US011590116B2

(12) United States Patent
Owens et al.

(10) Patent No.: US 11,590,116 B2
(45) Date of Patent: Feb. 28, 2023

(54) SUBSTITUTED PYRIDINES AND METHODS OF USE

(71) Applicant: THERAVANCE BIOPHARMA R&D IP, LLC, South San Francisco, CA (US)

(72) Inventors: Christina Owens, Oakland, CA (US); Svitlana Kulyk, Redwood City, CA (US); Steven D. E. Sullivan, San Francisco, CA (US); Paul Allegretti, Mountain View, CA (US); Mandy Loo, San Jose, CA (US); Jennifer Kozak, Pacifica, CA (US); Erik Fenster, San Bruno, CA (US); Adam D. Hughes, Half Moon Bay, CA (US)

(73) Assignee: THERAVANCE BIOPHARMA R&D IP, LLC, South San Francisco, CA (US)

( * ) Notice: Subject to any disclaimer, the term of this patent is extended or adjusted under 35 U.S.C. 154(b) by 152 days.

(21) Appl. No.: 16/949,915

(22) Filed: Nov. 20, 2020

(65) Prior Publication Data

US 2021/0154179 A1    May 27, 2021

Related U.S. Application Data

(60) Provisional application No. 63/198,637, filed on Oct. 30, 2020, provisional application No. 63/035,100, filed on Jun. 5, 2020, provisional application No. 62/939,186, filed on Nov. 22, 2019.

(51) Int. Cl.
| C07D 401/14 | (2006.01) |
| C07D 405/14 | (2006.01) |
| C07D 409/14 | (2006.01) |
| C07D 417/14 | (2006.01) |
| C07D 471/04 | (2006.01) |
| C07D 487/04 | (2006.01) |
| C07D 487/08 | (2006.01) |
| C07D 513/04 | (2006.01) |
| C07D 519/00 | (2006.01) |
| A61K 31/444 | (2006.01) |
| A61P 19/04 | (2006.01) |
| A61P 11/00 | (2006.01) |
| A61P 35/00 | (2006.01) |
| A61K 9/00 | (2006.01) |
| A61K 31/4709 | (2006.01) |
| A61K 31/496 | (2006.01) |
| A61K 31/4985 | (2006.01) |
| A61K 31/4995 | (2006.01) |
| A61K 31/519 | (2006.01) |
| A61K 31/5377 | (2006.01) |
| A61K 45/06 | (2006.01) |

(52) U.S. Cl.
CPC .......... *A61K 31/444* (2013.01); *A61K 9/0073* (2013.01); *A61K 31/4709* (2013.01); *A61K 31/496* (2013.01); *A61K 31/4985* (2013.01); *A61K 31/4995* (2013.01); *A61K 31/519* (2013.01); *A61K 31/5377* (2013.01); *A61K 45/06* (2013.01); *A61P 11/00* (2018.01); *A61P 19/04* (2018.01); *A61P 35/00* (2018.01); *C07D 401/14* (2013.01); *C07D 405/14* (2013.01); *C07D 409/14* (2013.01); *C07D 417/14* (2013.01); *C07D 471/04* (2013.01); *C07D 487/04* (2013.01); *C07D 487/08* (2013.01); *C07D 513/04* (2013.01); *C07D 519/00* (2013.01)

(58) Field of Classification Search
None
See application file for complete search history.

(56) References Cited

U.S. PATENT DOCUMENTS

| 2004/0176390 A1 | 9/2004 | Blumberg et al. |
| 2008/0319012 A1 | 12/2008 | Kim et al. |
| 2010/0022535 A1 | 1/2010 | Lee et al. |
| 2020/0147234 A1 | 5/2020 | Thomas-Karyat |
| 2020/0188370 A1 | 6/2020 | Kulyk et al. |

FOREIGN PATENT DOCUMENTS

| WO | 2001062756 A1 | 8/2001 |
| WO | 2001072737 A1 | 10/2001 |
| WO | 2002040468 A1 | 5/2002 |
| WO | 2002062794 A2 | 8/2002 |
| WO | 2002088107 A1 | 11/2002 |
| WO | 2004026306 A2 | 4/2004 |
| WO | 2004026859 A1 | 4/2004 |
| WO | 2004072033 A2 | 8/2004 |
| WO | 2004111036 A1 | 12/2004 |
| WO | 2006025988 A1 | 3/2006 |
| WO | 2007059359 A2 | 5/2007 |
| WO | 2008150827 A1 | 12/2008 |
| WO | 2009150547 A2 | 12/2009 |
| WO | 2010033906 A2 | 3/2010 |

(Continued)

OTHER PUBLICATIONS

International Search Report for PCT/US2020/070806 dated Feb. 8, 2021.

(Continued)

Primary Examiner — Samantha L Shterengarts
(74) Attorney, Agent, or Firm — Sheppard Mullin Richter & Hampton LLP

(57) ABSTRACT

The present disclosure provides inhibitors of activin receptor-like kinase 5 (ALK5). Also disclosed are methods to modulate the activity of ALK5 and methods of treatment of disorders mediated by ALK5.

25 Claims, No Drawings

(56) References Cited

FOREIGN PATENT DOCUMENTS

| WO | 2013009140 A2 | 1/2013 |
|---|---|---|
| WO | 2015046647 A1 | 4/2015 |
| WO | 2016081364 A1 | 5/2016 |
| WO | 2016140884 A1 | 9/2016 |
| WO | 2018017633 A1 | 1/2018 |
| WO | 2018132279 A1 | 7/2018 |
| WO | 2018183586 A1 | 10/2018 |
| WO | 2019005241 A1 | 1/2019 |
| WO | 2020123453 A2 | 6/2020 |
| WO | 2020123453 A3 | 7/2020 |

OTHER PUBLICATIONS

Ayers et al., "Transforming growth factor-B signaling in systemic sclerosis", The Journal of Biomedical Research, 32 (1): 3-12 (2018).
Written Opinion of the International Searching Authority for PCT/US2019/065389 dated Jun. 29, 2020.
Ebrahimi et al., "Interactions between Activin-like kinase 5 (ALK5) receptor and its inhibitors and the construction of a docking descriptor-based QSAR model", Journal Braz. Chem Soc, 23(11): 2043-2053 (2012).
Gellibert et al., "Identification of 1,5-naphthyridine derivatives as a novel series of potent and selective TGF-beta type I receptor inhibitors", J.Med.Chem, 47: 4494-4506 (2004).
Jin et al., "Discovery of N-((4-([1,2,4]triazolo[1,5-a]pyridin-6-yl)-5-(6-methylpyridin-2-yl)-1H-imidazol-2-yl)methyl)-2-fluoroaniline (EW-7197): A highly potent, selective, and orally bioavailable inhibitor of TGF-beta type I receptor kinase as cancer immunotherapeutic/antifobrotic agent", J.Med.Chem., 57: 4213-1238 (2014).
Jinnin et al., "Transforming growth factor beta-inhibitor repsox downregulates collagen expression of scleroderma dermal fibroblasts and prevents bleomycin-induced mice skin fibrosis", Exp. Dermatology, 26: 1139-1143 (2017).
Kelly et al., "Nephrogenic systemic fibrosis is associated with transforming growth factor B and Smad without evidence of renin-angiotensin system involvement", Journal of the American Academy of Dermatology, 58:1025-1030 (2008).
Li et al., "Synthesis and biological evaluation of 1-(6-methylpyridin-2-yl)-5-(quinoxalin-6-yl)-1,2,3-triazoles as transforming growth factor-beta type I receptor kinase inhibitors", Bioorganic & Med.Chem. Lett., 23: 1083-1086 (2013).
McCormick et al., "Anti-TGF-B treatment prevents skin and lung fibrosis in murine sclerodermatous graft-versus-host disease: a model for human scleroderma", The Journal of Immunology, 163: 5693-5699 (1999).
Pardali et al., "TGF-B-Induced endothelial-mesenchymal transition in fibrotic diseases", International Journal of Molecular Sciences, 18: 2157 (2017).
Ren et al., "Pharmacophore modeling and virtual screening for the discovery of new transforming growth factor-beta type I receptor (ALK5) inhibitors", Eur.J.Med.Chem., 44" 4259-4265 (2009).
Rosenbloom et al., "Human fibrotic diseases: current challenges in fibrosis research", Fibrosis: Methods and Protocols, Chapter 1, 1627: 1-23 (2017).
Song et al., "Vactosertib, a novel, orally bioavailable activin receptor-like kinase 5 inhibitor, promotes regression of fibrotic plaques in a rat model of peyronie's disease", The World of Men's Health, 12 pages (2019).
Yingling et al., "Development of TGF-B signalling inhibitors for cancer therapy", Nature Reviews: Drug Discovery, 3: 1011-1022(2004).
Yuan et al., "Targeting the immunity protein kinases for immuno-oncology", Eur.J.Med.Chem., 163: 413-427 (2019).
Zhu et al., "Design, synthesis, and antifibrosis evaluation of 4-(benzo-[c][1,2,5]thiadiazol-5-yl)-3(5)-(6-methyl-pyridin-2-yl)pyrazole and 3(5)-(6-methylpyridin-2-yl)-4-(thieno-l3,2,-c]pyridin-2-yl)pyrazole derivatives", Eur.J.Med.Chem., 180: 15-27 (2019).
U.S. Appl. No. 17/247,225, filed Dec. 4, 2020.

SUBSTITUTED PYRIDINES AND METHODS OF USE

CROSS-REFERENCE

This application claims the benefit of U.S. Provisional Application No. 62/939,186, filed Nov. 22, 2019; U.S. Provisional Application No. 63/035,100, filed Jun. 5, 2020; and U.S. Provisional Application No. 63/198,637, filed Oct. 30, 2020, each of which is incorporated herein by reference in its entirety.

BACKGROUND

Human fibrotic diseases such as systemic sclerosis (SSc), sclerodermatous graft vs. host disease, nephrogenic system fibrosis, and radiation-induced fibrosis, as well as cardiac, pulmonary, skin, liver, bladder and kidney fibrosis, constitute a major health problem. These diseases often progress to organ dysfunction with eventual organ failure and death due to lack of treatment available, mainly because the etiologic mechanisms of runaway fibrosis are complex, heterogeneous, and difficult to decipher. Activated myofibroblasts may be responsible for replacing normal tissues with nonfunctional fibrotic tissue. Therefore, signaling pathways responsible for stimulating profibrotic reactions in myofibroblasts have potential as targets for development of therapies to treat fibrotic diseases.

Normal tissue repair involves fibrotic reactions through homeostatic regulatory mechanisms. Uncontrolled fibrosis, however, may result in excess deposition of the extracellular matrix (ECM) macromolecules in interstitial space that stiffens over time. There are many sites along the molecular pathway leading up to myofibroblast activation, including, but not limited to, transforming growth factor-β (TGF-β) and bone morphogenic protein (BMP) signaling pathways. Of importance in this disclosure is the pathway involving transforming growth factor-β (TGF-β), TGF-β receptor I (TGF-βRI), and TGF-β receptor II (TGF-βRII).

TGF-β signaling is typically initiated by binding of a TGF-β ligand to a TGF-βRII. This in turn may recruit and phosphorylate TGF-βRI, also known as the activin receptor-like kinase 5 (ALK5). Once phosphorylated, ALK5 typically adopts an active conformation and is free to associate with and phosphorylate Smad2 or Smad3. Once phosphorylated, Smad 2 and 3 proteins then may form heterodimeric complexes with Smad4 which can translocate across the nuclear membrane and modulate Smad-mediated gene expression, including, for example, the production of collagen. Smad proteins are intracellular regulators of transcription and therefore may serve as modulators of TGF-β-regulated genes involving, inter alia, cell cycle arrest in epithelial and hematopoietic cells, control of mesenchymal cell proliferation and differentiation, wound healing, extracellular matrix production, immunosuppression and carcinogenesis.

ALK5 is believed to be the most relevant of the activin-like kinases (ALKs) in the fibrotic process (Rosenbloom, et al., *Fibrosis: Methods and Protocols, Methods in Molecular Biology*, 2017, Vol. 1627, Chapter 1, pp. 1-21). Several small molecules have been developed to inhibit the activity of ALK5 for various therapeutic indications, related mostly to oncology (see Yingling, et al., *Nature Reviews: Drug Discovery*, December 2004, Vol. 3, pp. 1011-1022).

SUMMARY OF THE INVENTION

One of the main problems with ALK5 inhibitors developed to date is that these molecules have been associated with ventricular or cardiac remodeling in preclinical safety studies resulting from significant systemic exposure from oral administration. In view of the foregoing, a need exists for small molecules that target ALK5 and for use of such compounds in the treatment of various diseases, such as cancer and fibrosis, while limiting adverse side effects. The present disclosure provides these and other related advantages. One objective of the present disclosure is to deliver a potent ALK5 inhibitor locally with minimal systemic exposure in order to address any unintended and unwanted systemic side effects of ALK5 inhibition during treatment. Therefore, in some aspects, the present disclosure provides inhaled, long-acting and lung-selective ALK5 inhibitors for the treatment of idiopathic pulmonary fibrosis. Compounds of the present disclosure may be used to treat other diseases, including, but not limited to, pulmonary fibrosis, liver fibrosis, renal glomerulosclerosis, and cancer. Compounds of the present disclosure may be used as a monotherapy or co-dosed with other therapies, whether delivered by inhalation, orally, intravenously, subcutaneously, or topically.

In certain aspects, the present disclosure provides a compound of Formula (I):

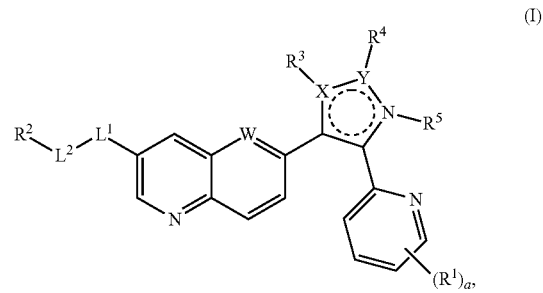

or a pharmaceutically acceptable salt thereof, wherein:

W is selected from CH and N;
X and Y are each independently selected from C and N;
a is an integer from 0 to 3;
$R^1$ is independently selected at each occurrence from $R^{10}$;
$L^1$ is selected from absent; $C_{1-6}$ alkylene, $C_{2-6}$ alkenylene, $C_{2-6}$ alkynylene, $C_{3-12}$ carbocycle, and 3- to 12-membered heterocycle, each of which is optionally substituted with one or more $R^{10}$;
$L^2$ is selected from absent, —O—, —S—, —N($R^{11}$)—, —C(O)—, —C(O)O—, —OC(O)—, —OC(O)O—, —C(O)N($R^{11}$)—, —C(O)N($R^{11}$)C(O)—, —C(O)N($R^{11}$)C(O)N($R^{11}$)—, —N($R^{11}$)C(O)—, —N($R^{11}$)C(O)N($R^{11}$)—, —N($R^{11}$)C(O)O—, —OC(O)N($R^{11}$)—, —C(N$R^{11}$)—, —N($R^{11}$)C(N$R^{11}$)—, —C(N$R^{11}$)N($R^{11}$)—, —N($R^{11}$)C(N$R^{11}$)N($R^{11}$)—, —S(O)$_2$—, —OS(O)—, —S(O)O—, —S(O)—, —OS(O)$_2$, —S(O)$_2$O—, —N($R^{11}$)S(O)$_2$—, —S(O)$_2$N($R^{11}$)—, —N($R^{11}$)S(O)—, —S(O)N($R^{11}$)—, —N($R^{11}$)S(O)$_2$N($R^{11}$)—, and —N($R^{11}$)S(O)N($R^{11}$)—;
$R^2$ is independently selected at each occurrence from $R^{10}$;
$R^3$, $R^4$, and $R^5$ are each independently absent or selected from $R^{11}$;
$R^{10}$ is independently selected at each occurrence from; halogen, —NO$_2$, —CN, —OR$^{12}$, —SR$^{12}$, —N(R$^{12}$)$_2$, —NR$^{13}$R$^{14}$, —S(=O)R$^{12}$—, —S(=O)$_2$R$^{12}$, —S(=O)$_2$N(R$^{12}$)$_2$, —S(=O)$_2$NR$^{13}$R$^{14}$, —NR$^{12}$S(=O)$_2$R$^{12}$, —NR$^{12}$S(=O)$_2$N(R$^{12}$)$_2$, —NR$^{12}$S(=O)$_2$NR$^{13}$R$^{14}$, —C(O)R$^{12}$, —C(O)OR$^{12}$, —OC(O)R$^{12}$, —OC(O)OR$^{12}$, —OC(O)N(R$^{12}$)$_2$, —OC(O)NR$^{13}$R$^{14}$, —NR$^{12}$C(O)R$^{12}$, —NR$^{12}$C(O)OR$^{12}$, —NR$^{12}$C(O)N(R$^{12}$)$_2$, —NR$^{12}$C(O)NR$^{13}$R$^{14}$, —C(O)N(R$^{12}$)$_2$, —C(O)NR$^{13}$R$^{14}$, —P(O)(OR$^{12}$)$_2$, —P(O)(R$^{12}$)$_2$, =O, =S, =N(R$^{12}$);

C$_{1-10}$ alkyl, C$_{2-10}$ alkenyl, and C$_{2-10}$ alkynyl, each of which is independently optionally substituted at each occurrence with one or more substituents selected from halogen, —NO$_2$, —CN, —OR$^{12}$, —SR$^{12}$, —N(R$^{12}$)$_2$, —NR$^{13}$R$^{14}$, —S(=O)R$^{12}$, —S(=O)$_2$R$^{12}$, —S(=O)$_2$N(R$^{12}$)$_2$, —S(=O)$_2$NR$^{13}$R$^{14}$, —NR$^{12}$S(=O)$_2$R$^{12}$, —NR$^{12}$S(=O)$_2$N(R$^{12}$)$_2$, —NR$^{12}$S(=O)$_2$NR$^{13}$R$^{14}$, —C(O)R$^{12}$, —C(O)OR$^{12}$, —OC(O)R$^{12}$, —OC(O)OR$^{12}$, —OC(O)N(R$^{12}$)$_2$, —OC(O)NR$^{13}$R$^{14}$, —NR$^{12}$C(O)R$^{12}$, —NR$^{12}$C(O)OR$^{12}$, —NR$^{12}$C(O)N(R$^{12}$)$_2$, —NR$^{12}$C(O)NR$^{13}$R$^{14}$, —C(O)N(R$^{12}$)$_2$, —C(O)NR$^{13}$R$^{14}$, —P(O)(OR$^{12}$)$_2$, —P(O)(R$^{12}$)$_2$, =O, =S, =N(R$^{12}$), C$_{3-12}$ carbocycle, and 3- to 12-membered heterocycle; and C$_{3-12}$ carbocycle and 3- to 12-membered heterocycle, wherein each C$_{3-12}$ carbocycle and 3- to 12-membered heterocycle in R$^{10}$ is independently optionally substituted with one or more substituents selected from halogen, —NO$_2$, —CN, —OR$^{12}$, —SR$^{12}$, —N(R$^{12}$)$_2$, —NR$^{13}$R$^{14}$, —S(=O)R$^{12}$, —S(=O)$_2$R$^{12}$, —S(=O)$_2$N(R$^{12}$)$_2$, —S(=O)$_2$NR$^{13}$R$^{14}$, —NR$^{12}$S(=O)$_2$R$^{12}$, —NR$^{12}$S(=O)$_2$N(R$^{12}$)$_2$, —NR$^{12}$S(=O)$_2$NR$^{13}$R$^{14}$, —C(O)R$^{12}$, —C(O)OR$^{12}$, —OC(O)R$^{12}$, —OC(O)OR$^{12}$, —OC(O)N(R$^{12}$)$_2$, —OC(O)NR$^{13}$R$^{14}$, —NR$^{12}$C(O)R$^{12}$, —NR$^{12}$C(O)OR$^{12}$, —NR$^{12}$C(O)N(R$^{12}$)$_2$, —NR$^{12}$C(O)NR$^{13}$R$^{14}$, —C(O)N(R$^{12}$)$_2$, —C(O)NR$^{13}$R$^{14}$, —P(O)(OR$^{12}$)$_2$, —P(O)(R$^{12}$)$_2$, =O, =S, =N(R$^{12}$), R$^{12}$, C$_{1-6}$ alkyl, C$_{1-6}$ haloalkyl, C$_{2-6}$ alkenyl, and C$_{2-6}$ alkynyl;

R$^{11}$ is independently selected at each occurrence from; hydrogen, —C(O)R$^{12}$, —C(O)OR$^{12}$, —C(O)N(R$^{12}$)$_2$, —C(O)NR$^{13}$R$^{14}$;

C$_{1-6}$ alkyl, C$_{2-6}$ alkenyl, and C$_{2-6}$ alkynyl, each of which is independently optionally substituted at each occurrence with one or more substituents selected from halogen, —NO$_2$, —CN, —OR$^{12}$, —SR$^{12}$, —N(R$^{12}$)$_2$, —NR$^{13}$R$^{14}$, —S(=O)R$^{12}$, —S(=O)$_2$R$^{12}$, —S(=O)$_2$N(R$^{12}$)$_2$, —S(=O)$_2$NR$^{13}$R$^{14}$, —NR$^{12}$S(=O)$_2$R$^{12}$, —NR$^{12}$S(=O)$_2$N(R$^{12}$)$_2$, —NR$^{12}$S(=O)$_2$NR$^{13}$R$^{14}$, —C(O)R$^{12}$, —C(O)OR$^{12}$, —OC(O)R$^{12}$, —OC(O)OR$^{12}$, —OC(O)N(R$^{12}$)$_2$, —OC(O)NR$^{13}$R$^{14}$, —NR$^{12}$C(O)R$^{12}$, —NR$^{12}$C(O)OR$^{12}$, —NR$^{12}$C(O)N(R$^{11}$)$_2$, —NR$^{12}$C(O)NR$^{13}$R$^{14}$, —C(O)N(R$^{12}$)$_2$, —C(O)NR$^{13}$R$^{14}$, —P(O)(OR$^{12}$)$_2$, —P(O)(R$^{12}$)$_2$, =O, =S, =N(R$^{12}$), C$_{3-12}$ carbocycle, and 3- to 12-membered heterocycle; and C$_{3-12}$ carbocycle and 3- to 12-membered heterocycle, wherein each C$_{3-12}$ carbocycle and 3- to 12-membered heterocycle in R$^{11}$ is independently optionally substituted with one or more substituents selected from halogen, —NO$_2$, —CN, —OR$^{12}$, —SR$^{12}$, —N(R$^{12}$)$_2$, —NR$^{13}$R$^{14}$, —S(=O)R$^{12}$, —S(=O)$_2$R$^{12}$, —S(=O)$_2$N(R$^{12}$)$_2$, —S(=O)$_2$NR$^{13}$R$^{14}$, —NR$^{12}$S(=O)$_2$R$^{12}$, —NR$^{12}$S(=O)$_2$N(R$^{12}$)$_2$, —NR$^{12}$S(=O)$_2$NR$^{13}$R$^{14}$, —C(O)R$^{12}$, —C(O)OR$^{12}$, —OC(O)R$^{12}$, —OC(O)OR$^{12}$, —OC(O)N(R$^{12}$)$_2$, —OC(O)NR$^{13}$R$^{14}$, —NR$^{12}$C(O)R$^{12}$, —NR$^{12}$C(O)OR$^{12}$, —NR$^{12}$C(O)N(R$^{12}$)$_2$, —NR$^{12}$C(O)NR$^{13}$R$^{14}$, —C(O)N(R$^{12}$)$_2$, —C(O)NR$^{13}$R$^{14}$, —P(O)(OR$^{12}$)$_2$, —P(O)(R$^{12}$)$_2$, =O, =S, =N(R$^{12}$), R$^{12}$, C$_{1-6}$ alkyl, C$_{1-6}$ haloalkyl, C$_{2-6}$ alkenyl, and C$_{2-6}$ alkynyl;

R$^{12}$ is independently selected at each occurrence from hydrogen; and C$_{1-10}$ alkyl, C$_{2-10}$ alkenyl, C$_{2-10}$ alkynyl, 1- to 6-membered heteroalkyl, C$_{3-12}$ carbocycle, and 3- to 12-membered heterocycle, each of which is optionally substituted by halogen, —CN, —NO$_2$, —NH$_2$, —NHCH$_3$, —NHCH$_2$CH$_3$, =O, —OH, —OCH$_3$, —OCH$_2$CH$_3$, —CH$_3$, —CH$_2$CH$_3$, —CH(CH$_3$)$_2$, —C(CH$_3$)$_3$, C$_{3-12}$ carbocycle, or 3- to 6-membered heterocycle; and R$^{13}$ and R$^{14}$ are taken together with the nitrogen atom to which they are attached to form a heterocycle, optionally substituted with one or more R$^{12}$.

For a compound of Formula (I), W may be N. In some embodiments, W is CH. In some embodiments, X is C and Y is N, optionally wherein R$^3$ is hydrogen, R$^4$ is hydrogen and R$^5$ is absent. In some embodiments, X is N and Y is C, optionally wherein R$^3$ is absent and R$^4$ and R$^5$ are each hydrogen. In some embodiments, X is N and Y is N, optionally wherein R$^3$ and R$^4$ are each absent and R$^5$ is hydrogen. In some embodiments, a is 1 or 2.

In certain aspects, the compound of Formula (I) is a compound of Formula (I-A)

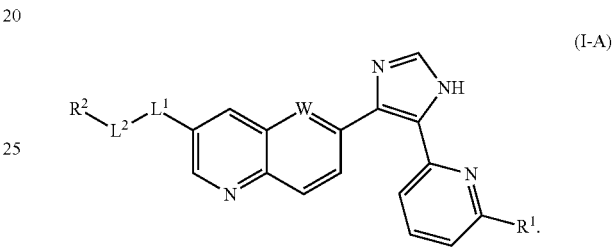

(I-A)

In certain aspects, the compound of Formula (I) is a compound of Formula (I-B):

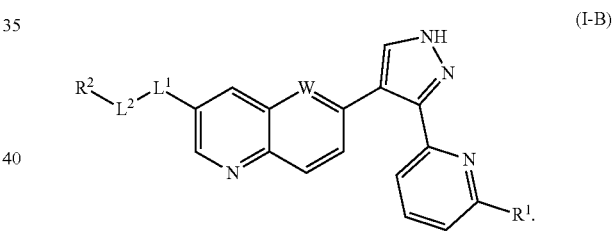

(I-B)

In certain aspects, the compound of Formula (I) is a compound of Formula (I-C):

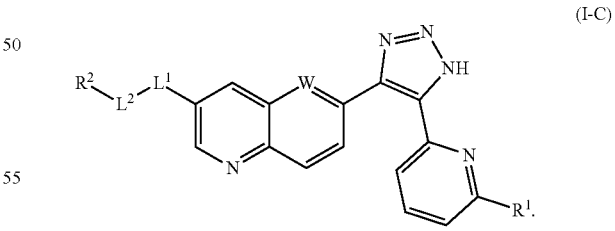

(I-C)

For a compound of Formula (I), (I-A), (I-B) or (I-C), R$^1$ may be selected from halogen, C$_{1-4}$ alkyl and C$_{1-4}$ haloalkyl, such as R is CH$_3$. In some embodiments, L$^1$ is selected from absent, C$_{1-6}$ alkylene, C$_{3-12}$ carbocycle and 3- to 12-membered heterocycle, such as L$^1$ is selected from 3- to 10-membered heterocycloalkylene, 5- to 10-membered heteroarylene and C$_{6-10}$ arylene. In some embodiments, L$^1$ is C$_{1-6}$ alkylene. In some embodiments, L$^1$ is absent. In some embodiments, L$^2$ is selected from absent, —O—, —N(R$^1$)—, —C(O)O—, —C(O)N(R$^{11}$)— and —N(R$^{11}$)C(O)—, such as L$^2$ is selected from absent, —O—, —NH—, —C(O)O—, —C(O)NH— and —NHC(O)—. In some embodiments, L$^2$ is —NH—. In some embodiments, L$^2$ is absent.

For a compound of Formula (I), (I-A), (I-B) or (I-C), R$^2$ may be selected from;
- halogen, —CN, —OR$^{12}$, —SR$^{12}$, —N(R$^{12}$)$_2$, —C(O)OR$^{12}$, —OC(O)R$^{12}$, —NR$^{12}$C(O)R$^{12}$, —NR$^{12}$C(O)N(R$^{12}$)$_2$, —C(O)N(R$^{12}$)$_2$;
- C$_{1-10}$ alkyl, optionally substituted with one or more substituents selected from halogen, —CN, —OR$^{12}$, —SR$^{12}$, —N(R$^{12}$)$_2$, —C(O)OR$^{12}$, —OC(O)R$^{12}$, —NR$^{12}$C(O)R$^{12}$, —NR$^{12}$C(O)N(R$^{12}$)$_2$, —C(O)N(R$^{12}$)$_2$, C$_{3-12}$ carbocycle, and 3- to 12-membered heterocycle; and
- C$_{3-12}$ carbocycle and 3- to 12-membered heterocycle,
  wherein each C$_{3-12}$ carbocycle and 3- to 12-membered heterocycle in R$^2$ is independently optionally substituted with one or more substituents selected from halogen, —CN, —OR$^{12}$, —SR$^{12}$, —N(R$^{12}$)$_2$, —C(O)OR$^{12}$, —OC(O)R$^{12}$, —NR$^{12}$C(O)R$^{12}$, —NR$^{12}$C(O)N(R$^{12}$)$_2$, —C(O)N(R$^{12}$)$_2$, =O, R$^{12}$, C$_{1-6}$ alkyl, and C$_{1-6}$ haloalkyl.

For a compound of Formula (I), (I-A), (I-B) or (I-C), R$^2$ may be selected from;
- —CN, —OR$^{12}$, —N(R$^{12}$)$_2$, —C(O)OR$^{12}$, —NR$^{12}$C(O)R$^{12}$, —C(O)N(R$^{12}$)$_2$;
- C$_{1-10}$ alkyl, optionally substituted with one or more substituents selected from halogen, —CN, —OR$^{12}$, —SR$^{12}$, —N(R$^{12}$)$_2$, —C(O)OR$^{12}$, C$_{3-12}$ carbocycle, and 3- to 12-membered heterocycle; and
- C$_{3-12}$ carbocycle and 3- to 12-membered heterocycle,
  wherein each C$_{3-12}$ carbocycle and 3- to 12-membered heterocycle in R$^2$ is independently optionally substituted with one or more substituents selected from —CN, —OR$^{12}$, —N(R$^{12}$)$_2$, —C(O)OR$^{12}$, —NR$^{12}$C(O)R, =O, R$^2$, C$_{1-6}$ alkyl, and C$_{1-6}$ haloalkyl.

For a compound of Formula (I), (I-A), (I-B) or (I-C), R$^{12}$ may independently be selected at each occurrence from hydrogen and C$_{1-6}$ alkyl, optionally substituted with one or more substituents selected from halogen, —NH$_2$, —NHCH$_3$, and —OCH$_3$.

For a compound of Formula (I), (I-A), (I-B) or (I-C), R$^2$ may be selected from C$_{3-6}$ cycloalkyl, C$_{3-6}$ cycloalkene, 3- to 6-membered heterocycloalkyl, and 5- to 6-membered heteroaryl, each of which is optionally substituted with one or more substituents selected from —NH$_2$, —NHCH$_3$, —N(CH$_3$)$_2$, —CH$_2$NH$_2$, —CH$_2$NHCH$_3$, —CH$_2$N(CH$_3$)$_2$, and —CH$_3$. In some embodiments, R$^2$ is C$_{1-3}$ alkyl substituted with C$_{3-6}$ cycloalkyl, C$_{3-6}$ cycloalkene, 3- to 6-membered heterocycloalkyl, or 5- to 6-membered heteroaryl, each of which is optionally substituted with one or more substituents selected from —NH$_2$, —NHCH$_3$, —N(CH$_3$)$_2$, —CH$_2$NH$_2$, —CH$_2$NHCH$_3$, —CH$_2$N(CH$_3$)$_2$, and —CH$_3$.

In some embodiments, for a compound of Formula (I), (I-A), (I-B) or (I-C), L$^1$ is selected from absent, C$_{3-12}$ carbocycle and 3- to 12-membered heterocycle;
L$^2$ is absent; and
R$^2$ is selected from;
- —CN, —OR$^{12}$, —N(R$^{12}$)$_2$, —C(O)OR$^{12}$, —NR$^{12}$C(O)R$^{12}$, —C(O)N(R$^{12}$)$_2$;
- C$_{1-10}$ alkyl, optionally substituted with one or more substituents selected from halogen, —CN, —OR$^{12}$, —SR$^{12}$, —N(R$^{12}$)$_2$, —C(O)OR$^{12}$, C$_{3-12}$ carbocycle, and 3- to 12-membered heterocycle; and
- C$_{3-12}$ carbocycle and 3- to 12-membered heterocycle,
  wherein each C$_{3-12}$ carbocycle and 3- to 12-membered heterocycle in R$^2$ is independently optionally substituted with one or more substituents selected from —CN, —OR$^{12}$, —N(R$^{12}$)$_2$, —C(O)OR$^{12}$, —NR$^{12}$C(O)R, =O, R$^{12}$, C$_{1-6}$ alkyl, and C$_{1-6}$ haloalkyl.

In some embodiments, for a compound of Formula (I), (I-A), (I-B) or (I-C), L$^1$ is selected from absent;
L$^2$ is selected from —O—, —NH—, —C(O)O—, —C(O)NH— and —NHC(O)—; and
R$^2$ is selected from;
- —CN, —OR$^{12}$, —N(R$^{12}$)$_2$, —C(O)OR$^{12}$, —NR$^{12}$C(O)R$^{12}$, —C(O)N(R$^{12}$)$_2$;
- C$_{1-10}$ alkyl, optionally substituted with one or more substituents selected from halogen, —CN, —OR$^{12}$, —SR$^{12}$, —N(R$^{12}$)$_2$, —C(O)OR$^{12}$, C$_{3-12}$ carbocycle, and 3- to 12-membered heterocycle; and
- C$_{3-12}$ carbocycle and 3- to 12-membered heterocycle,
  wherein each C$_{3-12}$ carbocycle and 3- to 12-membered heterocycle in R$^2$ is independently optionally substituted with one or more substituents selected from —CN, —OR$^{12}$, —N(R$^{12}$)$_2$, —C(O)OR$^{12}$, —NR$^{12}$C(O)R, =O, R$^{12}$, C$_{1-6}$ alkyl, and C$_{1-6}$ haloalkyl.

In some embodiments, for a compound of Formula (I), (I-A), (I-B) or (I-C), R$^1$ is CH$_3$;
L$^1$ is selected from absent, C$_{3-6}$ carbocycle and 3- to 6-membered heterocycle;
L$^2$ is selected from absent and —NH—;
R$^2$ is selected from;
- —NH$_2$;
- C$_{1-6}$ alkyl, optionally substituted with one or more substituents selected from C$_{3-6}$ carbocycle and 3- to 6-membered heterocycle; and
- C$_{3-6}$ carbocycle and 3- to 6-membered heterocycle,
  wherein each C$_{3-6}$ carbocycle and 3- to 6-membered heterocycle in R$^2$ is independently optionally substituted with one or more substituents selected from —N(R$^{12}$)$_2$, =O, R$^2$, and C$_{1-6}$ alkyl; and
R$^{12}$ is independently selected at each occurrence from hydrogen and C$_{1-6}$ alkyl, optionally substituted by halogen, —NH$_2$, —NHCH$_3$, and —NHCH$_2$CH$_3$.

In certain aspects, the present disclosure provides a substantially pure stereoisomer of a compound disclosed herein. The stereoisomer may be provided in at least 90% enantiomeric excess.

In certain aspects, the present disclosure provides a compound selected from Table 1.

In certain aspects, the present disclosure provides a pharmaceutical composition comprising a compound disclosed herein and a pharmaceutically acceptable carrier. The pharmaceutical composition may be formulated for inhalation.

In certain aspects, the present disclosure provides a method of inhibiting ALK5, comprising contacting ALK5 with an effective amount of a compound disclosed herein. In certain aspects, the present disclosure provides a method of treating an ALK5-mediated disease or condition in a subject, comprising administering to the subject a therapeutically effective amount of a compound disclosed herein. In practicing any of the subject methods, the disease or condition may be selected from fibrosis, alopecia and cancer. In some embodiments, the disease or condition is fibrosis. In some embodiments, the present disclosure provides a method of treating fibrosis, comprising administering to a patient a therapeutically effective amount of a compound disclosed herein. The fibrosis may be selected from systemic sclerosis, nephrogenic systemic fibrosis, organ-specific fibrosis, fibrosis associated with cancer, cystic fibrosis, and fibrosis associated with an autoimmune disease. Optionally, the organ-specific fibrosis is selected from cardiac fibrosis, kidney fibrosis, pulmonary fibrosis, liver fibrosis, portal vein fibrosis, skin fibrosis, bladder fibrosis, intestinal fibrosis, peritoneal fibrosis, myelofibrosis, oral submucous fibrosis, and retinal fibrosis. In some embodiments, the organ-specific fibrosis is intestinal fibrosis. Optionally, the pulmonary fibrosis is selected from idiopathic pulmonary fibrosis (IPF), familial pulmonary fibrosis (FPF), interstitial lung fibrosis, fibrosis associated with asthma, fibrosis associated with chronic obstructive pulmonary disease (COPD), silica-induced fibrosis, asbestos-induced fibrosis and chemotherapy-induced lung fibrosis. Optionally, the pulmonary fibrosis is idiopathic pulmonary fibrosis (IPF). In some embodiments, the pulmonary fibrosis was induced by a viral infection.

In practicing any of the subject methods, the disease or condition may be cancer, optionally wherein the cancer is selected from breast cancer, colon cancer, prostate cancer, lung cancer, hepatocellular carcinoma, glioblastoma, melanoma, and pancreatic cancer. In some embodiments, the cancer is lung cancer, optionally non-small cell lung cancer. A method of the subject disclosure may further comprise administering a second therapeutic agent. Optionally, the second therapeutic agent is an immunotherapeutic agent, such as a PD-1 inhibitor or a CTLA-4 inhibitor. In some embodiments, the immunotherapeutic agent is selected from pembrolizumab and durvalumab. A method of the present disclosure may further comprise administering an effective amount of radiation. In practicing any of the subject methods, the compound or salt disclosed herein may be administered by inhalation.

In certain aspects, the present disclosure provides a compound disclosed herein for use in treating fibrosis. In certain aspects, the present disclosure provides the use of a compound disclosed herein for the manufacture of a medicament for treating fibrosis.

INCORPORATION BY REFERENCE

All publications and patent applications mentioned in this specification are herein incorporated by reference to the same extent as if each individual publication or patent application was specifically and individually indicated to be incorporated by reference.

DETAILED DESCRIPTION

Unless defined otherwise, all technical and scientific terms used herein have the same meaning as is commonly understood by one of skill in the art to which this disclosure belongs.

Chemical structures are named herein according to IUPAC conventions as implemented in ChemDraw® software (Perkin Elmer, Inc., Cambridge, Mass.).

As used in the specification and claims, the singular forms "a", "an" and "the" include plural references unless the context clearly dictates otherwise.

The term "$C_{x-y}$" or "$C_x$-$C_y$" when used in conjunction with a chemical moiety, such as alkyl, alkenyl, or alkynyl, is meant to include groups that contain from x to y carbons in the chain. For example, the term "$C_{x-y}$ alkyl" refers to substituted or unsubstituted saturated hydrocarbon groups, including straight-chain alkyl and branched-chain alkyl groups, that contain from x to y carbons in the chain.

"Alkyl" refers to substituted or unsubstituted saturated hydrocarbon groups, including linear and branched alkyl groups. An alkyl group may contain from one to twelve carbon atoms (e.g., $C_{1-12}$ alkyl), such as one to eight carbon atoms ($C_{1-8}$ alkyl) or one to six carbon atoms ($C_{1-6}$ alkyl). Exemplary alkyl groups include methyl, ethyl, n-propyl, isopropyl, n-butyl, isobutyl, sec-butyl, tert-butyl, pentyl, isopentyl, neopentyl, hexyl, septyl, octyl, nonyl, and decyl. An alkyl group is attached to the rest of the molecule by a single bond. Unless stated otherwise specifically in the specification, an alkyl group is optionally substituted by one or more substituents such as those substituents described herein.

"Haloalkyl" refers to an alkyl group that is substituted by one or more halogens. Exemplary haloalkyl groups include trifluoromethyl, difluoromethyl, trichloro methyl, 2,2,2-trifluoroethyl, 1,2-difluoroethyl, 3-bromo-2-fluoropropyl, and 1,2-dibromoethyl.

"Alkenyl" refers to substituted or unsubstituted hydrocarbon groups, including linear and branched alkenyl groups, containing at least one double bond. An alkenyl group may contain from two to twelve carbon atoms (e.g., $C_{2-12}$ alkenyl), such as two to eight carbon atoms ($C_{2-8}$ alkenyl) or two to six carbon atoms ($C_{2-6}$ alkenyl). Exemplary alkenyl groups include ethenyl (i.e., vinyl), prop-1-enyl, but-1-enyl, pent-1-enyl, penta-1,4-dienyl, and the like. Unless stated otherwise specifically in the specification, an alkenyl group is optionally substituted by one or more substituents such as those substituents described herein.

"Alkynyl" refers to substituted or unsubstituted hydrocarbon groups, including linear and branched alkynyl groups, containing at least one triple bond. An alkynyl group may contain from two to twelve carbon atoms (e.g., $C_{2-12}$ alkynyl), such as two to eight carbon atoms ($C_{2-8}$ alkynyl) or two to six carbon atoms ($C_{2-6}$ alkynyl). Exemplary alkynyl groups include ethynyl, propynyl, butynyl, pentynyl, hexynyl, and the like. Unless stated otherwise specifically in the specification, an alkynyl group is optionally substituted by one or more substituents such as those substituents described herein.

"Alkylene" or "alkylene chain" refers to substituted or unsubstituted divalent saturated hydrocarbon groups, including linear alkylene and branched alkylene groups, that contain from one to twelve carbon atoms (e.g., $C_{1-12}$ alkylene), such as one to eight carbon atoms ($C_{1-8}$ alkylene) or one to six carbon atoms ($C_{1-6}$ alkylene). Exemplary alkylene groups include methylene, ethylene, propylene, and n-butylene. Similarly, "alkenylene" and "alkynylene" refer to alkylene groups, as defined above, which comprise one or more carbon-carbon double or triple bonds, respectively. The points of attachment of the alkylene, alkenylene or alkynylene chain to the rest of the molecule can be through one carbon or any two carbons of the chain. Unless stated otherwise specifically in the specification, an alkylene, alkenylene, or alkynylene group is optionally substituted by one or more substituents such as those substituents described herein.

"Heteroalkyl", "heteroalkenyl" and "heteroalkynyl" refer to substituted or unsubstituted alkyl, alkenyl and alkynyl groups, respectively, in which one or more, such as 1, 2 or 3, of the carbon atoms are replaced with a heteroatom, such as O, N, P, Si, S, or combinations thereof. Any nitrogen, phosphorus, and sulfur heteroatoms present in the chain may optionally be oxidized, and any nitrogen heteroatoms may optionally be quaternized. If given, a numerical range refers to the chain length in total. For example, a 3- to 8-membered heteroalkyl group has a chain length of 3 to 8 atoms. Connection to the rest of the molecule may be through either a heteroatom or a carbon in the heteroalkyl, heteroalkenyl or heteroalkynyl chain. Unless stated otherwise specifically in the specification, a heteroalkyl, heteroalkenyl, or heteroalkynyl group is optionally substituted by one or more substituents such as those substituents described herein.

"Heteroalkylene", "heteroalkenylene" and "heteroalkynylene" refer to substituted or unsubstituted alkylene, alkenylene and alkynylene groups, respectively, in which one or more, such as 1, 2 or 3, of the carbon atoms are replaced with a heteroatom, such as O, N, P, Si, S, or combinations thereof. Any nitrogen, phosphorus, and sulfur heteroatoms present in the chain may optionally be oxidized, and any nitrogen heteroatoms may optionally be quaternized. If given, a numerical range refers to the chain length in total. For example, a 3- to 8-membered heteroalkylene group has a chain length of 3 to 8 atoms. The points of attachment of the heteroalkylene, heteroalkenylene or heteroalkynylene chain to the rest of the molecule can be through either one heteroatom or one carbon, or any two heteroatoms, any two carbons, or any one heteroatom and any one carbon in the heteroalkylene, heteroalkenylene or heteroalkynylene chain. Unless stated otherwise specifically in the specification, a heteroalkylene, heteroalkenylene, or heteroalkynylene group is optionally substituted by one or more substituents such as those substituents described herein.

"Carbocycle" refers to a saturated, unsaturated or aromatic ring in which each atom of the ring is a carbon atom. Carbocycle may include $C_{3-10}$ monocyclic rings, $C_{6-12}$ bicyclic rings, $C_{6-12}$ spirocyclic rings, and $C_{6-12}$ bridged rings. Each ring of a bicyclic carbocycle may be selected from saturated, unsaturated, and aromatic rings. In some embodiments, the carbocycle is a $C_{6-12}$ aryl group, such as $C_{6-10}$ aryl. In some embodiments, the carbocycle is a $C_{6-12}$ cycloalkyl group. In some embodiments, the carbocycle is a $C_{6-12}$ cycloalkenyl group. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, are included in the definition of carbocycle. Exemplary carbocycles include cyclopentyl, cyclohexyl, cyclohexenyl, adamantyl, phenyl, indanyl, and naphthyl. Unless stated otherwise specifically in the specification, a carbocycle is optionally substituted by one or more substituents such as those substituents described herein.

"Heterocycle" refers to a saturated, unsaturated or aromatic ring comprising one or more heteroatoms, for example 1, 2 or 3 heteroatoms selected from O, S and N. Heterocycles include 3- to 10-membered monocyclic rings, 6- to 12-membered bicyclic rings, 6- to 12-membered spirocyclic rings, and 6- to 12-membered bridged rings. Each ring of a bicyclic heterocycle may be selected from saturated, unsaturated, and aromatic rings. The heterocycle may be attached to the rest of the molecule through any atom of the heterocycle, valence permitting, such as a carbon or nitrogen atom of the heterocycle. In some embodiments, the heterocycle is a 5- to 10-membered heteroaryl group, such as 5- or 6-membered heteroaryl. In some embodiments, the heterocycle is a 3- to 12-membered heterocycloalkyl group. In an exemplary embodiment, a heterocycle, e.g., pyridyl, may be fused to a saturated or unsaturated ring, e.g., cyclohexane, cyclopentane, or cyclohexene. Exemplary heterocycles include pyrrolidinyl, pyrrolyl, imidazolyl, pyrazolyl, triazolyl, piperidinyl, pyridinyl, pyrimidinyl, pyridazinyl, pyrazinyl, thiophenyl, oxazolyl, thiazolyl, morpholinyl, indazolyl, indolyl, and quinolinyl. Unless stated otherwise specifically in the specification, a heterocycle is optionally substituted by one or more substituents such as those substituents described herein.

"Heteroaryl" refers to a 5- to 12-membered aromatic ring that comprises at least one heteroatom, such as 1, 2 or 3 heteroatoms, selected from O, S and N. As used herein, the heteroaryl ring may be selected from monocyclic or bicyclic-including fused, spirocyclic and bridged ring systems—wherein at least one of the rings in the ring system is aromatic. The heteroatom(s) in the heteroaryl may optionally be oxidized. One or more nitrogen atoms, if present, are optionally quaternized. The heteroaryl may be attached to the rest of the molecule through any atom of the heteroaryl, valence permitting, such as a carbon or nitrogen atom of the heteroaryl. Examples of heteroaryl groups include, but are not limited to, azepinyl, benzimidazolyl, benzisothiazolyl, benzisoxazolyl, benzofuranyl, benzothiazolyl, benzothiophenyl, benzoxazolyl, furanyl, imidazolyl, indazolyl, indolyl, isoquinolinyl, isothiazolyl, isoxazolyl, oxadiazolyl, oxazolyl, purinyl, pyrazinyl, pyrazolidinyl, pyrazolyl, pyridazinyl, pyridazolyl, pyridyl, pyrimidinyl, pyrrolyl, quinazolinyl, quinolinyl, quinoxalinyl, tetrahydroquinolinyl, thiadiazolyl, thiazolyl, and thienyl groups. Unless stated otherwise specifically in the specification, a heteroaryl is optionally substituted by one or more substituents such as those substituents described herein.

Unless stated otherwise, hydrogen atoms are implied in structures depicted herein as necessary to satisfy the valence requirement.

A waved line "⌇" drawn across a bond or a dashed bond "---" are used interchangeably herein to denote where a bond disconnection or attachment occurs. For example, in the structure

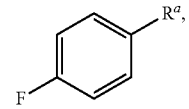

$R^a$ is attached to the para position of a fluorophenyl ring through a single bond. If $R^a$ is 2-pyridine as in

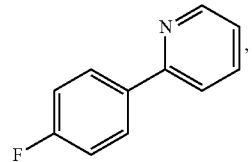 [SMILES: Fc1ccc(-c2ccccn2)cc1]

then $R^a$ may be depicted as

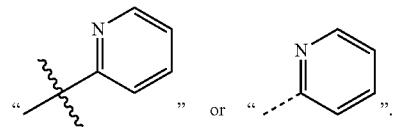

The term "substituted" refers to moieties having substituents replacing a hydrogen on one or more carbons or heteroatoms of the structure. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this disclosure, heteroatoms such as nitrogen may have any permissible substituents of organic compounds described herein which satisfy the valences of the heteroatoms.

A compound disclosed herein, such as a compound of Formula (I), is optionally substituted by one or more, such as 1, 2 or 3 substituents selected from:

halogen, —$NO_2$, —CN, —$OR^{12}$, —$SR^{12}$, —$N(R^{12})_2$, —$NR^{13}R^{14}$, —S(═O)$R^{12}$, —S(═O)$_2R^{12}$, —S(═O)$_2$N$(R^{12})_2$, —S(═O)$_2NR^{13}R^{14}$, —$NR^{12}$S(═O)$_2R^{12}$, —$NR^{12}$S(═O)$_2$N$(R^{12})_2$, —$NR^{12}$S(═O)$_2NR^{13}R^{14}$, —C(O)$R^{12}$, —C(O)O$R^{12}$, —OC(O)$R^{12}$, —OC(O)O$R^{12}$, —OC(O)N$(R^{12})_2$, —OC(O)N$R^{13}R^{14}$, —$NR^{12}$C(O)$R^{12}$, —$NR^{12}$C(O)O$R^{12}$, —$NR^{12}$C(O)N$(R^{12})_2$, —$NR^{12}$C(O)N$R^{13}R^{14}$, —C(O)N$(R^{12})_2$, —C(O)N$R^{13}R^{14}$, —P(O)(O$R^{12})_2$, —P(O)($R^{12})_2$, ═O, ═S, ═N($R^{12}$);

$C_{1-10}$ alkyl, $C_{2-10}$ alkenyl, and $C_{2-10}$ alkynyl, each of which is independently optionally substituted at each occurrence with one or more substituents selected from halogen, —$NO_2$, —CN, —$OR^{12}$, —$SR^{12}$, —$N(R^{12})_2$, —$NR^{13}R^{14}$, —S(═O)$R^{12}$, —S(═O)$_2R^{12}$, —S(═O)$_2$N$(R^{12})_2$, —S(═O)$_2NR^{13}R^{14}$, —$NR^{12}$S(═O)$_2R^{12}$, —$NR^{12}$S(═O)$_2$N$(R^{12})_2$, —$NR^{12}$S(═O)$_2NR^{13}R^{14}$, —C(O)$R^{12}$, —C(O)O$R^{12}$, —OC(O)$R^{12}$, —OC(O)O$R^{12}$, —OC(O)N$(R^{12})_2$, —OC(O)N$R^{13}R^{14}$, —$NR^{12}$C(O)$R^{12}$, —$NR^{12}$C(O)O$R^{12}$, —$NR^{12}$C(O)N$(R^{12})_2$, —$NR^{12}$C(O)N$R^{13}R^{14}$, —C(O)N$(R^{12})_2$, —C(O)N$R^{13}R^{14}$, —P(O)(O$R^{12})_2$, —P(O)($R^{12})_2$, ═O, ═S, ═N($R^{12}$), $C_{3-12}$ carbocycle, and 3- to 12-membered heterocycle; and $C_{3-12}$ carbocycle and 3- to 12-membered heterocycle, wherein each $C_{3-12}$ carbocycle and 3- to 12-membered heterocycle is independently optionally substituted with one or more substituents selected from halogen, —$NO_2$, —CN, —$OR^{12}$, —$SR^{12}$, —$N(R^{12})_2$, —$NR^{13}R^{14}$, —S(═O)$R^{12}$, —S(═O)$_2R^{12}$, —S(═O)$_2$N$(R^{12})_2$, —S(═O)$_2NR^{13}R^{14}$, —$NR^{12}$S(═O)$_2R^{12}$, —$NR^{12}$S(═O)$_2$N$(R^{11})_2$, —$NR^{12}$S(═O)$_2NR^{13}R^{14}$, —C(O)$R^{12}$, —C(O)O$R^{12}$, —OC(O)$R^{12}$, —OC(O)O$R^{12}$, —OC(O)N$(R^{12})_2$, —OC(O)N$R^{13}R^{14}$, —$NR^{12}$C(O)$R^{12}$, —$NR^{12}$C(O)O$R^{12}$, —$NR^{12}$C(O)N$(R^{12})_2$, —$NR^{12}$C(O)N$R^{13}R^{14}$, —C(O)N$(R^{12})_2$, —C(O)N$R^{13}R^{14}$, —P(O)(O$R^{12})_2$, —P(O)($R^{12})_2$, ═O, ═S, ═N($R^{12}$), $R^{12}$, $C_{1-6}$ alkyl, $C_{1-6}$ haloalkyl, $C_{2-6}$ alkenyl, and $C_{2-6}$ alkynyl;

$R^{12}$ is independently selected at each occurrence from hydrogen; and $C_{1-10}$ alkyl, $C_{2-10}$ alkenyl, $C_{2-10}$ alkynyl, 1- to 6-membered heteroalkyl, $C_{3-12}$ carbocycle, and 3- to 12-membered heterocycle, each of which is optionally substituted by halogen, —CN, —$NO_2$, —$NH_2$, —$NHCH_3$, —$NHCH_2CH_3$, ═O, —OH, —$OCH_3$, —$OCH_2CH_3$, —$CH_3$, —$CH_2CH_3$, —$CH(CH_3)_2$, —$C(CH_3)_3$, $C_{3-12}$ carbocycle, or 3- to 6-membered heterocycle; and $R^{13}$ and $R^{14}$ are taken together with the nitrogen atom to which they are attached to form a heterocycle, optionally substituted with one or more $R^{12}$.

In some embodiments, a compound disclosed herein, such as a compound of Formula (I), is optionally substituted by one or more, such as 1, 2 or 3 substituents selected from:

halogen, —$NO_2$, —CN, —$OR^{12}$, —$SR^{12}$, —$N(R^{12})_2$, —$NR^{13}R^{14}$, —S(═O)$R^{12}$, —S(═O)$_2R^{12}$, —S(═O)$_2$N$(R^{12})_2$, —S(═O)$_2NR^{13}R^{14}$, —$NR^{12}$S(═O)$_2R^{12}$, —$NR^{12}$S(═O)$_2$N$(R^{12})_2$, —$NR^{12}$S(═O)$_2NR^{13}R^{14}$, —C(O)$R^{12}$, —C(O)O$R^{12}$, —OC(O)$R^{12}$, —OC(O)O$R^{12}$, —OC(O)N$(R^{12})_2$, —OC(O)N$R^{13}R^{14}$, —$NR^{12}$C(O)$R^{12}$, —$NR^{12}$C(O)O$R^{12}$, —$NR^{12}$C(O)N$(R^{12})_2$, —$NR^{12}$C(O)N$R^{13}R^{14}$, —C(O)N$(R^{12})_2$, —C(O)N$R^{13}R^{14}$, —P(O)(O$R^{12})_2$, —P(O)($R^{12})_2$, ═O, ═S, ═N($R^{12}$);

$C_{1-10}$ alkyl, $C_{2-10}$ alkenyl, and $C_{2-10}$ alkynyl, each of which is independently optionally substituted at each occurrence with one or more substituents selected from halogen, ═O, ═S, ═N($R^{12}$), $C_{3-12}$ carbocycle, and 3- to 12-membered heterocycle; and $C_{3-12}$ carbocycle and 3- to 12-membered heterocycle, wherein each $C_{3-12}$ carbocycle and 3- to 12-membered heterocycle is independently optionally substituted with one or more substituents selected from halogen, ═O, ═S, ═N($R^{12}$), $C_{1-6}$ alkyl, $C_{1-6}$ haloalkyl, $C_{2-6}$ alkenyl, and $C_{2-6}$ alkynyl;

$R^{12}$ is independently selected at each occurrence from hydrogen; and $C_{1-10}$ alkyl, $C_{2-10}$ alkenyl, $C_{2-10}$ alkynyl, 1- to 6-membered heteroalkyl, $C_{3-12}$ carbocycle, and 3- to 12-membered heterocycle, each of which is optionally substituted by halogen, —CN, —$NO_2$, —$NH_2$, —$NHCH_3$, —$NHCH_2CH_3$, ═O, —OH, —$OCH_3$, —$OCH_2CH_3$, —$CH_3$, —$CH_2CH_3$, —$CH(CH_3)_2$, —$C(CH_3)_3$, $C_{3-12}$ carbocycle, or 3- to 6-membered heterocycle; and $R^{13}$ and $R^{14}$ are taken together with the nitrogen atom to which they are attached to form a heterocycle, optionally substituted with one or more $R^{12}$.

In some embodiments, a compound disclosed herein, such as a compound of Formula (I), is optionally substituted by one or more, such as 1, 2 or 3 substituents selected from halogen, —CN, —$NO_2$, —$NH_2$, —$NHCH_3$, —$NHCH_2CH_3$, ═O, —OH, —$OCH_3$, and —$OCH_2CH_3$; and $C_{1-10}$ alkyl, $C_{2-10}$ alkenyl, $C_{2-10}$ alkynyl, 1- to 6-membered heteroalkyl, $C_{3-12}$ carbocycle, and 3- to 12-membered heterocycle, each of which is optionally substituted by halogen, —CN, —$NO_2$, —$NH_2$, —$NHCH_3$, —$NHCH_2CH_3$, ═O, —OH, —$OCH_3$, —$OCH_2CH_3$, —$CH_3$, —$CH_2CH_3$, —$CH(CH_3)_2$, —$C(CH_3)_3$, $C_{3-12}$ carbocycle, or 3- to 6-membered heterocycle.

It will be understood by those skilled in the art that substituents can themselves be substituted, if appropriate. Unless specifically stated as "unsubstituted", references to chemical moieties herein are understood to include substituted variants. For example, reference to a "heteroaryl" group or moiety implicitly includes both substituted and unsubstituted variants.

Where bivalent substituent groups are specified herein by their conventional chemical formulae, written from left to right, they are intended to encompass the isomer that would result from writing the structure from right to left, e.g., —$CH_2O$— is also intended to encompass to —$OCH_2$—.

"Optional" or "optionally" means that the subsequently described event of circumstances may or may not occur, and that the description includes instances where the event or circumstance occurs and instances in which it does not. For example, an "optionally substituted" group may be either unsubstituted or substituted.

Compounds of the present disclosure also include crystalline and amorphous forms of those compounds, pharmaceutically acceptable salts, and active metabolites having the same type of activity, including, for example, polymorphs, pseudopolymorphs, solvates, hydrates, unsolvated polymorphs (including anhydrates), conformational polymorphs, amorphous forms of the compounds, and mixtures thereof.

The compounds described herein may exhibit their natural isotopic abundance, or one or more of the atoms may be artificially enriched in a particular isotope having the same atomic number, but an atomic mass or mass number different from the atomic mass or mass number predominantly found in nature. All isotopic variations of the compounds of the present disclosure, whether radioactive or not, are encompassed within the scope of the present disclosure. For example, hydrogen has three naturally occurring isotopes, denoted $^1$H (protium), $^2$H (deuterium), and $^3$H (tritium). Protium is the most abundant isotope of hydrogen in nature. Enriching for deuterium may afford certain therapeutic advantages, such as increased in vivo half-life and/or exposure, or may provide a compound useful for investigating in vivo routes of drug elimination and metabolism. Examples of isotopes that may be incorporated into compounds of the present disclosure include, but are not limited to, $^2$H, $^3$H, $^{13}$C, $^{14}$C, $^{15}$N, $^{18}$O, $^{17}$O, $^{35}$S, $^{36}$C, and $^{18}$F. Of particular interest are compounds of Formula (I) enriched in tritium or carbon-14, which can be used, for example, in tissue distribution studies; compounds of the disclosure enriched in deuterium especially at a site of metabolism, resulting, for example, in compounds having greater metabolic stability; and compounds of Formula (I) enriched in a positron emitting isotope, such as $^{11}$C, $^{18}$F, $^{15}$O and $^{13}$N, which can be used, for example, in Positron Emission Topography (PET) studies. Isotopically-enriched compounds may be prepared by conventional techniques well known to those skilled in the art.

As used herein, the phrase "of the formula" or "having the formula" or "having the structure" is not intended to be limiting and is used in the same way that the term "comprising" is commonly used. For example, if one structure is depicted, it is understood that all stereoisomer and tautomer forms are encompassed, unless stated otherwise.

Certain compounds described herein contain one or more asymmetric centers and can thus give rise to enantiomers, diastereomers, and other stereoisomeric forms, the asymmetric centers of which can be defined, in terms of absolute stereochemistry, as (R)- or (S)-. In some embodiments, in order to optimize the therapeutic activity of the compounds of the disclosure, e.g., to treat fibrosis, it may be desirable that the carbon atoms have a particular configuration (e.g., (R,R), (S,S), (S,R), or (R,S)) or are enriched in a stereoisomeric form having such configuration. The compounds of the disclosure may be provided as racemic mixtures. Accordingly, the disclosure relates to racemic mixtures, pure stereoisomers (e.g., enantiomers and diastereoisomers), stereoisomer-enriched mixtures, and the like, unless otherwise indicated. When a chemical structure is depicted herein without any stereochemistry, it is understood that all possible stereoisomers are encompassed by such structure. Similarly, when a particular stereoisomer is shown or named herein, it will be understood by those skilled in the art that minor amounts of other stereoisomers may be present in the compositions of the disclosure unless otherwise indicated, provided that the utility of the composition as a whole is not eliminated by the presence of such other isomers. Individual stereoisomers may be obtained by numerous methods that are known in the art, including preparation using chiral synthons or chiral reagents, resolution using chiral chromatography using a suitable chiral stationary phase or support, or by chemically converting them into diastereoisomers, separating the diastereoisomers by conventional means such as chromatography or recrystallization, then regenerating the original stereoisomer.

Additionally, where applicable, all cis-trans or E/Z isomers (geometric isomers), tautomeric forms and topoisomeric forms of the compounds of the invention are included within the scope of the invention unless otherwise specified.

The term "tautomer", as used herein, refers to each of two or more isomers of a compound that exist in equilibrium and which ready interconvert. For example, one skilled in the art would readily understand that 1,2,3-triazole exists in two tautomeric forms:

Unless otherwise specified, chemical entities described herein are intended to include all possible tautomers, even when a structure depicts only one of them. For example, even though a single tautomer of a compound of Formula (I-A) may be depicted herein, the disclosure is intended to include all possible tautomers, including:

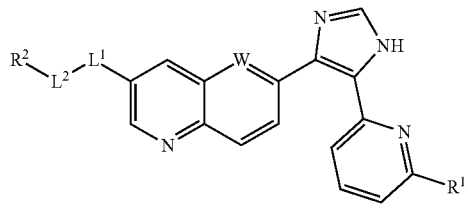 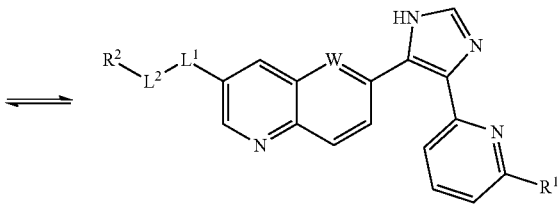

The term "pharmaceutically acceptable" refers to a material that is not biologically or otherwise unacceptable when used in the subject compositions and methods. For example, the term "pharmaceutically acceptable carrier" refers to a material—such as an adjuvant, excipient, glidant, sweetening agent, diluent, preservative, dye, colorant, flavor enhancer, surfactant, wetting agent, dispersing agent, suspending agent, stabilizer, isotonic agent, solvent or emulsifier—that can be incorporated into a composition and administered to a patient without causing unacceptable biological effects or interacting in an unacceptable manner with other components of the composition. Such pharmaceutically acceptable materials typically have met the required standards of toxicological and manufacturing testing, and include those materials identified as suitable inactive ingredients by the U.S. Food and Drug Administration.

The terms "salt" and "pharmaceutically acceptable salt" refer to a salt prepared from a base or an acid. Pharmaceutically acceptable salts are suitable for administration to a patient, such as a mammal (for example, salts having acceptable mammalian safety for a given dosage regime). Salts can be formed from inorganic bases, organic bases, inorganic acids and organic acids. In addition, when a compound contains both a basic moiety, such as an amine, pyridine or imidazole, and an acidic moiety, such as a carboxylic acid or tetrazole, zwitterions may be formed and are included within the term "salt" as used herein. Salts derived from inorganic bases include ammonium, calcium, copper, ferric, ferrous, lithium, magnesium, manganic, manganous, potassium, sodium, and zinc salts, and the like. Salts derived from organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. Salts derived from inorganic acids include salts of boric, carbonic, hydrohalic (hydrobromic, hydrochloric, hydrofluoric or hydroiodic), nitric, phosphoric, sulfamic and sulfuric acids. Salts derived from organic acids include salts of aliphatic hydroxyl acids (for example, citric, gluconic, glycolic, lactic, lactobionic, malic, and tartaric acids), aliphatic monocarboxylic acids (for example, acetic, butyric, formic, propionic and trifluoroacetic acids), amino acids (for example, aspartic and glutamic acids), aromatic carboxylic acids (for example, benzoic, p-chlorobenzoic, diphenylacetic, gentisic, hippuric, and triphenylacetic acids), aromatic hydroxyl acids (for example, o-hydroxybenzoic, p-hydroxybenzoic, 1-hydroxynaphthalene-2-carboxylic and 3-hydroxynaphthalene-2-carboxylic acids), ascorbic, dicarboxylic acids (for example, fumaric, maleic, oxalic and succinic acids), glucoronic, mandelic, mucic, nicotinic, orotic, pamoic, pantothenic, sulfonic acids (for example, benzenesulfonic, camphorsulfonic, edisylic, ethanesulfonic, isethionic, methanesulfonic, naphthalenesulfonic, naphthalene-1,5-disulfonic, naphthalene-2,6-disulfonic and p-toluenesulfonic acids), xinafoic acid, and the like.

The term "therapeutically effective amount" refers to that amount of a compound described herein that is sufficient to affect treatment when administered to a subject in need thereof. For example, a therapeutically effective amount for treating pulmonary fibrosis is an amount of compound needed to, for example, reduce, suppress, eliminate, or prevent the formation of fibrosis in a subject, or to treat the underlying cause of pulmonary fibrosis. The therapeutically effective amount may vary depending upon the intended treatment application (in vivo), or the subject and disease condition being treated, e.g., the weight and age of the subject, the severity of the disease condition, the manner of administration and the like, which can readily be determined by one of ordinary skill in the art. The specific dose will vary depending on the particular compound chosen, the dosing regimen to be followed, whether it is administered in combination with other compounds, timing of administration, the tissue to which it is administered, and the physical delivery system in which it is carried. The term "effective amount" refers to an amount sufficient to obtain a desired result, which may not necessarily be a therapeutic result. For example, an "effective amount" may be the amount needed to inhibit an enzyme.

As used herein, "treating" or "treatment" refers to an approach for obtaining beneficial or desired results with respect to a disease, disorder, or medical condition (such as pulmonary fibrosis) in a subject, including but not limited to the following: (a) preventing the disease or medical condition from occurring, e.g., preventing the reoccurrence of the disease or medical condition or prophylactic treatment of a subject that is pre-disposed to the disease or medical condition; (b) ameliorating the disease or medical condition, e.g., eliminating or causing regression of the disease or medical condition in a subject; (c) suppressing the disease or medical condition, e.g., slowing or arresting the development of the disease or medical condition in a subject; or (d) alleviating symptoms of the disease or medical condition in a subject. For example, "treating pulmonary fibrosis" would include preventing fibrosis from occurring, ameliorating fibrosis, suppressing fibrosis, and alleviating the symptoms of fibrosis (for example, increasing oxygen levels in blood or improved lung function tests). Also, a therapeutic benefit is achieved with the eradication or amelioration of one or more of the physiological symptoms associated with the underlying disorder such that an improvement is observed in the subject, notwithstanding that the subject may still be afflicted with the underlying disorder A "therapeutic effect", as that term is used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

The term "co-administration," "administered in combination with," and their grammatical equivalents, as used herein, encompass administration of two or more agents to an animal, including humans, so that both agents and/or their metabolites are present in the subject at the same time. Co-administration includes simultaneous administration in separate compositions, administration at different times in separate compositions, or administration in a composition in which both agents are present.

The terms "antagonist" and "inhibitor" are used interchangeably, and they refer to a compound having the ability to inhibit a biological function (e.g., activity, expression, binding, protein-protein interaction) of a target protein (e.g., ALK5). Accordingly, the terms "antagonist" and "inhibitor" are defined in the context of the biological role of the target protein. While preferred antagonists herein specifically interact with (e.g., bind to) the target, compounds that inhibit a biological activity of the target protein by interacting with other members of the signal transduction pathway of which the target protein is a member are also specifically included within this definition.

The term "selective inhibition" or "selectively inhibit" refers to the ability of a biologically active agent to preferentially reduce the target signaling activity as compared to off-target signaling activity, via direct or indirect interaction with the target.

The terms "subject" and "patient" refer to an animal, such as a mammal, for example a human. The methods described herein can be useful in both human therapeutics and veterinary applications. In some embodiments, the subject is a mammal, and in some embodiments, the subject is human. "Mammal" includes humans and both domestic animals such as laboratory animals and household pets (e.g., cats, dogs, swine, cattle, sheep, goats, horses, rabbits), and non-domestic animals such as wildlife and the like.

"Prodrug" is meant to indicate a compound that may be converted under physiological conditions or by solvolysis to a biologically active compound described herein (e.g., compound of Formula (I), (I-A), (I-B), (I-C), (I'), (I'-A), (I'-B), or (I'-C)). Thus, the term "prodrug" refers to a precursor of a biologically active compound that is pharmaceutically acceptable. In some aspects, a prodrug is inactive when administered to a subject but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam); Higuchi, T., et al., "Pro-drugs as Novel Delivery Systems," (1987) A.C.S. Symposium Series, Vol. 14; and Bioreversible Carriers in Drug Design, ed. Edward B. Roche, American Pharmaceutical Association and Pergamon Press) each of which is incorporated in full by reference herein. The term "prodrug" is also meant to include any covalently bonded carriers, which release the active compound in vivo when such prodrug is administered to a mammalian subject. Prodrugs of an active compound, as described herein, are typically prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of a hydroxy functional group, or acetamide, formamide and benzamide derivatives of an amine functional group in the active compound, and the like.

The term "in vivo" refers to an event that takes place in a subject's body.

The term "in vitro" refers to an event that takes places outside of a subject's body. For example, an in vitro assay encompasses any assay run outside of a subject. In vitro assays encompass cell-based assays in which cells alive or dead are employed. In vitro assays also encompass a cell-free assay in which no intact cells are employed.

The disclosure is also meant to encompass the in vivo metabolic products of the disclosed compounds. Such products may result from, for example, the oxidation, reduction, hydrolysis, amidation, esterification, and the like of the administered compound, primarily due to enzymatic processes. Accordingly, the disclosure includes compounds produced by a process comprising administering a compound of this disclosure to a mammal for a period of time sufficient to yield a metabolic product thereof. Such products are typically identified by administering a radiolabeled compound of the disclosure in a detectable dose to an animal, such as rat, mouse, guinea pig, monkey, or to a human, allowing sufficient time for metabolism to occur, and isolating its conversion products from the urine, blood or other biological samples.

Lung function tests include tests to check how well the lungs work. Spirometry, for example, measures the amount of air the lungs can hold as well as how forcefully one can empty air from the lungs. Forced expiratory volume (FEV) is a measure of the amount of air a person can exhale during a forced breath. FEV1, for example, is the amount of air a person can force from their lungs in one second. Forced vital capacity (FVC) is the total amount of air exhaled during an FEV test. The ratio of FEV1/FVC, also known as Index of Air Flow or Tiffeneau-Pinelli Index, is a measurement used to assess the health of a patient's lung function. A ratio of <80% indicates an obstructive defect is present in the lungs, such as chronic obstructive pulmonary disease (COPD). A ratio of >80% indicates a restrictive defect is present in the lungs, such as pulmonary fibrosis. The ratio of >80% in restrictive lung disease results from both FEV1 and FVC being reduced but that the decline in FVC is more than that of FEV1, resulting in a higher than 80% value.

The term "transforming growth factor-β" may also be referred to as TGF-β, transforming growth factor beta-1, or TGF-beta-1. It is also cleaved into latency-associated peptide (LAP).

The term "TGF-β receptor II" may also be referred to as TβRII, type II TGF-β receptor, TGF-βRII, TGF-beta receptor type-2, TGFR-2, TGF-beta type II receptor, transforming growth factor-beta receptor type II, TGF-beta receptor type II or TbetaR-II.

The term "TGF-β receptor I" may also be referred to as TβRI, type I TGF-β receptor, TGF-βRI, TGF-beta receptor type-1, TGFR-1, activin A receptor type II-like protein kinase of 53 kD, activin receptor-like kinase 5, ALK-5, ALK5, serine/threonine-protein kinase receptor R4, SKR4, TGF-beta type I receptor, transforming growth factor-beta receptor type I, TGF-beta receptor type I, transforming growth factor beta receptor I, TGF-beta receptor 1, or TbetaR-I.

The present disclosure provides compounds that are capable of selectively binding to and/or modulating ALK5. In some embodiments, the compounds modulate ALK5 by binding to or interacting with one or more amino acids and/or one or more metal ions. The binding of these compounds may disrupt ALK5 downstream signaling.

In certain aspects, the present disclosure provides a compound of Formula (I'):

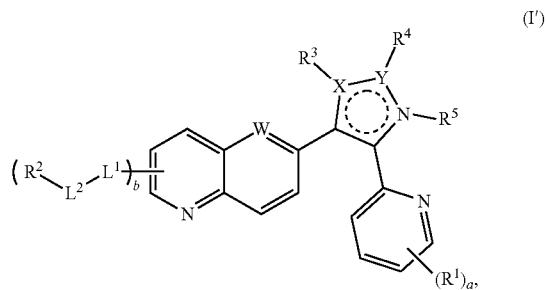

or a pharmaceutically acceptable salt thereof, wherein:
W is selected from CH and N;
X and Y are each independently selected from C and N;
a is an integer from 0 to 3;
b is an integer from 0 to 3;
$R^1$ is independently selected at each occurrence from $R^{10}$;
$L^1$ is independently selected at each occurrence from absent; $C_{1-6}$ alkylene, $C_{2-6}$ alkenylene, $C_{2-6}$ alkynylene, $C_{3-12}$ carbocycle, and 3- to 12-membered heterocycle, each of which is optionally substituted with one or more $R^{10}$;
$L^2$ is independently selected at each occurrence from absent, —O—, —S—, —N($R^{11}$)—, —C(O)—, —C(O)O—, —OC(O)—, —OC(O)O—, —C(O)N($R^{11}$)—, —C(O)N($R^{11}$)C(O)—, —C(O)N($R^{11}$)C(O)N($R^{11}$)—, —N($R^{11}$)C(O)—, —N($R^{11}$)C(O)N($R^{11}$)—, —N($R^{11}$)C(O)O—, —OC(O)N($R^{11}$)—, —C(N$R^{11}$)—, —N($R^{11}$)C(N$R^{11}$)—, —C(N$R^{11}$)N(R)—, —N($R^{11}$)C(N$R^{11}$)N($R^{11}$)—, —S(O)$_2$—, —OS(O)—, —S(O)O—, —S(O)—, —OS(O)$_2$, —S(O)$_2$O—, —N($R^{11}$)S(O)$_2$—, —S(O)$_2$N($R^{11}$)—, —N($R^{11}$)S(O)—, —S(O)N($R^{11}$)—, —N($R^{11}$)S(O)$_2$N($R^{11}$)—, and —N($R^{11}$)S(O)N($R^{11}$)—;

$R^2$ is independently selected at each occurrence from $R^{10}$;

$R^3$, $R^4$, and $R^5$ are each independently absent or selected from $R^{11}$; or $R^3$ and $R^4$ are taken together with the atoms to which they are attached to form a $C_{3-8}$ carbocycle or 3- to 8-membered heterocycle, each of which is optionally substituted with one or more $R^{10}$; or $R^4$ and $R^5$ are taken together with the atoms to which they are attached to form a 3- to 8-membered heterocycle, each of which is optionally substituted with one or more $R^{10}$;

$R^{10}$ is independently selected at each occurrence from; halogen, $-NO_2$, $-CN$, $-OR^{12}$, $-SR^{12}$, $-N(R^{12})_2$, $-NR^{13}R^{14}$, $-S(=O)R^{12}$, $-S(=O)_2R^{12}$, $-S(=O)_2N(R^{12})_2$, $-S(=O)_2NR^{13}R^{14}$, $-NR^{12}S(=O)_2R^{12}$, $-NR^{12}S(=O)_2N(R^{12})_2$, $-NR^{12}S(=O)_2NR^{13}R^{14}$, $-C(O)R^{12}$, $-C(O)OR^{12}$, $-OC(O)R^{12}$, $-OC(O)OR^{12}$, $-OC(O)N(R^{12})_2$, $-OC(O)NR^{13}R^{14}$, $-NR^{12}C(O)R^{12}$, $-NR^{12}C(O)OR^{12}$, $-NR^{12}C(O)N(R^{12})_2$, $-NR^{12}C(O)NR^{13}R^{14}$, $-C(O)N(R^{12})_2$, $-C(O)NR^{13}R^{14}$, $-P(O)(OR^{12})_2$, $-P(O)(R^{12})_2$, $=O$, $=S$, $=N(R^{12})$;

$C_{1-10}$ alkyl, $C_{2-10}$ alkenyl, and $C_{2-10}$ alkynyl, each of which is independently optionally substituted at each occurrence with one or more substituents selected from halogen, $-NO_2$, $-CN$, $-OR^{12}$, $-SR^{12}$, $-N(R^{12})_2$, $-NR^{13}R^{14}$, $-S(=O)R^{12}$, $-S(=O)_2R^{12}$, $-S(=O)_2N(R^{12})_2$, $-S(=O)_2NR^{13}R^{14}$, $-NR^{12}S(=O)_2R^{12}$, $-NR^{12}S(=O)_2N(R^{12})_2$, $-NR^{12}S(=O)_2NR^{13}R^{14}$, $-C(O)R^{12}$, $-C(O)OR^{12}$, $-OC(O)R^{12}$, $-OC(O)OR^{12}$, $-OC(O)N(R^{12})_2$, $-OC(O)NR^{13}R^{14}$, $-NR^{12}C(O)R^{12}$, $-NR^{12}C(O)OR^{12}$, $-NR^{12}C(O)N(R^{12})_2$, $-NR^{12}C(O)NR^{13}R^{14}$, $-C(O)N(R^{12})_2$, $-C(O)NR^{13}R^{14}$, $-P(O)(OR^{12})_2$, $-P(O)(R^{12})_2$, $=O$, $=S$, $=N(R^{12})$, $C_{3-12}$ carbocycle, and 3- to 12-membered heterocycle; and $C_{3-12}$ carbocycle and 3- to 12-membered heterocycle, wherein each $C_{3-12}$ carbocycle and 3- to 12-membered heterocycle in $R^{10}$ is independently optionally substituted with one or more substituents selected from halogen, $-NO_2$, $-CN$, $-OR^{12}$, $-SR^{12}$, $-N(R^{12})_2$, $-NR^{13}R^{14}$, $-S(=O)R^{12}$, $-S(=O)_2R^{12}$, $-S(=O)_2N(R^{12})_2$, $-S(=O)_2NR^{13}R^{14}$, $-NR^{12}S(=O)_2R^{12}$, $-NR^{12}S(=O)_2N(R^{12})_2$, $-NR^{12}S(=O)_2NR^{13}R^{14}$, $-C(O)R^{12}$, $-C(O)OR^{12}$, $-OC(O)R^{12}$, $-OC(O)OR^{12}$, $-OC(O)N(R^{12})_2$, $-OC(O)NR^{13}R^{14}$, $-NR^{12}C(O)R^{12}$, $-NR^{12}C(O)OR^{12}$, $-NR^{12}C(O)N(R^{12})_2$, $-NR^{12}C(O)NR^{13}R^{14}$, $-C(O)N(R^{12})_2$, $-C(O)NR^{13}R^{14}$, $-P(O)(OR^{12})_2$, $-P(O)(R^{12})_2$, $=O$, $=S$, $=N(R^{12})$, $R^{12}$, $C_{1-6}$ alkyl, $C_{1-6}$ haloalkyl, $C_{2-6}$ alkenyl, and $C_{2-6}$ alkynyl;

$R^{11}$ is independently selected at each occurrence from; hydrogen, $-C(O)R^{12}$, $-C(O)OR^{12}$, $-C(O)N(R^{12})_2$, $-C(O)NR^{13}R^{14}$;

$C_{1-6}$ alkyl, $C_{2-6}$ alkenyl, and $C_{2-6}$ alkynyl, each of which is independently optionally substituted at each occurrence with one or more substituents selected from halogen, $-NO_2$, $-CN$, $-OR^{12}$, $-SR^{12}$, $-N(R^{12})_2$, $-NR^{13}R^{14}$, $-S(=O)R^{12}$, $-S(=O)_2R^{12}$, $-S(=O)_2N(R^{12})_2$, $-S(=O)_2NR^{13}R^{14}$, $-NR^{12}S(=O)_2R^{12}$, $-NR^{12}S(=O)_2N(R^{12})_2$, $-NR^{12}S(=O)_2NR^{13}R^{14}$, $-C(O)R^{12}$, $-C(O)OR^{12}$, $-OC(O)R^{12}$, $-OC(O)OR^{12}$, $-OC(O)N(R^{12})_2$, $-OC(O)NR^{13}R^{14}$, $-NR^{12}C(O)R^{12}$, $-NR^{12}C(O)OR^{12}$, $-NR^{12}C(O)N(R^{12})_2$, $-NR^{12}C(O)NR^{13}R^{14}$, $-C(O)N(R^{12})_2$, $-C(O)NR^{13}R^{14}$, $-P(O)(OR^{12})_2$, $-P(O)(R^{12})_2$, $=O$, $=S$, $=N(R^{12})$, $C_{3-12}$ carbocycle, and 3- to 12-membered heterocycle; and $C_{3-12}$ carbocycle and 3- to 12-membered heterocycle, wherein each $C_{3-12}$ carbocycle and 3- to 12-membered heterocycle in $R^{11}$ is independently optionally substituted with one or more substituents selected from halogen, $-NO_2$, $-CN$, $-OR^{12}$, $-SR^{12}$, $-N(R^{12})_2$, $-NR^{13}R^{14}$, $-S(=O)R^{12}$, $-S(=O)_2R^{12}$, $-S(=O)_2N(R^{12})_2$, $-S(=O)_2NR^{13}R^{14}$, $-NR^{12}S(=O)_2R^{12}$, $-NR^{12}S(=O)_2N(R^{12})_2$, $-NR^{12}S(=O)_2NR^{13}R^{14}$, $-C(O)R^{12}$, $-C(O)OR^{12}$, $-OC(O)R^{12}$, $-OC(O)OR^{12}$, $-OC(O)N(R^{12})_2$, $-OC(O)NR^{13}R^{14}$, $-NR^{12}C(O)R^{12}$, $-NR^{12}C(O)OR^{12}$, $-NR^{12}C(O)N(R^{12})_2$, $-NR^{12}C(O)NR^{13}R^{14}$, $-C(O)N(R^{12})_2$, $-C(O)NR^{13}R^{14}$, $-P(O)(OR^{12})_2$, $-P(O)(R^{12})_2$, $=O$, $=S$, $=N(R^{12})$, $R^{12}$, $C_{1-6}$ alkyl, $C_{1-6}$ haloalkyl, $C_{2-6}$ alkenyl, and $C_{2-6}$ alkynyl;

$R^{12}$ is independently selected at each occurrence from hydrogen; and $C_{1-10}$ alkyl, $C_{2-10}$ alkenyl, $C_{2-10}$ alkynyl, 1- to 6-membered heteroalkyl, $C_{3-12}$ carbocycle, and 3- to 12-membered heterocycle, each of which is optionally substituted by halogen, $-CN$, $-NO_2$, $-NH_2$, $-NHCH_3$, $-NHCH_2CH_3$, $=O$, $-OH$, $-OCH_3$, $-OCH_2CH_3$, $-CH_3$, $-CH_2CH_3$, $-CH(CH_3)_2$, $-C(CH_3)_3$, $C_{3-12}$ carbocycle, or 3- to 6-membered heterocycle; and $R^{13}$ and $R^{14}$ are taken together with the nitrogen atom to which they are attached to form a heterocycle, optionally substituted with one or more $R^{12}$.

In some embodiments, for a compound of Formula (I'), b is an integer from 1 to 3, such as b is 1 or 2. In some embodiments, b is 1. In some embodiments, b is 2. In some embodiments, the compound of Formula (I') is a compound of Formula (I'-A), (I'-B) or (I'-C):

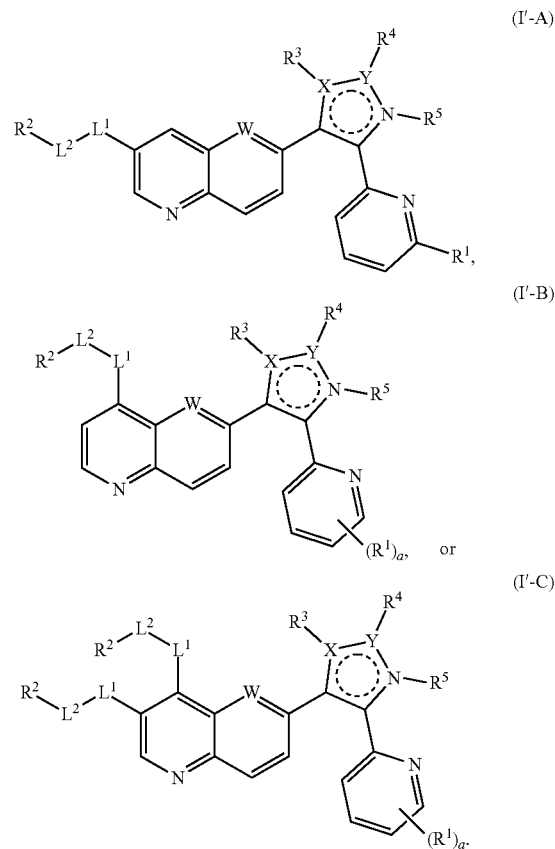

In some embodiments, for a compound of Formula (I'), (I'-A), (I'-B) or (I'-C), $R^3$ and $R^4$ are taken together with the atoms to which they are attached to form a $C_{3-8}$ carbocycle or 3- to 8-membered heterocycle, each of which is optionally substituted with one or more $R^{10}$. For example, $R^3$ and $R^4$ may be taken together to form

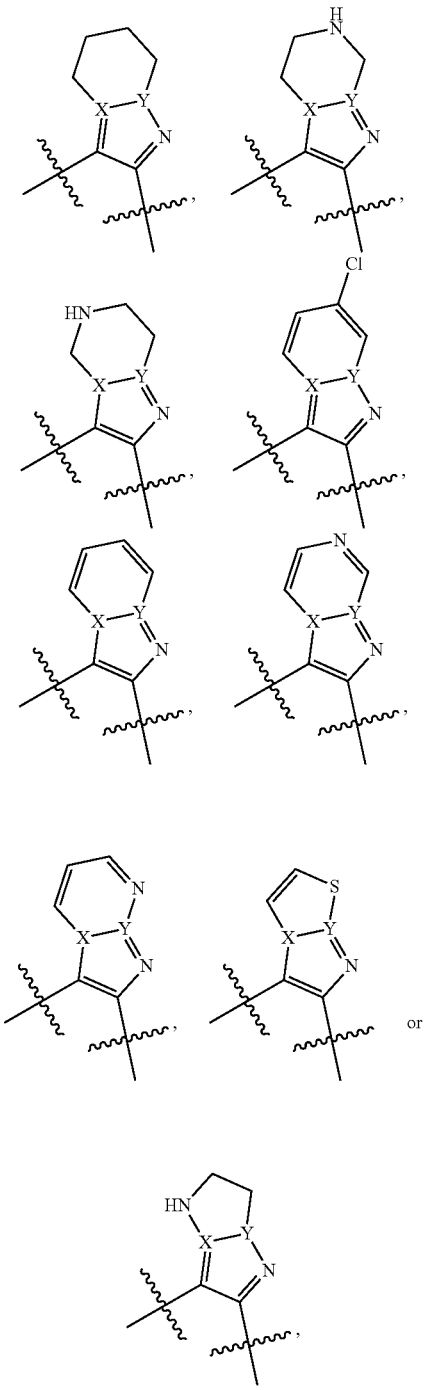

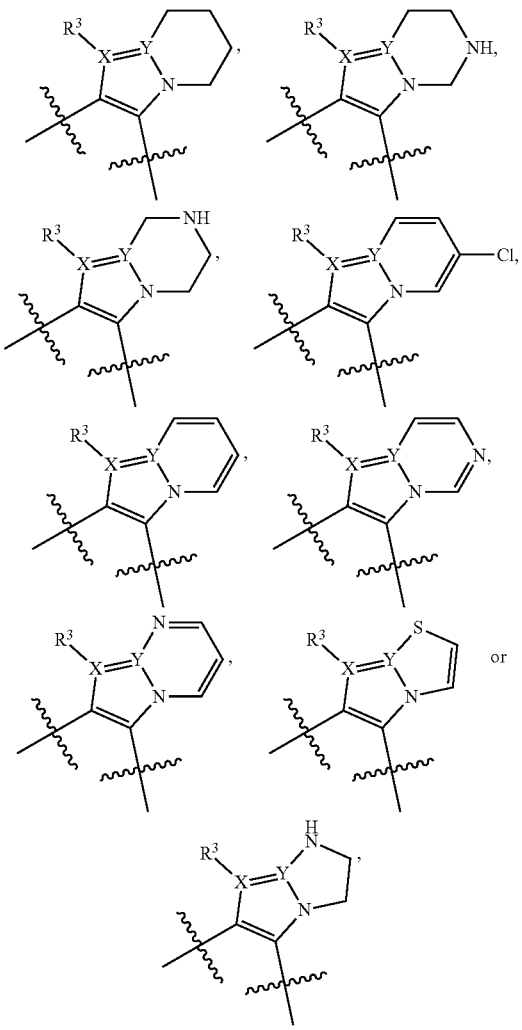

each of which may be optionally further substituted with one or more $R^{10}$.

In certain aspects, the present disclosure provides a compound of Formula (I):

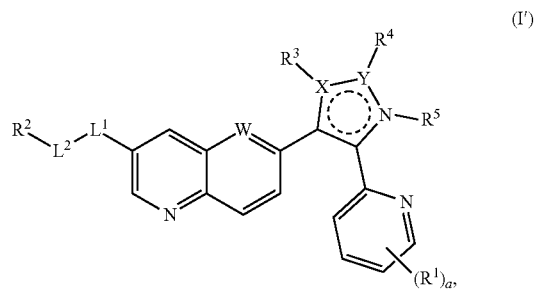

or a pharmaceutically acceptable salt thereof, wherein:

W is selected from CH and N;

X and Y are each independently selected from C and N;

a is an integer from 0 to 3;

$R^1$ is independently selected at each occurrence from $R^{10}$;

each of which may be optionally further substituted with one or more $R^{10}$. In some embodiments, $R^4$ and $R^5$ are taken together with the atoms to which they are attached to form a 3- to 8-membered heterocycle, each of which is optionally substituted with one or more $R^{10}$. For example, $R^4$ and $R^5$ may be taken together to form $L^1$ is selected from absent; $C_{1-6}$ alkylene, $C_{2-6}$ alkenylene, $C_{2-6}$ alkynylene, $C_{3-12}$ carbocycle, and 3- to 12-membered heterocycle, each of which is optionally substituted with one or more $R^{10}$;

$L^2$ is selected from absent, —O—, —S—, —N($R^{11}$)—, —C(O)—, —C(O)O—, —OC(O)—, —OC(O)O—, —C(O)N($R^{11}$)—, —C(O)N($R^{11}$)C(O)—, —C(O)N($R^{11}$)C(O)N($R^{11}$)—, —N($R^{11}$)C(O)—, —N($R^{11}$)C(O)N($R^{11}$)—, —N($R^{11}$)C(O)O—, —OC(O)N(R)—, —C(N$R^{11}$)—, —N($R^{11}$)C(N$R^{11}$)—, —C(N$R^{11}$)N($R^{11}$)—, —N(R)C(NR)N(R)—, —S(O)$_2$—, —OS(O)—, —S(O)O—, —S(O)—, —OS(O)$_2$, —S(O)$_2$O—, —N($R^{11}$)S(O)$_2$—, —S(O)$_2$N($R^{11}$)—, —N($R^{11}$)S(O)—, —S(O)N($R^{11}$)—, —N($R^{11}$)S(O)$_2$N($R^{11}$)—, and —N($R^{11}$)S(O)N($R^{11}$)—;

$R^2$ is independently selected at each occurrence from $R^{10}$;

$R^3$, $R^4$, and $R^5$ are each independently absent or selected from $R^{11}$;

$R^{10}$ is independently selected at each occurrence from; halogen, —NO$_2$, —CN, —OR$^{12}$—SR$^{12}$—N($R^{12}$)$_2$, —NR$^{13}$R$^{14}$, —S(=O)R$^{12}$—, —S(=O)$_2$R$^{12}$, —S(=O)$_2$N($R^{12}$)$_2$, —S(=O)$_2$NR$^{13}$R$^{14}$, —NR$^{12}$S(=O)$_2$R$^{12}$, —NR$^{12}$S(=O)$_2$N($R^{12}$)$_2$, —NR$^{12}$S(=O)$_2$NR$^{13}$R$^{14}$, —C(O)R$^{12}$, —C(O)OR$^{12}$, —OC(O)R$^{12}$, —OC(O)OR$^{12}$, —OC(O)N($R^{12}$)$_2$, —OC(O)NR$^{13}$R$^{14}$, —NR$^{12}$C(O)R$^{12}$, —NR$^{12}$C(O)OR$^{12}$, —NR$^{12}$C(O)N($R^{12}$)$_2$, —NR$^{12}$C(O)NR$^{13}$R$^{14}$, —C(O)N($R^{12}$)$_2$, —C(O)NR$^{13}$R$^{14}$, —P(O)(OR$^{12}$)$_2$, —P(O)($R^{12}$)$_2$, =O, =S, =N($R^{12}$);

$C_{1-10}$ alkyl, $C_{2-10}$ alkenyl, and $C_{2-10}$ alkynyl, each of which is independently optionally substituted at each occurrence with one or more substituents selected from halogen, —NO$_2$, —CN, —OR$^{12}$, —SR$^{12}$, —N($R^{12}$)$_2$, —NR$^{13}$R$^{14}$, —S(=O)R$^{12}$, —S(=O)$_2$R$^{12}$, —S(=O)$_2$N($R^{12}$)$_2$, —S(=O)$_2$NR$^{13}$R$^{14}$, —NR$^{12}$S(=O)$_2$R$^{12}$, —NR$^{12}$S(=O)$_2$N($R^{12}$)$_2$, —NR$^{12}$S(=O)$_2$NR$^{13}$R$^{14}$, —C(O)R$^{12}$, —C(O)OR$^{12}$, —OC(O)R$^{12}$, —OC(O)OR$^{12}$, —OC(O)N($R^{12}$)$_2$, —OC(O)NR$^{13}$R$^{14}$, —NR$^{12}$C(O)R$^{12}$, —NR$^{12}$C(O)OR$^{12}$, —NR$^{12}$C(O)N($R^{12}$)$_2$, —NR$^{12}$C(O)NR$^{13}$R$^{14}$, —C(O)N($R^{12}$)$_2$, —C(O)NR$^{13}$R$^{14}$, —P(O)(OR$^{12}$)$_2$, —P(O)($R^{12}$)$_2$, =O, =S, =N($R^{12}$), $C_{3-12}$ carbocycle, and 3- to 12-membered heterocycle; and $C_{3-12}$ carbocycle and 3- to 12-membered heterocycle, wherein each $C_{3-12}$ carbocycle and 3- to 12-membered heterocycle in $R^{10}$ is independently optionally substituted with one or more substituents selected from halogen, —NO$_2$, —CN, —OR$^{12}$, —SR$^{12}$, —N($R^{12}$)$_2$, —NR$^{13}$R$^{14}$, —S(=O)R$^{12}$, —S(=O)$_2$R$^{12}$, —S(=O)$_2$N($R^{12}$)$_2$, —S(=O)$_2$NR$^{13}$R$^{14}$, —NR$^{12}$S(=O)$_2$R$^{12}$, —NR$^{12}$S(=O)$_2$N($R^{12}$)$_2$, —NR$^{12}$S(=O)$_2$NR$^{13}$R$^{14}$, —C(O)R$^{12}$, —C(O)OR$^{12}$, —OC(O)R$^{12}$, —OC(O)OR$^{12}$, —OC(O)N($R^{12}$)$_2$, —OC(O)NR$^{13}$R$^{14}$, —NR$^{12}$C(O)R$^{12}$, —NR$^{12}$C(O)OR$^{12}$, —NR$^{12}$C(O)N($R^{12}$)$_2$, —NR$^{12}$C(O)NR$^{13}$R$^{14}$, —C(O)N($R^{12}$)$_2$, —C(O)NR$^{13}$R$^{14}$, —P(O)(OR$^{12}$)$_2$, —P(O)($R^{12}$)$_2$, =O, =S, =N($R^{12}$), $R^{12}$, $C_{1-6}$ alkyl, $C_{1-6}$ haloalkyl, $C_{2-6}$ alkenyl, and $C_{2-6}$ alkynyl;

$R^{11}$ is independently selected at each occurrence from; hydrogen, —C(O)R$^{12}$, —C(O)OR$^{12}$, —C(O)N($R^{12}$)$_2$, —C(O)NR$^{13}$R$^{14}$;

$C_{1-6}$ alkyl, $C_{2-6}$ alkenyl, and $C_{2-6}$ alkynyl, each of which is independently optionally substituted at each occurrence with one or more substituents selected from halogen, —NO$_2$, —CN, —OR$^{12}$, —SR$^{12}$, —N($R^{12}$)$_2$, —NR$^{13}$R$^{14}$, —S(=O)R$^{12}$, —S(=O)$_2$R$^{12}$, —S(=O)$_2$N($R^{12}$)$_2$, —S(=O)$_2$NR$^{13}$R$^{14}$, —NR$^{12}$S(=O)$_2$R$^{12}$, —NR$^{12}$S(=O)$_2$N($R^{12}$)$_2$, —NR$^{12}$S(=O)$_2$NR$^{13}$R$^{14}$, —C(O)R$^{12}$, —C(O)OR$^{12}$, —OC(O)R$^{12}$, —OC(O)OR$^{12}$, —OC(O)N($R^{12}$)$_2$, —OC(O)NR$^{13}$R$^{14}$, —NR$^{12}$C(O)R$^{12}$, —NR$^{12}$C(O)OR$^{12}$, —NR$^{12}$C(O)N($R^{12}$)$_2$, —NR$^{12}$C(O)NR$^{13}$R$^{14}$, —C(O)N($R^{12}$)$_2$, —C(O)NR$^{13}$R$^{14}$, —P(O)(OR$^{12}$)$_2$, —P(O)($R^{12}$)$_2$, =O, =S, =N($R^{12}$), $C_{3-12}$ carbocycle, and 3- to 12-membered heterocycle; and $C_{3-12}$ carbocycle and 3- to 12-membered heterocycle, wherein each $C_{3-12}$ carbocycle and 3- to 12-membered heterocycle in $R^{11}$ is independently optionally substituted with one or more substituents selected from halogen, —NO$_2$, —CN, —OR$^{12}$, —SR, —N($R^{12}$)$_2$, —NR$^{13}$R$^{14}$, —S(=O)R$^{12}$, —S(=O)$_2$R$^{12}$, —S(=O)$_2$N($R^{12}$)$_2$, —S(=O)$_2$NR$^{13}$R$^{14}$, —NR$^{12}$S(=O)$_2$R$^{12}$, —NR$^{12}$S(=O)$_2$N($R^{12}$)$_2$, —NR$^{12}$S(=O)$_2$NR$^{13}$R$^{14}$, —C(O)R$^{12}$, —C(O)OR$^{12}$, —OC(O)R$^{12}$, —OC(O)OR$^{12}$, —OC(O)N($R^{12}$)$_2$, —OC(O)NR$^{13}$R$^{14}$, —NR$^{12}$C(O)R$^{12}$, —NR$^{12}$C(O)OR$^{12}$, —NR$^{12}$C(O)N($R^{12}$)$_2$, —NR$^{12}$C(O)NR$^{13}$R$^{14}$, —C(O)N($R^{12}$)$_2$, —C(O)NR$^{13}$R$^{14}$, —P(O)(OR$^{12}$)$_2$, —P(O)($R^{12}$)$_2$, =O, =S, =N($R^{12}$), $R^{12}$, $C_{1-6}$ alkyl, $C_{1-6}$ haloalkyl, $C_{2-6}$ alkenyl, and $C_{2-6}$ alkynyl;

$R^{12}$ is independently selected at each occurrence from hydrogen; and $C_{1-10}$ alkyl, $C_{2-10}$ alkenyl, $C_{2-10}$ alkynyl, 1- to 6-membered heteroalkyl, $C_{3-12}$ carbocycle, and 3- to 12-membered heterocycle, each of which is optionally substituted by halogen, —CN, —NO$_2$, —NH$_2$, —NHCH$_3$, —NHCH$_2$CH$_3$, =O, —OH, —OCH$_3$, —OCH$_2$CH$_3$, —CH$_3$, —CH$_2$CH$_3$, —CH(CH$_3$)$_2$, —C(CH$_3$)$_3$, $C_{3-12}$ carbocycle, or 3- to 6-membered heterocycle; and $R^{13}$ and $R^{14}$ are taken together with the nitrogen atom to which they are attached to form a heterocycle, optionally substituted with one or more $R^{12}$.

In some embodiments, for a compound of Formula (I), (I'), (I'-B) or (I'-C), a is an integer from 1 to 3. For example, a may be 1 or 2.

In some embodiments, for a compound of Formula (I), (I'), (I'-A), (I'-B) or (I'-C), at least one of X and Y is N. In some embodiments, X is C and Y is N, optionally wherein $R^3$ is hydrogen, $R^4$ is hydrogen and $R^5$ is absent. In some embodiments, X is N and Y is C, optionally wherein $R^3$ is absent and $R^4$ and $R^5$ are each hydrogen. In some embodiments, X is N and Y is N, optionally wherein $R^3$ and $R^4$ are each absent and $R^5$ is hydrogen.

In some embodiments, for a compound of Formula (I), (I'), (I'-A), (I'-B) or (I'-C), $R^3$, $R^4$ and $R^5$ are each independently absent or selected from hydrogen; $C_{1-6}$ alkyl, optionally substituted with one or more substituents selected from halogen, —OR$^{12}$, —SR$^{12}$, —N($R^{12}$)$_2$, —NR$^{13}$R$^{14}$, —C(O)R$^{12}$, —C(O)OR$^{12}$, —OC(O)R$^{12}$, —OC(O)OR$^{12}$, —NR$^{12}$C(O)R$^{12}$, —C(O)N($R^{12}$)$_2$, $C_{3-12}$ carbocycle, and 3- to 12-membered heterocycle; and $C_{3-12}$ carbocycle and 3- to 12-membered heterocycle, wherein each $C_{3-12}$ carbocycle and 3- to 12-membered heterocycle is independently optionally substituted with one or more substituents selected from $R^{12}$. In some embodiments, $R^3$, $R^4$ and $R^5$ are each independently absent or selected from hydrogen, —CH$_3$, —CH$_2$-phenyl, —CH$_2$-pyridyl, —OCH$_3$, —NH$_2$, tetrahydropyranyl, —CH$_2$NH-(2-fluorophenyl), —NHCH$_2$CH$_2$-morpholinyl and —CH$_2$C(O)OH. In some embodiments, $R^3$, $R^4$ and $R^5$ are each independently absent or hydrogen. In some embodiments, $R^3$, $R^4$, and $R^5$ are each independently absent or selected from —O($C_{1-6}$ alkyl) and $R^{11}$. In some embodiments, $R^3$, $R^4$ and $R^5$ are each independently absent or selected from hydrogen, —CH$_3$, —CH$_2$-phenyl, —CH$_2$-pyridyl, —OH, —OCH$_3$, —OCH$_2$CH$_3$, —NH$_2$, tetrahydropyranyl, —CH$_2$NH-(2-fluorophenyl), —NHCH$_2$CH$_2$-morpholinyl and —CH₂C(O)OH. In some embodiments, R³, R⁴ and R⁵ are each independently absent or selected from hydrogen, —OH, —OCH₃ and —OCH₂CH₃.

In some embodiments, a compound of Formula (I), (I') or (I'-A), is a compound of Formula (I-A), (I-B) or (I-C):

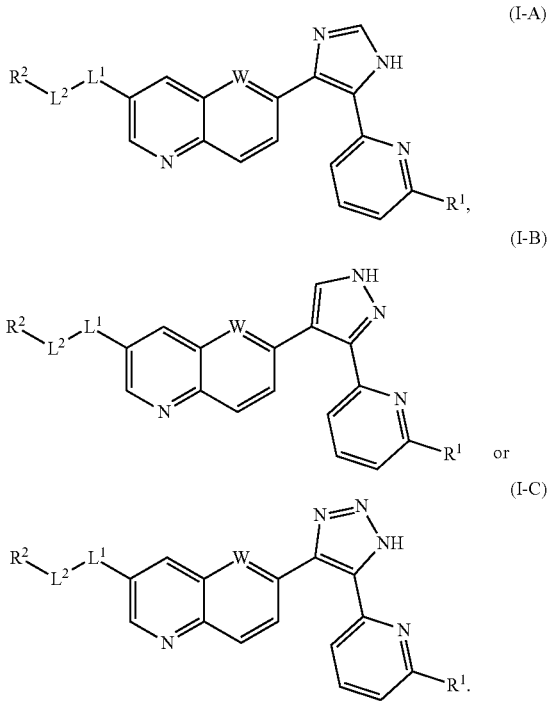

In some embodiments, for a compound of Formula (I-A), (I-B) or (I-C), R¹ is —CH₃.

In some embodiments, for a compound of Formula (I), (I'), (I-A), (I-B), (I-C), (I'-A), (I'-B) or (I'-C), W is N. In some embodiments, W is CH.

In some embodiments, for a compound of Formula (I), (I'), (I-A), (I-B), (I-C), (I'-A), (I'-B) or (I'-C), R¹ is independently selected at each occurrence from halogen, —O(C₁₋₄ alkyl), —S(C₁₋₄ alkyl), —N(C₁₋₄ alkyl), —C(O)(C₁₋₄ alkyl), —C(O)O(C₁₋₄ alkyl), —OC(O)(C₁₋₄ alkyl), C₁₋₄ alkyl, C₂₋₄ alkenyl, C₂₋₄ alkynyl, C₁₋₄ haloalkyl, C₃₋₆ carbocycle and 3- to 6-membered heterocycle. In some embodiments, R¹ is independently selected at each occurrence from halogen, C₁₋₄ alkyl and C₁₋₄ haloalkyl. In some embodiments, R¹ is independently selected at each occurrence from fluoro, C₁₋₄ alkyl and C₁₋₄ fluoroalkyl. In some embodiments, R¹ is independently selected at each occurrence from —F, —CH₃, —CH₂CH₃, —CH(CH₃)₂, —CH₂F, —CHF₂, and —CF₃. In some embodiments, a is 1 or 2, such as a is 1. In some embodiments, a is 1 and R¹ is selected from halogen, C₁₋₄ alkyl and C₁₋₄ haloalkyl. In some embodiments, a is 1 and R¹ is selected from —F, —CH₃, —CH₂CH₃, —CH(CH₃)₂, —CH₂F, —CHF₂, and —CF₃. In some embodiments, a is 1 and R¹ is CH₃, such as R¹ is 6-methyl. In some embodiments, a is 2 and R¹ is independently selected at each occurrence from halogen, C₁₋₄ alkyl and C₁₋₄ haloalkyl. In some embodiments, a is 2 and R¹ is independently selected at each occurrence from —F, —CH₃, —CH₂CH₃, —CH(CH₃)₂, —CH₂F, —CHF₂, and —CF₃. In some embodiments, a is 2 and R¹ is 5-fluoro-6-methyl.

In some embodiments, for a compound of Formula (I), (I'), (I-A), (I-B), (I-C), (I'-A), (I'-B) or (I'-C), L¹ is selected from absent; C₁₋₆ alkylene, C₃₋₁₂ carbocycle and 3- to 12-membered heterocycle, each of which is optionally substituted with one or more R¹⁰. In some embodiments, L¹ is selected from absent; C₁₋₆ alkylene, 3- to 10-membered heterocycloalkylene, 5- to 10-membered heteroarylene and C₆₋₁₀ arylene, each of which is optionally substituted with one or more R¹⁰. In some embodiments, L¹ is selected from 3- to 10-membered heterocycloalkylene, 5- to 10-membered heteroarylene and C₆₋₁₀ arylene, each of which is optionally substituted with one or more R¹⁰. In some embodiments, L¹ is C₁₋₆ alkylene, optionally substituted with one or more R¹⁰. In some embodiments, L¹ is selected from absent, pyrazolylene, triazolylene, imidazolylene, oxazolylene, imidazole[1,2-a]pyrazinylene, phenylene, pyridylene, pyrazinylene, azetidinylene, pyrrolidinylene, 2,5-dihydropyrrolylene, piperidylene, piperazinylene, diazepanylene, azabicyclo[3.2.1]octanylene, diazaspiro[4.4]nonanylene, azaspiro[3.3]heptanylene, cyclohexylene, cyclohexenylene, methylene, ethylene and propylene. In some embodiments, L¹ is selected from absent, pyrazolylene, piperidylene, piperazinylene, cyclohexenylene, methylene and ethylene. In some embodiments, L¹ is selected from absent, pyrazolylene, cyclohexenylene and methylene. In some embodiments, L¹ is absent. In some embodiments, L¹ is pyrazolylene. In some embodiments, L¹ is cyclohexenylene. In some embodiments, L¹ is methylene. In some embodiments, L¹ is unsubstituted.

In some embodiments, for a compound of Formula (I), (I'), (I-A), (I-B), (I-C), (I'-A), (I'-B) or (I'-C), L² is selected from absent, —O—, —S—, —N(R¹¹)—, —C(O)—, —C(O)O—, —OC(O)—, —OC(O)O—, —C(O)N(R¹¹)—, —C(O)N(R¹¹)C(O)—, —N(R¹¹)C(O)—, —N(R¹¹)C(O)N(R¹¹)—, —N(R¹¹)C(O)O—, —OC(O)N(R¹¹)—, —C(NR¹¹)—, —N(R¹¹)C(NR¹¹)—, —C(NR¹¹)N(R¹¹)—, —N(R¹¹)C(NR¹¹)N(R¹¹)—, —S(O)₂—, —S(O)—, —N(R)S(O)₂— and —S(O)₂N(R¹¹)—. In some embodiments, L² is selected from absent, —O—, —N(R¹¹)—, —C(O)O—, —C(O)N(R¹¹)— and —N(R¹¹)C(O)—. In some embodiments, L² is selected from absent, —O—, —NH—, —C(O)O—, —C(O)NH— and —NHC(O)—. In some embodiments, L² is absent. In some embodiments, L² is —O—. In some embodiments, L² is —NH—. In some embodiments, L² is —C(O)O—. In some embodiments, L² is —C(O)NH—. In some embodiments, L² is —NHC(O)—.

In some embodiments, for a compound of Formula (I), (I'), (I-A), (I-B), (I-C), (I'-A), (I'-B) or (I'-C), R² is selected from:

halogen, —CN, —OR¹², —SR¹², —N(R¹²)₂, —C(O)OR, —OC(O)R¹², —NR¹²C(O)R¹², —NR¹²C(O)N(R¹²)₂, —C(O)N(R¹²)₂;

C₁₋₁₀ alkyl, optionally substituted with one or more substituents selected from halogen, —CN, —OR¹², —SR¹², —N(R¹²)₂, —C(O)OR¹², —OC(O)R¹², —NR¹²C(O)R¹², —NR¹²C(O)N(R¹²)₂, —C(O)N(R¹²)₂, C₃₋₁₂ carbocycle, and 3- to 12-membered heterocycle; and C₃₋₁₂ carbocycle and 3- to 12-membered heterocycle, wherein each C₃₋₁₂ carbocycle and 3- to 12-membered heterocycle in R² is independently optionally substituted with one or more substituents selected from halogen, —CN, —OR¹², —SR¹², —N(R¹²)₂, —C(O)OR¹², —OC(O)R², —NR¹²C(O)R¹², —NR¹²C(O)N(R¹²)₂, —C(O)N(R¹²)₂, =O, R¹², C₁₋₆ alkyl, and C₁₋₆ haloalkyl. In some embodiments, R¹² is independently selected at each occurrence from hydrogen and C₁₋₆ alkyl, optionally substituted with one or more substituents selected from halogen, —NH₂, —NHCH₃, and —OCH₃.

In some embodiments, for a compound of Formula (I), (I'), (I-A), (I-B), (I-C), (I'-A), (I'-B) or (I'-C), $R^2$ is selected from:

—CN, —OR$^{12}$, —N(R$^{12}$)$_2$, —C(O)OR$^{12}$, —NR$^{12}$C(O)R$^{12}$, —C(O)N(R$^{12}$)$_2$;

$C_{1-10}$ alkyl, optionally substituted with one or more substituents selected from halogen, —CN, —OR$^{12}$, —SR$^2$, —N(R$^{12}$)$_2$, —C(O)OR$^{12}$, $C_{3-12}$ carbocycle, and 3- to 12-membered heterocycle; and $C_{3-12}$ carbocycle and 3- to 12-membered heterocycle, wherein each $C_{3-12}$ carbocycle and 3- to 12-membered heterocycle in $R^2$ is independently optionally substituted with one or more substituents selected from —CN, —OR$^{12}$, —N(R$^{12}$)$_2$, —C(O)OR$^{12}$, —NR$^{12}$C(O)R$^{12}$ ═O, R$^{12}$, $C_{1-6}$ alkyl, and $C_{1-6}$ haloalkyl. In some embodiments, R$^{12}$ is independently selected at each occurrence from hydrogen and $C_{1-6}$ alkyl, optionally substituted with one or more substituents selected from halogen, —NH$_2$, —NHCH$_3$, and —OCH$_3$.

In some embodiments, for a compound of Formula (I), (I'), (I-A), (I-B), (I-C), (I'-A), (I'-B) or (I'-C), $R^2$ is selected from $C_{3-6}$ cycloalkyl, $C_{3-6}$ cycloalkene, 3- to 6-membered heterocycloalkyl, and 5- to 6-membered heteroaryl, each of which is optionally substituted with one or more substituents selected from —NH$_2$, —NHCH$_3$, —N(CH$_3$)$_2$, —CH$_2$NH$_2$, —CH$_2$NHCH$_3$, —CH$_2$N(CH$_3$)$_2$, and —CH$_3$. In some embodiments, $R^2$ is $C_{1-3}$ alkyl substituted with $C_{3-6}$ cycloalkyl, $C_{3-6}$ cycloalkene, 3- to 6-membered heterocycloalkyl, or 5- to 6-membered heteroaryl, each of which is optionally substituted with one or more substituents selected from —NH$_2$, —NHCH$_3$, —N(CH$_3$)$_2$, —CH$_2$NH$_2$, —CH$_2$NHCH$_3$, —CH$_2$N(CH$_3$)$_2$, and —CH$_3$.

In some embodiments, for a compound of Formula (I), (I'), (I-A), (I-B), (I-C), (I'-A), (I'-B) or (I'-C):

$L^1$ is selected from absent, $C_{3-12}$ carbocycle and 3- to 12-membered heterocycle;

$L^2$ is absent; and $R^2$ is selected from;

—CN, —OR$^{12}$, —N(R$^{12}$)$_2$, —C(O)OR$^{12}$, —NR$^{12}$C(O)R$^{12}$, —C(O)N(R$^{12}$)$_2$;

$C_{1-10}$ alkyl, optionally substituted with one or more substituents selected from halogen, —CN, —OR$^{12}$, —SR$^{12}$, —N(R$^{12}$)$_2$, —C(O)OR$^{12}$, $C_{3-12}$ carbocycle, and 3- to 12-membered heterocycle; and $C_{3-12}$ carbocycle and 3- to 12-membered heterocycle, wherein each $C_{3-12}$ carbocycle and 3- to 12-membered heterocycle in $R^2$ is independently optionally substituted with one or more substituents selected from —CN, —OR, —N(R$^{12}$)$_2$, —C(O)OR$^{12}$, —NR$^{12}$C(O)R$^{12}$, ═O, R$^{12}$, $C_{1-6}$ alkyl, and $C_{1-6}$ haloalkyl.

In some embodiments, for a compound of Formula (I), (I'), (I-A), (I-B), (I-C), (I'-A), (I'-B) or (I'-C):

$L^1$ is selected from absent;

$L^2$ is selected from —O—, —NH—, —C(O)O—, —C(O)NH— and —NHC(O)—; and $R^2$ is selected from;

—CN, —OR$^{12}$, —N(R$^{12}$)$_2$, —C(O)OR$^{12}$, —NR$^{12}$C(O)R$^{12}$, —C(O)N(R$^{12}$)$_2$;

$C_{1-10}$ alkyl, optionally substituted with one or more substituents selected from halogen, —CN, —OR$^{12}$, —SR$^{12}$, —N(R$^{12}$)$_2$, —C(O)OR$^{12}$, $C_{3-12}$ carbocycle, and 3- to 12-membered heterocycle; and $C_{3-12}$ carbocycle and 3- to 12-membered heterocycle, wherein each $C_{3-12}$ carbocycle and 3- to 12-membered heterocycle in $R^2$ is independently optionally substituted with one or more substituents selected from —CN, —OR$^{12}$, —N(R$^{12}$)$_2$, —C(O)OR$^{12}$, —NR$^{12}$C(O)R, ═O, R$^{12}$, $C_{1-6}$ alkyl, and $C_{1-6}$ haloalkyl.

In some embodiments, for a compound of Formula (I), (I'), (I-A), (I-B), (I-C), (I'-A), (I'-B) or (I'-C), $R^2$-$L^2$-$L^1$- is selected from:

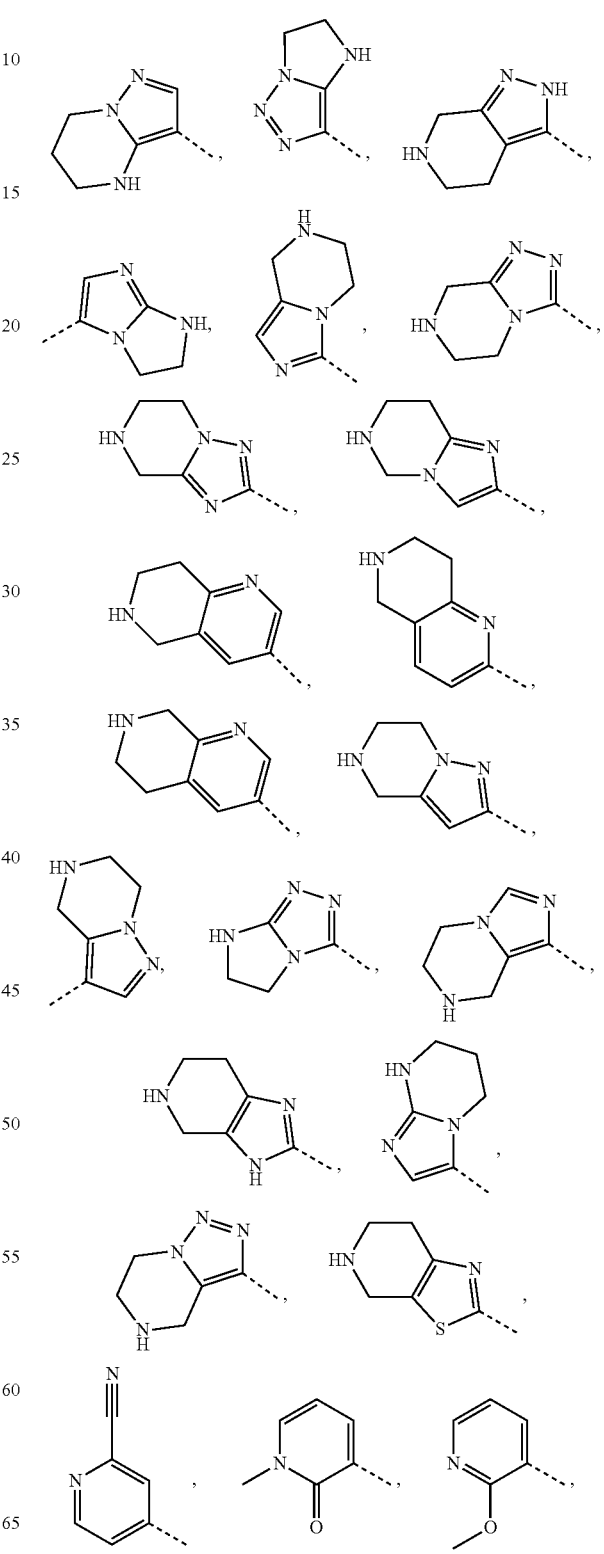

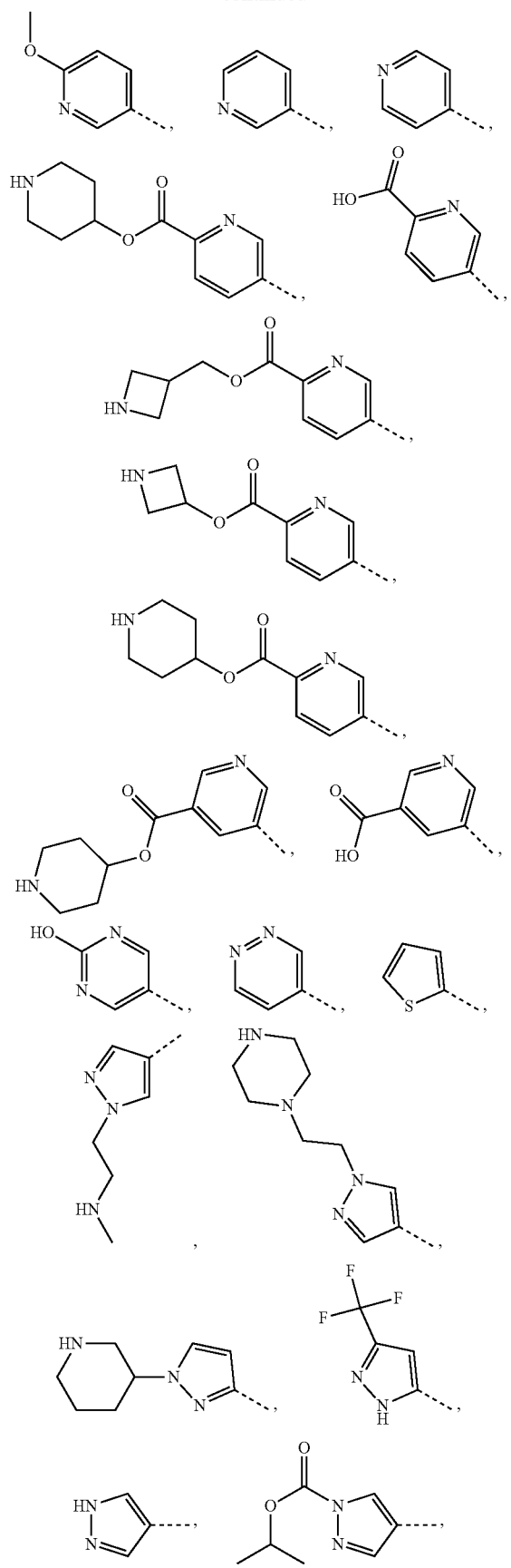
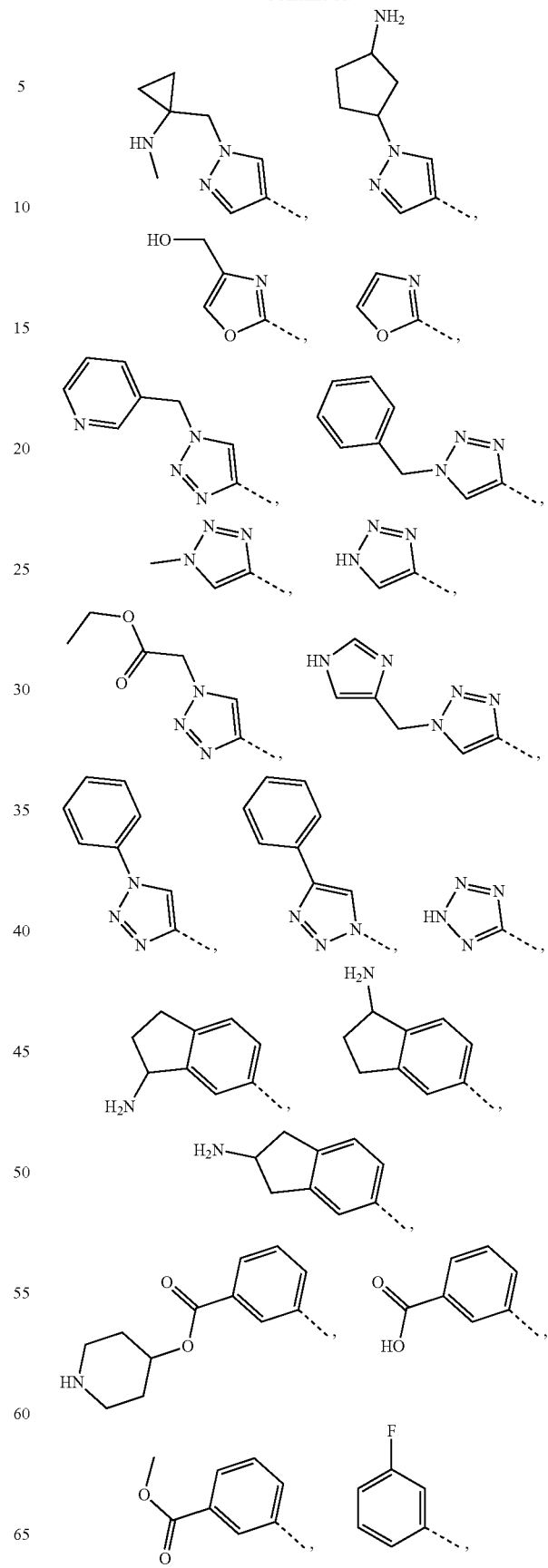

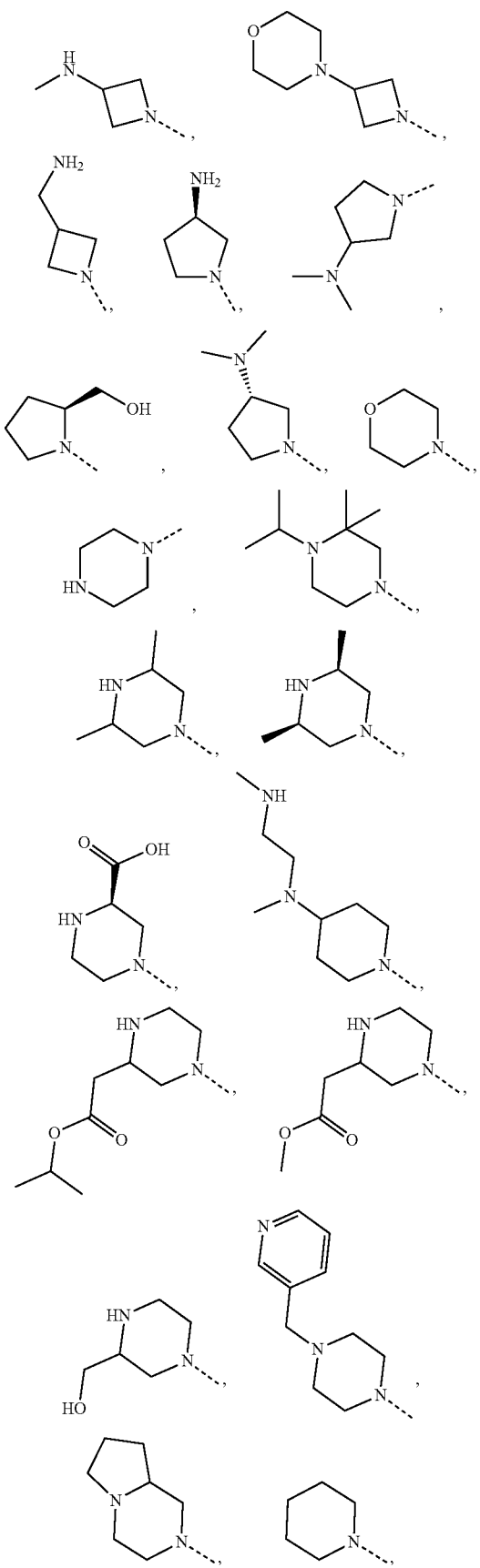
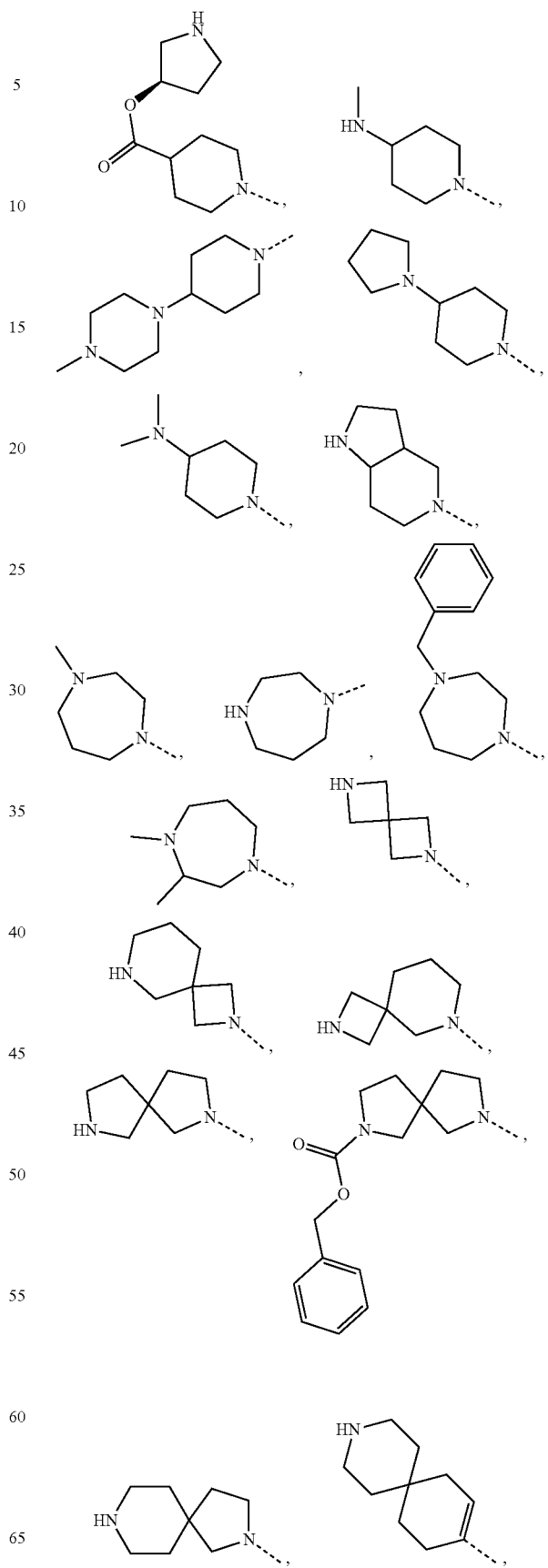

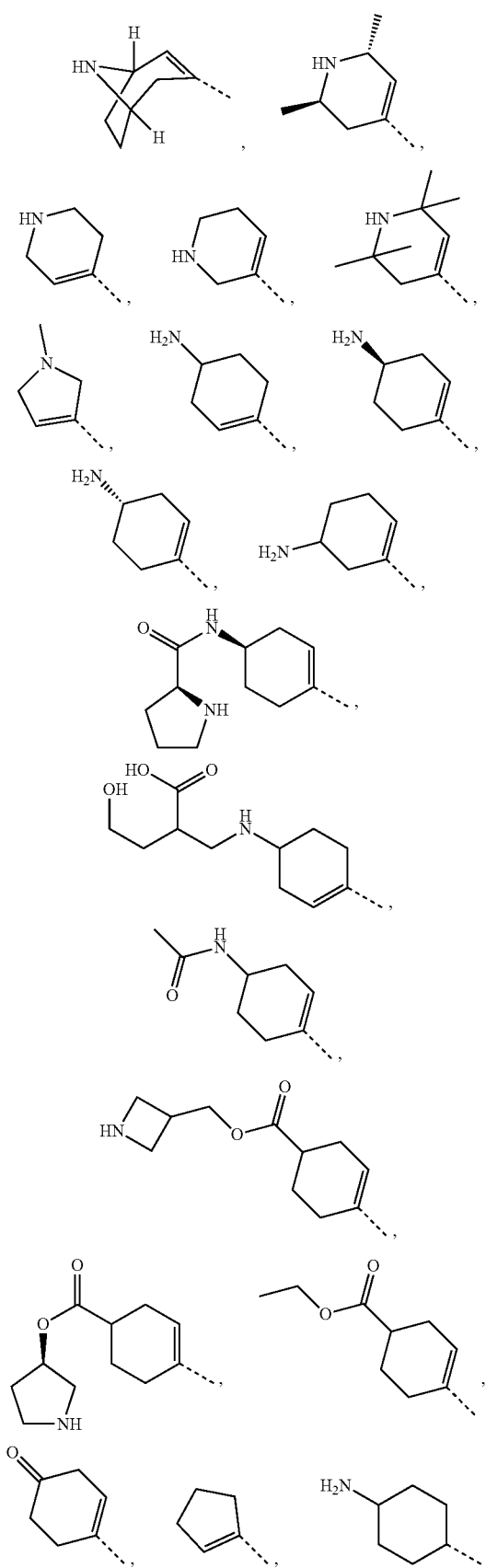
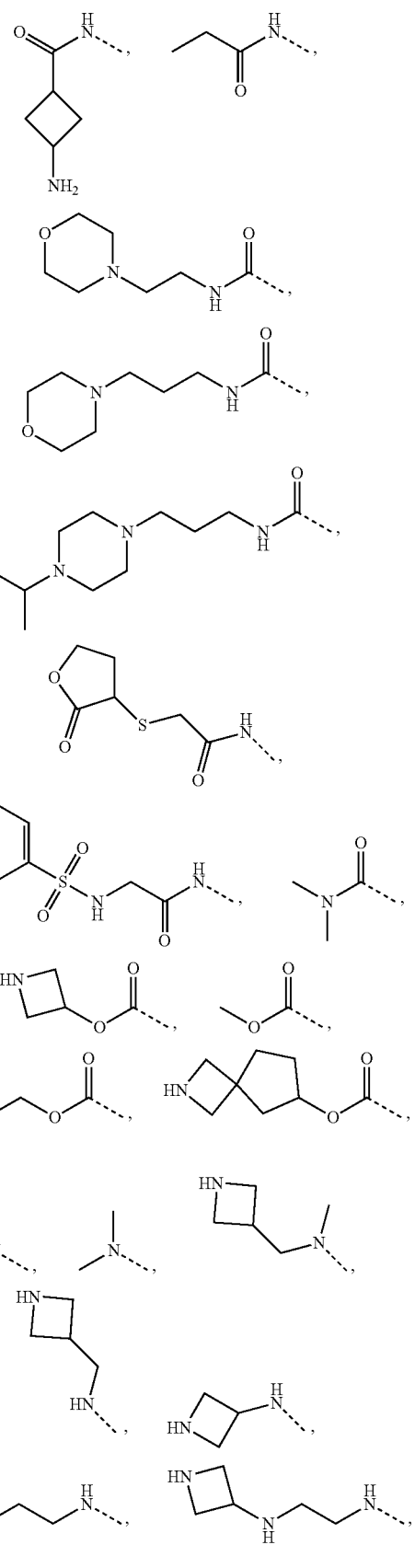

-continued
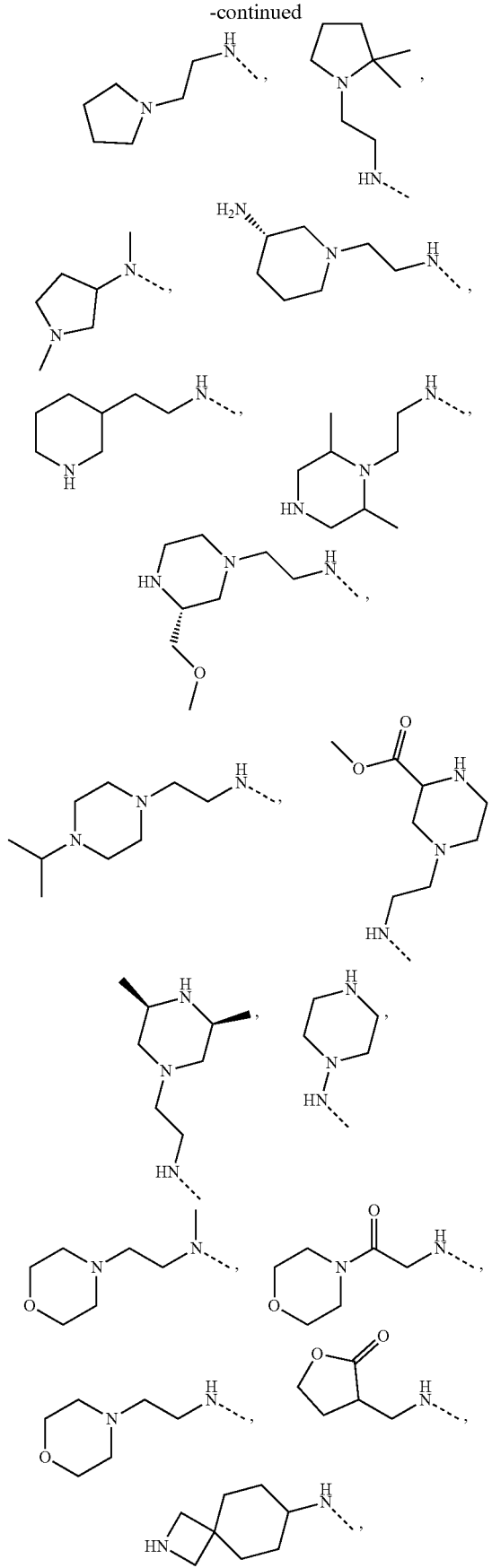
-continued
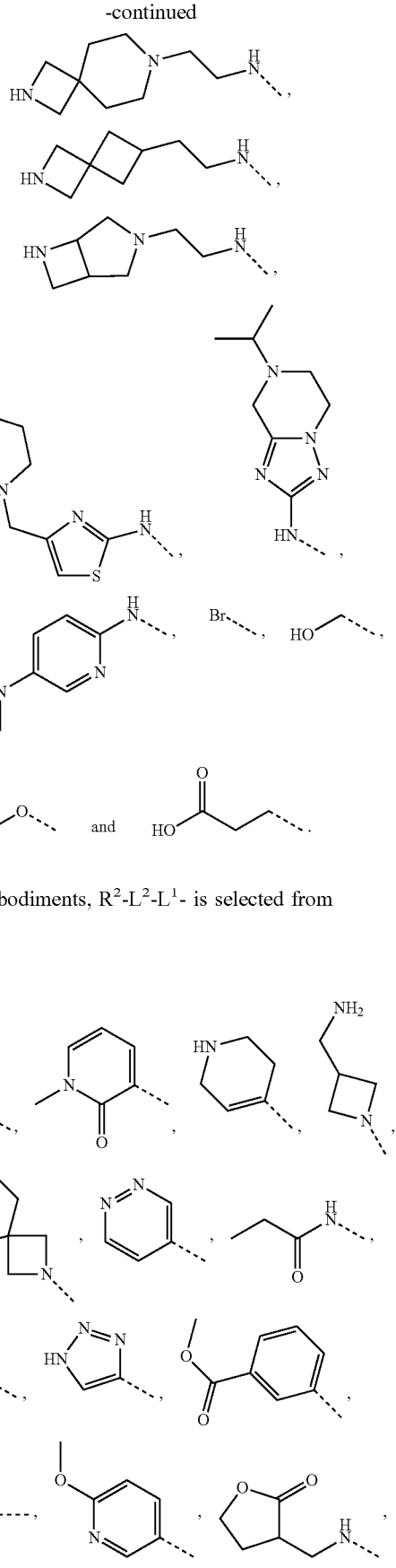
In some embodiments, $R^2$-$L^2$-$L^1$- is selected from

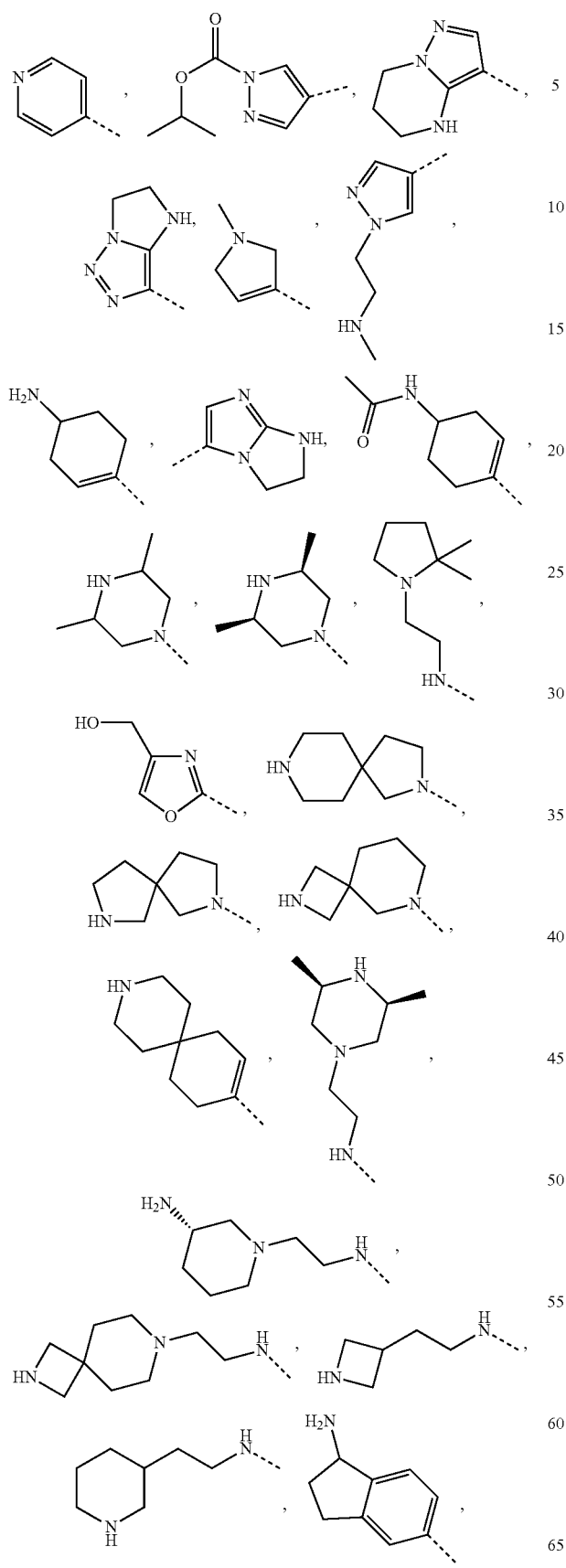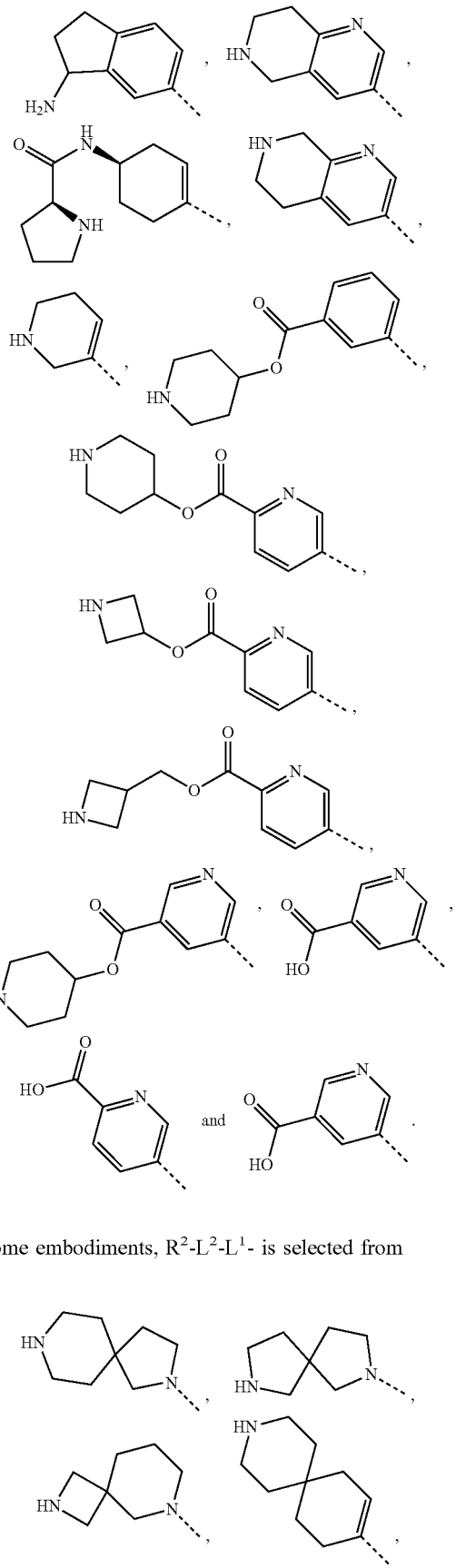
In some embodiments, $R^2$-$L^2$-$L^1$- is selected from

-continued
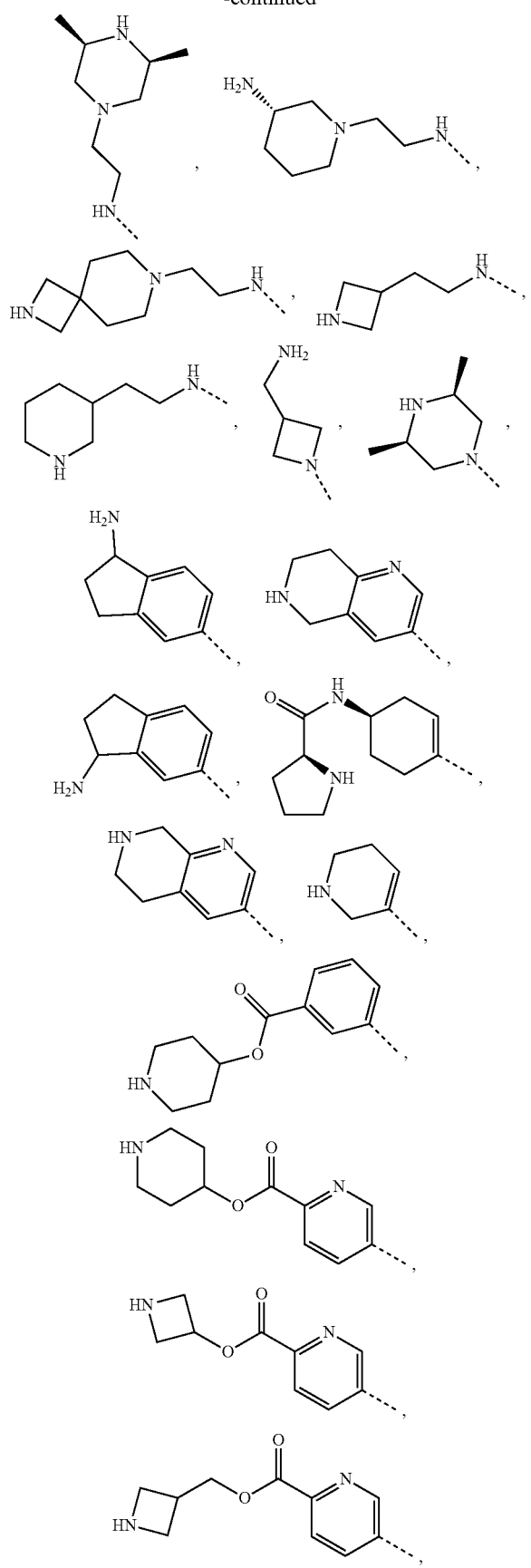
-continued
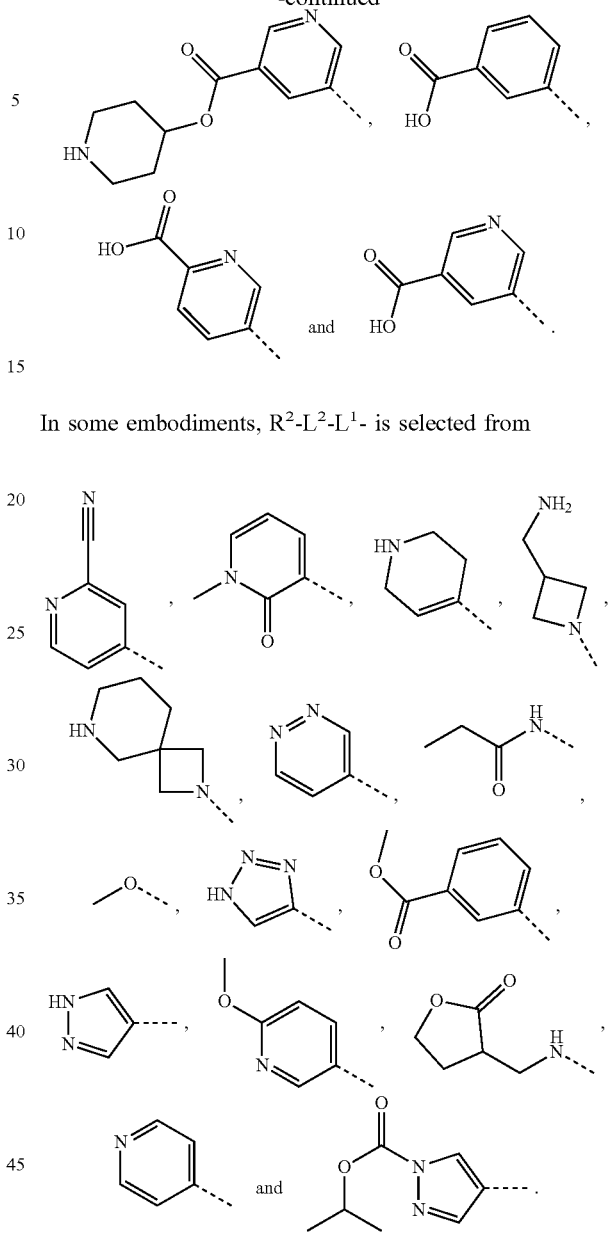
In some embodiments, $R^2$-$L^2$-$L^1$- is selected from
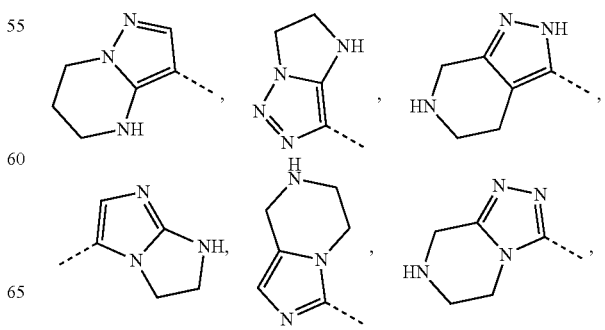
In some embodiments, for a compound of Formula (I), (P), (I-A), (I-B), (I-C), (P-A), (P-B) or (P-C), $R^2$-$L^2$-$L^1$- is selected from:

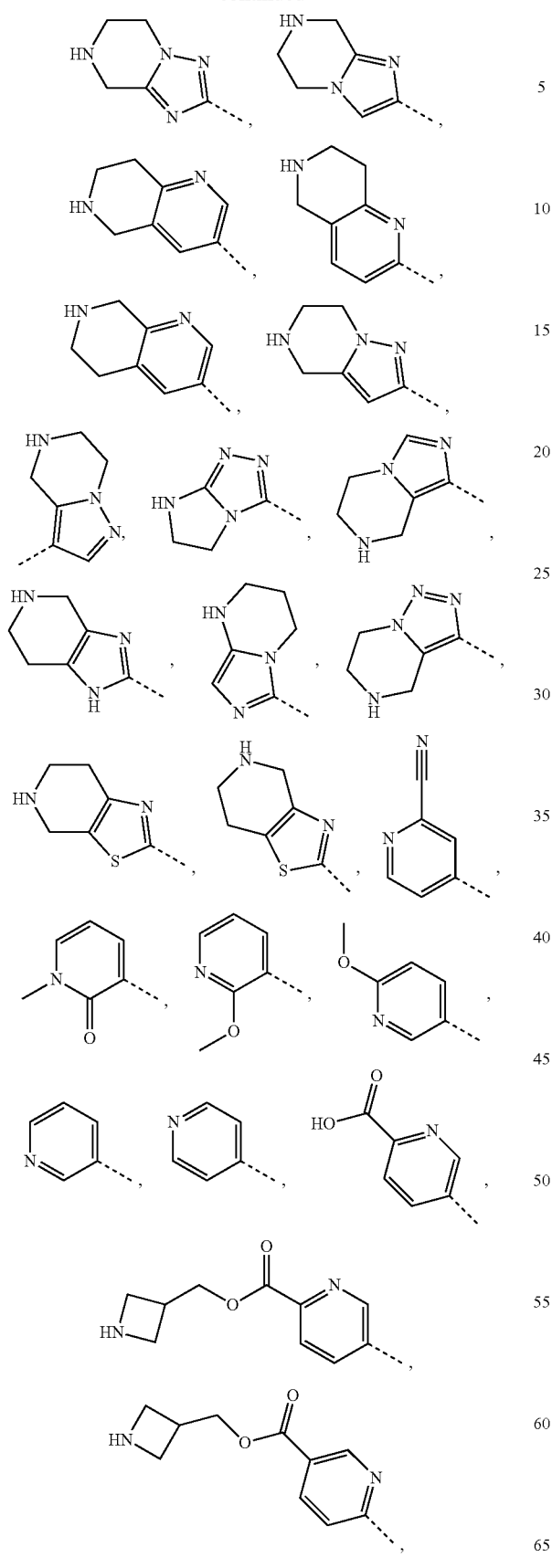
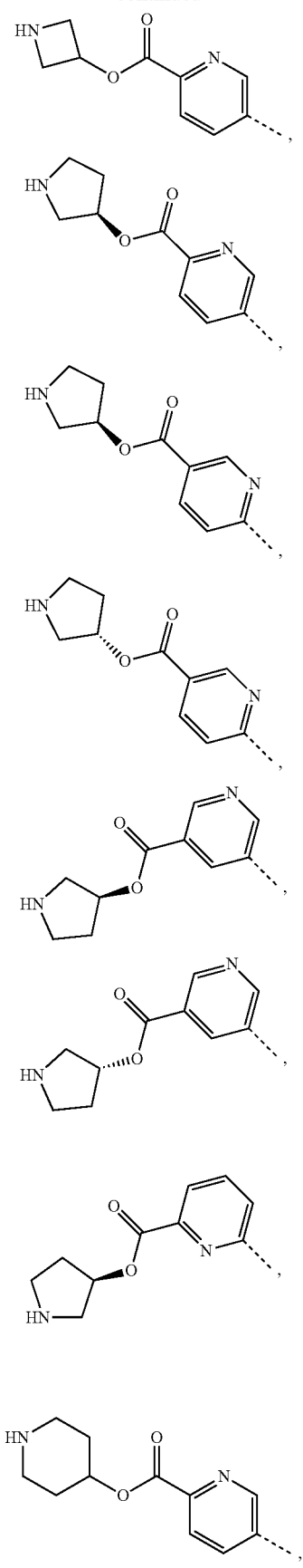

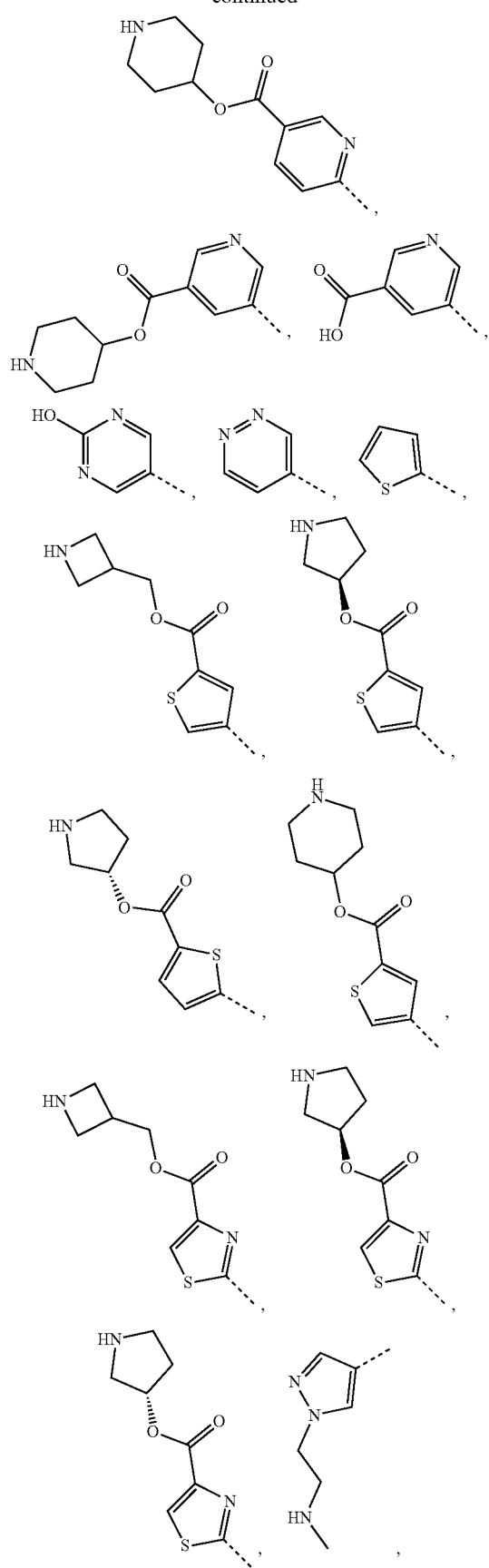
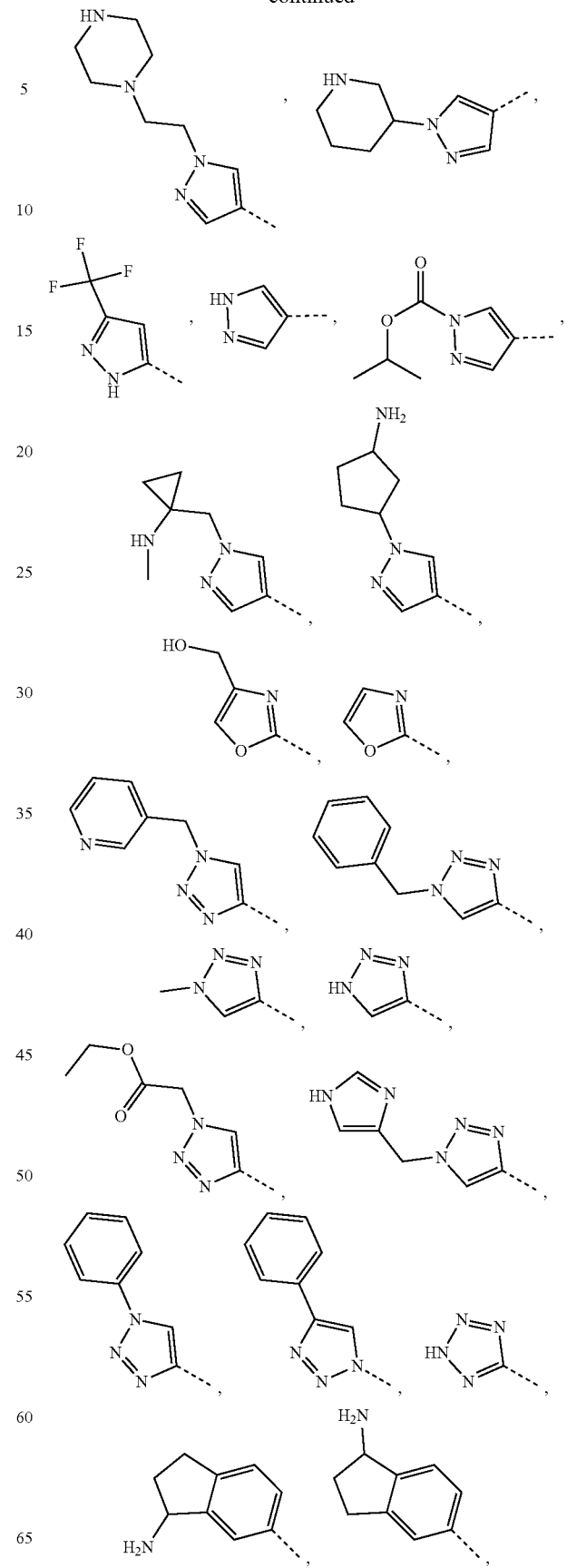

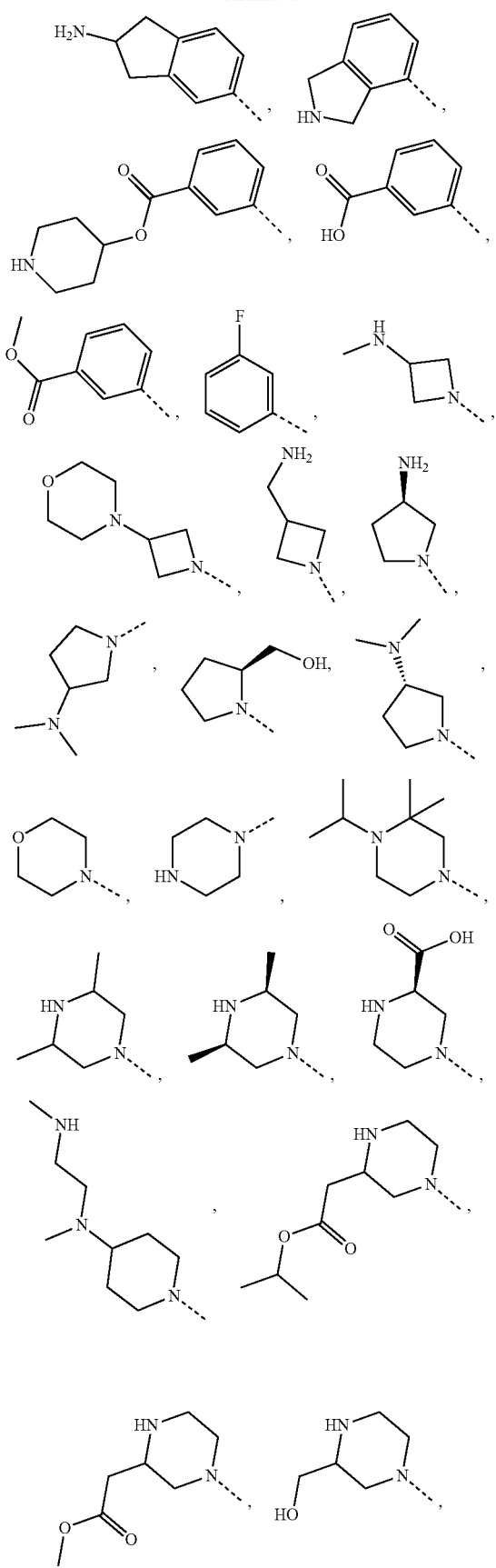
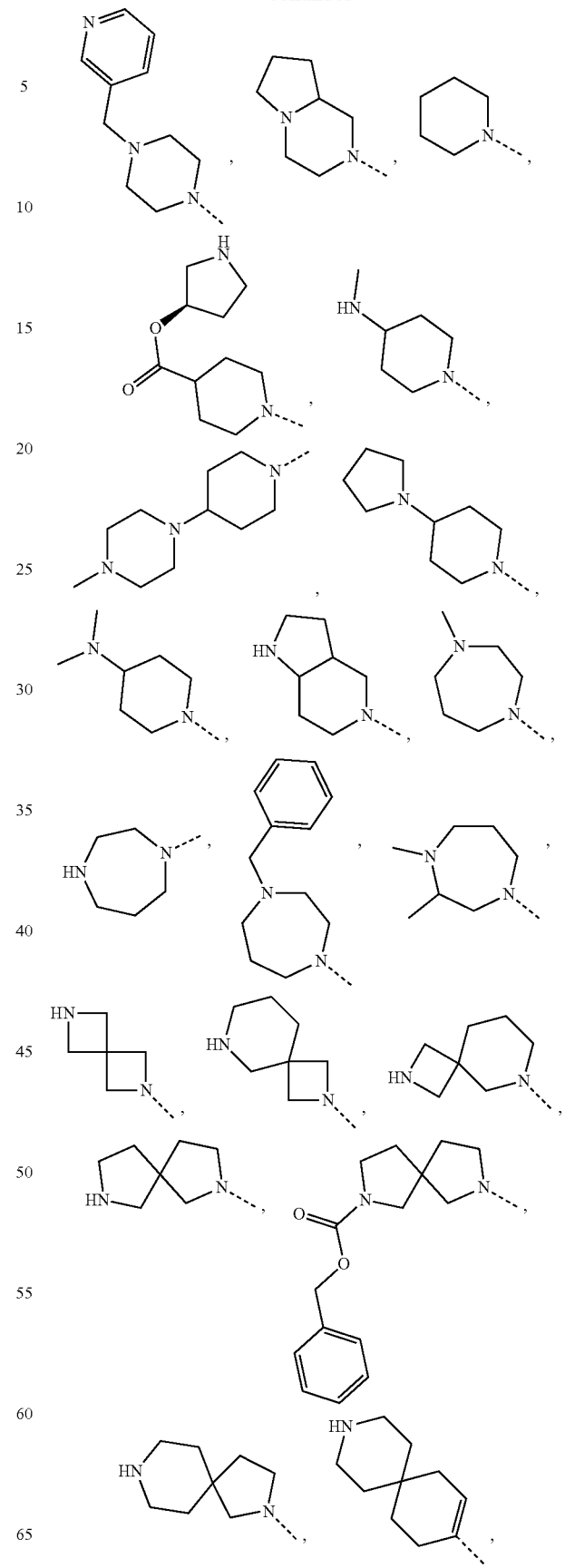

-continued
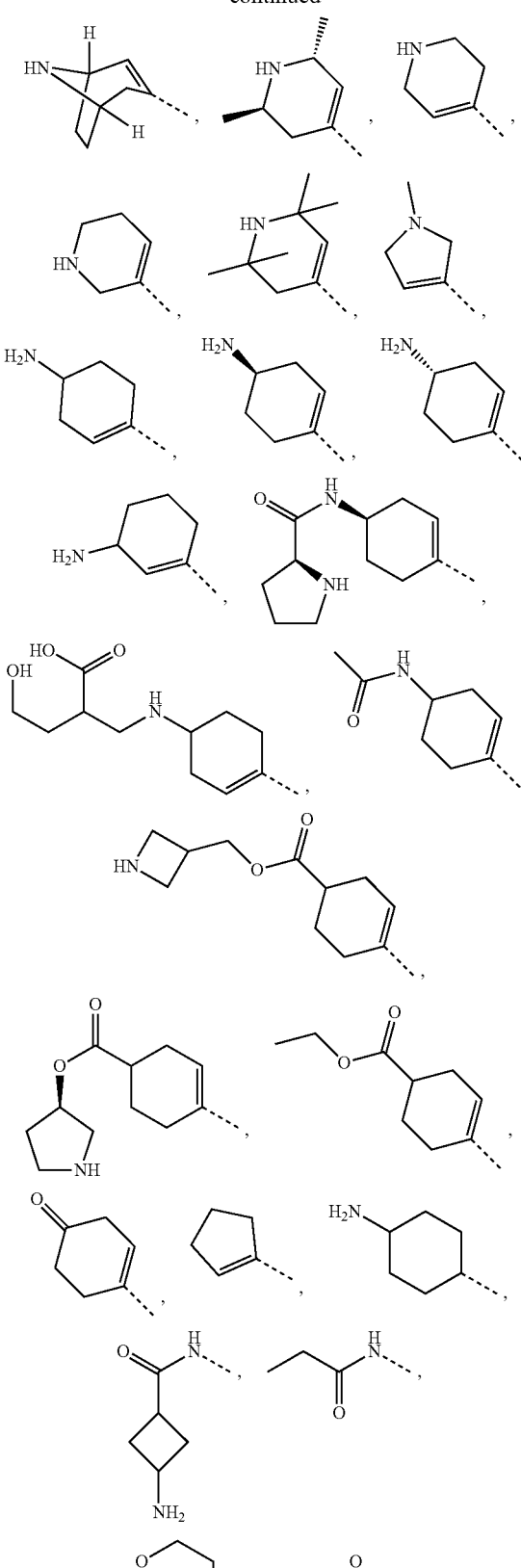
-continued
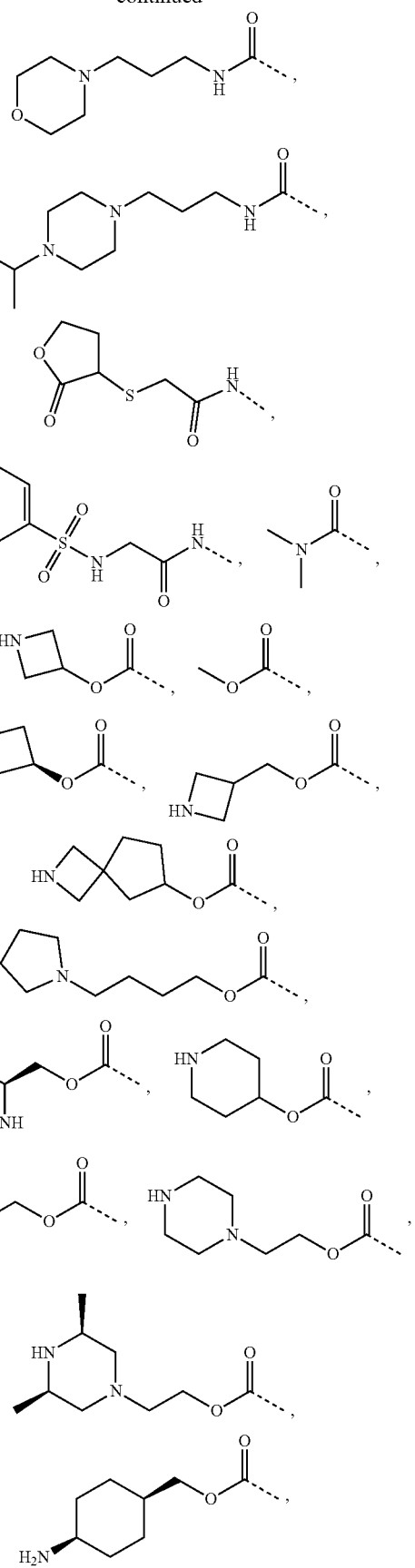

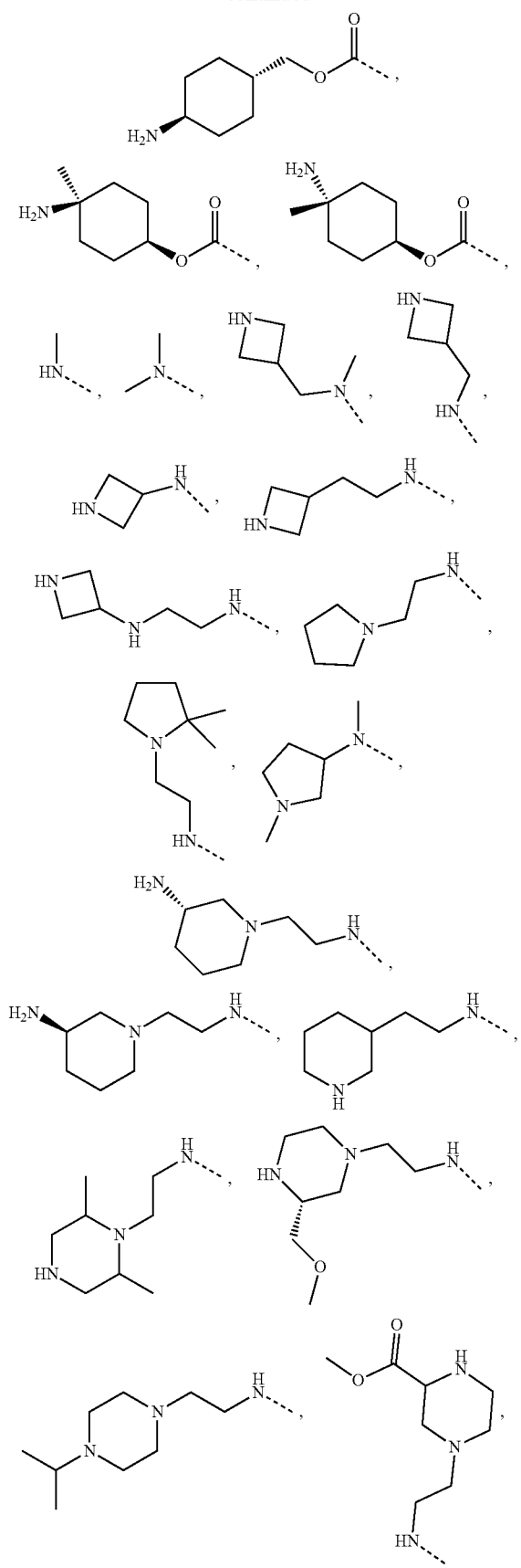
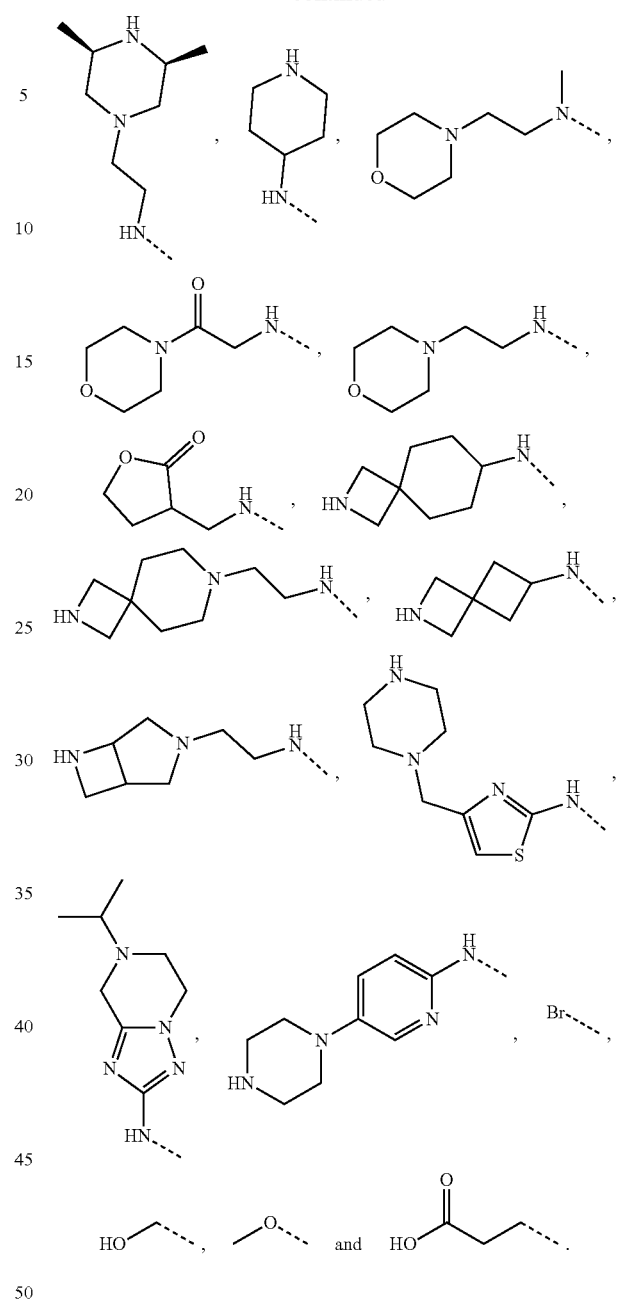
In some embodiments, $R^2$-$L^2$-$L^1$- is selected from
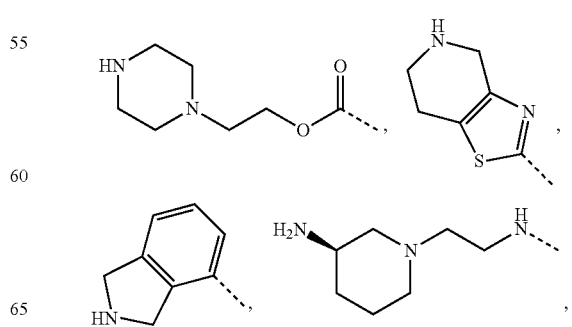

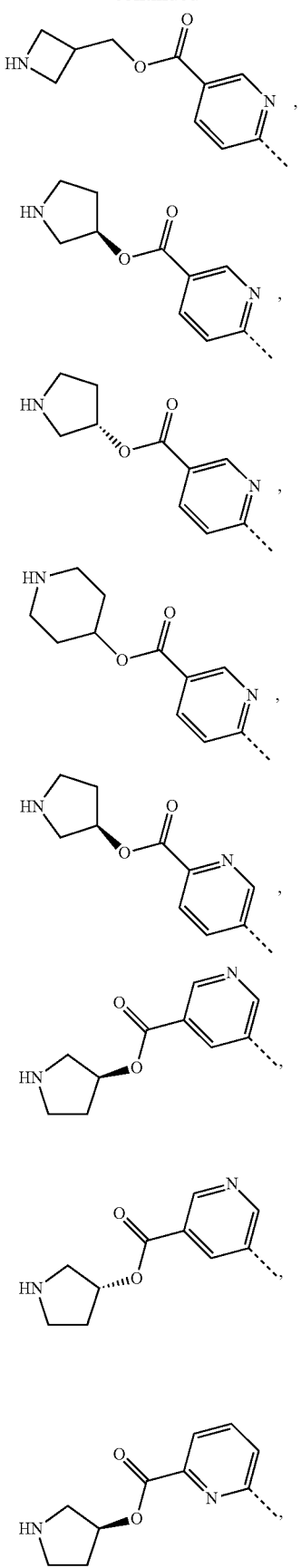
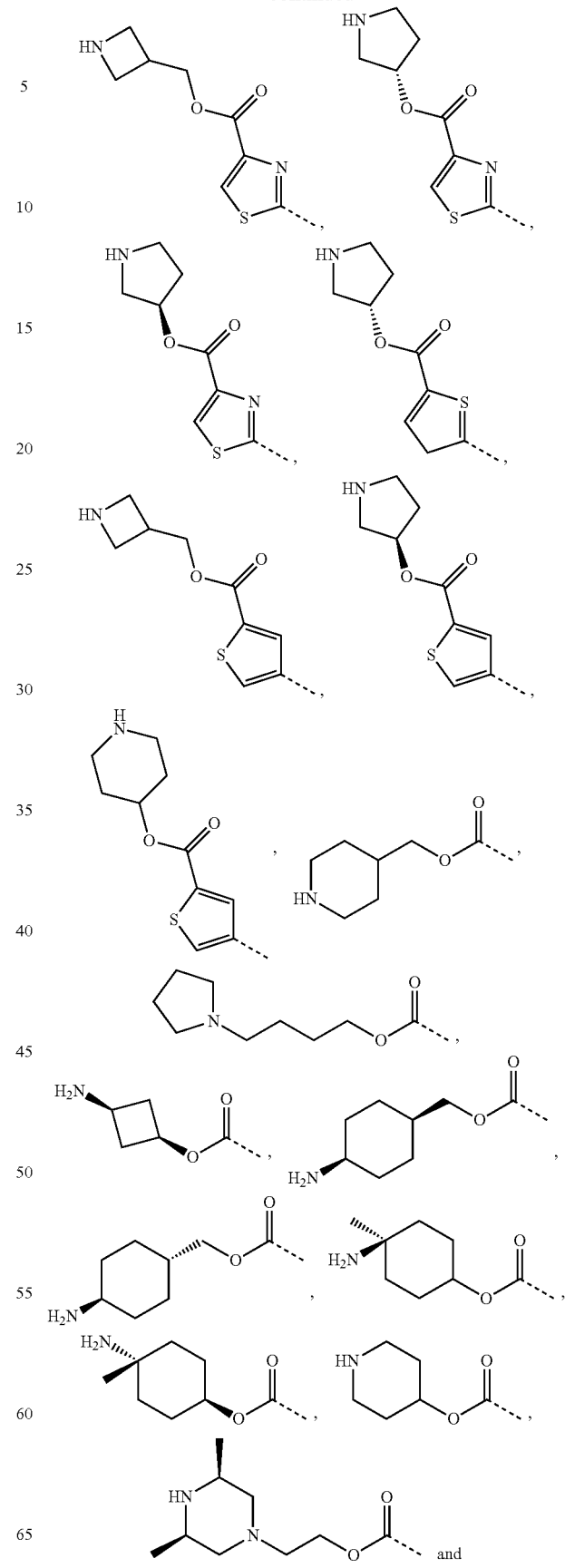

In some embodiments, $R^2$-$L^2$-$L^1$- is selected from

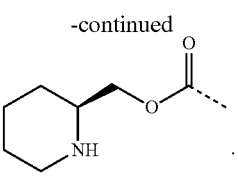

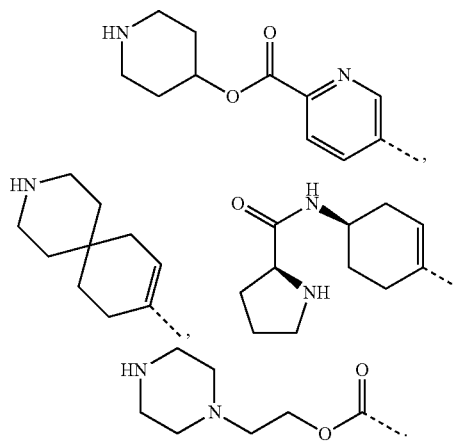

In some embodiments, a compound of Formula (I), (I'), (I-A), (I-B), (I-C), (I'-A), (I'-B) or (I'-C) comprises a terminal ester of the formula —C(O)OR$^{15}$ or —OC(O)R$^{15}$, wherein R$^{15}$ comprises 1 to 12 carbon atoms and at least one basic amine. In some embodiments, the molecular weight of R$^1$ is between 30 and 200 g/mol. The terminal ester may be metabolizable by one or more hydrolase (e.g., an esterase) present in human plasma and/or the human liver into a carboxylic acid and an alcohol. The biological activity of the compound may be greater than that of the carboxylic acid and the alcohol. For example, the compound may exhibit a BEAS2B pIC$_{50}$ of at least 1 unit or greater than the carboxylic acid and the alcohol (assessed according to the assay provided in Example 71). In some embodiments, R$^{15}$ is —(C$_{0-4}$ alkyl)(4- to 10-membered heterocycloalkyl), wherein the heterocycloalkyl comprises 1, 2 or 3 nitrogen atoms, and wherein the heterocycloalkyl is optionally substituted with one or more substituents selected from C$_{1-4}$ alkyl.

In some embodiments, for a compound of Formula (I), (I'), (I-A), (I-B), (I-C), (I'-A), (I'-B) or (I'-C), L$^2$ is —C(O)O— or —OC(O)—, or R$^2$ comprises —C(O)OR$^{12}$ or —OC(O)R$^{12}$. In some embodiments, L$^2$ is —C(O)O— and R$^2$ comprises at least one basic amine. In some embodiments, R$^2$ comprises —C(O)OR$^{12}$, wherein R$^{12}$ comprises at least one basic amine. In some embodiments, R$^2$-$L^2$-$L^1$- is selected from

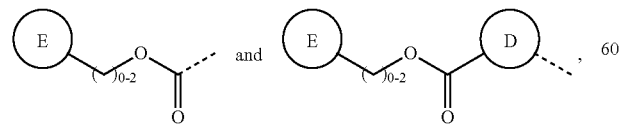

wherein D and E are each independently selected from 3- to 8-membered heterocycle, each of which is independently optionally substituted with one or more substituents selected from —NH$_2$, —NHCH$_3$, —N(CH$_3$)$_2$, —CH$_2$CH$_2$N(CH$_3$)$_2$, —C(O)CH$_3$, —C(O)OH, —C(O)NH$_2$, =O, —OH, —CH$_2$OH, —CH$_2$CH$_2$OH, —OCH$_3$, —OCH$_2$CH$_3$, —CH$_3$, —CH$_2$CH$_3$, —CH(CH$_3$)$_2$, —C(CH$_3$)$_3$, C$_3$ carbocycle, and 3- to 6-membered heterocycle. In some embodiments, D and E are each independently selected from 4- to 6-membered heterocycle, each of which is independently optionally substituted with one or more —CH$_3$. In some embodiments, the heterocycle comprises at least one nitrogen atom. In some embodiments, D and E are each unsubstituted. In some embodiments, $R^2$-$L^2$-$L^1$- is selected from

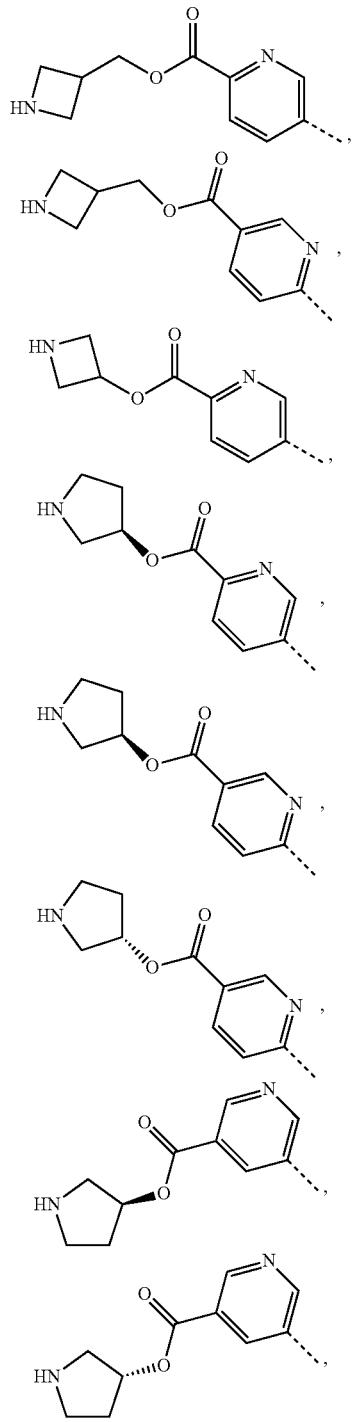

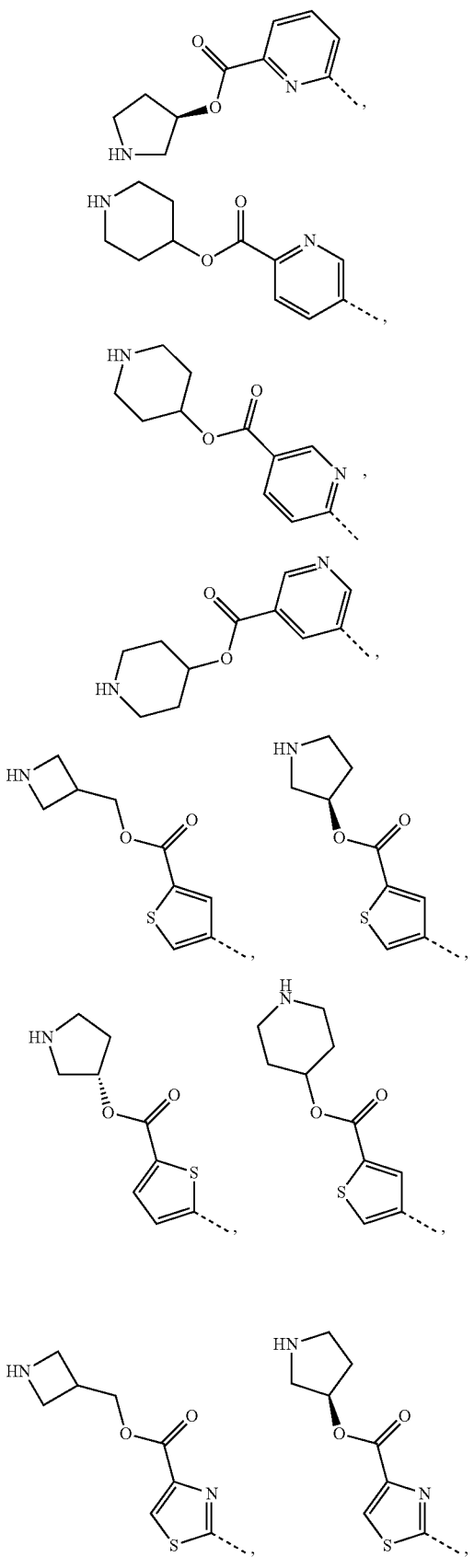
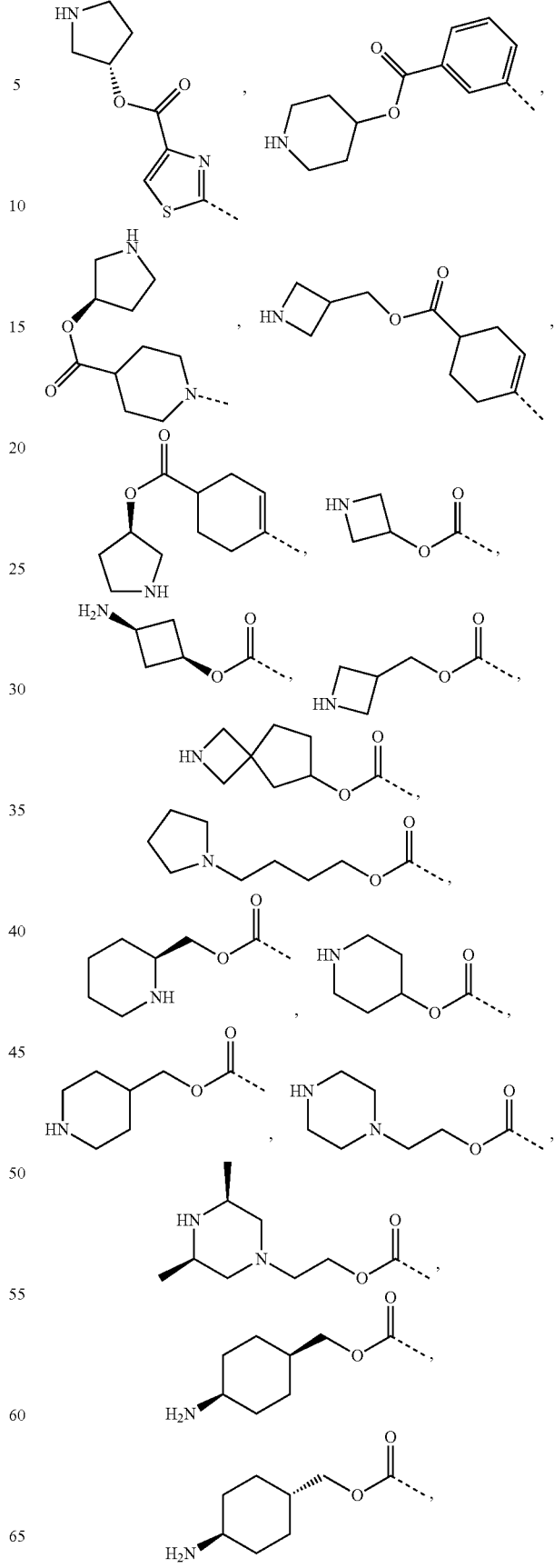

-continued
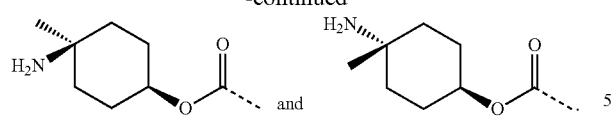 and 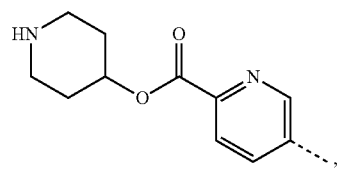
In some embodiments, $R^2\text{-}L^2\text{-}L^1\text{-}$ is selected from
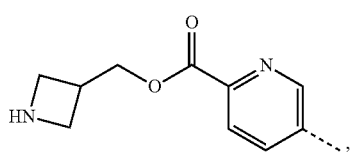
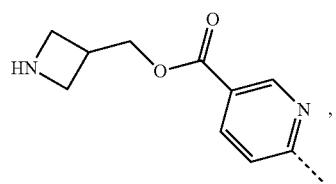
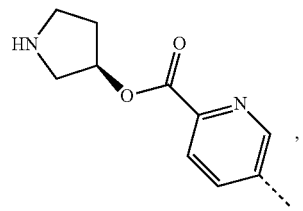
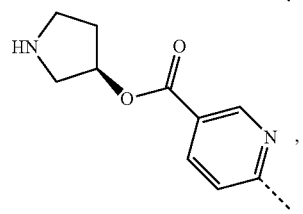
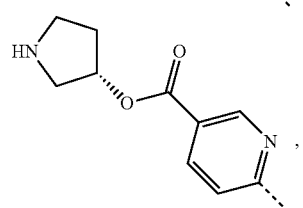
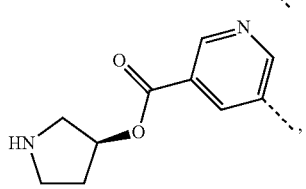
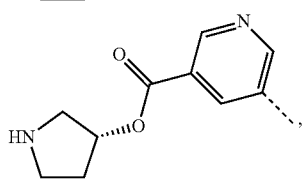
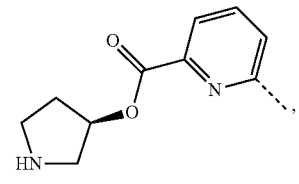
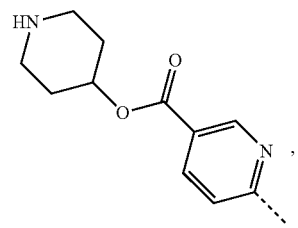
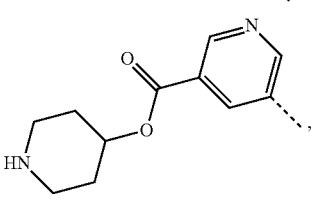
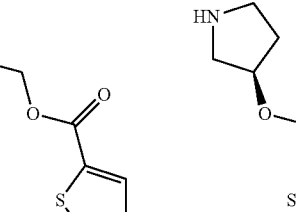
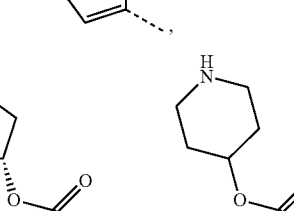
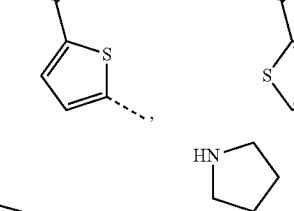
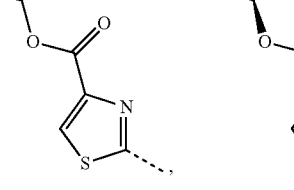
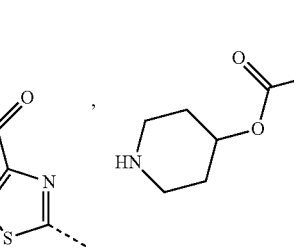

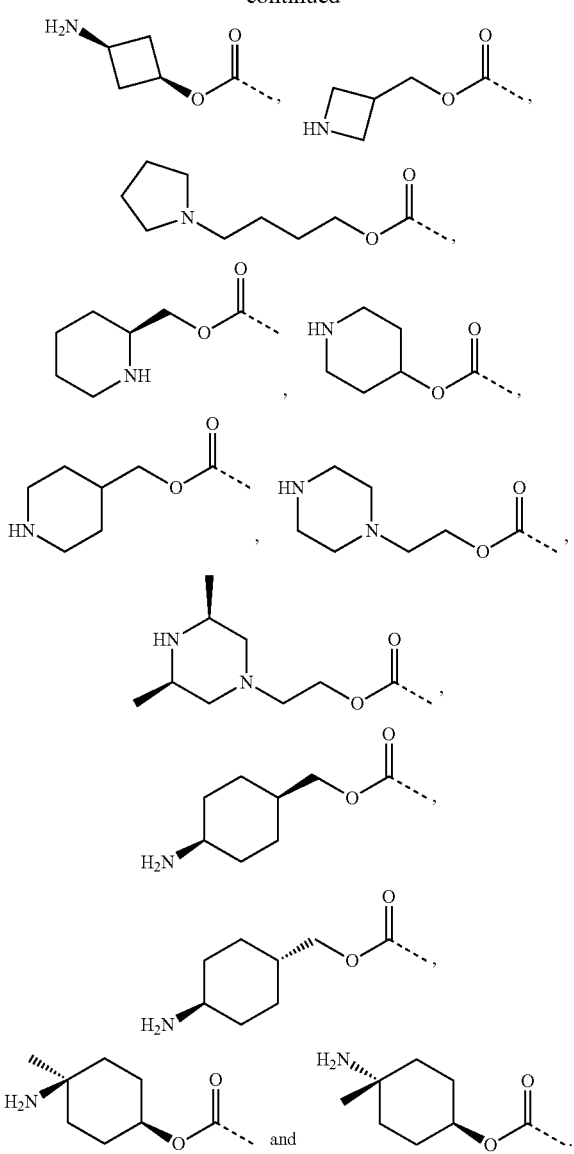

In some embodiments, $R^2$-$L^2$-$L^1$- is selected from

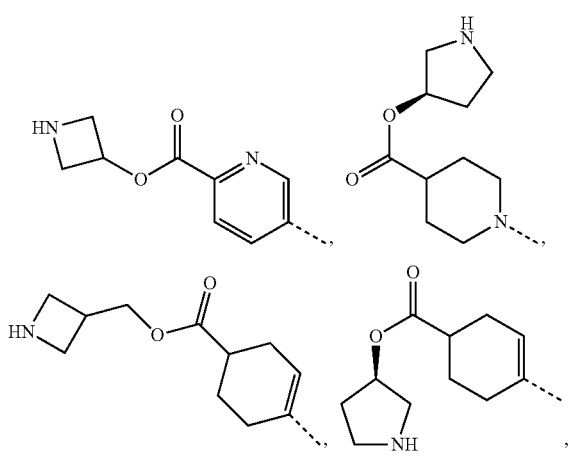

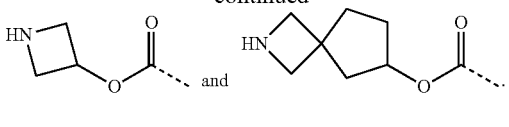

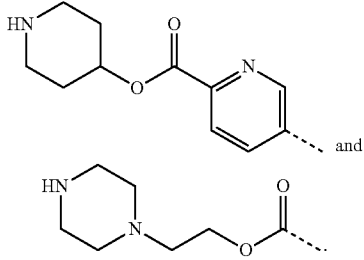

In some embodiments, for a compound of Formula (I), (I'), (I-A), (I-B), (I-C), (I'-A), (I'-B) or (I'-C):
$L^1$ is selected from absent; $C_{1-6}$ alkylene, $C_{3-12}$ carbocycle, and 3- to 12-membered heterocycle;
$L^2$ is selected from absent, —NH—, —C(O)O—, and —OC(O)—;
$R^2$ is selected from;
—C(O)OR$^{12}$ and —OC(O)R$^{12}$;
$C_{1-10}$ alkyl, optionally substituted with one or more substituents selected from —N(R$^{12}$)$_2$, —C(O)OR$^{12}$, —OC(O)R$^{12}$, $C_{3-12}$ carbocycle, and 3- to 12-membered heterocycle; and
$C_{3-12}$ carbocycle and 3- to 12-membered heterocycle,
wherein each $C_{3-12}$ carbocycle and 3- to 12-membered heterocycle in $R^2$ is independently optionally substituted with one or more substituents selected from —N(R$^{12}$)$_2$, —C(O)OR$^{12}$, —OC(O)R$^{12}$, and $C_{1-6}$ alkyl; and
$R^{12}$ is independently selected at each occurrence from hydrogen; and $C_{1-10}$ alkyl, $C_{3-12}$ carbocycle, and 3- to 12-membered heterocycle, each of which is optionally substituted by —NH$_2$, —CH$_3$, $C_{3-12}$ carbocycle-NH$_2$, or 3- to 6-membered heterocycle.

In some embodiments, for a compound of Formula (I), (I'), (I-A), (I-B), (I-C), (I'-A), (I'-B) or (I'-C):
$L^1$ is absent;
$L^2$ is selected from —C(O)O—, and —OC(O)—; and
$R^2$ is selected from;
$C_{1-10}$ alkyl, optionally substituted with one or more substituents selected from —NH$_2$, $C_{3-12}$ carbocycle, and 3- to 12-membered heterocycle; and
$C_{3-12}$ carbocycle and 3- to 12-membered heterocycle,
wherein each $C_{3-12}$ carbocycle and 3- to 12-membered heterocycle in $R^2$ is independently optionally substituted with one or more substituents selected from —NH$_2$ and $C_{1-6}$ alkyl.

In some embodiments, for a compound of Formula (I), (I'), (I-A), (I-B), (I-C), (I'-A), (I'-B) or (I'-C):
$L^1$ is 3- to 12-membered heterocycle;
$L^2$ is selected from —C(O)O— and —OC(O)—; and
$R^2$ is selected from;
$C_{1-10}$ alkyl, optionally substituted with one or more substituents selected from —NH$_2$, $C_{3-12}$ carbocycle, and 3- to 12-membered heterocycle; and
$C_{3-12}$ carbocycle and 3- to 12-membered heterocycle, wherein each $C_{3-12}$ carbocycle and 3- to 12-membered heterocycle in $R^2$ is independently optionally substituted with one or more substituents selected from —$NH_2$ and $C_{1-6}$ alkyl.

In some embodiments, for a compound of Formula (I), (I'), (I-A), (I-B), (I-C), (I'-A), (I'-B) or (I'-C):
$L^1$ is absent;
$L^2$ is —NH—; and
$R^2$ is selected from;
$C_{1-10}$ alkyl, substituted with $C_{3-12}$ carbocycle or 3- to 12-membered heterocycle; and $C_{3-12}$ carbocycle and 3- to 12-membered heterocycle,
wherein each $C_{3-12}$ carbocycle and 3- to 12-membered heterocycle in $R^2$ is substituted with —$C(O)OR^{12}$ or —$OC(O)R^{12}$;
$R^{12}$ is independently selected at each occurrence from hydrogen; and $C_{1-10}$ alkyl, $C_{3-12}$ carbocycle, and 3- to 12-membered heterocycle, each of which is optionally substituted by —$NH_2$, —$CH_3$, $C_{3-12}$ carbocycle-$NH_2$, or 3- to 6-membered heterocycle.

In some embodiments, for a compound of Formula (I), (I'), (I'-A), (I'-B) or (I'-C):
X and Y are each independently selected from C and N, wherein at least one of X and Y is N;
a is 1;
$R^1$ is $CH_3$;
$L^1$ is selected from absent, $C_{3-6}$ carbocycle and 3- to 6-membered heterocycle;
$L^2$ is selected from absent and —NH—;
$R^2$ is selected from;
—$NH_2$;
$C_{1-6}$ alkyl, optionally substituted with one or more substituents selected from $C_{3-6}$ carbocycle and 3- to 6-membered heterocycle; and
$C_{3-6}$ carbocycle and 3- to 6-membered heterocycle,
wherein each $C_{3-6}$ carbocycle and 3- to 6-membered heterocycle in $R^2$ is independently optionally substituted with one or more substituents selected from —$N(R^{12})_2$, =O, $R^{12}$, and $C_{1-6}$ alkyl;
$R^3$, $R^4$ and $R^5$ are each independently absent or selected from hydrogen, —$CH_3$, —$CH_2$-phenyl, —$CH_2$— pyridyl, —$OCH_3$, —$NH_2$, tetrahydropyranyl, —$CH_2NH$-(2-fluorophenyl), —$NHCH_2CH_2$-morpholinyl and —$CH_2C(O)OH$; or $R^3$ and $R^4$ are taken together with the atoms to which they are attached to form a $C_{3-8}$ carbocycle or 3- to 8-membered heterocycle, each of which is optionally substituted with one or more $R^{10}$; or $R^4$ and $R^5$ are taken together with the atoms to which they are attached to form a 3- to 8-membered heterocycle, each of which is optionally substituted with one or more $R^{10}$; and
$R^{12}$ is independently selected at each occurrence from hydrogen and $C_{1-6}$ alkyl, optionally substituted by halogen, —$NH_2$, —$NHCH_3$, and —$NHCH_2CH_3$. In some embodiments, W is CH. In some embodiments, W is N.

In some embodiments, for a compound of Formula (I), (I'), (I'-A), (I'-B) or (I'-C):
W is selected from CH and N;
X and Y are each independently selected from C and N;
a is an integer from 0 to 3;
b is an integer from 0 to 3;
$R^1$ is independently selected at each occurrence from $R^{10}$;
$L^1$ is independently selected at each occurrence from absent; $C_{1-6}$ alkylene, $C_{2-6}$ alkenylene, $C_{2-6}$ alkynylene, $C_{3-12}$ carbocycle, and 3- to 12-membered heterocycle, each of which is optionally substituted with one or more $R^{10}$;
$L^2$ is independently selected at each occurrence from absent, —O—, —S—, —$N(R^{11})$—, —$C(O)$—, —$C(O)O$—, —$OC(O)$—, —$OC(O)O$—, —$C(O)N(R^{11})$—, —$C(O)N(R^{11})C(O)$—, —$C(O)N(R^{11})C(O)N(R^{11})$—, —$N(R^{11})C(O)$—, —$N(R^{11})C(O)N(R^{11})$—, —$N(R^{11})C(O)O$—, —$OC(O)N(R^{11})$—, —$C(NR^{11})$—, —$N(R^{11})C(NR^{11})$—, —$C(NR^{11})N(R^{11})$—, —$N(R^{11})C(NR^{11})N(R^{11})$—, —$S(O)_2$—, —$OS(O)$—, —$S(O)O$—, —$S(O)$—, —$OS(O)_2$—, —$S(O)_2O$—, —$N(R^{11})S(O)_2$—, —$S(O)_2N(R^{11})$—, —$N(R^{11})S(O)$—, —$S(O)N(R^{11})$—, —$N(R^{11})S(O)_2N(R^{11})$—, and —$N(R^{11})S(O)N(R^{11})$—;
$R^2$ is independently selected at each occurrence from $R^{10}$; and
$R^3$, $R^4$, and $R^5$ are each independently absent or selected from —$O(C_{1-6}$ alkyl) and $R^{11}$; or $R^3$ and $R^4$ are taken together with the atoms to which they are attached to form a $C_{3-8}$ carbocycle or 3- to 8-membered heterocycle, each of which is optionally substituted with one or more $R^{10}$; or $R^4$ and $R^5$ are taken together with the atoms to which they are attached to form a 3- to 8-membered heterocycle, each of which is optionally substituted with one or more $R^{10}$.

In some embodiments, for a compound of Formula (I-A):
$R^1$ is $CH_3$;
W is CH;
$L^1$ is selected from absent, $C_{3-12}$ carbocycle and 3- to 12-membered heterocycle;
$L^2$ is selected from absent, —$C(O)O$— and —$NHC(O)$—; and
$R^2$ is selected from;
—$NH_2$; and
$C_{0-6}$ alkyl-(3- to 12-membered heterocycle).

In some embodiments, for a compound of Formula (I), (I'), (I-A), (I-B), (I-C), (I'-A), (I'-B) or (I'-C):
$R^1$ is $CH_3$;
$L^1$ is selected from absent, $C_{3-12}$ carbocycle and 3- to 12-membered heterocycle;
$L^2$ is absent; and
$R^2$ is selected from;
—CN, —$OR^{12}$, —$N(R^{12})_2$, —$C(O)OR^{12}$, —$NR^{12}C(O)R^{12}$, —$C(O)N(R^{12})_2$;
—$C_{1-10}$ alkyl, optionally substituted with one or more substituents selected from halogen, —CN, —$OR^{12}$, —$SR^{12}$, —$N(R^{12})_2$, —$C(O)OR^{12}$, $C_{3-12}$ carbocycle, and 3- to 12-membered heterocycle; and
$C_{3-12}$ carbocycle and 3- to 12-membered heterocycle,
wherein each $C_{3-12}$ carbocycle and 3- to 12-membered heterocycle in $R^2$ is independently optionally substituted with one or more substituents selected from —CN, —$OR^{12}$, —$N(R^{12})_2$, —$C(O)OR^{12}$, —$NR^{12}C(O)R^{12}$, =O, $R^{12}$, $C_{1-6}$ alkyl, and $C_{1-6}$ haloalkyl.

In some embodiments, W is CH. In some embodiments, W is N.

In some embodiments, for a compound of Formula (I), (I'), (I-A), (I-B), (I-C), (I'-A), (I'-B) or (I'-C):
$R^1$ is $CH_3$;
$L^1$ is selected from absent;
$L^2$ is selected from —O—, —NH—, —$C(O)O$—, —$C(O)NH$— and —$NHC(O)$—; and
$R^2$ is selected from;
—CN, —$OR^{12}$, —$N(R^{12})_2$, —$C(O)OR^{12}$, —$NR^{12}C(O)R^{12}$, —$C(O)N(R^{12})_2$;
—$C_{1-10}$ alkyl, optionally substituted with one or more substituents selected from halogen, —CN, —$OR^{12}$, —$SR^{12}$, —$N(R^{12})_2$, —$C(O)OR^{12}$, $C_{3-12}$ carbocycle, and 3- to 12-membered heterocycle; and
$C_{3-12}$ carbocycle and 3- to 12-membered heterocycle,
wherein each $C_{3-12}$ carbocycle and 3- to 12-membered heterocycle in $R^2$ is independently optionally substituted with one or more substituents selected from —CN, —OR$^{12}$, —N(R$^{12}$)$_2$, —C(O)OR$^{12}$, —NR$^{12}$C(O)R$^{12}$, =O, R$^{12}$, C$_{1-6}$ alkyl, and C$_{1-6}$ haloalkyl.

In some embodiments, W is CH. In some embodiments, W is N.

In some embodiments, for a compound of Formula (I), (I'), (I-A), (I-B), (I-C), (I'-A), (I'-B) or (I'-C):

R$^1$ is CH$_3$;

L$^1$ is selected from absent, C$_{3-6}$ carbocycle and 3- to 6-membered heterocycle;

L$^2$ is selected from absent and —NH—;

R$^2$ is selected from;

—NH$_2$;

C$_{1-6}$ alkyl, optionally substituted with one or more substituents selected from C$_{3-6}$ carbocycle and 3- to 6-membered heterocycle; and C$_{3-6}$ carbocycle and 3- to 6-membered heterocycle, wherein each C$_{3-6}$ carbocycle and 3- to 6-membered heterocycle in R$^2$ is independently optionally substituted with one or more substituents selected from —N(R$^{12}$)$_2$, =O, R$^{12}$, and C$_{1-6}$ alkyl; and R$^{12}$ is independently selected at each occurrence from hydrogen and C$_{1-6}$ alkyl, optionally substituted by halogen, —NH$_2$, —NHCH$_3$, and —NHCH$_2$CH$_3$. In some embodiments, W is CH. In some embodiments, W is N.

In some embodiments, for a compound of Formula (I), (I'), (I'-A), (I'-B) or (I'-C):

W is CH;

L$^1$ is selected from absent, C$_{3-6}$ carbocycle and 3- to 6-membered heterocycle;

L$^2$ is selected from absent and —NH—;

R$^2$ is selected from;

—NH$_2$;

C$_{1-6}$ alkyl, optionally substituted with one or more substituents selected from C$_{3-6}$ carbocycle and 3- to 6-membered heterocycle; and C$_{3-6}$ carbocycle and 3- to 6-membered heterocycle, wherein each C$_{3-6}$ carbocycle and 3- to 6-membered heterocycle in R$^2$ is independently optionally substituted with one or more substituents selected from —N(R$^{12}$)$_2$, =O, R$^{12}$, and C$_{1-6}$ alkyl;

R$^3$, R$^4$ and R$^5$ are each independently absent or selected from hydrogen, —CH$_3$, —CH$_2$-phenyl, —CH$_2$— pyridyl, —OCH$_3$, —NH$_2$, tetrahydropyranyl, —CH$_2$NH-(2-fluorophenyl), —NHCH$_2$CH$_2$-morpholinyl and —CH$_2$C(O)OH; and R$^{12}$ is independently selected at each occurrence from hydrogen and C$_{1-6}$ alkyl, optionally substituted by halogen, —NH$_2$, —NHCH$_3$, and —NHCH$_2$CH$_3$.

In some embodiments, for a compound of Formula (I), (I'), (I'-A), (I'-B) or (I'-C):

W is N;

L$^1$ is selected from absent, C$_{3-6}$ carbocycle and 3- to 6-membered heterocycle;

L$^2$ is selected from absent and —NH—;

R$^2$ is selected from;

—NH$_2$;

C$_{1-6}$ alkyl, optionally substituted with one or more substituents selected from C$_{3-6}$ carbocycle and 3- to 6-membered heterocycle; and C$_{3-6}$ carbocycle and 3- to 6-membered heterocycle, wherein each C$_{3-6}$ carbocycle and 3- to 6-membered heterocycle in R$^2$ is independently optionally substituted with one or more substituents selected from —N(R$^{12}$)$_2$, =O, R$^{12}$, and C$_{1-6}$ alkyl;

R$^3$, R$^4$ and R$^5$ are each independently absent or selected from hydrogen, —CH$_3$, —CH$_2$-phenyl, —CH$_2$— pyridyl, —OCH$_3$, —NH$_2$, tetrahydropyranyl, —CH$_2$NH-(2-fluorophenyl), —NHCH$_2$CH$_2$-morpholinyl and —CH$_2$C(O)OH; and R$^{12}$ is independently selected at each occurrence from hydrogen and C$_{1-6}$ alkyl, optionally substituted by halogen, —NH$_2$, —NHCH$_3$, and —NHCH$_2$CH$_3$.

In some embodiments, a compound of Formula (I') is a compound of a formula selected from:

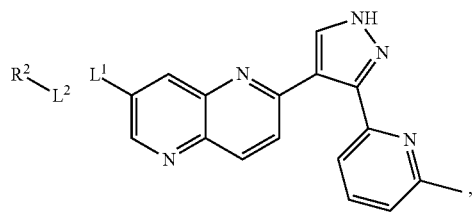

,

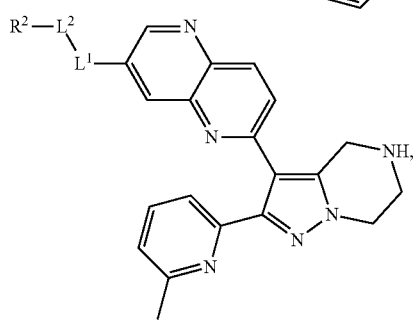

,

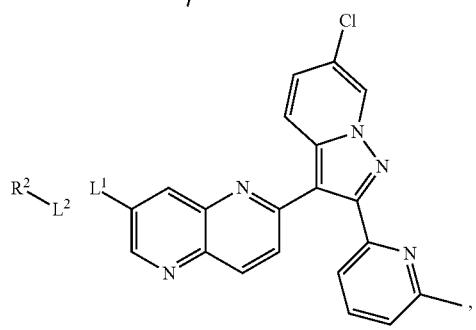

,

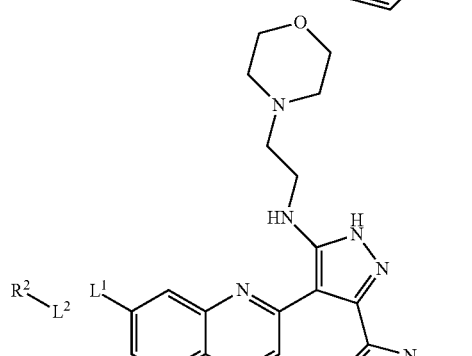

,

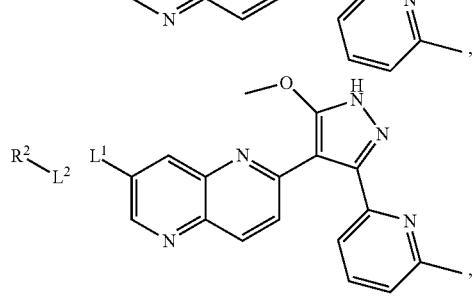

,

-continued
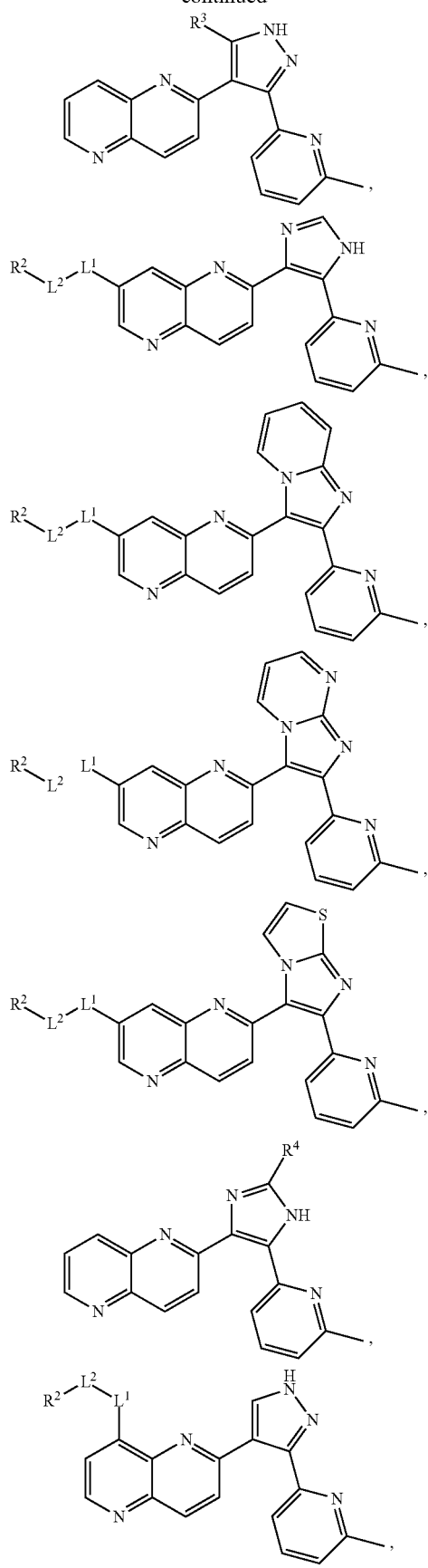
-continued
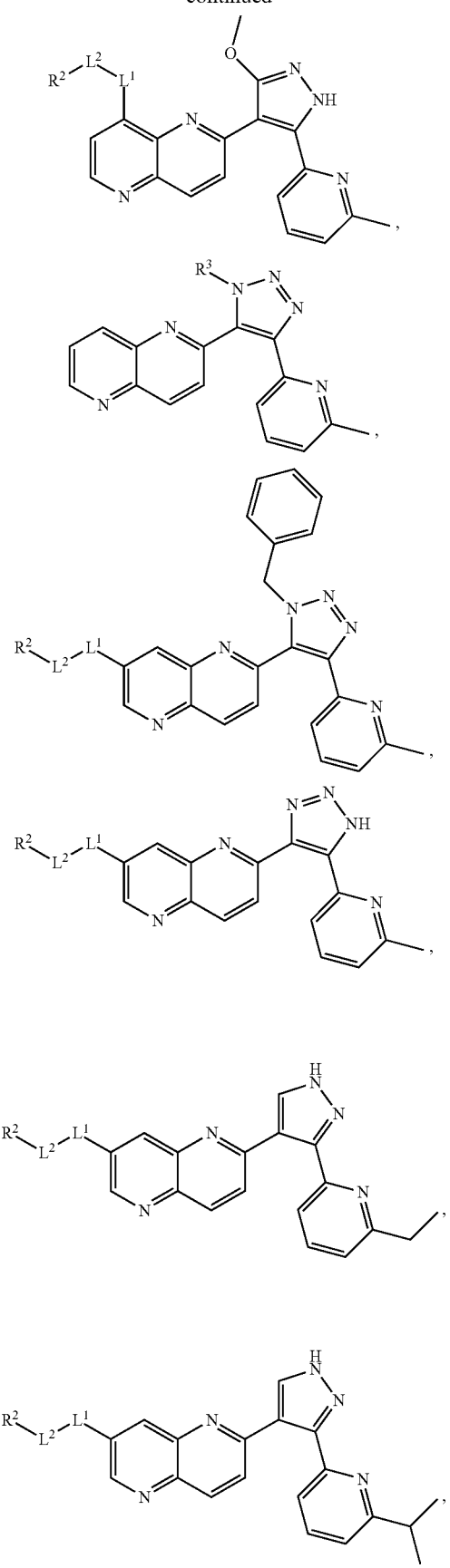

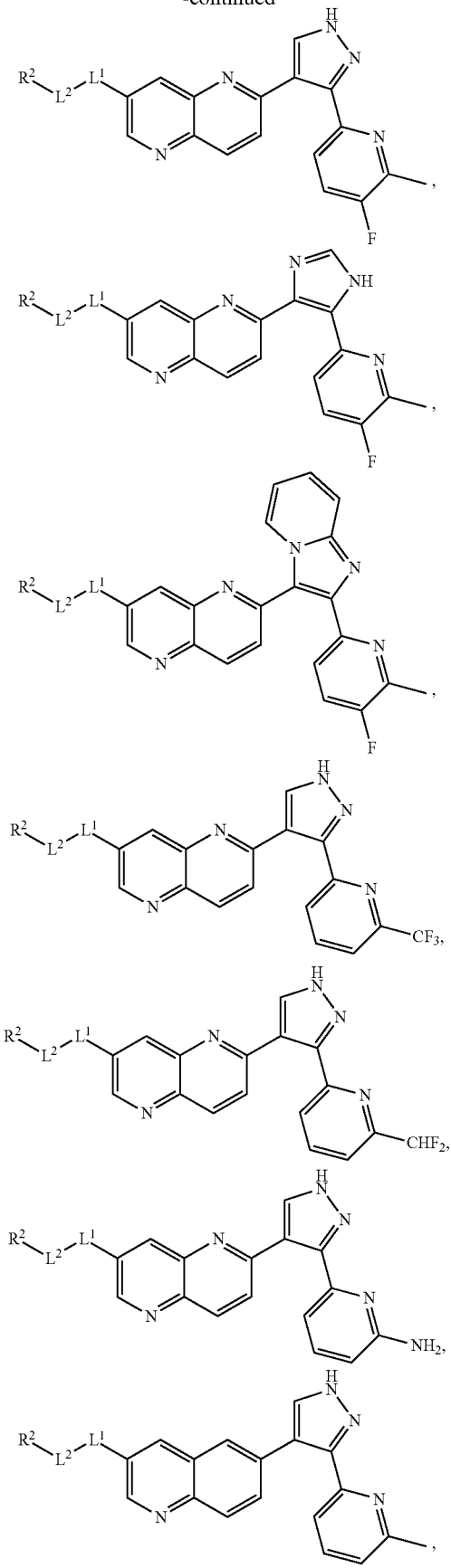
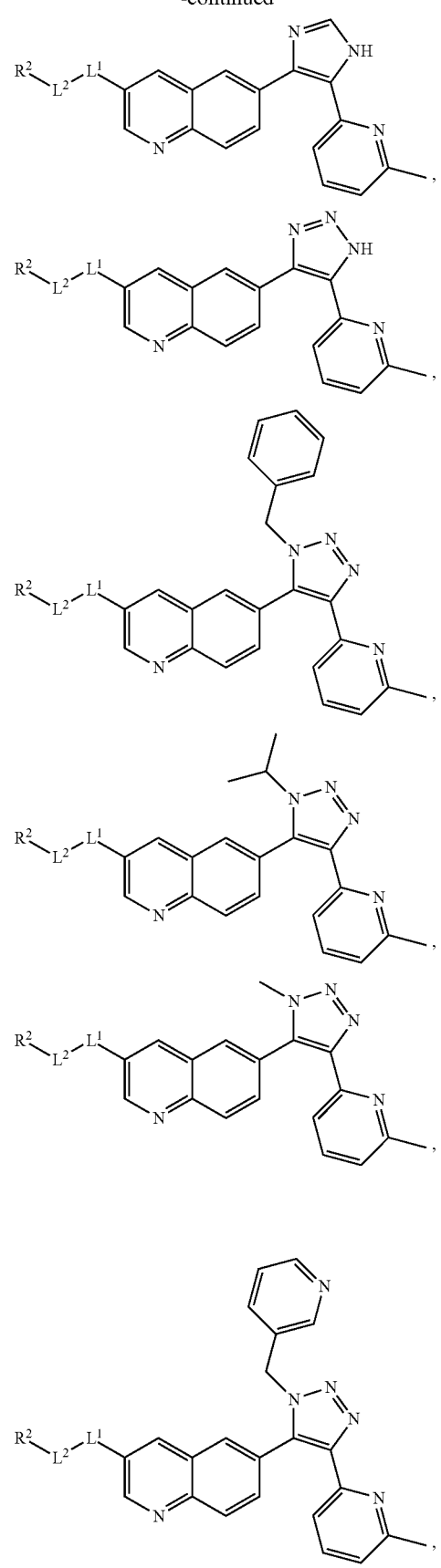

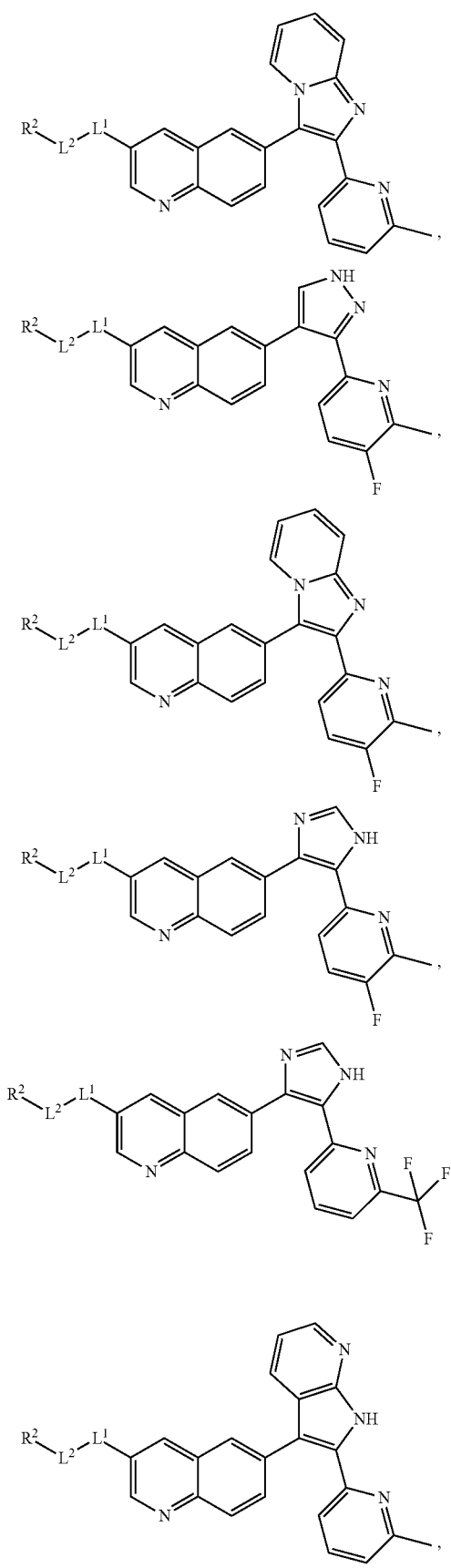
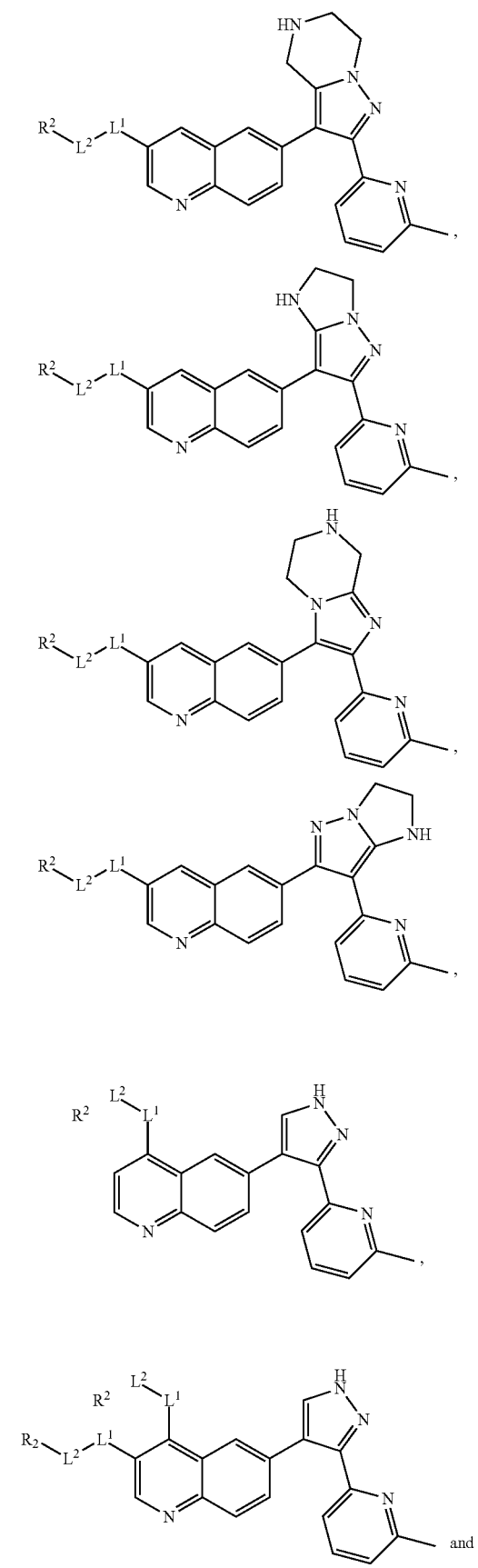

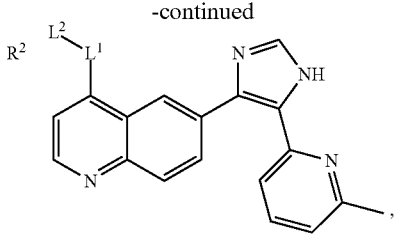

or a pharmaceutically acceptable salt thereof. In some embodiments, a compound of Formula (I') is a compound of the formula

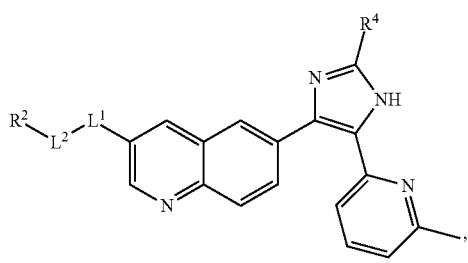

such as

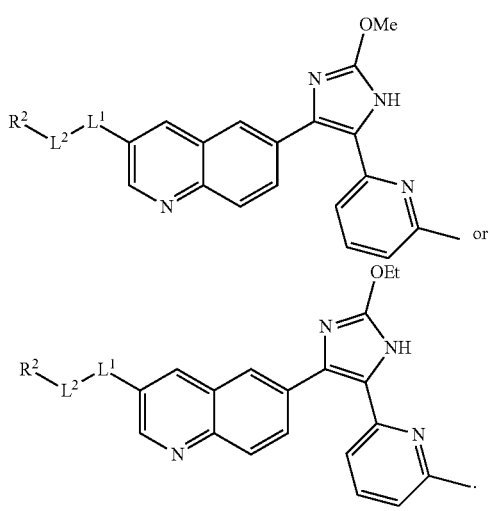

In some embodiments, a compound of Formula (I), (I'), (I-A), (I-B), (I-C), (I'-A), (I'-B) or (I'-C) is provided as a substantially pure stereoisomer. In some embodiments, the stereoisomer is provided in at least 80% enantiomeric excess, such as at least 85%, at least 90%, at least 95%, at least 96%, at least 97%, at least 98%, at least 99% or at least 99.9% enantiomeric excess.

In some embodiments, the present disclosure provides a soft ALK5 inhibitor. As used herein, the term "soft drug" or "soft ALK5 inhibitor" refers to a biologically active compound that is converted upon entering the systemic circulation into a predictable metabolite that exhibits reduced biological activity relative to the parent compound. A soft drug preferably exerts its desired therapeutic effect locally at the target organ or tissue, then is rapidly converted to a predictable metabolite designed to be less active than the parent soft drug upon entering the systemic circulation, thus reducing systemic exposure to the biologically active compound. Accordingly, soft drugs have a lower potential for undesired side effects relative to non-soft drug compounds having comparable biological activity. Preferably, a soft drug of the present disclosure exhibits good stability at the intended site of action (e.g., the lung), is rapidly metabolized upon entering systemic circulation, and displays more functional activity than the corresponding metabolite.

In some embodiments, a soft drug provided herein exhibits an ALK5 $pK_i$ of greater than or equal to 9, while the corresponding soft drug metabolite exhibits an ALK5 $pK_i$ of 9 or less, such as 8 or less (assessed according to the assay provided in Example 70). In some embodiments, the difference in $pK_i$ of the soft drug and the corresponding soft drug metabolite is at least 0.5, such as at least 0.6, 0.7, 0.8, 0.9, 1.0, 1.1, 1.2, 1.3, 1.4, 1.5, 1.6, 1.7, 1.8, 1.9, or at least 2.0. In some embodiments, a soft drug provided herein exhibits a BEAS2B $pIC_{50}$ of greater than or equal to 7, while the corresponding soft drug metabolite exhibits a BEAS2B $pIC_{50}$ of 6 or less (assessed according to the assay provided in Example 71). In some embodiments, the difference in $pIC_{50}$ of the soft drug and the corresponding soft drug metabolite is at least 1.0, such as at least 1.1, 1.2, 1.3, 1.4, 1.5, 1.6, 1.7, 1.8, 1.9, or at least 2.0. In some embodiments, the soft drug and corresponding soft drug metabolite exhibit similar ALK5 $pK_i$ values, but the soft drug is more active in cells (e.g., the soft drug exhibits a BEAS2B $pIC_{50}$ of at least 1.0 greater than the soft drug metabolite).

In some embodiments, the present disclosure provides a soft ALK5 inhibitor comprising an ester. Preferably, the ester inhibits ALK5 activity, while the corresponding carboxylic acid of the ester exhibits reduced ALK5 inhibitory activity. For example, the difference in ALK5 $pK_i$ of the ester and corresponding acid may be at least 1.0. In some embodiments, a soft drug ester of the present disclosure is administered to the lung, for example, by inhalation, and inhibits the activity of ALK5 in the lung. However, upon exiting the lung, the ester may be readily hydrolyzed to the corresponding carboxylic acid, thus reducing systemic exposure to the ester.

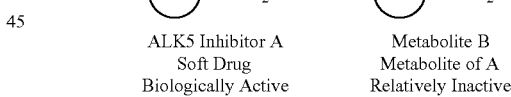

ALK5 Inhibitor A
Soft Drug
Biologically Active

Metabolite B
Metabolite of A
Relatively Inactive

The chemical entities described herein can be synthesized according to one or more illustrative schemes herein and/or techniques known in the art. Materials used herein are either commercially available or prepared by synthetic methods generally known in the art. These schemes are not limited to the compounds listed in the examples or by any particular substituents, which are employed for illustrative purposes. Although various steps are described and depicted in Schemes 1-5 and Examples 1-69, the steps in some cases may be performed in a different order than the order shown in Schemes 1-5 and Examples 1-69. Various modifications to these synthetic reaction schemes may be made and will be suggested to one skilled in the art having referred to the present disclosure. Numberings or R groups in each scheme typically have the same meanings as those defined elsewhere herein unless otherwise indicated.

Unless specified to the contrary, the reactions described herein take place at atmospheric pressure, generally within a temperature range from −10° C. to 200° C. Further, except as otherwise specified, reaction times and conditions are intended to be approximate, e.g. taking place at about atmospheric pressure within a temperature range of about −10° C. to about 110° C. over a period of about 1 to about 24 hours; reactions left to run overnight average a period of about 16 hours.

In general, compounds of the disclosure may be prepared by the following reaction schemes:

Scheme 1

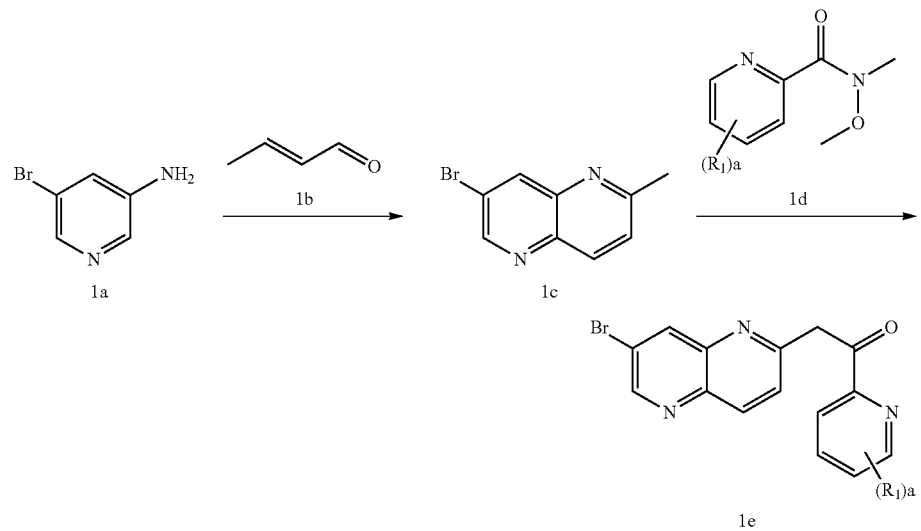

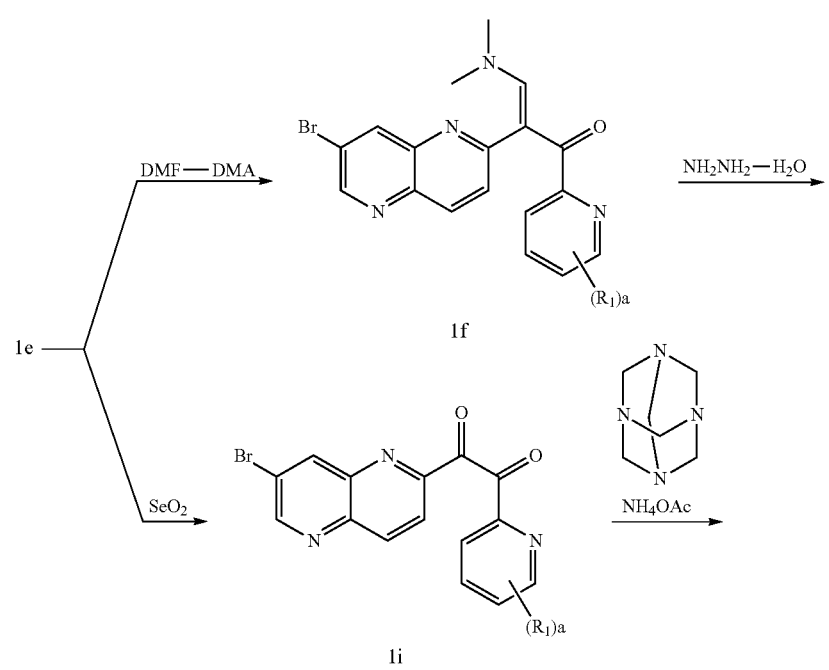

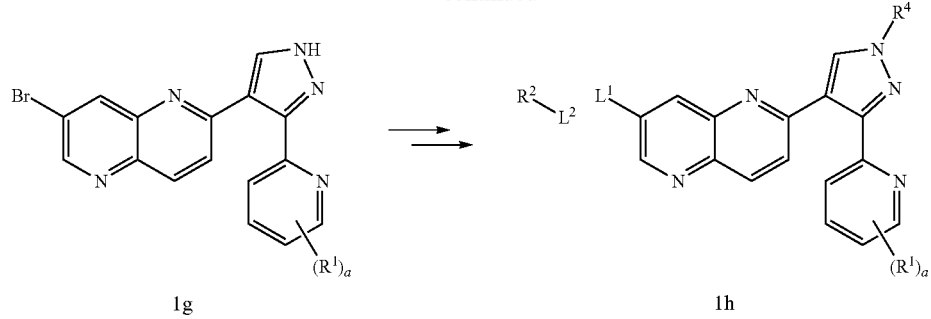

1g → 1h

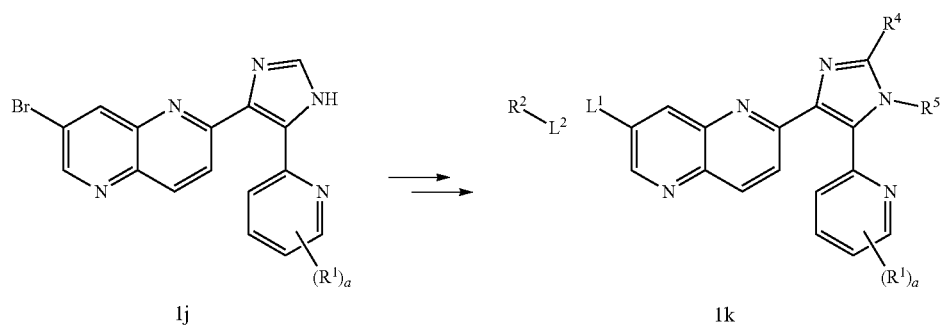

1j → 1k

In some embodiments, a compound of Formula 1h or Formula 1k may be prepared according to Scheme 1. For example, 3-aminopyridine 1a can be reacted with butenal 1b in the presence of a suitable acid to provide napthyridine 1c. Coupling of an unsubstituted or R¹-substituted N-methoxy-N-methylpicolinamide may proceed to give ethanone 1e. To convert 1e to a pyrazole, 1e may first be reacted with DMF.DMA at elevated temperatures to give intermediate 1f, which can be reacted with hydrazine monohydrate to provide pyrazole 1g. Optionally, 1g may be subjected to one or more coupling reactions, and optionally one or more protecting group manipulations, to provide a pyrazole of Formula 1h. Alternatively, oxidation of 1e can provide dione 1i, which can be converted to imidazole 1j in the presence of urotropine and ammonium acetate. Optionally, 1j may be subjected to one or more coupling reactions, and optionally one or more protecting group manipulations, to provide an imidazole of Formula 1k.

Scheme 2

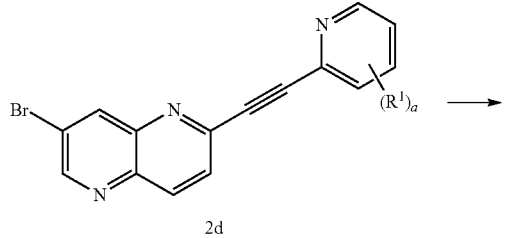

2d

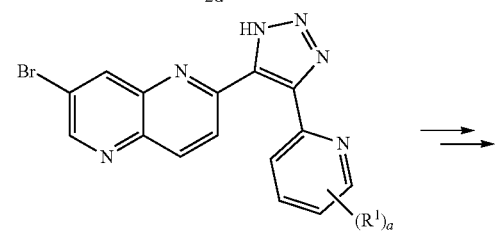

2e

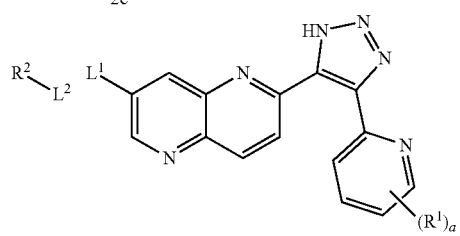

2f

In some embodiments, a compound of Formula 2f may be prepared according to Scheme 2. For example, napthyridine 1c can be oxidized to provide aldehyde 2a. The aldehyde can undergo a Seyferth-Gilbert homologation, optionally using Bestmann-Ohira reagent, to provide alkyne 2b. Cross-coupling of 2b with an unsubstituted or IV-substituted iodopyridine (2c) via a Sonogashira reaction provides alkyne 2d, which can be converted to triazole 2e in the presence of a suitable azide, such as TMS-$N_3$. Optionally, 2e may be subjected to one or more coupling reactions, and optionally one or more protecting group manipulations, to provide a triazole of Formula 2f.

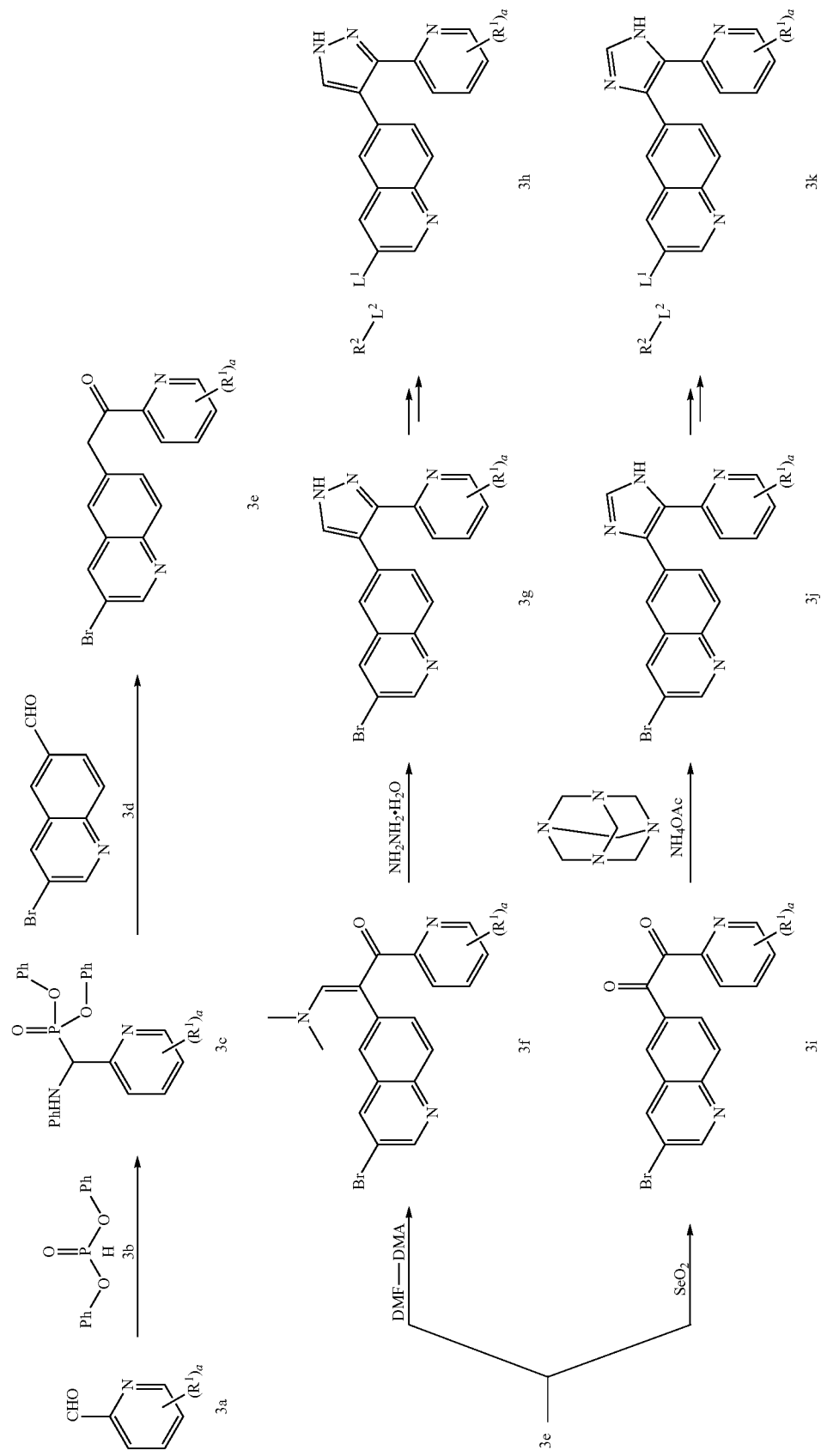

In some embodiments, a compound of Formula 3h or Formula 3k may be prepared according to Scheme 3. For example, unsubstituted or R¹-substituted picolinaldehyde (3a) can be reacted with phosphonate 3b in the presence of PhNH₂ to provide 3c, which can be coupled to aldehyde 3d to give ethanone 3e. From 3e, the same general procedure outlined in Scheme 1 may be followed to provide a pyrazole of Formula 3h or an imidazole of Formula 3k.

Scheme 4

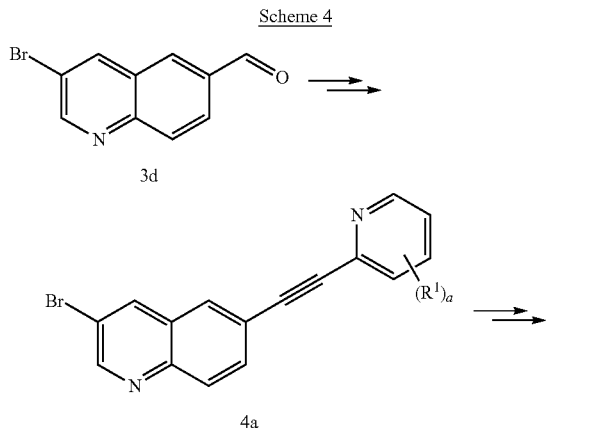

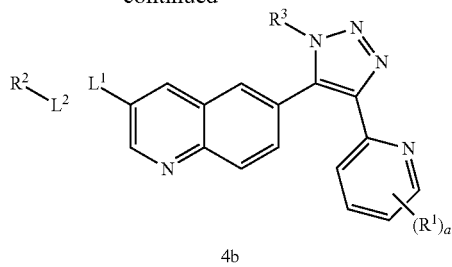

4b

In some embodiments, a compound of Formula 4b may be prepared according to Scheme 4. For example, following the same general procedure outlined in Scheme 2, quinoline 3d can be subjected to a Seyferth-Gilbert homologation and coupled to a suitable pyridine via a Sonogashira reaction to provide alkyne 4a. Following cyclization to the triazole, one or more optional coupling reactions and optionally one or more protecting group manipulations may provide a triazole of Formula 4b.

Scheme 5

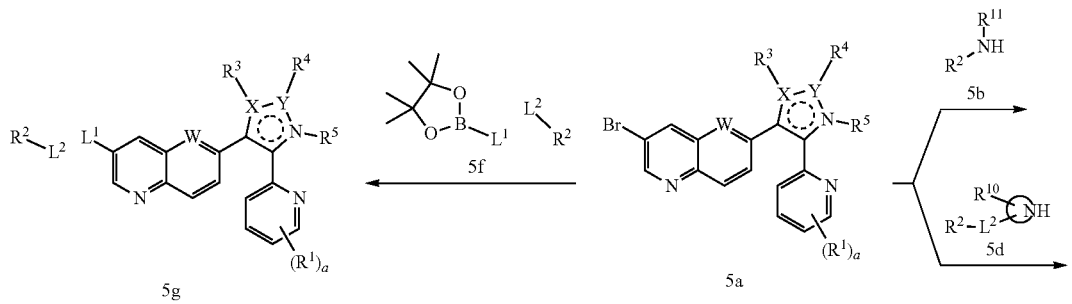

In some embodiments, a compound of Formula 5c, Formula 5e or Formula 5g may be prepared according to Scheme 5. For example, heteroaryl bromide 5a can be subjected to a C—N coupling reaction—optionally a Pd-catalyzed coupling reaction such as a Buchwald-Hartwig amination—with an acyclic primary or secondary amine (5b) or a cyclic secondary amine (5d) to provide a heteroaryl amine of Formula 5c or Formula 5e, respectively. Alternatively, installation of a desired -L$^1$L$^2$R$^2$ substituent may proceed via a Suzuki reaction to give a compound of Formula 5g.

In some embodiments, a compound of the present disclosure, for example, a compound of a formula given in Table 1, is synthesized according to one of the general routes outlined in Schemes 1-5, Examples 1-69, or by methods generally known in the art. In some embodiments, exemplary compounds may include, but are not limited to, a compound or salt thereof selected from Table 1.

TABLE 1

| No. | Structure | Chemical Name | [M + H]$^+$ |
|---|---|---|---|
| 1 | 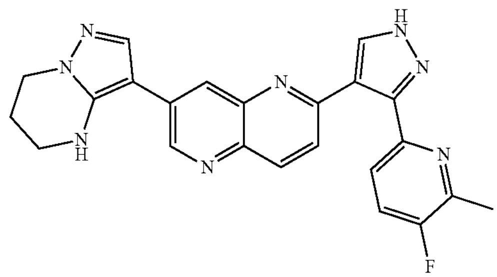 | 2-[3-(5-fluoro-6-methyl-2-pyridyl)-1H-pyrazol-4-yl]-7-(4,5,6,7-tetrahydropyrazolo[1,5-a]pyrimidin-3-yl)-1,5-naphthyridine | 427.2 |
| 2 | 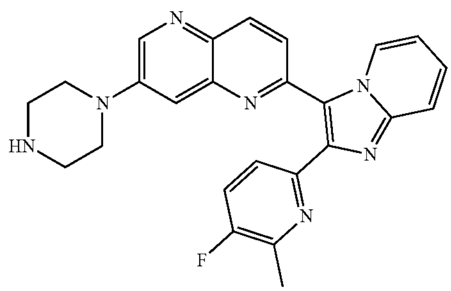 [SMILES: Cc1nc(-c2nc3ccccn3c2-c2ccc3ncc(N4CCNCC4)cc3n2)ccc1F] | 2-[2-(5-fluoro-6-methyl-2-pyridyl)imidazo[1,2-a]pyridin-3-yl]-7-piperazin-1-yl-1,5-naphthyridine | 440.1 |
| 3 | 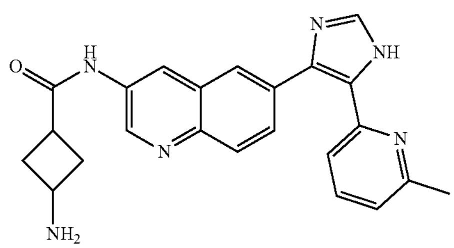 [SMILES: Cc1cccc(-c2[nH]cnc2-c2ccc3ncc(NC(=O)C4CC(N)C4)cc3c2)n1] | 3-amino-N-[6-[5-(6-methyl-2-pyridyl)-1H-imidazol-4-yl]-3-quinolyl]cyclobutanecarboxamide | 399.2 |
| 4 | 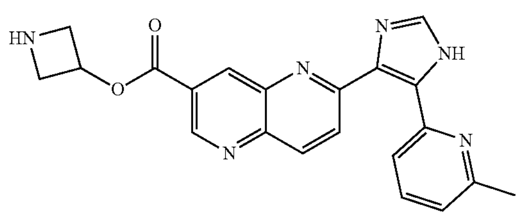 [SMILES: Cc1cccc(-c2[nH]cnc2-c2ccc3ncc(C(=O)OC4CNC4)cc3n2)n1] | azetidin-3-yl 6-[5-(6-methyl-2-pyridyl)-1H-pyrazol-4-yl]-1,5-naphthyridine-3-carboxylate | 387.0 |
| 5 | 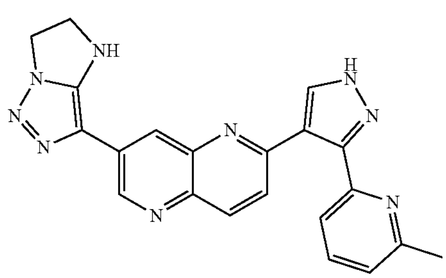 [SMILES: Cc1cccc(-c2n[nH]cc2-c2ccc3ncc(-c4nnn5c4NCC5)cc3n2)n1] | 7-(5,6-dihydro-4H-imidazo[1,2-c]triazol-3-yl)-2-[3-(6-methyl-2-pyridyl)-1H-pyrazol-4-yl]-1,5-naphthyridine | 396.1 |

TABLE 1-continued

| No. | Structure | Chemical Name | [M + H]+ |
|---|---|---|---|
| 6 | 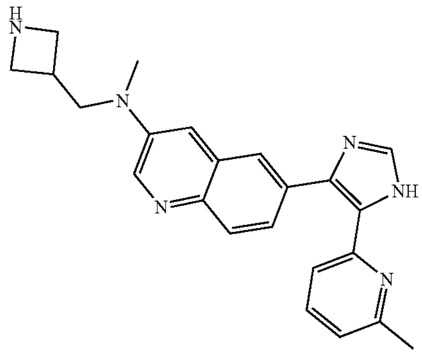 [SMILES: Cc1cccc(-c2[nH]cnc2-c2ccc3ncc(N(C)CC4CNC4)cc3c2)n1] | N-(azetidin-3-ylmethyl)-N-methyl-6-[5-(6-methyl-2-pyridyl)-1H-imidazol-4-yl]quinolin-3-amine | 385.1 |
| 7 | 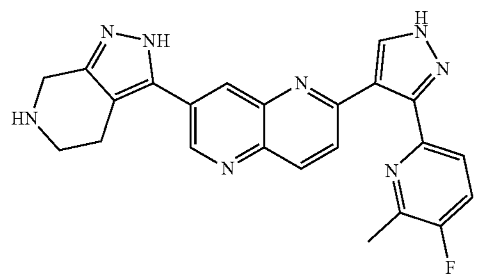 [SMILES: Cc1nc(-c2n[nH]cc2-c2ccc3ncc(-c4[nH]nc5c4CCNC5)cc3n2)ccc1F] | 2-[3-(5-fluoro-6-methyl-2-pyridyl)-1H-pyrazol-4-yl]-7-(4,5,6,7-tetrahydro-2H-pyrazolo[3,4-c]pyridin-3-yl)-1,5-naphthyridine | 427.1 |
| 8 | 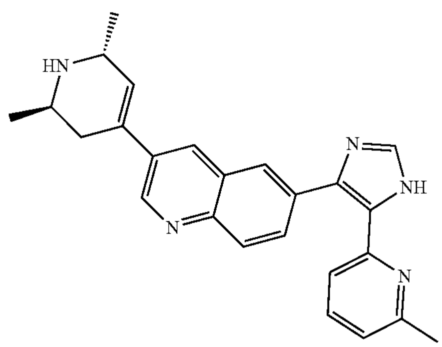 | 3-[(2R,6R)-2,6-dimethyl-1,2,3,6-tetrahydropyridin-4-yl]-6-[5-(6-methyl-2-pyridyl)-1H-imidazol-4-yl]quinoline | 396.0 |
| 9 | 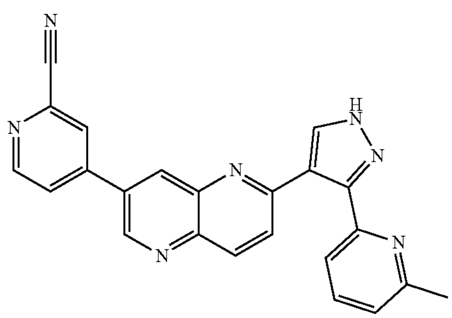 [SMILES: Cc1cccc(-c2n[nH]cc2-c2ccc3ncc(-c4ccnc(C#N)c4)cc3n2)n1] | 4-[6-[3-(6-methyl-2-pyridyl)-1H-pyrazol-4-yl]-1,5-naphthyridin-3-yl]pyridine-2-carbonitrile | 390.2 |
| 10 | 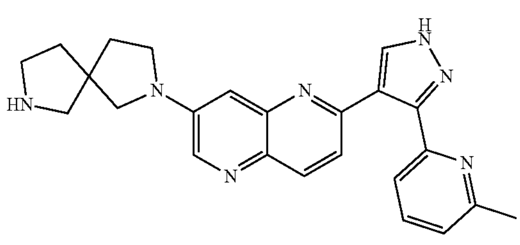 [SMILES: Cc1cccc(-c2n[nH]cc2-c2ccc3ncc(N4CCC5(CCNC5)C4)cc3n2)n1] | 7-(2,7-diazaspiro[4.4]nonan-2-yl)-2-[3-(6-methyl-2-pyridyl)-1H-pyrazol-4-yl]-1,5-naphthyridine | 412.1 |

TABLE 1-continued

| No. | Structure | Chemical Name | [M + H]+ |
|---|---|---|---|
| 11 | 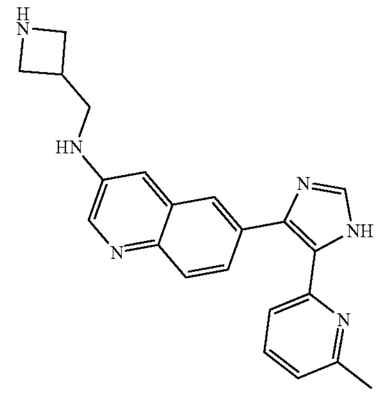 [SMILES: Cc1cccc(-c2[nH]cnc2-c2ccc3ncc(NCC4CNC4)cc3c2)n1] | N-(azetidin-3-ylmethyl)-6-[5-(6-methyl-2-pyridyl)-1H-imidazol-4-yl]quinolin-3-amine | 371.1 |
| 12 | 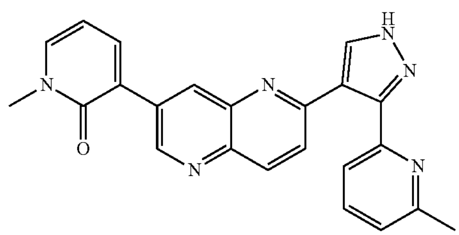 | 1-methyl-3-[6-[3-(6-methyl-2-pyridyl)-1H-pyrazol-4-yl]-1,5-naphthyridin-3-yl]pyridin-2-one | 395.4 |
| 13 | 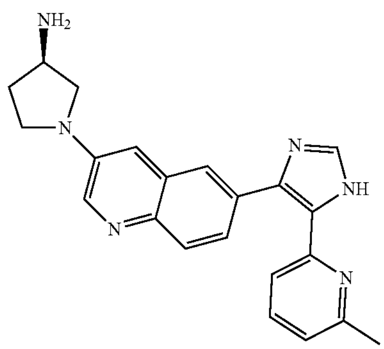 [SMILES: Cc1cccc(-c2[nH]cnc2-c2ccc3ncc(N4CC[C@@H](N)C4)cc3c2)n1] | (3R)-1-[6-[5-(6-methyl-2-pyridyl)-1H-imidazol-4-yl]-3-quinolyl]pyrrolidin-3-amine | 371.1 |
| 14 | 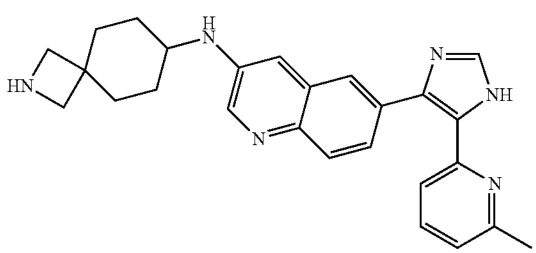 [SMILES: Cc1cccc(-c2[nH]cnc2-c2ccc3ncc(NC4CCC5(CC4)CNC5)cc3c2)n1] | N-(2-azaspiro[3.5]nonan-7-yl)-6-[5-(6-methyl-2-pyridyl)-1H-imidazol-4-yl]quinolin-3-amine | 425.1 |
| 15 | 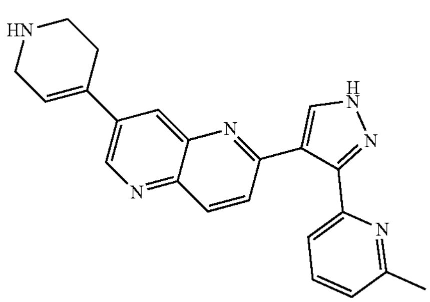 [SMILES: Cc1cccc(-c2n[nH]cc2-c2ccc3ncc(C4=CCNCC4)cc3n2)n1] | 2-[3-(6-methyl-2-pyridyl)-1H-pyrazol-4-yl]-7-(1,2,3,6-tetrahydropyridin-4-yl)-1,5-naphthyridine | 269.2 |

TABLE 1-continued

| No. | Structure | Chemical Name | [M + H]⁺ |
|---|---|---|---|
| 16 | 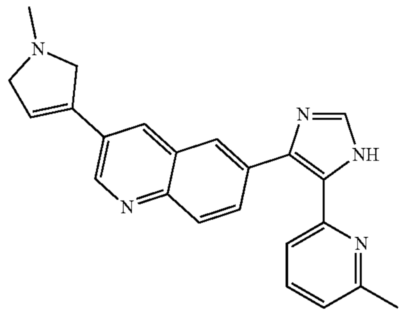 [SMILES: Cc1cccc(-c2[nH]cnc2-c2ccc3ncc(C4=CCN(C)C4)cc3c2)n1] | 3-(1-methyl-2,5-dihydropyrrol-3-yl)-6-[5-(6-methyl-2-pyridyl)-1H-imidazol-4-yl]quinoline | 368.2 |
| 17 | 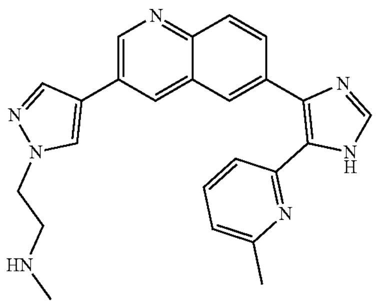 [SMILES: CNCCn1cc(-c2cnc3ccc(-c4nc[nH]c4-c4cccc(C)n4)cc3c2)cn1] | N-methyl-2-[4-[6-[5-(6-methyl-2-pyridyl)-1H-imidazol-4-yl]-3-quinolyl]pyrazol-1-yl]ethanamine | 410.2 |
| 18 | 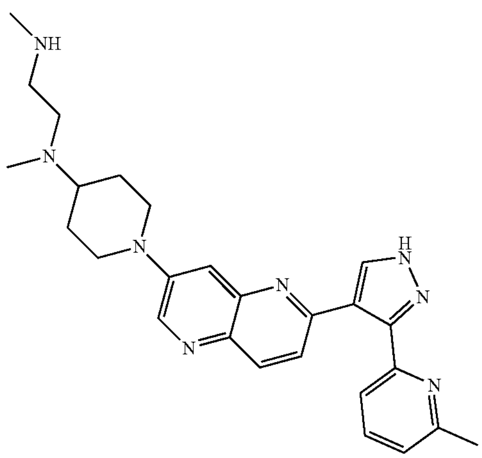 | N,N'-dimethyl-N'-[1-[6-[3-(6-methyl-2-pyridyl)-1H-pyrazol-4-yl]-1,5-naphthyridin-3-yl]-4-piperidyl]ethane-1,2-diamine | 457.2 |
| 19 | AND Enantiomer | 2-[3-(6-methyl-2-pyridyl)-1H-pyrazol-4-yl]-7-[rac-(3S)-3,4-dimethyl-1,4-diazepan-1-yl]-1,5-naphthyridine | 414.2 |

TABLE 1-continued

| No. | Structure | Chemical Name | [M + H]⁺ |
|---|---|---|---|
| 20 | 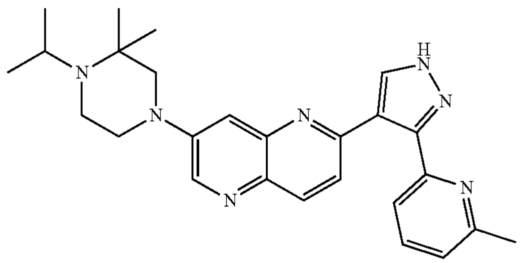 [SMILES: Cc1cccc(-c2n[nH]cc2-c2ccc3ncc(N4CCN(C(C)C)C(C)(C)C4)cc3n2)n1] | 7-(4-isopropyl-3,3-dimethyl-piperazin-1-yl)-2-[3-(6-methyl-2-pyridyl)-1H-pyrazol-4-yl]-1,5-naphthyridine | 442.2 |
| 21 | 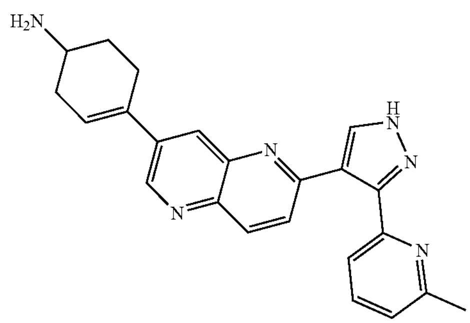 [SMILES: Cc1cccc(-c2n[nH]cc2-c2ccc3ncc(C4=CCC(N)CC4)cc3n2)n1] | 4-[6-[3-(6-methyl-2-pyridyl)-1H-pyrazol-4-yl]-1,5-naphthyridin-3-yl]cyclohex-3-en-1-amine | 383.2 |
| 22 | 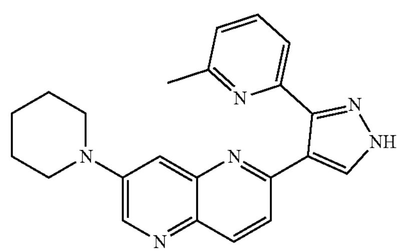 [SMILES: Cc1cccc(-c2n[nH]cc2-c2ccc3ncc(N4CCCCC4)cc3n2)n1] | 2-[3-(6-methyl-2-pyridyl)-1H-pyrazol-4-yl]-7-(1-piperidyl)-1,5-naphthyridine | 371.1 |
| 23 | 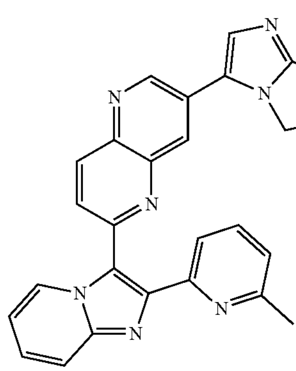 | 7-(6,7-dihydro-5H-imidazo[1,2-a]imidazol-3-yl)-2-[2-(6-methyl-2-pyridyl)imidazo[1,2-a]pyridin-3-yl]-1,5-naphthyridine | 445.2 |
| 24 | 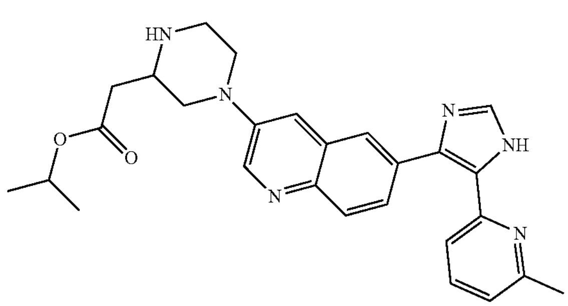 [SMILES: Cc1cccc(-c2[nH]cnc2-c2ccc3ncc(N4CCNC(CC(=O)OC(C)C)C4)cc3c2)n1] | isopropyl 2-[4-[6-[5-(6-methyl-2-pyridyl)-1H-imidazol-4-yl]-3-quinolyl]piperazin-2-yl]acetate | 471.2 |

TABLE 1-continued

| No. | Structure | Chemical Name | [M + H]+ |
|---|---|---|---|
| 25 | AND Entaniomer | rac-(3S)-N,N-dimethyl-1-[6-[3-methyl-5-(6-methyl-2-pyridyl)triazol-4-yl]-3-quinolyl]pyrrolidin-3-amine | 414.2 |
| 26 | 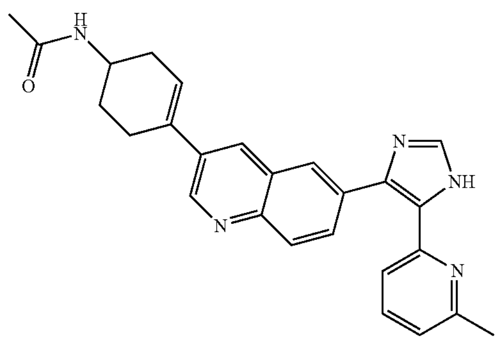 [SMILES: CC(=O)NC1CC=C(c2cnc3ccc(-c4nc[nH]c4-c4cccc(C)n4)cc3c2)CC1] | N-[4-[6-[5-(6-methyl-2-pyridyl)-1H-imidazol-4-yl]-3-quinolyl]cyclohex-3-en-1-yl]acetamide | 423.9 |
| 27 | 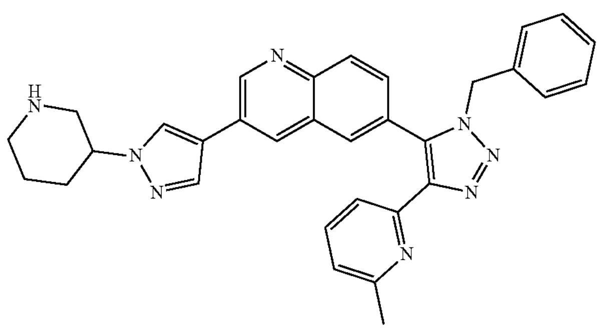 [SMILES: Cc1cccc(-c2nnn(Cc3ccccc3)c2-c2ccc3ncc(-c4cnn(C5CCCNC5)c4)cc3c2)n1] | 6-[3-benzyl-5-(6-methyl-2-pyridyl)triazol-4-yl]-3-[1-(3-piperidyl)pyrazol-4-yl]quinoline | 527.2 |
| 28 | 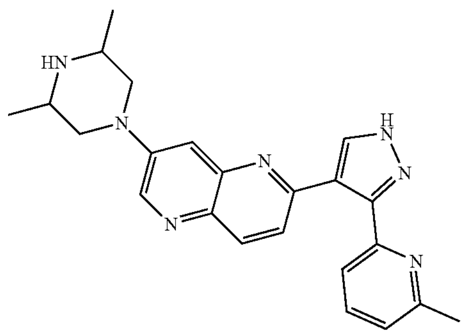 | 7-(3,5-dimethylpiperazin-1-yl)-2-[3-(6-methyl-2-pyridyl)-1H-pyrazol-4-yl]-1,5-naphthyridine | 400.2 |

TABLE 1-continued

| No. | Structure | Chemical Name | [M + H]⁺ |
|---|---|---|---|
| 29 | 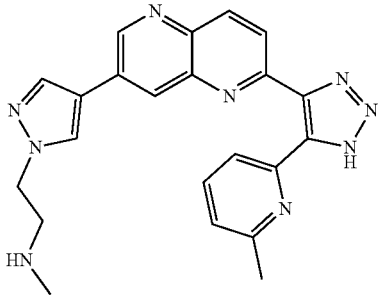 [SMILES: CNCCn1cc(-c2cnc3ccc(-c4nn[nH]c4-c4cccc(C)n4)nc3c2)cn1] | N-methyl-2-[4-[6-[5-(6-methyl-2-pyridyl)-1H-triazol-4-yl]-1,5-naphthyridin-3-yl]pyrazol-1-yl]ethanamine | 412.1 |
| 30 | 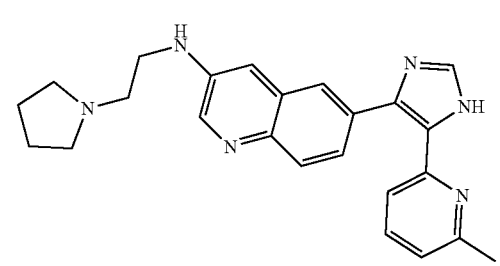 [SMILES: Cc1cccc(-c2[nH]cnc2-c2ccc3ncc(NCCN4CCCC4)cc3c2)n1] | 6-[5-(6-methyl-2-pyridyl)-1H-imidazol-4-yl]-N-(2-pyrrolidin-1-ylethyl)quinolin-3-amine | 399.2 |
| 31 | 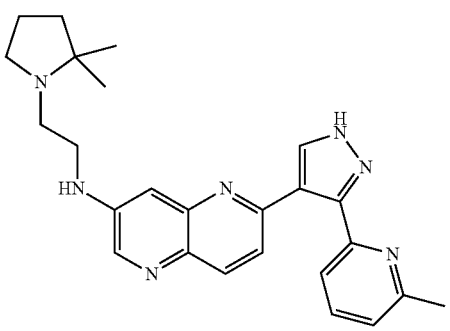 [SMILES: Cc1cccc(-c2n[nH]cc2-c2ccc3ncc(NCCN4CCCC4(C)C)cc3n2)n1] | N-[2-(2,2-dimethylpyrrolidin-1-yl)ethyl]-6-[3-(6-methyl-2-pyridyl)-1H-pyrazol-4-yl]-1,5-naphthyridin-3-amine | 428.2 |
| 32 | 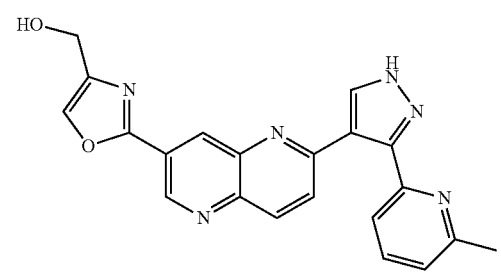 [SMILES: Cc1cccc(-c2n[nH]cc2-c2ccc3ncc(-c4nc(CO)co4)cc3n2)n1] | [2-[6-[3-(6-methyl-2-pyridyl)-1H-pyrazol-4-yl]-1,5-naphthyridin-3-yl]oxazol-4-yl]methanol | 385.1 |
| 33 | 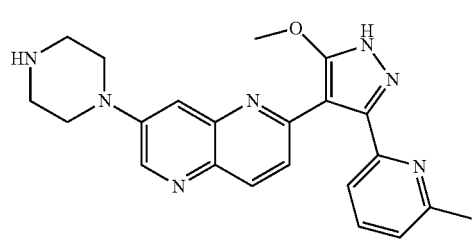 [SMILES: COc1[nH]nc(-c2cccc(C)n2)c1-c1ccc2ncc(N3CCNCC3)cc2n1] | 2-[5-methoxy-3-(6-methyl-2-pyridyl)-1H-pyrazol-4-yl]-7-piperazin-1-yl-1,5-naphthyridine | 402.1 |

TABLE 1-continued

| No. | Structure | Chemical Name | [M + H]+ |
|---|---|---|---|
| 34 | 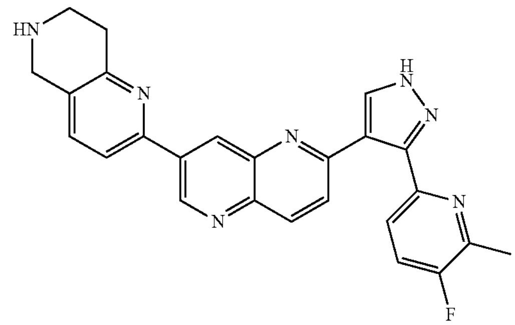 [SMILES: Cc1nc(-c2n[nH]cc2-c2ccc3ncc(-c4ccc5c(n4)CCNC5)cc3n2)ccc1F] | 2-[3-(5-fluoro-6-methyl-2-pyridyl)-1H-pyrazol-4-yl]-7-(5,6,7,8-tetrahydro-1,6-naphthyridin-2-yl)-1,5-naphthyridine | 438.0 |
| 35 | 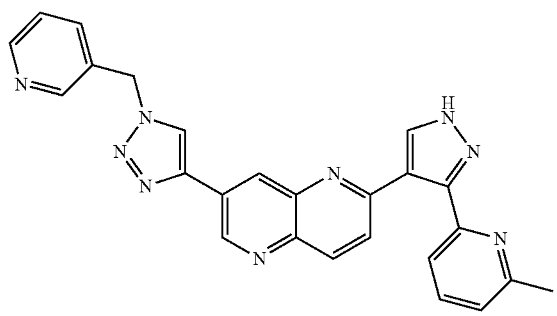 [SMILES: Cc1cccc(-c2n[nH]cc2-c2ccc3ncc(-c4cn(Cc5cccnc5)nn4)cc3n2)n1] | 2-[3-(6-methyl-2-pyridyl)-1H-pyrazol-4-yl]-7-[1-(3-pyridylmethyl)triazol-4-yl]-1,5-naphthyridine | 446.1 |
| 36 | 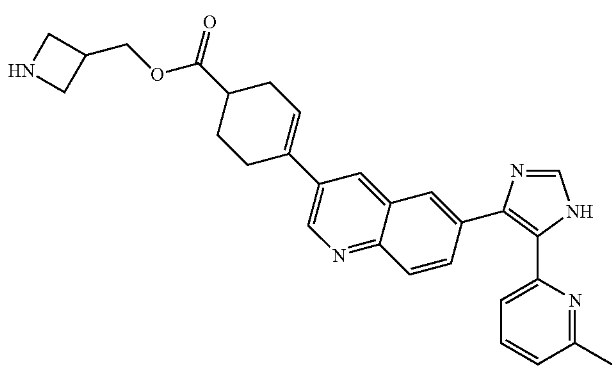 [SMILES: Cc1cccc(-c2[nH]cnc2-c2ccc3ncc(C4=CCC(C(=O)OCC5CNC5)CC4)cc3c2)n1] | azetidin-3-ylmethyl 4-[6-[5-(6-methyl-2-pyridyl)-1H-imidazol-4-yl]-3-quinolyl]cyclohex-3-ene-1-carboxylate | 480.1 |
| 37 | 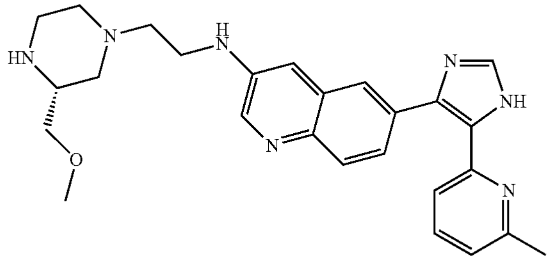 [SMILES: COC[C@H]1CN(CCNc2cnc3ccc(-c4nc[nH]c4-c4cccc(C)n4)cc3c2)CCN1] | N-[2-[(3R)-3-(methoxymethyl)piperazin-1-yl]ethyl]-6-[5-(6-methyl-2-pyridyl)-1H-imidazol-4-yl]quinolin-3-amine | 458.2 |
| 38 | 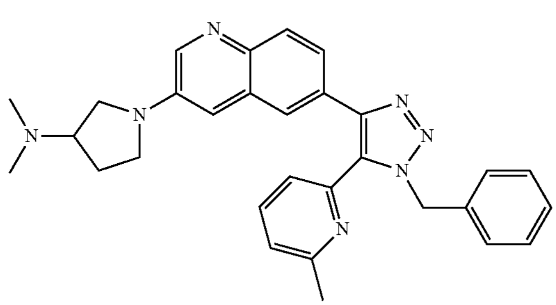 [SMILES: Cc1cccc(-c2c(-c3ccc4ncc(N5CCC(N(C)C)C5)cc4c3)nnn2Cc2ccccc2)n1] | 1-[6-[1-benzyl-5-(6-methyl-2-pyridyl)triazol-4-yl]-3-quinolyl]-N,N-dimethyl-pyrrolidin-3-amine | 490.3 |

TABLE 1-continued

| No. | Chemical Name | [M + H]+ |
|---|---|---|
| 39 | 2-[3-(5-fluoro-6-methyl-2-pyridyl)-1H-pyrazol-4-yl]-7-(5,6,7,8-tetrahydroimidazo[1,5-a]pyrazin-3-yl)-1,5-naphthyridine | 427.2 |
| 40 | 2-[3-(6-methyl-2-pyridyl)-1H-pyrazol-4-yl]-7-(5,6,7,8-tetrahydro-[1,2,4]triazolo[4,3-a]pyrazin-3-yl)-1,5-naphthyridine | 410.2 |
| 41 | [(3R)-pyrrolidin-3-yl] 1-[6-[5-(6-methyl-2-pyridyl)-1H-imidazol-4-yl]-3-quinolyl]piperidine-4-carboxylate | 483.2 |
| 42 | 7-bromo-2-[5-methoxy-3-(6-methyl-2-pyridyl)-1H-pyrazol-4-yl]-1,5-naphthyridine | 396.1 |
| 43 | 6-[3-(5-fluoro-6-methyl-2-pyridyl)-1H-pyrazol-4-yl]-N-[2-(4-isopropylpiperazin-1-yl)ethyl]-1,5-naphthyridin-3-amine | 475.2 |

TABLE 1-continued

| No. | Structure | Chemical Name | [M + H]+ |
|---|---|---|---|
| 44 | 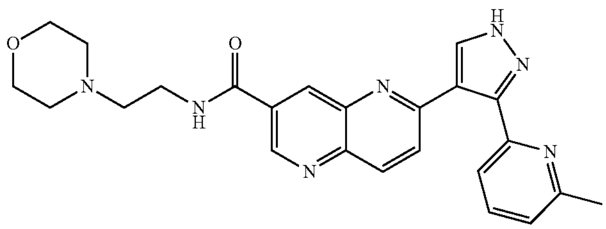 [SMILES: Cc1cccc(-c2n[nH]cc2-c2ccc3ncc(C(=O)NCCN4CCOCC4)cc3n2)n1] | 6-[3-(6-methyl-2-pyridyl)-1H-pyrazol-4-yl]-N-(2-morpholinoethyl)-1,5-naphthyridine-3-carboxamide | 444.2 |
| 45 | 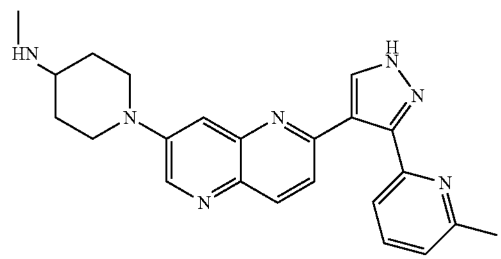 [SMILES: CNC1CCN(c2cnc3ccc(-c4c[nH]nc4-c4cccc(C)n4)nc3c2)CC1] | N-methyl-1-[6-[3-(6-methyl-2-pyridyl)-1H-pyrazol-4-yl]-1,5-naphthyridin-3-yl]piperidin-4-amine | 400.3 |
| 46 | 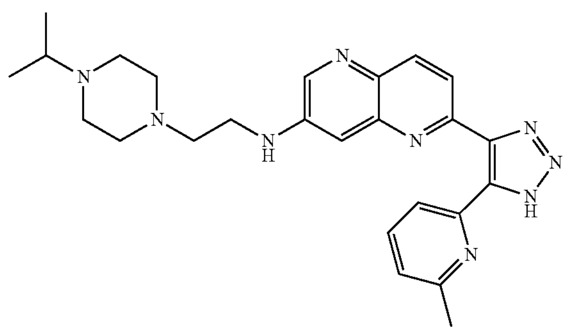 [SMILES: Cc1cccc(-c2[nH]nnc2-c2ccc3ncc(NCCN4CCN(C(C)C)CC4)cc3n2)n1] | N-[2-(4-isopropylpiperazin-1-yl)ethyl]-6-[5-(6-methyl-2-pyridyl)-1H-triazol-4-yl]-1,5-naphthyridin-3-amine | 458.3 |
| 47 | 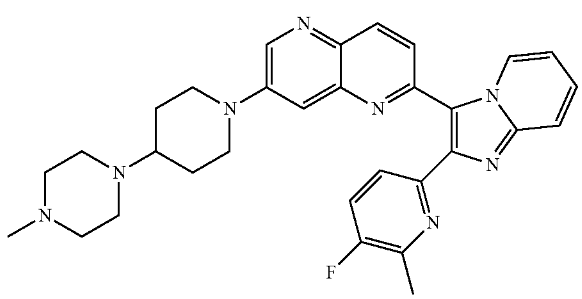 [SMILES: Cc1nc(-c2nc3ccccn3c2-c2ccc3ncc(N4CCC(N5CCN(C)CC5)CC4)cc3n2)ccc1F] | 2-[2-(5-fluoro-6-methyl-2-pyridyl)imidazo[1,2-a]pyridin-3-yl]-7-[4-(4-methylpiperazin-1-yl)-1-piperidyl]-1,5-naphthyridine | 537.1 |
| 48 | 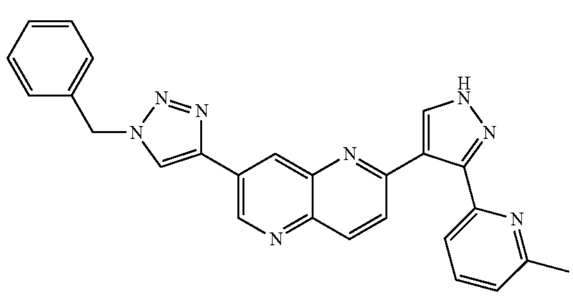 [SMILES: Cc1cccc(-c2n[nH]cc2-c2ccc3ncc(-c4cn(Cc5ccccc5)nn4)cc3n2)n1] | 7-(1-benzyltriazol-4-yl)-2-[3-(6-methyl-2-pyridyl)-1H-pyrazol-4-yl]-1,5-naphthyridine | 445.2 |

TABLE 1-continued

| No. | Structure | Chemical Name | [M + H]+ |
|---|---|---|---|
| 49 | 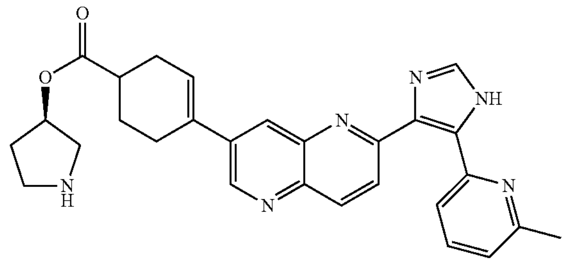 [SMILES: Cc1cccc(-c2[nH]cnc2-c2ccc3ncc(C4=CCC(C(=O)O[C@@H]5CCNC5)CC4)cc3n2)n1] | [(3R)-pyrrolidin-3-yl] 4-[6-[5-(6-methyl-2-pyridyl)-1H-imidazol-4-yl]-3-quinolyl]cyclohex-3-ene-1-carboxylate | 480.0 |
| 50 | 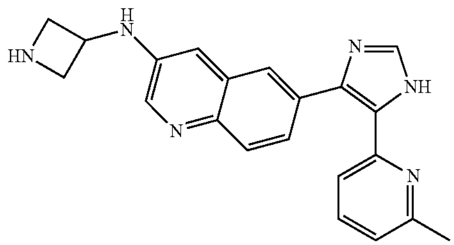 [SMILES: Cc1cccc(-c2[nH]cnc2-c2ccc3ncc(NC4CNC4)cc3c2)n1] | N-(azetidin-3-yl)-6-[5-(6-methyl-2-pyridyl)-1H-imidazol-4-yl]quinolin-3-amine | 357.1 |
| 51 | 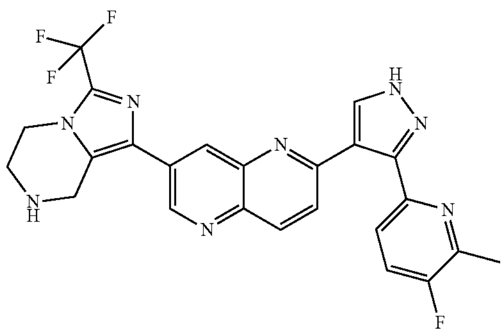 [SMILES: Cc1nc(-c2n[nH]cc2-c2ccc3ncc(-c4nc(C(F)(F)F)n5c4CNCC5)cc3n2)ccc1F] | 2-[3-(5-fluoro-6-methyl-2-pyridyl)-1H-pyrazol-4-yl]-7-[3-(trifluoromethyl)-5,6,7,8-tetrahydroimidazo[1,5-a]pyrazin-1-yl]-1,5-naphthyridine | 495.1 |
| 52 | 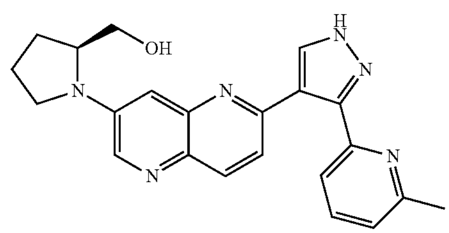 [SMILES: Cc1cccc(-c2n[nH]cc2-c2ccc3ncc(N4CCC[C@H]4CO)cc3n2)n1] | [(2S)-1-[6-[3-(6-methyl-2-pyridyl)-1H-pyrazol-4-yl]-1,5-naphthyridin-3-yl]pyrrolidin-2-yl]methanol | 387.1 |
| 53 | 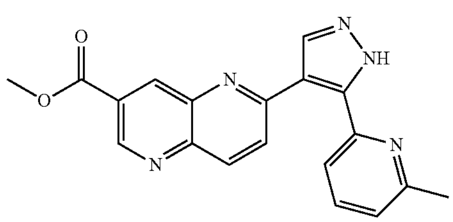 | methyl 6-[5-(6-methyl-2-pyridyl)-1H-pyrazol-4-yl]-1,5-naphthyridine-3-carboxylate | 345.9 |
| 54 | 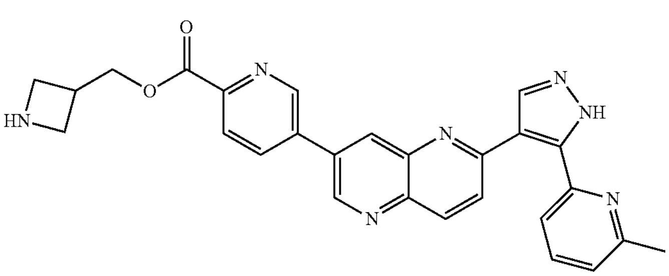 [SMILES: Cc1cccc(-c2[nH]ncc2-c2ccc3ncc(-c4ccc(C(=O)OCC5CNC5)nc4)cc3n2)n1] | azetidin-3-ylmethyl 5-[6-[5-(6-methyl-2-pyridyl)-1H-imidazol-4-yl]-3-quinolyl]pyridine-2-carboxylate | 477.1 |

TABLE 1-continued

| No. | Structure | Chemical Name | [M + H]+ |
|---|---|---|---|
| 55 | 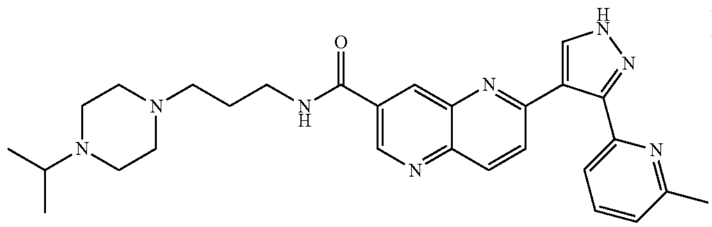 [SMILES: Cc1cccc(-c2n[nH]cc2-c2ccc3ncc(C(=O)NCCCN4CCN(C(C)C)CC4)cc3n2)n1] | N-[3-(4-isopropylpiperazin-1-yl)propyl]-6-[3-(6-methyl-2-pyridyl)-1H-pyrazol-4-yl]-1,5-naphthyridine-3-carboxamide | 499.2 |
| 56 | 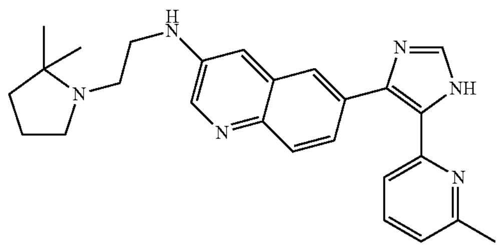 [SMILES: Cc1cccc(-c2[nH]cnc2-c2ccc3ncc(NCCN4CCCC4(C)C)cc3c2)n1] | N-[2-(2,2-dimethylpyrrolidin-1-yl)ethyl]-6-[5-(6-methyl-2-pyridyl)-1H-imidazol-4-yl]quinolin-3-amine | 427.1 |
| 57 | 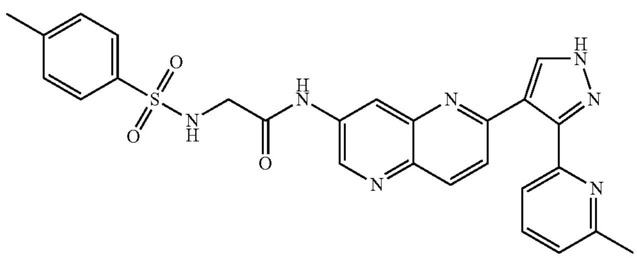 | N-[6-[3-(6-methyl-2-pyridyl)-1H-pyrazol-4-yl]-1,5-naphthyridin-3-yl]-2-(p-tolylsulfonylamino)acetamide | 513.7 |
| 58 | 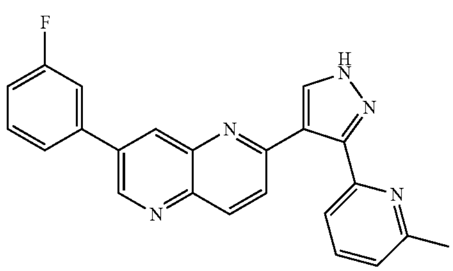 [SMILES: Cc1cccc(-c2n[nH]cc2-c2ccc3ncc(-c4cccc(F)c4)cc3n2)n1] | 7-(3-fluorophenyl)-2-[3-(6-methyl-2-pyridyl)-1H-pyrazol-4-yl]-1,5-naphthyridine | 382.0 |
| 59 | 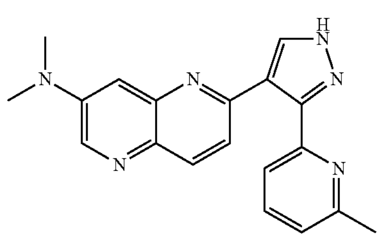 | N,N-dimethyl-6-[3-(6-methyl-2-pyridyl)-1H-pyrazol-4-yl]-1,5-naphthyridin-3-amine | 331.1 |
| 60 | 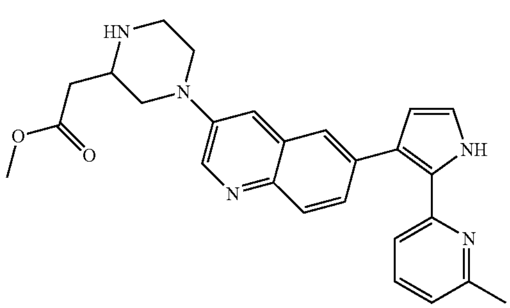 | methyl 2-[4-[6-[5-(6-methyl-2-pyridyl)-1H-imidazol-4-yl]-3-quinolyl]piperazin-2-yl]acetate | 443.1 |

TABLE 1-continued

| No. | Structure | Chemical Name | [M + H]+ |
|---|---|---|---|
| 61 | 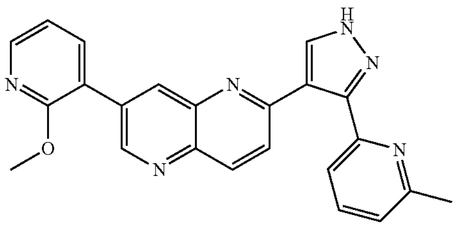 [SMILES: COc1ncccc1-c1cnc2ccc(-c3c[nH]nc3-c3cccc(C)n3)nc2c1] | 7-(2-methoxy-3-pyridyl)-2-[3-(6-methyl-2-pyridyl)-1H-pyrazol-4-yl]-1,5-naphthyridine | 395.0 |
| 62 | 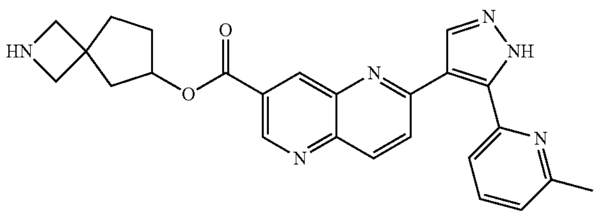 [SMILES: Cc1cccc(-c2[nH]ncc2-c2ccc3ncc(C(=O)OC4CCC5(CNC5)C4)cc3n2)n1] | 2-azaspiro[3.4]octan-6-yl 6-[5-(6-methyl-2-pyridyl)-1H-pyrazol-4-yl]-1,5-naphthyridine-3-carboxylate | 441.1 |
| 63 | 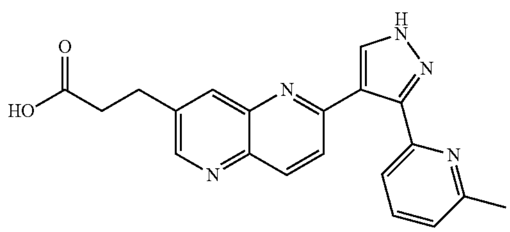 [SMILES: Cc1cccc(-c2n[nH]cc2-c2ccc3ncc(CCC(=O)O)cc3n2)n1] | 3-[6-[3-(6-methyl-2-pyridyl)-1H-pyrazol-4-yl]-1,5-naphthyridin-3-yl]propanoic acid | 360.2 |
| 64 | 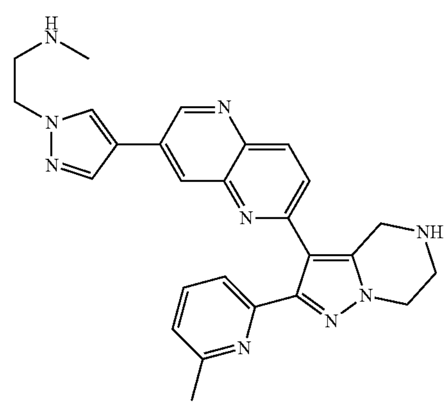 [SMILES: CNCCn1cc(-c2cnc3ccc(-c4c(-c5cccc(C)n5)nn5c4CNCC5)nc3c2)cn1] | N-methyl-2-[4-[6-[2-(6-methyl-2-pyridyl)-4,5,6,7-tetrahydropyrazolo[1,5-a]pyrazin-3-yl]-1,5-naphthyridin-3-yl]pyrazol-1-yl]ethanamine | 466.2 |
| 65 | 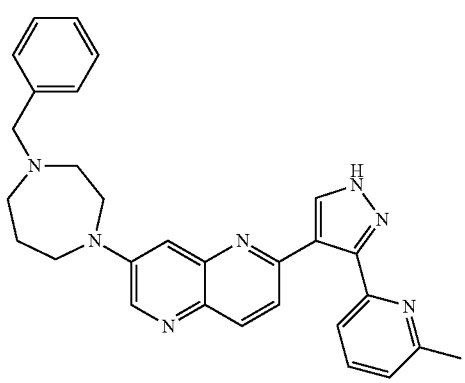 [SMILES: Cc1cccc(-c2n[nH]cc2-c2ccc3ncc(N4CCCN(Cc5ccccc5)CC4)cc3n2)n1] | 7-(4-benzyl-1,4-diazepan-1-yl)-2-[3-(6-methyl-2-pyridyl)-1H-pyrazol-4-yl]-1,5-naphthyridine | 476.2 |

TABLE 1-continued

| No. | Structure | Chemical Name | [M + H]+ |
|---|---|---|---|
| 66 | 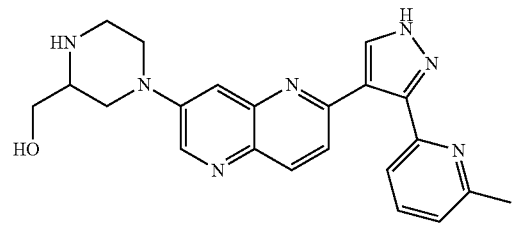 [SMILES: Cc1cccc(-c2n[nH]cc2-c2ccc3ncc(N4CCNC(CO)C4)cc3n2)n1] | [4-[6-[3-(6-methyl-2-pyridyl)-1H-pyrazol-4-yl]-1,5-naphthyridin-3-yl]piperazin-2-yl]methanol | 402.2 |
| 67 | 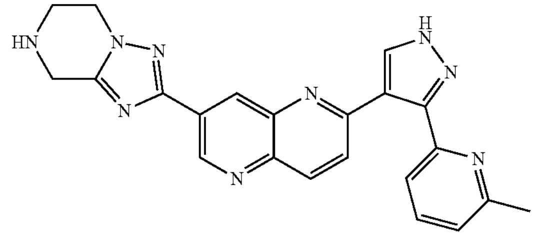 [SMILES: Cc1cccc(-c2n[nH]cc2-c2ccc3ncc(-c4nc5n(n4)CCNC5)cc3n2)n1] | 2-[3-(6-methyl-2-pyridyl)-1H-pyrazol-4-yl]-7-(5,6,7,8-tetrahydro-[1,2,4]triazolo[1,5-a]pyrazin-2-yl)-1,5-naphthyridine | 410.2 |
| 68 | 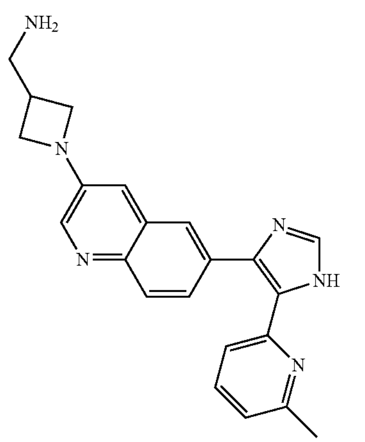 [SMILES: Cc1cccc(-c2[nH]cnc2-c2ccc3ncc(N4CC(CN)C4)cc3c2)n1] | [1-[6-[5-(6-methyl-2-pyridyl)-1H-imidazol-4-yl]-3-quinolyl]azetidin-3-yl]methanamine | 371.1 |
| 69 | 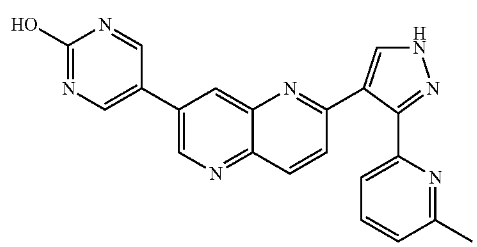 [SMILES: Cc1cccc(-c2n[nH]cc2-c2ccc3ncc(-c4cnc(O)nc4)cc3n2)n1] | 5-[6-[3-(6-methyl-2-pyridyl)-1H-pyrazol-4-yl]-1,5-naphthyridin-3-yl]pyrimidin-2-ol | 382.1 |
| 70 | 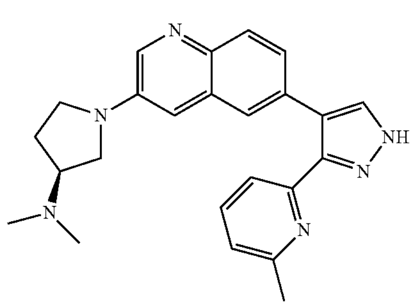 [SMILES: Cc1cccc(-c2n[nH]cc2-c2ccc3ncc(N4CC[C@H](N(C)C)C4)cc3c2)n1] | rac-(3S)-N,N-dimethyl-1-[6-[3-(6-methyl-2-pyridyl)-1H-pyrazol-4-yl]-3-quinolyl]pyrrolidin-3-amine | 399.3 |

TABLE 1-continued

| No. | Structure | Chemical Name | [M + H]+ |
|---|---|---|---|
| 71 | 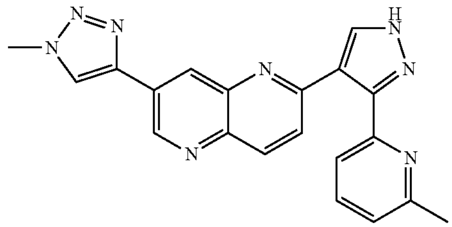 | 2-[3-(6-methyl-2-pyridyl)-1H-pyrazol-4-yl]-7-(1-methyltriazol-4-yl)-1,5-naphthyridine | 369.1 |
| 72 | 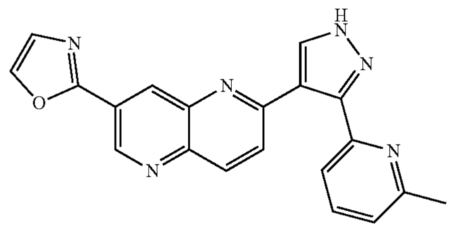 [SMILES: Cc1cccc(-c2n[nH]cc2-c2ccc3ncc(-c4ncco4)cc3n2)n1] | 2-[6-[3-(6-methyl-2-pyridyl)-1H-pyrazol-4-yl]-1,5-naphthyridin-3-yl]oxazole | 355.2 |
| 73 | 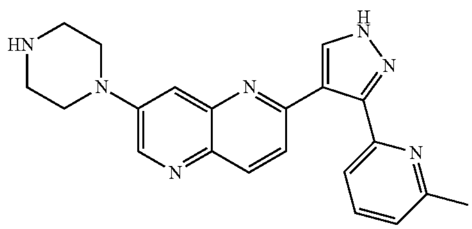 [SMILES: Cc1cccc(-c2n[nH]cc2-c2ccc3ncc(N4CCNCC4)cc3n2)n1] | 2-[3-(6-methyl-2-pyridyl)-1H-pyrazol-4-yl]-7-piperazin-1-yl-1,5-naphthyridine | 372.4 |
| 74 | 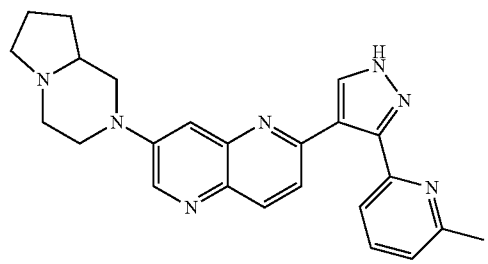 [SMILES: Cc1cccc(-c2n[nH]cc2-c2ccc3ncc(N4CCN5CCCC5C4)cc3n2)n1] | 7-(3,4,6,7,8,8a-hexahydro-1H-pyrrolo[1,2-a]pyrazin-2-yl)-2-[3-(6-methyl-2-pyridyl)-1H-pyrazol-4-yl]-1,5-naphthyridine | 412.2 |
| 75 | 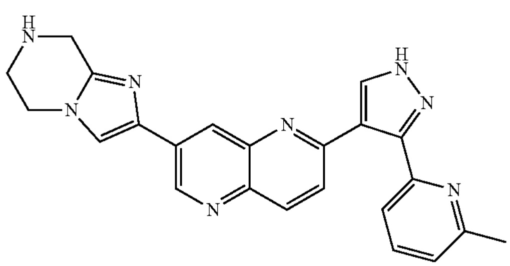 [SMILES: Cc1cccc(-c2n[nH]cc2-c2ccc3ncc(-c4cn5c(n4)CNCC5)cc3n2)n1] | 2-[3-(6-methyl-2-pyridyl)-1H-pyrazol-4-yl]-7-(5,6,7,8-tetrahydroimidazo[1,2-a]pyrazin-2-yl)-1,5-naphthyridine | 409.3 |
| 76 | 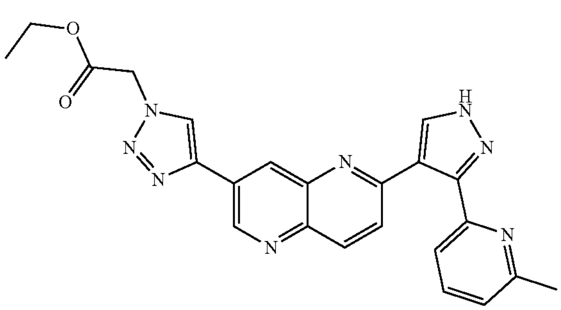 [SMILES: CCOC(=O)Cn1cc(-c2cnc3ccc(-c4c[nH]nc4-c4cccc(C)n4)nc3c2)nn1] | ethyl 2-[4-[6-[3-(6-methyl-2-pyridyl)-1H-pyrazol-4-yl]-1,5-naphthyridin-3-yl]triazol-1-yl]acetate | 441.2 |

TABLE 1-continued

| No. | Structure | Chemical Name | [M + H]+ |
|---|---|---|---|
| 77 | 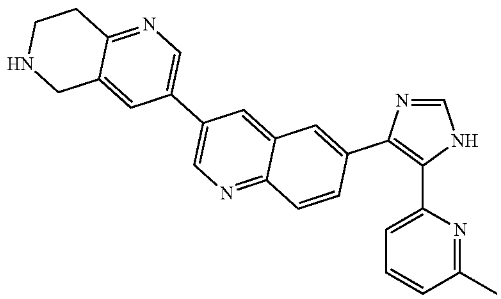 [SMILES: Cc1cccc(-c2[nH]cnc2-c2ccc3ncc(-c4cnc5c(c4)CNCC5)cc3c2)n1] | 3-[6-[5-(6-methyl-2-pyridyl)-1H-imidazol-4-yl]-3-quinolyl]-5,6,7,8-tetrahydro-1,6-naphthyridine | 419.2 |
| 78 | 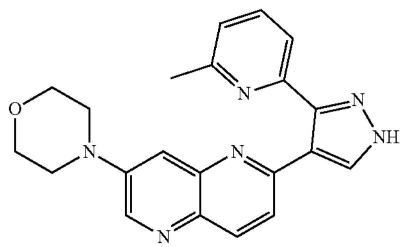 [SMILES: Cc1cccc(-c2n[nH]cc2-c2ccc3ncc(N4CCOCC4)cc3n2)n1] | 4-[6-[3-(6-methyl-2-pyridyl)-1H-pyrazol-4-yl]-1,5-naphthyridin-3-yl]morpholine | 373.2 |
| 79 | 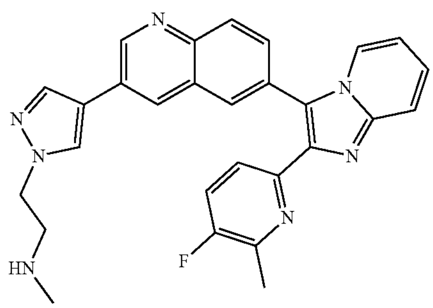 [SMILES: CNCCn1cc(-c2cnc3ccc(-c4c(-c5ccc(F)c(C)n5)nc5ccccn45)cc3c2)cn1] | 2-[4-[6-[2-(5-fluoro-6-methyl-2-pyridyl)imidazo[1,2-a]pyridin-3-yl]-3-quinolyl]pyrazol-1-yl]-N-methyl-ethanamine | 478.1 |
| 80 | 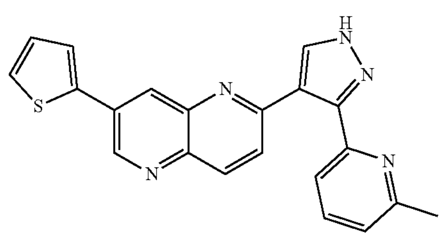 [SMILES: Cc1cccc(-c2n[nH]cc2-c2ccc3ncc(-c4cccs4)cc3n2)n1] | 2-[3-(6-methyl-2-pyridyl)-1H-pyrazol-4-yl]-7-(2-thienyl)-1,5-naphthyridine | 370.3 |
| 81 | 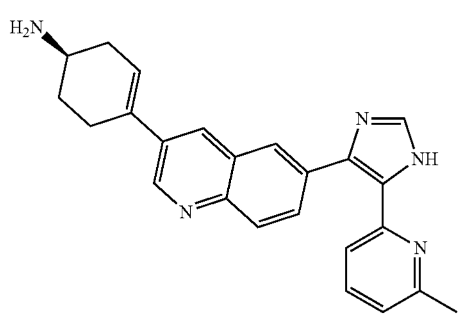 [SMILES: Cc1cccc(-c2[nH]cnc2-c2ccc3ncc(C4=CC[C@H](N)CC4)cc3c2)n1] | (1R)-4-[6-[5-(6-methyl-2-pyridyl)-1H-imidazol-4-yl]-3-quinolyl]cyclohex-3-en-1-amine | 382.1 |

TABLE 1-continued

| No. | Structure | Chemical Name | [M + H]+ |
|---|---|---|---|
| 82 | 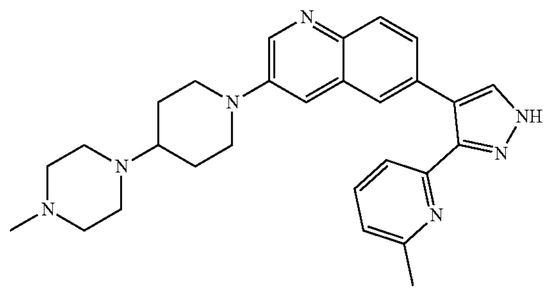 [SMILES: Cc1cccc(-c2n[nH]cc2-c2ccc3ncc(N4CCC(N5CCN(C)CC5)CC4)cc3c2)n1] | 3-[4-(4-methylpiperazin-1-yl)-1-piperidyl]-6-[3-(6-methyl-2-pyridyl)-1H-pyrazol-4-yl]quinoline | 468.2 |
| 83 | 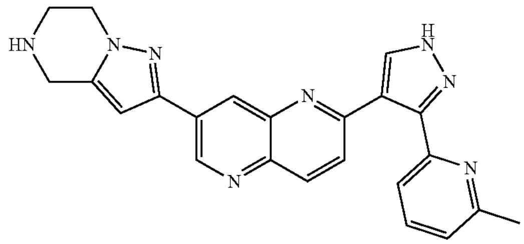 [SMILES: Cc1cccc(-c2n[nH]cc2-c2ccc3ncc(-c4cc5n(n4)CCNC5)cc3n2)n1] | 2-[3-(6-methyl-2-pyridyl)-1H-pyrazol-4-yl]-7-(4,5,6,7-tetrahydropyrazolo[1,5-a]pyrazin-2-yl)-1,5-naphthyridine | 409.2 |
| 84 | 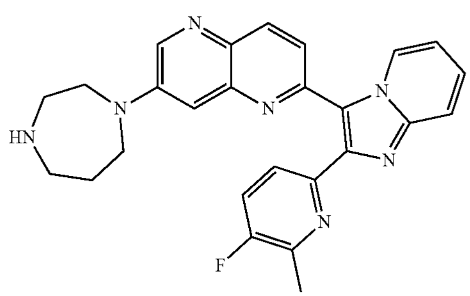 [SMILES: Cc1nc(-c2nc3ccccn3c2-c2ccc3ncc(N4CCCNCC4)cc3n2)ccc1F] | 7-(1,4-diazepan-1-yl)-2-[2-(5-fluoro-6-methyl-2-pyridyl)imidazo[1,2-a]pyridin-3-yl]-1,5-naphthyridine | 454.1 |
| 85 | 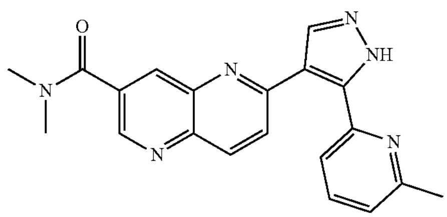 | N,N-dimethyl-6-[5-(6-methyl-2-pyridyl)-1H-pyrazol-4-yl]-1,5-naphthyridine-3-carboxamide | 359.0 |
| 86 | 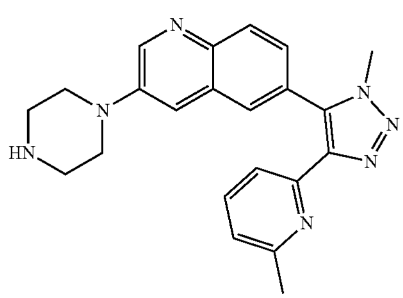 [SMILES: Cc1cccc(-c2nnn(C)c2-c2ccc3ncc(N4CCNCC4)cc3c2)n1] | 6-[3-methyl-5-(6-methyl-2-pyridyl)triazol-4-yl]-3-piperazin-1-yl-quinoline | 386.2 |
| 87 | 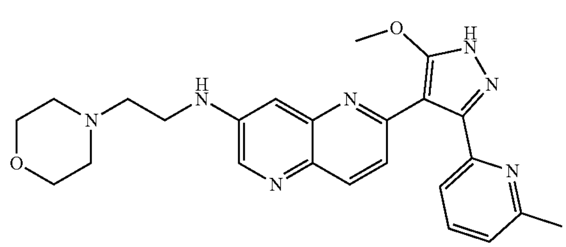 [SMILES: COc1[nH]nc(-c2cccc(C)n2)c1-c1ccc2ncc(NCCN3CCOCC3)cc2n1] | 6-[5-methoxy-3-(6-methyl-2-pyridyl)-1H-pyrazol-4-yl]-N-(2-morpholinoethyl)-1,5-naphthyridin-3-amine | 446.2 |

TABLE 1-continued

| No. | Structure | Chemical Name | [M + H]+ |
|---|---|---|---|
| 88 | 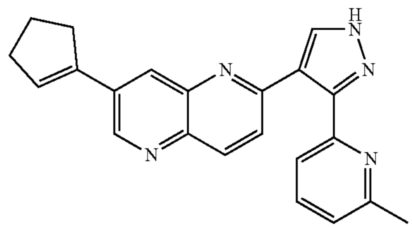 [SMILES: Cc1cccc(-c2n[nH]cc2-c2ccc3ncc(C4=CCCC4)cc3n2)n1] | 7-(cyclopenten-1-yl)-2-[3-(6-methyl-2-pyridyl)-1H-pyrazol-4-yl]-1,5-naphthyridine | 354.2 |
| 89 | 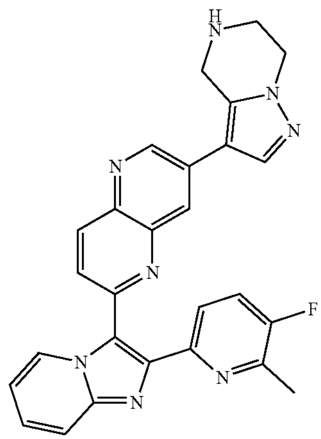 [SMILES: Cc1nc(-c2nc3ccccn3c2-c2ccc3ncc(-c4cnn5c4CNCC5)cc3n2)ccc1F] | 2-[2-(5-fluoro-6-methyl-2-pyridyl)imidazo[1,2-a]pyridin-3-yl]-7-(4,5,6,7-tetrahydropyrazolo[1,5-a]pyrazin-3-yl)-1,5-naphthyridine | 477.2 |
| 90 | 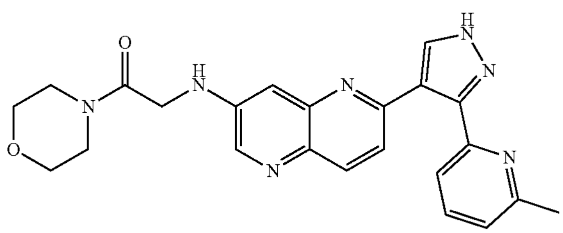 [SMILES: Cc1cccc(-c2n[nH]cc2-c2ccc3ncc(NCC(=O)N4CCOCC4)cc3n2)n1] | 2-[[6-[3-(6-methyl-2-pyridyl)-1H-pyrazol-4-yl]-1,5-naphthyridin-3-yl]amino]-1-morpholino-ethanone | 429.8 |
| 91 | 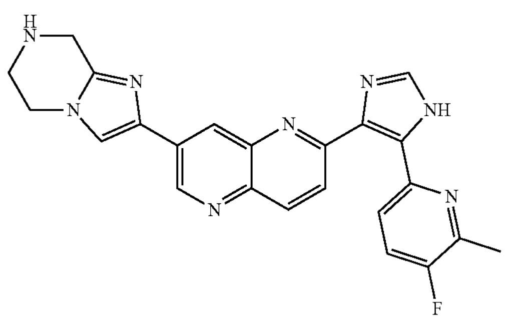 [SMILES: Cc1nc(-c2[nH]cnc2-c2ccc3ncc(-c4cn5c(n4)CNCC5)cc3n2)ccc1F] | 2-[5-(5-fluoro-6-methyl-2-pyridyl)-1H-imidazol-4-yl]-7-(5,6,7,8-tetrahydroimidazo[1,2-a]pyrazin-2-yl)-1,5-naphthyridine | 427.1 |
| 92 | 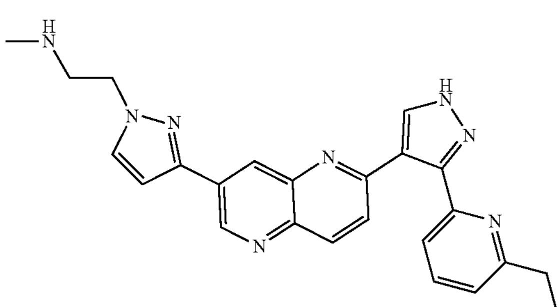 | 2-[3-[6-[3-(6-ethyl-2-pyridyl)-1H-pyrazol-4-yl]-1,5-naphthyridin-3-yl]pyrazol-1-yl]-N-methyl-ethanamine | 425.1 |

TABLE 1-continued

| No. | Structure | Chemical Name | [M + H]⁺ |
|---|---|---|---|
| 93 | 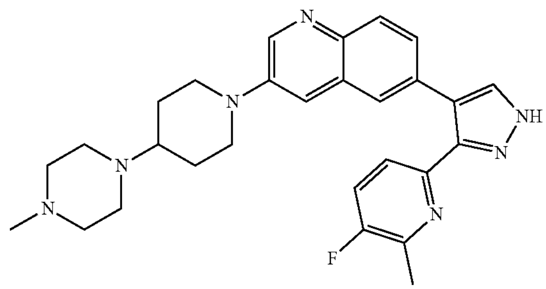 | 6-[3-(5-fluoro-6-methyl-2-pyridyl)-1H-pyrazol-4-yl]-3-[4-(4-methylpiperazin-1-yl)-1-piperidyl]quinoline | 486.2 |
| 94 | 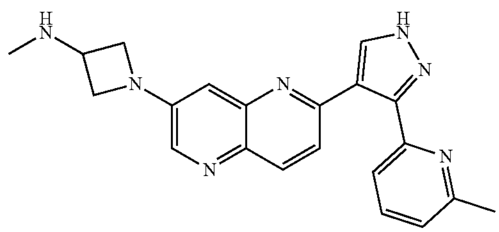 | N-methyl-1-[6-[3-(6-methyl-2-pyridyl)-1H-pyrazol-4-yl]-1,5-naphthyridin-3-yl]azetidin-3-amine | 372.2 |
| 95 | 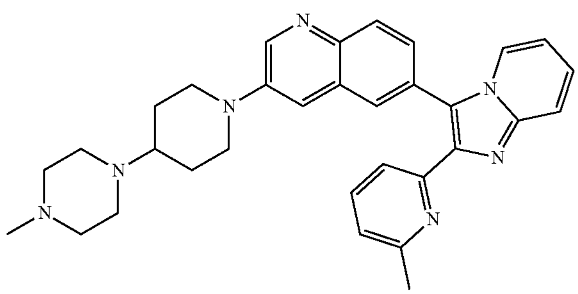 | 3-[4-(4-methylpiperazin-1-yl)-1-piperidyl]-6-[2-(6-methyl-2-pyridyl)imidazo[1,2-a]pyridin-3-yl]quinoline | 518.2 |
| 96 | AND Enantiomer | rac-(1R,3S)-3-[4-[6-[3-(5-fluoro-6-methyl-2-pyridyl)-1H-pyrazol-4-yl]-1,5-naphthyridin-3-yl]pyrazol-1-yl]cyclopentanamine | 455.1 |
| 97 | 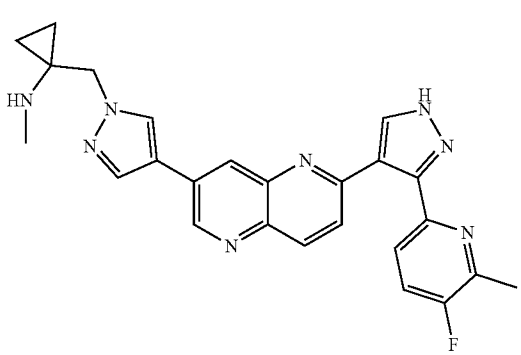 [SMILES: CNC1(Cn2cc(-c3cnc4ccc(-c5c[nH]nc5-c5ccc(F)c(C)n5)nc4c3)cn2)CC1] | 1-[[4-[6-[3-(5-fluoro-6-methyl-2-pyridyl)-1H-pyrazol-4-yl]-1,5-naphthyridin-3-yl]pyrazol-1-yl]methyl]-N-methyl-cyclopropanamine | 455.1 |

TABLE 1-continued

| No. | Structure | Chemical Name | [M + H]⁺ |
|---|---|---|---|
| 98 | 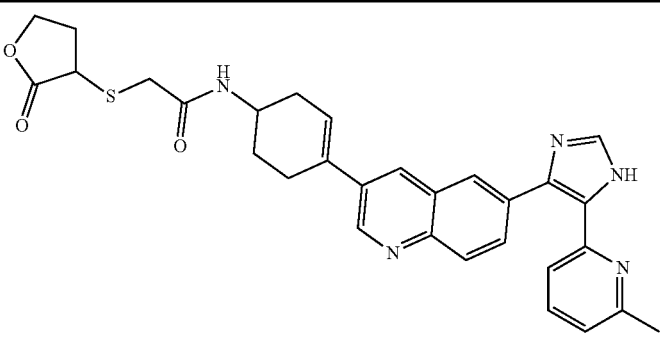 | N-[4-[6-[5-(6-methyl-2-pyridyl)-1H-imidazol-4-yl]-3-quinolyl]cyclohex-3-en-1-yl]-2-(2-oxotetrahydrofuran-3-yl)sulfanyl-acetamide | 540.1 |
| 99 | 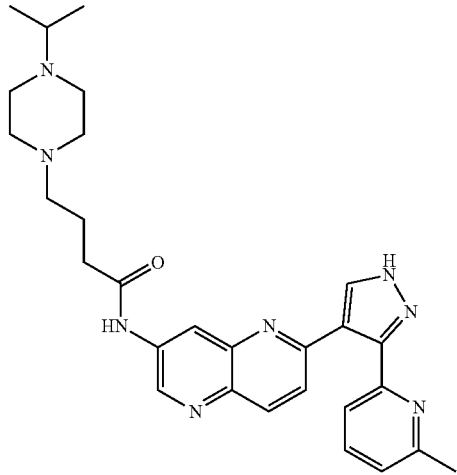 [SMILES: Cc1cccc(-c2n[nH]cc2-c2ccc3ncc(NC(=O)CCCN4CCN(C(C)C)CC4)cc3n2)n1] | 4-(4-isopropylpiperazin-1-yl)-N-[6-[3-(6-methyl-2-pyridyl)-1H-pyrazol-4-yl]-1,5-naphthyridin-3-yl]butanamide | 499.3 |
| 100 | 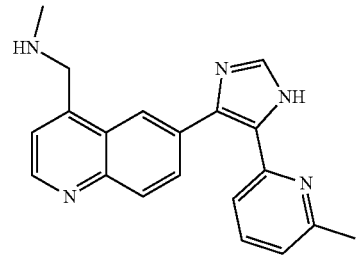 [SMILES: CNCc1ccnc2ccc(-c3nc[nH]c3-c3cccc(C)n3)cc12] | N-methyl-1-[6-[5-(6-methyl-2-pyridyl)-1H-imidazol-4-yl]-4-quinolyl]methanamine | 330.1 |
| 101 | 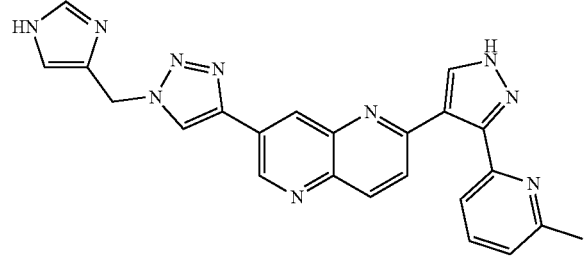 [SMILES: Cc1cccc(-c2n[nH]cc2-c2ccc3ncc(-c4cn(Cc5c[nH]cn5)nn4)cc3n2)n1] | 7-[1-(1H-imidazol-4-ylmethyl)triazol-4-yl]-2-[3-(6-methyl-2-pyridyl)-1H-pyrazol-4-yl]-1,5-naphthyridine | 435.2 |
| 102 | 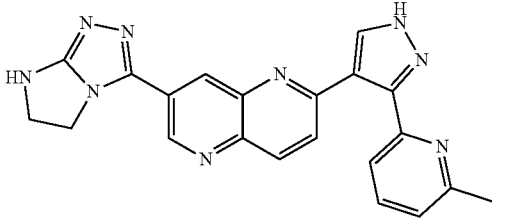 [SMILES: Cc1cccc(-c2n[nH]cc2-c2ccc3ncc(-c4nnc5n4CCN5)cc3n2)n1] | 7-(6,7-dihydro-5H-imidazo[2,1-c][1,2,4]triazol-3-yl)-2-[3-(6-methyl-2-pyridyl)-1H-pyrazol-4-yl]-1,5-naphthyridine | 396.2 |

TABLE 1-continued

| No. | Structure | Chemical Name | [M + H]+ |
|---|---|---|---|
| 103 | 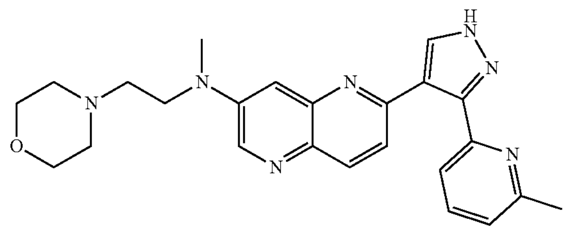 [SMILES: Cc1cccc(-c2n[nH]cc2-c2ccc3ncc(N(C)CCN4CCOCC4)cc3n2)n1] | N-methyl-6-[3-(6-methyl-2-pyridyl)-1H-pyrazol-4-yl]-N-(2-morpholinoethyl)-1,5-naphthyridin-3-amine | 429.9 |
| 104 | 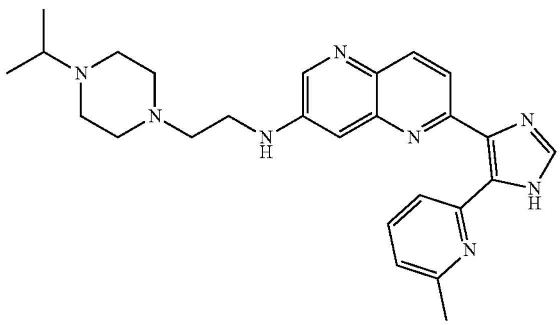 [SMILES: Cc1cccc(-c2[nH]cnc2-c2ccc3ncc(NCCN4CCN(C(C)C)CC4)cc3n2)n1] | N-[2-(4-isopropylpiperazin-1-yl)ethyl]-6-[5-(6-methyl-2-pyridyl)-1H-imidazol-4-yl]-1,5-naphthyridin-3-amine | 457.3 |
| 105 | 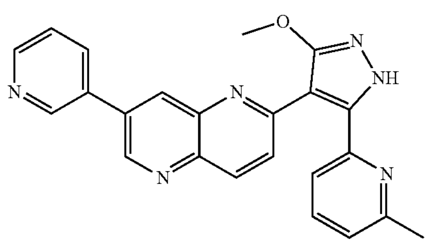 [SMILES: COc1n[nH]c(-c2cccc(C)n2)c1-c1ccc2ncc(-c3cccnc3)cc2n1] | 2-[3-methoxy-5-(6-methyl-2-pyridyl)-1H-pyrazol-4-yl]-7-(3-pyridyl)-1,5-naphthyridine | 395.2 |
| 106 | 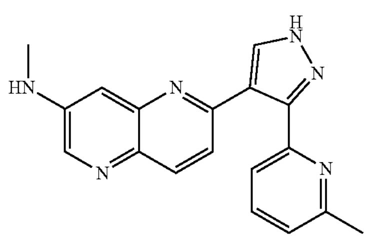 [SMILES: CNc1cnc2ccc(-c3c[nH]nc3-c3cccc(C)n3)nc2c1] | N-methyl-6-[3-(6-methyl-2-pyridyl)-1H-pyrazol-4-yl]-1,5-naphthyridin-3-amine | 317.1 |
| 107 | 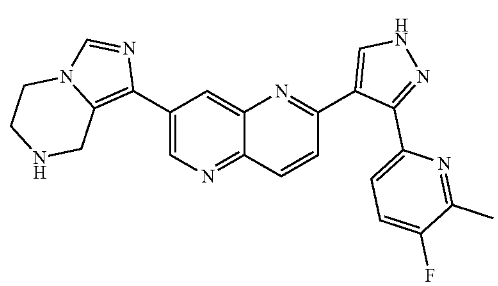 [SMILES: Cc1nc(-c2n[nH]cc2-c2ccc3ncc(-c4ncn5c4CNCC5)cc3n2)ccc1F] | 2-[3-(5-fluoro-6-methyl-2-pyridyl)-1H-pyrazol-4-yl]-7-(5,6,7,8-tetrahydroimidazo[1,5-a]pyrazin-1-yl)-1,5-naphthyridine | 427.2 |

TABLE 1-continued

| No. | Structure | Chemical Name | [M + H]+ |
|---|---|---|---|
| 108 | 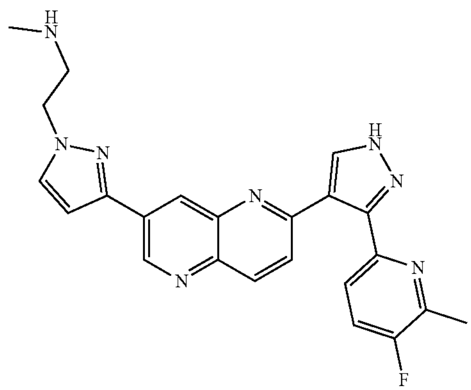 | 2-[3-[6-[3-(5-fluoro-6-methyl-2-pyridyl)-1H-pyrazol-4-yl]-1,5-naphthyridin-3-yl]pyrazol-1-yl]-N-methyl-ethanamine | 429.2 |
| 109 | 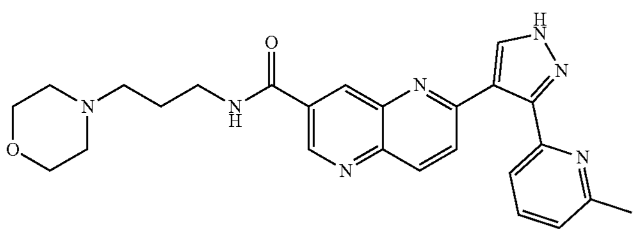 [SMILES: Cc1cccc(-c2n[nH]cc2-c2ccc3ncc(C(=O)NCCCN4CCOCC4)cc3n2)n1] | 6-[3-(6-methyl-2-pyridyl)-1H-pyrazol-4-yl]-N-(3-morpholinopropyl)-1,5-naphthyridine-3-carboxamide | 458.2 |
| 110 | 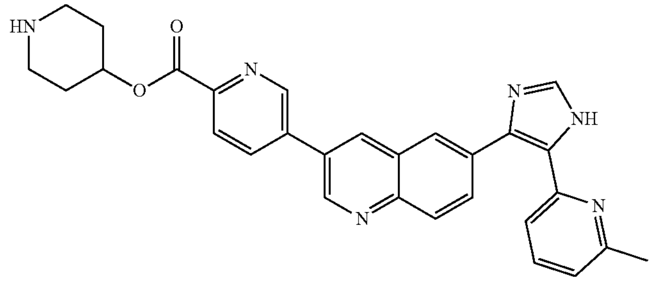 [SMILES: Cc1cccc(-c2[nH]cnc2-c2ccc3ncc(-c4ccc(C(=O)OC5CCNCC5)nc4)cc3c2)n1] | 4-piperidyl 5-[6-[5-(6-methyl-2-pyridyl)-1H-imidazol-4-yl]-3-quinolyl]pyridine-2-carboxylate | 491.2 |
| 111 | 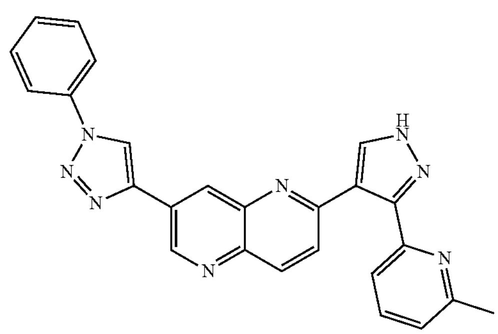 [SMILES: Cc1cccc(-c2n[nH]cc2-c2ccc3ncc(-c4cn(-c5ccccc5)nn4)cc3n2)n1] | 2-[3-(6-methyl-2-pyridyl)-1H-pyrazol-4-yl]-7-(1-phenyltriazol-4-yl)-1,5-naphthyridine | 431.2 |
| 112 | 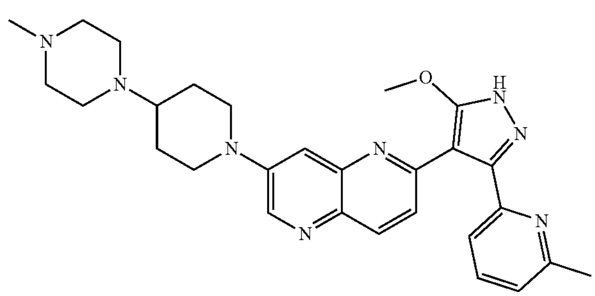 | 2-[5-methoxy-3-(6-methyl-2-pyridyl)-1H-pyrazol-4-yl]-7-[4-(4-methylpiperazin-1-yl)-1-piperidyl]-1,5-naphthyridine | 499.3 |

TABLE 1-continued

| No. | Structure | Chemical Name | [M + H]+ |
|---|---|---|---|
| 113 | 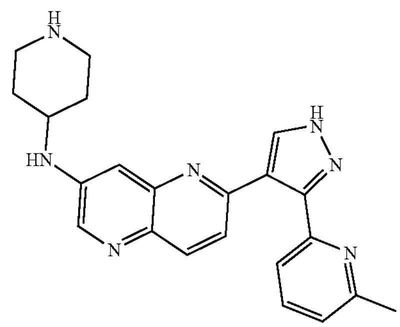 [SMILES: Cc1cccc(-c2n[nH]cc2-c2ccc3ncc(NC4CCNCC4)cc3n2)n1] | 6-[3-(6-methyl-2-pyridyl)-1H-pyrazol-4-yl]-N-(4-piperidyl)-1,5-naphthyridin-3-amine | 386.2 |
| 114 | 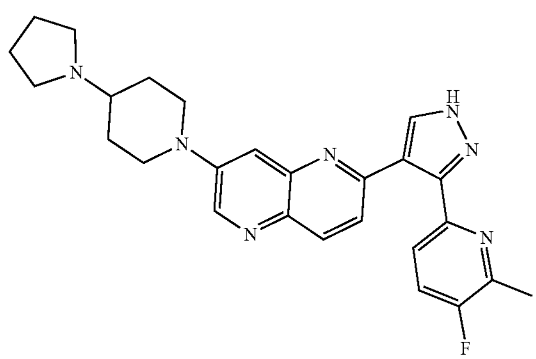 [SMILES: Cc1nc(-c2n[nH]cc2-c2ccc3ncc(N4CCC(N5CCCC5)CC4)cc3n2)ccc1F] | 2-[3-(5-fluoro-6-methyl-2-pyridyl)-1H-pyrazol-4-yl]-7-(4-pyrrolidin-1-yl-1-piperidyl)-1,5-naphthyridine | 458.1 |
| 115 | 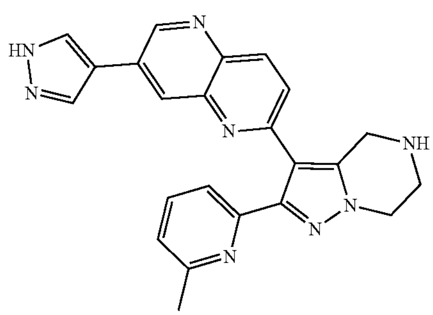 [SMILES: Cc1cccc(-c2nn3c(c2-c2ccc4ncc(-c5cn[nH]c5)cc4n2)CNCC3)n1] | 2-[2-(6-methyl-2-pyridyl)-4,5,6,7-tetrahydropyrazolo[1,5-a]pyrazin-3-yl]-7-(1H-pyrazol-4-yl)-1,5-naphthyridine | 409.2 |
| 116 | 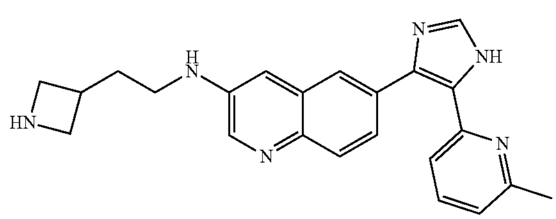 [SMILES: Cc1cccc(-c2[nH]cnc2-c2ccc3ncc(NCCC4CNC4)cc3c2)n1] | N-[2-(azetidin-3-yl)ethyl]-6-[5-(6-methyl-2-pyridyl)-1H-imidazol-4-yl]quinolin-3-amine | 385.2 |
| 117 | 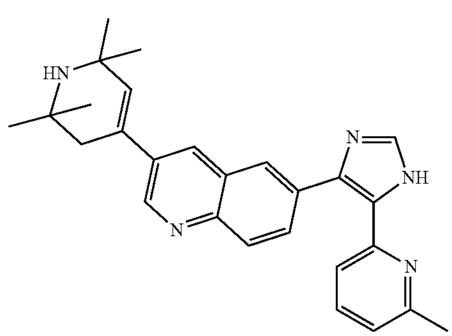 | 6-[5-(6-methyl-2-pyridyl)-1H-imidazol-4-yl]-3-(2,2,6,6-tetramethyl-1,3-dihydropyridin-4-yl)quinoline | 424.2 |

TABLE 1-continued

| No. | Structure | Chemical Name | [M + H]+ |
|---|---|---|---|
| 118 | 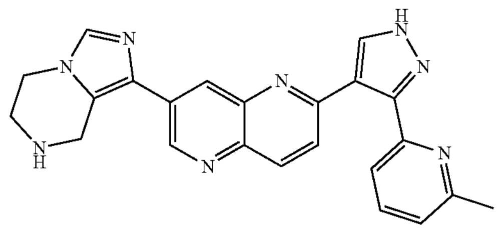 [SMILES: Cc1cccc(-c2n[nH]cc2-c2ccc3ncc(-c4ncn5c4CNCC5)cc3n2)n1] | 2-[3-(6-methyl-2-pyridyl)-1H-pyrazol-4-yl]-7-(5,6,7,8-tetrahydroimidazo[1,5-a]pyrazin-1-yl)-1,5-naphthyridine | 409.2 |
| 119 | 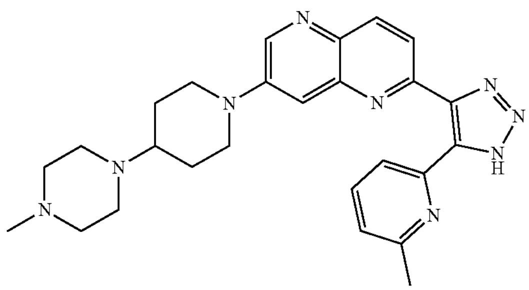 [SMILES: Cc1cccc(-c2[nH]nnc2-c2ccc3ncc(N4CCC(N5CCN(C)CC5)CC4)cc3n2)n1] | 7-[4-(4-methylpiperazin-1-yl)-1-piperidyl]-2-[5-(6-methyl-2-pyridyl)-1H-triazol-4-yl]-1,5-naphthyridine | 470.2 |
| 120 | 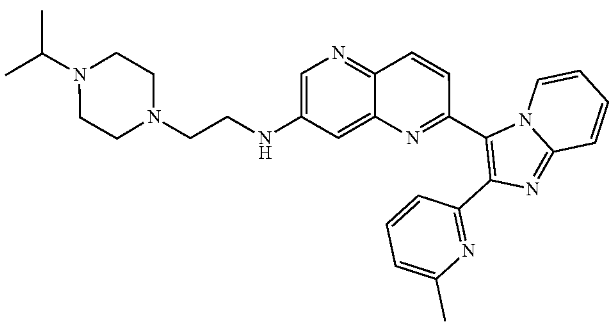 [SMILES: Cc1cccc(-c2nc3ccccn3c2-c2ccc3ncc(NCCN4CCN(C(C)C)CC4)cc3n2)n1] | N-[2-(4-isopropylpiperazin-1-yl)ethyl]-6-[2-(6-methyl-2-pyridyl)imidazo[1,2-a]pyridin-3-yl]-1,5-naphthyridin-3-amine | 507.2 |
| 121 | 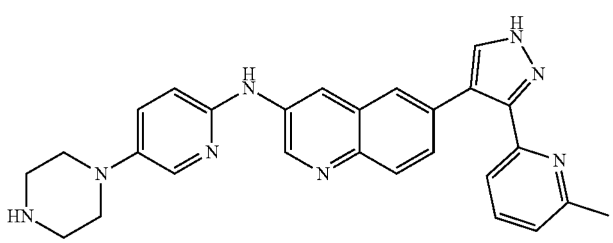 | 6-[3-(6-methyl-2-pyridyl)-1H-pyrazol-4-yl]-N-(5-piperazin-1-yl-2-pyridyl)quinolin-3-amine | 463.2 |
| 122 | 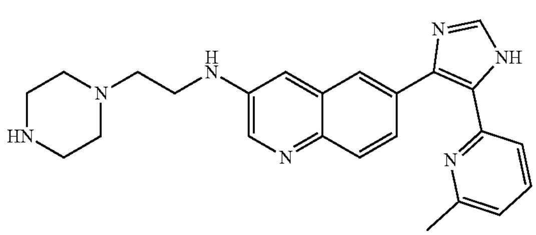 [SMILES: Cc1cccc(-c2[nH]cnc2-c2ccc3ncc(NCCN4CCNCC4)cc3c2)n1] | 6-[5-(6-methyl-2-pyridyl)-1H-imidazol-4-yl]-N-(2-piperazin-1-ylethyl)quinolin-3-amine | 414.3 |

TABLE 1-continued

| No. | Structure | Chemical Name | [M + H]+ |
|---|---|---|---|
| 123 | 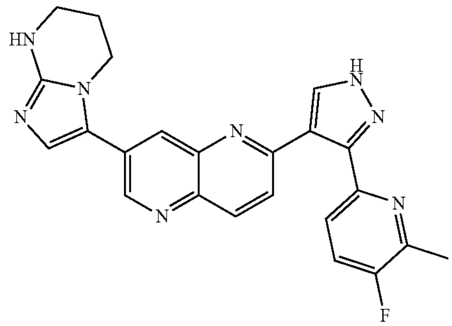 [SMILES: Cc1nc(-c2n[nH]cc2-c2ccc3ncc(-c4cnc5n4CCCN5)cc3n2)ccc1F] | 2-[3-(5-fluoro-6-methyl-2-pyridyl)-1H-pyrazol-4-yl]-7-(5,6,7,8-tetrahydroimidazo[1,2-a]pyrimidin-3-yl)-1,5-naphthyridine | 427.2 |
| 124 | 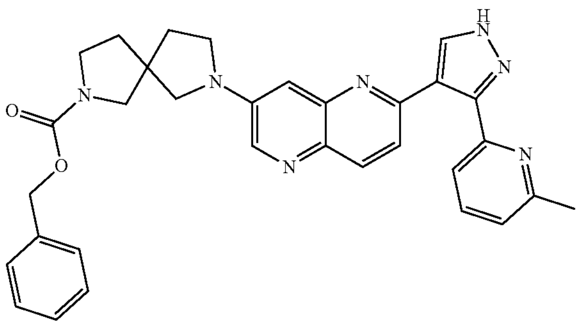 [SMILES: Cc1cccc(-c2n[nH]cc2-c2ccc3ncc(N4CCC5(CCN(C(=O)OCc6ccccc6)C5)C4)cc3n2)n1] | benzyl 7-[6-[3-(6-methyl-2-pyridyl)-1H-pyrazol-4-yl]-1,5-naphthyridin-3-yl]-2,7-diazaspiro[4.4]nonane-2-carboxylate | 546.2 |
| 125 | 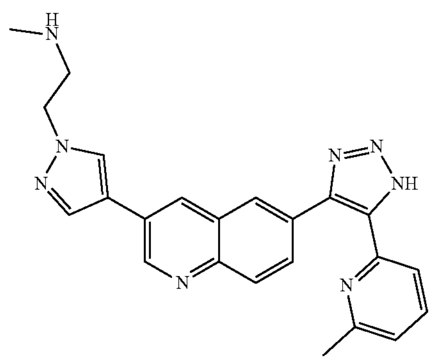 [SMILES: CNCCn1cc(-c2cnc3ccc(-c4nn[nH]c4-c4cccc(C)n4)cc3c2)cn1] | N-methyl-2-[4-[6-[5-(6-methyl-2-pyridyl)-1H-triazol-4-yl]-3-quinolyl]pyrazol-1-yl]ethanamine | 411.1 |
| 126 | 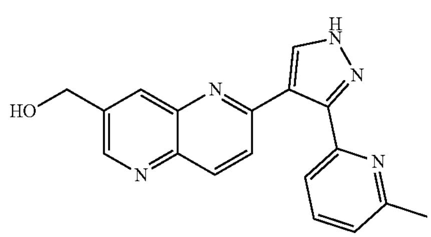 [SMILES: Cc1cccc(-c2n[nH]cc2-c2ccc3ncc(CO)cc3n2)n1] | [6-[3-(6-methyl-2-pyridyl)-1H-pyrazol-4-yl]-1,5-naphthyridin-3-yl]methanol | 318.0 |
| 127 | 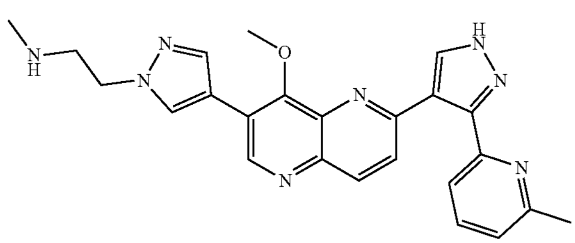 | 2-[4-[4-methoxy-6-[3-(6-methyl-2-pyridyl)-1H-pyrazol-4-yl]-1,5-naphthyridin-3-yl]pyrazol-1-yl]-N-methyl-ethanamine | 441.3 |

TABLE 1-continued
| No. | Structure | Chemical Name | [M + H]+ |
|---|---|---|---|
| 128 | 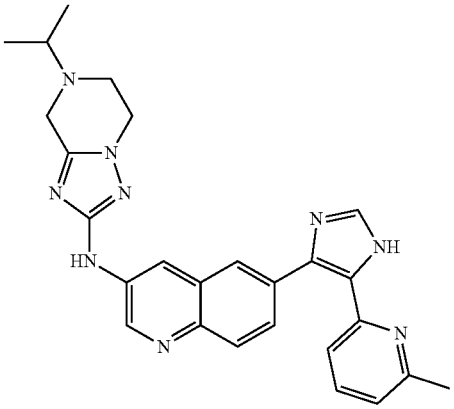 [SMILES: Cc1cccc(-c2[nH]cnc2-c2ccc3ncc(Nc4nc5n(n4)CCN(C(C)C)C5)cc3c2)n1] | N-(7-isopropyl-6,8-dihydro-5H-[1,2,4]triazolo[1,5-a]pyrazin-2-yl)-6-[5-(6-methyl-2-pyridyl)-1H-imidazol-4-yl]quinolin-3-amine | 466.2 |
| 129 | 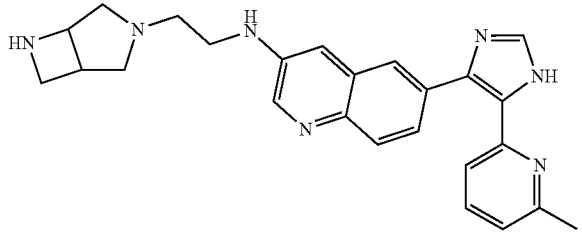 [SMILES: Cc1cccc(-c2[nH]cnc2-c2ccc3ncc(NCCN4CC5CNC5C4)cc3c2)n1] | N-[2-(3,6-diazabicyclo[3.2.0]heptan-3-yl)ethyl]-6-[5-(6-methyl-2-pyridyl)-1H-imidazol-4-yl]quinolin-3-amine | 426.2 |
| 130 | 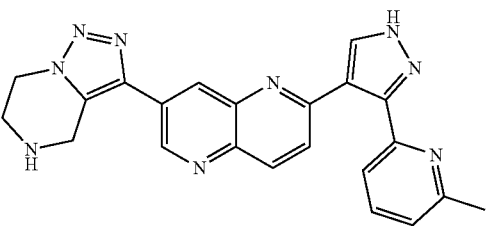 [SMILES: Cc1cccc(-c2n[nH]cc2-c2ccc3ncc(-c4nnn5c4CNCC5)cc3n2)n1] | 2-[3-(6-methyl-2-pyridyl)-1H-pyrazol-4-yl]-7-(4,5,6,7-tetrahydrotriazolo[1,5-a]pyrazin-3-yl)-1,5-naphthyridine | 410.2 |
| 131 | 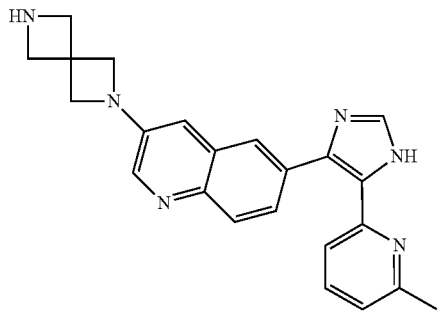 [SMILES: Cc1cccc(-c2[nH]cnc2-c2ccc3ncc(N4CC5(CNC5)C4)cc3c2)n1] | 3-(2,6-diazaspiro[3.3]heptan-2-yl)-6-[5-(6-methyl-2-pyridyl)-1H-imidazol-4-yl]quinoline | 383.2 |

TABLE 1-continued

| No. | Structure | Chemical Name | [M + H]+ |
|---|---|---|---|
| 132 | 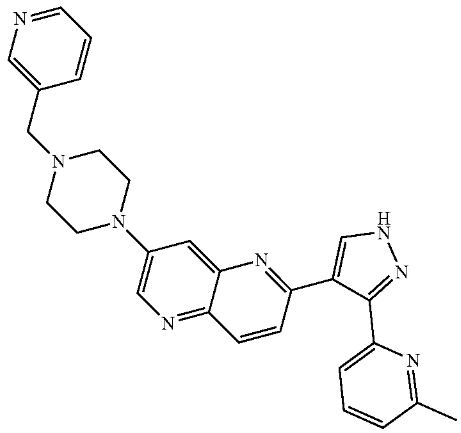 [SMILES: Cc1cccc(-c2n[nH]cc2-c2ccc3ncc(N4CCN(Cc5cccnc5)CC4)cc3n2)n1] | 2-[3-(6-methyl-2-pyridyl)-1H-pyrazol-4-yl]-7-[4-(3-pyridylmethyl)piperazin-1-yl]-1,5-naphthyridine | 463.2 |
| 133 | 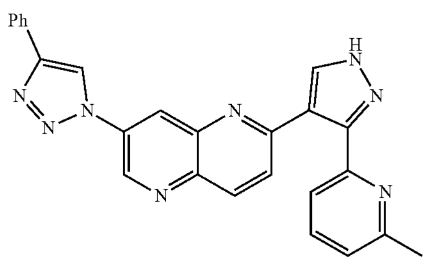 [SMILES: Cc1cccc(-c2n[nH]cc2-c2ccc3ncc(-n4cc(-c5ccccc5)nn4)cc3n2)n1] | 2-[3-(6-methyl-2-pyridyl)-1H-pyrazol-4-yl]-7-(4-phenyltriazol-1-yl)-1,5-naphthyridine | 431.1 |
| 134 | 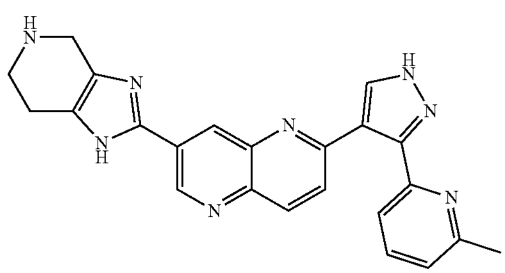 [SMILES: Cc1cccc(-c2n[nH]cc2-c2ccc3ncc(-c4nc5c([nH]4)CCNC5)cc3n2)n1] | 2-[3-(6-methyl-2-pyridyl)-1H-pyrazol-4-yl]-7-(4,5,6,7-tetrahydro-1H-imidazo[4,5-c]pyridin-2-yl)-1,5-naphthyridine | 409.2 |
| 135 | 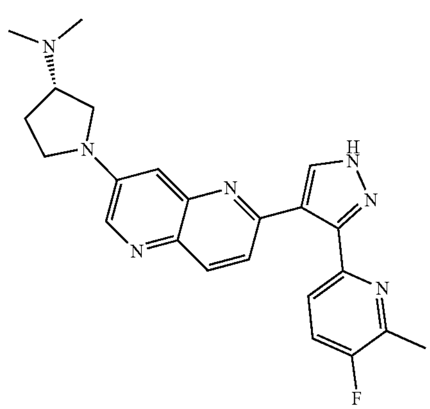 | (3S)-1-[6-[3-(5-fluoro-6-methyl-2-pyridyl)-1H-pyrazol-4-yl]-1,5-naphthyridin-3-yl]-N,N-dimethyl-pyrrolidin-3-amine | 418.3 |

TABLE 1-continued

| No. | Structure | Chemical Name | [M + H]+ |
|---|---|---|---|
| 136 | 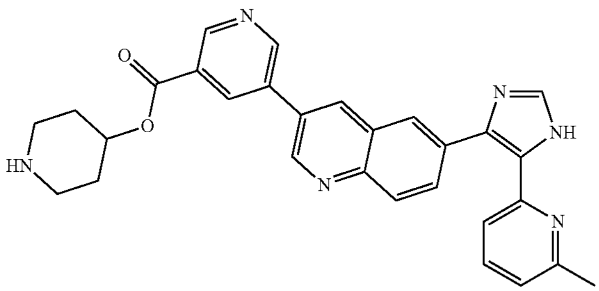 [SMILES: Cc1cccc(-c2[nH]cnc2-c2ccc3ncc(-c4cncc(C(=O)OC5CCNCC5)c4)cc3c2)n1] | 4-piperidyl 5-[6-[5-(6-methyl-2-pyridyl)-1H-imidazol-4-yl]-3-quinolyl]pyridine-3-carboxylate | 491.1 |
| 137 | 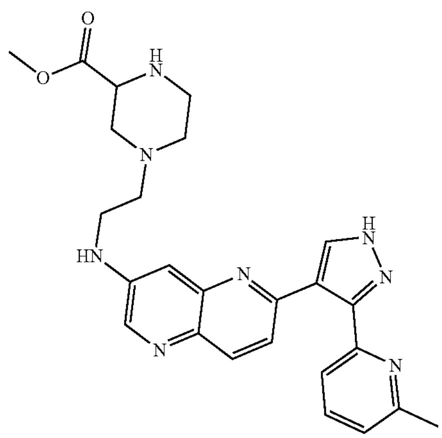 | methyl 4-[2-[[6-[3-(6-methyl-2-pyridyl)-1H-pyrazol-4-yl]-1,5-naphthyridin-3-yl]amino]ethyl]piperazine-2-carboxylate | 473.1 |
| 138 | 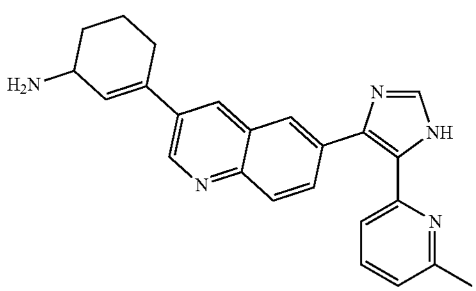 [SMILES: Cc1cccc(-c2[nH]cnc2-c2ccc3ncc(C4=CC(N)CCC4)cc3c2)n1] | 3-[6-[5-(6-methyl-2-pyridyl)-1H-imidazol-4-yl]-3-quinolyl]cyclohex-2-en-1-amine | 382.2 |
| 139 | 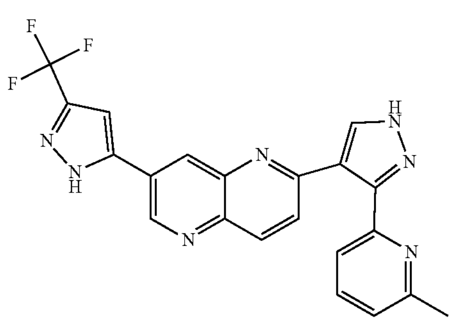 [SMILES: Cc1cccc(-c2n[nH]cc2-c2ccc3ncc(-c4cc(C(F)(F)F)n[nH]4)cc3n2)n1] | 2-[3-(6-methyl-2-pyridyl)-1H-pyrazol-4-yl]-7-[3-(trifluoromethyl)-1H-pyrazol-5-yl]-1,5-naphthyridine | 422.2 |
| 140 | AND Enantiomer | N-methyl-6-[3-(6-methyl-2-pyridyl)-1H-pyrazol-4-yl]-N-[rac-(3R)-1-methylpyrrolidin-3-yl]-1,5-naphthyridin-3-amine | 400.2 |

TABLE 1-continued

| No. | Structure | Chemical Name | [M + H]+ |
|---|---|---|---|
| 141 | 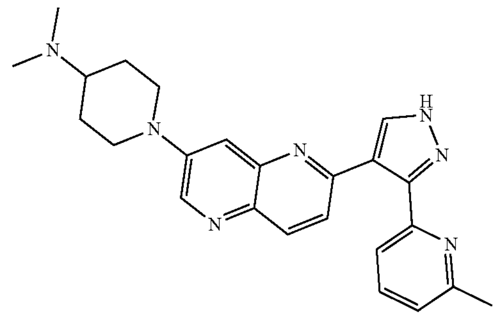 | N,N-dimethyl-1-[6-[3-(6-methyl-2-pyridyl)-1H-pyrazol-4-yl]-1,5-naphthyridin-3-yl]piperidin-4-amine | 414.2 |
| 142 | 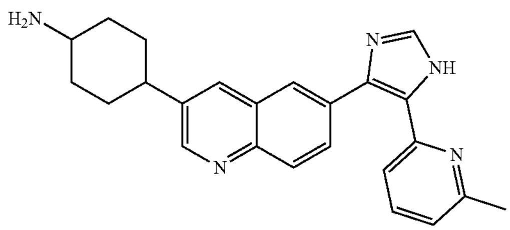 [SMILES: Cc1cccc(-c2[nH]cnc2-c2ccc3ncc(C4CCC(N)CC4)cc3c2)n1] | 4-[6-[5-(6-methyl-2-pyridyl)-1H-imidazol-4-yl]-3-quinolyl]cyclohexanamine | 384.1 |
| 143 | 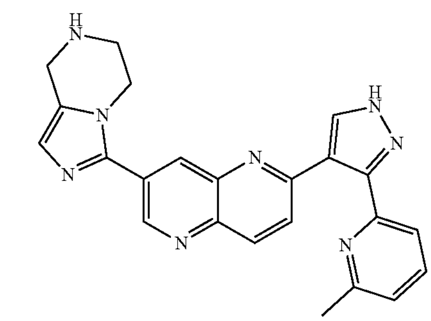 [SMILES: Cc1cccc(-c2n[nH]cc2-c2ccc3ncc(-c4ncc5n4CCNC5)cc3n2)n1] | 2-[3-(6-methyl-2-pyridyl)-1H-pyrazol-4-yl]-7-(5,6,7,8-tetrahydroimidazo[1,5-a]pyrazin-3-yl)-1,5-naphthyridine | 409.2 |
| 144 | 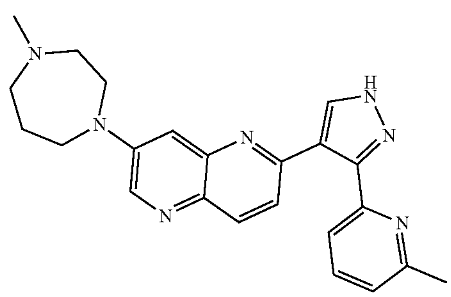 [SMILES: Cc1cccc(-c2n[nH]cc2-c2ccc3ncc(N4CCCN(C)CC4)cc3n2)n1] | 7-(4-methyl-1,4-diazepan-1-yl)-2-[3-(6-methyl-2-pyridyl)-1H-pyrazol-4-yl]-1,5-naphthyridine | 400.2 |
| 145 | 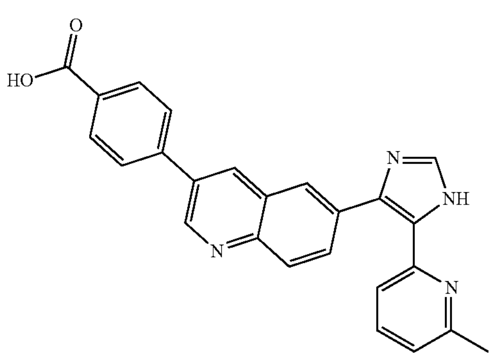 [SMILES: Cc1cccc(-c2[nH]cnc2-c2ccc3ncc(-c4ccc(C(=O)O)cc4)cc3c2)n1] | 4-[6-[5-(6-methyl-2-pyridyl)-1H-imidazol-4-yl]-3-quinolyl]benzoic acid | 407.1 |

TABLE 1-continued

| No. | Chemical Name | [M + H]+ |
|---|---|---|
| 146 | 4-pyrrolidin-1-ylbutyl 6-[5-(6-methyl-2-pyridyl)-1H-pyrazol-4-yl]-1,5-naphthyridine-3-carboxylate | 457.1 |
| 147 | 3-(cyclohexen-1-yl)-6-[5-(6-methyl-2-pyridyl)-1H-imidazol-4-yl]quinoline | 367.0 |
| 148 | 3-[(3R,5S)-3,5-dimethylpiperazin-1-yl]-6-[5-(6-methyl-2-pyridyl)-1H-imidazol-4-yl]quinoline | 399.1 |
| 149 | 4-[6-[5-(6-methyl-2-pyridyl)-1H-imidazol-4-yl]-1,5-naphthyridin-3-yl]cyclohex-3-en-1-amine | 383.2 |
| 150 | 4-hydroxy-2-[[[4-[6-[5-(6-methyl-2-pyridyl)-1H-imidazol-4-yl]-3-quinolyl]cyclohex-3-en-1-yl]amino]methyl]butanoic acid | 498.1 |

TABLE 1-continued
| No. | Structure | Chemical Name | [M + H]⁺ |
|---|---|---|---|
| 151 | 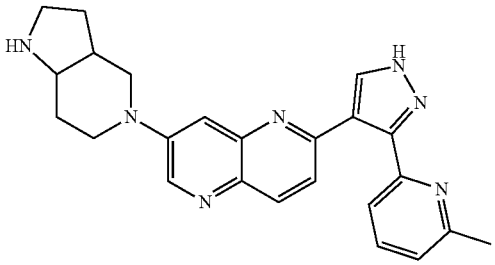 [SMILES: Cc1cccc(-c2n[nH]cc2-c2ccc3ncc(N4CCC5NCCC5C4)cc3n2)n1] | 7-(1,2,3,3a,4,6,7,7a-octahydropyrrolo[3,2-c]pyridin-5-yl)-2-[3-(6-methyl-2-pyridyl)-1H-pyrazol-4-yl]-1,5-naphthyridine | 412.2 |
| 152 | 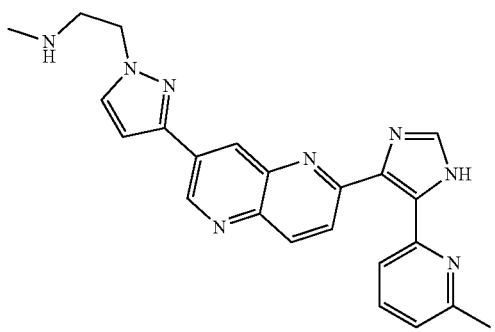 | N-methyl-2-[3-[6-[5-(6-methyl-2-pyridyl)-1H-imidazol-4-yl]-1,5-naphthyridin-3-yl]pyrazol-1-yl]ethanamine | 411.1 |
| 153 | 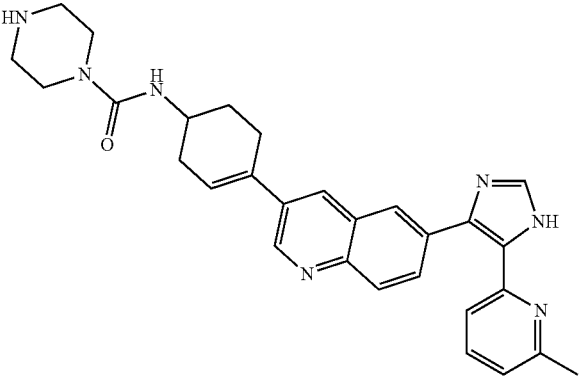 [SMILES: Cc1cccc(-c2[nH]cnc2-c2ccc3ncc(C4=CCC(NC(=O)N5CCNCC5)CC4)cc3c2)n1] | N-[4-[6-[5-(6-methyl-2-pyridyl)-1H-imidazol-4-yl]-3-quinolyl]cyclohex-3-en-1-yl]piperazine-1-carboxamide | 494.2 |
| 154 | 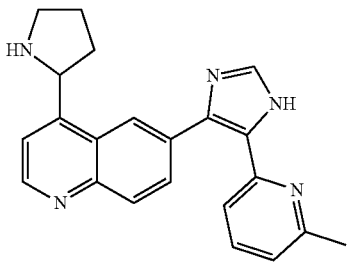 [SMILES: Cc1cccc(-c2[nH]cnc2-c2ccc3nccc(C4CCCN4)c3c2)n1] | 6-[5-(6-methyl-2-pyridyl)-1H-imidazol-4-yl]-4-pyrrolidin-2-yl-quinoline | 356.1 |

TABLE 1-continued

| No. | Structure | Chemical Name | [M + H]+ |
|---|---|---|---|
| 155 | 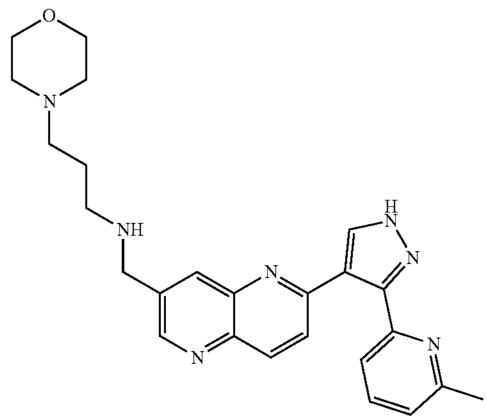 [SMILES: Cc1cccc(-c2n[nH]cc2-c2ccc3ncc(CNCCCN4CCOCC4)cc3n2)n1] | N-[[6-[3-(6-methyl-2-pyridyl)-1H-pyrazol-4-yl]-1,5-naphthyridin-3-yl]methyl]-3-morpholino-propan-1-amine | 443.8 |
| 156 | 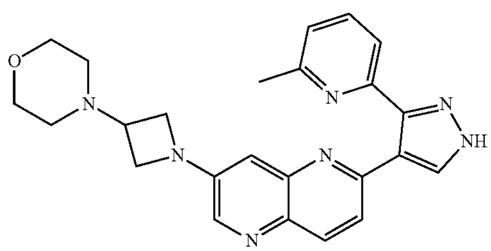 [SMILES: Cc1cccc(-c2n[nH]cc2-c2ccc3ncc(N4CC(N5CCOCC5)C4)cc3n2)n1] | 4-[1-[6-[3-(6-methyl-2-pyridyl)-1H-pyrazol-4-yl]-1,5-naphthyridin-3-yl]azetidin-3-yl]morpholine | 428.5 |
| 157 | 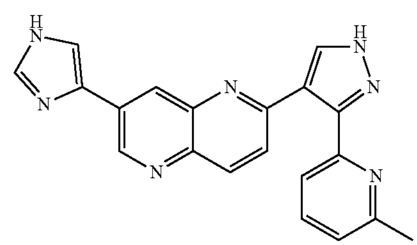 [SMILES: Cc1cccc(-c2n[nH]cc2-c2ccc3ncc(-c4c[nH]cn4)cc3n2)n1] | 7-(1H-imidazol-4-yl)-2-[3-(6-methyl-2-pyridyl)-1H-pyrazol-4-yl]-1,5-naphthyridine | 354.4 |
| 158 | 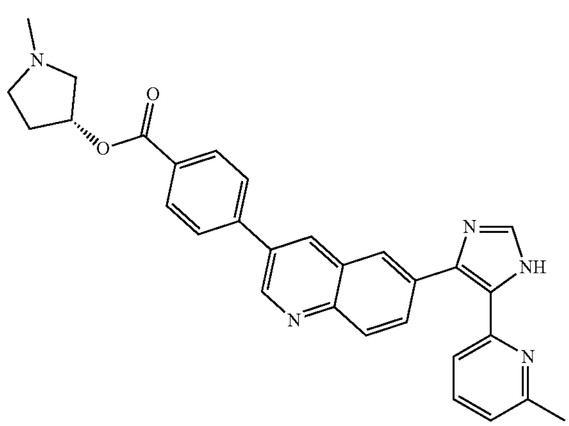 [SMILES: Cc1cccc(-c2[nH]cnc2-c2ccc3ncc(-c4ccc(C(=O)O[C@@H]5CCN(C)C5)cc4)cc3c2)n1] | [(3R)-1-methylpyrrolidin-3-yl] 4-[6-[5-(6-methyl-2-pyridyl)-1H-imidazol-4-yl]-3-quinolyl]benzoate | 490.2 |

TABLE 1-continued

| No. | Structure | Chemical Name | [M + H]+ |
|-----|-----------|---------------|----------|
| 159 | 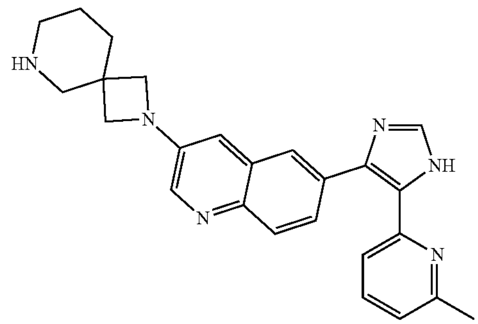 [SMILES: Cc1cccc(-c2[nH]cnc2-c2ccc3ncc(N4CC5(CCCNC5)C4)cc3c2)n1] | 3-(2,8-diazaspiro[3.5]nonan-2-yl)-6-[5-(6-methyl-2-pyridyl)-1H-imidazol-4-yl]quinoline | 411.3 |
| 160 | 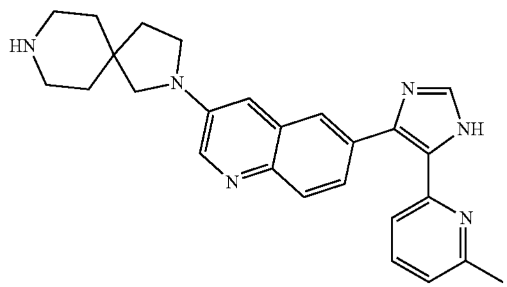 [SMILES: Cc1cccc(-c2[nH]cnc2-c2ccc3ncc(N4CCC5(CCNCC5)C4)cc3c2)n1] | 2-[6-[5-(6-methyl-2-pyridyl)-1H-imidazol-4-yl]-3-quinolyl]-2,8-diazaspiro[4.5]decane | 425.2 |
| 161 | AND Enantiomer | 2-[3-(6-methyl-2-pyridyl)-1H-pyrazol-4-yl]-7-[rac-(1R,5S)-8-azabicyclo[3.2.1]oct-2-en-3-yl]-1,5-naphthyridine | 395.1 |
| 162 | 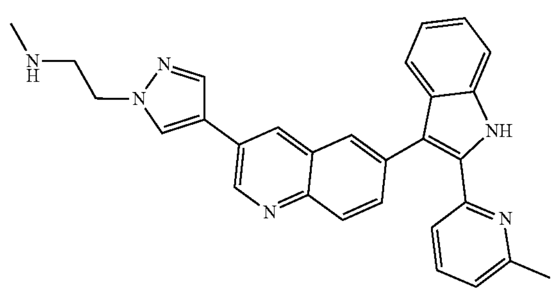 | N-methyl-2-[4-[6-[2-(6-methyl-2-pyridyl)-1H-indol-3-yl]-3-quinolyl]pyrazol-1-yl]ethanamine | 459.0 |
| 163 | 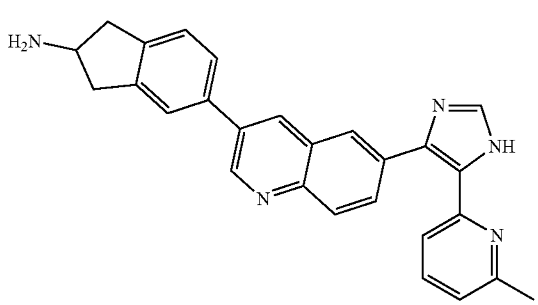 [SMILES: Cc1cccc(-c2[nH]cnc2-c2ccc3ncc(-c4ccc5c(c4)CC(N)C5)cc3c2)n1] | 5-[6-[5-(6-methyl-2-pyridyl)-1H-imidazol-4-yl]-3-quinolyl]indan-2-amine | 418.1 |

TABLE 1-continued

| No. | Structure | Chemical Name | [M + H]+ |
|---|---|---|---|
| 164 | 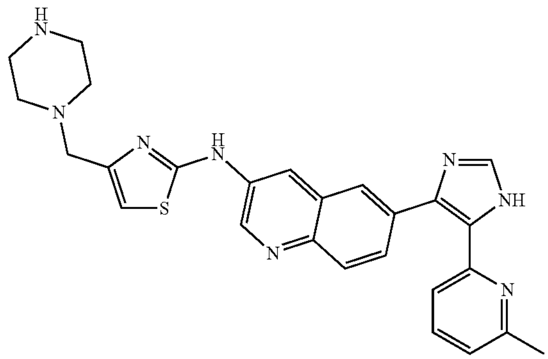 [SMILES: Cc1cccc(-c2[nH]cnc2-c2ccc3ncc(Nc4nc(CN5CCNCC5)cs4)cc3c2)n1] | N-[6-[5-(6-methyl-2-pyridyl)-1H-imidazol-4-yl]-3-quinolyl]-4-(piperazin-1-ylmethyl)thiazol-2-amine | 483.1 |
| 165 | 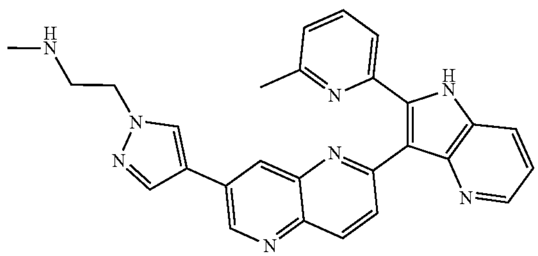 [SMILES: CNCCn1cc(-c2cnc3ccc(-c4c(-c5cccc(C)n5)[nH]c5cccnc45)nc3c2)cn1] | N-methyl-2-[4-[6-[2-(6-methyl-2-pyridyl)-1H-pyrrolo[3,2-b]pyridin-3-yl]-1,5-naphthyridin-3-yl]pyrazol-1-yl]ethanamine | 461.1 |
| 166 | 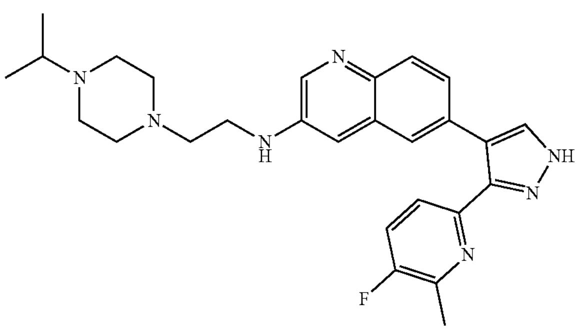 [SMILES: Cc1nc(-c2n[nH]cc2-c2ccc3ncc(NCCN4CCN(C(C)C)CC4)cc3c2)ccc1F] | 6-[3-(5-fluoro-6-methyl-2-pyridyl)-1H-pyrazol-4-yl]-N-[2-(4-isopropylpiperazin-1-yl)ethyl]quinolin-3-amine | 474.2 |
| 167 | 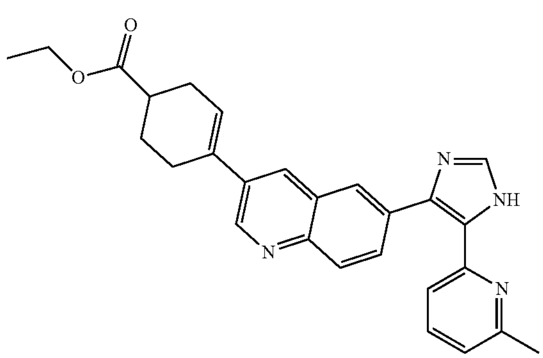 [SMILES: CCOC(=O)C1CC=C(c2cnc3ccc(-c4nc[nH]c4-c4cccc(C)n4)cc3c2)CC1] | ethyl 4-[6-[5-(6-methyl-2-pyridyl)-1H-imidazol-4-yl]-3-quinolyl]cyclohex-3-ene-1-carboxylate | 439.1 |

TABLE 1-continued

| No. | Structure | Chemical Name | [M + H]+ |
|---|---|---|---|
| 168 | 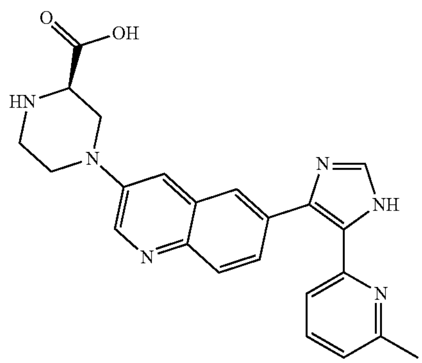 [SMILES: Cc1cccc(-c2[nH]cnc2-c2ccc3ncc(N4CCN[C@@H](C(=O)O)C4)cc3c2)n1] | (2R)-4-[6-[5-(6-methyl-2-pyridyl)-1H-imidazol-4-yl]-3-quinolyl]piperazine-2-carboxylic acid | 415.1 |
| 169 | 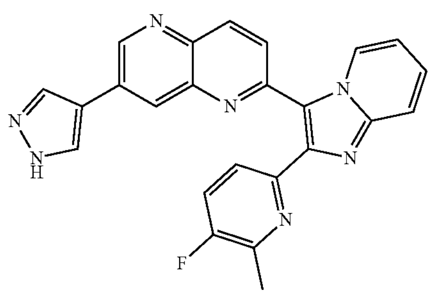 [SMILES: Cc1nc(-c2nc3ccccn3c2-c2ccc3ncc(-c4cn[nH]c4)cc3n2)ccc1F] | 2-[2-(5-fluoro-6-methyl-2-pyridyl)imidazo[1,2-a]pyridin-3-yl]-7-(1H-pyrazol-4-yl)-1,5-naphthyridine | 422.0 |
| 170 | 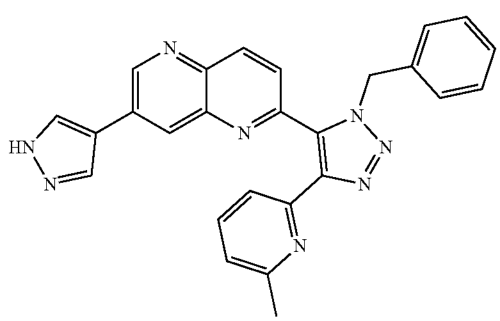 [SMILES: Cc1cccc(-c2nnn(Cc3ccccc3)c2-c2ccc3ncc(-c4cn[nH]c4)cc3n2)n1] | 2-[3-benzyl-5-(6-methyl-2-pyridyl)triazol-4-yl]-7-(1H-pyrazol-4-yl)-1,5-naphthyridine | 445.1 |
| 171 | 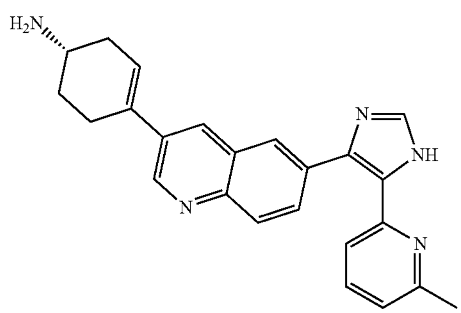 [SMILES: Cc1cccc(-c2[nH]cnc2-c2ccc3ncc(C4=CC[C@@H](N)CC4)cc3c2)n1] | (1S)-4-[6-[5-(6-methyl-2-pyridyl)-1H-imidazol-4-yl]-3-quinolyl]cyclohex-3-en-1-amine | 382.1 |
| 172 | 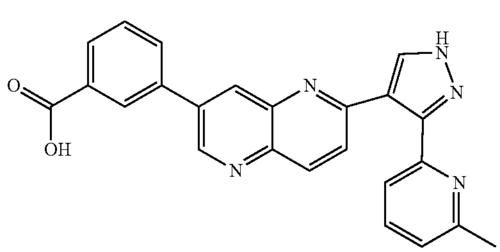 [SMILES: Cc1cccc(-c2n[nH]cc2-c2ccc3ncc(-c4cccc(C(=O)O)c4)cc3n2)n1] | 3-[6-[3-(6-methyl-2-pyridyl)-1H-pyrazol-4-yl]-1,5-naphthyridin-3-yl]benzoic acid | 408.1 |

TABLE 1-continued

| No. | Structure | Chemical Name | [M + H]+ |
|---|---|---|---|
| 173 | 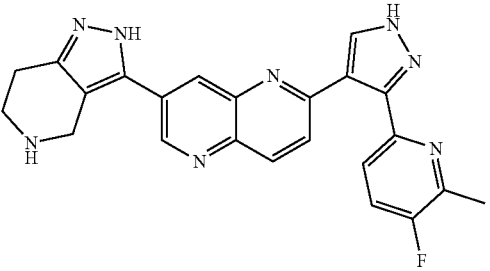 [SMILES: Cc1nc(-c2n[nH]cc2-c2ccc3ncc(-c4[nH]nc5c4CNCC5)cc3n2)ccc1F] | 2-[3-(5-fluoro-6-methyl-2-pyridyl)-1H-pyrazol-4-yl]-7-(4,5,6,7-tetrahydro-2H-pyrazolo[4,3-c]pyridin-3-yl)-1,5-naphthyridine | 427.2 |
| 174 | 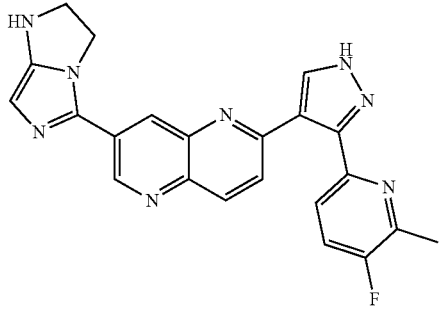 [SMILES: Cc1nc(-c2n[nH]cc2-c2ccc3ncc(-c4ncc5n4CCN5)cc3n2)ccc1F] | 7-(2,3-dihydro-1H-imidazo[1,2-c]imidazol-5-yl)-2-[3-(5-fluoro-6-methyl-2-pyridyl)-1H-pyrazol-4-yl]-1,5-naphthyridine | 413.0 |
| 175 | 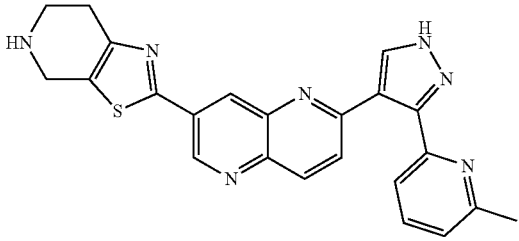 [SMILES: Cc1cccc(-c2n[nH]cc2-c2ccc3ncc(-c4nc5c(s4)CNCC5)cc3n2)n1] | 2-[6-[3-(6-methyl-2-pyridyl)-1H-pyrazol-4-yl]-1,5-naphthyridin-3-yl]-4,5,6,7-tetrahydrothiazolo[5,4-c]pyridine | 426.1 |
| 176 | 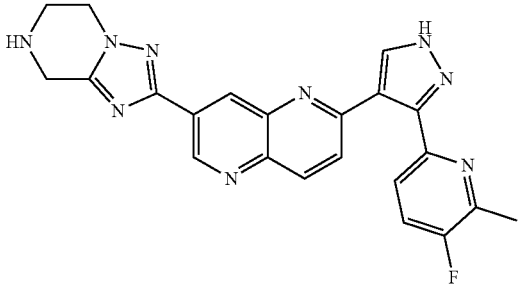 | 2-[3-(5-fluoro-6-methyl-2-pyridyl)-1H-pyrazol-4-yl]-7-(5,6,7,8-tetrahydro-[1,2,4]triazolo[1,5-a]pyrazin-2-yl)-1,5-naphthyridine | 428.1 |
| 177 | 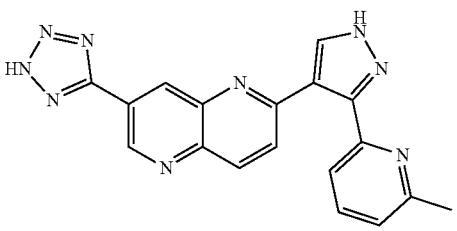 | 2-[3-(6-methyl-2-pyridyl)-1H-pyrazol-4-yl]-7-(2H-tetrazol-5-yl)-1,5-naphthyridine | 356.1 |

TABLE 1-continued

| No. | Structure | Chemical Name | [M + H]+ |
|---|---|---|---|
| 178 | 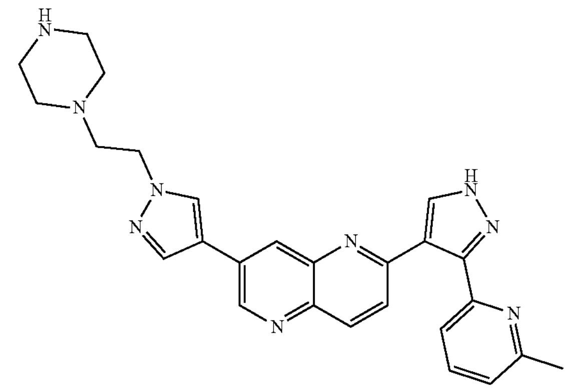 [SMILES: Cc1cccc(-c2n[nH]cc2-c2ccc3ncc(-c4cnn(CCN5CCNCC5)c4)cc3n2)n1] | 2-[3-(6-methyl-2-pyridyl)-1H-pyrazol-4-yl]-7-[1-(2-piperazin-1-ylethyl)pyrazol-4-yl]-1,5-naphthyridine | 466.2 |
| 179 | 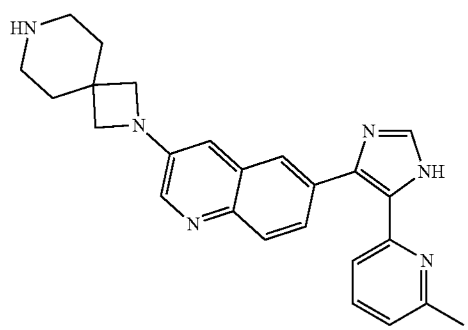 [SMILES: Cc1cccc(-c2[nH]cnc2-c2ccc3ncc(N4CC5(CCNCC5)C4)cc3c2)n1] | 3-(2,7-diazaspiro[3.5]nonan-2-yl)-6-[5-(6-methyl-2-pyridyl)-1H-imidazol-4-yl]quinoline | 411.2 |
| 180 | 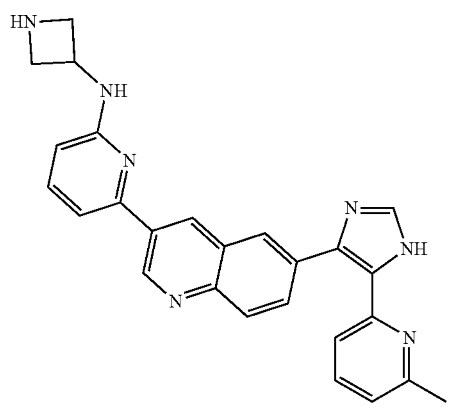 [SMILES: Cc1cccc(-c2[nH]cnc2-c2ccc3ncc(-c4cccc(NC5CNC5)n4)cc3c2)n1] | N-(azetidin-3-yl)-6-[6-[5-(6-methyl-2-pyridyl)-1H-imidazol-4-yl]-3-quinolyl]pyridin-2-amine | 434.1 |
| 181 | 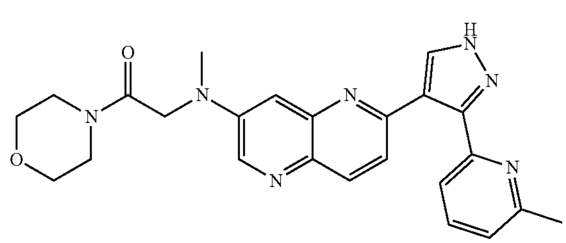 [SMILES: Cc1cccc(-c2n[nH]cc2-c2ccc3ncc(N(C)CC(=O)N4CCOCC4)cc3n2)n1] | 2-[methyl-[6-[3-(6-methyl-2-pyridyl)-1H-pyrazol-4-yl]-1,5-naphthyridin-3-yl]amino]-1-morpholino-ethanone | 444.3 |
| 182 | 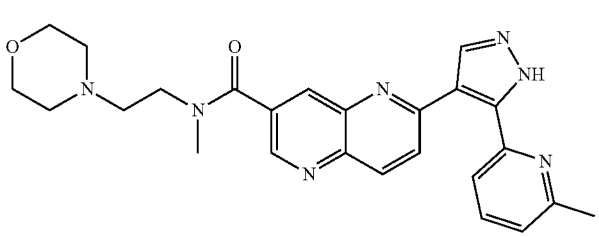 [SMILES: Cc1cccc(-c2[nH]ncc2-c2ccc3ncc(C(=O)N(C)CCN4CCOCC4)cc3n2)n1] | N-methyl-6-[5-(6-methyl-2-pyridyl)-1H-pyrazol-4-yl]-N-(2-morpholinoethyl)-1,5-naphthyridine-3-carboxamide | 457.8 |

TABLE 1-continued

| No. | Structure | Chemical Name | [M + H]+ |
|---|---|---|---|
| 183 | 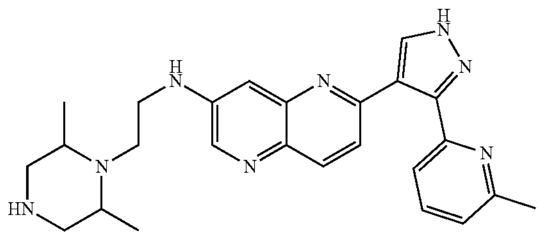 [SMILES: Cc1cccc(-c2n[nH]cc2-c2ccc3ncc(NCCN4C(C)CNCC4C)cc3n2)n1] | N-[2-(2,6-dimethylpiperazin-1-yl)ethyl]-6-[3-(6-methyl-2-pyridyl)-1H-pyrazol-4-yl]-1,5-naphthyridin-3-amine | 443.2 |
| 184 | 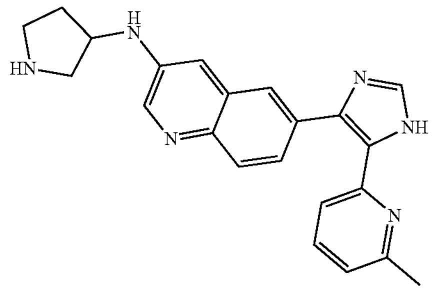 [SMILES: Cc1cccc(-c2[nH]cnc2-c2ccc3ncc(NC4CCNC4)cc3c2)n1] | 6-[5-(6-methyl-2-pyridyl)-1H-imidazol-4-yl]-N-pyrrolidin-3-yl-quinolin-3-amine | 371.0 |
| 185 | 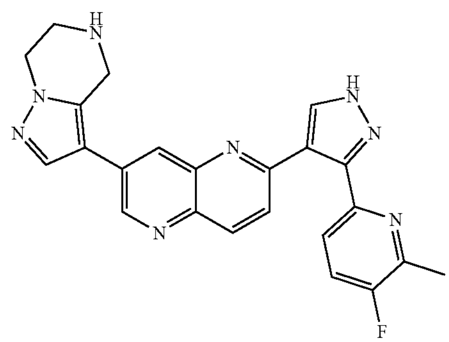 [SMILES: Cc1nc(-c2n[nH]cc2-c2ccc3ncc(-c4cnn5c4CNCC5)cc3n2)ccc1F] | 2-[3-(5-fluoro-6-methyl-2-pyridyl)-1H-pyrazol-4-yl]-7-(4,5,6,7-tetrahydropyrazolo[1,5-a]pyrazin-3-yl)-1,5-naphthyridine | 427.1 |
| 186 | 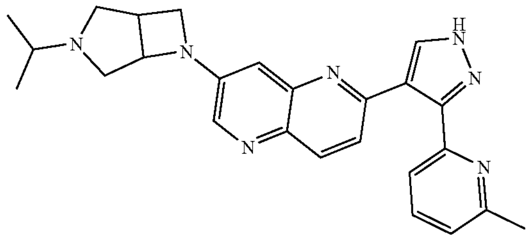 [SMILES: Cc1cccc(-c2n[nH]cc2-c2ccc3ncc(N4CC5CN(C(C)C)CC54)cc3n2)n1] | 7-(3-isopropyl-3,6-diazabicyclo[3.2.0]heptan-6-yl)-2-[3-(6-methyl-2-pyridyl)-1H-pyrazol-4-yl]-1,5-naphthyridine | 426.2 |
| 187 | 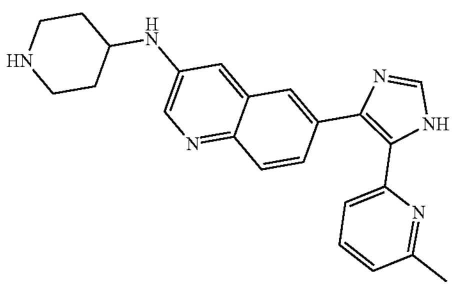 [SMILES: Cc1cccc(-c2[nH]cnc2-c2ccc3ncc(NC4CCNCC4)cc3c2)n1] | 6-[5-(6-methyl-2-pyridyl)-1H-imidazol-4-yl]-N-(4-piperidyl)quinolin-3-amine | 385.1 |

TABLE 1-continued

| No. | Structure | Chemical Name | [M + H]⁺ |
|---|---|---|---|
| 188 | AND Enantiomer | rac-(3S)-N,N-dimethyl-1-[6-[5-(6-methyl-2-pyridyl)-1H-triazol-4-yl]-1,5-naphthyridin-3-yl]pyrrolidin-3-amine | 401.3 |
| 189 | 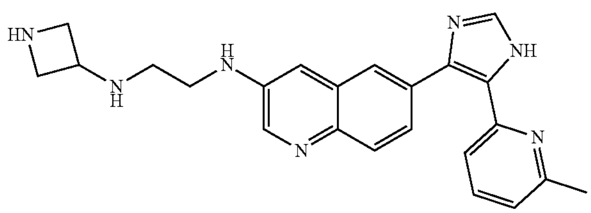 [SMILES: Cc1cccc(-c2[nH]cnc2-c2ccc3ncc(NCCNC4CNC4)cc3c2)n1] | N'-(azetidin-3-yl)-N-[6-[5-(6-methyl-2-pyridyl)-1H-imidazol-4-yl]-3-quinolyl]ethane-1,2-diamine | 400.2 |
| 190 | 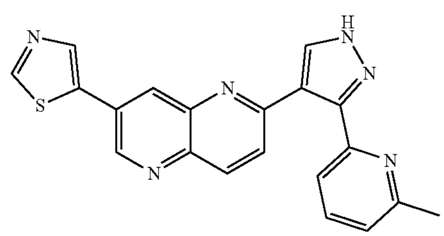 | 5-[6-[3-(6-methyl-2-pyridyl)-1H-pyrazol-4-yl]-1,5-naphthyridin-3-yl]thiazole | 372.2 |
| 191 | 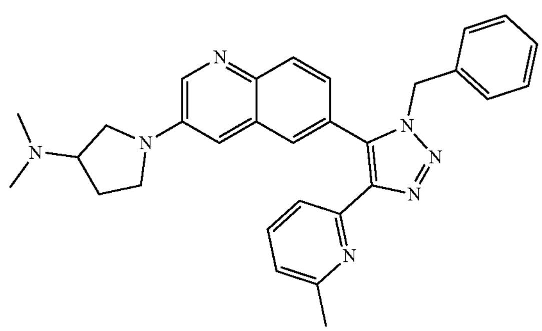 [SMILES: Cc1cccc(-c2nnn(Cc3ccccc3)c2-c2ccc3ncc(N4CCC(N(C)C)C4)cc3c2)n1] | 1-[6-[3-benzyl-5-(6-methyl-2-pyridyl)triazol-4-yl]-3-quinolyl]-N,N-dimethyl-pyrrolidin-3-amine | 490.2 |
| 192 | 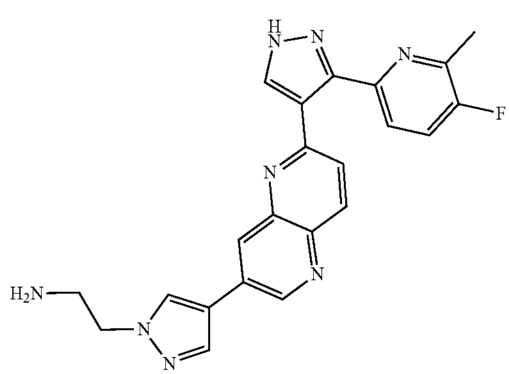 [SMILES: Cc1nc(-c2n[nH]cc2-c2ccc3ncc(-c4cnn(CCN)c4)cc3n2)ccc1F] | 2-[4-[6-[3-(5-fluoro-6-methyl-2-pyridyl)-1H-pyrazol-4-yl]-1,5-naphthyridin-3-yl]pyrazol-1-yl]ethanamine | 415.2 |

TABLE 1-continued

| No. | Structure | Chemical Name | [M + H]⁺ |
|---|---|---|---|
| 193 | 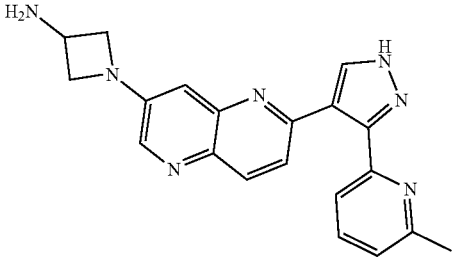 [SMILES: Cc1cccc(-c2n[nH]cc2-c2ccc3ncc(N4CC(N)C4)cc3n2)n1] | 1-[6-[3-(6-methyl-2-pyridyl)-1H-pyrazol-4-yl]-1,5-naphthyridin-3-yl]azetidin-3-amine | 358.1 |
| 194 | AND Enantiomer 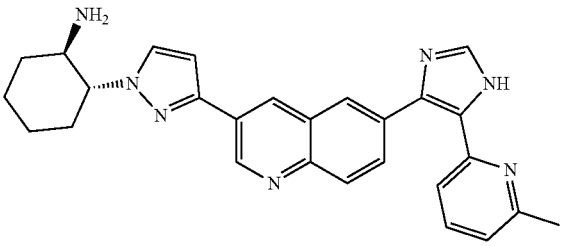 | rac-(1R,2R)-2-[3-[6-[5-(6-methyl-2-pyridyl)-1H-imidazol-4-yl]-3-quinolyl]pyrazol-1-yl]cyclohexanamine | 450.2 |
| 195 | 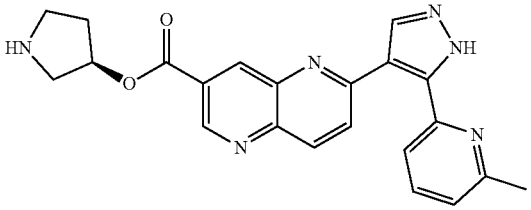 [SMILES: Cc1cccc(-c2[nH]ncc2-c2ccc3ncc(C(=O)O[C@@H]4CCNC4)cc3n2)n1] | [(3R)-pyrrolidin-3-yl] 6-[5-(6-methyl-2-pyridyl)-1H-pyrazol-4-yl]-1,5-naphthyridine-3-carboxylate | 401.1 |
| 196 | 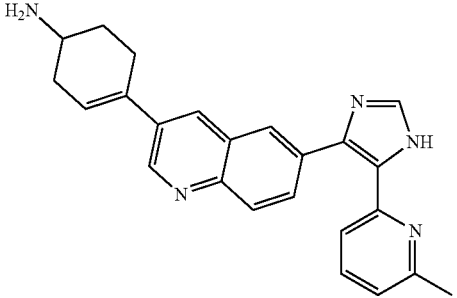 [SMILES: Cc1cccc(-c2[nH]cnc2-c2ccc3ncc(C4=CCC(N)CC4)cc3c2)n1] | 4-[6-[5-(6-methyl-2-pyridyl)-1H-imidazol-4-yl]-3-quinolyl]cyclohex-3-en-1-amine | 382.1 |
| 197 | 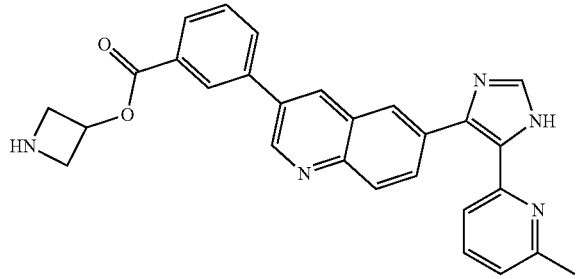 [SMILES: Cc1cccc(-c2[nH]cnc2-c2ccc3ncc(-c4cccc(C(=O)OC5CNC5)c4)cc3c2)n1] | azetidin-3-yl 3-[6-[5-(6-methyl-2-pyridyl)-1H-imidazol-4-yl]-3-quinolyl]benzoate | 462.1 |

TABLE 1-continued

| No. | Structure | Chemical Name | [M + H]+ |
|---|---|---|---|
| 198 | 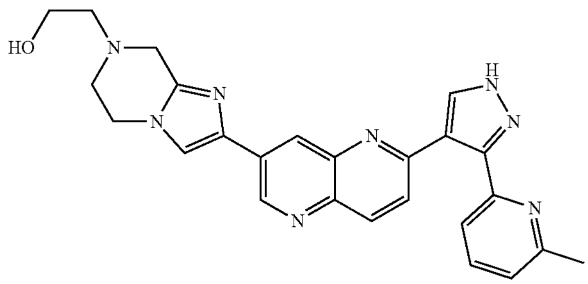 [SMILES: Cc1cccc(-c2n[nH]cc2-c2ccc3ncc(-c4cn5c(n4)CN(CCO)CC5)cc3n2)n1] | 2-[2-[6-[3-(6-methyl-2-pyridyl)-1H-pyrazol-4-yl]-1,5-naphthyridin-3-yl]-6,8-dihydro-5H-imidazo[1,2-a]pyrazin-7-yl]ethanol | 453.2 |
| 199 | 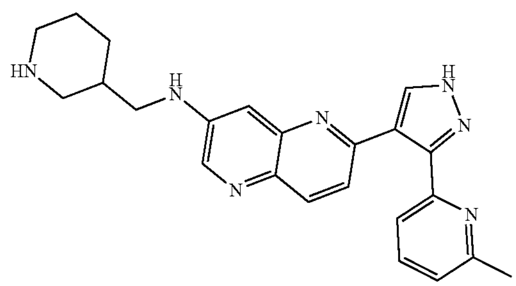 [SMILES: Cc1cccc(-c2n[nH]cc2-c2ccc3ncc(NCC4CCCNC4)cc3n2)n1] | 6-[3-(6-methyl-2-pyridyl)-1H-pyrazol-4-yl]-N-(3-piperidylmethyl)-1,5-naphthyridin-3-amine | 400.2 |
| 200 | 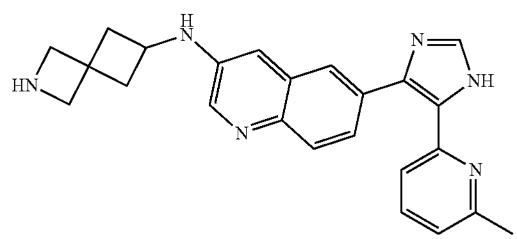 [SMILES: Cc1cccc(-c2[nH]cnc2-c2ccc3ncc(NC4CC5(CNC5)C4)cc3c2)n1] | N-(2-azaspiro[3.3]heptan-6-yl)-6-[5-(6-methyl-2-pyridyl)-1H-imidazol-4-yl]quinolin-3-amine | 397.1 |
| 201 | 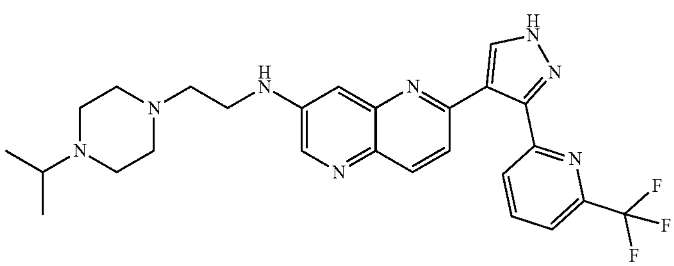 [SMILES: CC(C)N1CCN(CCNc2cnc3ccc(-c4c[nH]nc4-c4cccc(C(F)(F)F)n4)nc3c2)CC1] | N-[2-(4-isopropylpiperazin-1-yl)ethyl]-6-[3-[6-(trifluoromethyl)-2-pyridyl]-1H-pyrazol-4-yl]-1,5-naphthyridin-3-amine | 511.2 |
| 202 | 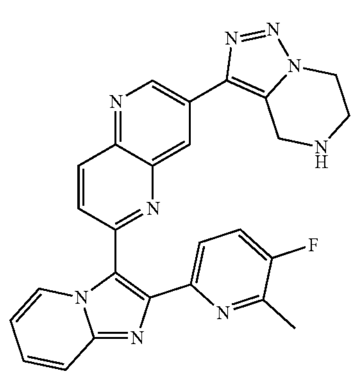 [SMILES: Cc1nc(-c2nc3ccccn3c2-c2ccc3ncc(-c4nnn5c4CNCC5)cc3n2)ccc1F] | 2-[2-(5-fluoro-6-methyl-2-pyridyl)imidazo[1,2-a]pyridin-3-yl]-7-(4,5,6,7-tetrahydrotriazolo[1,5-a]pyrazin-3-yl)-1,5-naphthyridine | 478.2 |

TABLE 1-continued

| No. | Structure | Chemical Name | [M + H]+ |
| --- | --- | --- | --- |
| 203 | 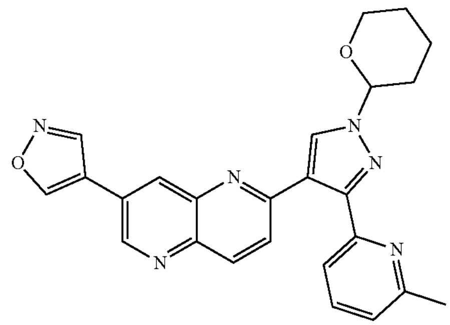 [SMILES: Cc1cccc(-c2nn(C3CCCCO3)cc2-c2ccc3ncc(-c4cnoc4)cc3n2)n1] | 4-[6-[3-(6-methyl-2-pyridyl)-1-tetrahydropyran-2-yl-pyrazol-4-yl]-1,5-naphthyridin-3-yl]isoxazole | 439.1 |
| 204 | 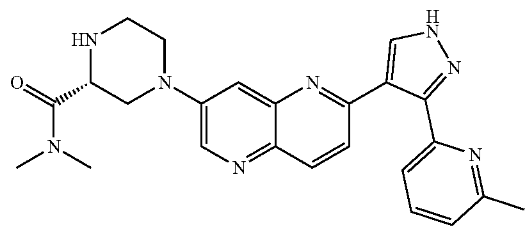 [SMILES: Cc1cccc(-c2n[nH]cc2-c2ccc3ncc(N4CCN[C@@H](C(=O)N(C)C)C4)cc3n2)n1] | (2R)-N,N-dimethyl-4-[6-[3-(6-methyl-2-pyridyl)-1H-pyrazol-4-yl]-1,5-naphthyridin-3-yl]piperazine-2-carboxamide | 443.1 |
| 205 | 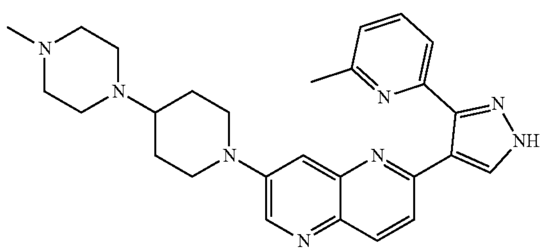 [SMILES: Cc1cccc(-c2n[nH]cc2-c2ccc3ncc(N4CCC(N5CCN(C)CC5)CC4)cc3n2)n1] | 7-[4-(4-methylpiperazin-1-yl)-1-piperidyl]-2-[3-(6-methyl-2-pyridyl)-1H-pyrazol-4-yl]-1,5-naphthyridine | 469.2 |
| 206 | 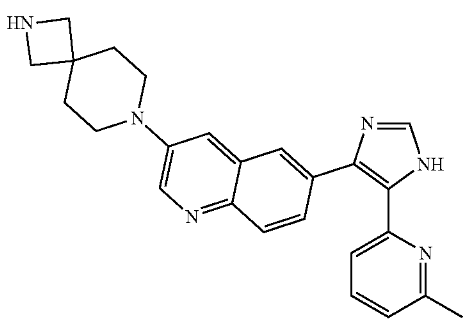 [SMILES: Cc1cccc(-c2[nH]cnc2-c2ccc3ncc(N4CCC5(CC4)CNC5)cc3c2)n1] | 3-(2,7-diazaspiro[3.5]nonan-7-yl)-6-[5-(6-methyl-2-pyridyl)-1H-imidazol-4-yl]quinoline | 411.2 |
| 207 | 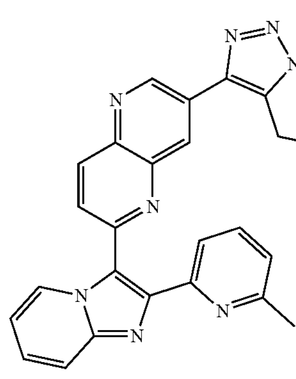 | 2-[2-(6-methyl-2-pyridyl)imidazo[1,2-a]pyridin-3-yl]-7-(4,5,6,7-tetrahydrotriazolo[1,5-a]pyrazin-3-yl)-1,5-naphthyridine | 460.1 |

TABLE 1-continued

| No. | Structure | Chemical Name | [M + H]+ |
|-----|-----------|---------------|----------|
| 208 | 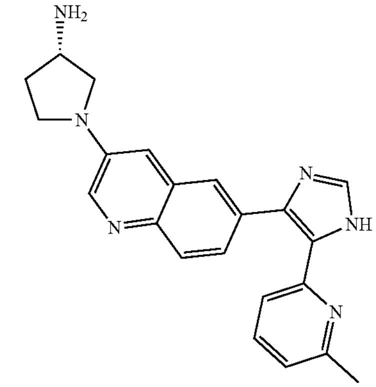 [SMILES: Cc1cccc(-c2[nH]cnc2-c2ccc3ncc(N4CC[C@H](N)C4)cc3c2)n1] | (3S)-1-[6-[5-(6-methyl-2-pyridyl)-1H-imidazol-4-yl]-3-quinolyl]pyrrolidin-3-amine | 371.1 |
| 209 | 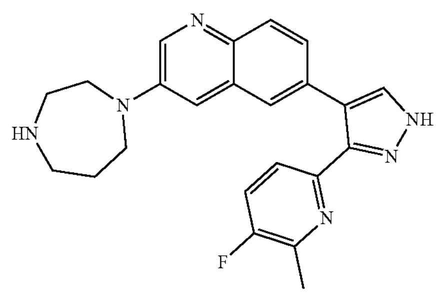 [SMILES: Cc1nc(-c2n[nH]cc2-c2ccc3ncc(N4CCCNCC4)cc3c2)ccc1F] | 3-(1,4-diazepan-1-yl)-6-[3-(5-fluoro-6-methyl-2-pyridyl)-1H-pyrazol-4-yl]quinoline | 403.2 |
| 210 | 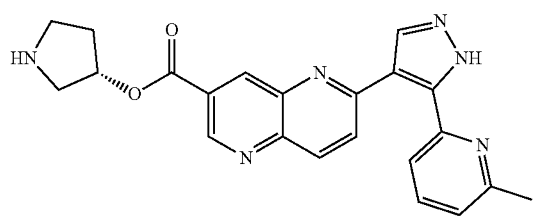 | [(3S)-pyrrolidin-3-yl]6-[5-(6-methyl-2-pyridyl)-1H-pyrazol-4-yl]-1,5-naphthyridine-3-carboxylate | 401.2 |
| 211 | 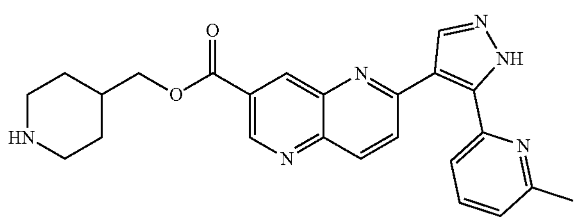 [SMILES: Cc1cccc(-c2[nH]ncc2-c2ccc3ncc(C(=O)OCC4CCNCC4)cc3n2)n1] | 4-piperidylmethyl 6-[5-(6-methyl-2-pyridyl)-1H-pyrazol-4-yl]-1,5-naphthyridine-3-carboxylate | 429.1 |
| 212 | 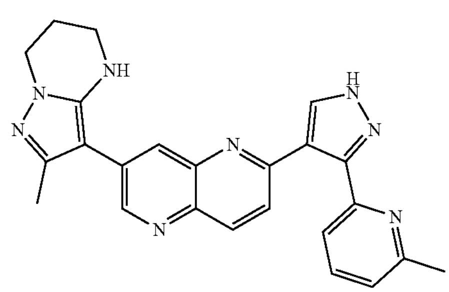 [SMILES: Cc1cccc(-c2n[nH]cc2-c2ccc3ncc(-c4c(C)nn5c4NCCC5)cc3n2)n1] | 2-[3-(6-methyl-2-pyridyl)-1H-pyrazol-4-yl]-7-(2-methyl-4,5,6,7-tetrahydropyrazolo[1,5-a]pyrimidin-3-yl)-1,5-naphthyridine | 423.1 |
| 213 | 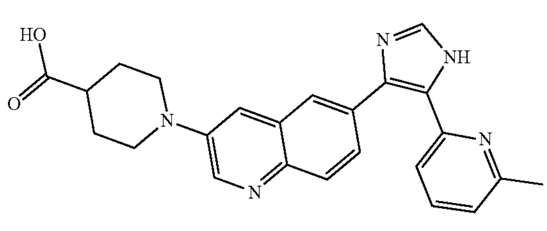 [SMILES: Cc1cccc(-c2[nH]cnc2-c2ccc3ncc(N4CCC(C(=O)O)CC4)cc3c2)n1] | 1-[6-[5-(6-methyl-2-pyridyl)-1H-imidazol-4-yl]-3-quinolyl]piperidine-4-carboxylic acid | 414.2 |

TABLE 1-continued

| No. | Structure | Chemical Name | [M + H]+ |
|---|---|---|---|
| 214 | 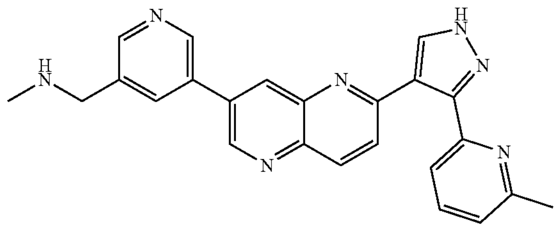 | N-methyl-1-[5-[6-[3-(6-methyl-2-pyridyl)-1H-pyrazol-4-yl]-1,5-naphthyridin-3-yl]-3-pyridyl]methanamine | 408.2 |
| 215 | 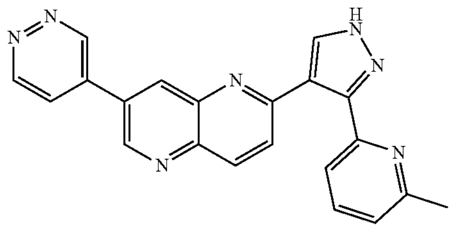 [SMILES: Cc1cccc(-c2n[nH]cc2-c2ccc3ncc(-c4ccnnc4)cc3n2)n1] | 2-[3-(6-methyl-2-pyridyl)-1H-pyrazol-4-yl]-7-pyridazin-4-yl-1,5-naphthyridine | 366.0 |
| 216 | 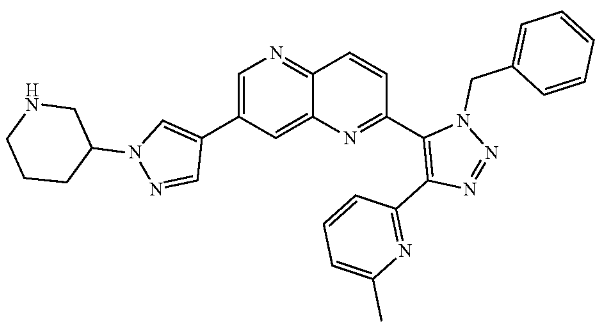 [SMILES: Cc1cccc(-c2nnn(Cc3ccccc3)c2-c2ccc3ncc(-c4cnn(C5CCCNC5)c4)cc3n2)n1] | 2-[3-benzyl-5-(6-methyl-2-pyridyl)triazol-4-yl]-7-[1-(3-piperidyl)pyrazol-4-yl]-1,5-naphthyridine | 528.1 |
| 217 | AND Enantiomer | N-[6-[5-(6-methyl-2-pyridyl)-1H-imidazol-4-yl]-3-quinolyl]-N'-[rac-(3R)-3-piperidyl]ethane-1,2-diamine | 428.2 |
| 218 | 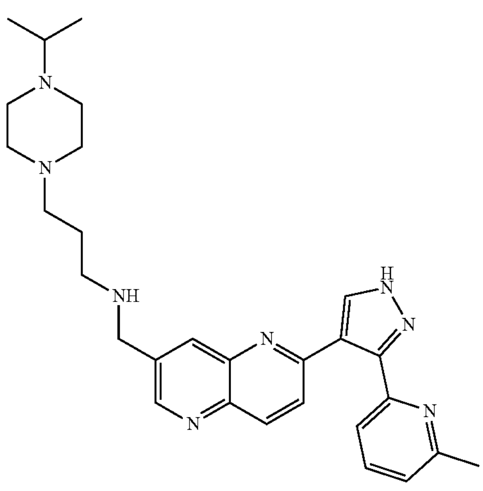 [SMILES: Cc1cccc(-c2n[nH]cc2-c2ccc3ncc(CNCCCN4CCN(C(C)C)CC4)cc3n2)n1] | 3-(4-isopropylpiperazin-1-yl)-N-[[6-[3-(6-methyl-2-pyridyl)-1H-pyrazol-4-yl]-1,5-naphthyridin-3-yl]methyl]propan-1-amine | 484.8 |

TABLE 1-continued

| No. | Structure | Chemical Name | [M + H]+ |
|---|---|---|---|
| 219 | 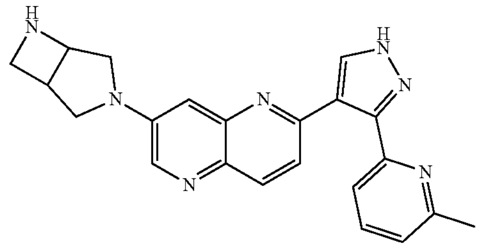 [SMILES: Cc1cccc(-c2n[nH]cc2-c2ccc3ncc(N4CC5CNC5C4)cc3n2)n1] | 7-(3,6-diazabicyclo[3.2.0]heptan-3-yl)-2-[3-(6-methyl-2-pyridyl)-1H-pyrazol-4-yl]-1,5-naphthyridine | 384.1 |
| 220 | 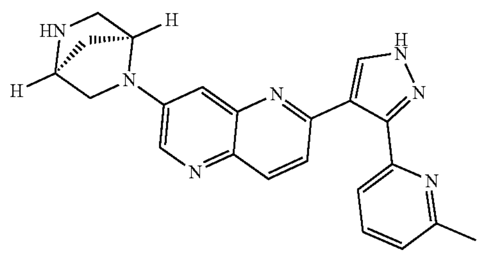 [SMILES: Cc1cccc(-c2n[nH]cc2-c2ccc3ncc(N4C[C@@H]5C[C@H]4CN5)cc3n2)n1] | 7-[(1S,4S)-2,5-diazabicyclo[2.2.1]heptan-2-yl]-2-[3-(6-methyl-2-pyridyl)-1H-pyrazol-4-yl]-1,5-naphthyridine | 384.5 |
| 221 | 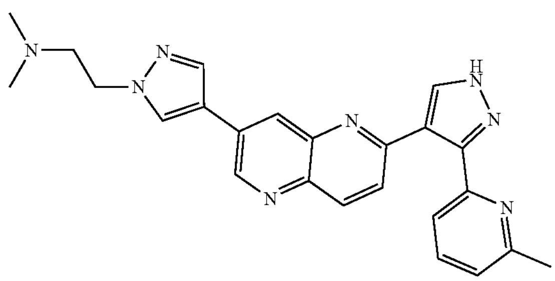 | N,N-dimethyl-2-[4-[6-[3-(6-methyl-2-pyridyl)-1H-pyrazol-4-yl]-1,5-naphthyridin-3-yl]pyrazol-1-yl]ethanamine | 425.1 |
| 222 | 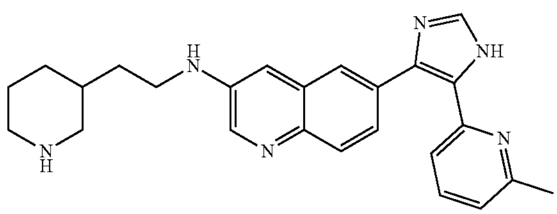 [SMILES: Cc1cccc(-c2[nH]cnc2-c2ccc3ncc(NCCC4CCCNC4)cc3c2)n1] | 6-[5-(6-methyl-2-pyridyl)-1H-imidazol-4-yl]-N-[2-(3-piperidyl)ethyl]quinolin-3-amine | 413.2 |
| 223 | 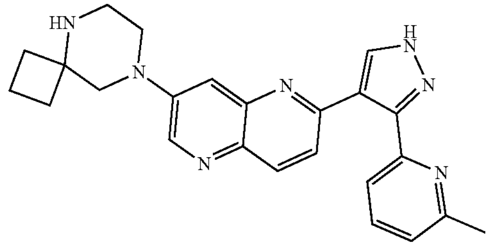 [SMILES: Cc1cccc(-c2n[nH]cc2-c2ccc3ncc(N4CCNC5(CCC5)C4)cc3n2)n1] | 7-(5,8-diazaspiro[3.5]nonan-8-yl)-2-[3-(6-methyl-2-pyridyl)-1H-pyrazol-4-yl]-1,5-naphthyridine | 412.2 |
| 224 | 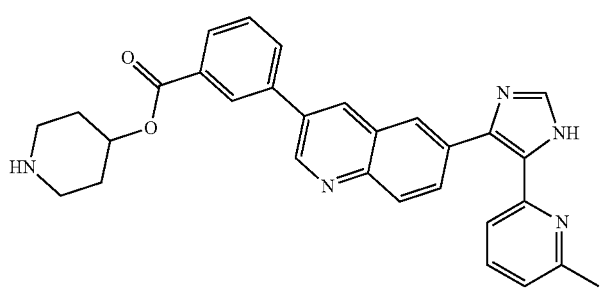 [SMILES: Cc1cccc(-c2[nH]cnc2-c2ccc3ncc(-c4cccc(C(=O)OC5CCNCC5)c4)cc3c2)n1] | 4-piperidyl 3-[6-[5-(6-methyl-2-pyridyl)-1H-imidazol-4-yl]-3-quinolyl]benzoate | 490.1 |

TABLE 1-continued

| No. | Structure | Chemical Name | [M + H]+ |
|---|---|---|---|
| 225 | 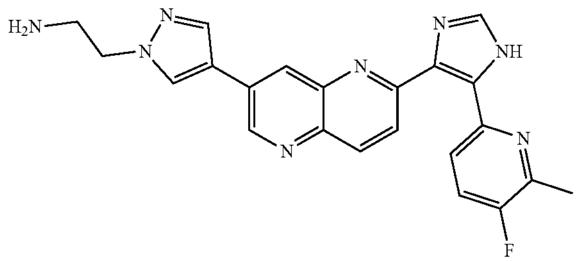 [SMILES: Cc1nc(-c2[nH]cnc2-c2ccc3ncc(-c4cnn(CCN)c4)cc3n2)ccc1F] | 2-[4-[6-[5-(5-fluoro-6-methyl-2-pyridyl)-1H-imidazol-4-yl]-1,5-naphthyridin-3-yl]pyrazol-1-yl]ethanamine | 415.1 |
| 226 | 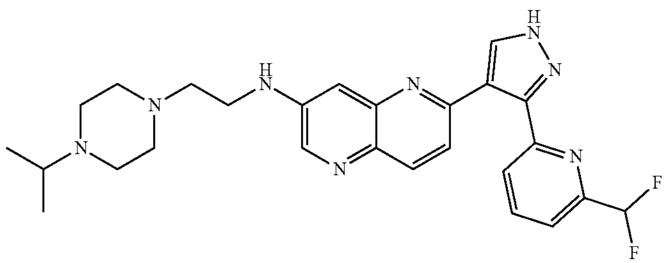 | 6-[3-[6-(difluoromethyl)-2-pyridyl]-1H-pyrazol-4-yl]-N-[2-(4-isopropylpiperazin-1-yl)ethyl]-1,5-naphthyridin-3-amine | 493.2 |
| 227 | 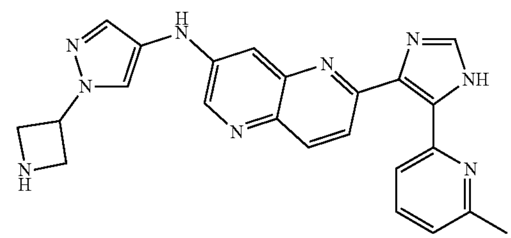 | N-[1-(azetidin-3-yl)pyrazol-4-yl]-6-[5-(6-methyl-2-pyridyl)-1H-imidazol-4-yl]quinolin-3-amine | 423.1 |
| 228 | 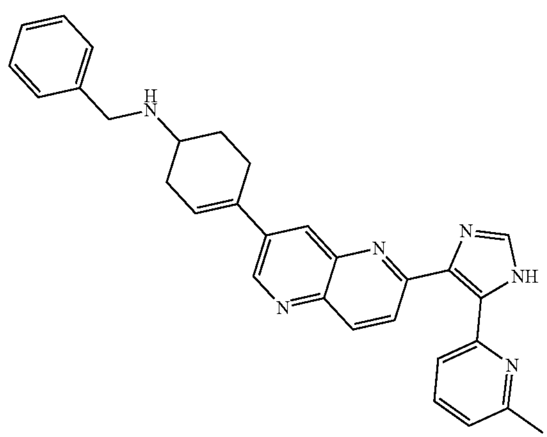 [SMILES: Cc1cccc(-c2[nH]cnc2-c2ccc3ncc(C4=CCC(NCc5ccccc5)CC4)cc3n2)n1] | N-benzyl-4-[6-[5-(6-methyl-2-pyridyl)-1H-imidazol-4-yl]-1,5-naphthyridin-3-yl]cyclohex-3-en-1-amine | 473.1 |
| 229 | 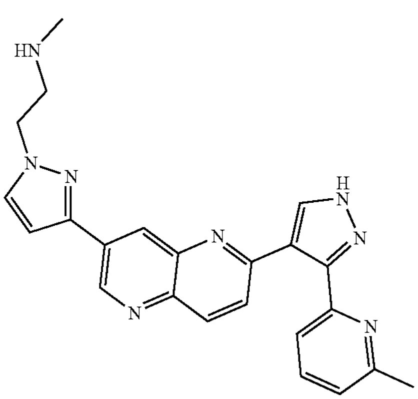 | N-methyl-2-[3-[6-[3-(6-methyl-2-pyridyl)-1H-pyrazol-4-yl]-1,5-naphthyridin-3-yl]pyrazol-1-yl]ethanamine | 411.2 |

TABLE 1-continued

| No. | Structure | Chemical Name | [M + H]⁺ |
|---|---|---|---|
| 230 | 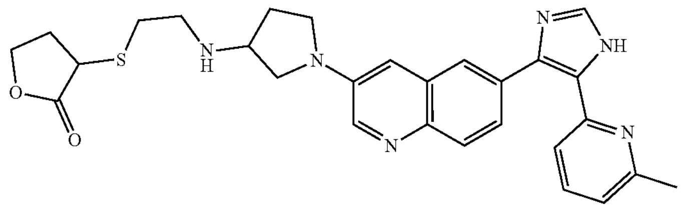 | 3-[2-[[1-[6-[5-(6-methyl-2-pyridyl)-1H-imidazol-4-yl]-3-quinolyl]pyrrolidin-3-yl]amino]ethylsulfanyl]tetrahydrofuran-2-one | 515.3 |
| 231 | 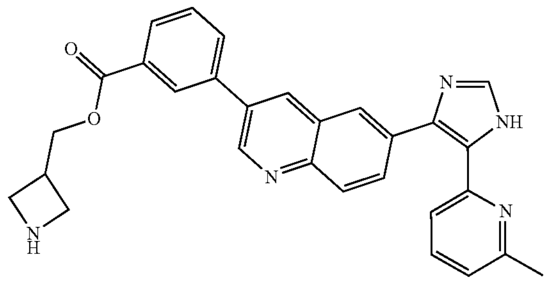 [SMILES: Cc1cccc(-c2[nH]cnc2-c2ccc3ncc(-c4cccc(C(=O)OCC5CNC5)c4)cc3c2)n1] | azetidin-3-ylmethyl 3-[6-[5-(6-methyl-2-pyridyl)-1H-imidazol-4-yl]-3-quinolyl]benzoate | 476.1 |
| 232 | 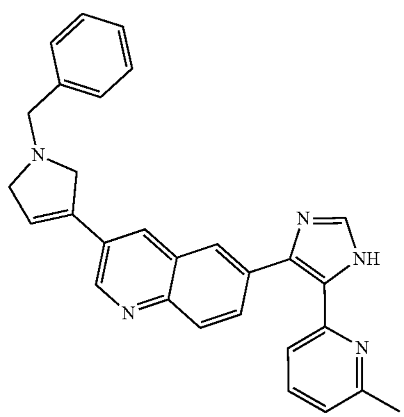 [SMILES: Cc1cccc(-c2[nH]cnc2-c2ccc3ncc(C4=CCN(Cc5ccccc5)C4)cc3c2)n1] | 3-(1-benzyl-2,5-dihydropyrrol-3-yl)-6-[5-(6-methyl-2-pyridyl)-1H-imidazol-4-yl]quinoline | 444.1 |
| 233 | 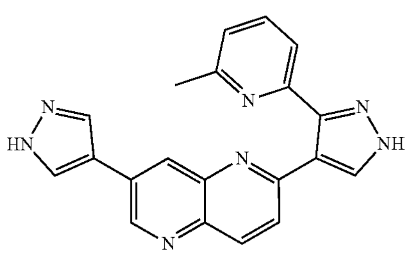 [SMILES: Cc1cccc(-c2n[nH]cc2-c2ccc3ncc(-c4cn[nH]c4)cc3n2)n1] | 2-[3-(6-methyl-2-pyridyl)-1H-pyrazol-4-yl]-7-(1H-pyrazol-4-yl)-1,5-naphthyridine | 354.4 |
| 234 | 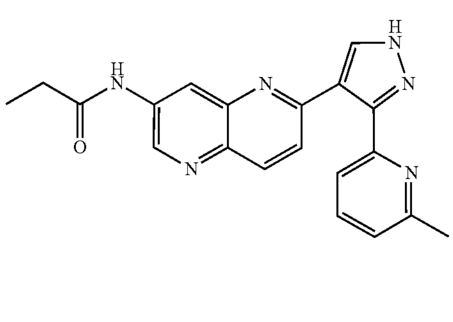 | N-[6-[3-(6-methyl-2-pyridyl)-1H-pyrazol-4-yl]-1,5-naphthyridin-3-yl]propanamide | 358.9 |

TABLE 1-continued

| No. | Structure | Chemical Name | [M + H]+ |
|---|---|---|---|
| 235 | 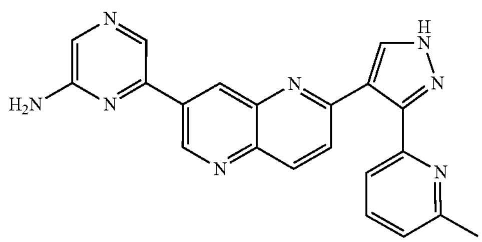 | 6-[6-[3-(6-methyl-2-pyridyl)-1H-pyrazol-4-yl]-1,5-naphthyridin-3-yl]pyrazin-2-amine | 381.2 |
| 236 | 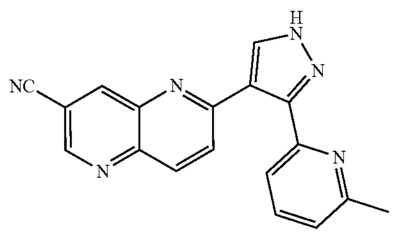 | 6-[3-(6-methyl-2-pyridyl)-1H-pyrazol-4-yl]-1,5-naphthyridine-3-carbonitrile | 313.1 |
| 237 | 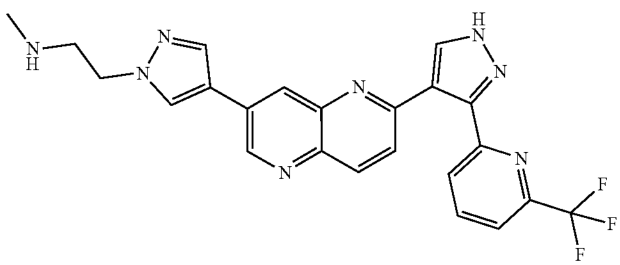 | N-methyl-2-[4-[6-[3-[6-(trifluoromethyl)-2-pyridyl]-1H-pyrazol-4-yl]-1,5-naphthyridin-3-yl]pyrazol-1-yl]ethanamine | 465.0 |
| 238 | 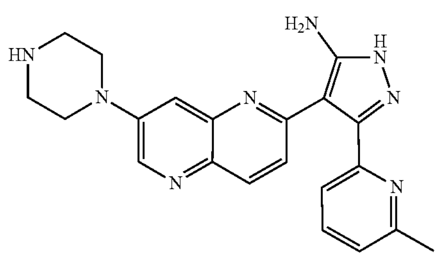 | 3-(6-methyl-2-pyridyl)-4-(7-piperazin-1-yl-1,5-naphthyridin-2-yl)-1H-pyrazol-5-amine | 387.3 |
| 239 | 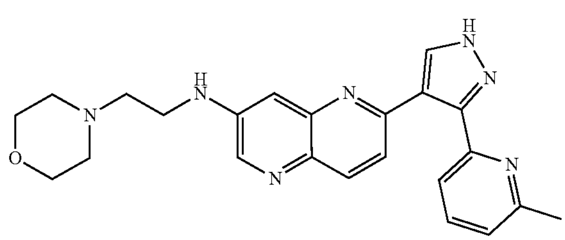 | 6-[3-(6-methyl-2-pyridyl)-1H-pyrazol-4-yl]-N-(2-morpholinoethyl)-1,5-naphthyridin-3-amine | 415.8 |
| 240 | 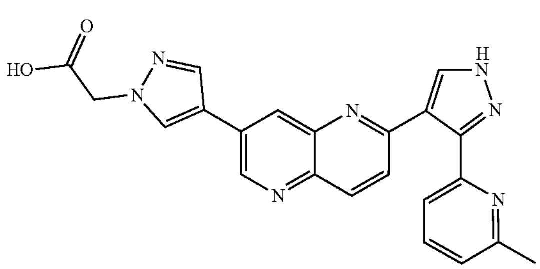 | 2-[4-[6-[3-(6-methyl-2-pyridyl)-1H-pyrazol-4-yl]-1,5-naphthyridin-3-yl]pyrazol-1-yl]acetic acid | 412.2 |

TABLE 1-continued

| No. | Structure | Chemical Name | [M + H]+ |
|---|---|---|---|
| 241 | 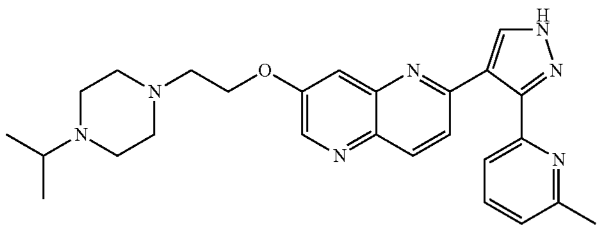 [SMILES: Cc1cccc(-c2n[nH]cc2-c2ccc3ncc(OCCN4CCN(C(C)C)CC4)cc3n2)n1] | 7-[2-(4-isopropylpiperazin-1-yl)ethoxy]-2-[3-(6-methyl-2-pyridyl)-1H-pyrazol-4-yl]-1,5-naphthyridine | 458.3 |
| 242 | AND Enantiomer | N-methyl-6-[3-(6-methyl-2-pyridyl)-1H-pyrazol-4-yl]-N-[rac-(3R)-pyrrolidin-3-yl]-1,5-naphthyridin-3-amine | 386.2 |
| 243 | 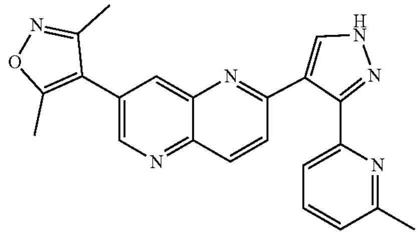 [SMILES: Cc1cccc(-c2n[nH]cc2-c2ccc3ncc(-c4c(C)noc4C)cc3n2)n1] | 3,5-dimethyl-4-[6-[3-(6-methyl-2-pyridyl)-1H-pyrazol-4-yl]-1,5-naphthyridin-3-yl]isoxazole | 388.3 |
| 244 | 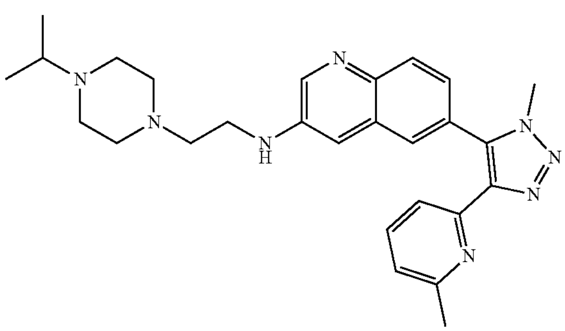 [SMILES: Cc1cccc(-c2nnn(C)c2-c2ccc3ncc(NCCN4CCN(C(C)C)CC4)cc3c2)n1] | N-[2-(4-isopropylpiperazin-1-yl)ethyl]-6-[3-methyl-5-(6-methyl-2-pyridyl)triazol-4-yl]quinolin-3-amine | 471.2 |
| 245 | 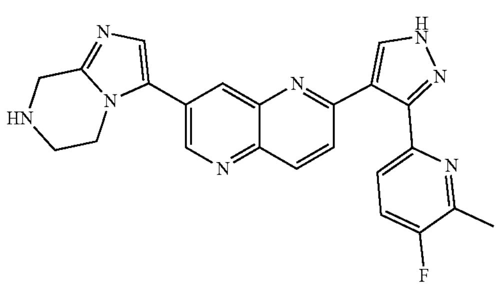 [SMILES: Cc1nc(-c2n[nH]cc2-c2ccc3ncc(-c4cnc5n4CCNC5)cc3n2)ccc1F] | 2-[3-(5-fluoro-6-methyl-2-pyridyl)-1H-pyrazol-4-yl]-7-(5,6,7,8-tetrahydroimidazo[1,2-a]pyrazin-3-yl)-1,5-naphthyridine | 427.2 |

TABLE 1-continued

| No. | Structure | Chemical Name | [M + H]+ |
|---|---|---|---|
| 246 | 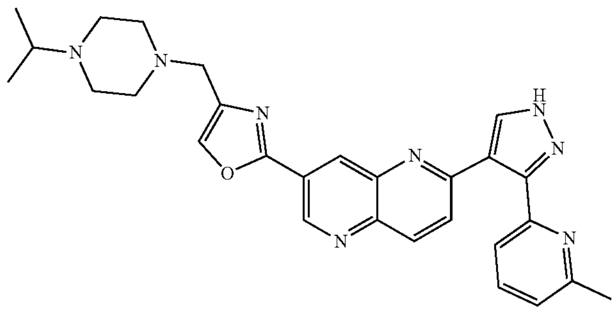 [SMILES: Cc1cccc(-c2n[nH]cc2-c2ccc3ncc(-c4nc(CN5CCN(C(C)C)CC5)co4)cc3n2)n1] | 4-[(4-isopropylpiperazin-1-yl)methyl]-2-[6-[3-(6-methyl-2-pyridyl)-1H-pyrazol-4-yl]-1,5-naphthyridin-3-yl]oxazole | 495.6 |
| 247 | 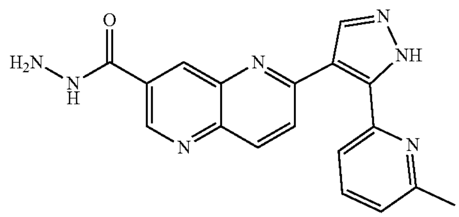 [SMILES: Cc1cccc(-c2[nH]ncc2-c2ccc3ncc(C(=O)NN)cc3n2)n1] | 6-[5-(6-methyl-2-pyridyl)-1H-pyrazol-4-yl]-1,5-naphthyridine-3-carbohydrazide | 346.1 |
| 248 | 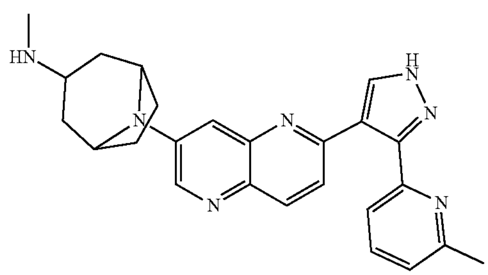 | N-methyl-8-[6-[3-(6-methyl-2-pyridyl)-1H-pyrazol-4-yl]-1,5-naphthyridin-3-yl]-8-azabicyclo[3.2.1]octan-3-amine | 426.1 |
| 249 | 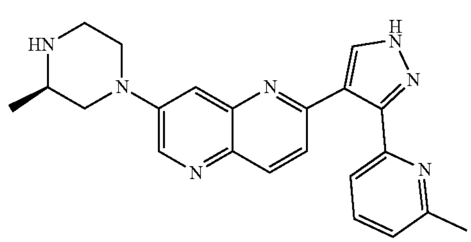 | 7-[(3R)-3-methylpiperazin-1-yl]-2-[3-(6-methyl-2-pyridyl)-1H-pyrazol-4-yl]-1,5-naphthyridine | 386.1 |
| 250 | 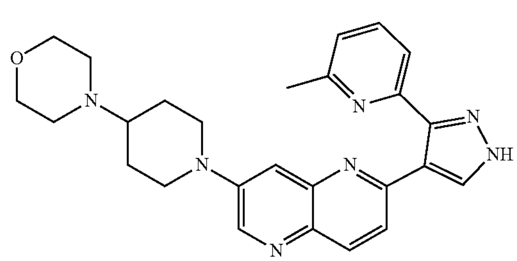 [SMILES: Cc1cccc(-c2n[nH]cc2-c2ccc3ncc(N4CCC(N5CCOCC5)CC4)cc3n2)n1] | 4-[1-[6-[3-(6-methyl-2-pyridyl)-1H-pyrazol-4-yl]-1,5-naphthyridin-3-yl]-4-piperidyl]morpholine | 456.2 |

TABLE 1-continued

| No. | Structure | Chemical Name | [M + H]+ |
|---|---|---|---|
| 251 | 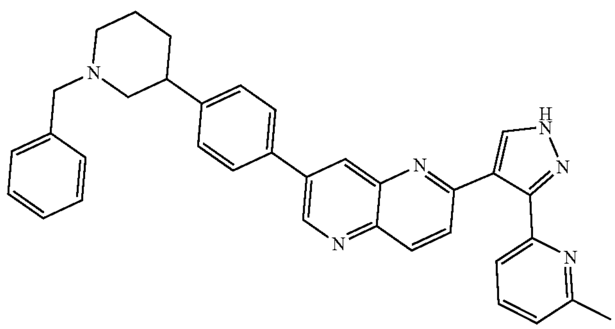 [SMILES: Cc1cccc(-c2n[nH]cc2-c2ccc3ncc(-c4ccc(C5CCCN(Cc6ccccc6)C5)cc4)cc3n2)n1] | 7-[4-(1-benzyl-3-piperidyl)phenyl]-2-[3-(6-methyl-2-pyridyl)-1H-pyrazol-4-yl]-1,5-naphthyridine | 537.1 |
| 252 | 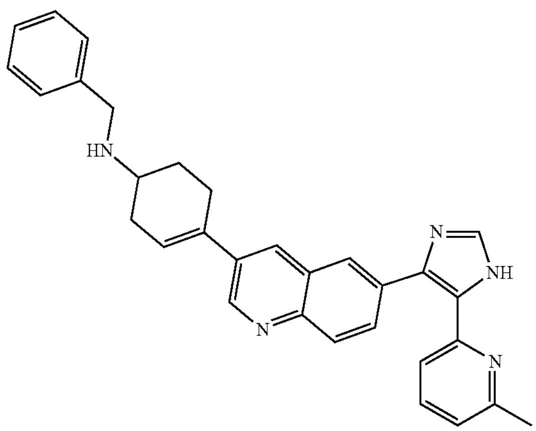 [SMILES: Cc1cccc(-c2[nH]cnc2-c2ccc3ncc(C4=CCC(NCc5ccccc5)CC4)cc3c2)n1] | N-benzyl-4-[6-[5-(6-methyl-2-pyridyl)-1H-imidazol-4-yl]-3-quinolyl]cyclohex-3-en-1-amine | 472.1 |
| 253 | 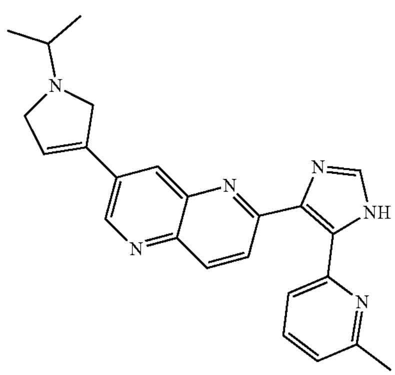 [SMILES: Cc1cccc(-c2[nH]cnc2-c2ccc3ncc(C4=CCN(C(C)C)C4)cc3n2)n1] | 7-(1-isopropyl-2,5-dihydropyrrol-3-yl)-2-[5-(6-methyl-2-pyridyl)-1H-imidazol-4-yl]-1,5-naphthyridine | 397.2 |
| 254 | 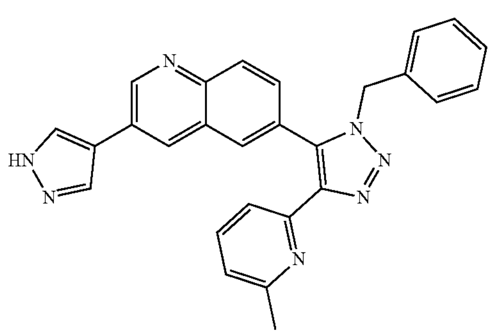 [SMILES: Cc1cccc(-c2nnn(Cc3ccccc3)c2-c2ccc3ncc(-c4cn[nH]c4)cc3c2)n1] | 6-[3-benzyl-5-(6-methyl-2-pyridyl)triazol-4-yl]-3-(1H-pyrazol-4-yl)quinoline | 444.2 |

TABLE 1-continued

| No. | Structure | Chemical Name | [M + H]+ |
|---|---|---|---|
| 255 | 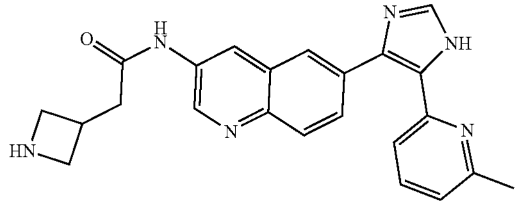 [SMILES: Cc1cccc(-c2[nH]cnc2-c2ccc3ncc(NC(=O)CC4CNC4)cc3c2)n1] | 2-(azetidin-3-yl)-N-[6-[5-(6-methyl-2-pyridyl)-1H-imidazol-4-yl]-3-quinolyl]acetamide | 399.2 |
| 256 | 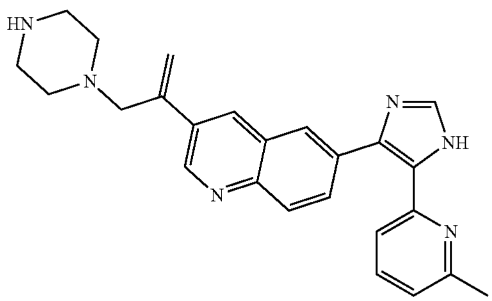 [SMILES: C=C(CN1CCNCC1)c1cnc2ccc(-c3nc[nH]c3-c3cccc(C)n3)cc2c1] | 6-[5-(6-methyl-2-pyridyl)-1H-imidazol-4-yl]-3-[1-(piperazin-1-ylmethyl)vinyl]quinoline | 411.1 |
| 257 | 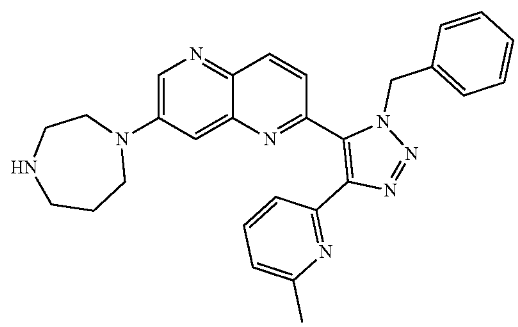 [SMILES: Cc1cccc(-c2nnn(Cc3ccccc3)c2-c2ccc3ncc(N4CCCNCC4)cc3n2)n1] | 2-[3-benzyl-5-(6-methyl-2-pyridyl)triazol-4-yl]-7-(1,4-diazepan-1-yl)-1,5-naphthyridine | 477.2 |
| 258 | 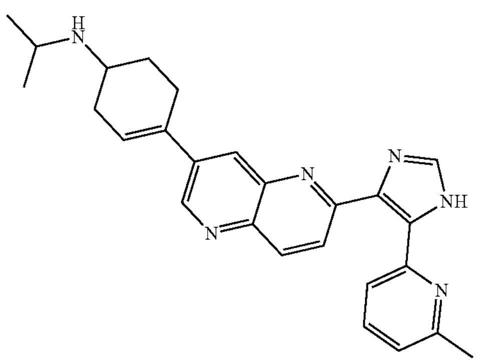 [SMILES: Cc1cccc(-c2[nH]cnc2-c2ccc3ncc(C4=CCC(NC(C)C)CC4)cc3n2)n1] | N-isopropyl-4-[6-[5-(6-methyl-2-pyridyl)-1H-imidazol-4-yl]-1,5-naphthyridin-3-yl]cyclohex-3-en-1-amine | 425.1 |
| 259 | 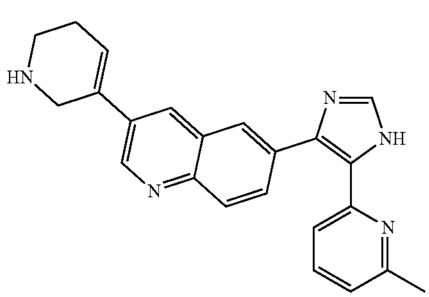 [SMILES: Cc1cccc(-c2[nH]cnc2-c2ccc3ncc(C4=CCCNC4)cc3c2)n1] | 6-[5-(6-methyl-2-pyridyl)-1H-imidazol-4-yl]-3-(1,2,3,6-tetrahydropyridin-5-yl)quinoline | 368.2 |

TABLE 1-continued

| No. | Structure | Chemical Name | [M + H]+ |
|---|---|---|---|
| 260 | 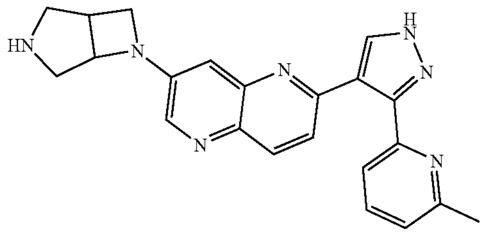 [SMILES: Cc1cccc(-c2n[nH]cc2-c2ccc3ncc(N4CC5CNCC54)cc3n2)n1] | 7-(3,6-diazabicyclo[3.2.0]heptan-6-yl)-2-[3-(6-methyl-2-pyridyl)-1H-pyrazol-4-yl]-1,5-naphthyridine | 384.2 |
| 261 | 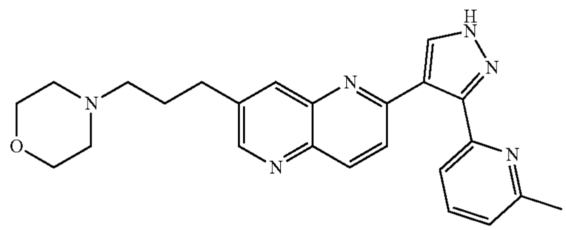 [SMILES: Cc1cccc(-c2n[nH]cc2-c2ccc3ncc(CCCN4CCOCC4)cc3n2)n1] | 4-[3-[6-[3-(6-methyl-2-pyridyl)-1H-pyrazol-4-yl]-1,5-naphthyridin-3-yl]propyl]morpholine | 414.8 |
| 262 | 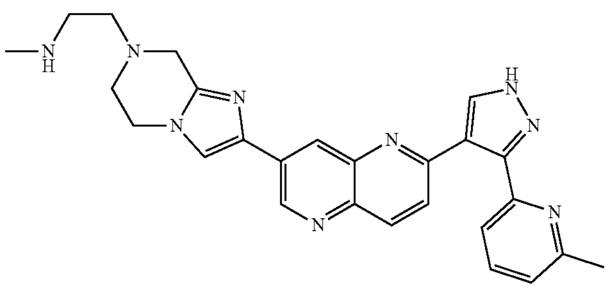 | N-methyl-2-[2-[6-[3-(6-methyl-2-pyridyl)-1H-pyrazol-4-yl]-1,5-naphthyridin-3-yl]-6,8-dihydro-5H-imidazo[1,2-a]pyrazin-7-yl]ethanamine | 466.1 |
| 263 | 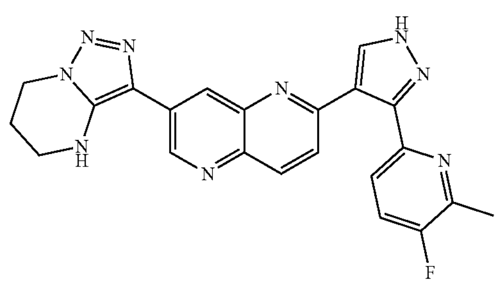 [SMILES: Cc1nc(-c2n[nH]cc2-c2ccc3ncc(-c4nnn5c4NCCC5)cc3n2)ccc1F] | 2-[3-(5-fluoro-6-methyl-2-pyridyl)-1H-pyrazol-4-yl]-7-(4,5,6,7-tetrahydrotriazolo[1,5-a]pyrimidin-3-yl)-1,5-naphthyridine | 428.1 |
| 264 | 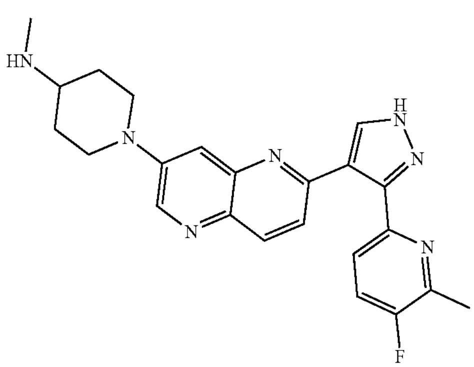 [SMILES: CNC1CCN(c2cnc3ccc(-c4c[nH]nc4-c4ccc(F)c(C)n4)nc3c2)CC1] | 1-[6-[3-(5-fluoro-6-methyl-2-pyridyl)-1H-pyrazol-4-yl]-1,5-naphthyridin-3-yl]-N-methyl-piperidin-4-amine | 418.2 |

TABLE 1-continued

| No. | Structure | Chemical Name | [M + H]+ |
|---|---|---|---|
| 265 | 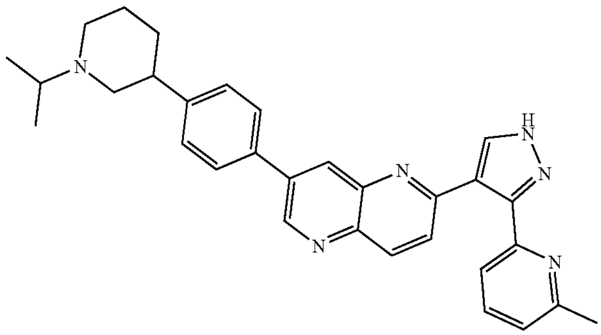 [SMILES: Cc1cccc(-c2n[nH]cc2-c2ccc3ncc(-c4ccc(C5CCCN(C(C)C)C5)cc4)cc3n2)n1] | 7-[4-(1-isopropyl-3-piperidyl)phenyl]-2-[3-(6-methyl-2-pyridyl)-1H-pyrazol-4-yl]-1,5-naphthyridine | 489.1 |
| 266 | 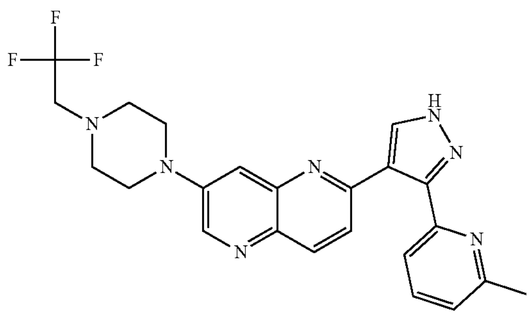 [SMILES: Cc1cccc(-c2n[nH]cc2-c2ccc3ncc(N4CCN(CC(F)(F)F)CC4)cc3n2)n1] | 2-[3-(6-methyl-2-pyridyl)-1H-pyrazol-4-yl]-7-[4-(2,2,2-trifluoroethyl)piperazin-1-yl]-1,5-naphthyridine | 411.3 |
| 267 | 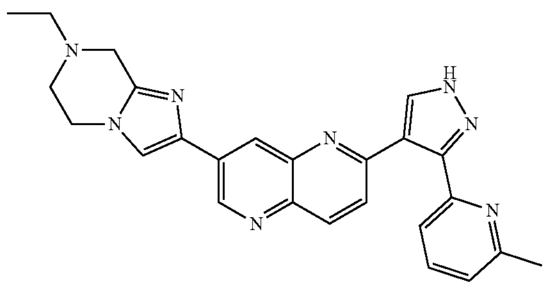 [SMILES: CCN1CCn2cc(-c3cnc4ccc(-c5c[nH]nc5-c5cccc(C)n5)nc4c3)nc2C1] | 7-(7-ethyl-6,8-dihydro-5H-imidazo[1,2-a]pyrazin-2-yl)-2-[3-(6-methyl-2-pyridyl)-1H-pyrazol-4-yl]-1,5-naphthyridine | 437.1 |
| 268 | 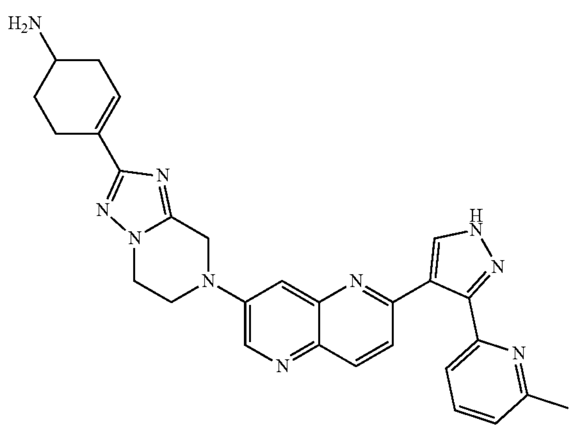 [SMILES: Cc1cccc(-c2n[nH]cc2-c2ccc3ncc(N4CCn5nc(C6=CCC(N)CC6)nc5C4)cc3n2)n1] | 4-[7-[6-[3-(6-methyl-2-pyridyl)-1H-pyrazol-4-yl]-1,5-naphthyridin-3-yl]-6,8-dihydro-5H-[1,2,4]triazolo[1,5-a]pyrazin-2-yl]cyclohex-3-en-1-amine | 505.1 |
| 269 | 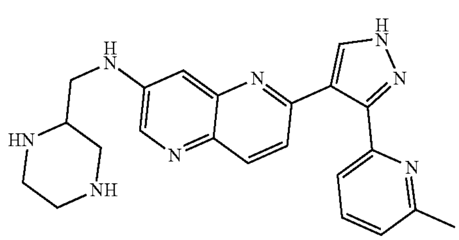 [SMILES: Cc1cccc(-c2n[nH]cc2-c2ccc3ncc(NCC4CNCCN4)cc3n2)n1] | 6-[3-(6-methyl-2-pyridyl)-1H-pyrazol-4-yl]-N-(piperazin-2-ylmethyl)-1,5-naphthyridin-3-amine | 401.2 |

TABLE 1-continued

| No. | Structure | Chemical Name | [M + H]+ |
|---|---|---|---|
| 270 | 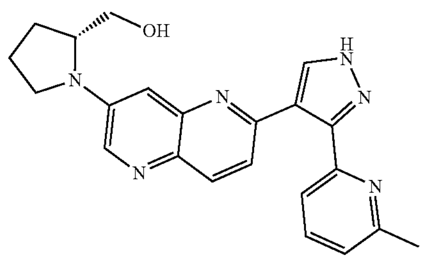 [SMILES: Cc1cccc(-c2n[nH]cc2-c2ccc3ncc(N4CCC[C@@H]4CO)cc3n2)n1] | [(2R)-1-[6-[3-(6-methyl-2-pyridyl)-1H-pyrazol-4-yl]-1,5-naphthyridin-3-yl]pyrrolidin-2-yl]methanol | 387.1 |
| 271 | 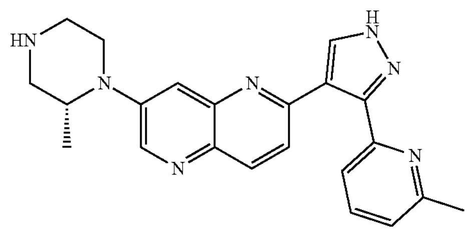 [SMILES: Cc1cccc(-c2n[nH]cc2-c2ccc3ncc(N4CCNC[C@H]4C)cc3n2)n1] | 7-[(2R)-2-methylpiperazin-1-yl]-2-[3-(6-methyl-2-pyridyl)-1H-pyrazol-4-yl]-1,5-naphthyridine | 386.2 |
| 272 | 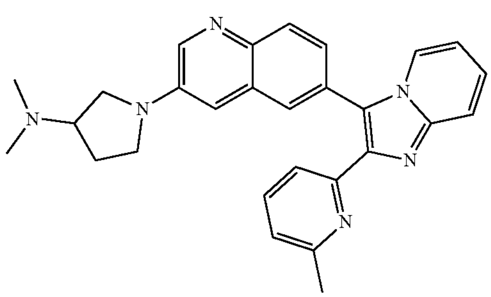 [SMILES: Cc1cccc(-c2nc3ccccn3c2-c2ccc3ncc(N4CCC(N(C)C)C4)cc3c2)n1] | N,N-dimethyl-1-[6-[2-(6-methyl-2-pyridyl)imidazo[1,2-a]pyridin-3-yl]-3-quinolyl]pyrrolidin-3-amine | 449.1 |
| 273 | 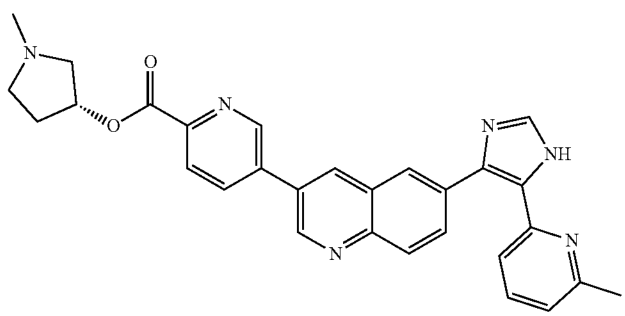 [SMILES: Cc1cccc(-c2[nH]cnc2-c2ccc3ncc(-c4ccc(C(=O)O[C@@H]5CCN(C)C5)nc4)cc3c2)n1] | [(3R)-1-methylpyrrolidin-3-yl] 5-[6-[5-(6-methyl-2-pyridyl)-1H-imidazol-4-yl]-3-quinolyl]pyridine-2-carboxylate | 491.1 |
| 274 | 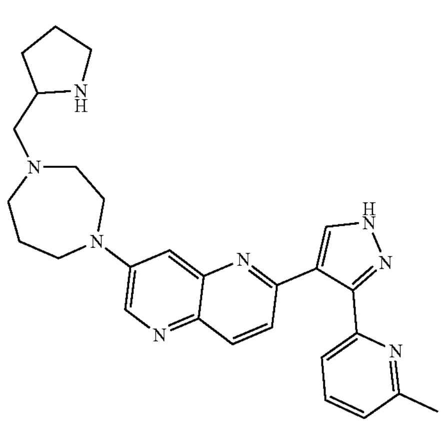 [SMILES: Cc1cccc(-c2n[nH]cc2-c2ccc3ncc(N4CCCN(CC5CCCN5)CC4)cc3n2)n1] | 2-[3-(6-methyl-2-pyridyl)-1H-pyrazol-4-yl]-7-[4-(pyrrolidin-2-ylmethyl)-1,4-diazepan-1-yl]-1,5-naphthyridine | 469.2 |

TABLE 1-continued

| No. | Structure | Chemical Name | [M + H]+ |
|---|---|---|---|
| 275 | 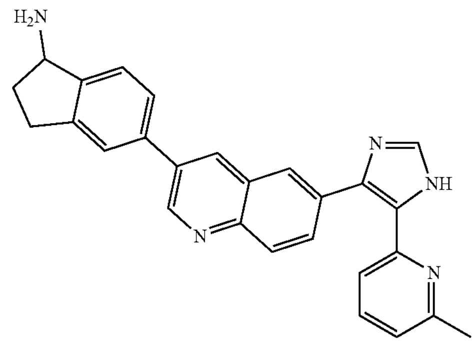 | 5-[6-[5-(6-methyl-2-pyridyl)-1H-imidazol-4-yl]-3-quinolyl]indan-1-amine | 418.1 |
| 276 | 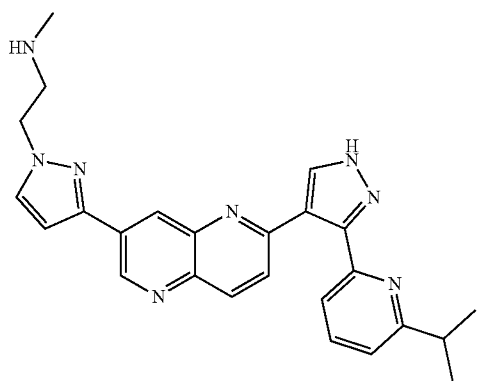 [SMILES: CNCCn1ccc(-c2cnc3ccc(-c4c[nH]nc4-c4cccc(C(C)C)n4)nc3c2)n1] | 2-[3-[6-[3-(6-isopropyl-2-pyridyl)-1H-pyrazol-4-yl]-1,5-naphthyridin-3-yl]pyrazol-1-yl]-N-methyl-ethanamine | 439.1 |
| 277 | 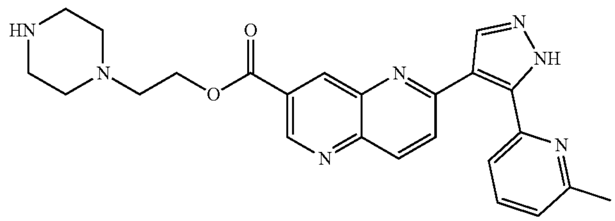 [SMILES: Cc1cccc(-c2[nH]ncc2-c2ccc3ncc(C(=O)OCCN4CCNCC4)cc3n2)n1] | 2-piperazin-1-ylethyl 6-[5-(6-methyl-2-pyridyl)-1H-pyrazol-4-yl]-1,5-naphthyridine-3-carboxylate | 444.1 |
| 278 | 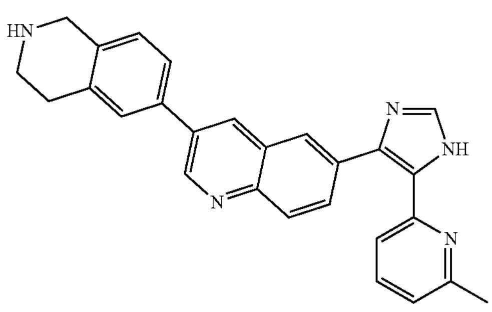 [SMILES: Cc1cccc(-c2[nH]cnc2-c2ccc3ncc(-c4ccc5c(c4)CCNC5)cc3c2)n1] | 6-[5-(6-methyl-2-pyridyl)-1H-imidazol-4-yl]-3-(1,2,3,4-tetrahydroisoquinolin-6-yl)quinoline | 418.1 |
| 279 | 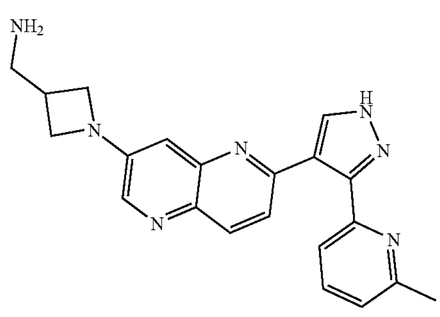 [SMILES: Cc1cccc(-c2n[nH]cc2-c2ccc3ncc(N4CC(CN)C4)cc3n2)n1] | [1-[6-[3-(6-methyl-2-pyridyl)-1H-pyrazol-4-yl]-1,5-naphthyridin-3-yl]azetidin-3-yl]methanamine | 372.3 |

TABLE 1-continued

| No. | Structure | Chemical Name | [M + H]+ |
|---|---|---|---|
| 280 | 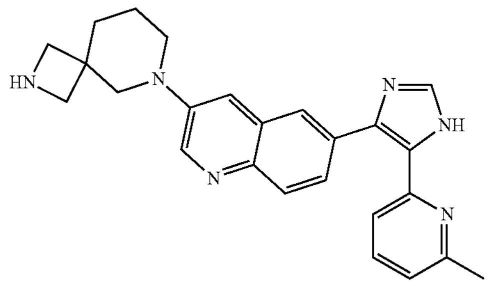 [SMILES: Cc1cccc(-c2[nH]cnc2-c2ccc3ncc(N4CCCC5(CNC5)C4)cc3c2)n1] | 3-(2,6-diazaspiro[3.5]nonan-6-yl)-6-[5-(6-methyl-2-pyridyl)-1H-imidazol-4-yl]quinoline | 411.2 |
| 281 | 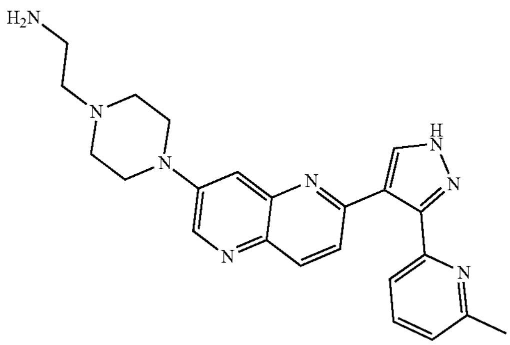 [SMILES: Cc1cccc(-c2n[nH]cc2-c2ccc3ncc(N4CCN(CCN)CC4)cc3n2)n1] | 2-[4-[6-[3-(6-methyl-2-pyridyl)-1H-pyrazol-4-yl]-1,5-naphthyridin-3-yl]piperazin-1-yl]ethanamine | 415.2 |
| 282 | 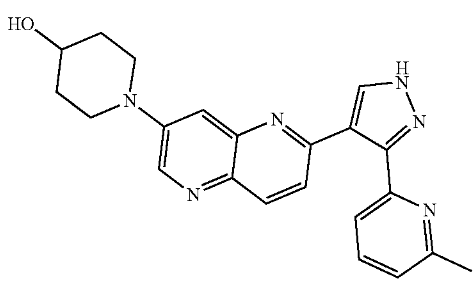 [SMILES: Cc1cccc(-c2n[nH]cc2-c2ccc3ncc(N4CCC(O)CC4)cc3n2)n1] | 1-[6-[3-(6-methyl-2-pyridyl)-1H-pyrazol-4-yl]-1,5-naphthyridin-3-yl]piperidin-4-ol | 387.2 |
| 283 | 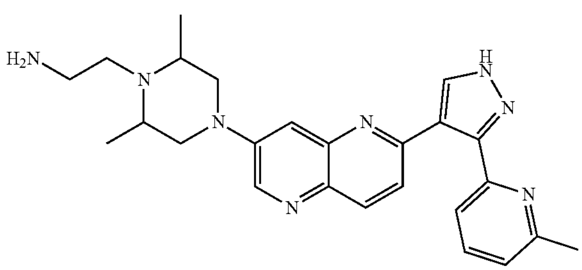 [SMILES: Cc1cccc(-c2n[nH]cc2-c2ccc3ncc(N4CC(C)N(CCN)C(C)C4)cc3n2)n1] | 2-[2,6-dimethyl-4-[6-[3-(6-methyl-2-pyridyl)-1H-pyrazol-4-yl]-1,5-naphthyridin-3-yl]piperazin-1-yl]ethanamine | 443.2 |
| 284 | 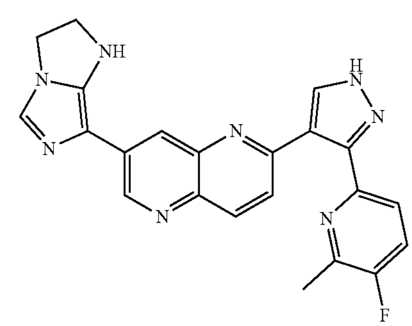 [SMILES: Cc1nc(-c2n[nH]cc2-c2ccc3ncc(-c4ncn5c4NCC5)cc3n2)ccc1F] | 7-(2,3-dihydro-1H-imidazo[1,5-a]imidazol-7-yl)-2-[3-(5-fluoro-6-methyl-2-pyridyl)-1H-pyrazol-4-yl]-1,5-naphthyridine | 413.1 |

| No. | Structure | Chemical Name | [M + H]+ |
|---|---|---|---|
| 285 | AND Enantiomer | rac-(3S)-N,N-dimethyl-1-[6-[2-(6-methyl-2-pyridyl)imidazo[1,2-a]pyridin-3-yl]-1,5-naphthyridin-3-yl]pyrrolidin-3-amine | 450.3 |
| 286 | 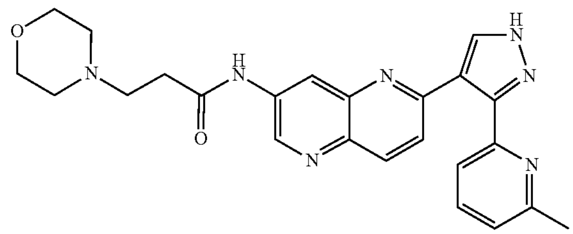 | N-[6-[3-(6-methyl-2-pyridyl)-1H-pyrazol-4-yl]-1,5-naphthyridin-3-yl]-3-morpholino-propanamide | 444.2 |
| 287 | 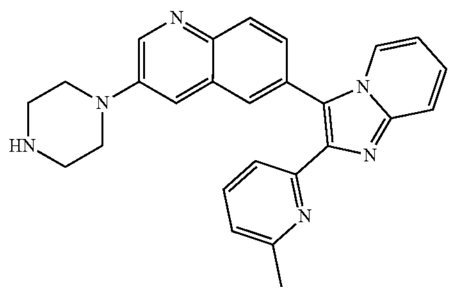 [SMILES: Cc1cccc(-c2nc3ccccn3c2-c2ccc3ncc(N4CCNCC4)cc3c2)n1] | 6-[2-(6-methyl-2-pyridyl)imidazo[1,2-a]pyridin-3-yl]-3-piperazin-1-yl-quinoline | 421.1 |
| 288 | 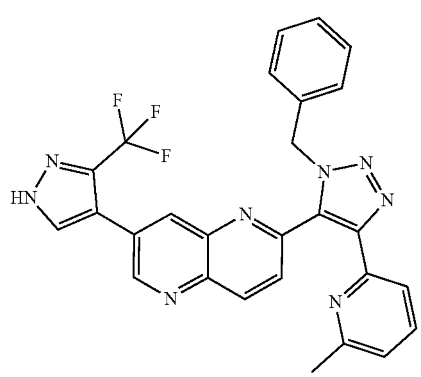 [SMILES: Cc1cccc(-c2nnn(Cc3ccccc3)c2-c2ccc3ncc(-c4c[nH]nc4C(F)(F)F)cc3n2)n1] | 2-[3-benzyl-5-(6-methyl-2-pyridyl)triazol-4-yl]-7-[3-(trifluoromethyl)-1H-pyrazol-4-yl]-1,5-naphthyridine | 513.1 |
| 289 | 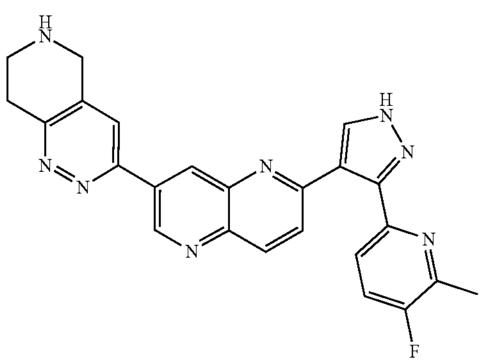 | 3-[6-[3-(5-fluoro-6-methyl-2-pyridyl)-1H-pyrazol-4-yl]-1,5-naphthyridin-3-yl]-5,6,7,8-tetrahydropyrido[4,3-c]pyridazine | 439.1 |

TABLE 1-continued

| No. | Structure | Chemical Name | [M + H]+ |
|---|---|---|---|
| 290 | 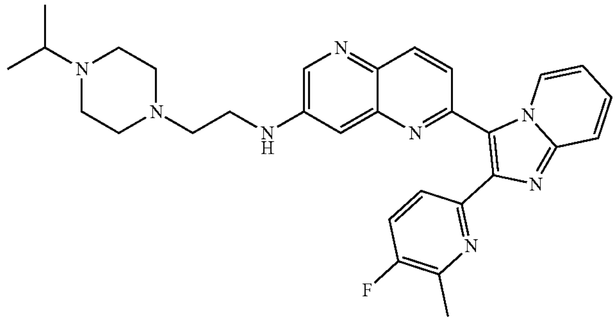 [SMILES: Cc1nc(-c2nc3ccccn3c2-c2ccc3ncc(NCCN4CCN(C(C)C)CC4)cc3n2)ccc1F] | 6-[2-(5-fluoro-6-methyl-2-pyridyl)imidazo[1,2-a]pyridin-3-yl]-N-[2-(4-isopropylpiperazin-1-yl)ethyl]-1,5-naphthyridin-3-amine | 525.2 |
| 291 | 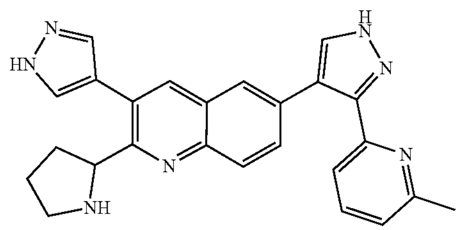 | 6-[3-(6-methyl-2-pyridyl)-1H-pyrazol-4-yl]-3-(1H-pyrazol-4-yl)-2-pyrrolidin-2-yl-quinoline | 422.1 |
| 292 | 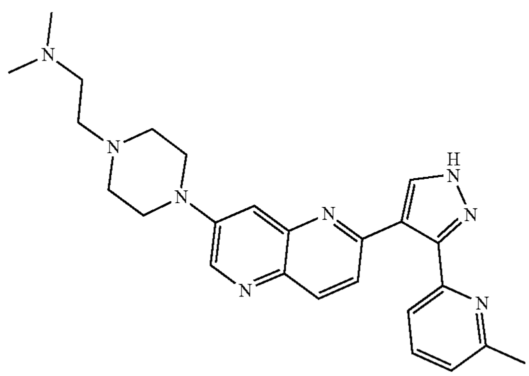 | N,N-dimethyl-2-[4-[6-[3-(6-methyl-2-pyridyl)-1H-pyrazol-4-yl]-1,5-naphthyridin-3-yl]piperazin-1-yl]ethanamine | 443.2 |
| 293 | 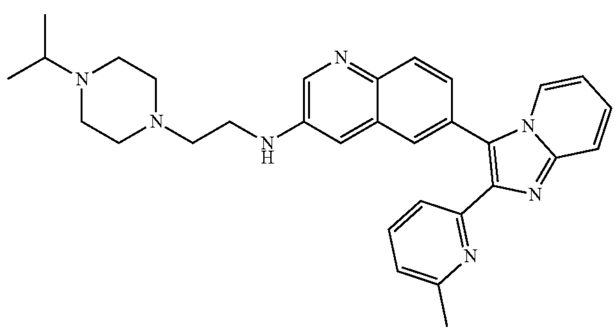 [SMILES: Cc1cccc(-c2nc3ccccn3c2-c2ccc3ncc(NCCN4CCN(C(C)C)CC4)cc3c2)n1] | N-[2-(4-isopropylpiperazin-1-yl)ethyl]-6-[2-(6-methyl-2-pyridyl)imidazo[1,2-a]pyridin-3-yl]quinolin-3-amine | 506.1 |
| 294 | 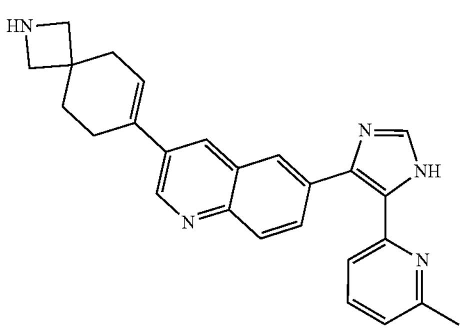 [SMILES: Cc1cccc(-c2[nH]cnc2-c2ccc3ncc(C4=CCC5(CC4)CNC5)cc3c2)n1] | 3-(2-azaspiro[3.5]non-6-en-7-yl)-6-[5-(6-methyl-2-pyridyl)-1H-imidazol-4-yl]quinoline | 408.3 |

TABLE 1-continued

| No. | Structure | Chemical Name | [M + H]⁺ |
|---|---|---|---|
| 295 | 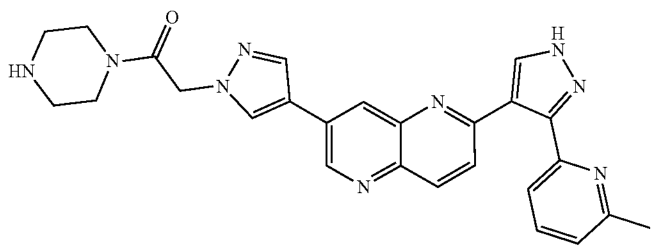 | 2-[4-[6-[3-(6-methyl-2-pyridyl)-1H-pyrazol-4-yl]-1,5-naphthyridin-3-yl]pyrazol-1-yl]-1-piperazin-1-yl-ethanone | 480.2 |
| 296 | AND Enantiomer | 2-[3-(6-methyl-2-pyridyl)-1H-pyrazol-4-yl]-7-[rac-(2R,5R)-2,4,5-trimethylpiperazin-1-yl]-1,5-naphthyridine | 414.2 |
| 297 | 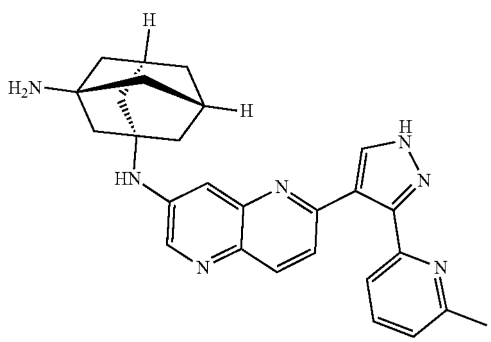 | rac-(5S,7R)-N1-[6-[3-(6-methyl-2-pyridyl)-1H-pyrazol-4-yl]-1,5-naphthyridin-3-yl]adamantane-1,3-diamine | 452.1 |
| 298 | AND Enantiomer | 2-[3-(6-methyl-2-pyridyl)-1H-pyrazol-4-yl]-7-[rac-(3R)-3-(methoxymethyl)piperazin-1-yl]-1,5-naphthyridine | 468.2 |
| 299 | 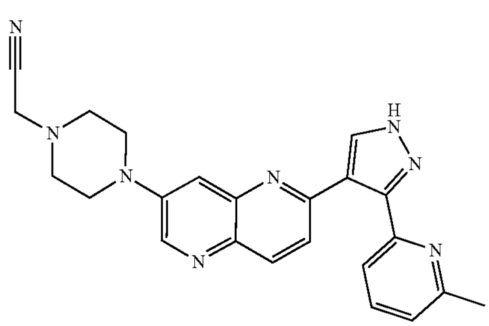 | 2-[4-[6-[3-(6-methyl-2-pyridyl)-1H-pyrazol-4-yl]-1,5-naphthyridin-3-yl]piperazin-1-yl]acetonitrile | 454.1 |

TABLE 1-continued

| No. | Structure | Chemical Name | [M + H]⁺ |
|---|---|---|---|
| 300 | 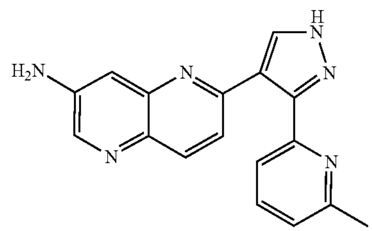 | 6-[3-(6-methyl-2-pyridyl)-1H-pyrazol-4-yl]-1,5-naphthyridin-3-amine | 302.9 |
| 301 | 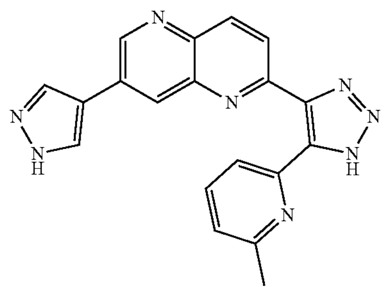 | 2-[5-(6-methyl-2-pyridyl)-1H-triazol-4-yl]-7-(1H-pyrazol-4-yl)-1,5-naphthyridine | 355.2 |
| 302 | 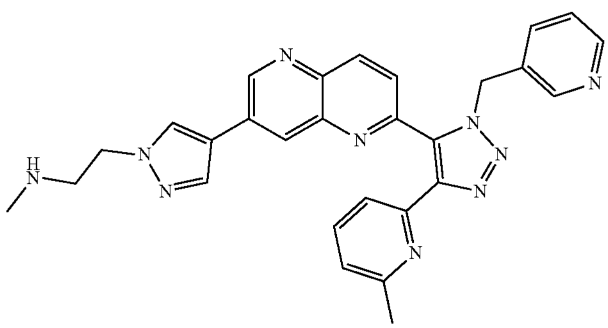 [SMILES: CNCCn1cc(-c2cnc3ccc(-c4c(-c5cccc(C)n5)nnn4Cc4cccnc4)nc3c2)cn1] | N-methyl-2-[4-[6-[5-(6-methyl-2-pyridyl)-3-(3-pyridylmethyl)triazol-4-yl]-3-quinolyl]pyrazol-1-yl]ethanamine | 502.2 |
| 303 | 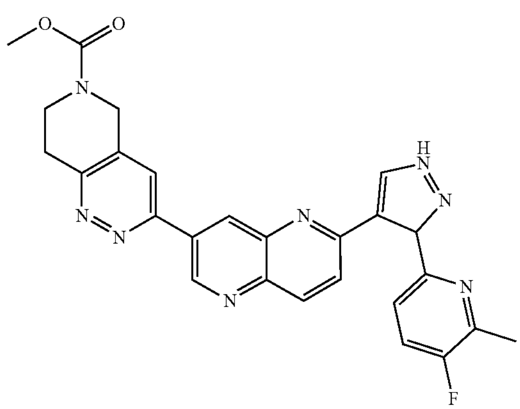 | methyl 3-[6-[3-(5-fluoro-6-methyl-2-pyridyl)-1H-pyrazol-4-yl]-1,5-naphthyridin-3-yl]-7,8-dihydro-5H-pyrido[4,3-c]pyridazine-6-carboxylate | 497.0 |
| 304 | 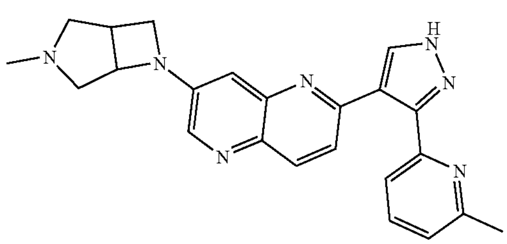 | 7-(3-methyl-3,6-diazabicyclo[3.2.0]heptan-6-yl)-2-[3-(6-methyl-2-pyridyl)-1H-pyrazol-4-yl]-1,5-naphthyridine | 398.1 |

TABLE 1-continued

| No. | Structure | Chemical Name | [M + H]+ |
|---|---|---|---|
| 305 | 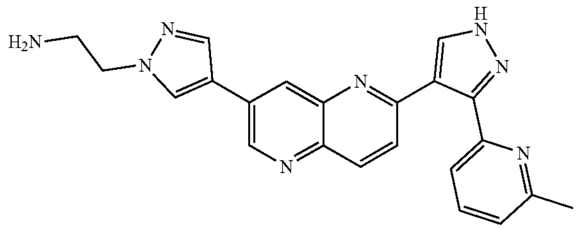 | 2-[4-[6-[3-(6-methyl-2-pyridyl)-1H-pyrazol-4-yl]-1,5-naphthyridin-3-yl]pyrazol-1-yl]ethanamine | 397.2 |
| 306 | 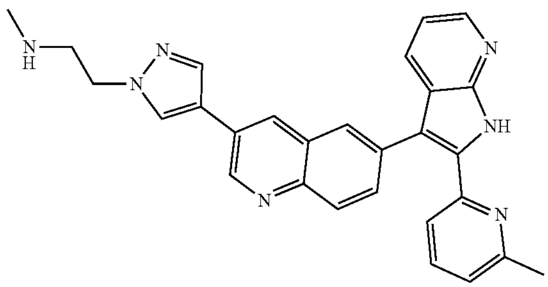 | N-methyl-2-[4-[6-[2-(6-methyl-2-pyridyl)-1H-pyrrolo[2,3-b]pyridin-3-yl]-3-quinolyl]pyrazol-1-yl]ethanamine | 460.1 |
| 307 | 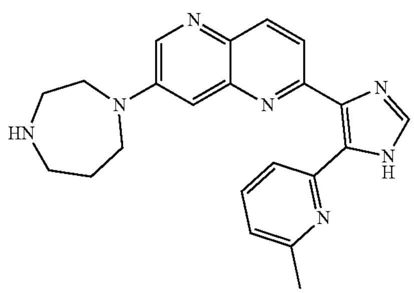 | 7-(1,4-diazepan-1-yl)-2-[5-(6-methyl-2-pyridyl)-1H-imidazol-4-yl]-1,5-naphthyridine | 386.2 |
| 308 | 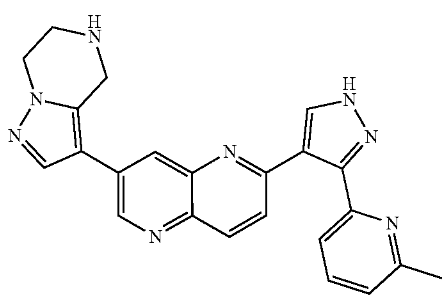 | 2-[3-(6-methyl-2-pyridyl)-1H-pyrazol-4-yl]-7-(4,5,6,7-tetrahydropyrazolo[1,5-a]pyrazin-3-yl)-1,5-naphthyridine | 409.2 |
| 309 | 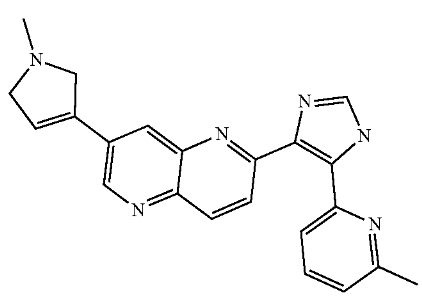 [SMILES: Cc1cccc(-c2[nH]cnc2-c2ccc3ncc(C4=CCN(C)C4)cc3n2)n1] | 7-(1-methyl-2,5-dihydropyrrol-3-yl)-2-[5-(6-methyl-2-pyridyl)-1H-imidazol-4-yl]-1,5-naphthyridine | 369.2 |

TABLE 1-continued

| No. | Structure | Chemical Name | [M + H]+ |
|---|---|---|---|
| 310 | 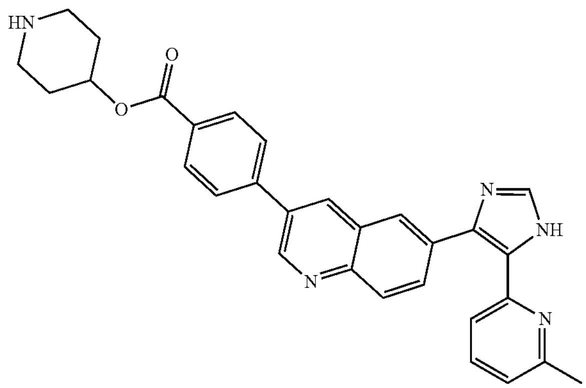 [SMILES: Cc1cccc(-c2[nH]cnc2-c2ccc3ncc(-c4ccc(C(=O)OC5CCNCC5)cc4)cc3c2)n1] | 4-piperidyl 4-[6-[5-(6-methyl-2-pyridyl)-1H-imidazol-4-yl]-3-quinolyl]benzoate | 490.1 |
| 311 | 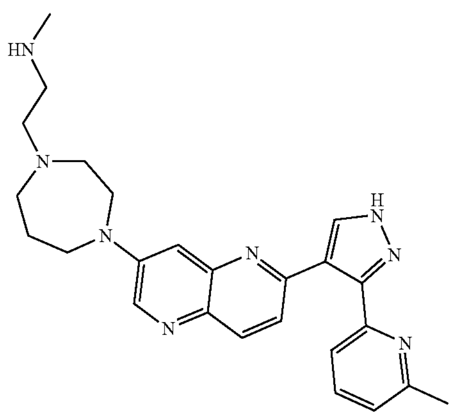 | N-methyl-2-[4-[6-[3-(6-methyl-2-pyridyl)-1H-pyrazol-4-yl]-1,5-naphthyridin-3-yl]-1,4-diazepan-1-yl]ethanamine | 443.2 |
| 312 | AND Enantiomer | rac-(3R)-1-[6-[3-(6-methyl-2-pyridyl)-1H-pyrazol-4-yl]-1,5-naphthyridin-3-yl]pyrrolidin-3-ol | 373.2 |
| 313 | 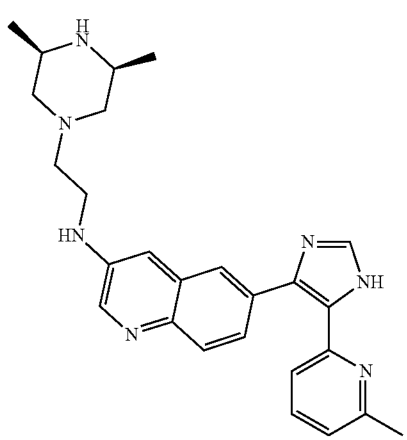 | N-[2-[(3R,5S)-3,5-dimethylpiperazin-1-yl]ethyl]-6-[5-(6-methyl-2-pyridyl)-1H-imidazol-4-yl]quinolin-3-amine | 442.2 |

TABLE 1-continued

| No. | Structure | Chemical Name | [M + H]+ |
|---|---|---|---|
| 314 | 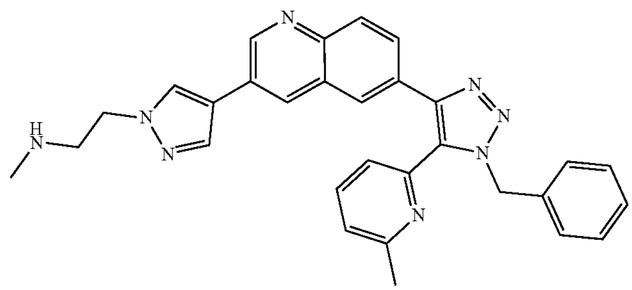 | 2-[4-[6-[1-benzyl-5-(6-methyl-2-pyridyl)triazol-4-yl]-3-quinolyl]pyrazol-1-yl]-N-methyl-ethanamine | 501.3 |
| 315 | 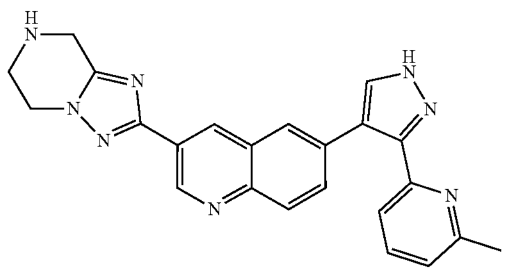 | 6-[3-(6-methyl-2-pyridyl)-1H-pyrazol-4-yl]-3-(5,6,7,8-tetrahydro-[1,2,4]triazolo[1,5-a]pyrazin-2-yl)quinoline | 409.2 |
| 316 | 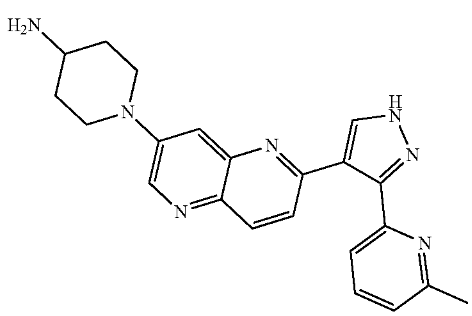 [SMILES: Cc1cccc(-c2n[nH]cc2-c2ccc3ncc(N4CCC(N)CC4)cc3n2)n1] | 1-[6-[3-(6-methyl-2-pyridyl)-1H-pyrazol-4-yl]-1,5-naphthyridin-3-yl]piperidin-4-amine | 386.2 |
| 317 | 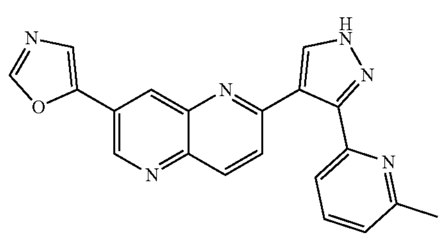 [SMILES: Cc1cccc(-c2n[nH]cc2-c2ccc3ncc(-c4cnco4)cc3n2)n1] | 5-[6-[3-(6-methyl-2-pyridyl)-1H-pyrazol-4-yl]-1,5-naphthyridin-3-yl]oxazole | 354.4 |
| 318 | 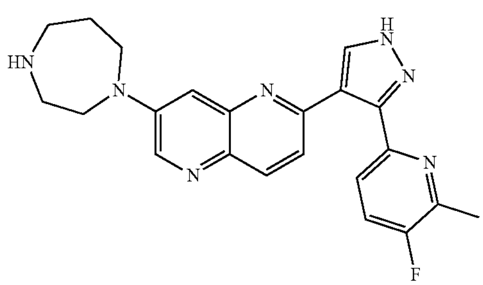 [SMILES: Cc1nc(-c2n[nH]cc2-c2ccc3ncc(N4CCCNCC4)cc3n2)ccc1F] | 7-(1,4-diazepan-1-yl)-2-[3-(5-fluoro-6-methyl-2-pyridyl)-1H-pyrazol-4-yl]-1,5-naphthyridine | 404.5 |

TABLE 1-continued

| No. | Structure | Chemical Name | [M + H]⁺ |
|---|---|---|---|
| 319 | 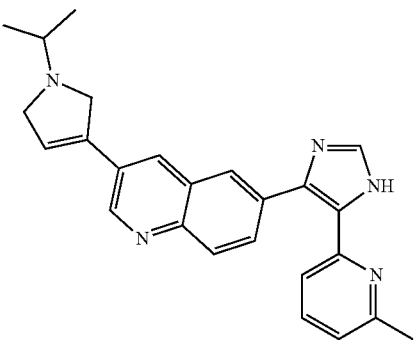 [SMILES: Cc1cccc(-c2[nH]cnc2-c2ccc3ncc(C4=CCN(C(C)C)C4)cc3c2)n1] | 3-(1-isopropyl-2,5-dihydropyrrol-3-yl)-6-[5-(6-methyl-2-pyridyl)-1H-imidazol-4-yl]quinoline | 369.2 |
| 320 | 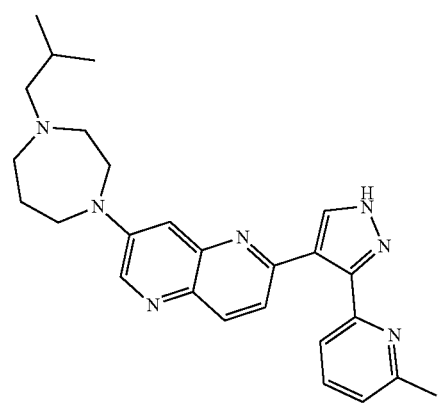 [SMILES: Cc1cccc(-c2n[nH]cc2-c2ccc3ncc(N4CCCN(CC(C)C)CC4)cc3n2)n1] | 7-(4-isobutyl-1,4-diazepan-1-yl)-2-[3-(6-methyl-2-pyridyl)-1H-pyrazol-4-yl]-1,5-naphthyridine | 442.2 |
| 321 | 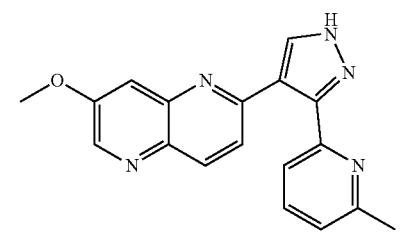 | 7-methoxy-2-[3-(6-methyl-2-pyridyl)-1H-pyrazol-4-yl]-1,5-naphthyridine | 318.4 |
| 322 | 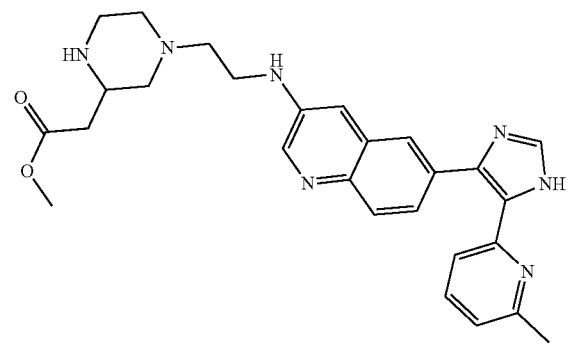 [SMILES: COC(=O)CC1CN(CCNc2cnc3ccc(-c4nc[nH]c4-c4cccc(C)n4)cc3c2)CCN1] | methyl 2-[4-[2-[[6-[5-(6-methyl-2-pyridyl)-1H-imidazol-4-yl]-3-quinolyl]amino]ethyl]piperazin-2-yl]acetate | 486.2 |
| 323 | 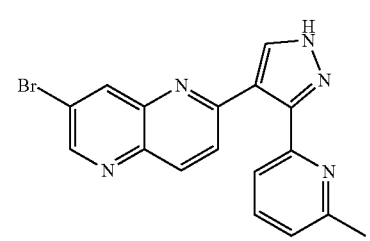 [SMILES: Cc1cccc(-c2n[nH]cc2-c2ccc3ncc(Br)cc3n2)n1] | 7-bromo-2-[3-(6-methyl-2-pyridyl)-1H-pyrazol-4-yl]-1,5-naphthyridine | 366.1 |

TABLE 1-continued

| No. | Structure | Chemical Name | [M + H]+ |
|---|---|---|---|
| 324 | 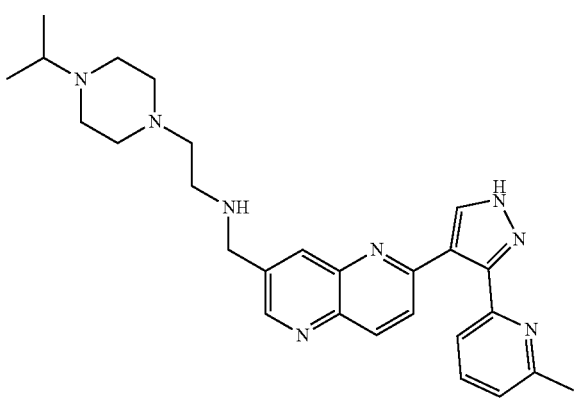 [SMILES: Cc1cccc(-c2n[nH]cc2-c2ccc3ncc(CNCCN4CCN(C(C)C)CC4)cc3n2)n1] | 2-(4-isopropylpiperazin-1-yl)-N-[[6-[3-(6-methyl-2-pyridyl)-1H-pyrazol-4-yl]-1,5-naphthyridin-3-yl]methyl]ethanamine | 470.9 |
| 325 | 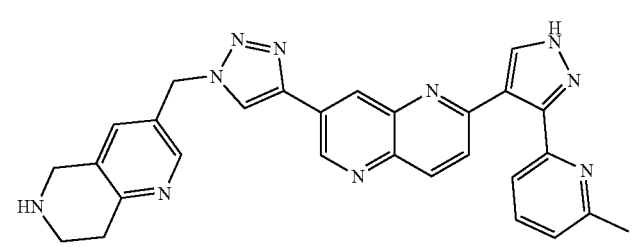 [SMILES: Cc1cccc(-c2n[nH]cc2-c2ccc3ncc(-c4cn(Cc5cnc6c(c5)CNCC6)nn4)cc3n2)n1] | 2-[3-(6-methyl-2-pyridyl)-1H-pyrazol-4-yl]-7-[1-(5,6,7,8-tetrahydro-1,6-naphthyridin-3-ylmethyl)triazol-4-yl]-1,5-naphthyridine | 501.3 |
| 326 | 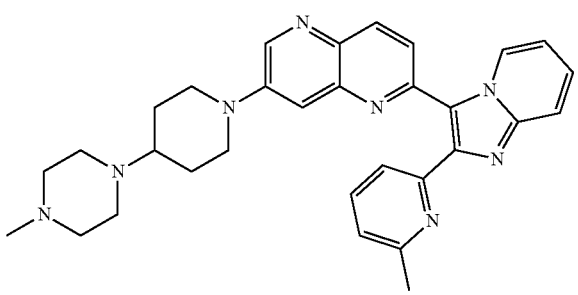 [SMILES: Cc1cccc(-c2nc3ccccn3c2-c2ccc3ncc(N4CCC(N5CCN(C)CC5)CC4)cc3n2)n1] | 7-[4-(4-methylpiperazin-1-yl)-1-piperidyl]-2-[2-(6-methyl-2-pyridyl)imidazo[1,2-a]pyridin-3-yl]-1,5-naphthyridine | 519.3 |
| 327 | 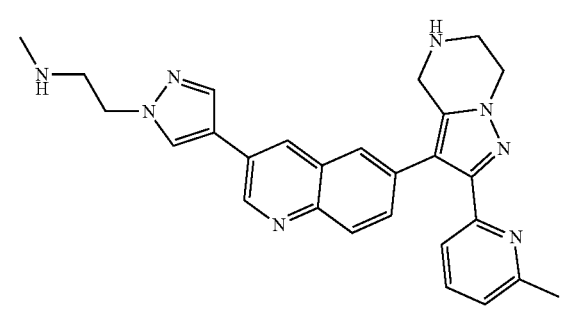 | N-methyl-2-[4-[6-[2-(6-methyl-2-pyridyl)-4,5,6,7-tetrahydropyrazolo[1,5-a]pyrazin-3-yl]-3-quinolyl]pyrazol-1-yl]ethanamine | 465.1 |
| 328 | 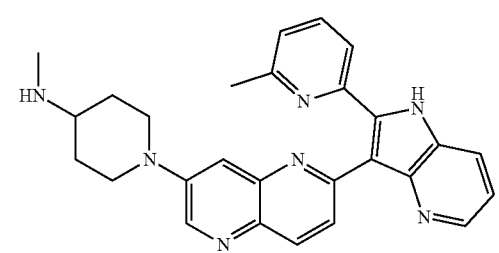 [SMILES: CNC1CCN(c2cnc3ccc(-c4c(-c5cccc(C)n5)[nH]c5cccnc45)nc3c2)CC1] | N-methyl-1-[6-[2-(6-methyl-2-pyridyl)-1H-pyrrolo[3,2-b]pyridin-3-yl]-1,5-naphthyridin-3-yl]piperidin-4-amine | 450.1 |

TABLE 1-continued

| No. | Structure | Chemical Name | [M + H]⁺ |
|---|---|---|---|
| 329 | 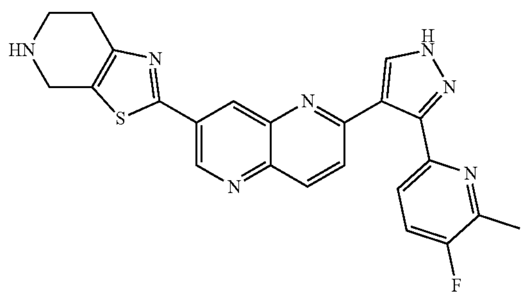 [SMILES: Cc1nc(-c2n[nH]cc2-c2ccc3ncc(-c4nc5c(s4)CNCC5)cc3n2)ccc1F] | 2-[6-[3-(5-fluoro-6-methyl-2-pyridyl)-1H-pyrazol-4-yl]-1,5-naphthyridin-3-yl]-4,5,6,7-tetrahydrothiazolo[5,4-c]pyridine | 444.1 |
| 330 | 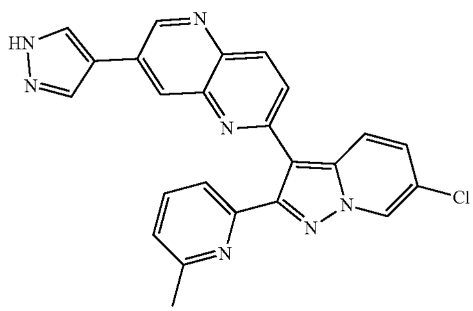 [SMILES: Cc1cccc(-c2nn3cc(Cl)ccc3c2-c2ccc3ncc(-c4cn[nH]c4)cc3n2)n1] | 2-[6-chloro-2-(6-methyl-2-pyridyl)pyrazolo[1,5-a]pyridin-3-yl]-7-(1H-pyrazol-4-yl)-1,5-naphthyridine | 438.1 |
| 331 | AND Enantiomer | rac-(3S)-1-[6-[3-benzyl-5-(6-methyl-2-pyridyl)triazol-4-yl]-1,5-naphthyridin-3-yl]-N,N-dimethyl-pyrrolidin-3-amine | 491.2 |
| 332 | 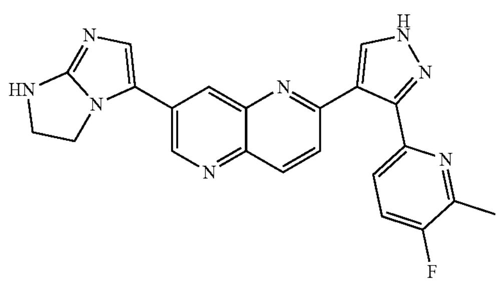 [SMILES: Cc1nc(-c2n[nH]cc2-c2ccc3ncc(-c4cnc5n4CCN5)cc3n2)ccc1F] | 7-(6,7-dihydro-5H-imidazo[1,2-a]imidazol-3-yl)-2-[3-(5-fluoro-6-methyl-2-pyridyl)-1H-pyrazol-4-yl]-1,5-naphthyridine | 413.4 |
| 333 | 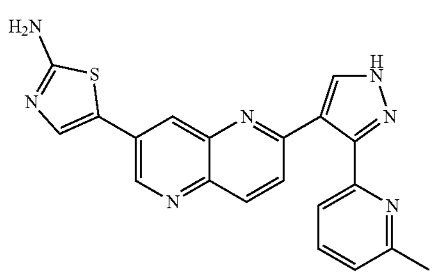 [SMILES: Cc1cccc(-c2n[nH]cc2-c2ccc3ncc(-c4cnc(N)s4)cc3n2)n1] | 5-[6-[3-(6-methyl-2-pyridyl)-1H-pyrazol-4-yl]-1,5-naphthyridin-3-yl]thiazol-2-amine | 386.1 |

TABLE 1-continued

| No. | Structure | Chemical Name | [M + H]+ |
|---|---|---|---|
| 334 | 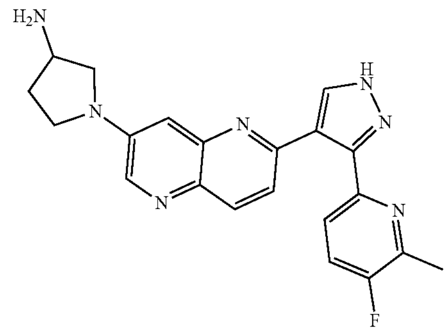 [SMILES: Cc1nc(-c2n[nH]cc2-c2ccc3ncc(N4CCC(N)C4)cc3n2)ccc1F] | 1-[6-[3-(5-fluoro-6-methyl-2-pyridyl)-1H-pyrazol-4-yl]-1,5-naphthyridin-3-yl]pyrrolidin-3-amine | 390.1 |
| 335 | 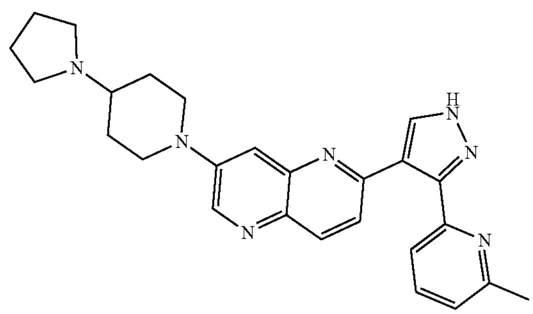 [SMILES: Cc1cccc(-c2n[nH]cc2-c2ccc3ncc(N4CCC(N5CCCC5)CC4)cc3n2)n1] | 2-[3-(6-methyl-2-pyridyl)-1H-pyrazol-4-yl]-7-(4-pyrrolidin-1-yl-1-piperidyl)-1,5-naphthyridine | 440.3 |
| 336 | 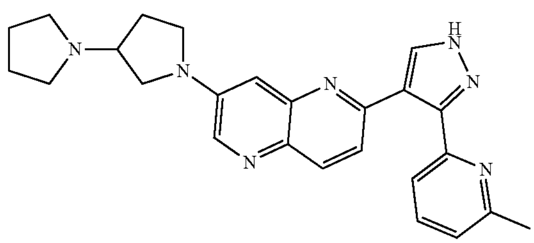 [SMILES: Cc1cccc(-c2n[nH]cc2-c2ccc3ncc(N4CCC(N5CCCC5)C4)cc3n2)n1] | 2-[3-(6-methyl-2-pyridyl)-1H-pyrazol-4-yl]-7-(3-pyrrolidin-1-ylpyrrolidin-1-yl)-1,5-naphthyridine | 426.2 |
| 337 | 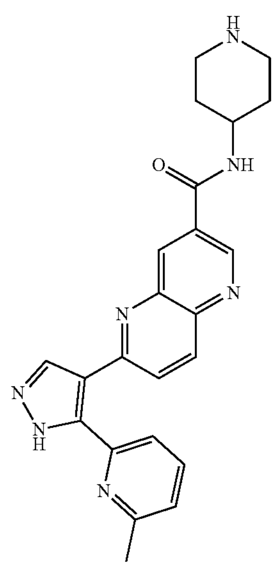 [SMILES: Cc1cccc(-c2[nH]ncc2-c2ccc3ncc(C(=O)NC4CCNCC4)cc3n2)n1] | 6-[5-(6-methyl-2-pyridyl)-1H-pyrazol-4-yl]-N-(4-piperidyl)-1,5-naphthyridine-3-carboxamide | 414.1 |

TABLE 1-continued

| No. | Structure | Chemical Name | [M + H]+ |
|---|---|---|---|
| 338 | 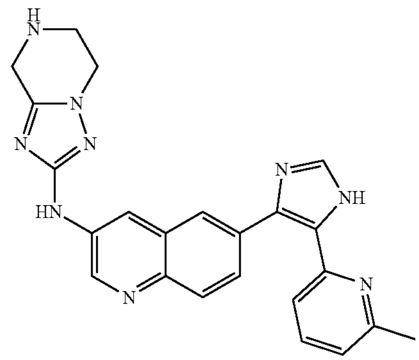 [SMILES: Cc1cccc(-c2[nH]cnc2-c2ccc3ncc(Nc4nc5n(n4)CCNC5)cc3c2)n1] | 6-[5-(6-methyl-2-pyridyl)-1H-imidazol-4-yl]-N-(5,6,7,8-tetrahydro-[1,2,4]triazolo[1,5-a]pyrazin-2-yl)quinolin-3-amine | 424.1 |
| 339 | 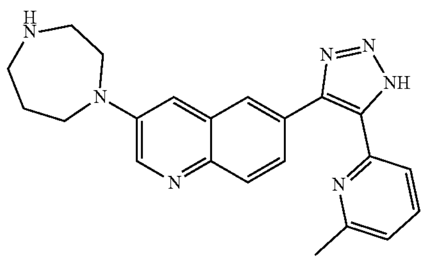 [SMILES: Cc1cccc(-c2[nH]nnc2-c2ccc3ncc(N4CCCNCC4)cc3c2)n1] | 3-(1,4-diazepan-1-yl)-6-[5-(6-methyl-2-pyridyl)-1H-triazol-4-yl]quinoline | 386.2 |
| 340 | 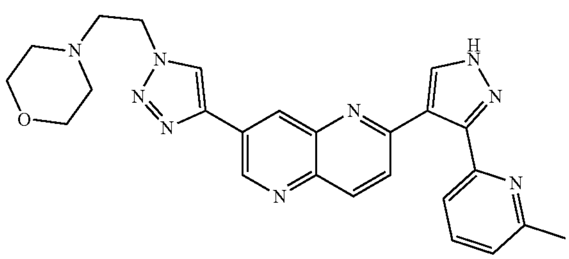 [SMILES: Cc1cccc(-c2n[nH]cc2-c2ccc3ncc(-c4cn(CCN5CCOCC5)nn4)cc3n2)n1] | 4-[2-[4-[6-[3-(6-methyl-2-pyridyl)-1H-pyrazol-4-yl]-1,5-naphthyridin-3-yl]triazol-1-yl]ethyl]morpholine | 468.2 |
| 341 | 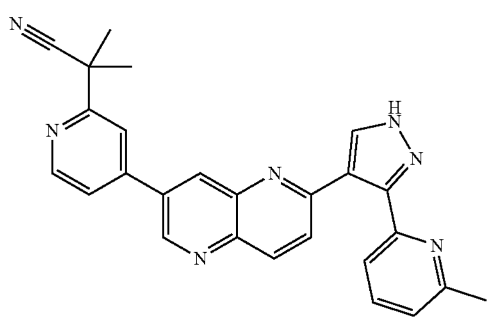 [SMILES: Cc1cccc(-c2n[nH]cc2-c2ccc3ncc(-c4ccnc(C(C)(C)C#N)c4)cc3n2)n1] | 2-methyl-2-[4-[6-[3-(6-methyl-2-pyridyl)-1H-pyrazol-4-yl]-1,5-naphthyridin-3-yl]-2-pyridyl]propanenitrile | 432.2 |
| 342 | 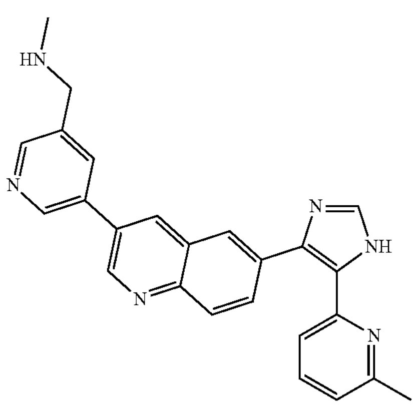 [SMILES: CNCc1cncc(-c2cnc3ccc(-c4nc[nH]c4-c4cccc(C)n4)cc3c2)c1] | N-methyl-1-[5-[6-[5-(6-methyl-2-pyridyl)-1H-imidazol-4-yl]-3-quinolyl]-3-pyridyl]methanamine | 407.1 |

TABLE 1-continued

| No. | Structure | Chemical Name | [M + H]+ |
|---|---|---|---|
| 343 | 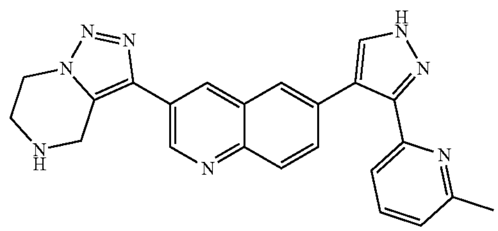 [SMILES: Cc1cccc(-c2n[nH]cc2-c2ccc3ncc(-c4nnn5c4CNCC5)cc3c2)n1] | 6-[3-(6-methyl-2-pyridyl)-1H-pyrazol-4-yl]-3-(4,5,6,7-tetrahydrotriazolo[1,5-a]pyrazin-3-yl)quinoline | 409.2 |
| 344 | 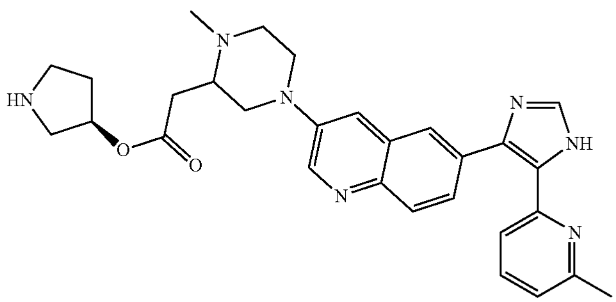 [SMILES: Cc1cccc(-c2[nH]cnc2-c2ccc3ncc(N4CCN(C)C(CC(=O)O[C@@H]5CCNC5)C4)cc3c2)n1] | [(3R)-pyrrolidin-3-yl]2-[1-methyl-4-[6-[5-(6-methyl-2-pyridyl)-1H-imidazol-4-yl]-3-quinolyl]piperazin-2-yl]acetate | 512.3 |
| 345 | 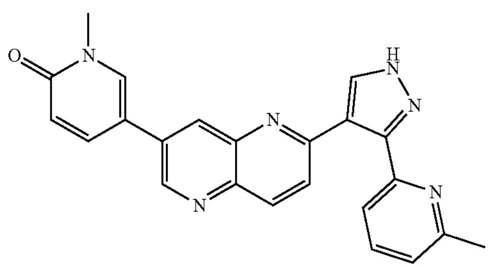 [SMILES: Cc1cccc(-c2n[nH]cc2-c2ccc3ncc(-c4ccc(=O)n(C)c4)cc3n2)n1] | 1-methyl-5-[6-[3-(6-methyl-2-pyridyl)-1H-pyrazol-4-yl]-1,5-naphthyridin-3-yl]pyridin-2-one | 395.3 |
| 346 | 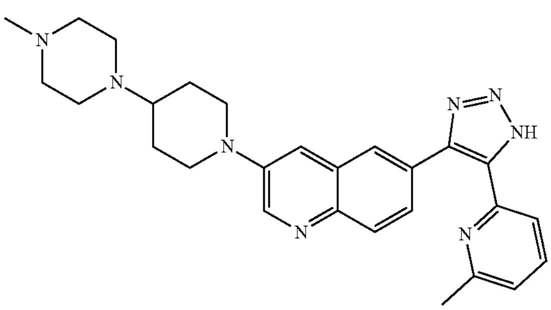 [SMILES: Cc1cccc(-c2[nH]nnc2-c2ccc3ncc(N4CCC(N5CCN(C)CC5)CC4)cc3c2)n1] | 3-[4-(4-methylpiperazin-1-yl)-1-piperidyl]-6-[5-(6-methyl-2-pyridyl)-1H-triazol-4-yl]quinoline | 469.3 |
| 347 | AND Enantiomer | rac-(3S)-1-[6-[2-(5-fluoro-6-methyl-2-pyridyl)imidazo[1,2-a]pyridin-3-yl]-1,5-naphthyridin-3-yl]-N,N-dimethyl-pyrrolidin-3-amine | 468.1 |

TABLE 1-continued

| No. | Structure | Chemical Name | [M + H]+ |
|---|---|---|---|
| 348 | 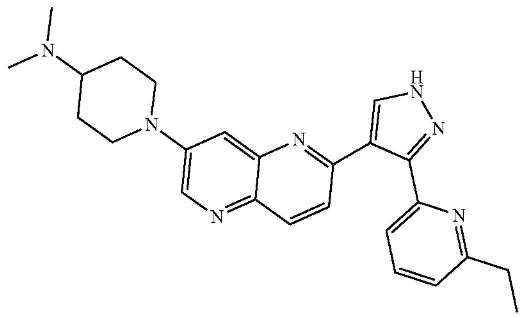 [SMILES: CCc1cccc(-c2n[nH]cc2-c2ccc3ncc(N4CCC(N(C)C)CC4)cc3n2)n1] | 1-[6-[3-(6-ethyl-2-pyridyl)-1H-pyrazol-4-yl]-1,5-naphthyridin-3-yl]-N,N-dimethyl-piperidin-4-amine | 428.2 |
| 349 | 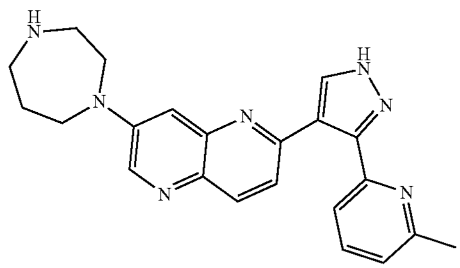 [SMILES: Cc1cccc(-c2n[nH]cc2-c2ccc3ncc(N4CCCNCC4)cc3n2)n1] | 7-(1,4-diazepan-1-yl)-2-[3-(6-methyl-2-pyridyl)-1H-pyrazol-4-yl]-1,5-naphthyridine | 386.2 |
| 350 | 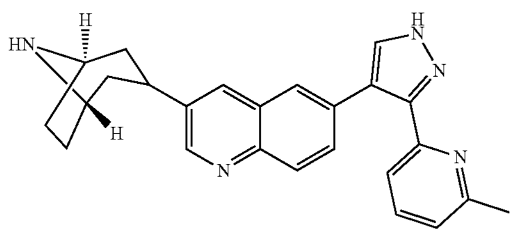 [SMILES: Cc1cccc(-c2n[nH]cc2-c2ccc3ncc(C4C[C@H]5CC[C@@H](C4)N5)cc3c2)n1] | 2-[3-(6-methyl-2-pyridyl)-1H-pyrazol-4-yl]-7-[rac-(1S,5R)-8-azabicyclo[3.2.1]octan-3-yl]-1,5-naphthyridine | 397.1 |
| 351 | 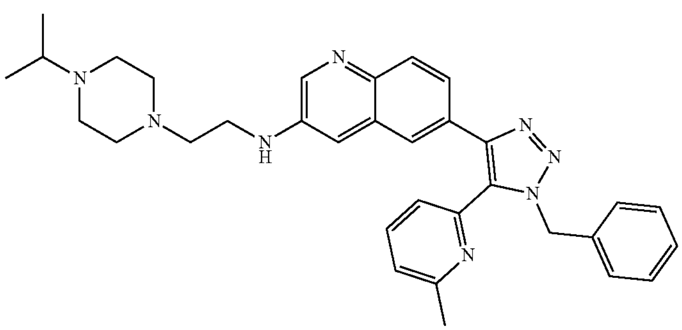 [SMILES: Cc1cccc(-c2c(-c3ccc4ncc(NCCN5CCN(C(C)C)CC5)cc4c3)nnn2Cc2ccccc2)n1] | 6-[1-benzyl-5-(6-methyl-2-pyridyl)triazol-4-yl]-N-[2-(4-isopropylpiperazin-1-yl)ethyl]quinolin-3-amine | 547.2 |
| 352 | 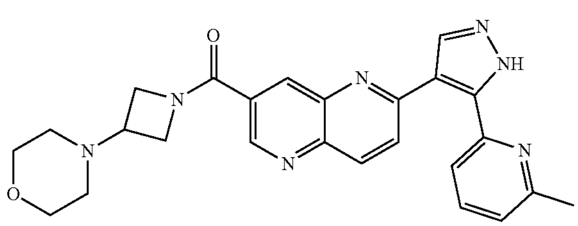 [SMILES: Cc1cccc(-c2[nH]ncc2-c2ccc3ncc(C(=O)N4CC(N5CCOCC5)C4)cc3n2)n1] | [6-[5-(6-methyl-2-pyridyl)-1H-pyrazol-4-yl]-1,5-naphthyridin-3-yl]-(3-morpholinoazetidin-1-yl)methanone | 455.5 |
| 353 | 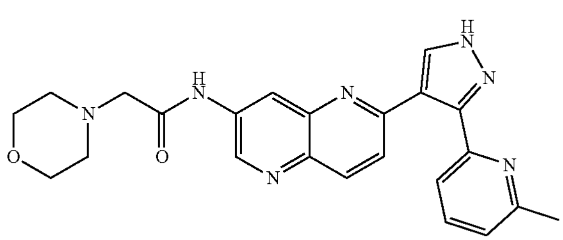 [SMILES: Cc1cccc(-c2n[nH]cc2-c2ccc3ncc(NC(=O)CN4CCOCC4)cc3n2)n1] | N-[6-[3-(6-methyl-2-pyridyl)-1H-pyrazol-4-yl]-1,5-naphthyridin-3-yl]-2-morpholino-acetamide | 430.2 |

TABLE 1-continued

| No. | Structure | Chemical Name | [M + H]+ |
|---|---|---|---|
| 354 | AND Enantiomer | 2-[3-(6-methyl-2-pyridyl)-1H-pyrazol-4-yl]-7-[rac-(3R)-3-(methoxymethyl)-4-methyl-piperazin-1-yl]-1,5-naphthyridine | 430.2 |
| 355 | 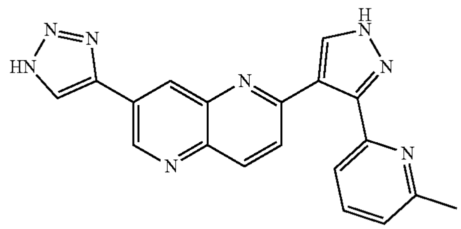 [SMILES: Cc1cccc(-c2n[nH]cc2-c2ccc3ncc(-c4c[nH]nn4)cc3n2)n1] | 2-[3-(6-methyl-2-pyridyl)-1H-pyrazol-4-yl]-7-(1H-triazol-4-yl)-1,5-naphthyridine | 355.2 |
| 356 | 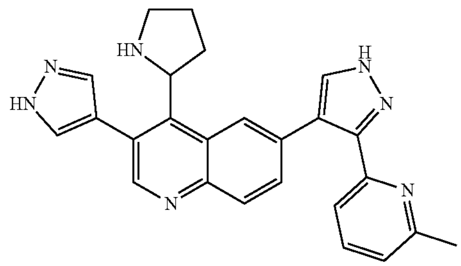 [SMILES: Cc1cccc(-c2n[nH]cc2-c2ccc3ncc(-c4cn[nH]c4)c(C4CCCN4)c3c2)n1] | 6-[3-(6-methyl-2-pyridyl)-1H-pyrazol-4-yl]-3-(1H-pyrazol-4-yl)-4-pyrrolidin-2-y-quinoline | 422.1 |
| 357 | 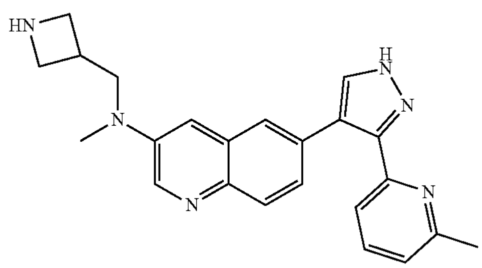 [SMILES: Cc1cccc(-c2n[nH]cc2-c2ccc3ncc(N(C)CC4CNC4)cc3c2)n1] | N-(azetidin-3-ylmethyl)-N-methyl-6-[3-(6-methyl-2-pyridyl)-1H-pyrazol-4-yl]-1,5-naphthyridin-3-amine | 386.3 |
| 358 | 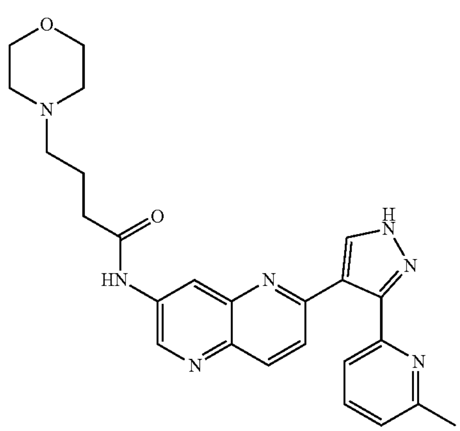 [SMILES: Cc1cccc(-c2n[nH]cc2-c2ccc3ncc(NC(=O)CCCN4CCOCC4)cc3n2)n1] | N-[6-[3-(6-methyl-2-pyridyl)-1H-pyrazol-4-yl]-1,5-naphthyridin-3-yl]-4-morpholino-butanamide | 458.2 |

TABLE 1-continued

| No. | Structure | Chemical Name | [M + H]+ |
|---|---|---|---|
| 359 | 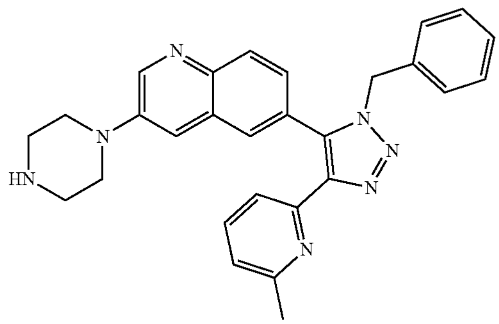 [SMILES: Cc1cccc(-c2nnn(Cc3ccccc3)c2-c2ccc3ncc(N4CCNCC4)cc3c2)n1] | 2-[3-benzyl-5-(6-methyl-2-pyridyl)triazol-4-yl]-7-piperazin-1-yl-1,5-naphthyridine | 463.1 |
| 360 | 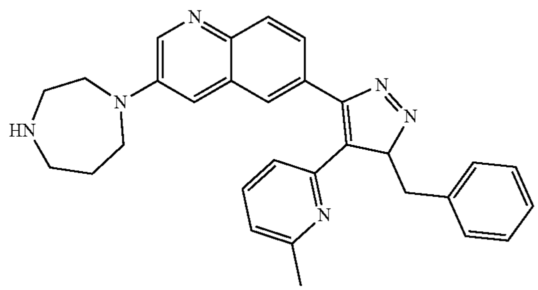 [SMILES: Cc1cccc(C2=C(c3ccc4ncc(N5CCCNCC5)cc4c3)N=NC2Cc2ccccc2)n1] | 6-[1-benzyl-5-(6-methyl-2-pyridyl)triazol-4-yl]-3-(1,4-diazepan-1-yl)quinoline | 476.2 |
| 361 | 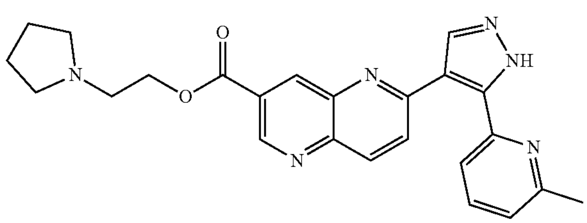 [SMILES: Cc1cccc(-c2[nH]ncc2-c2ccc3ncc(C(=O)OCCN4CCCC4)cc3n2)n1] | 2-pyrrolidin-1-ylethyl 6-[5-(6-methyl-2-pyridyl)-1H-pyrazol-4-yl]-1,5-naphthyridine-3-carboxylate | 429.1 |
| 362 | 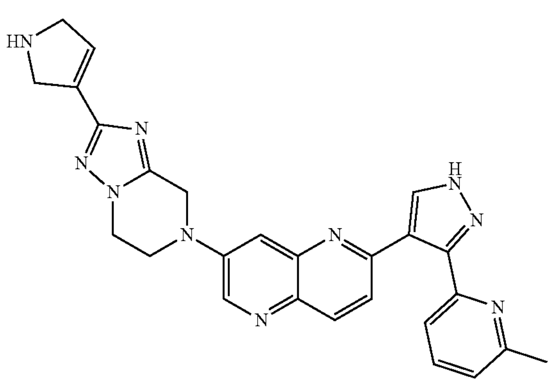 [SMILES: Cc1cccc(-c2n[nH]cc2-c2ccc3ncc(N4CCn5nc(C6=CCNC6)nc5C4)cc3n2)n1] | 7-[2-(2,5-dihydro-1H-pyrrol-3-yl)-6,8-dihydro-5H-[1,2,4]triazolo[1,5-a]pyrazin-7-yl]-2-[3-(6-methyl-2-pyridyl)-1H-pyrazol-4-yl]-1,5-naphthyridine | 477.2 |
| 363 | 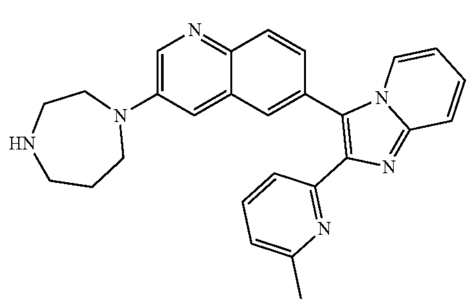 [SMILES: Cc1cccc(-c2nc3ccccn3c2-c2ccc3ncc(N4CCCNCC4)cc3c2)n1] | 3-(1,4-diazepan-1-yl)-6-[2-(6-methyl-2-pyridyl)imidazo[1,2-a]pyridin-3-yl]quinoline | 435.1 |

TABLE 1-continued

| No. | Structure | Chemical Name | [M + H]+ |
|---|---|---|---|
| 364 | 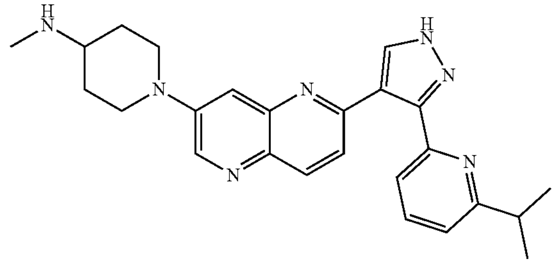 [SMILES: CNC1CCN(c2cnc3ccc(-c4c[nH]nc4-c4cccc(C(C)C)n4)nc3c2)CC1] | 1-[6-[3-(6-isopropyl-2-pyridyl)-1H-pyrazol-4-yl]-1,5-naphthyridin-3-yl]-N-methyl-piperidin-4-amine | 428.1 |
| 365 | 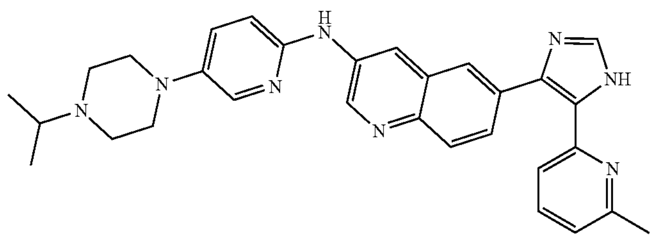 [SMILES: Cc1cccc(-c2[nH]cnc2-c2ccc3ncc(Nc4ccc(N5CCN(C(C)C)CC5)cn4)cc3c2)n1] | N-[5-(4-isopropylpiperazin-1-yl)-2-pyridyl]-6-[5-(6-methyl-2-pyridyl)-1H-imidazol-4-yl]quinolin-3-amine | 505.1 |
| 366 | 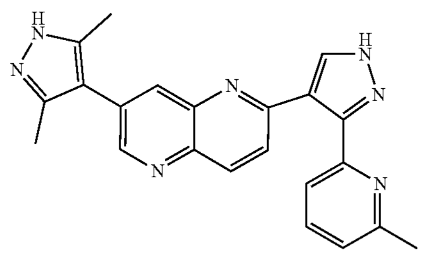 [SMILES: Cc1cccc(-c2n[nH]cc2-c2ccc3ncc(-c4c(C)n[nH]c4C)cc3n2)n1] | 7-(3,5-dimethyl-1H-pyrazol-4-yl)-2-[3-(6-methyl-2-pyridyl)-1H-pyrazol-4-yl]-1,5-naphthyridine | 382.2 |
| 367 | 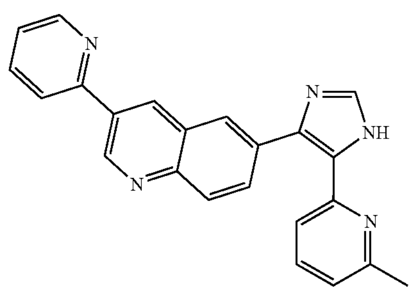 [SMILES: Cc1cccc(-c2[nH]cnc2-c2ccc3ncc(-c4ccccn4)cc3c2)n1] | 6-[5-(6-methyl-2-pyridyl)-1H-imidazol-4-yl]-3-(2-pyridyl)quinoline | 364.2 |
| 368 | 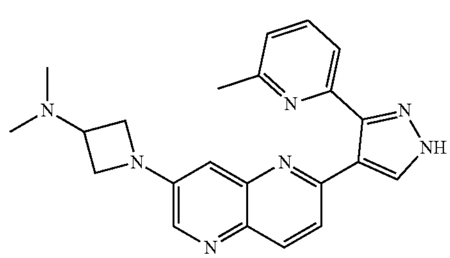 [SMILES: Cc1cccc(-c2n[nH]cc2-c2ccc3ncc(N4CC(N(C)C)C4)cc3n2)n1] | N,N-dimethyl-1-[6-[3-(6-methyl-2-pyridyl)-1H-pyrazol-4-yl]-1,5-naphthyridin-3-yl]azetidin-3-amine | 386.2 |
| 369 | 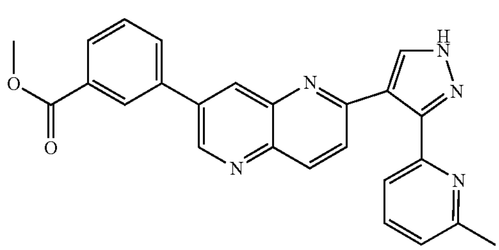 [SMILES: COC(=O)c1cccc(-c2cnc3ccc(-c4c[nH]nc4-c4cccc(C)n4)nc3c2)c1] | methyl 3-[6-[3-(6-methyl-2-pyridyl)-1H-pyrazol-4-yl]-1,5-naphthyridin-3-yl]benzoate | 422.2 |

TABLE 1-continued

| No. | Structure | Chemical Name | [M + H]+ |
|---|---|---|---|
| 370 | 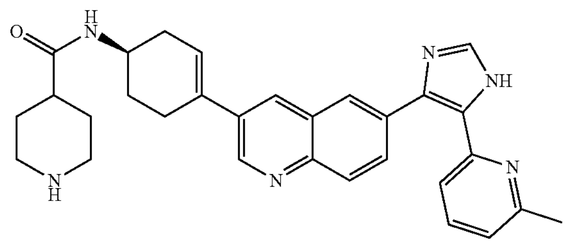 [SMILES: Cc1cccc(-c2[nH]cnc2-c2ccc3ncc(C4=CC[C@H](NC(=O)C5CCNCC5)CC4)cc3c2)n1] | N-[(1R)-4-[6-[5-(6-methyl-2-pyridyl)-1H-imidazol-4-yl]-3-quinolyl]cyclohex-3-en-1-yl]piperidine-4-carboxamide | 493.2 |
| 371 | 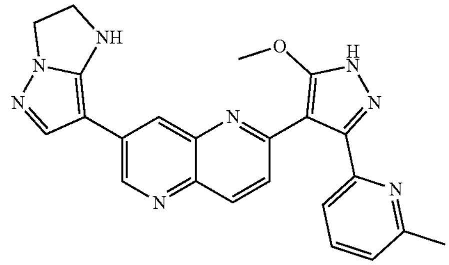 [SMILES: COc1[nH]nc(-c2cccc(C)n2)c1-c1ccc2ncc(-c3cnn4c3NCC4)cc2n1] | 7-(2,3-dihydro-1H-imidazo[1,2-b]pyrazol-7-yl)-2-[5-methoxy-3-(6-methyl-2-pyridyl)-1H-pyrazol-4-yl]-1,5-naphthyridine | 452.2 |
| 372 | 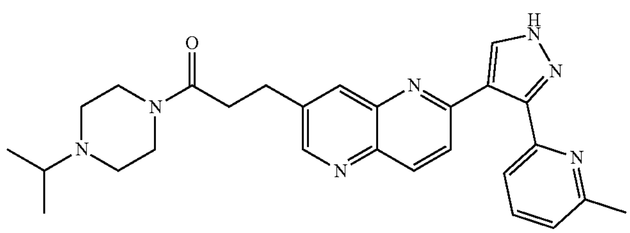 [SMILES: Cc1cccc(-c2n[nH]cc2-c2ccc3ncc(CCC(=O)N4CCN(C(C)C)CC4)cc3n2)n1] | 1-(4-isopropylpiperazin-1-yl)-3-[6-[3-(6-methyl-2-pyridyl)-1H-pyrazol-4-yl]-1,5-naphthyridin-3-yl]propan-1-one | 469.8 |
| 373 | 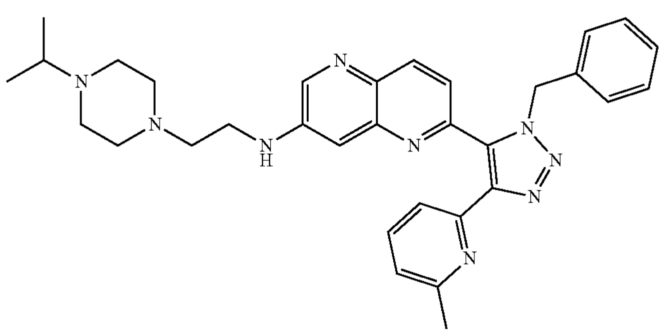 [SMILES: Cc1cccc(-c2nnn(Cc3ccccc3)c2-c2ccc3ncc(NCCN4CCN(C(C)C)CC4)cc3n2)n1] | 6-[3-benzyl-5-(6-methyl-2-pyridyl)triazol-4-yl]-N-[2-(4-isopropylpiperazin-1-yl)ethyl]-1,5-naphthyridin-3-amine | 548.2 |
| 374 | 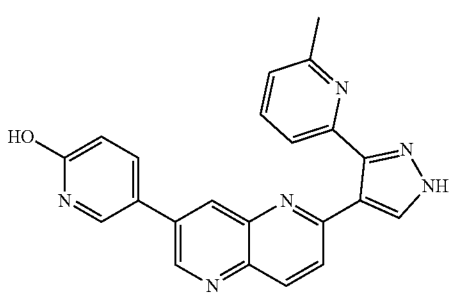 [SMILES: Cc1cccc(-c2n[nH]cc2-c2ccc3ncc(-c4ccc(O)nc4)cc3n2)n1] | 5-[6-[3-(6-methyl-2-pyridyl)-1H-pyrazol-4-yl]-1,5-naphthyridin-3-yl]pyridin-2-ol | 381.3 |

TABLE 1-continued

| No. | Structure | Chemical Name | [M + H]+ |
|---|---|---|---|
| 375 | 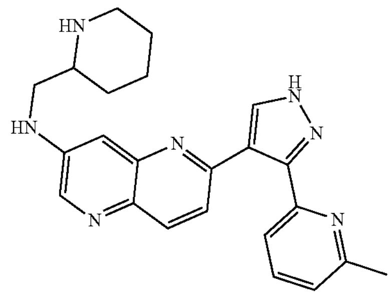 [SMILES: Cc1cccc(-c2n[nH]cc2-c2ccc3ncc(NCC4CCCCN4)cc3n2)n1] | 6-[3-(6-methyl-2-pyridyl)-1H-pyrazol-4-yl]-N-(2-piperidylmethyl)-1,5-naphthyridin-3-amine | 400.2 |
| 376 | 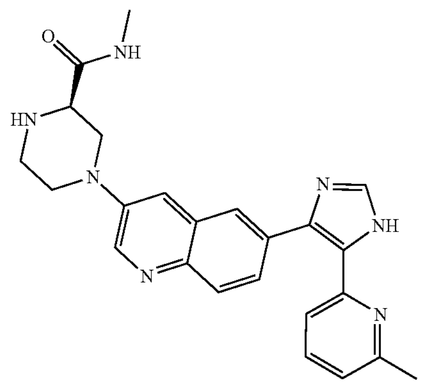 [SMILES: CNC(=O)[C@H]1CN(c2cnc3ccc(-c4nc[nH]c4-c4cccc(C)n4)cc3c2)CCN1] | (2R)-N-methyl-4-[6-[5-(6-methyl-2-pyridyl)-1H-imidazol-4-yl]-3-quinolyl]piperazine-2-carboxamide | 428.2 |
| 377 | 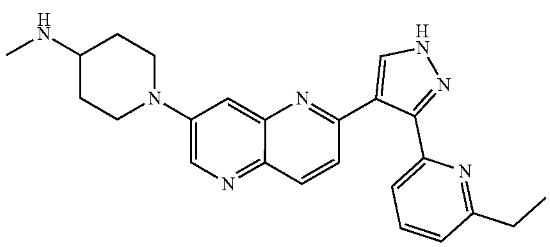 | 1-[6-[3-(6-ethyl-2-pyridyl)-1H-pyrazol-4-yl]-1,5-naphthyridin-3-yl]-N-methyl-piperidin-4-amine | 414.2 |
| 378 | 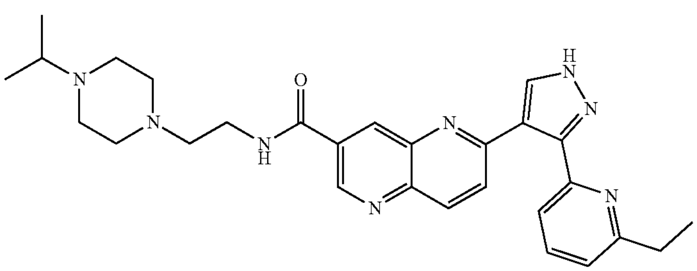 | N-[2-(4-isopropylpiperazin-1-yl)ethyl]-6-[3-(6-methyl-2-pyridyl)-1H-pyrazol-4-yl]-1,5-naphthyridine-3-carboxamide | 485.3 |
| 379 | 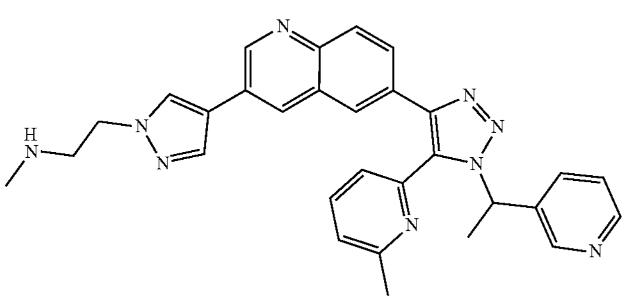 | N-methyl-2-[4-[6-[5-(6-methyl-2-pyridyl)-1-(3-pyridylmethyl)triazol-4-yl]-3-quinolyl]pyrazol-1-yl]ethanamine | 502.2 |

TABLE 1-continued

| No. | Structure | Chemical Name | [M + H]⁺ |
|---|---|---|---|
| 380 | 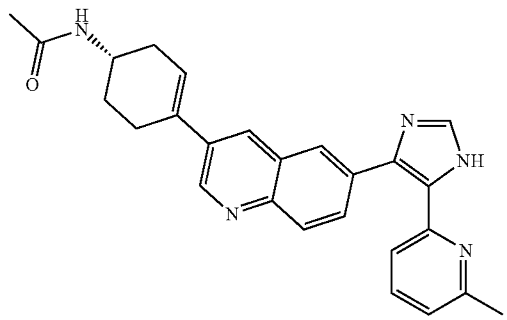 [SMILES: CC(=O)N[C@@H]1CC=C(c2cnc3ccc(-c4nc[nH]c4-c4cccc(C)n4)cc3c2)CC1] | N-[(1S)-4-[6-[5-(6-methyl-2-pyridyl)-1H-imidazol-4-yl]-3-quinolyl]cyclohex-3-en-1-yl]acetamide | 424.0 |
| 381 | 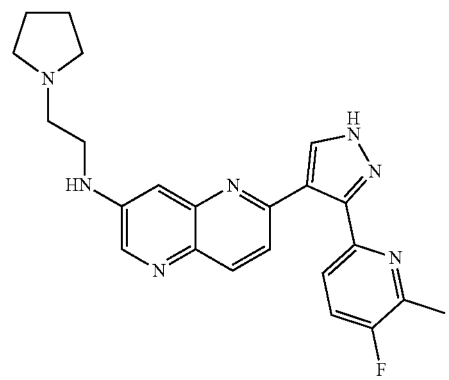 | 6-[3-(5-fluoro-6-methyl-2-pyridyl)-1H-pyrazol-4-yl]-N-(2-pyrrolidin-1-ylethyl)-1,5-naphthyridin-3-amine | 418.1 |
| 382 | 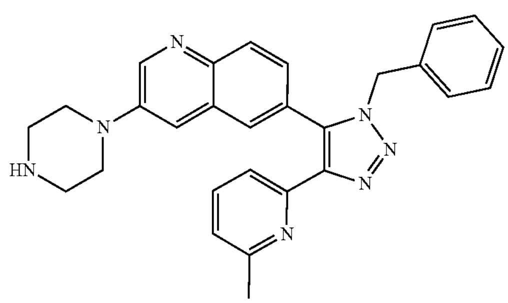 [SMILES: Cc1cccc(-c2nnn(Cc3ccccc3)c2-c2ccc3ncc(N4CCNCC4)cc3c2)n1] | 6-[3-benzyl-5-(6-methyl-2-pyridyl)triazol-4-yl]-3-piperazin-1-yl-quinoline | 462.1 |
| 383 | 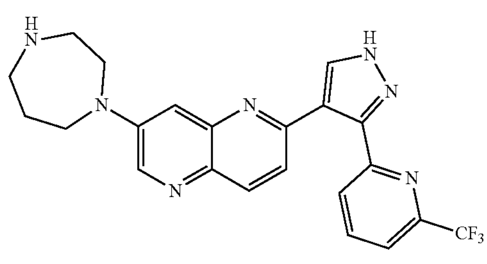 | 7-(1,4-diazepan-1-yl)-2-[3-[6-(trifluoromethyl)-2-pyridyl]-1H-pyrazol-4-yl]-1,5-naphthyridine | 440.2 |

TABLE 1-continued

| No. | Structure | Chemical Name | [M + H]+ |
|---|---|---|---|
| 384 | 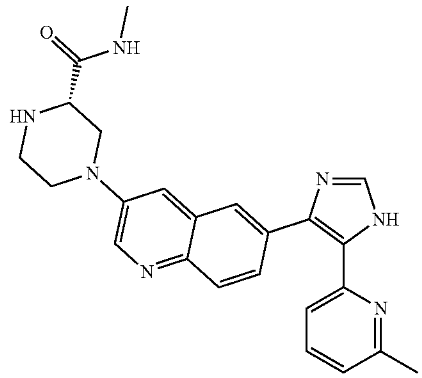 [SMILES: CNC(=O)[C@@H]1CN(c2cnc3ccc(-c4nc[nH]c4-c4cccc(C)n4)cc3c2)CCN1] | (2S)-N-methyl-4-[6-[5-(6-methyl-2-pyridyl)-1H-imidazol-4-yl]-3-quinolyl]piperazine-2-carboxamide | 428.1 |
| 385 | 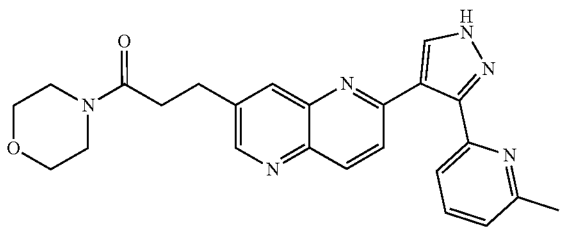 | 3-[6-[3-(6-methyl-2-pyridyl)-1H-pyrazol-4-yl]-1,5-naphthyridin-3-yl]-1-morpholino-propan-1-one | 428.8 |
| 386 | 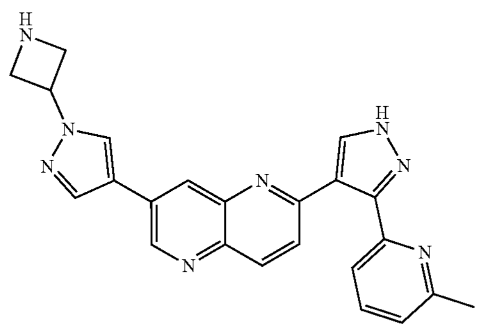 | 7-[1-(azetidin-3-yl)pyrazol-4-yl]-2-[3-(6-methyl-2-pyridyl)-1H-pyrazol-4-yl]-1,5-naphthyridine | 409.2 |
| 387 | 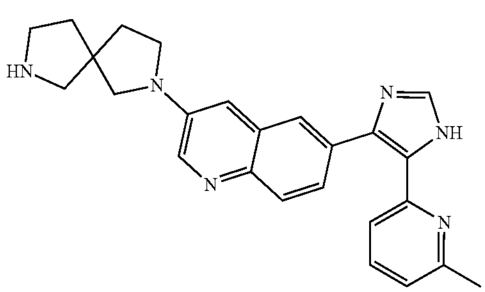 [SMILES: Cc1cccc(-c2[nH]cnc2-c2ccc3ncc(N4CCC5(CCNC5)C4)cc3c2)n1] | 3-(2,7-diazaspiro[4.4]nonan-2-yl)-6-[5-(6-methyl-2-pyridyl)-1H-imidazol-4-yl]quinoline | 411.1 |
| 388 | 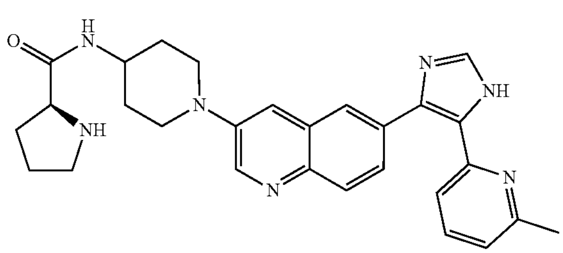 [SMILES: Cc1cccc(-c2[nH]cnc2-c2ccc3ncc(N4CCC(NC(=O)[C@@H]5CCCN5)CC4)cc3c2)n1] | (2S)-N-[1-[6-[5-(6-methyl-2-pyridyl)-1H-imidazol-4-yl]-3-quinolyl]-4-piperidyl]pyrrolidine-2-carboxamide | 482.1 |

TABLE 1-continued

| No. | Structure | Chemical Name | [M + H]+ |
|---|---|---|---|
| 389 | 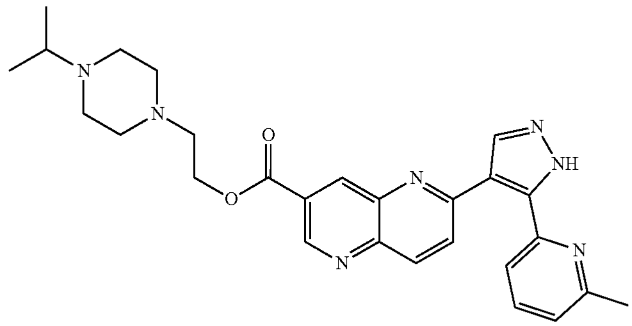 [SMILES: Cc1cccc(-c2[nH]ncc2-c2ccc3ncc(C(=O)OCCN4CCN(C(C)C)CC4)cc3n2)n1] | 2-(4-isopropylpiperazin-1-yl)ethyl 6-[5-(6-methyl-2-pyridyl)-1H-pyrazol-4-yl]-1,5-naphthyridine-3-carboxylate | 486.2 |
| 390 | 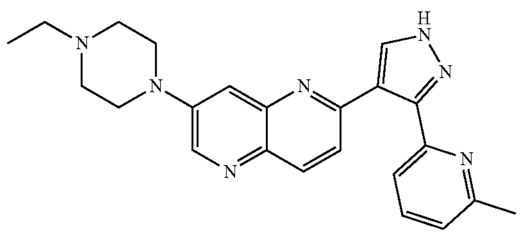 | 7-(4-ethylpiperazin-1-yl)-2-[3-(6-methyl-2-pyridyl)-1H-pyrazol-4-yl]-1,5-naphthyridine | 400.1 |
| 391 | 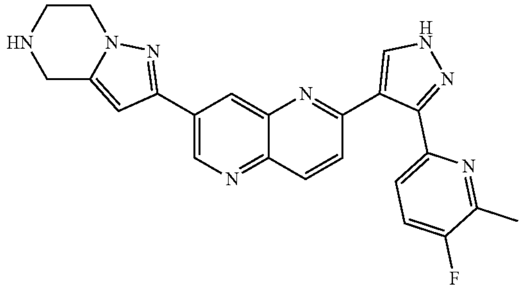 [SMILES: Cc1nc(-c2n[nH]cc2-c2ccc3ncc(-c4cc5n(n4)CCNC5)cc3n2)ccc1F] | 2-[3-(5-fluoro-6-methyl-2-pyridyl)-1H-pyrazol-4-yl]-7-(4,5,6,7-tetrahydropyrazolo[1,5-a]pyrazin-2-yl)-1,5-naphthyridine | 427.3 |
| 392 | 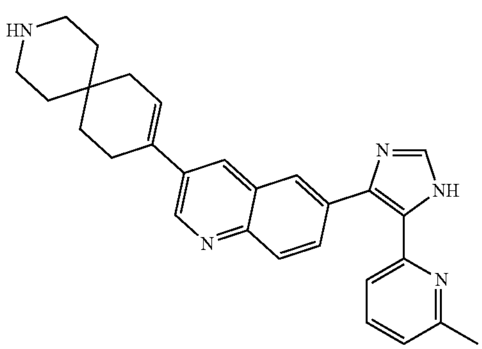 [SMILES: Cc1cccc(-c2[nH]cnc2-c2ccc3ncc(C4=CCC5(CCNCC5)CC4)cc3c2)n1] | 9-[6-[5-(6-methyl-2-pyridyl)-1H-imidazol-4-yl]-3-quinolyl]-3-azaspiro[5.5]undec-9-ene | 436.1 |
| 393 | 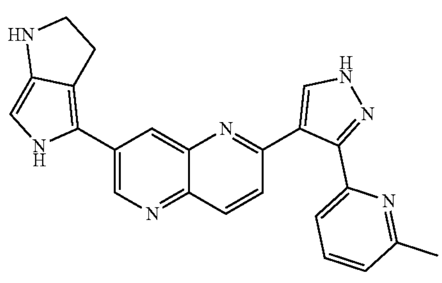 [SMILES: Cc1cccc(-c2n[nH]cc2-c2ccc3ncc(-c4[nH]cc5c4CCN5)cc3n2)n1] | 2-[3-(6-methyl-2-pyridyl)-1H-pyrazol-4-yl]-7-(2,4,5,6-tetrahydropyrrolo[2,3-c]pyrazol-3-yl)-1,5-naphthyridine | 395.0 |

TABLE 1-continued

| No. | Structure | Chemical Name | [M + H]+ |
|---|---|---|---|
| 394 | 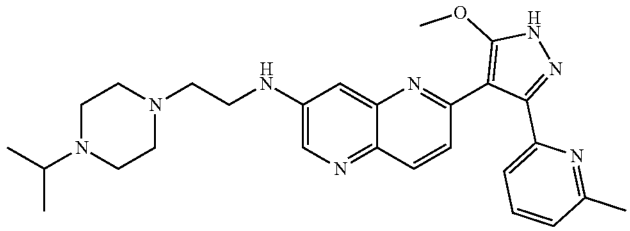 [SMILES: COc1[nH]nc(-c2cccc(C)n2)c1-c1ccc2ncc(NCCN3CCN(C(C)C)CC3)cc2n1] | N-[2-(4-isopropylpiperazin-1-yl)ethyl]-6-[5-methoxy-3-(6-methyl-2-pyridyl)-1H-pyrazol-4-yl]-1,5-naphthyridin-3-amine | 487.3 |
| 395 | AND Enantiomer | rac-(1S,3S)-3-[[4-[6-[3-(5-fluoro-6-methyl-2-pyridyl)-1H-pyrazol-4-yl]-1,5-naphthyridin-3-yl]pyrazol-1-yl]methyl]cyclohexanamine | 483.2 |
| 396 | 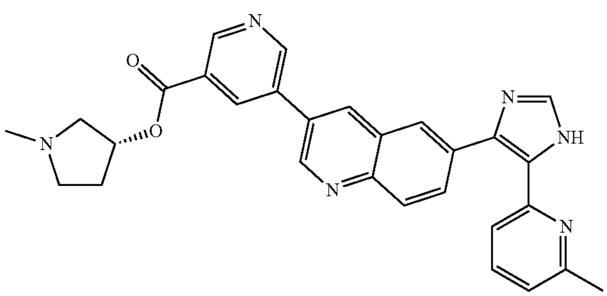 | [(3R)-1-methylpyrrolidin-3-yl] 5-[6-[5-(6-methyl-2-pyridyl)-1H-imidazol-4-yl]-3-quinolyl]pyridine-3-carboxylate | 491.2 |
| 397 | 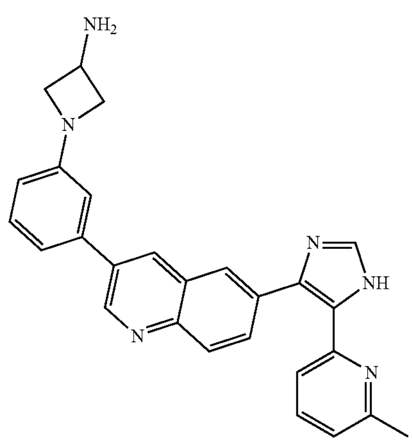 [SMILES: Cc1cccc(-c2[nH]cnc2-c2ccc3ncc(-c4cccc(N5CC(N)C5)c4)cc3c2)n1] | 1-[3-[6-[5-(6-methyl-2-pyridyl)-1H-imidazol-4-yl]-3-quinolyl]phenyl]azetidin-3-amine | 433.1 |
| 398 | 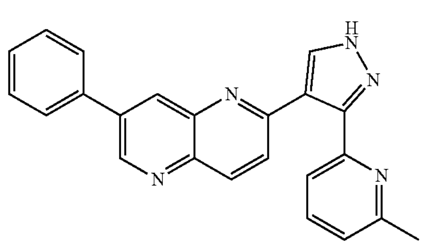 [SMILES: Cc1cccc(-c2n[nH]cc2-c2ccc3ncc(-c4ccccc4)cc3n2)n1] | 2-[3-(6-methyl-2-pyridyl)-1H-pyrazol-4-yl]-7-phenyl-1,5-naphthyridine | 364.3 |

TABLE 1-continued

| No. | Chemical Name | [M + H]+ |
|-----|---------------|----------|
| 399 | 6-[3-methyl-5-(6-methyl-2-pyridyl)triazol-4-yl]-3-(1H-pyrazol-4-yl)quinoline | 368.1 |
| 400 | 7-(4-cyclopentyl-1,4-diazepan-1-yl)-2-[3-(6-methyl-2-pyridyl)-1H-pyrazol-4-yl]-1,5-naphthyridine | 454.2 |
| 401 | 2-[4-[6-[5-(5-fluoro-6-methyl-2-pyridyl)-1H-imidazol-4-yl]-3-quinolyl]pyrazol-1-yl]-N-methyl-ethanamine | 428.1 |
| 402 | 6-[2-(6-methyl-2-pyridyl)-4,5,6,7-tetrahydropyrazolo[1,5-a]pyrazin-3-yl]-3-(1H-pyrazol-4-yl)quinoline | 408.2 |

TABLE 1-continued

| No. | Structure | Chemical Name | [M + H]+ |
|---|---|---|---|
| 403 | 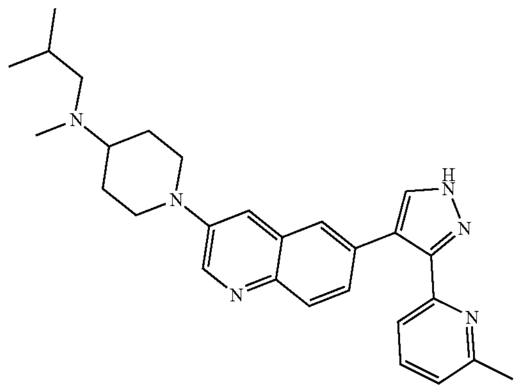 [SMILES: Cc1cccc(-c2n[nH]cc2-c2ccc3ncc(N4CCC(N(C)CC(C)C)CC4)cc3c2)n1] | N-isobutyl-N-methyl-1-[6-[3-(6-methyl-2-pyridyl)-1H-pyrazol-4-yl]-1,5-naphthyridin-3-yl]piperidin-4-amine | 456.2 |
| 404 | 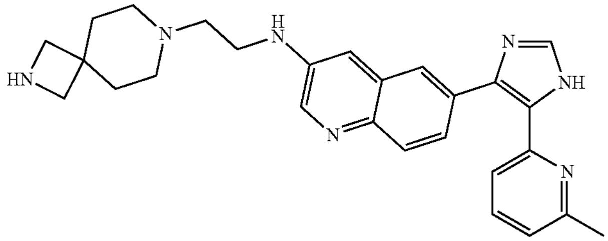 [SMILES: Cc1cccc(-c2[nH]cnc2-c2ccc3ncc(NCCN4CCC5(CC4)CNC5)cc3c2)n1] | N-[2-(2,7-diazaspiro[3.5]nonan-7-yl)ethyl]-6-[5-(6-methyl-2-pyridyl)-1H-imidazol-4-yl]quinolin-3-amine | 454.1 |
| 405 | 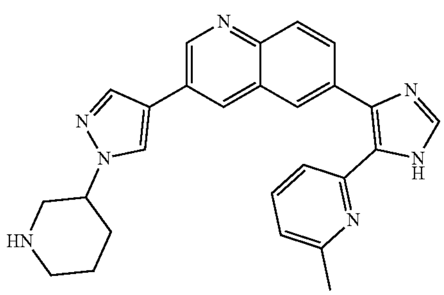 [SMILES: Cc1cccc(-c2[nH]cnc2-c2ccc3ncc(-c4cnn(C5CCCNC5)c4)cc3c2)n1] | 6-[5-(6-methyl-2-pyridyl)-1H-imidazol-4-yl]-3-[1-(3-piperidyl)pyrazol-4-yl]quinoline | 436.2 |
| 406 | 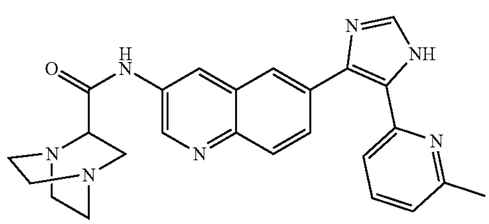 [SMILES: Cc1cccc(-c2[nH]cnc2-c2ccc3ncc(NC(=O)C4CN5CCN4CC5)cc3c2)n1] | N-[6-[5-(6-methyl-2-pyridyl)-1H-imidazol-4-yl]-3-quinolyl]-1,4-diazabicyclo[2.2.2]octane-2-carboxamide | 440.1 |
| 407 | 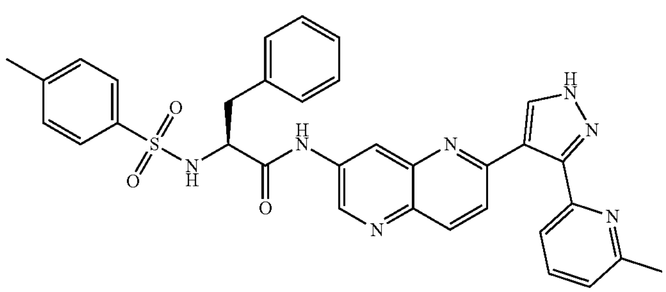 | rac-(2S)-N-[6-[3-(6-methyl-2-pyridyl)-1H-pyrazol-4-yl]-1,5-naphthyridin-3-yl]-3-phenyl-2-(p-tolylsulfonylamino)propanamide | 603.6 |

TABLE 1-continued

| No. | Structure | Chemical Name | [M + H]+ |
|---|---|---|---|
| 408 | 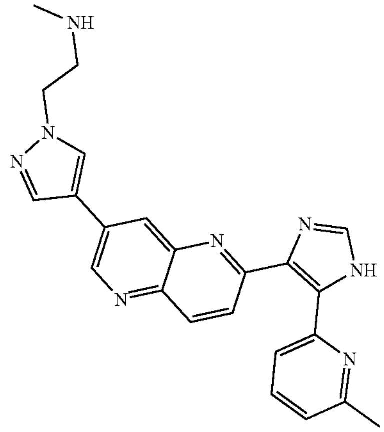 [SMILES: CNCCn1cc(-c2cnc3ccc(-c4nc[nH]c4-c4cccc(C)n4)nc3c2)cn1] | N-methyl-2-[4-[6-[5-(6-methyl-2-pyridyl)-1H-imidazol-4-yl]-1,5-naphthyridin-3-yl]pyrazol-1-yl]ethanamine | 411.1 |
| 409 | 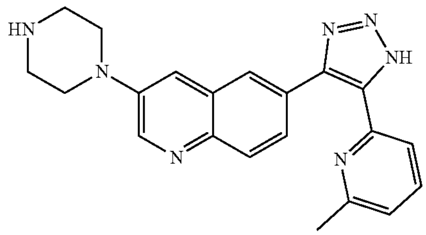 [SMILES: Cc1cccc(-c2[nH]nnc2-c2ccc3ncc(N4CCNCC4)cc3c2)n1] | 6-[5-(6-methyl-2-pyridyl)-1H-triazol-4-yl]-3-piperazin-1-yl-quinoline | 372.1 |
| 410 | 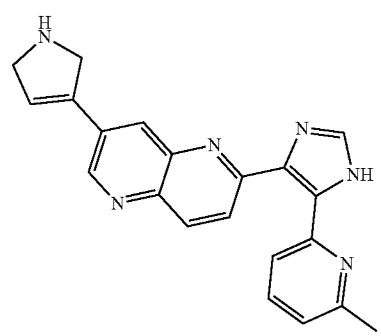 [SMILES: Cc1cccc(-c2[nH]cnc2-c2ccc3ncc(C4=CCNC4)cc3n2)n1] | 7-(2,5-dihydro-1H-pyrrol-3-yl)-2-[5-(6-methyl-2-pyridyl)-1H-imidazol-4-yl]-1,5-naphthyridine | 355.2 |
| 411 | 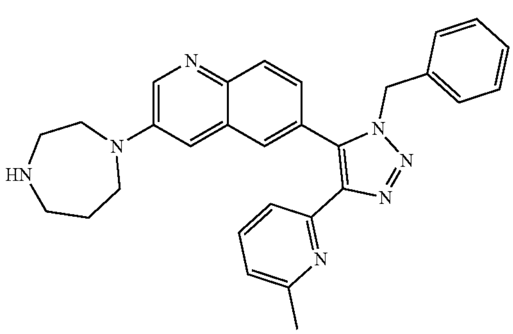 | 6-[3-benzyl-5-(6-methyl-2-pyridyl)triazol-4-yl]-3-(1,4-diazepan-1-yl)quinoline | 476.2 |

TABLE 1-continued

| No. | Structure | Chemical Name | [M + H]+ |
|---|---|---|---|
| 412 | 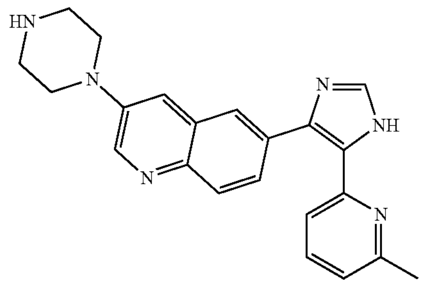 [SMILES: Cc1cccc(-c2[nH]cnc2-c2ccc3ncc(N4CCNCC4)cc3c2)n1] | 6-[5-(6-methyl-2-pyridyl)-1H-imidazol-4-yl]-3-piperazin-1-yl-quinoline | 371.1 |
| 413 | 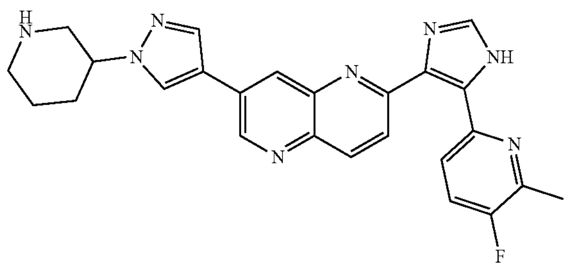 [SMILES: Cc1nc(-c2[nH]cnc2-c2ccc3ncc(-c4cnn(C5CCCNC5)c4)cc3n2)ccc1F] | 2-[5-(5-fluoro-6-methyl-2-pyridyl)-1H-imidazol-4-yl]-7-[1-(3-piperidyl)pyrazol-4-yl]-1,5-naphthyridine | 455.2 |
| 414 | 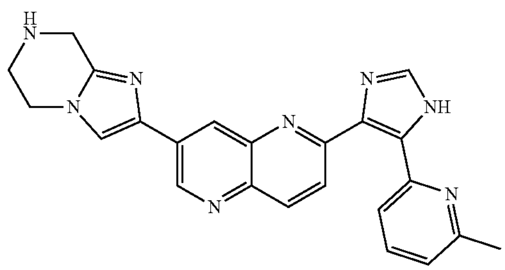 [SMILES: Cc1cccc(-c2[nH]cnc2-c2ccc3ncc(-c4cn5c(n4)CNCC5)cc3n2)n1] | 2-[5-(6-methyl-2-pyridyl)-1H-imidazol-4-yl]-7-(5,6,7,8-tetrahydroimidazo[1,2-a]pyrazin-2-yl)-1,5-naphthyridine | 409.2 |
| 415 | 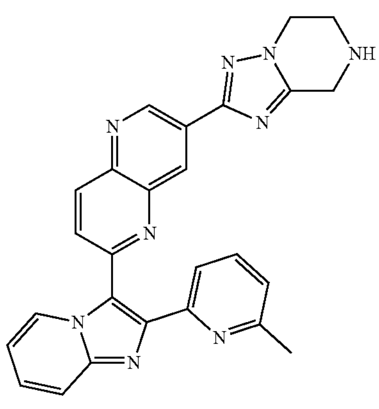 [SMILES: Cc1cccc(-c2nc3ccccn3c2-c2ccc3ncc(-c4nc5n(n4)CCNC5)cc3n2)n1] | 2-[2-(6-methyl-2-pyridyl)imidazo[1,2-a]pyridin-3-yl]-7-(5,6,7,8-tetrahydro-[1,2,4]triazolo[1,5-a]pyrazin-2-yl)-1,5-naphthyridine | 460.2 |
| 416 | 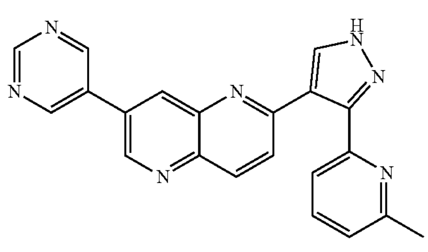 [SMILES: Cc1cccc(-c2n[nH]cc2-c2ccc3ncc(-c4cncnc4)cc3n2)n1] | 2-[3-(6-methyl-2-pyridyl)-1H-pyrazol-4-yl]-7-pyrimidin-5-yl-1,5-naphthyridine | 366.2 |

TABLE 1-continued

| No. | Structure | Chemical Name | [M + H]+ |
|---|---|---|---|
| 417 | 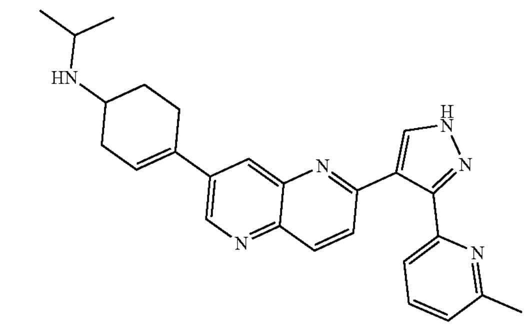 [SMILES: Cc1cccc(-c2n[nH]cc2-c2ccc3ncc(C4=CCC(NC(C)C)CC4)cc3n2)n1] | N-isopropyl-4-[6-[3-(6-methyl-2-pyridyl)-1H-pyrazol-4-yl]-1,5-naphthyridin-3-yl]cyclohex-3-en-1-amine | 425.1 |
| 418 | 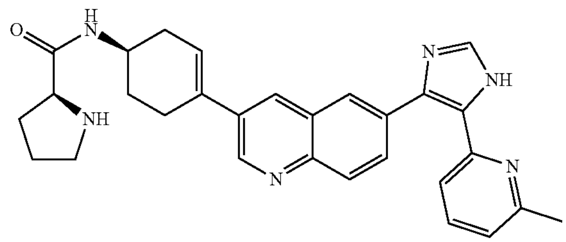 [SMILES: Cc1cccc(-c2[nH]cnc2-c2ccc3ncc(C4=CC[C@H](NC(=O)[C@@H]5CCCN5)CC4)cc3c2)n1] | (2S)-N-[(1R)-4-[6-[5-(6-methyl-2-pyridyl)-1H-imidazol-4-yl]-3-quinolyl]cyclohex-3-en-1-yl]pyrrolidine-2-carboxamide | 479.2 |
| 419 | 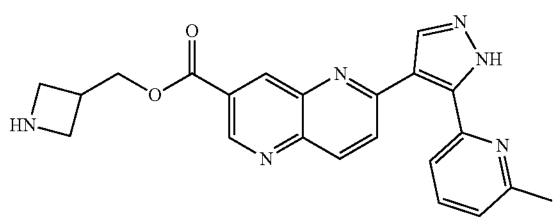 [SMILES: Cc1cccc(-c2[nH]ncc2-c2ccc3ncc(C(=O)OCC4CNC4)cc3n2)n1] | azetidin-3-ylmethyl 6-[5-(6-methyl-2-pyridyl)-1H-pyrazol-4-yl]-1,5-naphthyridine-3-carboxylate | 401.0 |
| 420 | 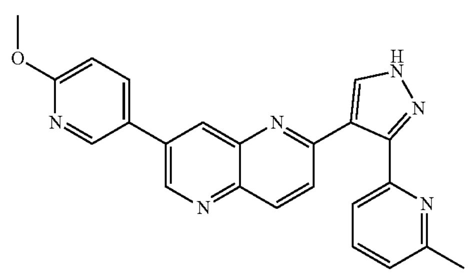 [SMILES: COc1ccc(-c2cnc3ccc(-c4c[nH]nc4-c4cccc(C)n4)nc3c2)cn1] | 7-(6-methoxy-3-pyridyl)-2-[3-(6-methyl-2-pyridyl)-1H-pyrazol-4-yl]-1,5-naphthyridine | 395.1 |
| 421 | 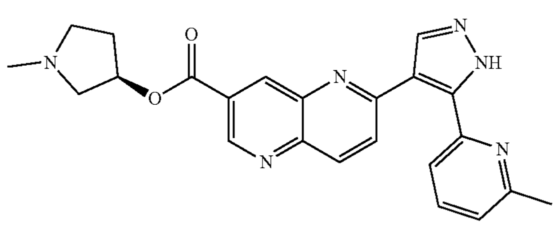 | [(3R)-1-methylpyrrolidin-3-yl] 6-[5-(6-methyl-2-pyridyl)-1H-pyrazol-4-yl]-1,5-naphthyridine-3-carboxylate | 415.2 |
| 422 | 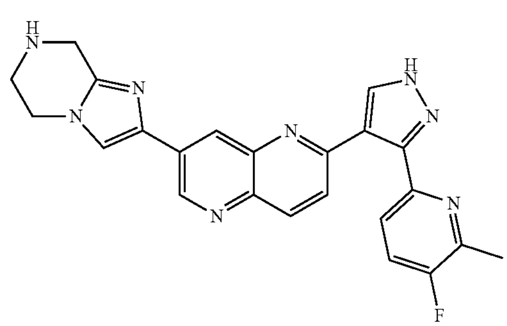 [SMILES: Cc1nc(-c2n[nH]cc2-c2ccc3ncc(-c4cn5c(n4)CNCC5)cc3n2)ccc1F] | 2-[3-(5-fluoro-6-methyl-2-pyridyl)-1H-pyrazol-4-yl]-7-(5,6,7,8-tetrahydroimidazo[1,2-a]pyrazin-2-yl)-1,5-naphthyridine | 427.1 |

TABLE 1-continued

| No. | Structure | Chemical Name | [M + H]+ |
|---|---|---|---|
| 423 | 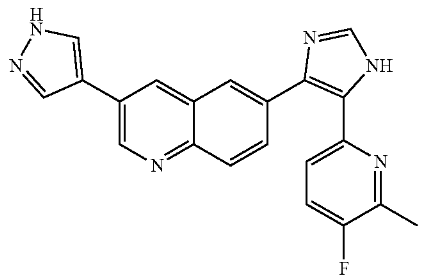 [SMILES: Cc1nc(-c2[nH]cnc2-c2ccc3ncc(-c4cn[nH]c4)cc3c2)ccc1F] | 6-[5-(5-fluoro-6-methyl-2-pyridyl)-1H-imidazol-4-yl]-3-(1H-pyrazol-4-yl)quinoline | 371.1 |
| 424 | 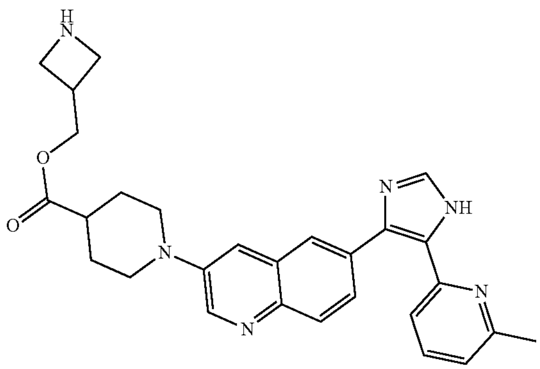 [SMILES: Cc1cccc(-c2[nH]cnc2-c2ccc3ncc(N4CCC(C(=O)OCC5CNC5)CC4)cc3c2)n1] | azetidin-3-ylmethyl 1-[6-[5-(6-methyl-2-pyridyl)-1H-imidazol-4-yl]-3-quinolyl]piperidine-4-carboxylate | 483.2 |
| 425 | 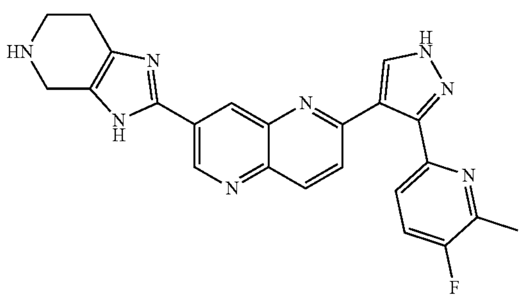 [SMILES: Cc1nc(-c2n[nH]cc2-c2ccc3ncc(-c4nc5c([nH]4)CNCC5)cc3n2)ccc1F] | 2-[3-(5-fluoro-6-methyl-2-pyridyl)-1H-pyrazol-4-yl]-7-(4,5,6,7-tetrahydro-3H-imidazo[4,5-c]pyridin-2-yl)-1,5-naphthyridine | 427.2 |
| 426 | 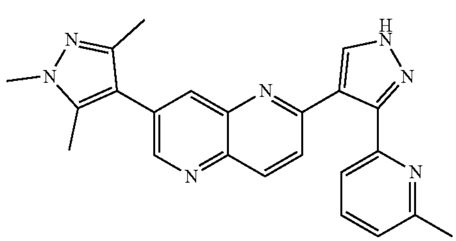 | 2-[3-(6-methyl-2-pyridyl)-1H-pyrazol-4-yl]-7-(1,3,5-trimethylpyrazol-4-yl)-1,5-naphthyridine | 396.1 |
| 427 | 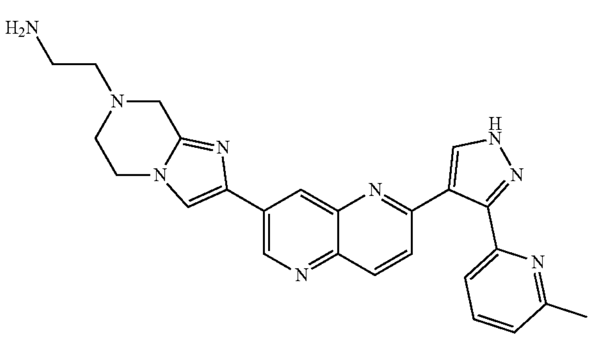 [SMILES: Cc1cccc(-c2n[nH]cc2-c2ccc3ncc(-c4cn5c(n4)CN(CCN)CC5)cc3n2)n1] | 2-[2-[6-[3-(6-methyl-2-pyridyl)-1H-pyrazol-4-yl]-1,5-naphthyridin-3-yl]-6,8-dihydro-5H-imidazo[1,2-a]pyrazin-7-yl]ethanamine | 452.1 |

TABLE 1-continued

| No. | Structure | Chemical Name | [M + H]+ |
|---|---|---|---|
| 428 | 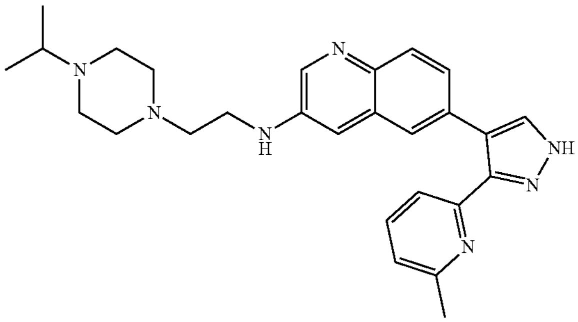 [SMILES: Cc1cccc(-c2n[nH]cc2-c2ccc3ncc(NCCN4CCN(C(C)C)CC4)cc3c2)n1] | N-[2-(4-isopropylpiperazin-1-yl)ethyl]-6-[3-(6-methyl-2-pyridyl)-1H-pyrazol-4-yl]quinolin-3-amine | 456.2 |
| 429 | 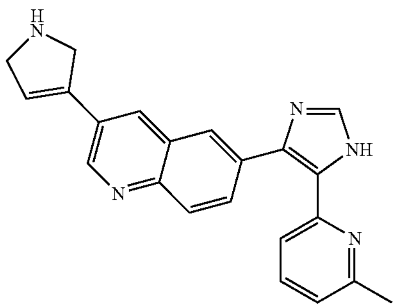 [SMILES: Cc1cccc(-c2[nH]cnc2-c2ccc3ncc(C4=CCNC4)cc3c2)n1] | 3-(2,5-dihydro-1H-pyrrol-3-yl)-6-[5-(6-methyl-2-pyridyl)-1H-imidazol-4-yl]quinoline | 354.2 |
| 430 | 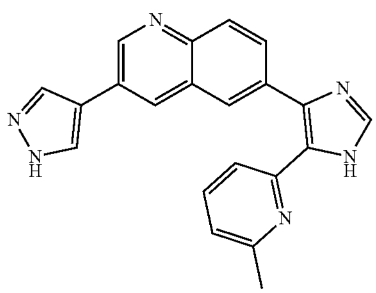 [SMILES: Cc1cccc(-c2[nH]cnc2-c2ccc3ncc(-c4cn[nH]c4)cc3c2)n1] | 6-[5-(6-methyl-2-pyridyl)-1H-imidazol-4-yl]-3-(1H-pyrazol-4-yl)quinoline | 353.3 |
| 431 | 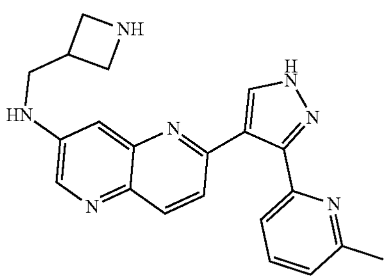 [SMILES: Cc1cccc(-c2n[nH]cc2-c2ccc3ncc(NCC4CNC4)cc3n2)n1] | N-(azetidin-3-ylmethyl)-6-[3-(6-methyl-2-pyridyl)-1H-pyrazol-4-yl]-1,5-naphthyridin-3-amine | 372.1 |
| 432 | 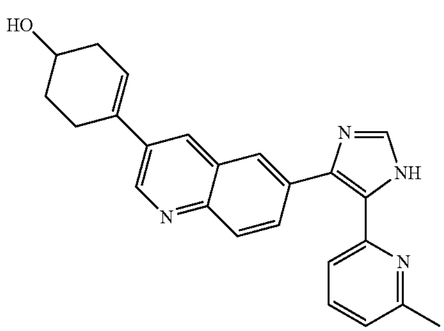 [SMILES: Cc1cccc(-c2[nH]cnc2-c2ccc3ncc(C4=CCC(O)CC4)cc3c2)n1] | 4-[6-[5-(6-methyl-2-pyridyl)-1H-imidazol-4-yl]-3-quinolyl]cyclohex-3-en-1-ol | 383.0 |

TABLE 1-continued

| No. | Structure | Chemical Name | [M + H]+ |
|---|---|---|---|
| 433 | 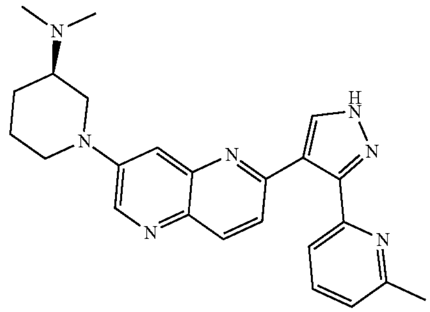 [SMILES: Cc1cccc(-c2n[nH]cc2-c2ccc3ncc(N4CCC[C@@H](N(C)C)C4)cc3n2)n1] | (3R)-N,N-dimethyl-1-[6-[3-(6-methyl-2-pyridyl)-1H-pyrazol-4-yl]-1,5-naphthyridin-3-yl]piperidin-3-amine | 414.3 |
| 434 | 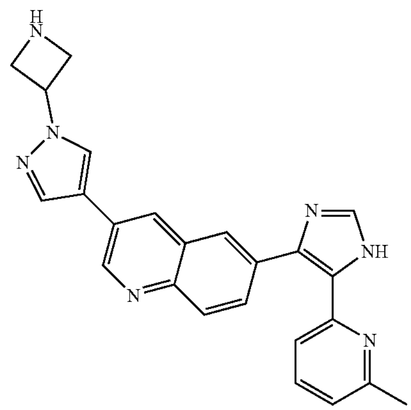 [SMILES: Cc1cccc(-c2[nH]cnc2-c2ccc3ncc(-c4cnn(C5CNC5)c4)cc3c2)n1] | 3-[1-(azetidin-3-yl)pyrazol-4-yl]-6-[5-(6-methyl-2-pyridyl)-1H-imidazol-4-yl]quinoline | 408.2 |
| 435 | 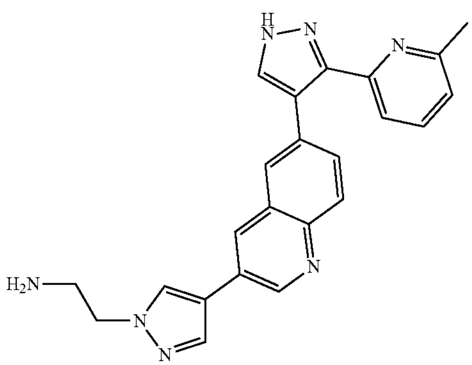 [SMILES: Cc1cccc(-c2n[nH]cc2-c2ccc3ncc(-c4cnn(CCN)c4)cc3c2)n1] | 2-[4-[6-[3-(6-methyl-2-pyridyl)-1H-pyrazol-4-yl]-3-quinolyl]pyrazol-1-yl]ethanamine | 396.1 |
| 436 | 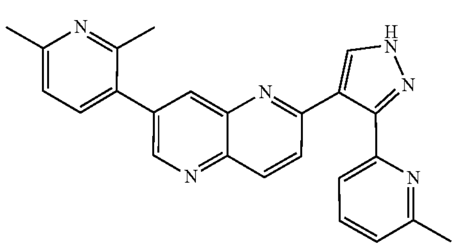 | 7-(2,6-dimethyl-3-pyridyl)-2-[3-(6-methyl-2-pyridyl)-1H-pyrazol-4-yl]-1,5-naphthyridine | 393.1 |

TABLE 1-continued

| No. | Structure | Chemical Name | [M + H]+ |
|---|---|---|---|
| 437 | AND Enantiomer | 2-[3-(6-methyl-2-pyridyl)-1H-pyrazol-4-yl]-7-[rac-(1R,4R)-5-methyl-2,5-diazabicyclo[2.2.1]heptan-2-yl]-1,5-naphthyridine | 398.2 |
| 438 | 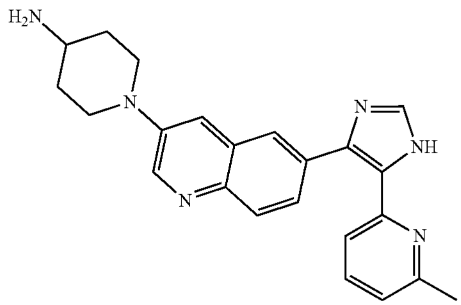 [SMILES: Cc1cccc(-c2[nH]cnc2-c2ccc3ncc(N4CCC(N)CC4)cc3c2)n1] | 1-[6-[5-(6-methyl-2-pyridyl)-1H-imidazol-4-yl]-3-quinolyl]piperidin-4-amine | 385.1 |
| 439 | 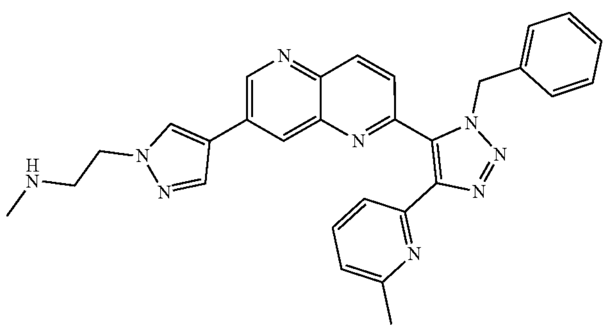 | 2-[4-[6-[3-benzyl-5-(6-methyl-2-pyridyl)triazol-4-yl]-1,5-naphthyridin-3-yl]pyrazol-1-yl]-N-methyl-ethanamine | 502.1 |
| 440 | 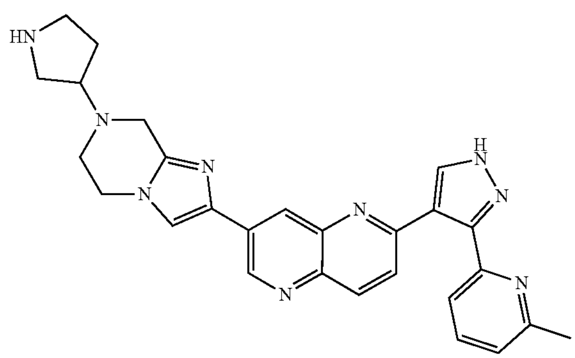 | 2-[3-(6-methyl-2-pyridyl)-1H-pyrazol-4-yl]-7-(7-pyrrolidin-3-yl-6,8-dihydro-5H-imidazo[1,2-a]pyrazin-2-yl)-1,5-naphthyridine | 478.1 |
| 441 | 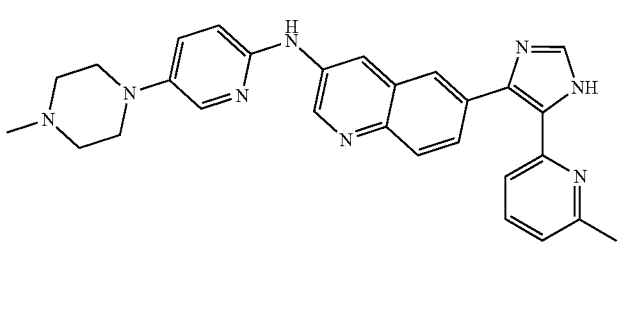 | N-[5-(4-methylpiperazin-1-yl)-2-pyridyl]-6-[5-(6-methyl-2-pyridyl)-1H-imidazol-4-yl]quinolin-3-amine | 477.1 |

TABLE 1-continued

| No. | Structure | Chemical Name | [M + H]⁺ |
|---|---|---|---|
| 442 | 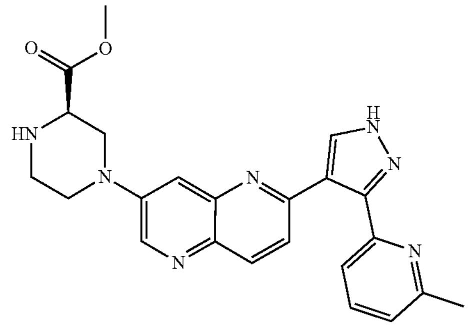 | methyl (2R)-4-[6-[3-(6-methyl-2-pyridyl)-1H-pyrazol-4-yl]-1,5-naphthyridin-3-yl]piperazine-2-carboxylate | 430.1 |
| 443 | 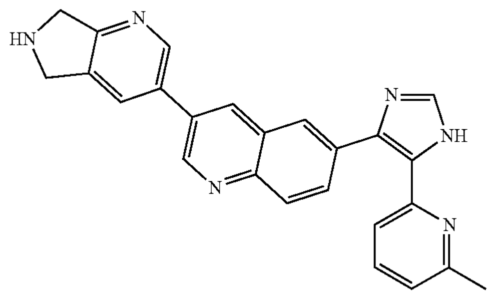 | 3-(6,7-dihydro-5H-pyrrolo[3,4-b]pyridin-3-yl)-6-[5-(6-methyl-2-pyridyl)-1H-imidazol-4-yl]quinoline | 405.0 |
| 444 | 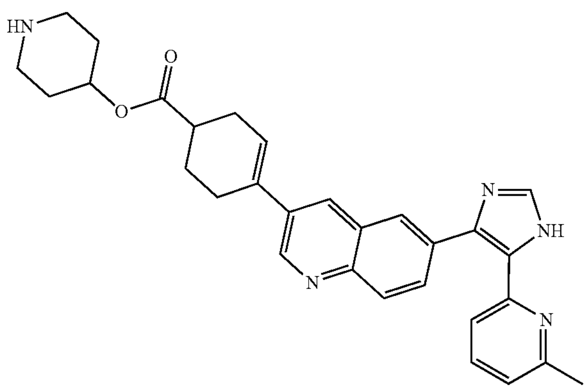 [SMILES: Cc1cccc(-c2[nH]cnc2-c2ccc3ncc(C4=CCC(C(=O)OC5CCNCC5)CC4)cc3c2)n1] | 4-piperidyl 4-[6-[5-(6-methyl-2-pyridyl)-1H-imidazol-4-yl]-3-quinolyl]cyclohex-3-ene-1-carboxylate | 494.0 |
| 445 | 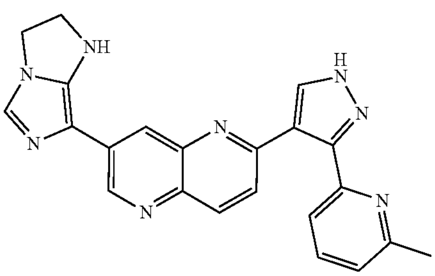 | 7-(2,3-dihydro-1H-imidazo[1,5-a]imidazol-7-yl)-2-[3-(6-methyl-2-pyridyl)-1H-pyrazol-4-yl]-1,5-naphthyridine | 395.2 |
| 446 | 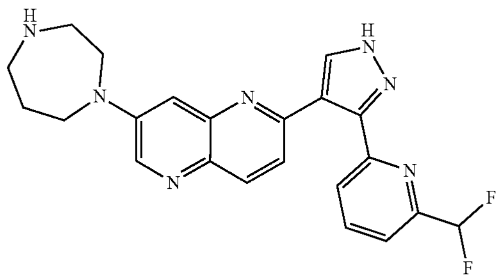 | 7-(1,4-diazepan-1-yl)-2-[3-[6-(difluoromethyl)-2-pyridyl]-1H-pyrazol-4-yl]-1,5-naphthyridine | 422.2 |

TABLE 1-continued

| No. | Structure | Chemical Name | [M + H]⁺ |
|---|---|---|---|
| 447 | 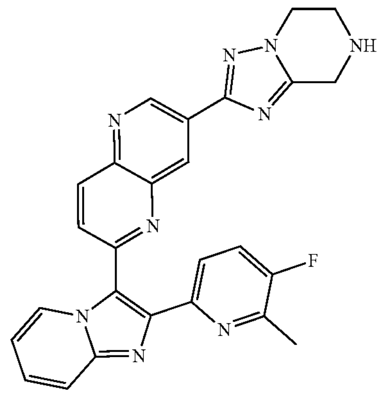 [SMILES: Cc1nc(-c2nc3ccccn3c2-c2ccc3ncc(-c4nc5n(n4)CCNC5)cc3n2)ccc1F] | 2-[2-(5-fluoro-6-methyl-2-pyridyl)imidazo[1,2-a]pyridin-3-yl]-7-(5,6,7,8-tetrahydro-[1,2,4]triazolo[1,5-a]pyrazin-2-yl)-1,5-naphthyridine | 478.1 |
| 448 | 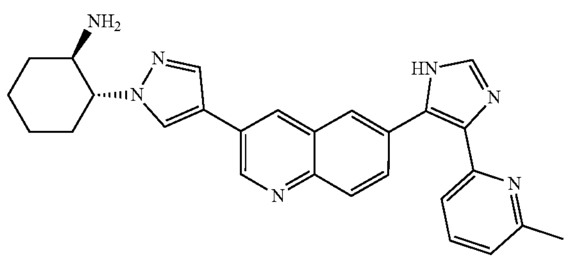 [SMILES: Cc1cccc(-c2nc[nH]c2-c2ccc3ncc(-c4cnn([C@@H]5CCCC[C@H]5N)c4)cc3c2)n1] | (1R,2R)-2-[4-[6-[4-(6-methyl-2-pyridyl)-1H-imidazol-5-yl]-3-quinolyl]pyrazol-1-yl]cyclohexanamine | 450.0 |
| 449 | 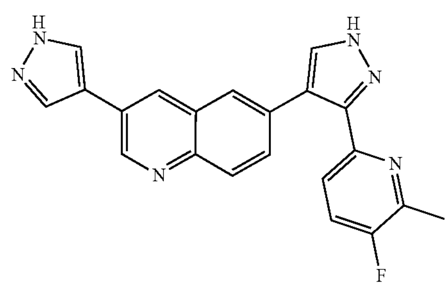 | 6-[3-(5-fluoro-6-methyl-2-pyridyl)-1H-pyrazol-4-yl]-3-(1H-pyrazol-4-yl)quinoline | 371.1 |
| 450 | 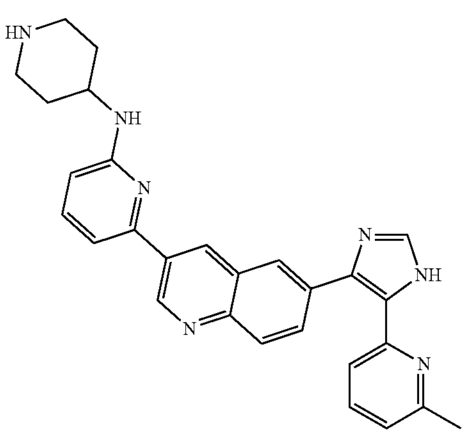 [SMILES: Cc1cccc(-c2[nH]cnc2-c2ccc3ncc(-c4cccc(NC5CCNCC5)n4)cc3c2)n1] | 6-[6-[5-(6-methyl-2-pyridyl)-1H-imidazol-4-yl]-3-quinolyl]-N-(4-piperidyl)pyridin-2-amine | 462.1 |

TABLE 1-continued

| No. | Structure | Chemical Name | [M + H]+ |
|---|---|---|---|
| 451 | 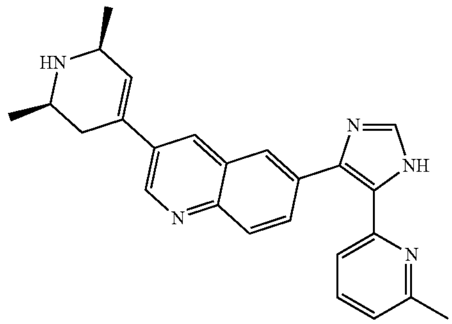 | 3-[(2R,6S)-2,6-dimethyl-1,2,3,6-tetrahydropyridin-4-yl]-6-[5-(6-methyl-2-pyridyl)-1H-imidazol-4-yl]quinoline | 396.1 |
| 452 | 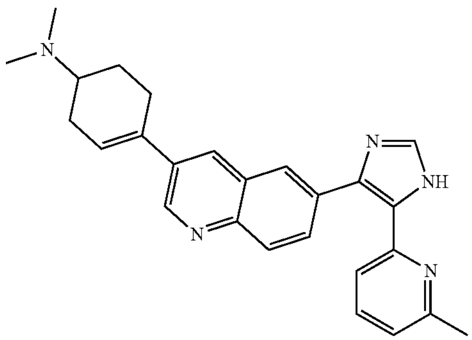 | N,N-dimethyl-4-[6-[5-(6-methyl-2-pyridyl)-1H-imidazol-4-yl]-1,5-naphthyridin-3-yl]cyclohex-3-en-1-amine | 411.1 |
| 453 | 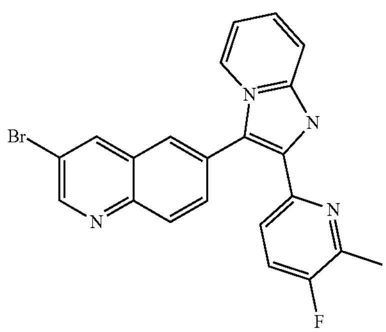 | 7-bromo-2-[2-(5-fluoro-6-methyl-2-pyridyl)imidazo[1,2-a]pyridin-3-yl]-1,5-naphthyridine | 434.2 |
| 454 | 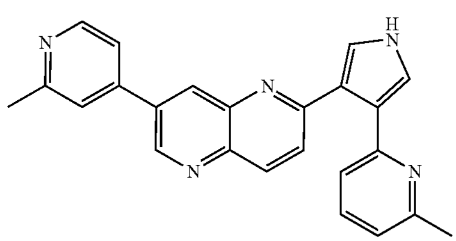 | 7-(2-methyl-4-pyridyl)-2-[3-(6-methyl-2-pyridyl)-1H-pyrazol-4-yl]-1,5-naphthyridine | 379.1 |
| 455 | 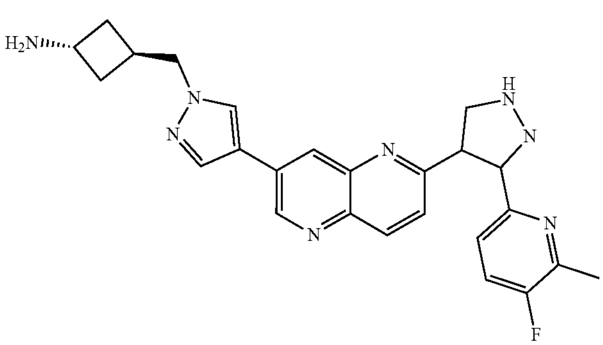 | 3-[[4-[6-[3-(5-fluoro-6-methyl-2-pyridyl)-1H-pyrazol-4-yl]-1,5-naphthyridin-3-yl]pyrazol-1-yl]methyl]cyclobutanamine | 455.1 |

TABLE 1-continued

| No. | Structure | Chemical Name | [M + H]+ |
|---|---|---|---|
| 456 | 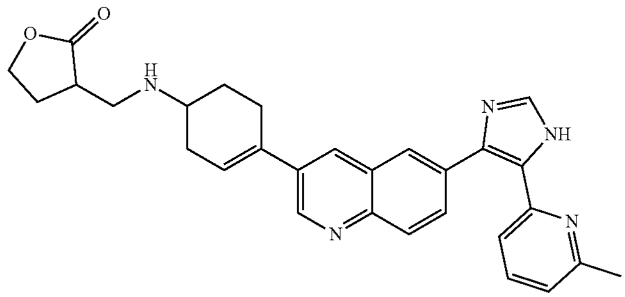 [SMILES: Cc1cccc(-c2[nH]cnc2-c2ccc3ncc(C4=CCC(NCC5CCOC5=O)CC4)cc3c2)n1] | 3-[[[4-[6-[5-(6-methyl-2-pyridyl)-1H-imidazol-4-yl]-3-quinolyl]cyclohex-3-en-1-yl]amino]methyl]tetrahydrofuran-2-one | 480.3 |
| 457 | 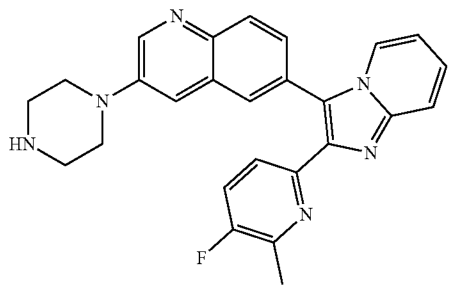 [SMILES: Cc1nc(-c2nc3ccccn3c2-c2ccc3ncc(N4CCNCC4)cc3c2)ccc1F] | 6-[2-(5-fluoro-6-methyl-2-pyridyl)imidazo[1,2-a]pyridin-3-yl]-3-piperazin-1-yl-quinoline | 439.2 |
| 458 | 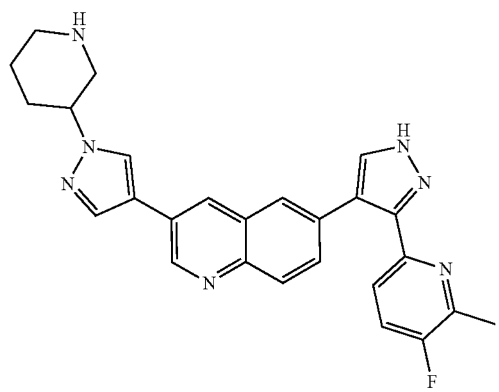 | 6-[3-(5-fluoro-6-methyl-2-pyridyl)-1H-pyrazol-4-yl]-3-[1-(3-piperidyl)pyrazol-4-yl]quinoline | 454.2 |
| 459 | 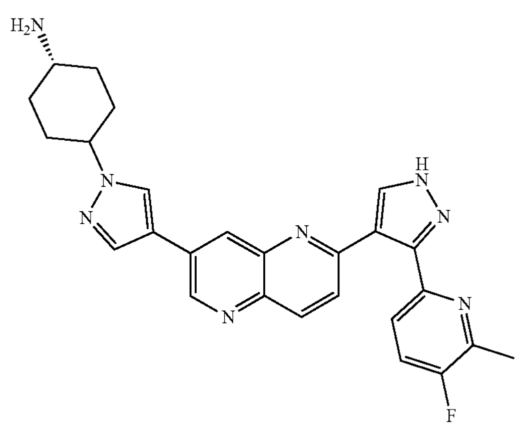 | 4-[4-[6-[3-(5-fluoro-6-methyl-2-pyridyl)-1H-pyrazol-4-yl]-1,5-naphthyridin-3-yl]pyrazol-1-yl]cyclohexanamine | 469.2 |

TABLE 1-continued

| No. | Structure | Chemical Name | [M + H]+ |
|---|---|---|---|
| 460 | 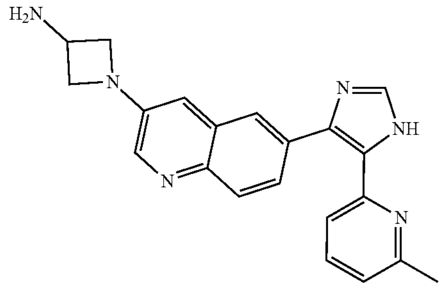 [SMILES: Cc1cccc(-c2[nH]cnc2-c2ccc3ncc(N4CC(N)C4)cc3c2)n1] | 1-[6-[5-(6-methyl-2-pyridyl)-1H-imidazol-4-yl]-3-quinolyl]azetidin-3-amine | 357.2 |
| 461 | 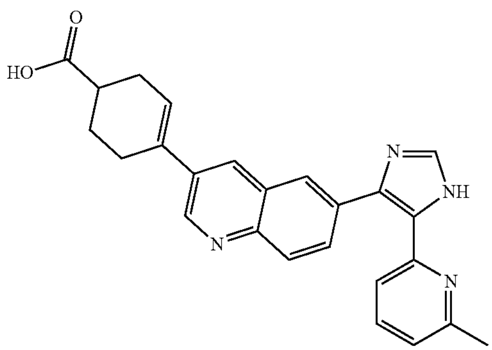 [SMILES: Cc1cccc(-c2[nH]cnc2-c2ccc3ncc(C4=CCC(C(=O)O)CC4)cc3c2)n1] | 4-[6-[5-(6-methyl-2-pyridyl)-1H-imidazol-4-yl]-3-quinolyl]cyclohex-3-ene-1-carboxylic acid | 411.0 |
| 462 | AND Enantiomer | 2-[3-(6-methyl-2-pyridyl)-1H-pyrazol-4-yl]-7-[rac-(2R,5R)-2,5-dimethylpiperazin-1-yl]-1,5-naphthyridine | 400.2 |
| 463 | AND Enantiomer | rac-(1R,3S)-3-[[4-[6-[3-(5-fluoro-6-methyl-2-pyridyl)-1H-pyrazol-4-yl]-1,5-naphthyridin-3-yl]pyrazol-1-yl]methyl]cyclohexanamine | 483.2 |
| 464 | 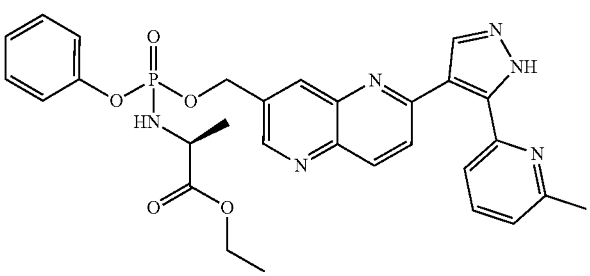 [SMILES: CCOC(=O)[C@H](C)NP(=O)(OCc1cnc2ccc(-c3cn[nH]c3-c3cccc(C)n3)nc2c1)Oc1ccccc1] | ethyl (2S)-2-[[[6-[5-(6-methyl-2-pyridyl)-1H-pyrazol-4-yl]-1,5-naphthyridin-3-yl]methoxy-phenoxy-phosphoryl]amino]propanoate | 573.3 |

TABLE 1-continued

| No. | Structure | Chemical Name | [M + H]+ |
|---|---|---|---|
| 465 | 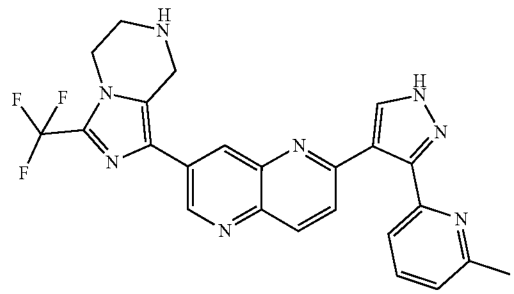 | 2-[3-(6-methyl-2-pyridyl)-1H-pyrazol-4-yl]-7-[3-(trifluoromethyl)-5,6,7,8-tetrahydroimidazo[1,5-a]pyrazin-1-yl]-1,5-naphthyridine | 477.1 |
| 466 | 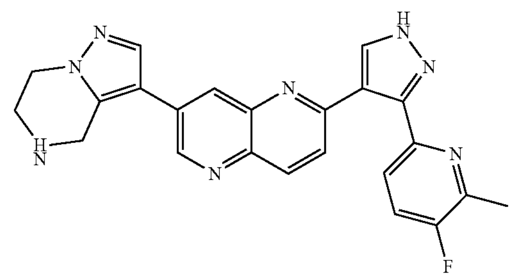 [SMILES: Cc1nc(-c2n[nH]cc2-c2ccc3ncc(-c4cnn5c4CNCC5)cc3n2)ccc1F] | 2-[3-(5-fluoro-6-methyl-2-pyridyl)-1H-pyrazol-4-yl]-7-(4,5,6,7-tetrahydrotriazolo[1,5-a]pyrazin-3-yl)-1,5-naphthyridine | 428.2 |
| 467 | 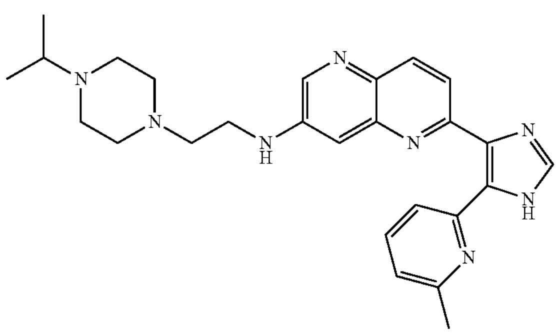 [SMILES: Cc1cccc(-c2[nH]cnc2-c2ccc3ncc(NCCN4CCN(C(C)C)CC4)cc3n2)n1] | N-[2-(4-isopropylpiperazin-1-yl)ethyl]-6-[5-(6-methyl-2-pyridyl)-1H-imidazol-4-yl]quinolin-3-amine | 456.2 |
| 468 | 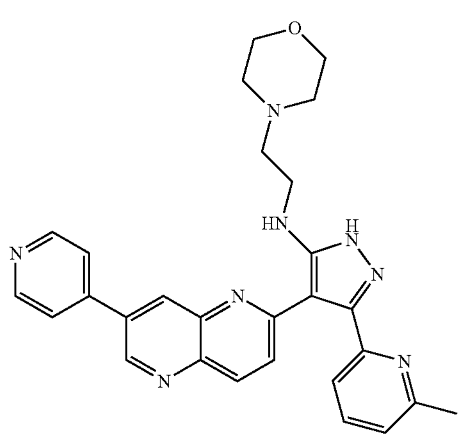 [SMILES: Cc1cccc(-c2n[nH]c(NCCN3CCOCC3)c2-c2ccc3ncc(-c4ccncc4)cc3n2)n1] | 3-(6-methyl-2-pyridyl)-N-(2-morpholinoethyl)-4-[7-(4-pyridyl)-1,5-naphthyridin-2-yl]-1H-pyrazol-5-amine | 493.2 |

TABLE 1-continued

| No. | Chemical Name | [M + H]+ |
|---|---|---|
| 469 | 2-[2-(6-methyl-2-pyridyl)imidazo[1,2-a]pyridin-3-yl]-7-(1H-pyrazol-4-yl)-1,5-naphthyridine | 404.2 |
| 470 | 2-[3-(6-methyl-2-pyridyl)-1H-pyrazol-4-yl]-7-(4-piperidyl)-1,5-naphthyridine | 371.1 |
| 471 | N-methyl-1-[6-[3-(6-methyl-2-pyridyl)-1H-pyrazol-4-yl]-3-(1H-pyrazol-4-yl)-4-quinolyl]methanamine | 396.5 |
| 472 | 6-[5-(6-methyl-2-pyridyl)-1H-imidazol-4-yl]-3-(1,2,3,6-tetrahydropyridin-4-yl)quinoline | 368.0 |
| 473 | 2-[2-(6-methyl-2-pyridyl)imidazo[1,2-a]pyridin-3-yl]-7-piperazin-1-yl-1,5-naphthyridine | 422.1 |

TABLE 1-continued

| No. | Structure | Chemical Name | [M + H]⁺ |
|---|---|---|---|
| 474 | 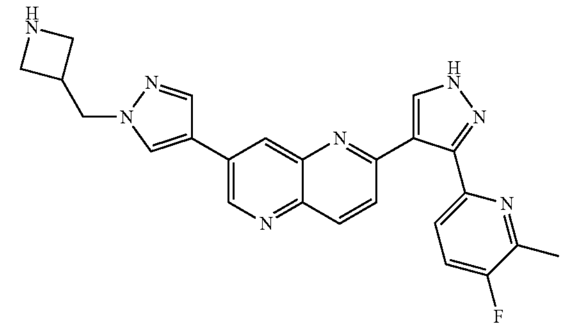 [SMILES: Cc1nc(-c2n[nH]cc2-c2ccc3ncc(-c4cnn(CC5CNC5)c4)cc3n2)ccc1F] | 7-[1-(azetidin-3-ylmethyl)pyrazol-4-yl]-2-[3-(5-fluoro-6-methyl-2-pyridyl)-1H-pyrazol-4-yl]-1,5-naphthyridine | 441.2 |
| 475 | 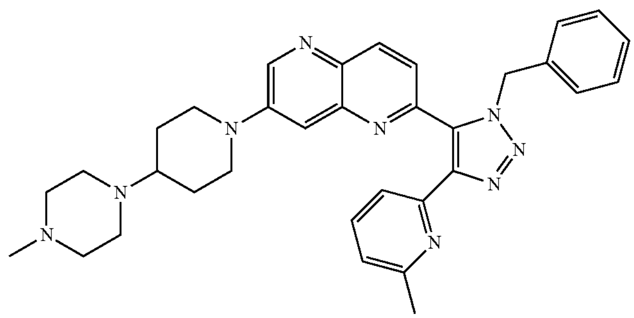 [SMILES: Cc1cccc(-c2nnn(Cc3ccccc3)c2-c2ccc3ncc(N4CCC(N5CCN(C)CC5)CC4)cc3n2)n1] | 2-[3-benzyl-5-(6-methyl-2-pyridyl)triazol-4-yl]-7-[4-(4-methylpiperazin-1-yl)-1-piperidyl]-1,5-naphthyridine | 560.3 |
| 476 | 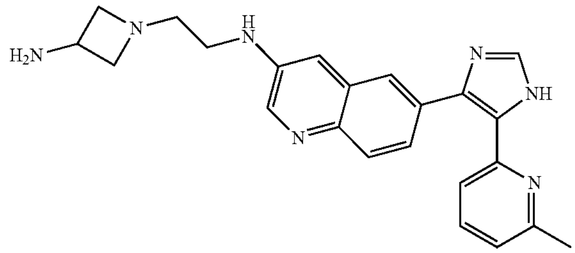 [SMILES: Cc1cccc(-c2[nH]cnc2-c2ccc3ncc(NCCN4CC(N)C4)cc3c2)n1] | N-[2-(3-aminoazetidin-1-yl)ethyl]-6-[5-(6-methyl-2-pyridyl)-1H-imidazol-4-yl]quinolin-3-amine | 400.2 |
| 477 | 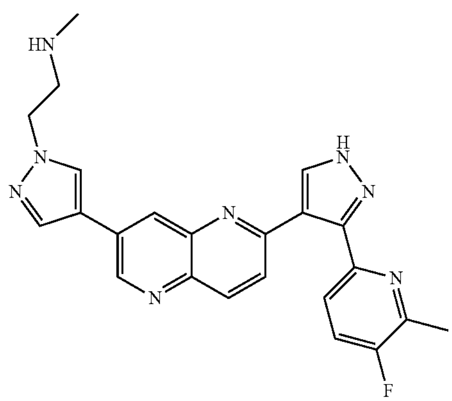 [SMILES: CNCCn1cc(-c2cnc3ccc(-c4c[nH]nc4-c4ccc(F)c(C)n4)nc3c2)cn1] | 2-[4-[6-[3-(5-fluoro-6-methyl-2-pyridyl)-1H-pyrazol-4-yl]-1,5-naphthyridin-3-yl]pyrazol-1-yl]-N-methyl-ethanamine | 429.2 |
| 478 | 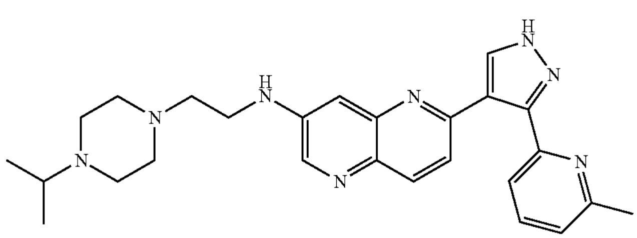 [SMILES: Cc1cccc(-c2n[nH]cc2-c2ccc3ncc(NCCN4CCN(C(C)C)CC4)cc3n2)n1] | N-[2-(4-isopropylpiperazin-1-yl)ethyl]-6-[3-(6-methyl-2-pyridyl)-1H-pyrazol-4-yl]-1,5-naphthyridin-3-amine | 457.2 |

TABLE 1-continued

| No. | Structure | Chemical Name | [M + H]+ |
|---|---|---|---|
| 479 | 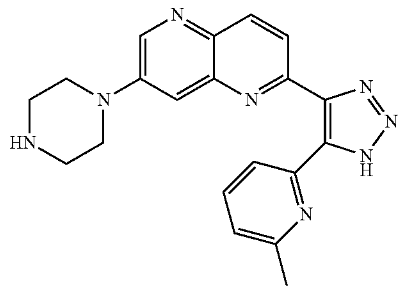 [SMILES: Cc1cccc(-c2[nH]nnc2-c2ccc3ncc(N4CCNCC4)cc3n2)n1] | 2-[5-(6-methyl-2-pyridyl)-1H-triazol-4-yl]-7-piperazin-1-yl-1,5-naphthyridine | 373.2 |
| 480 | 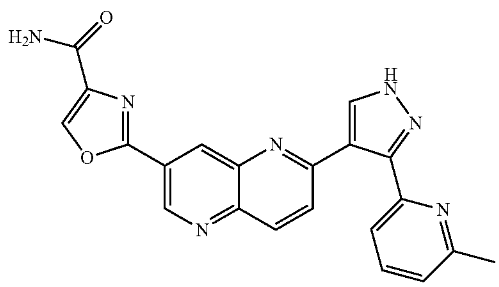 [SMILES: Cc1cccc(-c2n[nH]cc2-c2ccc3ncc(-c4nc(C(N)=O)co4)cc3n2)n1] | 2-[6-[3-(6-methyl-2-pyridyl)-1H-pyrazol-4-yl]-1,5-naphthyridin-3-yl]oxazole-4-carboxamide | 398.2 |
| 481 | 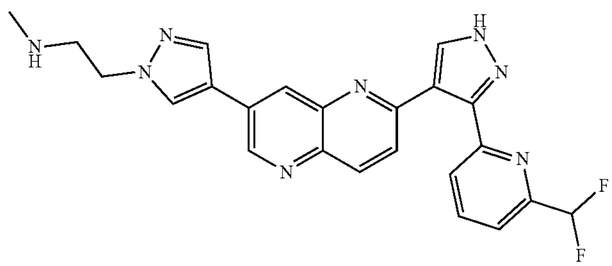 [SMILES: CNCCn1cc(-c2cnc3ccc(-c4c[nH]nc4-c4cccc(C(F)F)n4)nc3c2)cn1] | 2-[4-[6-[3-[6-(difluoromethyl)-2-pyridyl]-1H-pyrazol-4-yl]-1,5-naphthyridin-3-yl]pyrazol-1-yl]-N-methyl-ethanamine | 447.1 |
| 482 | 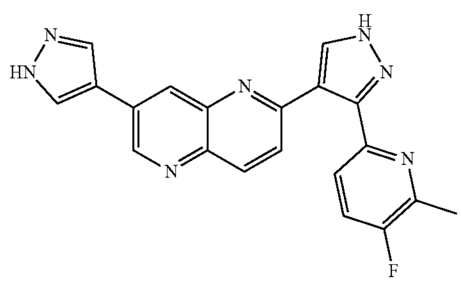 [SMILES: Cc1nc(-c2n[nH]cc2-c2ccc3ncc(-c4cn[nH]c4)cc3n2)ccc1F] | 2-[3-(5-fluoro-6-methyl-2-pyridyl)-1H-pyrazol-4-yl]-7-(1H-pyrazol-4-yl)-1,5-naphthyridine | 372.1 |
| 483 | 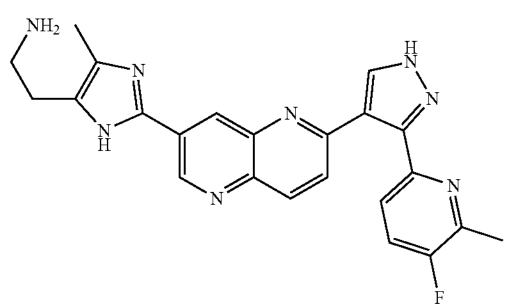 [SMILES: Cc1nc(-c2n[nH]cc2-c2ccc3ncc(-c4nc(C)c(CCN)[nH]4)cc3n2)ccc1F] | 2-[2-[6-[3-(5-fluoro-6-methyl-2-pyridyl)-1H-pyrazol-4-yl]-1,5-naphthyridin-3-yl]-4-methyl-1H-imidazol-5-yl]ethanamine | 429.1 |

TABLE 1-continued

| No. | Structure | Chemical Name | [M + H]+ |
|---|---|---|---|
| 484 | 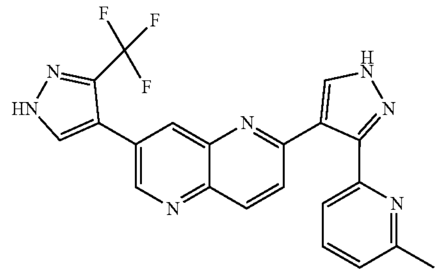 [SMILES: Cc1cccc(-c2n[nH]cc2-c2ccc3ncc(-c4c[nH]nc4C(F)(F)F)cc3n2)n1] | 2-[3-(6-methyl-2-pyridyl)-1H-pyrazol-4-yl]-7-[3-(trifluoromethyl)-1H-pyrazol-4-yl]-1,5-naphthyridine | 422.1 |
| 485 | 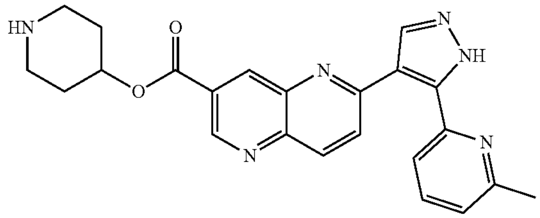 [SMILES: Cc1cccc(-c2[nH]ncc2-c2ccc3ncc(C(=O)OC4CCNCC4)cc3n2)n1] | 4-piperidyl 6-[5-(6-methyl-2-pyridyl)-1H-pyrazol-4-yl]-1,5-naphthyridine-3-carboxylate | 415.1 |
| 486 | 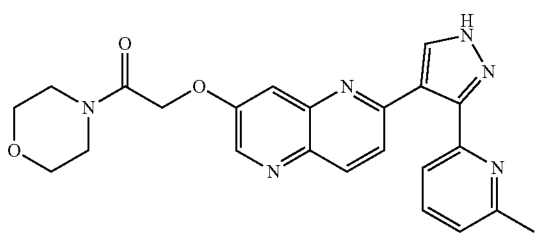 [SMILES: Cc1cccc(-c2n[nH]cc2-c2ccc3ncc(OCC(=O)N4CCOCC4)cc3n2)n1] | 2-[[6-[3-(6-methyl-2-pyridyl)-1H-pyrazol-4-yl]-1,5-naphthyridin-3-yl]oxy]-1-morpholino-ethanone | 431.5 |
| 487 | 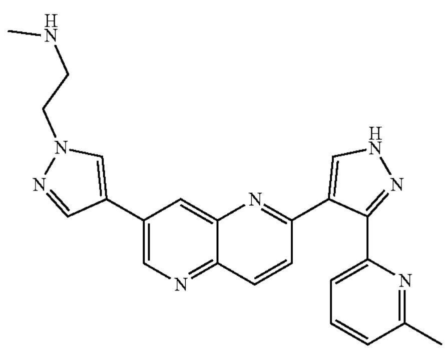 | N-methyl-2-[4-[6-[3-(6-methyl-2-pyridyl)-1H-pyrazol-4-yl]-1,5-naphthyridin-3-yl]pyrazol-1-yl]ethanamine | 411.2 |
| 488 | 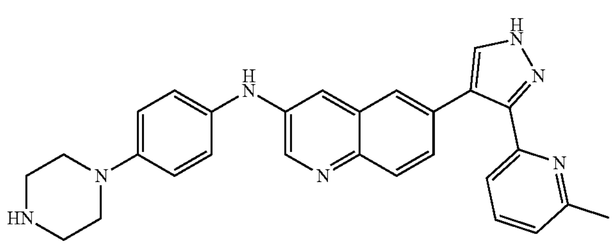 [SMILES: Cc1cccc(-c2n[nH]cc2-c2ccc3ncc(Nc4ccc(N5CCNCC5)cc4)cc3c2)n1] | 6-[3-(6-methyl-2-pyridyl)-1H-pyrazol-4-yl]-N-(4-piperazin-1-ylphenyl)quinolin-3-amine | 462.2 |
| 489 | 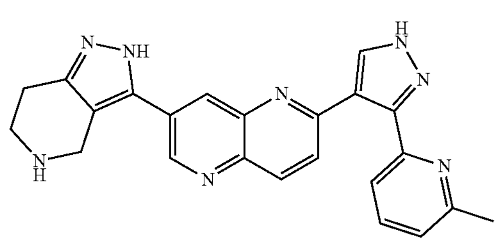 [SMILES: Cc1cccc(-c2n[nH]cc2-c2ccc3ncc(-c4[nH]nc5c4CNCC5)cc3n2)n1] | 2-[3-(6-methyl-2-pyridyl)-1H-pyrazol-4-yl]-7-(4,5,6,7-tetrahydro-2H-pyrazolo[4,3-c]pyridin-3-yl)-1,5-naphthyridine | 409.2 |

TABLE 1-continued

| No. | Structure | Chemical Name | [M + H]+ |
|---|---|---|---|
| 490 | 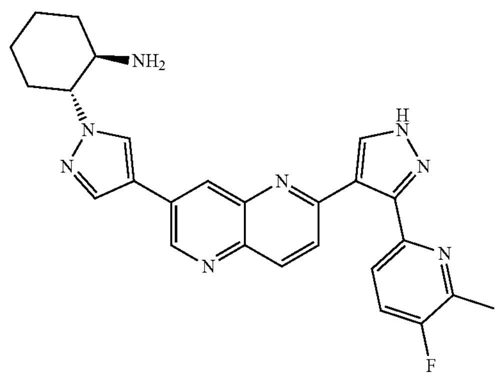 [SMILES: Cc1nc(-c2n[nH]cc2-c2ccc3ncc(-c4cnn([C@@H]5CCCC[C@H]5N)c4)cc3n2)ccc1F] | (1R,2R)-2-[4-[6-[3-(5-fluoro-6-methyl-2-pyridyl)-1H-pyrazol-4-yl]-1,5-naphthyridin-3-yl]pyrazol-1-yl]cyclohexanamine | 469..2 |
| 491 | 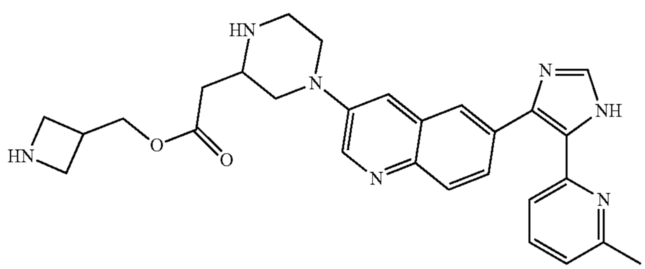 [SMILES: Cc1cccc(-c2[nH]cnc2-c2ccc3ncc(N4CCNC(CC(=O)OCC5CNC5)C4)cc3c2)n1] | azetidin-3-ylmethyl 2-[4-[6-[5-(6-methyl-2-pyridyl)-1H-imidazol-4-yl]-3-quinolyl]piperazin-2-yl]acetate | 498.3 |
| 492 | 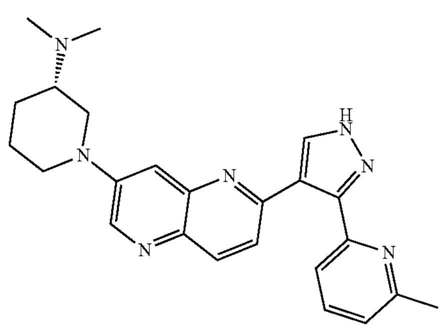 [SMILES: Cc1cccc(-c2n[nH]cc2-c2ccc3ncc(N4CCC[C@H](N(C)C)C4)cc3n2)n1] | (3S)-N,N-dimethyl-1-[6-[3-(6-methyl-2-pyridyl)-1H-pyrazol-4-yl]-1,5-naphthyridin-3-yl]piperidin-3-amine | 414.2 |
| 493 | 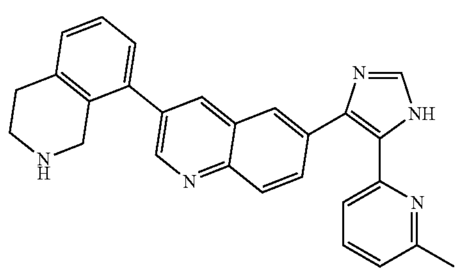 [SMILES: Cc1cccc(-c2[nH]cnc2-c2ccc3ncc(-c4cccc5c4CNCC5)cc3c2)n1] | 6-[5-(6-methyl-2-pyridyl)-1H-imidazol-4-yl]-3-(1,2,3,4-tetrahydroisoquinolin-8-yl)quinoline | 418.1 |
| 494 | 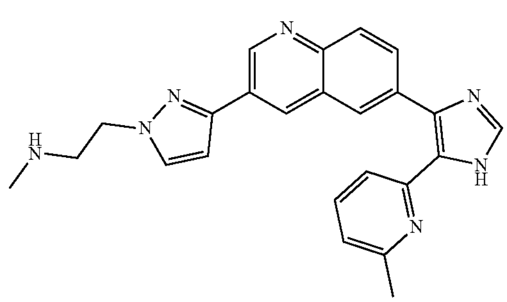 [SMILES: CNCCn1ccc(-c2cnc3ccc(-c4nc[nH]c4-c4cccc(C)n4)cc3c2)n1] | N-methyl-2-[3-[6-[5-(6-methyl-2-pyridyl)-1H-imidazol-4-yl]-3-quinolyl]pyrazol-1-yl]ethanamine | 410.1 |

TABLE 1-continued

| No. | Structure | Chemical Name | [M + H]+ |
|---|---|---|---|
| 495 | 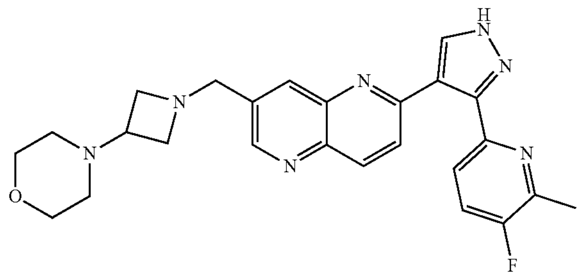 [SMILES: Cc1nc(-c2n[nH]cc2-c2ccc3ncc(CN4CC(N5CCOCC5)C4)cc3n2)ccc1F] | 4-[1-[[6-[3-(6-methyl-2-pyridyl)-1H-pyrazol-4-yl]-1,5-naphthyridin-3-yl]methyl]azetidin-3-yl]morpholine | 442.4 |
| 496 | 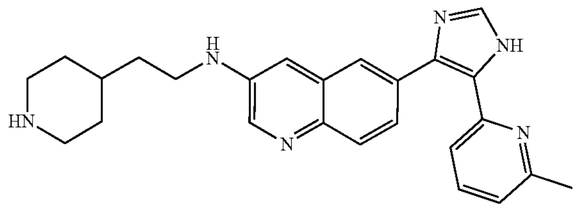 [SMILES: Cc1cccc(-c2[nH]cnc2-c2ccc3ncc(NCCC4CCNCC4)cc3c2)n1] | 6-[5-(6-methyl-2-pyridyl)-1H-imidazol-4-yl]-N-[2-(4-piperidyl)ethyl]quinolin-3-amine | 413.2 |
| 497 | AND Enantiomer | rac-(2S)-4-[6-[3-(6-methyl-2-pyridyl)-1H-pyrazol-4-yl]-1,5-naphthyridin-3-yl]piperazine-2-carboxamide | 415.2 |
| 498 | 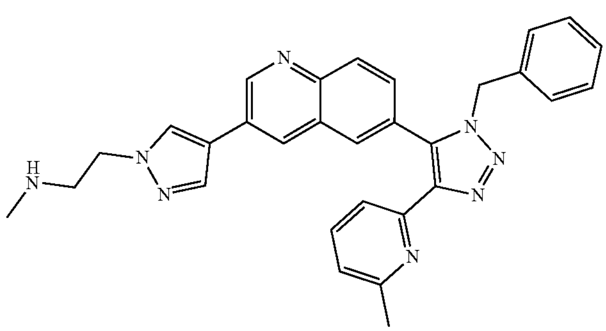 | 2-[4-[6-[3-benzyl-5-(6-methyl-2-pyridyl)triazol-4-yl]-3-quinolyl]pyrazol-1-yl]-N-methyl-ethanamine | 501.2 |
| 499 | 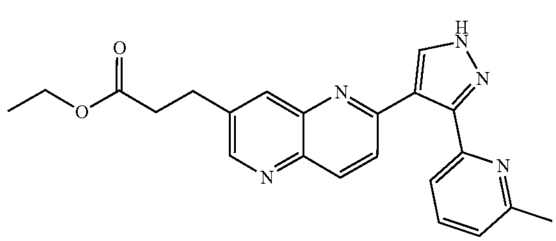 | ethyl 3-[6-[3-(6-methyl-2-pyridyl)-1H-pyrazol-4-yl]-1,5-naphthyridin-3-yl]propanoate | 388.1 |

TABLE 1-continued

| No. | Structure | Chemical Name | [M + H]⁺ |
|---|---|---|---|
| 500 | 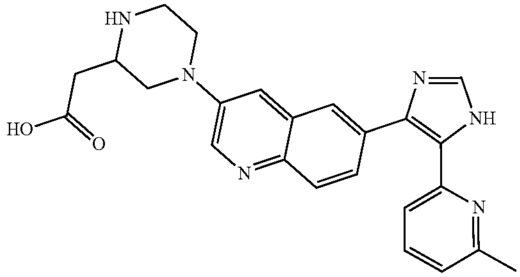 [SMILES: Cc1cccc(-c2[nH]cnc2-c2ccc3ncc(N4CCNC(CC(=O)O)C4)cc3c2)n1] | 2-[4-[6-[5-(6-methyl-2-pyridyl)-1H-imidazol-4-yl]-3-quinolyl]piperazin-2-yl]acetic acid | 429.1 |
| 501 | 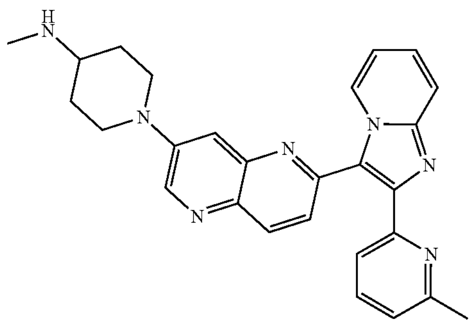 | N-methyl-1-[6-[2-(6-methyl-2-pyridyl)imidazo[1,2-a]pyridin-3-yl]-1,5-naphthyridin-3-yl]piperidin-4-amine | 450.2 |
| 502 | 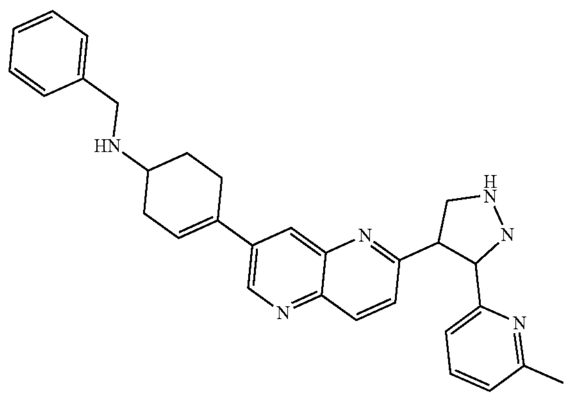 | N-benzyl-4-[6-[3-(6-methyl-2-pyridyl)-1H-pyrazol-4-yl]-1,5-naphthyridin-3-yl]cyclohex-3-en-1-amine | 473.1 |
| 503 | AND Enantiomer | N-methyl-6-[3-(6-methyl-2-pyridyl)-1H-pyrazol-4-yl]-N-[rac-(3R)-1-isopropylpyrrolidin-3-yl]-1,5-naphthyridin-3-amine | 428.2 |
| 504 | 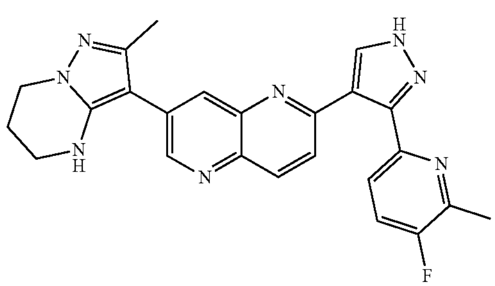 | 2-[3-(5-fluoro-6-methyl-2-pyridyl)-1H-pyrazol-4-yl]-7-(2-methyl-4,5,6,7-tetrahydropyrazolo[1,5-a]pyrimidin-3-yl)-1,5-naphthyridine | 441.1 |

TABLE 1-continued

| No. | Structure | Chemical Name | [M + H]+ |
|---|---|---|---|
| 505 | AND Enantiomer | rac-(3S)-N,N-dimethyl-1-[6-[3-(6-methyl-2-pyridyl)-1H-pyrazol-4-yl]-1,5-naphthyridin-3-yl]pyrrolidin-3-amine | 400.1 |
| 506 | 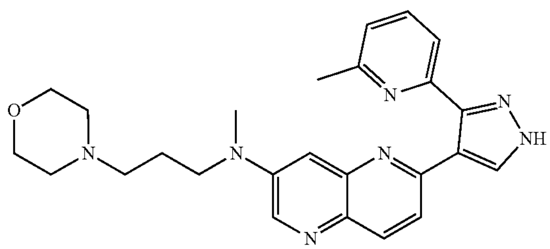 [SMILES: Cc1cccc(-c2n[nH]cc2-c2ccc3ncc(N(C)CCCN4CCOCC4)cc3n2)n1] | N-methyl-6-[3-(6-methyl-2-pyridyl)-1H-pyrazol-4-yl]-N-(3-morpholinopropyl)-1,5-naphthyridin-3-amine | 444.2 |
| 507 | 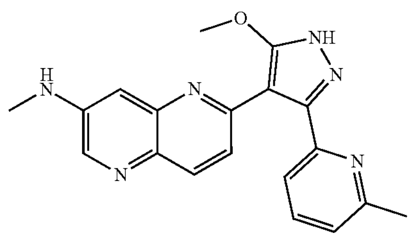 | 6-[5-methoxy-3-(6-methyl-2-pyridyl)-1H-pyrazol-4-yl]-N-methyl-1,5-naphthyridin-3-amine | 347.2 |
| 508 | 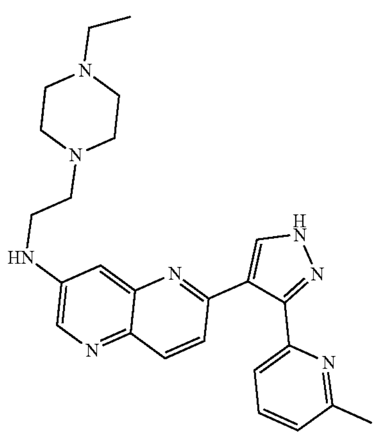 | N-[2-(4-ethylpiperazin-1-yl)ethyl]-6-[3-(6-methyl-2-pyridyl)-1H-pyrazol-4-yl]-1,5-naphthyridin-3-amine | 443.3 |
| 509 | 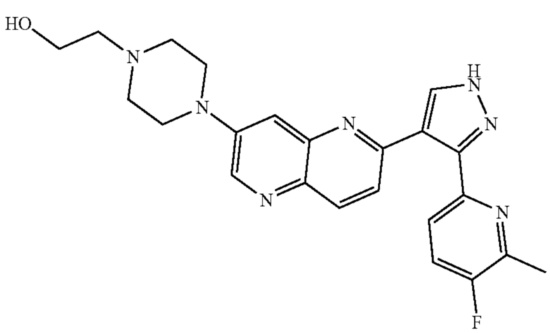 | 2-[4-[6-[3-(5-fluoro-6-methyl-2-pyridyl)-1H-pyrazol-4-yl]-1,5-naphthyridin-3-yl]piperazin-1-yl]ethanol | 434.1 |

TABLE 1-continued

| No. | Structure | Chemical Name | [M + H]+ |
|---|---|---|---|
| 510 | 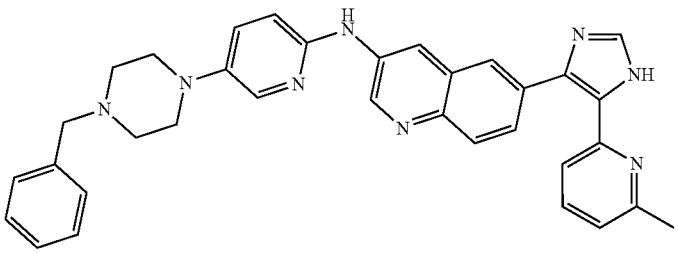 [SMILES: Cc1cccc(-c2[nH]cnc2-c2ccc3ncc(Nc4ccc(N5CCN(Cc6ccccc6)CC5)cn4)cc3c2)n1] | N-[5-(4-benzylpiperazin-1-yl)-2-pyridyl]-6-[5-(6-methyl-2-pyridyl)-1H-imidazol-4-yl]quinolin-3-amine | 553.1 |
| 511 | 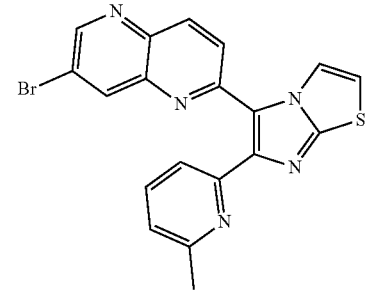 [SMILES: Cc1cccc(-c2nc3sccn3c2-c2ccc3ncc(Br)cc3n2)n1] | 5-(7-bromo-1,5-naphthyridin-2-yl)-6-(6-methyl-2-pyridyl)imidazo[2,1-b]thiazole | 422.9 |
| 512 | 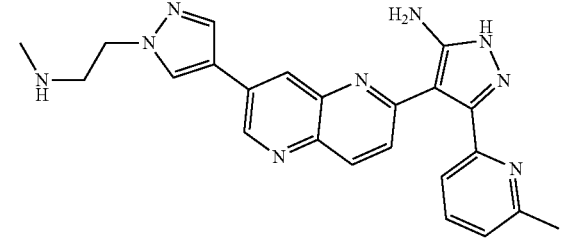 | 4-[7-[1-[2-(methylamino)ethyl]pyrazol-4-yl]-1,5-naphthyridin-2-yl]-3-(6-methyl-2-pyridyl)-1H-pyrazol-5-amine | 426.3 |
| 513 | AND Enantiomer 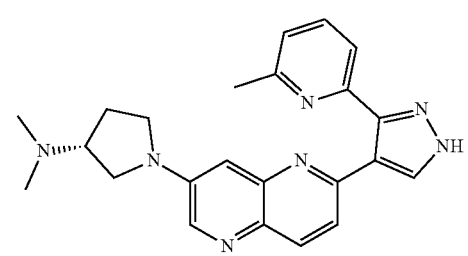 | rac-(3R)-N,N-dimethyl-1-[6-[3-(6-methyl-2-pyridyl)-1H-pyrazol-4-yl]-1,5-naphthyridin-3-yl]pyrrolidin-3-amine | 400.2 |
| 514 | 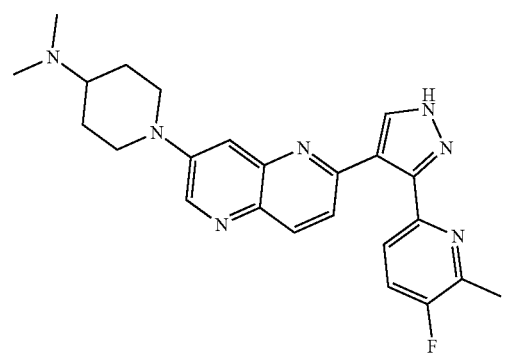 | 1-[6-[3-(5-fluoro-6-methyl-2-pyridyl)-1H-pyrazol-4-yl]-1,5-naphthyridin-3-yl]-N,N-dimethyl-piperidin-4-amine | 432.1 |

TABLE 1-continued

| No. | Structure | Chemical Name | [M + H]+ |
|---|---|---|---|
| 515 | 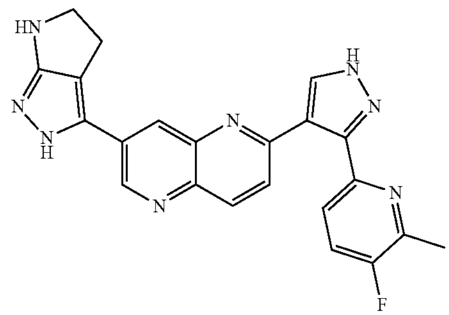 [SMILES: Cc1nc(-c2n[nH]cc2-c2ccc3ncc(-c4[nH]nc5c4CCN5)cc3n2)ccc1F] | 2-[3-(5-fluoro-6-methyl-2-pyridyl)-1H-pyrazol-4-yl]-7-(2,4,5,6-tetrahydropyrrolo[2,3-c]pyrazol-3-yl)-1,5-naphthyridine | 413.1 |
| 516 | 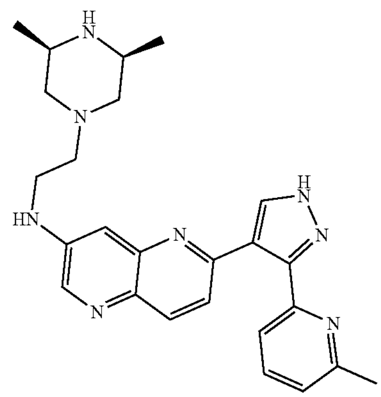 | 6-[3-(6-methyl-2-pyridyl)-1H-pyrazol-4-yl]-N-[2-[rac-(3R,5S)-3,5-dimethylpiperazin-1-yl]ethyl]-1,5-naphthyridin-3-amine | 443.1 |
| 517 | 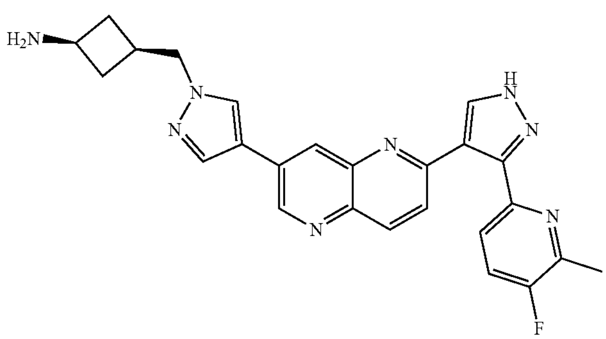 [SMILES: Cc1nc(-c2n[nH]cc2-c2ccc3ncc(-c4cnn(C[C@H]5C[C@@H](N)C5)c4)cc3n2)ccc1F] | 3-[[4-[6-[3-(5-fluoro-6-methyl-2-pyridyl)-1H-pyrazol-4-yl]-1,5-naphthyridin-3-yl]pyrazol-1-yl]methyl]cyclobutanamine | 455.1 |
| 518 | 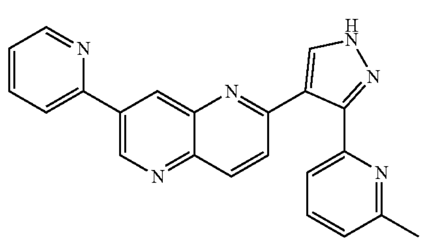 [SMILES: Cc1cccc(-c2n[nH]cc2-c2ccc3ncc(-c4ccccn4)cc3n2)n1] | 2-[3-(6-methyl-2-pyridyl)-1H-pyrazol-4-yl]-7-(2-pyridyl)-1,5-naphthyridine | 365.3 |
| 519 | 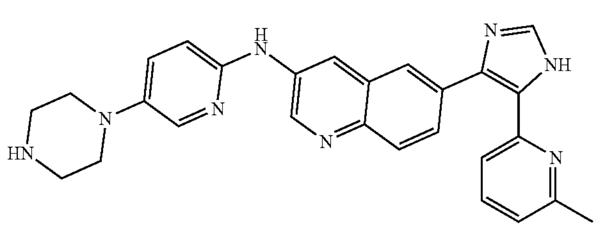 [SMILES: Cc1cccc(-c2[nH]cnc2-c2ccc3ncc(Nc4ccc(N5CCNCC5)cn4)cc3c2)n1] | 6-[5-(6-methyl-2-pyridyl)-1H-imidazol-4-yl]-N-(5-piperazin-1-yl-2-pyridyl)quinolin-3-amine | 463.2 |

TABLE 1-continued

| No. | Structure | Chemical Name | [M + H]⁺ |
|---|---|---|---|
| 520 | 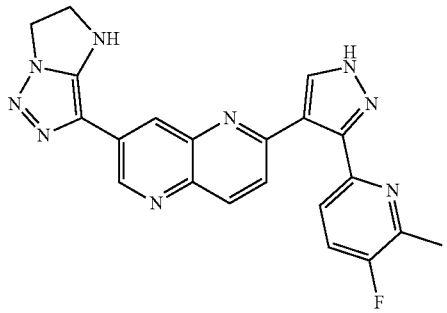 [SMILES: Cc1nc(-c2n[nH]cc2-c2ccc3ncc(-c4nnn5c4NCC5)cc3n2)ccc1F] | 7-(5,6-dihydro-4H-imidazo[1,2-c]triazol-3-yl)-2-[3-(5-fluoro-6-methyl-2-pyridyl)-1H-pyrazol-4-yl]-1,5-naphthyridine | 414.1 |
| 521 | 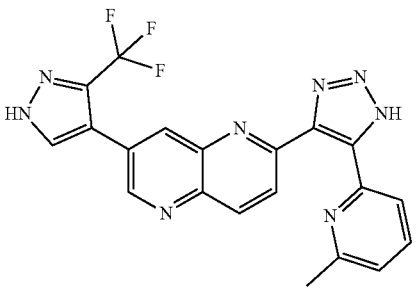 [SMILES: Cc1cccc(-c2[nH]nnc2-c2ccc3ncc(-c4c[nH]nc4C(F)(F)F)cc3n2)n1] | 2-[5-(6-methyl-2-pyridyl)-1H-triazol-4-yl]-7-[3-(trifluoromethyl)-1H-pyrazol-4-yl]-1,5-naphthyridine | 423.0 |
| 522 | 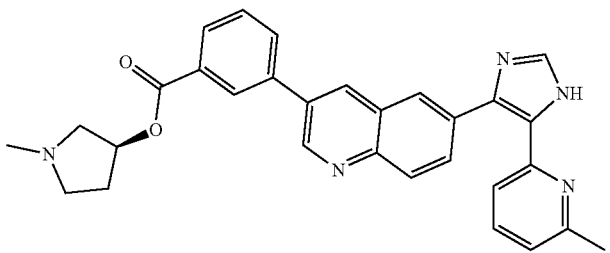 | [(3S)-1-methylpyrrolidin-3-yl] 3-[6-[5-(6-methyl-2-pyridyl)-1H-imidazol-4-yl]-3-quinolyl]benzoate | 490.1 |
| 523 | 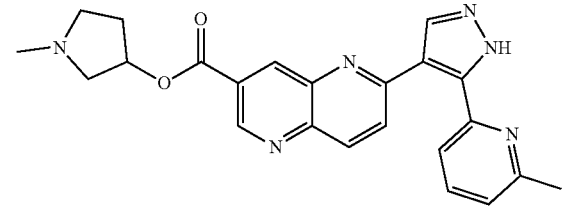 | (1-methylpyrrolidin-3-yl) 6-[5-(6-methyl-2-pyridyl)-1H-pyrazol-4-yl]-1,5-naphthyridine-3-carboxylate | 415.0 |
| 524 | 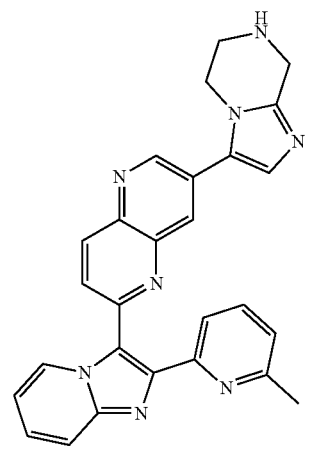 [SMILES: Cc1cccc(-c2nc3ccccn3c2-c2ccc3ncc(-c4cnc5n4CCNC5)cc3n2)n1] | 2-[2-(6-methyl-2-pyridyl)imidazo[1,2-a]pyridin-3-yl]-7-(5,6,7,8-tetrahydroimidazo[1,2-a]pyrazin-3-yl)-1,5-naphthyridine | 459.2 |

TABLE 1-continued

| No. | Structure | Chemical Name | [M + H]+ |
|---|---|---|---|
| 525 | 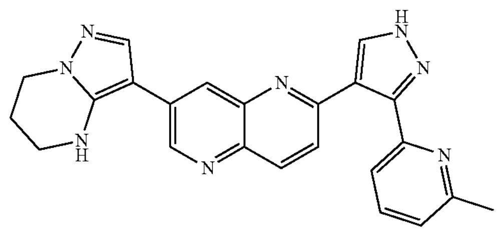 [SMILES: Cc1cccc(-c2n[nH]cc2-c2ccc3ncc(-c4cnn5c4NCCC5)cc3n2)n1] | 2-[3-(6-methyl-2-pyridyl)-1H-pyrazol-4-yl]-7-(4,5,6,7-tetrahydropyrazolo[1,5-a]pyrimidin-3-yl)-1,5-naphthyridine | 409.1 |
| 526 | 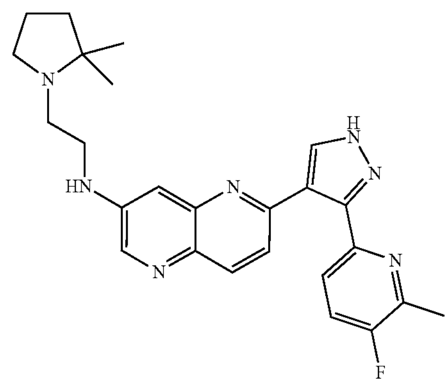 | N-[2-(2,2-dimethylpyrrolidin-1-yl)ethyl]-6-[3-(5-fluoro-6-methyl-2-pyridyl)-1H-pyrazol-4-yl]-1,5-naphthyridin-3-amine | 446.0 |
| 527 | 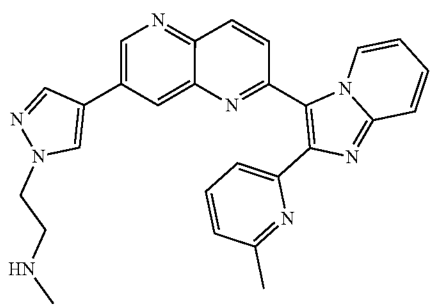 [SMILES: CNCCn1cc(-c2cnc3ccc(-c4c(-c5cccc(C)n5)nc5ccccn45)nc3c2)cn1] | N-methyl-2-[4-[6-[2-(6-methyl-2-pyridyl)imidazo[1,2-a]pyridin-3-yl]-1,5-naphthyridin-3-yl]pyrazol-1-yl]ethanamine | 461.2 |
| 528 | 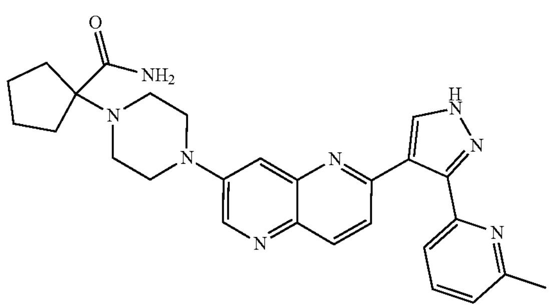 | 1-[4-[6-[3-(6-methyl-2-pyridyl)-1H-pyrazol-4-yl]-1,5-naphthyridin-3-yl]piperazin-1-yl]cyclopentanecarboxamide | 483.3 |
| 529 | 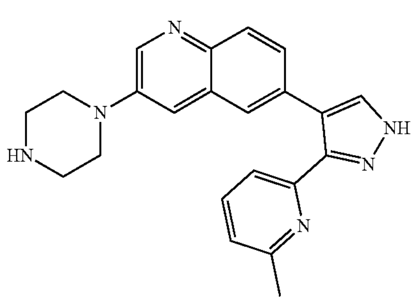 [SMILES: Cc1cccc(-c2n[nH]cc2-c2ccc3ncc(N4CCNCC4)cc3c2)n1] | 6-[3-(6-methyl-2-pyridyl)-1H-pyrazol-4-yl]-3-piperazin-1-yl-quinoline | 371.1 |

TABLE 1-continued

| No. | Structure | Chemical Name | [M + H]+ |
|---|---|---|---|
| 530 | 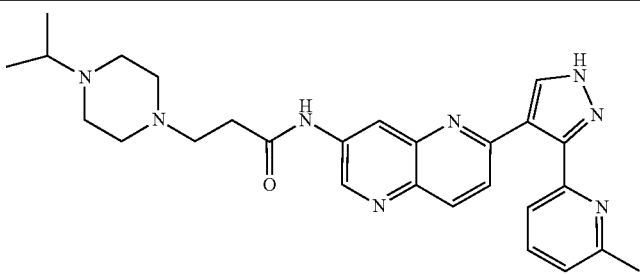 | 3-(4-isopropylpiperazin-1-yl)-N-[6-[3-(6-methyl-2-pyridyl)-1H-pyrazol-4-yl]-1,5-naphthyridin-3-yl]propanamide | 485.3 |
| 531 | 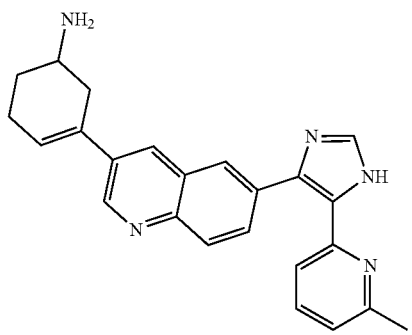 [SMILES: Cc1cccc(-c2[nH]cnc2-c2ccc3ncc(C4=CCCC(N)C4)cc3c2)n1] | 3-[6-[5-(6-methyl-2-pyridyl)-1H-imidazol-4-yl]-3-quinolyl]cyclohex-3-en-1-amine | 382.1 |
| 532 | 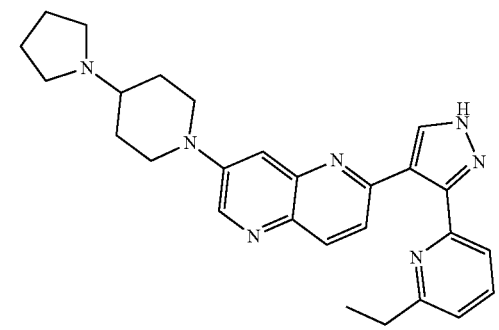 | 2-[3-(6-ethyl-2-pyridyl)-1H-pyrazol-4-yl]-7-(4-pyrrolidin-1-yl-1-piperidyl)-1,5-naphthyridine | 454.2 |
| 533 | 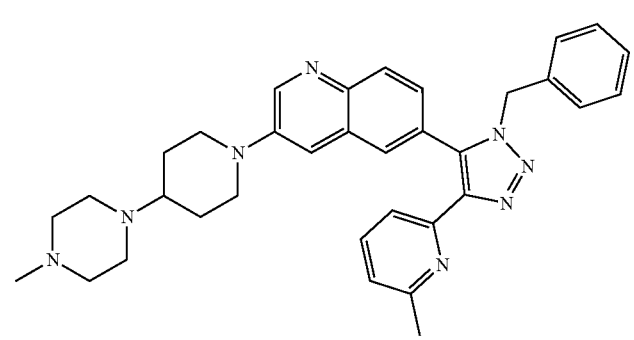 [SMILES: Cc1cccc(-c2nnn(Cc3ccccc3)c2-c2ccc3ncc(N4CCC(N5CCN(C)CC5)CC4)cc3c2)n1] | 6-[3-benzyl-5-(6-methyl-2-pyridyl)triazol-4-yl]-3-[4-(4-methylpiperazin-1-yl)-1-piperidyl]quinoline | 599.3 |
| 534 | 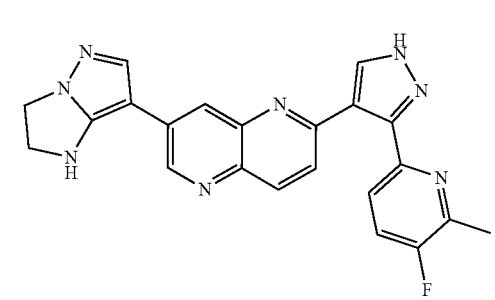 | 7-(2,3-dihydro-1H-imidazo[1,2-b]pyrazol-7-yl)-2-[3-(5-fluoro-6-methyl-2-pyridyl)-1H-pyrazol-4-yl]-1,5-naphthyridine | 413.2 |

TABLE 1-continued

| No. | Structure | Chemical Name | [M + H]⁺ |
|---|---|---|---|
| 535 | 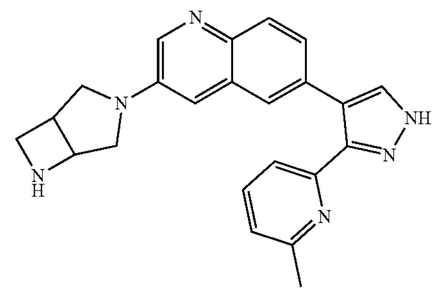 [SMILES: Cc1cccc(-c2n[nH]cc2-c2ccc3ncc(N4CC5CNC5C4)cc3c2)n1] | 3-(3,6-diazabicyclo[3.2.0]heptan-3-yl)-6-[3-(6-methyl-2-pyridyl)-1H-pyrazol-4-yl]quinoline | 383.1 |
| 536 | 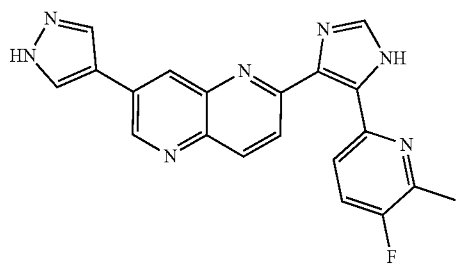 [SMILES: Cc1nc(-c2[nH]cnc2-c2ccc3ncc(-c4cn[nH]c4)cc3n2)ccc1F] | 2-[5-(5-fluoro-6-methyl-2-pyridyl)-1H-imidazol-4-yl]-7-(1H-pyrazol-4-yl)-1,5-naphthyridine | 372.1 |
| 537 | AND Enantiomer | N'-methyl-N-[6-[5-(6-methyl-2-pyridyl)-1H-imidazol-4-yl]-3-quinolyl]-N'-[rac-(3R)-pyrrolidin-3-yl]ethane-1,2-diamine | 428.2 |
| 538 | 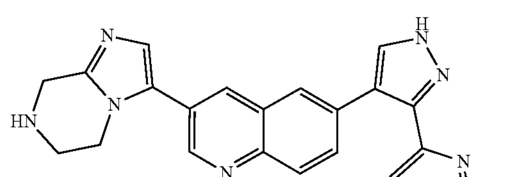 | 6-[3-(6-methyl-2-pyridyl)-1H-pyrazol-4-yl]-3-(5,6,7,8-tetrahydroimidazo[1,2-a]pyrazin-3-yl)quinoline | 408.2 |
| 539 | 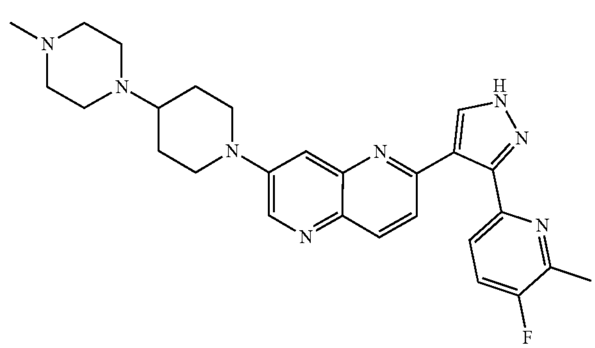 | 2-[3-(5-fluoro-6-methyl-2-pyridyl)-1H-pyrazol-4-yl]-7-[4-(4-methylpiperazin-1-yl)-1-piperidyl]-1,5-naphthyridine | 487.2 |

TABLE 1-continued

| No. | Structure | Chemical Name | [M + H]+ |
|---|---|---|---|
| 540 | 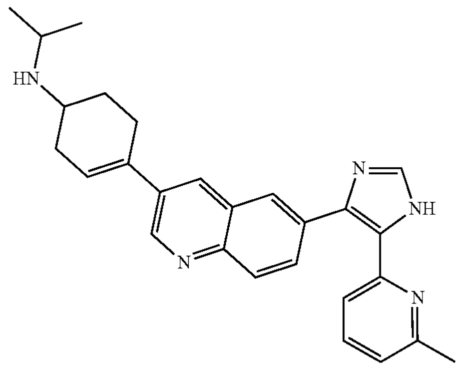 [SMILES: Cc1cccc(-c2[nH]cnc2-c2ccc3ncc(C4=CCC(NC(C)C)CC4)cc3c2)n1] | N-isopropyl-4-[6-[5-(6-methyl-2-pyridyl)-1H-imidazol-4-yl]-3-quinolyl]cyclohex-3-en-1-amine | 424.1 |
| 541 | 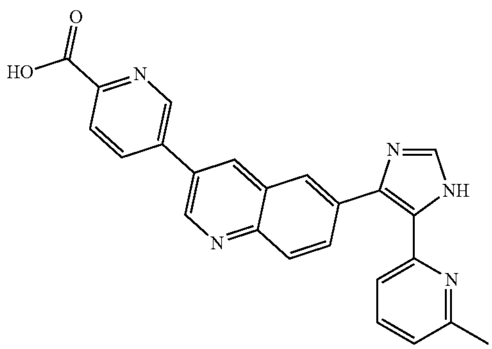 | 5-[6-[5-(6-methyl-2-pyridyl)-1H-imidazol-4-yl]-3-quinolyl]pyridine-2-carboxylic acid | 408.1 |
| 542 | 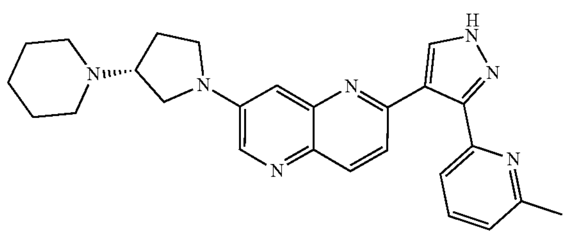 | 2-[3-(6-methyl-2-pyridyl)-1H-pyrazol-4-yl]-7-[(3R)-3-(1-piperidyl)pyrrolidin-1-yl]-1,5-naphthyridine | 440.2 |
| 543 | 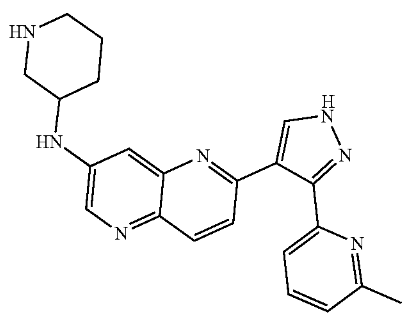 | 6-[3-(6-methyl-2-pyridyl)-1H-pyrazol-4-yl]-N-(3-piperidyl)-1,5-naphthyridin-3-amine | 386.3 |
| 544 | AND Enantiomer | rac-(3S)-1-[6-[2-(5-fluoro-6-methyl-2-pyridyl)imidazo[1,2-a]pyridin-3-yl]-3-quinolyl]-N,N-dimethyl-pyrrolidin-3-amine | 467.2 |

TABLE 1-continued

| No. | Structure | Chemical Name | [M + H]+ |
|---|---|---|---|
| 545 | 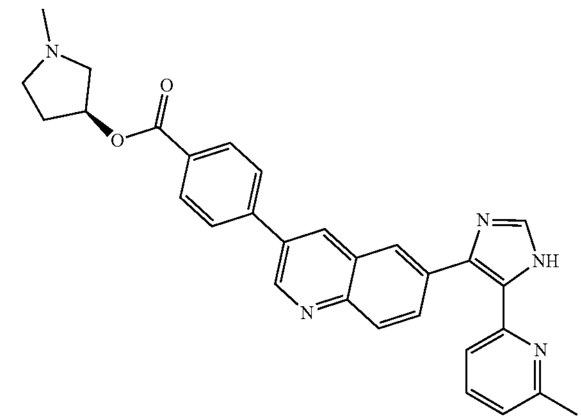 [SMILES: Cc1cccc(-c2[nH]cnc2-c2ccc3ncc(-c4ccc(C(=O)O[C@H]5CCN(C)C5)cc4)cc3c2)n1] | [(3S)-1-methylpyrrolidin-3-yl] 4-[6-[5-(6-methyl-2-pyridyl)-1H-imidazol-4-yl]-3-quinolyl]benzoate | 490.1 |
| 546 | 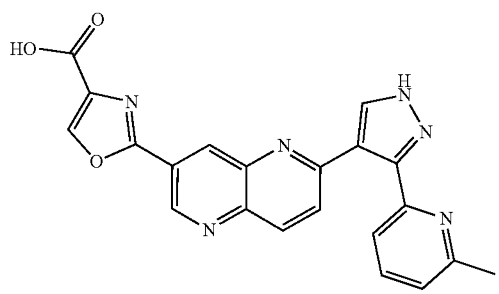 | 2-[6-[3-(6-methyl-2-pyridyl)-1H-pyrazol-4-yl]-1,5-naphthyridin-3-yl]oxazole-4-carboxylic acid | 399.4 |
| 547 | 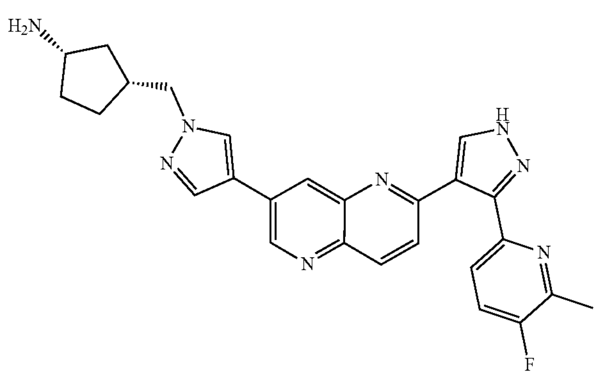 | rac-(1S,3R)-3-[[4-[6-[3-(5-fluoro-6-methyl-2-pyridyl)-1H-pyrazol-4-yl]-1,5-naphthyridin-3-yl]pyrazol-1-yl]methyl]cyclopentanamine | 469.1 |
| 548 | 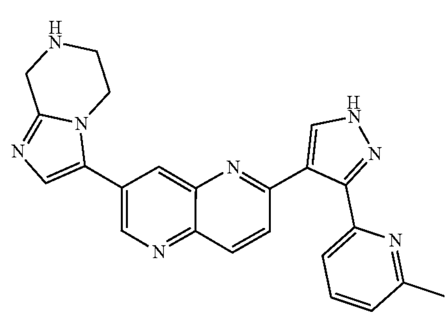 | 2-[3-(6-methyl-2-pyridyl)-1H-pyrazol-4-yl]-7-(5,6,7,8-tetrahydroimidazo[1,2-a]pyrazin-3-yl)-1,5-naphthyridine | 409.2 |

TABLE 1-continued

| No. | Structure | Chemical Name | [M + H]+ |
|---|---|---|---|
| 549 | 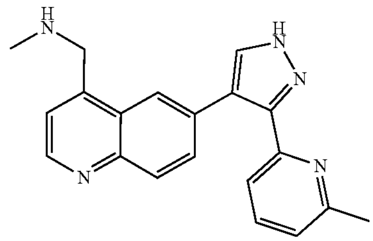 | N-methyl-1-[6-[3-(6-methyl-2-pyridyl)-1H-pyrazol-4-yl]-4-quinolyl]methanamine | 330.1 |
| 550 | 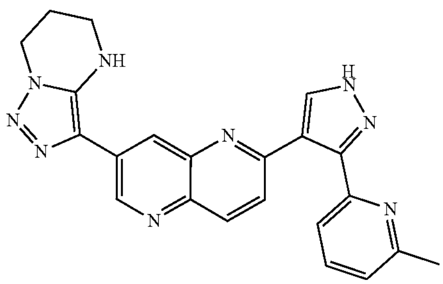 | 2-[3-(6-methyl-2-pyridyl)-1H-pyrazol-4-yl]-7-(4,5,6,7-tetrahydrotriazolo[1,5-a]pyrimidin-3-yl)-1,5-naphthyridine | 410.1 |
| 551 | 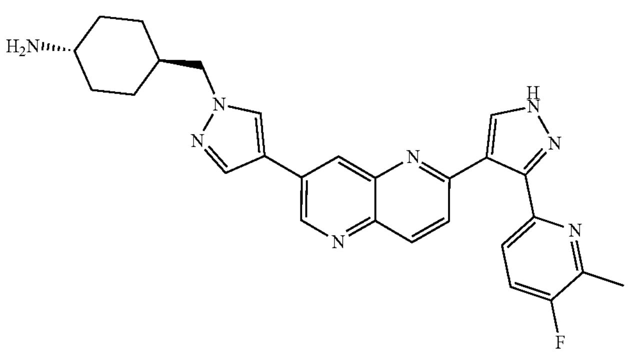 | 4-[[4-[6-[3-(5-fluoro-6-methyl-2-pyridyl)-1H-pyrazol-4-yl]-1,5-naphthyridin-3-yl]pyrazol-1-yl]methyl]cyclohexanamine | 483.2 |
| 552 | 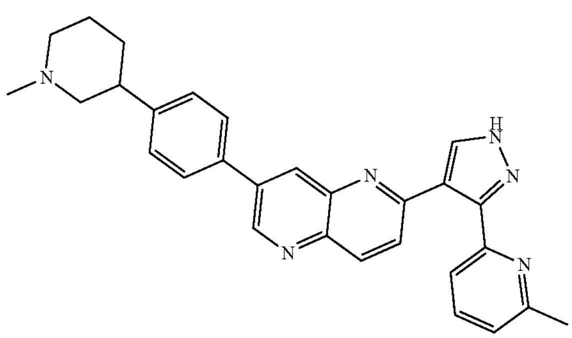 | 7-[4-(1-methyl-3-piperidyl)phenyl]-2-[3-(6-methyl-2-pyridyl)-1H-pyrazol-4-yl]-1,5-naphthyridine | 461.1 |
| 553 | 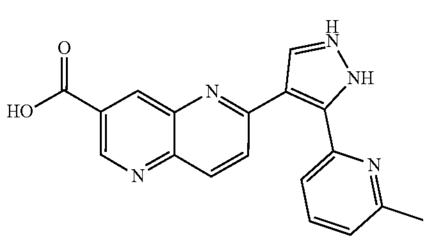 | 6-[5-(6-methyl-2-pyridyl)-1H-pyrazol-4-yl]-1,5-naphthyridine-3-carboxylic acid | 332.2 |

TABLE 1-continued

| No. | Structure | Chemical Name | [M + H]+ |
|-----|-----------|---------------|----------|
| 554 | 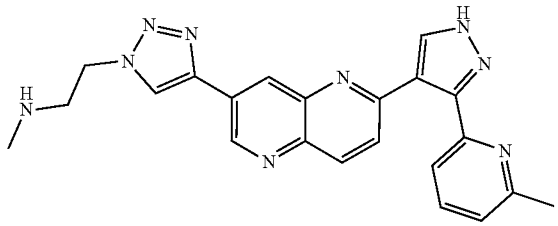 | N-methyl-2-[4-[6-[3-(6-methyl-2-pyridyl)-1H-pyrazol-4-yl]-1,5-naphthyridin-3-yl]triazol-1-yl]ethanamine | 412.1 |
| 555 | 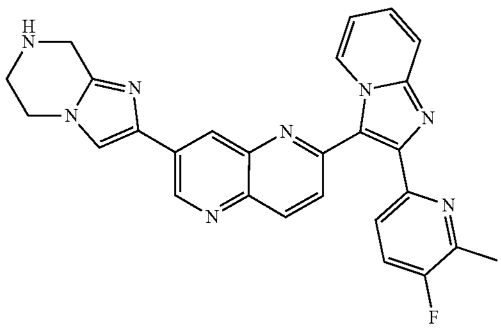 | 2-[2-(5-fluoro-6-methyl-2-pyridyl)imidazo[1,2-a]pyridin-3-yl]-7-(5,6,7,8-tetrahydroimidazo[1,2-a]pyrazin-2-yl)-1,5-naphthyridine | 477.1 |
| 556 | 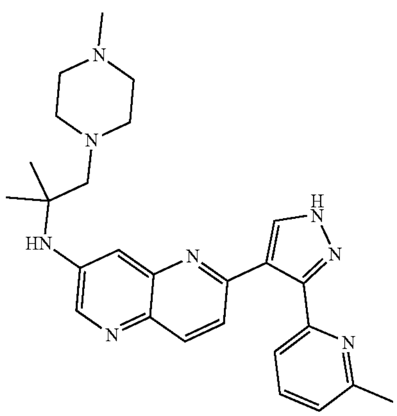 [SMILES: Cc1cccc(-c2n[nH]cc2-c2ccc3ncc(NC(C)(C)CN4CCN(C)CC4)cc3n2)n1] | N-[1,1-dimethyl-2-(4-methylpiperazin-1-yl)ethyl]-6-[3-(6-methyl-2-pyridyl)-1H-pyrazol-4-yl]-1,5-naphthyridin-3-amine | 457.2 |
| 557 | 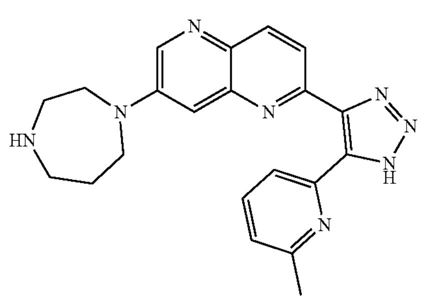 [SMILES: Cc1cccc(-c2[nH]nnc2-c2ccc3ncc(N4CCCNCC4)cc3n2)n1] | 7-(1,4-diazepan-1-yl)-2-[5-(6-methyl-2-pyridyl)-1H-triazol-4-yl]-1,5-naphthyridine | 387.1 |

TABLE 1-continued

| No. | Structure | Chemical Name | [M + H]⁺ |
|---|---|---|---|
| 558 | 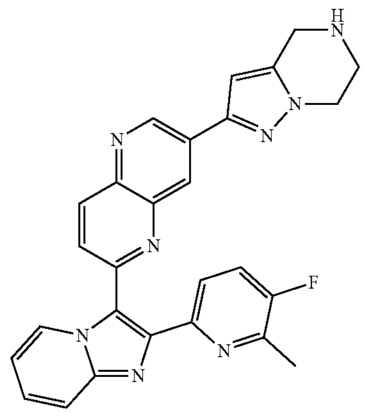 [SMILES: Cc1nc(-c2nc3ccccn3c2-c2ccc3ncc(-c4cc5n(n4)CCNC5)cc3n2)ccc1F] | 2-[2-(5-fluoro-6-methyl-2-pyridyl)imidazo[1,2-a]pyridin-3-yl]-7-(4,5,6,7-tetrahydropyrazolo[1,5-a]pyrazin-2-yl)-1,5-naphthyridine | 477.2 |
| 559 | 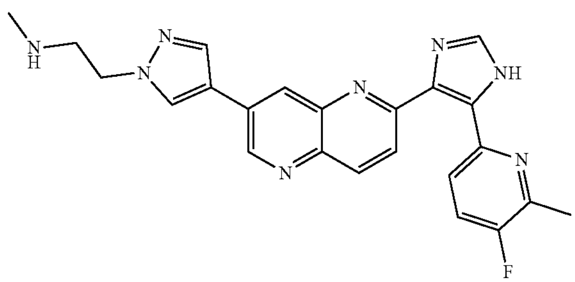 | 2-[4-[6-[5-(5-fluoro-6-methyl-2-pyridyl)-1H-imidazol-4-yl]-1,5-naphthyridin-3-yl]pyrazol-1-yl]-N-methyl-ethanamine | 429.2 |
| 560 | 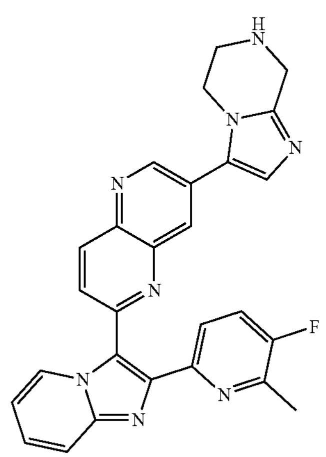 [SMILES: Cc1nc(-c2nc3ccccn3c2-c2ccc3ncc(-c4cnc5n4CCNC5)cc3n2)ccc1F] | 2-[2-(5-fluoro-6-methyl-2-pyridyl)imidazo[1,2-a]pyridin-3-yl]-7-(5,6,7,8-tetrahydroimidazo[1,2-a]pyrazin-3-yl)-1,5-naphthyridine | 477.2 |
| 561 | AND Enantiomer | rac-(3S)-N,N-dimethyl-1-[6-[5-(6-methyl-2-pyridyl)-1H-triazol-4-yl]-3-quinolyl]pyrrolidin-3-amine | 400.3 |

TABLE 1-continued

| No. | Structure | Chemical Name | [M + H]+ |
|---|---|---|---|
| 562 | 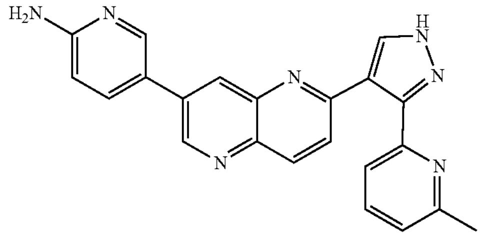 [SMILES: Cc1cccc(-c2n[nH]cc2-c2ccc3ncc(-c4ccc(N)nc4)cc3n2)n1] | 5-[6-[3-(6-methyl-2-pyridyl)-1H-pyrazol-4-yl]-1,5-naphthyridin-3-yl]pyridin-2-amine | 380.3 |
| 563 | 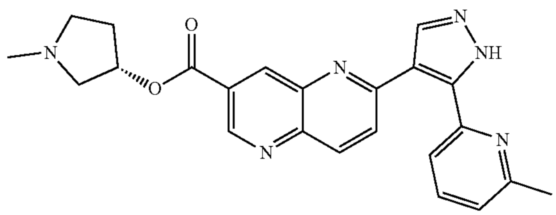 | [(3S)-1-methylpyrrolidin-3-yl]6-[5-(6-methyl-2-pyridyl)-1H-pyrazol-4-yl]-1,5-naphthyridine-3-carboxylate | 415.2 |
| 564 | 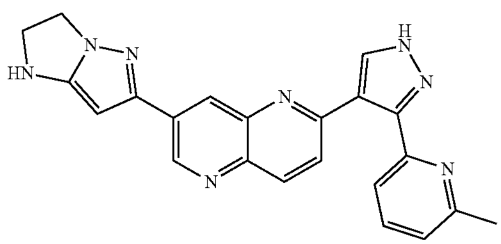 [SMILES: Cc1cccc(-c2n[nH]cc2-c2ccc3ncc(-c4cc5n(n4)CCN5)cc3n2)n1] | 7-(2,3-dihydro-1H-imidazo[1,2-b]pyrazol-6-yl)-2-[3-(6-methyl-2-pyridyl)-1H-pyrazol-4-yl]-1,5-naphthyridine | 395.4 |
| 565 | 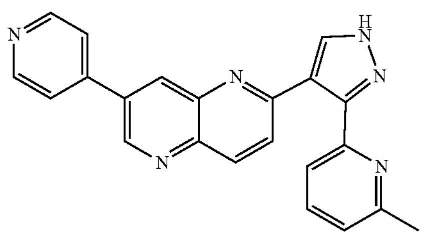 [SMILES: Cc1cccc(-c2n[nH]cc2-c2ccc3ncc(-c4ccncc4)cc3n2)n1] | 2-[3-(6-methyl-2-pyridyl)-1H-pyrazol-4-yl]-7-(4-pyridyl)-1,5-naphthyridine | 365.1 |
| 566 | 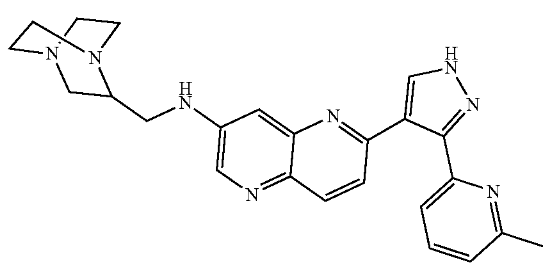 [SMILES: Cc1cccc(-c2n[nH]cc2-c2ccc3ncc(NCC4CN5CCN4CC5)cc3n2)n1] | N-(1,4-diazabicyclo[2.2.2]octan-2-ylmethyl)-6-[3-(6-methyl-2-pyridyl)-1H-pyrazol-4-yl]-1,5-naphthyridin-3-amine | 427.1 |
| 567 | 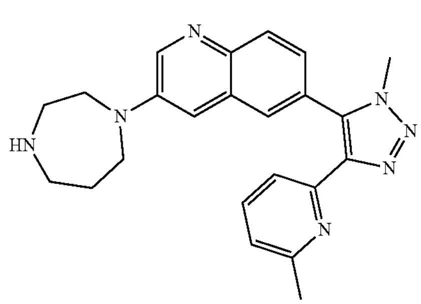 [SMILES: Cc1cccc(-c2nnn(C)c2-c2ccc3ncc(N4CCCNCC4)cc3c2)n1] | 3-(1,4-diazepan-1-yl)-6-[3-methyl-5-(6-methyl-2-pyridyl)triazol-4-yl]quinoline | 400.2 |

TABLE 1-continued

| No. | Structure | Chemical Name | [M + H]⁺ |
|---|---|---|---|
| 568 | 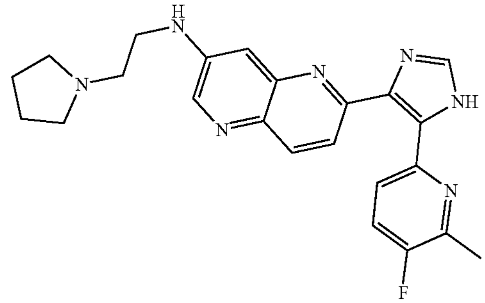 [SMILES: Cc1nc(-c2[nH]cnc2-c2ccc3ncc(NCCN4CCCC4)cc3n2)ccc1F] | 6-[5-(5-fluoro-6-methyl-2-pyridyl)-1H-imidazol-4-yl]-N-(2-pyrrolidin-1-ylethyl)-1,5-naphthyridin-3-amine | 418.2 |
| 569 | 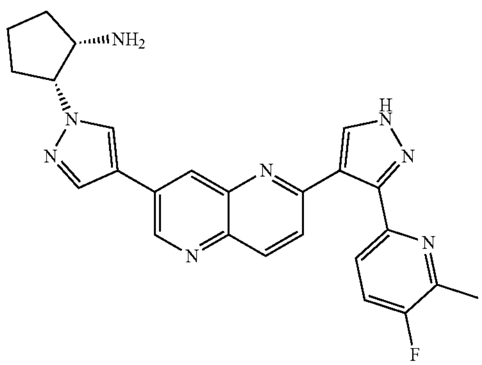 [SMILES: Cc1nc(-c2n[nH]cc2-c2ccc3ncc(-c4cnn([C@@H]5CCC[C@@H]5N)c4)cc3n2)ccc1F] | (1S,2R)-2-[4-[6-[3-(5-fluoro-6-methyl-2-pyridyl)-1H-pyrazol-4-yl]-1,5-naphthyridin-3-yl]pyrazol-1-yl]cyclopentanamine | 455.1 |
| 570 | 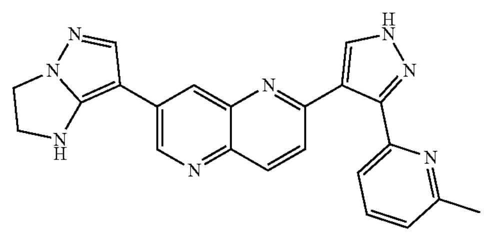 [SMILES: Cc1cccc(-c2n[nH]cc2-c2ccc3ncc(-c4cnn5c4NCC5)cc3n2)n1] | 7-(2,3-dihydro-1H-imidazo[1,2-b]pyrazol-7-yl)-2-[3-(6-methyl-2-pyridyl)-1H-pyrazol-4-yl]-1,5-naphthyridine | 395.1 |
| 571 | 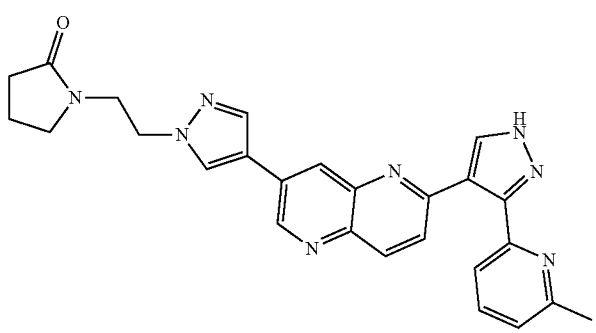 [SMILES: Cc1cccc(-c2n[nH]cc2-c2ccc3ncc(-c4cnn(CCN5CCCC5=O)c4)cc3n2)n1] | 1-[2-[4-[6-[3-(6-methyl-2-pyridyl)-1H-pyrazol-4-yl]-1,5-naphthyridin-3-yl]pyrazol-1-yl]ethyl]pyrrolidin-2-one | 465.1 |
| 572 | 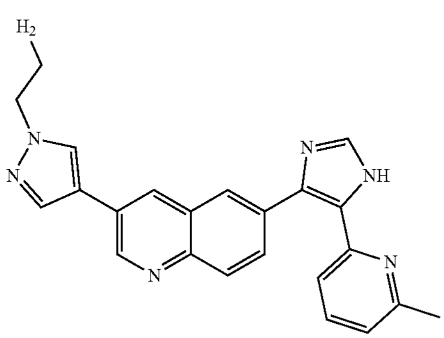 | 2-[4-[6-[5-(6-methyl-2-pyridyl)-1H-imidazol-4-yl]-3-quinolyl]pyrazol-1-yl]ethanamine | 396.3 |

TABLE 1-continued

| No. | Structure | Chemical Name | [M + H]+ |
|---|---|---|---|
| 573 | 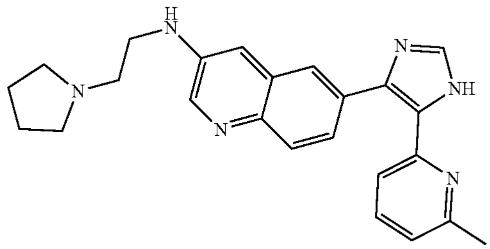 [SMILES: Cc1cccc(-c2[nH]cnc2-c2ccc3ncc(NCCN4CCCC4)cc3c2)n1] | 6-[5-(6-methyl-2-pyridyl)-1H-imidazol-4-yl]-N-(2-pyrrolidin-1-ylethyl)-1,5-naphthyridin-3-amine | 400.2 |
| 574 | 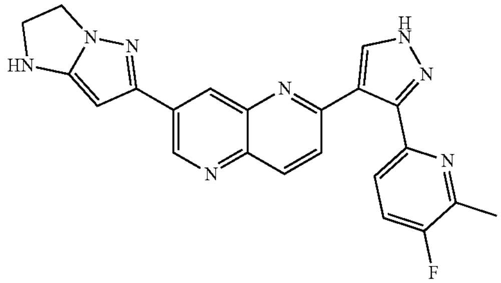 [SMILES: Cc1nc(-c2n[nH]cc2-c2ccc3ncc(-c4cc5n(n4)CCN5)cc3n2)ccc1F] | 7-(2,3-dihydro-1H-imidazo[1,2-b]pyrazol-6-yl)-2-[3-(5-fluoro-6-methyl-2-pyridyl)-1H-pyrazol-4-yl]-1,5-naphthyridine | 413.2 |
| 575 | 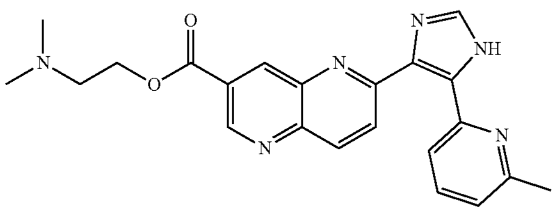 | 2-(dimethylamino)ethyl 6-[5-(6-methyl-2-pyridyl)-1H-pyrazol-4-yl]-1,5-naphthyridine-3-carboxylate | 403.0 |
| 576 | 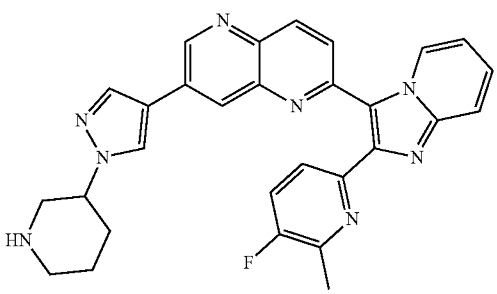 [SMILES: Cc1nc(-c2nc3ccccn3c2-c2ccc3ncc(-c4cnn(C5CCCNC5)c4)cc3n2)ccc1F] | 2-[2-(5-fluoro-6-methyl-2-pyridyl)imidazo[1,2-a]pyridin-3-yl]-7-[1-(3-piperidyl)pyrazol-4-yl]-1,5-naphthyridine | 505.1 |
| 577 | 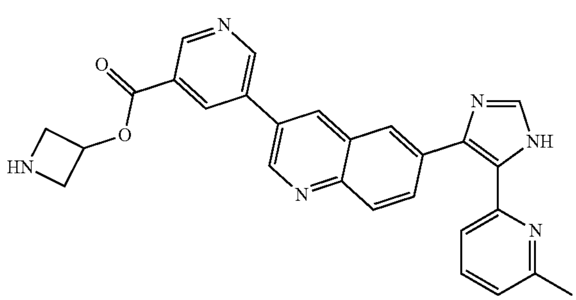 [SMILES: Cc1cccc(-c2[nH]cnc2-c2ccc3ncc(-c4cncc(C(=O)OC5CNC5)c4)cc3c2)n1] | azetidin-3-yl 5-[6-[5-(6-methyl-2-pyridyl)-1H-imidazol-4-yl]-3-quinolyl]pyridine-3-carboxylate | 463.1 |

TABLE 1-continued

| No. | Structure | Chemical Name | [M + H]+ |
|---|---|---|---|
| 578 | 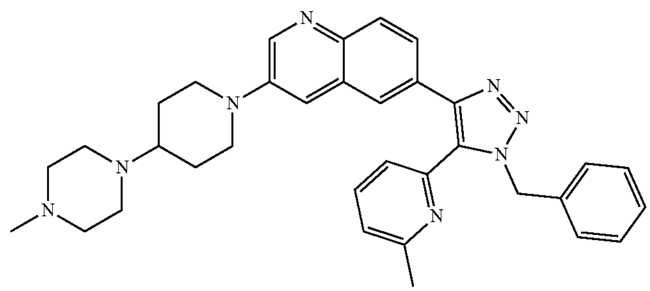 [SMILES: Cc1cccc(-c2c(-c3ccc4ncc(N5CCC(N6CCN(C)CC6)CC5)cc4c3)nnn2Cc2ccccc2)n1] | 6-[1-benzyl-5-(6-methyl-2-pyridyl)triazol-4-yl]-3-[4-(4-methylpiperazin-1-yl)-1-piperidyl]quinoline | 559.3 |
| 579 | 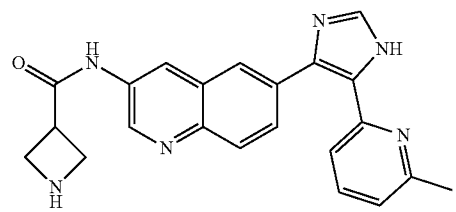 [SMILES: Cc1cccc(-c2[nH]cnc2-c2ccc3ncc(NC(=O)C4CNC4)cc3c2)n1] | N-[6-[5-(6-methyl-2-pyridyl)-1H-imidazol-4-yl]-3-quinolyl]azetidine-3-carboxamide | 385.1 |
| 580 | 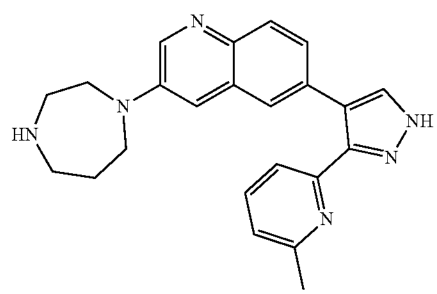 [SMILES: Cc1cccc(-c2n[nH]cc2-c2ccc3ncc(N4CCCNCC4)cc3c2)n1] | 3-(1,4-diazepan-1-yl)-6-[3-(6-methyl-2-pyridyl)-1H-pyrazol-4-yl]quinoline | 385.3 |
| 581 | 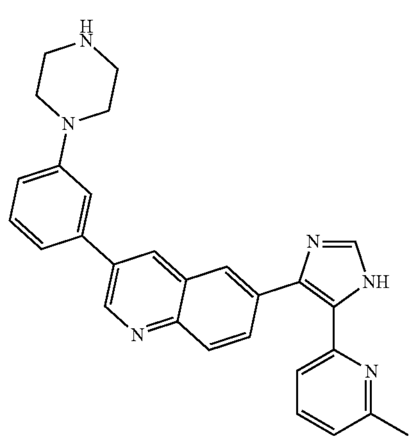 [SMILES: Cc1cccc(-c2[nH]cnc2-c2ccc3ncc(-c4cccc(N5CCNCC5)c4)cc3c2)n1] | 6-[5-(6-methyl-2-pyridyl)-1H-imidazol-4-yl]-3-(3-piperazin-1-ylphenyl)quinoline | 447.1 |
| 582 | 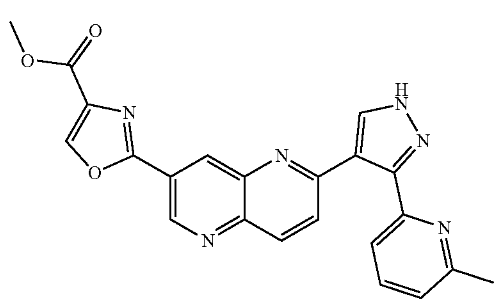 | methyl 2-[6-[3-(6-methyl-2-pyridyl)-1H-pyrazol-4-yl]-1,5-naphthyridin-3-yl]oxazole-4-carboxylate | 413.1 |

TABLE 1-continued

| No. | Structure | Chemical Name | [M + H]+ |
|---|---|---|---|
| 583 | 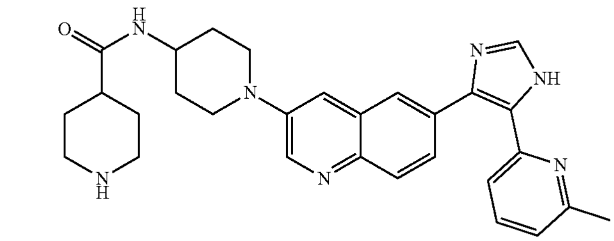 [SMILES: Cc1cccc(-c2[nH]cnc2-c2ccc3ncc(N4CCC(NC(=O)C5CCNCC5)CC4)cc3c2)n1] | N-[1-[6-[5-(6-methyl-2-pyridyl)-1H-imidazol-4-yl]-3-quinolyl]-4-piperidyl]piperidine-4-carboxamide | 496.2 |
| 584 | 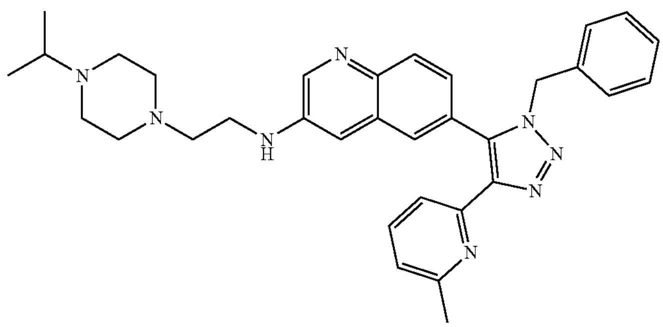 [SMILES: Cc1cccc(-c2nnn(Cc3ccccc3)c2-c2ccc3ncc(NCCN4CCN(C(C)C)CC4)cc3c2)n1] | 6-[3-benzyl-5-(6-methyl-2-pyridyl)triazol-4-yl]-N-[2-(4-isopropylpiperazin-1-yl)ethyl]quinolin-3-amine | 547.3 |
| 585 | 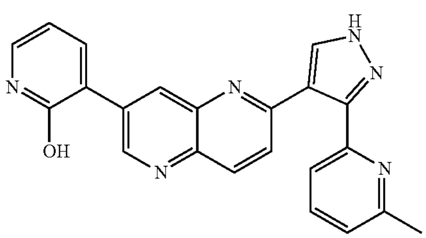 [SMILES: Cc1cccc(-c2n[nH]cc2-c2ccc3ncc(-c4cccnc4O)cc3n2)n1] | 3-[6-[3-(6-methyl-2-pyridyl)-1H-pyrazol-4-yl]-1,5-naphthyridin-3-yl]pyridin-2-ol | 381.1 |
| 586 | 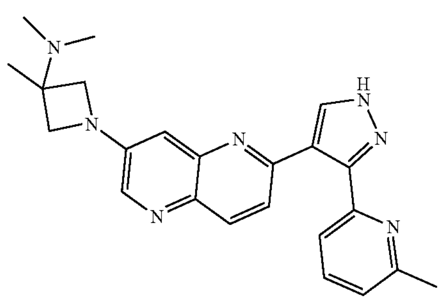 | N,N,3-trimethyl-1-[6-[3-(6-methyl-2-pyridyl)-1H-pyrazol-4-yl]-1,5-naphthyridin-3-yl]azetidin-3-amine | 400.2 |
| 587 | 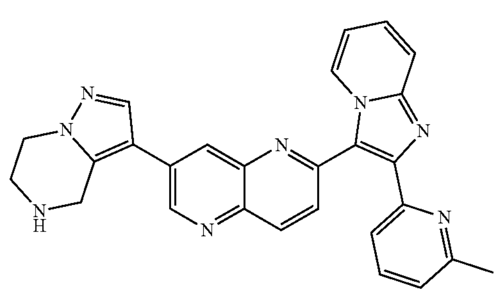 | 2-[2-(6-methyl-2-pyridyl)imidazo[1,2-a]pyridin-3-yl]-7-(4,5,6,7-tetrahydropyrazolo[1,5-a]pyrazin-3-yl)-1,5-naphthyridine | 459.2 |

TABLE 1-continued

| No. | Structure | Chemical Name | [M + H]+ |
|---|---|---|---|
| 588 | 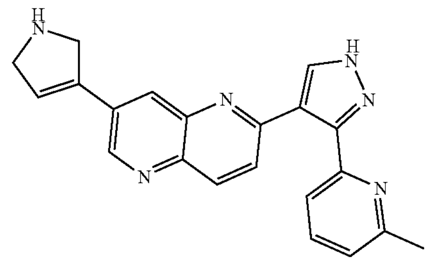 | 7-(2,5-dihydro-1H-pyrrol-3-yl)-2-[3-(6-methyl-2-pyridyl)-1H-pyrazol-4-yl]-1,5-naphthyridine | 355.3 |
| 589 | 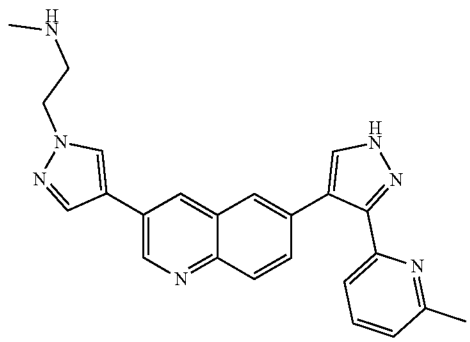 | N-methyl-2-[4-[6-[3-(6-methyl-2-pyridyl)-1H-pyrazol-4-yl]-3-quinolyl]pyrazol-1-yl]ethanamine | 410.1 |
| 590 | 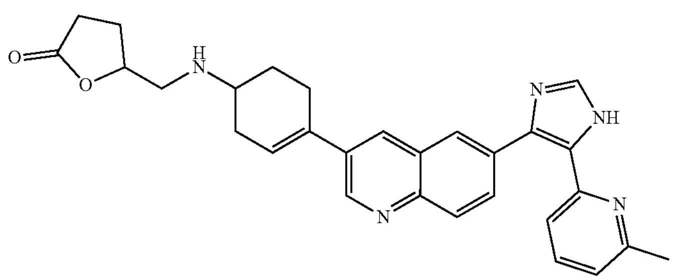 [SMILES: Cc1cccc(-c2[nH]cnc2-c2ccc3ncc(C4=CCC(NCC5CCC(=O)O5)CC4)cc3c2)n1] | 5-[[[4-[6-[5-(6-methyl-2-pyridyl)-1H-imidazol-4-yl]-3-quinolyl]cyclohex-3-en-1-yl]amino]methyl]tetrahydrofuran-2-one | 480.2 |
| 591 | 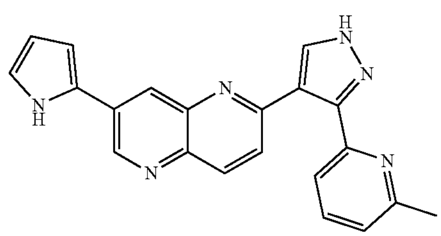 | 2-[3-(6-methyl-2-pyridyl)-1H-pyrazol-4-yl]-7-(1H-pyrrol-2-yl)-1,5-naphthyridine | 353.1 |
| 592 | 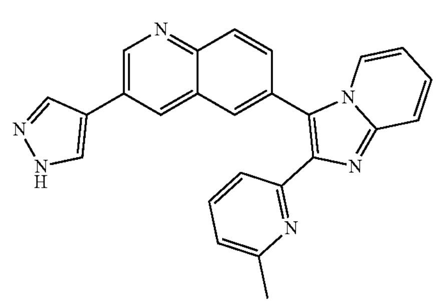 | 6-[2-(6-methyl-2-pyridyl)imidazo[1,2-a]pyridin-3-yl]-3-(1H-pyrazol-4-yl)quinoline | 403.1 |

TABLE 1-continued

| No. | Structure | Chemical Name | [M + H]+ |
|---|---|---|---|
| 593 | 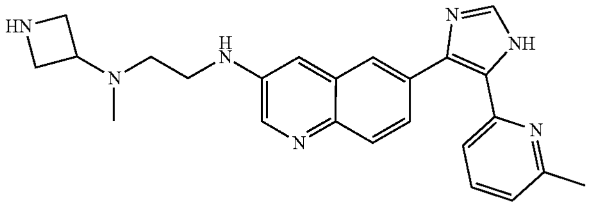 [SMILES: Cc1cccc(-c2[nH]cnc2-c2ccc3ncc(NCCN(C)C4CNC4)cc3c2)n1] | N'-(azetidin-3-yl)-N'-methyl-N-[6-[5-(6-methyl-2-pyridyl)-1H-imidazol-4-yl]-3-quinolyl]ethane-1,2-diamine | 414.3 |
| 594 | 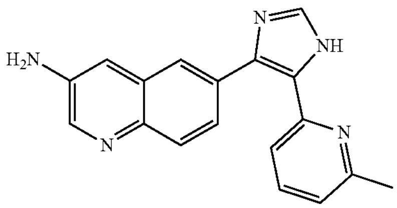 [SMILES: Cc1cccc(-c2[nH]cnc2-c2ccc3ncc(N)cc3c2)n1] | 6-[5-(6-methyl-2-pyridyl)-1H-imidazol-4-yl]quinolin-3-amine | 302.2 |
| 595 | 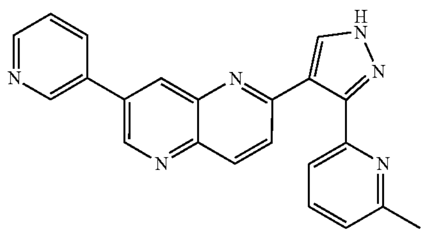 | 2-[3-(6-methyl-2-pyridyl)-1H-pyrazol-4-yl]-7-(3-pyridyl)-1,5-naphthyridine | 365.1 |
| 596 | 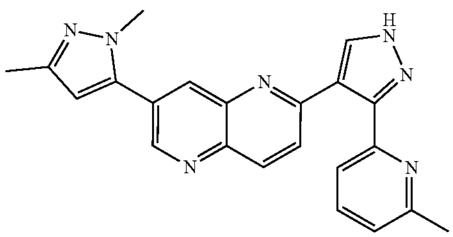 | 7-(2,5-dimethylpyrazol-3-yl)-2-[3-(6-methyl-2-pyridyl)-1H-pyrazol-4-yl]-1,5-naphthyridine | 382.3 |
| 597 | 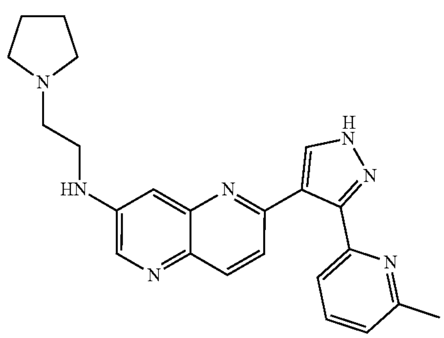 | 6-[3-(6-methyl-2-pyridyl)-1H-pyrazol-4-yl]-N-(2-pyrrolidin-1-ylethyl)-1,5-naphthyridin-3-amine | 400.2 |
| 598 | AND Enantiomer | 2-[3-(6-methyl-2-pyridyl)-1H-pyrazol-4-yl]-7-[rac-(3aS,6aS)-2,3,3a,4,6,6a-hexahydro-1H-pyrrolo[2,3-c]pyrrol-5-yl]-1,5-naphthyridine | 398.3 |

TABLE 1-continued

| No. | Structure | Chemical Name | [M + H]+ |
|---|---|---|---|
| 599 | 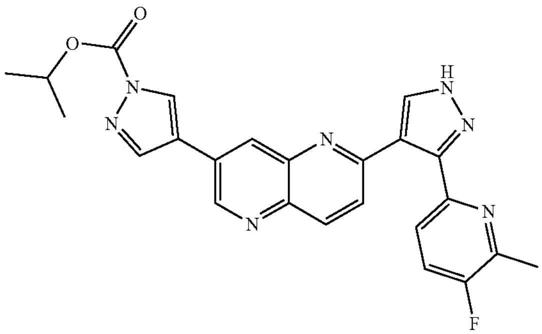 | isopropyl 4-[6-[3-(5-fluoro-6-methyl-2-pyridyl)-1H-pyrazol-4-yl]-1,5-naphthyridin-3-yl]pyrazole-1-carboxylate | 458.2 |
| 600 | 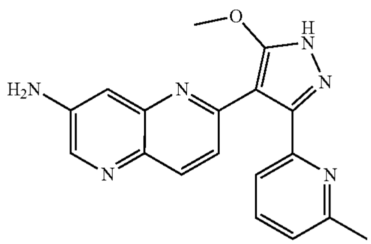 | 6-[5-methoxy-3-(6-methyl-2-pyridyl)-1H-pyrazol-4-yl]-1,5-naphthyridin-3-amine | 333.3 |
| 601 | 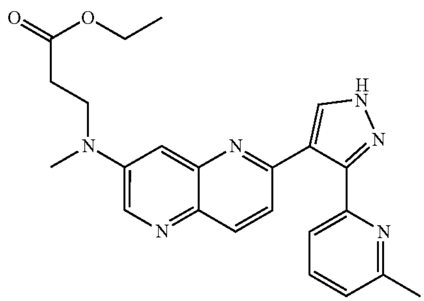 | ethyl 3-[methyl-[6-[3-(6-methyl-2-pyridyl)-1H-pyrazol-4-yl]-1,5-naphthyridin-3-yl]amino]propanoate | 417.3 |
| 602 | 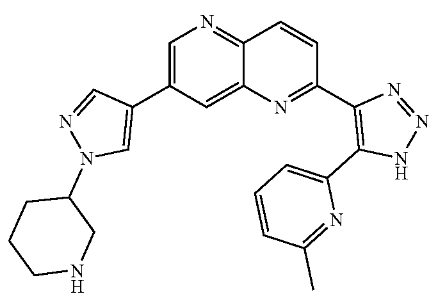 | 2-[5-(6-methyl-2-pyridyl)-1H-triazol-4-yl]-7-[1-(3-piperidyl)pyrazol-4-yl]-1,5-naphthyridine | 438.2 |
| 603 | 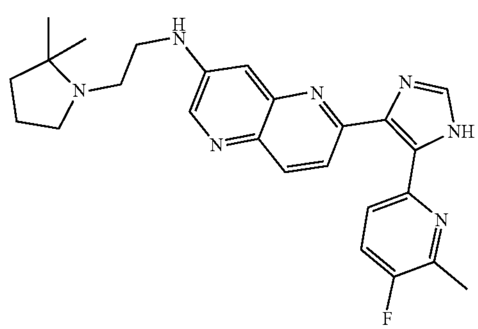 | N-[2-(2,2-dimethylpyrrolidin-1-yl)ethyl]-6-[5-(5-fluoro-6-methyl-2-pyridyl)-1H-imidazol-4-yl]-1,5-naphthyridin-3-amine | 446.2 |

TABLE 1-continued

| No. | Structure | Chemical Name | [M + H]+ |
|---|---|---|---|
| 604 | 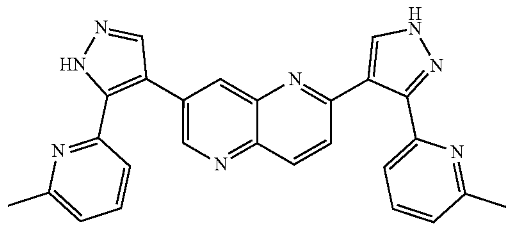 | 2-[3-(6-methyl-2-pyridyl)-1H-pyrazol-4-yl]-7-[5-(6-methyl-2-pyridyl)-1H-pyrazol-4-yl]-1,5-naphthyridine | 445.2 |
| 605 | 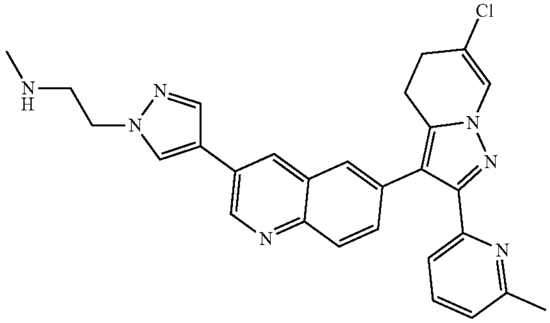 | 2-[4-[6-[6-chloro-2-(6-methyl-2-pyridyl)pyrazolo[1,5-a]pyridin-3-yl]-3-quinolyl]pyrazol-1-yl]-N-methyl-ethanamine | 494.1 |
| 606 | 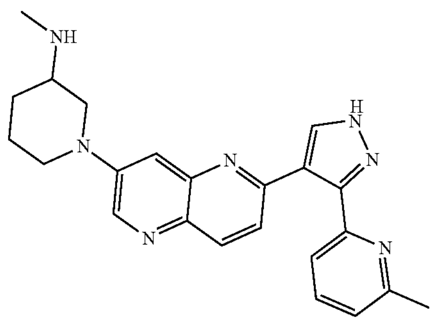 | N-methyl-1-[6-[3-(6-methyl-2-pyridyl)-1H-pyrazol-4-yl]-1,5-naphthyridin-3-yl]piperidin-3-amine | 400.2 |
| 607 | 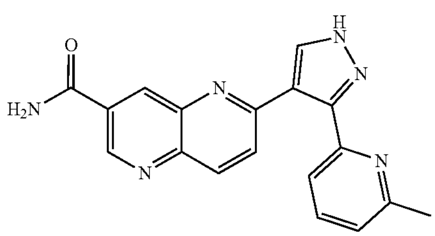 | 6-[3-(6-methyl-2-pyridyl)-1H-pyrazol-4-yl]-1,5-naphthyridine-3-carboxamide | 331.2 |
| 608 | 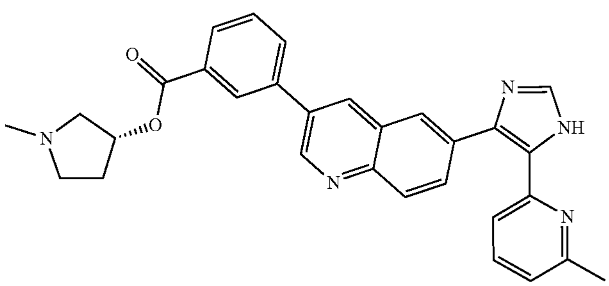 | [(3R)-1-methylpyrrolidin-3-yl] 3-[6-[5-(6-methyl-2-pyridyl)-1H-imidazol-4-yl]-3-quinolyl]benzoate | 490.2 |

TABLE 1-continued

| No. | Structure | Chemical Name | [M + H]+ |
|---|---|---|---|
| 609 | 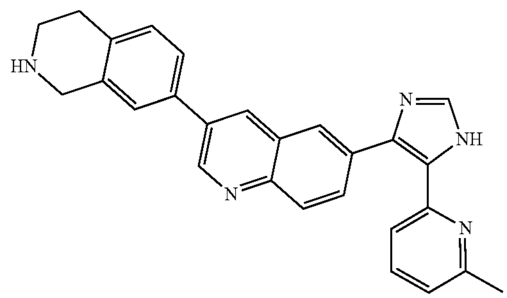 [SMILES: Cc1cccc(-c2[nH]cnc2-c2ccc3ncc(-c4ccc5c(c4)CNCC5)cc3c2)n1] | 6-[5-(6-methyl-2-pyridyl)-1H-imidazol-4-yl]-3-(1,2,3,4-tetrahydroisoquinolin-7-yl)quinoline | 418.1 |
| 610 | 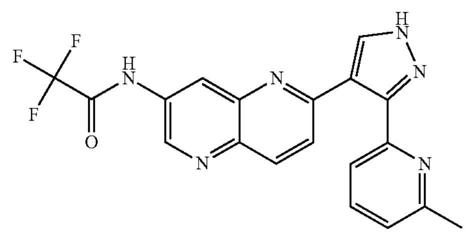 | 2,2,2-trifluoro-N-[6-[3-(6-methyl-2-pyridyl)-1H-pyrazol-4-yl]-1,5-naphthyridin-3-yl]acetamide | 398.7 |
| 611 | 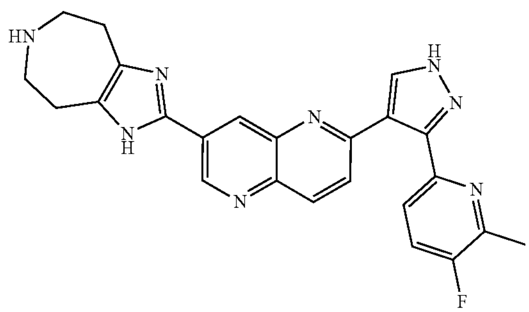 | 2-[6-[3-(5-fluoro-6-methyl-2-pyridyl)-1H-pyrazol-4-yl]-1,5-naphthyridin-3-yl]-1,4,5,6,7,8-hexahydroimidazo[4,5-d]azepine | 441.1 |
| 612 | 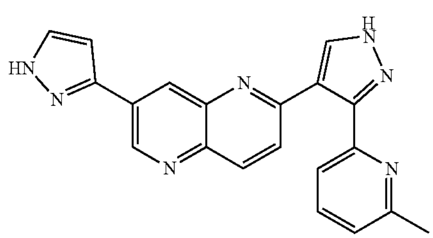 | 2-[3-(6-methyl-2-pyridyl)-1H-pyrazol-4-yl]-7-(1H-pyrazol-3-yl)-1,5-naphthyridine | 354.1 |
| 613 | 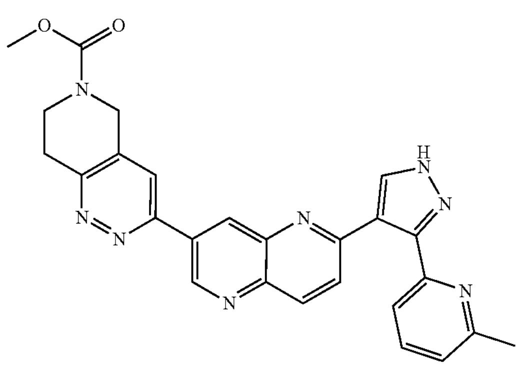 | methyl 3-[6-[3-(6-methyl-2-pyridyl)-1H-pyrazol-4-yl]-1,5-naphthyridin-3-yl]-7,8-dihydro-5H-pyrido[4,3-c]pyridazine-6-carboxylate | 479.0 |

TABLE 1-continued

| No. | Structure | Chemical Name | [M + H]+ |
|---|---|---|---|
| 614 | 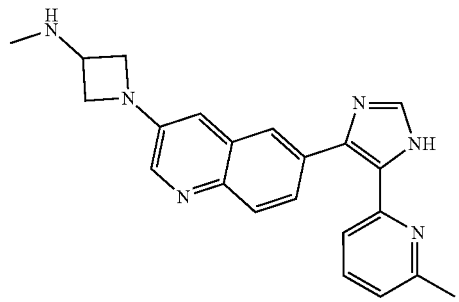 | N-methyl-1-[6-[5-(6-methyl-2-pyridyl)-1H-imidazol-4-yl]-3-quinolyl]azetidin-3-amine | 371.2 |
| 615 | 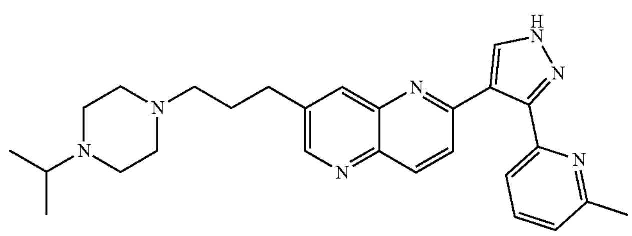 | 7-[3-(4-isopropylpiperazin-1-yl)propyl]-2-[3-(6-methyl-2-pyridyl)-1H-pyrazol-4-yl]-1,5-naphthyridine | 456.6 |
| 616 | 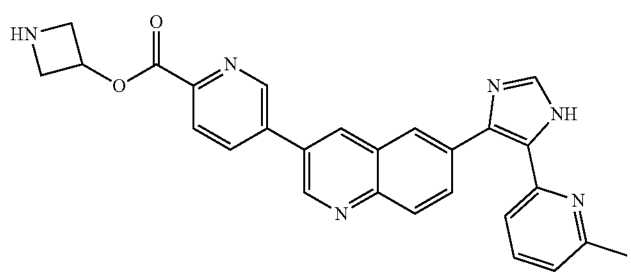 [SMILES: Cc1cccc(-c2[nH]cnc2-c2ccc3ncc(-c4ccc(C(=O)OC5CNC5)nc4)cc3c2)n1] | azetidin-3-yl 5-[6-[5-(6-methyl-2-pyridyl)-1H-imidazol-4-yl]-3-quinolyl]pyridine-2-carboxylate | 463.1 |
| 617 | 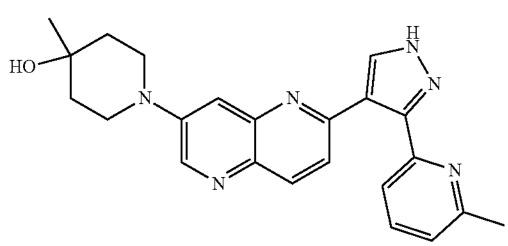 [SMILES: Cc1cccc(-c2n[nH]cc2-c2ccc3ncc(N4CCC(C)(O)CC4)cc3n2)n1] | 4-methyl-1-[6-[3-(6-methyl-2-pyridyl)-1H-pyrazol-4-yl]-1,5-naphthyridin-3-yl]piperidin-4-ol | 401.2 |
| 618 | 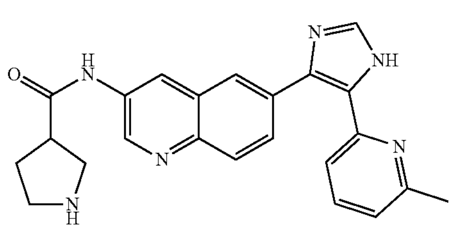 [SMILES: Cc1cccc(-c2[nH]cnc2-c2ccc3ncc(NC(=O)C4CCNC4)cc3c2)n1] | N-[6-[5-(6-methyl-2-pyridyl)-1H-imidazol-4-yl]-3-quinolyl]pyrrolidine-3-carboxamide | 399.1 |

TABLE 1-continued

| No. | Structure | Chemical Name | [M + H]+ |
|---|---|---|---|
| 619 | 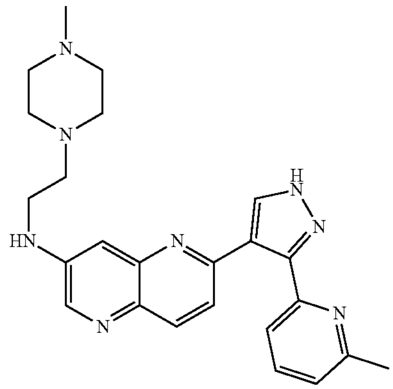 [SMILES: Cc1cccc(-c2n[nH]cc2-c2ccc3ncc(NCCN4CCN(C)CC4)cc3n2)n1] | N-[2-(4-methylpiperazin-1-yl)ethyl]-6-[3-(6-methyl-2-pyridyl)-1H-pyrazol-4-yl]-1,5-naphthyridin-3-amine | 429.2 |
| 620 | 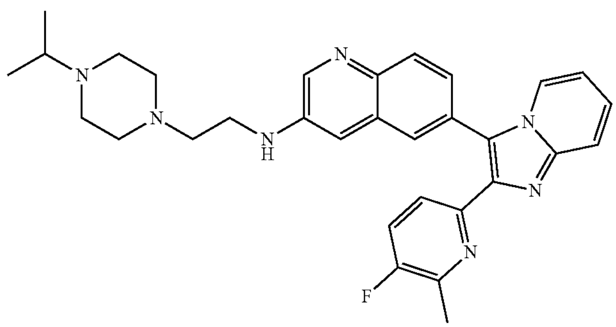 [SMILES: Cc1nc(-c2nc3ccccn3c2-c2ccc3ncc(NCCN4CCN(C(C)C)CC4)cc3c2)ccc1F] | 6-[2-(5-fluoro-6-methyl-2-pyridyl)imidazo[1,2-a]pyridin-3-yl]-N-[2-(4-isopropylpiperazin-1-yl)ethyl]quinolin-3-amine | 524.3 |
| 621 | 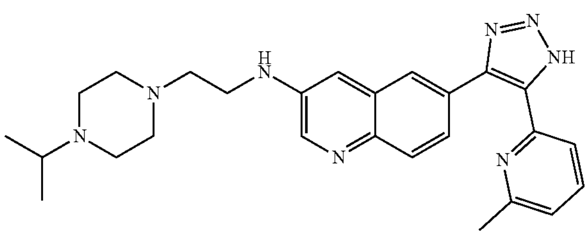 [SMILES: Cc1cccc(-c2[nH]nnc2-c2ccc3ncc(NCCN4CCN(C(C)C)CC4)cc3c2)n1] | N-[2-(4-isopropylpiperazin-1-yl)ethyl]-6-[5-(6-methyl-2-pyridyl)-1H-triazol-4-yl]quinolin-3-amine | 457.2 |
| 622 | 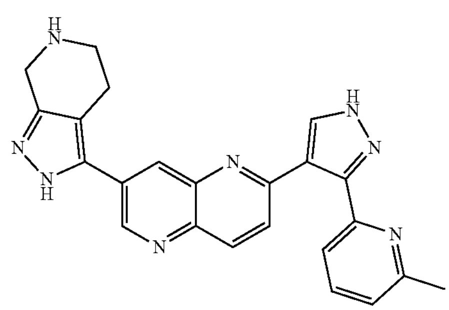 [SMILES: Cc1cccc(-c2n[nH]cc2-c2ccc3ncc(-c4[nH]nc5c4CCNC5)cc3n2)n1] | 2-[3-(6-methyl-2-pyridyl)-1H-pyrazol-4-yl]-7-(4,5,6,7-tetrahydro-2H-pyrazolo[3,4-c]pyridin-3-yl)-1,5-naphthyridine | 409.1 |
| 623 | 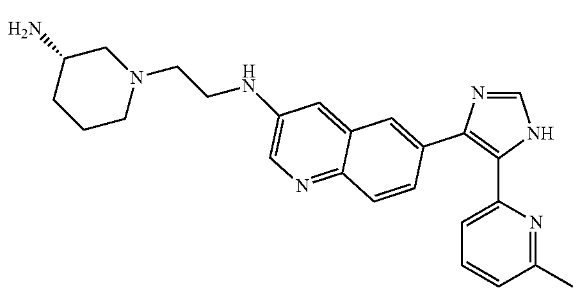 [SMILES: Cc1cccc(-c2[nH]cnc2-c2ccc3ncc(NCCN4CCC[C@H](N)C4)cc3c2)n1] | N-[2-[(3S)-3-amino-1-piperidyl]ethyl]-6-[5-(6-methyl-2-pyridyl)-1H-imidazol-4-yl]quinolin-3-amine | 428.3 |

TABLE 1-continued

| No. | Structure | Chemical Name | [M + H]+ |
|---|---|---|---|
| 624 | 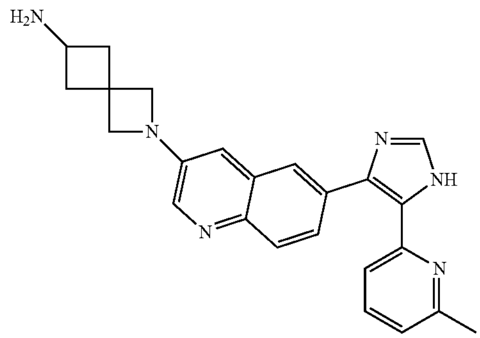 [SMILES: Cc1cccc(-c2[nH]cnc2-c2ccc3ncc(N4CC5(CC(N)C5)C4)cc3c2)n1] | 2-[6-[5-(6-methyl-2-pyridyl)-1H-imidazol-4-yl]-3-quinolyl]-2-azaspiro[3.3]heptan-6-amine | 397.1 |
| 625 | 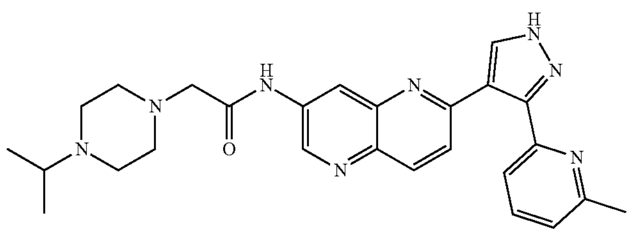 [SMILES: Cc1cccc(-c2n[nH]cc2-c2ccc3ncc(NC(=O)CN4CCN(C(C)C)CC4)cc3n2)n1] | 2-(4-isopropylpiperazin-1-yl)-N-[6-[3-(6-methyl-2-pyridyl)-1H-pyrazol-4-yl]-1,5-naphthyridin-3-yl]acetamide | 471.1 |
| 626 | 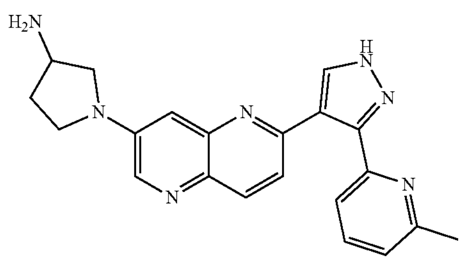 [SMILES: Cc1cccc(-c2n[nH]cc2-c2ccc3ncc(N4CCC(N)C4)cc3n2)n1] | 1-[6-[3-(6-methyl-2-pyridyl)-1H-pyrazol-4-yl]-1,5-naphthyridin-3-yl]pyrrolidin-3-amine | 372.2 |
| 627 | 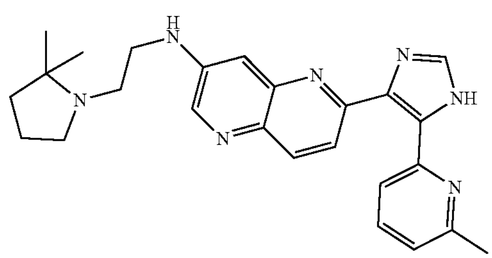 [SMILES: Cc1cccc(-c2[nH]cnc2-c2ccc3ncc(NCCN4CCCC4(C)C)cc3n2)n1] | N-[2-(2,2-dimethylpyrrolidin-1-yl)ethyl]-6-[5-(6-methyl-2-pyridyl)-1H-imidazol-4-yl]-1,5-naphthyridin-3-amine | 428.2 |
| 628 | 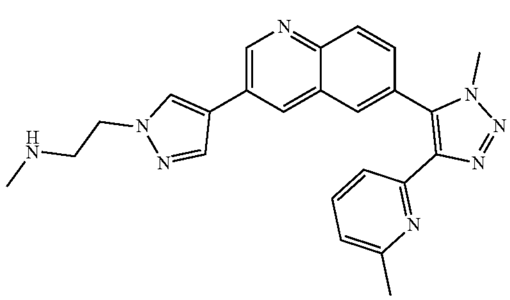 [SMILES: CNCCn1cc(-c2cnc3ccc(-c4c(-c5cccc(C)n5)nnn4C)cc3c2)cn1] | N-methyl-2-[4-[6-[3-methyl-5-(6-methyl-2-pyridyl)triazol-4-yl]-3-quinolyl]pyrazol-1-yl]ethanamine | 425.2 |

TABLE 1-continued

| No. | Structure | Chemical Name | [M + H]+ |
| --- | --- | --- | --- |
| 629 | 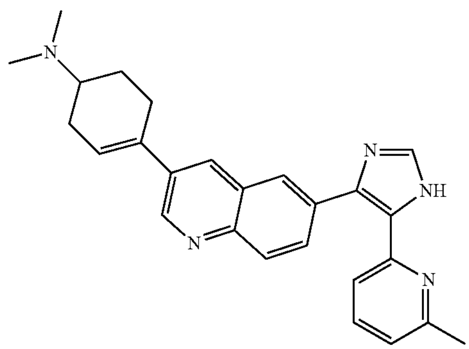 | N,N-dimethyl-4-[6-[5-(6-methyl-2-pyridyl)-1H-imidazol-4-yl]-3-quinolyl]cyclohex-3-en-1-amine | 410.1 |
| 630 | 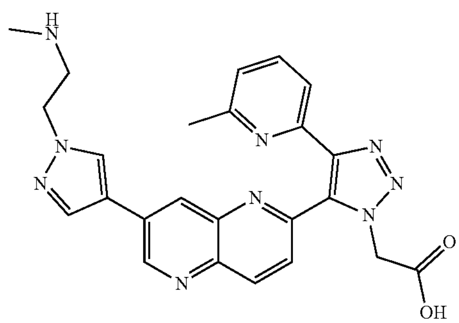 [SMILES: CNCCn1cc(-c2cnc3ccc(-c4c(-c5cccc(C)n5)nnn4CC(=O)O)nc3c2)cn1] | 2-[5-[7-[1-[2-(methylamino)ethyl]pyrazol-4-yl]-1,5-naphthyridin-2-yl]-4-(6-methyl-2-pyridyl)triazol-1-yl]acetic acid | 470.2 |
| 631 | 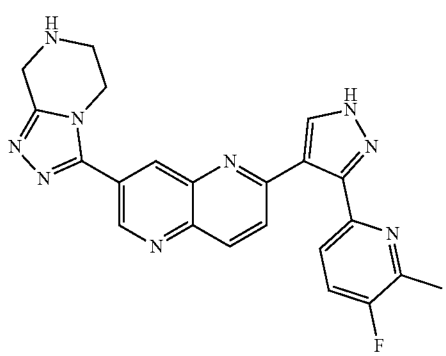 | 2-[3-(5-fluoro-6-methyl-2-pyridyl)-1H-pyrazol-4-yl]-7-(5,6,7,8-tetrahydro-[1,2,4]triazolo[4,3-a]pyrazin-3-yl)-1,5-naphthyridine | 428.1 |
| 632 | 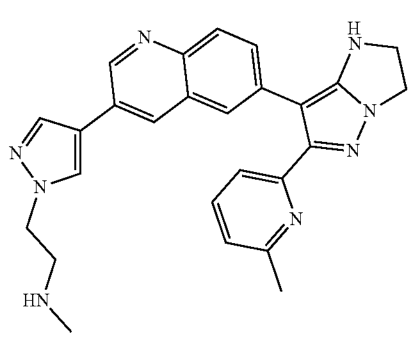 | N-methyl-2-[4-[6-[6-(6-methyl-2-pyridyl)-2,3-dihydro-1H-imidazo[1,2-b]pyrazol-7-yl]-3-quinolyl]pyrazol-1-yl]ethanamine | 451.1 |

TABLE 1-continued

| No. | Structure | Chemical Name | [M + H]+ |
|---|---|---|---|
| 633 | 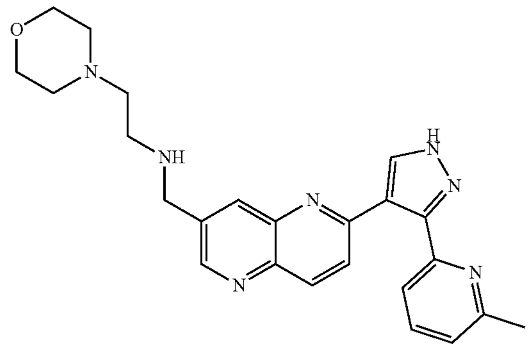 | N-[[6-[3-(6-methyl-2-pyridyl)-1H-pyrazol-4-yl]-1,5-naphthyridin-3-yl]methyl]-2-morpholino-ethanamine | 429.8 |
| 634 | 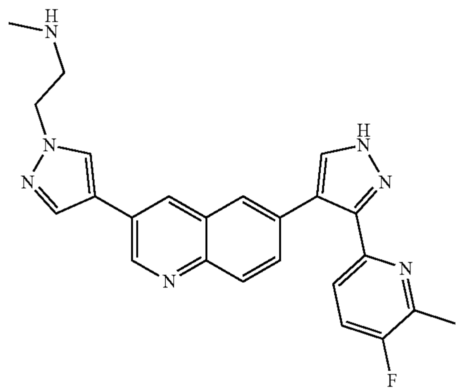 | 2-[4-[6-[3-(5-fluoro-6-methyl-2-pyridyl)-1H-pyrazol-4-yl]-3-quinolyl]pyrazol-1-yl]-N-methyl-ethanamine | 428.1 |
| 635 | 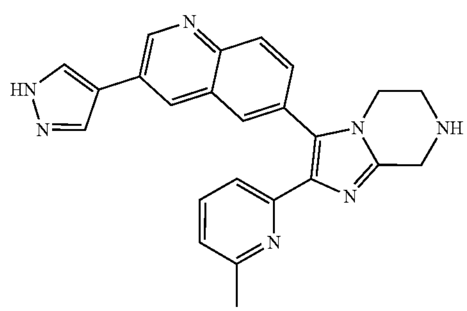 [SMILES: Cc1cccc(-c2nc3n(c2-c2ccc4ncc(-c5cn[nH]c5)cc4c2)CCNC3)n1] | 6-[2-(6-methyl-2-pyridyl)-5,6,7,8-tetrahydroimidazo[1,2-a]pyrazin-3-yl]-3-(1H-pyrazol-4-yl)quinoline | 408.1 |
| 636 | 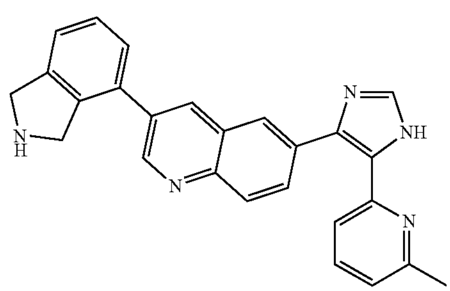 | 3-isoindolin-4-yl-6-[5-(6-methyl-2-pyridyl)-1H-imidazol-4-yl]quinoline | 404.0 |

TABLE 1-continued

| No. | Structure | Chemical Name | [M + H]+ |
|---|---|---|---|
| 637 | 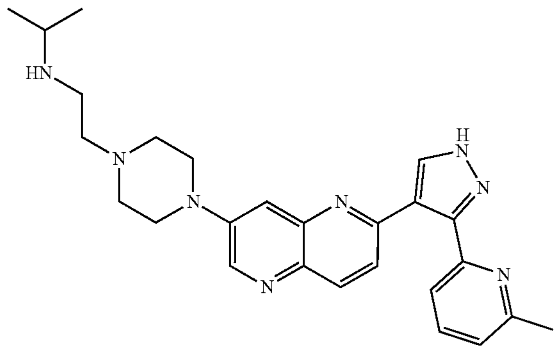 | N-[2-[4-[6-[3-(6-methyl-2-pyridyl)-1H-pyrazol-4-yl]-1,5-naphthyridin-3-yl]piperazin-1-yl]ethyl]propan-2-amine | 457.2 |
| 638 | 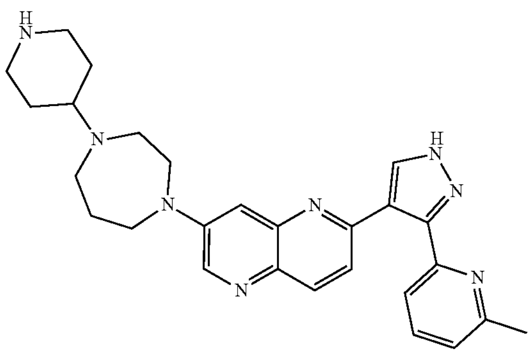 | 2-[3-(6-methyl-2-pyridyl)-1H-pyrazol-4-yl]-7-[4-(4-piperidyl)-1,4-diazepan-1-yl]-1,5-naphthyridine | 469.2 |
| 639 | 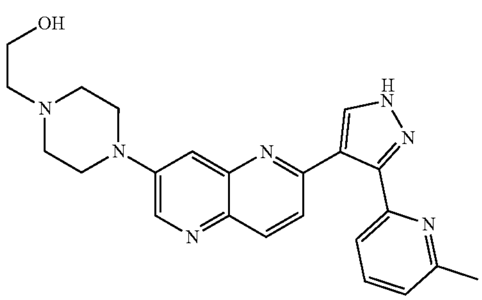 | 2-[4-[6-[3-(6-methyl-2-pyridyl)-1H-pyrazol-4-yl]-1,5-naphthyridin-3-yl]piperazin-1-yl]ethanol | 516.2 |
| 640 | 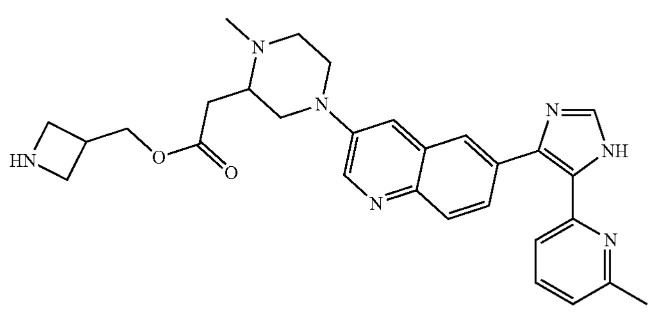 [SMILES: Cc1cccc(-c2[nH]cnc2-c2ccc3ncc(N4CCN(C)C(CC(=O)OCC5CNC5)C4)cc3c2)n1] | azetidin-3-ylmethyl 2-[1-methyl-4-[6-[5-(6-methyl-2-pyridyl)-1H-imidazol-4-yl]-3-quinolyl]piperazin-2-yl]acetate | 512.2 |
| 641 | 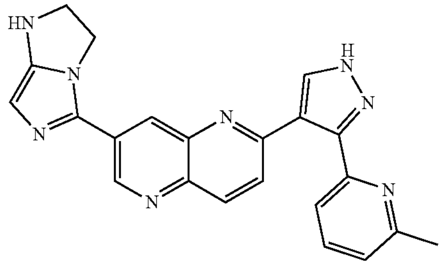 | 7-(2,3-dihydro-1H-imidazo[1,5-a]imidazol-5-yl)-2-[3-(6-methyl-2-pyridyl)-1H-pyrazol-4-yl]-1,5-naphthyridine | 395.0 |

TABLE 1-continued

| No. | Structure | Chemical Name | [M + H]+ |
|---|---|---|---|
| 642 | 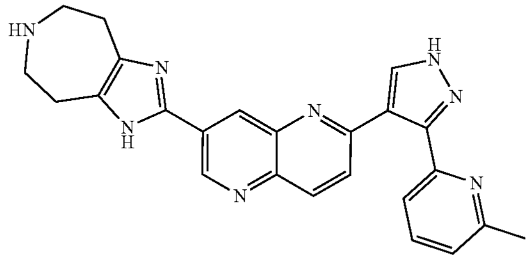 | 2-[6-[3-(6-methyl-2-pyridyl)-1H-pyrazol-4-yl]-1,5-naphthyridin-3-yl]-1,4,5,6,7,8-hexahydroimidazo[4,5-d]azepine | 423.1 |
| 643 | 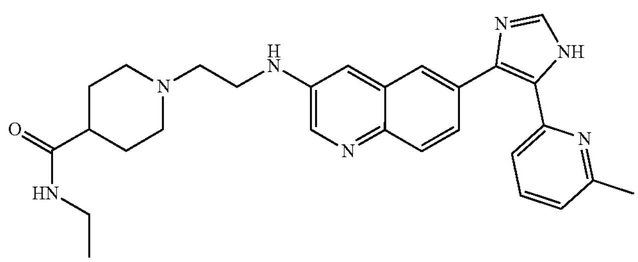 [SMILES: CCNC(=O)C1CCN(CCNc2cnc3ccc(-c4nc[nH]c4-c4cccc(C)n4)cc3c2)CC1] | N-ethyl-1-[2-[[6-[5-(6-methyl-2-pyridyl)-1H-imidazol-4-yl]-3-quinolyl]amino]ethyl]piperidine-4-carboxamide | 484.0 |
| 644 | 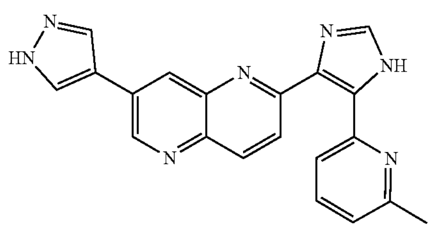 [SMILES: Cc1cccc(-c2[nH]cnc2-c2ccc3ncc(-c4cn[nH]c4)cc3n2)n1] | 2-[5-(6-methyl-2-pyridyl)-1H-imidazol-4-yl]-7-(1H-pyrazol-4-yl)-1,5-naphthyridine | 354.1 |
| 645 | 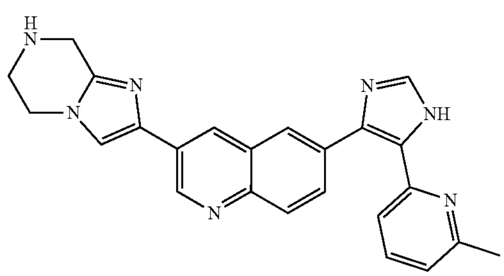 | 6-[5-(6-methyl-2-pyridyl)-1H-imidazol-4-yl]-3-(5,6,7,8-tetrahydroimidazo[1,2-a]pyrazin-2-yl)quinoline | 408.1 |
| 646 | 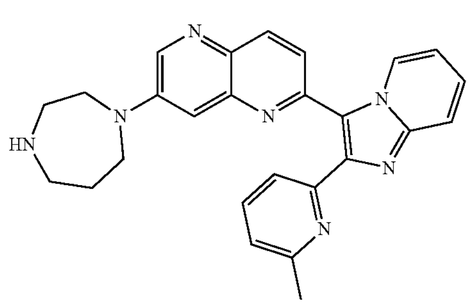 [SMILES: Cc1cccc(-c2nc3ccccn3c2-c2ccc3ncc(N4CCCNCC4)cc3n2)n1] | 7-(1,4-diazepan-1-yl)-2-[2-(6-methyl-2-pyridyl)imidazo[1,2-a]pyridin-3-yl]-1,5-naphthyridine | 436.2 |

TABLE 1-continued

| No. | Structure | Chemical Name | [M + H]+ |
|---|---|---|---|
| 647 | 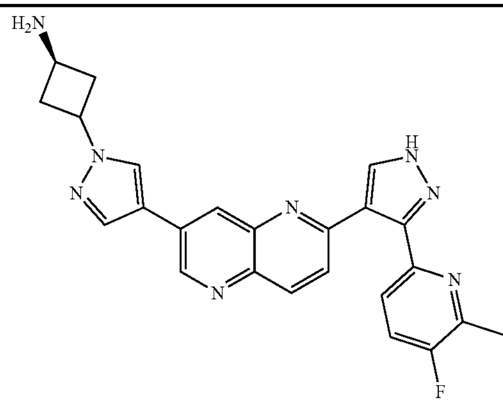 | 3-[4-[6-[3-(5-fluoro-6-methyl-2-pyridyl)-1H-pyrazol-4-yl]-1,5-naphthyridin-3-yl]pyrazol-1-yl]cyclobutanamine | 441.1 |
| 648 | 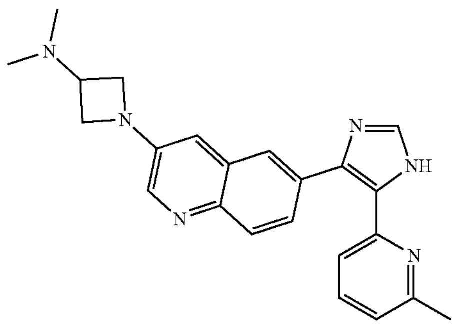 | N,N-dimethyl-1-[6-[5-(6-methyl-2-pyridyl)-1H-imidazol-4-yl]-3-quinolyl]azetidin-3-amine | 385.3 |
| 649 | 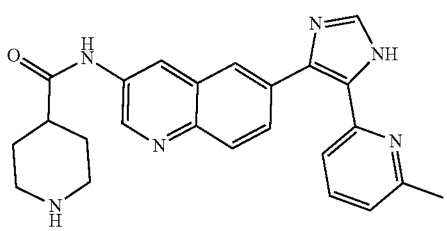 [SMILES: Cc1cccc(-c2[nH]cnc2-c2ccc3ncc(NC(=O)C4CCNCC4)cc3c2)n1] | N-[6-[5-(6-methyl-2-pyridyl)-1H-imidazol-4-yl]-3-quinolyl]piperidine-4-carboxamide | 413.1 |
| 650 | 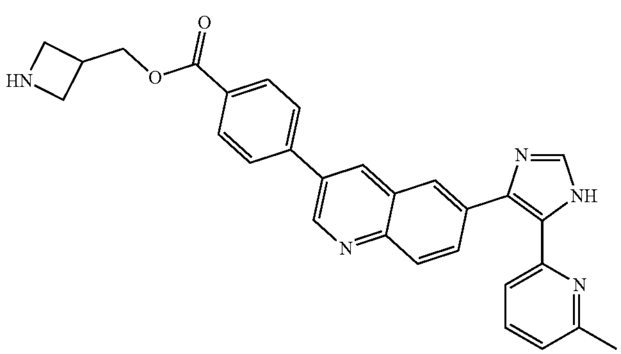 | azetidin-3-ylmethyl 4-[6-[5-(6-methyl-2-pyridyl)-1H-imidazol-4-yl]-3-quinolyl]benzoate | 476.0 |
| 651 | 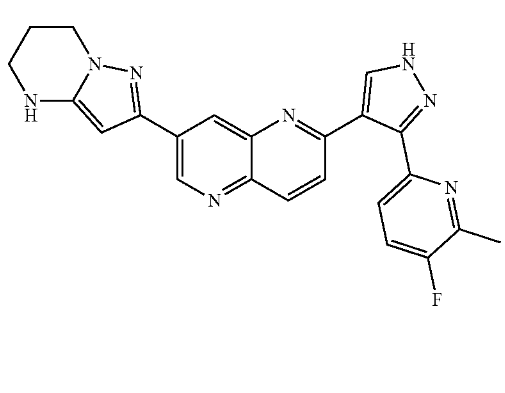 [SMILES: Cc1nc(-c2n[nH]cc2-c2ccc3ncc(-c4cc5n(n4)CCCN5)cc3n2)ccc1F] | 2-[3-(5-fluoro-6-methyl-2-pyridyl)-1H-pyrazol-4-yl]-7-(4,5,6,7-tetrahydropyrazolo[1,5-a]pyrimidin-2-yl)-1,5-naphthyridine | 427.1 |

TABLE 1-continued

| No. | Structure | Chemical Name | [M + H]+ |
|---|---|---|---|
| 652 | 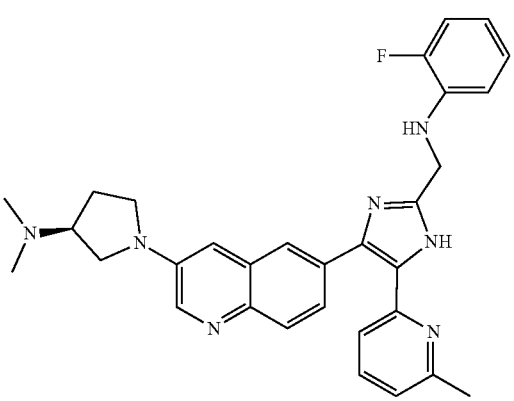 AND Enantiomer | rac-(3S)-1-[6-[2-[(2-fluoroanilino)methyl]-5-(6-methyl-2-pyridyl)-1H-imidazol-4-yl]-3-quinolyl]-N,N-dimethyl-pyrrolidin-3-amine | 522.2 |
| 653 | 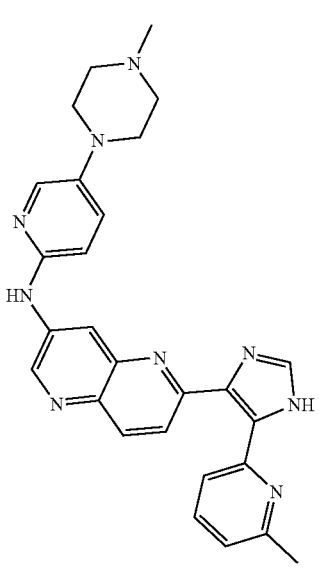 [SMILES: Cc1cccc(-c2[nH]cnc2-c2ccc3ncc(Nc4ccc(N5CCN(C)CC5)cn4)cc3n2)n1] | N-[5-(4-methylpiperazin-1-yl)-2-pyridyl]-6-[5-(6-methyl-2-pyridyl)-1H-imidazol-4-yl]-1,5-naphthyridin-3-amine | 478.1 |
| 654 | 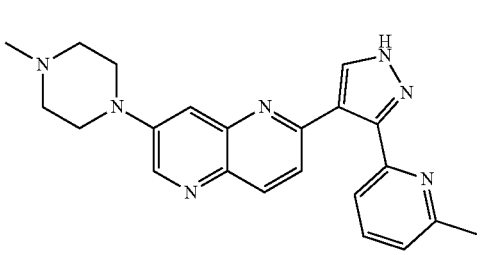 | 7-(4-methylpiperazin-1-yl)-2-[3-(6-methyl-2-pyridyl)-1H-pyrazol-4-yl]-1,5-naphthyridine | 386.1 |
| 655 | 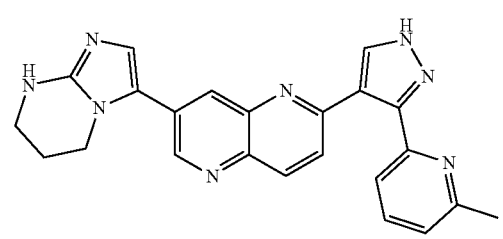 [SMILES: Cc1cccc(-c2n[nH]cc2-c2ccc3ncc(-c4cnc5n4CCCN5)cc3n2)n1] | 2-[3-(6-methyl-2-pyridyl)-1H-pyrazol-4-yl]-7-(5,6,7,8-tetrahydroimidazo[1,2-a]pyrimidin-3-yl)-1,5-naphthyridine | 409.1 |

TABLE 1-continued

| No. | Structure | Chemical Name | [M + H]+ |
|---|---|---|---|
| 656 | 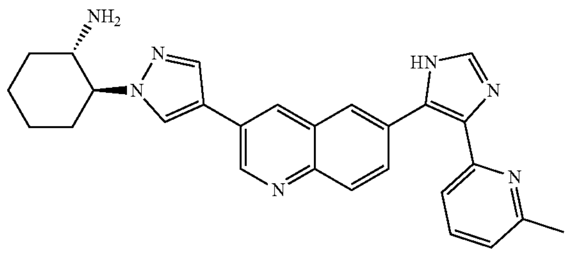 [SMILES: Cc1cccc(-c2nc[nH]c2-c2ccc3ncc(-c4cnn([C@H]5CCCC[C@@H]5N)c4)cc3c2)n1] | (1S,2S)-2-[4-[6-[4-(6-methyl-2-pyridyl)-1H-imidazol-5-yl]-3-quinolyl]pyrazol-1-yl]cyclohexanamine | 450.0 |
| 657 | 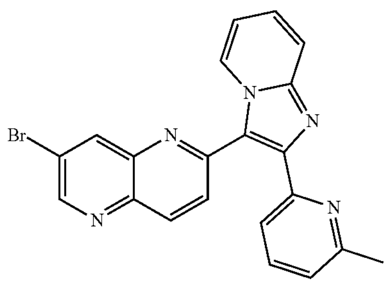 [SMILES: Cc1cccc(-c2nc3ccccn3c2-c2ccc3ncc(Br)cc3n2)n1] | 7-bromo-2-[2-(6-methyl-2-pyridyl)imidazo[1,2-a]pyridin-3-yl]-1,5-naphthyridine | 416.6 |
| 658 | 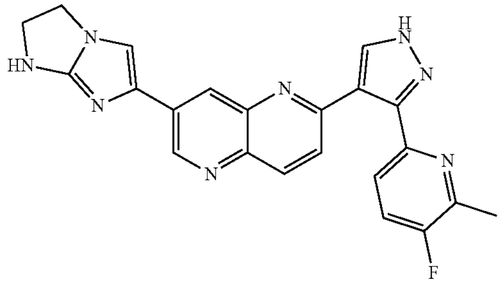 [SMILES: Cc1nc(-c2n[nH]cc2-c2ccc3ncc(-c4cn5c(n4)NCC5)cc3n2)ccc1F] | 7-(2,3-dihydro-1H-imidazo[1,2-a]imidazol-6-yl)-2-[3-(5-fluoro-6-methyl-2-pyridyl)-1H-pyrazol-4-yl]-1,5-naphthyridine | 413.1 |
| 659 | 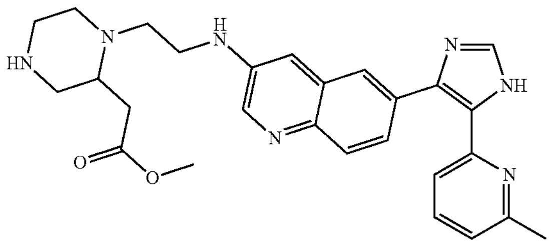 [SMILES: COC(=O)CC1CNCCN1CCNc1cnc2ccc(-c3nc[nH]c3-c3cccc(C)n3)cc2c1] | methyl 2-[1-[2-[[6-[5-(6-methyl-2-pyridyl)-1H-imidazol-4-yl]-3-quinolyl]amino]ethyl]piperazin-2-yl]acetate | 486.3 |
| 660 | 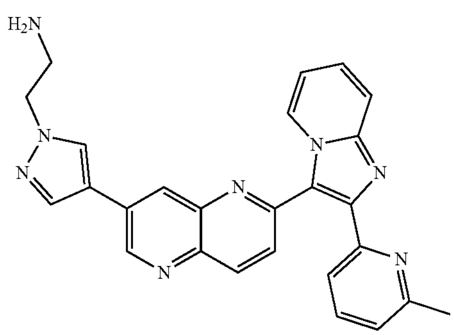 [SMILES: Cc1cccc(-c2nc3ccccn3c2-c2ccc3ncc(-c4cnn(CCN)c4)cc3n2)n1] | 2-[4-[6-[2-(6-methyl-2-pyridyl)imidazo[1,2-a]pyridin-3-yl]-1,5-naphthyridin-3-yl]pyrazol-1-yl]ethanamine | 447.2 |

TABLE 1-continued

| No. | Structure | Chemical Name | [M + H]+ |
|---|---|---|---|
| 661 | 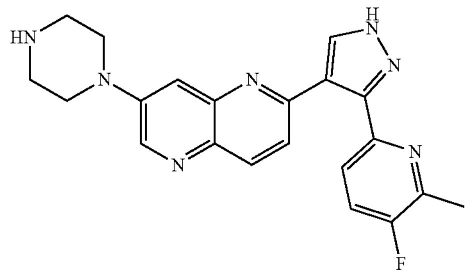 [SMILES: Cc1nc(-c2n[nH]cc2-c2ccc3ncc(N4CCNCC4)cc3n2)ccc1F] | 2-[3-(5-fluoro-6-methyl-2-pyridyl)-1H-pyrazol-4-yl]-7-piperazin-1-yl-1,5-naphthyridine | 390.2 |
| 662 | 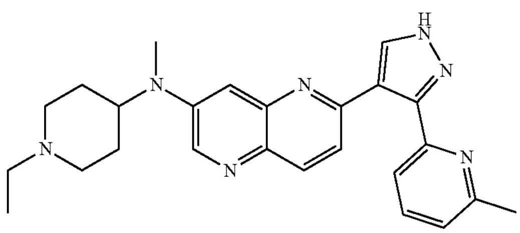 [SMILES: CCN1CCC(N(C)c2cnc3ccc(-c4c[nH]nc4-c4cccc(C)n4)nc3c2)CC1] | N-(1-ethyl-4-piperidyl)-N-methyl-6-[3-(6-methyl-2-pyridyl)-1H-pyrazol-4-yl]-1,5-naphthyridin-3-amine | 428.2 |
| 663 | 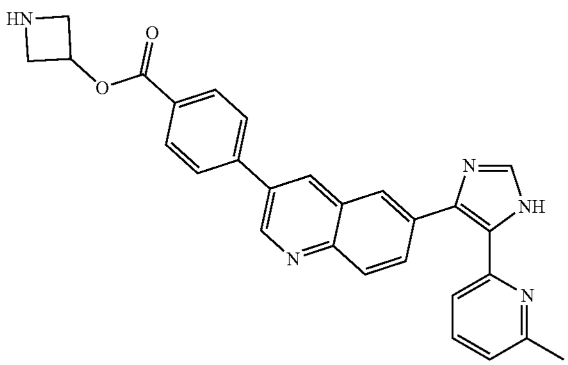 [SMILES: Cc1cccc(-c2[nH]cnc2-c2ccc3ncc(-c4ccc(C(=O)OC5CNC5)cc4)cc3c2)n1] | azetidin-3-yl 4-[6-[5-(6-methyl-2-pyridyl)-1H-imidazol-4-yl]-3-quinolyl]benzoate | 462.2 |
| 664 | 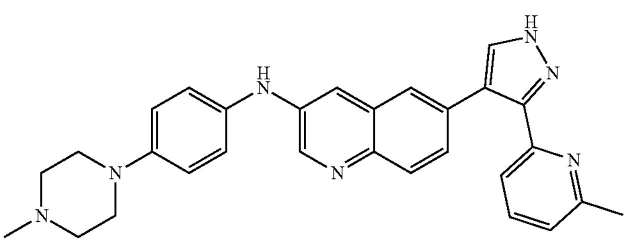 | N-[4-(4-methylpiperazin-1-yl)phenyl]-6-[3-(6-methyl-2-pyridyl)-1H-pyrazol-4-yl]quinolin-3-amine | 476.2 |
| 665 | 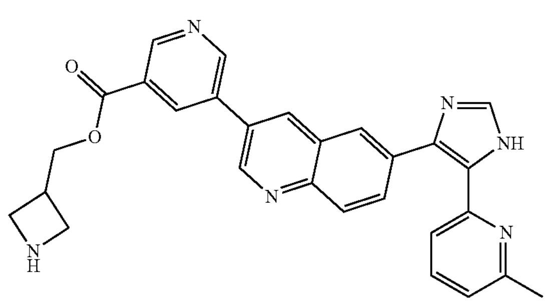 [SMILES: Cc1cccc(-c2[nH]cnc2-c2ccc3ncc(-c4cncc(C(=O)OCC5CNC5)c4)cc3c2)n1] | azetidin-3-ylmethyl 5-[6-[5-(6-methyl-2-pyridyl)-1H-imidazol-4-yl]-3-quinolyl]pyridine-3-carboxylate | 477.1 |

TABLE 1-continued

| No. | Structure | Chemical Name | [M + H]+ |
|---|---|---|---|
| 666 | 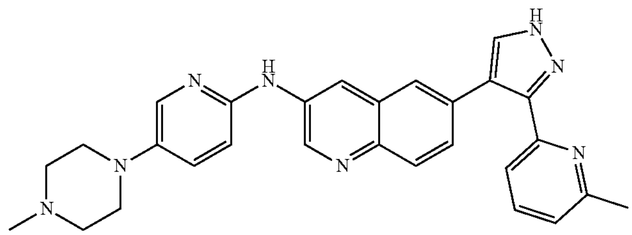 | N-[5-(4-methylpiperazin-1-yl)-2-pyridyl]-6-[3-(6-methyl-2-pyridyl)-1H-pyrazol-4-yl]quinolin-3-amine | 477.2 |
| 667 | 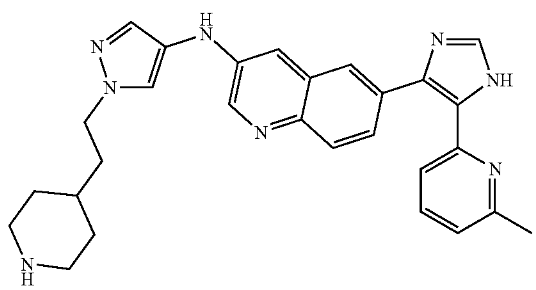 [SMILES: Cc1cccc(-c2[nH]cnc2-c2ccc3ncc(Nc4cnn(CCC5CCNCC5)c4)cc3c2)n1] | 6-[5-(6-methyl-2-pyridyl)-1H-imidazol-4-yl]-N-[1-[2-(4-piperidyl)ethyl]pyrazol-4-yl]quinolin-3-amine | 479.1 |
| 668 | 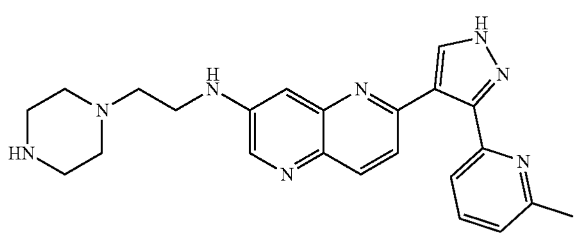 [SMILES: Cc1cccc(-c2n[nH]cc2-c2ccc3ncc(NCCN4CCNCC4)cc3n2)n1] | 6-[3-(6-methyl-2-pyridyl)-1H-pyrazol-4-yl]-N-(2-piperazin-1-ylethyl)-1,5-naphthyridin-3-amine | 415.2 |
| 669 | 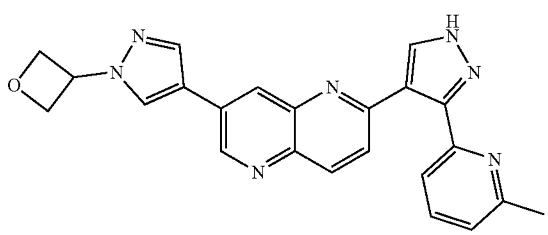 [SMILES: Cc1cccc(-c2n[nH]cc2-c2ccc3ncc(-c4cnn(C5COC5)c4)cc3n2)n1] | 2-[3-(6-methyl-2-pyridyl)-1H-pyrazol-4-yl]-7-[1-(oxetan-3-yl)pyrazol-4-yl]-1,5-naphthyridine | 410.1 |
| 670 | 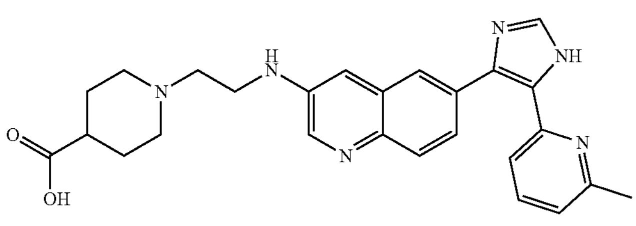 [SMILES: Cc1cccc(-c2[nH]cnc2-c2ccc3ncc(NCCN4CCC(C(=O)O)CC4)cc3c2)n1] | 1-[2-[[6-[5-(6-methyl-2-pyridyl)-1H-imidazol-4-yl]-3-quinolyl]amino]ethyl]piperidine-4-carboxylic acid | 457.1 |
| 671 | 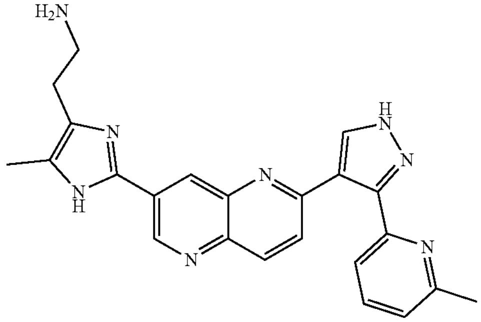 | 2-[5-methyl-2-[6-[3-(6-methyl-2-pyridyl)-1H-pyrazol-4-yl]-1,5-naphthyridin-3-yl]-1H-imidazol-4-yl]ethanamine | 411.3 |

TABLE 1-continued

| No. | Structure | Chemical Name | [M + H]+ |
|---|---|---|---|
| 672 | 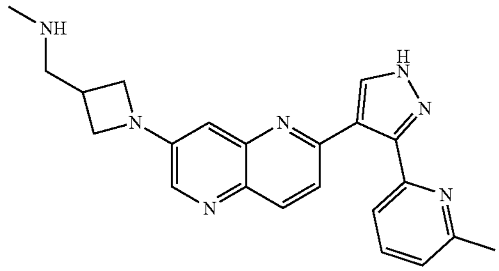 | N-methyl-1-[1-[6-[3-(6-methyl-2-pyridyl)-1H-pyrazol-4-yl]-1,5-naphthyridin-3-yl]azetidin-3-yl]methanamine | 386.2 |
| 673 | 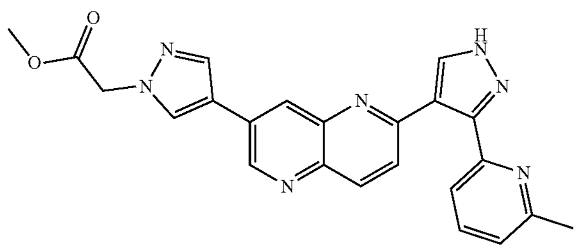 | methyl 2-[4-[6-[3-(6-methyl-2-pyridyl)-1H-pyrazol-4-yl]-1,5-naphthyridin-3-yl]pyrazol-1-yl]acetate | 426.3 |
| 674 | 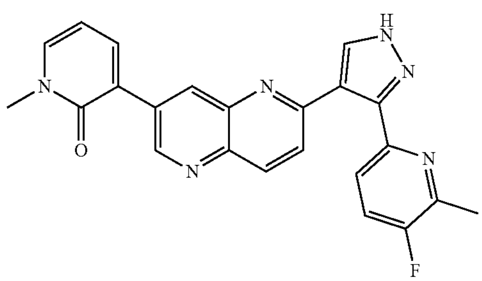 | 3-[6-[3-(5-fluoro-6-methyl-2-pyridyl)-1H-pyrazol-4-yl]-1,5-naphthyridin-3-yl]-1-methyl-pyridin-2-one | 413.2 |
| 675 | 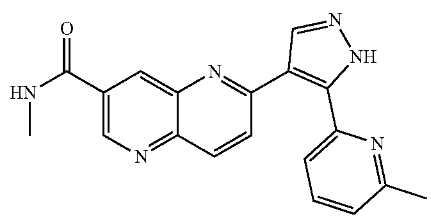 [SMILES: CNC(=O)c1cnc2ccc(-c3cn[nH]c3-c3cccc(C)n3)nc2c1] | N-methyl-6-[5-(6-methyl-2-pyridyl)-1H-pyrazol-4-yl]-1,5-naphthyridine-3-carboxamide | 345.2 |
| 676 | 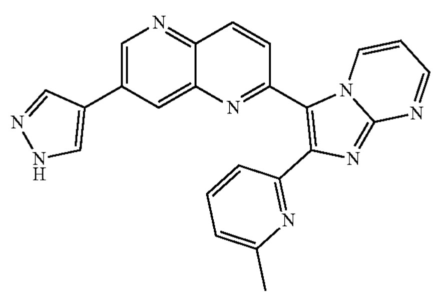 | 2-[2-(6-methyl-2-pyridyl)imidazo[1,2-a]pyrimidin-3-yl]-7-(1H-pyrazol-4-yl)-1,5-naphthyridine | 405.0 |
| 677 | 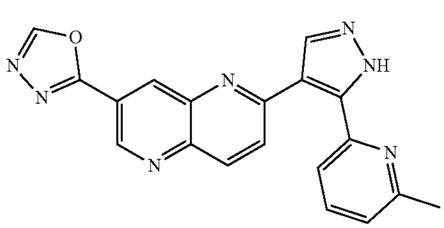 [SMILES: Cc1cccc(-c2[nH]ncc2-c2ccc3ncc(-c4nnco4)cc3n2)n1] | 2-[6-[5-(6-methyl-2-pyridyl)-1H-pyrazol-4-yl]-1,5-naphthyridin-3-yl]-1,3,4-oxadiazole | 356.1 |

TABLE 1-continued

| No. | Structure | Chemical Name | [M + H]+ |
|---|---|---|---|
| 678 | 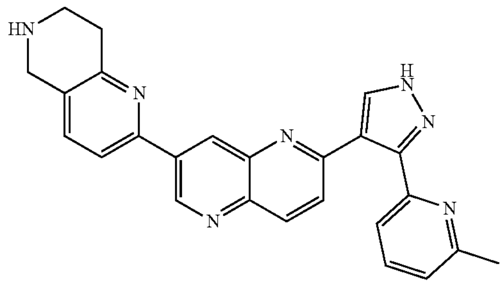 | 2-[3-(6-methyl-2-pyridyl)-1H-pyrazol-4-yl]-7-(5,6,7,8-tetrahydro-1,6-naphthyridin-2-yl)-1,5-naphthyridine | 420.1 |
| 679 | 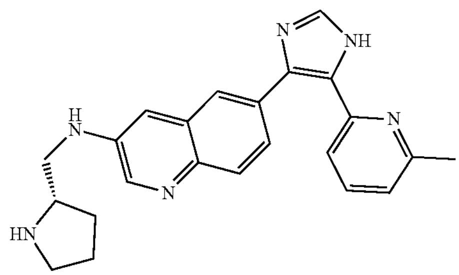 [SMILES: Cc1cccc(-c2[nH]cnc2-c2ccc3ncc(NC[C@@H]4CCCN4)cc3c2)n1] | 6-[5-(6-methyl-2-pyridyl)-1H-imidazol-4-yl]-N-[[(2S)-pyrrolidin-2-yl]methyl]quinolin-3-amine | 385.2 |
| 680 | 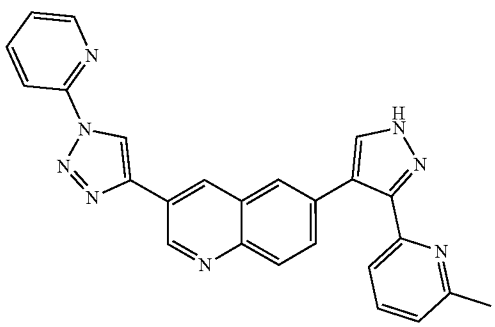 | 2-[3-(6-methyl-2-pyridyl)-1H-pyrazol-4-yl]-7-[1-(2-pyridyl)triazol-4-yl]-1,5-naphthyridine | 432.0 |
| 681 | 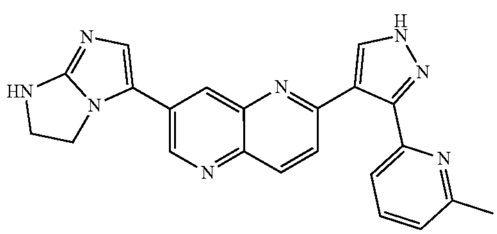 | 7-(6,7-dihydro-5H-imidazo[1,2-a]imidazol-3-yl)-2-[3-(6-methyl-2-pyridyl)-1H-pyrazol-4-yl]-1,5-naphthyridine | 395.1 |
| 682 | 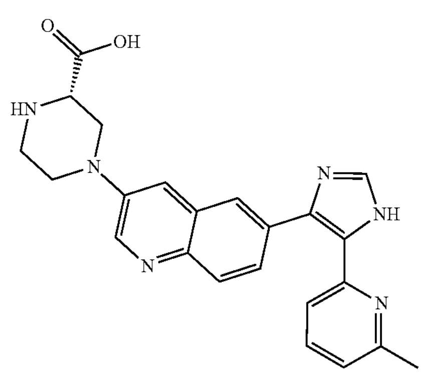 [SMILES: Cc1cccc(-c2[nH]cnc2-c2ccc3ncc(N4CCN[C@H](C(=O)O)C4)cc3c2)n1] | (2S)-4-[6-[5-(6-methyl-2-pyridyl)-1H-imidazol-4-yl]-3-quinolyl]piperazine-2-carboxylic acid | 415.1 |

TABLE 1-continued

| No. | Structure | Chemical Name | [M + H]+ |
|---|---|---|---|
| 683 | 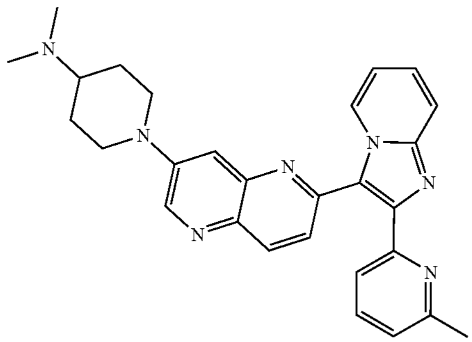 | N,N-dimethyl-1-[6-[2-(6-methyl-2-pyridyl)imidazo[1,2-a]pyridin-3-yl]-1,5-naphthyridin-3-yl]piperidin-4-amine | 464.2 |
| 684 | 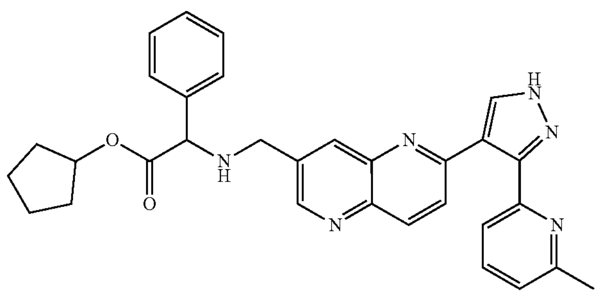 | cyclopentyl 2-[[6-[3-(6-methyl-2-pyridyl)-1H-pyrazol-4-yl]-1,5-naphthyridin-3-yl]methylamino]-2-phenyl-acetate | 519.4 |
| 685 | 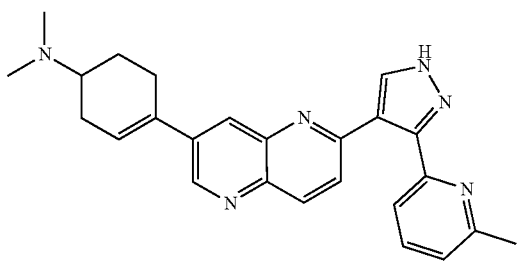 | N,N-dimethyl-4-[6-[3-(6-methyl-2-pyridyl)-1H-pyrazol-4-yl]-1,5-naphthyridin-3-yl]cyclohex-3-en-1-amine | 411.2 |
| 686 | 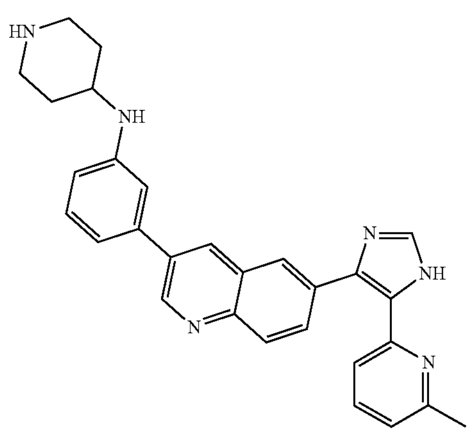 [SMILES: Cc1cccc(-c2[nH]cnc2-c2ccc3ncc(-c4cccc(NC5CCNCC5)c4)cc3c2)n1] | N-[3-[6-[5-(6-methyl-2-pyridyl)-1H-imidazol-4-yl]-3-quinolyl]phenyl]piperidin-4-amine | 461.1 |

TABLE 1-continued

| No. | Structure | Chemical Name | [M + H]+ |
|---|---|---|---|
| 687 | 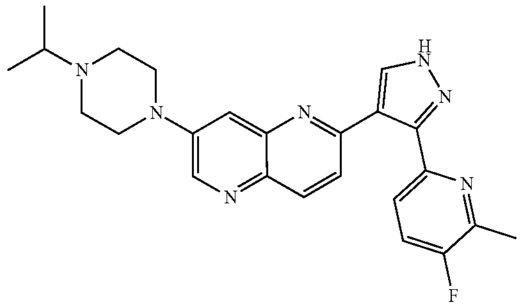 | 2-[3-(5-fluoro-6-methyl-2-pyridyl)-1H-pyrazol-4-yl]-7-(4-isopropylpiperazin-1-yl)-1,5-naphthyridine | 432.1 |
| 688 | 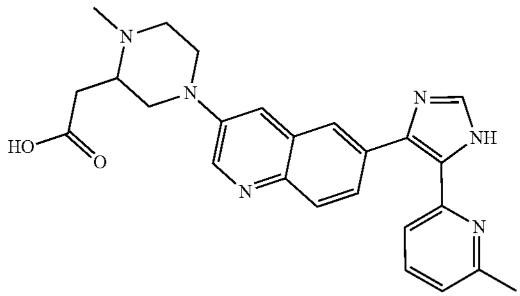 [SMILES: Cc1cccc(-c2[nH]cnc2-c2ccc3ncc(N4CCN(C)C(CC(=O)O)C4)cc3c2)n1] | 2-[1-methyl-4-[6-[5-(6-methyl-2-pyridyl)-1H-imidazol-4-yl]-3-quinolyl]piperazin-2-yl]acetic acid | 443.2 |
| 689 | 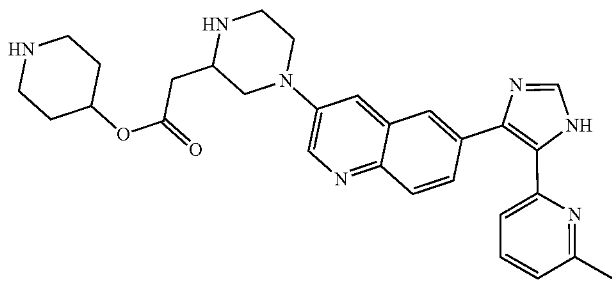 [SMILES: Cc1cccc(-c2[nH]cnc2-c2ccc3ncc(N4CCNC(CC(=O)OC5CCNCC5)C4)cc3c2)n1] | 4-piperidyl 2-[4-[6-[5-(6-methyl-2-pyridyl)-1H-imidazol-4-yl]-3-quinolyl]piperazin-2-yl]acetate | 512.3 |
| 690 | 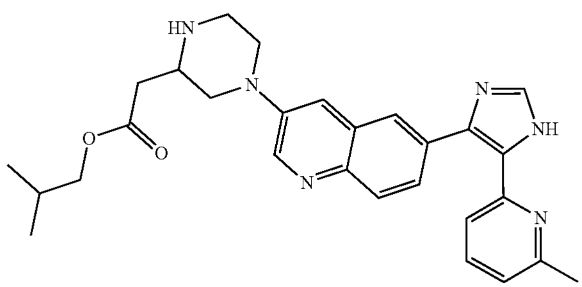 [SMILES: Cc1cccc(-c2[nH]cnc2-c2ccc3ncc(N4CCNC(CC(=O)OCC(C)C)C4)cc3c2)n1] | isobutyl 2-[4-[6-[5-(6-methyl-2-pyridyl)-1H-imidazol-4-yl]-3-quinolyl]piperazin-2-yl]acetate | 485.1 |
| 691 | 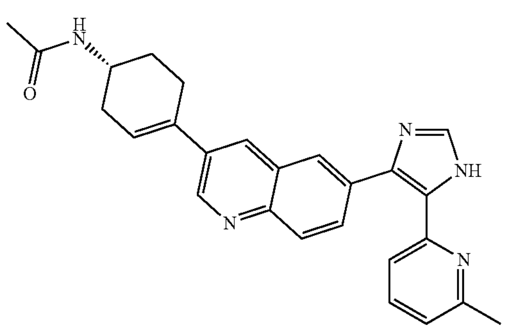 [SMILES: CC(=O)N[C@H]1CC=C(c2cnc3ccc(-c4nc[nH]c4-c4cccc(C)n4)cc3c2)CC1] | N-[(1R)-4-[6-[5-(6-methyl-2-pyridyl)-1H-imidazol-4-yl]-3-quinolyl]cyclohex-3-en-1-yl]acetamide | 424.1 |

TABLE 1-continued

| No. | Structure | Chemical Name | [M + H]+ |
|---|---|---|---|
| 692 | 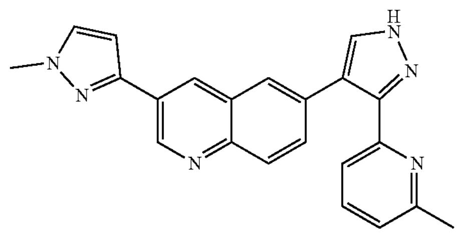 | 7-(1-methylpyrazol-3-yl)-2-[3-(6-methyl-2-pyridyl)-1H-pyrazol-4-yl]-1,5-naphthyridine | 368.2 |
| 693 | 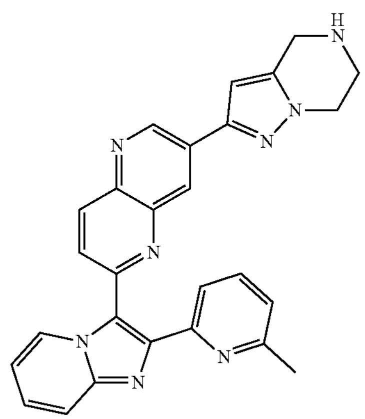 | 2-[2-(6-methyl-2-pyridyl)imidazo[1,2-a]pyridin-3-yl]-7-(4,5,6,7-tetrahydropyrazolo[1,5-a]pyrazin-2-yl)-1,5-naphthyridine | 459.2 |
| 694 | 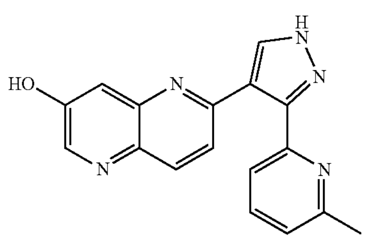 | 6-[3-(6-methyl-2-pyridyl)-1H-pyrazol-4-yl]-1,5-naphthyridin-3-ol | 304.1 |
| 695 | 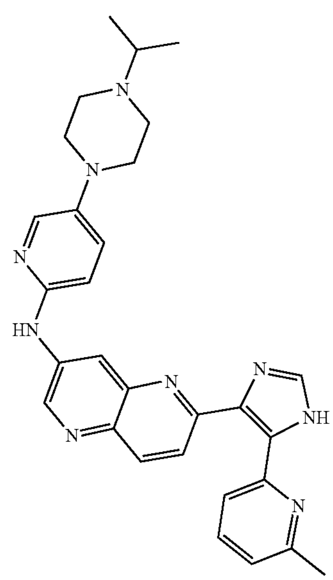 [SMILES: Cc1cccc(-c2[nH]cnc2-c2ccc3ncc(Nc4ccc(N5CCN(C(C)C)CC5)cn4)cc3n2)n1] | N-[5-(4-isopropylpiperazin-1-yl)-2-pyridyl]-6-[5-(6-methyl-2-pyridyl)-1H-imidazol-4-yl]-1,5-naphthyridin-3-amine | 506.1 |

TABLE 1-continued

| No. | Structure | Chemical Name | [M + H]+ |
|---|---|---|---|
| 696 | 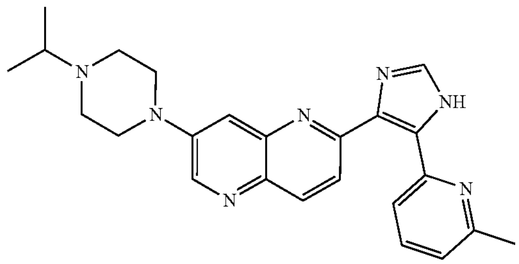 [SMILES: Cc1cccc(-c2[nH]cnc2-c2ccc3ncc(N4CCN(C(C)C)CC4)cc3n2)n1] | 7-(4-isopropylpiperazin-1-yl)-2-[3-(6-methyl-2-pyridyl)-1H-pyrazol-4-yl]-1,5-naphthyridine | 414.2 |
| 697 | 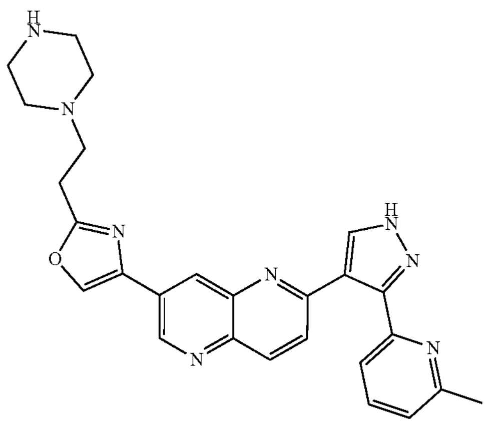 | 4-[6-[3-(6-methyl-2-pyridyl)-1H-pyrazol-4-yl]-1,5-naphthyridin-3-yl]-2-(2-piperazin-1-ylethyl)oxazole | 467.1 |
| 698 | 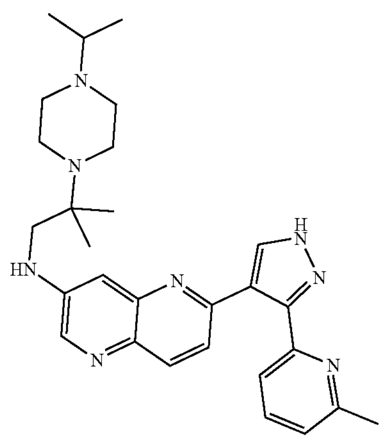 | N-[2-(4-isopropylpiperazin-1-yl)-2-methyl-propyl]-6-[3-(6-methyl-2-pyridyl)-1H-pyrazol-4-yl]-1,5-naphthyridin-3-amine | 485.2 |
| 699 | 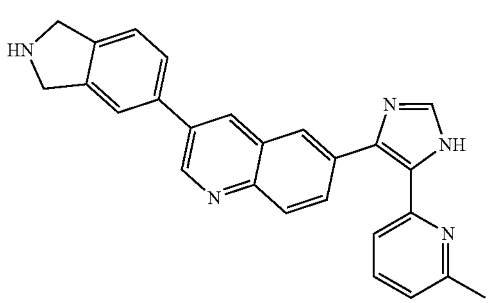 [SMILES: Cc1cccc(-c2[nH]cnc2-c2ccc3ncc(-c4ccc5c(c4)CNC5)cc3c2)n1] | 3-isoindolin-5-yl-6-[5-(6-methyl-2-pyridyl)-1H-imidazol-4-yl]quinoline | 404.1 |

| No. | Structure | Chemical Name | [M + H]+ |
|---|---|---|---|
| 700 | 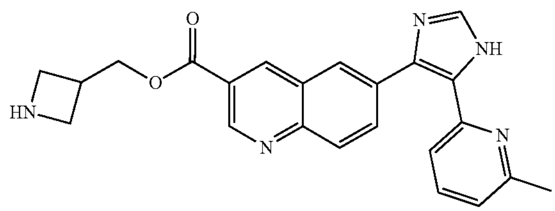 [SMILES: Cc1cccc(-c2[nH]cnc2-c2ccc3ncc(C(=O)OCC4CNC4)cc3c2)n1] | azetidin-3-ylmethyl 6-[5-(6-methyl-2-pyridyl)-1H-imidazol-4-yl]quinoline-3-carboxylate | 400.0 |
| 701 | 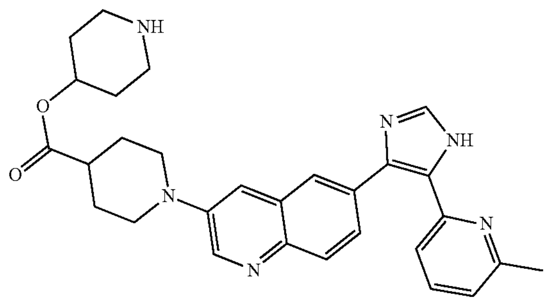 [SMILES: Cc1cccc(-c2[nH]cnc2-c2ccc3ncc(N4CCC(C(=O)OC5CCNCC5)CC4)cc3c2)n1] | 4-piperidyl 1-[6-[5-(6-methyl-2-pyridyl)-1H-imidazol-4-yl]-3-quinolyl]piperidine-4-carboxylate | 497.1 |
| 702 | 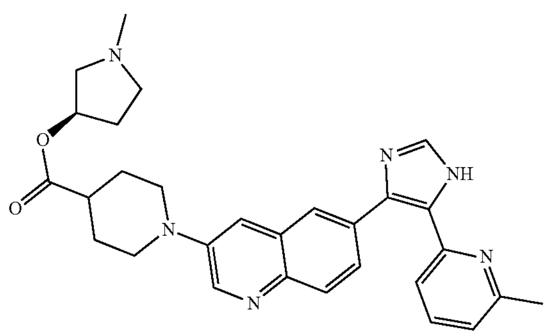 [SMILES: Cc1cccc(-c2[nH]cnc2-c2ccc3ncc(N4CCC(C(=O)O[C@@H]5CCN(C)C5)CC4)cc3c2)n1] | [(3R)-1-methylpyrrolidin-3-yl] 1-[6-[5-(6-methyl-2-pyridyl)-1H-imidazol-4-yl]-3-quinolyl]piperidine-4-carboxylate | 497.2 |
| 703 | 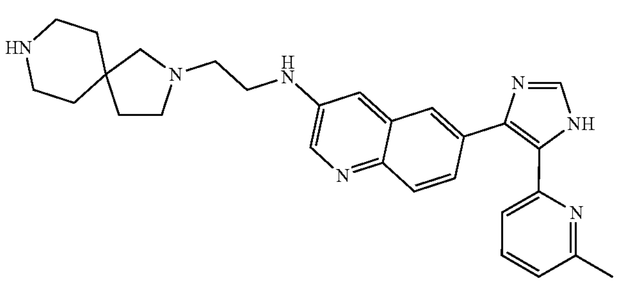 [SMILES: Cc1cccc(-c2[nH]cnc2-c2ccc3ncc(NCCN4CCC5(CCNCC5)C4)cc3c2)n1] | N-[2-(2,8-diazaspiro[4.5]decan-2-yl)ethyl]-6-[5-(6-methyl-2-pyridyl)-1H-imidazol-4-yl]quinolin-3-amine | 468.1 |
| 704 | 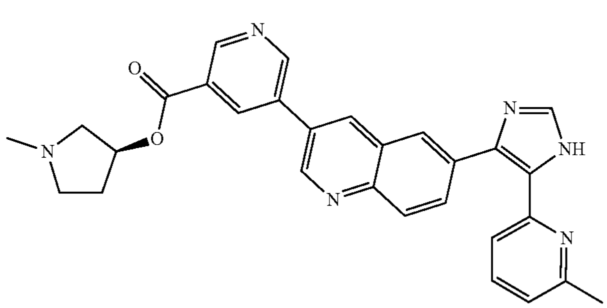 | [(3S)-1-methylpyrrolidin-3-yl] 5-[6-[5-(6-methyl-2-pyridyl)-1H-imidazol-4-yl]-3-quinolyl]pyridine-3-carboxylate | 491.0 |

TABLE 1-continued

| No. | Structure | Chemical Name | [M + H]+ |
|---|---|---|---|
| 705 | 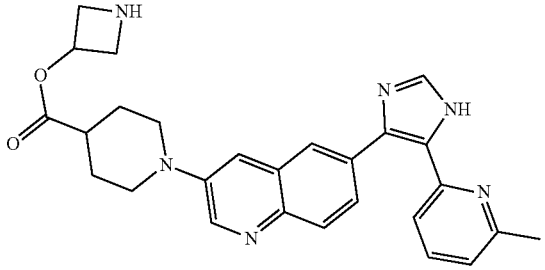 [SMILES: Cc1cccc(-c2[nH]cnc2-c2ccc3ncc(N4CCC(C(=O)OC5CNC5)CC4)cc3c2)n1] | azetidin-3-yl 1-[6-[5-(6-methyl-2-pyridyl)-1H-imidazol-4-yl]-3-quinolyl]piperidine-4-carboxylate | 469.1 |
| 706 | 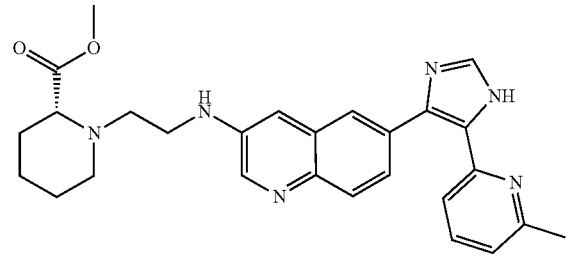 [SMILES: COC(=O)[C@H]1CCCCN1CCNc1cnc2ccc(-c3nc[nH]c3-c3cccc(C)n3)cc2c1] | methyl (2R)-1-[2-[[6-[5-(6-methyl-2-pyridyl)-1H-imidazol-4-yl]-3-quinolyl]amino]ethyl]piperidine-2-carboxylate | 471.1 |
| 707 | 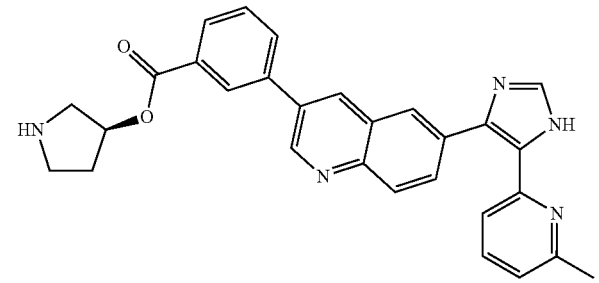 [SMILES: Cc1cccc(-c2[nH]cnc2-c2ccc3ncc(-c4cccc(C(=O)O[C@H]5CCNC5)c4)cc3c2)n1] | [(3S)-pyrrolidin-3-yl] 3-[6-[5-(6-methyl-2-pyridyl)-1H-imidazol-4-yl]-3-quinolyl]benzoate | 476.1 |
| 708 | 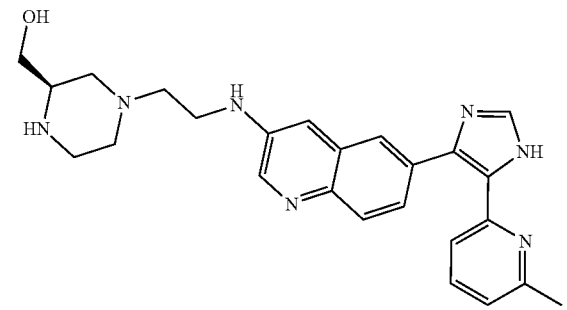 [SMILES: Cc1cccc(-c2[nH]cnc2-c2ccc3ncc(NCCN4CCN[C@@H](CO)C4)cc3c2)n1] | [(2R)-4-[2-[[6-[5-(6-methyl-2-pyridyl)-1H-imidazol-4-yl]-3-quinolyl]amino]ethyl]piperazin-2-yl]methanol | 444.1 |
| 709 | 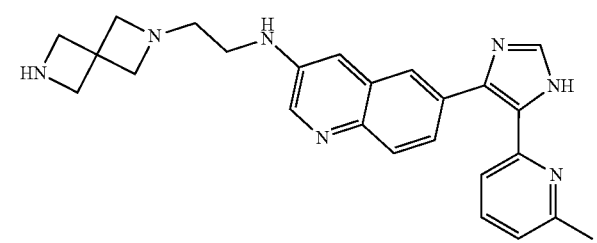 [SMILES: Cc1cccc(-c2[nH]cnc2-c2ccc3ncc(NCCN4CC5(CNC5)C4)cc3c2)n1] | N-[2-(2,6-diazaspiro[3.3]heptan-2-yl)ethyl]-6-[5-(6-methyl-2-pyridyl)-1H-imidazol-4-yl]quinolin-3-amine | 426.1 |

TABLE 1-continued

| No. | Structure | Chemical Name | [M + H]+ |
|---|---|---|---|
| 710 | 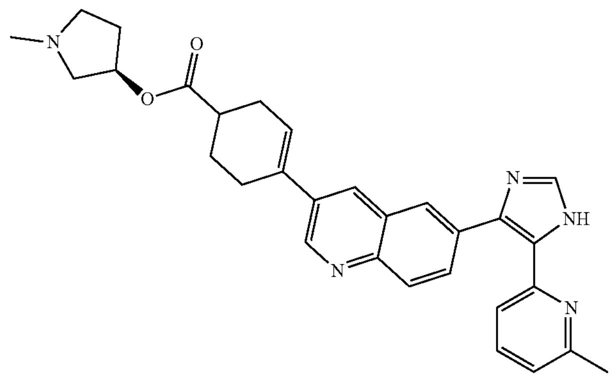 | [(3R)-1-methylpyrrolidin-3-yl] 4-[6-[5-(6-methyl-2-pyridyl)-1H-imidazol-4-yl]-3-quinolyl]cyclohex-3-ene-1-carboxylate | 494.1 |
| 711 | 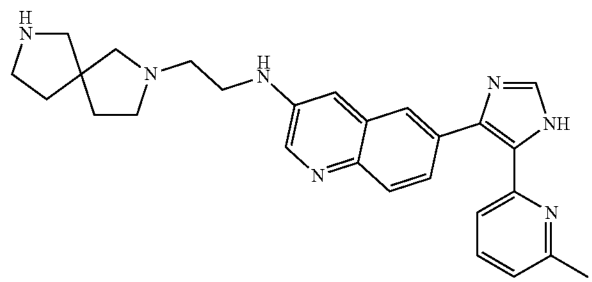 | N-[2-(2,7-diazaspiro[4.4]nonan-2-yl)ethyl]-6-[5-(6-methyl-2-pyridyl)-1H-imidazol-4-yl]quinolin-3-amine | 454.1 |
| 712 | 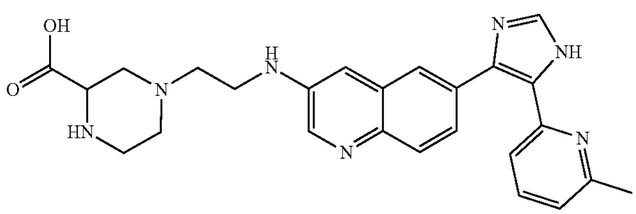 [SMILES: Cc1cccc(-c2[nH]cnc2-c2ccc3ncc(NCCN4CCNC(C(=O)O)C4)cc3c2)n1] | 4-[2-[[6-[5-(6-methyl-2-pyridyl)-1H-imidazol-4-yl]-3-quinolyl]amino]ethyl]piperazine-2-carboxylic acid | 485.2 |
| 713 | 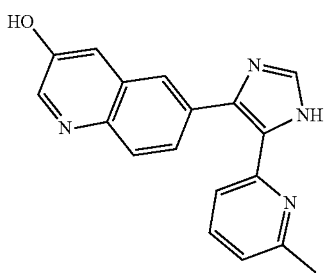 [SMILES: Cc1cccc(-c2[nH]cnc2-c2ccc3ncc(O)cc3c2)n1] | 6-[5-(6-methyl-2-pyridyl)-1H-pyrazol-4-yl]quinolin-3-ol | 303.1 |
| 714 | 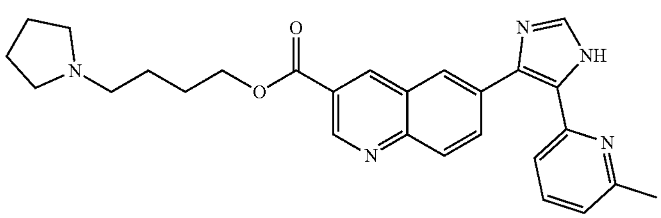 [SMILES: Cc1cccc(-c2[nH]cnc2-c2ccc3ncc(C(=O)OCCCCN4CCCC4)cc3c2)n1] | 4-pyrrolidin-1-ylbutyl 6-[5-(6-methyl-2-pyridyl)-1H-imidazol-4-yl]quinoline-3-carboxylate | 456.1 |
| 715 | 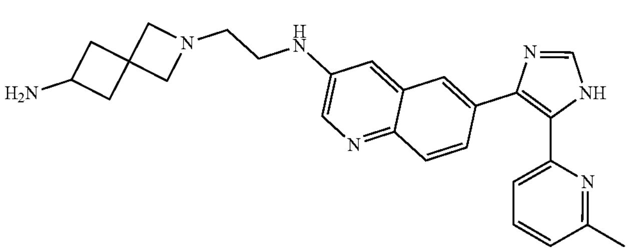 [SMILES: Cc1cccc(-c2[nH]cnc2-c2ccc3ncc(NCCN4CC5(CC(N)C5)C4)cc3c2)n1] | N-[2-(6-amino-2-azaspiro[3.3]heptan-2-yl)ethyl]-6-[5-(6-methyl-2-pyridyl)-1H-imidazol-4-yl]quinolin-3-amine | 440.1 |

TABLE 1-continued

| No. | Structure | Chemical Name | [M + H]+ |
|---|---|---|---|
| 716 | 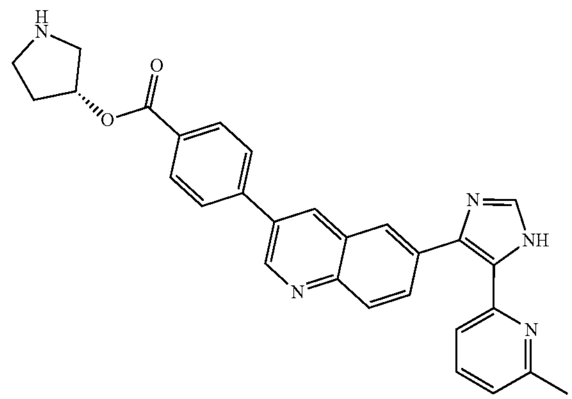 [SMILES: Cc1cccc(-c2[nH]cnc2-c2ccc3ncc(-c4ccc(C(=O)O[C@@H]5CCNC5)cc4)cc3c2)n1] | [(3R)-pyrrolidin-3-yl] 4-[6-[5-(6-methyl-2-pyridyl)-1H-imidazol-4-yl]-3-quinolyl]benzoate | 476.0 |
| 717 | 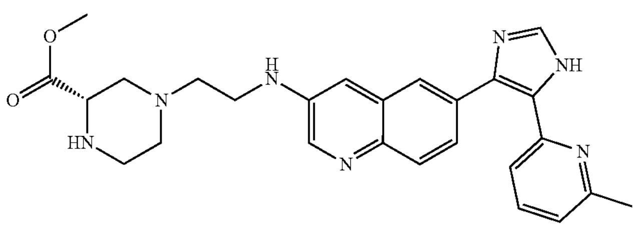 [SMILES: COC(=O)[C@@H]1CN(CCNc2cnc3ccc(-c4nc[nH]c4-c4cccc(C)n4)cc3c2)CCN1] | methyl (2S)-4-[2-[[6-[5-(6-methyl-2-pyridyl)-1H-imidazol-4-yl]-3-quinolyl]amino]ethyl]piperazine-2-carboxylate | 472.1 |
| 718 | 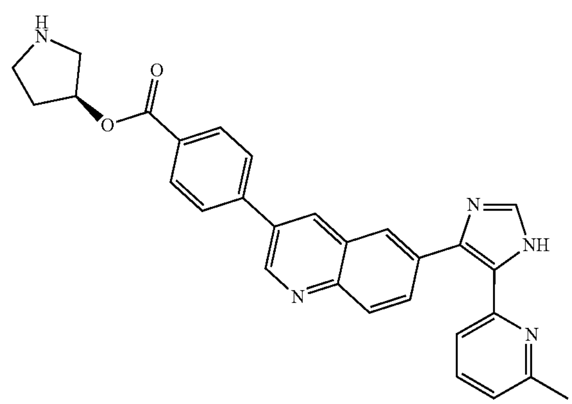 [SMILES: Cc1cccc(-c2[nH]cnc2-c2ccc3ncc(-c4ccc(C(=O)O[C@H]5CCNC5)cc4)cc3c2)n1] | [(3S)-pyrrolidin-3-yl]4-[6-[5-(6-methyl-2-pyridyl)-1H-imidazol-4-yl]-3-quinolyl]benzoate | 476.0 |
| 719 | 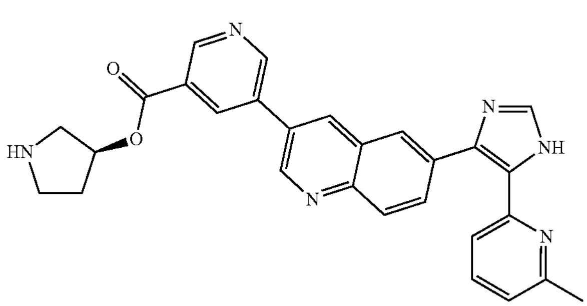 [SMILES: Cc1cccc(-c2[nH]cnc2-c2ccc3ncc(-c4cncc(C(=O)O[C@H]5CCNC5)c4)cc3c2)n1] | [(3S)-pyrrolidin-3-yl] 5-[6-[5-(6-methyl-2-pyridyl)-1H-imidazol-4-yl]-3-quinolyl]pyridine-3-carboxylate | 477.0 |
| 720 | 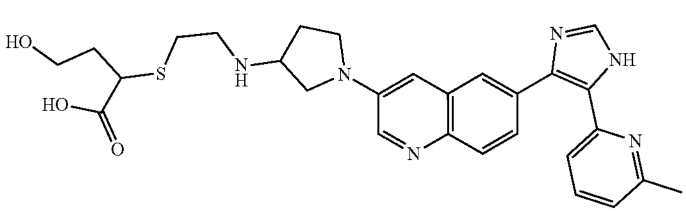 | 4-hydroxy-2-[2-[[1-[6-[5-(6-methyl-2-pyridyl)-1H-imidazol-4-yl]-3-quinolyl]pyrrolidin-3-yl]amino]ethylsulfanyl]butanoic acid | 533.0 |

TABLE 1-continued

| No. | Structure | Chemical Name | [M + H]+ |
|---|---|---|---|
| 721 | 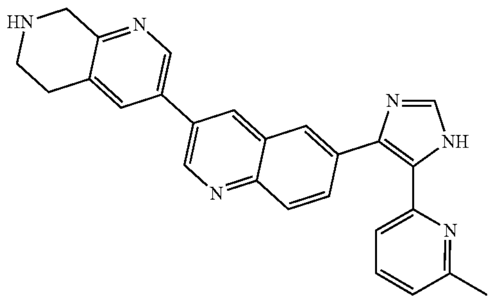 [SMILES: Cc1cccc(-c2[nH]cnc2-c2ccc3ncc(-c4cnc5c(c4)CCNC5)cc3c2)n1] | 3-[6-[5-(6-methyl-2-pyridyl)-1H-imidazol-4-yl]-3-quinolyl]-5,6,7,8-tetrahydro-1,7-naphthyridine | 419.0 |
| 722 | 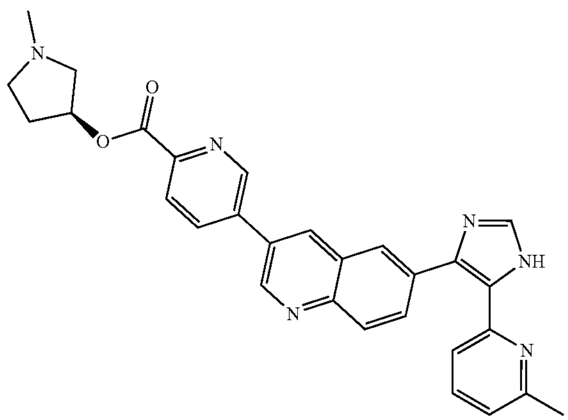 [SMILES: Cc1cccc(-c2[nH]cnc2-c2ccc3ncc(-c4ccc(C(=O)O[C@H]5CCN(C)C5)nc4)cc3c2)n1] | [(3S)-1-methylpyrrolidin-3-yl] 5-[6-[5-(6-methyl-2-pyridyl)-1H-imidazol-4-yl]-3-quinolyl]pyridine-2-carboxylate | 491.0 |
| 723 | 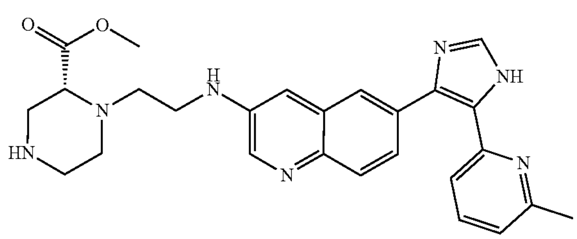 [SMILES: COC(=O)[C@H]1CNCCN1CCNc1cnc2ccc(-c3nc[nH]c3-c3cccc(C)n3)cc2c1] | methyl (2R)-1-[2-[[6-[5-(6-methyl-2-pyridyl)-1H-imidazol-4-yl]-3-quinolyl]amino]ethyl]piperazine-2-carboxylate | 472.1 |
| 724 | 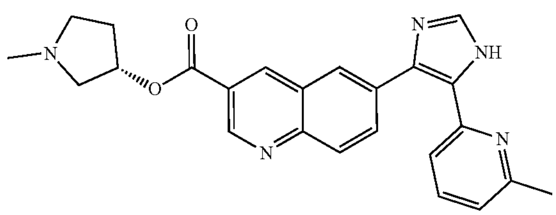 | [(3S)-1-methylpyrrolidin-3-yl] 6-[5-(6-methyl-2-pyridyl)-1H-imidazol-4-yl]quinoline-3-carboxylate | 414.1 |
| 725 | 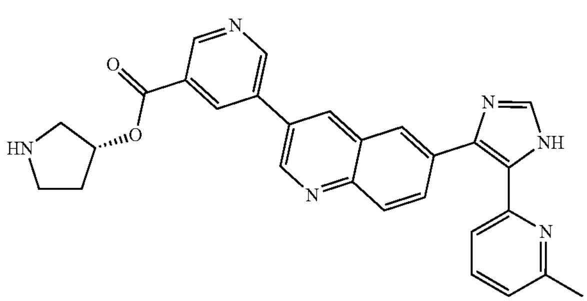 [SMILES: Cc1cccc(-c2[nH]cnc2-c2ccc3ncc(-c4cncc(C(=O)O[C@@H]5CCNC5)c4)cc3c2)n1] | [(3R)-pyrrolidin-3-yl] 5-[6-[5-(6-methyl-2-pyridyl)-1H-imidazol-4-yl]-3-quinolyl]pyridine-3-carboxylate | 477.0 |

TABLE 1-continued

| No. | Structure | Chemical Name | [M + H]+ |
|---|---|---|---|
| 726 | 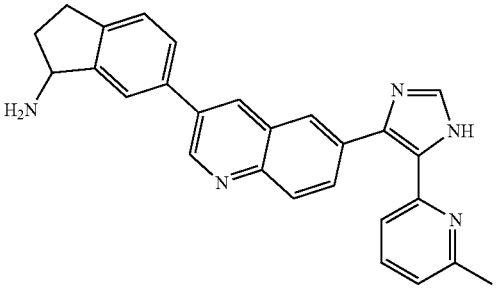 [SMILES: Cc1cccc(-c2[nH]cnc2-c2ccc3ncc(-c4ccc5c(c4)C(N)CC5)cc3c2)n1] | 6-[6-[5-(6-methyl-2-pyridyl)-1H-imidazol-4-yl]-3-quinolyl]indan-1-amine | 418.1 |
| 727 | 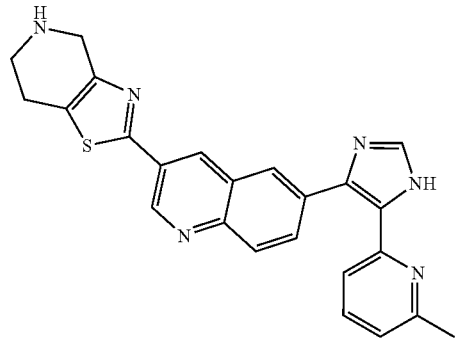 [SMILES: Cc1cccc(-c2[nH]cnc2-c2ccc3ncc(-c4nc5c(s4)CCNC5)cc3c2)n1] | 2-[6-[5-(6-methyl-2-pyridyl)-1H-imidazol-4-yl]-3-quinolyl]-4,5,6,7-tetrahydrothiazolo[4,5-c]pyridine | 425.1 |
| 728 | 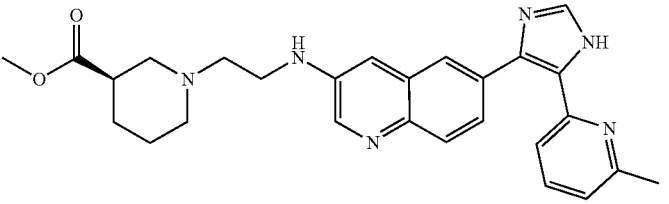 | methyl (3R)-1-[2-[[6-[5-(6-methyl-2-pyridyl)-1H-imidazol-4-yl]-3-quinolyl]amino]ethyl]piperidine-3-carboxylate | 471.2 |
| 729 | 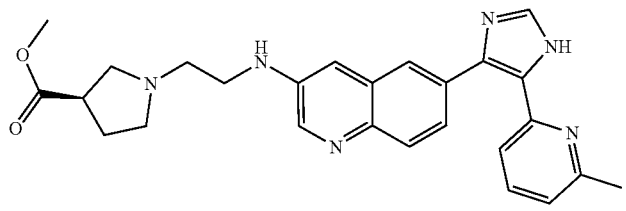 [SMILES: COC(=O)[C@@H]1CCN(CCNc2cnc3ccc(-c4nc[nH]c4-c4cccc(C)n4)cc3c2)C1] | methyl (3R)-1-[2-[[6-[5-(6-methyl-2-pyridyl)-1H-imidazol-4-yl]-3-quinolyl]amino]ethyl]pyrrolidine-3-carboxylate | 457.2 |
| 730 | 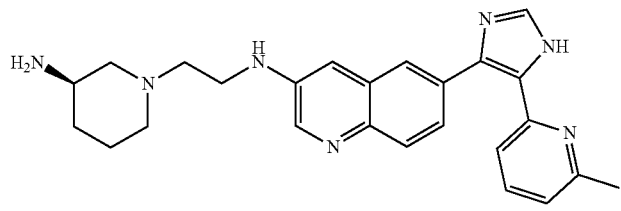 [SMILES: Cc1cccc(-c2[nH]cnc2-c2ccc3ncc(NCCN4CCC[C@@H](N)C4)cc3c2)n1] | N-[2-[(3R)-3-amino-1-piperidyl]ethyl]-6-[5-(6-methyl-2-pyridyl)-1H-imidazol-4-yl]quinolin-3-amine | 428.2 |

TABLE 1-continued

| No. | Structure | Chemical Name | [M + H]+ |
|---|---|---|---|
| 731 | 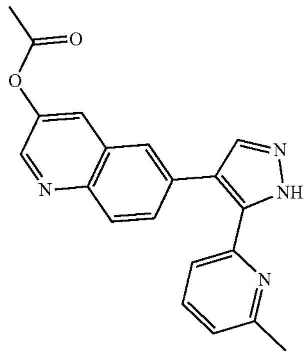 [SMILES: CC(=O)Oc1cnc2ccc(-c3cn[nH]c3-c3cccc(C)n3)cc2c1] | [6-[5-(6-methyl-2-pyridyl)-1H-pyrazol-4-yl]-3-quinolyl]acetate | 345.1 |
| 732 | 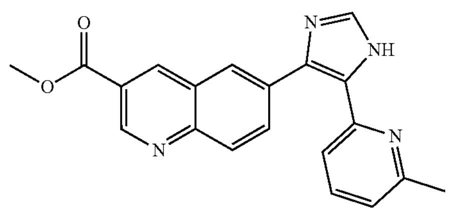 | methyl 6-[5-(6-methyl-2-pyridyl)-1H-imidazol-4-yl]quinoline-3-carboxylate | 345.0 |
| 733 | 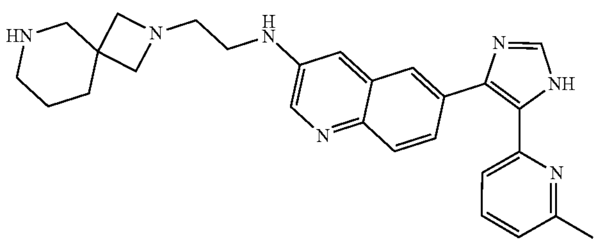 [SMILES: Cc1cccc(-c2[nH]cnc2-c2ccc3ncc(NCCN4CC5(CCCNC5)C4)cc3c2)n1] | N-[2-(2,8-diazaspiro[3.5]nonan-2-yl)ethyl]-6-[5-(6-methyl-2-pyridyl)-1H-imidazol-4-yl]quinolin-3-amine | 454.1 |
| 734 | 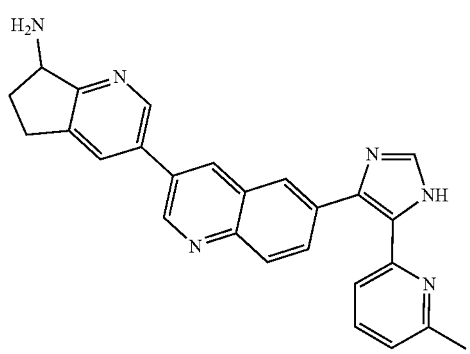 [SMILES: Cc1cccc(-c2[nH]cnc2-c2ccc3ncc(-c4cnc5c(c4)CCC5N)cc3c2)n1] | 3-[6-[5-(6-methyl-2-pyridyl)-1H-imidazol-4-yl]-3-quinolyl]-6,7-dihydro-5H-cyclopenta[b]pyridin-7-amine | 419.2 |
| 735 | 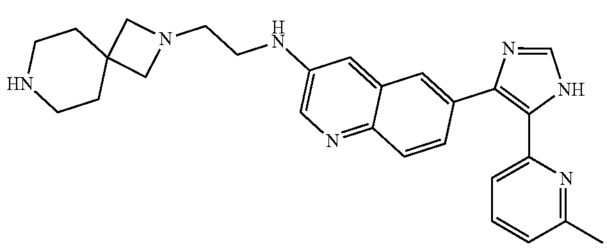 [SMILES: Cc1cccc(-c2[nH]cnc2-c2ccc3ncc(NCCN4CC5(CCNCC5)C4)cc3c2)n1] | N-[2-(2,7-diazaspiro[3.5]nonan-2-yl)ethyl]-6-[5-(6-methyl-2-pyridyl)-1H-imidazol-4-yl]quinolin-3-amine | 454.1 |

TABLE 1-continued

| No. | Structure | Chemical Name | [M + H]+ |
|---|---|---|---|
| 736 | 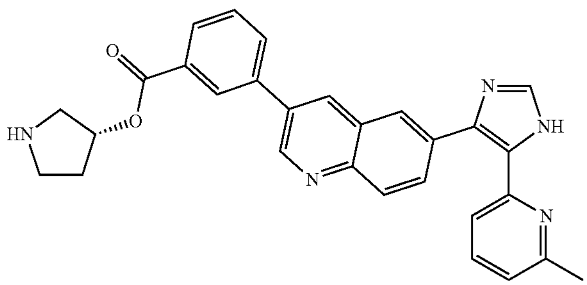 [SMILES: Cc1cccc(-c2[nH]cnc2-c2ccc3ncc(-c4cccc(C(=O)O[C@@H]5CCNC5)c4)cc3c2)n1] | [(3R)-pyrrolidin-3-yl] 3-[6-[5-(6-methyl-2-pyridyl)-1H-imidazol-4-yl]-3-quinolyl]benzoate | 476.0 |
| 737 | 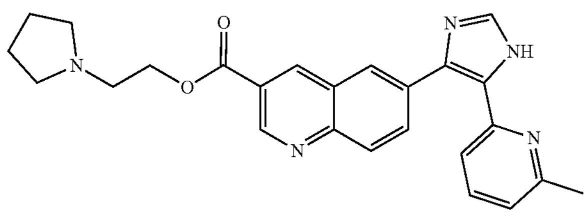 [SMILES: Cc1cccc(-c2[nH]cnc2-c2ccc3ncc(C(=O)OCCN4CCCC4)cc3c2)n1] | 2-pyrrolidin-1-ylethyl 6-[5-(6-methyl-2-pyridyl)-1H-imidazol-4-yl]quinoline-3-carboxylate | 428.2 |
| 738 | 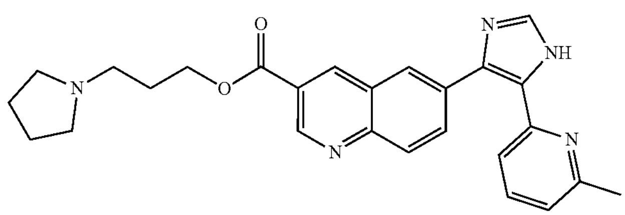 [SMILES: Cc1cccc(-c2[nH]cnc2-c2ccc3ncc(C(=O)OCCCN4CCCC4)cc3c2)n1] | 3-pyrrolidin-1-ylpropyl 6-[5-(6-methyl-2-pyridyl)-1H-imidazol-4-yl]quinoline-3-carboxylate | 442.1 |
| 739 | 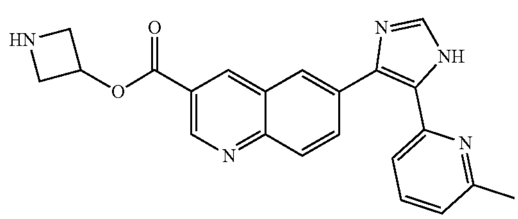 [SMILES: Cc1cccc(-c2[nH]cnc2-c2ccc3ncc(C(=O)OC4CNC4)cc3c2)n1] | azetidin-3-yl 6-[5-(6-methyl-2-pyridyl)-1H-imidazol-4-yl]quinoline-3-carboxylate | 386.2 |
| 740 | 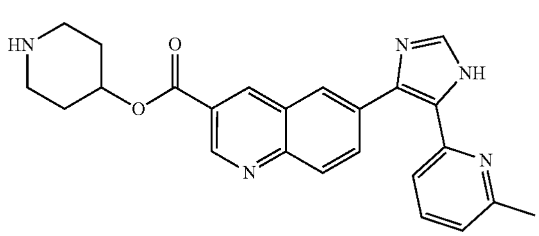 [SMILES: Cc1cccc(-c2[nH]cnc2-c2ccc3ncc(C(=O)OC4CCNCC4)cc3c2)n1] | 4-piperidyl 6-[5-(6-methyl-2-pyridyl)-1H-imidazol-4-yl]quinoline-3-carboxylate | 414.2 |
| 741 | 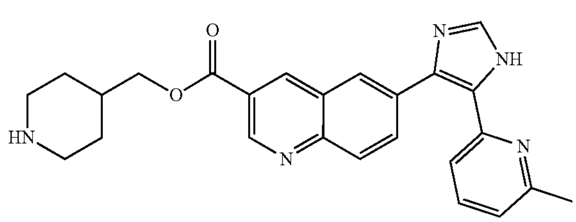 [SMILES: Cc1cccc(-c2[nH]cnc2-c2ccc3ncc(C(=O)OCC4CCNCC4)cc3c2)n1] | 4-piperidylmethyl 6-[5-(6-methyl-2-pyridyl)-1H-imidazol-4-yl]quinoline-3-carboxylate | 428.2 |

TABLE 1-continued

| No. | Structure | Chemical Name | [M + H]+ |
|---|---|---|---|
| 742 | 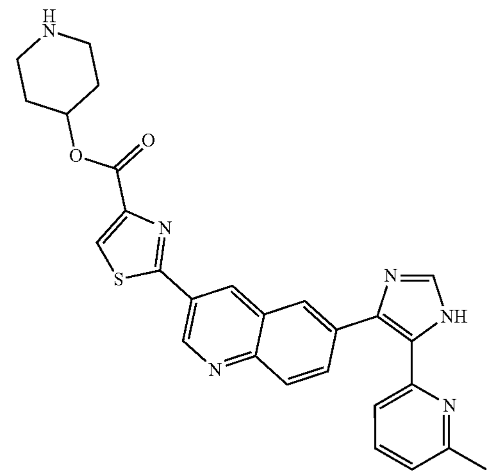 [SMILES: Cc1cccc(-c2[nH]cnc2-c2ccc3ncc(-c4nc(C(=O)OC5CCNCC5)cs4)cc3c2)n1] | 4-piperidyl 2-[6-[5-(6-methyl-2-pyridyl)-1H-imidazol-4-yl]-3-quinolyl]thiazole-4-carboxylate | 497.0 |
| 743 | 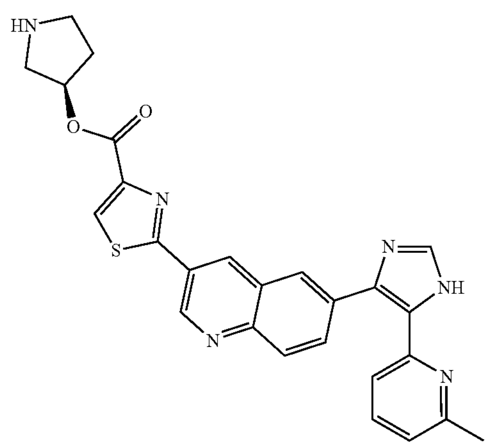 [SMILES: Cc1cccc(-c2[nH]cnc2-c2ccc3ncc(-c4nc(C(=O)O[C@@H]5CCNC5)cs4)cc3c2)n1] | [(3R)-pyrrolidin-3-yl]2-[6-[5-(6-methyl-2-pyridyl)-1H-imidazol-4-yl]-3-quinolyl]thiazole-4-carboxylate | 483.0 |
| 744 | 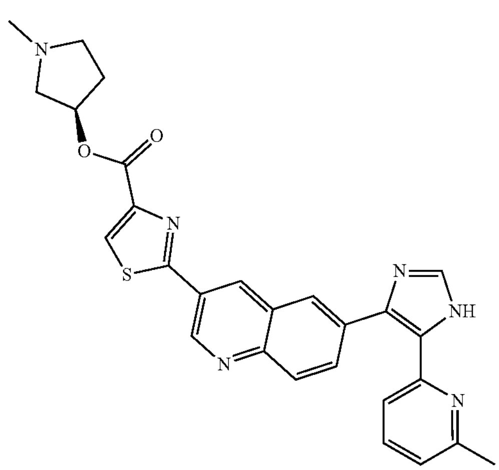 | [(3R)-1-methylpyrrolidin-3-yl] 2-[6-[5-(6-methyl-2-pyridyl)-1H-imidazol-4-yl]-3-quinolyl]thiazole-4-carboxylate | 497.0 |

TABLE 1-continued

| No. | Structure | Chemical Name | [M + H]+ |
|---|---|---|---|
| 745 | 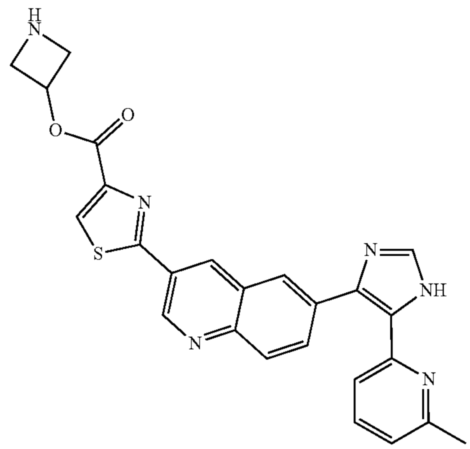 [SMILES: Cc1cccc(-c2[nH]cnc2-c2ccc3ncc(-c4nc(C(=O)OC5CNC5)cs4)cc3c2)n1] | azetidin-3-yl 2-[6-[5-(6-methyl-2-pyridyl)-1H-imidazol-4-yl]-3-quinolyl]thiazole-4-carboxylate | 469.0 |
| 746 | 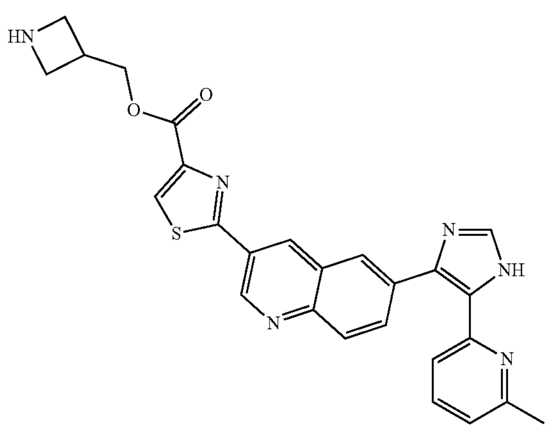 [SMILES: Cc1cccc(-c2[nH]cnc2-c2ccc3ncc(-c4nc(C(=O)OCC5CNC5)cs4)cc3c2)n1] | azetidin-3-ylmethyl 2-[6-[5-(6-methyl-2-pyridyl)-1H-imidazol-4-yl]-3-quinolyl]thiazole-4-carboxylate | 483.0 |
| 747 | 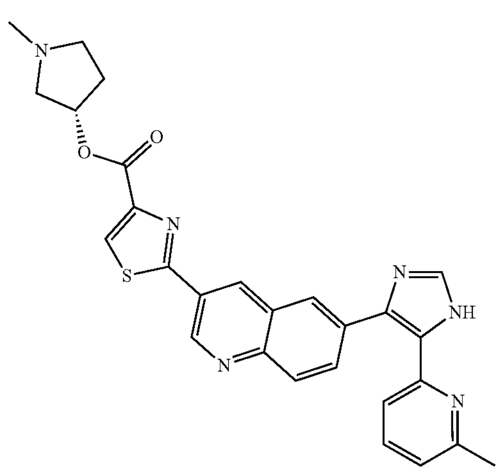 | [(3S)-1-methylpyrrolidin-3-yl] 2-[6-[5-(6-methyl-2-pyridyl)-1H-imidazol-4-yl]-3-quinolyl]thiazole-4-carboxylate | 497.0 |

TABLE 1-continued

| No. | Structure | Chemical Name | [M + H]+ |
|---|---|---|---|
| 748 | 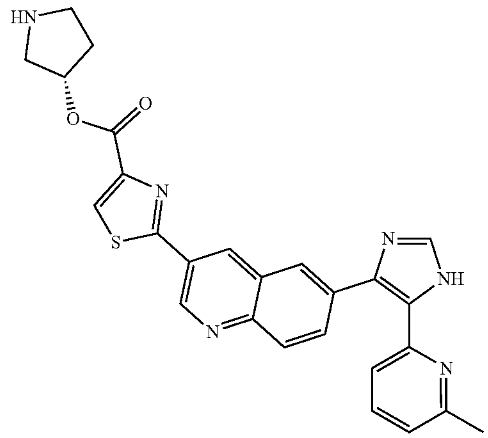 [SMILES: Cc1cccc(-c2[nH]cnc2-c2ccc3ncc(-c4nc(C(=O)O[C@H]5CCNC5)cs4)cc3c2)n1] | [(3S)-pyrrolidin-3-yl] 2-[6-[5-(6-methyl-2-pyridyl)-1H-imidazol-4-yl]-3-quinolyl]thiazole-4-carboxylate | 483.0 |
| 749 | 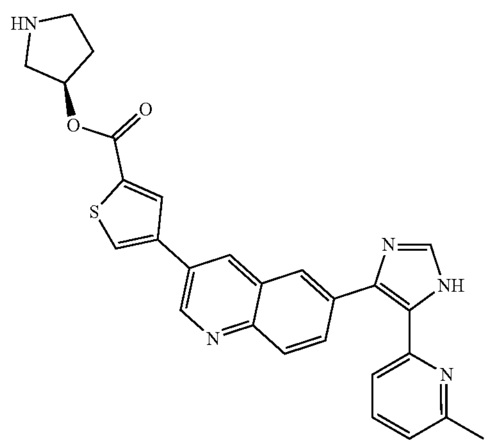 [SMILES: Cc1cccc(-c2[nH]cnc2-c2ccc3ncc(-c4csc(C(=O)O[C@@H]5CCNC5)c4)cc3c2)n1] | [(3R)-pyrrolidin-3-yl] 4-[6-[5-(6-methyl-2-pyridyl)-1H-imidazol-4-yl]-3-quinolyl]thiophene-2-carboxylate | 482.0 |
| 750 | 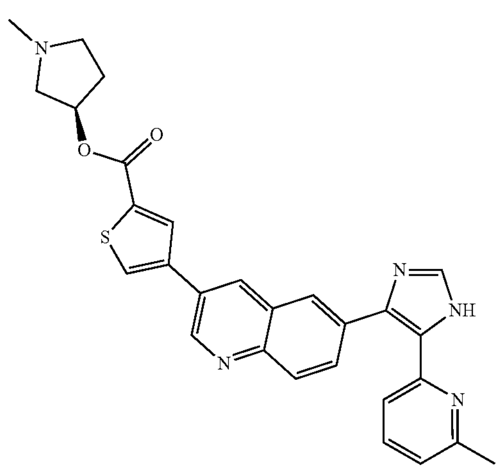 | [(3R)-1-methylpyrrolidin-3-yl] 4-[6-[5-(6-methyl-2-pyridyl)-1H-imidazol-4-yl]-3-quinolyl]thiophene-2-carboxylate | 496.0 |

TABLE 1-continued

| No. | Structure | Chemical Name | [M + H]⁺ |
|---|---|---|---|
| 751 | 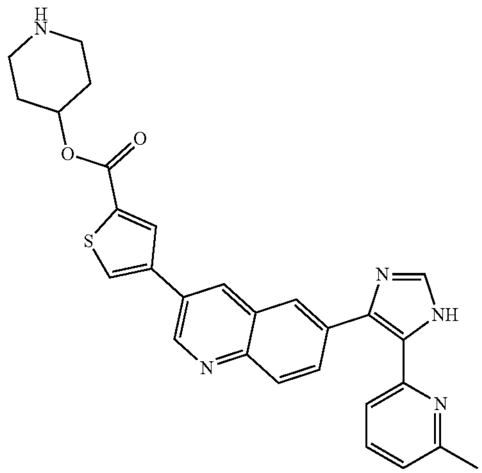 [SMILES: Cc1cccc(-c2[nH]cnc2-c2ccc3ncc(-c4csc(C(=O)OC5CCNCC5)c4)cc3c2)n1] | 4-piperidyl 4-[6-[5-(6-methyl-2-pyridyl)-1H-imidazol-4-yl]-3-quinolyl]thiophene-2-carboxylate | 496.0 |
| 752 | 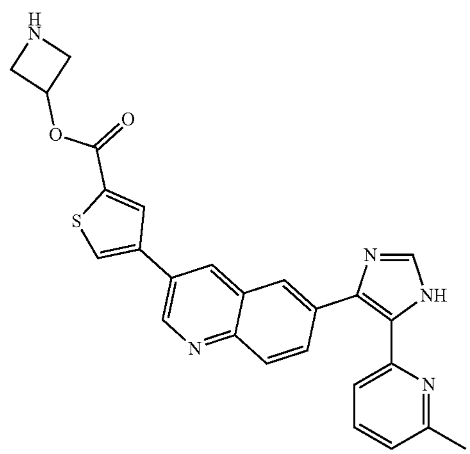 [SMILES: Cc1cccc(-c2[nH]cnc2-c2ccc3ncc(-c4csc(C(=O)OC5CNC5)c4)cc3c2)n1] | azetidin-3-yl 4-[6-[5-(6-methyl-2-pyridyl)-1H-imidazol-4-yl]-3-quinolyl]thiophene-2-carboxylate | 468.0 |
| 753 | 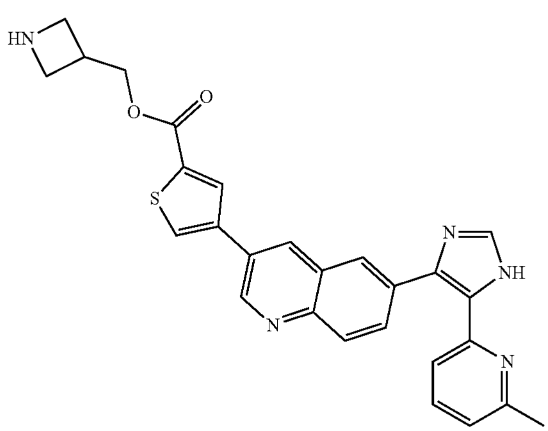 [SMILES: Cc1cccc(-c2[nH]cnc2-c2ccc3ncc(-c4csc(C(=O)OCC5CNC5)c4)cc3c2)n1] | azetidin-3-ylmethyl 4-[6-[5-(6-methyl-2-pyridyl)-1H-imidazol-4-yl]-3-quinolyl]thiophene-2-carboxylate | 482.1 |

TABLE 1-continued

| No. | Structure | Chemical Name | [M + H]+ |
|---|---|---|---|
| 754 | 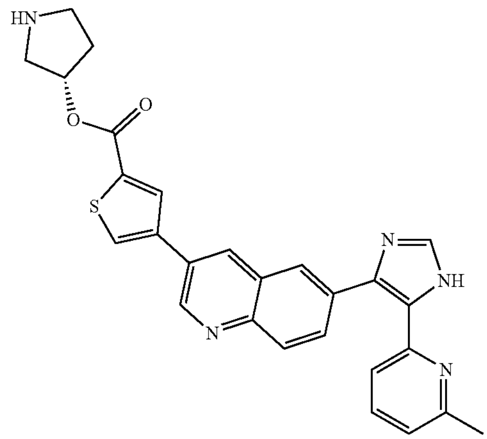 [SMILES: Cc1cccc(-c2[nH]cnc2-c2ccc3ncc(-c4csc(C(=O)O[C@H]5CCNC5)c4)cc3c2)n1] | [(3S)-pyrrolidin-3-yl] 4-[6-[5-(6-methyl-2-pyridyl)-1H-imidazol-4-yl]-3-quinolyl]thiophene-2-carboxylate | 482.0 |
| 755 | 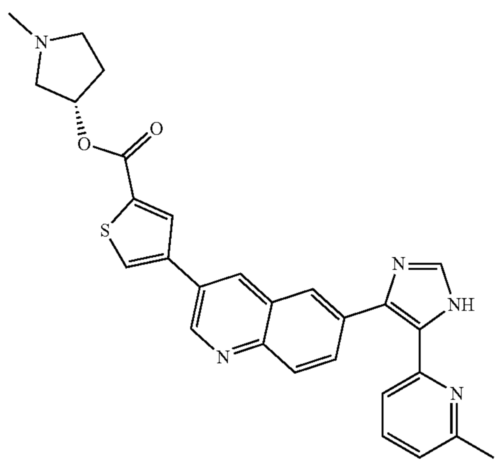 | [(3S)-1-methylpyrrolidin-3-yl] 4-[6-[5-(6-methyl-2-pyridyl)-1H-imidazol-4-yl]-3-quinolyl]thiophene-2-carboxylate | 496.0 |
| 756 | 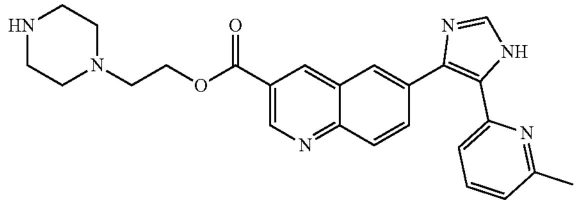 [SMILES: Cc1cccc(-c2[nH]cnc2-c2ccc3ncc(C(=O)OCCN4CCNCC4)cc3c2)n1] | 2-piperazin-1-ylethyl 6-[5-(6-methyl-2-pyridyl)-1H-imidazol-4-yl]quinoline-3-carboxylate | 443.1 |
| 757 | 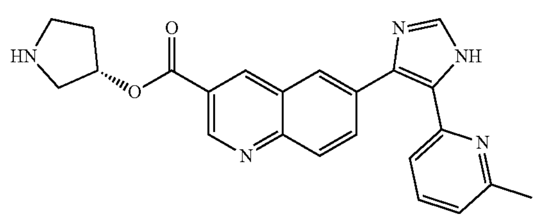 [SMILES: Cc1cccc(-c2[nH]cnc2-c2ccc3ncc(C(=O)O[C@H]4CCNC4)cc3c2)n1] | [(3S)-pyrrolidin-3-yl] 6-[5-(6-methyl-2-pyridyl)-1H-imidazol-4-yl]quinoline-3-carboxylate | 400.1 |
| 758 | 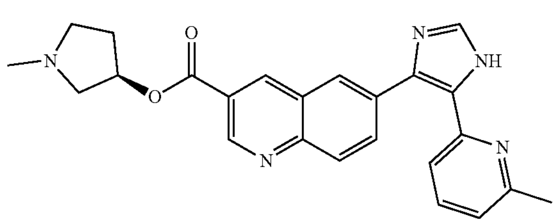 | [(3R)-1-methylpyrrolidin-3-yl] 6-[5-(6-methyl-2-pyridyl)-1H-imidazol-4-yl]quinoline-3-carboxylate | 414.2 |

TABLE 1-continued

| No. | Structure | Chemical Name | [M + H]+ |
|---|---|---|---|
| 759 | 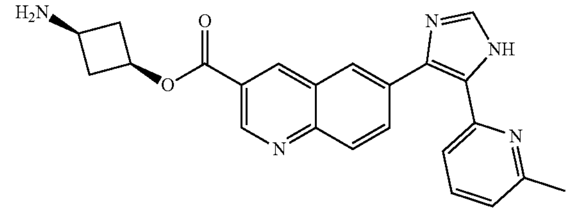 [SMILES: Cc1cccc(-c2[nH]cnc2-c2ccc3ncc(C(=O)O[C@H]4C[C@@H](N)C4)cc3c2)n1] | (3-aminocyclobutyl) 6-[5-(6-methyl-2-pyridyl)-1H-imidazol-4-yl]quinoline-3-carboxylate | 400.1 |
| 760 | 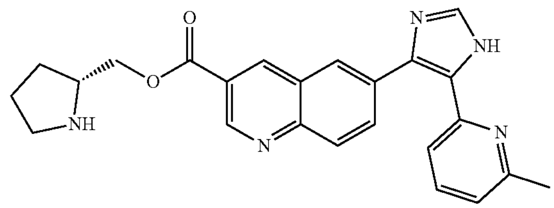 [SMILES: Cc1cccc(-c2[nH]cnc2-c2ccc3ncc(C(=O)OC[C@H]4CCCN4)cc3c2)n1] | [(2R)-pyrrolidin-2-yl]methyl 6-[5-(6-methyl-2-pyridyl)-1H-imidazol-4-yl]quinoline-3-carboxylate | 414.1 |
| 761 | 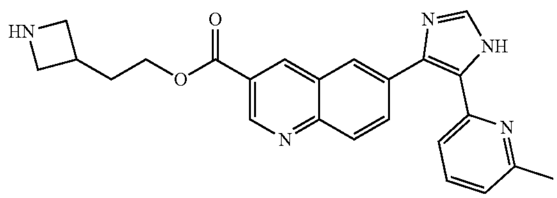 [SMILES: Cc1cccc(-c2[nH]cnc2-c2ccc3ncc(C(=O)OCCC4CNC4)cc3c2)n1] | 2-(azetidin-3-yl)ethyl 6-[5-(6-methyl-2-pyridyl)-1H-imidazol-4-yl]quinoline-3-carboxylate | 414.1 |
| 762 | 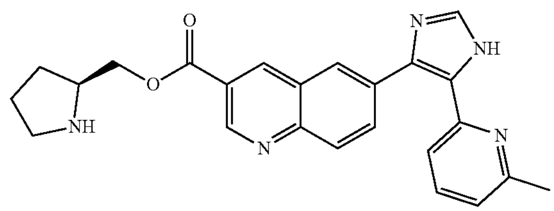 [SMILES: Cc1cccc(-c2[nH]cnc2-c2ccc3ncc(C(=O)OC[C@@H]4CCCN4)cc3c2)n1] | [(2S)-pyrrolidin-2-yl]methyl 6-[5-(6-methyl-2-pyridyl)-1H-imidazol-4-yl]quinoline-3-carboxylate | 414.1 |
| 763 | 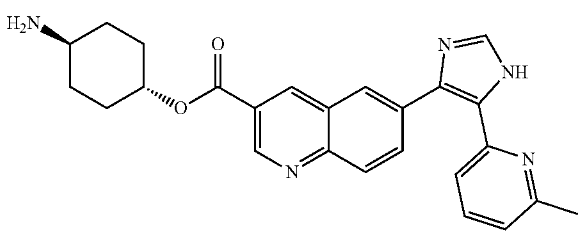 [SMILES: Cc1cccc(-c2[nH]cnc2-c2ccc3ncc(C(=O)O[C@H]4CC[C@H](N)CC4)cc3c2)n1] | (4-aminocyclohexyl) 6-[5-(6-methyl-2-pyridyl)-1H-imidazol-4-yl]quinoline-3-carboxylate | 428.1 |
| 764 | 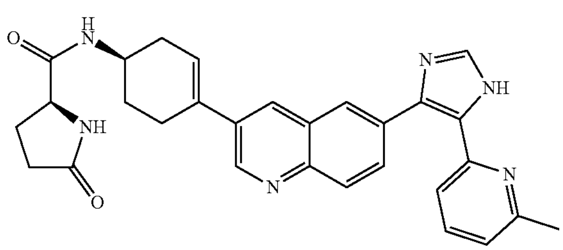 [SMILES: Cc1cccc(-c2[nH]cnc2-c2ccc3ncc(C4=CC[C@H](NC(=O)[C@@H]5CCC(=O)N5)CC4)cc3c2)n1] | (2S)-N-[(1R)-4-[6-[5-(6-methyl-2-pyridyl)-1H-imidazol-4-yl]-3-quinolyl]cyclohex-3-en-1-yl]-5-oxo-pyrrolidine-2-carboxamide | 493.1 |
| 765 | 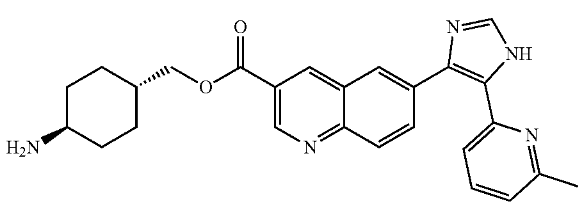 [SMILES: Cc1cccc(-c2[nH]cnc2-c2ccc3ncc(C(=O)OC[C@H]4CC[C@H](N)CC4)cc3c2)n1] | (4-aminocyclohexyl)methyl 6-[5-(6-methyl-2-pyridyl)-1H-imidazol-4-yl]quinoline-3-carboxylate | 442.2 |

TABLE 1-continued

| No. | Structure | Chemical Name | [M + H]+ |
|---|---|---|---|
| 766 | AND Enantiomer | [rac-(1R,3R)-3-aminocyclopentyl] 6-[5-(6-methyl-2-pyridyl)-1H-imidazol-4-yl]quinoline-3-carboxylate | 414.1 |
| 767 | AND Enantiomer | [rac-(1R,3S)-3-aminocyclohexyl]methyl 6-[5-(6-methyl-2-pyridyl)-1H-imidazol-4-yl]quinoline-3-carboxylate | 442.1 |
| 768 | 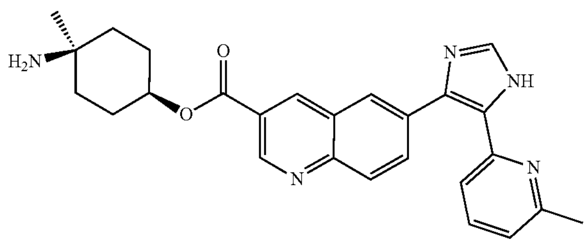 [SMILES: Cc1cccc(-c2[nH]cnc2-c2ccc3ncc(C(=O)O[C@H]4CC[C@@](C)(N)CC4)cc3c2)n1] | (4-amino-4-methyl-cyclohexyl) 6-[5-(6-methyl-2-pyridyl)-1H-imidazol-4-yl]quinoline-3-carboxylate | 442.2 |
| 769 | AND Enantiomer | [rac-(1S,3S)-3-aminocyclohexyl]methyl 6-[5-(6-methyl-2-pyridyl)-1H-imidazol-4-yl]quinoline-3-carboxylate | 442.1 |
| 770 | 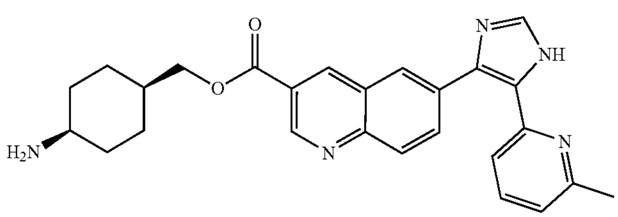 [SMILES: Cc1cccc(-c2[nH]cnc2-c2ccc3ncc(C(=O)OC[C@H]4CC[C@@H](N)CC4)cc3c2)n1] | (4-aminocyclohexyl)methyl 6-[5-(6-methyl-2-pyridyl)-1H-imidazol-4-yl]quinoline-3-carboxylate | 442.2 |
| 771 | 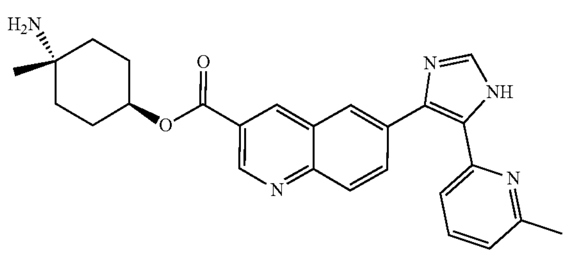 | (4-amino-4-methyl-cyclohexyl) 6-[5-(6-methyl-2-pyridyl)-1H-imidazol-4-yl]quinoline-3-carboxylate | 442.2 |

TABLE 1-continued

| No. | Structure | Chemical Name | [M + H]+ |
|---|---|---|---|
| 772 | 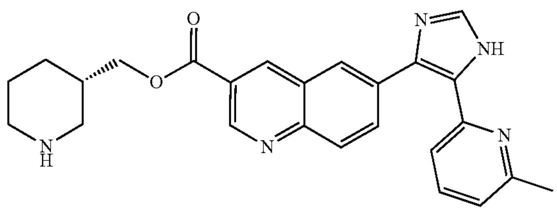 [SMILES: Cc1cccc(-c2[nH]cnc2-c2ccc3ncc(C(=O)OC[C@H]4CCCNC4)cc3c2)n1] | [(3S)-3-piperidyl]methyl 6-[5-(6-methyl-2-pyridyl)-1H-imidazol-4-yl]quinoline-3-carboxylate | 428.1 |
| 773 | 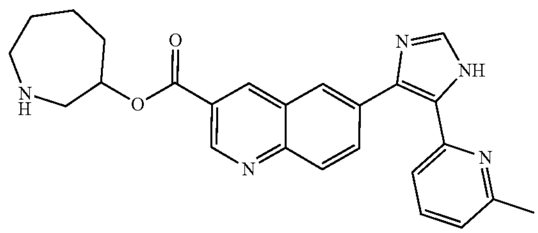 | azepan-3-yl 6-[5-(6-methyl-2-pyridyl)-1H-imidazol-4-yl]quinoline-3-carboxylate | 428.1 |
| 774 | AND Enantiomer | [rac-(1S,3S)-3-aminocyclohexyl] 6-[5-(6-methyl-2-pyridyl)-1H-imidazol-4-yl]quinoline-3-carboxylate | 428.0 |
| 775 | 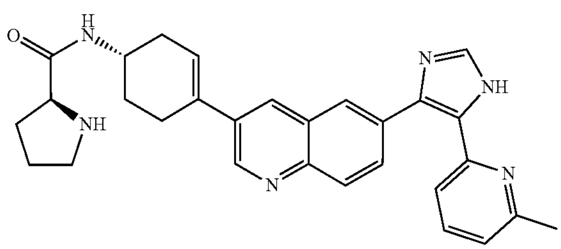 [SMILES: Cc1cccc(-c2[nH]cnc2-c2ccc3ncc(C4=CC[C@@H](NC(=O)[C@@H]5CCCN5)CC4)cc3c2)n1] | (2S)-N-[(1S)-4-[6-[5-(6-methyl-2-pyridyl)-1H-imidazol-4-yl]-3-quinolyl]cyclohex-3-en-1-yl]pyrrolidine-2-carboxamide | 479.2 |
| 776 | 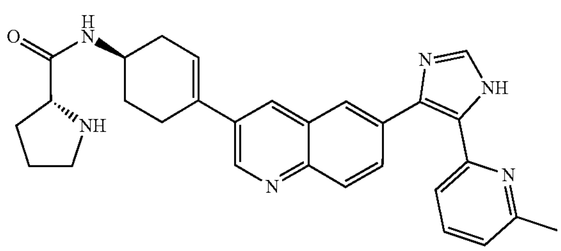 [SMILES: Cc1cccc(-c2[nH]cnc2-c2ccc3ncc(C4=CC[C@H](NC(=O)[C@H]5CCCN5)CC4)cc3c2)n1] | (2R)-N-[(1R)-4-[6-[5-(6-methyl-2-pyridyl)-1H-imidazol-4-yl]-3-quinolyl]cyclohex-3-en-1-yl]pyrrolidine-2-carboxamide | 479.2 |
| 777 | 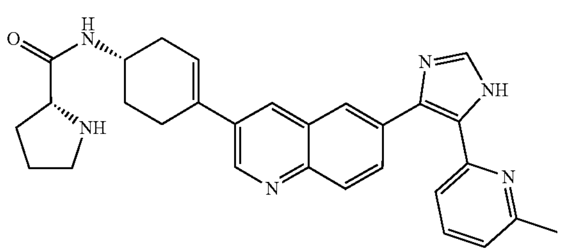 [SMILES: Cc1cccc(-c2[nH]cnc2-c2ccc3ncc(C4=CC[C@@H](NC(=O)[C@H]5CCCN5)CC4)cc3c2)n1] | (2R)-N-[(1S)-4-[6-[5-(6-methyl-2-pyridyl)-1H-imidazol-4-yl]-3-quinolyl]cyclohex-3-en-1-yl]pyrrolidine-2-carboxamide | 479.2 |

TABLE 1-continued

| No. | Structure | Chemical Name | [M + H]+ |
|---|---|---|---|
| 778 | 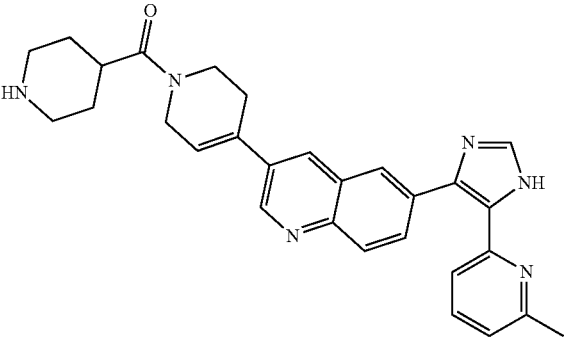 [SMILES: Cc1cccc(-c2[nH]cnc2-c2ccc3ncc(C4=CCN(C(=O)C5CCNCC5)CC4)cc3c2)n1] | [4-[6-[5-(6-methyl-2-pyridyl)-1H-imidazol-4-yl]-3-quinolyl]-3,6-dihydro-2H-pyridin-1-yl]-(4-piperidyl)methanone | 479.2 |
| 779 | 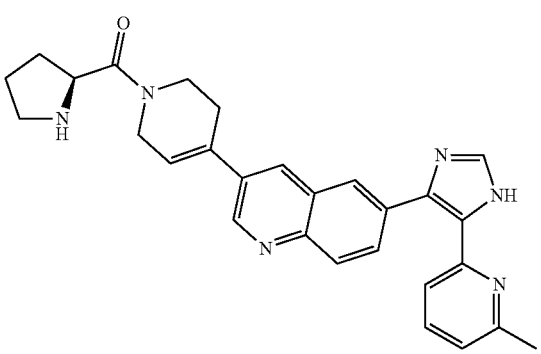 | [4-[6-[5-(6-methyl-2-pyridyl)-1H-imidazol-4-yl]-3-quinolyl]-3,6-dihydro-2H-pyridin-1-yl]-[(2S)-pyrrolidin-2-yl]methanone | 465.1 |
| 780 | 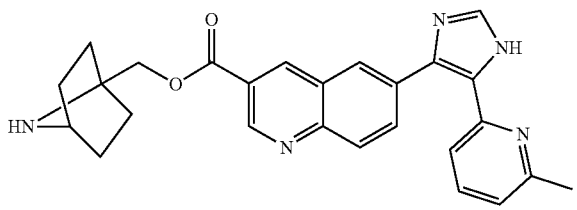 [SMILES: Cc1cccc(-c2[nH]cnc2-c2ccc3ncc(C(=O)OCC45CCC(CC4)NC5)cc3c2)n1] | 7-azabicyclo[2.2.1]heptan-1-ylmethyl 6-[5-(6-methyl-2-pyridyl)-1H-imidazol-4-yl]quinoline-3-carboxylate | 440.1 |
| 781 | 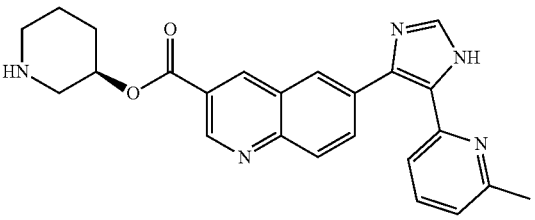 | [(3R)-3-piperidyl] 6-[5-(6-methyl-2-pyridyl)-1H-imidazol-4-yl]quinoline-3-carboxylate | 414.1 |
| 782 | 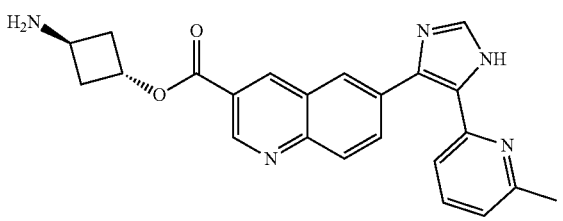 [SMILES: Cc1cccc(-c2[nH]cnc2-c2ccc3ncc(C(=O)O[C@H]4C[C@H](N)C4)cc3c2)n1] | (3-aminocyclobutyl) 6-[5-(6-methyl-2-pyridyl)-1H-imidazol-4-yl]quinoline-3-carboxylate | 400.0 |
| 783 | 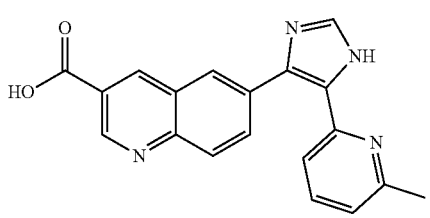 [SMILES: Cc1cccc(-c2[nH]cnc2-c2ccc3ncc(C(=O)O)cc3c2)n1] | 6-[5-(6-methyl-2-pyridyl)-1H-pyrazol-4-yl]quinoline-3-carboxylic acid | 331.0 |

TABLE 1-continued

| No. | Chemical Name | [M + H]+ |
|---|---|---|
| 784 | methyl 6-[5-(6-methyl-2-pyridyl)-1H-pyrazol-4-yl]quinoline-3-carboxylate | 345.0 |
| 785 | [(2R)-pyrrolidin-2-yl]methyl 6-[5-(6-methyl-2-pyridyl)-1H-pyrazol-4-yl]quinoline-3-carboxylate | 414.0 |
| 786 | 4-piperidyl 6-[5-(6-methyl-2-pyridyl)-1H-pyrazol-4-yl]quinoline-3-carboxylate | 414.1 |
| 787 | 3-pyrrolidin-1-ylpropyl 6-[5-(6-methyl-2-pyridyl)-1H-pyrazol-4-yl]quinoline-3-carboxylate | 442.0 |
| 788 | 4-pyrrolidin-1-ylbutyl 6-[5-(6-methyl-2-pyridyl)-1H-pyrazol-4-yl]quinoline-3-carboxylate | 456.2 |
| 789 | azetidin-3-yl 6-[5-(6-methyl-2-pyridyl)-1H-pyrazol-4-yl]quinoline-3-carboxylate | 386.0 |
| 790 | azetidin-3-ylmethyl 6-[5-(6-methyl-2-pyridyl)-1H-pyrazol-4-yl]quinoline-3-carboxylate | 400.0 |

TABLE 1-continued

| No. | Structure | Chemical Name | [M + H]+ |
|---|---|---|---|
| 791 | 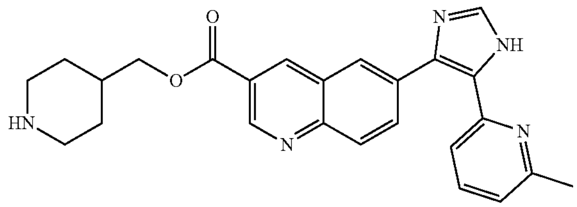 [SMILES: Cc1cccc(-c2[nH]cnc2-c2ccc3ncc(C(=O)OCC4CCNCC4)cc3c2)n1] | 4-piperidylmethyl 6-[5-(6-methyl-2-pyridyl)-1H-pyrazol-4-yl]quinoline-3-carboxylate | 428.1 |
| 792 | 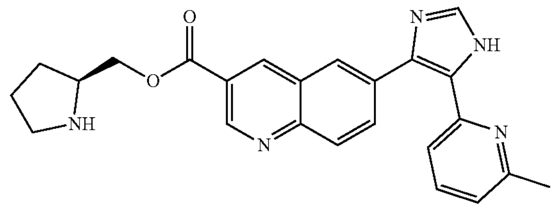 [SMILES: Cc1cccc(-c2[nH]cnc2-c2ccc3ncc(C(=O)OC[C@@H]4CCCN4)cc3c2)n1] | [(2S)-pyrrolidin-2-yl]methyl 6-[5-(6-methyl-2-pyridyl)-1H-pyrazol-4-yl]quinoline-3-carboxylate | 414.1 |
| 793 | 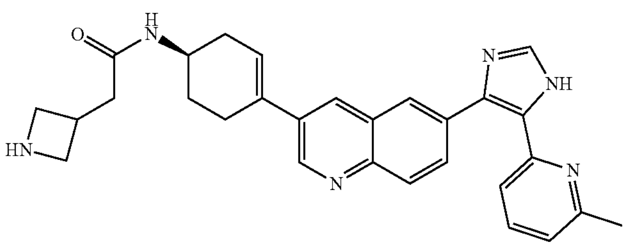 [SMILES: Cc1cccc(-c2[nH]cnc2-c2ccc3ncc(C4=CC[C@H](NC(=O)CC5CNC5)CC4)cc3c2)n1] | 2-(azetidin-3-yl)-N-[rac-(1R)-4-[6-[5-(6-methyl-2-pyridyl)-1H-imidazol-4-yl]-3-quinolyl]cyclohex-3-en-1-yl]acetamide | 479.1 |
| 794 | 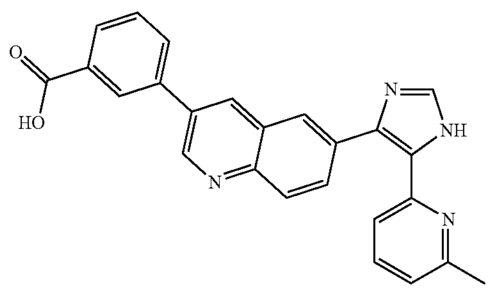 [SMILES: Cc1cccc(-c2[nH]cnc2-c2ccc3ncc(-c4cccc(C(=O)O)c4)cc3c2)n1] | 3-[6-[5-(6-methyl-2-pyridyl)-1H-imidazol-4-yl]-3-quinolyl]benzoic acid | 407.1 |
| 795 | 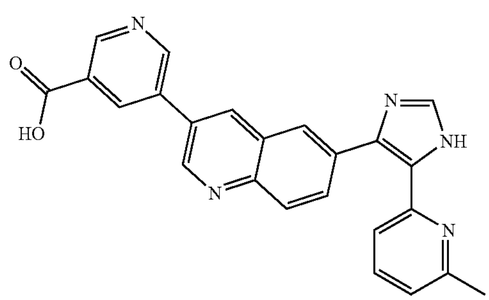 [SMILES: Cc1cccc(-c2[nH]cnc2-c2ccc3ncc(-c4cncc(C(=O)O)c4)cc3c2)n1] | 5-[6-[5-(6-methyl-2-pyridyl)-1H-imidazol-4-yl]-3-quinolyl]pyridine-3-carboxylic acid | 408.1 |
| 796 | 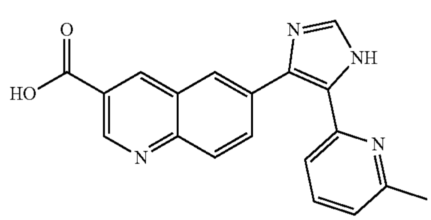 [SMILES: Cc1cccc(-c2[nH]cnc2-c2ccc3ncc(C(=O)O)cc3c2)n1] | 6-[5-(6-methyl-2-pyridyl)-1H-imidazol-4-yl]quinoline-3-carboxylic acid | 331.0 |

TABLE 1-continued

| No. | Structure | Chemical Name | [M + H]⁺ |
|---|---|---|---|
| 797 | 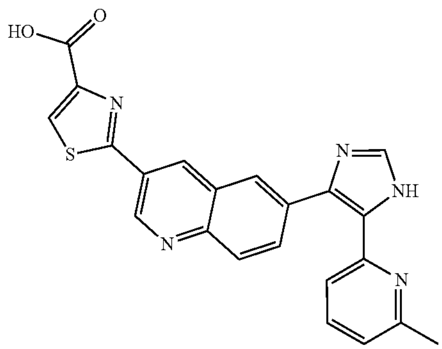 [SMILES: Cc1cccc(-c2[nH]cnc2-c2ccc3ncc(-c4nc(C(=O)O)cs4)cc3c2)n1] | 2-[6-[5-(6-methyl-2-pyridyl)-1H-imidazol-4-yl]-3-quinolyl]thiazole-4-carboxylic acid | 414.1 |
| 798 | 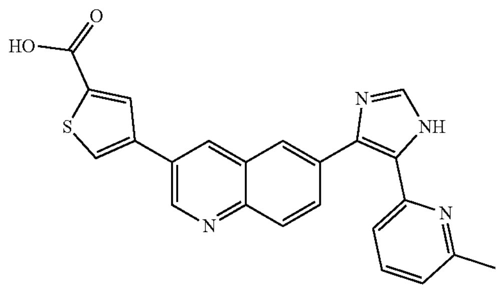 [SMILES: Cc1cccc(-c2[nH]cnc2-c2ccc3ncc(-c4csc(C(=O)O)c4)cc3c2)n1] | 4-[6-[5-(6-methyl-2-pyridyl)-1H-imidazol-4-yl]-3-quinolyl]thiophene-2-carboxylic acid | 413.1 |
| 799 | 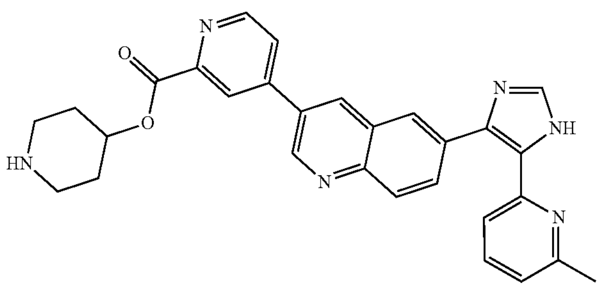 [SMILES: Cc1cccc(-c2[nH]cnc2-c2ccc3ncc(-c4ccnc(C(=O)OC5CCNCC5)c4)cc3c2)n1] | 4-piperidyl 4-[6-[5-(6-methyl-2-pyridyl)-1H-imidazol-4-yl]-3-quinolyl]pyridine-2-carboxylate | 491.1 |
| 800 | 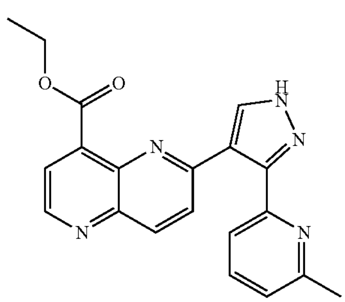 | ethyl 6-[3-(6-methyl-2-pyridyl)-1H-pyrazol-4-yl]-1,5-naphthyridine-4-carboxylate | 360.0 |
| 801 | 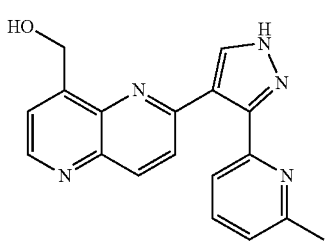 | [6-[3-(6-methyl-2-pyridyl)-1H-pyrazol-4-yl]-1,5-naphthyridin-4-yl]methanol | 318.2 |

TABLE 1-continued

| No. | Structure | Chemical Name | [M + H]+ |
|---|---|---|---|
| 802 | 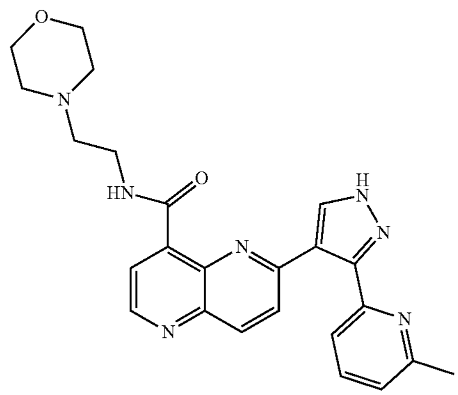 | 6-[3-(6-methyl-2-pyridyl)-1H-pyrazol-4-yl]-N-(2-morpholinoethyl)-1,5-naphthyridine-4-carboxamide | 444.2 |
| 803 | 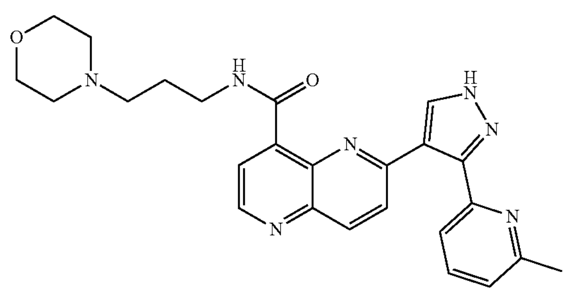 | 6-[3-(6-methyl-2-pyridyl)-1H-pyrazol-4-yl]-N-(3-morpholinopropyl)-1,5-naphthyridine-4-carboxamide | 458.2 |
| 804 | AND Enantiomer | rac-(2S)-6-[[6-[3-(6-methyl-2-pyridyl)-1H-pyrazol-4-yl]-1,5-naphthyridine-4-carbonyl]amino]-2-[[rac-(2R)-2-aminopropanoyl]amino]hexanoic acid | 531.3 |
| 805 | AND Enantiomer | rac-(2S)-2-[(2-aminoacetyl)amino]-6-[[6-[3-(6-methyl-2-pyridyl)-1H-pyrazol-4-yl]-1,5-naphthyridine-4-carbonyl]amino]hexanoic acid | 517.2 |

TABLE 1-continued

| No. | Structure | Chemical Name | [M + H]+ |
|---|---|---|---|
| 806 | 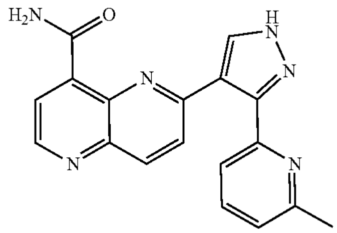 | 6-[3-(6-methyl-2-pyridyl)-1H-pyrazol-4-yl]-1,5-naphthyridine-4-carboxamide | 331.1 |
| 807 | 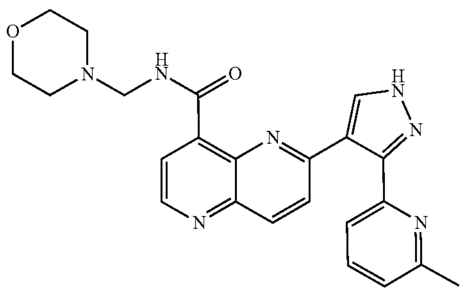 | 6-[3-(6-methyl-2-pyridyl)-1H-pyrazol-4-yl]-N-(morpholinomethyl)-1,5-naphthyridine-4-carboxamide | 430.3 |
| 808 | 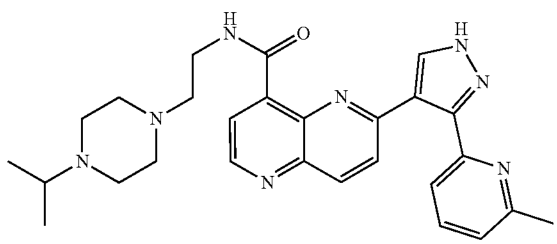 | N-[2-(4-isopropylpiperazin-1-yl)ethyl]-6-[3-(6-methyl-2-pyridyl)-1H-pyrazol-4-yl]-1,5-naphthyridine-4-carboxamide | 485.2 |
| 809 | 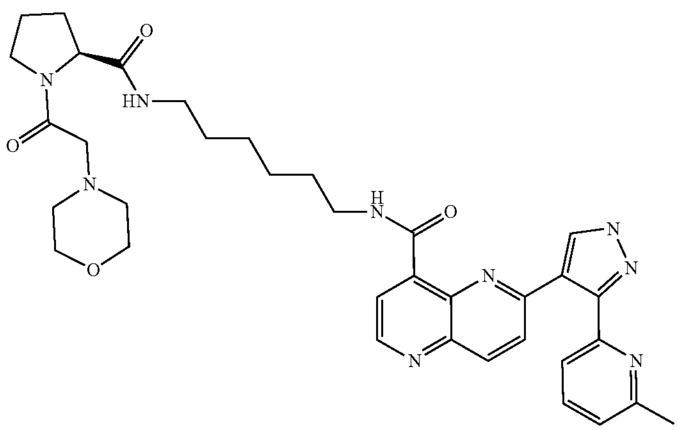 [SMILES: Cc1cccc(-c2n[nH]cc2-c2ccc3nccc(C(=O)NCCCCCCNC(=O)[C@@H]4CCCN4C(=O)CN4CCOCC4)c3n2)n1] | 6-[3-(6-methyl-2-pyridyl)-1H-pyrazol-4-yl]-N-[6-[[rac-(2S)-1-(2-morpholinoacetyl)pyrrolidine-2-carbonyl]amino]hexyl]-1,5-naphthyridine-4-carboxamide | 654.3 |
| 810 | 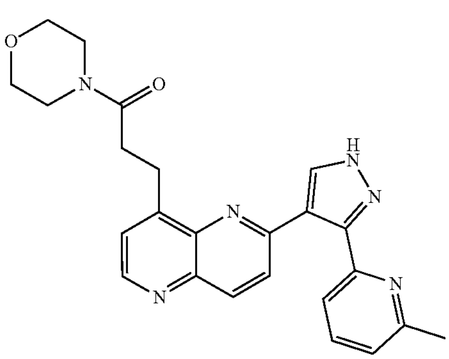 | 3-[6-[3-(6-methyl-2-pyridyl)-1H-pyrazol-4-yl]-1,5-naphthyridin-4-yl]-1-morpholino-propan-1-one | 429.3 |

TABLE 1-continued

| No. | Structure | Chemical Name | [M + H]⁺ |
|---|---|---|---|
| 811 | 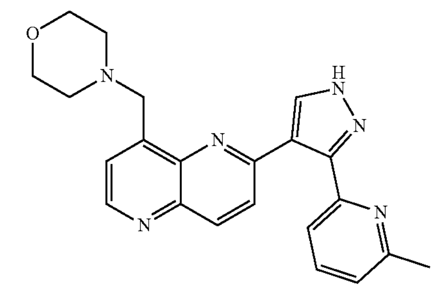 | 4-[[6-[3-(6-methyl-2-pyridyl)-1H-pyrazol-4-yl]-1,5-naphthyridin-4-yl]methyl]morpholine | 387.1 |
| 812 | 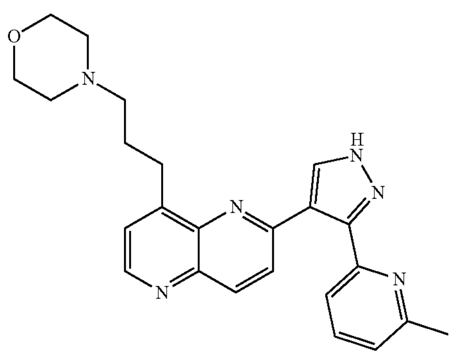 | 4-[3-[6-[3-(6-methyl-2-pyridyl)-1H-pyrazol-4-yl]-1,5-naphthyridin-4-yl]propyl]morpholine | 415.1 |
| 814 | 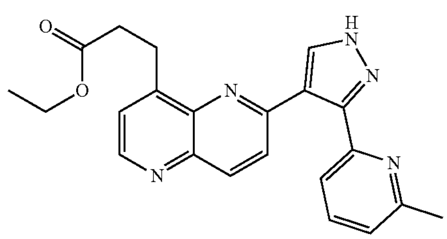 | ethyl 3-[6-[3-(6-methyl-2-pyridyl)-1H-pyrazol-4-yl]-1,5-naphthyridin-4-yl]propanoate | 388.1 |
| 815 | 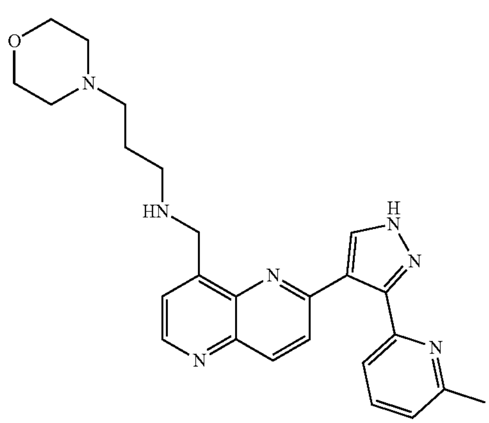 | N-[[6-[3-(6-methyl-2-pyridyl)-1H-pyrazol-4-yl]-1,5-naphthyridin-4-yl]methyl]-3-morpholino-propan-1-amine | 444.2 |

TABLE 1-continued

| No. | Structure | Chemical Name | [M + H]+ |
|---|---|---|---|
| 816 | 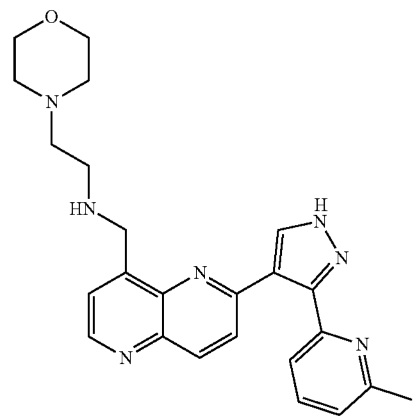 | N-[[6-[3-(6-methyl-2-pyridyl)-1H-pyrazol-4-yl]-1,5-naphthyridin-4-yl]methyl]-2-morpholino-ethanamine | 430.2 |
| 817 | 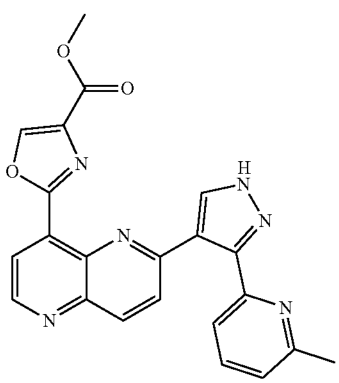 | methyl 2-[6-[3-(6-methyl-2-pyridyl)-1H-pyrazol-4-yl]-1,5-naphthyridin-4-yl]oxazole-4-carboxylate | 413.1 |
| 818 | 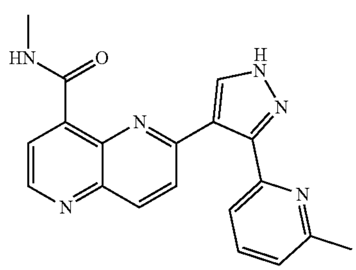 | N-methyl-6-[5-(6-methyl-2-pyridyl)-1H-pyrazol-4-yl]-1,5-naphthyridine-4-carboxamide | 344.9 |
| 819 | 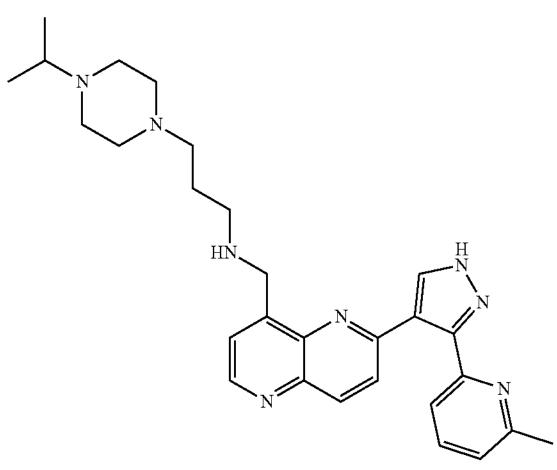 | 3-(4-isopropylpiperazin-1-yl)-N-[[6-[3-(6-methyl-2-pyridyl)-1H-pyrazol-4-yl]-1,5-naphthyridin-4-yl]methyl]propan-1-amine | 484.8 |

TABLE 1-continued

| No. | Structure | Chemical Name | [M + H]+ |
|---|---|---|---|
| 820 | 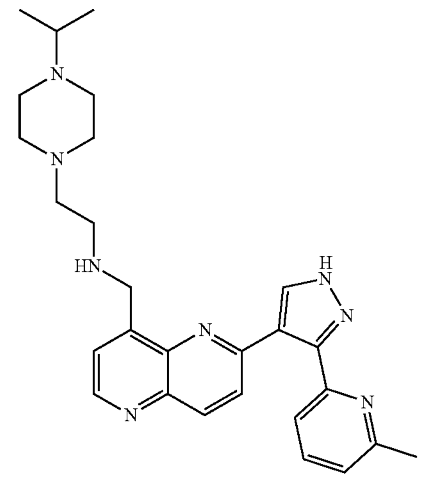 | 2-(4-isopropylpiperazin-1-yl)-N-[[6-[3-(6-methyl-2-pyridyl)-1H-pyrazol-4-yl]-1,5-naphthyridin-4-yl]methyl]ethanamine | 470.8 |
| 821 | 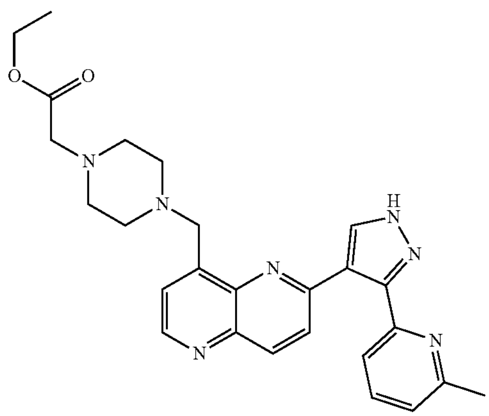 | ethyl 2-[4-[[6-[3-(6-methyl-2-pyridyl)-1H-pyrazol-4-yl]-1,5-naphthyridin-4-yl]methyl]piperazin-1-yl]acetate | 471.8 |
| 822 | 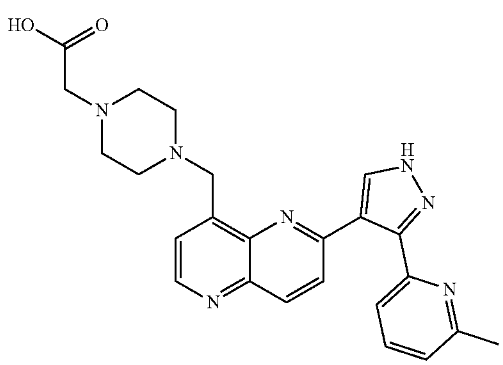 | 2-[4-[[6-[3-(6-methyl-2-pyridyl)-1H-pyrazol-4-yl]-1,5-naphthyridin-4-yl]methyl]piperazin-1-yl]acetic acid | 443.5 |
| 823 | 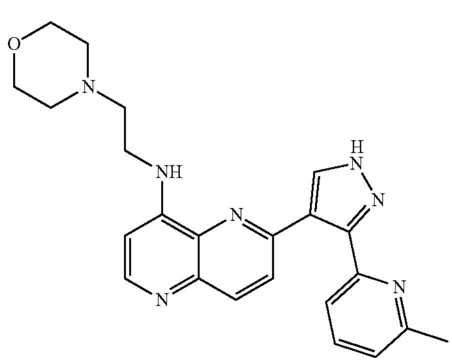 | 6-[3-(6-methyl-2-pyridyl)-1H-pyrazol-4-yl]-N-(2-morpholinoethyl)-1,5-naphthyridin-4-amine | 415.8 |

TABLE 1-continued

| No. | Structure | Chemical Name | [M + H]+ |
|---|---|---|---|
| 824 | 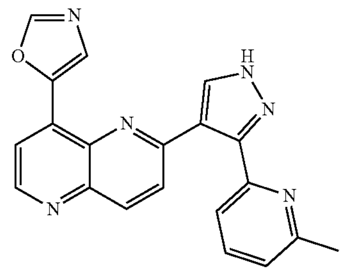 | 5-[6-[3-(6-methyl-2-pyridyl)-1H-pyrazol-4-yl]-1,5-naphthyridin-4-yl]oxazole | 355.0 |
| 825 | 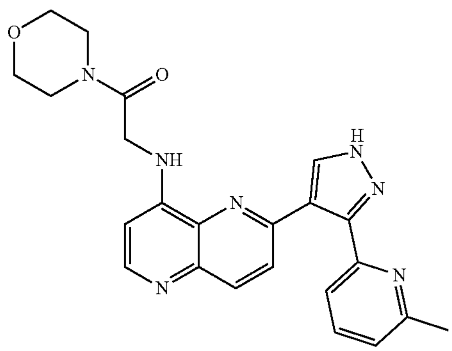 | 2-[[6-[3-(6-methyl-2-pyridyl)-1H-pyrazol-4-yl]-1,5-naphthyridin-4-yl]amino]-1-morpholino-ethanone | 430.1 |
| 826 | 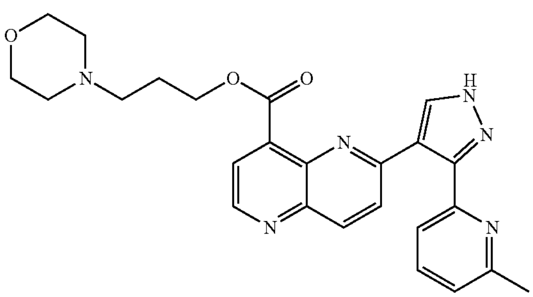 | 3-morpholinopropyl 6-[3-(6-methyl-2-pyridyl)-1H-pyrazol-4-yl]-1,5-naphthyridine-4-carboxylate | 459.1 |
| 827 | 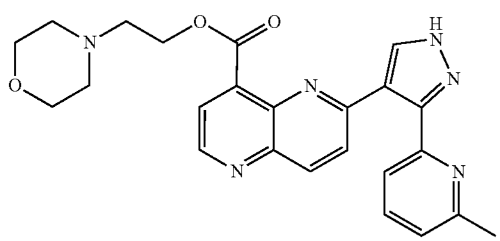 | 2-morpholinoethyl 6-[3-(6-methyl-2-pyridyl)-1H-pyrazol-4-yl]-1,5-naphthyridine-4-carboxylate | 445.1 |
| 828 | 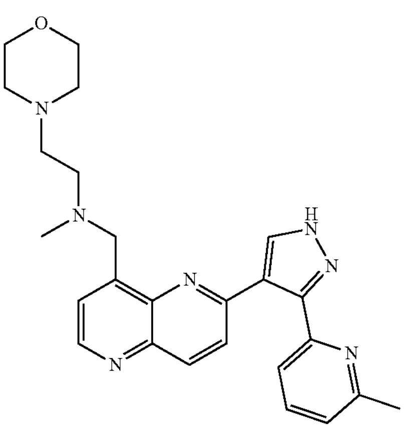 | N-methyl-N-[[6-[3-(6-methyl-2-pyridyl)-1H-pyrazol-4-yl]-1,5-naphthyridin-4-yl]methyl]-2-morpholino-ethanamine | 443.7 |

TABLE 1-continued

| No. | Structure | Chemical Name | [M + H]⁺ |
|---|---|---|---|
| 829 | 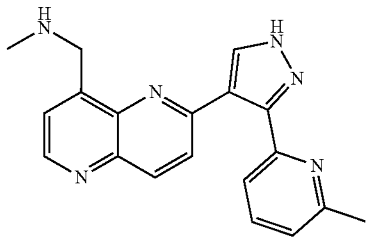 | N-methyl-1-[6-[3-(6-methyl-2-pyridyl)-1H-pyrazol-4-yl]-1,5-naphthyridin-4-yl]methanamine | 331.0 |
| 830 | 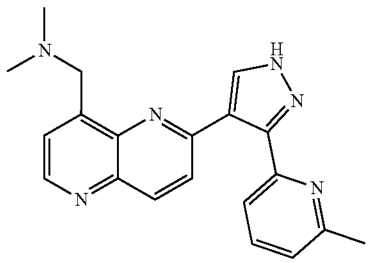 | N,N-dimethyl-1-[6-[3-(6-methyl-2-pyridyl)-1H-pyrazol-4-yl]-1,5-naphthyridin-4-yl]methanamine | 344.9 |
| 831 | 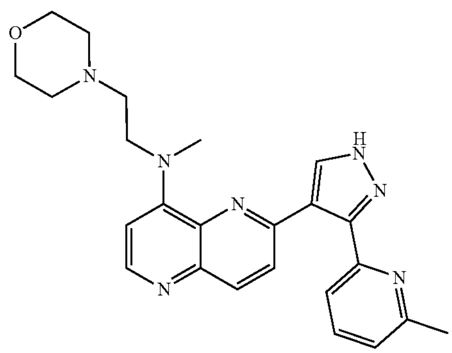 | N-methyl-6-[3-(6-methyl-2-pyridyl)-1H-pyrazol-4-yl]-N-(2-morpholinoethyl)-1,5-naphthyridin-4-amine | 430.2 |
| 832 | 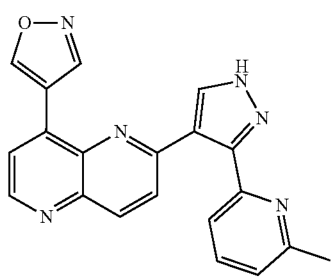 | 4-[6-[3-(6-methyl-2-pyridyl)-1H-pyrazol-4-yl]-1,5-naphthyridin-4-yl]isoxazole | 355.1 |
| 833 | 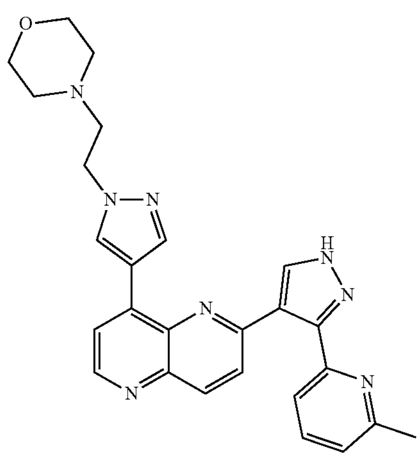 | 4-[2-[4-[6-[3-(6-methyl-2-pyridyl)-1H-pyrazol-4-yl]-1,5-naphthyridin-4-yl]pyrazol-1-yl]ethyl]morpholine | 467.2 |

TABLE 1-continued

| No. | Structure | Chemical Name | [M + H]+ |
|---|---|---|---|
| 834 | 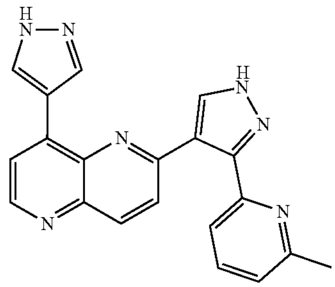 | 2-[3-(6-methyl-2-pyridyl)-1H-pyrazol-4-yl]-8-(1H-pyrazol-4-yl)-1,5-naphthyridine | 354.1 |
| 835 | 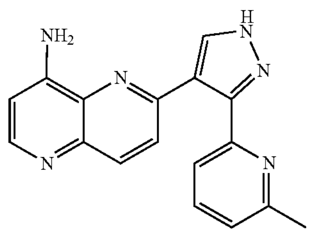 | 6-[3-(6-methyl-2-pyridyl)-1H-pyrazol-4-yl]-1,5-naphthyridin-4-amine | 303.0 |
| 836 | 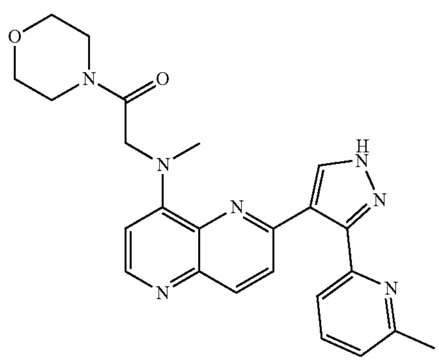 | 2-[methyl-[6-[3-(6-methyl-2-pyridyl)-1H-pyrazol-4-yl]-1,5-naphthyridin-4-yl]amino]-1-morpholino-ethanone | 444.1 |
| 837 | 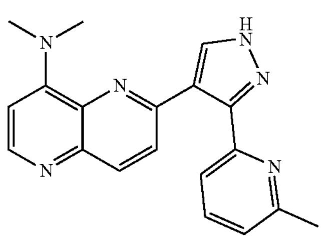 | N,N-dimethyl-6-[3-(6-methyl-2-pyridyl)-1H-pyrazol-4-yl]-1,5-naphthyridin-4-amine | 331.1 |
| 838 | 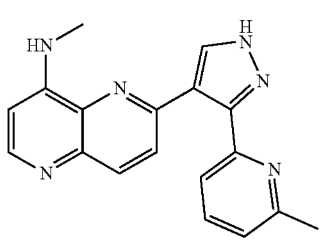 | N-methyl-6-[3-(6-methyl-2-pyridyl)-1H-pyrazol-4-yl]-1,5-naphthyridin-4-amine | 317.1 |

TABLE 1-continued

| No. | Structure | Chemical Name | [M + H]+ |
|---|---|---|---|
| 839 | 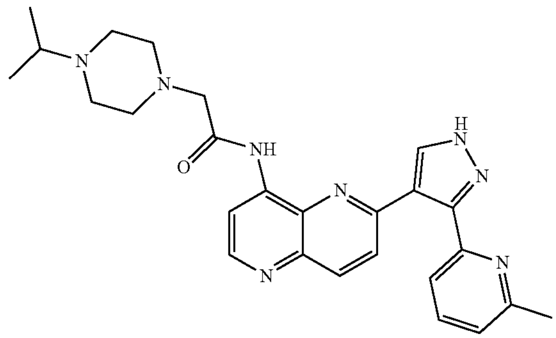 | 2-(4-isopropylpiperazin-1-yl)-N-[6-[3-(6-methyl-2-pyridyl)-1H-pyrazol-4-yl]-1,5-naphthyridin-4-yl]acetamide | 471.2 |
| 840 | 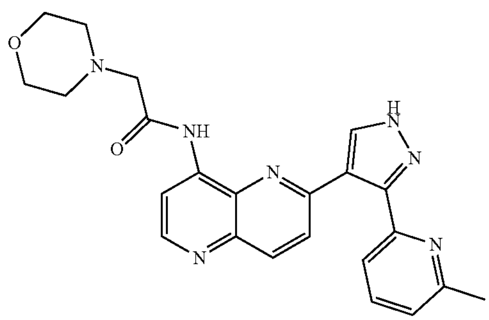 | N-[6-[3-(6-methyl-2-pyridyl)-1H-pyrazol-4-yl]-1,5-naphthyridin-4-yl]-2-morpholino-acetamide | 430.1 |
| 841 | 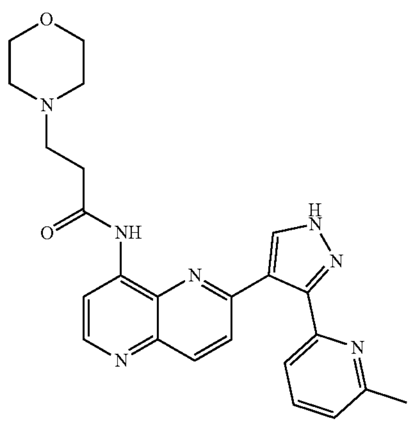 | N-[6-[3-(6-methyl-2-pyridyl)-1H-pyrazol-4-yl]-1,5-naphthyridin-4-yl]-3-morpholino-propanamide | 443.8 |
| 842 | 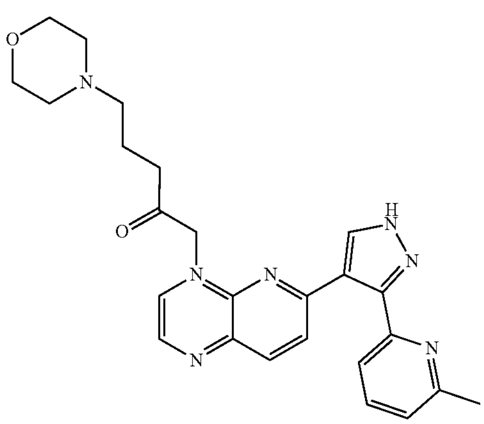 | N-[6-[3-(6-methyl-2-pyridyl)-1H-pyrazol-4-yl]-1,5-naphthyridin-4-yl]-4-morpholino-butanamide | 457.8 |

TABLE 1-continued

| No. | Structure | Chemical Name | [M + H]+ |
|---|---|---|---|
| 843 | 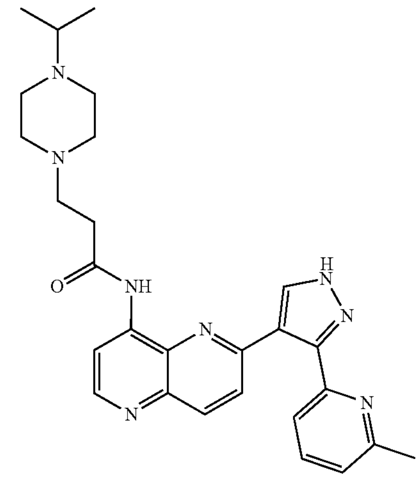 | 3-(4-isopropylpiperazin-1-yl)-N-[6-[3-(6-methyl-2-pyridyl)-1H-pyrazol-4-yl]-1,5-naphthyridin-4-yl]propanamide | 484.7 |
| 844 | 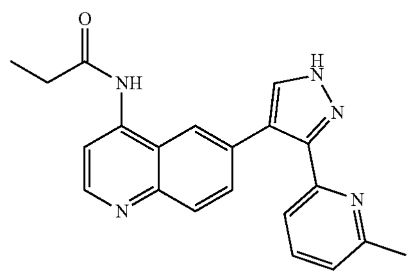 | N-[6-[3-(6-methyl-2-pyridyl)-1H-pyrazol-4-yl]-1,5-naphthyridin-4-yl]propanamide | 358.4 |
| 845 | 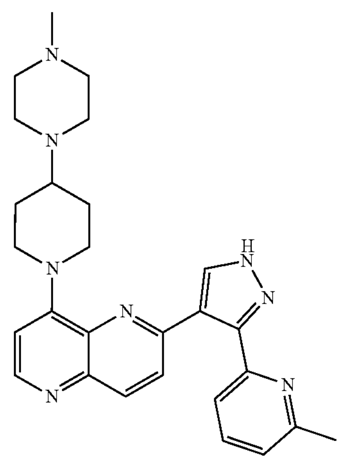 | 8-[4-(4-methylpiperazin-1-yl)-1-piperidyl]-2-[3-(6-methyl-2-pyridyl)-1H-pyrazol-4-yl]-1,5-naphthyridine | 468.9 |
| 846 | 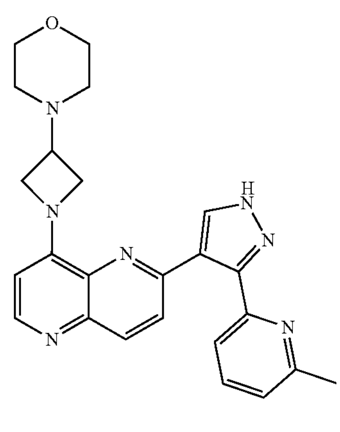 | 4-[1-[6-[3-(6-methyl-2-pyridyl)-1H-pyrazol-4-yl]-1,5-naphthyridin-4-yl]azetidin-3-yl]morpholine | 427.8 |

TABLE 1-continued

| No. | Structure | Chemical Name | [M + H]⁺ |
|---|---|---|---|
| 847 | 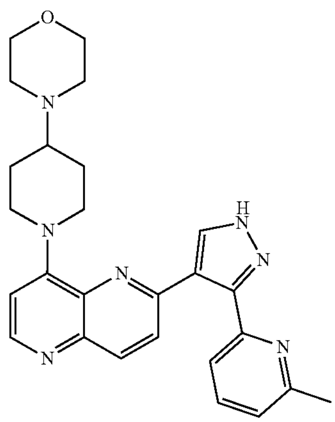 | 4-[1-[6-[3-(6-methyl-2-pyridyl)-1H-pyrazol-4-yl]-1,5-naphthyridin-4-yl]-4-piperidyl]morpholine | 455.8 |
| 848 | 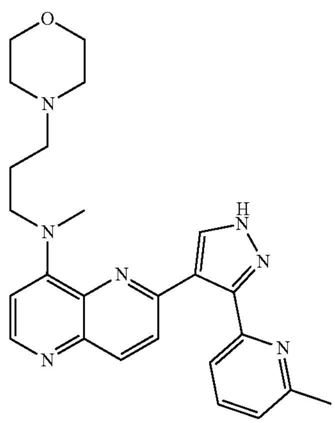 | N-methyl-6-[3-(6-methyl-2-pyridyl)-1H-pyrazol-4-yl]-N-(3-morpholinopropyl)-1,5-naphthyridin-4-amine | 443.8 |
| 849 | 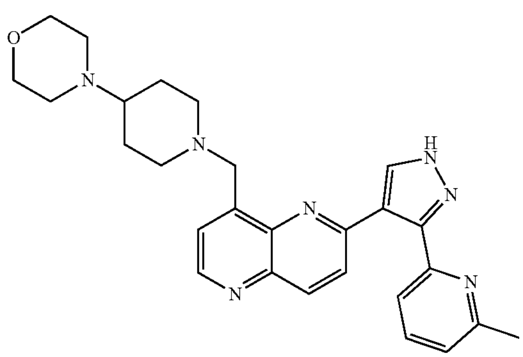 | 4-[1-[[6-[3-(6-methyl-2-pyridyl)-1H-pyrazol-4-yl]-1,5-naphthyridin-4-yl]methyl]-4-piperidyl]morpholine | 470.2 |
| 850 | 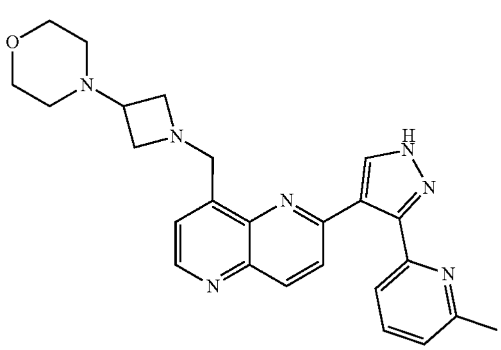 | 4-[1-[[6-[3-(6-methyl-2-pyridyl)-1H-pyrazol-4-yl]-1,5-naphthyridin-4-yl]methyl]azetidin-3-yl]morpholine | 442.2 |

TABLE 1-continued

| No. | Structure | Chemical Name | [M + H]+ |
|---|---|---|---|
| 851 | 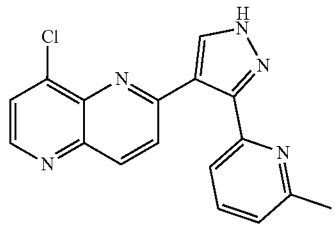 | 8-chloro-2-[3-(6-methyl-2-pyridyl)-1H-pyrazol-4-yl]-1,5-naphthyridine | 322.0 |
| 852 | 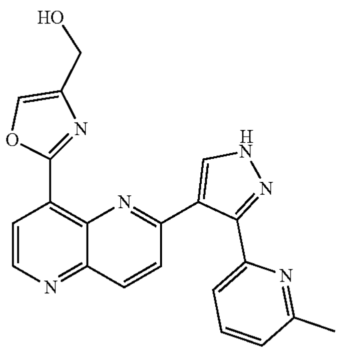 | [2-[6-[3-(6-methyl-2-pyridyl)-1H-pyrazol-4-yl]-1,5-naphthyridin-4-yl]oxazol-4-yl]methanol | 385.3 |
| 853 | 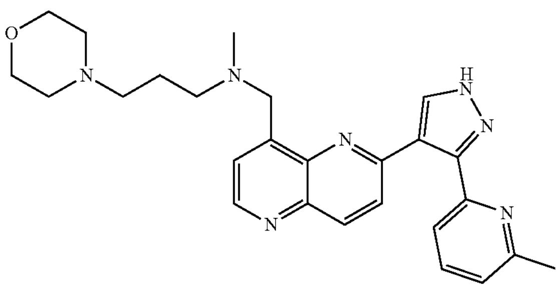 | N-methyl-N-[[6-[3-(6-methyl-2-pyridyl)-1H-pyrazol-4-yl]-1,5-naphthyridin-4-yl]methyl]-3-morpholino-propan-1-amine | 458.0 |
| 854 | 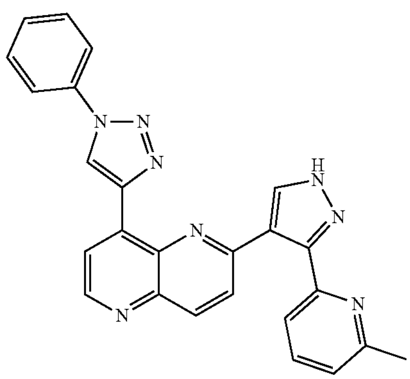 | 2-[3-(6-methyl-2-pyridyl)-1H-pyrazol-4-yl]-8-(1-phenyltriazol-4-yl)-1,5-naphthyridine | 431.2 |
| 855 | 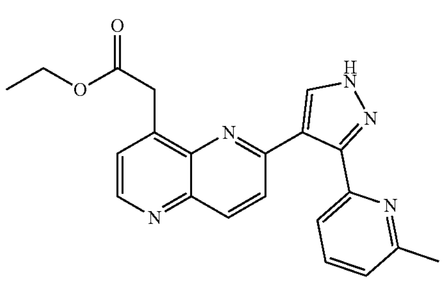 | ethyl 2-[6-[3-(6-methyl-2-pyridyl)-1H-pyrazol-4-yl]-1,5-naphthyridin-4-yl]acetate | 374.1 |

TABLE 1-continued

| No. | Structure | Chemical Name | [M + H]+ |
|---|---|---|---|
| 856 | 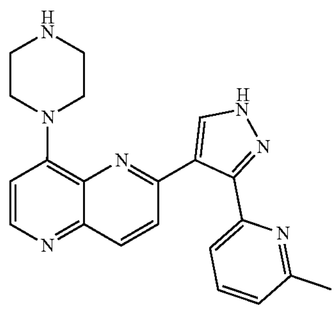 | 2-[3-(6-methyl-2-pyridyl)-1H-pyrazol-4-yl]-8-piperazin-1-yl-1,5-naphthyridine | 372.1 |
| 857 | 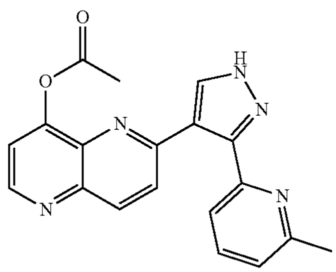 [SMILES: CC(=O)Oc1ccnc2ccc(-c3c[nH]nc3-c3cccc(C)n3)nc12] | [6-[3-(6-methyl-2-pyridyl)-1H-pyrazol-4-yl]-1,5-naphthyridin-4-yl]acetate | 346.3 |
| 858 | 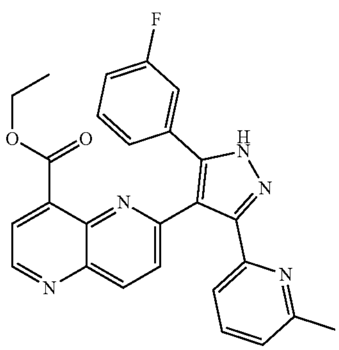 [SMILES: CCOC(=O)c1ccnc2ccc(-c3c(-c4cccc(C)n4)n[nH]c3-c3cccc(F)c3)nc12] | ethyl 6-[5-(3-fluorophenyl)-3-(6-methyl-2-pyridyl)-1H-pyrazol-4-yl]-1,5-naphthyridine-4-carboxylate | 454.2 |
| 859 | 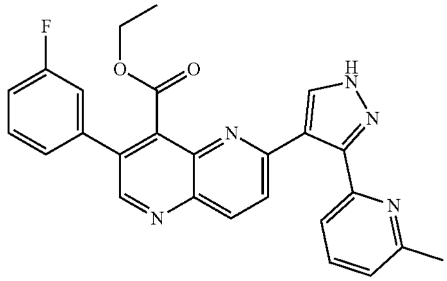 [SMILES: CCOC(=O)c1c(-c2cccc(F)c2)cnc2ccc(-c3c[nH]nc3-c3cccc(C)n3)nc12] | ethyl 3-(3-fluorophenyl)-6-[3-(6-methyl-2-pyridyl)-1H-pyrazol-4-yl]-1,5-naphthyridine-4-carboxylate | 454.1 |
| 860 | 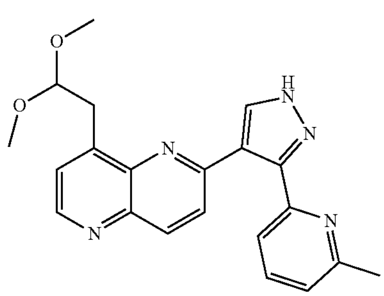 | 8-(2,2-dimethoxyethyl)-2-[3-(6-methyl-2-pyridyl)-1H-pyrazol-4-yl]-1,5-naphthyridine | 376.2 |

TABLE 1-continued

| No. | Structure | Chemical Name | [M + H]+ |
|---|---|---|---|
| 861 | 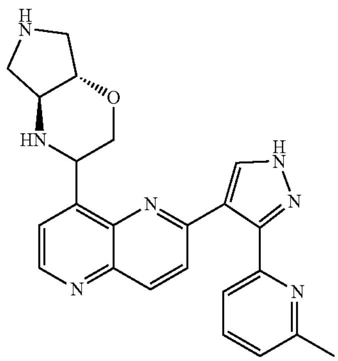 | rac-(4aS,7aS)-3-[6-[3-(6-methyl-2-pyridyl)-1H-pyrazol-4-yl]-1,5-naphthyridin-4-yl]-2,3,4,4a,5,6,7,7a-octahydropyrrolo[3,4-b][1,4]oxazine | 414.5 |
| 862 | 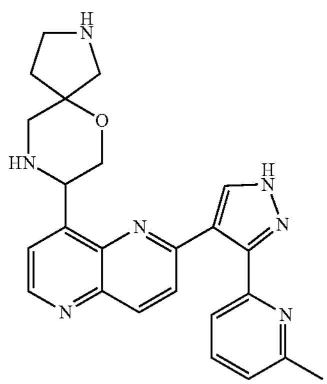 [SMILES: Cc1cccc(-c2n[nH]cc2-c2ccc3nccc(C4COC5(CCNC5)CN4)c3n2)n1] | 8-[6-[3-(6-methyl-2-pyridyl)-1H-pyrazol-4-yl]-1,5-naphthyridin-4-yl]-6-oxa-2,9-diazaspiro[4.5]decane | 428.1 |
| 863 | 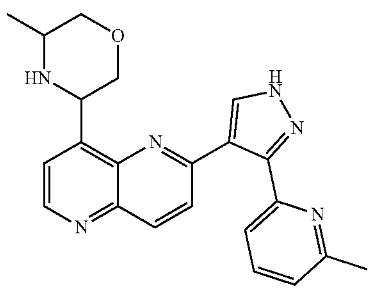 | 3-methyl-5-[6-[3-(6-methyl-2-pyridyl)-1H-pyrazol-4-yl]-1,5-naphthyridin-4-yl]morpholine | 387.1 |
| 864 | 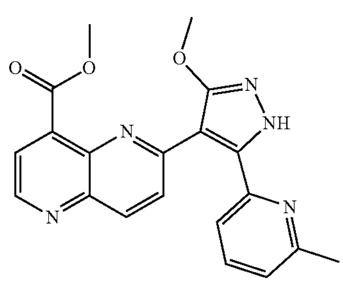 [SMILES: COC(=O)c1ccnc2ccc(-c3c(OC)n[nH]c3-c3cccc(C)n3)nc12] | methyl 6-[3-methoxy-5-(6-methyl-2-pyridyl)-1H-pyrazol-4-yl]-1,5-naphthyridine-4-carboxylate | 376.2 |

TABLE 1-continued

| No. | Structure | Chemical Name | [M + H]+ |
|---|---|---|---|
| 865 | 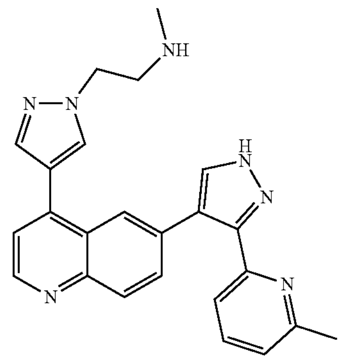 [SMILES: CNCCn1cc(-c2ccnc3ccc(-c4c[nH]nc4-c4cccc(C)n4)cc23)cn1] | N-methyl-2-[4-[6-[3-(6-methyl-2-pyridyl)-1H-pyrazol-4-yl]-4-quinolyl]pyrazol-1-yl]ethanamine | 410.2 |
| 866 | 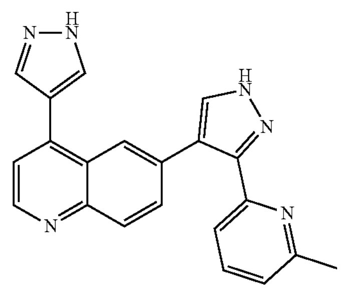 [SMILES: Cc1cccc(-c2n[nH]cc2-c2ccc3nccc(-c4cn[nH]c4)c3c2)n1] | 6-[3-(6-methyl-2-pyridyl)-1H-pyrazol-4-yl]-4-(1H-pyrazol-4-yl)quinoline | 353.2 |
| 867 | 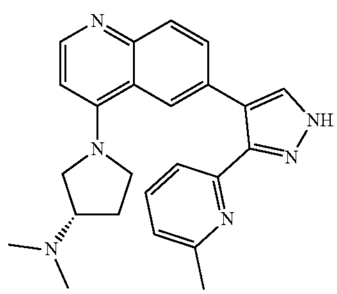 [SMILES: Cc1cccc(-c2n[nH]cc2-c2ccc3nccc(N4CC[C@H](N(C)C)C4)c3c2)n1] | rac-(3S)-N,N-dimethyl-1-[6-[3-(6-methyl-2-pyridyl)-1H-pyrazol-4-yl]-4-quinolyl]pyrrolidin-3-amine | 399.2 |
| 868 | 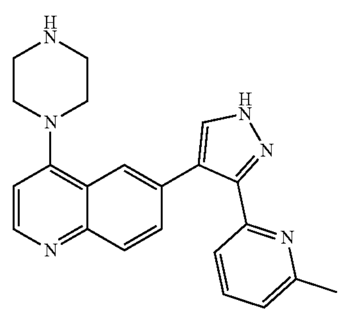 [SMILES: Cc1cccc(-c2n[nH]cc2-c2ccc3nccc(N4CCNCC4)c3c2)n1] | 6-[3-(6-methyl-2-pyridyl)-1H-pyrazol-4-yl]-4-piperazin-1-yl-quinoline | 371.2 |
| 869 | 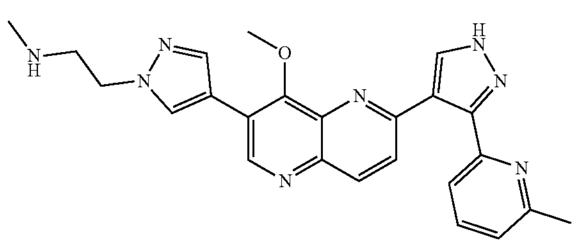 | 2-[4-[4-methoxy-6-[3-(6-methyl-2-pyridyl)-1H-pyrazol-4-yl]-1,5-naphthyridin-3-yl]pyrazol-1-yl]-N-methyl-ethanamine | 441.2 |

TABLE 1-continued

| No. | Structure | Chemical Name | [M + H]+ |
|---|---|---|---|
| 870 | 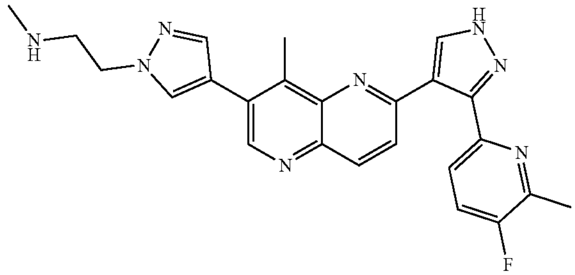 | 2-[4-[6-[3-(5-fluoro-6-methyl-2-pyridyl)-1H-pyrazol-4-yl]-4-methyl-1,5-naphthyridin-3-yl]pyrazol-1-yl]-N-methyl-ethanamine | 441.3 |
| 871 | 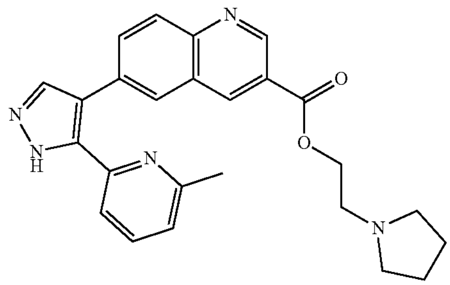 [SMILES: Cc1cccc(-c2[nH]ncc2-c2ccc3ncc(C(=O)OCCN4CCCC4)cc3c2)n1] | 2-(pyrrolidin-1-yl)ethyl 6-(5-(6-methylpyridin-2-yl)-1H-pyrazol-4-yl)quinoline-3-carboxylate | |
| 872 | 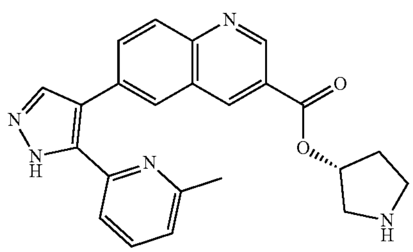 [SMILES: Cc1cccc(-c2[nH]ncc2-c2ccc3ncc(C(=O)O[C@@H]4CCNC4)cc3c2)n1] | (R)-pyrrolidin-3-yl 6-(5-(6-methylpyridin-2-yl)-1H-pyrazol-4-yl)quinoline-3-carboxylate | |
| 873 | 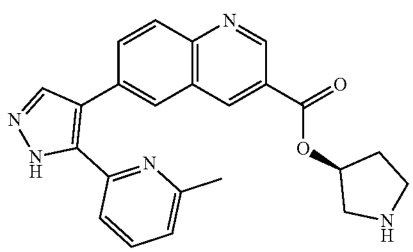 [SMILES: Cc1cccc(-c2[nH]ncc2-c2ccc3ncc(C(=O)O[C@H]4CCNC4)cc3c2)n1] | (S)-pyrrolidin-3-yl 6-(5-(6-methylpyridin-2-yl)-1H-pyrazol-4-yl)quinoline-3-carboxylate | |
| 874 | 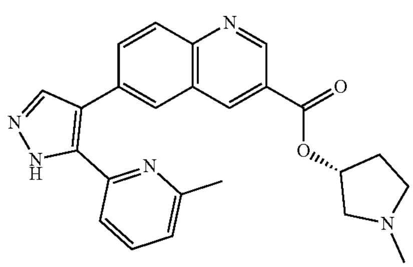 [SMILES: Cc1cccc(-c2[nH]ncc2-c2ccc3ncc(C(=O)O[C@@H]4CCN(C)C4)cc3c2)n1] | (R)-1-methylpyrrolidin-3-yl 6-(5-(6-methylpyridin-2-yl)-1H-pyrazol-4-yl)quinoline-3-carboxylate | |
| 875 | 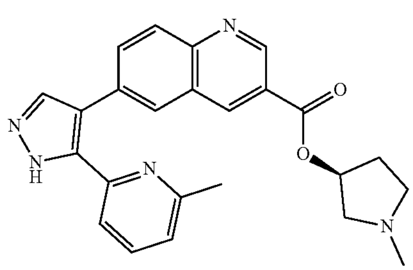 [SMILES: Cc1cccc(-c2[nH]ncc2-c2ccc3ncc(C(=O)O[C@H]4CCN(C)C4)cc3c2)n1] | (S)-1-methylpyrrolidin-3-yl 6-(5-(6-methylpyridin-2-yl)-1H-pyrazol-4-yl)quinoline-3-carboxylate | |

TABLE 1-continued

| No. | Structure | Chemical Name | [M + H]⁺ |
|---|---|---|---|
| 876 | 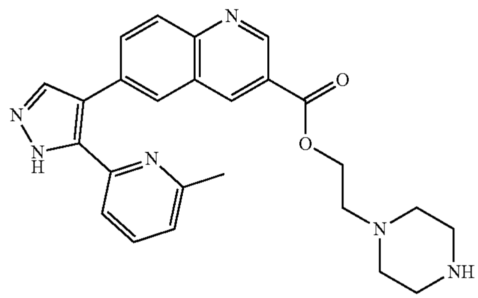 [SMILES: Cc1cccc(-c2[nH]ncc2-c2ccc3ncc(C(=O)OCCN4CCNCC4)cc3c2)n1] | 2-(piperazin-1-yl)ethyl 6-(5-(6-methylpyridin-2-yl)-1H-pyrazol-4-yl)quinoline-3-carboxylate | 443.2 |
| 877 | 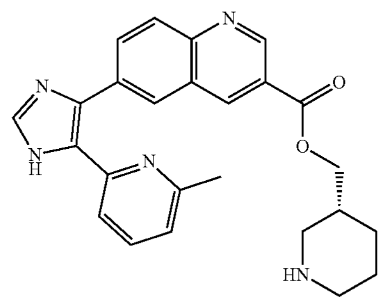 [SMILES: Cc1cccc(-c2[nH]cnc2-c2ccc3ncc(C(=O)OC[C@@H]4CCCNC4)cc3c2)n1] | (R)-piperidin-3-ylmethyl 6-(5-(6-methylpyridin-2-yl)-1H-imidazol-4-yl)quinoline-3-carboxylate | 428.1 |
| 878 | 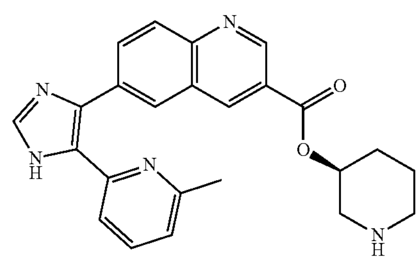 [SMILES: Cc1cccc(-c2[nH]cnc2-c2ccc3ncc(C(=O)O[C@H]4CCCNC4)cc3c2)n1] | (S)-piperidin-3-yl 6-(5-(6-methylpyridin-2-yl)-1H-imidazol-4-yl)quinoline-3-carboxylate | 414.1 |
| 879 | 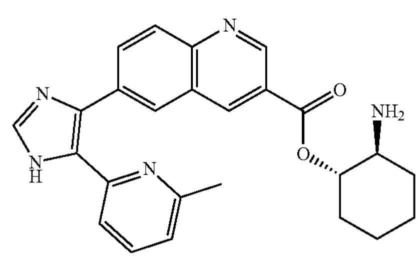 [SMILES: Cc1cccc(-c2[nH]cnc2-c2ccc3ncc(C(=O)O[C@H]4CCCC[C@@H]4N)cc3c2)n1] | (1S,2S)-2-aminocyclohexyl 6-(5-(6-methylpyridin-2-yl)-1H-imidazol-4-yl)quinoline-3-carboxylate | 428.1 |
| 880 | 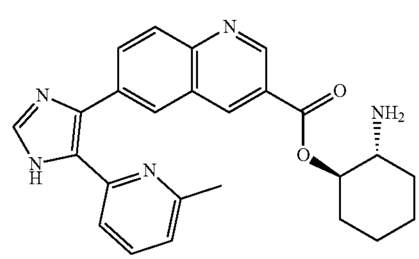 [SMILES: Cc1cccc(-c2[nH]cnc2-c2ccc3ncc(C(=O)O[C@@H]4CCCC[C@H]4N)cc3c2)n1] | (1R,2R)-2-aminocyclohexyl 6-(5-(6-methylpyridin-2-yl)-1H-imidazol-4-yl)quinoline-3-carboxylate | 428.2 |

TABLE 1-continued

| No. | Structure | Chemical Name | [M + H]+ |
|---|---|---|---|
| 881 | 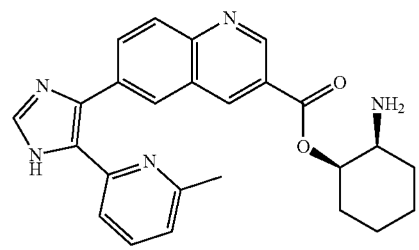 [SMILES: Cc1cccc(-c2[nH]cnc2-c2ccc3ncc(C(=O)O[C@@H]4CCCC[C@@H]4N)cc3c2)n1] | (1R,2S)-2-aminocyclohexyl 6-(5-(6-methylpyridin-2-yl)-1H-imidazol-4-yl)quinoline-3-carboxylate | 428.1 |
| 882 | 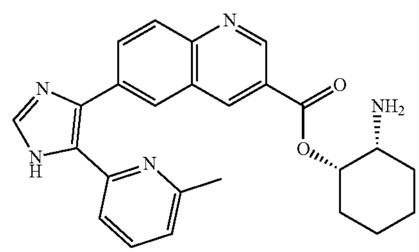 [SMILES: Cc1cccc(-c2[nH]cnc2-c2ccc3ncc(C(=O)O[C@H]4CCCC[C@H]4N)cc3c2)n1] | (1S,2R)-2-aminocyclohexyl 6-(5-(6-methylpyridin-2-yl)-1H-imidazol-4-yl)quinoline-3-carboxylate | 428.1 |
| 883 | 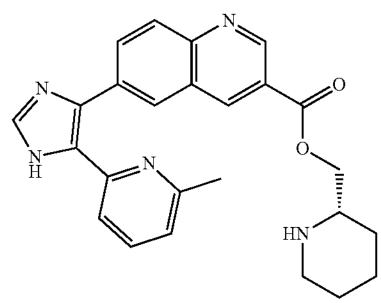 [SMILES: Cc1cccc(-c2[nH]cnc2-c2ccc3ncc(C(=O)OC[C@@H]4CCCCN4)cc3c2)n1] | (S)-piperidin-2-ylmethyl 6-(5-(6-methylpyridin-2-yl)-1H-imidazol-4-yl)quinoline-3-carboxylate | 428.1 |
| 884 | 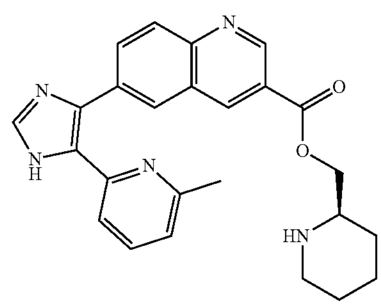 [SMILES: Cc1cccc(-c2[nH]cnc2-c2ccc3ncc(C(=O)OC[C@H]4CCCCN4)cc3c2)n1] | (R)-piperidin-2-ylmethyl 6-(5-(6-methylpyridin-2-yl)-1H-imidazol-4-yl)quinoline-3-carboxylate | 428.1 |
| 885 | 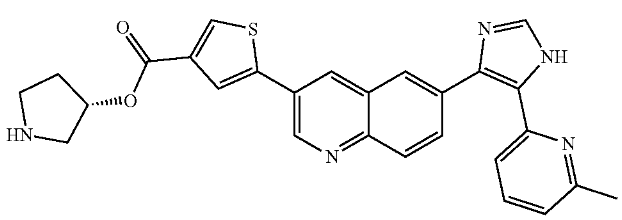 [SMILES: Cc1cccc(-c2[nH]cnc2-c2ccc3ncc(-c4cc(C(=O)O[C@H]5CCNC5)cs4)cc3c2)n1] | [(3S)-pyrrolidin-3-yl] 5-[6-[5-(6-methyl-2-pyridyl)-1H-imidazol-4-yl]-3-quinolyl]thiophene-3-carboxylate | 482.1 |

TABLE 1-continued

| No. | Structure | Chemical Name | [M + H]+ |
| --- | --- | --- | --- |
| 886 | 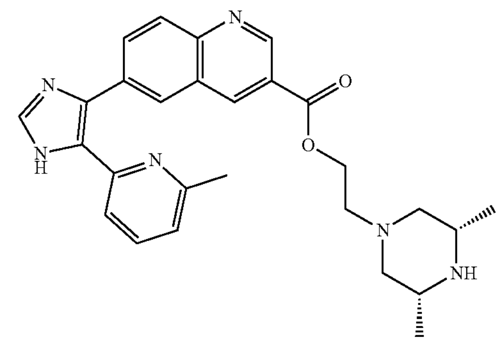 [SMILES: Cc1cccc(-c2[nH]cnc2-c2ccc3ncc(C(=O)OCCN4C[C@@H](C)N[C@@H](C)C4)cc3c2)n1] | 2-((3S,5R)-3,5-dimethylpiperazin-1-yl)ethyl 6-(5-(6-methylpyridin-2-yl)-1H-imidazol-4-yl)quinoline-3-carboxylate | 471.2 |
| 887 | 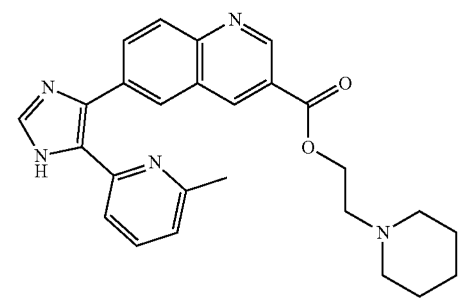 | 2-(piperidin-1-yl)ethyl 6-(5-(6-methylpyridin-2-yl)-1H-imidazol-4-yl)quinoline-3-carboxylate | 442.2 |
| 888 | 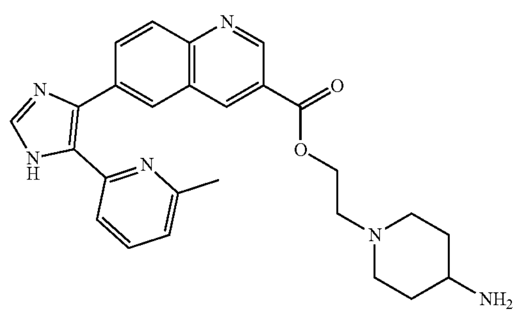 | 2-(4-aminopiperidin-1-yl)ethyl 6-(5-(6-methylpyridin-2-yl)-1H-imidazol-4-yl)quinoline-3-carboxylate | |
| 889 | 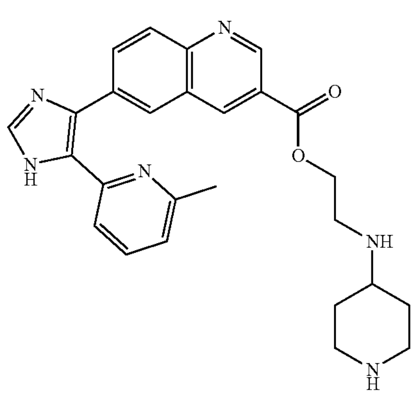 | 2-(piperidin-4-ylamino)ethyl 6-(5-(6-methylpyridin-2-yl)-1H-imidazol-4-yl)quinoline-3-carboxylate | |

TABLE 1-continued

| No. | Structure | Chemical Name | [M + H]+ |
|---|---|---|---|
| 890 | 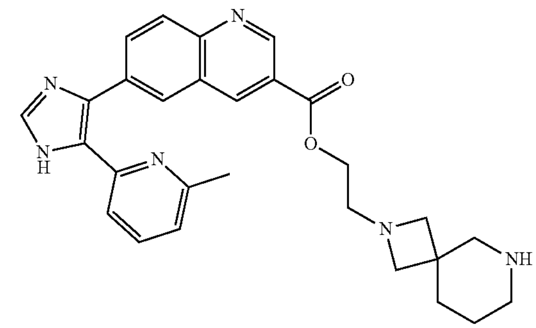 | 2-(2,6-diazaspiro[3.5]nonan-2-yl)ethyl 6-(5-(6-methylpyridin-2-yl)-1H-imidazol-4-yl)quinoline-3-carboxylate | 483.3 |
| 891 | 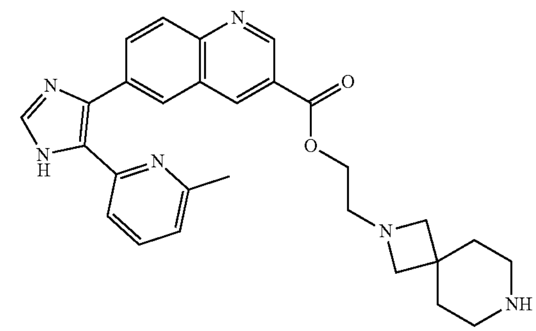 | 2-(2,7-diazaspiro[3.5]nonan-2-yl)ethyl 6-(5-(6-methylpyridin-2-yl)-1H-imidazol-4-yl)quinoline-3-carboxylate | 483.2 |
| 892 | 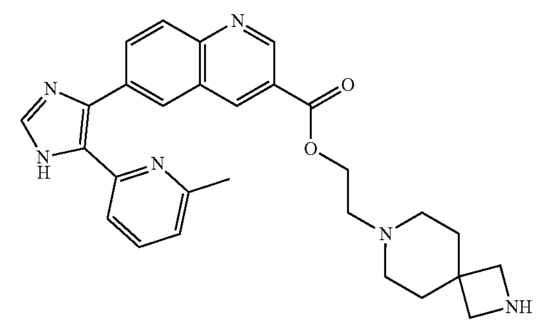 | 2-(2,7-diazaspiro[3.5]nonan-7-yl)ethyl 6-(5-(6-methylpyridin-2-yl)-1H-imidazol-4-yl)quinoline-3-carboxylate | 483.2 |
| 893 | 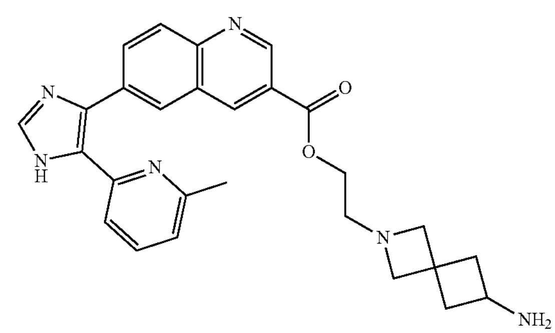 | 2-(6-amino-2-azaspiro[3.3]heptan-2-yl)ethyl 6-(5-(6-methylpyridin-2-yl)-1H-imidazol-4-yl)quinoline-3-carboxylate | |
| 894 | 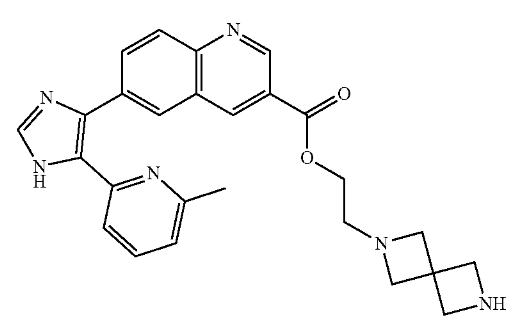 | 2-(2,6-diazaspiro[3.3]heptan-2-yl)ethyl 6-(5-(6-methylpyridin-2-yl)-1H-imidazol-4-yl)quinoline-3-carboxylate | 455.2 |

TABLE 1-continued

| No. | Structure | Chemical Name | [M + H]+ |
|---|---|---|---|
| 895 | 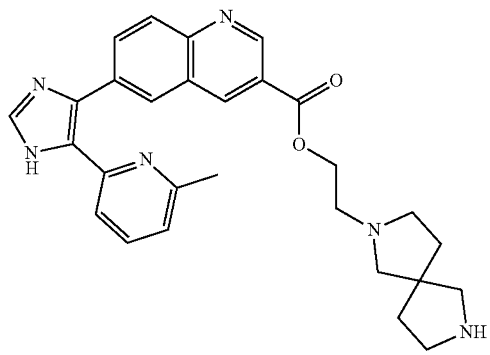 | 2-(2,7-diazaspiro[4.4]nonan-2-yl)ethyl 6-(5-(6-methylpyridin-2-yl)-1H-imidazol-4-yl)quinoline-3-carboxylate | |
| 896 | 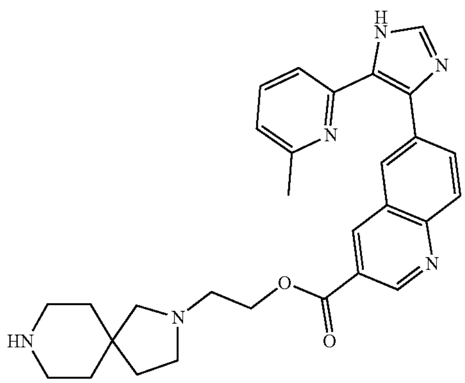 | 2-(2,8-diazaspiro[4.5]decan-2-yl)ethyl 6-(5-(6-methylpyridin-2-yl)-1H-imidazol-4-yl)quinoline-3-carboxylate | 497.2 |
| 897 | 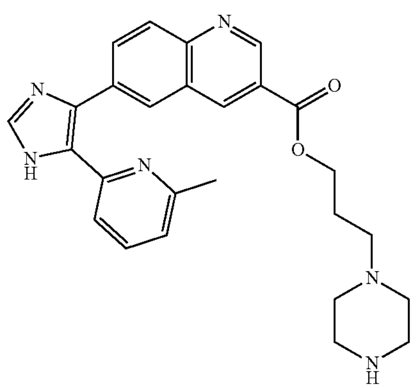 | 3-(piperazin-1-yl)propyl 6-(5-(6-methylpyridin-2-yl)-1H-imidazol-4-yl)quinoline-3-carboxylate | 457.2 |
| 898 | 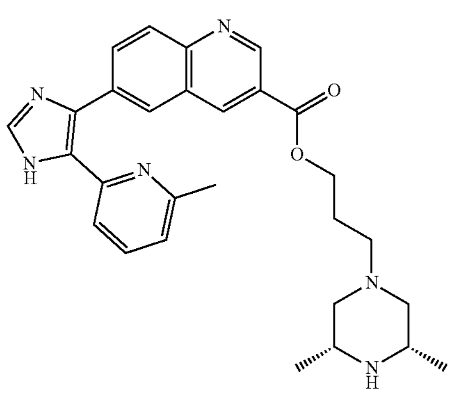 | 3-((3S,5R)-3,5-dimethylpiperazin-1-yl)propyl 6-(5-(6-methylpyridin-2-yl)-1H-imidazol-4-yl)quinoline-3-carboxylate | 485.2 |

TABLE 1-continued

| No. | Structure | Chemical Name | [M + H]+ |
|---|---|---|---|
| 899 | 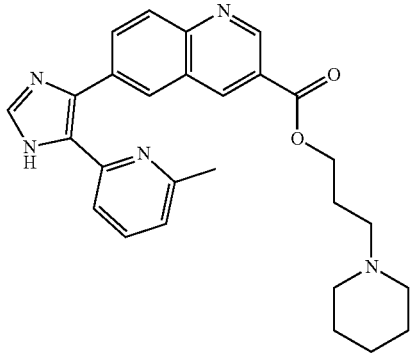 | 3-(piperidin-1-yl)propyl 6-(5-(6-methylpyridin-2-yl)-1H-imidazol-4-yl)quinoline-3-carboxylate | |
| 900 | 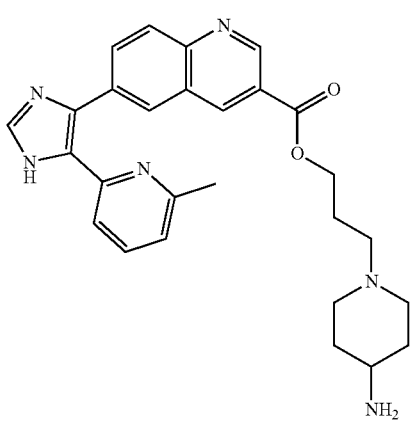 | 3-(4-aminopiperidin-1-yl)propyl 6-(5-(6-methylpyridin-2-yl)-1H-imidazol-4-yl)quinoline-3-carboxylate | |
| 901 | 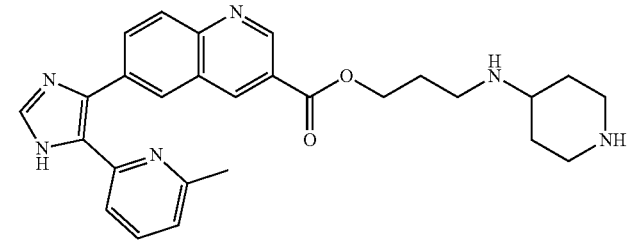 | 3-(piperidin-4-ylamino)propyl 6-(5-(6-methylpyridin-2-yl)-1H-imidazol-4-yl)quinoline-3-carboxylate | |
| 902 | 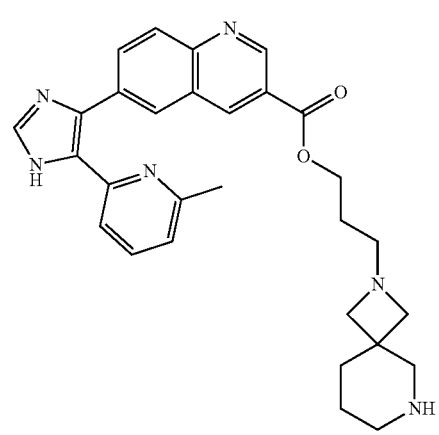 | 3-(2,6-diazaspiro[3.5]nonan-2-yl)propyl 6-(5-(6-methylpyridin-2-yl)-1H-imidazol-4-yl)quinoline-3-carboxylate | |

TABLE 1-continued

| No. | Structure | Chemical Name | [M + H]⁺ |
|---|---|---|---|
| 903 | 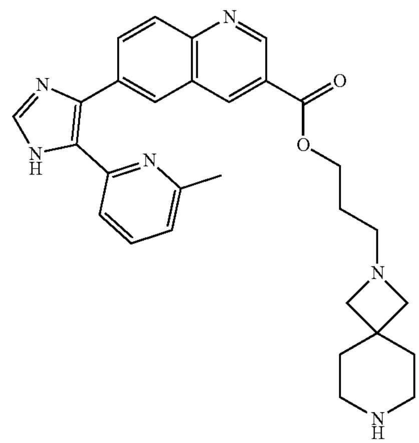 | 3-(2,7-diazaspiro[3.5]nonan-2-yl)propyl 6-(5-(6-methylpyridin-2-yl)-1H-imidazol-4-yl)quinoline-3-carboxylate | 497.2 |
| 904 | 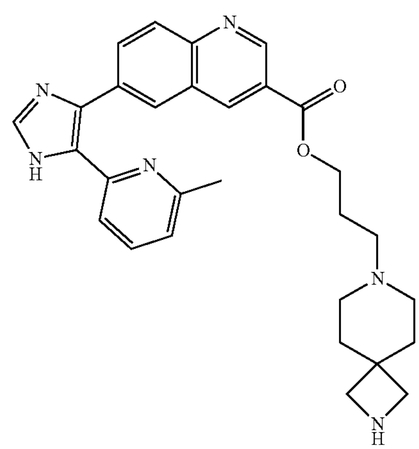 | 3-(2,7-diazaspiro[3.5]nonan-7-yl)propyl 6-(5-(6-methylpyridin-2-yl)-1H-imidazol-4-yl)quinoline-3-carboxylate | 497.2 |
| 905 | 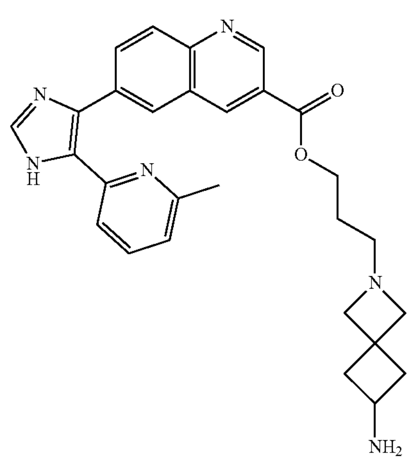 | 3-(6-amino-2-azaspiro[3.3]heptan-2-yl)propyl 6-(5-(6-methylpyridin-2-yl)-1H-imidazol-4-yl)quinoline-3-carboxylate | |

TABLE 1-continued

| No. | Structure | Chemical Name | [M + H]+ |
| --- | --- | --- | --- |
| 906 | 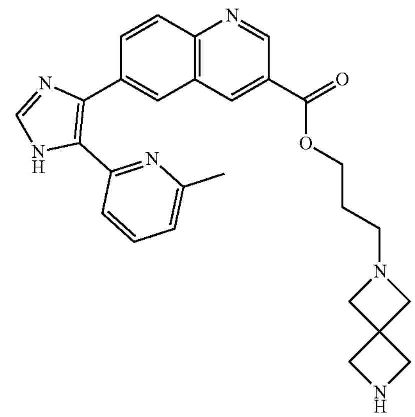 | 3-(2,6-diazaspiro[3.3]heptan-2-yl)propyl 6-(5-(6-methylpyridin-2-yl)-1H-imidazol-4-yl)quinoline-3-carboxylate | |
| 907 | 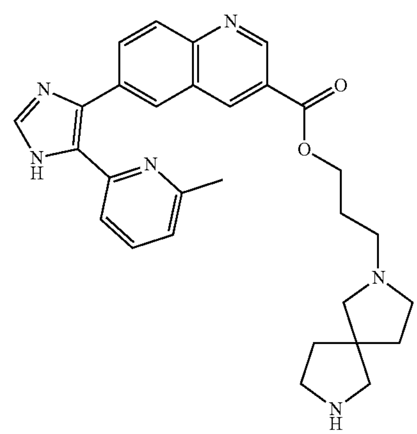 | 3-(2,7-diazaspiro[4.4]nonan-2-yl)propyl 6-(5-(6-methylpyridin-2-yl)-1H-imidazol-4-yl)quinoline-3-carboxylate | |
| 908 | 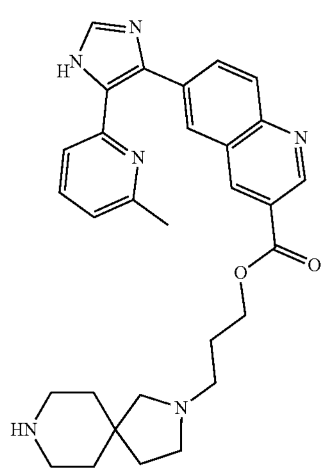 | 3-(2,8-diazaspiro[4.5]decan-2-yl)propyl 6-(5-(6-methylpyridin-2-yl)-1H-imidazol-4-yl)quinoline-3-carboxylate | |

TABLE 1-continued

| No. | Structure | Chemical Name | [M + H]+ |
|---|---|---|---|
| 909 | 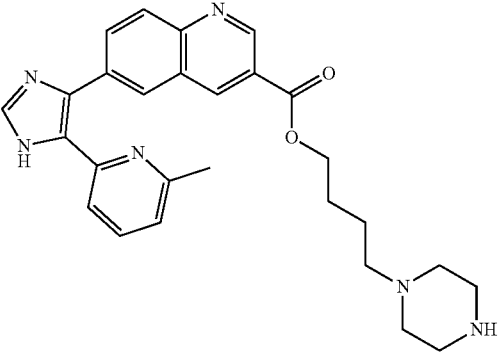 | 4-(piperazin-1-yl)butyl 6-(5-(6-methylpyridin-2-yl)-1H-imidazol-4-yl)quinoline-3-carboxylate | |
| 910 | 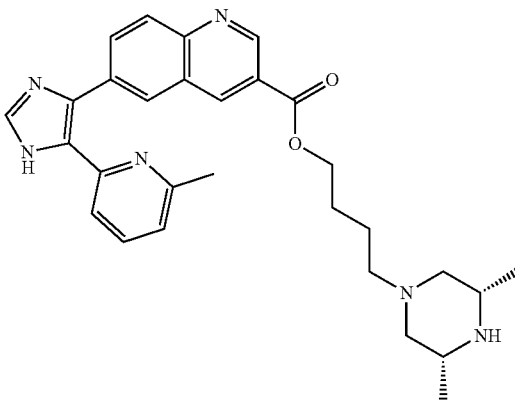 | 4-((3S,5R)-3,5-dimethylpiperazin-1-yl)butyl 6-(5-(6-methylpyridin-2-yl)-1H-imidazol-4-yl)quinoline-3-carboxylate | |
| 911 | 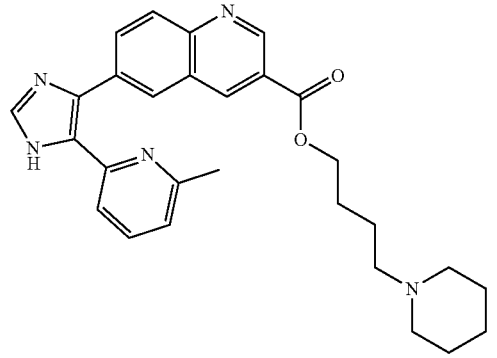 | 4-(piperidin-1-yl)butyl 6-(5-(6-methylpyridin-2-yl)-1H-imidazol-4-yl)quinoline-3-carboxylate | |
| 912 | 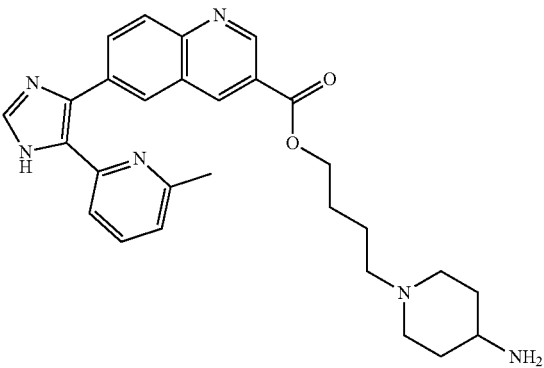 | 4-(4-aminopiperidin-1-yl)butyl 6-(5-(6-methylpyridin-2-yl)-1H-imidazol-4-yl)quinoline-3-carboxylate | |

TABLE 1-continued

| No. | Structure | Chemical Name | [M + H]+ |
|---|---|---|---|
| 913 | 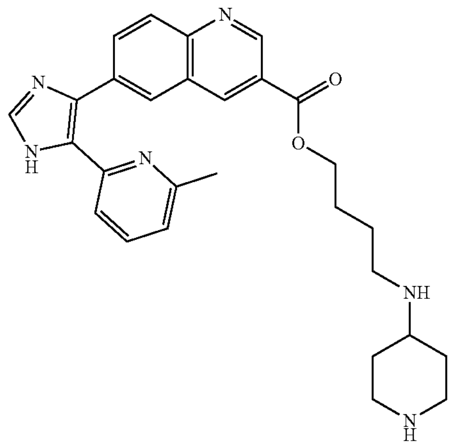 | 4-(piperidin-4-ylamino)butyl 6-(5-(6-methylpyridin-2-yl)-1H-imidazol-4-yl)quinoline-3-carboxylate | |
| 914 | 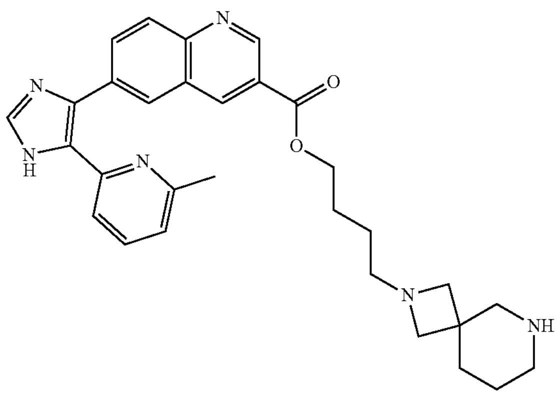 | 4-(2,6-diazaspiro[3.5]nonan-2-yl)butyl 6-(5-(6-methylpyridin-2-yl)-1H-imidazol-4-yl)quinoline-3-carboxylate | |
| 915 | 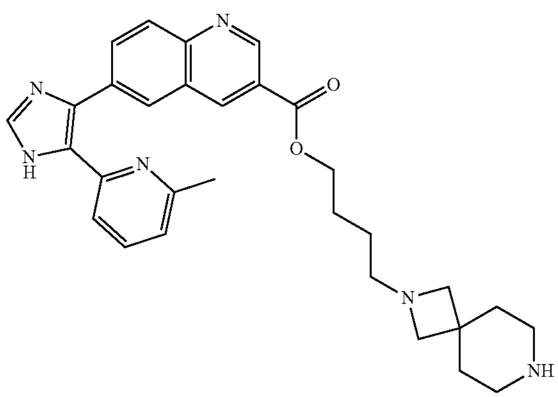 | 4-(2,7-diazaspiro[3.5]nonan-2-yl)butyl 6-(5-(6-methylpyridin-2-yl)-1H-imidazol-4-yl)quinoline-3-carboxylate | |
| 916 | 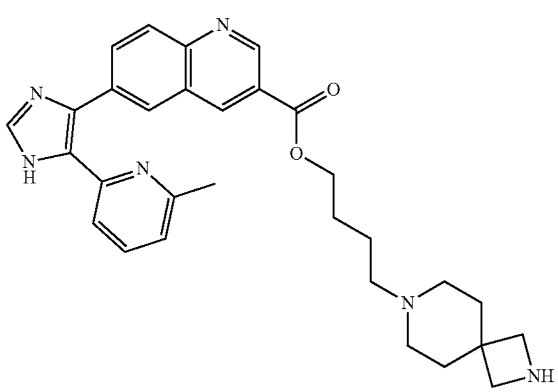 | 4-(2,7-diazaspiro[3.5]nonan-7-yl)butyl 6-(5-(6-methylpyridin-2-yl)-1H-imidazol-4-yl)quinoline-3-carboxylate | |

TABLE 1-continued

| No. | Structure | Chemical Name | [M + H]+ |
|---|---|---|---|
| 917 | 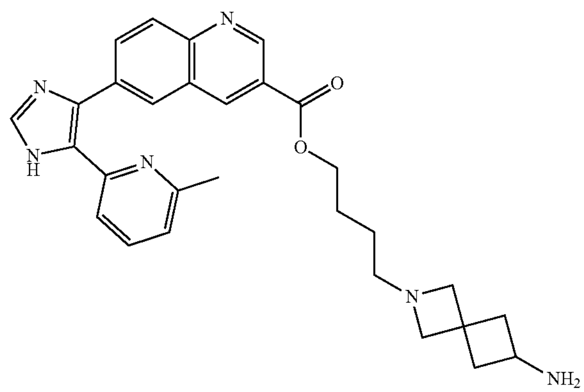 [SMILES: Cc1cccc(-c2[nH]cnc2-c2ccc3ncc(C(=O)OCCCCN4CC5(CC(N)C5)C4)cc3c2)n1] | 4-(6-amino-2-azaspiro[3.3]heptan-2-yl)butyl 6-(5-(6-methylpyridin-2-yl)-1H-imidazol-4-yl)quinoline-3-carboxylate | |
| 918 | 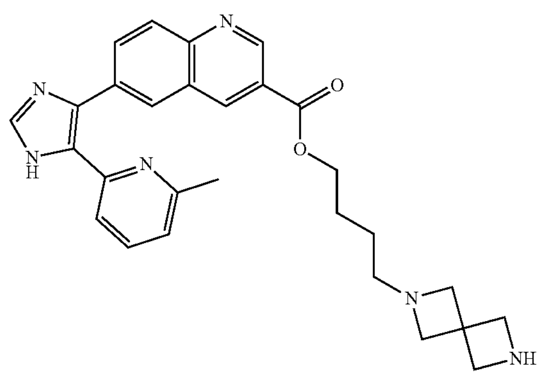 [SMILES: Cc1cccc(-c2[nH]cnc2-c2ccc3ncc(C(=O)OCCCCN4CC5(CNC5)C4)cc3c2)n1] | 4-(2,6-diazaspiro[3.3]heptan-2-yl)butyl 6-(5-(6-methylpyridin-2-yl)-1H-imidazol-4-yl)quinoline-3-carboxylate | |
| 919 | 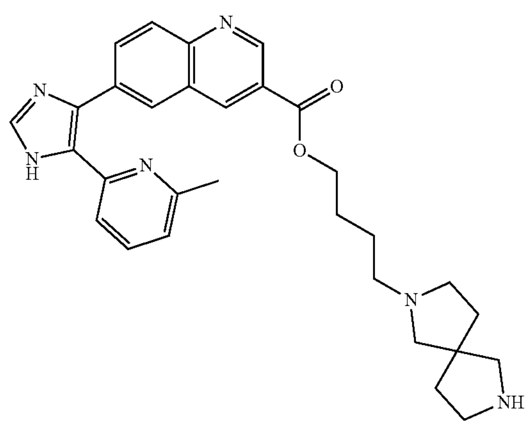 [SMILES: Cc1cccc(-c2[nH]cnc2-c2ccc3ncc(C(=O)OCCCCN4CCC5(CCNC5)C4)cc3c2)n1] | 4-(2,7-diazaspiro[4.4]nonan-2-yl)butyl 6-(5-(6-methylpyridin-2-yl)-1H-imidazol-4-yl)quinoline-3-carboxylate | |
| 920 | 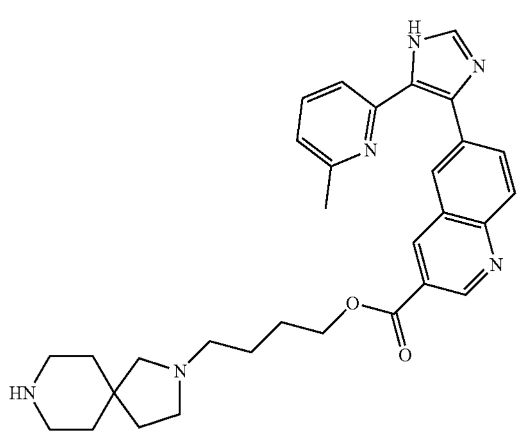 [SMILES: Cc1cccc(-c2[nH]cnc2-c2ccc3ncc(C(=O)OCCCCN4CCC5(CCNCC5)C4)cc3c2)n1] | 4-(2,8-diazaspiro[4.5]decan-2-yl)butyl 6-(5-(6-methylpyridin-2-yl)-1H-imidazol-4-yl)quinoline-3-carboxylate | |

TABLE 1-continued

| No. | Structure | Chemical Name | [M + H]⁺ |
|---|---|---|---|
| 921 | 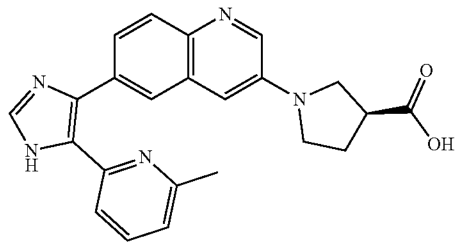 [SMILES: Cc1cccc(-c2[nH]cnc2-c2ccc3ncc(N4CC[C@H](C(=O)O)C4)cc3c2)n1] | (S)-1-(6-(5-(6-methylpyridin-2-yl)-1H-imidazol-4-yl)quinolin-3-yl)pyrrolidine-3-carboxylic acid | |
| 922 | 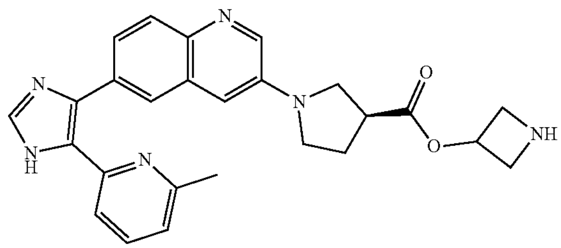 [SMILES: Cc1cccc(-c2[nH]cnc2-c2ccc3ncc(N4CC[C@H](C(=O)OC5CNC5)C4)cc3c2)n1] | azetidin-3-yl (S)-1-(6-(5-(6-methylpyridin-2-yl)-1H-imidazol-4-yl)quinolin-3-yl)pyrrolidine-3-carboxylate | |
| 923 | 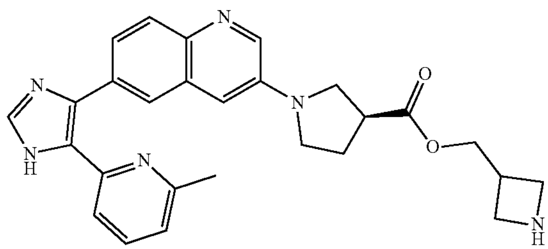 [SMILES: Cc1cccc(-c2[nH]cnc2-c2ccc3ncc(N4CC[C@H](C(=O)OCC5CNC5)C4)cc3c2)n1] | azetidin-3-ylmethyl (S)-1-(6-(5-(6-methylpyridin-2-yl)-1H-imidazol-4-yl)quinolin-3-yl)pyrrolidine-3-carboxylate | |
| 924 | 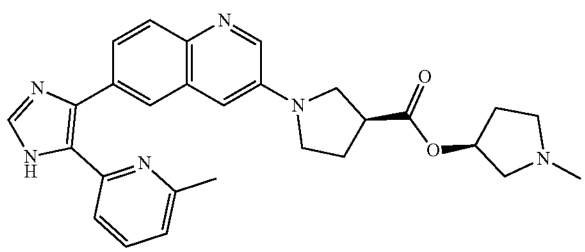 [SMILES: Cc1cccc(-c2[nH]cnc2-c2ccc3ncc(N4CC[C@H](C(=O)O[C@H]5CCN(C)C5)C4)cc3c2)n1] | (S)-1-methylpyrrolidin-3-yl (S)-1-(6-(5-(6-methylpyridin-2-yl)-1H-imidazol-4-yl)quinolin-3-yl)pyrrolidine-3-carboxylate | |
| 925 | 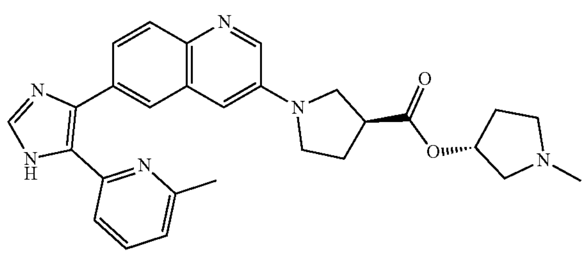 [SMILES: Cc1cccc(-c2[nH]cnc2-c2ccc3ncc(N4CC[C@H](C(=O)O[C@@H]5CCN(C)C5)C4)cc3c2)n1] | (R)-1-methylpyrrolidin-3-yl (S)-1-(6-(5-(6-methylpyridin-2-yl)-1H-imidazol-4-yl)quinolin-3-yl)pyrrolidine-3-carboxylate | |
| 926 | 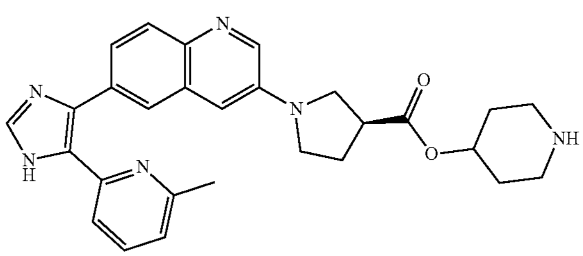 [SMILES: Cc1cccc(-c2[nH]cnc2-c2ccc3ncc(N4CC[C@H](C(=O)OC5CCNCC5)C4)cc3c2)n1] | piperidin-4-yl (S)-1-(6-(5-(6-methylpyridin-2-yl)-1H-imidazol-4-yl)quinolin-3-yl)pyrrolidine-3-carboxylate | |

TABLE 1-continued

| No. | Structure | Chemical Name | [M + H]+ |
|---|---|---|---|
| 927 | 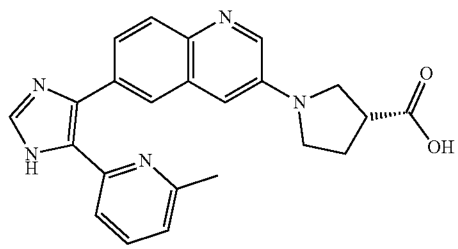 | (R)-1-(6-(5-(6-methylpyridin-2-yl)-1H-imidazol-4-yl)quinolin-3-yl)pyrrolidine-3-carboxylic acid | |
| 928 | 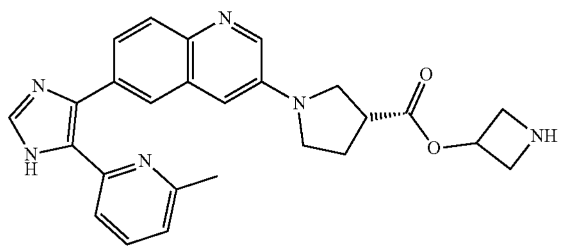 | azetidin-3-yl (R)-1-(6-(5-(6-methylpyridin-2-yl)-1H-imidazol-4-yl)quinolin-3-yl)pyrrolidine-3-carboxylate | |
| 929 | 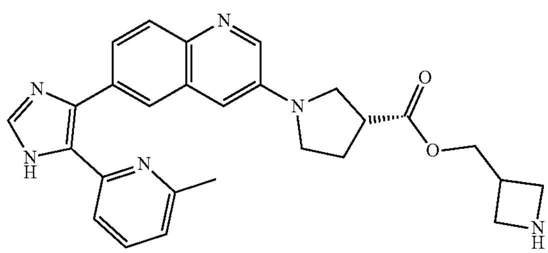 | azetidin-3-ylmethyl (R)-1-(6-(5-(6-methylpyridin-2-yl)-1H-imidazol-4-yl)quinolin-3-yl)pyrrolidine-3-carboxylate | |
| 930 | 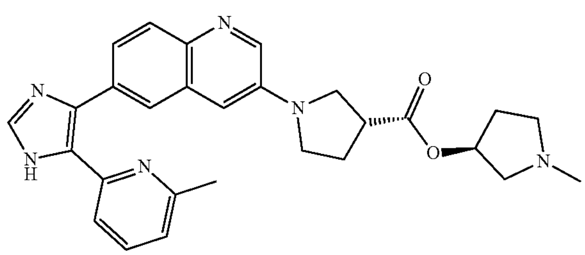 | (S)-1-methylpyrrolidin-3-yl (R)-1-(6-(5-(6-methylpyridin-2-yl)-1H-imidazol-4-yl)quinolin-3-yl)pyrrolidine-3-carboxylate | |
| 931 | 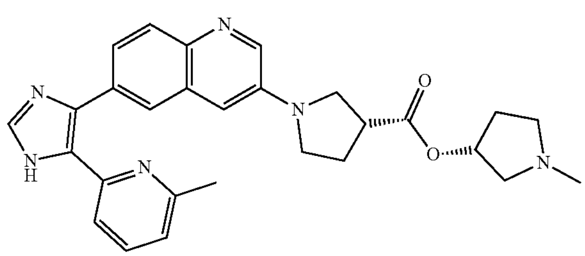 | (R)-1-methylpyrrolidin-3-yl (R)-1-(6-(5-(6-methylpyridin-2-yl)-1H-imidazol-4-yl)quinolin-3-yl)pyrrolidine-3-carboxylate | |
| 932 | 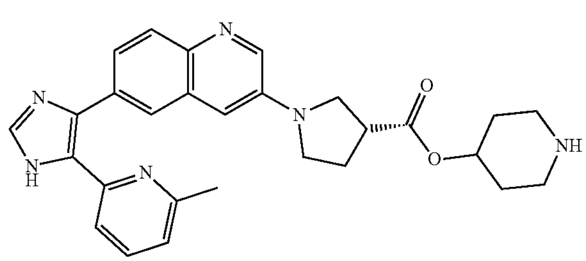 | piperidin-4-yl (R)-1-(6-5-(6-methylpyridin-2-yl)-1H-imidazol-4-yl)quinolin-3-yl)pyrrolidine-3-carboxylate | |

TABLE 1-continued

| No. | Structure | Chemical Name | [M + H]⁺ |
|---|---|---|---|
| 933 | 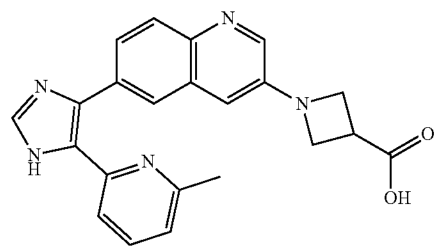 [SMILES: Cc1cccc(-c2[nH]cnc2-c2ccc3ncc(N4CC(C(=O)O)C4)cc3c2)n1] | 1-(6-(5-(6-methylpyridin-2-yl)-1H-imidazol-4-yl)quinolin-3-yl)azetidine-3-carboxylic acid | |
| 934 | 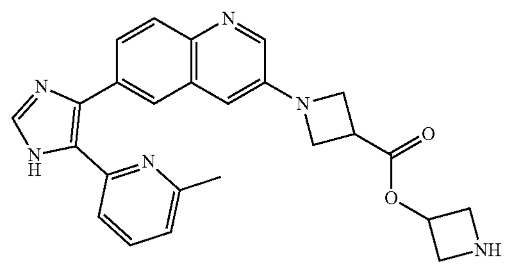 [SMILES: Cc1cccc(-c2[nH]cnc2-c2ccc3ncc(N4CC(C(=O)OC5CNC5)C4)cc3c2)n1] | azetidin-3-yl 1-(6-(5-(6-methylpyridin-2-yl)-1H-imidazol-4-yl)quinolin-3-yl)azetidine-3-carboxylate | |
| 935 | 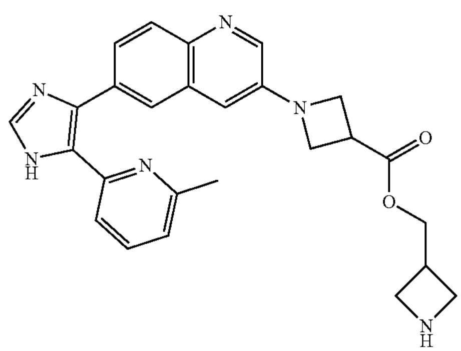 [SMILES: Cc1cccc(-c2[nH]cnc2-c2ccc3ncc(N4CC(C(=O)OCC5CNC5)C4)cc3c2)n1] | azetidin-3-ylmethyl 1-(6-(5-(6-methylpyridin-2-yl)-1H-imidazol-4-yl)quinolin-3-yl)azetidine-3-carboxylate | |
| 936 | 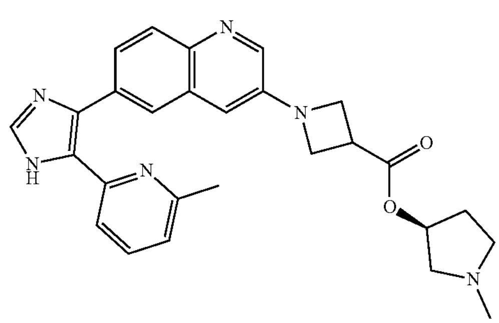 [SMILES: Cc1cccc(-c2[nH]cnc2-c2ccc3ncc(N4CC(C(=O)O[C@H]5CCN(C)C5)C4)cc3c2)n1] | (S)-1-methylpyrrolidin-3-yl 1-(6-(5-(6-methylpyridin-2-yl)-1H-imidazol-4-yl)quinolin-3-yl)azetidine-3-carboxylate | |
| 937 | 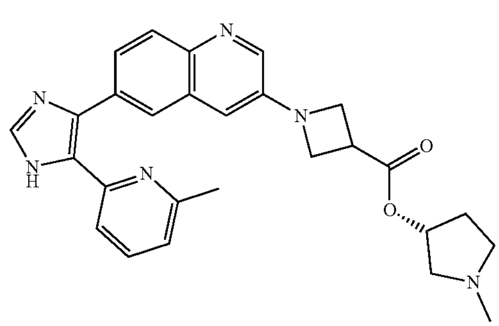 | (R)-1-methylpyrrolidin-3-yl 1-(6-(5-(6-methylpyridin-2-yl)-1H-imidazol-4-yl)quinolin-3-yl)azetidine-3-carboxylate | |

TABLE 1-continued

| No. | Structure | Chemical Name | [M + H]+ |
|---|---|---|---|
| 938 | 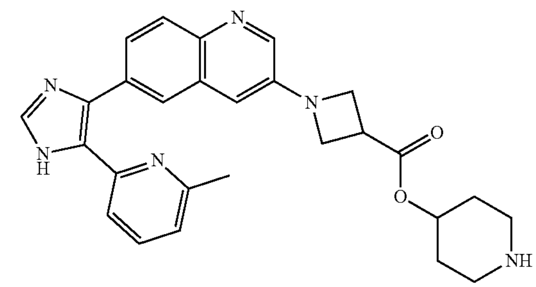 [SMILES: Cc1cccc(-c2[nH]cnc2-c2ccc3ncc(N4CC(C(=O)OC5CCNCC5)C4)cc3c2)n1] | piperidin-4-yl 1-(6-(5-(6-methylpyridin-2-yl)-1H-imidazol-4-yl)quinolin-3-yl)azetidine-3-carboxylate | |
| 939 | 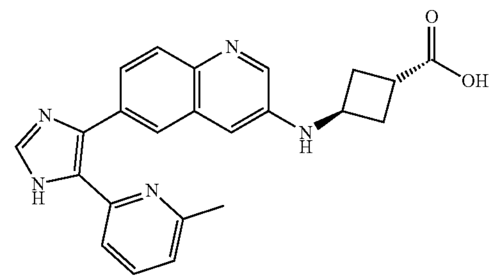 | (1r,3r)-3-((6-(5-(6-methylpyridin-2-yl)-1H-imidazol-4-yl)quinolin-3-yl)amino)cyclobutane-1-carboxylic acid | |
| 940 | 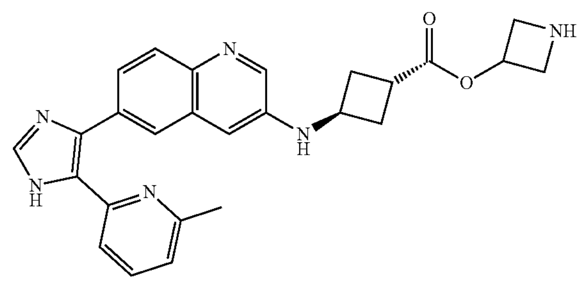 | azetidin-3-yl (1r,3r)-3-((6-(5-(6-methylpyridin-2-yl)-1H-imidazol-4-yl)quinolin-3-yl)amino)cyclobutane-1-carboxylate | |
| 941 | 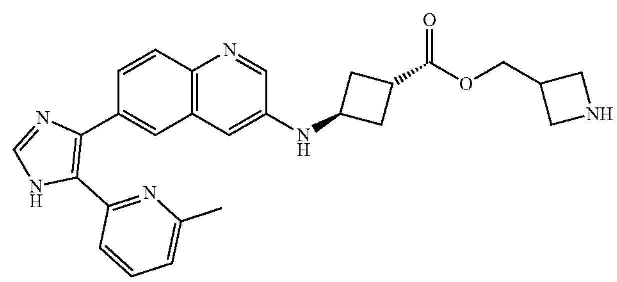 | azetidin-3-ylmethyl (1r,3r)-3-((6-(5-(6-methylpyridin-2-yl)-1H-imidazol-4-yl)quinolin-3-yl)amino)cyclobutane-1-carboxylate | |
| 942 | 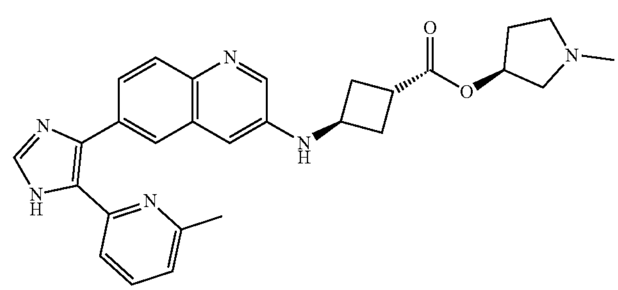 | (S)-1-methylpyrrolidin-3-yl (1r,3s)-3-((6-(5-(6-methylpyridin-2-yl)-1H-imidazol-4-yl)quinolin-3-yl)amino)cyclobutane-1-carboxylate | |

TABLE 1-continued

| No. | Structure | Chemical Name | [M + H]+ |
|---|---|---|---|
| 943 | 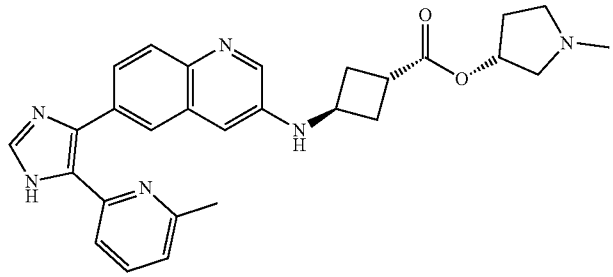 | (R)-1-methylpyrrolidin-3-yl (1r,3r)-3-((6-(5-(6-methylpyridin-2-yl)-1H-imidazol-4-yl)quinolin-3-yl)amino)cyclobutane-1-carboxylate | |
| 944 | 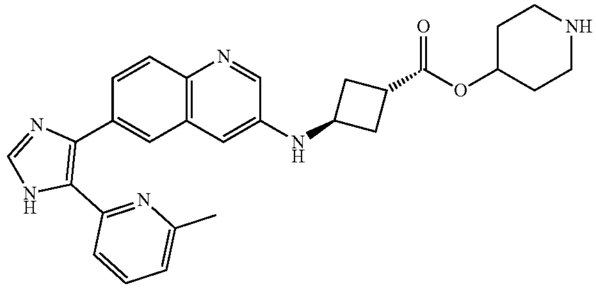 | piperidin-4-yl (1r,3r)-3-((6-(5-(6-methylpyridin-2-yl)-1H-imidazol-4-yl)quinolin-3-yl)amino)cyclobutane-1-carboxylate | |
| 945 | 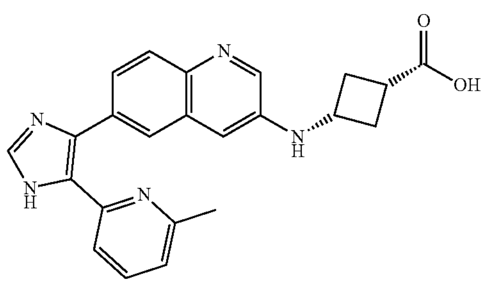 | (1s,3s)-3-((6-(5-(6-methylpyridin-2-yl)-1H-imidazol-4-yl)quinolin-3-yl)amino)cyclobutane-1-carboxylic acid | |
| 946 | 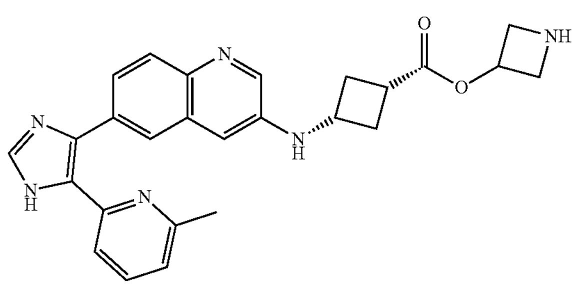 | azetidin-3-yl (1s,3s)-3-((6-(5-(6-methylpyridin-2-yl)-1H-imidazol-4-yl)quinolin-3-yl)amino)cyclobutane-1-carboxylate | |
| 947 | 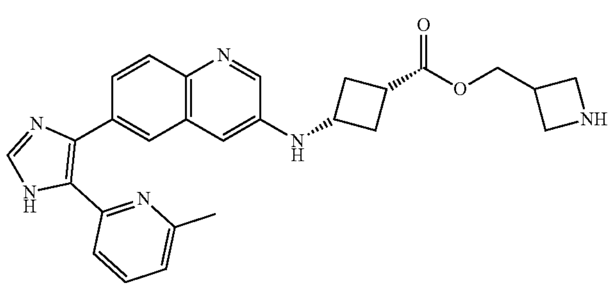 | azetidin-3-ylmethyl (1s,3s)-3-((6-(5-(6-methylpyridin-2-yl)-1H-imidazol-4-yl)quinolin-3-yl)amino)cyclobutane-1-carboxylate | |

TABLE 1-continued

| No. | Structure | Chemical Name | [M + H]⁺ |
|---|---|---|---|
| 948 | 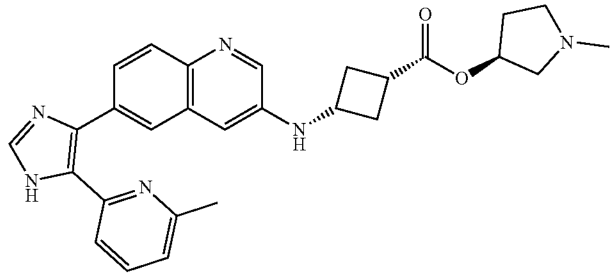 | (S)-1-methylpyrrolidin-3-yl (1s,3r)-3-(((6-(5-(6-methylpyridin-2-yl)-1H-imidazol-4-yl)quinolin-3-yl)amino)cyclobutane-1-carboxylate | |
| 949 | 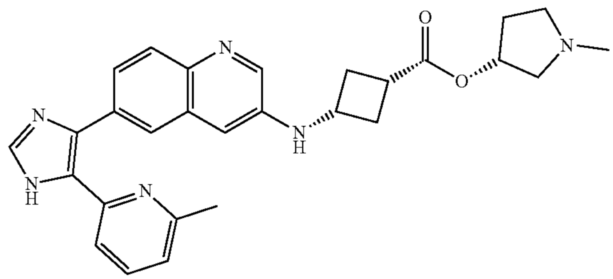 | (R)-1-methylpyrrolidin-3-yl (1s,3s)-3-(((6-(5-(6-methylpyridin-2-yl)-1H-imidazol-4-yl)quinolin-3-yl)amino)cyclobutane-1-carboxylate | |
| 950 | 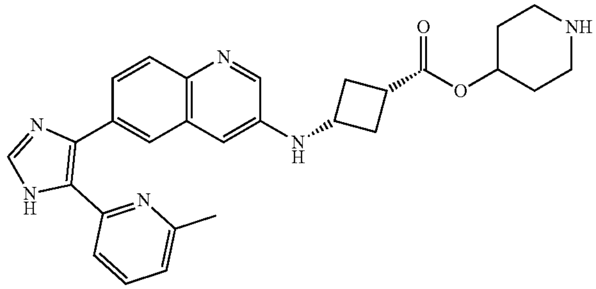 | piperidin-4-yl (1s,3s)-3-((6-(5-(6-methylpyridin-2-yl)-1H-imidazol-4-yl)quinolin-3-yl)amino)cyclobutane-1-carboxylate | |
| 951 | 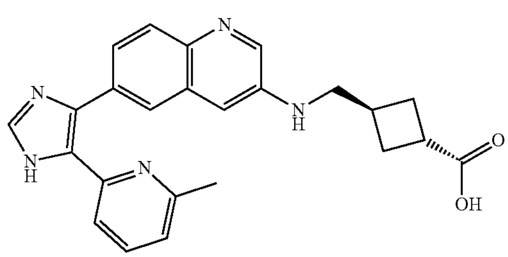 | (1r,3r)-3-(((6-(5-(6-methylpyridin-2-yl)-1H-imidazol-4-yl)quinolin-3-yl)amino)methyl)cyclobutane-1-carboxylic acid | |
| 952 | 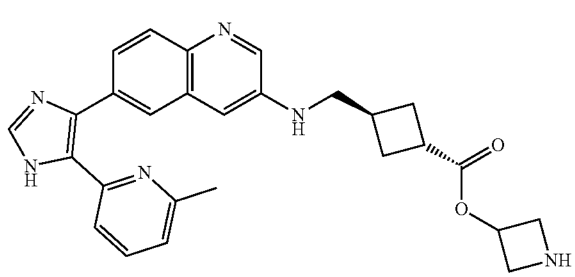 | azetidin-3-yl (1r,3r)-3-(((6-(5-(6-methylpyridin-2-yl)-1H-imidazol-4-yl)quinolin-3-yl)amino)methyl)cyclobutane-1-carboxylate | |

TABLE 1-continued

| No. | Structure | Chemical Name | [M + H]+ |
|---|---|---|---|
| 953 | 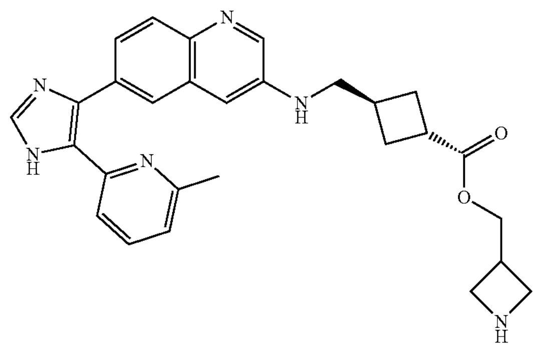 | azetidin-3-ylmethyl (1r,3r)-3-(((6-(5-(6-methylpyridin-2-yl)-1H-imidazol-4-yl)quinolin-3-yl)amino)methyl)cyclobutane-1-carboxylate | |
| 954 | 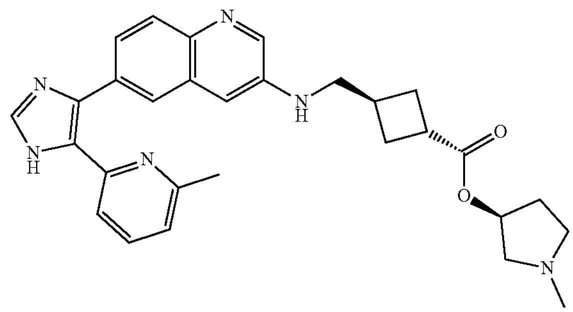 | (S)-1-methylpyrrolidin-3-yl (1r,3s)-3-(((6-(5-(6-methylpyridin-2-yl)-1H-imidazol-4-yl)quinolin-3-yl)amino)methyl)cyclobutane-1-carboxylate | |
| 955 | 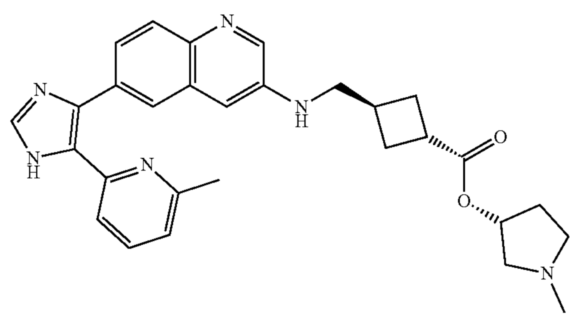 | (R)-1-methylpyrrolidin-3-yl (1r,3r)-3-(((6-(5-(6-methylpyridin-2-yl)-1H-imidazol-4-yl)quinolin-3-yl)amino)methyl)cyclobutane-1-carboxylate | |
| 956 | 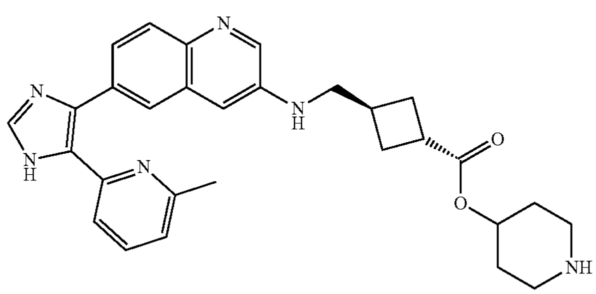 | piperidin-4-yl (1r,3r)-3-(((6-(5-(6-methylpyridin-2-yl)-1H-imidazol-4-yl)quinolin-3-yl)amino)methyl)cyclobutane-1-carboxylate | |
| 957 | 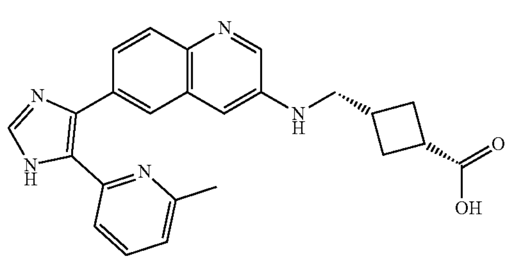 | (1s,3s)-3-(((6-(5-(6-methylpyridin-2-yl)-1H-imidazol-4-yl)quinolin-3-yl)amino)methyl)cyclobutane-1-carboxylic acid | |

TABLE 1-continued

| No. | Structure | Chemical Name | [M + H]⁺ |
|---|---|---|---|
| 958 | 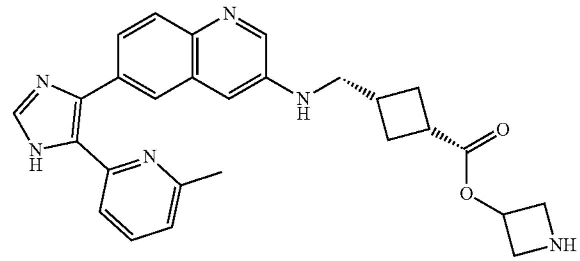 | azetidin-3-yl (1s,3s)-3-(((6-(5-(6-methylpyridin-2-yl)-1H-imidazol-4-yl)quinolin-3-yl)amino)methyl)cyclobutane-1-carboxylate | |
| 959 | 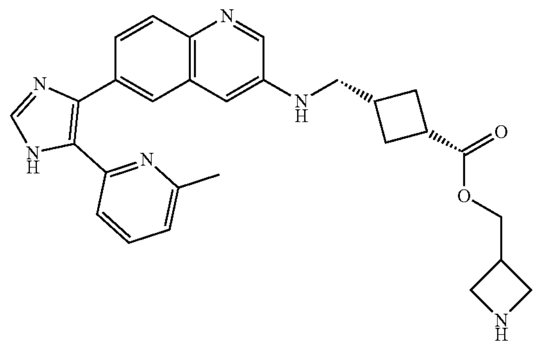 | azetidin-3-ylmethyl (1s,3s)-3-(((6-(5-(6-methylpyridin-2-yl)-1H-imidazol-4-yl)quinolin-3-yl)amino)methyl)cyclobutane-1-carboxylate | |
| 960 | 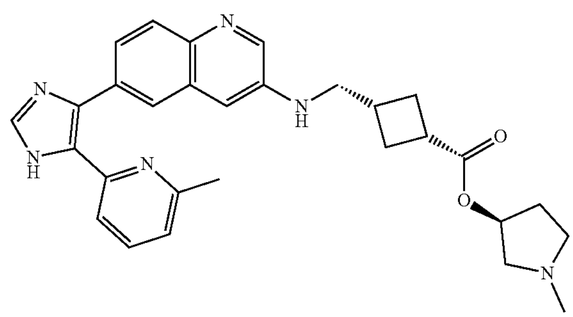 | (S)-1-methylpyrrolidin-3-yl (1r,3s)-3-(((6-(5-(6-methylpyridin-2-yl)-1H-imidazol-4-yl)quinolin-3-yl)amino)methyl)cyclobutane-1-carboxylate | |
| 961 | 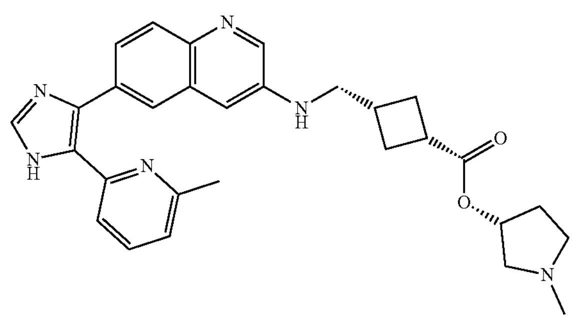 | (R)-1-methylpyrrolidin-3-yl (1s,3s)-3-(((6-(5-(6-methylpyridin-2-yl)-1H-imidazol-4-yl)quinolin-3-yl)amino)methyl)cyclobutane-1-carboxylate | |
| 962 | 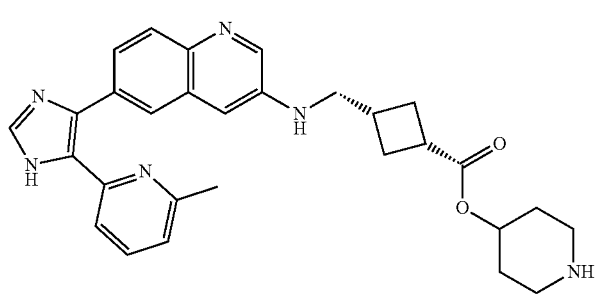 | piperidin-4-yl (1s,3s)-3-(((6-(5-(6-methylpyridin-2-yl)-1H-imidazol-4-yl)quinolin-3-yl)amino)methyl)cyclobutane-1-carboxylate | |

TABLE 1-continued

| No. | Structure | Chemical Name | [M + H]⁺ |
|---|---|---|---|
| 963 | 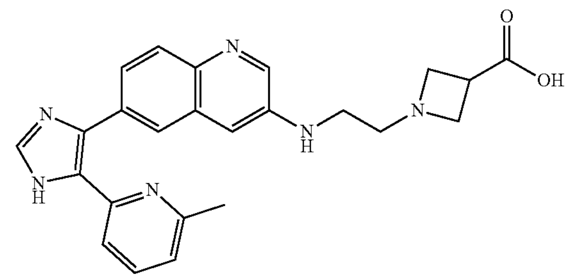 [SMILES: Cc1cccc(-c2[nH]cnc2-c2ccc3ncc(NCCN4CC(C(=O)O)C4)cc3c2)n1] | 1-(2-((6-(5-(6-methylpyridin-2-yl)-1H-imidazol-4-yl)quinolin-3-yl)amino)ethyl)azetidine-3-carboxylic acid | |
| 964 | 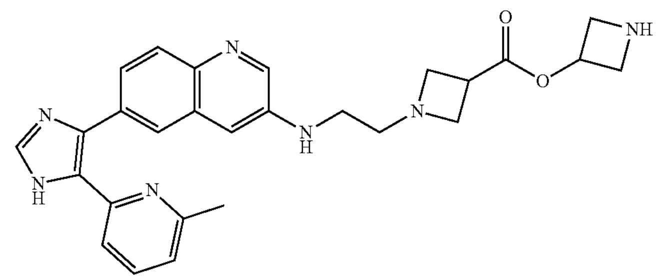 [SMILES: Cc1cccc(-c2[nH]cnc2-c2ccc3ncc(NCCN4CC(C(=O)OC5CNC5)C4)cc3c2)n1] | azetidin-3-yl 1-(2-((6-(5-(6-methylpyridin-2-yl)-1H-imidazol-4-yl)quinolin-3-yl)amino)ethyl)azetidine-3-carboxylate | |
| 965 | 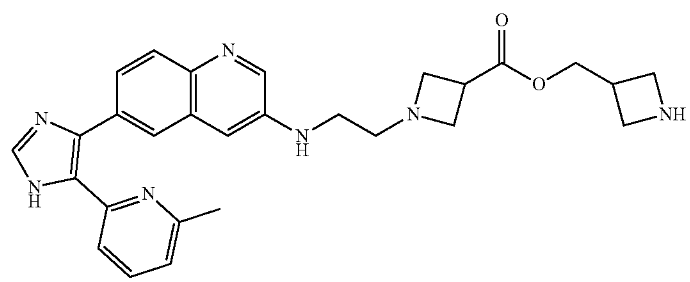 [SMILES: Cc1cccc(-c2[nH]cnc2-c2ccc3ncc(NCCN4CC(C(=O)OCC5CNC5)C4)cc3c2)n1] | azetidin-3-ylmethyl 1-(2-((6-(5-(6-methylpyridin-2-yl)-1H-imidazol-4-yl)quinolin-3-yl)amino)ethyl)azetidine-3-carboxylate | |
| 966 | 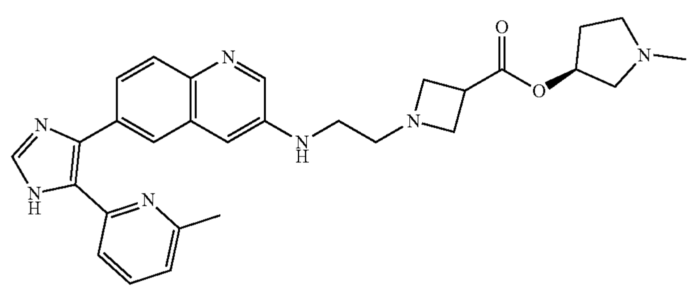 [SMILES: Cc1cccc(-c2[nH]cnc2-c2ccc3ncc(NCCN4CC(C(=O)O[C@H]5CCN(C)C5)C4)cc3c2)n1] | (S)-1-methylpyrrolidin-3-yl 1-(2-((6-(5-(6-methylpyridin-2-yl)-1H-imidazol-4-yl)quinolin-3-yl)amino)ethyl)azetidine-3-carboxylate | |
| 967 | 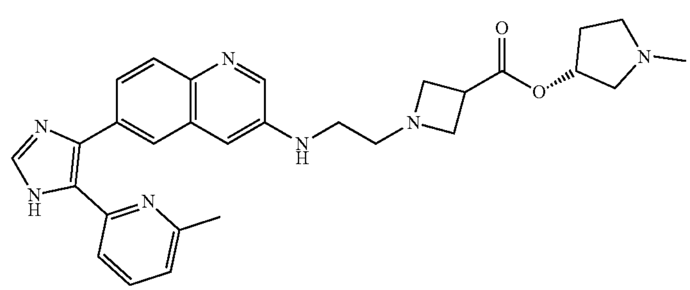 | (R)-1-methylpyrrolidin-3-yl 1-(2-((6-(5-(6-methylpyridin-2-yl)-1H-imidazol-4-yl)quinolin-3-yl)amino)ethyl)azetidine-3-carboxylate | |

| No. | Structure | Chemical Name | [M + H]+ |
|---|---|---|---|
| 968 | 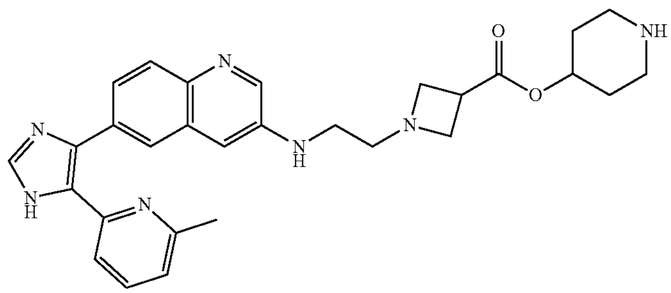 [SMILES: Cc1cccc(-c2[nH]cnc2-c2ccc3ncc(NCCN4CC(C(=O)OC5CCNCC5)C4)cc3c2)n1] | piperidin-4-yl 1-(2-((6-(5-(6-methylpyridin-2-yl)-1H-imidazol-4-yl)quinolin-3-yl)amino)ethyl)azetidine-3-carboxylate | |
| 969 | 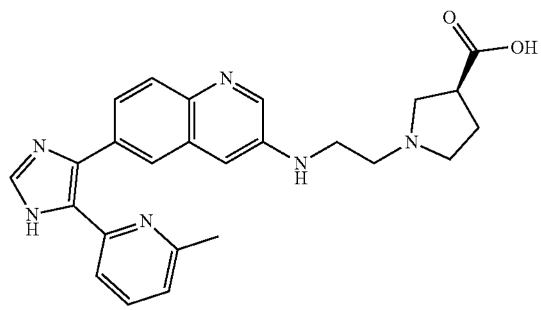 [SMILES: Cc1cccc(-c2[nH]cnc2-c2ccc3ncc(NCCN4CC[C@H](C(=O)O)C4)cc3c2)n1] | (S)-1-(2-((6-(5-(6-methylpyridin-2-yl)-1H-imidazol-4-yl)quinolin-3-yl)amino)ethyl)pyrrolidine-3-carboxylic acid | |
| 970 | 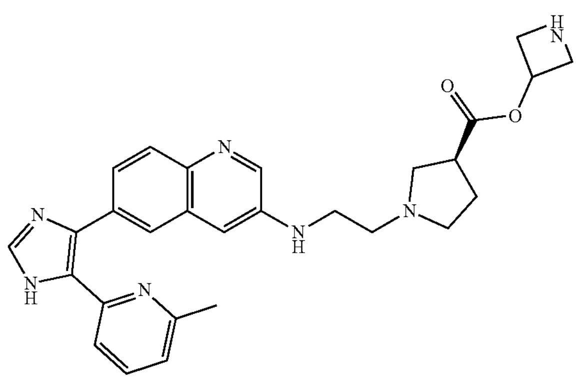 [SMILES: Cc1cccc(-c2[nH]cnc2-c2ccc3ncc(NCCN4CC[C@H](C(=O)OC5CNC5)C4)cc3c2)n1] | azetidin-3-yl (S)-1-(2-((6-(5-(6-methylpyridin-2-yl)-1H-imidazol-4-yl)quinolin-3-yl)amino)ethyl)pyrrolidine-3-carboxylate | |
| 971 | 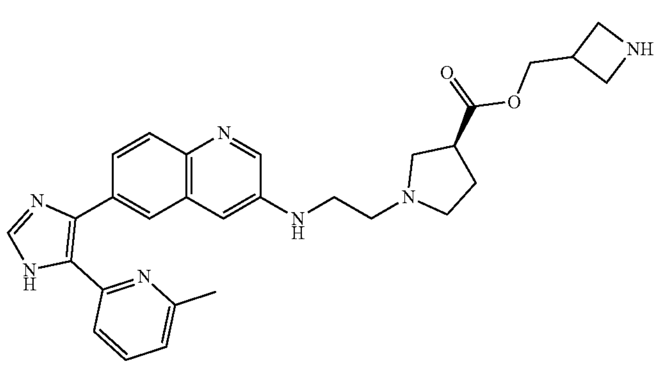 [SMILES: Cc1cccc(-c2[nH]cnc2-c2ccc3ncc(NCCN4CC[C@H](C(=O)OCC5CNC5)C4)cc3c2)n1] | azetidin-3-ylmethyl (S)-1-(2-((6-(5-(6-methylpyridin-2-yl)-1H-imidazol-4-yl)quinolin-3-yl)amino)ethyl)pyrrolidine-3-carboxylate | |

TABLE 1-continued

| No. | Structure | Chemical Name | [M + H]⁺ |
|---|---|---|---|
| 972 | 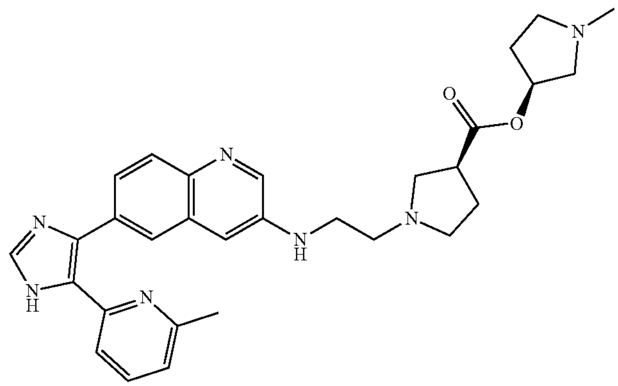 [SMILES: Cc1cccc(-c2[nH]cnc2-c2ccc3ncc(NCCN4CC[C@H](C(=O)O[C@H]5CCN(C)C5)C4)cc3c2)n1] | (S)-1-methylpyrrolidin-3-yl (S)-1-(2-((6-(5-(6-methylpyridin-2-yl)-1H-imidazol-4-yl)quinolin-3-yl)amino)ethyl)pyrrolidine-3-carboxylate | |
| 973 | 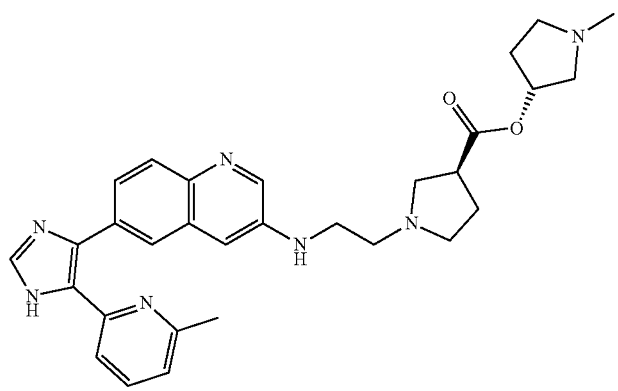 | (R)-1-methylpyrrolidin-3-yl (S)-1-(2-((6-(5-(6-methylpyridin-2-yl)-1H-imidazol-4-yl)quinolin-3-yl)amino)ethyl)pyrrolidine-3-carboxylate | |
| 974 | 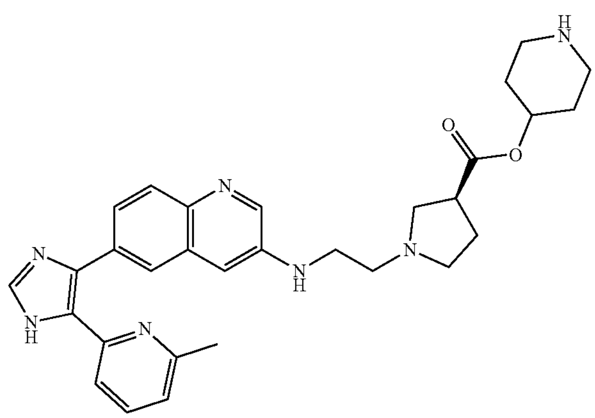 [SMILES: Cc1cccc(-c2[nH]cnc2-c2ccc3ncc(NCCN4CC[C@H](C(=O)OC5CCNCC5)C4)cc3c2)n1] | piperidin-4-yl (S)-1-(2-((6-(5-(6-methylpyridin-2-yl)-1H-imidazol-4-yl)quinolin-3-yl)amino)ethyl)pyrrolidine-3-carboxylate | |
| 975 | 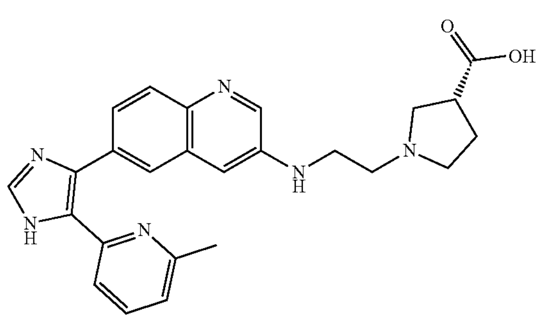 | (R)-1-(2-((6-(5-(6-methylpyridin-2-yl)-1H-imidazol-4-yl)quinolin-3-yl)amino)ethyl)pyrrolidine-3-carboxylic acid | |

TABLE 1-continued

| No. | Structure | Chemical Name | [M + H]+ |
|---|---|---|---|
| 976 | 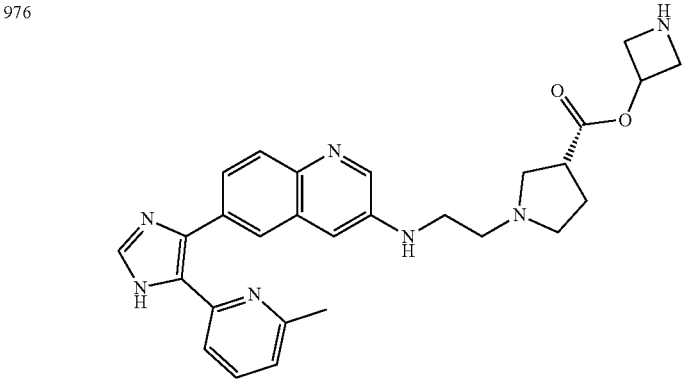 | azetidin-3-yl (R)-1-(2-((6-(5-(6-methylpyridin-2-yl)-1H-imidazol-4-yl)quinolin-3-yl)amino)ethyl)pyrrolidine-3-carboxylate | |
| 977 | 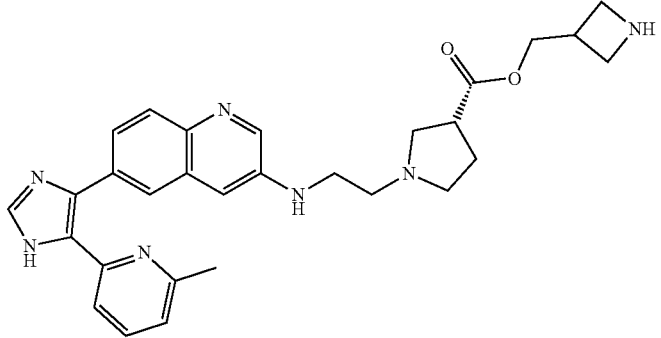 | azetidin-3-ylmethyl (R)-1-(2-((6-(5-(6-methylpyridin-2-yl)-1H-imidazol-4-yl)quinolin-3-yl)amino)ethyl)pyrrolidine-3-carboxylate | |
| 978 | 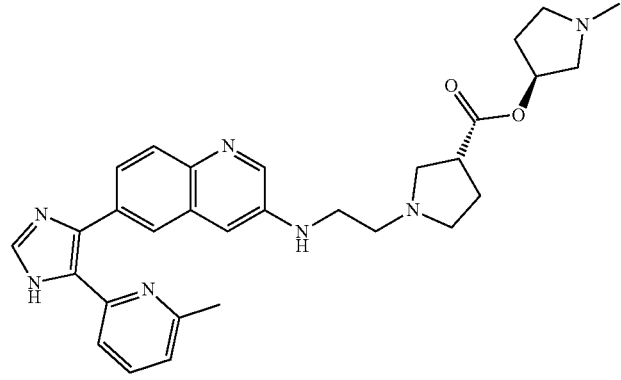 | (S)-1-methylpyrrolidin-3-yl (R)-1-(2-((6-(5-(6-methylpyridin-2-yl)-1H-imidazol-4-yl)quinolin-3-yl)amino)ethyl)pyrrolidine-3-carboxylate | |
| 979 | 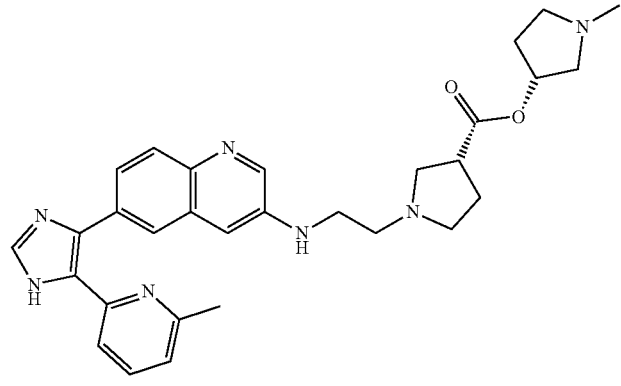 | (R)-1-methylpyrrolidin-3-yl (R)-1-(2-((6-(5-(6-methylpyridin-2-yl)-1H-imidazol-4-yl)quinolin-3-yl)amino)ethyl)pyrrolidine-3-carboxylate | |

TABLE 1-continued

| No. | Structure | Chemical Name | [M + H]+ |
|---|---|---|---|
| 980 | 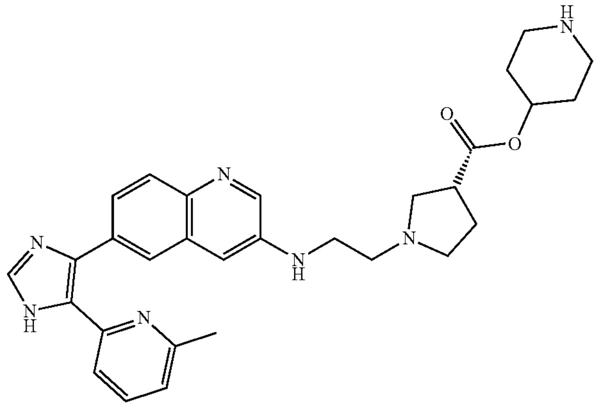 | piperidin-4-yl (R)-1-(2-((6-(5-(6-methylpyridin-2-yl)-1H-imidazol-4-yl)quinolin-3-yl)amino)ethyl)pyrrolidine-3-carboxylate | |
| 981 | 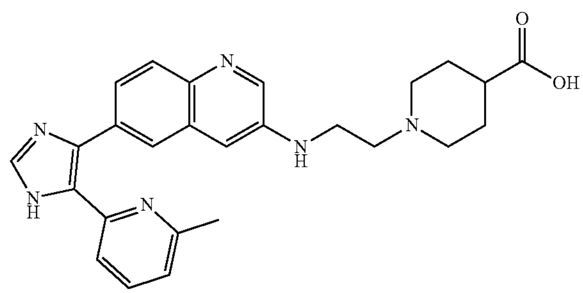 [SMILES: Cc1cccc(-c2[nH]cnc2-c2ccc3ncc(NCCN4CCC(C(=O)O)CC4)cc3c2)n1] | 1-(2-((6-(5-(6-methylpyridin-2-yl)-1H-imidazol-4-yl)quinolin-3-yl)amino)ethyl)piperidine-4-carboxylic acid | 457.1 |
| 982 | 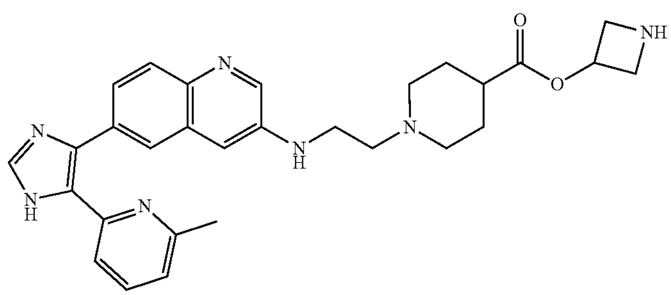 [SMILES: Cc1cccc(-c2[nH]cnc2-c2ccc3ncc(NCCN4CCC(C(=O)OC5CNC5)CC4)cc3c2)n1] | azetidin-3-yl 1-(2-((6-(5-(6-methylpyridin-2-yl)-1H-imidazol-4-yl)quinolin-3-yl)amino)ethyl)piperidine-4-carboxylate | |
| 983 | 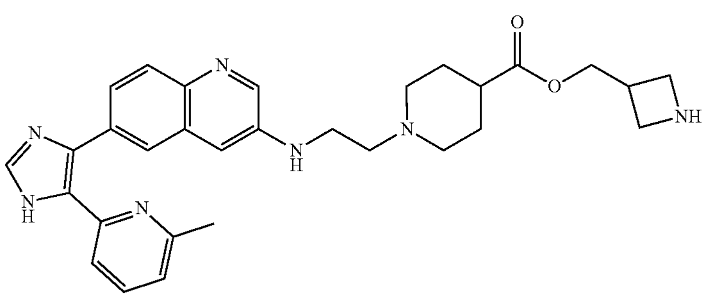 [SMILES: Cc1cccc(-c2[nH]cnc2-c2ccc3ncc(NCCN4CCC(C(=O)OCC5CNC5)CC4)cc3c2)n1] | azetidin-3-ylmethyl 1-(2-((6-(5-(6-methylpyridin-2-yl)-1H-imidazol-4-yl)quinolin-3-yl)amino)ethyl)piperidine-4-carboxylate | |
| 984 | 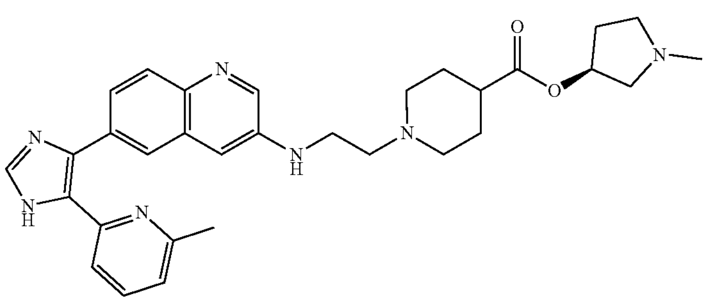 [SMILES: Cc1cccc(-c2[nH]cnc2-c2ccc3ncc(NCCN4CCC(C(=O)O[C@H]5CCN(C)C5)CC4)cc3c2)n1] | (S)-1-methylpyrrolidin-3-yl 1-(2-((6-(5-(6-methylpyridin-2-yl)-1H-imidazol-4-yl)quinolin-3-yl)amino)ethyl)piperidine-4-carboxylate | |

TABLE 1-continued

| No. | Structure | Chemical Name | [M + H]⁺ |
|---|---|---|---|
| 985 | 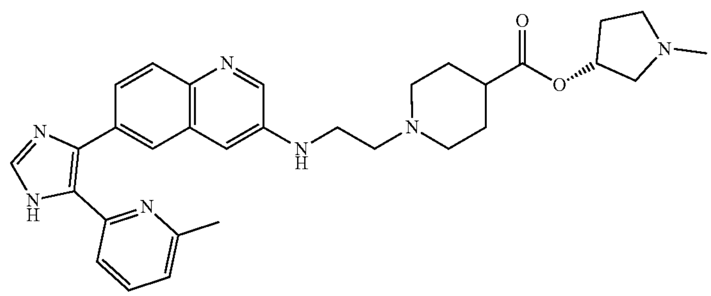 | (R)-1-methylpyrrolidin-3-yl 1-(2-((6-(5-(6-methylpyridin-2-yl)-1H-imidazol-4-yl)quinolin-3-yl)amino)ethyl)piperidine-4-carboxylate | |
| 986 | 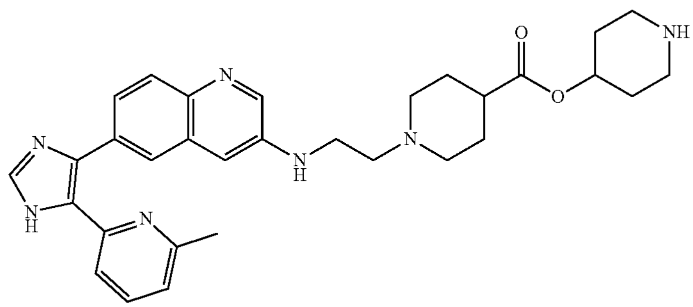 [SMILES: Cc1cccc(-c2[nH]cnc2-c2ccc3ncc(NCCN4CCC(C(=O)OC5CCNCC5)CC4)cc3c2)n1] | piperidin-4-yl 1-(2-((6-(5-(6-methylpyridin-2-yl)-1H-imidazol-4-yl)quinolin-3-yl)amino)ethyl)piperidine-4-carboxylate | |
| 987 | 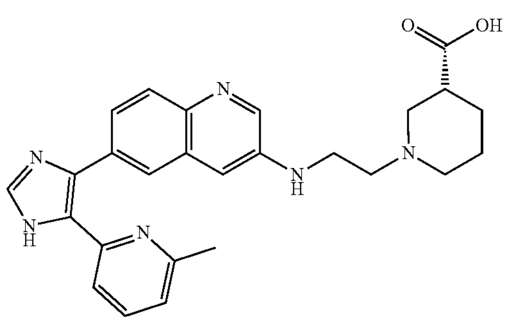 | (R)-1-(2-((6-(5-(6-methylpyridin-2-yl)-1H-imidazol-4-yl)quinolin-3-yl)amino)ethyl)piperidine-3-carboxylic acid | |
| 988 | 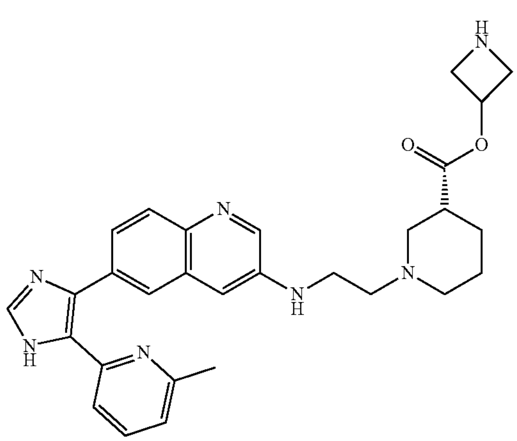 | azetidin-3-yl (R)-1-(2-((6-(5-(6-methylpyridin-2-yl)-1H-imidazol-4-yl)quinolin-3-yl)amino)ethyl)piperidine-3-carboxylate | |

TABLE 1-continued

| No. | Structure | Chemical Name | [M + H]+ |
|---|---|---|---|
| 989 | 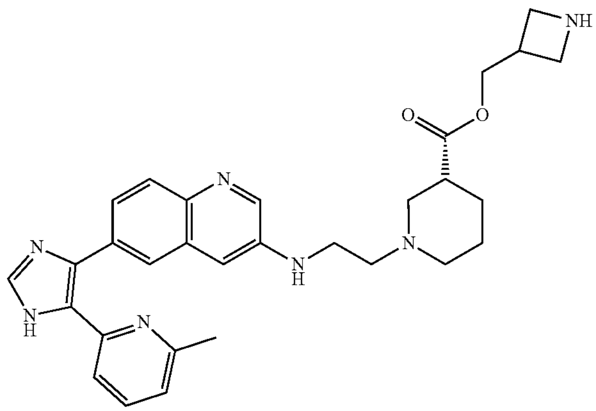 | azetidin-3-ylmethyl (R)-1-(2-((6-(5-(6-methylpyridin-2-yl)-1H-imidazol-4-yl)quinolin-3-yl)amino)ethyl)piperidine-3-carboxylate | |
| 990 | 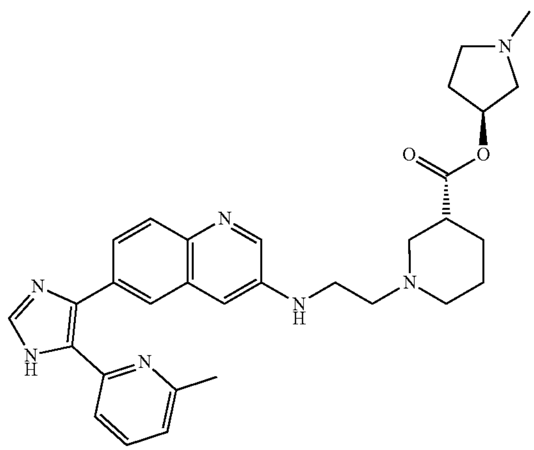 | (S)-1-methylpyrrolidin-3-yl (R)-1-(2-((6-(5-(6-methylpyridin-2-yl)-1H-imidazol-4-yl)quinolin-3-yl)amino)ethyl)piperidine-3-carboxylate | |
| 991 | 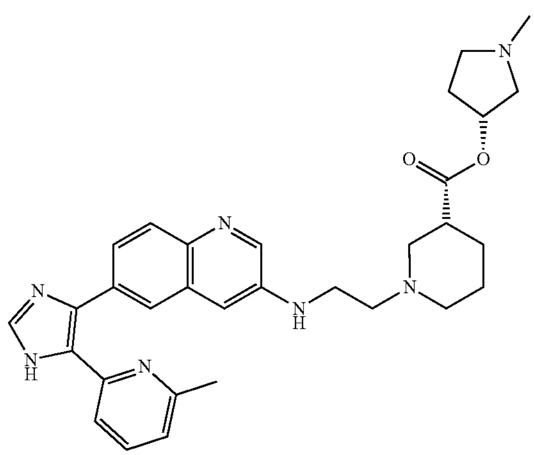 | (R)-1-methylpyrrolidin-3-yl (R)-1-(2-((6-(5-(6-methylpyridin-2-yl)-1H-imidazol-4-yl)quinolin-3-yl)amino)ethyl)piperidine-3-carboxylate | |

TABLE 1-continued

| No. | Structure | Chemical Name | [M + H]+ |
|---|---|---|---|
| 992 | 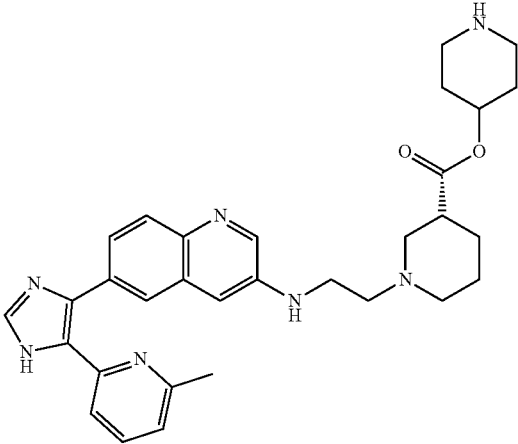 | piperidin-4-yl (R)-1-(2-((6-(5-(6-methylpyridin-2-yl)-1H-imidazol-4-yl)quinolin-3-yl)amino)ethyl)piperidine-3-carboxylate | |
| 993 | 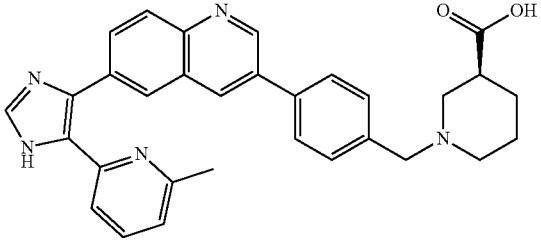 [SMILES: Cc1cccc(-c2[nH]cnc2-c2ccc3ncc(-c4ccc(CN5CCC[C@H](C(=O)O)C5)cc4)cc3c2)n1] | (S)-1-(4-(6-(5-(6-methylpyridin-2-yl)-1H-imidazol-4-yl)quinolin-3-yl)benzyl)piperidine-3-carboxylic acid | |
| 994 | 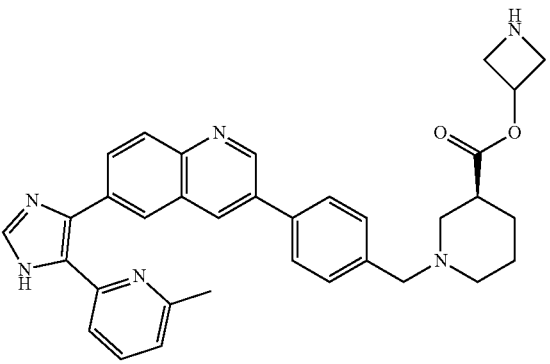 [SMILES: Cc1cccc(-c2[nH]cnc2-c2ccc3ncc(-c4ccc(CN5CCC[C@H](C(=O)OC6CNC6)C5)cc4)cc3c2)n1] | azetidin-3-yl (S)-1-(4-(6-(5-(6-methylpyridin-2-yl)-1H-imidazol-4-yl)quinolin-3-yl)benzyl)piperidine-3-carboxylate | |
| 995 | 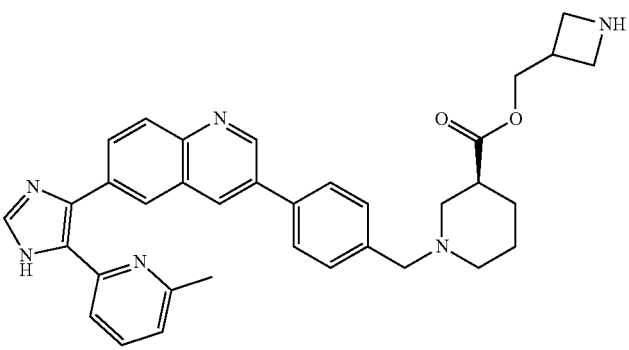 [SMILES: Cc1cccc(-c2[nH]cnc2-c2ccc3ncc(-c4ccc(CN5CCC[C@H](C(=O)OCC6CNC6)C5)cc4)cc3c2)n1] | azetidin-3-ylmethyl (S)-1-(4-(6-(5-(6-methylpyridin-2-yl)-1H-imidazol-4-yl)quinolin-3-yl)benzyl)piperidine-3-carboxylate | |

TABLE 1-continued

| No. | Structure | Chemical Name | [M + H]⁺ |
|---|---|---|---|
| 996 | 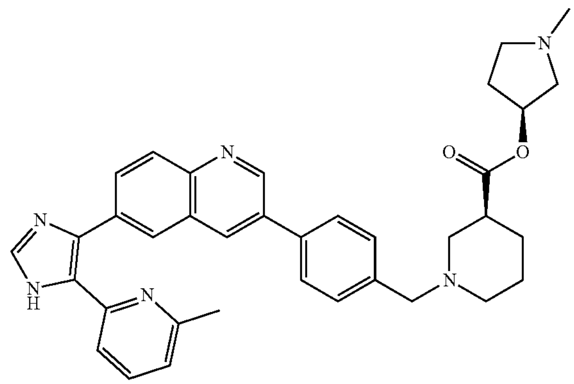 [SMILES: Cc1cccc(-c2[nH]cnc2-c2ccc3ncc(-c4ccc(CN5CCC[C@H](C(=O)O[C@H]6CCN(C)C6)C5)cc4)cc3c2)n1] | (S)-1-methylpyrrolidin-3-yl (S)-1-(4-(6-(5-(6-methylpyridin-2-yl)-1H-imidazol-4-yl)quinolin-3-yl)benzyl)piperidine-3-carboxylate | |
| 997 | 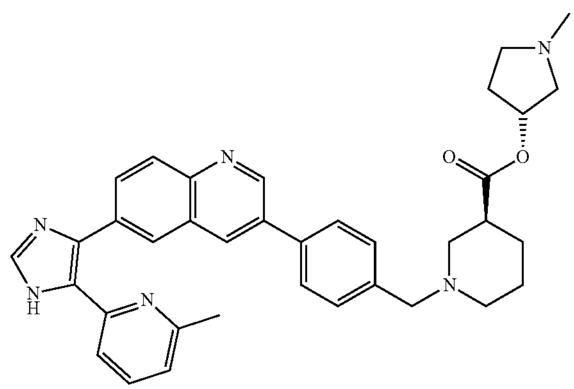 | (R)-1-methylpyrrolidin-3-yl (S)-1-(4-(6-(5-(6-methylpyridin-2-yl)-1H-imidazol-4-yl)quinolin-3-yl)benzyl)piperidine-3-carboxylate | |
| 998 | 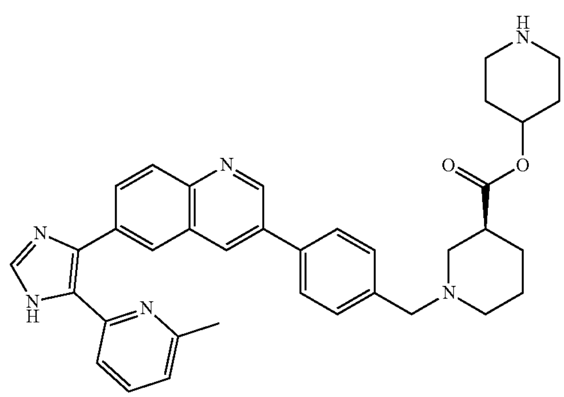 [SMILES: Cc1cccc(-c2[nH]cnc2-c2ccc3ncc(-c4ccc(CN5CCC[C@H](C(=O)OC6CCNCC6)C5)cc4)cc3c2)n1] | piperidin-4-yl (S)-1-(4-(6-(5-(6-methylpyridin-2-yl)-1H-imidazol-4-yl)quinolin-3-yl)benzyl)piperidine-3-carboxylate | |
| 999 | 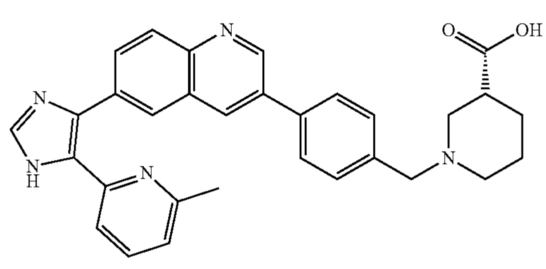 | (R)-1-(4-(6-(5-(6-methylpyridin-2-yl)-1H-imidazol-4-yl)quinolin-3-yl)benzyl)piperidine-3-carboxylic acid | |

TABLE 1-continued

| No. | Structure | Chemical Name | [M + H]+ |
|---|---|---|---|
| 1000 | 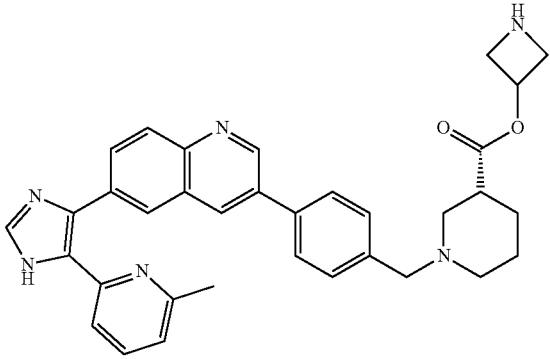 | azetidin-3-yl (R)-1-(4-(6-(5-(6-methylpyridin-2-yl)-1H-imidazol-4-yl)quinolin-3-yl)benzyl)piperidine-3-carboxylate | |
| 1001 | 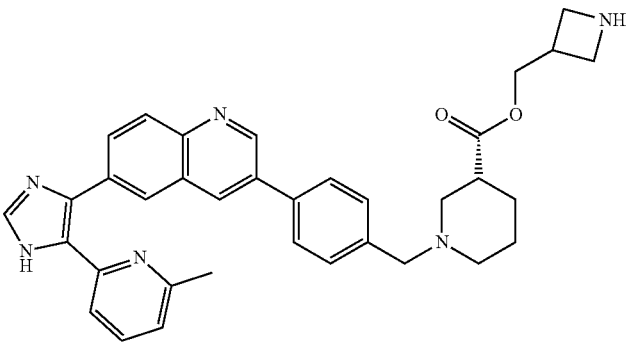 | azetidin-3-ylmethyl (R)-1-(4-(6-(5-(6-methylpyridin-2-yl)-1H-imidazol-4-yl)quinolin-3-yl)benzyl)piperidine-3-carboxylate | |
| 1002 | 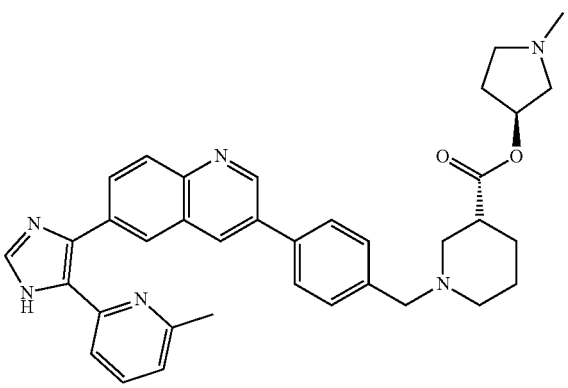 | (S)-1-methylpyrrolidin-3-yl (R)-1-(4-(6-(5-(6-methylpyridin-2-yl)-1H-imidazol-4-yl)quinolin-3-yl)benzyl)piperidine-3-carboxylate | |
| 1003 | 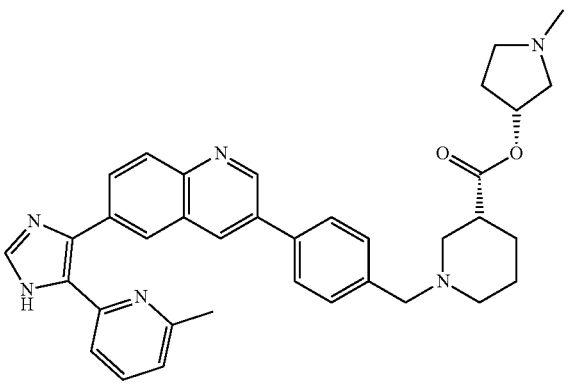 | (R)-1-methylpyrrolidin-3-yl (R)-1-(4-(6-(5-(6-methylpyridin-2-yl)-1H-imidazol-4-yl)quinolin-3-yl)benzyl)piperidine-3-carboxylate | |

TABLE 1-continued

| No. | Structure | Chemical Name | [M + H]+ |
|---|---|---|---|
| 1004 | 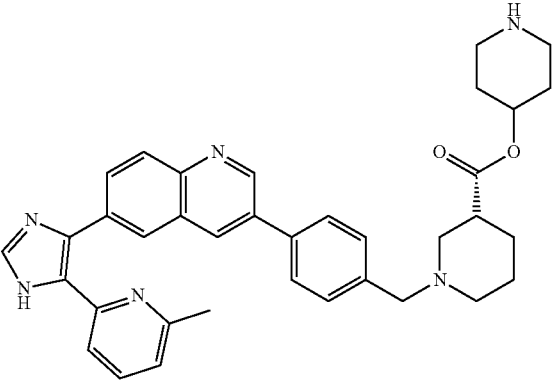 | piperidin-4-yl (R)-1-(4-(6-(5-(6-methylpyridin-2-yl)-1H-imidazol-4-yl)quinolin-3-yl)benzyl)piperidine-3-carboxylate | |
| 1005 | 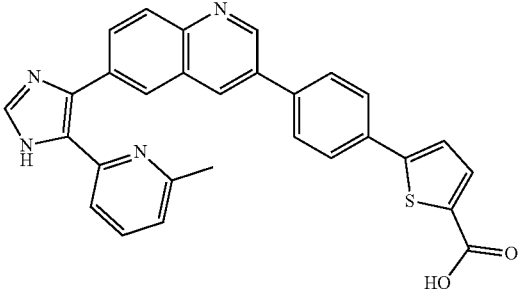 [SMILES: Cc1cccc(-c2[nH]cnc2-c2ccc3ncc(-c4ccc(-c5ccc(C(=O)O)s5)cc4)cc3c2)n1] | 5-(6-(5-(6-methylpyridin-2-yl)-1H-imidazol-4-yl)quinolin-3-yl)thiophene-2-carboxylic acid | 413.0 |
| 1006 | 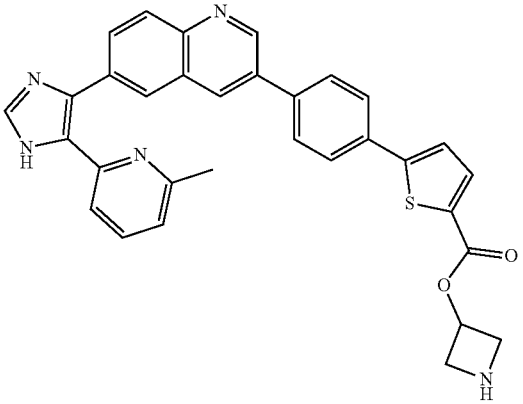 [SMILES: Cc1cccc(-c2[nH]cnc2-c2ccc3ncc(-c4ccc(-c5ccc(C(=O)OC6CNC6)s5)cc4)cc3c2)n1] | azetidin-3-yl 5-(6-(5-(6-methylpyridin-2-yl)-1H-imidazol-4-yl)quinolin-3-yl)thiophene-2-carboxylate | 468.1 |
| 1007 | 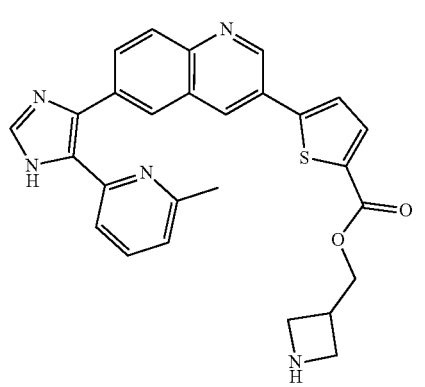 | azetidin-3-ylmethyl 5-(6-(5-(6-methylpyridin-2-yl)-1H-imidazol-4-yl)quinolin-3-yl)thiophene-2-carboxylate | 482.1 |

| No. | Structure | Chemical Name | [M + H]+ |
|---|---|---|---|
| 1008 | 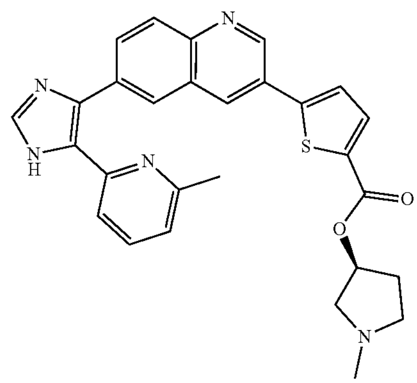 | (S)-1-methylpyrrolidin-3-yl 5-(6-(5-(6-methylpyridin-2-yl)-1H-imidazol-4-yl)quinolin-3-yl)thiophene-2-carboxylate | 482.1 |
| 1009 | 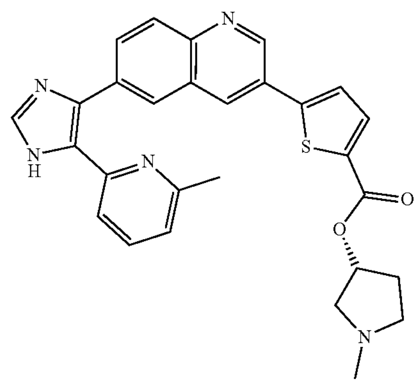 | (R)-1-methylpyrrolidin-3-yl 5-(6-(5-(6-methylpyridin-2-yl)-1H-imidazol-4-yl)quinolin-3-yl)thiophene-2-carboxylate | 482.1 |
| 1010 | 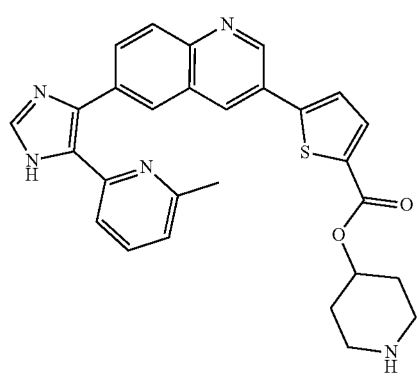 | piperidin-4-yl 5-(6-(5-(6-methylpyridin-2-yl)-1H-imidazol-4-yl)quinolin-3-yl)thiophene-2-carboxylate | 496.0 |
| 1011 | 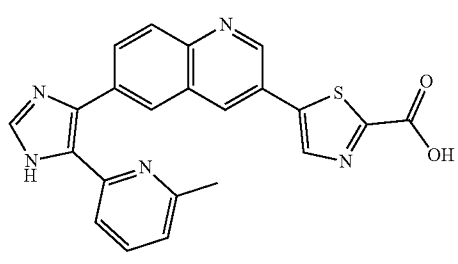 | 5-(6-(5-(6-methylpyridin-2-yl)-1H-imidazol-4-yl)quinolin-3-yl)thiazole-2-carboxylic acid | |

501
502

TABLE 1-continued

| No. | Structure | Chemical Name | [M + H]+ |
|---|---|---|---|
| 1012 | 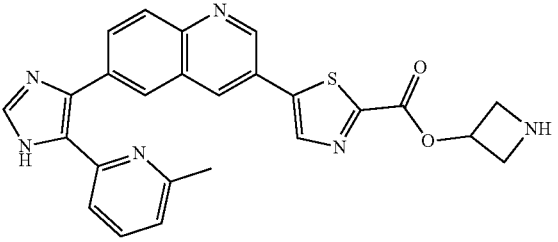 | azetidin-3-yl 5-(6-(5-(6-methylpyridin-2-yl)-1H-imidazol-4-yl)quinolin-3-yl)thiazole-2-carboxylate | |
| 1013 | 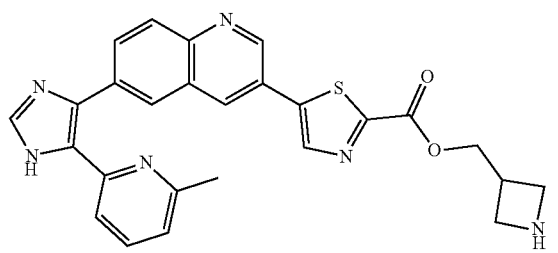 | azetidin-3-ylmethyl 5-(6-(5-(6-methylpyridin-2-yl)-1H-imidazol-4-yl)quinolin-3-yl)thiazole-2-carboxylate | |
| 1014 | 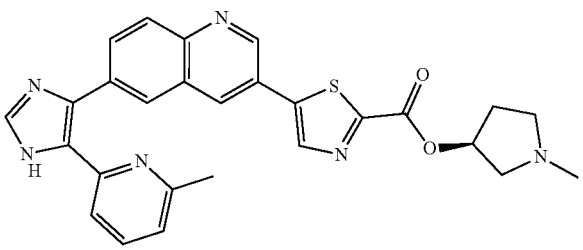 | (S)-1-methylpyrrolidin-3-yl 5-(6-(5-(6-methylpyridin-2-yl)-1H-imidazol-4-yl)quinolin-3-yl)thiazole-2-carboxylate | |
| 1015 | 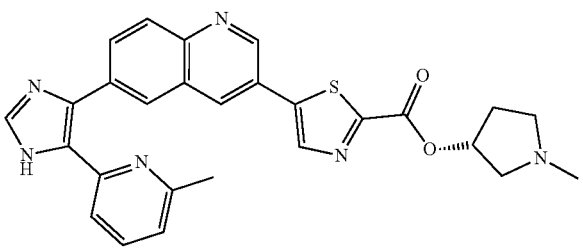 | (R)-1-methylpyrrolidin-3-yl 5-(6-(5-(6-methylpyridin-2-yl)-1H-imidazol-4-yl)quinolin-3-yl)thiazole-2-carboxylate | |
| 1016 | 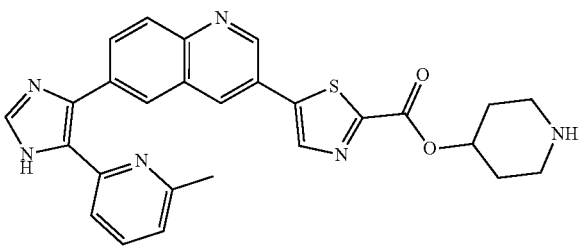 | piperidin-4-yl 5-(6-(5-(6-methylpyridin-2-yl)-1H-imidazol-4-yl)quinolin-3-yl)thiazole-2-carboxylate | |
| 1017 | 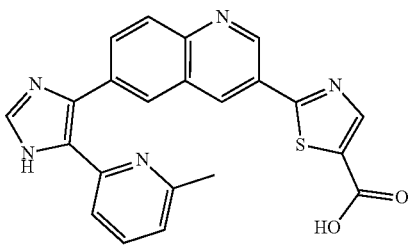 | 2-(6-(5-(6-methylpyridin-2-yl)-1H-imidazol-4-yl)quinolin-3-yl)thiazole-5-carboxylic acid | 414.1 |

TABLE 1-continued

| No. | Structure | Chemical Name | [M + H]⁺ |
|---|---|---|---|
| 1018 | 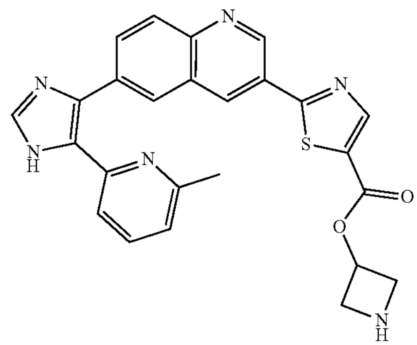 | azetidin-3-yl 2-(6-(5-(6-methylpyridin-2-yl)-1H-imidazol-4-yl)quinolin-3-yl)thiazole-5-carboxylate | 469.1 |
| 1019 | 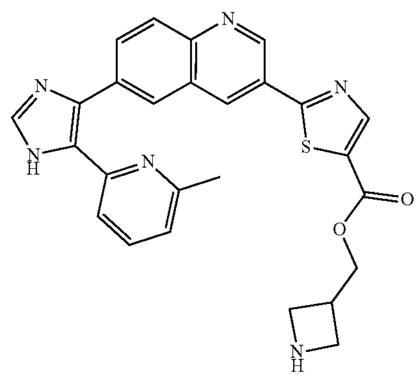 | azetidin-3-ylmethyl 2-(6-(5-(6-methylpyridin-2-yl)-1H-imidazol-4-yl)quinolin-3-yl)thiazole-5-carboxylate | |
| 1020 | 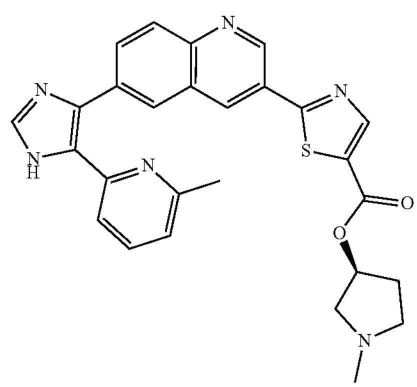 | (S)-1-methylpyrrolidin-3-yl 2-(6-(5-(6-methylpyridin-2-yl)-1H-imidazol-4-yl)quinolin-3-yl)thiazole-5-carboxylate | |
| 1021 | 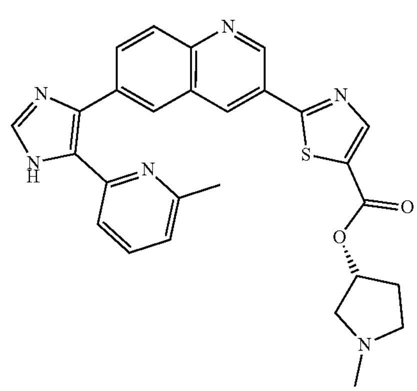 | (R)-1-methylpyrrolidin-3-yl 2-(6-(5-(6-methylpyridin-2-yl)-1H-imidazol-4-yl)quinolin-3-yl)thiazole-5-carboxylate | |

| No. | Structure | Chemical Name | [M + H]⁺ |
|---|---|---|---|
| 1022 | 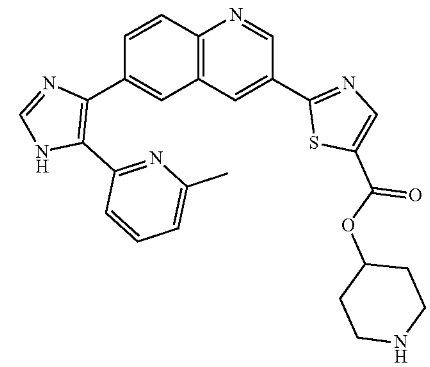 [SMILES: Cc1cccc(-c2[nH]cnc2-c2ccc3ncc(-c4ncc(C(=O)OC5CCNCC5)s4)cc3c2)n1] | piperidin-4-yl 2-(6-(5-(6-methylpyridin-2-yl)-1H-imidazol-4-yl)quinolin-3-yl)thiazole-5-carboxylate | 497.1 |
| 1023 | 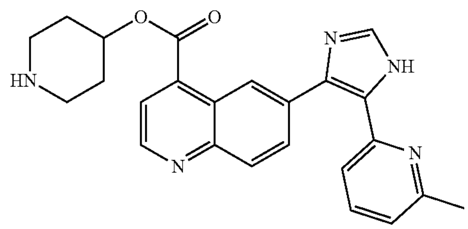 [SMILES: Cc1cccc(-c2[nH]cnc2-c2ccc3nccc(C(=O)OC4CCNCC4)c3c2)n1] | 4-piperidyl 6-[5-(6-methyl-2-pyridyl)-1H-imidazol-4-yl]quinoline-4-carboxylate | |
| 1024 | 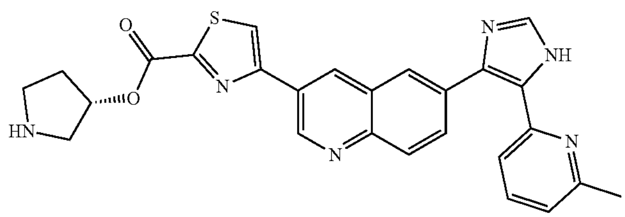 [SMILES: Cc1cccc(-c2[nH]cnc2-c2ccc3ncc(-c4csc(C(=O)O[C@H]5CCNC5)n4)cc3c2)n1] | [(3S)-pyrrolidin-3-yl] 4-[6-[5-(6-methyl-2-pyridyl)-1H-imidazol-4-yl]-3-quinolyl]thiazole-2-carboxylate | 483.2 |
| 1025 | 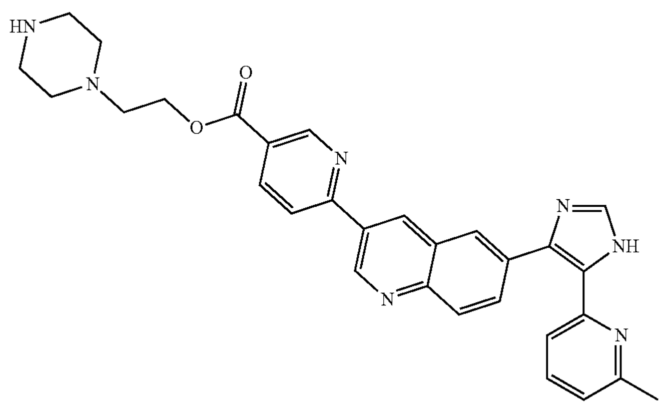 | 2-piperazin-1-ylethyl 6-[6-[5-(6-methyl-2-pyridyl)-1H-imidazol-4-yl]-3-quinolyl]pyridine-3-carboxylate | 520.2 |
| 1026 | 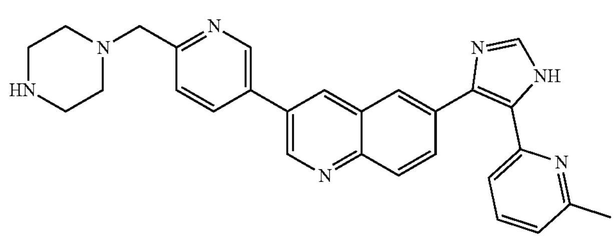 [SMILES: Cc1cccc(-c2[nH]cnc2-c2ccc3ncc(-c4ccc(CN5CCNCC5)nc4)cc3c2)n1] | 6-[5-(6-methyl-2-pyridyl)-1H-imidazol-4-yl]-3-[6-(piperazin-1-ylmethyl)-3-pyridyl]quinoline | 462.1 |

TABLE 1-continued

| No. | Structure | Chemical Name | [M + H]+ |
| --- | --- | --- | --- |
| 1027 | 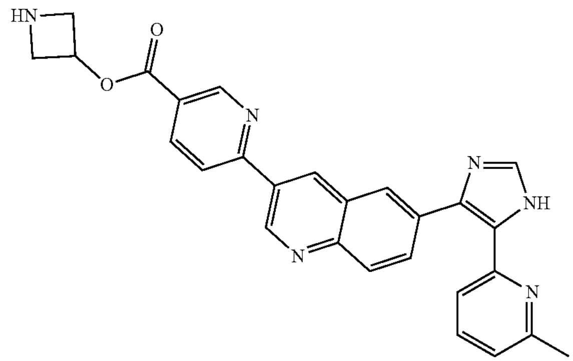 [SMILES: Cc1cccc(-c2[nH]cnc2-c2ccc3ncc(-c4ccc(C(=O)OC5CNC5)cn4)cc3c2)n1] | azetidin-3-yl 6-[6-[5-(6-methyl-2-pyridyl)-1H-imidazol-4-yl]-3-quinolyl]pyridine-3-carboxylate | 463.2 |
| 1028 | 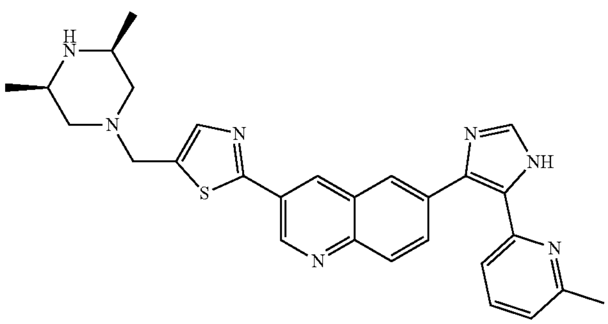 | 5-[[(3S,5R)-3,5-dimethylpiperazin-1-yl]methyl]-2-[6-[5-(6-methyl-2-pyridyl)-1H-imidazol-4-yl]-3-quinolyl]thiazole | 496.1 |
| 1029 | 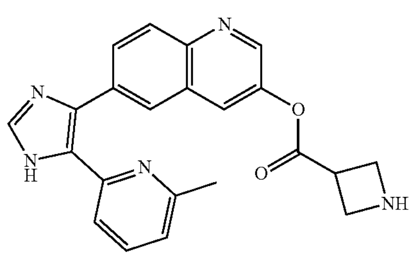 [SMILES: Cc1cccc(-c2[nH]cnc2-c2ccc3ncc(OC(=O)C4CNC4)cc3c2)n1] | 6-(5-(6-methylpyridin-2-yl)-1H-pyrazol-4-yl)quinolin-3-yl azetidine-3-carboxylate | |
| 1030 | 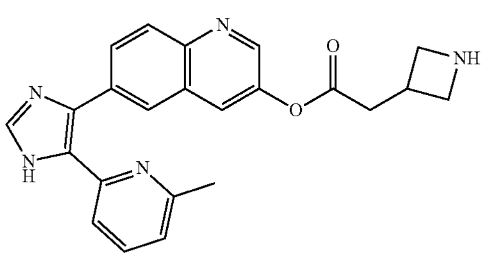 [SMILES: Cc1cccc(-c2[nH]cnc2-c2ccc3ncc(OC(=O)CC4CNC4)cc3c2)n1] | 6-(5-(6-methylpyridin-2-yl)-1H-pyrazol-4-yl)quinolin-3-yl 2-(azetidin-3-yl)acetate | |
| 1031 | 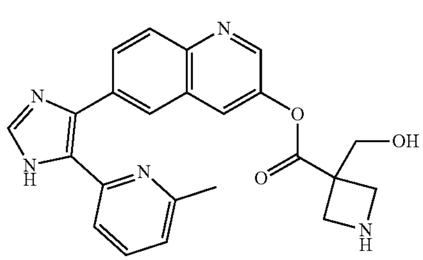 [SMILES: Cc1cccc(-c2[nH]cnc2-c2ccc3ncc(OC(=O)C4(CO)CNC4)cc3c2)n1] | 6-(5-(6-methylpyridin-2-yl)-1H-pyrazol-4-yl)quinolin-3-yl 3-(hydroxymethyl)azetidine-3-carboxylate | |

TABLE 1-continued

| No. | Structure | Chemical Name | [M + H]+ |
|---|---|---|---|
| 1032 | 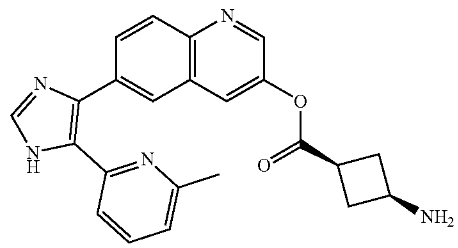 [SMILES: Cc1cccc(-c2[nH]cnc2-c2ccc3ncc(OC(=O)[C@H]4C[C@@H](N)C4)cc3c2)n1] | 6-(5-(6-methylpyridin-2-yl)-1H-pyrazol-4-yl)quinolin-3-yl (1s,3s)-3-aminocyclobutane-1-carboxylate | 400.1 |
| 1033 | 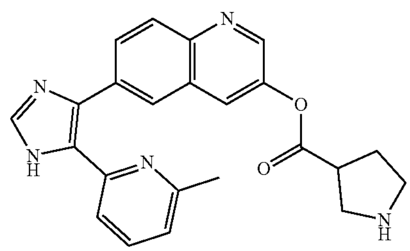 [SMILES: Cc1cccc(-c2[nH]cnc2-c2ccc3ncc(OC(=O)C4CCNC4)cc3c2)n1] | 6-(5-(6-methylpyridin-2-yl)-1H-pyrazol-4-yl)quinolin-3-yl pyrrolidine-3-carboxylate | |
| 1034 | 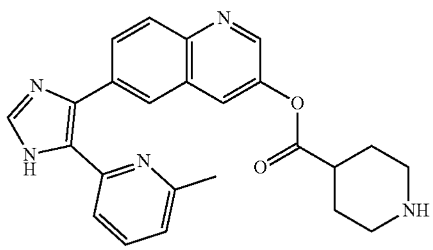 [SMILES: Cc1cccc(-c2[nH]cnc2-c2ccc3ncc(OC(=O)C4CCNCC4)cc3c2)n1] | 6-(5-(6-methylpyridin-2-yl)-1H-pyrazol-4-yl)quinolin-3-yl piperidine-4-carboxylate | |
| 1035 | 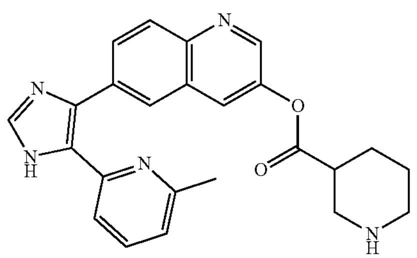 [SMILES: Cc1cccc(-c2[nH]cnc2-c2ccc3ncc(OC(=O)C4CCCNC4)cc3c2)n1] | 6-(5-(6-methylpyridin-2-yl)-1H-pyrazol-4-yl)quinolin-3-yl piperidine-3-carboxylate | |
| 1036 | 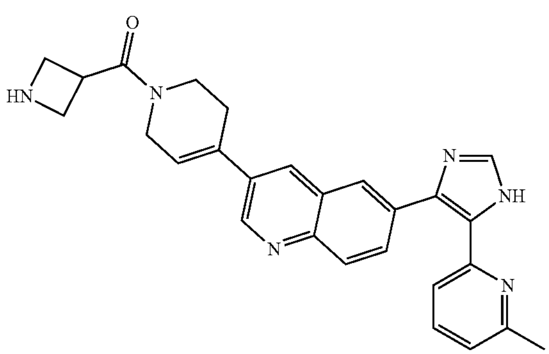 [SMILES: Cc1cccc(-c2[nH]cnc2-c2ccc3ncc(C4=CCN(C(=O)C5CNC5)CC4)cc3c2)n1] | azetidin-3-yl-[4-[6-[5-(6-methyl-2-pyridyl)-1H-imidazol-4-yl]-3-quinolyl]-3,6-dihydro-2H-pyridin-1-yl]methanone | 451.2 |

TABLE 1-continued

| No. | Structure | Chemical Name | [M + H]+ |
|---|---|---|---|
| 1037 | 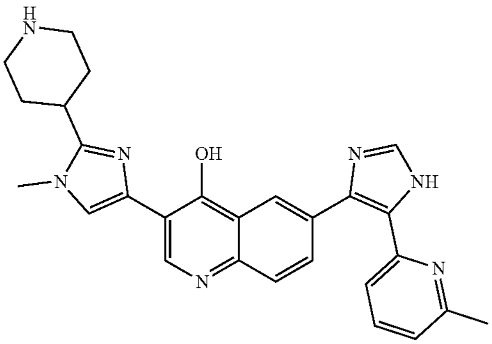 [SMILES: Cc1cccc(-c2[nH]cnc2-c2ccc3ncc(-c4cn(C)c(C5CCNCC5)n4)c(O)c3c2)n1] | 3-[1-methyl-2-(4-piperidyl)imidazol-4-yl]-6-[5-(6-methyl-2-pyridyl)-1H-imidazol-4-yl]quinolin-4-ol | |
| 1038 | 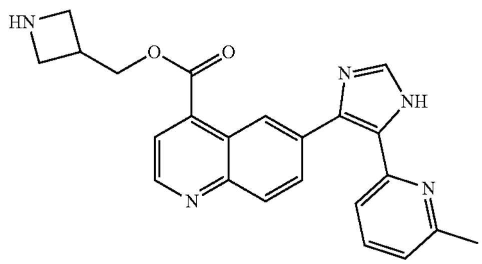 [SMILES: Cc1cccc(-c2[nH]cnc2-c2ccc3nccc(C(=O)OCC4CNC4)c3c2)n1] | azetidin-3-ylmethyl 6-[5-(6-methyl-2-pyridyl)-1H-imidazol-4-yl]quinoline-4-carboxylate | 400.2 |
| 1039 | 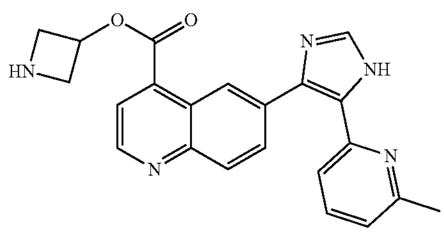 [SMILES: Cc1cccc(-c2[nH]cnc2-c2ccc3nccc(C(=O)OC4CNC4)c3c2)n1] | azetidin-3-yl 6-[5-(6-methyl-2-pyridyl)-1H-imidazol-4-yl]quinoline-4-carboxylate | |
| 1040 | 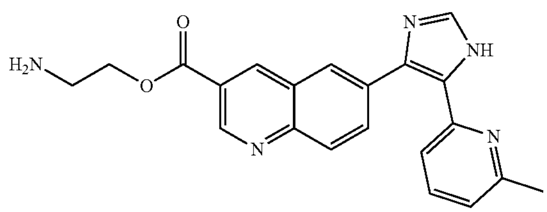 [SMILES: Cc1cccc(-c2[nH]cnc2-c2ccc3ncc(C(=O)OCCN)cc3c2)n1] | 2-aminoethyl 6-[5-(6-methyl-2-pyridyl)-1H-imidazol-4-yl]quinoline-3-carboxylate | 374.2 |
| 1041 | 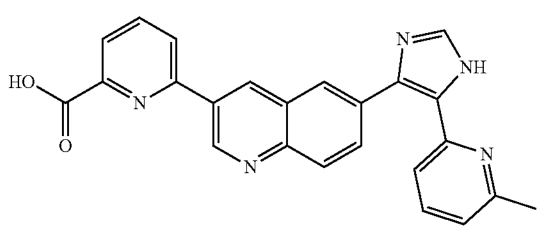 [SMILES: Cc1cccc(-c2[nH]cnc2-c2ccc3ncc(-c4cccc(C(=O)O)n4)cc3c2)n1] | 6-[6-[5-(6-methyl-2-pyridyl)-1H-imidazol-4-yl]-3-quinolyl]pyridine-2-carboxylic acid | 408.1 |
| 1042 | 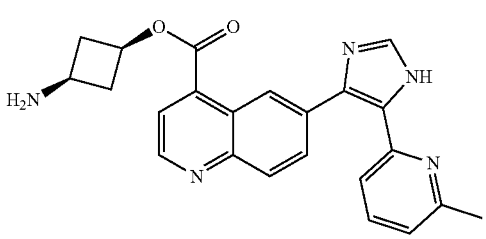 [SMILES: Cc1cccc(-c2[nH]cnc2-c2ccc3nccc(C(=O)O[C@H]4C[C@@H](N)C4)c3c2)n1] | (3-aminocyclobutyl) 6-[5-(6-methyl-2-pyridyl)-1H-imidazol-4-yl]quinoline-4-carboxylate | 400.1 |

TABLE 1-continued

| No. | Structure | Chemical Name | [M + H]+ |
|---|---|---|---|
| 1043 | 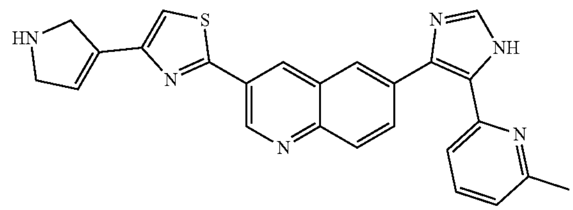 [SMILES: Cc1cccc(-c2[nH]cnc2-c2ccc3ncc(-c4nc(C5=CCNC5)cs4)cc3c2)n1] | 4-(2,5-dihydro-1H-pyrrol-3-yl)-2-[6-[5-(6-methyl-2-pyridyl)-1H-imidazol-4-yl]-3-quinolyl]thiazole | 437.0 |
| 1044 | 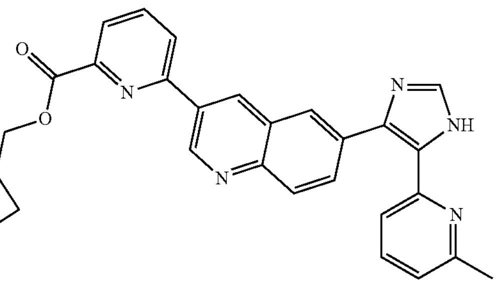 | azetidin-3-ylmethyl 6-[6-[5-(6-methyl-2-pyridyl)-1H-imidazol-4-yl]-3-quinolyl]pyridine-2-carboxylate | 477.2 |
| 1045 | 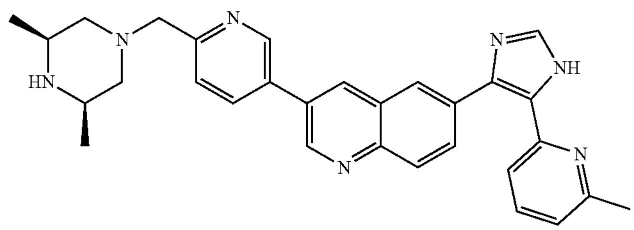 | 6-[5-(6-methyl-2-pyridyl)-1H-imidazol-4-yl]-3-[6-[[rac-(3S,5R)-3,5-dimethylpiperazin-1-yl]methyl]-3-pyridyl]quinoline | 490.2 |
| 1046 | 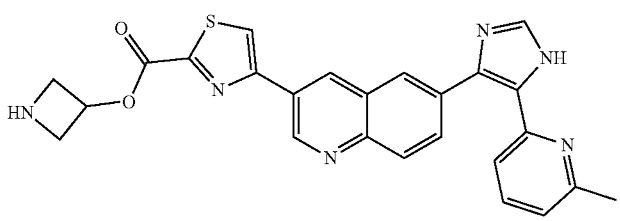 [SMILES: Cc1cccc(-c2[nH]cnc2-c2ccc3ncc(-c4csc(C(=O)OC5CNC5)n4)cc3c2)n1] | azetidin-3-yl 4-[6-[5-(6-methyl-2-pyridyl)-1H-imidazol-4-yl]-3-quinolyl]thiazole-2-carboxylate | 469.1 |
| 1047 | 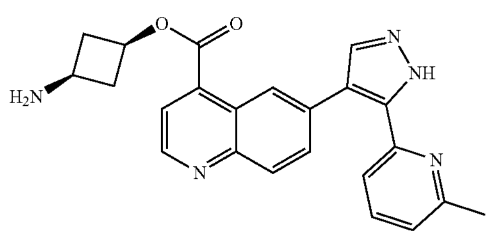 [SMILES: Cc1cccc(-c2[nH]ncc2-c2ccc3nccc(C(=O)O[C@H]4C[C@@H](N)C4)c3c2)n1] | (3-aminocyclobutyl) 6-[5-(6-methyl-2-pyridyl)-1H-pyrazol-4-yl]quinoline-4-carboxylate | 400.2 |
| 1048 | 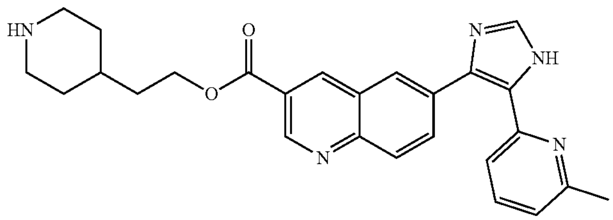 [SMILES: Cc1cccc(-c2[nH]cnc2-c2ccc3ncc(C(=O)OCCC4CCNCC4)cc3c2)n1] | 2-(4-piperidyl)ethyl 6-[5-(6-methyl-2-pyridyl)-1H-imidazol-4-yl]quinoline-3-carboxylate | 442.2 |

TABLE 1-continued

| No. | Structure | Chemical Name | [M + H]+ |
|---|---|---|---|
| 1049 | 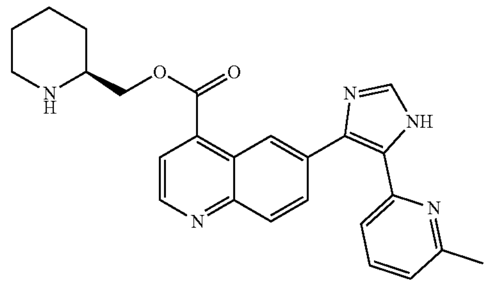 [SMILES: Cc1cccc(-c2[nH]cnc2-c2ccc3nccc(C(=O)OC[C@@H]4CCCCN4)c3c2)n1] | [(2S)-2-piperidyl]methyl 6-[5-(6-methyl-2-pyridyl)-1H-imidazol-4-yl]quinoline-4-carboxylate | |
| 1050 | 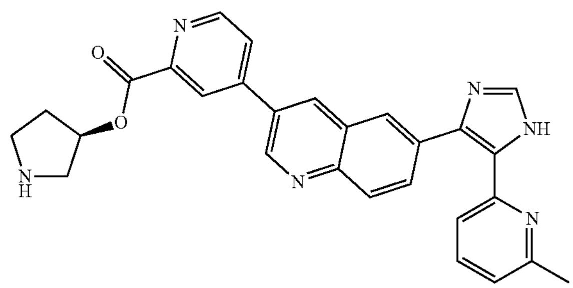 [SMILES: Cc1cccc(-c2[nH]cnc2-c2ccc3ncc(-c4ccnc(C(=O)O[C@@H]5CCNC5)c4)cc3c2)n1] | [(3R)-pyrrolidin-3-yl] 4-[6-[5-(6-methyl-2-pyridyl)-1H-imidazol-4-yl]-3-quinolyl]pyridine-2-carboxylate | 477.1 |
| 1051 | 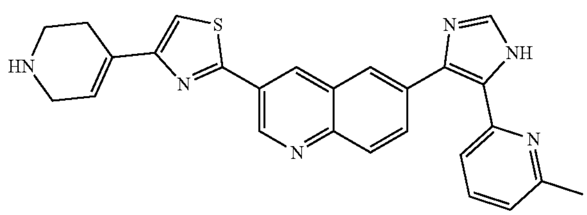 [SMILES: Cc1cccc(-c2[nH]cnc2-c2ccc3ncc(-c4nc(C5=CCNCC5)cs4)cc3c2)n1] | 2-[6-[5-(6-methyl-2-pyridyl)-1H-imidazol-4-yl]-3-quinolyl]-4-(1,2,3,6-tetrahydropyridin-4-yl)thiazole | 451.2 |
| 1052 | 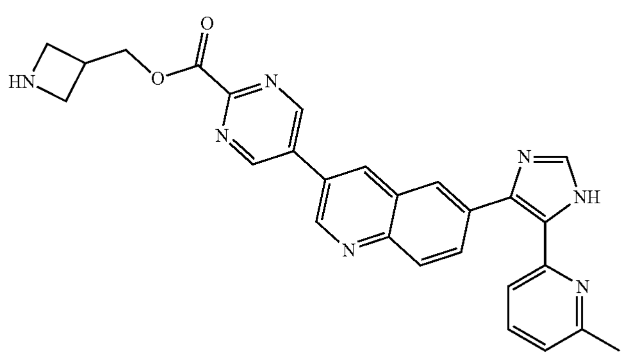 [SMILES: Cc1cccc(-c2[nH]cnc2-c2ccc3ncc(-c4cnc(C(=O)OCC5CNC5)nc4)cc3c2)n1] | azetidin-3-ylmethyl 5-[6-[5-(6-methyl-2-pyridyl)-1H-imidazol-4-yl]-3-quinolyl]pyrimidine-2-carboxylate | 478.3 |
| 1053 | 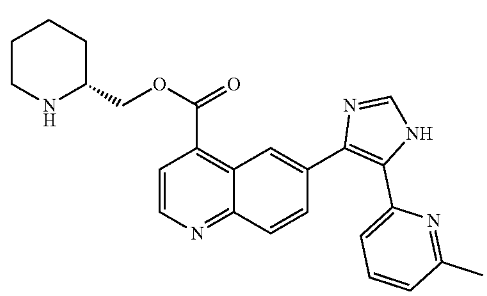 | [(2R)-2-piperidyl]methyl 6-[5-(6-methyl-2-pyridyl)-1H-imidazol-4-yl]quinoline-4-carboxylate | |

TABLE 1-continued

| No. | Structure | Chemical Name | [M + H]+ |
|---|---|---|---|
| 1054 | 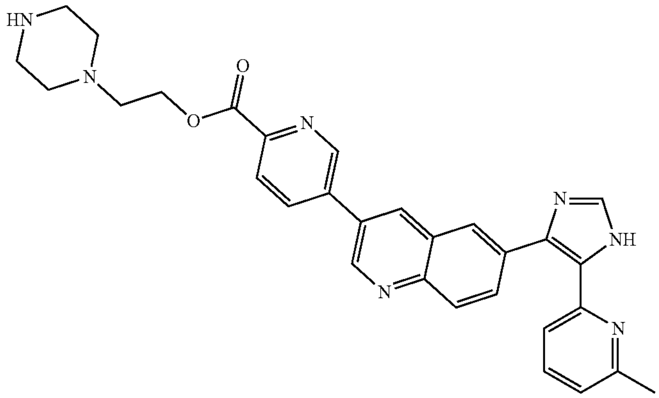 [SMILES: Cc1cccc(-c2[nH]cnc2-c2ccc3ncc(-c4ccc(C(=O)OCCN5CCNCC5)nc4)cc3c2)n1] | 2-piperazin-1-ylethyl 5-[6-[5-(6-methyl-2-pyridyl)-1H-imidazol-4-yl]-3-quinolyl]pyridine-2-carboxylate | 520.2 |
| 1055 | 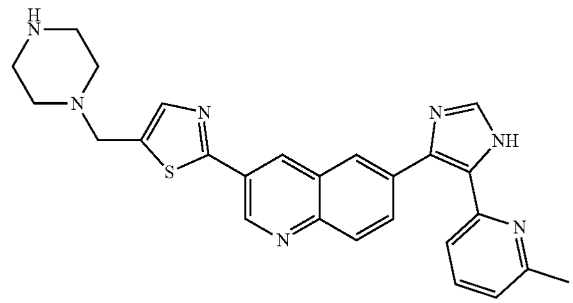 [SMILES: Cc1cccc(-c2[nH]cnc2-c2ccc3ncc(-c4ncc(CN5CCNCC5)s4)cc3c2)n1] | 2-[6-[5-(6-methyl-2-pyridyl)-1H-imidazol-4-yl]-3-quinolyl]-5-(piperazin-1-ylmethyl)thiazole | 468.1 |
| 1056 | 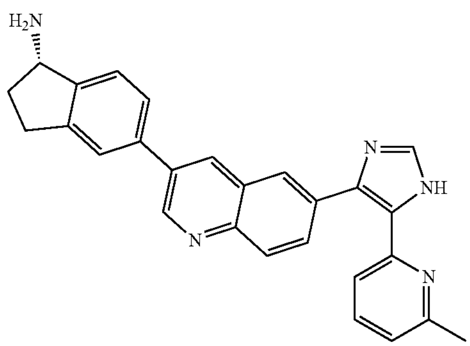 [SMILES: Cc1cccc(-c2[nH]cnc2-c2ccc3ncc(-c4ccc5c(c4)CC[C@@H]5N)cc3c2)n1] | (1S)-5-[6-[5-(6-methyl-2-pyridyl)-1H-imidazol-4-yl]-3-quinolyl]indan-1-amine | 418.2 |
| 1057 | 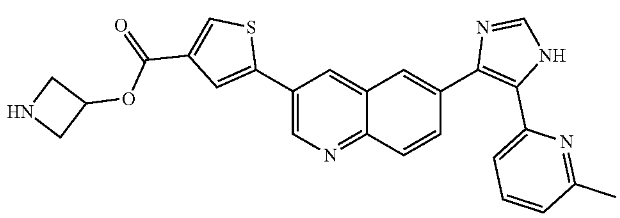 [SMILES: Cc1cccc(-c2[nH]cnc2-c2ccc3ncc(-c4cc(C(=O)OC5CNC5)cs4)cc3c2)n1] | azetidin-3-yl 5-[6-[5-(6-methyl-2-pyridyl)-1H-imidazol-4-yl]-3-quinolyl]thiophene-3-carboxylate | 468.1 |
| 1058 | 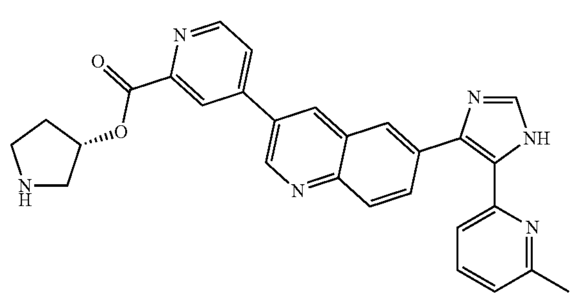 [SMILES: Cc1cccc(-c2[nH]cnc2-c2ccc3ncc(-c4ccnc(C(=O)O[C@H]5CCNC5)c4)cc3c2)n1] | [(3S)-pyrrolidin-3-yl] 4-[6-[5-(6-methyl-2-pyridyl)-1H-imidazol-4-yl]-3-quinolyl]pyridine-2-carboxylate | 477.1 |

TABLE 1-continued

| No. | Structure | Chemical Name | [M + H]+ |
|---|---|---|---|
| 1059 | 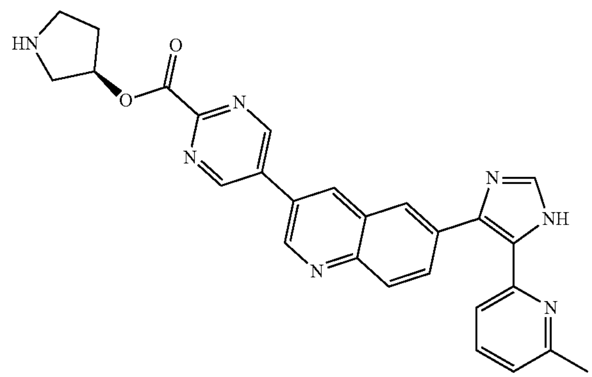 [SMILES: Cc1cccc(-c2[nH]cnc2-c2ccc3ncc(-c4cnc(C(=O)O[C@@H]5CCNC5)nc4)cc3c2)n1] | [(3R)-pyrrolidin-3-yl] 5-[6-[5-(6-methyl-2-pyridyl)-1H-imidazol-4-yl]-3-quinolyl]pyrimidine-2-carboxylate | 478.1 |
| 1060 | 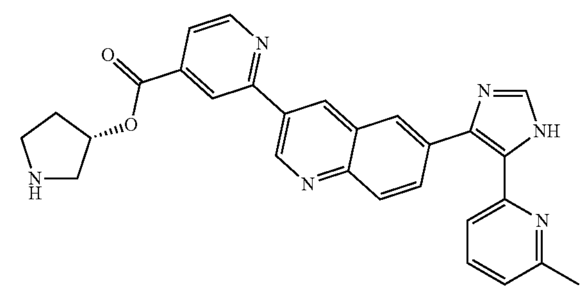 [SMILES: Cc1cccc(-c2[nH]cnc2-c2ccc3ncc(-c4cc(C(=O)O[C@H]5CCNC5)ccn4)cc3c2)n1] | [(3S)-pyrrolidin-3-yl] 2-[6-[5-(6-methyl-2-pyridyl)-1H-imidazol-4-yl]-3-quinolyl]pyridine-4-carboxylate | 477.1 |
| 1061 | 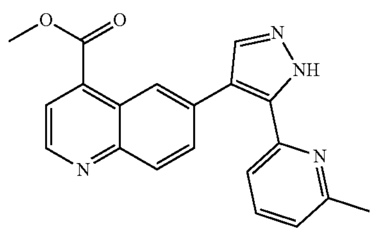 | methyl 6-[5-(6-methyl-2-pyridyl)-1H-pyrazol-4-yl]quinoline-4-carboxylate | 345.1 |
| 1062 | 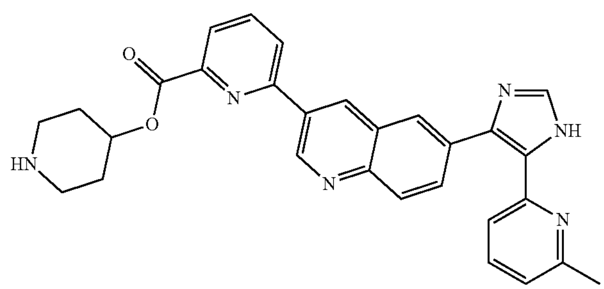 [SMILES: Cc1cccc(-c2[nH]cnc2-c2ccc3ncc(-c4cccc(C(=O)OC5CCNCC5)n4)cc3c2)n1] | 4-piperidyl 6-[6-[5-(6-methyl-2-pyridyl)-1H-imidazol-4-yl]-3-quinolyl]pyridine-2-carboxylate | 491.2 |
| 1063 | 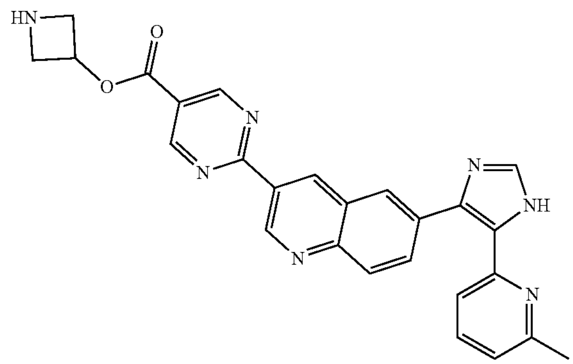 [SMILES: Cc1cccc(-c2[nH]cnc2-c2ccc3ncc(-c4ncc(C(=O)OC5CNC5)cn4)cc3c2)n1] | azetidin-3-yl 2-[6-[5-(6-methyl-2-pyridyl)-1H-imidazol-4-yl]-3-quinolyl]pyrimidine-5-carboxylate | 464.1 |

TABLE 1-continued

| No. | Structure | Chemical Name | [M + H]+ |
|---|---|---|---|
| 1064 | 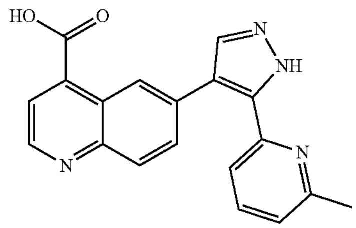 [SMILES: Cc1cccc(-c2[nH]ncc2-c2ccc3nccc(C(=O)O)c3c2)n1] | 6-[5-(6-methyl-2-pyridyl)-1H-pyrazol-4-yl]quinoline-4-carboxylic acid | 331.1 |
| 1065 | 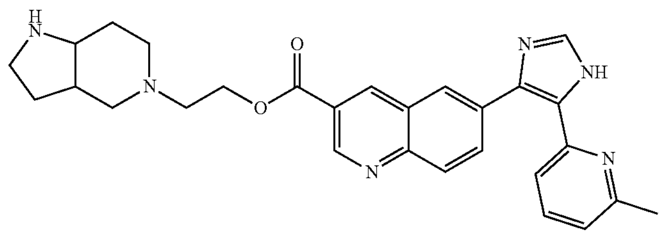 [SMILES: Cc1cccc(-c2[nH]cnc2-c2ccc3ncc(C(=O)OCCN4CCC5NCCC5C4)cc3c2)n1] | 2-(1,2,3,3a,4,6,7,7a-octahydropyrrolo[3,2-c]pyridin-5-yl)ethyl 6-[5-(6-methyl-2-pyridyl)-1H-imidazol-4-yl]quinoline-3-carboxylate | 483.2 |
| 1066 | 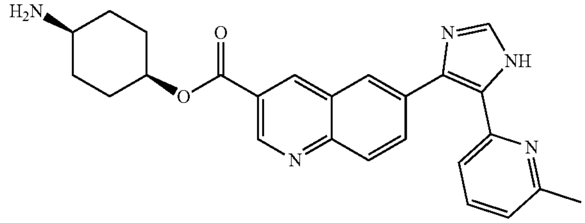 [SMILES: Cc1cccc(-c2[nH]cnc2-c2ccc3ncc(C(=O)O[C@H]4CC[C@@H](N)CC4)cc3c2)n1] | (4-aminocyclohexyl) 6-[5-(6-methyl-2-pyridyl)-1H-imidazol-4-yl]quinoline-3-carboxylate | 428.2 |
| 1067 | 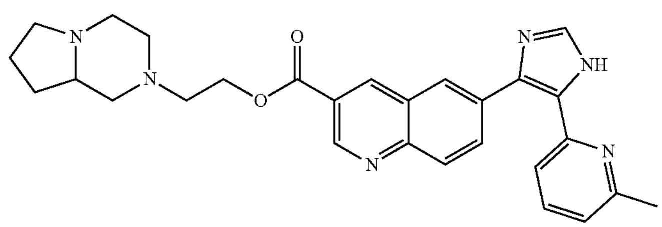 [SMILES: Cc1cccc(-c2[nH]cnc2-c2ccc3ncc(C(=O)OCCN4CCN5CCCC5C4)cc3c2)n1] | 2-(3,4,6,7,8,8a-hexahydro-1H-pyrrolo[1,2-a]pyrazin-2-yl)ethyl 6-[5-(6-methyl-2-pyridyl)-1H-imidazol-4-yl]quinoline-3-carboxylate | 483.2 |
| 1068 | 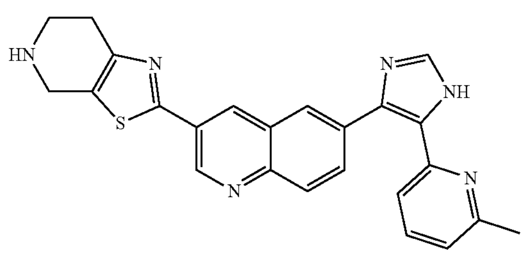 [SMILES: Cc1cccc(-c2[nH]cnc2-c2ccc3ncc(-c4nc5c(s4)CNCC5)cc3c2)n1] | 2-[6-[5-(6-methyl-2-pyridyl)-1H-imidazol-4-yl]-3-quinolyl]-4,5,6,7-tetrahydrothiazolo[5,4-c]pyridine | 425.3 |
| 1069 | 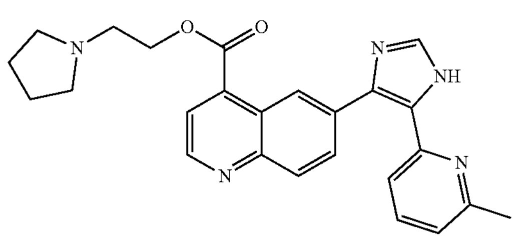 [SMILES: Cc1cccc(-c2[nH]cnc2-c2ccc3nccc(C(=O)OCCN4CCCC4)c3c2)n1] | 2-pyrrolidin-1-ylethyl 6-[5-(6-methyl-2-pyridyl)-1H-imidazol-4-yl]quinoline-4-carboxylate | |

TABLE 1-continued

| No. | Structure | Chemical Name | [M + H]+ |
|---|---|---|---|
| 1070 | 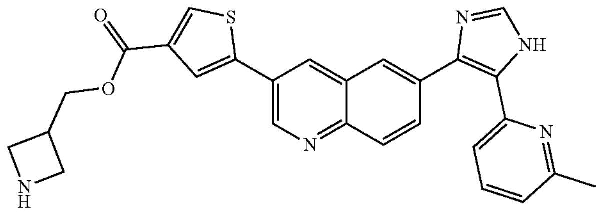 | azetidin-3-ylmethyl 5-[6-[5-(6-methyl-2-pyridyl)-1H-imidazol-4-yl]-3-quinolyl]thiophene-3-carboxylate | 482.1 |
| 1071 | 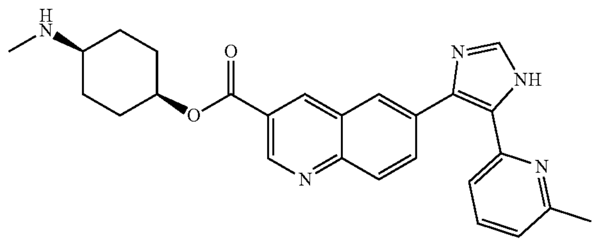 | [4-(methylamino)cyclohexyl] 6-[5-(6-methyl-2-pyridyl)-1H-imidazol-4-yl]quinoline-3-carboxylate | 442.2 |
| 1072 | 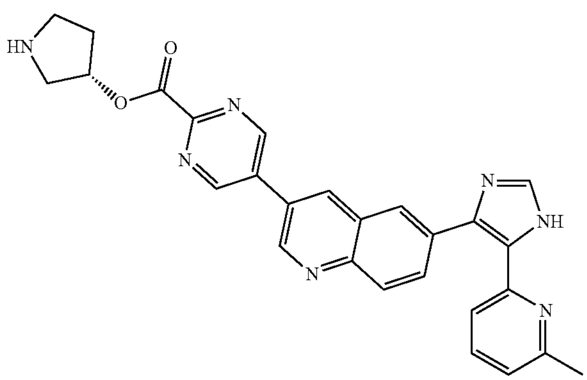 [SMILES: Cc1cccc(-c2[nH]cnc2-c2ccc3ncc(-c4cnc(C(=O)O[C@H]5CCNC5)nc4)cc3c2)n1] | [(3S)-pyrrolidin-3-yl] 5-[6-[5-(6-methyl-2-pyridyl)-1H-imidazol-4-yl]-3-quinolyl]pyrimidine-2-carboxylate | 478.2 |
| 1073 | 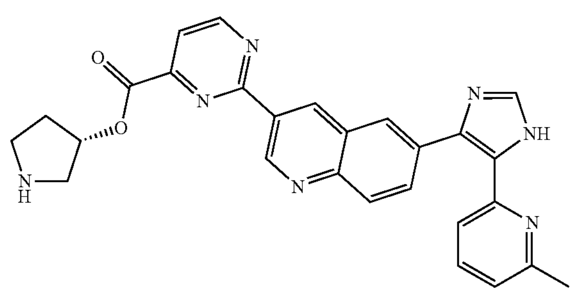 | [(3S)-pyrrolidin-3-yl] 2-[6-[5-(6-methyl-2-pyridyl)-1H-imidazol-4-yl]-3-quinolyl]pyrimidine-4-carboxylate | 478.1 |
| 1074 | 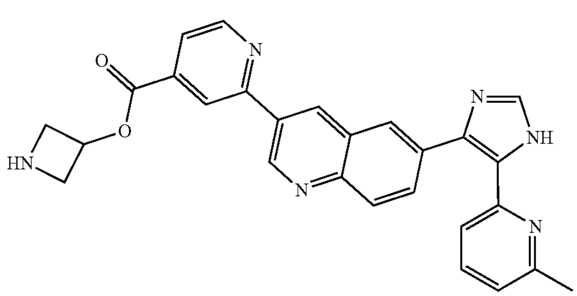 | azetidin-3-yl 2-[6-[5-(6-methyl-2-pyridyl)-1H-imidazol-4-yl]-3-quinolyl]pyridine-4-carboxylate | 463.1 |

TABLE 1-continued

| No. | Structure | Chemical Name | [M + H]⁺ |
|---|---|---|---|
| 1075 | 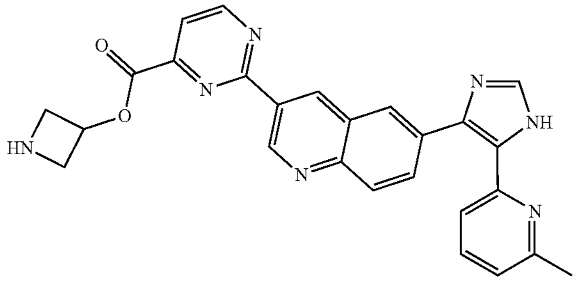 [SMILES: Cc1cccc(-c2[nH]cnc2-c2ccc3ncc(-c4nccc(C(=O)OC5CNC5)n4)cc3c2)n1] | azetidin-3-yl 2-[6-[5-(6-methyl-2-pyridyl)-1H-imidazol-4-yl]-3-quinolyl]pyrimidine-4-carboxylate | 464.2 |
| 1076 | 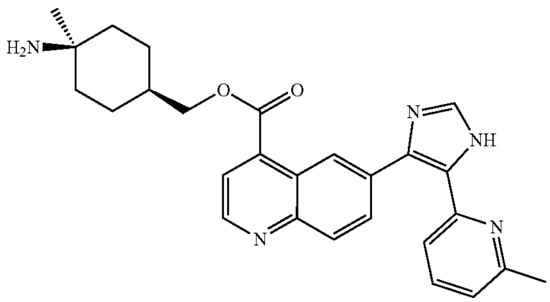 [SMILES: Cc1cccc(-c2[nH]cnc2-c2ccc3nccc(C(=O)OC[C@H]4CC[C@@](C)(N)CC4)c3c2)n1] | (4-amino-4-methyl-cyclohexyl)methyl 6-[5-(6-methyl-2-pyridyl)-1H-imidazol-4-yl]quinoline-4-carboxylate | |
| 1077 | 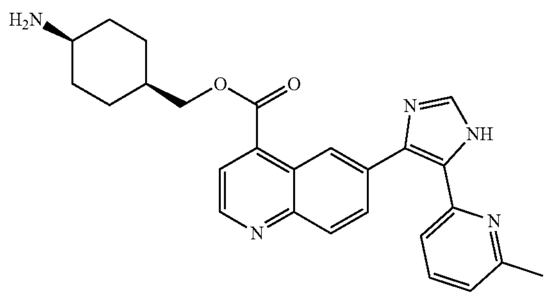 [SMILES: Cc1cccc(-c2[nH]cnc2-c2ccc3nccc(C(=O)OC[C@H]4CC[C@@H](N)CC4)c3c2)n1] | (4-aminocyclohexyl)methyl 6-[5-(6-methyl-2-pyridyl)-1H-imidazol-4-yl]quinoline-4-carboxylate | 442.1 |
| 1078 | 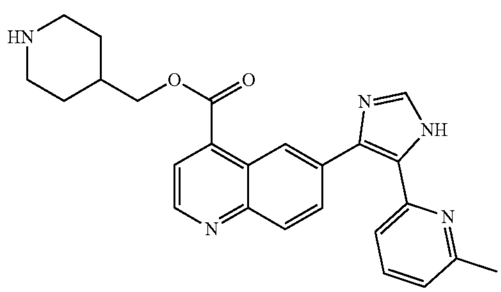 [SMILES: Cc1cccc(-c2[nH]cnc2-c2ccc3nccc(C(=O)OCC4CCNCC4)c3c2)n1] | 4-piperidylmethyl 6-[5-(6-methyl-2-pyridyl)-1H-imidazol-4-yl]quinoline-4-carboxylate | 428.1 |
| 1079 | 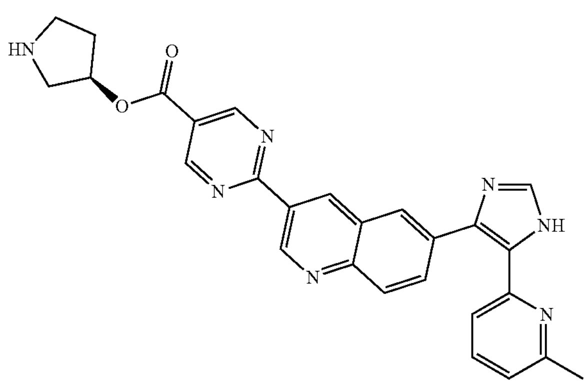 | [(3R)-pyrrolidin-3-yl] 2-[6-[5-(6-methyl-2-pyridyl)-1H-imidazol-4-yl]-3-quinolyl]pyrimidine-5-carboxylate | 478.2 |

TABLE 1-continued

| No. | Structure | Chemical Name | [M + H]+ |
|---|---|---|---|
| 1080 | 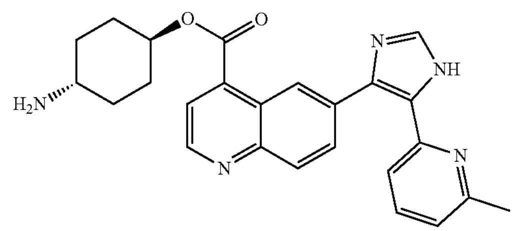 [SMILES: Cc1cccc(-c2[nH]cnc2-c2ccc3nccc(C(=O)O[C@H]4CC[C@H](N)CC4)c3c2)n1] | (4-aminocyclohexyl) 6-[5-(6-methyl-2-pyridyl)-1H-imidazol-4-yl]quinoline-4-carboxylate | |
| 1081 | 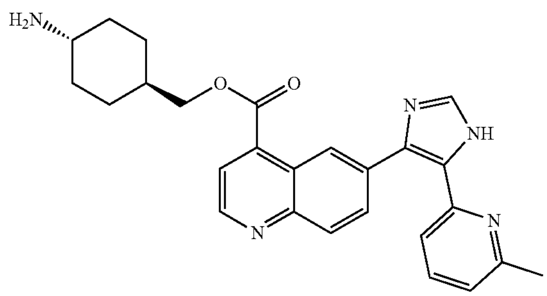 [SMILES: Cc1cccc(-c2[nH]cnc2-c2ccc3nccc(C(=O)OC[C@H]4CC[C@H](N)CC4)c3c2)n1] | (4-aminocyclohexyl)methyl 6-[5-(6-methyl-2-pyridyl)-1H-imidazol-4-yl]quinoline-4-carboxylate | 442.1 |
| 1082 | 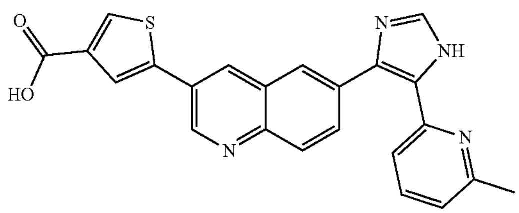 [SMILES: Cc1cccc(-c2[nH]cnc2-c2ccc3ncc(-c4cc(C(=O)O)cs4)cc3c2)n1] | 5-[6-[5-(6-methyl-2-pyridyl)-1H-imidazol-4-yl]-3-quinolyl]thiophene-3-carboxylic acid | 413.0 |
| 1083 | 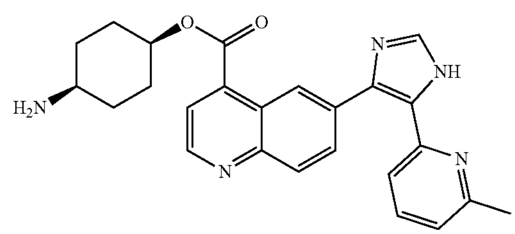 | (4-aminocyclohexyl) 6-[5-(6-methyl-2-pyridyl)-1H-imidazol-4-yl]quinoline-4-carboxylate | |
| 1084 | 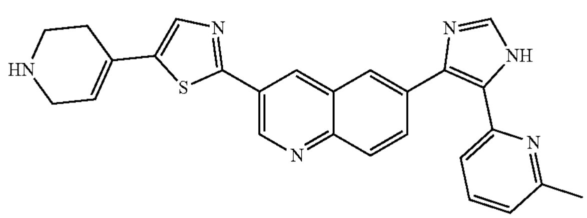 [SMILES: Cc1cccc(-c2[nH]cnc2-c2ccc3ncc(-c4ncc(C5=CCNCC5)s4)cc3c2)n1] | 2-[6-[5-(6-methyl-2-pyridyl)-1H-imidazol-4-yl]-3-quinolyl]-5-(1,2,3,6-tetrahydropyridin-4-yl)thiazole | 451.1 |
| 1085 | 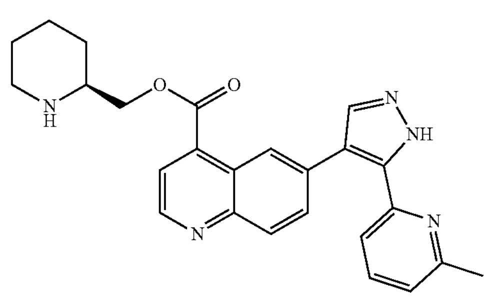 [SMILES: Cc1cccc(-c2[nH]ncc2-c2ccc3nccc(C(=O)OC[C@@H]4CCCCN4)c3c2)n1] | [(2S)-2-piperidyl]methyl 6-[5-(6-methyl-2-pyridyl)-1H-pyrazol-4-yl]quinoline-4-carboxylate | 428.1 |

TABLE 1-continued

| No. | Structure | Chemical Name | [M + H]+ |
|---|---|---|---|
| 1086 | 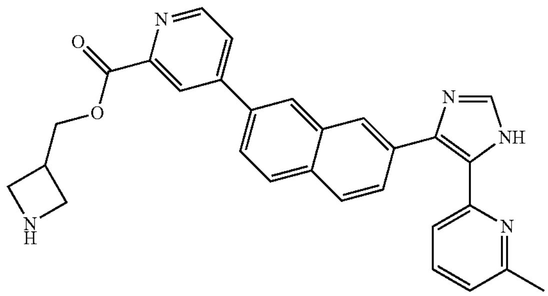 [SMILES: Cc1cccc(-c2[nH]cnc2-c2ccc3ccc(-c4ccnc(C(=O)OCC5CNC5)c4)cc3c2)n1] | azetidin-3-ylmethyl 4-[6-[5-(6-methyl-2-pyridyl)-1H-imidazol-4-yl]-3-quinolyl]pyridine-2-carboxylate | 477.1 |
| 1087 | 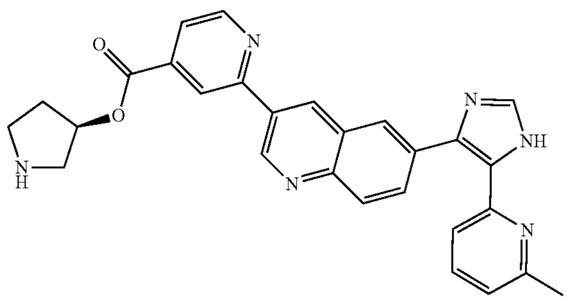 [SMILES: Cc1cccc(-c2[nH]cnc2-c2ccc3ncc(-c4cc(C(=O)O[C@@H]5CCNC5)ccn4)cc3c2)n1] | [(3R)-pyrrolidin-3-yl] 2-[6-[5-(6-methyl-2-pyridyl)-1H-imidazol-4-yl]-3-quinolyl]pyridine-4-carboxylate | 477.1 |
| 1088 | 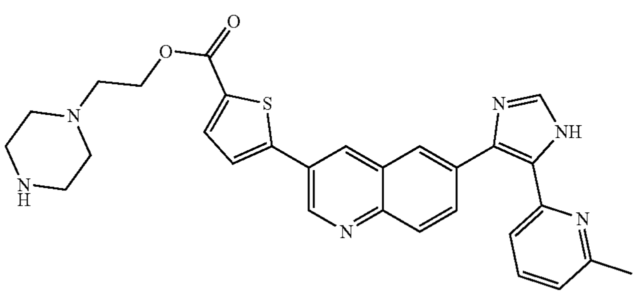 [SMILES: Cc1cccc(-c2[nH]cnc2-c2ccc3ncc(-c4ccc(C(=O)OCCN5CCNCC5)s4)cc3c2)n1] | 2-piperazin-1-ylethyl 5-[6-[5-(6-methyl-2-pyridyl)-1H-imidazol-4-yl]-3-quinolyl]thiophene-2-carboxylate | 525.1 |
| 1089 | 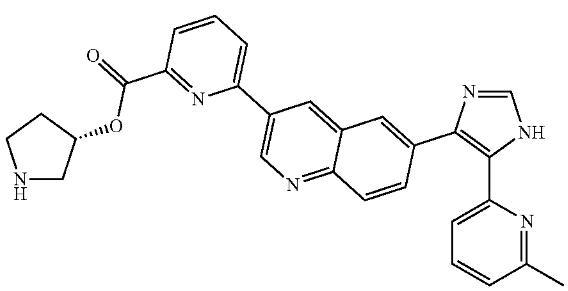 | [(3S)-pyrrolidin-3-yl] 6-[6-[5-(6-methyl-2-pyridyl)-1H-imidazol-4-yl]-3-quinolyl]pyridine-2-carboxylate | 477.1 |
| 1090 | 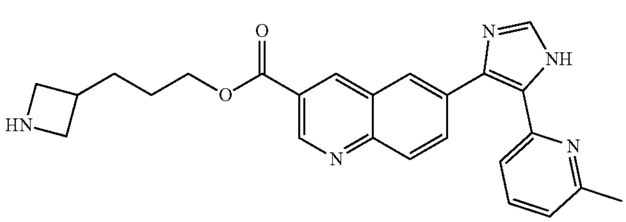 [SMILES: Cc1cccc(-c2[nH]cnc2-c2ccc3ncc(C(=O)OCCCC4CNC4)cc3c2)n1] | 3-(azetidin-3-yl)propyl 6-[5-(6-methyl-2-pyridyl)-1H-imidazol-4-yl]quinoline-3-carboxylate | 428.2 |

TABLE 1-continued

| No. | Structure | Chemical Name | [M + H]+ |
|---|---|---|---|
| 1091 | 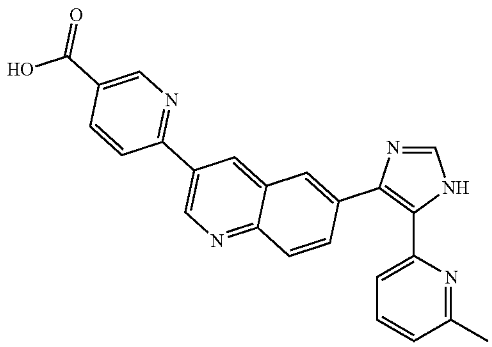 [SMILES: Cc1cccc(-c2[nH]cnc2-c2ccc3ncc(-c4ccc(C(=O)O)cn4)cc3c2)n1] | 6-[6-[5-(6-methyl-2-pyridyl)-1H-imidazol-4-yl]-3-quinolyl]pyridine-3-carboxylic acid | 408.1 |
| 1092 | 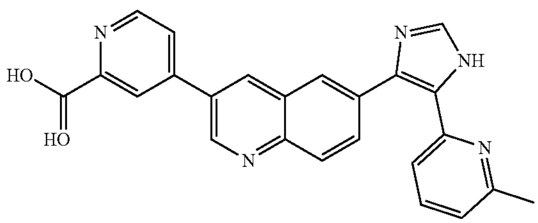 [SMILES: Cc1cccc(-c2[nH]cnc2-c2ccc3ncc(-c4ccnc(C(=O)O)c4)cc3c2)n1] | 4-[6-[5-(6-methyl-2-pyridyl)-1H-imidazol-4-yl]-3-quinolyl]pyridine-2-carboxylic acid | 408.1 |
| 1093 | 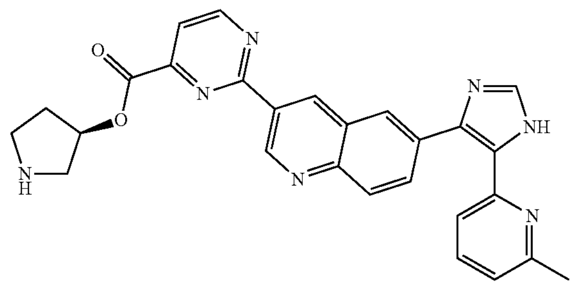 [SMILES: Cc1cccc(-c2[nH]cnc2-c2ccc3ncc(-c4nccc(C(=O)O[C@@H]5CCNC5)n4)cc3c2)n1] | [(3R)-pyrrolidin-3-yl] 2-[6-[5-(6-methyl-2-pyridyl)-1H-imidazol-4-yl]-3-quinolyl]pyrimidine-4-carboxylate | 478.1 |
| 1094 | 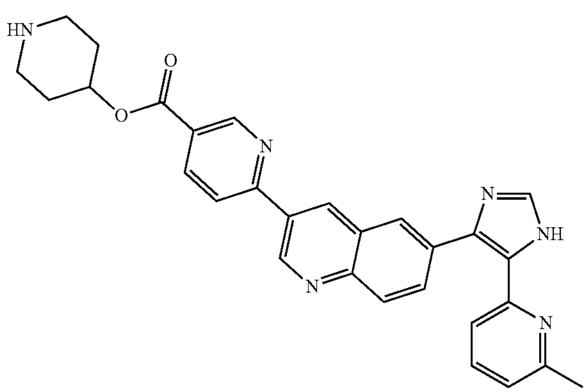 | 4-piperidyl 6-[6-[5-(6-methyl-2-pyridyl)-1H-imidazol-4-yl]-3-quinolyl]pyridine-3-carboxylate | 491.2 |
| 1095 | 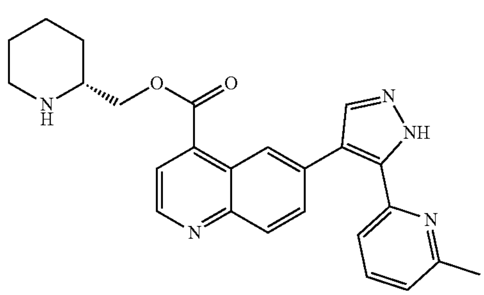 [SMILES: Cc1cccc(-c2[nH]ncc2-c2ccc3nccc(C(=O)OC[C@H]4CCCCN4)c3c2)n1] | [(2R)-2-piperidyl]methyl 6-[5-(6-methyl-2-pyridyl)-1H-pyrazol-4-yl]quinoline-4-carboxylate | 428.1 |

TABLE 1-continued

| No. | Structure | Chemical Name | [M + H]⁺ |
|---|---|---|---|
| 1096 | 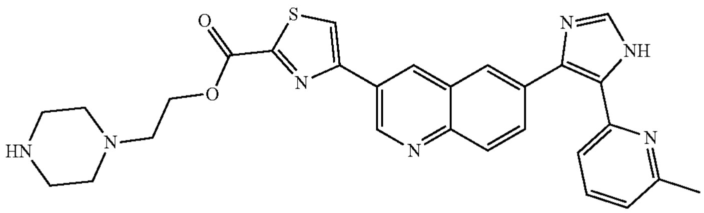 [SMILES: Cc1cccc(-c2[nH]cnc2-c2ccc3ncc(-c4csc(C(=O)OCCN5CCNCC5)n4)cc3c2)n1] | 2-piperazin-1-ylethyl 4-[6-[5-(6-methyl-2-pyridyl)-1H-imidazol-4-yl]-3-quinolyl]thiazole-2-carboxylate | 526.1 |
| 1097 | 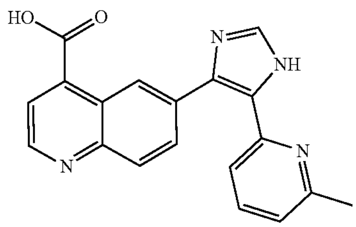 [SMILES: Cc1cccc(-c2[nH]cnc2-c2ccc3nccc(C(=O)O)c3c2)n1] | 6-[5-(6-methyl-2-pyridyl)-1H-imidazol-4-yl]quinoline-4-carboxylic acid | 331.0 |
| 1098 | 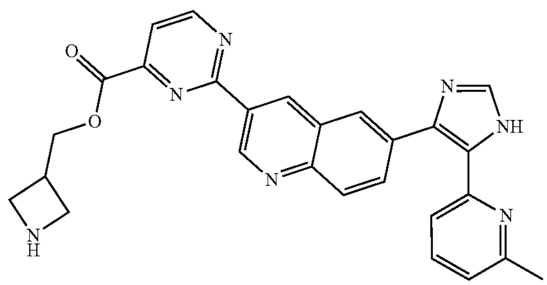 [SMILES: Cc1cccc(-c2[nH]cnc2-c2ccc3ncc(-c4nccc(C(=O)OCC5CNC5)n4)cc3c2)n1] | azetidin-3-ylmethyl 2-[6-[5-(6-methyl-2-pyridyl)-1H-imidazol-4-yl]-3-quinolyl]pyrimidine-4-carboxylate | 478.2 |
| 1099 | 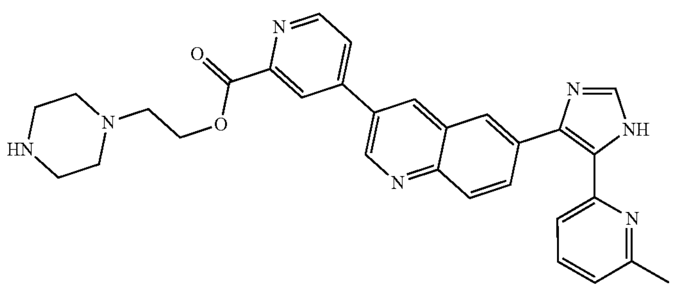 [SMILES: Cc1cccc(-c2[nH]cnc2-c2ccc3ncc(-c4ccnc(C(=O)OCCN5CCNCC5)c4)cc3c2)n1] | 2-piperazin-1-ylethyl 4-[6-[5-(6-methyl-2-pyridyl)-1H-imidazol-4-yl]-3-quinolyl]pyridine-2-carboxylate | 520.2 |
| 1100 | 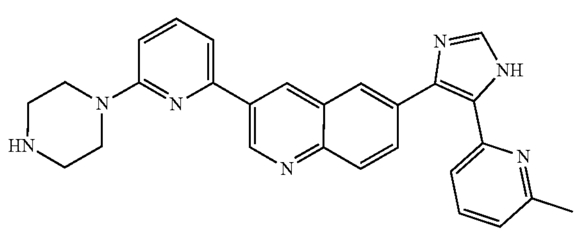 [SMILES: Cc1cccc(-c2[nH]cnc2-c2ccc3ncc(-c4cccc(N5CCNCC5)n4)cc3c2)n1] | 6-[5-(6-methyl-2-pyridyl)-1H-imidazol-4-yl]-3-(6-piperazin-1-yl-2-pyridyl)quinoline | 448.2 |

TABLE 1-continued

| No. | Structure | Chemical Name | [M + H]⁺ |
|---|---|---|---|
| 1101 | 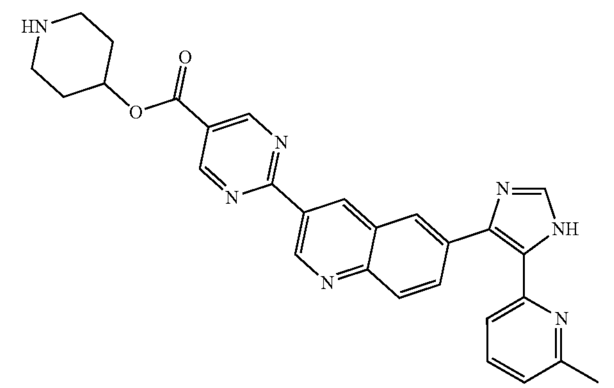 [SMILES: Cc1cccc(-c2[nH]cnc2-c2ccc3ncc(-c4ncc(C(=O)OC5CCNCC5)cn4)cc3c2)n1] | 4-piperidyl 2-[6-[5-(6-methyl-2-pyridyl)-1H-imidazol-4-yl]-3-quinolyl]pyrimidine-5-carboxylate | 492.1 |
| 1102 | 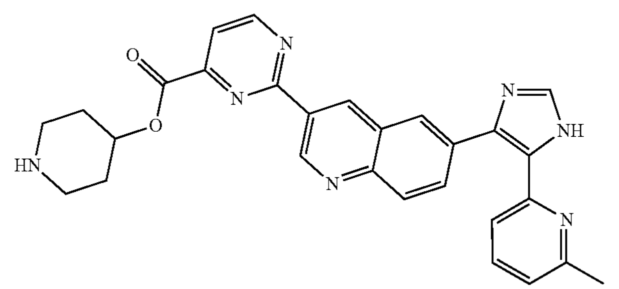 [SMILES: Cc1cccc(-c2[nH]cnc2-c2ccc3ncc(-c4nccc(C(=O)OC5CCNCC5)n4)cc3c2)n1] | 4-piperidyl 2-[6-[5-(6-methyl-2-pyridyl)-1H-imidazol-4-yl]-3-quinolyl]pyrimidine-4-carboxylate | 492.1 |
| 1103 | 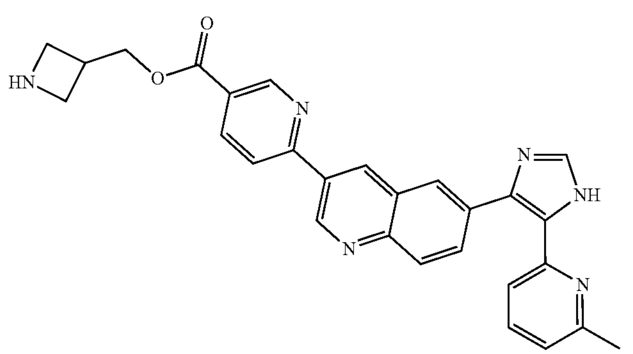 [SMILES: Cc1cccc(-c2[nH]cnc2-c2ccc3ncc(-c4ccc(C(=O)OCC5CNC5)cn4)cc3c2)n1] | azetidin-3-ylmethyl 6-[6-[5-(6-methyl-2-pyridyl)-1H-imidazol-4-yl]-3-quinolyl]pyridine-3-carboxylate | 477.2 |
| 1104 | 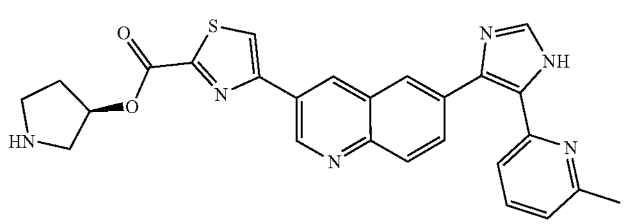 [SMILES: Cc1cccc(-c2[nH]cnc2-c2ccc3ncc(-c4csc(C(=O)O[C@@H]5CCNC5)n4)cc3c2)n1] | [(3R)-pyrrolidin-3-yl] 4-[6-[5-(6-methyl-2-pyridyl)-1H-imidazol-4-yl]-3-quinolyl]thiazole-2-carboxylate | 483.1 |
| 1105 | 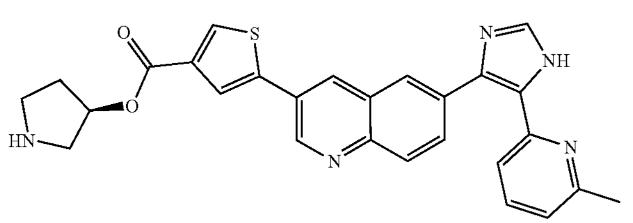 [SMILES: Cc1cccc(-c2[nH]cnc2-c2ccc3ncc(-c4cc(C(=O)O[C@@H]5CCNC5)cs4)cc3c2)n1] | [(3R)-pyrrolidin-3-yl] 5-[6-[5-(6-methyl-2-pyridyl)-1H-imidazol-4-yl]-3-quinolyl]thiophene-3-carboxylate | 482.1 |

TABLE 1-continued

| No. | Structure | Chemical Name | [M + H]+ |
|---|---|---|---|
| 1106 | 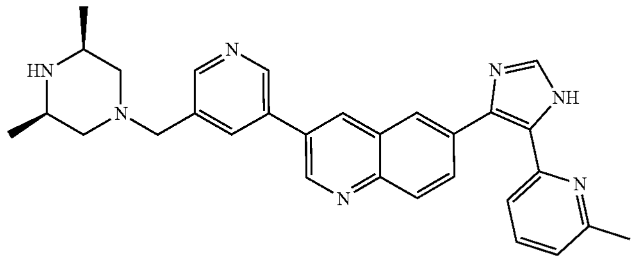 | 3-[5-[[(3S,5R)-3,5-dimethylpiperazin-1-yl]methyl]-3-pyridyl]-6-[5-(6-methyl-2-pyridyl)-1H-imidazol-4-yl]quinoline | 490.1 |
| 1107 | 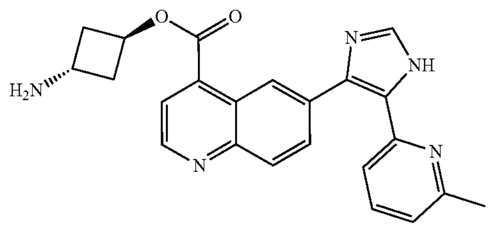 [SMILES: Cc1cccc(-c2[nH]cnc2-c2ccc3nccc(C(=O)O[C@H]4C[C@H](N)C4)c3c2)n1] | (3-aminocyclobutyl) 6-[5-(6-methyl-2-pyridyl)-1H-imidazol-4-yl]quinoline-4-carboxylate | 400.1 |
| 1108 | 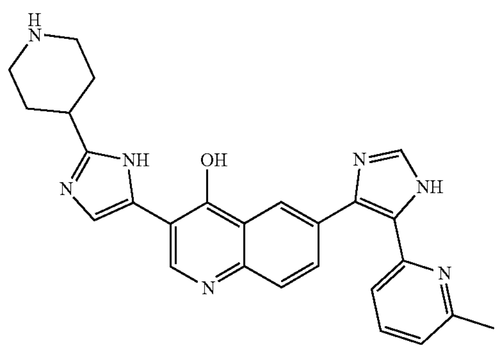 | 6-[5-(6-methyl-2-pyridyl)-1H-imidazol-4-yl]-3-[2-(4-piperidyl)-1H-imidazol-5-yl]quinolin-4-ol | |
| 1109 | 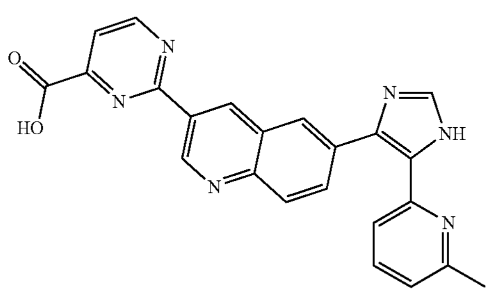 [SMILES: Cc1cccc(-c2[nH]cnc2-c2ccc3ncc(-c4nccc(C(=O)O)n4)cc3c2)n1] | 2-[6-[5-(6-methyl-2-pyridyl)-1H-imidazol-4-yl]-3-quinolyl]pyrimidine-4-carboxylic acid | 409.1 |
| 1110 | 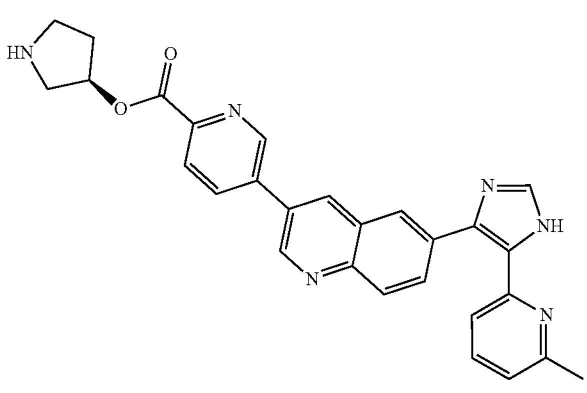 [SMILES: Cc1cccc(-c2[nH]cnc2-c2ccc3ncc(-c4ccc(C(=O)O[C@@H]5CCNC5)cn4)cc3c2)n1] | [(3R)-pyrrolidin-3-yl] 5-[6-[5-(6-methyl-2-pyridyl)-1H-imidazol-4-yl]-3-quinolyl]pyridine-2-carboxylate | 477.1 |

TABLE 1-continued

| No. | Structure | Chemical Name | [M + H]+ |
|---|---|---|---|
| 1111 | 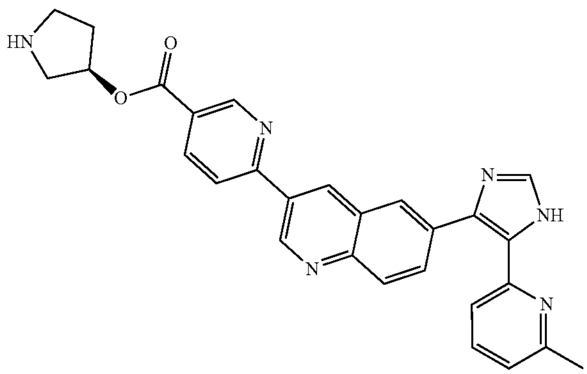 | [(3R)-pyrrolidin-3-yl] 6-[6-[5-(6-methyl-2-pyridyl)-1H-imidazol-4-yl]-3-quinolyl]pyridine-3-carboxylate | 477.1 |
| 1112 | 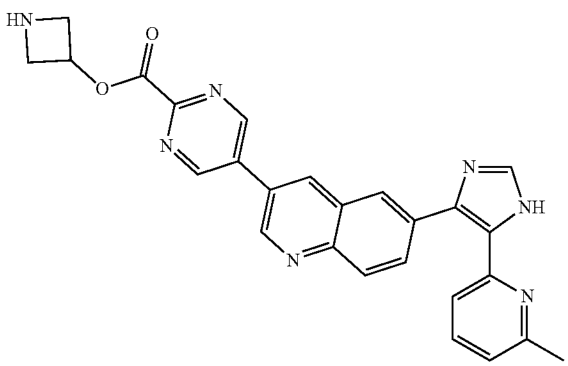 [SMILES: Cc1cccc(-c2[nH]cnc2-c2ccc3ncc(-c4cnc(C(=O)OC5CNC5)nc4)cc3c2)n1] | azetidin-3-yl 5-[6-[5-(6-methyl-2-pyridyl)-1H-imidazol-4-yl]-3-quinolyl]pyrimidine-2-carboxylate | 464.1 |
| 1113 | 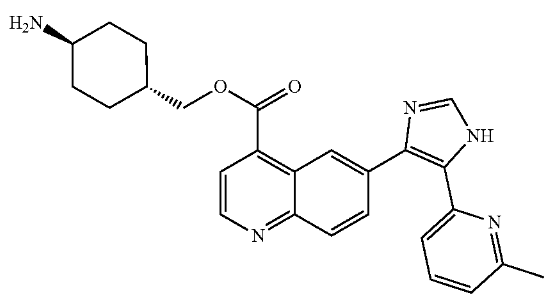 [SMILES: Cc1cccc(-c2[nH]cnc2-c2ccc3nccc(C(=O)OC[C@H]4CC[C@H](N)CC4)c3c2)n1] | (4-aminocyclohexyl)methyl 6-[5-(6-methyl-2-pyridyl)-1H-pyrazol-4-yl]quinoline-4-carboxylate | 442.2 |
| 1114 | 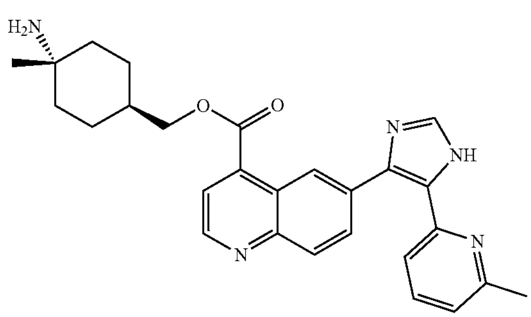 | (4-amino-4-methyl-cyclohexyl)methyl 6-[5-(6-methyl-2-pyridyl)-1H-imidazol-4-yl]quinoline-4-carboxylate | |

TABLE 1-continued

| No. | Structure | Chemical Name | [M + H]+ |
|---|---|---|---|
| 1115 | 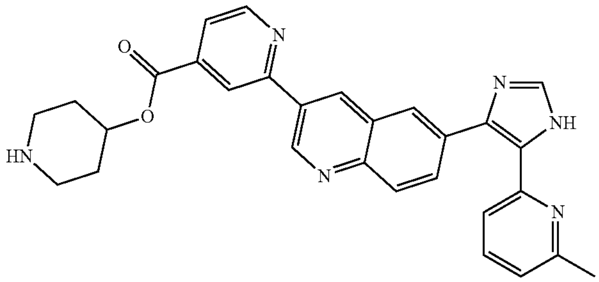 [SMILES: Cc1cccc(-c2[nH]cnc2-c2ccc3ncc(-c4cc(C(=O)OC5CCNCC5)ccn4)cc3c2)n1] | 4-piperidyl 2-[6-[5-(6-methyl-2-pyridyl)-1H-imidazol-4-yl]-3-quinolyl]pyridine-4-carboxylate | 491.2 |
| 1116 | 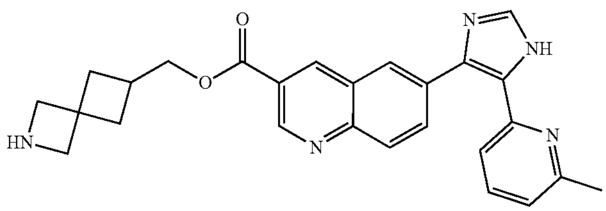 [SMILES: Cc1cccc(-c2[nH]cnc2-c2ccc3ncc(C(=O)OCC4CC5(CNC5)C4)cc3c2)n1] | 2-azaspiro[3.3]heptan-6-ylmethyl 6-[5-(6-methyl-2-pyridyl)-1H-imidazol-4-yl]quinoline-3-carboxylate | 440.1 |
| 1117 | 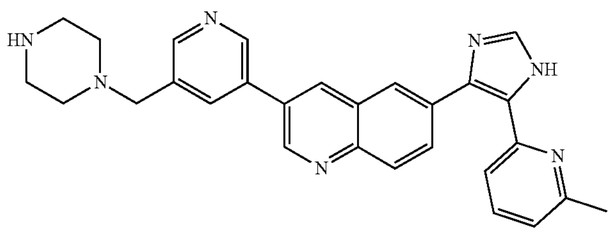 [SMILES: Cc1cccc(-c2[nH]cnc2-c2ccc3ncc(-c4cncc(CN5CCNCC5)c4)cc3c2)n1] | 6-[5-(6-methyl-2-pyridyl)-1H-imidazol-4-yl]-3-[5-(piperazin-1-ylmethyl)-3-pyridyl]quinoline | 462.1 |
| 1118 | 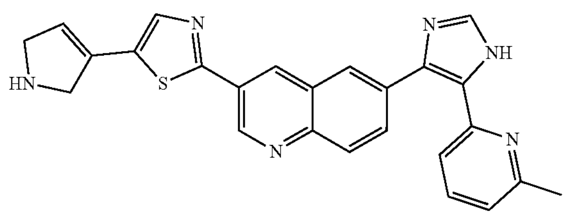 [SMILES: Cc1cccc(-c2[nH]cnc2-c2ccc3ncc(-c4ncc(C5=CCNC5)s4)cc3c2)n1] | 5-(2,5-dihydro-1H-pyrrol-3-yl)-2-[6-[5-(6-methyl-2-pyridyl)-1H-imidazol-4-yl]-3-quinolyl]thiazole | 437.0 |
| 1119 | 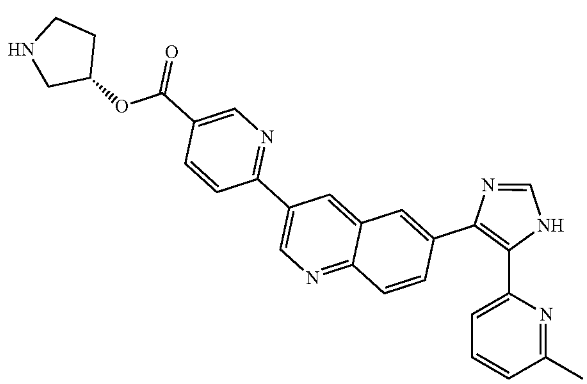 | [(3S)-pyrrolidin-3-yl] 6-[6-[5-(6-methyl-2-pyridyl)-1H-imidazol-4-yl]-3-quinolyl]pyridine-3-carboxylate | 477.2 |
| 1120 | 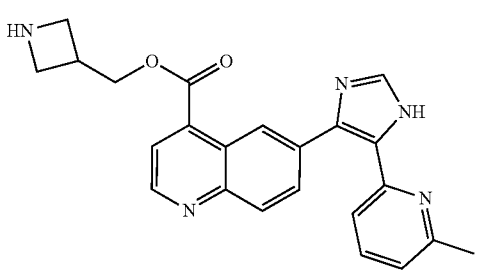 [SMILES: Cc1cccc(-c2[nH]cnc2-c2ccc3nccc(C(=O)OCC4CNC4)c3c2)n1] | azetidin-3-ylmethyl 6-[5-(6-methyl-2-pyridyl)-1H-pyrazol-4-yl]quinoline-4-carboxylate | 400.2 |

TABLE 1-continued

| No. | Structure | Chemical Name | [M + H]+ |
|---|---|---|---|
| 1121 | 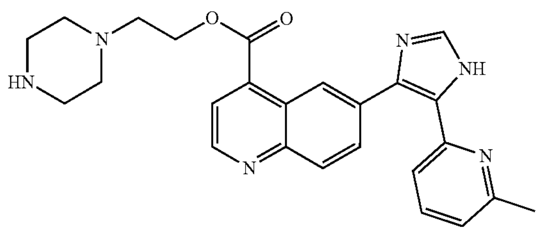 [SMILES: Cc1cccc(-c2[nH]cnc2-c2ccc3nccc(C(=O)OCCN4CCNCC4)c3c2)n1] | 2-piperazin-1-ylethyl 6-[5-(6-methyl-2-pyridyl)-1H-imidazol-4-yl]quinoline-4-carboxylate | 443.2 |
| 1122 | 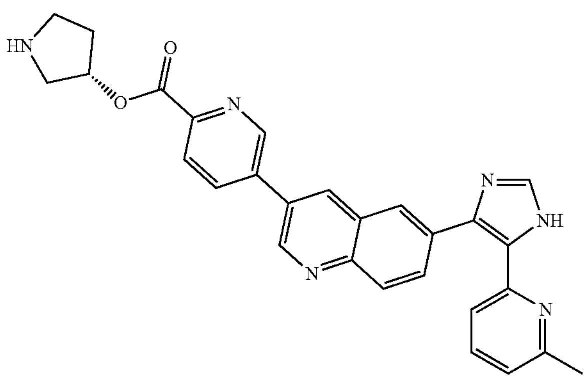 [SMILES: Cc1cccc(-c2[nH]cnc2-c2ccc3ncc(-c4ccc(C(=O)O[C@H]5CCNC5)nc4)cc3c2)n1] | [(3S)-pyrrolidin-3-yl] 5-[6-[5-(6-methyl-2-pyridyl)-1H-imidazol-4-yl]-3-quinolyl]pyridine-2-carboxylate | 477.2 |
| 1123 | 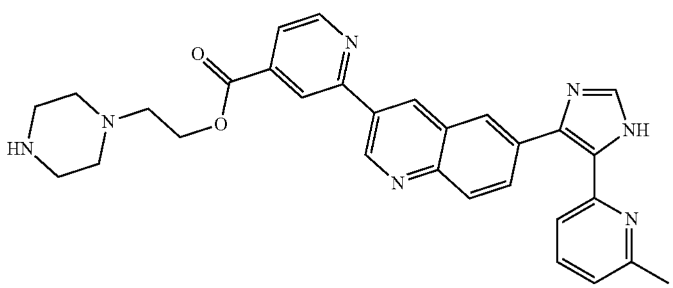 | 2-piperazin-1-ylethyl 2-[6-[5-(6-methyl-2-pyridyl)-1H-imidazol-4-yl]-3-quinolyl]pyridine-4-carboxylate | 520.2 |
| 1124 | 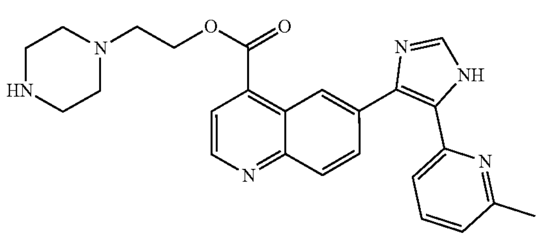 [SMILES: Cc1cccc(-c2[nH]cnc2-c2ccc3nccc(C(=O)OCCN4CCNCC4)c3c2)n1] | 2-piperazin-1-ylethyl 6-[5-(6-methyl-2-pyridyl)-1H-pyrazol-4-yl]quinoline-4-carboxylate | 443.2 |
| 1125 | 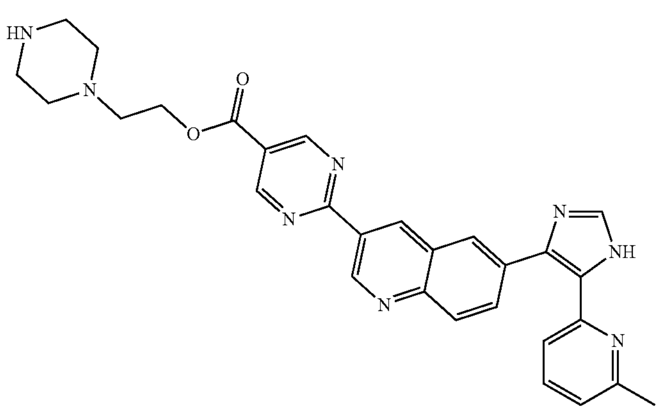 [SMILES: Cc1cccc(-c2[nH]cnc2-c2ccc3ncc(-c4ncc(C(=O)OCCN5CCNCC5)cn4)cc3c2)n1] | 2-piperazin-1-ylethyl 2-[6-[5-(6-methyl-2-pyridyl)-1H-imidazol-4-yl]-3-quinolyl]pyrimidine-5-carboxylate | 521.2 |

TABLE 1-continued

| No. | Structure | Chemical Name | [M + H]+ |
|---|---|---|---|
| 1126 | 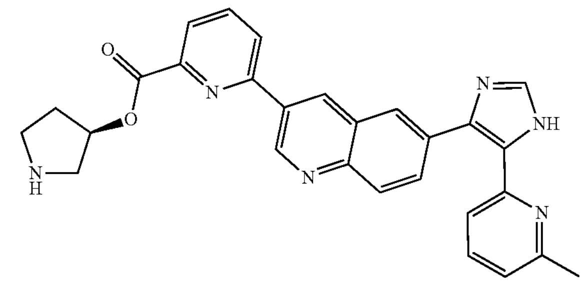 | [(3R)-pyrrolidin-3-yl] 6-[6-[5-(6-methyl-2-pyridyl)-1H-imidazol-4-yl]-3-quinolyl]pyridine-2-carboxylate | 477.1 |
| 1127 | 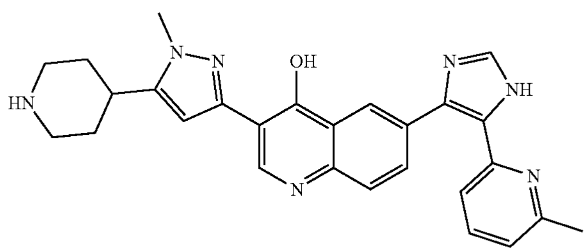 [SMILES: Cc1cccc(-c2[nH]cnc2-c2ccc3ncc(-c4cc(C5CCNCC5)n(C)n4)c(O)c3c2)n1] | 3-[1-methyl-5-(4-piperidyl)pyrazol-3-yl]-6-[5-(6-methyl-2-pyridyl)-1H-imidazol-4-yl]quinolin-4-ol | |
| 1128 | 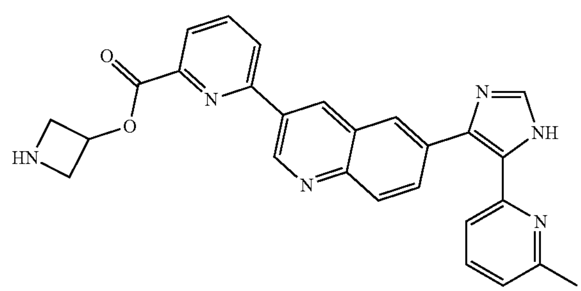 [SMILES: Cc1cccc(-c2[nH]cnc2-c2ccc3ncc(-c4cccc(C(=O)OC5CNC5)n4)cc3c2)n1] | azetidin-3-yl 6-[6-[5-(6-methyl-2-pyridyl)-1H-imidazol-4-yl]-3-quinolyl]pyridine-2-carboxylate | 463.1 |
| 1129 | 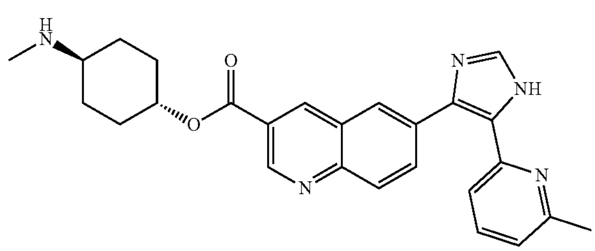 | [4-(methylamino)cyclohexyl] 6-[5-(6-methyl-2-pyridyl)-1H-imidazol-4-yl]quinoline-3-carboxylate | 442.2 |
| 1130 | 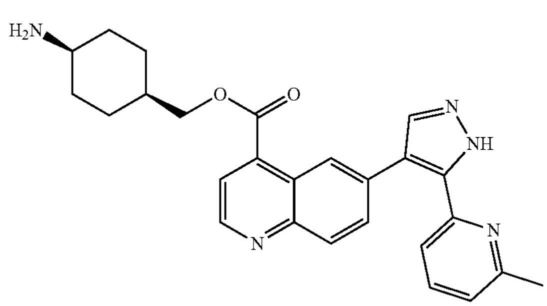 [SMILES: Cc1cccc(-c2[nH]ncc2-c2ccc3nccc(C(=O)OC[C@H]4CC[C@@H](N)CC4)c3c2)n1] | (4-aminocyclohexyl)methyl 6-[5-(6-methyl-2-pyridyl)-1H-pyrazol-4-yl]quinoline-4-carboxylate | 442.2 |

TABLE 1-continued

| No. | Structure | Chemical Name | [M + H]⁺ |
|-----|-----------|---------------|----------|
| 1131 | 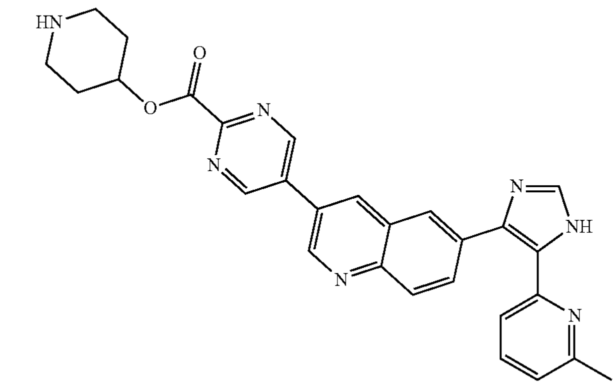 [SMILES: Cc1cccc(-c2[nH]cnc2-c2ccc3ncc(-c4cnc(C(=O)OC5CCNCC5)nc4)cc3c2)n1] | 4-piperidyl 5-[6-[5-(6-methyl-2-pyridyl)-1H-imidazol-4-yl]-3-quinolyl]pyrimidine-2-carboxylate | 492.2 |
| 1132 | 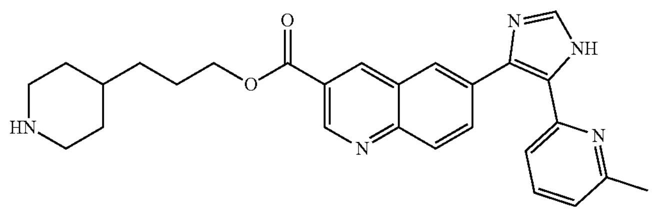 [SMILES: Cc1cccc(-c2[nH]cnc2-c2ccc3ncc(C(=O)OCCCC4CCNCC4)cc3c2)n1] | 3-(4-piperidyl)propyl 6-[5-(6-methyl-2-pyridyl)-1H-imidazol-4-yl]quinoline-3-carboxylate | 456.2 |
| 1133 | 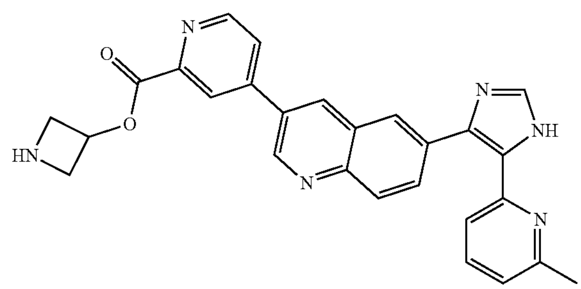 [SMILES: Cc1cccc(-c2[nH]cnc2-c2ccc3ncc(-c4ccnc(C(=O)OC5CNC5)c4)cc3c2)n1] | azetidin-3-yl 4-[6-[5-(6-methyl-2-pyridyl)-1H-imidazol-4-yl]-3-quinolyl]pyridine-2-carboxylate | 463.1 |
| 1134 | 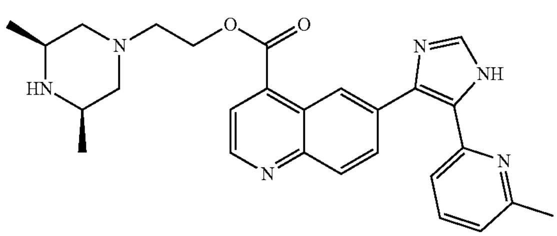 | 2-[rac-(3R,5S)-3,5-dimethylpiperazin-1-yl]ethyl 6-[5-(6-methyl-2-pyridyl)-1H-imidazol-4-yl]quinoline-4-carboxylate | |
| 1135 | 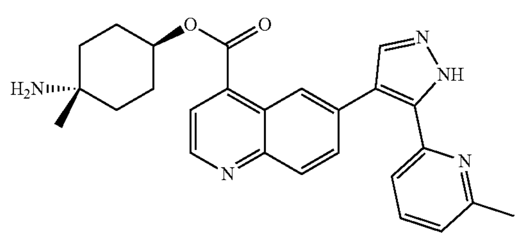 [SMILES: Cc1cccc(-c2[nH]ncc2-c2ccc3nccc(C(=O)O[C@H]4CC[C@](C)(N)CC4)c3c2)n1] | (4-amino-4-methyl-cyclohexyl) 6-[5-(6-methyl-2-pyridyl)-1H-pyrazol-4-yl]quinoline-4-carboxylate | 442.2 |
| 1136 | 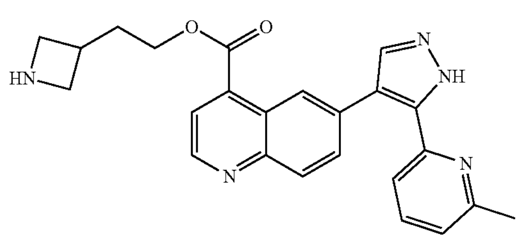 [SMILES: Cc1cccc(-c2[nH]ncc2-c2ccc3nccc(C(=O)OCCC4CNC4)c3c2)n1] | 2-(azetidin-3-yl)ethyl 6-[5-(6-methyl-2-pyridyl)-1H-pyrazol-4-yl]quinoline-4-carboxylate | 414.1 |

TABLE 1-continued

| No. | Structure | Chemical Name | [M + H]+ |
|---|---|---|---|
| 1137 | 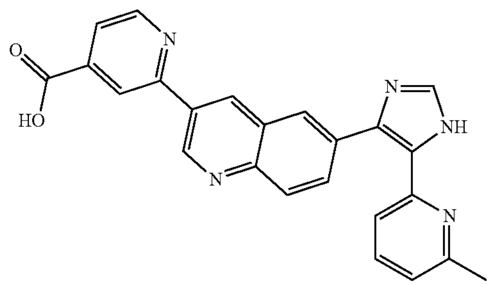 [SMILES: Cc1cccc(-c2[nH]cnc2-c2ccc3ncc(-c4cc(C(=O)O)ccn4)cc3c2)n1] | 2-[6-[5-(6-methyl-2-pyridyl)-1H-imidazol-4-yl]-3-quinolyl]pyridine-4-carboxylic acid | 408.2 |
| 1138 | 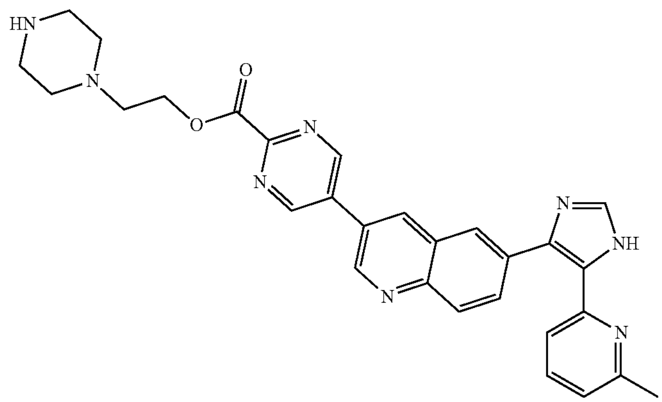 | 2-piperazin-1-ylethyl 5-[6-[5-(6-methyl-2-pyridyl)-1H-imidazol-4-yl]-3-quinolyl]pyrimidine-2-carboxylate | 521.2 |
| 1139 | 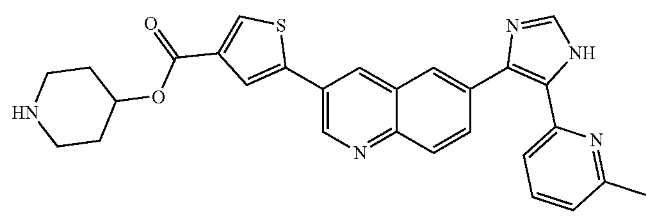 | 4-piperidyl 5-[6-[5-(6-methyl-2-pyridyl)-1H-imidazol-4-yl]-3-quinolyl]thiophene-3-carboxylate | 496.1 |
| 1140 | 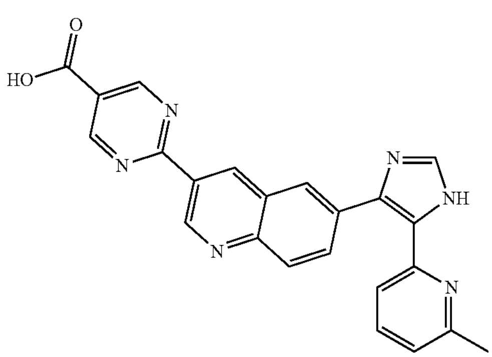 | 2-[6-[5-(6-methyl-2-pyridyl)-1H-imidazol-4-yl]-3-quinolyl]pyrimidine-5-carboxylic acid | 409.8 |
| 1141 | 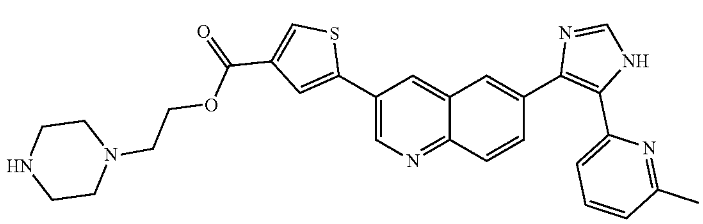 [SMILES: Cc1cccc(-c2[nH]cnc2-c2ccc3ncc(-c4cc(C(=O)OCCN5CCNCC5)cs4)cc3c2)n1] | 2-piperazin-1-ylethyl 5-[6-[5-(6-methyl-2-pyridyl)-1H-imidazol-4-yl]-3-quinolyl]thiophene-3-carboxylate | 525.2 |

TABLE 1-continued

| No. | Structure | Chemical Name | [M + H]⁺ |
|---|---|---|---|
| 1142 | 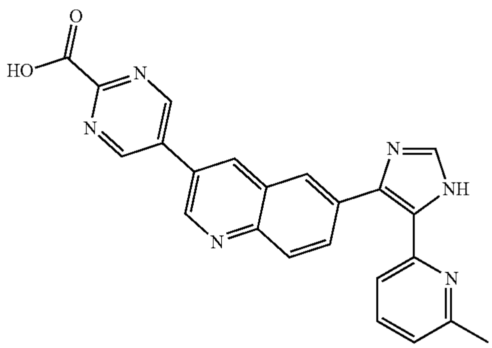 [SMILES: Cc1cccc(-c2[nH]cnc2-c2ccc3ncc(-c4cnc(C(=O)O)nc4)cc3c2)n1] | 5-[6-[5-(6-methyl-2-pyridyl)-1H-imidazol-4-yl]-3-quinolyl]pyrimidine-2-carboxylic acid | 409.1 |
| 1143 | 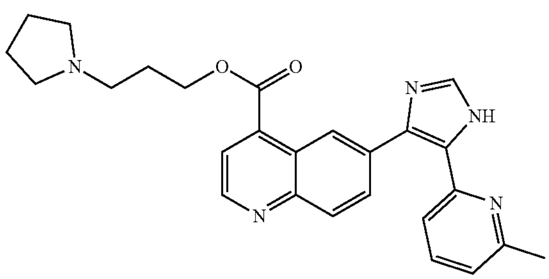 [SMILES: Cc1cccc(-c2[nH]cnc2-c2ccc3nccc(C(=O)OCCCN4CCCC4)c3c2)n1] | 3-pyrrolidin-1-ylpropyl 6-[5-(6-methyl-2-pyridyl)-1H-imidazol-4-yl]quinoline-4-carboxylate | |
| 1144 | 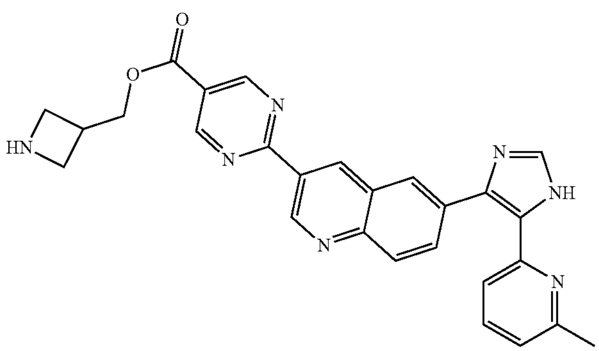 [SMILES: Cc1cccc(-c2[nH]cnc2-c2ccc3ncc(-c4ncc(C(=O)OCC5CNC5)cn4)cc3c2)n1] | azetidin-3-ylmethyl 2-[6-[5-(6-methyl-2-pyridyl)-1H-imidazol-4-yl]-3-quinolyl]pyrimidine-5-carboxylate | 478.1 |
| 1145 | 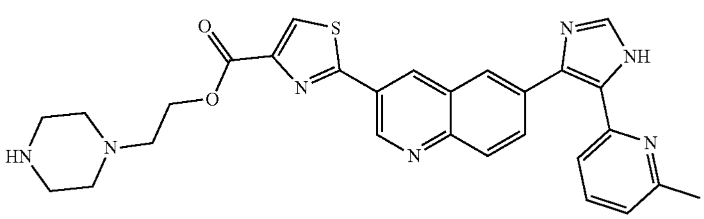 [SMILES: Cc1cccc(-c2[nH]cnc2-c2ccc3ncc(-c4nc(C(=O)OCCN5CCNCC5)cs4)cc3c2)n1] | 2-piperazin-1-ylethyl 2-[6-[5-(6-methyl-2-pyridyl)-1H-imidazol-4-yl]-3-quinolyl]thiazole-4-carboxylate | 526.1 |
| 1146 | 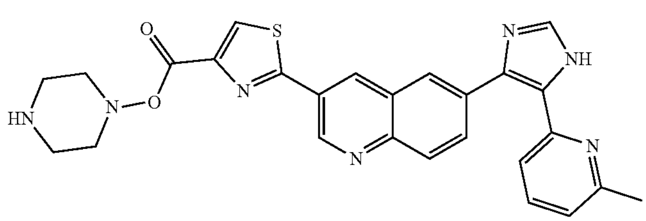 [SMILES: Cc1cccc(-c2[nH]cnc2-c2ccc3ncc(-c4nc(C(=O)ON5CCNCC5)cs4)cc3c2)n1] | 4-piperidyl 4-[6-[5-(6-methyl-2-pyridyl)-1H-imidazol-4-yl]-3-quinolyl]thiazole-2-carboxylate | 497.2 |

TABLE 1-continued

| No. | Structure | Chemical Name | [M + H]+ |
|---|---|---|---|
| 1147 | 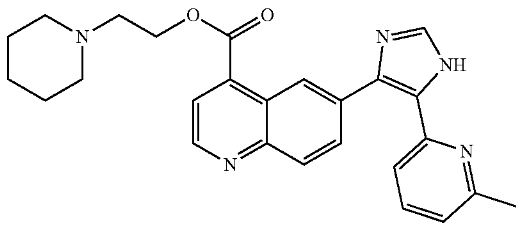 [SMILES: Cc1cccc(-c2[nH]cnc2-c2ccc3nccc(C(=O)OCCN4CCCCC4)c3c2)n1] | 2-(1-piperidyl)ethyl 6-[5-(6-methyl-2-pyridyl)-1H-pyrazol-4-yl]quinoline-4-carboxylate | 442.2 |
| 1148 | 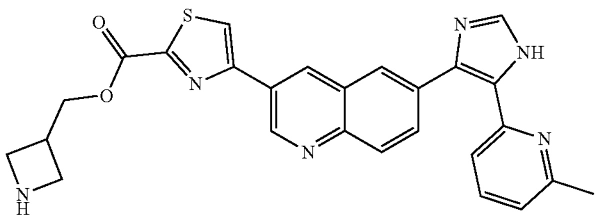 [SMILES: Cc1cccc(-c2[nH]cnc2-c2ccc3ncc(-c4csc(C(=O)OCC5CNC5)n4)cc3c2)n1] | azetidin-3-ylmethyl 4-[6-[5-(6-methyl-2-pyridyl)-1H-imidazol-4-yl]-3-quinolyl]thiazole-2-carboxylate | 483.2 |
| 1149 | 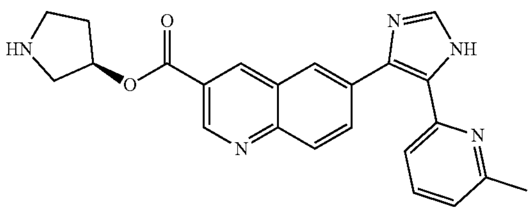 [SMILES: Cc1cccc(-c2[nH]cnc2-c2ccc3ncc(C(=O)O[C@@H]4CCNC4)cc3c2)n1] | [(3R)-pyrrolidin-3-yl] 6-[5-(6-methyl-2-pyridyl)-1H-imidazol-4-yl]quinoline-3-carboxylate | 400.2 |
| 1150 | 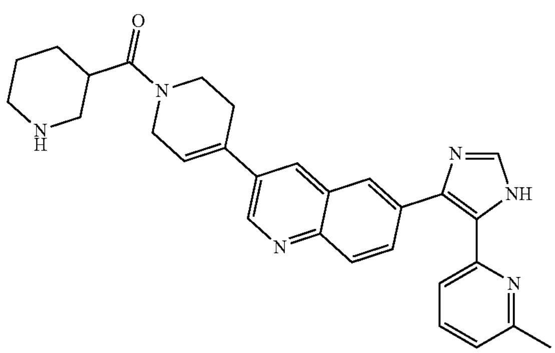 [SMILES: Cc1cccc(-c2[nH]cnc2-c2ccc3ncc(C4=CCN(C(=O)C5CCCNC5)CC4)cc3c2)n1] | [4-[6-[5-(6-methyl-2-pyridyl)-1H-imidazol-4-yl]-3-quinolyl]-3,6-dihydro-2H-pyridin-1-yl]-(3-piperidyl)methanone | 479.1 |
| 1151 | 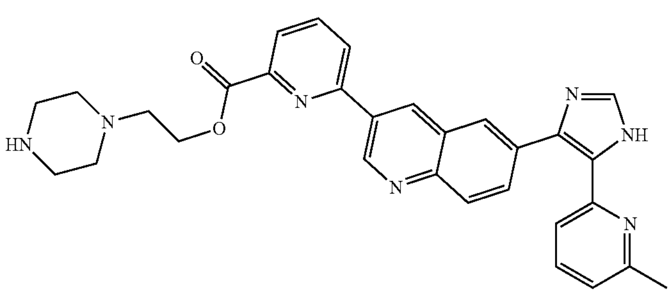 [SMILES: Cc1cccc(-c2[nH]cnc2-c2ccc3ncc(-c4cccc(C(=O)OCCN5CCNCC5)n4)cc3c2)n1] | 2-piperazin-1-ylethyl 6-[6-[5-(6-methyl-2-pyridyl)-1H-imidazol-4-yl]-3-quinolyl]pyridine-2-carboxylate | 520.2 |
| 1152 | 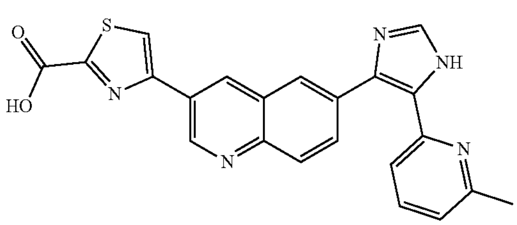 [SMILES: Cc1cccc(-c2[nH]cnc2-c2ccc3ncc(-c4csc(C(=O)O)n4)cc3c2)n1] | 4-[6-[5-(6-methyl-2-pyridyl)-1H-imidazol-4-yl]-3-quinolyl]thiazole-2-carboxylic acid | 414.1 |

TABLE 1-continued

| No. | Structure | Chemical Name | [M + H]+ |
|---|---|---|---|
| 1153 | 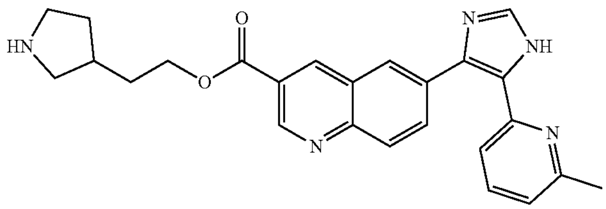 [SMILES: Cc1cccc(-c2[nH]cnc2-c2ccc3ncc(C(=O)OCCC4CCNC4)cc3c2)n1] | 2-pyrrolidin-3-ylethyl 6-[5-(6-methyl-2-pyridyl)-1H-imidazol-4-yl]quinoline-3-carboxylate | 482.2 |
| 1154 | 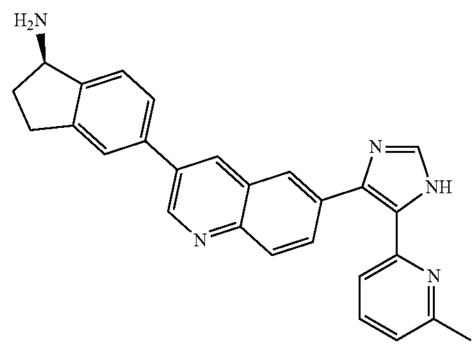 [SMILES: Cc1cccc(-c2[nH]cnc2-c2ccc3ncc(-c4ccc5c(c4)CC[C@H]5N)cc3c2)n1] | (1R)-5-[6-[5-(6-methyl-2-pyridyl)-1H-imidazol-4-yl]-3-quinolyl]indan-1-amine | 418.2 |
| 1155 | 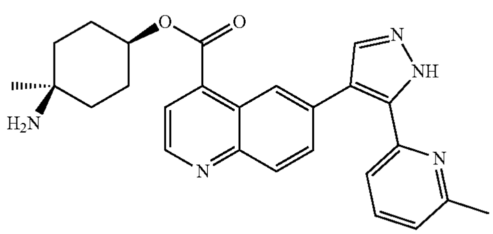 | (4-amino-4-methyl-cyclohexyl) 6-[5-(6-methyl-2-pyridyl)-1H-pyrazol-4-yl]quinoline-4-carboxylate | 442.2 |
| 1156 | 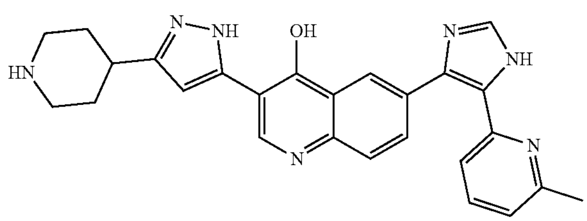 [SMILES: Cc1cccc(-c2[nH]cnc2-c2ccc3ncc(-c4cc(C5CCNCC5)n[nH]4)c(O)c3c2)n1] | 6-[5-(6-methyl-2-pyridyl)-1H-imidazol-4-yl]-3-[3-(4-piperidyl)-1H-pyrazol-5-yl]quinolin-4-ol | |
| 1157 | 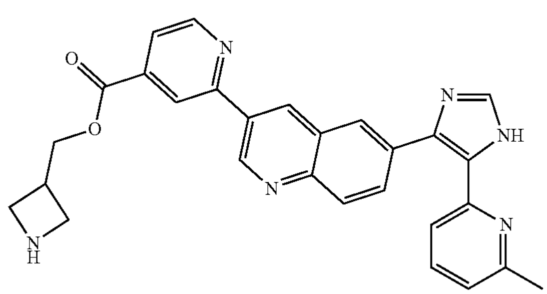 [SMILES: Cc1cccc(-c2[nH]cnc2-c2ccc3ncc(-c4cc(C(=O)OCC5CNC5)ccn4)cc3c2)n1] | azetidin-3-ylmethyl 2-[6-[5-(6-methyl-2-pyridyl)-1H-imidazol-4-yl]-3-quinolyl]pyridine-4-carboxylate | 477.1 |

TABLE 1-continued

| No. | Structure | Chemical Name | [M + H]+ |
|---|---|---|---|
| 1158 | 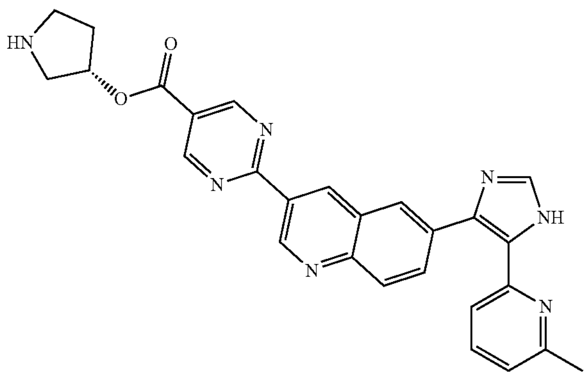 [SMILES: Cc1cccc(-c2[nH]cnc2-c2ccc3ncc(-c4ncc(C(=O)O[C@H]5CCNC5)cn4)cc3c2)n1] | [(3S)-pyrrolidin-3-yl] 2-[6-[5-(6-methyl-2-pyridyl)-1H-imidazol-4-yl]-3-quinolyl]pyrimidine-5-carboxylate | 478.1 |
| 1159 | 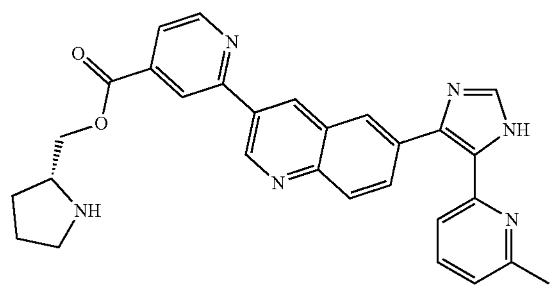 [SMILES: Cc1cccc(-c2[nH]cnc2-c2ccc3ncc(-c4cc(C(=O)OC[C@H]5CCCN5)ccn4)cc3c2)n1] | [(2R)-pyrrolidin-2-yl]methyl 2-[6-[5-(6-methyl-2-pyridyl)-1H-imidazol-4-yl]-3-quinolyl]pyridine-4-carboxylate | 491.1 |
| 1160 | 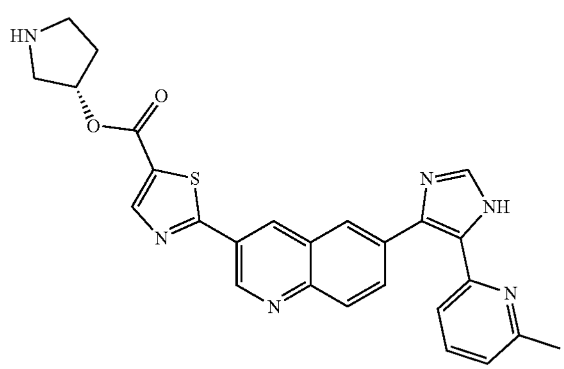 [SMILES: Cc1cccc(-c2[nH]cnc2-c2ccc3ncc(-c4ncc(C(=O)O[C@H]5CCNC5)s4)cc3c2)n1] | [(3S)-pyrrolidin-3-yl] 2-[6-[5-(6-methyl-2-pyridyl)-1H-imidazol-4-yl]-3-quinolyl]thiazole-5-carboxylate | 483.1 |
| 1161 | 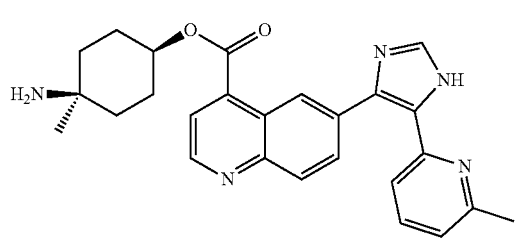 [SMILES: Cc1cccc(-c2[nH]cnc2-c2ccc3nccc(C(=O)O[C@H]4CC[C@@](C)(N)CC4)c3c2)n1] | (4-amino-4-methyl-cyclohexyl) 6-[5-(6-methyl-2-pyridyl)-1H-imidazol-4-yl]quinoline-4-carboxylate | 442.2 |
| 1162 | 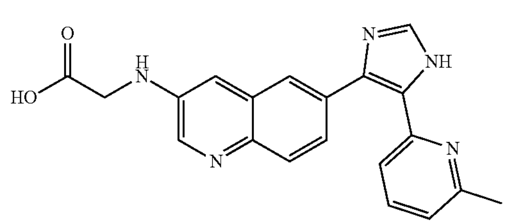 [SMILES: Cc1cccc(-c2[nH]cnc2-c2ccc3ncc(NCC(=O)O)cc3c2)n1] | 2-[[6-[5-(6-methyl-2-pyridyl)-1H-imidazol-4-yl]-3-quinolyl]amino]acetic acid | 360.1 |

TABLE 1-continued

| No. | Structure | Chemical Name | [M + H]+ |
|---|---|---|---|
| 1163 | 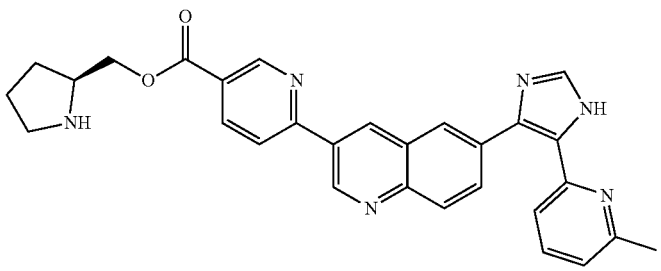 [SMILES: Cc1cccc(-c2[nH]cnc2-c2ccc3ncc(-c4ccc(C(=O)OC[C@@H]5CCCN5)cn4)cc3c2)n1] | [(2S)-pyrrolidin-2-yl]methyl 6-[6-[5-(6-methyl-2-pyridyl)-1H-imidazol-4-yl]-3-quinolyl]pyridine-3-carboxylate | 491.1 |
| 1164 | 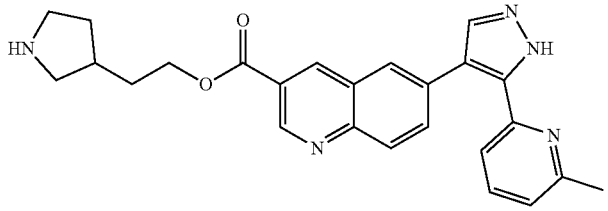 [SMILES: Cc1cccc(-c2[nH]ncc2-c2ccc3ncc(C(=O)OCCC4CCNC4)cc3c2)n1] | 2-pyrrolidin-3-ylethyl 6-[5-(6-methyl-2-pyridyl)-1H-pyrazol-4-yl]quinoline-3-carboxylate | 428.1 |
| 1165 | 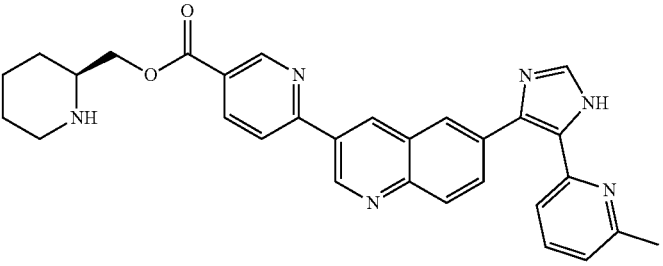 [SMILES: Cc1cccc(-c2[nH]cnc2-c2ccc3ncc(-c4ccc(C(=O)OC[C@@H]5CCCCN5)cn4)cc3c2)n1] | [(2S)-2-piperidyl]methyl 6-[6-[5-(6-methyl-2-pyridyl)-1H-imidazol-4-yl]-3-quinolyl]pyridine-3-carboxylate | 505.1 |
| 1166 | 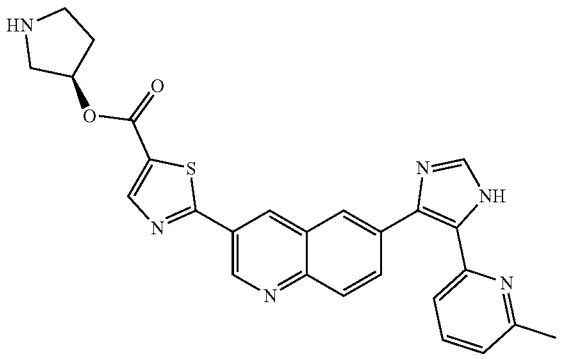 [SMILES: Cc1cccc(-c2[nH]cnc2-c2ccc3ncc(-c4ncc(C(=O)O[C@@H]5CCNC5)s4)cc3c2)n1] | [(3R)-pyrrolidin-3-yl] 2-[6-[5-(6-methyl-2-pyridyl)-1H-imidazol-4-yl]-3-quinolyl]thiazole-5-carboxylate | 483.1 |
| 1167 | 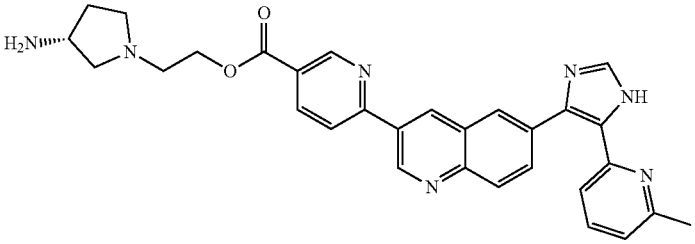 [SMILES: Cc1cccc(-c2[nH]cnc2-c2ccc3ncc(-c4ccc(C(=O)OCCN5CC[C@@H](N)C5)cn4)cc3c2)n1] | 2-[(3R)-3-aminopyrrolidin-1-yl]ethyl 6-[6-[5-(6-methyl-2-pyridyl)-1H-imidazol-4-yl]-3-quinolyl]pyridine-3-carboxylate | 520.1 |

TABLE 1-continued

| No. | Structure | Chemical Name | [M + H]+ |
|---|---|---|---|
| 1168 | 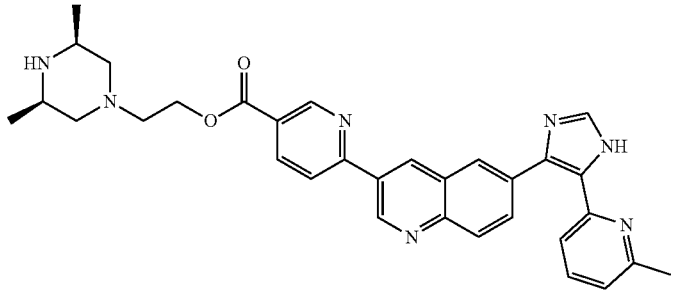 | 2-[rac-(3S,5R)-3,5-dimethylpiperazin-1-yl]ethyl 6-[6-[5-(6-methyl-2-pyridyl)-1H-imidazol-4-yl]-3-quinolyl]pyridine-3-carboxylate | 548.3 |
| 1169 | 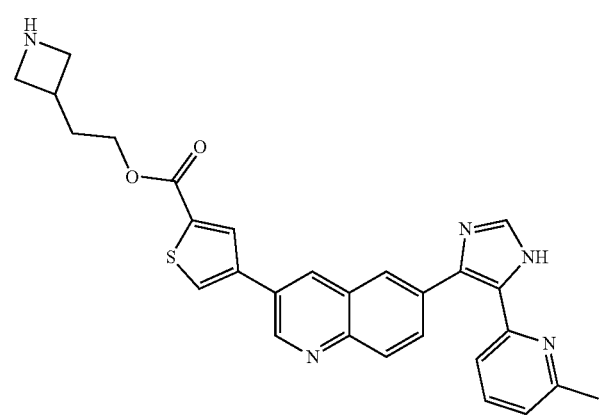 [SMILES: Cc1cccc(-c2[nH]cnc2-c2ccc3ncc(-c4csc(C(=O)OCCC5CNC5)c4)cc3c2)n1] | 2-(azetidin-3-yl)ethyl 4-[6-[5-(6-methyl-2-pyridyl)-1H-imidazol-4-yl]-3-quinolyl]thiophene-2-carboxylate | 496.1 |
| 1170 | 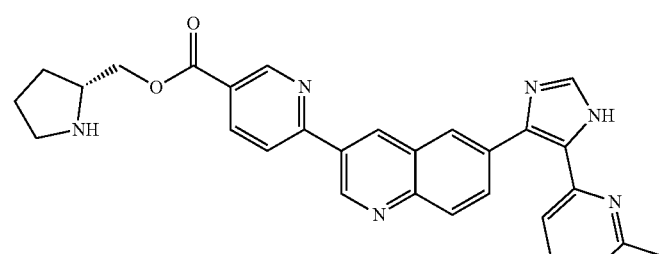 | [(2R)-pyrrolidin-2-yl]methyl 6-[6-[5-(6-methyl-2-pyridyl)-1H-imidazol-4-yl]-3-quinolyl]pyridine-3-carboxylate | 491.1 |
| 1171 | 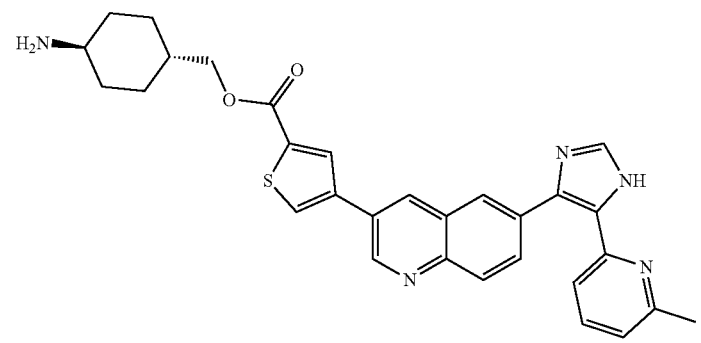 [SMILES: Cc1cccc(-c2[nH]cnc2-c2ccc3ncc(-c4csc(C(=O)OC[C@H]5CC[C@H](N)CC5)c4)cc3c2)n1] | (4-aminocyclohexyl)methyl 4-[6-[5-(6-methyl-2-pyridyl)-1H-imidazol-4-yl]-3-quinolyl]thiophene-2-carboxylate | 524.1 |

TABLE 1-continued

| No. | Structure | Chemical Name | [M + H]+ |
|---|---|---|---|
| 1172 | 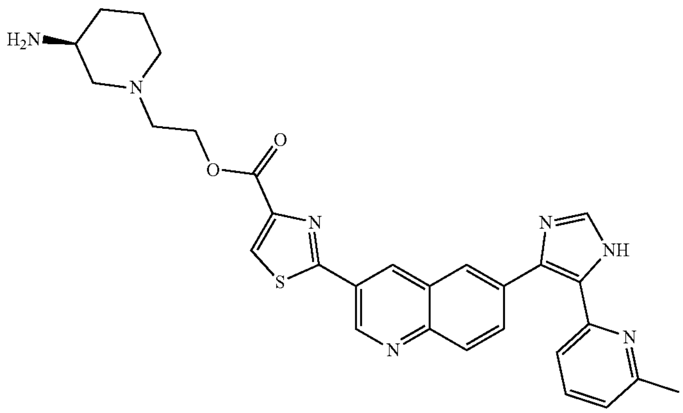 [SMILES: Cc1cccc(-c2[nH]cnc2-c2ccc3ncc(-c4nc(C(=O)OCCN5CCC[C@H](N)C5)cs4)cc3c2)n1] | 2-[(3S)-3-amino-1-piperidyl]ethyl 2-[6-[5-(6-methyl-2-pyridyl)-1H-imidazol-4-yl]-3-quinolyl]thiazole-4-carboxylate | 540.1 |
| 1173 | 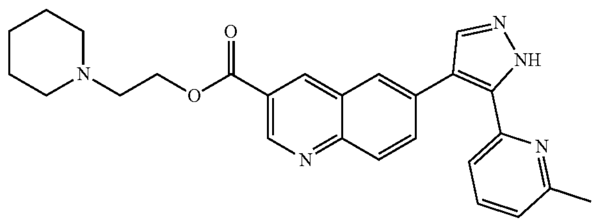 [SMILES: Cc1cccc(-c2[nH]ncc2-c2ccc3ncc(C(=O)OCCN4CCCCC4)cc3c2)n1] | 2-(1-piperidyl)ethyl 6-[5-(6-methyl-2-pyridyl)-1H-pyrazol-4-yl]quinoline-3-carboxylate | 442.1 |
| 1174 | 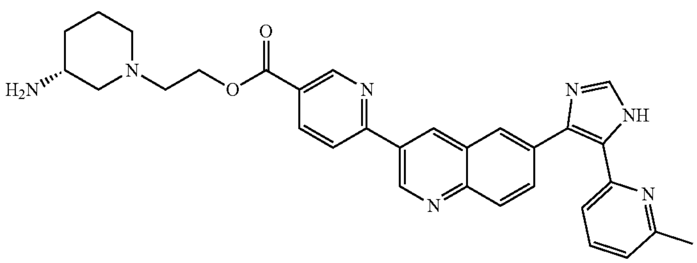 [SMILES: Cc1cccc(-c2[nH]cnc2-c2ccc3ncc(-c4ccc(C(=O)OCCN5CCC[C@@H](N)C5)cn4)cc3c2)n1] | 2-[(3R)-3-amino-1-piperidyl]ethyl 6-[6-[5-(6-methyl-2-pyridyl)-1H-imidazol-4-yl]-3-quinolyl]pyridine-3-carboxylate | 534.2 |
| 1175 | 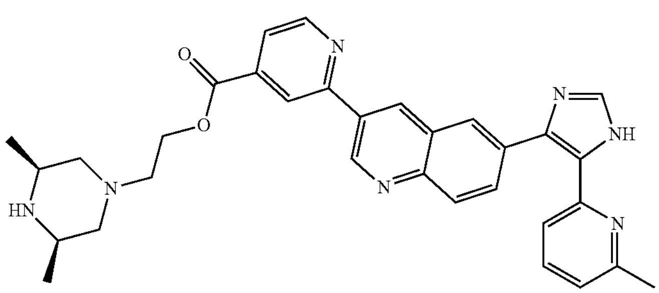 | 2-[(3R,5S)-3,5-dimethylpiperazin-1-yl]ethyl 2-[6-[5-(6-methyl-2-pyridyl)-1H-imidazol-4-yl]-3-quinolyl]pyridine-4-carboxylate | 548.2 |
| 1176 | 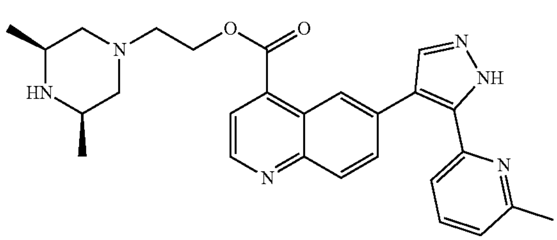 | 2-[(3R,5S)-3,5-dimethylpiperazin-1-yl]ethyl 6-[5-(6-methyl-2-pyridyl)-1H-pyrazol-4-yl]quinoline-4-carboxylate | 471.2 |

TABLE 1-continued

| No. | Structure | Chemical Name | [M + H]+ |
|---|---|---|---|
| 1177 | 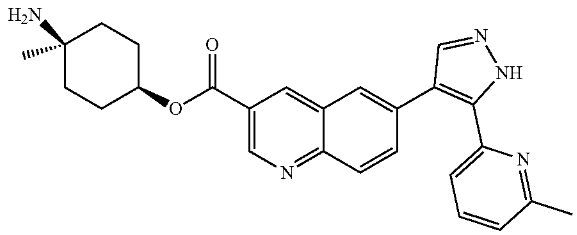 | (4-amino-4-methyl-cyclohexyl) 6-[5-(6-methyl-2-pyridyl)-1H-pyrazol-4-yl]quinoline-3-carboxylate | 442.1 |
| 1178 | 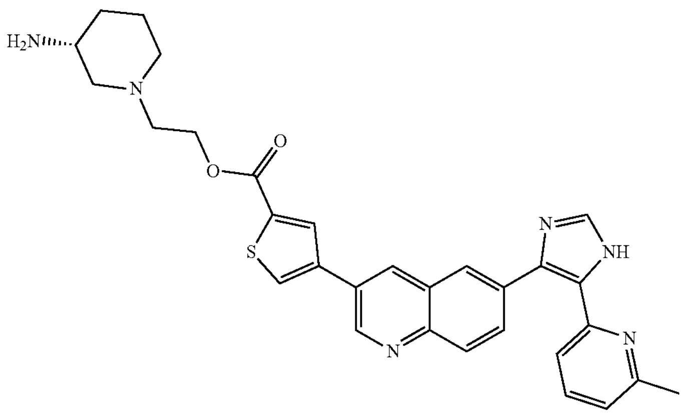 [SMILES: Cc1cccc(-c2[nH]cnc2-c2ccc3ncc(-c4csc(C(=O)OCCN5CCC[C@@H](N)C5)c4)cc3c2)n1] | 2-[(3R)-3-amino-1-piperidyl]ethyl 4-[6-[5-(6-methyl-2-pyridyl)-1H-imidazol-4-yl]-3-quinolyl]thiophene-2-carboxylate | 539.2 |
| 1179 | 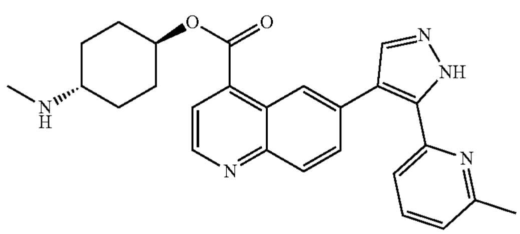 | [4-(methylamino)cyclohexyl] 6-[5-(6-methyl-2-pyridyl)-1H-pyrazol-4-yl]quinoline-4-carboxylate | 442.2 |
| 1180 | 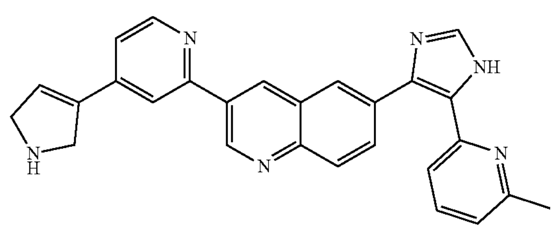 [SMILES: Cc1cccc(-c2[nH]cnc2-c2ccc3ncc(-c4cc(C5=CCNC5)ccn4)cc3c2)n1] | 3-[5-(2,5-dihydro-1H-pyrrol-3-yl)-3-pyridyl]-6-[5-(6-methyl-2-pyridyl)-1H-imidazol-4-yl]quinoline | |
| 1181 | 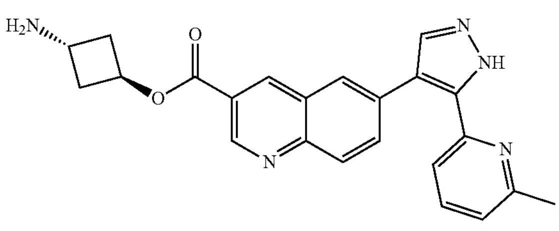 [SMILES: Cc1cccc(-c2[nH]ncc2-c2ccc3ncc(C(=O)O[C@H]4C[C@H](N)C4)cc3c2)n1] | (3-aminocyclobutyl) 6-[5-(6-methyl-2-pyridyl)-1H-pyrazol-4-yl]quinoline-3-carboxylate | 400.1 |
| 1182 | 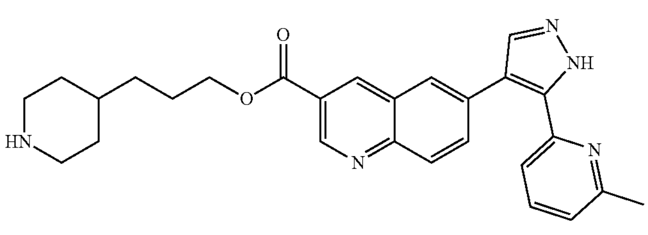 [SMILES: Cc1cccc(-c2[nH]ncc2-c2ccc3ncc(C(=O)OCCCC4CCNCC4)cc3c2)n1] | 3-(4-piperidyl)propyl 6-[5-(6-methyl-2-pyridyl)-1H-pyrazol-4-yl]quinoline-3-carboxylate | 456.2 |

TABLE 1-continued

| No. | Structure | Chemical Name | [M + H]+ |
|---|---|---|---|
| 1183 | 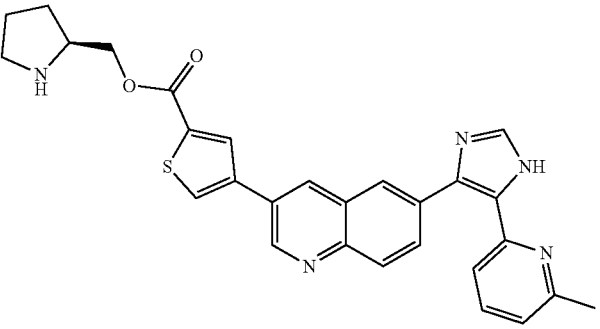 [SMILES: Cc1cccc(-c2[nH]cnc2-c2ccc3ncc(-c4csc(C(=O)OC[C@@H]5CCCN5)c4)cc3c2)n1] | [(2S)-pyrrolidin-2-yl]methyl 4-[6-[5-(6-methyl-2-pyridyl)-1H-imidazol-4-yl]-3-quinolyl]thiophene-2-carboxylate | 496.1 |
| 1184 | 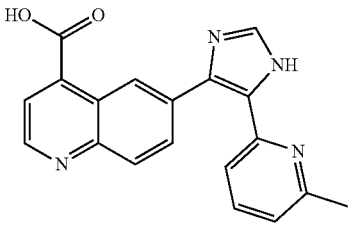 | 6-[5-(6-methyl-2-pyridyl)-1H-imidazol-4-yl]quinoline-4-carboxylic acid | 331.0 |
| 1185 | 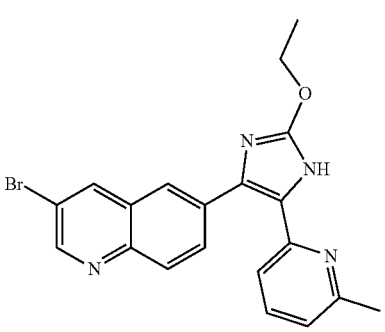 [SMILES: CCOc1nc(-c2ccc3ncc(Br)cc3c2)c(-c2cccc(C)n2)[nH]1] | 3-bromo-6-[2-ethoxy-5-(6-methyl-2-pyridyl)-1H-imidazol-4-yl]quinoline | 409.0 |
| 1186 | 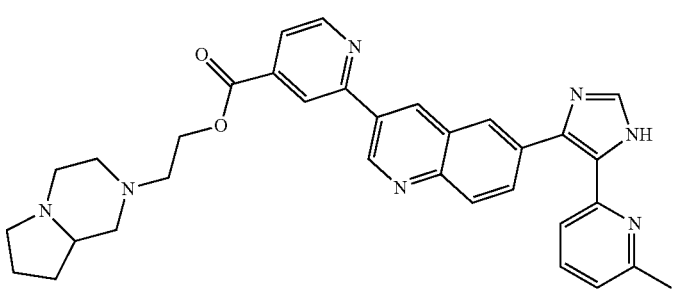 [SMILES: Cc1cccc(-c2[nH]cnc2-c2ccc3ncc(-c4cc(C(=O)OCCN5CCN6CCCC6C5)ccn4)cc3c2)n1] | 2-(3,4,6,7,8,8a-hexahydro-1H-pyrrolo[1,2-a]pyrazin-2-yl)ethyl 2-[6-[5-(6-methyl-2-pyridyl)-1H-imidazol-4-yl]-3-quinolyl]pyridine-4-carboxylate | 560.2 |
| 1187 | 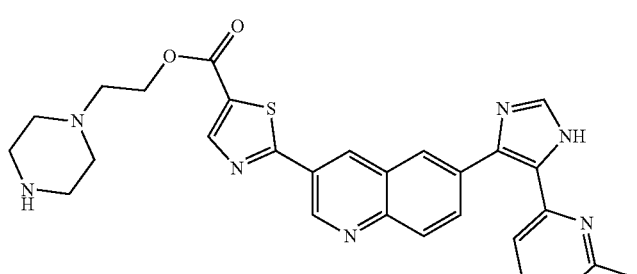 | 2-piperazin-1-ylethyl 2-[6-[5-(6-methyl-2-pyridyl)-1H-imidazol-4-yl]-3-quinolyl]thiazole-5-carboxylate | 526.1 |

TABLE 1-continued

| No. | Structure | Chemical Name | [M + H]+ |
|---|---|---|---|
| 1188 | 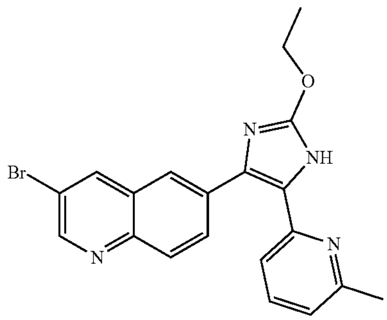 [SMILES: CCOc1nc(-c2ccc3ncc(Br)cc3c2)c(-c2cccc(C)n2)[nH]1] | 3-bromo-6-[2-ethoxy-5-(6-methyl-2-pyridyl)-1H-imidazol-4-yl]quinoline | |
| 1189 | 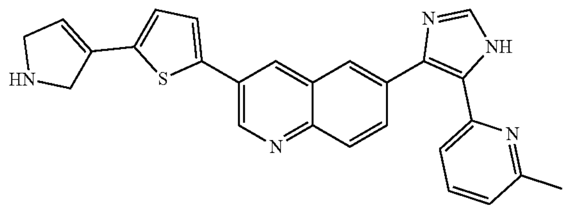 [SMILES: Cc1cccc(-c2[nH]cnc2-c2ccc3ncc(-c4ccc(C5=CCNC5)s4)cc3c2)n1] | 3-[5-(2,5-dihydro-1H-pyrrol-3-yl)-2-thienyl]-6-[5-(6-methyl-2-pyridyl)-1H-imidazol-4-yl]quinoline | |
| 1190 | 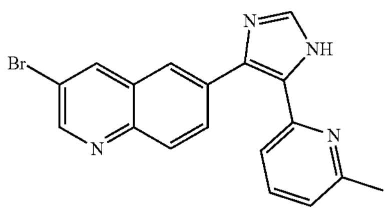 [SMILES: Cc1cccc(-c2[nH]cnc2-c2ccc3ncc(Br)cc3c2)n1] | 3-bromo-6-[5-(6-methyl-2-pyridyl)-1H-imidazol-4-yl]quinoline | 365.0 |
| 1191 | 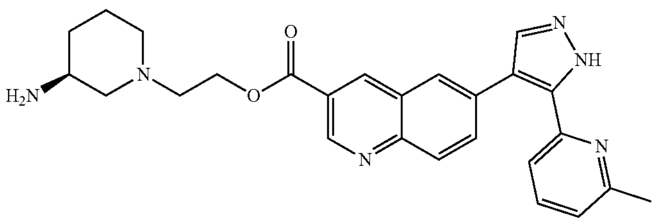 [SMILES: Cc1cccc(-c2[nH]ncc2-c2ccc3ncc(C(=O)OCCN4CCC[C@H](N)C4)cc3c2)n1] | 2-[(3S)-3-amino-1-piperidyl]ethyl 6-[5-(6-methyl-2-pyridyl)-1H-pyrazol-4-yl]quinoline-3-carboxylate | 457.2 |
| 1192 | 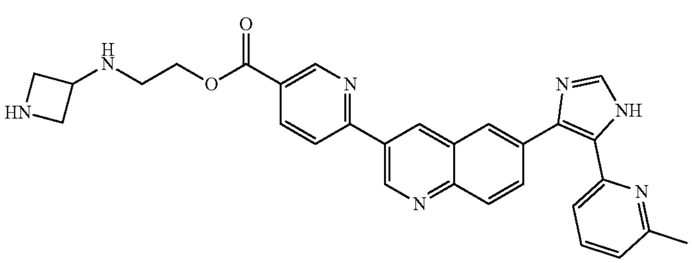 [SMILES: Cc1cccc(-c2[nH]cnc2-c2ccc3ncc(-c4ccc(C(=O)OCCNC5CNC5)cn4)cc3c2)n1] | 2-(azetidin-3-ylamino)ethyl 6-[6-[5-(6-methyl-2-pyridyl)-1H-imidazol-4-yl]-3-quinolyl]pyridine-3-carboxylate | 506.1 |
| 1193 | 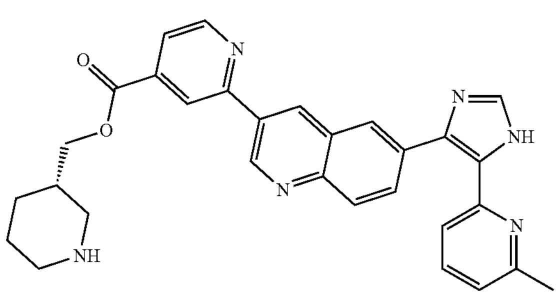 [SMILES: Cc1cccc(-c2[nH]cnc2-c2ccc3ncc(-c4cc(C(=O)OC[C@H]5CCCNC5)ccn4)cc3c2)n1] | [(3S)-3-piperidyl]methyl 2-[6-[5-(6-methyl-2-pyridyl)-1H-imidazol-4-yl]-3-quinolyl]pyridine-4-carboxylate | 505.2 |

TABLE 1-continued

| No. | Structure | Chemical Name | [M + H]+ |
|---|---|---|---|
| 1194 | 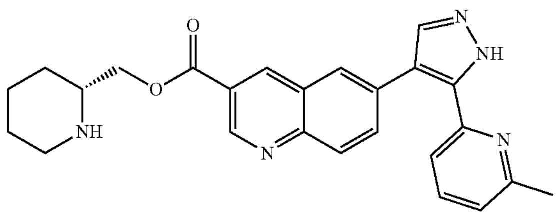 [SMILES: Cc1cccc(-c2[nH]ncc2-c2ccc3ncc(C(=O)OC[C@H]4CCCCN4)cc3c2)n1] | [rac-(2R)-2-piperidyl]methyl 6-[5-(6-methyl-2-pyridyl)-1H-pyrazol-4-yl]quinoline-3-carboxylate | 428.2 |
| 1195 | 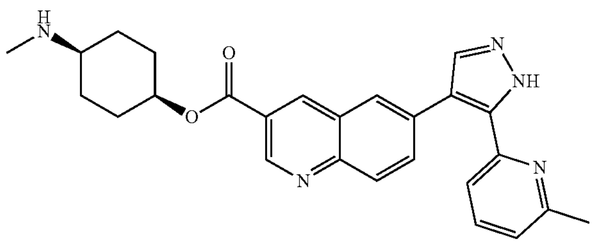 | [4-(methylamino)cyclohexyl] 6-[5-(6-methyl-2-pyridyl)-1H-pyrazol-4-yl]quinoline-3-carboxylate | 442.1 |
| 1196 | 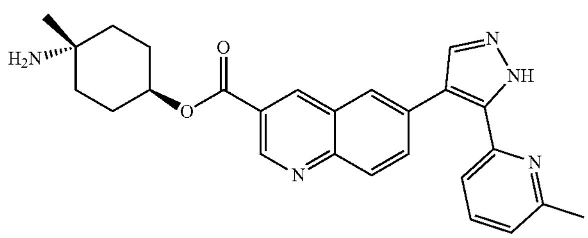 [SMILES: Cc1cccc(-c2[nH]ncc2-c2ccc3ncc(C(=O)O[C@H]4CC[C@](C)(N)CC4)cc3c2)n1] | (4-amino-4-methyl-cyclohexyl) 6-[5-(6-methyl-2-pyridyl)-1H-pyrazol-4-yl]quinoline-3-carboxylate | 442.2 |
| 1197 | 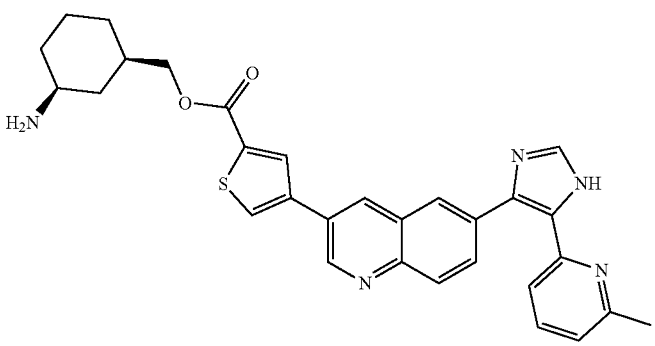 [SMILES: Cc1cccc(-c2[nH]cnc2-c2ccc3ncc(-c4csc(C(=O)OC[C@@H]5CCC[C@H](N)C5)c4)cc3c2)n1] | [rac-(1R,3S)-3-aminocyclohexyl]methyl 4-[6-[5-(6-methyl-2-pyridyl)-1H-imidazol-4-yl]-3-quinolyl]thiophene-2-carboxylate | 524.1 |
| 1198 | 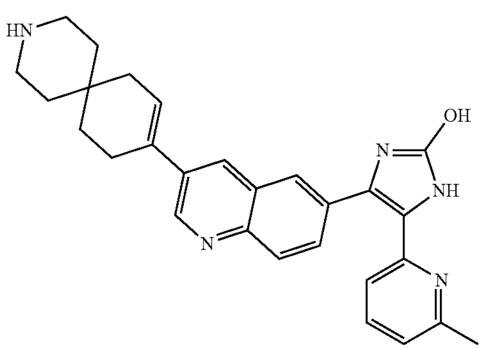 [SMILES: Cc1cccc(-c2[nH]c(O)nc2-c2ccc3ncc(C4=CCC5(CCNCC5)CC4)cc3c2)n1] | 4-[3-(3-azaspiro[5.5]undec-9-en-9-yl)-6-quinolyl]-5-(6-methyl-2-pyridyl)-1H-imidazol-2-ol | 452.2 |

TABLE 1-continued

| No. | Structure | Chemical Name | [M + H]⁺ |
|---|---|---|---|
| 1199 | 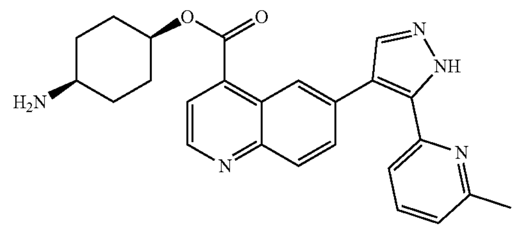 [SMILES: Cc1cccc(-c2[nH]ncc2-c2ccc3nccc(C(=O)O[C@H]4CC[C@@H](N)CC4)c3c2)n1] | (4-aminocyclohexyl) 6-[5-(6-methyl-2-pyridyl)-1H-pyrazol-4-yl]quinoline-4-carboxylate | 428.1 |
| 1200 | 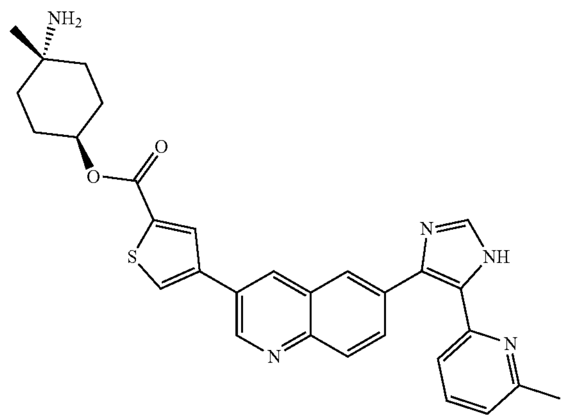 | (4-amino-4-methyl-cyclohexyl) 4-[6-[5-(6-methyl-2-pyridyl)-1H-imidazol-4-yl]-3-quinolyl]thiophene-2-carboxylate | 524.1 |
| 1201 | 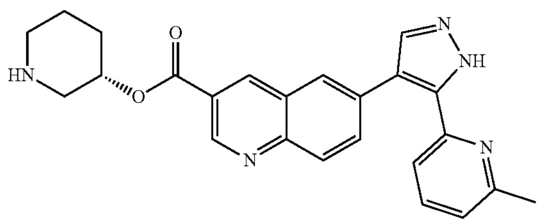 [SMILES: Cc1cccc(-c2[nH]ncc2-c2ccc3ncc(C(=O)O[C@H]4CCCNC4)cc3c2)n1] | [(3S)-3-piperidyl] 6-[5-(6-methyl-2-pyridyl)-1H-pyrazol-4-yl]quinoline-3-carboxylate | 414.1 |
| 1202 | 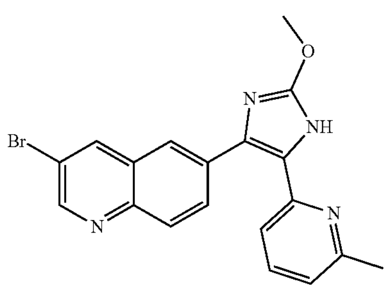 [SMILES: COc1nc(-c2ccc3ncc(Br)cc3c2)c(-c2cccc(C)n2)[nH]1] | 3-bromo-6-[2-methoxy-5-(6-methyl-2-pyridyl)-1H-imidazol-4-yl]quinoline | 395.0 |
| 1203 | 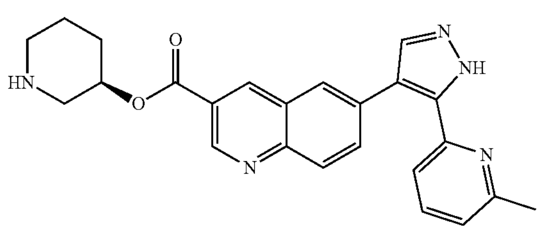 [SMILES: Cc1cccc(-c2[nH]ncc2-c2ccc3ncc(C(=O)O[C@@H]4CCCNC4)cc3c2)n1] | [(3R)-3-piperidyl] 6-[5-(6-methyl-2-pyridyl)-1H-pyrazol-4-yl]quinoline-3-carboxylate | 414.2 |
| 1204 | 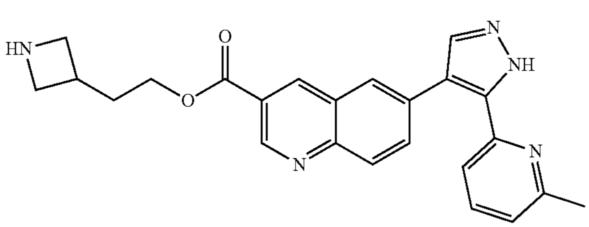 [SMILES: Cc1cccc(-c2[nH]ncc2-c2ccc3ncc(C(=O)OCCC4CNC4)cc3c2)n1] | 2-(azetidin-3-yl)ethyl 6-[5-(6-methyl-2-pyridyl)-1H-pyrazol-4-yl]quinoline-3-carboxylate | 414.1 |

TABLE 1-continued

| No. | Structure | Chemical Name | [M + H]+ |
|---|---|---|---|
| 1205 | 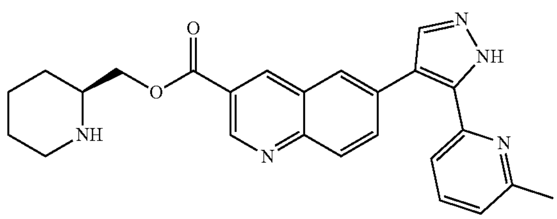 [SMILES: Cc1cccc(-c2[nH]ncc2-c2ccc3ncc(C(=O)OC[C@@H]4CCCCN4)cc3c2)n1] | [(2S)-2-piperidyl]methyl 6-[5-(6-methyl-2-pyridyl)-1H-pyrazol-4-yl]quinoline-3-carboxylate | 428.1 |
| 1206 | 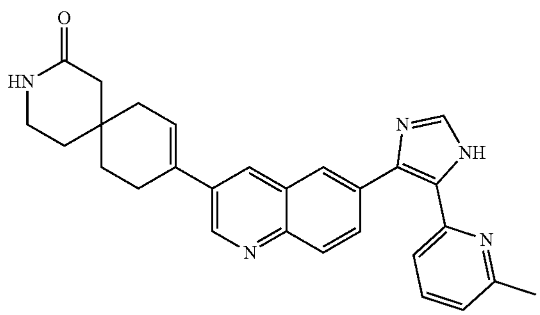 [SMILES: Cc1cccc(-c2[nH]cnc2-c2ccc3ncc(C4=CCC5(CCNC(=O)C5)CC4)cc3c2)n1] | 9-[6-[5-(6-methyl-2-pyridyl)-1H-imidazol-4-yl]-3-quinolyl]-3-azaspiro[5.5]undec-9-en-4-one | 450.1 |
| 1207 | 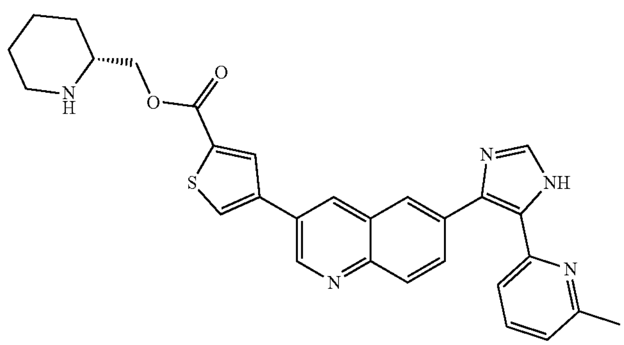 [SMILES: Cc1cccc(-c2[nH]cnc2-c2ccc3ncc(-c4csc(C(=O)OC[C@H]5CCCCN5)c4)cc3c2)n1] | [(2R)-2-piperidyl]methyl 4-[6-[5-(6-methyl-2-pyridyl)-1H-imidazol-4-yl]-3-quinolyl]thiophene-2-carboxylate | 510.1 |
| 1208 | 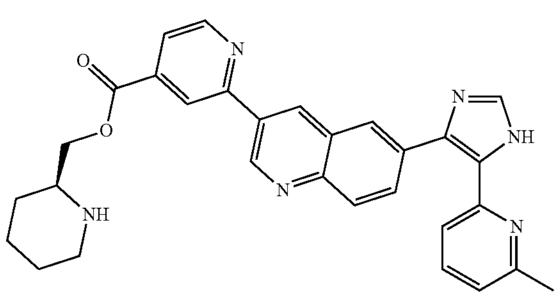 [SMILES: Cc1cccc(-c2[nH]cnc2-c2ccc3ncc(-c4cc(C(=O)OC[C@@H]5CCCCN5)ccn4)cc3c2)n1] | [(2S)-2-piperidyl]methyl 2-[6-[5-(6-methyl-2-pyridyl)-1H-imidazol-4-yl]-3-quinolyl]pyridine-4-carboxylate | 505.2 |
| 1209 | 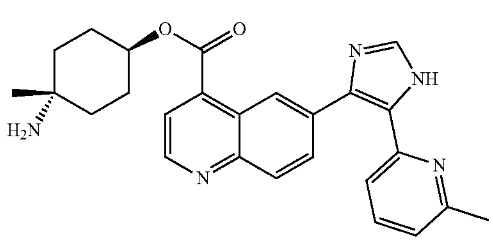 | (4-amino-4-methyl-cyclohexyl) 6-[5-(6-methyl-2-pyridyl)-1H-imidazol-4-yl]quinoline-4-carboxylate | 442.2 |

TABLE 1-continued

| No. | Structure | Chemical Name | [M + H]+ |
|---|---|---|---|
| 1210 | 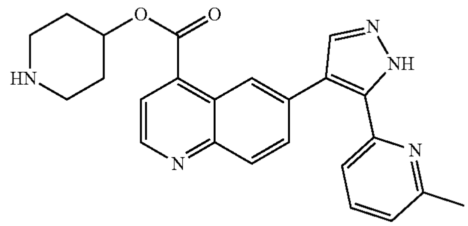 [SMILES: Cc1cccc(-c2[nH]ncc2-c2ccc3nccc(C(=O)OC4CCNCC4)c3c2)n1] | 4-piperidyl 6-[5-(6-methyl-2-pyridyl)-1H-pyrazol-4-yl]quinoline-4-carboxylate | 414.1 |
| 1211 | 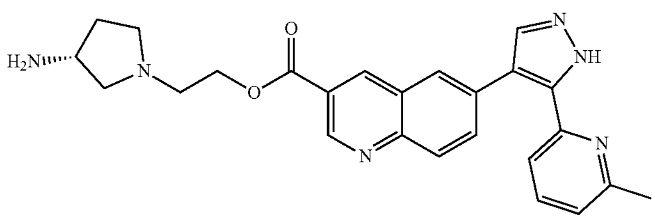 [SMILES: Cc1cccc(-c2[nH]ncc2-c2ccc3ncc(C(=O)OCCN4CC[C@@H](N)C4)cc3c2)n1] | 2-[(3R)-3-aminopyrrolidin-1-yl]ethyl 6-[5-(6-methyl-2-pyridyl)-1H-pyrazol-4-yl]quinoline-3-carboxylate | 443.2 |
| 1212 | 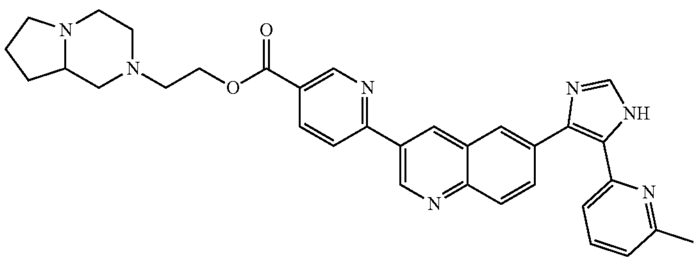 [SMILES: Cc1cccc(-c2[nH]cnc2-c2ccc3ncc(-c4ccc(C(=O)OCCN5CCN6CCCC6C5)cn4)cc3c2)n1] | 2-(3,4,6,7,8,8a-hexahydro-1H-pyrrolo[1,2-a]pyrazin-2-yl)ethyl 6-[6-[5-(6-methyl-2-pyridyl)-1H-imidazol-4-yl]-3-quinolyl]pyridine-3-carboxylate | 560.2 |
| 1213 | 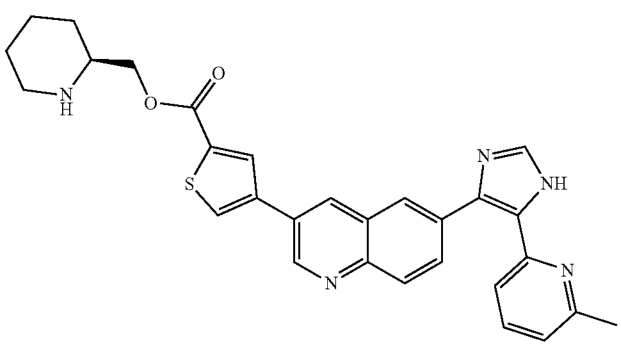 [SMILES: Cc1cccc(-c2[nH]cnc2-c2ccc3ncc(-c4csc(C(=O)OC[C@@H]5CCCCN5)c4)cc3c2)n1] | [(2S)-2-piperidyl]methyl 4-[6-[5-(6-methyl-2-pyridyl)-1H-imidazol-4-yl]-3-quinolyl]thiophene-2-carboxylate | 510.1 |
| 1214 | 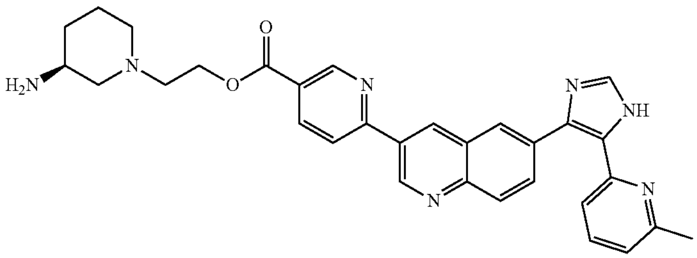 [SMILES: Cc1cccc(-c2[nH]cnc2-c2ccc3ncc(-c4ccc(C(=O)OCCN5CCC[C@H](N)C5)cn4)cc3c2)n1] | 2-[(3S)-3-amino-1-piperidyl]ethyl 6-[6-[5-(6-methyl-2-pyridyl)-1H-imidazol-4-yl]-3-quinolyl]pyridine-3-carboxylate | 534.2 |

TABLE 1-continued

| No. | Structure | Chemical Name | [M + H]⁺ |
|---|---|---|---|
| 1215 | 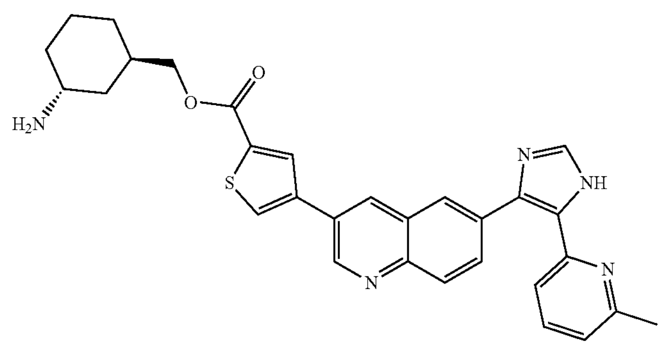 [SMILES: Cc1cccc(-c2[nH]cnc2-c2ccc3ncc(-c4csc(C(=O)OC[C@@H]5CCC[C@@H](N)C5)c4)cc3c2)n1] | [rac-(1R,3R)-3-aminocyclohexyl]methyl 4-[6-[5-(6-methyl-2-pyridyl)-1H-imidazol-4-yl]-3-quinolyl]thiophene-2-carboxylate | 524.1 |
| 1216 | 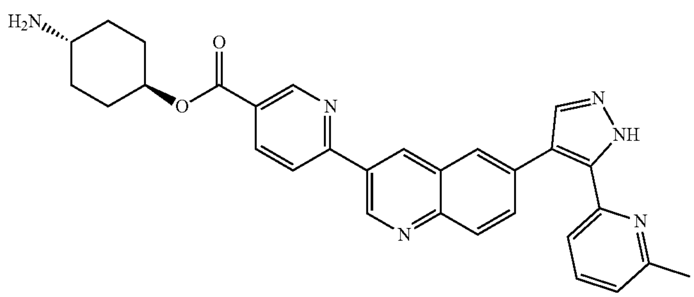 [SMILES: Cc1cccc(-c2[nH]ncc2-c2ccc3ncc(-c4ccc(C(=O)O[C@H]5CC[C@H](N)CC5)cn4)cc3c2)n1] | (4-aminocyclohexyl) 6-[5-(6-methyl-2-pyridyl)-1H-pyrazol-4-yl]quinoline-3-carboxylate | 428.1 |
| 1217 | 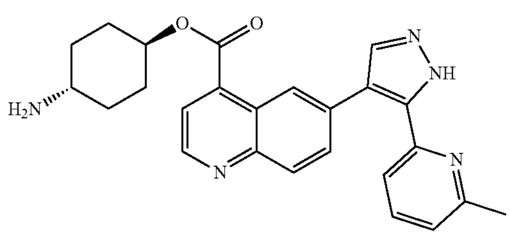 [SMILES: Cc1cccc(-c2[nH]ncc2-c2ccc3nccc(C(=O)O[C@H]4CC[C@H](N)CC4)c3c2)n1] | (4-aminocyclohexyl) 6-[5-(6-methyl-2-pyridyl)-1H-pyrazol-4-yl]quinoline-4-carboxylate | 428.2 |
| 1218 | 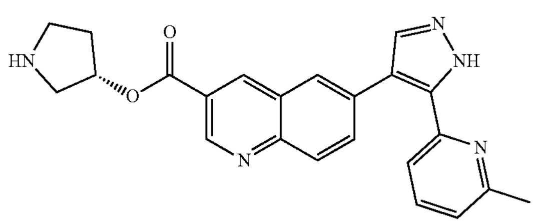 [SMILES: Cc1cccc(-c2[nH]ncc2-c2ccc3ncc(C(=O)O[C@H]4CCNC4)cc3c2)n1] | [(3S)-pyrrolidin-3-yl]6-[5-(6-methyl-2-pyridyl)-1H-pyrazol-4-yl]quinoline-3-carboxylate | 400.1 |
| 1219 | 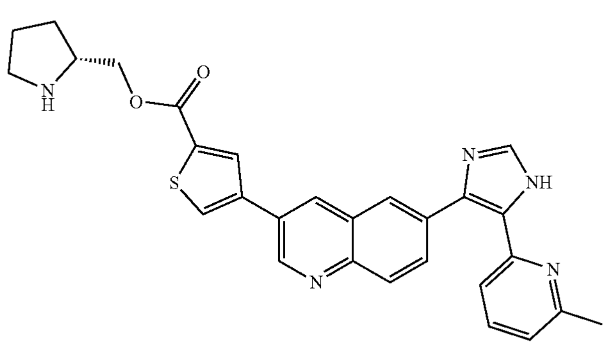 [SMILES: Cc1cccc(-c2[nH]cnc2-c2ccc3ncc(-c4csc(C(=O)OC[C@H]5CCCN5)c4)cc3c2)n1] | [(2R)-pyrrolidin-2-yl]methyl 4-[6-[5-(6-methyl-2-pyridyl)-1H-imidazol-4-yl]-3-quinolyl]thiophene-2-carboxylate | 496.1 |

TABLE 1-continued

| No. | Chemical Name | [M + H]+ |
|---|---|---|
| 1220 | 2-[(3R)-3-aminopyrrolidin-1-yl]ethyl 4-[6-[5-(6-methyl-2-pyridyl)-1H-imidazol-4-yl]-3-quinolyl]thiophene-2-carboxylate | 525.1 |
| 1221 | [4-(methylamino)cyclohexyl] 6-[5-(6-methyl-2-pyridyl)-1H-pyrazol-4-yl]quinoline-3-carboxylate | 442.1 |
| 1222 | 2-[(3S,5R)-3,5-dimethylpiperazin-1-yl]ethyl 4-[6-[5-(6-methyl-2-pyridyl)-1H-imidazol-4-yl]-3-quinolyl]thiophene-2-carboxylate | 553.2 |
| 1223 | [(2R)-pyrrolidin-2-yl]methyl 6-[5-(6-methyl-2-pyridyl)-1H-pyrazol-4-yl]quinoline-4-carboxylate | 414.2 |

TABLE 1-continued

| No. | Structure | Chemical Name | [M + H]+ |
|---|---|---|---|
| 1224 | 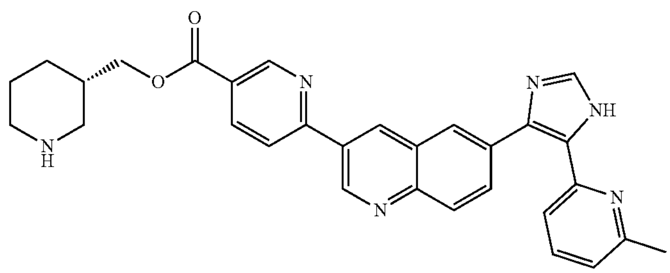 [SMILES: Cc1cccc(-c2[nH]cnc2-c2ccc3ncc(-c4ccc(C(=O)OC[C@H]5CCCNC5)cn4)cc3c2)n1] | [(3S)-3-piperidyl]methyl 6-[6-[5-(6-methyl-2-pyridyl)-1H-imidazol-4-yl]-3-quinolyl]pyridine-3-carboxylate | 505.1 |
| 1225 | 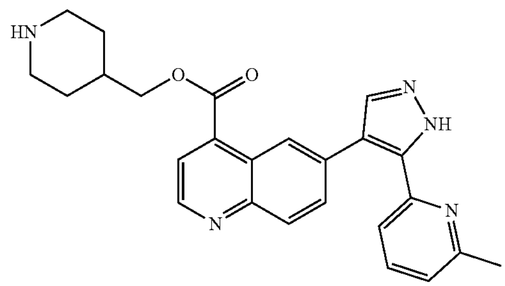 [SMILES: Cc1cccc(-c2[nH]ncc2-c2ccc3nccc(C(=O)OCC4CCNCC4)c3c2)n1] | 4-piperidylmethyl 6-[5-(6-methyl-2-pyridyl)-1H-pyrazol-4-yl]quinoline-4-carboxylate | 428.1 |
| 1226 | 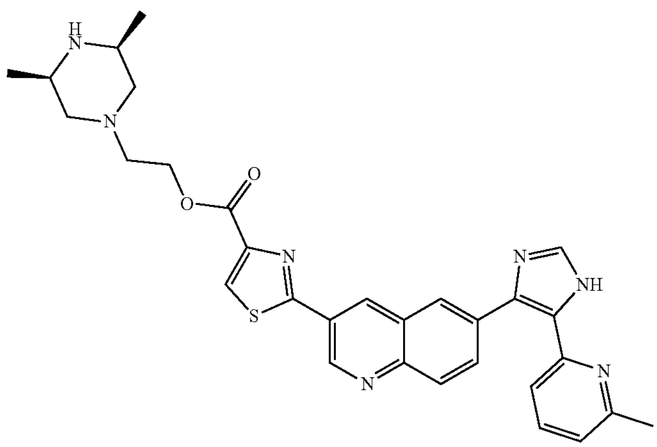 | 2-[(3R,5S)-3,5-dimethylpiperazin-1-yl]ethyl 2-[6-[5-(6-methyl-2-pyridyl)-1H-imidazol-4-yl]-3-quinolyl]thiazole-4-carboxylate | 554.2 |
| 1227 | 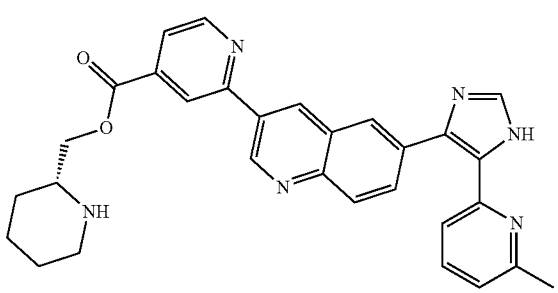 [SMILES: Cc1cccc(-c2[nH]cnc2-c2ccc3ncc(-c4cc(C(=O)OC[C@H]5CCCCN5)ccn4)cc3c2)n1] | [(2R)-2-piperidyl]methyl 2-[6-[5-(6-methyl-2-pyridyl)-1H-imidazol-4-yl]-3-quinolyl]pyridine-4-carboxylate | 505.2 |
| 1228 | 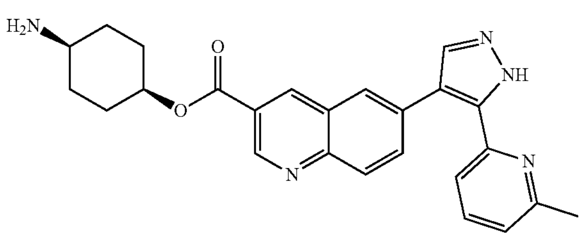 [SMILES: Cc1cccc(-c2[nH]ncc2-c2ccc3ncc(C(=O)O[C@H]4CC[C@@H](N)CC4)cc3c2)n1] | (4-aminocyclohexyl) 6-[5-(6-methyl-2-pyridyl)-1H-pyrazol-4-yl]quinoline-3-carboxylate | 428.2 |

TABLE 1-continued

| No. | Structure | Chemical Name | [M + H]+ |
|---|---|---|---|
| 1229 | 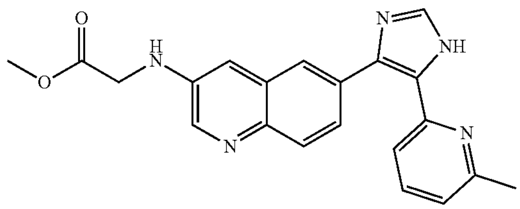 | methyl 2-[[6-[5-(6-methyl-2-pyridyl)-1H-imidazol-4-yl]-3-quinolyl]amino]acetate | 374.1 |
| 1230 | 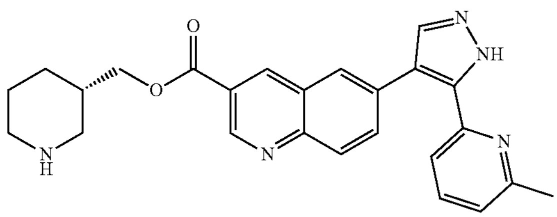 [SMILES: Cc1cccc(-c2[nH]ncc2-c2ccc3ncc(C(=O)OC[C@H]4CCCNC4)cc3c2)n1] | [(3S)-3-piperidyl]methyl 6-[5-(6-methyl-2-pyridyl)-1H-pyrazol-4-yl]quinoline-3-carboxylate | 428.1 |
| 1231 | 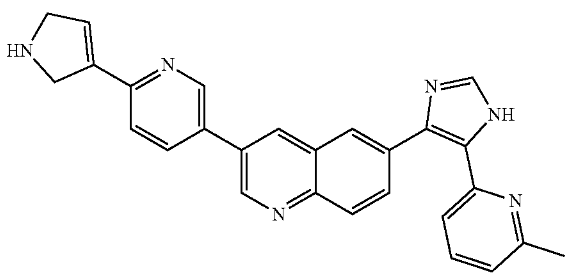 [SMILES: Cc1cccc(-c2[nH]cnc2-c2ccc3ncc(-c4ccc(C5=CCNC5)nc4)cc3c2)n1] | 3-[6-(2,5-dihydro-1H-pyrrol-3-yl)-3-pyridyl]-6-[5-(6-methyl-2-pyridyl)-1H-imidazol-4-yl]quinoline | |
| 1232 | 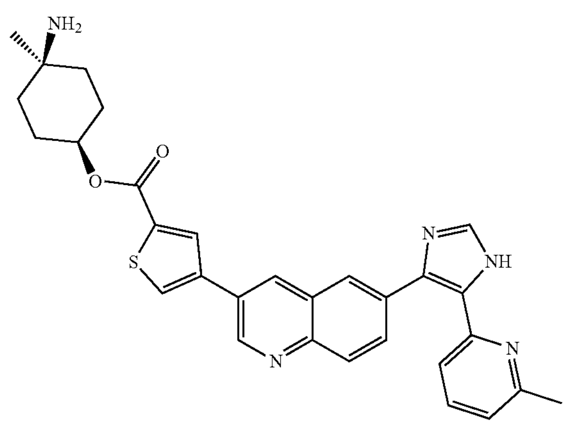 | (4-amino-4-methyl-cyclohexyl) 4-[6-[5-(6-methyl-2-pyridyl)-1H-imidazol-4-yl]-3-quinolyl]thiophene-2-carboxylate | 524.1 |
| 1233 | 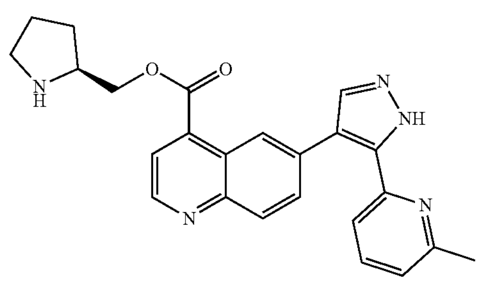 [SMILES: Cc1cccc(-c2[nH]ncc2-c2ccc3nccc(C(=O)OC[C@@H]4CCCN4)c3c2)n1] | [(2S)-pyrrolidin-2-yl]methyl 6-[5-(6-methyl-2-pyridyl)-1H-pyrazol-4-yl]quinoline-4-carboxylate | 414.1 |

TABLE 1-continued

| No. | Structure | Chemical Name | [M + H]+ |
|---|---|---|---|
| 1234 | 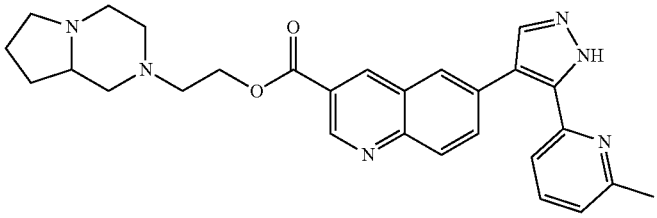 [SMILES: Cc1cccc(-c2[nH]ncc2-c2ccc3ncc(C(=O)OCCN4CCN5CCCC5C4)cc3c2)n1] | 2-(3,4,6,7,8,8a-hexahydro-1H-pyrrolo[1,2-a]pyrazin-2-yl)ethyl 6-[5-(6-methyl-2-pyridyl)-1H-pyrazol-4-yl]quinoline-3-carboxylate | 483.1 |
| 1235 | 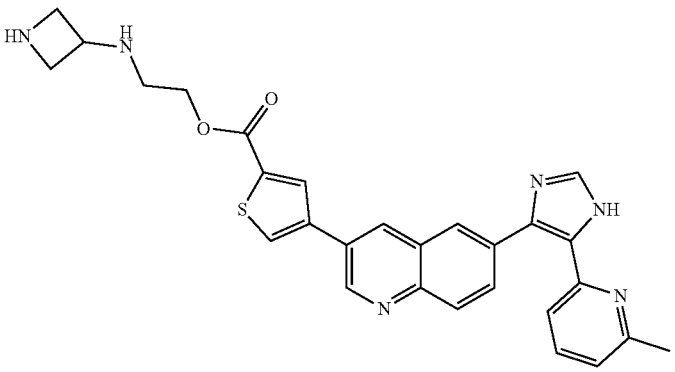 [SMILES: Cc1cccc(-c2[nH]cnc2-c2ccc3ncc(-c4csc(C(=O)OCCNC5CNC5)c4)cc3c2)n1] | 2-(azetidin-3-ylamino)ethyl 4-[6-[5-(6-methyl-2-pyridyl)-1H-imidazol-4-yl]-3-quinolyl]thiophene-2-carboxylate | 511.1 |
| 1236 | 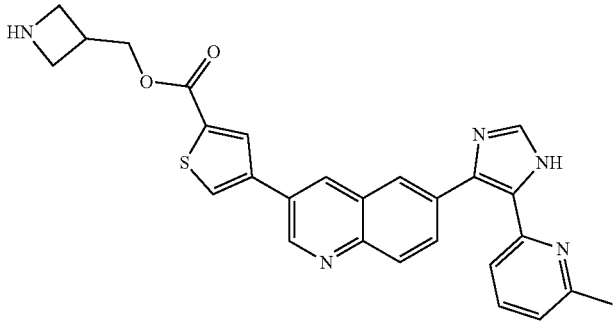 [SMILES: Cc1cccc(-c2[nH]cnc2-c2ccc3ncc(-c4csc(C(=O)OCC5CNC5)c4)cc3c2)n1] | azetidin-3-ylmethyl 2-[6-[5-(6-methyl-2-pyridyl)-1H-imidazol-4-yl]-3-quinolyl]thiazole-5-carboxylate | 483.1 |
| 1237 | 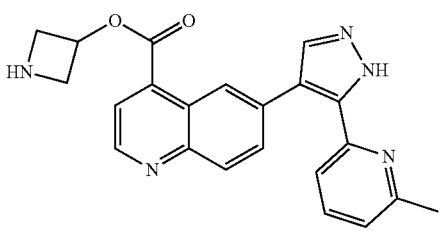 [SMILES: Cc1cccc(-c2[nH]ncc2-c2ccc3nccc(C(=O)OC4CNC4)c3c2)n1] | azetidin-3-yl 6-[5-(6-methyl-2-pyridyl)-1H-pyrazol-4-yl]quinoline-4-carboxylate | 386.1 |
| 1238 | 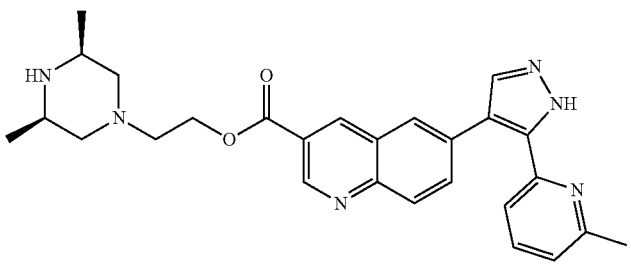 | 2-[(3S,5R)-3,5-dimethylpiperazin-1-yl]ethyl 6-[5-(6-methyl-2-pyridyl)-1H-pyrazol-4-yl]quinoline-3-carboxylate | 471.1 |

| No. | Structure | Chemical Name | [M + H]+ |
|---|---|---|---|
| 1239 | 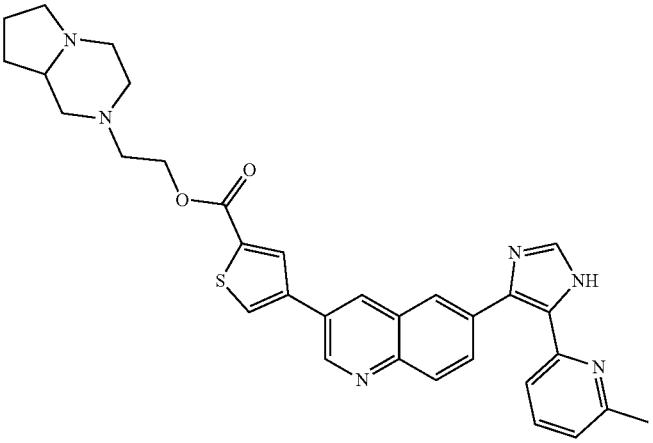 [SMILES: Cc1cccc(-c2[nH]cnc2-c2ccc3ncc(-c4csc(C(=O)OCCN5CCN6CCCC6C5)c4)cc3c2)n1] | 2-(3,4,6,7,8,8a-hexahydro-1H-pyrrolo[1,2-a]pyrazin-2-yl)ethyl 2-[6-[5-(6-methyl-2-pyridyl)-1H-imidazol-4-yl]-3-quinolyl]thiazole-4-carboxylate | 566.2 |
| 1240 | 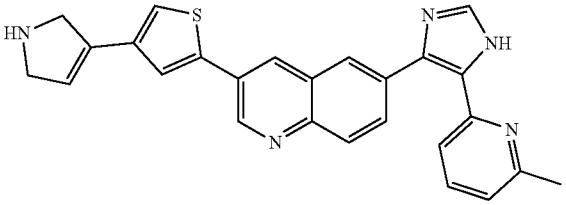 [SMILES: Cc1cccc(-c2[nH]cnc2-c2ccc3ncc(-c4cc(C5=CCNC5)cs4)cc3c2)n1] | 3-[4-(2,5-dihydro-1H-pyrrol-3-yl)-2-thienyl]-6-[5-(6-methyl-2-pyridyl)-1H-imidazol-4-yl]quinoline | |
| 1241 | 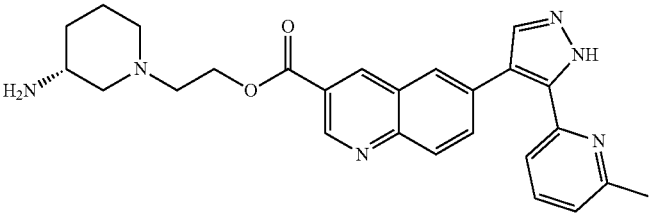 [SMILES: Cc1cccc(-c2[nH]ncc2-c2ccc3ncc(C(=O)OCCN4CCC[C@@H](N)C4)cc3c2)n1] | 2-[(3R)-3-amino-1-piperidyl]ethyl 6-[5-(6-methyl-2-pyridyl)-1H-pyrazol-4-yl]quinoline-3-carboxylate | 457.2 |
| 1242 | 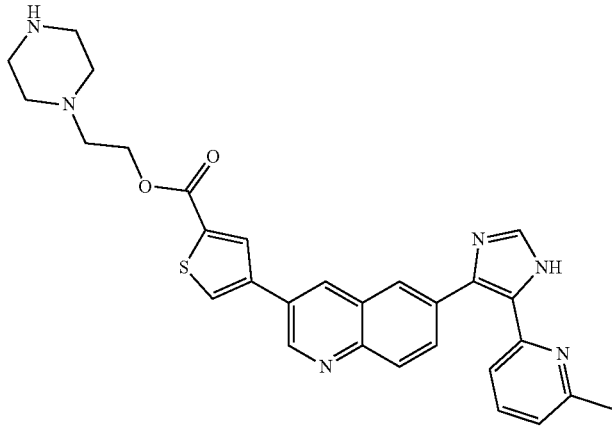 [SMILES: Cc1cccc(-c2[nH]cnc2-c2ccc3ncc(-c4csc(C(=O)OCCN5CCNCC5)c4)cc3c2)n1] | 2-piperazin-1-ylethyl 4-[6-[5-(6-methyl-2-pyridyl)-1H-imidazol-4-yl]-3-quinolyl]thiophene-2-carboxylate | 525.2 |

TABLE 1-continued

| No. | Structure | Chemical Name | [M + H]+ |
|---|---|---|---|
| 1243 | 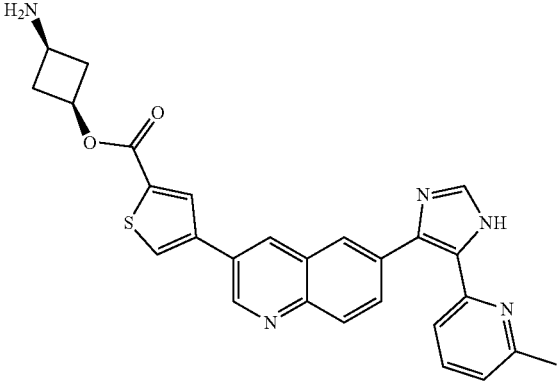 [SMILES: Cc1cccc(-c2[nH]cnc2-c2ccc3ncc(-c4csc(C(=O)O[C@H]5C[C@@H](N)C5)c4)cc3c2)n1] | (3-aminocyclobutyl) 4-[6-[5-(6-methyl-2-pyridyl)-1H-imidazol-4-yl]-3-quinolyl]thiophene-2-carboxylate | 482.1 |
| 1244 | 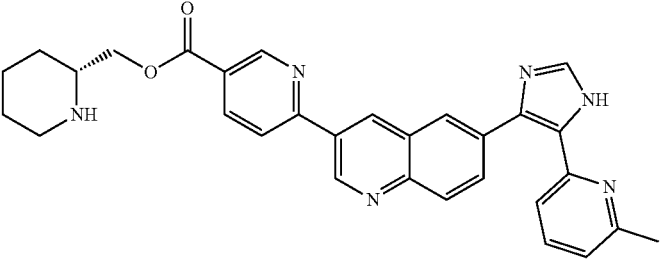 [SMILES: Cc1cccc(-c2[nH]cnc2-c2ccc3ncc(-c4ccc(C(=O)OC[C@H]5CCCCN5)cn4)cc3c2)n1] | [(2R)-2-piperidyl]methyl 6-[6-[5-(6-methyl-2-pyridyl)-1H-imidazol-4-yl]-3-quinolyl]pyridine-3-carboxylate | 505.2 |
| 1245 | 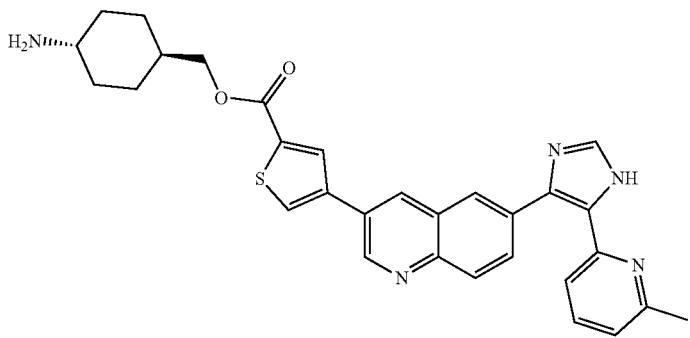 [SMILES: Cc1cccc(-c2[nH]cnc2-c2ccc3ncc(-c4csc(C(=O)OC[C@H]5CC[C@H](N)CC5)c4)cc3c2)n1] | (4-aminocyclohexyl)methyl 4-[6-[5-(6-methyl-2-pyridyl)-1H-imidazol-4-yl]-3-quinolyl]thiophene-2-carboxylate | 524.1 |
| 1246 | 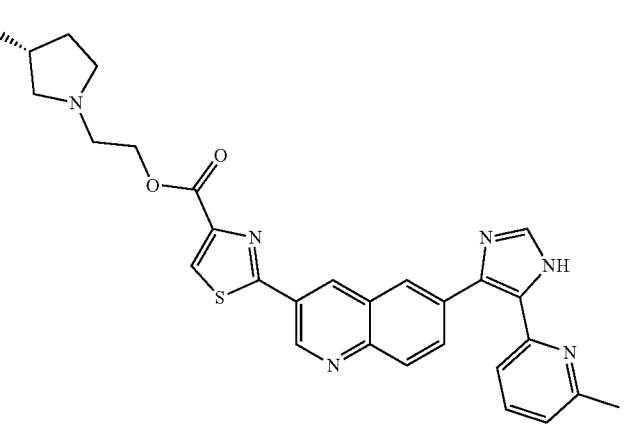 | 2-[(3R)-3-aminopyrrolidin-1-yl]ethyl 2-[6-[5-(6-methyl-2-pyridyl)-1H-imidazol-4-yl]-3-quinolyl]thiazole-4-carboxylate | 526.1 |

TABLE 1-continued

| No. | Structure | Chemical Name | [M + H]+ |
|---|---|---|---|
| 1247 | 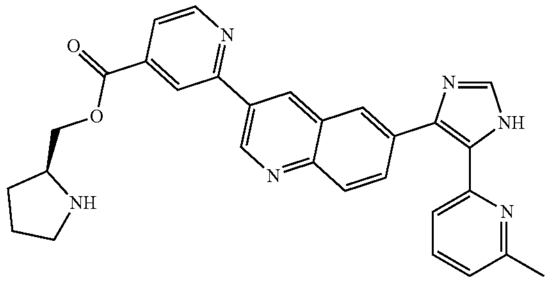 [SMILES: Cc1cccc(-c2[nH]cnc2-c2ccc3ncc(-c4cc(C(=O)OC[C@@H]5CCCN5)ccn4)cc3c2)n1] | [(2S)-pyrrolidin-2-yl]methyl 2-[6-[5-(6-methyl-2-pyridyl)-1H-imidazol-4-yl]-3-quinolyl]pyridine-4-carboxylate | 491.1 |
| 1248 | 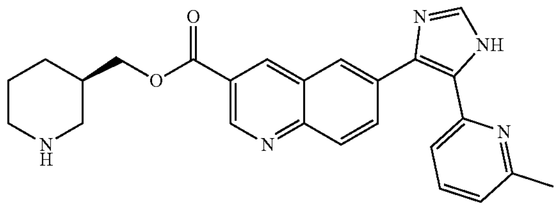 [SMILES: Cc1cccc(-c2[nH]cnc2-c2ccc3ncc(C(=O)OC[C@@H]4CCCNC4)cc3c2)n1] | [(3R)-3-piperidyl]methyl 6-[5-(6-methyl-2-pyridyl)-1H-pyrazol-4-yl]quinoline-3-carboxylate | 428.2 |
| 1249 | 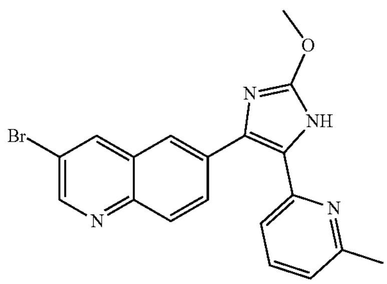 [SMILES: COc1nc(-c2ccc3ncc(Br)cc3c2)c(-c2cccc(C)n2)[nH]1] | 3-bromo-6-[2-methoxy-5-(6-methyl-2-pyridyl)-1H-imidazol-4-yl]quinoline | |
| 1250 | 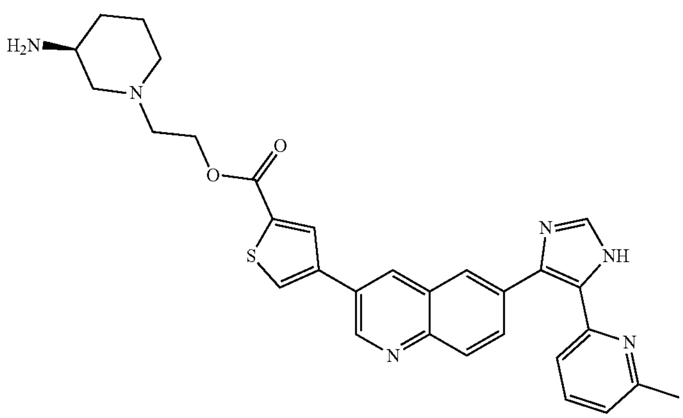 [SMILES: Cc1cccc(-c2[nH]cnc2-c2ccc3ncc(-c4csc(C(=O)OCCN5CCC[C@H](N)C5)c4)cc3c2)n1] | 2-[(3S)-3-amino-1-piperidyl]ethyl 4-[6-[5-(6-methyl-2-pyridyl)-1H-imidazol-4-yl]-3-quinolyl]thiophene-2-carboxylate | 539.2 |
| 1251 | 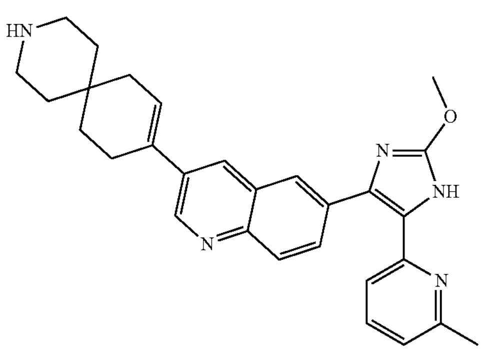 [SMILES: COc1nc(-c2ccc3ncc(C4=CCC5(CCNCC5)CC4)cc3c2)c(-c2cccc(C)n2)[nH]1] | 9-[6-[2-methoxy-5-(6-methyl-2-pyridyl)-1H-imidazol-4-yl]-3-quinolyl]-3-azaspiro[5.5]undec-9-ene | 466.2 |

TABLE 1-continued

| No. | Structure | Chemical Name | [M + H]⁺ |
|---|---|---|---|
| 1252 | 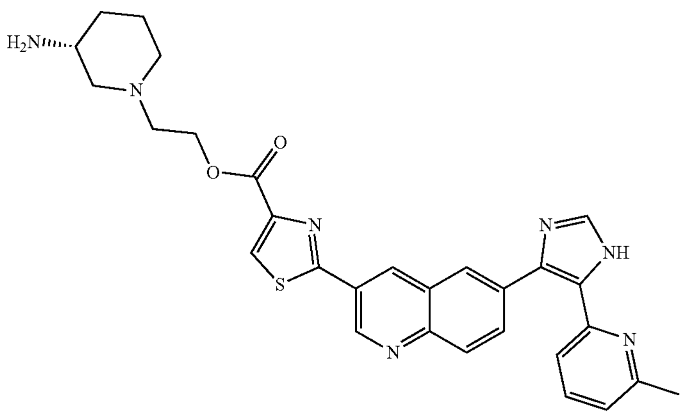 [SMILES: Cc1cccc(-c2[nH]cnc2-c2ccc3ncc(-c4nc(C(=O)OCCN5CCC[C@@H](N)C5)cs4)cc3c2)n1] | 2-[(3R)-3-amino-1-piperidyl]ethyl 2-[6-[5-(6-methyl-2-pyridyl)-1H-imidazol-4-yl]-3-quinolyl]thiazole-4-carboxylate | 540.1 |
| 1253 | 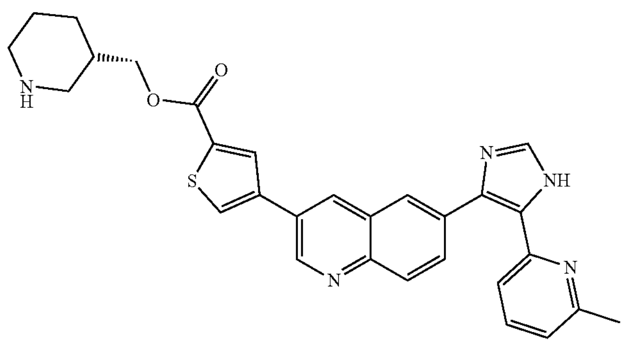 | [(3S)-3-piperidyl]methyl 4-[6-[5-(6-methyl-2-pyridyl)-1H-imidazol-4-yl]-3-quinolyl]thiophene-2-carboxylate | 510.1 |
| 1254 | 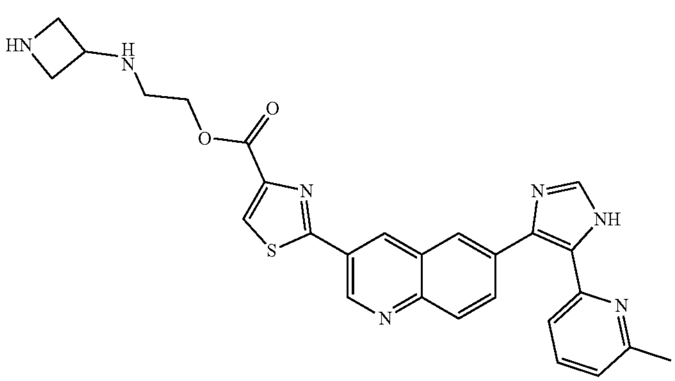 [SMILES: Cc1cccc(-c2[nH]cnc2-c2ccc3ncc(-c4nc(C(=O)OCCNC5CNC5)cs4)cc3c2)n1] | 2-(azetidin-3-ylamino)ethyl 2-[6-[5-(6-methyl-2-pyridyl)-1H-imidazol-4-yl]-3-quinolyl]thiazole-4-carboxylate | 512.2 |
| 1255 | 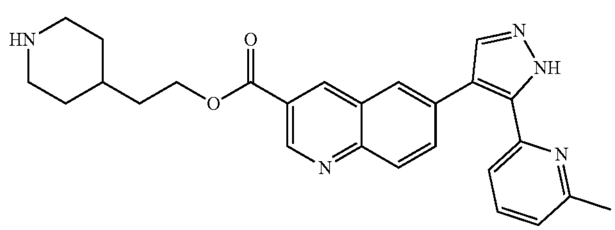 [SMILES: Cc1cccc(-c2[nH]ncc2-c2ccc3ncc(C(=O)OCCC4CCNCC4)cc3c2)n1] | 2-(4-piperidyl)ethyl 6-[5-(6-methyl-2-pyridyl)-1H-pyrazol-4-yl]quinoline-3-carboxylate | 442.2 |
| 1256 | 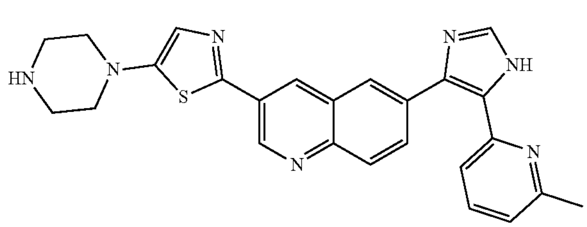 [SMILES: Cc1cccc(-c2[nH]cnc2-c2ccc3ncc(-c4ncc(N5CCNCC5)s4)cc3c2)n1] | 2-[6-[5-(6-methyl-2-pyridyl)-1H-imidazol-4-yl]-3-quinolyl]-5-piperazin-1-yl-thiazole | |

TABLE 1-continued

| No. | Structure | Chemical Name | [M + H]+ |
|---|---|---|---|
| 1257 | 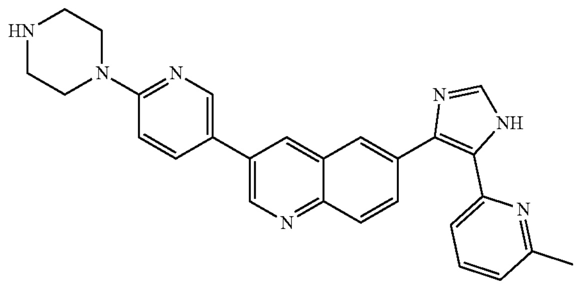 [SMILES: Cc1cccc(-c2[nH]cnc2-c2ccc3ncc(-c4ccc(N5CCNCC5)nc4)cc3c2)n1] | 6-[5-(6-methyl-2-pyridyl)-1H-imidazol-4-yl]-3-(6-piperazin-1-yl-3-pyridyl)quinoline | |
| 1258 | 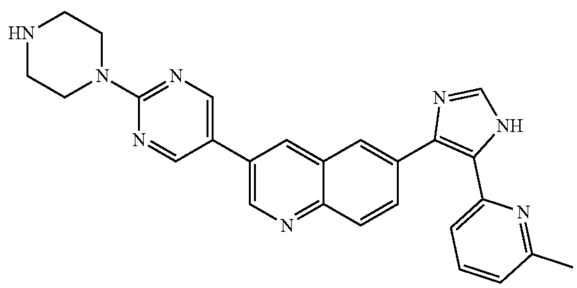 [SMILES: Cc1cccc(-c2[nH]cnc2-c2ccc3ncc(-c4cnc(N5CCNCC5)nc4)cc3c2)n1] | 6-[5-(6-methyl-2-pyridyl)-1H-imidazol-4-yl]-3-(2-piperazin-1-ylpyrimidin-5-yl)quinoline | |
| 1259 | 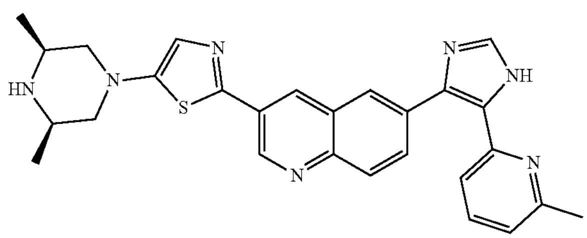 | 5-[(3R,5S)-3,5-dimethylpiperazin-1-yl]-2-[6-[5-(6-methyl-2-pyridyl)-1H-imidazol-4-yl]-3-quinolyl]thiazole | |
| 1260 | 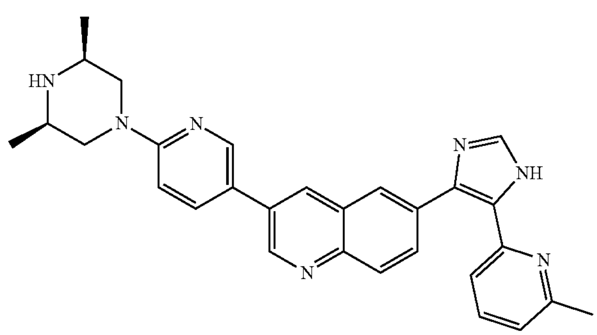 | 3-[6-[(3S,5R)-3,5-dimethylpiperazin-1-yl]-3-pyridyl]-6-[5-(6-methyl-2-pyridyl)-1H-imidazol-4-yl]quinoline | |
| 1261 | 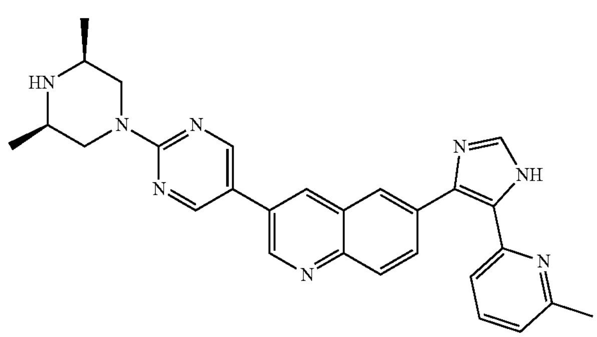 | 3-[2-[(3S,5R)-3,5-dimethylpiperazin-1-yl]pyrimidin-5-yl]-6-[5-(6-methyl-2-pyridyl)-1H-imidazol-4-yl]quinoline | |

Methods

In some aspects, the present disclosure provides a method of inhibiting TGFβ signaling, comprising contacting a cell with an effective amount of a compound disclosed herein, such as a compound of Formula (I), (I-A), (I-B), (I-C), (I'), (I'-A), (I'-B) or (I'-C). In some embodiments, the present disclosure provides a method of inhibiting ALK5, comprising contacting ALK5 with an effective amount of a compound disclosed herein. Inhibition of ALK5 or TGFβ signaling can be assessed by a variety of methods known in the art. Non-limiting examples include a showing of (a) a decrease in kinase activity of ALK5; (b) a decrease in binding affinity between the TGFβ/TGFβ-RII complex and ALK5; (c) a decrease in the levels of phosphorylated intracellular signaling molecules downstream in the TGFβ signaling pathway, such as a decrease in pSMAD2 or pSMAD3 levels; (d) a decrease in binding of ALK5 to downstream signaling molecules, such as SMAD2 and SMAD3; and/or (e) an increase in ATP levels or a decrease in ADP levels. Kits and commercially available assays can be utilized for determining one or more of the above.

In some aspects, the present disclosure provides a method of treating an ALK5-mediated disease or condition in a subject, comprising administering to the subject a therapeutically effective amount of a compound disclosed herein. In some embodiments, the disease or condition is selected from fibrosis and cancer. In some embodiments, the disease or condition is pulmonary fibrosis, such as idiopathic pulmonary fibrosis or virus-induced fibrosis. In some embodiments, the disease or condition is intestinal fibrosis. In some embodiments, the disease or condition is alopecia. In some embodiments, the disease is a neurodegenerative disease, such as Alzheimer's disease. In some embodiments, the present disclosure provides a method of reversing symptoms of aging. For example, the method may enhance neurogenesis, reduce neuroinflammation, improve cognitive performance, regenerate liver tissue, and reduce p16 levels.

In some aspects, the present disclosure provides a method of treating fibrosis, comprising administering to a patient an effective amount of a compound disclosed herein. In some embodiments, the fibrosis is mediated by ALK5. In some embodiments, the fibrosis is selected from systemic sclerosis, systemic fibrosis, organ-specific fibrosis, kidney fibrosis, pulmonary fibrosis, liver fibrosis, portal vein fibrosis, skin fibrosis, bladder fibrosis, intestinal fibrosis, peritoneal fibrosis, myelofibrosis, oral submucous fibrosis, and retinal fibrosis. In some embodiments, the fibrosis is pulmonary fibrosis, such as idiopathic pulmonary fibrosis (IPF), familial pulmonary fibrosis (FPF), interstitial lung fibrosis, fibrosis associated with asthma, fibrosis associated with chronic obstructive pulmonary disease (COPD), silica-induced fibrosis, asbestos-induced fibrosis or chemotherapy-induced lung fibrosis. In some embodiments, the fibrosis is idiopathic pulmonary fibrosis (IPF). In some embodiments, the fibrosis is TGF-β-mediated pulmonary fibrosis. In some embodiments, the patient has been diagnosed with acute respiratory distress syndrome (ARDS). In some embodiments, the fibrosis is acute fibrosis. In some embodiments, the fibrosis is chronic fibrosis.

In some aspects, the present disclosure provides a method of treating pulmonary fibrosis induced by a viral infection, comprising administering to a patient an effective amount of a compound disclosed herein. The pulmonary fibrosis may be induced by an erythrovirus, a dependovirus, a papillomavirus, a polyomavirus, a mastadenovirus, an alphaherpesvirinae, a varicellovirus, a gammaherpesvirinae, a betaherpesvirinae, a roseolovirus, an orthopoxvirus, a parapoxvirus, a molluscipoxvirus, an orthohepadnavirus, an enterovirus, a rhinovirus, a hepatovirus, an aphthovirus, a calicivirus, an astrovirus, an alphavirus, a rubivirus, a flavivirus, a Hepatitis C virus, a reovirus, an orbivirus, a rotavirus, an influenzavirus A, an influenzavirus B, an influenzavirus C, a paramyxovirus, a morbillivirus, a rubulavirus, a pneumovirus, a vesiculovirus, a lyssavirus, a bunyavirus, a hantavirus, a nairovirus, a phlebovirus, a coronavirus, an arenavirus, a BLV-HTLV-retrovirus, a lentivirinae, a spumavirinae or a filovirus. In some embodiments, the fibrosis is virus-induced fibrosis, such as virus-induced pulmonary fibrosis. In some embodiments, the fibrosis is selected from EBV-induced pulmonary fibrosis, CMV-induced pulmonary fibrosis, herpesvirus-induced pulmonary fibrosis and coronavirus-induced pulmonary fibrosis. In some embodiments, the fibrosis is selected from EBV-induced pulmonary fibrosis, CMV-induced pulmonary fibrosis, HHV-6-induced pulmonary fibrosis, HHV-7-induced pulmonary fibrosis, HHV-8-induced pulmonary fibrosis, H5N1 virus-induced pulmonary fibrosis, SARS-CoV-induced pulmonary fibrosis, MERS-CoV-induced pulmonary fibrosis and SARS-CoV-2-induced pulmonary fibrosis. In some embodiments, the pulmonary fibrosis is coronavirus-induced pulmonary fibrosis. In some embodiments, the pulmonary fibrosis is SARS-CoV-2-induced pulmonary fibrosis. In some embodiments, the pulmonary fibrosis is COVID-19-induced pulmonary fibrosis.

In some aspects, the present disclosure provides a method of treating acute lung injury (ALI), comprising administering to a patient an effective amount of a compound disclosed herein. In some embodiments, the present disclosure provides a method of treating acute respiratory distress syndrome (ARDS), comprising administering to a patient an effective amount of a compound disclosed herein. The ARDS may be in the early acute injury phase or the fibroproliferative phase. In some embodiments, the ARDS is fibroproliferative ARDS. In some embodiments, the present disclosure provides a method of treating fibrosis resulting from ARDS, comprising administering to a patient an effective amount of a compound disclosed herein. The fibrosis resulting from ARDS may be pulmonary fibrosis. In some embodiments, the present disclosure provides a method of treating fibrosis resulting from ALI, comprising administering to a patient an effective amount of a compound disclosed herein. The fibrosis resulting from ALI may be pulmonary fibrosis.

In some aspects, the present disclosure provides a method of treating intestinal fibrosis, comprising administering to a patient an effective amount of a compound disclosed herein. In some embodiments, the intestinal fibrosis is mediated by ALK5. In some embodiments, the compound is administered in an amount effective to delay progression of, reduce the incidence of, or reduce the degree of one or more characteristics associated with intestinal fibrosis. In some embodiments, the compound is administered, either in a single dose or over multiple doses, in an amount effective to reverse established fibrosis.

In some aspects, the present disclosure provides a method of treating cancer, comprising administering to a patient an effective amount of a compound disclosed herein. In some embodiments, the cancer is mediated by ALK5. In some embodiments, the cancer is selected from breast cancer, colon cancer, prostate cancer, lung cancer, hepatocellular carcinoma, glioblastoma, melanoma and pancreatic cancer. In some embodiments, the cancer is lung cancer, such as non-small cell lung cancer. In some aspects, the present disclosure provides a method of treating cancer, such as non-small cell lung cancer, comprising administering to a patient an effective amount of a compound disclosed herein and an immunotherapeutic agent. In some embodiments, the cancer is stage III non-small cell lung cancer. In some embodiments, the method further comprises administering radiation to the patient. In some embodiments, the immunotherapeutic agent is a PD-1 inhibitor or a CTLA-4 inhibitor. In some embodiments, the immunotherapeutic agent is selected from atezolizumab, avelumab, nivolumab, pembrolizumab, durvalumab, BGB-A317, tremelimumab and ipilimumab. In some embodiments, the immunotherapeutic agent is selected from pembrolizumab and durvalumab.

The compounds described herein, including compounds of Formula (I), (I-A), (I-B), (I-C), (I'), (I'-A), (I'-B) and (I'-C), are ALK5 inhibitors that limit the activity of TGFβ. TGFβ is one of several factors involved in the initiation and development of fibrotic diseases throughout the body. As such, the compounds of the disclosure are expected to be useful for the treatment, prevention and/or reduction of fibrosis in a patient by administering a therapeutically effective amount of a compound disclosed herein. By inhibiting ALK5, the compound is expected to potentiate the formation of fibrosis in areas of the body that suffer from excessive deposition of the extracellular matrix. Those areas are described below.

Systemic Fibrotic Diseases

Systemic sclerosis (SSc) is an autoimmune disorder that affects the skin and internal organs and results in autoantibody production, vascular endothelial activation of small blood vessels, and tissue fibrosis as a result of fibroblast dysfunction. Transforming growth factor β (TGF-β) has been identified as a regulator of pathological fibrogenesis in SSc (Ayers, N. B., et al., *Journal of Biomedical Research*, 2018, 32(1), pp. 3-12). According to the authors, "understanding the essential role TGF-β pathways play in the pathology of systemic sclerosis could provide a potential outlet for treatment and a better understanding of this severe disease." In some embodiments, the present disclosure provides a method of treating SSc, comprising administering to a subject an effective amount of a compound disclosed herein.

Multifocal fibrosclerosis (MF) and idiopathic multifocal fibrosclerosis (IMF) are disorders characterized by fibrous lesions at varying sites and include retroperitoneal fibrosis, mediastinal fibrosis and Riedel's thyroiditis. Both multifocal fibrosclerosis and idiopathic multifocal fibrosclerosis are considered to be an outcome of $IgG_4$-associated fibrosis/disease and TGF-β is believed to be one factor involved in the initiation and development of fibrosis (Pardali, E., et. al., *Int. J. Mol. Sci.*, 18, 2157, pp. 1-22). In some embodiments, the present disclosure provides a method of treating multifocal fibrosclerosis or idiopathic multifocal fibrosclerosis, comprising administering to a subject an effective amount of a compound disclosed herein.

In some embodiments, the present disclosure provides a method of treating nephrogenic systemic fibrosis, comprising administering to a subject an effective amount of a compound disclosed herein. Nephrogenic systemic fibrosis is a rare disease occurring mainly in people with advanced kidney failure with or without dialysis. In a study performed by Kelly et al. (*J. Am. Acad. Dermatol.*, 2008, 58, 6, pp. 1025-1030), it was shown that TGF-β, as well as Smad 2/3, appear to be associated with fibrosis seen in nephrogenic systemic fibrosis.

Sclerodermatous graft-versus-host disease (GVHD) is a prevalent complication of allogeneic hematopoietic stem cell graft appearing two to three months after allogeneic bone marrow transplantation. The disease results in production of autoantibodies and fibrosis of skin and inner organs. Using a murine cutaneous GVHD model, it has been shown that progression of early skin and lung disease can be inhibited with TGF-β neutralizing antibodies (McCormick, L. L., et al., *J. Immunol.*, 1999, 163, pp. 5693-5699). In some embodiments, the present disclosure provides a method of treating sclerodermatous GVHD, comprising administering to a subject an effective amount of a compound disclosed herein.

Organ-Specific Fibrotic Diseases

Cardiac fibrosis refers to the abnormal thickening of heart valves due to the abnormal proliferation of cardiac fibroblasts resulting in excess deposition of ECM in heart muscle. Fibroblasts secrete collagen, which serves as structural support for the heart. However, when collagen is excessively secreted in the heart, wall and valve thickening can result in tissue build-up on the tricuspid and pulmonary valves. This in turn causes loss of flexibility and ultimately valvular dysfunction leading to heart failure. A specific type of cardiac fibrosis is hypertension-associated cardiac fibrosis as described by J. Diez (*J. Clin. Hypertens.*, 2007, July 9(7), pp. 546-550). According to Diez, changes in the composition of cardiac tissue develop in hypertensive patients with left ventricular hypertrophy and lead to structural remodeling of the heart tissue. One change relates to the disruption of the equilibrium between the synthesis and degradation of collagen types I and III molecules, resulting in excessive accumulation of collagen fibers in the heart tissue. Other types of cardiac fibrosis include post-myocardial infarction and Chagas disease-induced myocardial fibrosis. In Chagas disease, transforming growth factor β1 (TGF-β1) has been implicated in Chagas disease physiopathology, where animal models suggest that the TGF-β1-pathway is up-regulated during infection (Araujo-Jorge, T. C., et al., *Clin. Pharmacol. Ther.*, 2012, 92(5), pp. 613-621; Curvo, E., *Mem Inst Oswaldo Cruz*, 2018, Vol. 113(4), e170440, pp. 1-8). In some embodiments, the present disclosure provides a method of treating various forms of cardiac fibrosis, such as hypertension-associated cardiac fibrosis, post-myocardial infarction or Chagas disease-induced myocardial fibrosis, comprising administering to a subject an effective amount of a compound disclosed herein.

Renal fibrosis encompasses a variety of disorders associated with the aberrant expression and activity of TGF-β, including, but not limited to, diabetic and hypertensive nephropathy, urinary tract obstruction-induced kidney fibrosis, inflammatory/autoimmune-induced kidney fibrosis, aristolochic acid nephropathy, progressive kidney fibrosis, and polysystic kidney disease. As discussed above, fibrosis involves an excess accumulation of the ECM, which in turn causes loss of function when normal tissue is replaced with scar tissue (Wynn, T. A., J Clin Invest., 2007, 117, pp. 524-529). As early as 2005, ALK5 inhibitors were being studied in models for renal disease (Laping, N. J., *Current Opinion in Pharmacology*, 2003, 3, pp. 204-208). In some embodiments, the present disclosure provides a method of treating renal fibrosis, comprising administering to a subject an effective amount of a compound disclosed herein.

One fibrotic disease that has been particularly difficult to treat is idiopathic pulmonary fibrosis (IPF). IPF is a chronic, progressive and fatal fibrotic lung disease with survival only improved by lung transplantation. Current oral therapies such as nintedanib and pirfenidone have been shown to slow the progression of the disease, but have adverse effects that lead to discontinuation and lack of compliance by the patient. Although there are other therapies in development targeting various pathways, an unmet need remains for patients with IPF.

Although ALK5 is an important and known component in the fibrotic disease pathway, the efficacy of ALK5 inhibitors in IPF have not been realized due to systemic adverse effects, especially in the heart. Thus, one of the goals of this disclosure is to develop ALK5 inhibitors with high lung selectivity and rapid clearance. One preferred embodiment of this disclosure is to treat patients with idiopathic pulmonary fibrosis with a compound described herein, for example, by once or twice daily administration of inhalable ALK5 inhibitor having minimal systemic exposure. The inhaled ALK5 inhibitor may be administered as a monotherapy or co-dosed with other orally available IPF therapies. In some embodiments, the present disclosure provides a method of treating idiopathic pulmonary fibrosis, comprising administering to a subject an effective amount of a compound disclosed herein. In some embodiments, the compound is administered by inhalation.

Familial pulmonary fibrosis is a hereditary disease where two or more family members have confirmed IPF. In some embodiments, the present disclosure provides a method of treating familial pulmonary fibrosis, comprising administering to a subject an effective amount of a compound disclosed herein.

Pulmonary fibrosis is a typical clinical feature associated with viral infection, such as SARS and COVID-19. SARS-mediated TGF-β signaling has been shown to promote fibrosis and block apoptosis of SARS-CoV-infected host cells (Zhao, X. et al., *J. Biol. Chem.*, 2008, 283(6), pp. 3272-3280). Increased TGF-β expression was similarly observed in patients infected with SARS-CoV-2, ultimately leading to the development of pulmonary fibrosis. TGF-β signaling mediated by SARS-CoV-2 can promote fibroblast proliferation and myofibroblast differentiation and block host cell apoptosis. (Xiong, Y. et al., *Emerging Microbes & Infections*, 2020, 9(1), pp. 761-770). Compounds of the present disclosure are expected to inhibit increased TGF-β signaling mediated by viral infection and prevent, halt, slow or reverse the progression of pulmonary fibrosis associated with the infection. Accordingly, in some embodiments, the present disclosure provides a method of treating pulmonary fibrosis induced by a viral infection, comprising administering to a subject an effective amount of a compound disclosed herein. In some embodiments, the pulmonary fibrosis is induced by SARS-CoV or SARS-CoV-2. In some embodiments, the compound is administered by inhalation.

Chronic lung disease, such as interstitial lung disease (ILD), chronic obstructive pulmonary disease (COPD) and idiopathic pulmonary fibrosis (IPF), may lead to pulmonary hypertension (PH). Pulmonary hypertension is a progressive disease characterized by high blood pressure in the lungs. The World Health Organization (WHO) has defined five classifications of PH (WHO Group I: Pulmonary arterial hypertension (PAH); WHO Group II: Pulmonary hypertension due to left heart disease; WHO Group III: Pulmonary hypertension due to lung disease and/or hypoxia; WHO Group IV: Chronic thromboembolic pulmonary hypertension (CTEPH); and WHO Group V: Pulmonary hypertension with unclear multifactorial mechanisms). TGF-β signaling has been implicated in the pathogenesis of PH. Moreover, inhibition of ALK5 in a monocrotaline (MCT) model of severe PH was shown to attenuate the development of PH and reduce pulmonary vascular remodeling in a dose-dependent manner, namely by reducing RV systolic pressure, reducing RV diastolic pressure, increasing cardiac output and reducing RV hypertrophy (Zaiman, A. L.; et al., *Am. J. Respir. Crit. Care Med.*, 2008, 177, pp. 896-905). Compounds of the present disclosure are expected to inhibit TGF-β signaling in lung tissue and prevent, halt, slow or reverse the progression of PH, particularly in WHO Group III PH. Accordingly, in some embodiments, the present disclosure provides a method of treating pulmonary hypertension, comprising administering to a subject an effective amount of a compound disclosed herein. The pulmonary hypertension may be WHO Group III pulmonary hypertension, such as pulmonary fibrosis-related pulmonary hypertension (PH-PF) or interstitial lung disease-related pulmonary hypertension (PH-ILD). In some embodiments, the compound is administered by inhalation.

Other types of interstitial lung diseases include, but are not limited to, (1) interstitial pneumonia caused by bacteria, viruses, or fungi; (2) nonspecific interstitial pneumonitis usually associated with autoimmune conditions such as rheumatoid arthritis or scleroderma; (3) hypersensitivity pneumonitis caused by inhalation of dust, mold, or other irritants; (4) cryptogenic organizing pneumonia; (5) acute interstitial pneumonitis; (6) desquamative interstitial pneumonitis; (7) sarcoidosis; (8) drug-induced interstitial lung disease; and (9) progressive fibrosing interstitial lung disease (PF-ILD). In some embodiments, the present disclosure provides a method of treating an interstitial lung disease, comprising administering to a subject an effective amount of a compound disclosed herein.

Both transforming growth factor (TGF)-beta(1) and activin-A have been implicated in airway remodeling in asthma (Kariyawasam, H. H., *J Allergy Clin Immunol.*, 2009, September, 124(3), pp. 454-462). In some embodiments, the present disclosure provides a method of treating asthma, comprising administering to a subject an effective amount of a compound disclosed herein.

Chronic obstructive pulmonary disease (COPD) is a pulmonary disorder characterized by a poorly reversible and progressive airflow limitation caused by airway inflammation and emphysema, whereas IPF is associated with impaired diffusion capacity (Chilosi, M., et al., *Respir. Res.*, 2012, 13(1), 3, pp. 1-9). Both diseases, however, demonstrate a progressive loss of alveolar parenchyma leading to severe impairment of respiratory function. Fibrosis associated with emphysema is known and research has demonstrated TGF-β1 involvement in chronic sinus disease, pulmonary fibrosis, asthma, and COPD (Yang, Y. C., et al., *Allergy*, 2012, 67, pp. 1193-1202). In some embodiments, the present disclosure provides a method of treating COPD, comprising administering to a subject an effective amount of a compound disclosed herein.

Other types of lung injury that result in fibrosis include silica-induced pneumoconiosis (silicosis), asbestos-induced pulmonary fibrosis (asbestosis), and chemotherapeutic agent-induced pulmonary fibrosis. In some embodiments, the present disclosure provides a method of treating injury-induced fibrosis, comprising administering to a subject an effective amount of a compound disclosed herein.

In some embodiments, the present disclosure provides a method of treating liver fibrosis, comprising administering to a subject an effective amount of a compound disclosed herein. Fibrosis develops in the liver when it is repeatedly or continuously damaged, for example, in patients with chronic hepatitis. TGF-β signaling participates in all stages of disease progression, from initial liver injury through inflammation and fibrosis, to cirrhosis and cancer (Fabregat, I., et al., *The FEBS J.*, 2016, 283(12), pp. 2219-2232).

A related condition involves fibrosis resulting from idiopathic non-cirrhotic portal hypertension (INCPH). This disease is of uncertain etiology characterized by periportal fibrosis and involvement of small and medium branches of the portal vein. According to Nakanuma et al., small portal veins and skin findings are similar between patients with scleroderma and INCPH (Nakanuma, Y., Hepatol. Res., 2009, 39, pp. 1023-1031). Transforming growth factor-β (TGF-β) and connective tissue growth factor, which are fibrosis-related and vascular endothelial growth factors, respectively, increase in serum, skin, and the portal vein, suggesting that these could be mechanisms of the portal vein occlusion in INCPH. Moreover, endothelial mesenchymal transition (EndMT) theory was proposed by Kitao et al. based on these findings (Kitao, A., et al., Am. J. Pathol., 2009, 175, pp. 616-626). The increase of TGF-β in sera may act as a potent inducer of EndMT. In some embodiments, the present disclosure provides a method of treating INCPH, comprising administering to a subject an effective amount of a compound disclosed herein.

Other types of liver fibrosis include alcoholic and non-alcoholic liver fibrosis, hepatitis C-induced liver fibrosis, primary biliary cirrhosis or cholangitis, and parasite-induced liver fibrosis (schistosomiasis). In some embodiments, the present disclosure provides a method of treating alcoholic liver fibrosis, non alcoholic liver fibrosis, hepatitis C-induced liver fibrosis, primary biliary cirrhosis, primary biliary cholangitis, or parasite-induced liver fibrosis (schistosomiasis), comprising administering to a subject an effective amount of a compound disclosed herein.

Primary biliary cholangitis (PBC) and primary sclerosing cholangitis (PSC) are two types of chronic liver disease that often lead to cirrhosis and liver failure. Liver biopsies of patients with PBC or PSC typically reveal inflammation and fibrosis. Inhibition of integrin αvβ6, which has been shown to bind to and activate TGFβ1 on epithelial cells, suppresses biliary fibrosis in rodents. (Peng, Z-W., et al., Hepatology, 2016, 63, pp. 217-232). Accordingly, inhibition of the TGF-β pathway is also expected to suppress fibrotic processes in both PBC and PSC. Compounds of the present disclosure are expected to inhibit TGF-β signaling in liver tissue and prevent, halt, slow or reverse the progression of PBC and PSC. Thus, in some embodiments, the present disclosure provides a method of treating primary biliary cholangitis or primary sclerosing cholangitis, comprising administering to a subject an effect amount of a compound described herein. In some embodiments, the present disclosure provides a method of treating liver fibrosis, optionally in a subject that suffers from PBC or PSC, comprising administering to the subject an effective amount of a compound described herein.

Fibrotic skin conditions include, but are not limited to, hypertrophic scarring, keloids, and localized or systemic sclerosis (scleroderma). As discussed previously, TGF-β is a potent stimulus of connective tissue accumulation and has been implicated in the pathogenesis of scleroderma and other fibrotic disorders (Lakos, G., et al., Am. J. Pathol., 2004, 165(1), pp. 203-217). Lakos et. al. demonstrated that Smad3 functions as a key intracellular signal transducer for profibrotic TGF-β responses in normal skin fibroblasts and found that the targeted disruption of TGF-β/Smad3 signaling modulated skin fibrosis in the mouse model of scleroderma. In some embodiments, the present disclosure provides a method of treating skin fibrosis, comprising administering to a subject an effective amount of a compound disclosed herein.

Intestinal fibrosis is a common complication of inflammatory bowel disease (IBD) and is a serious clinical problem. TGF-β has been implicated as a major driving factor of intestinal fibrosis. Moreover, TGF-β1 signaling contributes to stricture formation in fibrostenotic Crohn's disease by inducing insulin-like growth factor I (IGF-I) and mechano-growth factor (MGF) production in intestinal smooth muscle. (Latella, G., Rieder, F., Curr. Opin. Gastroenterol., 2017, 33(4), pp. 239-245). Inhibition of TGF-β signaling could thus slow, halt or reverse the progression of fibrosis in the intestine. However, adverse side effects of concern to patients with IBD—such as inflammation and neoplasia—would likely result from systemic inhibition of TGF-β signaling. One goal of the present disclosure is to develop ALK5 inhibitors with high selectivity for the gastrointestinal tract and rapid clearance. In some embodiments, the present disclosure provides a method of treating intestinal fibrosis, comprising administering to a subject an effective amount of a compound described herein, for example, by once or twice daily administration of an oral ALK5 inhibitor having minimal systemic exposure. In some embodiments, the subject suffers from inflammatory bowel disease, such as Crohn's disease or colitis. The degree of therapeutic efficacy may be with respect to a starting condition of the subject (e.g., a baseline Mayo score, baseline Lichtiger score, or severity or incidence of one or more symptoms), or with respect to a reference population (e.g., an untreated population, or a population treated with a different agent). Severity of intestinal fibrosis may be assessed using any suitable method, such as delayed enhancement MRI, ultrasound elastography, shear wave elastography, magnetization MRI, or by the direct detection of macromolecules such as collagen. Preferably, treatment with a compound of the present disclosure reduces the severity of the fibrosis, such as from severe fibrosis to moderate or mild fibrosis. In some embodiments, the treatment increases intestinal tissue elasticity, reduces tissue stiffness, and/or reduces collagen levels. In some embodiments, the treatment prevents myofibroblast accumulation, inhibits expression of pro-fibrotic factors, and/or inhibits accumulation of fibrotic tissue.

Other types of organ-specific fibrosis or fibrotic diseases involving the TGF-β pathway include, but are not limited to, radiation-induced fibrosis (various organs), bladder fibrosis, intestinal fibrosis, peritoneal sclerosis, diffuse fasciitis, Dupuytren's disease, myelofibrosis, oral submucous fibrosis, and retinal fibrosis. In some embodiments, the present disclosure provides a method of treating radiation-induced fibrosis, bladder fibrosis, intestinal fibrosis, peritoneal sclerosis, diffuse fasciitis, Dupuytren's disease, myelofibrosis, oral submucous fibrosis, or retinal fibrosis, comprising administering to a subject an effective amount of a compound disclosed herein.

Although one of the goals of this disclosure is to treat fibrotic and pulmonary diseases locally or in a targeted way, the compounds described herein may also be used to treat patients systemically. Diseases that may be treated systemically, include, for example, oncologic diseases such as glioblastoma, pancreatic cancer and hepatocellular carcinoma, breast cancer metastasized to lungs, non-small cell lung cancer, small cell lung cancer, cystic fibrosis, and metastasis of other forms of primary cancer subtypes. Some of the forgoing diseases may also be treated locally as well.

Other fibrotic diseases that compounds disclosed herein may treat include angioedema, anti-aging, and alopecia. Alopecia includes alopecia totalis, alopecia universalis, androgenetic alopecia, alopecia areata, diffuse alopecia, postpartum alopecia, and traction alopecia.

Other Indications

In certain aspects, the present disclosure provides a method of reversing one or more symptoms of aging, comprising administering to a subject an ALK5 inhibitor. The method may further comprise administering an activator of the MAPK pathway, such as oxytocin. The method may be effective in one or more of enhancing neurogenesis in the hippocampus, reducing neuroinflammation, improving cognitive ability, reducing liver adiposity, reducing liver fibrosis, and decreasing the number of p16$^+$ cells. In some embodiments, a method described herein increases stem cell activity. The increase in stem cell activity may allow the subject to generate new muscle fibers and/or to form new neurons in the hippocampus. Treatment with an ALK5 inhibitor, such as a compound described herein, may prevent or slow the onset of age-related diseases, such as Alzheimer's disease. (see Mehdipour, M. et al. *Aging* 2018, 10, 5628-5645).

Pharmaceutical Compositions

In some aspects, the present disclosure provides a pharmaceutical composition. The pharmaceutical composition may comprise a compound disclosed herein, such as a compound of Formula (I), (I-A), (I-B), (I C), (I'), (I'-A), (I'-B) or (I'-C), and a pharmaceutically acceptable carrier. In some embodiments, the pharmaceutical composition is formulated for oral administration. In some embodiments, the pharmaceutical composition is formulated for inhalation. In some embodiments, the pharmaceutical composition comprises a compound disclosed herein and an additional therapeutic agent. Non-limiting examples of such therapeutic agents are described herein below.

Pharmaceutical compositions typically include at least one pharmaceutically acceptable carrier, diluent or excipient and at least one compound of Formula (I), (I-A), (I-B), (I-C), (I'), (I'-A), (I'-B) or (I'-C), or a compound provided in Table 1—described herein as the active agent. The active agent may be provided in any form suitable for the particular mode of administration, such as a free base, a free acid, or a pharmaceutically acceptable salt. Additionally, the methods and pharmaceutical compositions of the present disclosure include the use of N-oxides, crystalline forms (e.g., polymorphs), as well as metabolites of these compounds having similar activity. All tautomers of the compounds described herein are included within the scope of the present disclosure. Additionally, the compounds described herein encompass unsolvated as well as solvated forms with pharmaceutically acceptable solvents such as water, ethanol and the like.

Suitable routes of administration include, but are not limited to, oral, intravenous, rectal, vaginal, aerosol, pulmonary, nasal, transmucosal, topical, transdermal, otic, ocular, and parenteral modes of administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In certain embodiments, a compound described herein is administered in a local rather than systemic manner, for example, via injection of the compound directly into an organ, often in a depot preparation or sustained release formulation. In some embodiments, a long acting formulation is administered by implantation (e.g., subcutaneously or intramuscularly) or by intramuscular injection. In some embodiments, a compound described herein is provided in the form of a rapid release formulation, an extended release formulation, or an intermediate release formulation. In some embodiments, a compound described herein is provided in the form of a nebulized formulation. In some embodiments, a compound described herein is administered locally to the lungs by inhalation.

Compounds of the present disclosure are effective over a wide dosage range. For example, in the treatment of adult humans, dosages from 0.01 to 1000 mg, 0.5 to 100 mg, 1 to 50 mg, or from 5 to 40 mg per day may be administered to a subject in need thereof. The exact dosage will depend upon the route of administration, the form in which the compound is administered, the subject to be treated, the body weight of the subject to be treated, and the preference and experience of the attending physician.

A compound of the present disclosure may be administered in a single dose. In some embodiments, a compound of the disclosure is administered in multiple doses, such as about once, twice, three times, four times, five times, six times, or more than six times per day. In some embodiments, dosing is about once a month, once every two weeks, once a week, or once every other day. In some embodiments, a compound of the disclosure and an additional therapeutic agent are administered together about once per day to about 6 times per day. In some embodiments, the administration continues for more than about 6, 10, 14, 28 days, two months, six months, or more than about one year. In some embodiments, a dosing schedule is maintained as long as necessary. A compound of the present disclosure may be administered chronically on an ongoing basis, e.g., for the treatment of chronic effects.

Pharmaceutical compositions of the present disclosure typically contain a therapeutically effective amount of a compound of the present disclosure. Those skilled in the art will recognize, however, that a pharmaceutical composition may contain more than a therapeutically effective amount, e.g., bulk compositions, or less than a therapeutically effective amount, e.g., individual unit doses designed for co-administration to achieve a therapeutically effective amount.

Typically, pharmaceutical compositions of the present disclosure contain from about 0.01 to about 95% by weight of the active agent; including, for example, from about 0.05 to about 30% by weight; and from about 0.1% to about 10% by weight of the active agent.

Any conventional carrier or excipient may be used in the pharmaceutical compositions of the present disclosure. The choice of a particular carrier or excipient, or combinations of carriers or excipients, will depend on the mode of administration being used to treat a particular patient or type of medical condition or disease state. Additionally, the carriers or excipients used in the pharmaceutical compositions of this disclosure may be commercially-available. Conventional formulation techniques are described in Remington; The Science and Practice of Pharmacy, 20th Edition, Lippincott Williams & White, Baltimore, Md. (2000); and H. C. Ansel et al., Pharmaceutical Dosage Forms and Drug Delivery Systems, 7th Edition, Lippincott Williams & White, Baltimore, Md. (1999).

Representative examples of materials which can serve as pharmaceutically acceptable carriers include, but are not limited to, the following: sugars, such as lactose, glucose and sucrose; starches, such as corn starch and potato starch; cellulose, such as microcrystalline cellulose and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical compositions.

Pharmaceutical compositions are typically prepared by thoroughly and intimately mixing or blending the active agent with a pharmaceutically-acceptable carrier and one or more optional ingredients. The resulting uniformly blended mixture can then be shaped or loaded into tablets, capsules, pills and the like using conventional procedures and equipment.

In one aspect, the pharmaceutical composition is suitable for inhaled administration. Pharmaceutical compositions for inhaled administration are typically in the form of an aerosol or a powder. Such compositions are generally administered using inhaler delivery devices, such as a dry powder inhaler (DPI), a metered-dose inhaler (MDI), a nebulizer inhaler, or a similar delivery device.

In a particular embodiment, the pharmaceutical composition is administered by inhalation using a dry powder inhaler. Such dry powder inhalers typically administer the pharmaceutical composition as a free-flowing powder that is dispersed in a patient's air-stream during inspiration. In order to achieve a free-flowing powder composition, the therapeutic agent is typically formulated with a suitable excipient such as lactose, starch, mannitol, dextrose, poly-lactic acid (PLA), polylactide-co-glycolide (PLGA) or combinations thereof. Typically, the therapeutic agent is micronized and combined with a suitable carrier to form a composition suitable for inhalation.

A representative pharmaceutical composition for use in a dry powder inhaler comprises lactose and a micronized form of a compound disclosed herein. Such a dry powder composition can be made, for example, by combining dry milled lactose with the therapeutic agent and then dry blending the components. The composition is then typically loaded into a dry powder dispenser, or into inhalation cartridges or capsules for use with a dry powder delivery device.

Dry powder inhaler delivery devices suitable for administering therapeutic agents by inhalation are described in the art and examples of such devices are commercially available. For example, representative dry powder inhaler delivery devices or products include Aeolizer (Novartis); Airmax (IVAX); ClickHaler (Innovata Biomed); Diskhaler (GlaxoSmithKline); Diskus/Accuhaler (GlaxoSmithKline); Ellipta (GlaxoSmithKline); Easyhaler (Orion Pharma); Eclipse (Aventis); FlowCaps (Hovione); Handihaler (Boehringer Ingelheim); Pulvinal (Chiesi); Rotahaler (GlaxoSmithKline); SkyeHaler/Certihaler (SkyePharma); Twisthaler (Schering-Plough); Turbuhaler (AstraZeneca); Ultrahaler (Aventis); and the like.

A pharmaceutical composition of the present disclosure may be administered by inhalation using a metered-dose inhaler. Such metered-dose inhalers typically discharge a measured amount of a therapeutic agent using a compressed propellant gas. Accordingly, pharmaceutical compositions administered using a metered-dose inhaler typically comprise a solution or suspension of the therapeutic agent in a liquefied propellant. Any suitable liquefied propellant may be employed, including hydrofluoroalkanes (HFAs), such as 1,1,1,2-tetrafluoroethane (HFA 134a) and 1,1,1,2,3,3,3-heptafluoro-n-propane, (HFA 227); and chlorofluorocarbons, such as $CCl_3F$. In a particular embodiment, the propellant is a hydrofluoroalkane. In some embodiments, the hydrofluoroalkane formulation contains a co-solvent, such as ethanol or pentane, and/or a surfactant, such as sorbitan trioleate, oleic acid, lecithin, and glycerin.

A representative pharmaceutical composition for use in a metered-dose inhaler comprises from about 0.01% to about 5% by weight of a compound of the present disclosure; from about 0% to about 20% by weight ethanol; and from about 0% to about 5% by weight surfactant; with the remainder being an HFA propellant. Such compositions are typically prepared by adding chilled or pressurized hydrofluoroalkane to a suitable container containing the therapeutic agent, ethanol (if present) and the surfactant (if present). To prepare a suspension, the therapeutic agent is micronized and then combined with the propellant. The composition is then loaded into an aerosol canister, which typically forms a portion of a metered-dose inhaler device.

Metered-dose inhaler devices suitable for administering therapeutic agents by inhalation are described in the art and examples of such devices are commercially available. For example, representative metered-dose inhaler devices or products include AeroBid Inhaler System (Forest Pharmaceuticals); Atrovent Inhalation Aerosol (Boehringer Ingelheim); Flovent (GlaxoSmithKline); Maxair Inhaler (3M); Proventil Inhaler (Schering); Serevent Inhalation Aerosol (GlaxoSmithKline); and the like.

A pharmaceutical composition of the present disclosure may be administered by inhalation using a nebulizer inhaler. Such nebulizer devices typically produce a stream of high velocity air that causes the pharmaceutical composition to spray as a mist that is carried into the patient's respiratory tract. Accordingly, when formulated for use in a nebulizer inhaler, the therapeutic agent can be dissolved in a suitable carrier to form a solution. Alternatively, the therapeutic agent can be micronized or nanomilled and combined with a suitable carrier to form a suspension.

A representative pharmaceutical composition for use in a nebulizer inhaler comprises a solution or suspension comprising from about 0.05 µg/mL to about 20 mg/mL of a compound of the present disclosure and excipients compatible with nebulized formulations. In one embodiment, the solution has a pH of about 3 to about 8.

Nebulizer devices suitable for administering therapeutic agents by inhalation are described in the art and examples of such devices are commercially available. For example, representative nebulizer devices or products include the Respimat® Softmist™ Inhalaler (Boehringer Ingelheim); the AERx® Pulmonary Delivery System (Aradigm Corp.); the PARI LC Plus® Reusable Nebulizer or PARI eFlow® rapid Nebulizer System (Pari GmbH); and the like.

A pharmaceutical composition of the present disclosure may be prepared in a dosage form intended for oral administration. Suitable pharmaceutical compositions for oral administration may be in the form of capsules, tablets, pills, lozenges, cachets, dragees, powders, granules; or as a solution or a suspension in an aqueous or non-aqueous liquid; or as an oil-in-water or water-in-oil liquid emulsion; or as an elixir or syrup; and the like; each containing a predetermined amount of a compound of the present disclosure as an active ingredient.

When intended for oral administration in a solid dosage form, the pharmaceutical compositions of the disclosure will typically comprise the active agent and one or more pharmaceutically-acceptable carriers, such as sodium citrate or dicalcium phosphate. Optionally or alternatively, such solid dosage forms may also comprise: fillers or extenders, binders, humectants, solution retarding agents, absorption accelerators, wetting agents, absorbents, lubricants, coloring agents, and buffering agents. Release agents, wetting agents, coating agents, sweetening, flavoring and perfuming agents, preservatives and antioxidants can also be present in the present pharmaceutical compositions.

Alternative formulations may include controlled release formulations, liquid dosage forms for oral administration, transdermal patches, and parenteral formulations. Conventional excipients and methods of preparation of such alternative formulations are described, for example, in the reference by Remington, supra.

The following non-limiting examples illustrate representative pharmaceutical compositions of the present disclosure.

Dry Powder Composition

A micronized compound of the present disclosure (1 g) is blended with milled lactose (25 g). This blended mixture is then loaded into individual blisters of a peelable blister pack in an amount sufficient to provide between about 0.1 mg to about 4 mg of the compound per dose. The contents of the blisters are administered using a dry powder inhaler.

Dry Powder Composition

A micronized compound of the present disclosure (1 g) is blended with milled lactose (20 g) to form a bulk composition having a weight ratio of compound to milled lactose of 1:20. The blended composition is packed into a dry powder inhalation device capable of delivering between about 0.1 mg to about 4 mg of the compound per dose.

Metered-Dose Inhaler Composition

A micronized compound of the present disclosure (10 g) is dispersed in a solution prepared by dissolving lecithin (0.2 g) in demineralized water (200 mL). The resulting suspension is spray dried and then micronized to form a micronized composition comprising particles having a mean diameter less than about 1.5 µm. The micronized composition is then loaded into metered-dose inhaler cartridges containing pressurized 1,1,1,2-tetrafluoroethane in an amount sufficient to provide about 0.1 mg to about 4 mg of the compound per dose when administered by the metered dose inhaler.

Nebulizer Composition

A representative nebulizer composition is as follows. A compound of the present disclosure (2 g of free-base equivalents) is dissolved in a solution containing 80 mL reverse-osmosis water, 0.1-1% by weight of anhydrous citric acid, and 0.5-1.5 equivalents of hydrochloric acid, followed by addition of sodium hydroxide to adjust the pH to 3.5 to 5.5. Thereafter, between 4-6% by weight of D-mannitol is added and solution q.s. to 100 mL. The solution is then filtered through a 0.2 µm filter and stored at room temperature prior to use. The solution is administered using a nebulizer device that provides about 0.1 mg to about 4 mg of the compound per dose.

Kits

In certain aspects, the present disclosure provides a kit comprising one or more unit doses of a compound or pharmaceutical composition described herein, optionally wherein the kit further comprises instructions for using the compound or pharmaceutical composition. In some embodiments, the kit comprises a carrier, package, or container that is compartmentalized to receive one or more containers, such as vials, tubes, and the like, each of the container(s) comprising one of the separate elements to be used in a method described herein. Suitable containers include, for example, bottles, vials, syringes, and test tubes. The containers may be formed from a variety of materials, such as glass or plastic.

The articles of manufacture provided herein may contain packaging materials. Packaging materials for use in packaging pharmaceutical products include those found in, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. For example, the container(s) may include one or more compounds described herein, optionally in a composition or in combination with another agent as disclosed herein. The container(s) may optionally have a sterile access port (for example, the container is an intravenous solution bag or a vial having a stopper pierceable by a hypodermic injection needle). Such kits may optionally comprise a compound with an identifying description or label or instructions relating to its use in the methods described herein.

In some embodiments, a kit includes one or more containers, each with one or more of various materials (such as reagents, optionally in concentrated form, and/or devices) desirable from a commercial and user standpoint for use of a compound described herein. Nonlimiting examples of such materials include, but are not limited to, buffers, diluents, filters, needles, syringes, carrier, package, container, vial and/or tube labels listing contents and/or instructions for use, and package inserts with instructions for use. A set of instructions will also typically be included. A label is optionally on or associated with the container. For example, a label is on a container when letters, numbers or other characters forming the label are attached, molded, or etched onto the container itself, a label is associated with a container when it is present within a receptacle or carrier that also holds the container, e.g., as a package insert. In addition, a label is used to indicate that the contents are to be used for a specific therapeutic application. In addition, the label indicates directions for use of the contents, such as in the methods described herein. In certain embodiments, the pharmaceutical composition is presented in a pack or dispenser device which contains one or more unit dosage forms containing a compound provided herein. The pack may contain metal or plastic foil, such as a blister pack. In some embodiments, the pack or dispenser device is accompanied by instructions for administration. Optionally, the pack or dispenser is accompanied with a notice associated with the container in a form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for prescription drugs, or the approved product insert. In some embodiments, compositions containing a compound provided herein formulated in a compatible pharmaceutical carrier are prepared, placed in an appropriate container, and labeled for treatment of an indicated condition.

Combination Therapy

The compounds and pharmaceutical compositions of the disclosure may be used in combination with one or more therapeutic agents which act by the same mechanism or by a different mechanism to treat a disease. The one or more agents may be administered sequentially or simultaneously, in separate compositions or in the same composition. Useful classes of agents for combination therapy include, but are not limited to, compounds used to treat cardiac, kidney, pulmonary, liver, skin, immunological and oncological conditions.

In practicing any of the subject methods, an ALK5 inhibitor and a second therapeutic agent can be administered sequentially, wherein the two agents are introduced into a subject at two different time points. The two time points can be separated by more than 2 hours, 1 or more days, 1 or more weeks, 1 or more months, or according to any intermittent regimen schedule disclosed herein.

In some embodiments, the ALK5 inhibitor and the second therapeutic agent are administered simultaneously. The two agents may form part of the same composition, or the two agents may be provided in one or more unit doses.

In some embodiments, the ALK5 inhibitor or the second therapeutic agent are administered parenterally, orally, inhalatively, intraperitoneally, intravenously, intraarterially, transdermally, intramuscularly, liposomally, via local delivery by catheter or stent, subcutaneously, intraadiposally, or intrathecally. As used herein, a therapeutically effective amount of a combination of an ALK5 inhibitor and a second therapeutic agent refers to a combination of an ALK5 inhibitor and a second therapeutic agent, wherein the combination is sufficient to affect the intended application, including but not limited to, disease treatment, as defined herein. Also contemplated in the subject methods is the use of a sub-therapeutic amount of an ALK5 inhibitor and a second therapeutic agent in combination for treating an intended disease condition. The individual components of the combination, though present in sub-therapeutic amounts, synergistically yield an efficacious effect and/or reduced a side effect in an intended application.

The amount of the ALK5 inhibitor and the second therapeutic agent administered may vary depending upon the intended application (in vitro or in vivo), or the subject and disease condition being treated, e.g., the weight and age of the subject, the severity of the disease condition, the manner of administration and the like, which can readily be determined by one of ordinary skill in the art.

Measuring an immune response and/or the inhibition of biological effects of ALK5 can comprise performing an assay on a biological sample, such as a sample from a subject. Any of a variety of samples may be selected, depending on the assay. Examples of samples include, but are not limited to blood samples (e.g. blood plasma or serum), exhaled breath condensate samples, bronchoalveolar lavage fluid, sputum samples, urine samples, and tissue samples.

A subject being treated with an ALK5 inhibitor and a second therapeutic agent may be monitored to determine the effectiveness of treatment, and the treatment regimen may be adjusted based on the subject's physiological response to treatment. For example, if inhibition of a biological effect of ALK5 inhibition is above or below a threshold, the dosing amount or frequency may be decreased or increased, respectively. Alternatively, the treatment regimen may be adjusted with respect to an immune response. The methods can further comprise continuing the therapy if the therapy is determined to be efficacious. The methods can comprise maintaining, tapering, reducing, or stopping the administered amount of a compound or compounds in the therapy if the therapy is determined to be efficacious. The methods can comprise increasing the administered amount of a compound or compounds in the therapy if it is determined not to be efficacious. Alternatively, the methods can comprise stopping therapy if it is determined not to be efficacious. In some embodiments, treatment with an ALK5 inhibitor and a second therapeutic agent is discontinued if inhibition of the biological effect is above or below a threshold, such as in a lack of response or an adverse reaction. The biological effect may be a change in any of a variety of physiological indicators.

Specific agents that may be used in combination with the compounds disclosed herein include, but are not limited to, OFEV® (nintedanib) and Esbriet® (pirfenidone). In some embodiments, a compound disclosed herein is administered in combination with pirfenidone, optionally wherein the pirfenidone is administered by inhalation. In some embodiments, the present disclosure provides a method of treating fibrosis, such as idiopathic pulmonary fibrosis, in a subject, comprising administering to the subject an ALK5 inhibitor, such as a compound disclosed in Table 1, and nintedanib or pirfenidone. In some embodiments, the present disclosure provides a method of treating cancer, such as lung cancer, in a subject, comprising administering to the subject an ALK5 inhibitor, such as a compound disclosed in Table 1, and nintedanib or pirfenidone.

In some embodiments, the present disclosure provides a method for treating a proliferative disorder (e.g., lung cancer) in a subject in need thereof, comprising administering to said subject an ALK5 inhibitor and an immunotherapeutic agent. TGF-β has been shown to regulate lymphocyte differentiation, suppress T cell proliferation and to enhance tumor growth. Moreover, TGF-β has been shown to prevent optimal activation of the immune system in immunotherapy-resistant patients (see Löffek, S. *J. Oncolo.* 2018, 1-9; incorporated herein by reference in its entirety). Not wishing to be bound by any particular theory, the present inventors expect that inhibition of ALK5 may enhance the efficacy of a particular immunotherapy. As such, treatment with an immunotherapeutic agent, such as durvalumab or pembrolizumab, and an ALK5 inhibitor, such as a compound of the present disclosure, is expected to improve the clinical outcome of a subject with cancer, such as a subject with non-small cell lung cancer. The combination is expected to produce a synergistic effect. A synergistic combination is also expected for a triple combination of radiation therapy, immunotherapy, and ALK5 inhibition. In addition, the ALK5 inhibitor, even when administered locally (e.g., to the lung by inhalation), may stimulate both local and systemic immune responses, allowing for the treatment of primary or metastatic tumors in tissues beyond the site of the local delivery. For example, an inhaled ALK5 inhibitor may be administered in combination with an immunotherapeutic agent to treat melanoma, renal cell carcinoma, colon cancer, or breast cancer.

In some embodiments, the ALK5 inhibitor and the immunotherapeutic agent are administered sequentially or simultaneously. In some embodiments, the ALK5 inhibitor and the immunotherapeutic agent are more effective in treating the proliferative disorder than either agent alone. In some embodiments, the ALK5 inhibitor and the immunotherapeutic agent yield a synergistic effect in treating the proliferative disorder. The synergistic effect may be a therapeutic effect that is greater than either agent used alone in comparable amounts under comparable conditions. The synergistic effect may be a therapeutic effect that is greater than results expected by adding the effects of each agent alone. In some embodiments, the proliferative disorder is a cancer condition. In some embodiments, the cancer condition is lung cancer, such as non-small cell lung cancer.

The term "immunotherapeutic agent" refers to any agent that induces, enhances, suppresses or otherwise modifies an immune response. This includes the administration of an active agent to, or any type of intervention or process performed on, the subject, with the objective of modifying an immune response. An immunotherapeutic agent may, for example, increase or enhance the effectiveness or potency of an existing immune response in a subject, for example, by stimulating mechanisms that enhance the endogenous host immune response or overcoming mechanisms that suppress the endogenous host immune response.

"Immune response" refers to the action of a cell of the immune system including, for example, B lymphocytes, T lymphocytes, natural killer (NK) cells, macrophages, eosinophils, mast cells, myeloid-derived suppressor cells, dendritic cells and neutrophils and soluble macromolecules produced by any of these cells or the liver (including antibodies, cytokines and complement), that results in selective targeting, binding to, damage to, destruction of, and/or elimination of invading pathogens, cells or tissues infected with pathogens, cancerous or other abnormal cells, or, in cases of autoimmunity or pathological inflammation, normal human cells or tissues, from the body of a subject.

In one embodiment, an immunotherapeutic agent may comprise a PD-1 inhibitor. In another embodiment, an immunotherapeutic agent may comprise a CTLA-4 inhibitor. In still another embodiment, an immunotherapeutic agent may comprise a B7 inhibitor.

Exemplary PD-1 inhibitors: A PD-1 inhibitor suitable for use in the subject methods can be selected from a variety of types of molecules. For example, the PD-1 inhibitor can be a biological or chemical compound, such as an organic or inorganic molecule, peptide, peptide mimetic, antibody or an antigen-binding fragment of an antibody. Some exemplary classes of agents suitable for use in the subject methods are detailed in the sections below. A PD-1 inhibitor for use in the present disclosure can be any PD-1 inhibitor that is known in the art, and can include any entity that, upon administration to a patient, results in inhibition of the PD-1 pathway in the patient. A PD-1 inhibitor can inhibit PD-1 by any biochemical mechanism, including disruption of any one or more of PD-1/PD-L1, PD1/PD-L2 and PD-L1/CD80 interactions.

In some embodiments, the PD-1 inhibitor is a molecule that inhibits the binding of PD-1 to its ligand binding partners. In a specific aspect, the PD-1 ligand binding partners are PD-L1 and/or PD-L2. In another embodiment, a PD-1 inhibitor is a molecule that inhibits the binding of PD-L1 to its binding partners. In a specific aspect, PD-L1 binding partners are PD1 and/or CD80. In another embodiment, the PD-1 inhibitor is a molecule that inhibits the binding of PD-L2 to its binding partners. In a specific aspect, a PD-L2 binding partner is PD1. The inhibitor may be an antibody, an antigen binding fragment thereof, an immunoadhesin, a fusion protein or oligopeptide.

In some embodiments, the PD-1 inhibitor is an anti-PD-1 antibody. In some further embodiments, the anti-PD-1 antibody is capable of inhibiting binding between PD-1 and PD-L1. In another embodiment, the anti-PD-1 antibody is capable of inhibiting binding between PD-1 and PD-L2. In some embodiments, the PD-1 inhibitor is an anti-PD-L1 antibody. In some embodiments, the anti-PD-L1 antibody is capable of inhibiting binding between PD-L1 and PD-1 and/or between PD-L1 and CD80. In some embodiments, the PD-1 inhibitor is an anti-PD-L2 antibody. In some further embodiments, the anti-PD-L2 antibody is capable of inhibiting binding between PD-1 and PD-L2. In yet another embodiment, the PD-1 inhibitor is nivolumab or pembrolizumab. In some embodiments, the PD-1 inhibitor is selected from atezolizumab, avelumab, nivolumab, pembrolizumab, durvalumab and BGB-A317.

Inhibition of the PD-1 pathway can enhance the immune response to cancerous cells in a patient. The interaction between PD-1 and PD-L1 impairs T cell response as manifested by a decrease in tumor-infiltrating lymphocytes (TILs) and a decrease in T-cell receptor mediated proliferation, resulting in T cell anergy, exhaustion or apoptosis, and immune evasion by the cancerous cells. This immune suppression can be reversed by inhibiting the local interaction between PD-L1 and PD-1 using a PD-1 inhibitor, including, for example, an anti-PD-1 and/or an anti-PD-L1 Ab. A PD-1 inhibitor may improve or restore antitumor T-cell functions.

Anti-PD-1 antibodies suitable for use in the disclosure can be generated using methods well known in the art. Exemplary PD-1 inhibitors include, but are not limited to: nivolumab (BMS936558), pembrolizumab (MK-3475), pidilizumab (CT-011), AMP-224, AMP-514, BMS-936559, RG7446 (MPDL3280A), MDX-1106 (Medarex Inc.), MSB0010718C, MEDI4736, and HenGrui mAB005 (WO 15/085847). Further PD-1 antibodies and other PD-1 inhibitors include those described in WO 04/056875, WO 06/121168, WO 07/005874, WO 08/156712, WO 09/014708, WO 09/114335, WO 09/101611, WO 10/036959, WO 10/089411, WO 10/027827, WO 10/077634, WO 11/066342, WO 12/145493, WO 13/019906, WO 13/181452, WO 14/022758, WO 14/100079, WO 14/206107, WO 15/036394, WO 15/085847, WO 15/112900, WO 15/112805, WO 15/112800, WO 15/109124, WO 15/061668, WO 15/048520, WO 15/044900, WO 15/036927, WO 15/035606; U. S. Pub. No. 2015/0071910; and U.S. Pat. Nos. 7,488,802; 7,521,051; 7,595,048; 7,722, 868; 7,794, 710; 8,008,449; 8,354,509; 8,383,796; 8,652,465; and 8,735,553; all of which are incorporated herein by reference. Some anti-PD-1 antibodies are commercially available, for example from ABCAM (AB137132), BIOLEGEND (EH12.2H7, RMP 1-14) and AFFYMETRIX EBIOSCIENCE (J105, J116, M1H4).

Exemplary CTLA-4 inhibitors: A CTLA-4 inhibitor suitable for use in the subject methods can be selected from a variety of types of molecules. For example, the CTLA-4 inhibitor can be a biological or chemical compound, such as an organic or inorganic molecule, peptide, peptide mimetic, antibody or an antigen-binding fragment of an antibody. Some exemplary classes of agents suitable for use in the subject methods are detailed in the sections below. A CTLA-4 inhibitor for use in the present disclosure can be any CTLA-4 inhibitor that is known in the art, and can include any entity that, upon administration to a patient, results in inhibition of the CTLA-4 pathway in the patient. A CTLA-4 inhibitor can inhibit CTLA-4 by any biochemical mechanism, including disruption of either one or both of CTLA-4/CD80 and CTLA-4/CD86 interactions.

In some embodiments, the CTLA-4 inhibitor is a molecule that inhibits the binding of CTLA-4 to its ligand binding partners. In a specific aspect, the CTLA-4 ligand binding partners are CD80 and/or CD86. In another embodiment, a CTLA-4 inhibitor is a molecule that inhibits the binding of CD80 to its binding partners. In a specific aspect, a CD80 binding partner is CTLA-4. In another embodiment, the CTLA-4 inhibitor is a molecule that inhibits the binding of CD86 to its binding partners. In a specific aspect, a CD86 binding partner is CTLA-4. The inhibitor may be an antibody, an antigen binding fragment thereof, an immunoadhesin, a fusion protein or oligopeptide.

In some embodiments, the CTLA-4 inhibitor is an anti-CTLA-4 antibody. In some further embodiments, the anti-CTLA-4 antibody is capable of inhibiting binding between CTLA-4 and CD80. In another embodiment, the anti-CTLA-4 antibody is capable of inhibiting binding between CTLA-4 and CD86. In some embodiments, the CTLA-4 inhibitor is an anti-CD80 antibody. In some embodiments, the anti-CD80 antibody is capable of inhibiting binding between CTLA-4 and CD80. In some embodiments, the CTLA-4 inhibitor is an anti-CD86 antibody. In some further embodiments, the anti-CD86 antibody is capable of inhibiting binding between CTLA-4 and CD86. In yet another embodiment, the CTLA-4 inhibitor is tremelimumab or ipilimumab.

Inhibition of the CTLA-4 pathway can enhance the immune response to cancerous cells in a patient. The interaction between CTLA-4 and one of its natural ligands, CD80 and CD86, delivers a negative regulatory signal to T cells. This immune suppression can be reversed by inhibiting the local interaction between CD80 or CD86 and CTLA-4 using a CTLA-4 inhibitor, including, for example, an anti-CTLA-4 Ab, anti-CD80 Ab or an antiCD86 Ab. A CTLA-4 inhibitor may improve or restore antitumor T-cell functions.

Anti-CTLA-4 antibodies suitable for use in the disclosure can be generated using methods well known in the art. Exemplary CTLA-4 inhibitors include but are not limited to tremelimumab and ipilimumab (also known as 10D1 or MDX-010). Further CTLA-4 antibodies and other CTLA-4 inhibitors include those described in WO 98/042752, WO 00/037504, WO 01/014424 and WO 04/035607; U. S. Pub. Nos. 2002/0039581, 2002/086014 and 2005/0201994; U.S. Pat. Nos. 5,811,097; 5,855,887; 5,977,318; 6,051,227; 6,207, 156; 6,682,736; 6,984,720; 7, 109,003; 7, 132,281; 7,605,238; 8, 143,379; 8,318,916; 8,435,516; 8,784,815; and 8,883,984; EP Pat. No. 1212422; Hurwitz et al., PNAS 1998, 95(17): 10067-10071; Camacho et al., J Clin Oncology 2004, 22(145): abstract no. 2505 (antibody CP675206); and Mokyr, et al., Cancer Research 1998, 58:5301-5304; each of which is incorporated herein by reference.

Also provided herein is a pharmaceutical composition comprising a compound of the disclosure or a pharmaceutically acceptable salt thereof and one or more other therapeutic agents. The therapeutic agent may be selected from the classes of agents specified above and from the lists of specific agents described above. In some embodiments, the pharmaceutical composition is suitable for delivery to the lungs. In some embodiments, the pharmaceutical composition is suitable for inhaled or nebulized administration. In some embodiments, the pharmaceutical composition is a dry powder or a liquid composition.

Further, in a method aspect, the disclosure provides a method of treating a disease or disorder in a mammal comprising administering to the mammal a compound of the disclosure or a pharmaceutically acceptable salt thereof and one or more other therapeutic agents.

When used in combination therapy, the agents may be formulated in a single pharmaceutical composition, or the agents may be provided in separate compositions that are administered simultaneously or at separate times, by the same or by different routes of administration. Such compositions can be packaged separately or may be packaged together as a kit. The two or more therapeutic agents in the kit may be administered by the same route of administration or by different routes of administration.

EXAMPLES

The following examples are given for the purpose of illustrating various embodiments of the disclosure and are not meant to limit the present disclosure in any fashion. The present examples, along with the methods and compositions described herein, are presently representative of preferred embodiments, are exemplary, and are not intended as limitations on the scope of the disclosure. Changes therein and other uses which are encompassed within the spirit of the disclosure as defined by the scope of the claims will occur to those skilled in the art.

The following abbreviations have the following meanings unless otherwise indicated and any other abbreviations used herein and not defined have their standard, generally accepted meaning;

AcOH=acetic acid
AcONa=sodium acetate
ACN=acetonitrile
Atm=atmosphere
$Boc_2O$=di-tert-butyl dicarbonate
$(Bpin)_2$=bis(pinacolato)diboron
BrettPhos=2-(dicyclohexylphosphino)-3,6-dimethoxy-2', 4',6'-triisopropyl-1,1'-biphenyl
BrettPhos Pd G4=N-substituted 2-aminobiphenylpalladium methanesulfonate precatalyst
BSA=bovine serum albumin, Fraction V
$Cp*RuCl(PPh_3)_2$=pentamethylcyclopentadienylbis (triphenylphosphine)ruthenium(II) chloride
d=day(s)
DCE=1,2-dichloroethane
DCM=dichloromethane or methylene chloride
DHP=dihydropyran
DIAD=diisopropyl azodicarboxylate
DIBAH=diisobutylaluminium hydride
DIPEA=N,N-diisopropylethylamine
DMA or DMAc=dimethylacetamide
DMAP=4-dimethylaminopyridine
DMEDA=1,2-bis(methylamino)ethane
DMF=N,N-dimethylformamide
DMSO=dimethyl sulfoxide
DPPA=diphenylphosphoryl azide
DTT=dithiothreitol
EDCI=N-ethyl-N'-(3-dimethylaminopropyl) carbodiimide hydrochloride
EDTA=ethylenediaminetetraacetic acid
EGTA=ethylene glycol-bis(β-aminoethyl ether)-N,N,N', N'-tetraacetic acid
EtOH=ethanol
EtOAc or EA=ethyl acetate
g=gram(s)
h=hour(s)
HATU=N,N,N',N'-tetramethyl-O-(7-azabenzotriazol-1-yl)uronium hexafluorophosphate
HEPES=4-(2-hyrdroxyethyl)-1-piperazine ethanesulfonic acid
HOBT=hydroxybenzotriazole
i-PrOBPin=2-isopropyl-4,4,5,5-tetramethyl-1,3,2-dioxaborolane
KHMDS=potassium bis(trimethylsilyl)amide
LDA=lithium diisopropylamide
LiHDMS=hexamethyldisilazane lithium salt
m-CPBA=meta-chloroperoxybenzoic acid
MeCN=acetonitrile
MeOH=methanol
min=minute(s)
MTBE=methyl tert-butyl ether
NBS=N-bromosuccinimide
n-BuLi=n-butyl lithium
$Pd(dppf)Cl_2$=[1,1'-bis(diphenylphosphino)ferrocene]-dichloropalladium(II)
$Pd(OAc)_2$=palladium(II) acetate
$Pd(PPh_3)_4$=tetrakis(triphenylphosphine)palladium(O)
Pd/C=palladium on activated carbon, 10% loading
$Pd_2(dba)_3$=tris(dibenzylideneacetone)dipalladium(O)
PE=petroleum ether PhN₂=benzene diazonium ion
RT, rt, or r.t.=room temperature
RuPhos=2-dicyclohexylphosphino-2',6'-diisopropoxybiphenyl
RuPhos Pd G2=chloro(2-dicyclohexylphosphino-2',6'-diisopropoxy-1,1'-biphenyl) [2-(2'-amino-1,1'-biphenyl)]palladium(II)
RuPhos Pd G4=ligand for Buchwald 4th generation Palladacycle
SEMCl=2-(trimethylsilyl)ethoxymethyl chloride
SiO₂=silicon dioxide or silica
SPhos Pd G3=(2-dicyclohexylphosphino-2',6'-dimethoxybiphenyl) [2-(2'-amino-1,1'-biphenyl)]palladium(II) methanesulfonate
TBAB=tetrabutylammonium bromide
TBSCl=tert-butyldimethylchlorosilane
t-BuOK=potassium tert-butoxide
TEA, Et₃N=triethylamine
TFA=trifluoroacetic acid
THF=tetrahydrofuran
TMS=tetramethylsilane
TosCl=p-toluenesulfonyl chloride
Tris-HCl=tris(hydroxymethyl)aminomethane hydrochloride
Tween-20=polyoxyethylene sorbitan monolaurate
Xantphos=4,5-bis(diphenylphosphino)-9,9-dimethylxanthene
XPhos Pd G4=Buchwald 4th generation palladacycle Unless noted otherwise, all materials, such as reagents, starting materials and solvents, were purchased from commercial suppliers, such as Sigma-Aldrich, Fluka Riedel-de Haën, and the like, and were used without further purification.

Reactions were run under nitrogen atmosphere, unless noted otherwise. The progress of reactions was monitored by thin layer chromatography (TLC), analytical high performance liquid chromatography (anal. HPLC), and mass spectrometry, the details of which are given in specific examples.

Reactions were worked up as described specifically in each preparation; commonly, reaction mixtures were purified by extraction and other purification methods such as temperature- and solvent-dependent crystallization, and precipitation. In addition, reaction mixtures were routinely purified by preparative HPLC, typically using Microsorb C18 and Microsorb BDS column packings and conventional eluents. Progress of reactions was typically monitored by liquid chromatography mass spectrometry (LCMS). Characterization of isomers was typically done by Nuclear Overhauser effect spectroscopy (NOE). Characterization of reaction products was routinely carried out by mass spectrometry and/or ¹H-NMR spectroscopy. For NMR measurement, samples were dissolved in deuterated solvent (CD₃OD, CDCl₃, or DMSO-d₆), and ¹H-NMR spectra were acquired with a Varian Gemini 2000 instrument (400 MHz) under standard observation conditions. Mass spectrometric identification of compounds was typically conducted using an electrospray ionization method (ESMS) with an Applied Biosystems (Foster City, Calif.) model API 150 EX instrument or an Agilent (Palo Alto, Calif.) model 1200 LC/MSD instrument.

Example 1: Synthesis of 6-[3-(6-methyl-2-pyridyl)-1H-pyrazol-4-yl]-N-(2-pyrrolidin-1-ylethyl)-1,5-naphthyridin-3-amine (597)

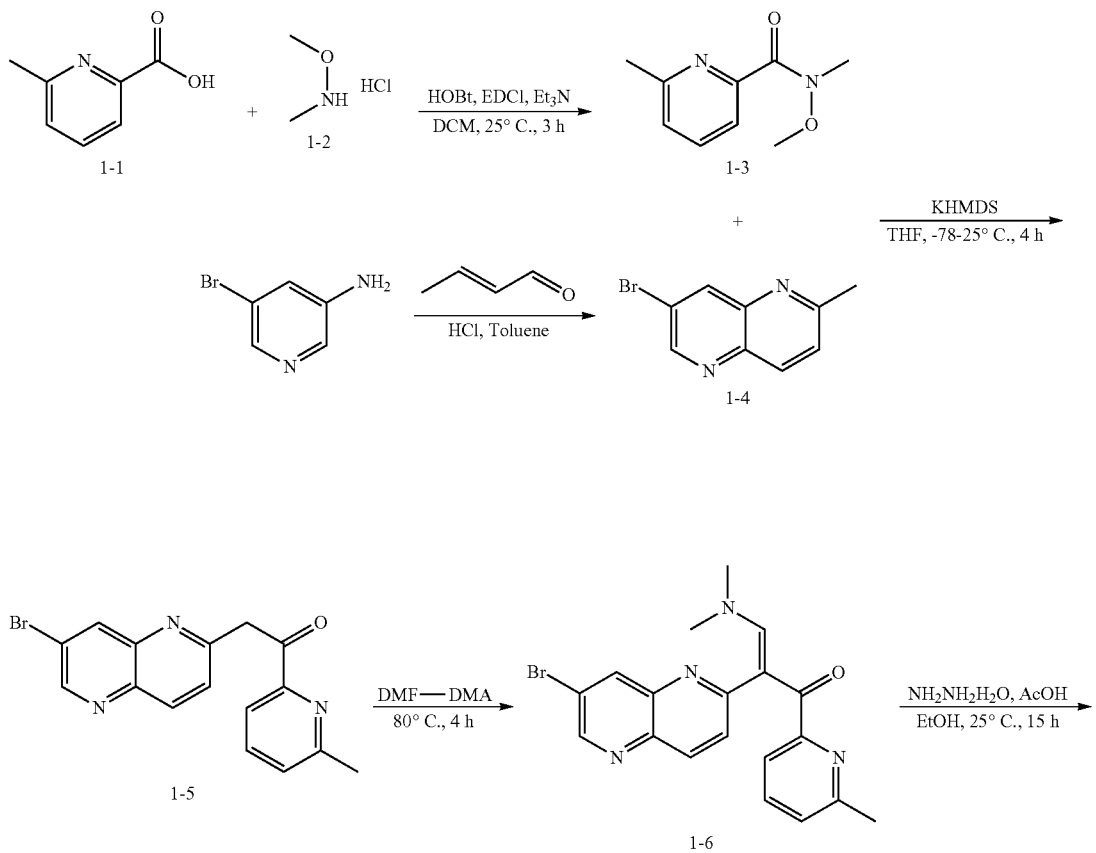

-continued

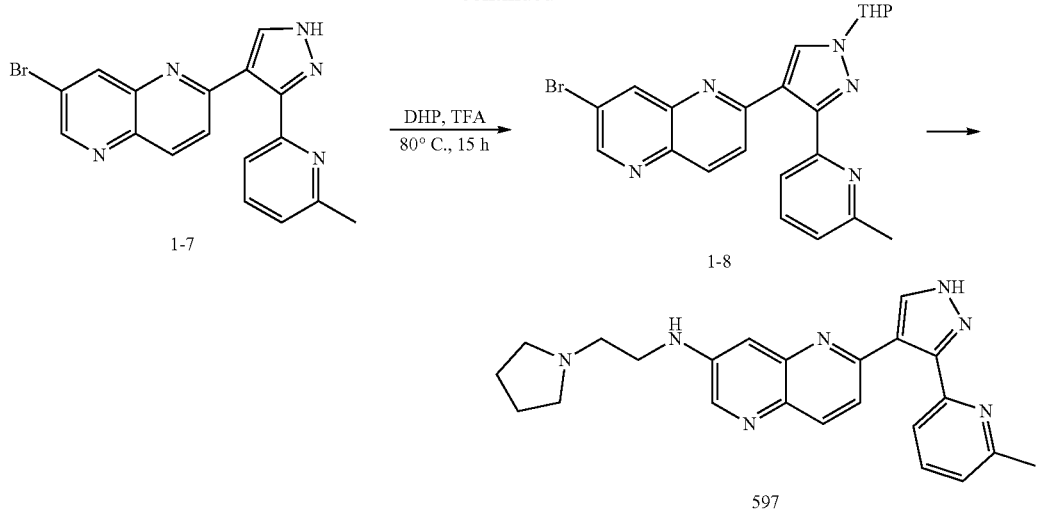

Step A: Preparation of N-methoxy-N,6-dimethylpicolinamide. To a solution of 1-1 (25.0 g, 0.182 mol), 1-2 (26.6 g, 0.273 mol), HOBt (29.5 g, 0.218 mol) and EDCI (41.8 g, 0.218 mol) in DCM (500 mL) was added Et$_3$N (73.7 g, 0.728 mol) dropwise at 25° C. The mixture was then stirred at 25° C. for 3 h. The mixture was concentrated in vacuo. The residue was extracted with EA (3×300 mL). The combined organic layers were washed with brine (2×500 mL) and dried over Na$_2$SO$_4$. After concentration, the crude product was purified via column (DCM:MeOH=20:1-10:1) to give 1-3 (23 g, 70% yield) as yellow oil.

Step B: Preparation of 7-bromo-2-methyl-1,5-napthyridine (1-4). (E)-but-2-enal (30.66 g, 437 mmol) in toluene (90 mL) was added dropwise to 5-bromopyridin-3-amine (18.0 g, 104.0 mmol) in HCl (1.8 L, 6 M) at 100° C. and the mixture was stirred for 1 h at 100° C. A further amount of (E)-but-2-enal (30.66 g, 437 mmol) in toluene (90 mL) was added in one portion and the mixture was stirred at 100° C. for another 4 h. The solvent was removed in vacuum to dryness and the pH of the residue was adjusted to pH 8.0 with NaHCO$_3$ solid. This procedure was repeated four times and the crude products were combined and purified by column chromatography (PE:EA=100:1 to 5:1) to yield title compound 1-4 as a yellow solid (71 g, 95% purity, 15.3% yield). [M+H]$^+$ calcd for C$_9$H$_8$BrN$_2$ 222.99, found 222.9. $^1$H NMR (400 MHz, CDCl$_3$) δ 8.89 (d, J=1.6 Hz, 1H), 8.46 (d, J=1.6 Hz, 1H), 8.23 (d, J=8.8 Hz, 1H), 7.50 (d, J=8.4 Hz, 1H), 2.76 (s, 3H).

Step C: Preparation of 2-(7-bromo-1,5-naphthyridin-2-yl)-1-(6-methylpyridin-2-yl)ethan-1-one (1-5). A solution of 1-4 (23.0 g, 103.6 mmol) and 1-3 (18.7 g, 103.6 mmol) in THF (250 mL) was added KHMDS (155 mL, 155.4 mmol) at −78° C. under N2. The mixture was stirred at −78° C. for 2 h. The mixture was warmed to 25° C. and stirred at 25° C. for 2 h. The mixture was quenched with H$_2$O (800 mL) and extracted with EA (3×1200 mL). The combined organic phase was dried over Na$_2$SO$_4$ and concentrated. The residue was washed with EA (2×100 mL) to afford 1-5 (11 g, 31% yield) as a yellow solid. 15 g compound 1-4 was recovered.

Step D: Preparation of (E)-2-(7-bromo-1,5-naphthyridin-2-yl)-3-(dimethylamino)-1-(6-methylpyridin-2-yl)prop-2-en-1-one (1-6). A solution of 1-5 (11 g, 32.3 mmol) in DMF-DMA (120 mL) was stirred for 4 h at 80° C. to afford 1-6. The mixture was concentrated under vacuum and the residue was used directly in next step (16 g). [M+H]$^+$ calcd for C$_{19}$H$_{17}$BrN$_4$O, 397.06, found 397.1.

Step E: Preparation of 7-bromo-2-(3-(6-methylpyridin-2-yl)-1H-pyrazol-4-yl)-1,5-naphthyridine (1-7). To a solution of 1-6 (16 g, crude) in EtOH (80 mL) was added AcOH (13.8 g, 229.3 mmol) and hydrazine monohydrate (8.9 g, 177.7 mmol). The mixture was stirred for 15 h at 25° C. The mixture was concentrated under vacuum and the residue was purified by column chromatography (PE:EA=1:61:1) to afford 1-7 (6.0 g, 51% yield) as brown solid, which was used directly without further purification.

Step F: Preparation of 7-bromo-2-(3-(6-methylpyridin-2-yl)-1-(tetrahydro-2H-pyran-2-yl)-1H-pyrazol-4-yl)-1,5-naphthyridine (1-8). To a solution of 1-7 (5.0 g, 13.7 mmol) in DHP (40 mL) was added TFA (0.15 mL, catalytic amount). The mixture was stirred for 15 h at 80° C. The mixture was combined with another batch of the same reaction (starting with 1.0 g of 1-7). The reaction was poured into 100 mL H$_2$O. The mixture was extracted with EA (3×50 mL). The organic layer was washed with sat.NaHCO$_3$ (50 mL), dried over with Na$_2$SO$_4$ and concentrated in vacuum to dryness to give crude product. The crude product was purified by column (PE:EA=10:1~1:1) to give 1-8 (5.4 g, 73% yield, 98% purity) as yellow solid. [M+H]$^+$ calcd for C$_{22}$H$_{20}$BrN$_5$O, 450.09, found 450.2.

Step G: Preparation of 6-(3-(6-methylpyridin-2-yl)-1H-pyrazol-4-yl)-N-(2-(pyrrolidin-1-yl)ethyl)-1,5-naphthyridin-3-amine (597). To compound 1-8 (30 mg, 0.067 mmol) and 1-(2-aminoethyl)pyrrolidine (11.4 mg, 0.100 mmol) were added BrettPhos, (7.15 mg, 0.013 mmol), BrettPhos Pd G4 (12.26 mg, 0.013 mmol) and cesium carbonate, (65.1 mg, 0.200 mmol). To the resulting mixture was added dioxane (666 μL) and subsequently sparged with nitrogen for 5 min. The resulting yellow reaction mixture was capped and stirred at 85° C. for 16 h. The reaction was cooled and concentrated in vacuo. The resulting residue was treated with TFA (0.5 mL) and stirred at 50° C. for 1 h. The crude product was concentrated in vacuo and purified by preparative HPLC chromatography using a gradient (7 to 35%) of acetonitrile in water with 0.05% trifluoroacetic acid to yield a TFA salt of the title compound (34 mg). [M+H]$^+$ calcd for C$_{23}$H$_{25}$N$_7$ 40.22 found 400.2. $^1$H NMR (400 MHz, Methanol-d$_4$) δ 8.87 (s, 1H), 8.64 (d, J=2.6 Hz, 1H), 8.55 (d, J=8.8 Hz, 1H), 8.43 (d, J=8.1 Hz, 1H), 8.20-8.08 (m, 2H), 7.65-

7.58 (m, 1H), 7.44 (d, J=2.5 Hz, 1H), 3.76 (t, J=5.9 Hz, 3H), 3.70-3.57 (m, 3H), 3.58-3.51 (m, 1H), 3.06 (s, 3H), 2.17 (s, 2H), 2.08 (s, 3H).

Example 2: Synthesis of 2-(3-(6-methylpyridin-2-yl)-1H-pyrazol-4-yl)-7-(4-(pyrrolidin-1-yl)piperidin-1-yl)-1,5-naphthyridine (335)

1-8 →

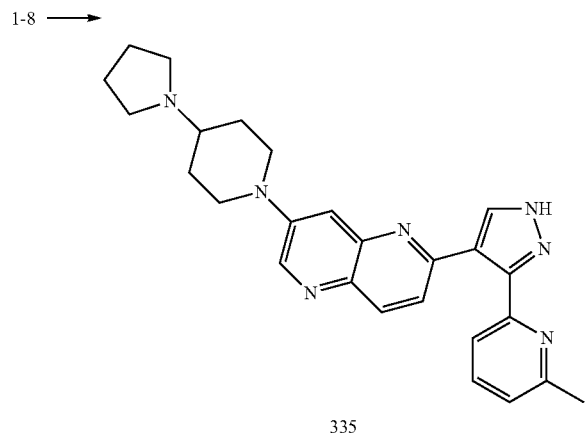

335

To a vial charged with compound 1-8 (60 mg, 0.133 mmol) and 4-(1-pyrrolidinyl)piperidine (31 mg, 0.200 mmol) was added RuPhos, (6.22 mg, 0.013 mmol), RuPhos Pd G2 (10.35 mg, 0.013 mmol) and sodium tert-butoxide, (38.4 mg, 0.400 mmol). To the resulting mixture was added dioxane (700 μL) and subsequently sparged with nitrogen for 5 min. The resulting yellow reaction mixture was capped stirred at 105° C. for 16 h. The reaction was cooled and then concentrated in vacuo. The resulting residue was treated with 1 mL of TFA and stirred at 55° C. for 1 h. The crude product was concentrated in vacuo, and purified by preparative HPLC chromatography using a gradient (13 to 27%) of acetonitrile in water with 0.05% trifluoroacetic acid to yield a TFA salt of the title compound (20 mg). [M+H]+ calcd for $C_{26}H_{29}N_7$ 440.25 found 440.3.

Example 3: Synthesis of 2-(3-(6-Methylpyridin-2-yl)-1H-pyrazol-4-yl)-7-(5,6,7,8-tetrahydroimidazo[1,2-a]pyrazin-2-yl)-1,5-naphthyridine (75)

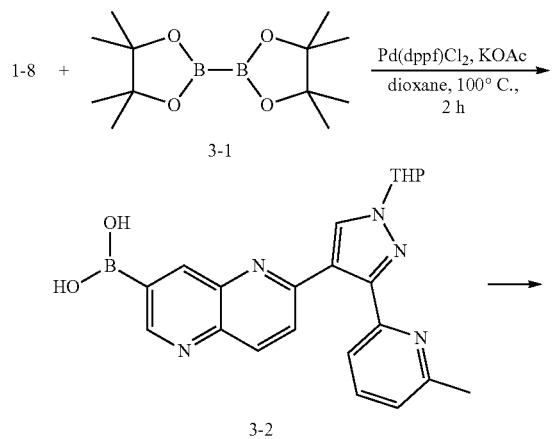

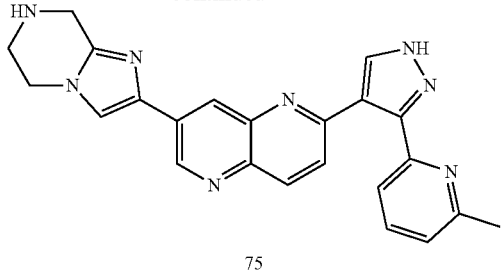

75

Step A: Preparation of (6-(3-(6-methylpyridin-2-yl)-1-(tetrahydro-2H-pyran-2-yl)-1H-pyrazol-4-yl)-1,5-naphthyridin-3-yl)boronic acid (3-2). To a solution of 1-8 (5×500 mg, 5×1.11 mmol), 3-1 (5×423 mg, 5×1.67 mmol) and KOAc (5×327 mg, 5×3.33 mmol) in dioxane (5×25 mL) was added Pd(dppf)Cl₂ (5×81 mg, 5×0.111 mmol). The mixture was stirred at 100° C. for 2 h under N₂. The mixture was poured into H₂O (250 mL) and extracted with EA (4×100 mL). The organic layer was concentrated in vacuum to dryness to give crude product. The crude product was purified by prep-HPLC (Water with 0.05% NH₃H₂O/ACN 5-25%, column (Gemini 150×25, 5 μm), 100 mL/min) to give 3-2 (1.2 g, 52% yield, 98% purity) as a yellow solid. [M+H]+ calcd for $C_{22}H_{22}BN_5O_3$ 416.18, found 416.4.

Step B: Preparation of 2-(3-(6-methylpyridin-2-yl)-1H-pyrazol-4-yl)-7-(5,6,7,8-tetrahydroimidazo[1,2-a]pyrazin-2-yl)-1,5-naphthyridine (75). To a vial containing compound 3-2 (70 mg, 0.169 mmol) was added tert-butyl 2-bromo-5,6-dihydroimidazo[1,2-a]pyrazine-7(8H)-carboxylate (61.1 mg, 0.202 mmol) followed by potassium phosphate tribasic (107 mg, 0.506 mmol), Xphos Pd G4 (14.51 mg, 0.017 mmol), and Xphos (8.04 mg, 0.017 mmol). The resulting mixture was purged with nitrogen before degassed water (337 μL) and 1,4-dioxane (337 μL) was added. The vial was capped and stirred at 105° C. for 1.5 h. The reaction was then cooled, filtered through a plug of celite, washed with THF (7 mL) and concentrated in vacuo. The resulting residue was treated with 1.2 mL of TFA and stirred at 55° C. for 1 h. The crude product was concentrated in vacuo and purified by preparative HPLC chromatography using a gradient (10 to 40%) of acetonitrile in water with 0.05% trifluoroacetic acid to yield a TFA salt of the title compound (41.3 mg). [M+H]+ calcd for $C_{23}H_{20}N_8$ 409.18 found 409.3.

Example 4: Synthesis of 2-(2-(6-Methylpyridin-2-yl)-4,5,6,7-tetrahydropyrazolo[1,5-a]pyrazin-3-yl)-7-(1H-pyrazol-4-yl)-1,5-naphthyridine (115)

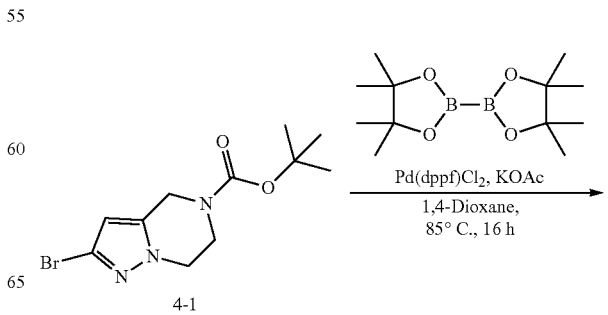

4-1

625
-continued
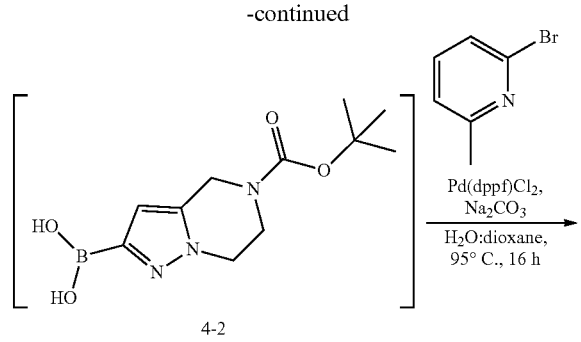
4-2
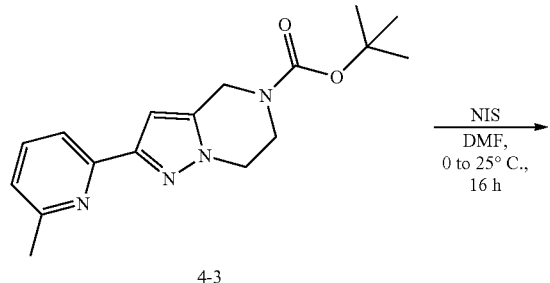
4-3
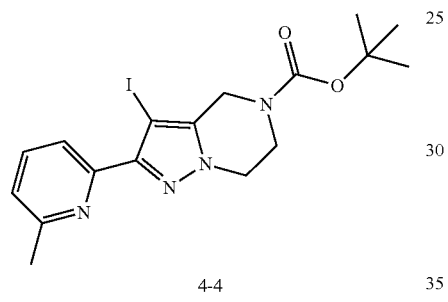
4-4
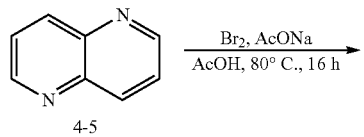
4-5
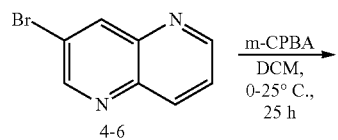
4-6
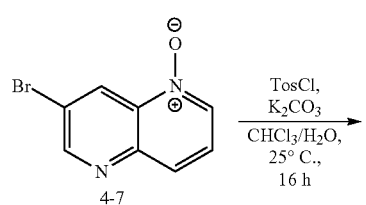
4-7
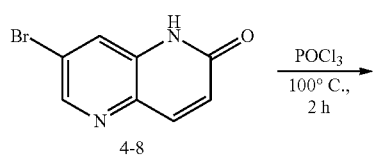
4-8
626
-continued
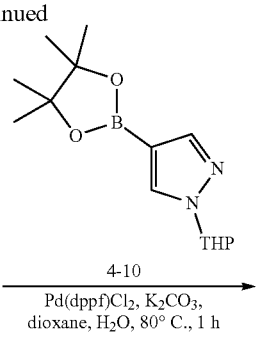
4-10
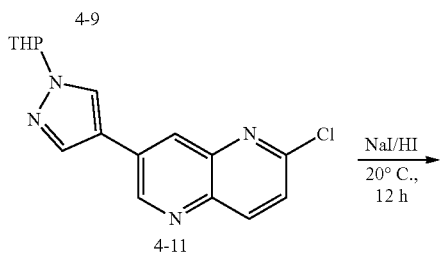
4-11
4-12
4-13
4-14
4-4 + 4-14
115
Step A: Preparation of (5-(tert-butoxycarbonyl)-4,5,6,7-tetrahydropyrazolo[1,5-a]pyrazin-2-yl)boronic acid and tert-butyl 2-(6-methylpyridin-2-yl)-6,7-dihydropyrazolo[1,5-a]pyrazine-5(4H)-carboxylate (4-3). A vial of tert-butyl 2-bromo-6,7-dihydropyrazolo[1,5-a]pyrazine-5(4H)-carboxylate 4-1 (300 mg, 0.993 mmol), potassium acetate (292 mg, 2.98 mmol), bis(pinacolato)diboron (504 mg, 1.986 mmol), and Pd(dppf)Cl$_2$ (145 mg, 0.199 mmol) in 1,4-dioxane (4.7 mL) was sparged with N$_2$ for 10 min before heating to 100° C. 16 h. The reaction was cooled and 4-2 used in the next step as a 0.21 M solution. [M+H]$^+$ calcd for C$_{11}$H$_{18}$BN$_3$O$_4$ 268.14, found 268.0. A vial of 2-bromo-6-methyl-pyridine (0.226 mL, 1.986 mmol), 4-2 in dioxane (4.7 mL, 0.993 mmol Pd(dppf)Cl$_2$ (0.145 g, 0.199 mmol), and sodium carbonate (0.316 g, 2.98 mmol) in water (1.8 mL) was sparged with N$_2$ for 10 min before heating to 100° C. for 16 h. The reaction mixture was filtered through a pad of celite and concentrated in vacuum. The residue was purified via normal phase chromatography (0 to 100% EA in hexanes) yielding 4-3 (152 mg, 49% yield) as a brown solid. [M+H]$^+$ calcd for C$_{17}$H$_{22}$N$_4$O$_2$ 315.17, found 315.0.

Step B: Preparation of tert-butyl 3-iodo-2-(6-methylpyridin-2-yl)-6,7-dihydropyrazolo[1,5-a]pyrazine-5(4H)-carboxylate (4-4). A vial of 4-3 (41 mg, 0.130 mmol) in DMF (195 µL) was cooled to 0° C. and NIS (58.7 mg, 0.261 mmol) was added. After 5 min, the mixture was then heated to 90° C. for 16 h. The reaction mixture was concentrated onto a pad of silica and purified via normal phase chromatography (0 to 20% of MeOH in DCM) to afford 4-4 (29.8 mg, 51.9% yield) as a yellow solid. [M+H]$^+$ calcd for C$_{17}$H$_{21}$IN$_4$O$_2$ 441.07, found 441.0.

Step C: Preparation of 3-bromo-1,5-naphthyridine (4-6). A mixture of 4-5 (44.0 g, 338 mmol) and AcONa (55.4 g, 676 mmol) in AcOH (350 mL) was added dropwise a solution of Br$_2$ (59.2 g, 372 mmol) in AcOH (150 mL) at 80° C. The mixture was stirred for 16 h at 80° C. The mixture was concentrated to remove AcOH, then diluted with water (100 mL) slowly, neutralized with solid Na$_2$CO$_3$ to pH 7, extracted with EA (3×400 mL). The combined organic phase was washed with brine (300 mL), dried with anhydrous Na$_2$SO$_4$, and concentrated in vacuum. The residue was purified by silica gel column (PE:EA=100:1-10:1) to obtain 4-6 (30.0 g, 42% yield) as yellow solid.

Step D: Preparation of 7-bromo-1,5-naphthyridine 1-oxide (4-7). A solution of 4-6 (30.0 g, 144 mmol) in DCM (400 mL) was added m-CPBA (35.0 g, 172 mmol) in portions at 0° C. The mixture was stirred for 25 h at 25° C. The reaction mixture was washed with saturated Na$_2$SO$_3$ (200 mL) and saturated NaHCO$_3$ (300 mL) sequentially, and then washed with brine (300 mL), dried over Na$_2$SO$_4$ and filtered, and concentrated in vacuum. The residue was purified by trituration from EA (200 mL) to afford 4-7 (18.0 g, 56% yield) as a yellow solid. [M+H]$^+$ calcd for C$_8$H$_5$BrN$_2$O, 224.96, found 225.0.

Step E: Preparation of 7-bromo-1,5-naphthyridin-2(1H)-one (4-8).

To a mixture of 4-7 (13.0 g, 57.8 mmol), TosCl (13.2 g, 69.4 mmol) in CHCl$_3$ (130 mL) was added K$_2$CO$_3$ (23.9 g, 173 mmol) in H$_2$O (43 mL) dropwise. The mixture was stirred for 16 h at 25° C. The reaction mixture was diluted with water (200 mL) and filtered. The filter cake was washed with water (200 mL) and dried to afford 4-8 (15.0 g, 83% purity) as a white solid.

Step F: Preparation of 7-bromo-2-chloro-1,5-naphthyridine (4-9). A solution of 4-8 (12.0 g, 53.3 mmol) in POCl$_3$ (220.0 g) was stirred for 2 h at 100° C. The reaction mixture was concentrated in vacuum. The reaction mixture was quenched with H$_2$O (200 mL), basified with 3.0 M NaOH to pH 8. The cake was washed with H$_2$O (100 mL). The residue was dried in vacuum to afford 4-9 (13.0 g, 80% yield, 91% purity) as a gray solid. [M+H]$^+$ calcd for C$_8$H$_4$BrClN$_2$ 242.92, found 242.9.

Step G: Preparation of 2-chloro-7-(1-(tetrahydro-2H-pyran-2-yl)-1H-pyrazol-4-yl)-1,5-naphthyridine (4-11). To a mixture of 4-9 (9.0 g, 37.0 mmol), 4-10 (10.3 g, 37.0 mmol), K$_2$CO$_3$ (15.3 g, 111 mmol), Pd(dppf)Cl$_2$ (2.7 g, 3.70 mmol) in dioxane (150 mL) and H$_2$O (15 mL) was stirred under N$_2$ for 1 h at 80° C. The reaction mixture was purified by column (EA:PE=1:5 to 1:1) to afford 4-11 (5.7 g, 50% yield) as a yellow solid.

Step H: Preparation of 2-iodo-7-(1H-pyrazol-4-yl)-1,5-naphthyridine (4-12). To a mixture of 4-11 (5.0 g, 15.9 mmol), NaI (14.3 g, 95.4 mmol) in HI (100 mL) was stirred for 12 h at 20° C. The reaction mixture was basified with solid NaHCO$_3$ to pH 8, extracted with EA (3×200 mL). The organic layer was washed with Na$_2$SO$_3$ (100 mL), dried over Na$_2$SO$_4$, filtered. The filtrate was concentrated in vacuum to afford 4-12 (3.5 g, 70% yield) as a yellow solid.

Step I: Preparation of tert-butyl 4-(6-iodo-1,5-naphthyridin-3-yl)-1H-pyrazole-1-carboxylate (4-13). A mixture of 4-12 (1.0 g, 3.11 mmol), Boc$_2$O (1.4 g, 6.22 mmol), DMAP (189 mg, 1.55 mmol) in DCM (20 mL) was stirred for 2 h at 20° C. The reaction mixture was concentrated in vacuum. The residue was purified by column (EA:PE=1:5 to 1:1) to afford 4-13 (1.0 g, 76% yield, 95% yield) as a white solid. [M+H]$^+$ calcd for C$_{16}$H$_{15}$IN$_4$O$_2$ 423.02, found 422.9.

Step J: Preparation of tert-butyl 4-(6-(trimethylstannyl)-1,5-naphthyridin-3-yl)-1H-pyrazole-1-carboxylate (4-14). A solution of 4-13 (850 mg, 2.01 mmol), Sn$_2$Me$_6$ (3.4 g, 10.2 mmol), Pd(PPh$_3$)$_2$Cl$_2$ (142 mg, 0.201 mmol) in dioxane (10.0 mL) was stirred at 80° C. for 6 h under N$_2$. The reaction mixture was concentrated in vacuum. The residue was purified by preparative HPLC using a gradient (50 to 80%) of acetonitrile in water with 0.05% ammonia hydroxide to afford 4-14 (450 mg, 38% yield, 95% purity) as a white solid. [M+H]$^+$ calcd for C$_{19}$H$_{24}$N$_4$O$_2$Sn, 461.09, found 461.2.

Step K: Preparation of 2-(2-(6-methylpyridin-2-yl)-4,5,6,7-tetrahydropyrazolo[1,5-a]pyrazin-3-yl)-7-(1H-pyrazol-4-yl)-1,5-naphthyridine (115). A vial of 4-14 (24.06 mg, 0.052 mmol), 4-4 (30 mg, 0.068 mmol), and tetrakis(triphenylphosphine) palladium (3.03 mg, 2.62 µmol) in dioxane (524 µL) was sparged with N$_2$ for 10 min before allowing to stir for 1 h at 25° C. The reaction was then heated to 100° C. for 16 h. SilaMetS® Cysteine (0.052 mmol) was added to the reaction mixture and allowed to stir for 2 h at 25° C. The reaction mixture was filtered through a pad of celite and concentrated in vacuum. TFA (300 µL) was added to the residue and heated to 50° C. for 1 h. TFA was removed in vacuum and the residue was purified by preparative HPLC chromatography using a gradient (2 to 50%) of acetonitrile in water with 0.05% trifluoroacetic acid to yield a TFA salt of the title compound (5.8 mg). [M+H]$^+$ calcd for C$_{23}$H$_{20}$N$_8$ 409.18, found 409.2.

Example 5: Synthesis of 2-(6-chloro-2-(6-methylpyridin-2-yl)pyrazolo[1,5-a]pyridin-3-yl)-1,5-naphthyridine (5-1)

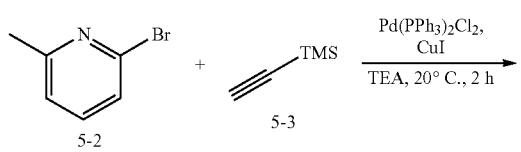

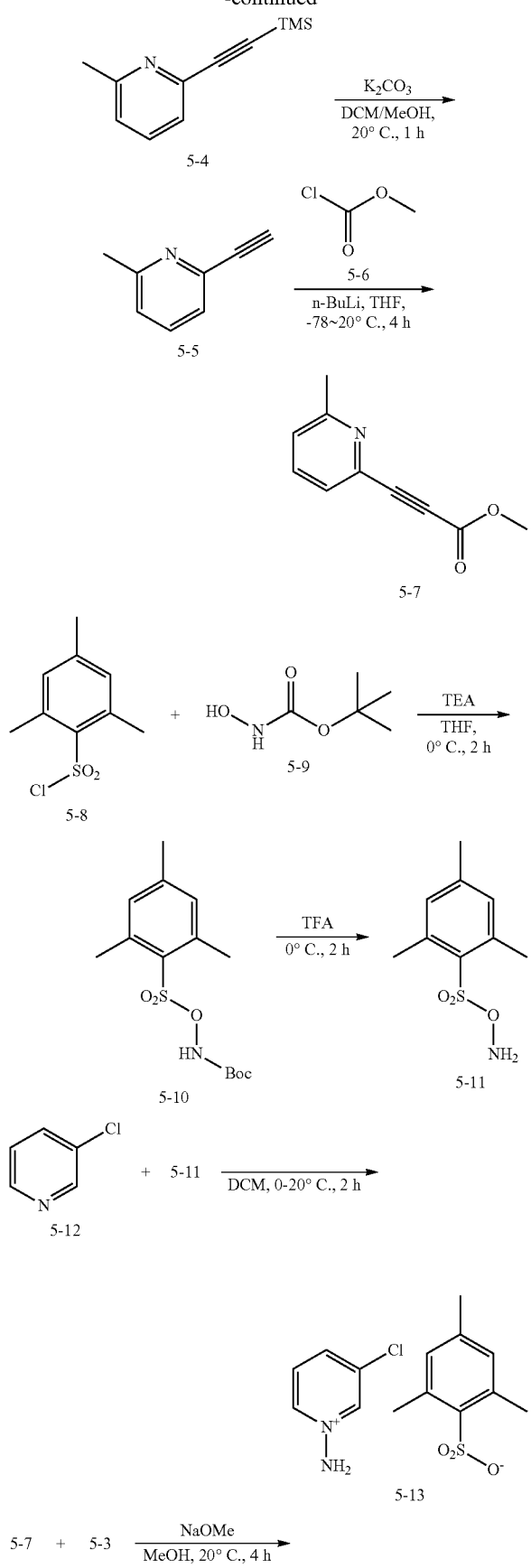
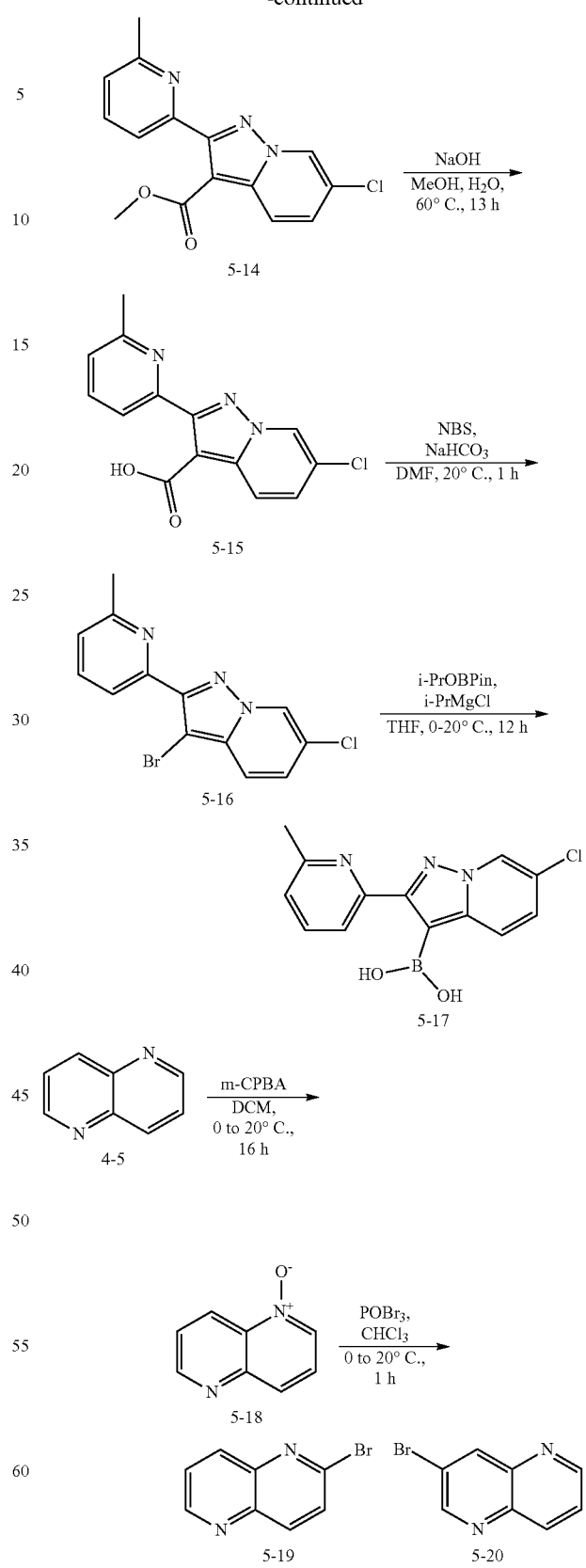

-continued

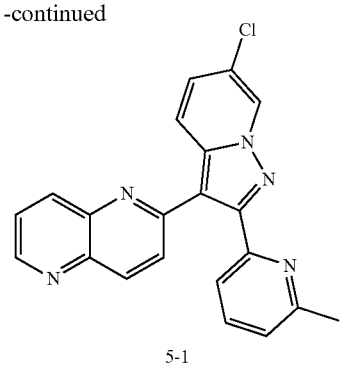

5-1

Step A: Preparation of 2-methyl-6-((trimethylsilyl)ethynyl)pyridine (5-4). A solution of 5-2 (100.0 g, 582 mmol), 5-3 (114.2 g, 1162 mmol), Pd(PPh$_3$)$_2$Cl$_2$ (10.0 g, 14.6 mmol) and CuI (11.0 g, 58.2 mmol) in TEA (1000 mL) was stirred at 20° C. for 2 h. The reaction mixture was filtered through celite. The filtrate was concentrated in vacuum to afford crude 5-4 (120.0 g, 75% purity) as brown oil, which was used for next step without further purification. [M+H]$^+$ calcd for C$_{11}$H$_{15}$NSi 190.10, found 190.0.

Step B: Preparation of 2-ethynyl-6-methylpyridine (5-5). A solution of 5-4 (120 g, 476 mmol), K$_2$CO$_3$ (197 g, 1428 mmol) in DCM (800 mL) and MeOH (400 mL) was stirred at 20° C. for 1 h. The reaction mixture was concentrated in vacuum. The residue was diluted with H$_2$O (300 mL), extracted with EA (3×500 mL). The organic layer was washed with brine (200 mL), dried over Na$_2$SO$_4$, filtered, and concentrated in vacuum. The residue was purified by column (EA:PE=1:20 to 1:10) to afford 5-5 (36.0 g, 53% yield, via two steps) as yellow oil.

Step C: Preparation of methyl 3-(6-methylpyridin-2-yl)propiolate (5-7). To a solution of 5-5 (36.0 g, 290 mmol) in THF (500 mL) was added n-BuLi (128.0 mL, 319 mmol) at −78° C. The reaction mixture was stirred at this temperature for 1 h. Then added 5-6 (134.7 g, 1425 mmol) at −78° C. The reaction was warmed to 20° C. and stirred at this temperature for 3 h. The reaction mixture was quenched with H$_2$O (500 mL), extracted with EA (500 mL×3). The organic layer was washed with brine (300 mL×3), dried over Na$_2$SO$_4$, filtered, and concentrated in vacuum. The residue was purified by column (EA/PE=1/50 to 1/5) to afford 5-7 (38.7 g, 72% yield) as a yellow solid.

Step D: Preparation of tert-butyl ((mesitylsulfonyl)oxy)carbamate (5-11). To a mixture of 5-8 (80.0 g, 367 mmol), 5-9 (53.7 g, 404 mmol) in THF (800 mL) was added TEA (44.4 g, 440 mmol) at 0° C. The reaction mixture was stirred at 0° C. for 2 h. The reaction mixture was concentrated in vacuum, diluted with H$_2$O (500 mL), extracted with DCM (500 mL×3). The organic layer was washed with brine (500 mL), dried over Na$_2$SO$_4$, filtered. The filtrate was concentrated in vacuum to afford 5-10 (110.0 g, 95% yield) as a yellow solid.

Step E: Preparation of O-(mesitylsulfonyl)hydroxylamine (5-11). To a solution of TFA (400 mL) was added 5-10 (110.0 g, 360 mmol) at 0° C. The reaction mixture was stirred at 0° C. for 2 h. The reaction mixture was poured into ice water (2 L). The precipitation was filtered, washed with H$_2$O (200 mL×6) to pH=7. The cake was diluted with DCM (500 mL), dried over MgSO$_4$, filtered. Filtrate 5-11 was used for next step (500 mL, 0.72 M in DCM) directly.

Step F: Preparation of 1-amino-3-chloropyridin-1-ium 2,4,6-trimethylbenzenesulfonate (5-13). To a solution of 5-11 (500 mL, 0.72 M in DCM) was added 5-12 (25.0 g, 221.2 mmol) in DCM (200 mL) at 0° C. The reaction mixture was stirred at 20° C. for 2 h. The reaction mixture was added PE (2 L). The precipitation was filtered; the cake was dried in vacuum to afford 5-13 (35.0 g, 81% yield) as a white solid.

Step G: Preparation of methyl 6-chloro-2-(6-methylpyridin-2-yl)pyrazolo[1,5-a]pyridine-3-carboxylate (5-14). To a solution of 5-7 (15.0 g, 85.7 mmol), 5-13 (31.0 g, 94.3 mmol) in MeOH (200 mL) was added NaOMe (9.3 g, 171.4 mmol). The reaction mixture was stirred at 20° C. for 4 h. The reaction mixture was concentrated in vacuum. The residue was purified by column (EA/PE=1/10 to 1/3) to afford 5-14 (3.0 g, 12% yield) as a yellow solid. [M+H]$^+$ calcd for C$_{15}$H$_{12}$ClN$_3$O$_2$ 302.06, found 302.0.

Step H: Preparation of 6-chloro-2-(6-methylpyridin-2-yl)pyrazolo[1,5-a]pyridine-3-carboxylic acid (5-15). To a solution of 5-14 (3.0 g, 9.97 mmol) in MeOH (30 mL) was added NaOH (2.0 g, 49.85 mmol) in H$_2$O (30 mL). The reaction mixture was stirred at 60° C. for 13 h. The reaction mixture was concentrated in vacuum. The residue was diluted with H$_2$O (10 mL), acidized with HOAc to pH=6, Extracted with DCM (30 mL×3). The organic layer was washed with brine (50 mL), dried over Na$_2$SO$_4$, filtered. The filtrate was concentrated in vacuum to afford 5-15 (2.4 g, 85% yield, 90% purity) as a yellow solid. [M+H]$^+$ calcd for C$_{14}$H$_{10}$ClN$_3$O$_2$ 288.05, found 288.0.

Step I: Preparation of 3-bromo-6-chloro-2-(6-methylpyridin-2-yl)pyrazolo[1,5-a]pyridine (5-16). To a mixture of 5-15 (2.4 g, 8.36 mmol), NaHCO$_3$ (1.4 g, 16.72 mmol) in DMF (30 mL) was added NBS (1.8 g, 10.03 mmol). The reaction mixture was stirred at 20° C. for 1 h. The reaction mixture was diluted with H$_2$O (50 mL), extracted with EA (50 mL×3). The organic layer was washed with brine (50 mL×3), dried over Na$_2$SO$_4$, filtered. The filtrate was concentrated in vacuum to afford 5-16 (2.5 g, 93% yield, 86% purity) as a yellow solid. [M+H]$^+$ calcd for C$_{13}$H$_9$BrClN$_3$ 321.97, found 321.9.

Step J: Preparation of (6-chloro-2-(6-methylpyridin-2-yl)pyrazolo[1,5-a]pyridin-3-yl)boronic acid (5-17). To a mixture of 5-16 (300 mg, 0.93 mmol) and i-PrOBPin (1.04 g 5.58 mmol) in THF (16 mL) was dropwise added i-PrMgCl (2.4 mL, 4.66 mmol) at 0° C. under N$_2$. The reaction mixture was stirred at 20° C. for 12 h. The reaction mixture was quenched with saturated aq.NH$_4$Cl (80 mL) and extracted with EA (150 mL×3). The organic layer was washed with brine (150 mL×2), dried over Na$_2$SO$_4$, filtered, and concentrated in vacuum. The residue was purified by preparative HPLC using a gradient (50 to 80%) of acetonitrile in water with 0.05% ammonia hydroxide to afford to afford 5-17 (60 mg, 20% yield, 96% purity) as yellow solid. [M+H]$^+$ calcd for C$_{13}$H$_{11}$BClN$_3$O$_2$ 288.06, found 288.2.

Step K: Preparation of 1,5-naphthyridine 1-oxide (5-18). To a solution of 4-5 (40.0 g, 306 mmol) in DCM (0.8 L) was added m-CPBA (58.4 g, 338 mmol) in several portions at 0° C. After addition, the mixture was stirred at 20° C. for 16 h. The mixture was filtered. The mother filtrate was concentrated to dryness, triturated with PE (2×200 mL) and purified by silica gel column (PE/EA=10/1 to DCM/MeOH=100/1~10/1) to give 5-18 (39.0 g, 84% yield, 99% purity) as white solid. [M+H]$^+$ calcd for C$_8$H$_6$N$_2$O, 147.05, found 147.3.

Step L: Preparation of 2-bromo-1,5-naphthyridine and 3-bromo-1,5-naphthyridine (5-19 and 5-20). To a solution of 5-18 (36 g, 246.3 mmol) in CHCl$_3$ (0.26 L) was dropwise added a solution of POBr$_3$ (84.6 g*3, 295.5 mmol) in CHCl$_3$ (0.18 L) at 0° C. After additions, the mixture was stirred at 0° C. for 30 min and then stirred at 20° C. for another 30 min. The reaction mixture was poured into saturated NaHCO$_3$ (300 mL) in portions. The resulting mixture was extracted with DCM (200 mL*3). The combined organic layers were concentrated in vacuum and purified by silica gel column (PE/EA=100/1~1/1) twice to give 5-19 (13.3 g, 15% yield, 99% purity) as white solid, 5-20 (6.8 g, 87% purity) as white solid and a mixture of 5-19 with 5-20 (3.8 g) as white solid. [M+H]$^+$ calcd for C$_8$H$_5$BrN$_2$ 208.96, found 209.0.

Step M: Preparation of 2-(6-chloro-2-(6-methylpyridin-2-yl)pyrazolo[1,5-a]pyridin-3-yl)-1,5-naphthyridine (5-1). A vial of 5-19 (29.1 mg, 0.139 mmol), 5-17 (20 mg, 0.070 mmol), sodium carbonate (22.12 mg, 0.209 mmol), and Pd(dppf)Cl$_2$ (10.18 mg, 0.014 mmol) in degassed water (116 µL):DMF (232 µL) was heated to 95° C. for 16 h. The reaction mixture was filtered through a pad of celite and concentrated in vacuum. The residue was purified by preparative HPLC chromatography using a gradient (5 to 75%) of acetonitrile in water with 0.05% trifluoroacetic acid to yield a TFA salt of the title compound (10.9 mg). [M+H]$^+$ calcd for C$_{21}$H$_{14}$ClN$_5$ 372.09, found 372.2.

Example 6: Synthesis of 3-(6-methylpyridin-2-yl)-N-(2-morpholinoethyl)-4-(7-(pyridin-4-yl)-1,5-naphthyridin-2-yl)-1H-pyrazol-5-amine (468)

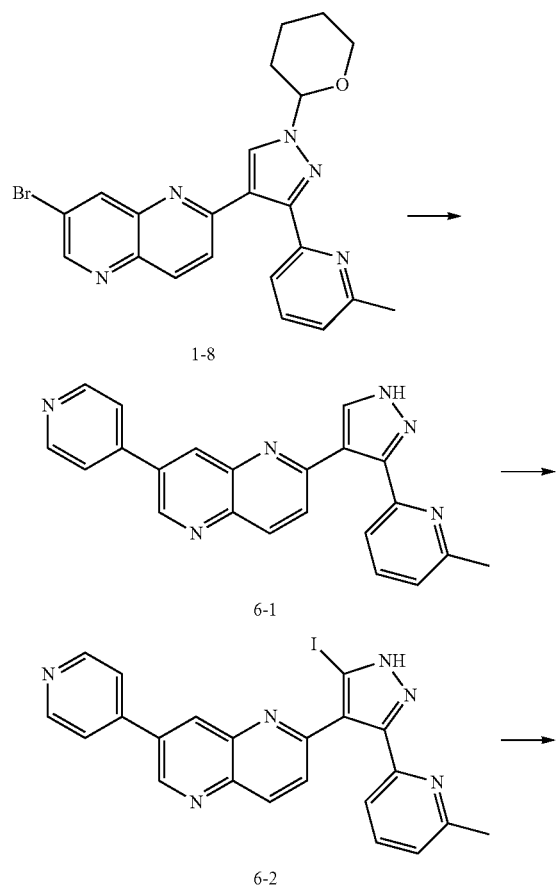

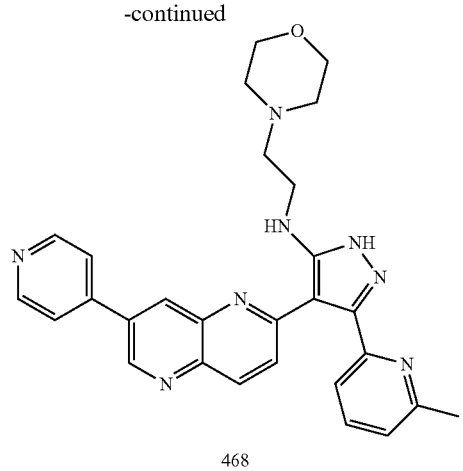

468

Step A: Preparation of intermediate 6-1. To a vial was added 4-pyridineboronic acid (12.0 mg, 0.096 mmol), palladium(II) acetate (1.658 mg, 7.38 µmol), dicyclohexyl(2′,4′,6′-triisopropyl-[1,1′-biphenyl]-2-yl)phosphine (7.04 mg, 0.015 mmol), cesium carbonate (72.2 mg, 0.222 mmol) and the resulting mixture was purged with nitrogen before degassed water (250 µL) was added under air-free conditions followed by a stock solution of 1-8 (35.0 mg, 0.074 mmol) in degassed THF (250 µL). The resulting mixture was capped and stirred at 85° C. for 16 h, then filtered through a pad of celite, washed on a filter with THF (3 mL) and concentrated. The residue was treated with TFA (1 mL) at 55° C. for 1 h. The crude mixture was concentrated and purified by preparative HPLC chromatography using a gradient (7 to 22%) of acetonitrile in water with 0.05% trifluoroacetic acid to yield a 2TFA salt of intermediate 6-1 (18.0 mg, 41% yield) as a white solid. [M+H]$^+$ calcd for C$_{22}$H$_{16}$N$_6$ 365.14, found 365.1.

Step B: Preparation of intermediate 6-2. The solution of 6-1, 2TFA (14 mg, 0.024 mmol) in DMF (350 µL) was treated with n-iodosuccinimide (15 mg, 0.067 mmol) at RT and then stirred at 80° C. overnight. Clear yellow solution turned cloudy yellow upon heating. After 15 h an additional amount of n-iodosuccinimide (25 g) (26 mg, 0.116 mmol) was introduced into reaction mixture and heating was continued for additional 7 hours. The reaction mixture was concentrated and purified by silica gel column chromatography (0 to 15% methanol in DCM gradient) to intermediate 6-2 (13 mg, 80% purity, 90% yield) as a yellow solid. [M+H]$^+$ calcd for C$_{22}$H$_{15}$IN$_6$ 491.04, found 491.0.

Step C: Preparation of 3-(6-methylpyridin-2-yl)-N-(2-morpholinoethyl)-4-(7-(pyridin-4-yl)-1,5-naphthyridin-2-yl)-1H-pyrazol-5-amine (468). To a vial containing 6-2 (13 mg, 0.021 mmol) was added 4-(2-aminoethyl)morpholine (4.18 µL, 0.032 mmol), BrettPhos Pd G4 (1.953 mg, 2.121 µcool), BrettPhos (1.139 mg, 2.121 µmol) and the resulting mixture was purged with nitrogen and treated with LiHMDS, 1M in THF (70 µL, 0.070 mmol) under nitrogen atmosphere. The resulting dark mixture was stirred at 85° C. for 16 h. Following that the reaction mixture was filtered through a plug of celite, washed with THF (2 mL), concentrated and purified by preparative HPLC chromatography using a gradient (2 to 22%) of acetonitrile in water with 0.05% trifluoroacetic acid to yield a TFA salt of the title compound (3.9 mg) as a light-yellow solid. [M+H]$^+$ calcd for C$_{28}$H$_{28}$N$_8$O, 493.24, found 493.2.

Example 7. Synthesis of 6-(5-methoxy-3-(6-methylpyridin-2-yl)-1H-pyrazol-4-yl)-1,5-naphthyridin-3-amine (600)

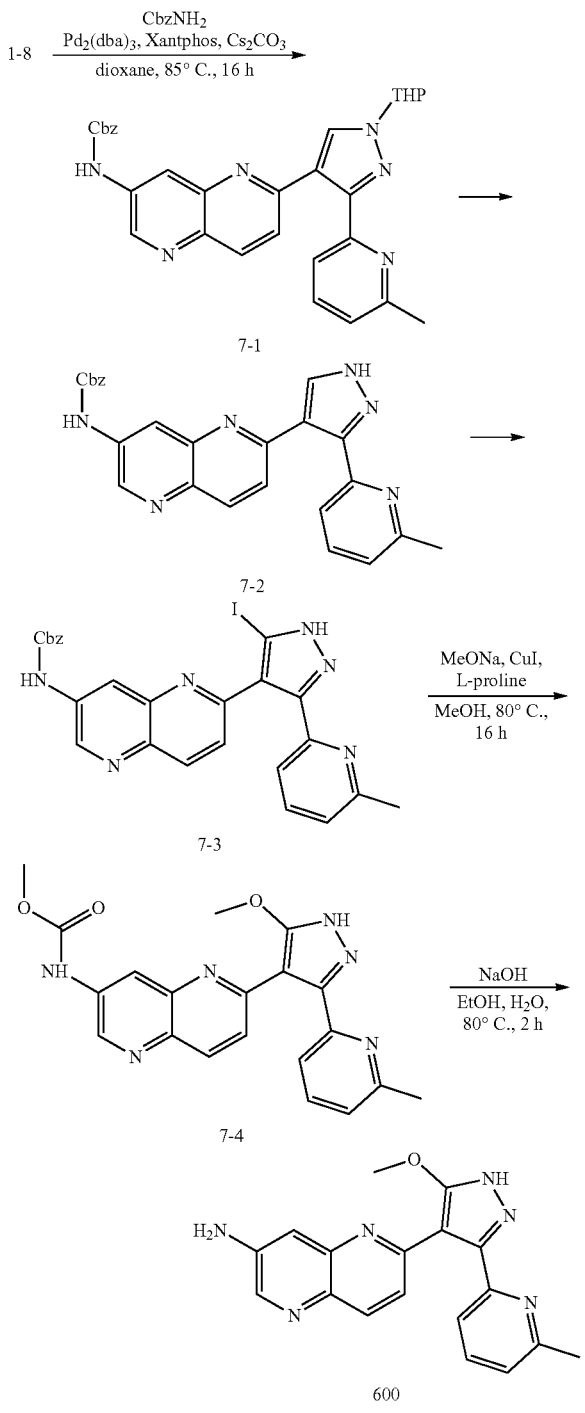

Step A: Preparation of benzyl (6-(3-(6-methylpyridin-2-yl)-1-(tetrahydro-2H-pyran-2-yl)-1H-pyrazol-4-yl)-1,5-naphthyridin-3-yl)carbamate (7-1). To a solution of 1-8 (3.0 g, 6.66 mmol) in dioxane (40 mL) was added benzyl chloroformate (1.51 g, 9.99 mmol), Pd₂(dba)₃ (610 mg, 0.666 mmol), Xantphos (1.15 g, 2.0 mmol), and cesium carbonate (3.25 g, 9.99 mmol). The mixture was degassed under vacuum and purged N₂ 3 times. Then the reaction mixture was heated to 85° C. and stirred for 16 hours. The mixture was poured into water (50 mL) and extracted with EA (50 mL×3). The organic layer was washed with sat. NaCl (50 mL×3) and dried over sodium sulfate. The solvent was removed in vacuum to give crude product which was purified by silica gel column chromatography (PE/EA 6:1 to 1:2 gradient) to yield 7-1 (2.0 g, 60%) as light yellow solid. [M+H]⁺ 521.4.

Step B: Preparation of intermediate 7-2. 7-1 (2.0 g, 3.8 mmol) was added to 1M hydrogen chloride in ethyl acetate (40 mL). The mixture was stirred at 25° C. for 3.0 h. The solvent was removed and the residue was diluted with EA (80 mL). The mixture was washed with sat. aq. sodium bicarbonate (30 mL×3) and brine (40 mL×3). The mixture was dried over sodium sulfate and concentrated in vacuum to dryness to give 7-2 (1.6 g) as yellow solid, which was used directly in the next step without further purification.

Step C: Preparation of benzyl (6-(5-iodo-3-(6-methylpyridin-2-yl)-1H-pyrazol-4-yl)-1,5-naphthyridin-3-yl)carbamate (7-3). To a solution of 7-2 (1.5 g, 3.43 mmol) in DMF (10 mL) was added NIS (3.1 g, 13.75 mmol). The mixture was stirred at 85° C. for 15 h. The reaction was poured into water (80 mL). The mixture was filtrated. The cake was dried and washed with EA (5 mL×2) to give 7-3 (1.0 g) as yellow solid. [M+H]⁺ calcd for $C_{20}H_{19}IN_6O_2$ 563.06, found 563.0.

Step D: Preparation of methyl (6-(5-methoxy-3-(6-methylpyridin-2-yl)-1H-pyrazol-4-yl)-1,5-naphthyridin-3-yl)carbamate (7-4). To a solution of 7-3 (450 mg, 0.8 mmol) in methanol (50 mL) was added sodium methoxide (432 mg, 8.0 mmol), copper(I) iodide (76 mg, 0.4 mmol) and L-proline (92 mg, 0.8 mmol). The reaction was stirred at 80° C. for 16 h. mixture was filtrated. The filtrate was concentrated in vacuum to dryness to give crude product. The crude product was purified by silica gel column chromatography (PE/EA 5:1 to 1:2 gradient) to give 7-4 (220 mg, 31% yield) as yellow solid. [M+H]⁺ calcd for $C_{20}H_{18}N_6O_3$ 391.14, found 391.3.

Step E: Preparation of 6-(5-methoxy-3-(6-methylpyridin-2-yl)-1H-pyrazol-4-yl)-1,5-naphthyridin-3-amine (600). To a mixture of 7-4 (180 mg, 0.46 mmol) in EtOH/H₂O (2 mL/2 mL) was added NaOH (110.0 mg, 2.77 mmol). The reaction mixture was stirred at 80° C. for 2 h. Following that the mixture was concentrated. Trituration with EtOH/H₂O (3 mL/3 mL) yielded the title compound (88 mg) as a yellow solid. [M+H]⁺ calcd for $C_{18}H_{16}N_6O$, 333.14, found 333.1.

Example 8: Synthesis of 7-bromo-2-(5-methoxy-3-(6-methylpyridin-2-yl)-1H-pyrazol-4-yl)-1,5-naphthyridine (42)

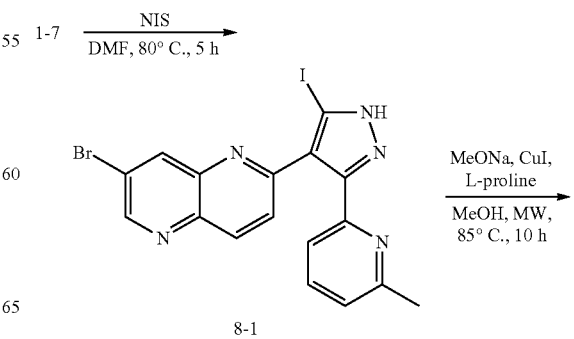

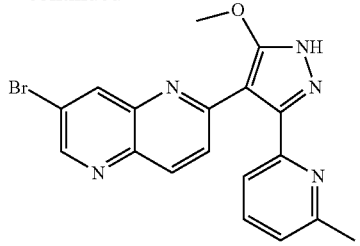

42

Step A: Preparation of 7-bromo-2-(5-iodo-3-(6-methylpyridin-2-yl)-1H-pyrazol-4-yl)-1,5-naphthyridine (8-1). To a solution of 1-7 (3.0 g, 8.19 mmol) in DMF (30 mL) was added NIS (2.8 g, 12.29 mmol). The mixture was stirred at 80° C. for 5 h. Following that the mixture was poured into ice water (100 mL) and then extracted with EA (50 mL×3). The organic layer was washed with brine (50 mL×2), dried over with sodium sulfate and concentrated under vacuum. The solid was triturated with EA (5 mL) and collected by filtration to afford 8-1 (3.0 g, 75% yield) as a yellow solid. [M+H]$^+$ calcd for $C_{17}H_{11}BrIN_5$ 491.92, found 492.1. $^1$H NMR (400 MHz, Methanol-$d_4$) δ 9.04 (s, 1H), 8.67 (d, J=1.9 Hz, 1H), 8.65-8.54 (m, 2H), 8.47 (t, J=7.5 Hz, 1H), 8.27 (d, J=7.5 Hz, 1H), 7.90 (d, J=7.5 Hz, 1H), 4.21 (s, 3H), 3.00 (s, 3H).

Step B: Preparation of 7-bromo-2-(5-methoxy-3-(6-methylpyridin-2-yl)-1H-pyrazol-4-yl)-1,5-naphthyridine (42). To a solution of 8-1 (100 mg×4, 0.20 mmol×4) in MeOH (10 mL×4) was added sodium methoxide (55 mg×4, 1.02 mmol×4), CuI (19 mg×4, 0.10 mmol×4) and L-proline (22 mg×4, 0.20 mmol×4). The mixture was heated under microwave irradiation at 85° C. for 10 h. The solvent was removed under vacuum. The crude product was purified by silica gel column chromatography (PE/EA 5:1 to 1:2 gradient) to give the title compound (42) (400 mg, 25%) as a yellow solid. [M+H]$^+$ calcd for $C_{15}H_{14}BrN_5O$, 396.04, found 396.1.

Example 9: Synthesis of 2-(5-methoxy-3-(6-methylpyridin-2-yl)-1H-pyrazol-4-yl)-7-(piperazin-1-yl)-1,5-naphthyridine (33)

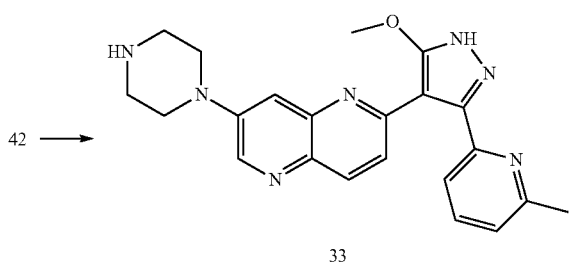 [SMILES: COc1[nH]nc(-c2cccc(C)n2)c1-c1ccc2ncc(N3CCNCC3)cc2n1]

33

To a vial containing 42 (16.19 mg, 0.041 mmol) was added piperazine (14.07 mg, 0.163 mmol), tris(dibenzylideneacetone)dipalladium(O) (3.74 mg, 4.08 µmol), RuPhos (3.81 mg, 8.17 µmol) and sodium tertbutoxide (5.89 mg, 0.061 mmol). The contents of the vial were purged with nitrogen and dioxane (163 µL) was added. The reaction mixture was allowed to sit at room temperature for 10 min and then stirred at 105° C. for 50 min. The dark slurry was filtered through a plug of celite and washed on a filter with THF (3 mL). The combined filtrates were concentrated and purified by preparative HPLC chromatography using a gradient (5 to 45%) of acetonitrile in water with 0.05% trifluoroacetic acid to yield a TFA salt of the title compound (8.8 mg) as a light yellow solid. [M+H]$^+$ calcd for $C_{22}H_{23}N_7O$ 402.20, found 402.1. $^1$H NMR (400 MHz, Methanol-$d_4$) δ 9.06 (d, J=2.6 Hz, 1H), 8.65 (d, J=8.9 Hz, 1H), 8.43 (d, J=8.9 Hz, 1H), 8.02 (t, J=7.8 Hz, 1H), 7.89-7.84 (m, 1H), 7.69 (s, 1H), 7.55 (d, J=7.8 Hz, 1H), 4.17 (s, 3H), 3.82 (t, J=5.2 Hz, 4H), 3.49 (t, J=5.2 Hz, 4H), 2.91 (s, 3H).

Example 10: Synthesis of 2-(5-methoxy-3-(6-methylpyridin-2-yl)-1H-pyrazol-4-yl)-7-(pyridin-3-yl)-1,5-naphthyridine (105)

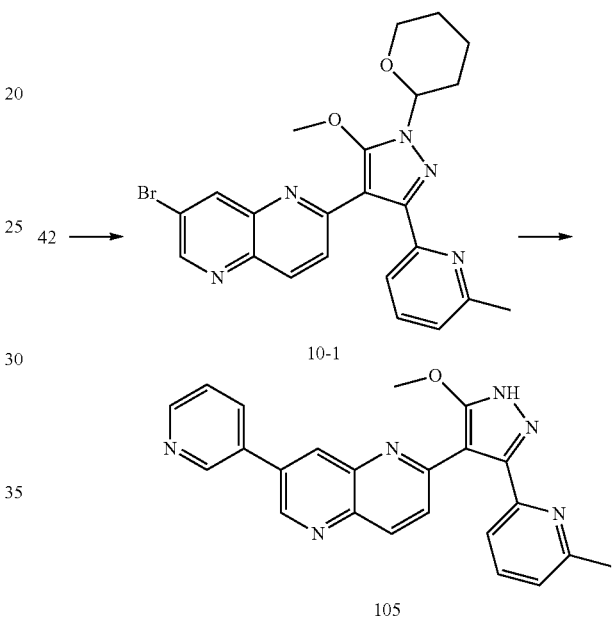

Step A: To a vial containing 42 (100 mg, 0.252 mmol) was added p-toluenesulfonic acid monohydrate (7.20 mg, 0.038 mmol) followed by DMF (1.2 mL). The resulting yellow slurry was treated with 3,4-dihydro-2H-pyran (0.115 mL, 1.262 mmol) and stirred at 85° C. for 18 h. Following that triethylamine (10.55 µL, 0.076 mmol) was added and the resulting mixture was concentrated and purified using silica gel chromatography (0 to 100% EA in hexanes) to yield the desired intermediate 7-bromo-2-(5-methoxy-3-(6-methylpyridin-2-yl)-1-(tetrahydro-2H-pyran-2-yl)-1H-pyrazol-4-yl)-1,5-naphthyridine (10-1) (32 mg, 26% yield) as a white solid. [M+H]$^+$ calcd for $C_{23}H_{22}BrN_5O_2$ 480.10, found 480.0.

Step B: To a vial containing pyridine-3-boronic acid (4.98 mg, 0.031 mmol) was added palladium (II) acetate (0.935 mg, 4.16 µmol), XPhos (3.97 mg, 8.33 µmol) and cesium carbonate (20.35 mg, 0.062 mmol). The content of the vial was purged with nitrogen before solution of 10-1 (10 mg, 0.021 mmol) in dioxane (95 µL) and water (9.46 µL) was added. The mixture was stirred at 105° C. for 3.5 h before being cooled down to RT, filtered through a plug of celite and washed with 2 mL of THF. The combined filtrates were concentrated and the residue was treated with 0.7 mL of TFA at 50 for 1 h. The resulting mixture was concentrated and purified by preparative HPLC chromatography using a gradient (15 to 40%) of acetonitrile in water with 0.05% trifluoroacetic acid to yield a TFA salt of the title compound (5.2 mg) as a light yellow solid. [M+H]+ calcd for C23H18N6O, 395.15, found 395.3.

Example 11: Synthesis of 2-(5-(6-methylpyridin-2-yl)-1H-imidazol-4-yl)-7-(1H-pyrazol-4-yl)-1,5-naphthyridine (644)

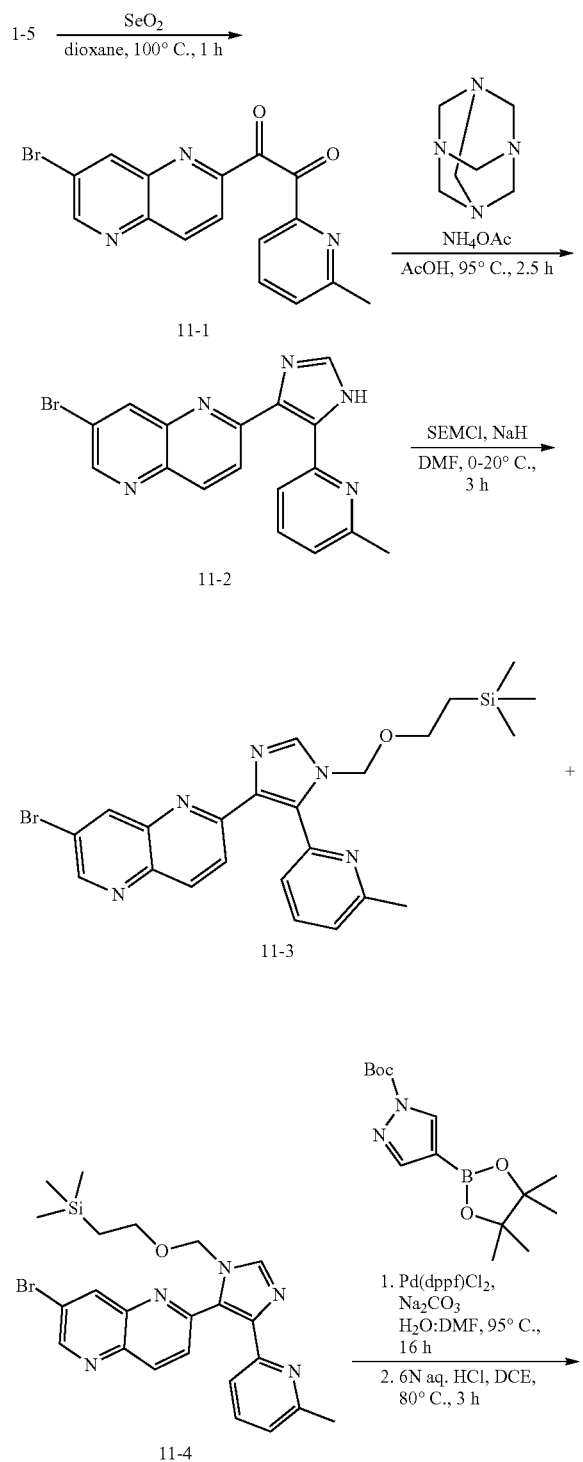

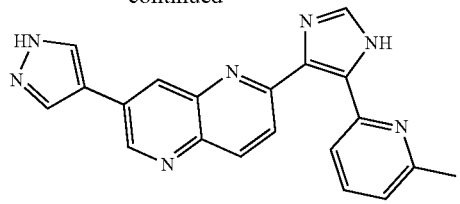

644

Step A: Preparation of 1-(7-bromo-1,5-naphthyridin-2-yl)-2-(6-methylpyridin-2-yl)ethane-1,2-dione (11-1). A solution of 1-5 (7.0 g, 20.5 mmol), SeO2 (6.8 g, 61.5 mmol) in dioxane (100 mL) was stirred at 100° C. for 1 h. The reaction mixture was filtered through a pad of celite. The filtrate was concentrated in vacuum to afford 11-1 (7.0 g, crude) as a yellow solid. [M+H]+ calcd for C16H10BrN3O2 356.00, found 356.1.

Step B: Preparation of 7-bromo-2-(5-(6-methylpyridin-2-yl)-1H-imidazol-4-yl)-1,5-naphthyridine (11-2). A solution of crude 11-1 (7.0 g, 19.7 mmol), hexamine (8.3 g, 59.1 mmol) and NH4OAc (9.1 g, 118 mmol) in AcOH (100 mL) was stirred at 95° C. for 2.5 h. The reaction mixture was concentrated in vacuum and basified with sat. aq NaHCO3 (100 mL) to pH=9. The mixture was extracted with EA (400 mL×3). The combined organic phase was washed with brine (400 mL×2), dried over Na2SO4, filtered, and concentrated under reduced pressure to give a residue. The residue was purified by silica gel column (EA:MeOH=1:0 to 10:1) to afford 11-2 (3.6 g, 39% yield, 74% purity) as yellow solid. [M+H]+ calcd for C17H12BrN5 366.03, found 366.2.

Step C: Preparation of 7-bromo-2-(5-(6-methylpyridin-2-yl)-1-((2-(trimethylsilyl)ethoxy)methyl)-1H-imidazol-4-yl)-1,5-naphthyridine (11-3) and 7-bromo-2-(4-(6-methylpyridin-2-yl)-1-((2-(trimethylsilyl)ethoxy)methyl)-1H-imidazol-5-yl)-1,5-naphthyridine (11-4). To a solution of 11-2 (3.3 g, 9.01 mmol) in DMF (50 mL) was added NaH (469 mg, 11.7 mmol) at 0° C. The reaction mixture was stirred at 0° C. for 1 h. Then the mixture was added SEMCl (1.8 g, 10.8 mmol). The reaction mixture was stirred at 20° C. for 2 h. The reaction mixture was diluted with H2O (100 mL), extracted with EA (200 mL×3). The organic layer was washed with brine (200 mL×2), dried over Na2SO4, filtered, and concentrated in vacuum. The residue was purified by silica gel column (PE:EA=10:1~1:1) to afford mixture of isomers 11-3 and 11-4 (2.0 g, 43% yield, 96% yield) as yellow solid. [M+H]+ calcd for C23H26BrN5OSi 496.11, found 496.3.

Step D: Preparation of 2-(5-(6-methylpyridin-2-yl)-1H-imidazol-4-yl)-7-(1H-pyrazol-4-yl)-1,5-naphthyridine (644). A vial of 1-Boc-pyrazole-4-boronic acid pinacol ester (28.5 mg, 0.097 mmol), 11-3 and 11-4 (40.0 mg, 0.081 mmol), sodium carbonate (34.2 mg, 0.322 mmol), and Pd(dppf)Cl2 (11.8 mg, 0.016 mmol) in degassed water (161 µL):DMF (645 µL) was heated to 95° C. for 16 h. The reaction mixture was filtered through a pad of celite and concentrated in vacuum. The crude material was dissolved in DCE (0.300 mL) and 6 M aq. HCl (0.200 mL) was added. The mixture was heated to 80° C. for 3 h. The reaction mixture was concentrated in vacuum. The residue was purified by preparative HPLC chromatography using a gradient (10 to 95%) of acetonitrile in water with 0.05% trifluoroacetic acid to yield a TFA salt of the title compound (14.3 mg). [M+H]+ calcd for C20H15N7 354.14, found 354.1.

Example 12: Synthesis of N-(2-(4-isopropylpiperazin-1-yl)ethyl)-6-(5-(6-methylpyridin-2-yl)-1H-imidazol-4-yl)-1,5-naphthyridin-3-amine (104)

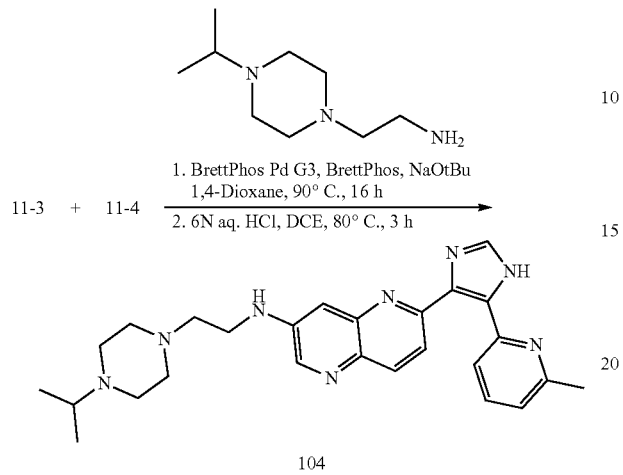

A vial of 11-3 and 11-4 (19.0 mg, 0.038 mmol), 2-(4-isopropyl-piperazin-1-yl)-ethylamine (24.69 mg, 0.144 mmol), sodium tert-butoxide (11.03 mg, 0.115 mmol), BrettPhos (2.05 mg, 3.83 µmol), and BrettPhos Pd G3 (3.47 mg, 3.83 µmol) in degassed 1,4-dioxane (382 µL) was heated to 90° C. for 16 h. The reaction mixture was filtered through a pad of celite and concentrated in vacuum. The crude material was dissolved in DCE (0.300 mL) and 6 M aq. HCl (0.200 mL) was added. The mixture was heated to 80° C. for 3 h. The reaction mixture was concentrated in vacuum. The residue was purified by preparative HPLC chromatography using a gradient (2 to 60%) of acetonitrile in water with 0.05% trifluoroacetic acid to yield a TFA salt of the title compound (7.4 mg). [M+H]$^+$ calcd for $C_{26}H_{32}N_8$ 457.28, found 457.3.

Example 13: Synthesis of 7-(1,4-diazepan-1-yl)-2-(5-(6-methylpyridin-2-yl)-1H imidazol-4-yl)-1,5-naphthyridine (307)

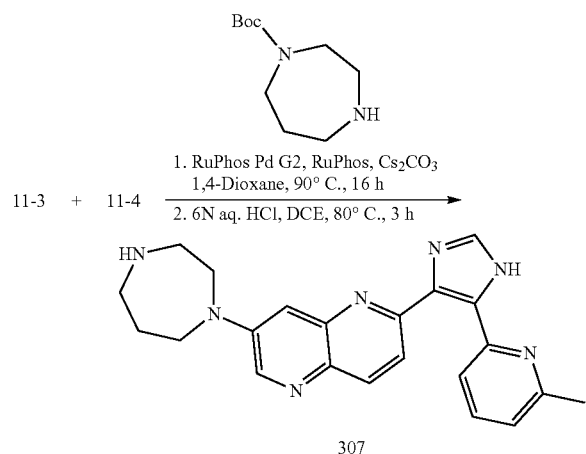

A vial of 11-3 and 11-4 (19 mg, 0.038 mmol), RuPhos (3.57 mg, 7.65 µmol), 1-Boc-hexahydro-1,4-diazepine (30.7 mg, 0.153 mmol), sodium tert-butoxide (11.03 mg, 0.115 mmol), and RuPhos Pd G2 (5.94 mg, 7.65 µmol) in 1,4-dioxane (250 µL) was heated to 90° C. for 16 h. The reaction mixture was filtered through a pad of celite and concentrated in vacuum. The crude material was dissolved in DCE (0.300 mL) and 6 M aq. HCl (0.200 mL) was added. The mixture was heated to 80° C. for 3 h. The reaction mixture was concentrated in vacuum. The residue was purified by preparative HPLC chromatography using a gradient (2 to 60%) of acetonitrile in water with 0.05% trifluoroacetic acid to yield a TFA salt of the title compound (5.7 mg). [M+H]$^+$ calcd for $C_{22}H_{23}N_7$ 386.20, found 386.2.

Example 14: Synthesis of 2-(5-(6-methylpyridin-2-yl)-1H-imidazol-4-yl)-7-(5,6,7,8-tetrahydroimidazo[1,2-a]pyrazin-2-yl)-1,5-naphthyridine (414)

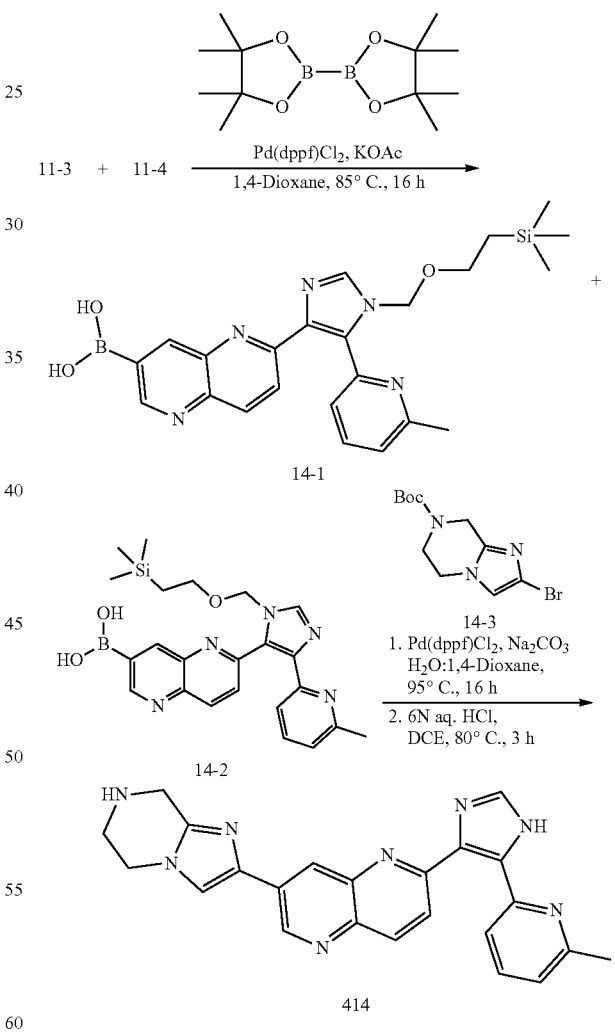

Step A: Preparation of 6-(5-(6-methylpyridin-2-yl)-1-((2-(trimethylsilyl)ethoxy)methyl)-1H-imidazol-4-yl)-1,5-naphthyridin-3-yl)boronic acid and (6-(4-(6-methylpyridin-2-yl)-1-((2-(trimethylsilyl)ethoxy)methyl)-1H-imidazol-5-yl)-1,5-naphthyridin-3-yl)boronic acid. A vial of 11-3 and 11-4 (50 mg, 0.101 mmol), bis(pinacolato)diboron (33.2 mg, 0.131 mmol), Pd(dppf)Cl$_2$ (14.74 mg, 0.020 mmol), and potassium acetate (29.7 mg, 0.302 mmol) in 1,4-dioxane (0.480 mL) was sparged with N$_2$ for 5 min before heating to 85° C. for 16 h. Crude 14-1 and 14-2 were used directly as a 0.21 M solution in dioxane in the next reaction. [M+H]$^+$ calcd for C$_{23}$H$_{28}$BN$_5$O$_3$Si, 462.21, found 462.0.

Step B: Preparation of 2-(5-(6-methylpyridin-2-yl)-1H-imidazol-4-yl)-7-(5,6,7,8-tetrahydroimidazo[1,2-a]pyrazin-2-yl)-1,5-naphthyridine (414). A vial of 14-1 and 14-2 (480 µL, 0.101 mmol, crude, 0.21 M in dioxane), 14-3 (30.5 mg, 0.101 mmol), sodium carbonate (32.1 mg, 0.303 mmol), and Pd(dppf)Cl$_2$ (14.78 mg, 0.020 mol) in water (240 µL) was sparged for 10 min with N$_2$ before heating to 95° C. for 16 h. The reaction mixture was filtered through a pad of celite and concentrated in vacuum. The crude material was dissolved in DCE (0.300 mL) and 6 M aq. HCl (0.200 mL) was added. The mixture was heated to 80° C. for 3 h. The reaction mixture was concentrated in vacuum. The residue was purified by preparative HPLC chromatography using a gradient (5 to 65%) of acetonitrile in water with 0.05% trifluoroacetic acid to yield a TFA salt of the title compound (12.4 mg). [M+H]$^+$ calcd for C$_{23}$H$_{20}$N$_8$ 409.18, found 409.2.

Example 15: Synthesis of N-(5-(4-methylpiperazin-1-yl)pyridin-2-yl)-6-(5-(6-methylpyridin-2-yl)-1H imidazol-4-yl)-1,5-naphthyridin-3-amine (653)

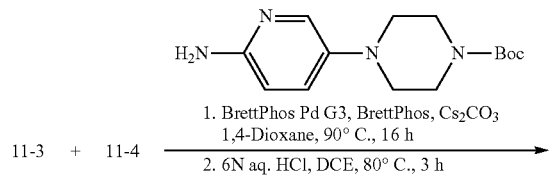

11-3 + 11-4 →
1. BrettPhos Pd G3, BrettPhos, Cs$_2$CO$_3$
1,4-Dioxane, 90° C., 16 h
2. 6N aq. HCl, DCE, 80° C., 3 h

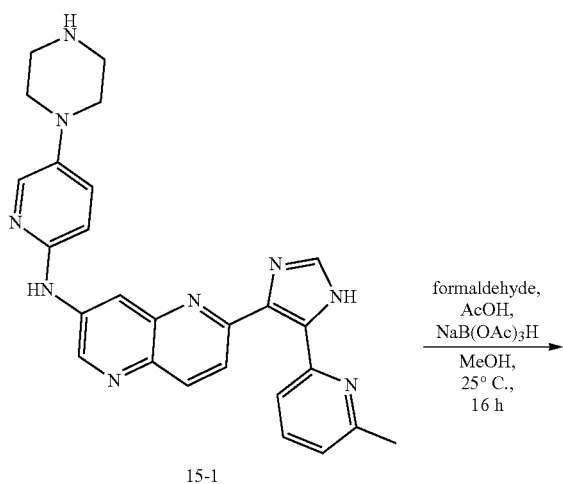

15-1 formaldehyde,
AcOH,
NaB(OAc)$_3$H
MeOH,
25° C.,
16 h

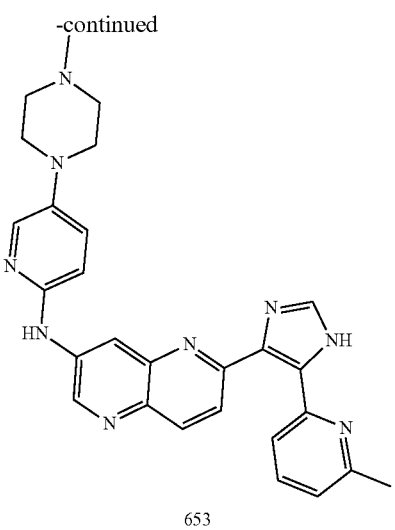

653

Step A: Preparation of 6-(5-(6-methylpyridin-2-yl)-1H imidazol-4-yl)-N-(5-(piperazin-1-yl)pyridin-2-yl)-1,5-naphthyridin-3-amine (15-1). A vial of 11-3 and 11-4 (50.1 mg, 0.101 mmol), tert-butyl 4-(6-aminopyridin-3-yl)piperazine-1-carboxylate (33.7 mg, 0.121 mmol), cesium carbonate (99.0 mg, 0.303 mmol), BrettPhos (10.83 mg, 0.020 mmol), and BrettPhos Pd G4 (18.6 mg, 0.020 mmol) in degassed 1,4-dioxane (673 µL) was heated to 90° C. for 16 h. The reaction mixture was filtered through a pad of celite and concentrated in vacuum. The crude material was dissolved in DCE (0.300 mL) and 6 M aq. HCl (0.200 mL) was added. The mixture was heated to 80° C. for 3 h. The reaction mixture was concentrated in vacuum. The residue was purified by preparative HPLC chromatography using a gradient (10 to 80%) of acetonitrile in water with 0.05% trifluoroacetic acid to yield a TFA salt of 15-1 (44.6 mg). [M+H]$^+$ calcd for C$_{26}$H$_{25}$N$_9$ 464.22, found 464.2.

Step B: Preparation of N-(5-(4-methylpiperazin-1-yl) pyridin-2-yl)-6-(5-(6-methylpyridin-2-yl)-1H imidazol-4-yl)-1,5-naphthyridin-3-amine (653). A vial of 15-1 (10.38 mg, 0.022 mmol), formaldehyde 37 wt. % in H$_2$O (3.33 µL, 0.045 mmol), and AcOH (1.28 µL, 0.022 mmol) in methanol (0.2 mL) was stirred at 25° C. for 1 h before adding sodium triacetoxyborohydride (16.67 mg, 0.079 mmol). The resulting mixture was allowed to stir at 25° C. for 16 h. The reaction was quenched with H$_2$O (0.2 mL) and concentrated in vacuum. The residue was purified by preparative HPLC chromatography using a gradient (5 to 75%) of acetonitrile in water with 0.05% trifluoroacetic acid to yield a TFA salt of the title compound (5.8 mg). [M+H]+ calcd for C$_{27}$H$_{27}$N$_9$ 478.24, found 478.1.

Example 16: Synthesis of N-isopropyl-4-(6-(5-(6-methylpyridin-2-yl)-1H imidazol-4-yl)-1,5-naphthyridin-3-yl)cyclohex-3-en-1-amine (258)

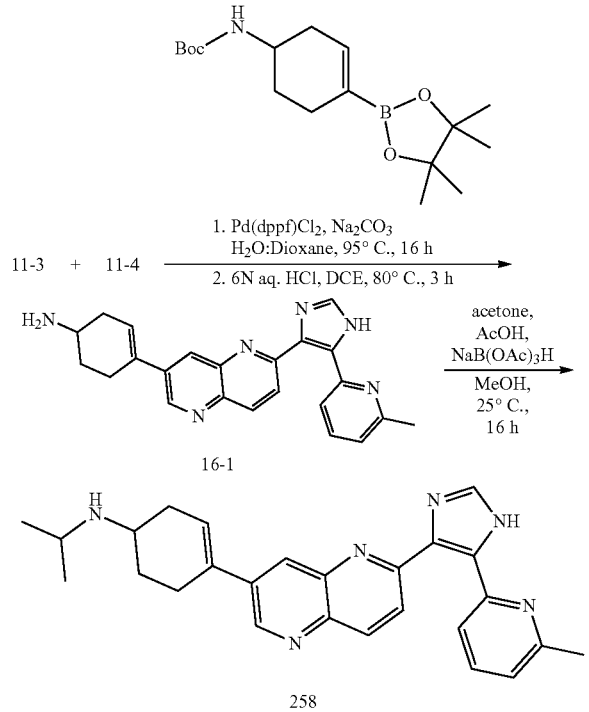

Example 17: Synthesis of 2-(2-(6-methylpyridin-2-yl)imidazo[1,2-a]pyridin-3-yl)-7-(1H-pyrazol-4-yl)-1,5-naphthyridine (469)

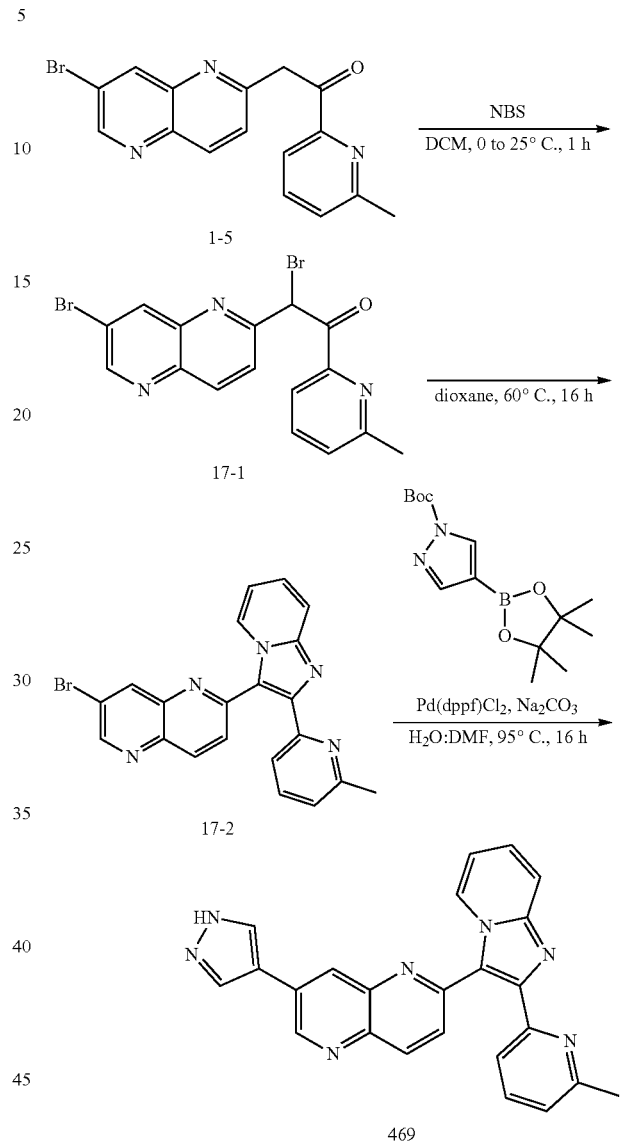

Step A: Preparation of 4-(6-(5-(6-methylpyridin-2-yl)-1H-imidazol-4-yl)-1,5-naphthyridin-3-yl)cyclohex-3-en-1-amine (16-1). A mixture of 4-(N-Boc-amino) cyclohex-1-enyl-1-boronic acid pinacol ester (33.9 mg, 0.105 mmol), 11-3 and 11-4 (40.0 mg, 0.081 mmol), sodium carbonate (34.2 mg, 0.322 mmol), and Pd(dppf)Cl$_2$ (11.8 mg, 0.016 mmol) in degassed water (130 µL):dioxane (300 µL) was heated to 95° C. for 16 h. The reaction mixture was filtered through a pad of celite and concentrated in vacuum. The crude material was dissolved in DCE (0.300 mL) and 6 M aq. HCl (0.200 mL) was added. The mixture was heated to 80° C. for 3 h. The reaction mixture was concentrated in vacuum. The residue was purified by preparative HPLC chromatography using a gradient (2 to 60%) of acetonitrile in water with 0.05% trifluoroacetic acid to yield a TFA salt of 16-1 (45.5 mg). [M+H]$^+$ calcd for C$_{23}$H$_{22}$N$_6$ 383.19, found 383.2.

Step B: A vial of 16-1 (10.0 mg, 0.026 mmol), acetone (3.85 µl, 0.052 mmol), and AcOH (1.50 µL, 0.061 mmol) in methanol (0.2 mL) was stirred at 25° C. for 1 h before adding sodium triacetoxyborohydride (16.67 mg, 0.079 mmol). The resulting mixture was allowed to stir at 25° C. for 16 h. The reaction was quenched with H$_2$O (0.2 mL) and concentrated in vacuum. The residue was purified by preparative HPLC chromatography using a gradient (2 to 60%) of acetonitrile in water with 0.05% trifluoroacetic acid to yield a TFA salt of the title compound (6.0 mg). [M+H]+ calcd for C$_{26}$H$_{28}$N$_6$ 425.24, found 425.1.

Step A: Preparation of 2-bromo-2-(7-bromo-1,5-naphthyridin-2-yl)-1-(6-methylpyridin-2-yl)ethan-1-one (17-1). To a mixture of 1-5 (2.3 g, 6.9 mmol) in DCM (50 mL) was cooled to 0° C., then NBS (1.2 g, 6.9 mmol) was added and the mixture was stirred at 25° C. for 1 h. The mixture was concentrated in vacuum. The residue was purified by column chromatography (PE/EA=3/1) to afford 17-1 (2.6 g, 81% yield, 91% purity) as a brown oil. [M+H]$^+$ calcd for C$_{16}$H$_{11}$Br$_2$N$_3$O, 421.92, found 421.8.

Step B: Preparation of 7-bromo-2-(2-(6-methylpyridin-2-yl)imidazo[1,2-a]pyridin-3-yl)-1,5-naphthyridine (17-2). To a mixture of 17-1 (2.6 g, 6.17 mmol) in dioxane (50 mL) was added 2-aminopyridine (1.8 g, 18.52 mmol), the mixture was stirred at 60° C. for 16 h. The mixture was triturated with EA (50 mL), the filter cake was collected and dried in vacuum to afford 17-2 (1.7 g, 63% yield, 98% purity) as a white solid. [M+H]$^+$ calcd for C$_{21}$H$_{14}$BrN$_5$ 416.04, found 415.9.

Step C: Preparation of 2-(2-(6-methylpyridin-2-yl)imidazo[1,2-a]pyridin-3-yl)-7-(1H-pyrazol-4-yl)-1,5-naphthyridine (469). A vial of 1-Boc-pyrazole-4-boronic acid pinacol ester (14.13 mg, 0.048 mmol), 17-2 (10.0 mg, 0.024 mmol), sodium carbonate (7.64 mg, 0.072 mmol), and Pd(dppf)Cl$_2$ (3.92 mg, 4.80 µmol) in degassed water (200 µL):DMF (400 µL) was heated to 95° C. for 16 h. The reaction mixture was filtered through a pad of celite and concentrated in vacuum. The Boc group was removed during the Suzuki reaction. The residue was purified by preparative HPLC chromatography using a gradient (5 to 65%) of acetonitrile in water with 0.05% trifluoroacetic acid to yield a TFA salt of the title compound (2.7 mg). [M+H]$^+$ calcd for C$_{24}$H$_{17}$N$_7$ 404.15, found 404.2.

Example 18: Synthesis N-methyl-2-(4-(6-(2-(6-methylpyridin-2-yl)imidazo[1,2-a]pyridin-3-yl)-1,5-naphthyridin-3-yl)-1H-pyrazol-1-yl)ethan-1-amine (527)

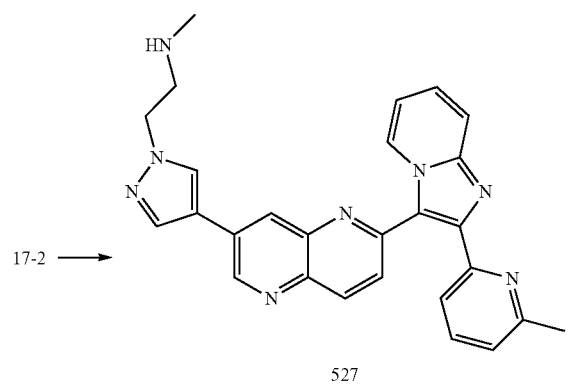 [SMILES: CNCCn1cc(-c2cnc3ccc(-c4c(-c5cccc(C)n5)nc5ccccn45)nc3c2)cn1]

527

The procedure of Example 17 was used to make the title compound with an additional Boc deprotection step. TFA (300 µL) was added to the residue and heated to 50° C. for 1 h. TFA was removed in vacuum before purification. [M+H]$^+$ calcd for C$_{27}$H$_{24}$N$_8$ 461.21, found 461.2.

Example 19: Synthesis of N-(2-(4-isopropylpiperazin-1-yl)ethyl)-6-(2-(6-methylpyridin-2-yl)imidazo[1,2-a]pyridin-3-yl)-1,5-naphthyridin-3-amine (120)

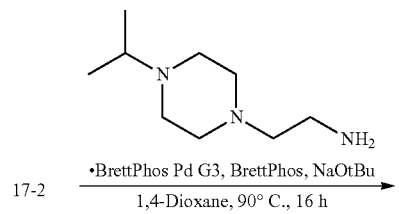

17-2 •BrettPhos Pd G3, BrettPhos, NaOtBu
1,4-Dioxane, 90° C., 16 h

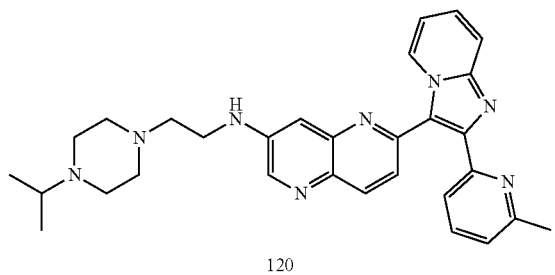

120

A vial of 17-2 (30 mg, 0.072 mmol), 2-(4-isopropylpiperazin-1-yl)-ethylamine (24.69 mg, 0.144 mmol), sodium tert-butoxide (20.78 mg, 0.216 mmol), BrettPhos (3.87 mg, 7.21 µmol), and BrettPhos Pd G3 (6.53 mg, 7.21 µmol) in degassed 1,4-dioxane (360 µL) was heated to 90° C. for 16 h. The reaction mixture was concentrated in vacuum and the residue was purified by preparative HPLC chromatography using a gradient (5 to 75%) of acetonitrile in water with 0.05% trifluoroacetic acid to yield a TFA salt of the title compound (36.1 mg). [M+H]$^+$ calcd for C$_{30}$H$_{34}$N$_8$ 507.29, found 507.2.

Example 20: Synthesis of 2-(2-(6-methylpyridin-2-yl)imidazo[1,2-a]pyridin-3-yl)-7-(4,5,6,7-tetrahydropyrazolo[1,5-a]pyrazin-3-yl)-1,5-naphthyridine (587)

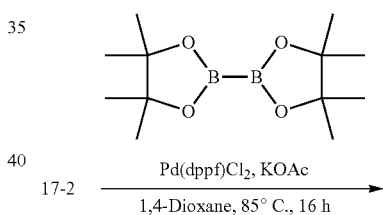

17-2 Pd(dppf)Cl$_2$, KOAc
1,4-Dioxane, 85° C., 16 h

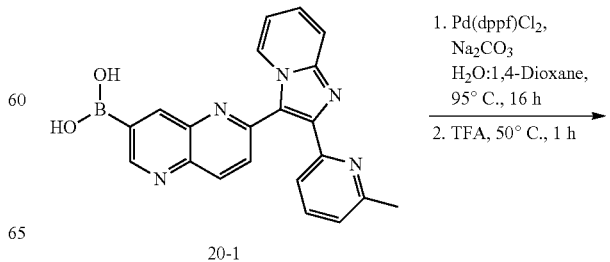

20-1

20-2

1. Pd(dppf)Cl$_2$, Na$_2$CO$_3$
H$_2$O:1,4-Dioxane, 95° C., 16 h
2. TFA, 50° C., 1 h

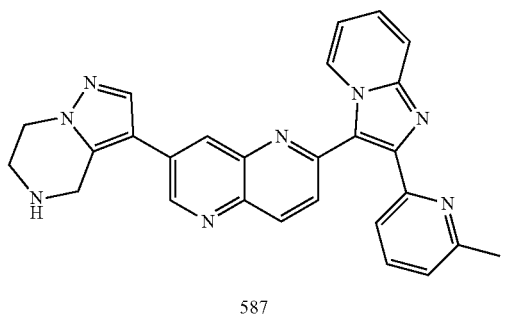

587

Step A: Preparation of (6-(2-(6-methylpyridin-2-yl)imidazo[1,2-a]pyridin-3-yl)-1,5-naphthyridin-3-yl)boronic acid (20-1). A vial of 17-2 (550 mg, 1.32 mmol), bis(pinacolato)diboron (671 mg, 2.64 mmol), Pd(dppf)Cl$_2$ (193 mg, 0.264 mmol), and potassium acetate (389 mg, 3.96 mmol) in 1,4-dioxane (6.30 mL) was sparged with N$_2$ for 5 min before heating to 85° C. for 16 h. Crude 20-1 was used directly as a 0.21 M solution in dioxane in the next reaction. [M+H]$^+$ calcd for C$_{21}$H$_{16}$BN$_5$O$_2$ 382.14, found 382.0.

Step B: Preparation of 2-(2-(6-methylpyridin-2-yl)imidazo[1,2-a]pyridin-3-yl)-7-(4,5,6,7-tetrahydropyrazolo[1,5-a]pyrazin-3-yl)-1,5-naphthyridine (587). A vial of 20-1 (15 mg, 0.039 mmol, crude, 0.21 M in dioxane), 20-2 (17.84 mg, 0.059 mmol), sodium carbonate (8.34 mg, 0.079 mmol), and Pd(dppf)Cl$_2$ (5.76 mg, 7.87 μmol) in water (65.6 μL):1,4-dioxane (131 μL) was sparged for 10 min with N$_2$ before heating to 95° C. for 16 h. The reaction mixture was filtered through a pad of celite and concentrated in vacuum. TFA (300 μL) was added to the residue and heated to 50° C. for 1 h. TFA was removed in vacuum and the residue was purified by preparative HPLC chromatography using a gradient (2 to 60%) of acetonitrile in water with 0.05% trifluoroacetic acid to yield a TFA salt of the title compound (23.5 mg). [M+H]$^+$ calcd for C$_{27}$H$_{22}$N$_8$ 459.20, found 459.2. $^1$H NMR (400 MHz, methanol-d$_4$) δ 9.45 (dt, J=7.1, 1.2 Hz, 1H), 9.19 (d, J=2.2 Hz, 1H), 8.53 (dd, J=2.2, 0.8 Hz, 1H), 8.44 (dd, J=8.8, 0.8 Hz, 1H), 8.21 (s, 1H), 7.99-7.83 (m, 4H), 7.70 (d, J=7.8 Hz, 1H), 7.50 (d, J=7.8 Hz, 1H), 7.38 (td, J=6.9, 1.3 Hz, 1H), 4.94 (s, 2H), 4.57 (t, J=5.8 Hz, 2H), 3.90 (t, J=5.9 Hz, 2H), 2.59 (s, 3H).

Example 21: Synthesis of 2-(2-(6-methylpyridin-2-yl)imidazo[1,2-a]pyrimidin-3-yl)-7-(1H-pyrazol-4-yl)-1,5-naphthyridine (676)

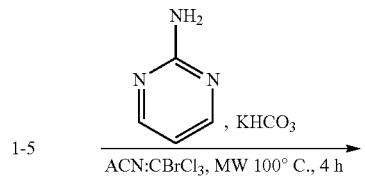

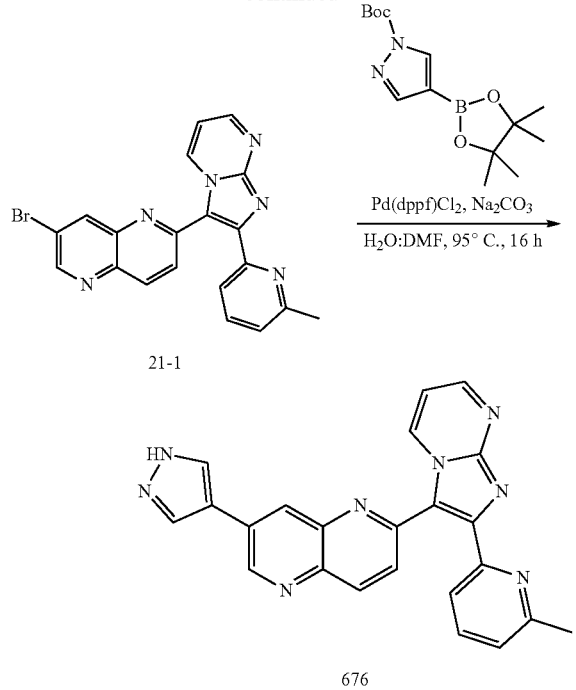

Step A: Preparation of 7-bromo-2-(2-(6-methylpyridin-2-yl)imidazo[1,2-a]pyrimidin-3-yl)-1,5-naphthyridine (21-1). A vial of 1-5 (100 mg, 0.292 mmol), pyrimidin-2-amine (30.6 mg, 0.321 mmol) and potassium bicarbonate (29.3 mg, 0.292 mmol) in 9:1 acetonitrile (526 μl):CBrCl$_3$ (58.4 μl) was heated to 100° C. for 4 h in the microwave. The reaction mixture was concentrated in vacuum. The residue was purified by normal phase chromatography (0 to 10% of MeOH in DCM) to afford 21-1 (53.6 mg, 44.1% yield) as a beige solid. [M+H]$^+$ calcd for C$_{20}$H$_{13}$BrN$_6$ 417.04, found 416.9.

Step B: Preparation of 2-(2-(6-methylpyridin-2-yl)imidazo[1,2-a]pyrimidin-3-yl)-7-(1H-pyrazol-4-yl)-1,5-naphthyridine (676). A vial of 1-Boc-pyrazole-4-boronic acid pinacol ester (17.48 mg, 0.059 mmol), 21-1 (12.4 mg, 0.030 mmol), sodium carbonate (9.45 mg, 0.089 mmol), and Pd(dppf)Cl$_2$ (4.85 mg, 5.94 μmol) in degassed water (200 μL):DMF (400 μL) was heated to 95° C. for 16 h. The reaction mixture was filtered through a pad of celite and concentrated in vacuum. The Boc group is removed during the Suzuki reaction. The residue was purified by preparative HPLC chromatography using a gradient (5 to 65%) of acetonitrile in water with 0.05% trifluoroacetic acid to yield a TFA salt of the title compound (3.4 mg). [M+H]$^+$ calcd for C$_{23}$H$_{16}$N$_8$ 405.15, found 405.0.

Example 22: Synthesis of 5-(7-Bromo-1,5-naphthyridin-2-yl)-6-(6-methylpyridin-2-yl)imidazo[2,1-b]thiazole (511)

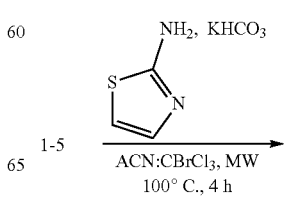

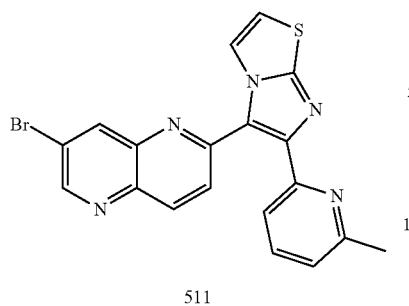

511

A vial of 1-5 (100 mg, 0.292 mmol), 2-amino-1,3-thiazole (32.2 mg, 0.321 mmol) and potassium bicarbonate (29.3 mg, 0.292 mmol) in 9:1 acetonitrile (526 µl):CBrCl$_3$ (58.4 µl) was heated to 100° C. for 4 h in the microwave. The reaction mixture was concentrated in vacuum. The residue was purified by preparative HPLC chromatography using a gradient (20 to 80%) of acetonitrile in water with 0.05% trifluoroacetic acid to yield a TFA salt of the title compound (5.3 mg). [M+H]$^+$ calcd for C$_{19}$H$_{12}$BrN$_5$S, 422.00, found 421.9.

Example 23: Synthesis of 6-(1-benzyl-4-(6-methylpyridin-2-yl)-1H-1,2,3-triazol-5-yl)-N-(2-(4-isopropylpiperazin-1-yl)ethyl)-1,5-naphthyridin-3-amine (373)

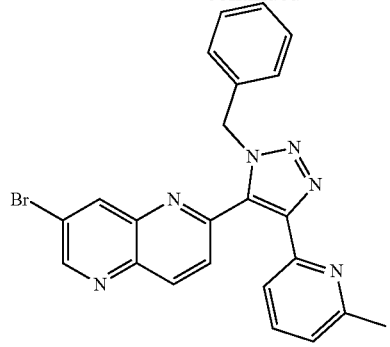

23-6

373

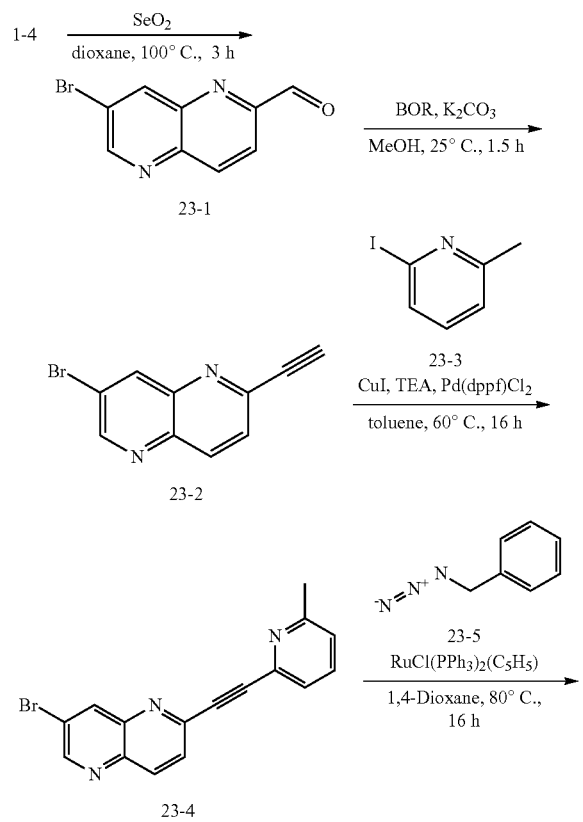

Step A: Preparation of 7-bromo-1,5-napthyridine-2-carbaldehyde (23-1). To a solution of 1-4 (16.0 g, 71.7 mmol) in dioxane (300 mL) was added SeO$_2$ (9.5 g, 86.1 mmol). The mixture was stirred at 100° C. for 3 h under N$_2$ atmosphere. The mixture was filtered and concentrated in vacuum, the residue was purified by column chromatography (PE/EA=10/1~5/1) to afford 23-1 (12.8 g, 54% yield, 72% purity) as a brown solid. [M+H]$^+$ calcd for C$_9$H$_5$BrN$_2$O, 236.96, found 236.9.

Step B: Preparation of 7-bromo-2-ethynyl-1,5-naphthyridine (23-2). To a solution of 23-1 (7.8 g, 32.5 mmol) in MeOH (250 mL) was added K$_2$CO$_3$ (9.0 g, 65.0 mmol) and BOR (7.5 g, 39.0 mmol). The mixture was stirred at 25° C. for 1.5 h under N$_2$ atmosphere. The mixture was diluted with H$_2$O (300 mL), the aqueous phase was extracted with EA (300 mL*3). The organic phase was washed with brine, dried over anhydrous Na$_2$SO$_4$, filtered and concentrated under vacuum. The residue was purified by prep-HPLC (Phenomenex luna C18 250*50 mm*10 µm, water (0.1% TFA)-ACN) and column chromatography (PE/EA=10/1~1/1) to afford to afford 23-2 (5.8 g, 46% yield, 99% purity) as a yellow solid. [M+H]$^+$ calcd for C$_{10}$H$_5$BrN$_2$ 232.96, found 233.0.

Step C: Preparation of 7-bromo-2-((6-methylpyridin-2-yl)ethynyl)-1,5-naphthyridine (23-4). To a mixture of 23-2 (2.9 g, 12.5 mmol) and 23-3 (3.6 g, 16.2 mmol), Pd(dppf)Cl$_2$ (455 mg, 0.62 mmol), CuI (237 mg, 1.25 mmol) and TEA (2.5 g, 24.9 mmol) in toluene (80 mL) was stirred at 60° C. for 16 hours under N$_2$. The mixture was diluted with H$_2$O (100 mL), the aqueous phase was extracted with EA (80 mL*3), the organic phase was washed with brine, dried over anhydrous Na$_2$SO$_4$, filtered and concentrated in vacuum, then purified by column (PE/EA=10/1~1/1) to obtain 23-4

(2.0 g, 48% yield, 98% purity) as yellow solid. [M+H]+ calcd for $C_{16}H_{10}BrN_3$ 324.01, found 323.9.

Step D: Preparation of 2-(1-benzyl-4-(6-methylpyridin-2-yl)-1H-1,2,3-triazol-5-yl)-7-bromo-1,5-naphthyridine (23-6). A vial of 23-4 (300 mg, 0.925 mmol), pentamethylcyclopentadienylbis-(triphenylphosphine)ruthenium(II) chloride, (36.8 mg, 0.046 mmol), and 23-5 (2036 μl, 1.018 mmol) in 1,4-dioxane (9.25 mL) was degassed for 10 minutes. The reaction mixture was then sealed, heated to 80° C. and let stir for 16 h. The resulting mixture was cooled and concentrated in vacuo. The crude product was purified by silica gel column (EA/Hexanes 0%-70%) to obtain 23-6 (211 mg, 50% yield) as a mixture of both possible isomers. [M+H]+ calcd for $C_{23}H_{17}BrN_6$ 457.07, found 457.

Step E: Preparation of 6-(1-benzyl-4-(6-methylpyridin-2-yl)-1H-1,2,3-triazol-5-yl)-N-(2-(4-isopropylpiperazin-1-yl)ethyl)-1,5-naphthyridin-3-amine (373). To 2-(1-benzyl-4-(6-methylpyridin-2-yl)-1H-1,2,3-triazol-5-yl)-7-bromo-1,5-naphthyridine (23-6) (as a mixture of both triazole isomers) (30 mg, 0.066 mmol) and 2-(4-isopropylpiperazin-1-yl)ethan-1-amine (33.7 mg, 0.197 mmol) was added BrettPhos, (3.52 mg, 6.56 μmol), BrettPhos Pd G3 (5.95 mg, 6.56 μmol) and sodium tert-butoxide, (18.91 mg, 0.197 mmol). To the resulting mixture was added dioxane (328 μL) and subsequently sparged with nitrogen for 5 m. The resulting yellow reaction mixture was capped and stirred at 80° C. for 16 hr. The reaction was cooled and concentrated in vacuo. The crude product purified (and separated from the undesired triazole regioisomer) by preparative HPLC chromatography using a gradient (10 to 50%) of acetonitrile in water with 0.05% trifluoroacetic acid to yield a TFA salt of the title compound (9.8 mg). [M+H]+ calcd for $C_{32}H_{37}N_9$ 548.32 found 548.2.

Example 24: Synthesis of 2-(1-benzyl-4-(6-methylpyridin-2-yl)-1H-1,2,3-triazol-5-yl)-7-(piperazin-1-yl)-1,5-naphthyridine (359)

23-6 ⟶

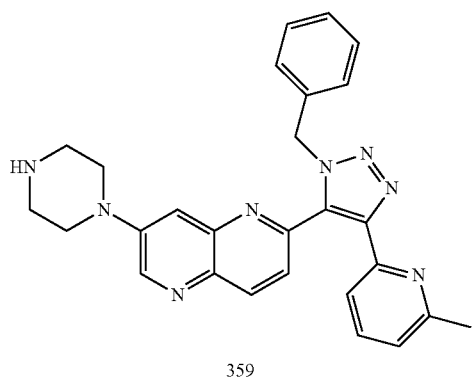

359

To a vial charged with 2-(1-benzyl-4-(6-methylpyridin-2-yl)-1H-1,2,3-triazol-5-yl)-7-bromo-1,5-naphthyridine (23-6) (as a mixture of both triazole isomers) (30 mg, 0.066 mmol) and 1-Boc-piperazine (48.9 mg, 0.262 mmol) was added RuPhos, (6.12 mg, 0.013 mmol), RuPhos Pd G2 (10.19 mg, 0.013 mmol) and sodium tert-butoxide, (18.91 mg, 0.197 mmol). To the resulting mixture was added dioxane (219 μL) and subsequently sparged with nitrogen for 5 m. The resulting yellow reaction mixture was capped and stirred at 90° C. for 16 hr. The reaction was cooled and then concentrated in vacuo. The resulting residue was treated with 1 mL of TFA and stirred at 55° C. for 1 h. The crude product was concentrated in vacuo and purified (and separated from the undesired triazole regiosomer) by preparative HPLC chromatography using a gradient (10 to 50%) of acetonitrile in water with 0.05% trifluoroacetic acid to yield a TFA salt of the title compound (11.1 mg). [M+H]+ calcd for $C_{27}H_{26}N_8$ 463.23 found 462.1.

Example 25: Synthesis of 2-(1-benzyl-4-(6-methylpyridin-2-yl)-1H-1,2,3-triazol-5-yl)-7-(1-(piperidin-3-yl)-1H-pyrazol-4-yl)-1,5-naphthyridine (216)

23-6 ⟶

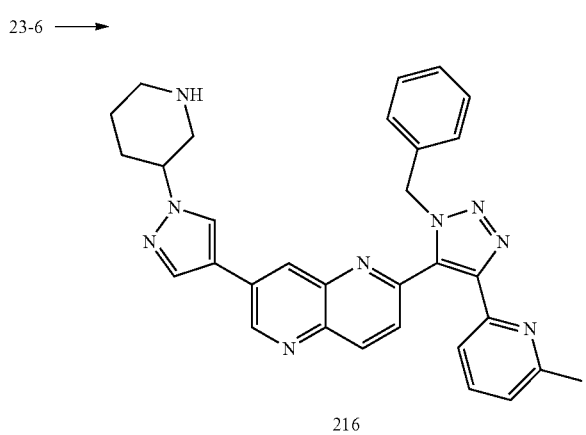

216

To a vial charged with 2-(1-benzyl-4-(6-methylpyridin-2-yl)-1H-1,2,3-triazol-5-yl)-7-bromo-1,5-naphthyridine (23-6) (as a mixture of both triazole isomers) (30 mg, 0.067 mmol) was added 3-(4-(4,4,5,5-tetramethyl-1,3,2-dioxaborolan-2-yl)-1H-pyrazol-1-yl)piperidine HCl (41.1 mg, 0.131 mmol) followed by sodium carbonate (20.86 mg, 0.197 mmol), and Pd(dppf)Cl₂ (10.71 mg, 0.013 mmol). The resulting mixture was purged with nitrogen before degassed water (164 μl) and DMF (325 μl) was added. The vial was capped and stirred at 95° C. for 16 hr. The reaction was then cooled, filtered through a plug of celite, washed with THF (5 mL) and concentrated in vacuo. The resulting residue was treated with 0.3 mL of TFA and stirred at RT for 3 hr. The crude product was concentrated in vacuo and purified (and separated from the undesired triazole regioisomer) by preparative HPLC chromatography using a gradient (15 to 55%) of acetonitrile in water with 0.05% trifluoroacetic acid to yield a TFA salt of the title compound (9.1 mg). [M+H]+ calcd for $C_{24}H_{23}N_7$ 410.20 found 410.1.

Example 26: Synthesis of N-methyl-2-(4-(6-(5-(6-methylpyridin-2-yl)-1H-1,2,3-triazol-4-yl)-1,5-naphthyridin-3-yl)-1H-pyrazol-1-yl)ethan-1-amine (29)

23-4 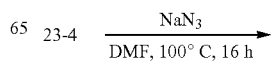

655

-continued

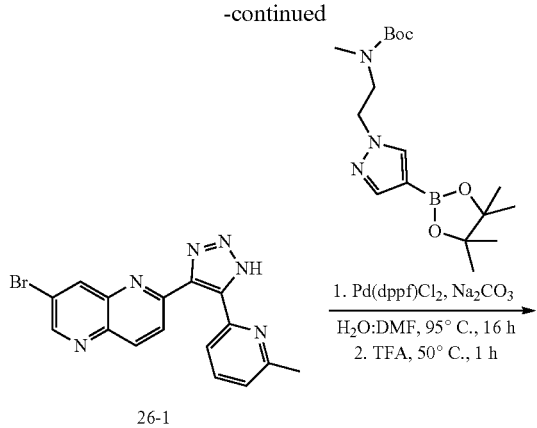

26-1

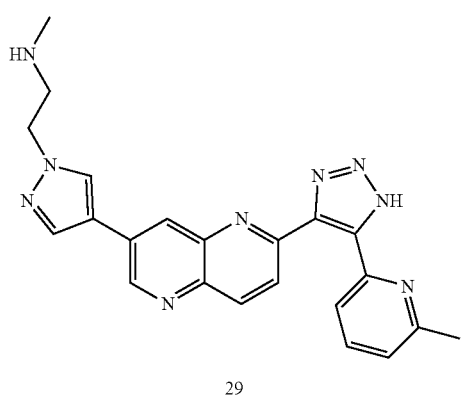

29

Step A: Preparation of 7-bromo-2-(5-(6-methylpyridin-2-yl)-1H-1,2,3-triazol-4-yl)-1,5-naphthyridine (26-1). A vial of 23-4 (300 mg, 0.925 mmol) and sodium azide (180 mg, 2.78 mmol) in DMF (9.25 mL) was heated 100° C. for 16 h. The reaction was quenched with water (10 mL) and extracted with DCM (30 mL×3). The organic layer was dried over $Na_2SO_4$, filtered, and concentrated in vacuum. The residue was purified via normal phase chromatography (0 to 20% MeOH in DCM) yielding 26-1 (311 mg, 92% yield) as a beige solid. [M+H]$^+$ calcd for $C_{16}H_{11}BrN_6$ 367.02, found 367.0.

Step B: Preparation of N-methyl-2-(4-(6-(5-(6-methylpyridin-2-yl)-1H-1,2,3-triazol-4-yl)-1,5-naphthyridin-3-yl)-1H-pyrazol-1-yl)ethan-1-amine (29). A vial of tert-butyl methyl(2-(4-(4,4,5,5-tetramethyl-1,3,2-dioxaborolan-2-yl)-1H-pyrazol-1-yl)ethyl)carbamate (57.4 mg, 0.163 mmol), 26-1 (30 mg, 0.082 mmol), sodium carbonate (26.0 mg, 0.245 mmol), and Pd(dppf)Cl$_2$ (13.34 mg, 0.016 mmol) in degassed water (272 μL):DMF (545 μL) was heated to 95° C. for 16 h. The reaction mixture was filtered through a pad of celite and concentrated in vacuum. TFA (300 μL) was added to the residue and heated to 50° C. for 1 h. TFA was removed in vacuum and the residue was purified by preparative HPLC chromatography using a gradient (2 to 60%) of acetonitrile in water with 0.05% trifluoroacetic acid to yield a TFA salt of the title compound (16.9 mg). [M+H]$^+$ calcd for $C_{22}H_{21}N_9$ 412.19, found 412.1.

656

Example 27: Synthesis of (S)—N,N-dimethyl-1-(6-(5-(6-methylpyridin-2-yl)-1H-1,2,3-triazol-4-yl)-1,5-naphthyridin-3-yl)pyrrolidin-3-amine (188)

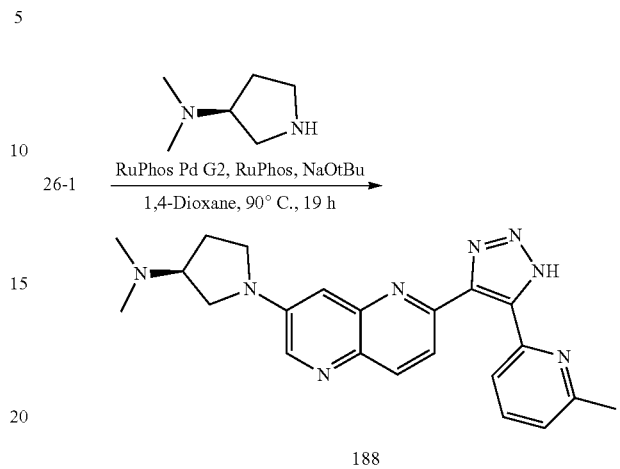

A vial of 26-1 (30 mg, 0.082 mmol), (S)-(−)-3-(dimethylamino)pyrrolidine (18.66, 0.163 mmol), RuPhos (7.62 mg, 0.016 mmol), sodium tert-butoxide (23.55 mg, 0.245 mmol), and RuPhos Pd G2 (63.4 mg, 0.064 mmol) in 1,4-dioxane (272 μL) (degassed with $N_2$) was heated to 90° C. for 72 h. The reaction mixture was filtered through a pad of celite and concentrated in vacuum. The residue was purified by preparative HPLC chromatography using a gradient (2 to 40%) of acetonitrile in water with 0.05% trifluoroacetic acid to yield a TFA salt of the title compound (20.1 mg). [M+H]$^+$ calcd for $C_{22}H_{24}N_8$ 401.21, found 401.3.

Example 28: Synthesis of 2-(3-(6-ethylpyridin-2-yl)-1H-pyrazol-4-yl)-7-(4-(pyrrolidin-1-yl)piperidin-1-yl)-1,5-naphthyridine (532)

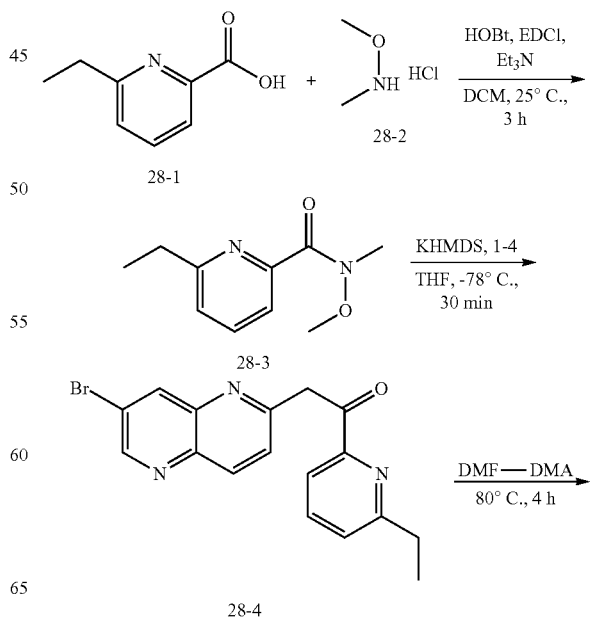

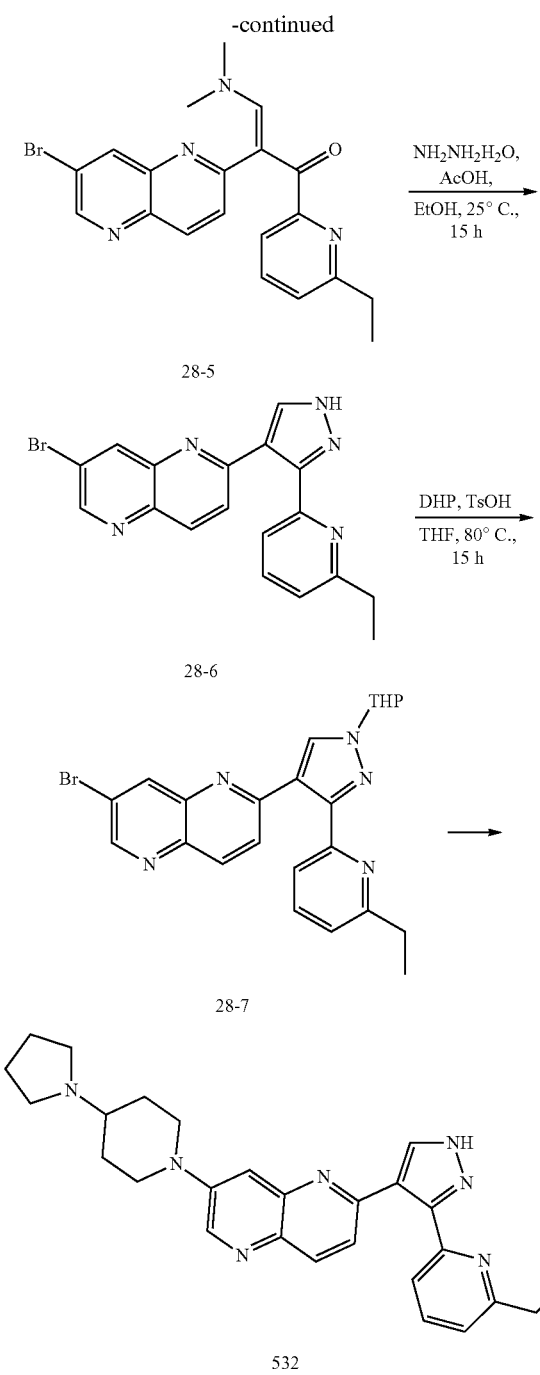

Step A: Preparation of 6-ethyl-N-methoxy-N-methylpicolinamide (28-3). To a solution of 28-1 (850 mg, 5.62 mmol), 28-2 (822 mg, 8.43 mmol), HOBt (911 mg, 6.74 mmol) and EDCI (1.3 g, 6.74 mmol) in DCM (20 mL) was added Et$_3$N (2.3 g, 22.5 mmol) dropwise at 25° C. The mixture was then stirred at 25° C. for 3 h. The reaction was diluted with H$_2$O (20 mL), extracted with DCM (50 mL×3). The organic layer was washed with brine (20 mL×2), dried over Na$_2$SO$_4$, filtered, and concentrated in vacuum to give crude product. The crude product was purified by column (PE:EA=10:1~1:1) to give 28-3 (800 mg, 73% yield, 85% purity) as yellow oil. [M+H]$^+$ calcd for C$_{10}$H$_{14}$N$_2$O$_2$ 195.11, found 195.3.

Step B: Preparation of 2-(7-bromo-1,5-naphthyridin-2-yl)-1-(6-ethylpyridin-2-yl)ethan-1-one (28-4). To a mixture of 1-4 (765 mg, 3.43 mmol) and 28-3 (800 mg, 4.12 mmol) in THF (20 mL) was dropwise added KHMDS (6.9 mL, 6.86 mmol) at −78° C. The mixture was stirred at −78° C. for 30 min. The mixture was combined with another batch of the same reaction (starting with 143 mg of 1-4), and then was quenched with H$_2$O (30 mL) and extracted with EA (50 mL×3). The combined organic phase was dried over Na$_2$SO$_4$, and concentration to give the crude product 28-4 (1.6 g) as yellow solid. [M+H]$^+$ calcd for C$_{17}$H$_{14}$BrN$_3$O, 356.03, found 356.2.

Step C: Preparation of (E)-2-(7-bromo-1,5-naphthyridin-2-yl)-3-(dimethylamino)-1-(6-ethylpyridin-2-yl)prop-2-en-1-one (28-5). To a solution of 28-4 (1.5 g, 4.21 mmol) in DMF-DMA (20 mL) was stirred for 4 hours at 80° C. The mixture was concentrated in vacuum and the residue crude 28-5 (1.5 g) was used directly in the next step. [M+H]$^+$ calcd for C$_{20}$H$_{19}$BrN$_4$O, 411.08, found 413.3.

Step D: Preparation of 7-bromo-2-(3-(6-ethylpyridin-2-yl)-1H-pyrazol-4-yl)-1,5-naphthyridine (28-6). To a solution of 28-5 (1.5 g, 2.70 mmol) in EtOH (20 mL) was added AcOH (1.2 g, 19.2 mmol) and NH$_2$NH$_2$H$_2$O (746 mg, 14.9 mmol). The mixture was stirred for 15 h at 25° C. The mixture (combined with another batch of the same reaction starting with 100 mg of 28-5) was concentrated in vacuum and the residue was purified by column (PE:EA=6/1~1:1) to afford 28-6 (780 mg, 71% yield, 95% purity) as brown solid. [M+H]$^+$ calcd for C$_{18}$H$_{14}$BrN$_5$ 380.04, found 380.2.

Step E: Preparation of 7-bromo-2-(3-(6-ethylpyridin-2-yl)-1-(tetrahydro-2H-pyran-2-yl)-1H-pyrazol-4-yl)-1,5-naphthyridine (28-7). To a solution of 28-6 (680 mg, 1.79 mmol) in THF (20 mL) was added DHP (1.5 g, 17.9 mmol) and TsOH (31 mg, 0.179 mmol). The mixture was stirred for 15 h at 80° C. The reaction mixture (combined with another batch of the same reaction starting with 100 mg of 28-6) was diluted with H$_2$O (100 mL), basified with solid NaHCO$_3$ to pH=9 and extracted with EA (200 mL×3). The organic layer was washed with brine (200 mL×2), dried over Na$_2$SO$_4$, filtered, and concentrated in vacuum. The residue was purified by column (PE:EA=10:1~3:1) to afford 28-7 (260 mg, 27% yield, 94% purity) as yellow oil. [M+H]$^+$ calcd for C$_{23}$H$_{22}$BrN$_5$O, 464.10, found 466.3.

Step F: Preparation of 2-(3-(6-ethylpyridin-2-yl)-1H-pyrazol-4-yl)-7-(4-(pyrrolidin-1-yl)piperidin-1-yl)-1,5-naphthyridine (532). To a vial charged with 7-bromo-2-(3-(6-ethylpyridin-2-yl)-1-(tetrahydro-2H-pyran-2-yl)-1H-pyrazol-4-yl)-1,5-naphthyridine (28-7) (21 mg, 0.044 mmol) and 4-(1-pyrrolidinyl)-piperidine (10 mg, 0.066 mmol) was added RuPhos, (2.05 mg, 4.40 µmol), RuPhos Pd G2 (3.42 mg, 4.40 µmol) and sodium tert-butoxide, (13 mg, 0.132 mmol). To the resulting mixture was added dioxane (400 µL) and subsequently sparged with nitrogen for 5 m. The resulting yellow reaction mixture was capped stirred at 105° C. for 16 hr. The reaction was cooled and then concentrated in vacuo. The resulting residue was treated with 1 mL of TFA and stirred at 45° C. for 1 h. The crude product was concentrated in vacuo and purified by preparative HPLC chromatography using a gradient (10 to 43%) of acetonitrile in water with 0.05% trifluoroacetic acid to yield a TFA salt of the title compound (8.2 mg). [M+H]$^+$ calcd for C$_{27}$H$_{31}$N$_7$ 454.26 found 454.2.

Example 29: Synthesis of 2-(3-(6-(3-(6-ethylpyridin-2-yl)-1H-pyrazol-4-yl)-1,5-naphthyridin-3-yl)-1H-pyrazol-1-yl)-N-methylethan-1-amine (92)

28-7 ⟶

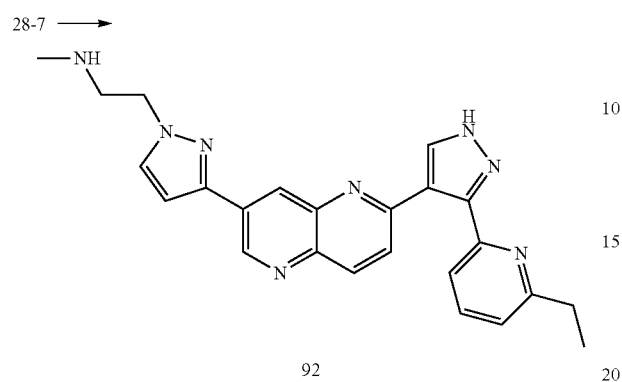

92

To a vial charged with 7-bromo-2-(3-(6-ethylpyridin-2-yl)-1-(tetrahydro-2H-pyran-2-yl)-1H-pyrazol-4-yl)-1,5-naphthyridine (28-7) (35 mg, 0.075 mmol) was added tert-butyl methyl(2-(4-(4,4,5,5-tetramethyl-1,3,2-dioxaborolan-2-yl)-1H-pyrazol-1-yl)ethyl) carbamate (30.5 mg, 0.087 mmol) followed by potassium phosphate tribasic (48 mg, 0.226 mmol), Xphos Pd G4 (6.49 mg, 7.54 µmol), and Xphos (3.59 mg, 7.54 µmol). The resulting mixture was purged with nitrogen before degassed water (151 µl) and 1,4-dioxane (151 µl) was added. The vial was capped and stirred at 105° C. for 16 hr. The reaction was then cooled, filtered through a plug of celite, washed with THE (5 mL) and concentrated in vacuo. The resulting residue was treated with 1 mL of TFA and stirred at 55° C. for 1 hr. The crude product was concentrated in vacuo and purified by preparative HPLC chromatography using a gradient (10 to 60%) of acetonitrile in water with 0.05% trifluoroacetic acid to yield a TFA salt of the title compound (21.1 mg). [M+H]+ calcd for $C_{24}H_{24}N_8$ 425.21 found 425.1. $^1$H NMR (400 MHz, methanol-$d_4$) δ 9.55 (d, J=2.0 Hz, 1H), 8.91-8.84 (m, 1H), 8.88 (s, 1H), 8.64 (dd, J=8.2, 1.2 Hz, 1H), 8.58 (dd, J=8.9, 0.8 Hz, 1H), 8.50 (t, J=8.0 Hz, 1H), 8.35 (d, J=9.0 Hz, 1H), 7.95-7.87 (m, 2H), 7.02 (d, J=2.4 Hz, 1H), 4.70-4.62 (m, 2H), 3.68-3.61 (m, 2H), 3.49 (q, J=7.6 Hz, 2H), 2.81 (s, 3H), 1.53 (t, J=7.6 Hz, 3H).

Example 30: N-(2-(2,2-dimethylpyrrolidin-1-yl)ethyl)-6-(3-(5-fluoro-6-methylpyridin-2-yl)-1H-pyrazol-4-yl)-1,5-naphthyridin-3-amine (526)

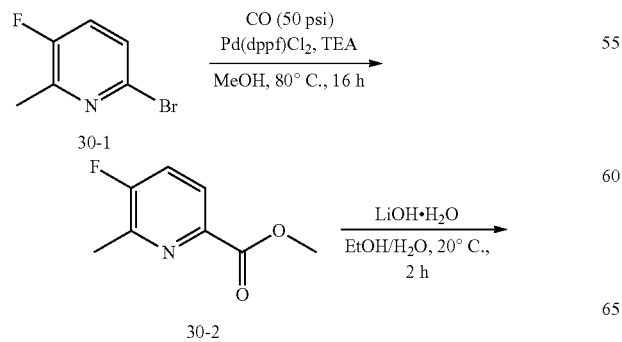

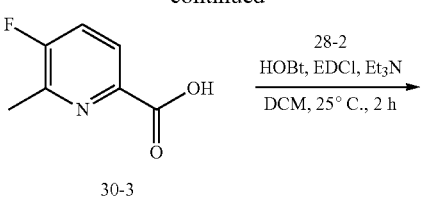

30-3

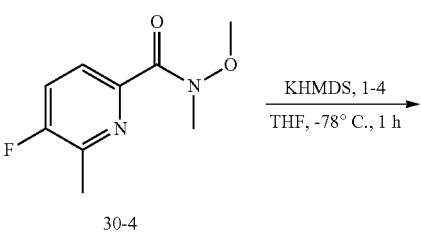

30-4

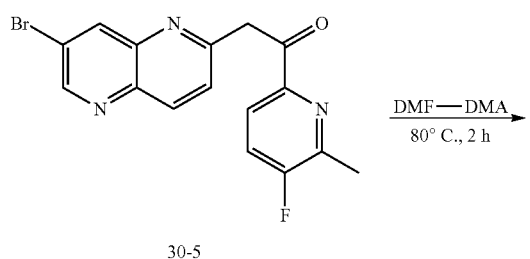

30-5

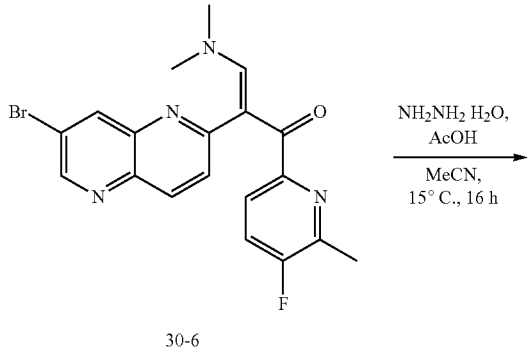

30-6

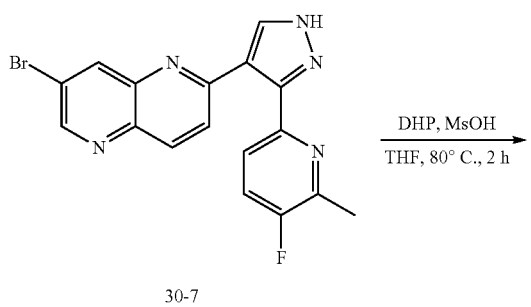

30-7

-continued

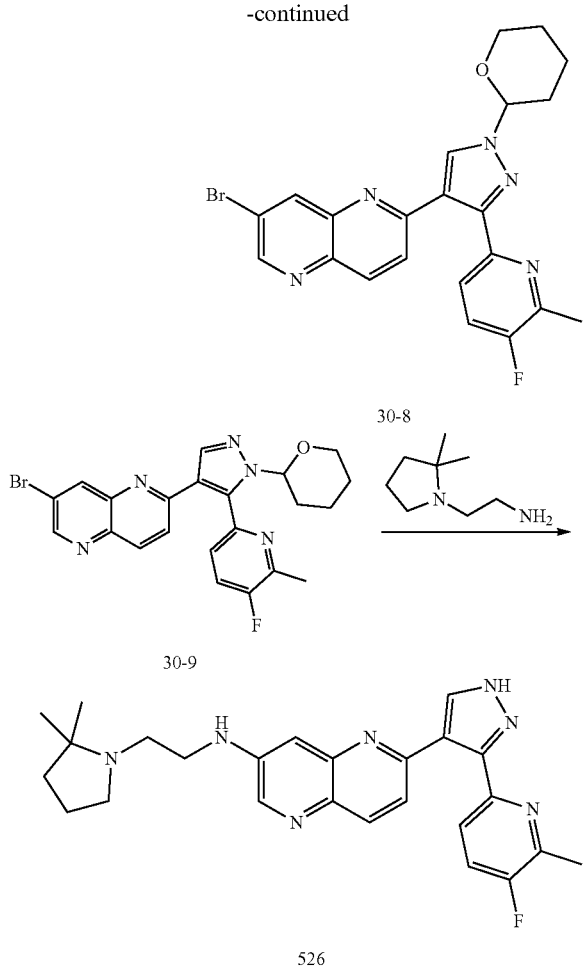

Step A: Preparation of methyl 5-fluoro-6-methylpicolinate (30-2). To a solution of 30-1 (29.0 g, 153 mmol) and Pd(dppf)Cl$_2$ (3.5 g, 4.58 mmol) in MeOH (500 mL) was added TEA (46.3 g, 458 mmol). The mixture was stirred at 80° C. for 16 h under CO (50 psi). The mixture was concentrated under reduced pressure. The residue was purified by column chromatography (0~20% of EA in PE) to give 30-2 (24.4 g, 94% yield, 99% purity) as white solid.

Step B: Preparation of 5-fluoro-6-methylpicolinic acid (30-3). To a solution of 30-2 (13.8 g, 81.6 mmol) in EtOH (150 mL) and H$_2$O (50 mL) was added LiOH.H$_2$O (17.1 g, 408 mmol). The mixture was stirred at 20° C. for 2 h. The mixture was combined with another batch of the same reaction (starting with 13.8 g of 30-2). 2M HCl was added to pH=6, EtOH was removed under reduced pressure. The mixture was extracted with EA (400 mL*3). The combined organic phase was dried over Na$_2$SO$_4$, concentrated under reduced pressure and dried in vacuum to give 30-3 (20.7 g, 82% yield) as white solid.

Step C: Preparation of 5-fluoro-N-methoxy-N,6-dimethylpicolinamide (30-4). To a solution of 30-3 (19.7 g, 127 mmol), 28-2 (18.6 g, 190 mmol), HOBt (20.6 g, 152 mmol) and EDCI (29.2 g, 152 mmol) in DCM (800 mL) was added Et$_3$N (51.4 g, 508 mmol) dropwise, the mixture was stirred at 25° C. for 2 h. The mixture was combined with another batch of the same reaction (starting with 1.0 g of 30-3). The combined mixture was diluted with H$_2$O (800 mL), the DCM layer separated, the aqueous layer was extracted with EA (80 mL*2), the DCM layer was combined with organic layer, dried over Na$_2$SO$_4$, concentrated under reduced pressure. The residue was purified by column (0~20% of EA in PE) to give 30-4 (15.3 g, 55% yield, 95% purity) as light yellow oil. [M+H]$^+$ calcd for C$_9$H$_{11}$FN$_2$O$_2$ 199.08, found 199.1.

Step D: Preparation of 2-(7-bromo-1,5-naphthyridin-2-yl)-1-(5-fluoro-6-methylpyridin-2-yl)ethan-1-one (30-5). To a mixture of 1-4 (1.25 g*2, 5.60 mmol*2) and 30-4 (1.33 g*2, 6.72 mmol*2) in THF (30 mL*2) was added KHMDS (11.2 mL*2, 11.2 mmol*2) at −78° C. under N$_2$. The mixture was stirred at −78° C. for 1.0 h. The reaction was quenched with H$_2$O (20 mL*2) at −78° C. The mixture was combined with 7 other batches of the same reaction (starting with 1.0 g of 30-4 each). The combined mixture was filtered and the filtrate was extracted with EA (300 mL*3), the combined organic phase was combined with the filter cake. The combined mixture was concentrated under reduced pressure, dried in vacuum to give crude 30-5 (14.0 g, 50% yield, 52% purity) as a yellow solid. [M+H]$^+$ calcd for C$_{16}$H$_{11}$BrFN$_3$O, 360.01, found 360.1.

Step E: Preparation of (E)-2-(7-bromo-1,5-naphthyridin-2-yl)-3-(dimethylamino)-1-(5-fluoro-6-methylpyridin-2-yl)prop-2-en-1-one (30-6). A solution of 30-5 (13.0 g*2, 16.3*2 mmol) in DMF.DMA (130*2 mL) was stirred at 80° C. for 2 h under N$_2$. The mixture was concentrated under reduced pressure and dried in vacuum to give crude 30-6 (15.0 g, 79% yield, 41% purity) as brown solid. [M+H]$^+$ calcd for C$_{19}$H$_{16}$BrFN$_4$O, 415.05, found 415.1.

Step F: Preparation of 7-bromo-2-(3-(5-fluoro-6-methylpyridin-2-yl)-1H-pyrazol-4-yl)-1,5-naphthyridine (30-7). To a solution of 30-6 (15.0 g, 14.8 mmol) in MeCN (150 mL) was added AcOH (6.3 g, 105 mmol) and NH$_2$NH$_2$H$_2$O (4.1 g, 81.5 mmol). The mixture was stirred at 15° C. for 16 h. The mixture was combined with 2 other batches of the same reaction (starting with 1.0 g and 1.5 g of 30-6). The combined mixture was filtered, the filter cake was washed with H$_2$O (50 mL*3), the filtrate was basified with sat. NaHCO$_3$ to pH=8. The filtrate was diluted with H$_2$O (300 mL), extracted with EA (500 mL*3), the combined mixture was dried over Na$_2$SO$_4$, the combined mixture was concentrated under reduced pressure. The residue was combined with the filter cake and dried in vacuum to give crude 30-7 (17.6 g) as brown solid. [M+H]$^+$ calcd for C$_{17}$H$_{11}$BrFN$_5$ 384.02, found 386.1.

Step G: Preparation of 7-bromo-2-(3-(5-fluoro-6-methylpyridin-2-yl)-1-(tetrahydro-2H-pyran-2-yl)-1H-pyrazol-4-yl)-1,5-naphthyridine (30-8). To a solution of 30-7 (12.5 g, 32.5 mmol) in THF (130 mL) was added MsOH (50 drops) and DHP (13.7 g, 163 mmol). The mixture was stirred for 2 h at 80° C. The mixture was combined with another batch of the same reaction (starting with 100 mg of 30-7). The combined mixture was washed with sat. NaHCO$_3$ (200 mL) and sat. NaCl (200 mL). The organic layer was dried over Na$_2$SO$_4$ and concentrated under reduced pressure. The residue was purified by column (5%~30% of EA in PE) to give 30-8 (4.9 g, 22% yield, 95% purity) as yellow solid and a mixture of 30-8 and 30-9 (0.7 g) as yellow oil. [M+H]$^+$ calcd for C$_{22}$H$_{19}$BrFN$_5$O, 468.08, found 470.1.

Step H: Preparation of N-(2-(2,2-dimethylpyrrolidin-1-yl)ethyl)-6-(3-(5-fluoro-6-methylpyridin-2-yl)-1H-pyrazol-4-yl)-1,5-naphthyridin-3-amine (526). 7-bromo-2-(3-(5-fluoro-6-methylpyridin-2-yl)-1-(tetrahydro-2H-pyran-2-yl)-1H-pyrazol-4-yl)-1,5-naphthyridine (30-8) (29.3 mg, 0.063 mmol) and 2-(2,2-dimethylpyrrolidin-1-yl)ethan-1-amine (11.6 mg, 0.081 mmol) was added BrettPhos, (6.72 mg, 0.013 mmol), BrettPhos Pd G4 (11.52 mg, 0.013 mmol) and sodium tert-butoxide (18.04 mg, 0.188 mmol). To the resulting mixture was added dioxane (417 μL) and subsequently sparged with nitrogen for 5 m. The resulting yellow reaction mixture was capped and stirred at 85° C. for 16 hr. The reaction was cooled and concentrated in vacuo. The resulting residue was treated with TFA (0.5 mL) and stirred at 50° C. for 1 h. The crude product was concentrated in vacuo and purified by preparative HPLC chromatography using a gradient (5 to 45%) of acetonitrile in water with 0.05% trifluoroacetic acid to yield a TFA salt of the title compound (17.5 mg). [M+H]+ calcd for $C_{25}H_{28}FN_7$ 446.24 found 446. $^1$H NMR (400 MHz, Methanol-$d_4$) δ 8.86 (s, 1H), 8.73-8.63 (m, 2H), 8.28 (dd, J=8.8, 4.0 Hz, 1H), 8.11 (d, J=8.8 Hz, 1H), 7.81 (t, J=8.8 Hz, 1H), 7.38 (d, J=2.5 Hz, 1H), 3.92 (s, 1H), 3.78 (t, J=6.1 Hz, 2H), 3.64 (s, 1H), 3.36 (s, 2H), 2.86 (d, J=2.8 Hz, 3H), 2.17 (s, 1H), 2.08 (s, 3H), 1.53 (s, 3H), 1.34 (s, 3H).

Example 31: Synthesis of (1R,2R)-2-(4-(6-(3-(5-fluoro-6-methylpyridin-2-yl)-1H-pyrazol-4-yl)-1,5-naphthyridin-3-yl)-1H-pyrazol-1-yl)cyclohexan-1-amine (490)

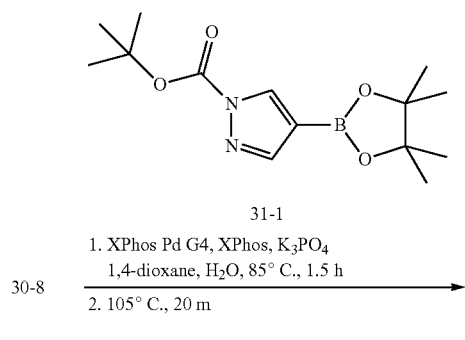

31-1

30-8
1. XPhos Pd G4, XPhos, $K_3PO_4$
1,4-dioxane, $H_2O$, 85° C., 1.5 h
2. 105° C., 20 m

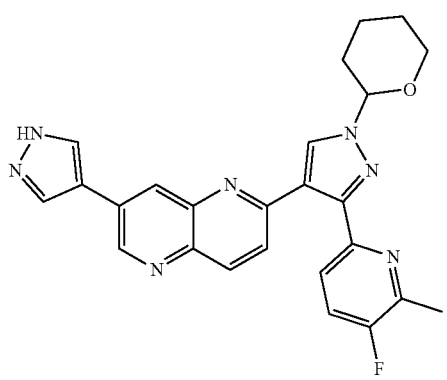

31-2

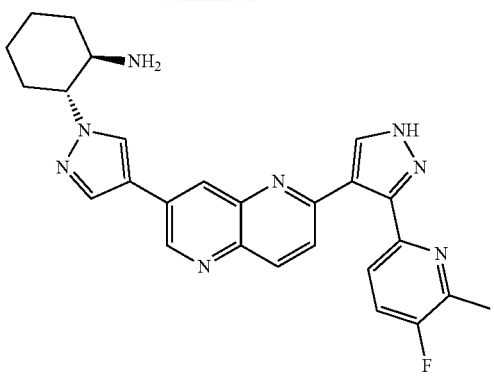

490

Step A: Preparation of 2-(3-(5-fluoro-6-methylpyridin-2-yl)-1-(tetrahydro-2H-pyran-2-yl)-1H-pyrazol-4-yl)-7-(1H-pyrazol-4-yl)-1,5-naphthyridine (31-2). To a vial containing 30-8 (150 mg, 0.320 mmol) was added 31-1 (122 mg, 0.416 mmol) followed by potassium phosphate tribasic (204 mg, 0.384 mmol), Xphos Pd G4 (27.6 mg, 0.032 mmol), and Xphos (15.27 mg, 0.032 mmol). The resulting mixture was purged with nitrogen before degassed water (650 μl) and 1,4-dioxane (650 μl) was added. The vial was capped and stirred at 85° C. for 1.5 hr. Afterwards, the reaction was stirred at 105° C. for 20 m. The reaction was then cooled and concentrated in vacuo. The residue was purified by column (0%~15% of MeOH in DCM), yielding 31-2 (117 mg, 72% yield, 90% purity). [M+H]+ calcd for $C_{25}H_{22}FN_7O$, 456.19 found 456.

Step B: Preparation of (1R,2S)-2-(4-(6-(3-(5-fluoro-6-methylpyridin-2-yl)-1H-pyrazol-4-yl)-1,5-naphthyridin-3-yl)-1H-pyrazol-1-yl)cyclohexan-1-amine (490). To a vial containing (1R,2R)-trans-N-Boc-2-aminocyclohexanol (35.4 mg, 0.165 mmol) was added DCM (1 mL) and triethylamine (0.038 mL, 0.274 mmol) and the resulting mixture was cooled to 0° C. before being treated with methanesulfonyl chloride (0.015 mL, 0.198 mmol). The resulting clear solution was stirred at 0° C. and slowly allowed to warm up to RT overnight. The reaction was quenched with $NaHCO_3$ (sat), and the aq. layer was extracted with DCM. The combined organics were dried over $Na_2SO_4$ and concentrated in vacuo. To the resulting white solid was added cesium carbonate (71.5 mg, 0.220 mmol) followed by a solution containing 31-2 (50 mg, 0.110 mmol) in acetonitrile (1000 μL) and the resulting mixture was capped and stirred at 100° C. for 6 hr. Afterwards, the reaction was concentrated in vacuo. The resulting residue was treated with 1 mL of TFA and stirred at 50° C. for 1 hr. The crude product was concentrated in vacuo and purified by preparative HPLC chromatography using a gradient (10 to 50%) of acetonitrile in water with 0.05% trifluoroacetic acid to yield a TFA salt of the title compound (40.4 mg). [M+H]+ calcd for $C_{26}H_{25}FN_8$ 469.22 found 469.2. The stereochemistry of the product was confirmed by NOE.

Example 32: Synthesis of N-methyl-2-(4-(6-(3-(6-(trifluoromethyl)pyridin-2-yl)-1H-pyrazol-4-yl)-1,5-naphthyridin-3-yl)-1H-pyrazol-1-yl)ethan-1-amine (237)

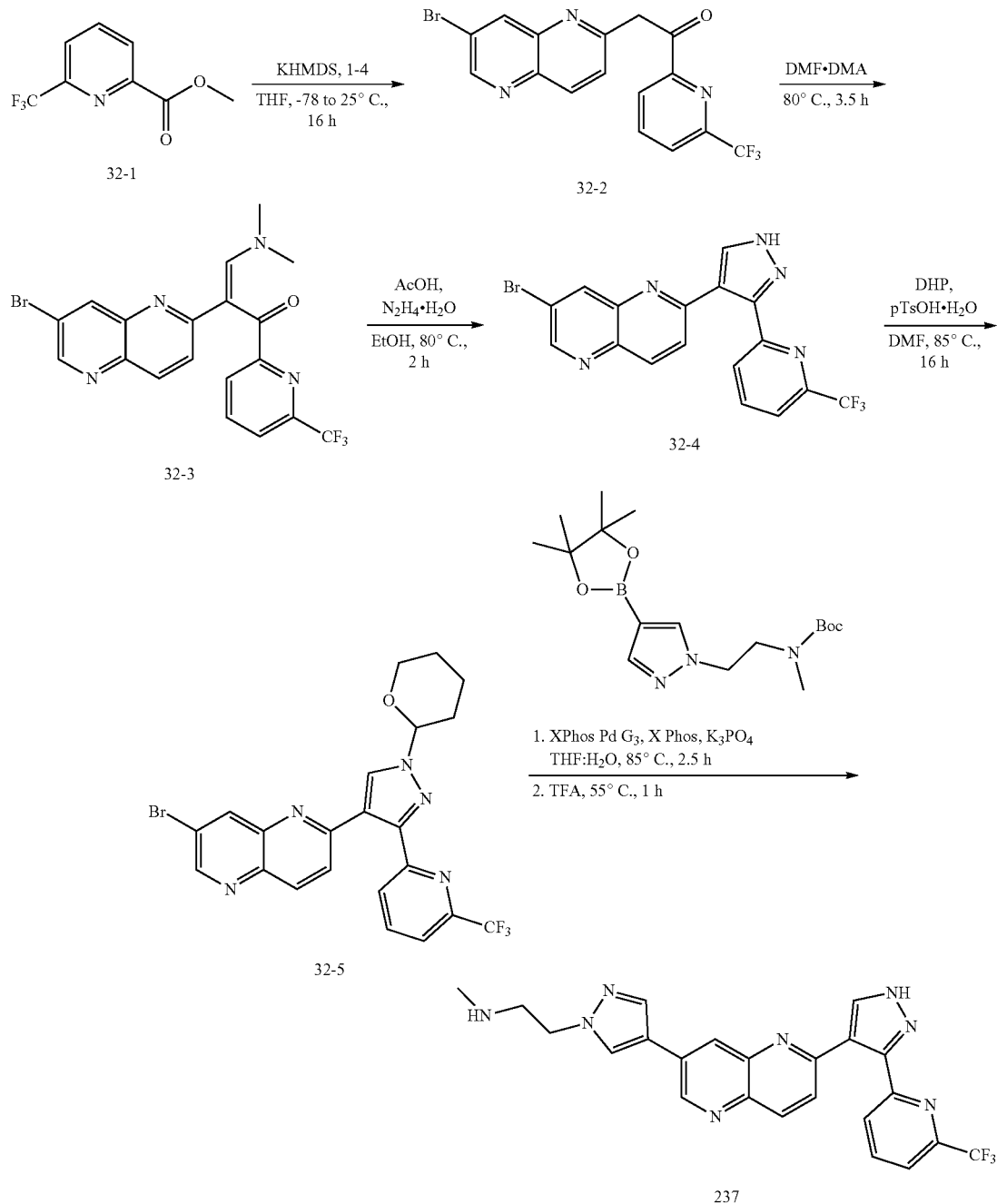

Step A: Preparation of 2-(7-bromo-1,5-naphthyridin-2-yl)-1-(6-(trifluoromethyl)pyridin-2-yl)ethan-1-one (32-2). A solution, under an atmosphere of nitrogen, containing 32-1 (36.8 mg, 0.179 mmol) and 1-4 (40 mg, 0.179 mmol) in dry THF (897 µL) was cooled to −78° C. After 15 min, a solution of 1.0 M KHMDS in THF (215 µL, 0.215 mmol) was added dropwise. The resulting mixture was allowed to slowly warm up to 25° C. and stir for 16 h. The reaction was quenched with 200 µL of H$_2$O. MeOH (2 mL) was added and the mixture was concentrated. The residue was purified by silica gel column chromatography (0 to 100% of EA in Hex) to afford 32-2 (49.2 mg, 69.3% yield). [M+H]$^+$ calcd for C$_{16}$H$_9$BrF$_3$N$_3$O, 395.99, found 396.0.

Step B: Preparation of 7-bromo-2-(3-(6-(trifluoromethyl)pyridin-2-yl)-1H-pyrazol-4-yl)-1,5-naphthyridine (32-4). To a vial containing 32-2 (49.2 mg, 0.124 mmol) was added N,N-dimethylformamide dimethyl acetal (412 μL, 3.10 mmol) and the resulting mixture was stirred at 80° C. for 3.5 h. The reaction mixture was concentrated to afford crude 32-3. [M+H]+ calcd for $C_{19}H_{14}BrF_3N_4O$ 451.03, found 451.0. To a solution of crude 32-3 in EtOH (621 μL) was added acetic acid (35.5 μL, 0.621 mmol) and hydrazine hydrate (31.1 μL, 0.621 mmol). The resulting mixture was stirred at 80° C. for 2 h. The reaction mixture was concentrated in vacuum. The residue was purified by silica gel column chromatography (0 to 15% of MeOH in DCM) to afford 32-4 (26.5 mg, 50.8% yield). [M+H]+ calcd for $C_{17}H_9BrF_3N_5$ 420.00, found 420.0.

Step C: Preparation of 7-bromo-2-(1-(tetrahydro-2H-pyran-2-yl)-3-(6-(trifluoromethyl)pyridin-2-yl)-1H-pyrazol-4-yl)-1,5-naphthyridine (32-5). To a solution of 32-4 (26.5 mg, 0.063 mmol) in DMF (420 μL) was added p-toluenesulfonic acid monohydrate (1.799 mg, 9.46 μmol) and 3,4-dihydro-2h-pyran (17.26 μL, 0.189 mmol). The resulting mixture was stirred at 85° C. for 16 h. The reaction mixture was treated with triethylamine (2.198 μL, 0.016 mmol) and concentrated in vacuum. The residue was purified by silica gel column chromatography (0 to 10% of MeOH in DCM) to afford 32-5 (7.3 mg, 23% yield). [M+H]+ calcd for $C_{22}H_{17}BrF_3N_5O$ 504.06, found 504.0.

Step D: Preparation of N-methyl-2-(4-(6-(3-(6-(trifluoromethyl)pyridin-2-yl)-1H-pyrazol-4-yl)-1,5-naphthyridin-3-yl)-1H-pyrazol-1-yl)ethan-1-amine (237). To a vial containing 32-5 (6.8 mg, 0.013 mmol) and carbamic acid, tert-butyl methyl(2-(4-(4,4,5,5-tetramethyl-1,3,2-dioxaborolan-2-yl)-1H-pyrazol-1-yl)ethyl)carbamate (7.10 mg, 0.020 mmol) was added XPhos Pd G3 (1.141 mg, 1.348 μmol), 2-dicyclohexylphosphino-2',4',6'-triisopropylbiphenyl (0.643 mg, 1.348 μmol) and potassium phosphate, tribasic (10.02 mg, 0.047 mmol) followed by THF (33.7 μL) and water (33.7 μL). The reaction mixture was sparged with $N_2$ for 3 min before being capped and stirred at 85° C. for 2.5 h. The reaction mixture was concentrated in vacuum. The resulting residue was treated with 0.5 mL of TFA and stirred at 55° C. for 1 h. The reaction mixture was concentrated in vacuum. The residue was purified using preparative HPLC chromatography using a gradient (10 to 50%) of acetonitrile in water with 0.05% trifluoroacetic acid to yield a TFA salt of the title compound (3.7 mg). [M+H]+ calcd for $C_{23}H_{19}F_3N_8$ 465.17, found 465.0.

Example 33: Synthesis of N-(2-(4-isopropylpiperazin-1-yl)ethyl)-6-(3-(6-(trifluoromethyl)pyridin-2-yl)-1H-pyrazol-4-yl)-1,5-naphthyridin-3-amine (201)

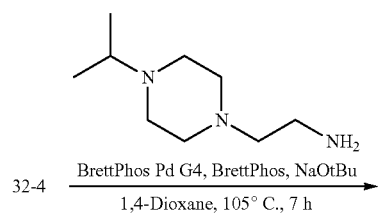

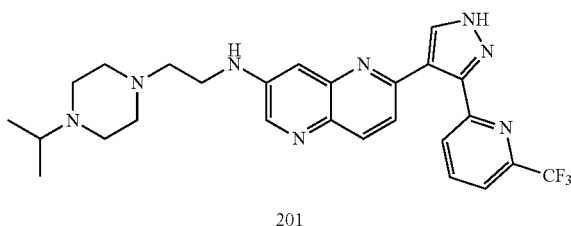

201

To a vial charged with BrettPhos Pd G4 (6.57 mg, 7.14 μmol), BrettPhos (3.83 mg, 7.14 μmol), sodium tert-butoxide (9.15 mg, 0.095 mmol), 2-(4-isopropyl-piperazin-1-yl)-ethylamine (13.00 μL, 0.071 mmol) and 32-4 (20 mg, 0.048 mmol) in dioxane (238 μL) was sparged with nitrogen for 10 min and stirred at 105° C. for 7 h. The reaction mixture was filtered through a pad of celite and concentrated in vacuum. The residue was purified by preparative HPLC chromatography using a gradient (5 to 65%) of acetonitrile in water with 0.05% trifluoroacetic acid to yield a TFA salt of the title compound (24.8 mg). [M+H]+ calcd for $C_{26}H_{29}F_3N_8$ 511.25, found 511.2.

Example 34: Synthesis of N-(4-(4-methylpiperazin-1-yl)phenyl)-6-(3-(6-methylpyridin-2-yl)-1H-pyrazol-4-yl)quinolin-3-amine (664)

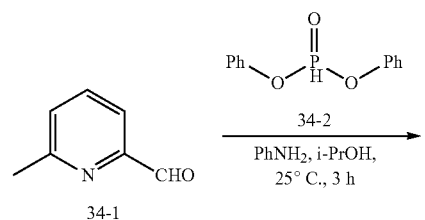

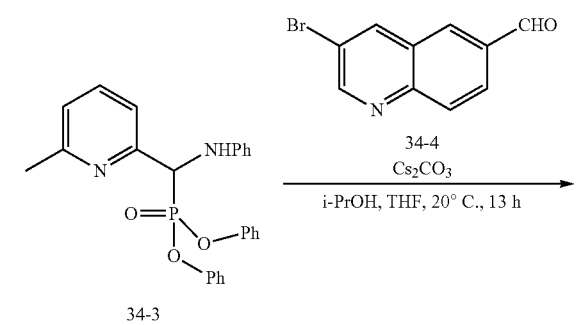

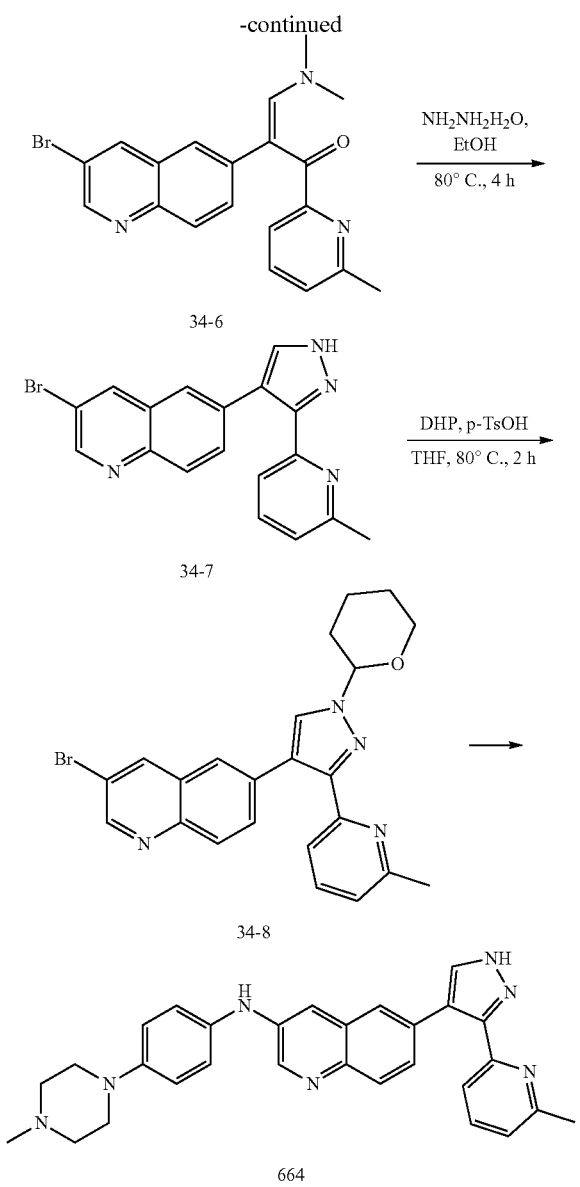

Step A: Preparation of diphenyl ((6-methylpyridin-2-yl)(phenylamino)methyl)phosphonate (34-3). To a mixture of 34-1 (20.0 g, 165 mmol), PhNH₂ (18.4 g, 198 mmol) in i-PrOH (500 mL) was added 34-2 (67.1 g, 215 mmol) at 25° C. The reaction mixture was stirred at 25° C. for 3 h. The mixture was filtered. The solid was concentrated in vacuum to afford 34-3 (29.0 g, 41% yield, 100% purity) as white solid. [M+H]⁺ calcd for $C_{25}H_{23}N_2O_3P$, 431.14, found 431.2.

Step B: Preparation of 2-(3-bromoquinolin-6-yl)-1-(6-methylpyridin-2-yl)ethan-1-one (34-5). To a mixture of 34-3 (18.8 g, 43.6 mmol), Cs₂CO₃ (21.3 g, 65.4 mmol) in THF (200 mL) and i-PrOH (40 mL) was added 34-4 (10.3 g, 43.6 mmol) at 20° C. The reaction mixture was stirred at 20° C. for 12 h. The reaction mixture was diluted with 3.0 M HCl (80 mL) and stirred at 20° C. for 1 h. The reaction mixture was basified with solid NaOH to pH=8, extracted with EA (200 mL×3). The organic layer was washed with brine (150 mL×2), dried over Na₂SO₄, filtered, and concentrated in vacuum. One part was purified by recrystallizaiton to obtain 34-5 (9.2 g, 88% purity) as yellow solid. [M+H]⁺ calcd for $C_{17}H_{13}BrN_2O$ 341.02, found 342.9. Another part was purified by silica gel column to obtain 34-5 (6.0 g, 40% yield, 99% purity) as a white solid. [M+H]⁺ calcd for $C_{17}H_{13}BrN_2O$, 341.02, found 342.9.

Step C: Preparation of (Z)-2-(3-bromoquinolin-6-yl)-3-(dimethylamino)-1-(6-methylpyridin-2-yl)prop-2-en-1-one (34-6). A solution of 34-5 (11.2 g, 32.8 mmol) in DMF.DMA (100 mL) was stirred at 80° C. for 4 h. The reaction was concentrated in vacuum to obtain crude 34-6 (17.5 g) as red oil.

Step D: Preparation of 3-bromo-6-(3-(6-methylpyridin-2-yl)-1H-pyrazol-4-yl)quinoline (34-7). A solution of crude 34-6 (17.5 g, 32.8 mmol) and NH₂NH₂H₂O (8.2 g, 164 mmol) in EtOH (100 mL) was stirred at 80° C. for 4 h. The mixture was concentrated in vacuum and purified by silica gel column (20%~60% of EA in PE) to obtain 34-7 (8.0 g, 66% yield (over 2 steps), 91% purity) as red solid. [M+H]⁺ calcd for $C_{18}H_{13}BrN_4$ 365.03, found 366.9.

Step E: Preparation of 3-bromo-6-(3-(6-methylpyridin-2-yl)-1-(tetrahydro-2H-pyran-2-yl)-1H-pyrazol-4-yl)quinoline (34-8). A solution of 34-7 (8.0 g, 21.9 mmol), DHP (9.2 g, 110 mmol) and p-TsOH (377 mg, 2.19 mmol) in THF (100 mL) was stirred at 80° C. for 2 h. The reaction was detected by TLC. The mixture was concentrated in vacuum and purified by silica gel column (10%~60% of EA in PE) which was combined with another batch of the same reaction (starting with 460 mg of 34-7) to obtain 34-8 (8.0 g, 76% yield, 98% purity) as yellow solid. [M+H]⁺ calcd for $C_{23}H_{21}BrN_4O$, 449.09, found 450.9.

Step F: Preparation of N-(4-(4-methylpiperazin-1-yl)phenyl)-6-(3-(6-methylpyridin-2-yl)-1H-pyrazol-4-yl)quinolin-3-amine (664). 3-bromo-6-(3-(6-methylpyridin-2-yl)-1-(tetrahydro-2H-pyran-2-yl)-1H-pyrazol-4-yl)quinoline (34-8) (20 mg, 0.045 mmol) and 4-(4-methyl-1-piperazinyl)aniline, (17.03 mg, 0.089 mmol) was added BrettPhos, (2.389 mg, 4.45 μmol), BrettPhos Pd G4 (4.10 mg, 4.45 μmol) and sodium tert-butoxide, (12.83 mg, 0.089 mmol). To the resulting mixture was added dioxane (223 μL) and subsequently sparged with nitrogen for 5 m. The resulting yellow reaction mixture was capped and stirred at 85° C. for 16 hr. The reaction was cooled and concentrated in vacuo. The resulting residue was treated with TFA (0.3 mL) and stirred at 60° C. for 1 h. The crude product was concentrated in vacuo and purified by preparative HPLC chromatography using a gradient (2 to 40%) of acetonitrile in water with 0.05% trifluoroacetic acid to yield a TFA salt of the title compound (21.5 mg). [M+H]⁺ calcd for $C_{29}H_{29}N_7$ 476.25 found 476.2.

Example 35: Synthesis of 3-(4-(4-Methylpiperazin-1-yl)piperidin-1-yl)-6-(3-(6-methylpyridin-2-yl)-1H-pyrazol-4-yl)quinoline (82)

34-8 ⟶

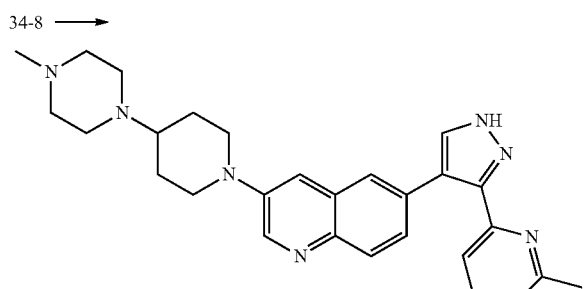

82

To a vial charged with 3-bromo-6-(3-(6-methylpyridin-2-yl)-1-(tetrahydro-2H-pyran-2-yl)-1H-pyrazol-4-yl)quinoline (34-8) (30 mg, 0.067 mmol) and 1-methyl-4-(piperidin-4-yl)piperazine (49.0 mg, 0.267 mmol) was added RuPhos, (6.23 mg, 0.013 mmol), RuPhos Pd G2 (10.37 mg, 0.013 mmol) and sodium tert-butoxide, (19.25 mg, 0.200 mmol). To the resulting mixture was added dioxane (223 μL) and subsequently sparged with nitrogen for 5 m. The resulting yellow reaction mixture was capped stirred at 80° C. for 16 hr. The reaction was cooled and then concentrated in vacuo. The resulting residue was treated with 0.5 mL of TFA and stirred at 50° C. for 1 h. The crude product was concentrated in vacuo and purified by preparative HPLC chromatography using a gradient (2 to 30%) of acetonitrile in water with 0.05% trifluoroacetic acid to yield a TFA salt of the title compound (11.2 mg). [M+H]$^+$ calcd for $C_{27}H_{31}FN_8$ 487.27 found 487.2. $^1$H NMR (400 MHz, Methanol-$d_4$) δ 9.03 (d, J=2.8 Hz, 1H), 8.21-8.12 (m, 3H), 8.05-7.98 (m, 2H), 7.72 (dd, J=8.9, 1.7 Hz, 2H), 7.56 (d, J=8.0 Hz, 1H), 4.17-4.09 (m, 2H), 3.50 (s, 4H), 3.41 (s, 4H), 3.24 (tt, J=11.6, 3.7 Hz, 1H), 3.07 (td, J=12.7, 2.3 Hz, 2H), 2.92 (s, 3H), 2.78 (s, 3H), 2.26-2.17 (m, 2H), 1.95-1.79 (m, 2H).

Example 36: Synthesis of N-methyl-2-(4-(6-(5-(6-methylpyridin-2-yl)-1H-imidazol-4-yl)quinolin-3-yl)-1H-pyrazol-1-yl)ethan-1-amine (17)

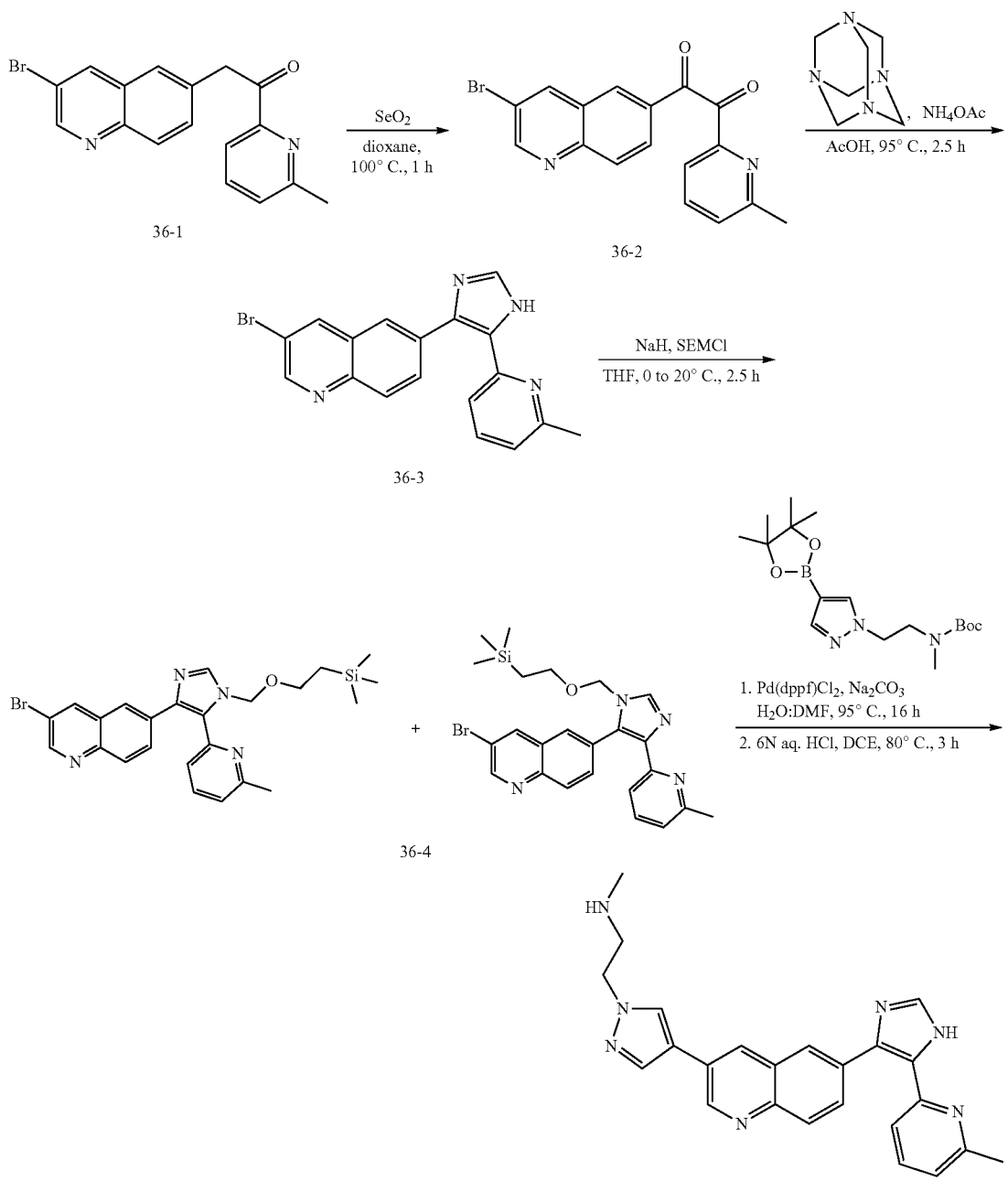

Step A: Preparation of 1-(3-bromoquinolin-6-yl)-2-(6-methylpyridin-2-yl)ethane-1,2-dione (36-2). A mixture of 36-1 (7.0 g, 20.5 mmol) and SeO$_2$ (4.6 g, 41.0 mmol) in dioxane (100 mL) was stirred at 100° C. for 1 h. The mixture was filtered and the filtrate was concentrated under reduced pressure to give 36-2 (9.5 g, 70% purity) as yellow oil, which was used into next step directly. [M+H]$^+$ calcd for C$_{17}$H$_{11}$BrN$_2$O$_2$ 355.00, found 355.0.

Step B: Preparation of 3-bromo-6-(5-(6-methylpyridin-2-yl)-1H-imidazol-4-yl)quinoline (36-3). A mixture of 36-2 (9.5 g, 18.7 mmol), hexamine (7.9 g, 56.2 mmol) and NH$_4$OAc (8.6 g, 112 mmol) in AcOH (100 mL) was stirred at 95° C. for 2.5 h. The mixture was concentrated in vacuum to about 40 mL. The residue was diluted with H$_2$O (100 mL), basified with solid NaOH at 0° C. to pH=7. The mixture was extracted with DCM (150 mL×3). The combined organic layers were dried in vacuum to give the residue. The residue was purified by column (0 to 10% of MeOH in EA) to give 36-3 (3.4 g, 40% yield, 80% purity) as brown solid. [M+H]$^+$ calcd for C$_{18}$H$_{13}$BrN$_4$ 365.03, found 364.9.

Step C: Preparation of 3-bromo-6-(5-(6-methylpyridin-2-yl)-1-((2-(trimethylsilyl)ethoxy)methyl)-1H-imidazol-4-yl)quinoline and 3-bromo-6-(4-(6-methylpyridin-2-yl)-1-((2-(trimethylsilyl)ethoxy)methyl)-1H-imidazol-5-yl)quinoline (36-4). To a solution of 36-3 (3.3 g, 9.04 mmol) in THF (40 mL) was added NaH (723 mg, 18.1 mmol) stirred at 0° C. for 0.5 h. SEMCl (2.3 g, 13.6 mmol) was added, the mixture was stirred at 20° C. for 2 h. The reaction was quenched with H$_2$O (100 mL) and extracted with EA (100 mL×3). The combined organic layer was dried over Na$_2$SO$_4$ and concentrated under reduced pressure to give a residue. The residue was purified by column (0 to 100% of EA (containing 25% of DCM) in PE) to give 36-4 (1.9 g, 43% yield, 98% purity, 2 isomers combined) as brown oil. [M+H]$^+$ calcd for C$_{24}$H$_{27}$BrN$_4$OSi 495.11, found 495.0.

Step D: Preparation of N-methyl-2-(4-(6-(5-(6-methylpyridin-2-yl)-1H-imidazol-4-yl)quinolin-3-yl)-1H-pyrazol-1-yl)ethan-1-amine (17). A vial of tert-butyl methyl(2-(4-(4,4,5,5-tetramethyl-1,3,2-dioxaborolan-2-yl)-1H-pyrazol-1-yl)ethyl)carbamate (25.1 mg, 0.072 mmol), 36-4 (27.3 mg, 0.055 mmol), sodium carbonate (17.49 mg, 0.165 mmol), and Pd(dppf)Cl$_2$ (8.98 mg, 0.011 mmol) in degassed water (137 µL):DMF (274 µL) was heated to 95° C. for 16 h. The reaction mixture was filtered through a pad of celite and concentrated in vacuum. The crude material was dissolved in DCE (0.300 mL) and 6 M aq. HCl (0.200 mL) was added. The mixture was heated to 80° C. for 3 h. The reaction mixture was concentrated in vacuum. The residue was purified by preparative HPLC chromatography using a gradient (2 to 40%) of acetonitrile in water with 0.05% trifluoroacetic acid to yield a TFA salt of the title compound (32.7 mg). [M+H]$^+$ calcd for C$_{24}$H$_{23}$N$_7$ 410.20, found 410.2. $^1$H NMR (400 MHz, Methanol-d$_4$) δ 9.27 (d, J=2.2 Hz, 1H), 8.93 (s, 1H), 8.67 (dd, J=2.2, 0.8 Hz, 1H), 8.40 (d, J=0.7 Hz, 1H), 8.28 (d, J=1.9 Hz, 1H), 8.22-8.12 (m, 2H), 7.90 (dd, J=8.8, 2.0 Hz, 1H), 7.75 (t, J=7.9 Hz, 1H), 7.36 (ddt, J=9.5, 7.8, 0.8 Hz, 2H), 4.65-4.57 (m, 2H), 3.63-3.51 (m, 2H), 2.78 (s, 3H), 2.63 (s, 3H).

Example 37: Synthesis of 4-[6-[5-(6-methyl-2-pyridyl)-1H-imidazol-4-yl]-3-quinolyl]cyclohex-3-en-1-amine (196)

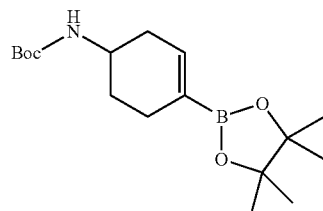

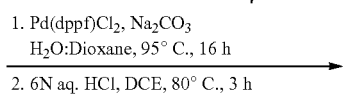

36-4

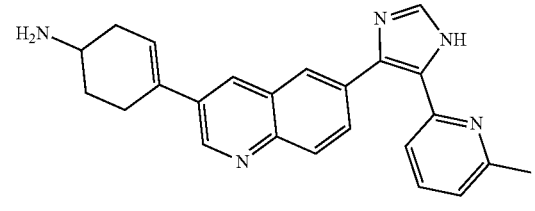

196

A mixture of 4-(N-boc-amino) cyclohex-1-enyl-1-boronic acid pinacol ester (33.9 mg, 0.105 mmol), 36-4 (40.1 mg, 0.081 mmol), sodium carbonate (34.2 mg, 0.322 mmol), and Pd(dppf)Cl$_2$ (11.8 mg, 0.016 mmol) in degassed water (130 µL):dioxane (300 µL) was heated to 95° C. for 16 h. The reaction mixture was filtered through a pad of celite and concentrated in vacuum. The crude material was dissolved in DCE (0.300 mL) and 6 M aq. HCl (0.200 mL) was added. The mixture was heated to 80° C. for 3 h. The reaction mixture was concentrated in vacuum. The residue was purified by preparative HPLC chromatography using a gradient (2 to 60%) of acetonitrile in water with 0.05% trifluoroacetic acid to yield a TFA salt of 196 (48.2 mg). [M+H]$^+$ calcd for C$_{24}$H$_{23}$N$_5$ 382.20, found 382.1. $^1$H NMR (400 MHz, Methanol-d$_4$) δ 9.19 (d, J=2.2 Hz, 1H), 8.93 (s, 1H), 8.52 (d, J=2.2 Hz, 1H), 8.32 (d, J=2.0 Hz, 1H), 8.23-8.14 (m, 1H), 7.94 (dd, J=8.8, 2.0 Hz, 1H), 7.74 (t, J=7.9 Hz, 1H), 7.35 (ddt, J=21.7, 7.9, 0.8 Hz, 2H), 6.47 (td, J=3.2, 1.6 Hz, 1H), 3.61-3.47 (m, 1H), 2.85-2.71 (m, 3H), 2.64 (s, 3H), 2.48-2.22 (m, 2H), 1.95 (dddd, J=12.6, 10.7, 8.5, 7.1 Hz, 1H).

Example 38: Synthesis of N,N-dimethyl-4-(6-(5-(6-methylpyridin-2-yl)-1H-imidazol-4-yl)quinolin-3-yl)cyclohex-3-en-1-amine (629)

196 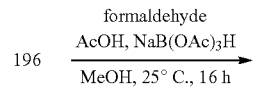

-continued

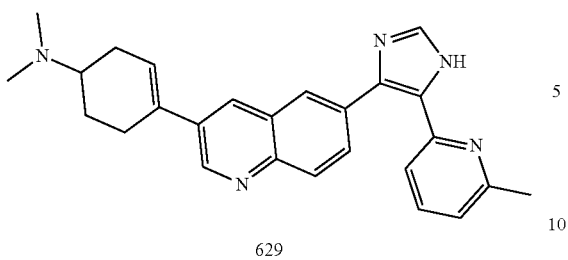

629

A vial of 196 (10.0 mg, 0.026 mmol), formaldehyde 37 wt. % in H₂O (3.90 μl, 0.052 mmol), and AcOH (1.50 μl, 0.061 mmol) in methanol (0.2 mL) was stirred at 25° C. for 1 h before adding sodium triacetoxyborohydride (16.67 mg, 0.079 mmol). The resulting mixture was allowed to stir at 25° C. for 16 h. The reaction was quenched with H₂O (0.2 mL) and concentrated in vacuum. The residue was purified by preparative HPLC chromatography using a gradient (2 to 60%) of acetonitrile in water with 0.05% trifluoroacetic acid to yield a TFA salt of the title compound (5.1 mg). [M+H]⁺ calcd for $C_{26}H_{27}N_5$ 410.23, found 410.1.

Example 39: Synthesis of N-(4-(6-(5-(6-methylpyridin-2-yl)-1H-imidazol-4-yl)quinolin-3-yl)cyclohex-3-en-1-yl)-2-((2-oxotetrahydrofuran-3-yl)thio)acetamide (98)

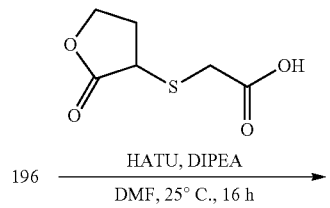

196 —HATU, DIPEA→
DMF, 25° C., 16 h

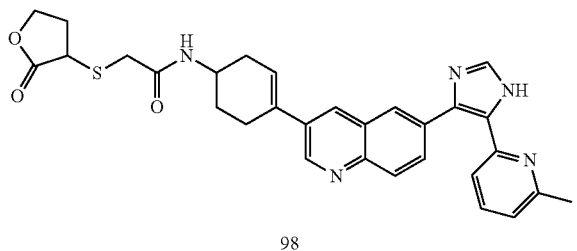

98

A vial of 2-[(2-oxooxolan-3-yl)sulfanyl]acetic acid (10 mg, 0.057 mmol), DIPEA (39.7 μL, 0.227 mmol), and HATU (21.58 mg, 0.057 mmol) in DMF (568 μL) was stirred for 1 h before adding 196 (25 mg, 0.041 mmol). The resulting mixture was stirred at 25° C. for 16 h. The reaction mixture was concentrated in vacuum and the residue was purified by preparative HPLC chromatography using a gradient (5 to 75%) of acetonitrile in water with 0.05% trifluoroacetic acid to yield a TFA salt of the title compound (2.2 mg). [M+H]⁺ calcd for $C_{30}H_{29}N_5O_3S$, 540.20, found 540.1.

Example 40: Synthesis of 2-(4-(6-(5-(6-methylpyridin-2-yl)-1H-imidazol-4-yl)quinolin-3-yl)piperazin-2-yl)acetic acid (500)

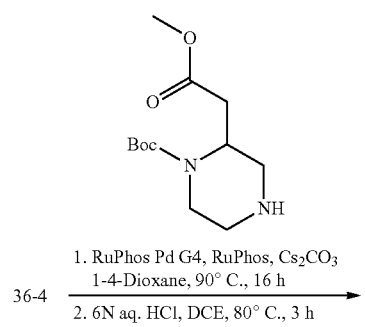

36-4 —1. RuPhos Pd G4, RuPhos, Cs₂CO₃
1-4-Dioxane, 90° C., 16 h
2. 6N aq. HCl, DCE, 80° C., 3 h→

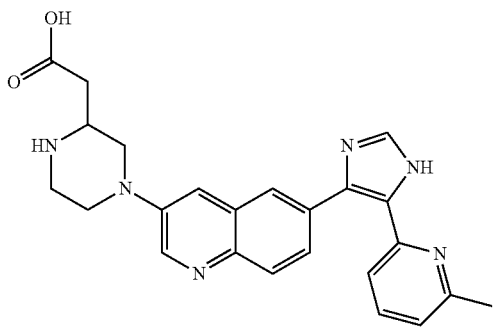

500

A vial of 36-4 (80 mg, 0.161 mmol), RuPhos (15.07 mg, 0.032 mmol), 1-Boc-2-methoxycarbonylmethylpiperazine (50.0 mg, 0.194 mmol), cesium carbonate (158 mg, 0.484 mmol), and RuPhos Pd G4 (13.73 mg, 0.016 mmol) in 1,4-dioxane (807 μL) was heated to 90° C. for 16 h. The reaction mixture was filtered through a pad of celite and concentrated in vacuum. The crude material was dissolved in DCE (0.300 mL) and 6 M aq. HCl (0.200 mL) was added. The mixture was heated to 80° C. for 3 h. The reaction mixture was concentrated in vacuum to afford the title compound. and 2-(4-(6-(5-(6-methylpyridin-2-yl)-1H-imidazol-4-yl)quinolin-3-yl)piperazin-2-yl)acetic acid was used directly in the next reaction. [M+H]⁺ calcd for $C_{24}H_{24}N_6O_2$ 429.20, found 429.0.

Example 41: Synthesis of methyl 2-(4-(6-(5-(6-methylpyridin-2-yl)-1H-imidazol-4-yl)quinolin-3-yl)piperazin-2-yl)acetate (60)

500 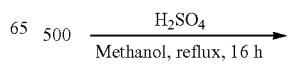 
H₂SO₄ / Methanol, reflux, 16 h

-continued

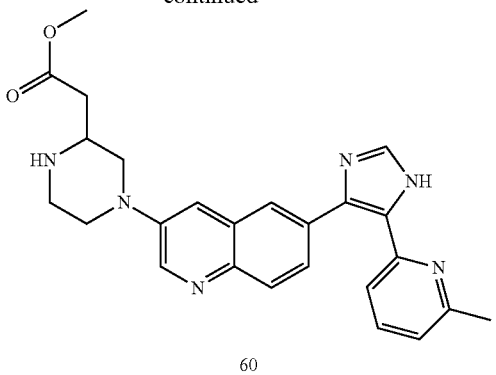

60

A mixture of crude 2-(4-(6-(5-(6-methylpyridin-2-yl)-1H-imidazol-4-yl)quinolin-3-yl)piperazin-2-yl)acetic acid (500) (23 mg, 0.054 mmol) and sulfuric acid (2.86 µL, 0.054 mmol) in MeOH (0.5 mL) was heated to a reflux for 16 h. The reaction mixture was concentrated in vacuum. The residue was purified by preparative HPLC chromatography using a gradient (5 to 75%) of acetonitrile in water with 0.05% trifluoroacetic acid to yield a TFA salt of the title compound (12.2 mg). [M+H]$^+$ calcd for $C_{25}H_{26}N_6O_2$ 443.21, found 443.1.

Example 42: Synthesis of 6-(5-(6-methylpyridin-2-yl)-1H-imidazol-4-yl)-N-(5,6,7,8-tetrahydro-triazolo[1,5-a]pyrazin-2-yl)quinolin-3-amine (338)

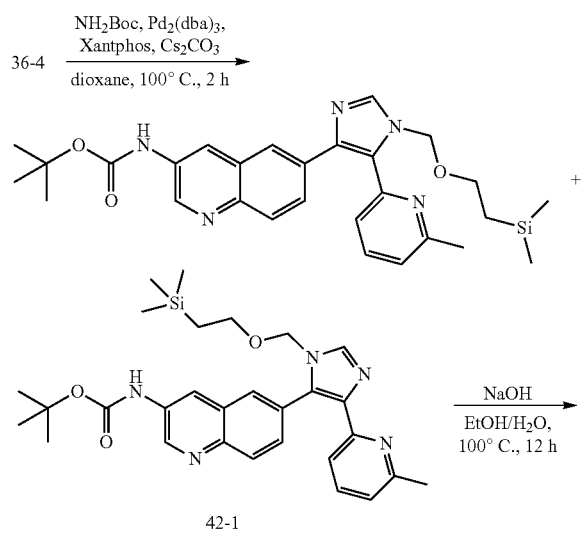

42-1

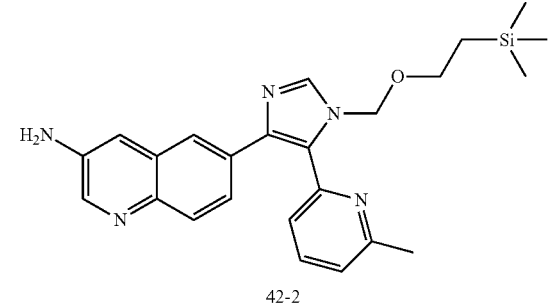

42-2

-continued

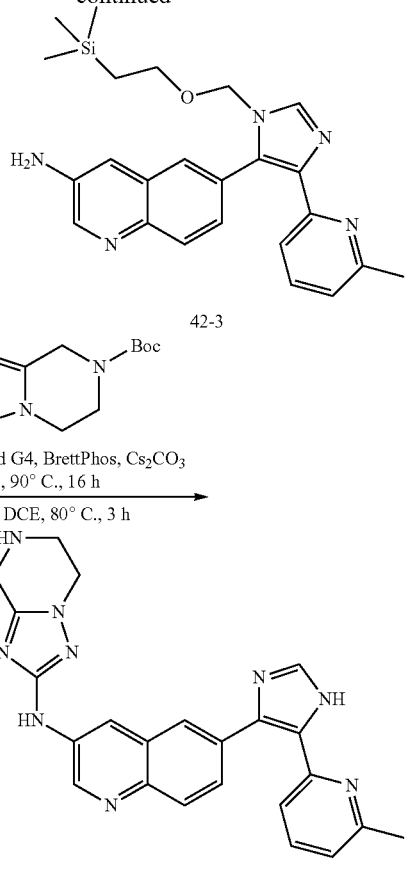

Step A: Preparation of tert-butyl (6-(5-(6-methylpyridin-2-yl)-1-((2-(trimethylsilyl)ethoxy)methyl)-1H-imidazol-4-yl)quinolin-3-yl)carbamate and tert-butyl (6-(4-(6-methylpyridin-2-yl)-1-((2-(trimethylsilyl)ethoxy)methyl)-1H-imidazol-5-yl)quinolin-3-yl)carbamate (42-1). A mixture of 36-4 (3.7 g, 7.47 mmol), NH$_2$Boc (1.3 g, 11.2 mmol), Pd$_2$(dba)$_3$ (684 mg, 0.747 mmol), Xantphos (432 mg, 0.747 mmol) and Cs$_2$CO$_3$ (7.3 g, 22.4 mmol) in dioxane (40 mL) was stirred at 100° C. under N$_2$ for 2 h. The mixture was combined with a second reaction. The combined mixture was concentrated under reduced pressure. The residue was purified by column chromatography (20 to 100% of EA in PE) to give 42-1 (1.7 g, 92% purity, 2 isomers combined) as a yellow solid. [M+H]$^+$ calcd for $C_{29}H_{37}N_5O_3Si$, 532.27, found 532.4.

Step B: Preparation of 6-(5-(6-methylpyridin-2-yl)-1-((2-(trimethylsilyl)ethoxy)methyl)-1H-imidazol-4-yl)quinolin-3-amine (42-2) and 6-(4-(6-methylpyridin-2-yl)-1-((2-(trimethylsilyl)ethoxy)methyl)-1H-imidazol-5-yl)quinolin-3-amine (42-3). A mixture of 42-1 (1.1 g, 2.07 mmol) and NaOH (828 mg, 20.7 mmol) in EtOH (40 mL) and H$_2$O (20 mL) was stirred at 100° C. for 12 h. The mixture was combined with a second reaction. The combined mixture was acidified with AcOH to pH=6. EtOH was removed under reduced pressure. The mixture was extracted with EA (20 mL×3), the combined organic layers were dried over Na$_2$SO$_4$, and concentrated under reduced pressure. The residue was purified by preparative HPLC chromatography using a gradient (22 to 52%) of acetonitrile in water with 0.25% trifluoroacetic acid to yield a to give 42-2 (730 mg, 56% purity, 99% yield) as a yellow solid and 42-3 (220 mg, 17% purity, 97% purity) as a light yellow solid. [M+H]+ calcd for $C_{24}H_{29}N_5OSi$ 432.21, found 432.3.

Step C: Preparation of 6-(5-(6-methylpyridin-2-yl)-1H-imidazol-4-yl)-N-(5,6,7,8-tetrahydro-[1,2,4]triazolo[1,5-a]pyrazin-2-yl)quinolin-3-amine (338). A vial of tert-butyl-2-iodo-5,6-dihydro[1,2,4]triazolo[1,5-a]pyrazine-7(8H)-carboxylate (26.8 mg, 0.076 mmol), 42-2 (30 mg, 0.070 mmol), BrettPhos (7.46 mg, 0.014 mmol), BrettPhos Pd G4 (12.80 mg, 0.014 mmol), and cesium carbonate (67.9 mg, 0.209 mmol) in 1,4-dioxane (695 µl) was heated to 90° C. for 16 h. The reaction mixture was filtered through a pad of celite and concentrated in vacuum. The crude material was dissolved in DCE (0.300 mL) and 6 M aq. HCl (0.200 mL) was added. The mixture was heated to 80° C. for 3 h. The reaction mixture was concentrated in vacuum and purified by preparative HPLC chromatography using a gradient (2 to 60%) of acetonitrile in water with 0.05% trifluoroacetic acid to yield a TFA salt of the title compound (3.5 mg). [M+H]+ calcd for $C_{23}H_{21}N_9$ 424.19, found 424.1.

Example 43: Synthesis of (R)—N-(6-(5-(6-methylpyridin-2-yl)-1H-imidazol-4-yl)quinolin-3-yl)-1,4-diazabicyclo[2.2.2]octane-2-carboxamide (407)

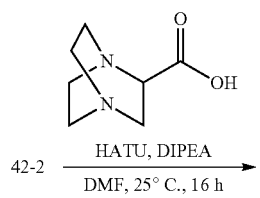

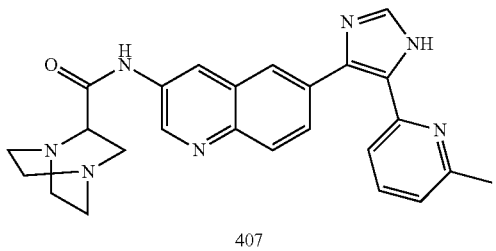

407

A solution of (1S,2R,4S)-1,4-diazabicyclo[2.2.2]octane-2-carboxylic acid (14.11 mg, 0.090 mmol), DIPEA (60.7 µL, 0.348 mmol), and HATU (39.6 mg, 0.104 mmol) in DMF (348 µl) was allowed to stir for 0.5 h before adding 42-2 (30 mg, 0.070 mmol). The resulting mixture was stirred 25° C. for 16 h. The reaction mixture was concentrated in vacuum. The crude material was dissolved in DCE (0.300 mL) and 6 M aq. HCl (0.200 mL) was added. The mixture was heated to 80° C. for 3 h. The reaction mixture was concentrated in vacuum and purified by preparative HPLC chromatography using a gradient (2 to 20%) of acetonitrile in water with 0.05% trifluoroacetic acid to yield a TFA salt of the title compound (8.2 mg). [M+H]+ calcd for $C_{25}H_{25}N_7O$, 440.21, found 440.1.

Example 44: Synthesis of N-(2-((3R,5S)-3,5-dimethylpiperazin-1-yl)ethyl)-6-(5-(6-methylpyridin-2-yl)-1H-imidazol-4-yl)quinolin-3-amine (313)

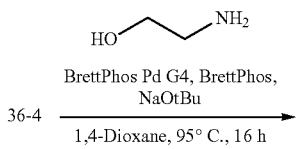

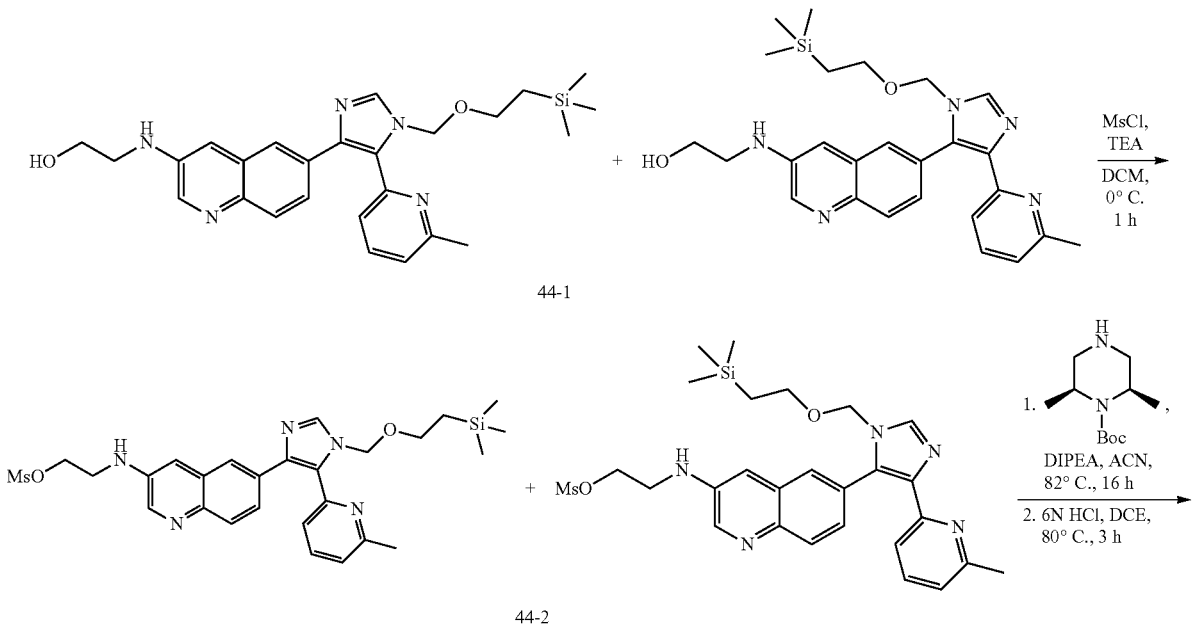

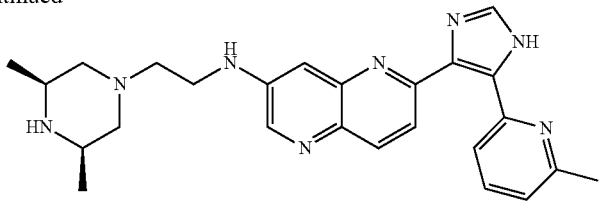

313

Step A: Preparation of 2-((6-(5-(6-methylpyridin-2-yl)-1-((2-(trimethylsilyl)ethoxy)methyl)-1H-imidazol-4-yl)quinolin-3-yl)amino)ethan-1-ol and 2-((6-(4-(6-methylpyridin-2-yl)-1-((2-(trimethylsilyl)ethoxy)methyl)-1H-imidazol-5-yl)quinolin-3-yl)amino)ethan-1-ol. To a vial charged with 36-4 (272 mg, 0.549 mmol) and ethanolamine (132.8 μL, 2.196 mmol) was added BrettPhos Pd G4 (50.5 mg, 0.055 mmol), BrettPhos (29.5 mg, 0.055 mmol) and sodium tert-butoxide (158 mg, 1.647 mmol). The resulting mixture was purged with $N_2$ and dioxane (2745 μL) was added. The resulting mixture was capped and stirred at 95° C. for 32 h. LCMS showed formation of 44-1. The reaction was filtered through a pad of celite and concentrated in vacuum. The residue was purified via normal phase chromatography (0 to 15% of MeOH in DCM) to afford 44-1 (76 mg, 29.1% yield) as a yellow oil. $[M+H]^+$ calcd for $C_{26}H_{33}N_5O_2Si$, 476.24, found 476.0.

Step B: Preparation of 2-((6-(5-(6-methylpyridin-2-yl)-1-((2-(trimethylsilyl)ethoxy)methyl)-1H-imidazol-4-yl)quinolin-3-yl)amino)ethyl methanesulfonate and 2-((6-(4-(6-methylpyridin-2-yl)-1-((2-(trimethylsilyl)ethoxy) methyl)-1H-imidazol-5-yl)quinolin-3-yl)amino)ethyl methanesulfonate (44-2). To a vial containing 44-1 (76 mg, 0.160 mmol) in DCM (1.6 mL) was added TEA (44.5 μL, 0.320 mmol). The resulting solution was cooled to 0° C. before being treated with methanesulfonyl chloride (24.73 μL, 0.320 mmol). The reaction mixture was heated to 25° C. and stirred for 1 h. The reaction mixture was quenched with sat. aq $NaHCO_3$ (1 mL) and extracted with DCM (3 mL×3). The combined organic layers were dried over $Na_2SO_4$ and concentrated in vacuum to afford 44-2 (68.5 mg, two isomers combined, crude) as a yellow oil. $[M+H]^+$ calcd for $C_{27}H_{35}N_5O_4SSi$ 554.22, found 554.0. $^1H$ NMR (400 MHz, Methanol-$d_4$) δ 8.92 (s, 1H), 8.72 (d, J=2.7 Hz, 1H), 8.16 (d, J=1.9 Hz, 1H), 8.07 (dd, J=8.8, 0.8 Hz, 1H), 7.81-7.69 (m, 3H), 7.36 (ddt, J=21.6, 7.9, 0.8 Hz, 2H), 3.71-3.55 (m, 6H), 3.24 (t, J=6.1 Hz, 2H), 2.76 (dd, J=12.9, 11.3 Hz, 2H), 2.64 (s, 3H), 1.37 (d, J=6.5 Hz, 6H).

Step C: Preparation of N-(2-((3R,5S)-3,5-dimethylpiperazin-1-yl)ethyl)-6-(5-(6-methylpyridin-2-yl)-1H-imidazol-4-yl)quinolin-3-amine (313). A solution of a crude mixture of 44-2 (17 mg, 0.031 mmol), DIPEA (21.45 μL, 0.123 mmol), and (2R,6S)-tert-butyl 2,6-dimethylpiperazine-1-carboxylate (14.53 mg, 0.068 mmol) in acetonitrile (0.3 mL) was heated to 80° C. for 16 h. The reaction was concentrated in vacuum. The crude material was dissolved in DCE (0.300 mL) and 6 M aq. HCl (0.200 mL) was added. The mixture was heated to 80° C. for 3 h. The reaction mixture was concentrated in vacuum. The residue was purified by preparative HPLC chromatography using a gradient (2 to 15%) of acetonitrile in water with 0.05% trifluoroacetic acid to yield a TFA salt of the title compound (4.8 mg). $[M+H]^+$ calcd for $C_{26}H_3, N_7$ 442.26, found 442.2. $^1H$ NMR (400 MHz, Methanol-$d_4$) δ 8.92 (s, 1H), 8.72 (d, J=2.7 Hz, 1H), 8.16 (d, J=1.9 Hz, 1H), 8.07 (dd, J=8.8, 0.8 Hz, 1H), 7.81-7.69 (m, 3H), 7.36 (ddt, J=21.6, 7.9, 0.8 Hz, 2H), 3.71-3.55 (m, 6H), 3.24 (t, J=6.1 Hz, 2H), 2.76 (dd, J=12.9, 11.3 Hz, 2H), 2.64 (s, 3H), 1.37 (d, J=6.5 Hz, 6H).

Example 45: Synthesis of N-methyl-2-(4-(6-(5-(6-methylpyridin-2-yl)-1H-1,2,3-triazol-4-yl)quinolin-3-yl)-1H-pyrazol-1-yl)ethan-1-amine (125)

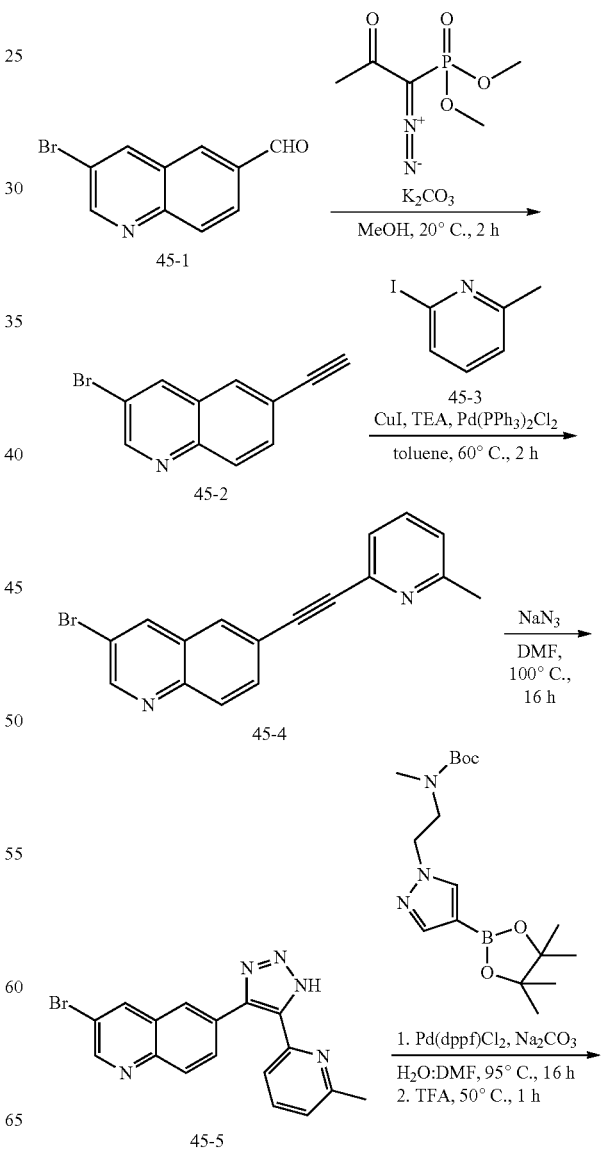

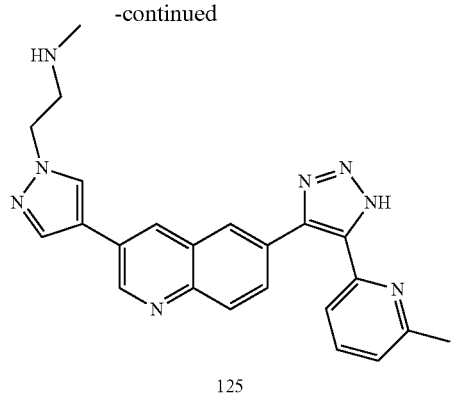

125

Step A: Preparation of 3-bromo-6-ethynylquinoline (45-2). To a suspension of 45-1 (2.8 g, 11.86 mmol) and $K_2CO_3$ (3.3 g, 23.72 mmol) in MeOH (40 mL) was added dropwise dimethyl (1-diazo-2-oxopropyl)phosphonate (4.6 g, 23.72 mmol) and stirred at 25° C. for 2 h. The mixture was diluted with water (100 mL) and extracted with EA (100 mL×3). The organic layer was concentrated in vacuum. The residue was purified by silica gel column (0 to 10% of EA in PE) to obtain 45-2 (2.2 g, 80% yield, 100% purity) as white solid. $[M+H]^+$ calcd for $C_{11}H_6BrN$ 231.97, found 231.9.

Step B: Preparation of 3-bromo-6-((6-methylpyridin-2-yl)ethynyl)quinoline (45-4). A mixture of 45-2 (1.0 g, 4.4 mmol), 45-3 (1.7 g, 5.2 mmol), $Pd(PPh_3)_2Cl_2$ (300 mg, 0.44 mmol), CuI (80 mg, 0.44 mmol) and TEA (900 mg, 8.8 mmol) in toluene (20 mL) was stirred at 60° C. for 2 h under $N_2$. The mixture was filtered and the filtrate was concentrated in vacuum. The residue was purified by silica gel column (0 to 30% of EA in PE) to give 45-4 (2.85 g, 75% yield, 97% purity) as yellow solid. $[M+H]^+$ calcd for $C_{17}H_{11}BrN_2$ 323.01, found 323.0.

Step C: Preparation of 3-bromo-6-(5-(6-methylpyridin-2-yl)-1H-1,2,3-triazol-4-yl)quinoline (45-5). A vial of 45-4 (100 mg, 0.309 mmol) and sodium azide (60.3 mg, 0.928 mmol) in DMF (3.09 mL) was heated 100° C. for 16 h. The reaction was quenched with water (10 mL) and extracted with DCM (20 mL×3). The organic layer was dried over $Na_2SO_4$, filtered, and concentrated in vacuum. The residue was purified via normal phase chromatography (0 to 20% MeOH in DCM) yielding 45-5 (58 mg, 51.2% yield) as a yellow solid. $[M+H]^+$ calcd for $C_{17}H_{12}BrN_5$ 366.03, found 366.0.

Step D: Preparation of N-methyl-2-(4-(6-(5-(6-methylpyridin-2-yl)-1H-1,2,3-triazol-4-yl)quinolin-3-yl)-1H-pyrazol-1-yl)ethan-1-amine (125). A vial of tert-butyl methyl(2-(4-(4,4,5,5-tetramethyl-1,3,2-dioxaborolan-2-yl)-1H-pyrazol-1-yl)ethyl)carbamate (55.6 mg, 0.158 mmol), 45-5 (29 mg, 0.079 mmol), sodium carbonate (25.2 mg, 0.238 mmol), and $Pd(dppf)Cl_2$ (12.93 mg, 0.016 mmol) in degassed water (264 µL):DMF (528 µL) was heated to 95° C. for 16 h. The reaction mixture was filtered through a pad of celite and concentrated in vacuum. TFA (300 µL) was added to the residue and heated to 50° C. for 1 h. TFA was removed in vacuum and the residue was purified by preparative HPLC chromatography using a gradient (2 to 40%) of acetonitrile in water with 0.05% trifluoroacetic acid to yield a TFA salt of the title compound (13.2 mg). $[M+H]^+$ calcd for $C_{23}H_{22}N_8$ 411.20, found 411.1.

Example 46: Synthesis of N-(2-(4-isopropylpiperazin-1-yl)ethyl)-6-(5-(6-methylpyridin-2-yl)-1H-1,2,3-triazol-4-yl)quinolin-3-amine (621)

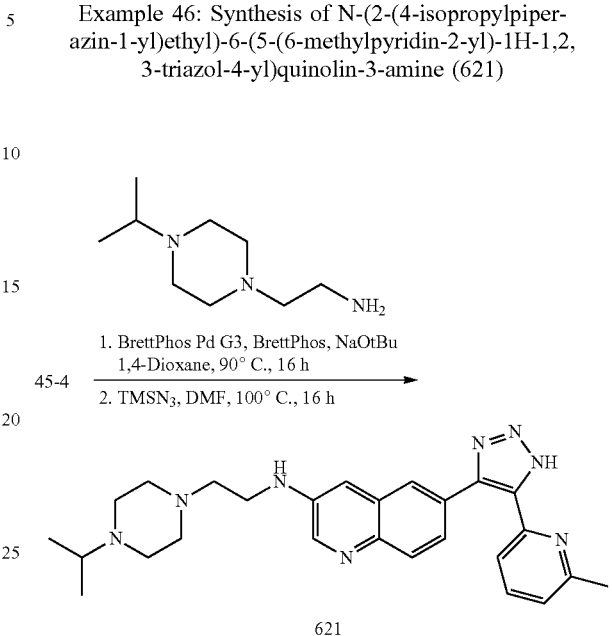

621

A vial of 45-4 (50 mg, 0.155 mmol), 2-(4-isopropylpiperazin-1-yl)-ethylamine (79 mg, 0.464 mmol), sodium tert-butoxide (44.6 mg, 0.464 mmol), BrettPhos (8.30 mg, 0.015 mmol), BrettPhos Pd G3 (14.02 mg, 0.015 mmol) in 1,4-dioxane (774 µL) (degassed with $N_2$) was heated to 90° C. for 16 h. The reaction mixture was filtered through a pad of celite and concentrated in vacuum. The residue was purified by column chromatography (0 to 70% of EA in Hex) yielding N-(2-(4-isopropylpiperazin-1-yl)ethyl)-6-((6-methylpyridin-2-yl)ethynyl)quinolin-3-amine (61 mg). N-(2-(4-isopropylpiperazin-1-yl)ethyl)-6-((6-methylpyridin-2-yl)ethynyl)quinolin-3-amine (58 mg, 0.140 mmol) and trimethylsilyl azide (74.1 µL, 0.561 mmol) in DMF (0.815 mL) were heated 100° C. for 16 h. The reaction mixture was concentrated in vacuum. The residue was purified by preparative HPLC chromatography using a gradient (2 to 40%) of acetonitrile in water with 0.05% trifluoroacetic acid to yield a TFA salt of the title compound (2.1 mg). $[M+H]^+$ calcd for $C_{26}H_{32}N_8$ 457.28, found 457.2.

Example 47: Synthesis of N-methyl-2-(4-(6-(1-methyl-4-(6-methylpyridin-2-yl)-1H-1,2,3-triazol-5-yl)quinolin-3-yl)-1H-pyrazol-1-yl)ethan-1-amine (628)

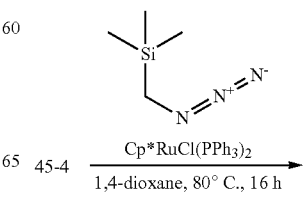

45-4  $\xrightarrow{\text{Cp*RuCl(PPh}_3)_2}{\text{1,4-dioxane, 80° C., 16 h}}$

685
-continued

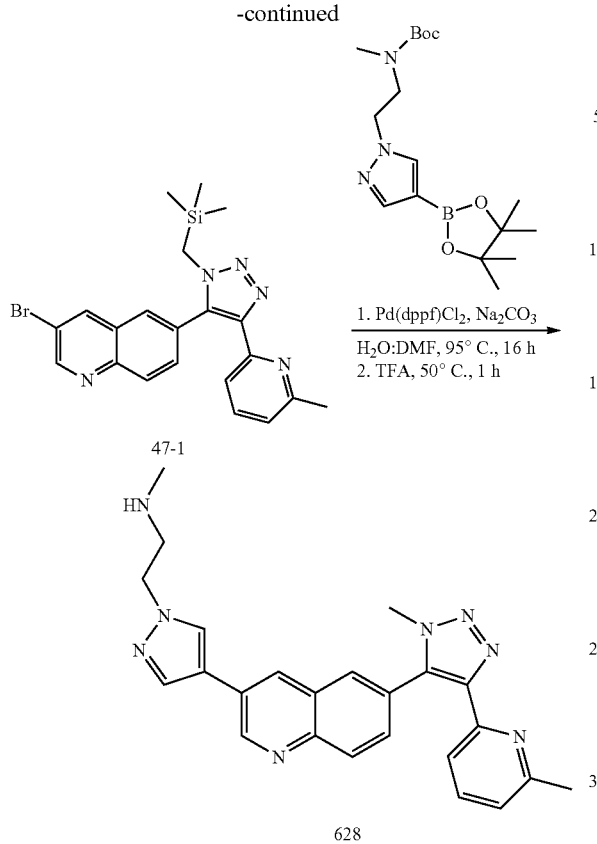

Step A: Preparation of 3-bromo-6-(4-(6-methylpyridin-2-yl)-1-((trimethylsilyl)methyl)-1H-1,2,3-triazol-5-yl)quinoline (47-1). A vial of 45-4 (150 mg, 0.464 mmol), trimethylsilylmethylazide (96 mg, 0.743 mmol), and Cp*RuCl(PPh₃)₂ (37.0 mg, 0.046 mmol) in 1,4-dioxane (2.47 mL) was sparged with N₂ for 10 minutes. The reaction mixture was then heated to 80° C. for 16 h. Two isomers were formed. The reaction mixture was filtered through a pad of celite and concentrated in vacuum. The residue was purified via normal phase chromatography (0 to 85% of EA in Hex) to yield 47-1 (139 mg, 66.2% yield, two isomers combined). [M+H]⁺ calcd for $C_{21}H_{22}BrN_5Si$, 452.08, found 452.0.

Step B: Preparation of N-methyl-2-(4-(6-(1-methyl-4-(6-methylpyridin-2-yl)-1H-1,2,3-triazol-5-yl)quinolin-3-yl)-1H-pyrazol-1-yl)ethan-1-amine (628). A vial of tert-butyl methyl(2-(4-(4,4,5,5-tetramethyl-1,3,2-dioxaborolan-2-yl)-1H-pyrazol-1-yl)ethyl)carbamate (40.4 mg, 0.115 mmol), 47-1 (26 mg, 0.057 mmol), sodium carbonate (18.27 mg, 0.172 mmol), and Pd(dppf)Cl₂ (9.39 mg, 0.011 mmol) in degassed water (192 µL):DMF (383 µL) was heated to 95° C. for 16 h. The TMS group was removed during the Suzuki-Miyaura reaction. The reaction mixture was filtered through a pad of celite and concentrated in vacuum. TFA (300 µL) was added to the residue and heated to 50° C. for 1 h. TFA was removed in vacuum and the residue was purified by preparative HPLC chromatography using a gradient (5 to 65%) of acetonitrile in water with 0.05% trifluoroacetic acid to yield a TFA salt of the title compound (28.4 mg). [M+H]⁺ calcd for $C_{24}H_{24}N_8$ 425.21, found 425.2.

686

Example 48: Synthesis of N-(2-(4-isopropylpiperazin-1-yl)ethyl)-6-(2-(6-methylpyridin-2-yl)imidazo[1,2-a]pyridin-3-yl)quinolin-3-amine (293)

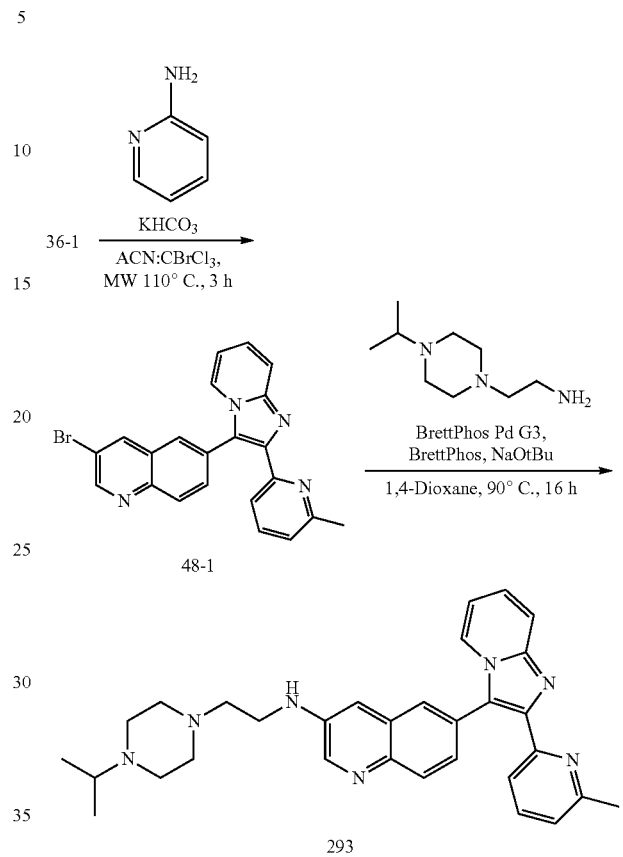

Step A: Preparation of 3-bromo-6-(2-(6-methylpyridin-2-yl)imidazo[1,2-a]pyridin-3-yl)quinoline (48-1). A vial of 36-1 (200 mg, 0.586 mmol), 2-aminopyridine (112 mg, 0.645 mmol) and potassium bicarbonate (58.7 mg, 0.586 mmol) in 9:2 acetonitrile (1.05 mL):CBrCl₃ (0.117 mL) was heated to 110° C. for 3 h in the microwave. The reaction mixture was concentrated in vacuum. The residue was purified by normal phase chromatography (0 to 10% of MeOH in DCM) to afford 48-1 (222 mg, 91% yield) as a beige solid. [M+H]⁺ calcd for $C_{22}H_{15}BrN_4$ 415.05, found 415.0.

Step B: Preparation of N-(2-(4-isopropylpiperazin-1-yl)ethyl)-6-(2-(6-methylpyridin-2-yl)imidazo[1,2-a]pyridin-3-yl)quinolin-3-amine (293). A vial of 48-1 (30 mg, 0.072 mmol), 2-(4-isopropyl-piperazin-1-yl)-ethylamine (24.72 mg, 0.144 mmol), sodium tert-butoxide (20.83 mg, 0.217 mmol), BrettPhos (3.88 mg, 7.22 µmol), BrettPhos Pd G3 (6.55 mg, 7.22 µmol) in 1,4-dioxane (346 µL) (degassed with N₂) was heated to 90° C. for 16 h. The reaction mixture was filtered through a pad of celite and concentrated in vacuum. The residue was purified by preparative HPLC chromatography using a gradient (2 to 50%) of acetonitrile in water with 0.05% trifluoroacetic acid to yield a TFA salt of the title compound (25.8 mg). [M+H]⁺ calcd for $C_{31}H_{35}N_7$ 506.30, found 506.1.

Example 49: Synthesis of N-methyl-2-(4-(6-(2-(6-methylpyridin-2-yl)-1H-pyrrolo[2,3-b]pyridin-3-yl)quinolin-3-yl)-1H-pyrazol-1-yl)ethan-1-amine (306)
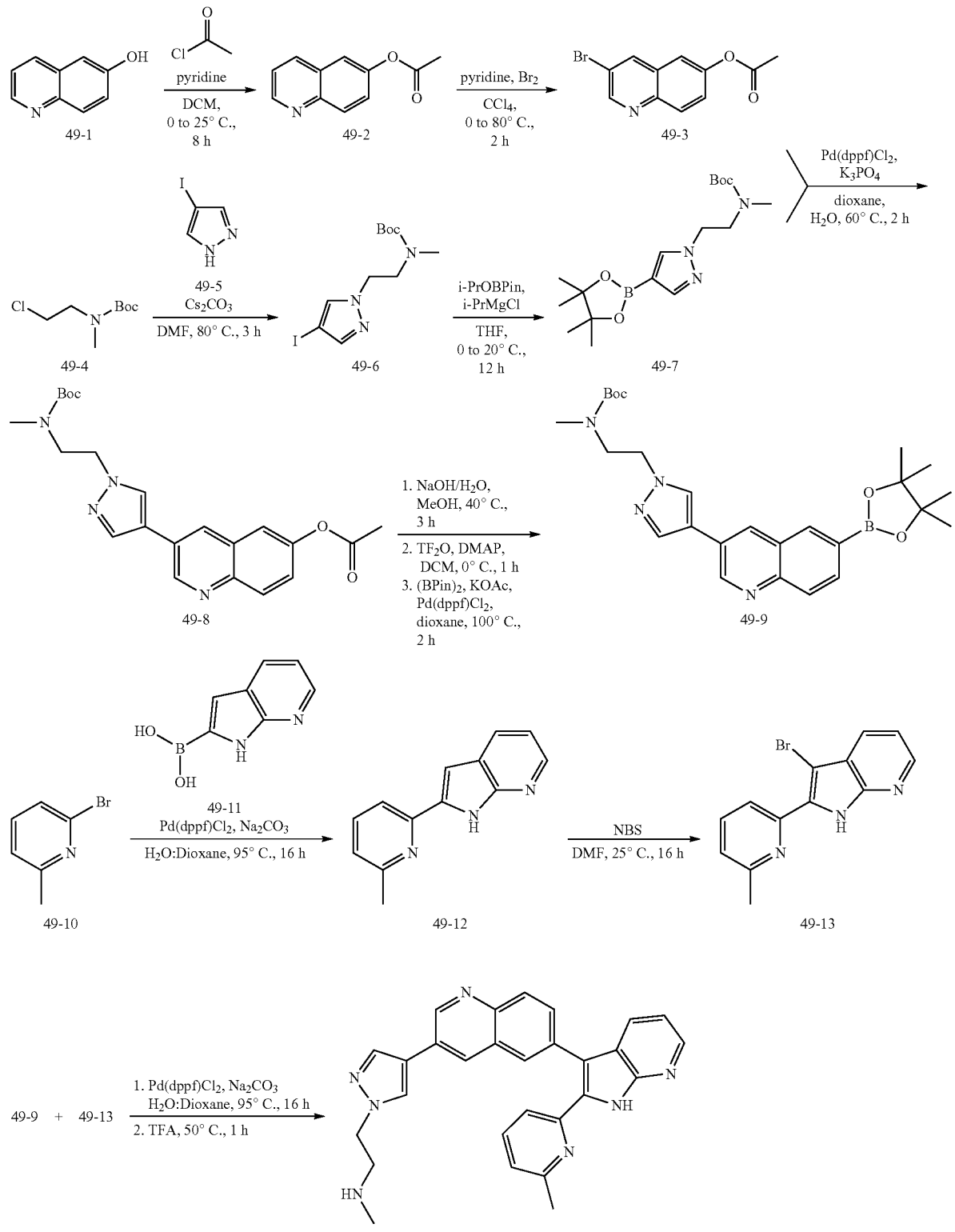

Step A: Preparation of quinolin-6-yl acetate (49-2). To a solution of 49-1 (24.0 g, 165 mmol) and pyridine (15.7 g, 198 mmol) in DCM (300 mL) was added acetyl chloride (15.5 g, 198 mmol) dropwise at 0° C. Then the mixture was stirred at 25° C. for 8 h under $N_2$. The mixture was basified by sat. $NaHCO_3$ solution to pH=8 and extracted by EA (300 mL*2). The organic layer was concentrated in vacuum and purified by silica gel column (0 to 36% of EA in PE) to obtain 49-2 (26.8 g, 86% yield, 99% purity) as yellow solid. $[M+H]^+$ calcd for $C_{11}H_9NO_2$ 188.06, found 188.0.

Step B: Preparation of 3-bromoquinolin-6-yl acetate (49-3). To a solution of 49-2 (26.8 g, 143 mmol) and pyridine (24.9 g, 315 mmol) in $CCl_4$ (400 mL) was added $Br_2$ (45.7 g, 286 mmol) at 0° C. The mixture was stirred at 80° C. for 2 h. The mixture was filtered and the filtrate was concentrated in vacuum. The residue was purified by trituration (10% of EA in PE (50 mL)) to obtain 49-3 (32.8 g, 86% yield, 87% purity) as white solid. $[M+H]^+$ calcd for $C_{11}H_8BrNO_2$ 265.97, found 265.8.

Step C: Preparation of tert-Butyl (2-(4-iodo-1H-pyrazol-1-yl)ethyl)(methyl)carbamate (49-6). A mixture of 49-5 (24.0 g, 124 mmol), 49-4 (47.9 g, 247 mmol), and $Cs_2CO_3$ (80.5 g, 247 mmol) in DMF (400 mL) was stirred at 80° C. for 3 h. The mixture was filtered. The filtrate was diluted with brine (1 L) and extracted with EA (500 mL×2). The organic layer was concentrated in vacuum and purified by silica gel column (0 to 20% of EA in PE) to obtain 49-6 (40.0 g, 93% yield, 97% purity) as yellow oil. $[M+H]^+$ calcd for $C_{11}H_{18}INO_2$ 352.04, found 351.9.

Step D: Preparation of tert-butyl methyl(2-(4-(4,4,5,5-tetramethyl-1,3,2-dioxaborolan-2-yl)-1H-pyrazol-1-yl)ethyl)carbamate (49-7). To a mixture of 49-6 (40.0 g, 114 mmol), i-PrOBPin (31.8 g, 171 mmol) in THF (300 mL) was added i-PrMgCl (114 mL, 228 mmol) at 0° C. The reaction was stirred at 20° C. for 12 h. The reaction mixture was concentrated in vacuum to afford 49-7 (91.0 g, 51% purity) as yellow solid which was used directly. $[M+H]^+$ calcd for $C_{17}H_{30}BN_3O_4$ 352.23, found 352.0.

Step E: Preparation of 3-(1-(2-((tert-butoxycarbonyl)(methyl)amino)ethyl)-1H-pyrazol-4-yl)quinolin-6-yl acetate (49-8). To a solution of 49-3 (9.2 g, 34.6 mmol), 49-7 (30.0 g, 38.1 mmol) and $K_3PO_4$ (14.7 g, 69.3 mmol) in dioxane (160 mL) and $H_2O$ (32 mL) was added $Pd(dppf)Cl_2$ (2.5 g, 3.46 mmol). The mixture was stirred at 60° C. for 2 h under $N_2$. The mixture was concentrated in vacuum and purified by silica gel column chromatography (40% to 80% of EA in PE) to obtain 49-8 as a black oil (6.3 g, 41% yield).

Step F: Preparation of tert-butyl (2-(4-(6-hydroxyquinolin-3-yl)-1H-pyrazol-1-yl)ethyl)(methyl)carbamate. A solution of 49-8 (6.3 g, 15.3 mmol) in $NaOH/H_2O$ (14 mL, 40%) and MeOH (80 mL) was stirred at 40° C. for 3 h. TLC showed starting material was consumed. The mixture was concentrated in vacuum. The residue was acidified by HCl (2 M) to pH=7. The mixture was diluted with water (100 mL) and extracted with EA (100 mL*3). The organic layer was concentrated in vacuum and purified by silica gel column chromatography (40 to 90% of EA in PE) to obtain the title alcohol (4.6 g, 81% yield) as a white solid.

Step G: Preparation of 3-(1-(2-((tert-butoxycarbonyl)(methyl)amino)ethyl)-1H-pyrazol-4-yl)quinolin-6-yl trifluoromethanesulfonate. To a solution of tert-butyl (2-(4-(6-hydroxyquinolin-3-yl)-1H-pyrazol-1-yl)ethyl)(methyl)carbamate (4.6 g, 12.5 mmol) and DMAP (3.1 g, 25.0 mmol) in DCM (50 mL) was dropwise added trifluoromethanesulfonic anhydride (4.2 g, 15.0 mmol) over 0.5 h at 0° C. The mixture was stirred at 0° C. for 0.5 h. TLC showed starting material was consumed. The mixture was concentrated in vacuum and purified by silica gel column chromatography (30 to 60% of EA in PE) to obtain the title triflate (4.0 g, 64% yield) as a white solid.

Step H: Preparation of tert-butyl methyl(2-(4-(6-(4,4,5-trimethyl-1,3,2-dioxaborolan-2-yl)quinolin-3-yl)-1H-pyrazol-1-yl)ethyl)carbamate (49-9). To a mixture of 3-(1-(2-((tert-butoxycarbonyl)(methyl)amino) ethyl)-1H-pyrazol-4-yl)quinolin-6-yl trifluoromethanesulfonate (4.0 g, 7.99 mmol) and $(BPin)_2$ (2.4 g, 9.59 mmol) in dioxane (60 mL) was added $Pd(dppf)Cl_2$ (584 mg, 0.799 mmol) and KOAc (1.6 g, 16.0 mmol). The mixture was stirred at 100° C. for 2 h under $N_2$ atmosphere. The mixture was concentrated in vacuum and purified by silica gel column chromatography (30 to 70% of EA in PE) to obtain 49-9 (4.1 g, 76% yield, 99% purity) as a white solid.

Step I: Preparation of 2-(6-methylpyridin-2-yl)-1H-pyrrolo[2,3-b]pyridine (49-12). A mixture of 49-10 (60.8 µl, 0.535 mmol), 49-11 (66.6 mg, 0.411 mmol), $Pd(dppf)Cl_2$ (60.2 mg, 0.082 mmol), and sodium carbonate (131 mg, 1.234 mmol) in water (686 µl):1,4-dioxane (1371 µl) was sparged with $N_2$ for 5 min before heating to 95° C. for 16 h. The reaction mixture was filtered through a pad of celite and concentrated in vacuum yielding 49-12 (86 mg), which was used directly in the next step without further purification. $[M+H]^+$ calcd for $C_{13}H_{11}N_3$ 210.10, found 210.0.

Step J: Preparation of 3-bromo-2-(6-methylpyridin-2-yl)-1H-pyrrolo[2,3-b]pyridine (49-13). To a solution of 49-12 (86 mg, 0.411 mmol, crude) in anhydrous DMF (2.0 mL) was added N-bromosuccinimide (117 mg, 0.658 mmol). The resulting mixture was allowed to stir at 25° C. for 16 h. The reaction was concentrated and the residue was purified via normal phase chromatography (5 to 80% of EA in Hex) to afford 49-13 (21 mg, 17.7% yield) as a beige solid. $[M+H]^+$ calcd for $C_{13}H_{10}BrN_3$ 288.01, found 288.0.

Step K: Preparation of N-methyl-2-(4-(6-(2-(6-methylpyridin-2-yl)-1H-pyrrolo[2,3-b]pyridin-3-yl)quinolin-3-yl)-1H-pyrazol-1-yl)ethan-1-amine (306). A vial of 49-9 (16.50 mg, 0.042 mmol), 49-13 (10.0 mg, 0.035 mmol), sodium carbonate (14.7 mg, 0.139 mmol), and $Pd(dppf)Cl_2$ (5.1 mg, 6.94 µmol) in degassed water (69 µL):1,4-dioxane (278 µL) was heated to 95° C. for 16 h. The reaction mixture was filtered through a pad of celite and concentrated in vacuum. TFA (300 µL) was added to the residue and heated to 50° C. for 1 hour. TFA was removed in vacuum. The residue was purified by preparative HPLC chromatography using a gradient (5 to 75%) of acetonitrile in water with 0.05% trifluoroacetic acid to yield a TFA salt of the title compound (4.4 mg). $[M+H]^+$ calcd for $C_{28}H_{25}N_7$ 460.22, found 460.1.

Example 50: Synthesis of 6-(2-(6-methylpyridin-2-yl)-5,6,7,8-tetrahydroimidazo[1,2-a]pyrazin-3-yl)-3-(1H-pyrazol-4-yl)quinoline (635)

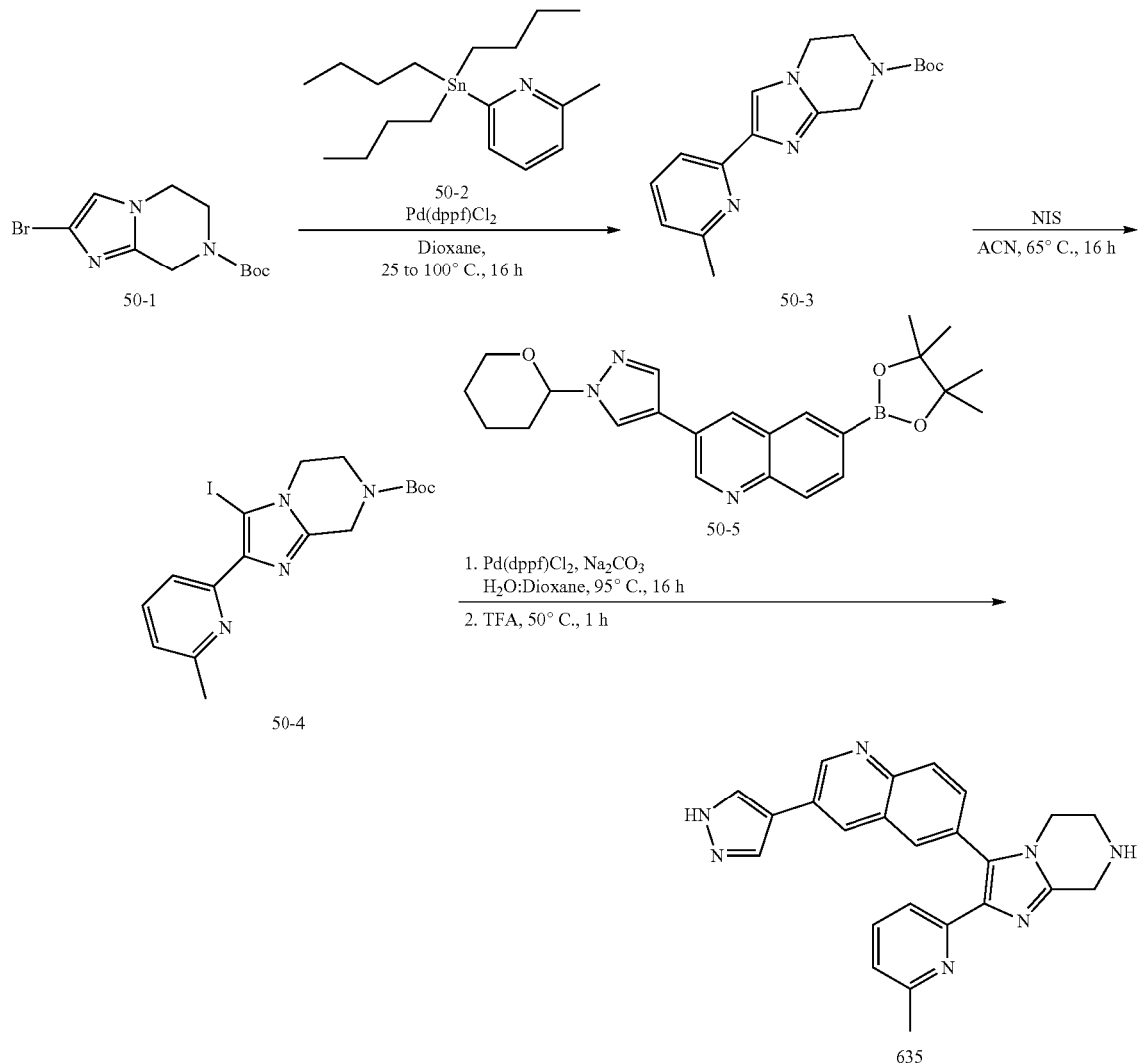

Step A: Preparation of tert-butyl 2-(6-methylpyridin-2-yl)-5,6-dihydroimidazo[1,2-a]pyrazine-7(8H)-carboxylate (50-3). A vial of 50-1 (80 mg, 0.265 mmol), 50-2 (172 mg, 0.450 mmol), and Pd(dppf)Cl$_2$ (38.7 mg, 0.053 mmol) in 1,4-dioxane (1324 μl) was sparged with N$_2$ for 10 min before allowing to stir for 1 h at 25° C. The reaction was then heated to 100° C. for 16 h. SilaMetS® Cysteine (0.691 mmol) was added to the reaction mixture and allowed to stir for 2 h at 25° C. The reaction mixture was filtered through a pad of celite and concentrated in vacuum. The residue was purified via column chromatography (0 to 20% of MeOH in DCM) to afford 50-3 (55 mg, 66.1% yield). [M+H]$^+$ calcd for C$_{17}$H$_{22}$N$_4$O$_2$ 315.17, found 315.0.

Step B: Preparation of tert-butyl 3-iodo-2-(6-methylpyridin-2-yl)-5,6-dihydroimidazo[1,2-a]pyrazine-7(8H)-carboxylate (50-4). To a vial of 50-3 (55 mg, 0.175 mmol) in ACN (875 μL) was added N-iodosuccinimide (55.1 mg, 0.245 mmol). The mixture was allowed to stir for 16 h at 65° C. The reaction mixture was concentrated in vacuum. The residue was purified via column chromatography (0 to 10% of MeOH in DCM) to afford 50-4 (37 mg, 48% yield) as a yellow solid. [M+H]$^+$ calcd for C$_{17}$H$_{21}$IN$_4$O$_2$ 441.07, found 441.0.

Step C: Preparation of 6-(2-(6-methylpyridin-2-yl)-5,6,7,8-tetrahydroimidazo[1,2-a]pyrazin-3-yl)-3-(1H-pyrazol-4-yl)quinoline (635). A vial of 50-5 (44.3 mg, 0.109 mmol), 50-4 (37.0 mg, 0.084 mmol), Pd(dppf)Cl$_2$ (12.3 mg, 0.017 mmol), and sodium carbonate (26.7 mg, 0.252 mmol) in 1,4-dioxane (336 μL):water (84 μL) was sparged with N$_2$ for 10 min before heating to 100° C. for 16 h. The reaction mixture was filtered through a pad of celite and concentrated in vacuum. TFA (300 μL) was added to the residue and heated to 50° C. for 1 hour. TFA was removed in vacuum. The residue was purified by preparative HPLC chromatography using a gradient (2 to 20%) of acetonitrile in water with 0.05% trifluoroacetic acid to yield a TFA salt of the title compound (6.4 mg). [M+H]$^+$ calcd for C$_{24}$H$_{21}$N$_7$ 408.19, found 408.1.

Example 51: Synthesis of N-methyl-1-(6-(3-(6-methylpyridin-2-yl)-1H-pyrazol-4-yl)quinolin-4-yl)methanamine (356)

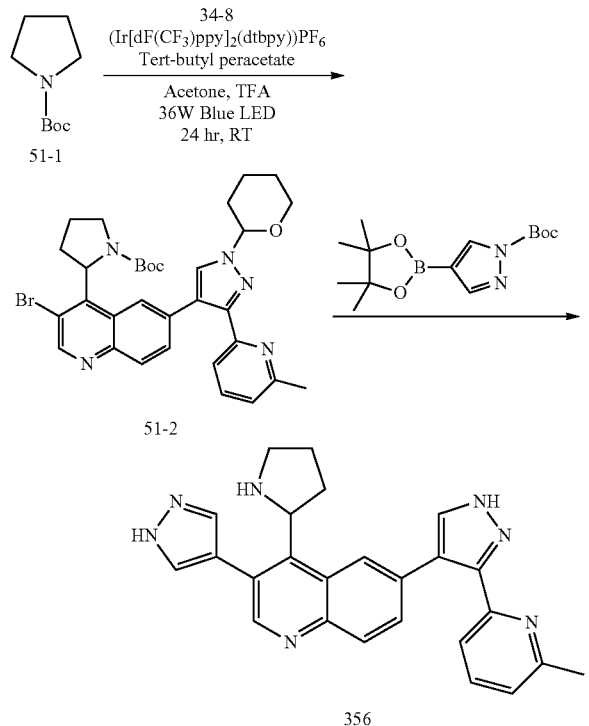

Step A: Preparation of tert-butyl 2-(3-bromo-6-(3-(6-methylpyridin-2-yl)-1-(tetrahydro-2H-pyran-2-yl)-1H-pyrazol-4-yl)quinolin-4-yl)pyrrolidine-1-carboxylate (51-2). To a vial containing 34-8 (15.06 mg, 0.034 mmol) was added 51-1 (14.35 mg, 0.084 mmol), (Ir[dF(CF$_3$)ppy]$_2$(dtbpy))PF$_6$ (0.752 mg, 0.670 μmol), acetone (335 μL), TFA (5.16 μL, 0.067 mmol) and tert-butyl peracetate, 50 WT. % solution in odorless mineral spirits (21.40 μL, 0.067 mmol). The resulting yellow mixture was sparged with nitrogen for 1 min, and then sealed and let stir under irradiation with a 36 W Blue LED at RT for 24 hr. The resulting mixture was treated with TEA (23.36 μL, 0.168 mmol), and then concentrated in vacuo. The crude product was purified by column chromatography (MeOH/DCM=0%~10%) to afford 51-2 (12.6 mg, 55% yield, 90% purity) as a white solid. [M+H]$^+$ calcd for C$_{32}$H$_{36}$BrN$_5$O$_3$ 618.10, found 618.

Step B: Preparation of N-methyl-1-(6-(3-(6-methylpyridin-2-yl)-1H-pyrazol-4-yl)quinolin-4-yl)methanamine (356). To a vial containing 51-2 (12.6 mg, 0.020 mmol) was added tert-butyl 4-(4,4,5,5-tetramethyl-1,3,2-dioxaborolan-2-yl)-1H-pyrazole-1-carboxylate (15.45 mg, 0.053 mmol) followed by potassium phospate, tribasic (16.7 mg, 0.079 mmol), Xphos (1.25 mg, 2.63 μmol), and Xphos Pd G4 (2.26 mg, 2.63 μmol). The resulting mixture was purged with nitrogen before degassed water (13 μl) and 1,4-dioxane (118 μl) was added. The vial was capped and stirred at 100° C. for 2 hr. The reaction was then cooled and concentrated in vacuo. The resulting residue was treated with 0.3 mL of TFA and stirred at 50° C. for 1 hr. The crude product was concentrated in vacuo and purified by preparative HPLC chromatography using a gradient (2 to 40%) of acetonitrile in water with 0.05% trifluoroacetic acid to yield a TFA salt of the title compound (2.3 mg). [M+H]+ calcd for C$_{25}$H$_{23}$N$_7$ 422.20 found 422.1.

Example 52: Synthesis of (1R,2R)-2-(4-(6-(5-(6-methylpyridin-2-yl)-1H-imidazol-4-yl)quinolin-3-yl)-1H-pyrazol-1-yl)cyclohexan-1-amine (194)

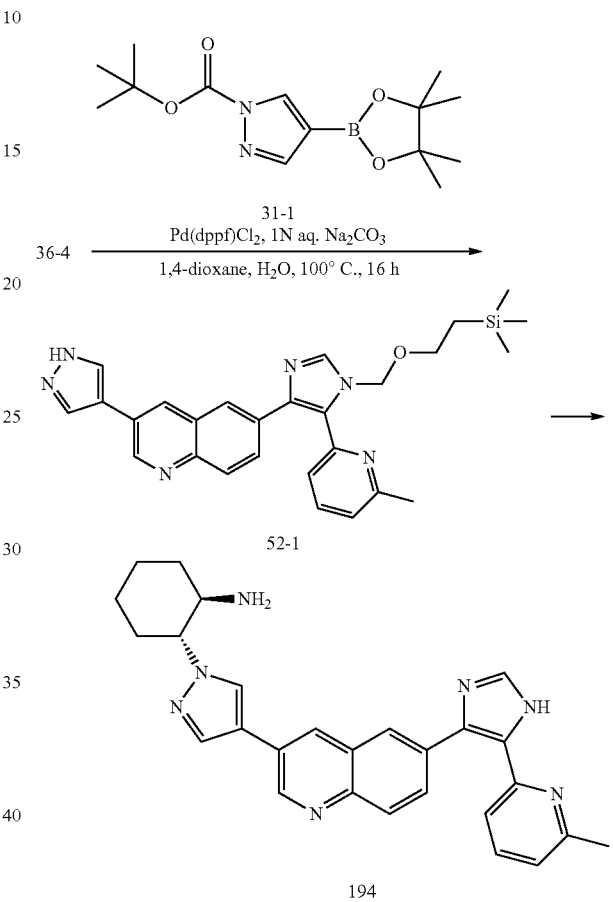

Step A: Preparation of 6-(5-(6-methylpyridin-2-yl)-1-((2-(trimethylsilyl)ethoxy)methyl)-1H-imidazol-4-yl)-3-(1H-pyrazol-4-yl)quinoline (52-1). To a vial containing 36-4 (303 mg, 0.612 mmol) was added 31-1 (234 mg, 0.795 mmol) followed by 1 N aq. sodium carbonate (3.06 mL, 3.06 mmol) and Pd(dppf)Cl$_2$ (45 mg, 0.061 mmol). The resulting mixture was purged with N$_2$ before 1,4-dioxane (3.06 mL) was added. The resulting mixture was stirred at 100° C. for 16 hr. Afterwards, the reaction was filtered through a pad of celite and concentrated in vacuo. The residue was purified by column (0 to 10% of MeOH in DCM), yielding 52-1 (238 mg) as a brown oil. [M+H]+ calcd for C$_{27}$H$_{30}$N$_{60}$Si, 483.23 found 483.1.

Step B: Preparation of (1R,2R)-2-(4-(6-(5-(6-methylpyridin-2-yl)-1H-imidazol-4-yl)quinolin-3-yl)-1H-pyrazol-1-yl)cyclohexan-1-amine (194). To a vial containing (1R,2R)-trans-N-Boc-2-aminocyclohexanol (194 mg, 0.902 mmol) was added DCM (4.51 mL) and triethylamine (0.314 mL, 2.25 mmol) and the resulting mixture was cooled to 0° C. before being treated with methanesulfonyl chloride (0.126 mL, 1.624 mmol). The resulting clear solution was stirred at 0° C. and slowly allowed to warm up to 25° C. for 7 h. The reaction was quenched with NaHCO₃ (sat), and the aq. layer was extracted with DCM. The combined organics were dried over Na₂SO₄ and concentrated in vacuo. To the resulting white solid was added cesium carbonate (399 mg, 1.22 mmol) followed by a solution containing 52-1 (295 mg, 0.612 mmol) in acetonitrile (3.06 mL) and the resulting mixture was capped and stirred at 100° C. for 16 h. Afterwards, the reaction was concentrated in vacuo. The resulting residue was treated with 5 mL of TFA and stirred at 50° C. for 1 hr. The crude product was concentrated in vacuo and purified by preparative HPLC chromatography using a gradient (5 to 75%) of acetonitrile in water with 0.05% trifluoroacetic acid to yield a TFA salt of the title compound (103.8 mg). [M+H]+ calcd for $C_{27}H_{27}N_7$ 450.23 found 450.2. $^1$H NMR (400 MHz, Methanol-d₄) δ 9.29 (d, J=2.2 Hz, 1H), 8.94 (s, 1H), 8.65 (dd, J=2.2, 0.8 Hz, 1H), 8.45 (d, J=0.8 Hz, 1H), 8.27 (d, J=1.9 Hz, 1H), 8.24-8.14 (m, 2H), 7.90 (dd, J=8.7, 2.0 Hz, 1H), 7.74 (t, J=7.9 Hz, 1H), 7.36 (ddt, J=16.8, 7.9, 0.8 Hz, 2H), 4.41-4.29 (m, 1H), 3.72 (td, J=11.2, 4.1 Hz, 1H), 2.65 (s, 3H), 2.30-2.17 (m, 2H), 1.96 (q, J=9.0, 7.0 Hz, 4H), 1.55 (q, J=11.1, 9.9 Hz, 2H). The stereochemistry of the product was confirmed by NOE.

Example 53: Synthesis of 6-[5-(6-methyl-2-pyridyl)-1H-imidazol-4-yl]quinoline-3-carboxylic Acid (796)

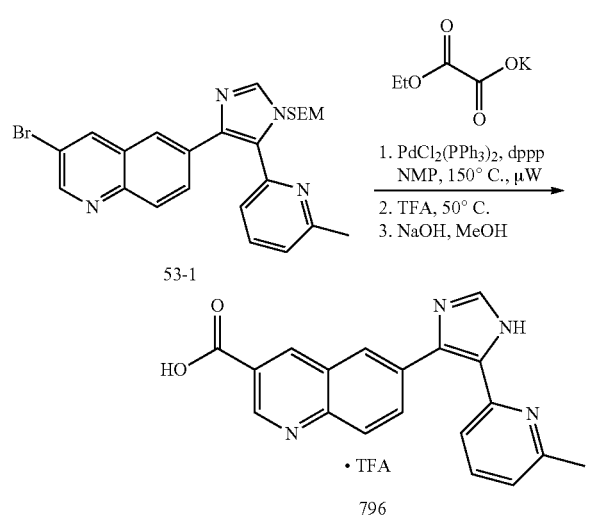

3-Bromo-6-(5-(6-methylpyridin-2-yl)-1-((2-(trimethylsilyl)ethoxy)methyl)-1H-imidazol-4-yl)quinoline (1.25 g, 2.52 mmol), potassium ethyl oxalate, 5 g (0.492 g, 3.15 mmol), 1,3-bis(diphenylphosphino)propane (0.031 g, 0.076 mmol), and trans-dichlorobis(triphenylphosphine) palladium(II) (0.035 g, 0.050 mmol) were added to a 0.5-2.0 mL μW vial and placed under vacuum for 2 min. The vial was backfilled with N₂, then N-methyl-2-pyrrolidinone (5.05 mL) was added and the resulting mixture was degassed via vacuum/N₂ backfill (5×), sealed, and heated to 150° C. for 8 h. The reaction was cooled and the solvent was removed under reduced pressure. The resulting residue was dissolved in TFA (10 mL) and heated to 50° C. for 30 min. The reaction was concentrated, azeotroped with toluene (2×5 mL), then dissolved in MeOH (25 mL). NaOH (10 mL, 3.0 M, 30.0 mmol) was added and the mixture was stirred at 23° C. for 2 h. The reaction was deemed complete by LCMS, and was acidified with TFA (1.0 mL), then concentrated. The residue was purified via prep HPLC to afford the product (1.01 g, 90% yield) as a yellow powder.

Example 54: Synthesis of piperidin-4-yl 6-(5-(6-methylpyridin-2-yl)-1H-imidazol-4-yl)quinoline-3-carboxylate (740)

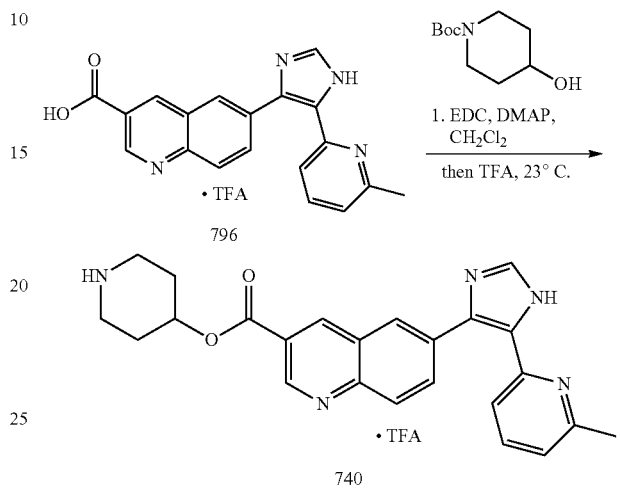

To a vial containing 6-(5-(6-methylpyridin-2-yl)-1H-imidazol-4-yl)quinoline-3-carboxylic acid (796), TFA (15.0 mg, 0.034 mmol) was added 1-Boc-4-hydroxypiperidine (10.2 mg, 0.051 mmol)) followed by a solution of n-(3-dimethylaminopropyl)-n'-ethylcarbodiimide hydrochloride (9.71 mg, 0.051 mmol) and DMAP (0.825 mg, 6.75 μmol) in CH₂Cl₂ (300 μL). The vial was sealed and the reaction was run at 23° C. for 3d. TFA (200 μL, 2.60 mmol) was added and the reaction was stirred for an additional 1 h, then was concentrated under reduced pressure. The crude residue was purified by prep HPLC to afford the desired ester (9.9 mg, 53% yield) as a pale yellow powder.

Example 55: Synthesis of 6-[5-(6-methyl-2-pyridyl)-1H-pyrazol-4-yl]quinoline-3-carboxylic Acid (783)

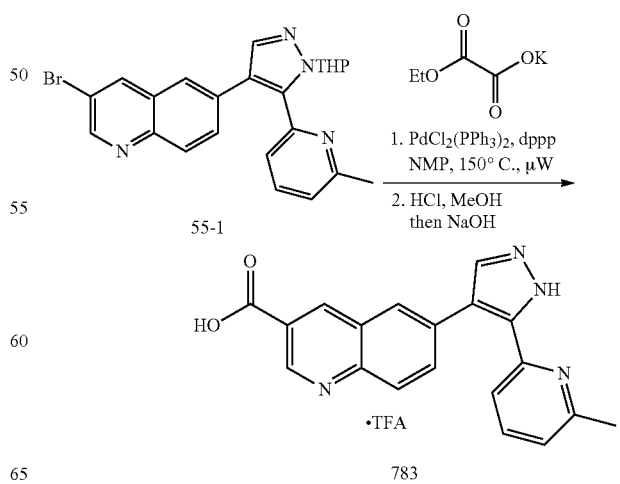

3-Bromo-6-(5-(6-methylpyridin-2-yl)-1-(tetrahydro-2H-pyran-2-yl)-1H-pyrazol-4-yl)quinoline (0.300 g, 0.668 mmol), potassium ethyl oxalate (0.130 g, 0.835 mmol), 1,3-bis(diphenylphosphino)propane (8.26 mg, 0.020 mmol), and trans-dichlorobis(triphenylphosphine)palladium(II) (9.37 mg, 0.013 mmol) were added to a 0.5-2.0 mL μW vial and placed under vacuum for 2 min. The vial was backfilled with $N_2$, then N-methyl-2-pyrrolidinone (1.34 mL) was added and the resulting mixture was degassed via vacuum/$N_2$ backfill (5×), sealed, and heated to 150° C. for 8 h. The reaction was concentrated under reduced pressure and the crude material was dissolved in TFA (5.0 mL) and heated to 50° C. for 1 h. The reaction was concentrated, azeotroping with PhMe (3×5 mL). The crude residue was dissolved in MeOH (5.0 mL) and NaOH (3.20 mL, 9.60 mmol) was added. The mixture was stirred for 3 d. Upon completion, the reaction was acidified with TFA (1.0 mL), then concentrated under reduced pressure. The residue was purified via prep HPLC to afford the product (0.175 g, 59% yield) as a yellow powder.

Example 56: Synthesis of azetidin-3-ylmethyl 6-(5-(6-methylpyridin-2-yl)-1H-pyrazol-4-yl)quinoline-3-carboxylate (790)

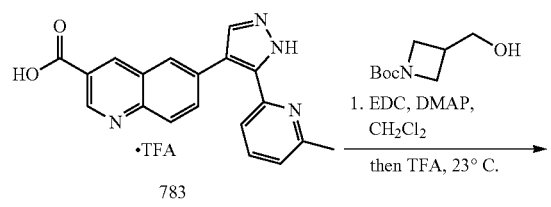

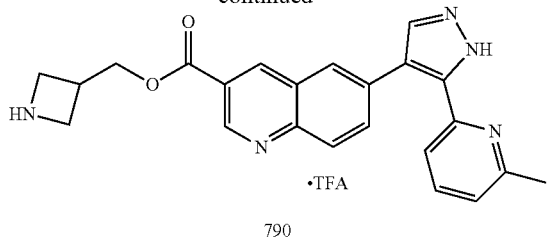

To a vial containing 6-(5-(6-methylpyridin-2-yl)-1H-pyrazol-4-yl)quinoline-3-carboxylic acid (783), TFA (15.0 mg, 0.034 mmol) was added 1-Boc-azetidine-3-yl-methanol (9.5 mg, 0.051 mmol)) followed by a solution of n-(3-dimethylaminopropyl)-n'-ethylcarbodiimide hydrochloride (9.71 mg, 0.051 mmol) and DMAP (0.825 mg, 6.75 μmol) in $CH_2Cl_2$ (300 μL). The vial was sealed and the reaction was run at 23° C. for 3 d. TFA (200 μL, 2.60 mmol) was added and the reaction was stirred for an additional 1 h, then was concentrated under reduced pressure. The crude residue was purified by prep HPLC to afford the desired ester (4.6 mg, 20% yield) as a pale yellow powder.

Example 57: Synthesis of 2-(6-(5-(6-methylpyridin-2-yl)-1H-imidazol-4-yl)quinolin-3-yl)-4,5,6,7-tetrahydrothiazolo[4,5-c]pyridine (727)

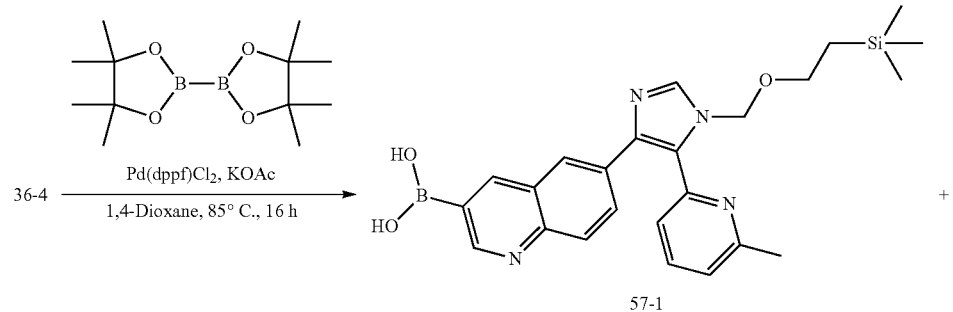

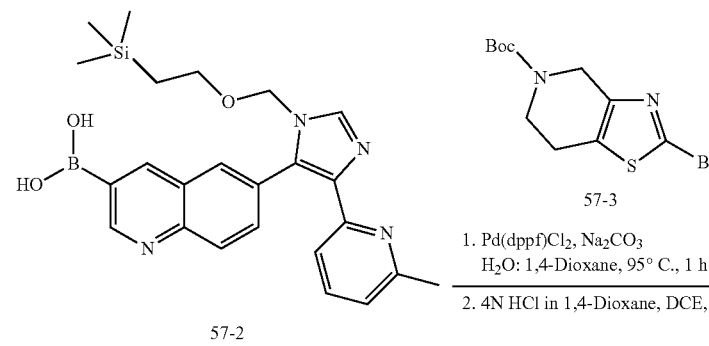

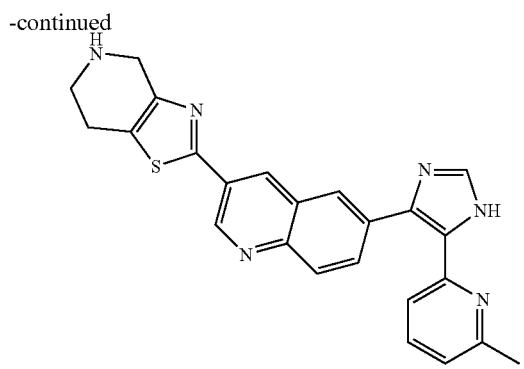

727

Step A: Preparation of (6-(5-(6-methylpyridin-2-yl)-1-((2-(trimethylsilyl)ethoxy)methyl)-1H-imidazol-4-yl)quinolin-3-yl)boronic acid and (6-(4-(6-methylpyridin-2-yl)-1-((2-(trimethylsilyl)ethoxy)methyl)-1H-imidazol-5-yl)quinolin-3-yl)boronic acid. A vial of 36-4 (65 mg, 0.131 mmol), bis(pinacolato)diboron (43.3 mg, 0.171 mmol), Pd(dppf)Cl$_2$ (19.20 mg, 0.026 mmol), and potassium acetate (38.6 mg, 0.394 mmol) in 1,4-dioxane (0.625 mL) was sparged with N$_2$ for 5 min before heating to 85° C. for 16 h. Crude 57-1 and 57-2 were used directly as a 0.21 M solution in dioxane in the next reaction. [M+H]$^+$ calcd for C$_{24}$H$_{29}$BN$_4$O$_3$Si, 461.21, found 461.0.

Step B: Preparation of 2-(6-(5-(6-methylpyridin-2-yl)-1H-imidazol-4-yl)quinolin-3-yl)-4,5,6,7-tetrahydrothiazolo[4,5-c]pyridine (727). A vial of crude 57-1 and 57-2 (71.0 mg, 0.131 mmol, 0.21 M in dioxane), 57-3 (50.0 mg, 0.157 mmol), sodium carbonate (42.0 mg, 0.393 mmol), and Pd(dppf)Cl$_2$ (19.0 mg, 0.026 mmol) in a mixture of 1,4-dioxane (0.524 mL) and water (0.131 mL) was sparged for 10 min with N$_2$ before heating to 95° C. for 1 h. The reaction mixture was filtered through a pad of celite and concentrated in vacuo. The crude material was treated with 4 N HCl/dioxane (0.426 mL) and EtOH (0.421 mL) was added. The mixture was heated to 50° C. for 1 h. The reaction mixture was concentrated in vacuo. The residue was purified by preparative HPLC chromatography using a gradient (2 to 50%) of acetonitrile in water with 0.05% trifluoroacetic acid to yield a TFA salt of the title compound (46.8 mg). [M+H]$^+$ calcd for C$_{24}$H$_{20}$N$_6$S, 425.15, found 425.1.

Example 58: Synthesis of 5-(6-(5-(6-methylpyridin-2-yl)-1H-imidazol-4-yl)quinolin-3-yl)picolinic Acid (541)

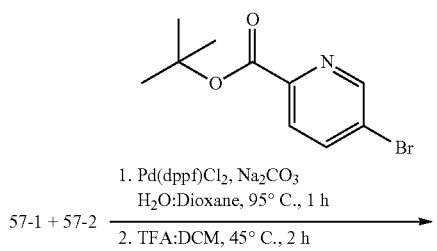

541

A vial of crude 57-1 and 57-2 (350 mg, 0.645 mmol, 0.21 M in dioxane), tert-butyl 5-bromopicolinate (183 mg, 0.710 mmol), sodium carbonate (205 mg, 1.93 mmol), and Pd(dppf)Cl$_2$ (94 mg, 0.129 mmol) in a mixture of 1,4-dioxane (2.58 mL) and water (0.645 mL) was sparged for 10 min with N$_2$ before heating to 95° C. for 1 h. The reaction mixture was concentrated in vacuo and purified by column chromatography (0 to 15% of MeOH in DCM). Fractions containing desired product were combined and concentrated in vacuo. A mixture of TFA (1.16 mL):DCM (1.36 mL) was added to the residue and heated gently at 45° C. for 2 h. The reaction mixture was concentrated in vacuo. The residue was purified by preparative HPLC chromatography using a gradient (2 to 50%) of acetonitrile in water with 0.05% trifluoroacetic acid to yield a TFA salt of the title compound (26 mg). [M+H]$^+$ calcd for C$_{24}$H$_{17}$N$_5$O$_2$ 408.14, found 408.1.

Example 59: Synthesis of (R)-1-methylpyrrolidin-3-yl 5-(6-(5-(6-methylpyridin-2-yl)-1H-imidazol-4-yl)quinolin-3-yl)picolinate (273)

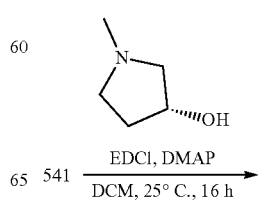

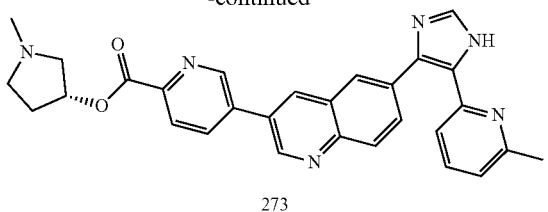

273

To a solution of 541 (50.0 mg, 0.079 mmol) and EDCI (22.63 mg, 0.118 mmol) dissolved in DCM (0.500 mL) was added DMAP (1.92 mg, 0.016 mmol) and (R)-(−)-1-methyl-3-pyrrolidinol (11.94 mg, 0.118 mmol). The resulting mixture was stirred at 25° C. for 16 h. The reaction mixture was concentrated in vacuo. The residue was purified by preparative HPLC chromatography using a gradient (2 to 50%) of acetonitrile in water with 0.05% trifluoroacetic acid to yield a TFA salt of the title compound (21.6 mg). [M+H]$^+$ calcd for $C_{29}H_{26}N_6O_2$ 491.21, found 491.1.

Example 60: Synthesis of 1-(6-(5-(6-methylpyridin-2-yl)-1H-imidazol-4-yl)quinolin-3-yl)piperidine-4-carboxylic acid (213)

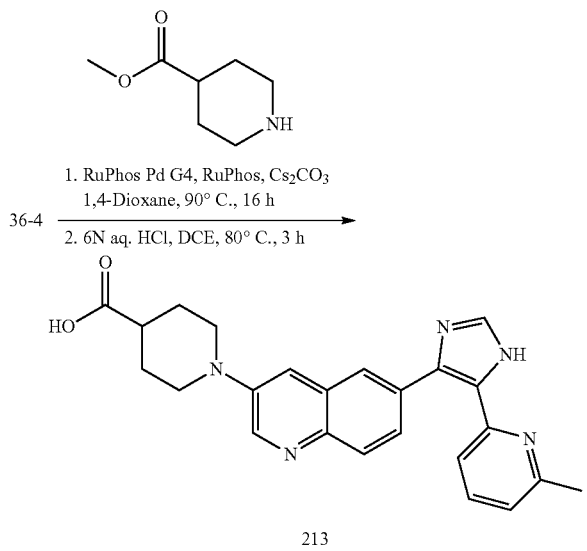

213

To a vial charged with 36-4 (100 mg, 0.202 mmol) and methyl isonipecotate (87 mg, 0.605 mmol) was added RuPhos (18.8 mg, 0.040 mmol), RuPhos Pd G4 (34.3 mg, 0.040 mmol), and cesium carbonate (263 mg, 0.807 mmol). To the resulting mixture was added dioxane (1.00 mL) and subsequently sparged with $N_2$ for 10 min. The resulting mixture was stirred at 90° C. for 16 h. The reaction was concentrated in vacuo. The crude material was dissolved in DCE (0.300 mL) and 6 M aq. HCl (0.200 mL) was added. The mixture was heated to 80° C. for 3 h. The reaction mixture was concentrated in vacuo. The residue was purified by preparative HPLC chromatography using a gradient (2 to 50%) of acetonitrile in water with 0.05% trifluoroacetic acid to yield a TFA salt of the title compound (13.3 mg). [M+H]$^+$ calcd for $C_{24}H_{23}N_5O_2$ 414.19, found 414.2.

Example 61: Synthesis of piperidin-4-yl 1-(6-(5-(6-methylpyridin-2-yl)-1H-imidazol-4-yl)quinolin-3-yl)piperidine-4-carboxylate (701)

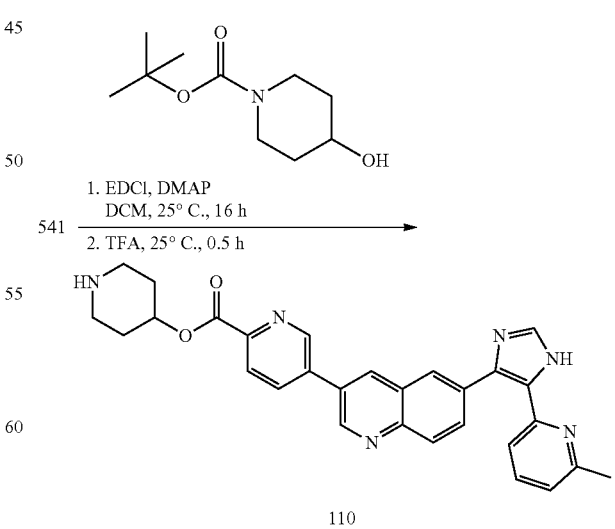

701

A solution of 213 (19.5 mg, 0.047 mmol), HATU (35.9 mg, 0.094 mmol), and DIPEA (0.041 mL, 0.236 mmol) in DMF (0.200 mL) was stirred at 25° C. for 0.5 h before adding 1-boc-hydroxypiperidine (18.98 mg, 0.094 mmol). The resulting mixture was stirred for 16 h at 25° C. The reaction mixture was concentrated in vacuo. TFA (0.200 mL) was added to the residue and stirred at 50° C. for 1 h. The reaction mixture was concentrated in vacuo. The residue was purified by preparative HPLC chromatography using a gradient (2 to 50%) of acetonitrile in water with 0.05% trifluoroacetic acid to yield a TFA salt of the title compound (1.6 mg). [M+H]$^+$ calcd for $C_{29}H_{32}N_6O_2$ 497.25, found 497.1.

Example 62: Synthesis of piperidin-4-yl 5-(6-(5-(6-methylpyridin-2-yl)-1H-imidazol-4-yl)quinolin-3-yl)picolinate (110)

110

To a solution of 541 (35.0 mg, 0.067 mmol) and EDCI (19.30 mg, 0.101 mmol) dissolved in DCM (0.800 mL) was added DMAP (1.64 mg, 0.013 mmol) and tert-butyl 4-hydroxypiperidine-1-carboxylate (20.26 mg, 0.101 mmol). The resulting mixture was stirred at 25° C. for 16 h. The reaction mixture was concentrated in vacuo. TFA (200 μL) was added to the reaction mixture and was stirred at 25° C. for 30 min. The reaction mixture was concentrated in vacuum and was purified by preparative HPLC chromatography using a gradient (2 to 50%) of acetonitrile in water with 0.05% trifluoroacetic acid to yield a TFA salt of the title compound (44.7 mg). [M+H]$^+$ calcd for $C_{29}H_{26}N_6O_2$ 490.57, found 491.2.

Example 63: Synthesis of (S)-pyrrolidin-3-yl 2-(6-(5-(6-methylpyridin-2-yl)-1H-imidazol-4-yl)quinolin-3-yl)thiazole-4-carboxylate (748)

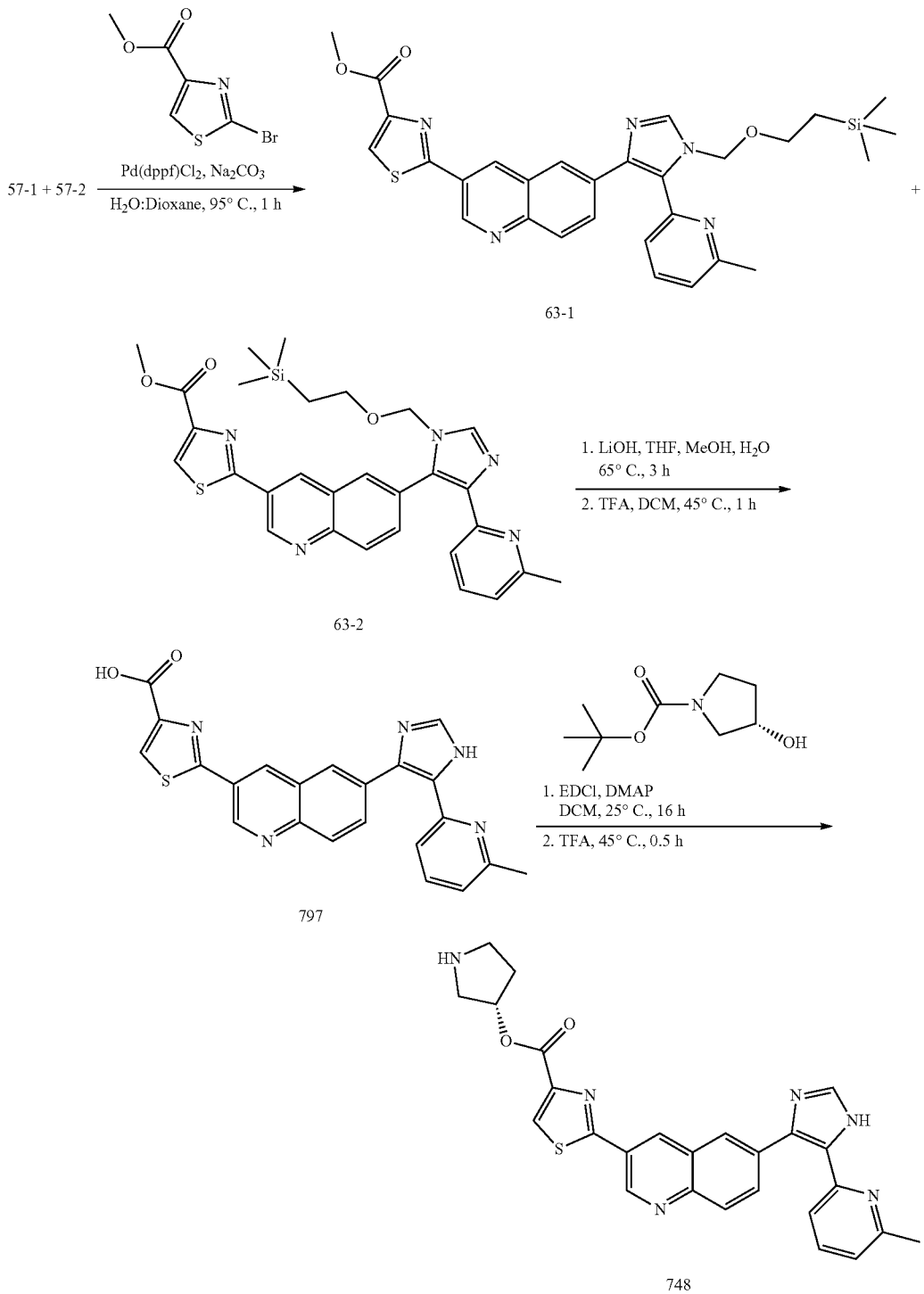

Step A: Preparation of methyl 2-(6-(5-(6-methylpyridin-2-yl)-1-((2-(trimethylsilyl)ethoxy)methyl)-1H-imidazol-4-yl)quinolin-3-yl)thiazole-4-carboxylate (63-1, 63-2). A vial of crude 57-1 and 57-2 (547 mg, 1.01 mmol), methyl 2-bromothiazole-4-carboxylate (269 mg, 1.21 mmol), sodium carbonate (321 mg, 3.03 mmol), and Pd(dppf)Cl$_2$ (74 mg, 0.101 mmol) in a mixture of 1,4-dioxane (4.0 mL) and water (1.0 mL) was sparged for 10 min with N$_2$ before heating to 95° C. for 1 h. The reaction mixture was concentrated in vacuo and purified by column chromatography (0 to 15% of MeOH in DCM). Fractions containing desired product were combined and concentrated in vacuo to give a mixture of 63-1 and 63-2 (313 mg). [M+H]$^+$ calcd for C$_{29}$H$_{31}$N$_5$O$_3$SSi 557.74, found 558.1.

Step B: Preparation of 2-(6-(5-(6-methylpyridin-2-yl)-1H-imidazol-4-yl)quinolin-3-yl)thiazole-4-carboxylic acid (797). To a vial of 63-1 and 63-2 (313 mg, 0.561 mmol) dissolved in a 3:2:1 mixture of THF:MeOH:H$_2$O (1.4 mL, 0.9 mL, 0.5 mL) was added lithium hydroxide (26.9 mg, 1.122 mmol). The reaction mixture was heated at 65° C. for 3 h. The reaction mixture was concentrated in vacuo to give a crude residue. To the residue was directly added DCM (1.6 mL) and TFA (1.9 mL) and was heated at 45° C. for 1 h. The reaction mixture was concentrated in vacuum and was purified by preparative HPLC chromatography using a gradient (5 to 30%) of acetonitrile in water with 0.05% trifluoroacetic acid to yield a TFA salt of 797 (59.8 mg). [M+H]$^+$ calcd for C$_{22}$H$_{15}$N$_5$O$_2$S, 413.46, found 414.1.

Step C: Preparation of (S)-pyrrolidin-3-yl 2-(6-(5-(6-methylpyridin-2-yl)-1H-imidazol-4-yl)quinolin-3-yl)thiazole-4-carboxylate (748). To a solution of 797 (20.0 mg, 0.038 mmol) and EDCI (10.9 mg, 0.057 mmol) dissolved in DCM (0.500 mL) was added DMAP (0.93 mg, 7.58 μmol) and tert-butyl (S)-3-hydroxypyrrolidine-1-carboxylate (10.65 mg, 0.057 mmol). The resulting mixture was stirred at 25° C. for 16 h. The reaction mixture was concentrated in vacuo. TFA (200 μL) was added to the reaction mixture and was heated at 45° C. for 30 min. The reaction mixture was concentrated in vacuum and was purified by preparative HPLC chromatography using a gradient (5 to 65%) of acetonitrile in water with 0.05% trifluoroacetic acid to yield a TFA salt of the title compound (14.5 mg). [M+H]$^+$ calcd for C$_{26}$H$_{22}$N$_6$O$_2$S, 482.56, found 483.0.

Example 64: Synthesis of azetidin-3-ylmethyl 4-(6-(5-(6-methylpyridin-2-yl)-1H-imidazol-4-yl)quinolin-3-yl)thiophene-2-carboxylate (753)

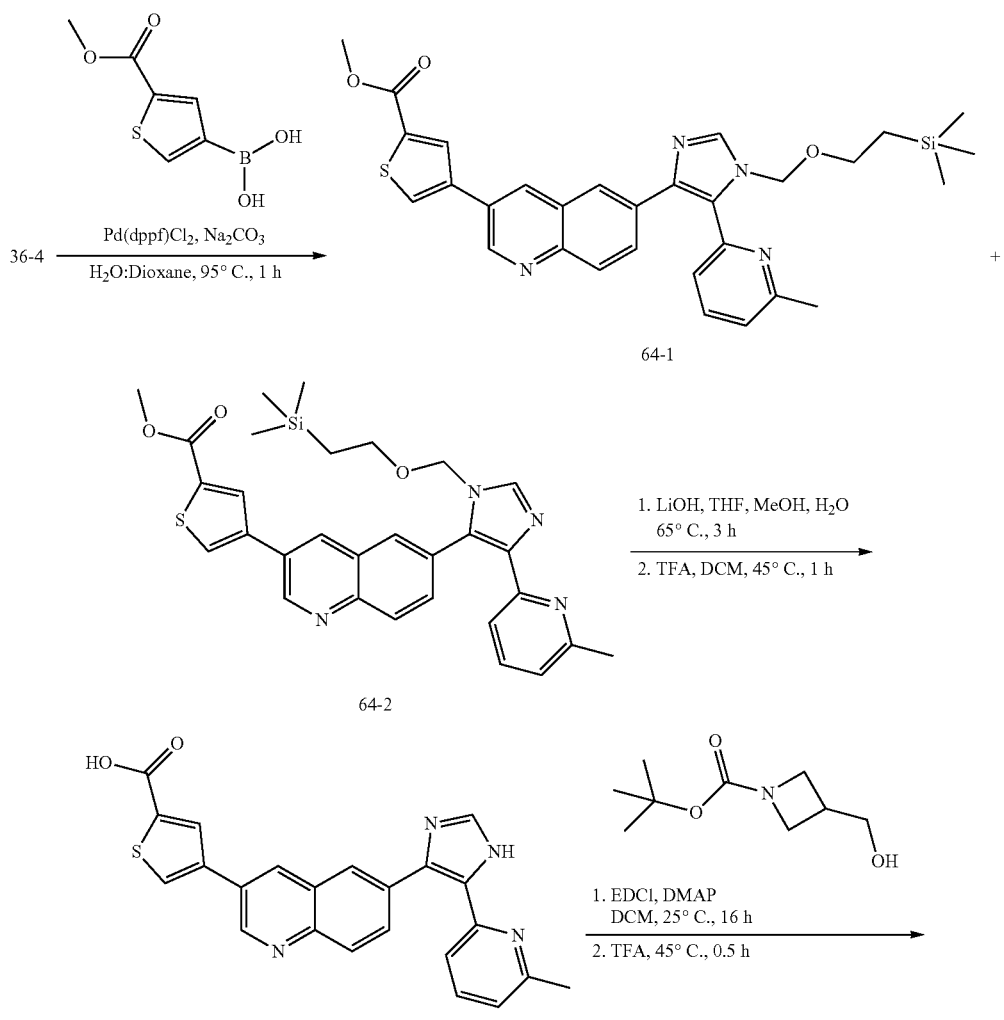

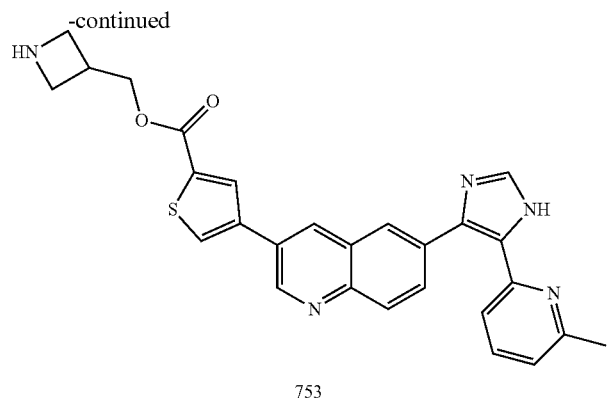

753

Step A: Preparation of methyl 4-(6-(5-(6-methylpyridin-2-yl)-1-((2-(trimethylsilyl)ethoxy)methyl)-1H-imidazol-4-yl)quinolin-3-yl)thiophene-2-carboxylate (64-1, 64-2). A vial of 36-4 (350 mg, 0.706 mmol), (5-(methoxycarbonyl)thiophen-3-yl)boronic acid (158 mg, 0.847 mmol), sodium carbonate (224 mg, 2.118 mmol), and Pd(dppf)Cl$_2$ (103 mg, 0.141 mmol) in a mixture of 1,4-dioxane (2.8 mL) and water (0.7 mL) was sparged for 10 min with N$_2$ before heating to 95° C. for 1 h. The reaction mixture was concentrated in vacuo and purified by column chromatography (0 to 15% of MeOH in DCM). Fractions containing desired product were combined and concentrated in vacuo to give a mixture of 64-1 and 64-2 (349 mg). [M+H]$^+$ calcd for C$_{30}$H$_{32}$N$_4$O$_3$SSi 556.76, found 557.1.

Step B: Preparation of 4-(6-(5-(6-methylpyridin-2-yl)-1H-imidazol-4-yl)quinolin-3-yl)thiophene-2-carboxylic acid (798). To a vial of 64-1 and 64-2 (349 mg, 0.627 mmol) dissolved in a 3:2:1 mixture of THF:MeOH:H$_2$O (1.4 mL, 0.9 mL, 0.5 mL) was added lithium hydroxide (26.9 mg, 1.122 mmol). The reaction mixture was heated at 65° C. for 3 h. The reaction mixture was concentrated in vacuo to give a crude residue. To the residue was directly added DCM (1.6 mL) and TFA (1.9 mL) and was heated at 45° C. for 1 h. The reaction mixture was concentrated in vacuum and was purified by preparative HPLC chromatography using a gradient (5 to 30%) of acetonitrile in water with 0.05% trifluoroacetic acid to yield a TFA salt of 798 (49.7 mg). [M+H]$^+$ calcd for C$_{23}$H$_{16}$N$_4$O$_2$S, 412.47, found 413.1.

Step C: Preparation of azetidin-3-ylmethyl 4-(6-(5-(6-methylpyridin-2-yl)-1H-imidazol-4-yl)quinolin-3-yl)thiophene-2-carboxylate (753). To a solution of 798 (20.0 mg, 0.038 mmol) and EDCI (10.9 mg, 0.057 mmol) dissolved in DCM (0.500 mL) was added DMAP (0.93 mg, 7.58 μmol) and tert-butyl 3-(hydroxymethyl)azetidine-1-carboxylate (10.67 mg, 0.057 mmol). The resulting mixture was stirred at 25° C. for 16 h. The reaction mixture was concentrated in vacuo. TFA (200 μL) was added to the reaction mixture and was heated at 45° C. for 30 min. The reaction mixture was concentrated in vacuum and was purified by preparative HPLC chromatography using a gradient (5 to 65%) of acetonitrile in water with 0.05% trifluoroacetic acid to yield a TFA salt of the title compound (17.2 mg). [M+H]$^+$ calcd for C$_{27}$H$_{23}$N$_5$O$_2$S, 481.57, found 482.1.

Example 65: Synthesis of 2-(6-(5-(6-methylpyridin-2-yl)-1H-imidazol-4-yl)quinolin-3-yl)-4-(1,2,3,6-tetrahydropyridin-4-yl)thiazole (1051)

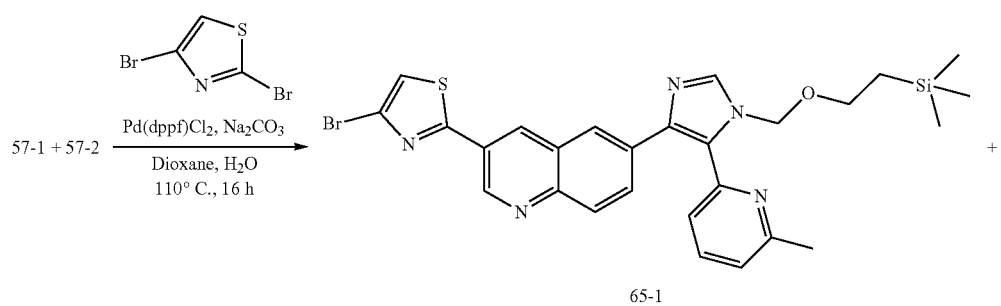

65-1

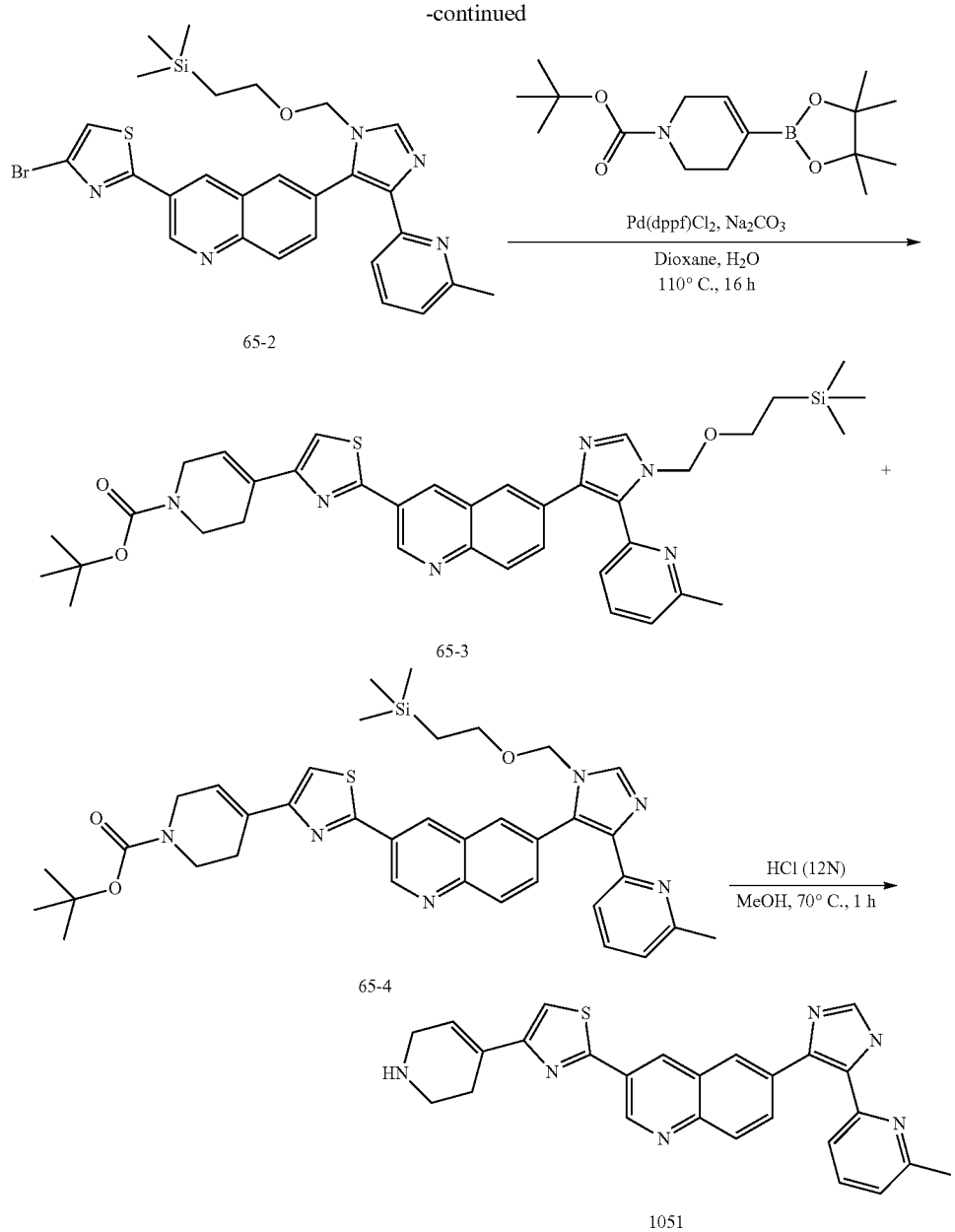

Step A: Preparation of 4-bromo-2-(6-(5-(6-methylpyridin-2-yl)-1-((2-(trimethylsilyl)ethoxy)methyl)-1H-imidazol-4-yl)quinolin-3-yl)thiazole (65-1 and 65-2). A mixture of compound 57-1 and 57-2 (2.50 g, 5.43 mmol), 2,4-dibromothiazole (923 mg, 3.80 mmol), and $Na_2CO_3$ (2.30 g, 21.7 mmol) in dioxane (15.0 mL) and $H_2O$ (1.5 mL) was degassed and purged with $N_2$. Pd(dppf)$Cl_2$ (159 mg, 217 µmol) was added and the mixture degassed, purged with $N_2$, and stirred at 110° C. for 16 h under $N_2$ atmosphere. The reaction mixture was partitioned between $H_2O$ (20.0 mL) and DCM (40.0 mL). The organic phase was separated, washed with brine (15.0 mL), dried over $Na_2SO_4$, filtered and concentrated under reduced pressure to give a residue. The residue was purified by column chromatography ($SiO_2$, petroleum ether:ethyl acetate=2:1 to 0:1, $NH_3H_2O$ 2%) to give the title compound as a mixture of regioisomers 65-1 and 65-2 (950 mg, 1.64 mmol) as a brown oil. [M+H]$^+$ calcd for $C_{27}H_{28}BrN_5OSSi$ 578.60, found 578.2.

Step B: Preparation of tert-butyl 4-(2-(6-(5-(6-methylpyridin-2-yl)-1-((2-(trimethylsilyl)ethoxy)methyl)-1H-imidazol-4-yl)quinolin-3-yl)thiazol-4-yl)-3,6-dihydropyridine-1(2H)-carboxylate (65-3 and 65-4). A mixture of 65-1 and 65-2 (0.50 g, 864 µmol), $Na_2CO_3$ (366 mg, 3.46 mmol), and tert-butyl 4-(4,4,5,5-tetramethyl-1,3,2-dioxaborolan-2-yl)-3,6-dihydropyridine-1(2H)-carboxylate (401 mg, 1.30 mmol) in dioxane (4.0 mL) and $H_2O$ (0.4 mL) was degassed and purged with $N_2$. Pd(dppf)$Cl_2$ (63.2 mg, 86.4 µmol) was added and the resulting mixture degassed, purged with $N_2$, and stirred at 110° C. for 16 h under $N_2$ atmosphere. The reaction mixture was partitioned between $H_2O$ (15.0 mL) and DCM (25.0 mL), the organic phase was separated, washed with brine (15.0 mL), dried over $Na_2SO_4$ filtered and concentrated under reduced pressure to give a residue. The residue was purified by column chromatography ($SiO_2$, petroleum ether:ethyl acetate=30:1 to 0:1, $NH_3H_2O$) to give the title compound as a mixture of regioisomers 65-3 and 65-4 (370 mg, 543 µmol) as a yellow solid. [M+H]⁺ calcd for $C_{37}H_{44}N_6O_3SSi$ 680.94, found 681.4.

Step C: Preparation of 2-(6-(5-(6-methylpyridin-2-yl)-1H-imidazol-4-yl)quinolin-3-yl)-4-(1,2,3,6-tetrahydropyridin-4-yl)thiazole (1051). To a solution of 65-3 and 65-4 (350 mg, 514 µmol) in MeOH (4.0 mL) was added aq. HCl (12.0 M, 214 µL). The mixture was stirred at 70° C. for 1 h. The reaction was filtered and the filter cake was concentrated under reduced pressure to give the title compound 1051 (57.0 mg, 109 µmol HCl salt) as a yellow solid. [M+H]⁺ calcd for $C_{26}H_{22}N_6S$, 450.56, found 451.2.

Example 66: Synthesis of 3-(5-(((3S,5R)-3,5-dimethylpiperazin-1-yl)methyl)pyridin-3-yl)-6-(5-(6-methylpyridin-2-yl)-1H-imidazol-4-yl)quinoline (1045)

with EtOAc (10.0 mL×3). The combined organic layers were washed with brine (20.0 mL), dried over anhydrous $Na_2SO_4$, filtered and concentrated under reduced pressure to give the title compound 66-2 (0.4 g, crude) as a white solid.

Step B: Preparation of tert-butyl (2S,6R)-4-((5-bromopyridin-2-yl)methyl)-2,6-dimethylpiperazine-1-carboxylate (66-3). To a solution of 66-2 (0.20 g, 1.08 mmol) in DCM (2.0 mL) was added tert-butyl (2S,6R)-2,6-dimethylpiperazine-1-carboxylate (215 mg, 1.00 mmol). The mixture was stirred at 25° C. for 0.5 h. Then $NaBH(OAc)_3$ (639 mg, 3.01 mmol) was added at 25° C. The mixture was stirred at 25° C. for 12 h, then quenched by $H_2O$ (10.0 mL) at 0~10° C., diluted with DCM (20.0 mL) and extracted with DCM (10.0 mL). The combined organic layers were washed with brine (20.0 mL), dried over anhydrous $Na_2SO_4$, filtered and concentrated under reduced pressure to give the title compound 66-3 (0.3 g, crude) as a yellow oil.

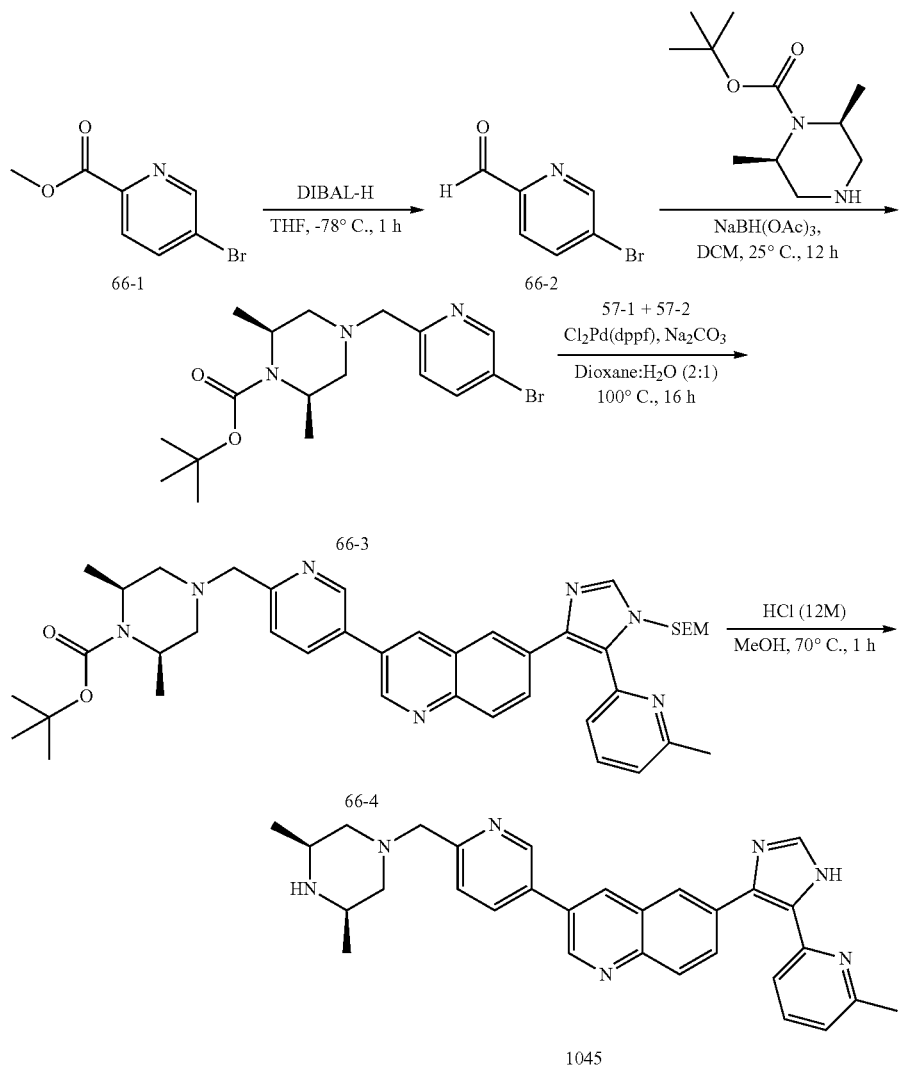

Step A: Preparation of 5-bromopicolinaldehyde (66-2). To a solution of 66-1 (0.5 g, 2.31 mmol) in THF (5.0 mL) was added DIBAL-H (1 M, 4.63 mL) at −78° C. The mixture was stirred at −78° C. for 2 h, then quenched by $H_2O$ (10.0 mL) at 0~10° C., diluted with EtOAc (20.0 mL) and extracted Step C: Preparation of tert-butyl (2S,6R)-2,6-dimethyl-4-((5-(6-(5-(6-methylpyridin-2-yl)-1-((2-(trimethylsilyl)ethoxy)methyl)-1H-imidazol-4-yl)quinolin-3-yl)pyridin-2-yl)methyl)piperazine-1-carboxylate (66-4). A mixture of 66-3 (0.3 g, 780.62 µmol), 57-1 and 57-2 (359.4 mg, 781

µmol), Na$_2$CO$_3$ (248 mg, 2.34 mmol), and Pd(PPh$_3$)$_4$ (36.1 mg, 31.2 µmol) in dioxane (4.00 mL) and H$_2$O (2.0 mL) was degassed and purged with N$_2$, and the mixture was stirred at 100° C. for 16 h under N$_2$ atmosphere. The reaction mixture was quenched by H$_2$O (10.0 mL) at 0~10° C., diluted with EtOAc (20.0 mL) and extracted with EtOAc (10.0 mL×3). The combined organic layers were washed with brine (20.0 mL), dried over anhydrous Na$_2$SO$_4$, filtered and concentrated under reduced pressure to give the title compound 66-4 (0.3 g, crude) as a brown oil. [M+H]$^+$ calcd for C$_{41}$H$_{53}$N$_7$O$_3$Si, 720.01, found 720.3.

Step D: Preparation of 3-(6-(((3S,5R)-3,5-dimethylpiperazin-1-yl)methyl)pyridin-3-yl)-6-(5-(6-methylpyridin-2-yl)-1H-imidazol-4-yl)quinoline (1045). To a solution of compound 66-4 (0.3 g, 416.67 µmol) in MeOH (1.0 mL) was added 12 M of aq. HCl (15.2 mg, 417 µmol, 14.9 µL). The mixture was stirred at 70° C. for 1 h, then concentrated and the resulting residue purified by prep-HPLC (column: Phenomenex luna C18 80*40 mm*3 µm; mobile phase: [water (0.04% HCl)-ACN]; B %: 1%-20%, 7 min) to give the title compound 1045 (80.0 mg, 163 µmol) as a yellow solid. [M+H]$^+$ calcd for C$_{30}$H$_{31}$N$_7$ 489.63, found 490.2.

Example 67: Synthesis of 9-(6-(5-(6-methylpyridin-2-yl)-1H-imidazol-4-yl)quinolin-3-yl)-3-azaspiro[5.5]undec-8-ene (392)

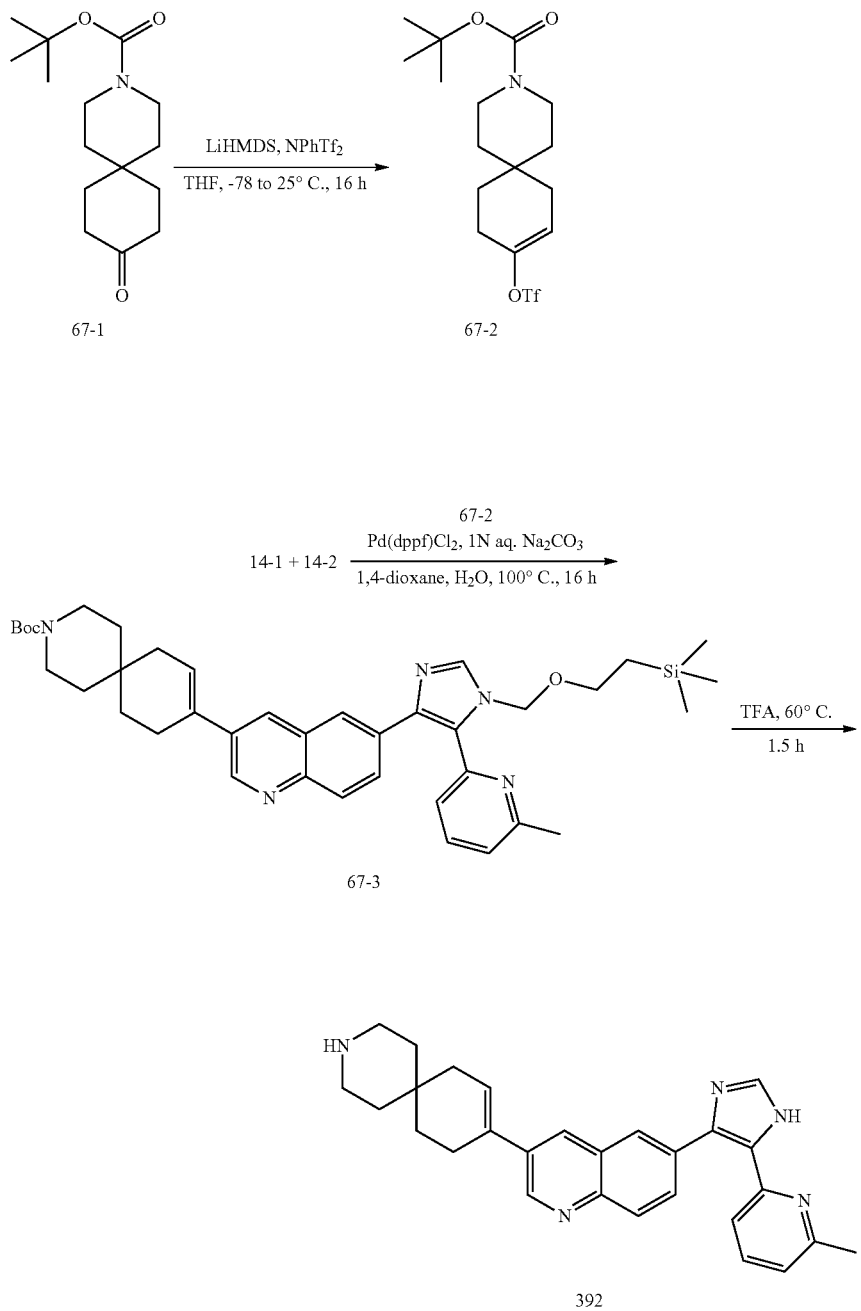

Step A: Preparation of tert-butyl 9-(((trifluoromethyl)sulfonyl)oxy)-3-azaspiro[5.5]undec-8-ene-3-carboxylate (67-2). Under a nitrogen atmosphere, to a solution of 9-oxo-3-aza-spiro[5.5]undecane-3-carboxylic acid tert-butyl ester 67-1 (300 mg, 1.122 mmol) in THF (6234 μL) cooled to −78° C. was added lithium bis(trimethylsilyl)amide solution 1.0 M in THF (1290 μL, 1.290 mmol) dropwise. The mixture was stirred at −78° C. for 45 min. N-phenyl-bis(trifluoromethanesulfonimide) (633 mg, 1.773 mmol) was added. The mixture was allowed to warm to room temperature and stir overnight. The reaction was quenched with aq sat. NH₄Cl. The resulting aqueous phase was extracted with ethyl acetate (×3) and the organic extracts were combined, washed with saturated aqueous sodium bicarbonate solution (×2), water (×2), brine, dried, filtered, and concentrated. The residue was purified via normal phase chromatography (0 to 40% of EA in Hex) to yield 67-2 (552 mg) as a clear colorless oil.

Step B: Preparation of 9-(6-(5-(6-methylpyridin-2-yl)-1H-imidazol-4-yl)quinolin-3-yl)-3-azaspiro[5.5]undec-8-ene (392). A mixture of 14-1 and 14-2 (232 mg, 0.504 mmol, crude), 67-2 (241 mg, 0.603 mmol), sodium carbonate (214 mg, 2.016 mmol), and Pd(dppf)Cl₂ (73.8 mg, 0.101 mmol) in 1,4-dioxane (2016 μl):water (504 μl) was sparged for 10 min with N₂ before heating to 95° C. for 16 h. The reaction mixture was filtered through a pad of celite and concentrated in vacuum yielding crude 67-3. TFA (500 μl) was added to 67-3 and the resulting mixture heated to 60° C. for 1.5 h. The reaction mixture was concentrated in vacuum. The residue was purified by preparative HPLC chromatography using a gradient (10 to 30%) of acetonitrile in water with 0.05% trifluoroacetic acid to yield a TFA salt of the title compound (155 mg). [M+H]⁺ calcd for $C_{28}H_{29}N_5$ 436.24, found 436.2.

Example 68: Synthesis of (2S)—N-[(1R)-4-[6-[5-(6-methyl-2-pyridyl)-1H-imidazol-4-yl]-3-quinolyl]cyclohex-3-en-1-yl]pyrrolidine-2-carboxamide (418)

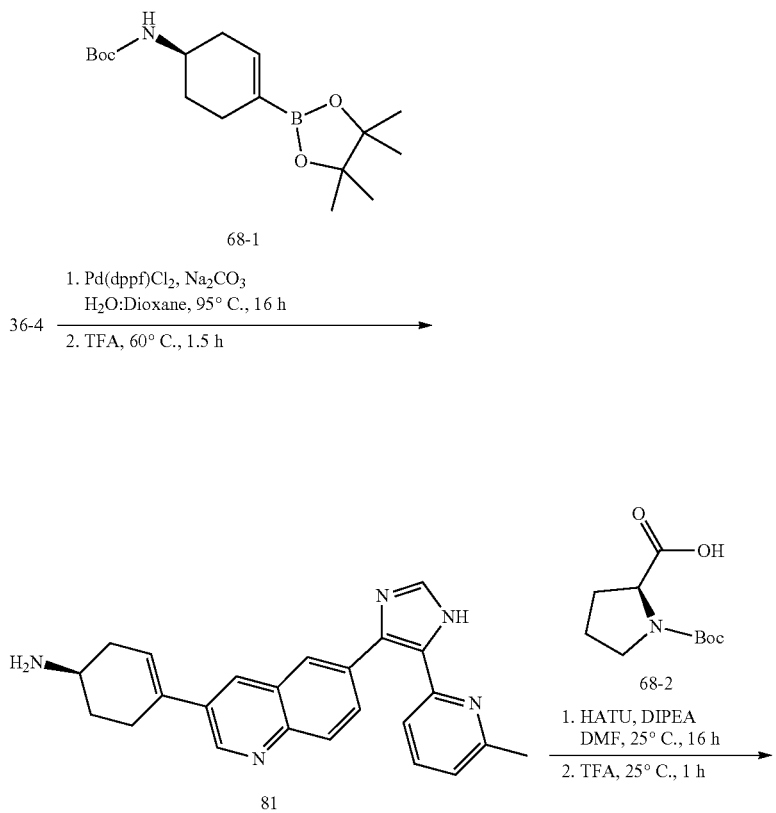

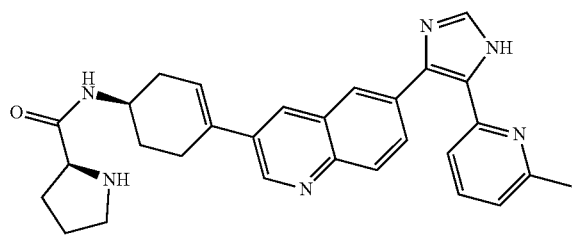

Step A: Preparation of (1R)-4-[6-[5-(6-methyl-2-pyridyl)-1H-imidazol-4-yl]-3-quinolyl]cyclohex-3-en-1-amine (81). A mixture of tert-butyl (R)-(4-(4,4,5,5-tetramethyl-1,3,2-dioxaborolan-2-yl)cyclohex-3-en-1-yl)carbamate 68-1 (22.4 mg, 0.069 mmol), 36-4 (30 mg, 0.061 mmol), sodium carbonate (25.7 mg, 0.242 mmol), and Pd(dppf)Cl$_2$ (8.86 mg, 0.012 mmol) in degassed water (60.5 µL):dioxane (242 µL) was heated to 95° C. for 16 h. The reaction mixture was filtered through a pad of celite and concentrated in vacuum. The crude material was dissolved in TFA (500 µl). The mixture was heated to 60° C. for 1.5 h. The reaction mixture was concentrated in vacuum. The residue was purified by preparative HPLC chromatography using a gradient (10 to 20%) of acetonitrile in water with 0.05% trifluoroacetic acid to yield a TFA salt of 81 (3.9 mg). [M+H]$^+$ calcd for $C_{24}H_{23}N_5$ 382.20, found 382.1.

Step B: Preparation of (2S)—N-[(1R)-4-[6-[5-(6-methyl-2-pyridyl)-1H-imidazol-4-yl]-3-quinolyl]cyclohex-3-en-1-yl]pyrrolidine-2-carboxamide (418). A mixture of Boc-Pro-OH 68-2 (33.9 mg, 0.157 mmol), DIPEA (68.7 µL, 0.393 mmol), and HATU (71.8 mg, 0.189 mmol) in DMF (393 µL) was allowed to stir for 0.5 h before adding 81 (30 mg, 0.079 mmol). The resulting mixture was stirred for 16 h at room temperature. The solvent was removed in vacuum. TFA (500 µL) was added and the resulting mixture was heated to 50° C. for 1 h. The reaction mixture was concentrated in vacuum. The residue was purified by preparative HPLC chromatography using a gradient (13 to 48%) of acetonitrile in water with 0.05% trifluoroacetic acid to yield a TFA salt of title compound (40 mg). [M+H]$^+$ calcd for $C_{29}H_{30}N_6O$, 479.25, found 479.2.

Example 69: Synthesis of 2-(piperazin-1-yl)ethyl 6-(5-(6-methylpyridin-2-yl)-1H-imidazol-4-yl)quinoline-3-carboxylate (756)

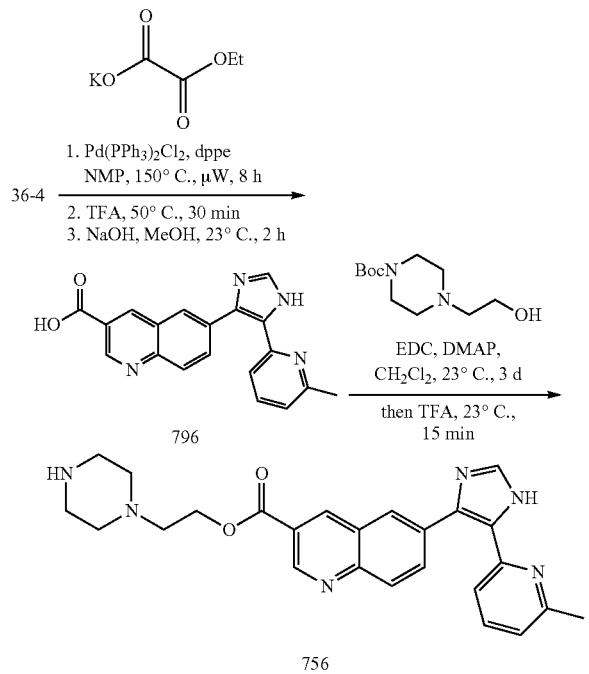

Step A: Preparation of 6-[5-(6-methyl-2-pyridyl)-1H-imidazol-4-yl]quinoline-3-carboxylic acid (796). 3-bromo-6-(5-(6-methylpyridin-2-yl)-1-((2-(trimethylsilyl)ethoxy)methyl)-1H-imidazol-4-yl)quinoline 36-4 (1.00 g, 2.02 mmol), potassium ethyl oxalate (0.394 g, 2.52 mmol), 1,3 bis(diphenylphosphino)-propane (0.025 g, 0.061 mmol), and trans-dichlorobis(triphenylphosphine)palladium(II) (0.028 g, 0.040 mmol) were added to a vial and placed under vacuum for 2 min. The vial was backfilled with N$_2$, then N-methyl-2-pyrrolidinone (4.04 mL) was added and the resulting mixture was degassed via vacuum/N$_2$ backfill (5×), sealed, and heated to 150° C. for 8 h. LCMS confirmed full conversion of the 36-4 to a mixture of the desired ethyl ester/SEM protected material, free acid/SEM protected, free acid/SEM deprotected, and fully deprotected 796. The mixture was diluted with water (25 mL) and extracted with EtOAc (2×30 mL). The combined organics were washed with water, brine, dried over MgSO$_4$, filtered, and concentrated affording the mixture of products as a brown oil. This mixture was deprotected via the TFA/NaOH sequence described below. The aqueous washes were acidified with TFA to pH~3, then extracted with 3:1 CHCl$_3$/iPrOH (2×15 mL) to recover the 796 formed in the reaction. This was dried over MgSO$_4$, filtered, and concentrated. The residue from the EtOAc extracts was dissolved in TFA (10 mL) and heated to 50° C. for 30 min. The reaction was concentrated, azeotroped with toluene (2×5 mL), then dissolved in MeOH (20 mL). NaOH (5.38 mL, 16.14 mmol) was added and the mixture was stirred at 23° C. for 2 h. The reaction was deemed complete by LCMS, acidified with TFA (1.0 mL), then concentrated. The residue was combined with crude 796 and purified via reverse phase chromatography to afford the TFA salt of 796 (0.564 g) as a yellow powder. [M+H]$^+$ calcd for $C_{19}H_{14}N_4O_2$ 331.1, found 331.2.

Step B: Preparation of 2-(piperazin-1-yl)ethyl 6-(5-(6-methylpyridin-2-yl)-1H-imidazol-4-yl)quinoline-3-carboxylate (756). To a vial containing tert-butyl 4-(2-hydroxyethyl)piperazine-1-carboxylate (34.5 mg, 0.150 mmol), and 6-(5-(6-methylpyridin-2-yl)-1H-imidazol-4-yl)quinoline-3-carboxylic acid, HCl 796 (36.7 mg, 0.100 mmol) in CH$_2$Cl$_2$ (500 µL) was added EDC (28.8 mg, 0.150 mmol) followed by DMAP (1.22 mg, 10.0 µmol) and DIPEA (34.8 µL, 0.200 mmol). The reaction was stirred for 3 d. The reaction was diluted with TFA (500 µL) stirred for 15 min, and then was concentrated. The residue was purified via reverse phase chromatography to afford the bis-TFA salt of 756 (0.0484 g) as a yellow powder. [M+H]$^+$ calcd for $C_{25}H_{26}N_6O_2$ 443.2, found 443.2.

Example 70: Biochemical ALK5 (TGF-βR1) Assay to Measure pKi

Apparent pKi values for compounds of the present disclosure were determined using a recombinant human ALK5 (TGF-βR1) protein (Product No. PR9075A or equivalent, Life Technologies) and a commercially-available kinase assay (LANCE® (lanthanide chelate excite) Ultra ULight™ kinase assay, Product Nos. TRF0130-M and TRF02108-M, Perkin Elmer) as described below.

The assays were performed in a 384-well plate (24 columns×16 wells/rows). An Echo® 550 Liquid Handler (Labcyte) was used to prepare various intermediate concentrations of compounds of the present disclosure in 100% DMSO. From the intermediate concentrations, a range of concentrations (from 10 µM to 25 pM corresponding to volumes up to 105 nL) were prepared and ejected into a final assay plate to be used to create individual dose response curves for each of the subject compounds. To a separate column within the assay plate, 105 nL of DMSO in each well was used to establish a maximum assay signal. Additionally, 105 nL of 100 µM SD-208, a selective TGF-βR1 inhibitor (Catalog #S7624, Selleck Chemicals), was used in another column of wells to establish a minimal assay signal.

With a multidrop dispenser, 8 µL of enzyme mixture (1.25× final) was added to each well. The enzyme mixture consisted of 250 pM ALK5 enzyme and 62.5 nM peptide substrate (LANCE® (lanthanide chelate excite) Ultra ULight™-DNA Topoisomerase 2-alpha (Thr1342)) prepared in assay buffer (50 mM HEPES, 10 mM $MgCl_2$, 1 mM EGTA, 0.01% Tween-20, pH 7.5 at room temperature) with 2 mM DTT added prior to use. The plate was then sealed with an adhesive seal and allowed to equilibrate for 60 minutes at room temperature.

Next, 2 µL of 125 µM ATP (5× final, 125 µM ATP prepared in assay buffer with 2 mM DTT) was added to the incubated mixtures, covered with a MicroClime® Environmental Lid (Product No. LLS-0310, Labcyte) and immediately transferred to 37° C. The reactions were allowed to proceed at 37° C. for 60 minutes before terminating with the addition of 10 µL of detection antibody (LANCE® (lanthanide chelate excite) Ultra Europium-anti-phospo-DNA Topoisomerase 2-alpha (Thr1342)) in detection mixture (12 mM EDTA, 4 nM detection antibody prepared in detection buffer (50 mM Tris-HCl, 150 mM NaCl, 0.5% BSA (Fraction V), pH 7.0)) at room temperature. The plate was then read on a Perkin Elmer EnVision Plate Reader using europium specific reader settings with excitation and emission wavelengths set to 320 or 340 nm and 665 nm, respectively. These data were used to calculate percent enzyme inhibition values based on DMSO and SD-208 background controls.

For dose-response analyses, percent inhibition versus compound concentrations were plotted, and $pIC_{50}$ values were determined from a 4-parameter robust fit model with GraphPad Prism V5 Software (GraphPad Software, Inc., La Jolla, Calif.). This model obtains $pIC_{50}$ values by fitting the sigmoidal dose-response (variable slope) equation to the data. Results were expressed as $pIC_{50}$ (negative logarithm of $IC_{50}$) and subsequently converted to $pK_i$ (negative logarithm of dissociate constant, K) using the Cheng-Prusoff equation. The higher the value of $pK_i$ (lower value of $K_i$), the greater the inhibition of ALK5 activity. Certain compounds disclosed herein exhibited $pK_i$ values of greater than 8 or greater than 9 when tested in the biochemical ALK5 assay.

Table 2 shows biological activities of selected compounds in a biochemical ALK5 assay. Compound numbers correspond to the numbers and structures provided in Table 1 and Examples 1-69.

TABLE 2

| | 7.5 to 8.4 (+) | 8.5 to 9.4 (++) | 9.5 to 10.4 (+++) | ≥10.5 (++++) |
|---|---|---|---|---|
| ALK5 $pK_i$ | 20, 40, 63, 85, 154, 182, 248, 291, 297, 314, 350, 351, 352, 379, 486, 493, 495, 553, 557, 578, 601, 631, 684, 783, 785, 792, 796, 808, 828, 830, 836, 858, 861, 862, 863, 879, 881, 882, 1064, 1135, 1155, 1161, 1199, 1223 | 38, 39, 46, 86, 87, 90, 100, 117, 133, 142, 155, 181, 186, 195, 203, 210, 212, 218, 220, 236, 238, 243, 260, 288, 289, 324, 328, 339, 360, 361, 371, 372, 383, 385, 421, 437, 453, 462, 470, 479, 504, 507, 510, 511, 521, 528, 538, 546, 549, 556, 567, 575, 604, 630, 633, 643, 680, 682, 689, 724, 737, 757, 758, 760, 762, 774, 780, 781, 795, 801, 803, 804, 805, 806, 807, 809, 810, 812, 817, 821, 822, 823, 825, 826, 827, 829, 835, 838, 839, 841, 842, 843, 845, 846, 849, 850, 857, 859, 860, 864, 867, 868, 880, 883, 884, 890, 894, 1038, 1040, 1042, 1047, 1052, 1066, 1071, 1073, 1075, 1077, 1078, 1081, 1085, 1093, 1095, 1097, 1107, 1109, 1112, 1120, 1121, 1124, 1130, | 2, 3, 4, 6, 7, 8, 10, 11, 13, 14, 18, 19, 22, 24, 25, 27, 30, 33, 35, 36, 37, 41, 42, 43, 47, 48, 49, 50, 51, 52, 53, 54, 55, 57, 58, 59, 60, 61, 62, 64, 65, 66, 67, 68, 69, 72, 76, 77, 79, 80, 82, 84, 89, 91, 92, 94, 95, 98, 99, 102, 103, 104, 105, 106, 107, 108, 109, 110, 111, 112, 113, 115, 116, 118, 119, 120, 122, 123, 124, 126, 128, 129, 130, 132, 134, 136, 137, 138, 139, 143, 144, 145, 146, 147, 148, 151, 153, 157, 158, 161, 162, 163, 164, 165, 166, 167, 168, 169, 170, 173, 174, 175, 176, 177, 179, 180, 183, 184, 185, 187, 188, 189, 191, 193, 197, 198, 199, 200, 201, 202, 204, 205, 206, 207, 208, 209, 211, 213, 214, 216, 217, 219, 222, 223, 224, 225, 226, 227, 228, 231, 235, 239, 241, 242, 244, 245, 246, 247, 249, 251, 253, 254, 255, 256, 257, 259, 261, 262, 263, 265, 266, 268, 269, 270, 271, 274, 275, 277, 278, 279, 280, 283, 284, 285, 286, 287, 290, 293, 294, 295, 296, 298, 301, 302, 303, 304, 307, 308, 310, 311, 313, 315, 317, 318, 320, 322, 323, 326, 327, 329, 330, 331, 333, 334, 337, 338, 340, 342, 343, 344, 346, 347, 349, 353, 356, 358, 359, 362, 363, 364, 365, 366, 367, 370, 373, 375, 376, 378, 382, 384, 388, 389, 390, 392, 394, 396, 400, 402, 403, 404, 406, 407, 408, 409, 410, 411, 412, 413, 414, 415, 416, 418, 419, 424, 425, 426, 427, 428, 429, 431, 433, 436, 438, 439, 440, 442, 443, 444, 445, 446, 447, 450, 451, 455, 457, 460, 461, 464, 465, 466, 467, 468, 469, 471, 473, 475, 476, 480, 483, 484, 485, 488, 489, 491, 492, 494, 496, 497, 498, 499, 500, 501, 506, 508, 512, 514, 516, 517, 518, 519, 522, 523, 524, 527, 530, 533, 535, 537, 543, 544, 545, 547, 548, 550, 555, 558, 559, 560, 563, 566, 568, 569, 572, 573, 576, 577, 579, 580, 583, 584, 587, 588, 590, 593, 594, 600, 605, 606, 607, 608, 609, 610, 612, 613, 614, 615, 616, 618, 619, 620, 621, 622, 623, 624, 625, 627, 632, 635, 636, 637, 638, 640, 641, 642, 645, 646, 648, 649, 650, | 1, 5, 9, 12, 15, 16, 17, 21, 23, 26, 28, 29, 31, 32, 34, 44, 45, 56, 70, 71, 73, 74, 75, 78, 81, 83, 88, 93, 96, 97, 101, 114, 121, 125, 127, 131, 135, 140, 141, 149, 150, 152, 156, 159, 160, 171, 172, 178, 190, 192, 194, 196, 215, 221, 229, 230, 232, 233, 234, 237, 240, 250, 252, 258, 264, 272, 273, 276, 281, 282, 292, 299, 300, 305, 306, 309, 312, 316, 319, 321, 325, 332, 335, 336, 341, 345, 348, 354, 355, 357, 368, 369, 374, 377, 380, 381, 386, 387, 391, 393, 395, 397, 398, 399, 401, 405, 417, 420, 422, 423, 430, 432, 434, 435, 441, 448, 449, 452, 454, 456, 458, 459, 463, 472, 474, 477, 478, 481, 482, 487, 490, 502, 503, 505, 509, 513, 515, 520, 525, 526, 529, 531, 532, 534, 536, 539, 540, 541, 542, 551, 552, 554, 561, 562, 564, 565, 570, 571, 574, 581, 582, 585, 586, 589, 591, 592, 595, 596, 597, 598, 599, 602, 603, 611, 617, 626, 628, 629, 634, 639, 644, 647, 651, 656, 658, 668, 669, 678, 681, 686, 687, 691, 692, 693, 699, |

TABLE 2-continued

| 7.5 to 8.4 (+) | 8.5 to 9.4 (++) | 9.5 to 10.4 (+++) | ≥10.5 (++++) |
|---|---|---|---|
| | 1136, 1138, 1142, 1147, 1149, 1162, 1179, 1184, 1185, 1202, 1209, 1217, 1250 | 652, 653, 654, 655, 657, 659, 660, 661, 662, 663, 664, 665, 666, 667, 670, 671, 672, 673, 674, 675, 676, 677, 679, 683, 685, 688, 690, 694, 695, 696, 697, 698, 700, 701, 702, 703, 704, 705, 706, 707, 708, 709, 710, 711, 712, 713, 714, 715, 716, 717, 718, 719, 720, 721, 722, 723, 725, 728, 729, 730, 731, 732, 733, 734, 735, 736, 738, 739, 740, 741, 742, 743, 744, 745, 747, 748, 750, 752, 753, 754, 755, 756, 759, 761, 763, 764, 765, 766, 767, 768, 769, 770, 771, 772, 773, 775, 776, 777, 778, 779, 782, 784, 786, 787, 788, 789, 790, 791, 793, 794, 797, 798, 799, 800, 802, 811, 814, 815, 816, 818, 819, 820, 824, 831, 832, 833, 834, 837, 840, 844, 847, 848, 851, 852, 853, 854, 855, 856, 865, 876, 877, 878, 886, 887, 891, 892, 896, 897, 898, 903, 904, 1005, 1006, 1007, 1008, 1009, 1010, 1017, 1018, 1022, 1024, 1025, 1026, 1027, 1028, 1032, 1036, 1041, 1043, 1045, 1046, 1048, 1050, 1051, 1054, 1055, 1056, 1058, 1059, 1060, 1061, 1062, 1063, 1065, 1067, 1068, 1072, 1074, 1079, 1084, 1086, 1088, 1089, 1090, 1096, 1098, 1099, 1100, 1101, 1102, 1104, 1106, 1110, 1113, 1115, 1116, 1117, 1118, 1119, 1122, 1123, 1128, 1129, 1131, 1132, 1133, 1137, 1140, 1141, 1144, 1145, 1148, 1150, 1151, 1153, 1157, 1158, 1163, 1164, 1165, 1166, 1167, 1168, 1170, 1173, 1174, 1176, 1177, 1178, 1181, 1182, 1187, 1190, 1192, 1194, 1195, 1196, 1197, 1198, 1200, 1201, 1203, 1205, 1210, 1211, 1212, 1214, 1216, 1218, 1220, 1221, 1222, 1224, 1225, 1226, 1228, 1229, 1230, 1233, 1234, 1235, 1236, 1237, 1238, 1239, 1241, 1244, 1245, 1246, 1248, 1252, 1255 | 726, 727, 746, 749, 751, 866, 869, 885, 1044, 1057, 1070, 1082, 1087, 1091, 1092, 1094, 1103, 1105, 1111, 1125, 1126, 1139, 1146, 1152, 1154, 1160, 1169, 1171, 1172, 1183, 1191, 1204, 1206, 1207, 1213, 1215, 1219, 1232, 1242, 1243, 1251, 1253, 1254 |

Example 71: Cellular ALK5 Potency Assay to Measure $pIC_{50}$, Inhibition of TGF-β Stimulated pSMAD3 Formation in BEAS-2B Cells The potency of compounds of the present disclosure for inhibition of TGF-β-stimulated SMAD3 phosphorylation was measured in BEAS-2B cells, a human lung epithelial cell line. TGF-β signals through activin receptor-like kinase 5 (ALK5) immediately prior to SMAD3 phosphorylation. As the AlphaLISA SureFire Ultra kit (Perkin Elmer) quantitatively measures pSMAD3 levels in lysate, the assay demonstrates the ALK5 cellular potency of a test compound.

BEAS-2B cells were grown using 50% DMEM (Life Technologies) and 50% F-12 (Life Technologies) media, supplemented with 10% Fetal Bovine Serum (ATCC), 25 mM HEPES (Life Technologies), and 1× Pen-Strep (Life Technologies). Cells were cultured in a humidified incubator set at 37° C., 5% $CO_2$, and trypsonized using 0.25% Trypsin with 0.5% polyvinylpyrrolidone (PVP).

For the assay, BEAS-2B cells were seeded at 7,500 cells/well (25 µL/well) in a 384-well plate and cultured overnight. Before dosing, growth media was aspirated and the wells were rinsed with HBSS Buffer (HBSS with Calcium and Magnesium, Life Technologies) supplemented with 25 mM HEPES (Life Technologies) and 1% Bovine Serum Albumin (Roche). Compounds were serially diluted in DMSO, then further diluted with supplemented HBSS Buffer (50 µL/well) to create a compound plate 3× of the final assay concentration, at 0.3% DMSO. The diluted compounds were then added to the cells (8 µL/well) and incubated at 37° C., 5% $CO_2$ for 1 hour. After the compound incubation, TGF-β (R&D Systems) reconstituted in supplemented HBSS Buffer was added to the cells (12 µL/well, final concentration 10 ng/mL) and incubated for a further 30 minutes, after which the cells were immediately lysed with AlphaLISA lysis buffer (PerkinElmer). AlphaLISA Acceptor and Detector beads (PerkinElmer) were added 2 hours apart, then incubated overnight to be read the next day. The potency of the compound was determined through analysis of dose-dependent quantified changes in pSMAD3 signal from baseline (non-compound treated TGF-β stimulated cells). Data are expressed as $pIC_{50}$ (negative decadic logarithm $IC_{50}$) values. Certain compounds disclosed herein exhibited $pIC_{50}$ values of greater than 6 or greater than 7 when tested in BEAS-2B cells.

Table 3 shows biological activities of selected compounds in a cellular ALK5 potency assay. Compound numbers correspond to the numbers and structures provided in Table 1 and Examples 1-69.

TABLE 3

| | 5 to 5.8 (+) | 5.9 to 6.7 (++) | 6.8 to 7.6 (+++) | ≥7.7 (++++) |
|---|---|---|---|---|
| BEAS2B pIC$_{50}$ | 38, 40, 63, 69, 102, 134, 137, 168, 172, 177, 180, 238, 269, 291, 314, 360, 370, 379, 431, 453, 486, 500, 541, 546, 553, 557, 578, 579, 583, 611, 630, 631, 638, 640, 688, 783, 794, 795, 796, 797, 798, 804, 805, 1005, 1017, 1041, 1064, 1073, 1091, 1092, 1109, 1112, 1137, 1142, 1147 | 3, 7, 10, 14, 18, 20, 29, 39, 46, 47, 54, 55, 62, 64, 65, 85, 87, 101, 112, 113, 119, 129, 136, 143, 145, 150, 153, 154, 162, 164, 165, 173, 174, 182, 183, 187, 188, 189, 199, 200, 202, 203, 213, 217, 218, 227, 228, 241, 248, 251, 255, 257, 260, 262, 265, 268, 274, 277, 280, 281, 283, 289, 295, 297, 302, 311, 320, 322, 325, 327, 328, 331, 337, 338, 339, 344, 350, 351, 352, 356, 362, 366, 371, 373, 376, 383, 384, 388, 394, 400, 404, 406, 407, 424, 425, 427, 440, 468, 475, 479, 483, 489, 491, 493, 495, 497, 507, 512, 519, 528, 533, 537, 547, 552, 577, 584, 593, 601, 602, 605, 618, 622, 623, 635, 642, 645, 649, 652, 659, 665, 667, 668, 670, 671, 679, 680, 682, 684, 689, 697, 701, 705, 708, 711, 712, 715, 719, 723, 733, 735, 761, 764, 774, 785, 792, 793, 799, 801, 802, 809, 810, 811, 812, 817, 823, 831, 836, 845, 846, 848, 849, 850, 858, 859, 861, 862, 863, 864, 867, 881, 890, 891, 892, 894, 896, 903, 904, 1036, 1044, 1050, 1052, 1054, 1058, 1059, 1065, 1066, 1072, 1075, 1081, 1082, 1086, 1090, 1093, 1097, 1098, 1099, 1102, 1110, 1116, 1121, 1122, 1131, 1133, 1136, 1138, 1140, 1149, 1151, 1155, 1161, 1162, | 1, 2, 4, 5, 6, 8, 11, 17, 19, 21, 22, 23, 24, 25, 27, 28, 30, 31, 32, 33, 34, 36, 37, 41, 42, 43, 44, 45, 49, 50, 51, 52, 53, 56, 57, 58, 60, 61, 66, 67, 70, 71, 72, 74, 75, 76, 77, 79, 80, 82, 84, 86, 89, 90, 91, 92, 93, 94, 95, 96, 98, 99, 100, 103, 104, 105, 107, 108, 109, 110, 114, 115, 116, 117, 118, 120, 121, 122, 123, 124, 125, 126, 127, 128, 130, 131, 132, 133, 135, 138, 139, 140, 141, 142, 144, 146, 147, 148, 149, 151, 152, 155, 157, 158, 160, 161, 166, 167, 170, 175, 176, 178, 179, 181, 184, 186, 191, 193, 194, 195, 197, 198, 201, 204, 205, 206, 207, 209, 210, 211, 212, 214, 216, 219, 220, 221, 222, 223, 224, 225, 226, 229, 230, 231, 232, 235, 236, 237, 239, 240, 242, 243, 244, 245, 246, 247, 249, 250, 252, 253, 254, 256, 258, 261, 263, 264, 266, 270, 271, 272, 273, 275, 276, 279, 284, 285, 286, 287, 288, 290, 292, 293, 294, 296, 298, 301, 303, 304, 305, 306, 307, 309, 310, 313, 315, 316, 318, 319, 324, 326, 329, 330, 332, 333, 334, 335, 336, 340, 342, 343, 346, 347, 348, 349, 353, 354, 357, 358, 359, 361, 363, 364, 365, 367, 368, 372, 374, 375, 377, 378, 381, 382, 385, 386, 387, 389, 390, 392, 393, 395, 396, 397, 401, 402, 403, 405, 408, 409, 410, 411, 413, 414, 417, 418, 419, 421, 422, 426, 428, 433, 434, 435, 436, 437, 438, 439, 441, 442, 443, 444, 445, 446, 447, 448, 450, 451, 452, 455, 457, 459, 460, 461, 462, 463, 464, 465, 466, 467, 470, 471, 473, 474, 476, 478, 480, 481, 485, 488, 492, 494, 496, 498, 499, 501, 502, 503, 504, 505, 506, 508, 509, 510, 511, 513, 514, 515, 516, 517, 520, 521, 522, 523, 524, 526, 527, 530, 532, 535, 538, 539, 540, 542, 543, 544, 545, 548, 549, 550, 551, 554, 555, 556, 558, 559, 560, 561, 563, 566, 567, 568, 569, 571, 572, 573, 575, 576, 580, 581, 582, 585, 586, 587, 590, 597, 598, 600, 603, 604, 606, 607, 608, 610, 612, 613, 614, 615, 616, 619, 620, 621, 624, 625, 626, 627, 628, 629, 632, 633, 636, 637, 639, 641, 643, 646, 647, 648, 650, 653, 654, 655, 657, 660, 662, 663, 664, 666, 672, 673, 675, 676, 677, 678, 681, 683, 685, 686, 687, 690, 695, 696, 698, 700, 702, 703, 704, 706, 707, 709, 710, 714, 716, 717, 718, 721, 724, 725, 726, 728, 729, 730, 734, 736, 737, 738, 739, 740, 741, 742, 743, 744, 745, 746, 748, 749, 751, 752, 753, 754, 756, 757, 758, 759, 760, 762, 763, 765, 766, 767, 768, 769, 770, 771, 772, 773, 775, 776, 777, 778, 779, 780, 781, 782, 786, 789, 790, 800, 806, 814, 815, 816, 818, 819, 820, 821, 822, 825, 826, 827, 828, 829, 830, 832, 833, 835, 837, 838, 839, 840, 841, 842, 843, 844, 847, 852, 853, 854, 855, 856, 857, 860, 865, 866, 868, 869, 870, 877, 878, 879, 880, 882, 883, 884, 885, 886, 887, 897, 898, 1006, 1007, 1008, 1009, 1010, 1018, 1024, 1025, 1026, 1027, 1038, 1040, 1042, 1045, 1046, 1047, 1048, 1056, 1057, 1060, 1061, 1062, 1063, 1067, 1070, 1071, 1074, 1077, 1078, 1079, 1085, 1087, 1088, 1089, 1094, 1095, 1096, 1101, 1103, 1104, 1105, 1106, 1107, 1111, 1113, 1115, 1117, 1119, 1120, 1123, 1124, 1125, 1126, 1128, 1129, 1130, 1132, 1139, 1141, 1144, 1145, 1146, 1148, 1150, 1153, 1157, 1158, 1163, 1164, 1165, 1166, 1167, 1168, 1169, 1170, 1171, 1173, 1174, 1176, | 9, 12, 13, 15, 16, 26, 35, 48, 59, 68, 73, 78, 81, 83, 88, 97, 106, 111, 156, 159, 163, 169, 171, 185, 190, 192, 196, 208, 215, 233, 234, 259, 278, 282, 299, 300, 308, 312, 317, 321, 323, 341, 345, 355, 369, 380, 391, 398, 399, 412, 415, 416, 420, 423, 429, 430, 432, 449, 454, 456, 458, 469, 472, 477, 482, 484, 487, 490, 518, 525, 529, 531, 534, 536, 562, 564, 565, 570, 574, 588, 589, 591, 592, 594, 595, 596, 599, 609, 617, 634, 644, 651, 656, 658, 661, 669, 674, 691, 692, 693, 694, 699, 713, 722, 727, 731, 732, 747, 750, 755, 784, 787, 788, 791, 824, 834, 851, 876, 1028, 1032, 1043, 1051, 1055, 1068, 1084, 1100, 1118, 1152, 1154, 1160, 1181, 1190, 1194, 1196, 1205, 1216, 1221, 1248 |

TABLE 3-continued

| 5 to 5.8 (+) | 5.9 to 6.7 (++) | 6.8 to 7.6 (+++) | ≥7.7 (++++) |
|---|---|---|---|
| | 1172, 1184, 1192, 1198, 1199, 1246, 1254 | 1177, 1178, 1179, 1182, 1183, 1185, 1187, 1191, 1195, 1197, 1200, 1201, 1202, 1203, 1204, 1206, 1207, 1209, 1210, 1211, 1212, 1213, 1214, 1215, 1217, 1218, 1219, 1220, 1222, 1223, 1224, 1225, 1226, 1228, 1229, 1230, 1232, 1233, 1234, 1235, 1236, 1237, 1238, 1239, 1241, 1242, 1243, 1244, 1245, 1250, 1251, 1252, 1253, 1255 | |

Example 72: Cytotoxicity Measured by Premature Chromosome Condensation [15] ($pCC_{15}$)

The impact of a compound of the present disclosure on cellular adenosine triphosphate (ATP) levels was measured in Beas2B cells, a human lung epithelial cell line. Levels of ATP are correlated with the viability of cells and are often measured to determine the potential cytotoxicity of compounds. CellTiter-Glo, which lyses the cells and produces a luminescent signal proportional to the amount of ATP present, was used to determine the effect of test compound on cell viability.

Beas2B cells were grown in 50% DMEM (Life Technologies) and 50% F-12 (Life Technologies) media, supplemented with 10% Fetal Bovine Serum (ATCC), 25 mM HEPES (Life Technologies), and 1× Pen-Strep (Life Technologies). Cells were cultured in a humidified incubator set at 37° C., 5% $CO_2$, and trypsinized using 0.25% Trypsin with 0.5% polyvinylpyrrolidone (PVP).

For the assay, Beas2B cells were seeded at 500 cells/well (25 μL/well) in a 384-well plate and cultured overnight. Compounds were serially diluted in DMSO, then further diluted with growth media (40 μL/well) to create a compound plate 6× of the final assay concentration, at 0.6% DMSO. The diluted compounds were then added to the cells (5 μL/well) and incubated at 37° C., 5% $CO_2$ for 48 hours. After the compound incubation, CellTiter-Glo (Promega) was added directly to the cells (30 μL/mL). The assay plate was sealed and shaken at 700 rpm for 15 minutes in a darkened environment, then centrifuged for 2 minutes at 1500 rpm to settle the lysate at the bottom of the well. The effect of the compound on cell viability was determined through analysis of dose-dependent quantified changes in ATP from baseline (non-compound treated cells) and wells treated with 60 μM AT9283, a well-characterized cytotoxic compound. Data are expressed as $pCC_{15}$ (negative decadic logarithm $CC_{15}$) values. Certain compounds disclosed herein exhibited $pCC_{15}$ values of less than 6 or less than 5.5 when tested in Beas2B cells.

Table 4 shows cytotoxicities of selected compounds in a premature chromosome condensation assay. Compound numbers correspond to the numbers and structures provided in Table 1 and Examples 1-69.

TABLE 4

| | ≤5 (+++) | 5.1 to 5.7 (++) | 5.8 to 7.0 (+) |
|---|---|---|---|
| Cytotoxicity $pCC_{15}$ | 2, 3, 4, 6, 7, 8, 9, 11, 12, 14, 15, 18, 20, 22, 24, 25, 29, 30, 32, 33, 36, 37, 38, 39, 40, 41, 42, 44, 46, 47, 49, 50, 51, 53, 54, 55, 56, 58, 60, 61, 62, 63, 64, 66, 67, 68, 69, 70, 72, 76, 80, 84, 85, 86, 87, 89, 90, 95, 98, 100, 101, 102, 103, 107, 109, 110, 111, 114, 115, 116, 117, 118, 122, 123, 125, 126, 128, 129, 130, 131, 133, 134, 135, 136, 137, 142, 143, 145, 146, 150, 153, 154, 155, 157, 158, 159, 161, 164, 165, 166, 168, 169, 170, 172, 173, 174, 177, 179, 180, 181, 182, 184, 185, 187, 189, 191, 195, 197, 200, 201, 202, 203, 204, 206, 207, 208, 210, 211, 213, 214, 215, 217, 218, 222, 225, 226, 227, 231, 234, 236, 238, 241, 243, 244, 245, 246, 247, 253, 254, 255, 256, 257, 259, 261, 264, 266, 268, 269, 273, 277, 279, 280, 285, 286, 287, 288, 289, 290, 291, 293, 294, 295, 302, 303, 309, 310, 313, 314, 315, 319, 321, 322, 323, 324, 325, 326, 327, 328, 330, 331, 334, 337, 338, 339, 342, 343, 344, 346, 350, 351, 352, 353, 355, 356, 358, 359, 360, 361, 362, 363, 366, 367, 369, 370, 372, 373, 374, 376, 378, 379, 381, 382, 384, 385, 387, 388, 389, 390, 394, 399, 402, 404, 406, 409, 410, 411, 412, 415, 416, 419, 420, 421, 424, 425, 426, 427, 428, 429, 431, 436, 438, 439, 442, 443, 447, 451, 453, | 1, 5, 10, 13, 16, 19, 23, 26, 27, 28, 31, 35, 43, 45, 48, 52, 57, 59, 65, 73, 74, 77, 78, 82, 83, 88, 91, 92, 93, 94, 99, 104, 105, 106, 108, 112, 113, 119, 120, 121, 124, 132, 138, 139, 141, 147, 148, 152, 156, 160, 162, 167, 175, 183, 186, 188, 190, 192, 193, 196, 198, 199, 205, 209, 212, 216, 219, 220, 223, 224, 228, 229, 230, 232, 235, 237, 239, 240, 242, 248, 249, 250, 251, 252, 258, 260, 262, 263, 270, 271, 272, 274, 276, 281, 282, 283, 284, 292, 296, 297, 298, 299, 300, 304, 305, 306, 308, 311, 312, 316, 317, 318, 320, 332, 333, 335, 340, 341, 345, 347, 348, 349, 354, 357, 364, 365, 368, 371, 375, 377, 380, 383, 391, 392, 395, 396, 397, 398, 400, 401, 403, 407, 408, 414, 418, 422, | 17, 21, 34, 71, 75, 79, 81, 96, 97, 127, 140, 144, 149, 151, 163, 171, 176, 178, 194, 221, 233, 265, 275, 278, 301, 307, 329, 336, 386, 393, 405, 413, 417, 430, 435, 458, 459, 487, 502, 503, 505, 513, 517, 525, 542, 544, 551, 552, 555, 562, 564, 570, 571, 576, 591, 609, 626, 632, 647, 651, 653, 656, 658, 662, 669, 672, 678, 692, 693, 695, 699, 726, 727, 869, 870, 1010, 1056, 1068, 1084, 1100, 1154, 1200, 1206 |

TABLE 4-continued

| ≤5 (+++) | 5.1 to 5.7 (++) | 5.8 to 7.0 (+) |
|---|---|---|
| 456, 460, 465, 466, 467, 468, 469, 470, 471, 472, 473, 474, 475, 476, 480, 483, 484, 485, 486, 488, 489, 491, 492, 495, 496, 497, 498, 499, 500, 501, 504, 507, 509, 511, 512, 514, 515, 518, 519, 520, 521, 523, 524, 526, 528, 533, 535, 536, 537, 538, 539, 541, 545, 546, 548, 553, 556, 557, 558, 560, 561, 563, 565, 567, 568, 572, 575, 577, 578, 579, 582, 583, 584, 585, 588, 590, 593, 594, 599, 600, 601, 602, 603, 607, 608, 611, 613, 614, 615, 616, 618, 620, 621, 622, 623, 624, 625, 628, 630, 631, 633, 635, 636, 640, 641, 642, 643, 646, 648, 649, 650, 652, 654, 657, 659, 663, 665, 666, 667, 670, 671, 674, 675, 676, 677, 679, 680, 682, 683, 687, 688, 689, 690, 694, 696, 697, 700, 701, 702, 703, 705, 706, 708, 709, 710, 711, 712, 713, 714, 715, 716, 717, 719, 720, 722, 723, 724, 725, 728, 729, 730, 731, 733, 735, 736, 737, 738, 739, 740, 741, 742, 743, 744, 745, 746, 748, 753, 756, 757, 758, 759, 760, 761, 762, 763, 764, 765, 766, 767, 768, 769, 770, 771, 772, 773, 774, 775, 778, 780, 781, 782, 783, 784, 785, 786, 787, 788, 789, 790, 791, 792, 793, 794, 795, 796, 797, 798, 799, 800, 804, 805, 806, 809, 810, 811, 812, 814, 815, 816, 817, 818, 819, 820, 821, 822, 823, 826, 827, 828, 829, 830, 831, 833, 835, 836, 837, 839, 840, 841, 842, 843, 845, 846, 847, 848, 849, 850, 851, 852, 853, 855, 856, 857, 858, 859, 860, 861, 862, 863, 864, 865, 867, 876, 877, 878, 879, 880, 881, 882, 883, 884, 886, 887, 890, 891, 892, 894, 896, 897, 898, 903, 904, 1005, 1007 1017, 1018, 1024, 1025, 1026, 1027, 1032, 1036, 1038, 1040, 1041, 1042, 1044, 1045, 1046, 1047, 1048, 1050, 1052, 1054, 1055, 1058, 1059, 1060, 1061, 1062, 1063, 1064, 1065, 1066, 1067, 1070, 1071, 1072, 1073, 1074, 1075, 1077, 1078, 1079, 1081, 1082, 1085, 1086, 1087, 1088, 1089, 1090, 1091, 1092, 1093, 1095, 1097, 1098, 1099, 1102, 1103, 1104, 1106, 1107, 1109, 1110, 1111, 1112, 1113, 1116, 1117, 1119, 1120, 1121, 1122, 1123, 1124, 1125, 1126, 1128, 1129, 1130, 1131, 1132, 1133, 1135, 1136, 1137, 1138, 1140, 1141, 1142, 1144, 1145, 1146, 1147, 1148, 1149, 1150, 1151, 1153, 1155, 1157, 1158, 1160, 1161, 1162, 1163, 1164, 1165, 1166, 1167, 1168, 1169, 1170, 1172, 1173, 1174, 1176, 1179, 1181, 1184, 1185, 1187, 1190, 1191, 1192, 1194, 1195, 1196, 1198, 1199, 1201, 1202, 1203, 1204, 1205, 1209, 1210, 1211, 1212, 1214, 1217, 1218, 1220, 1223, 1224, 1225, 1226, 1228, 1229, 1230, 1233, 1234, 1235, 1236, 1237, 1238, 1239, 1241, 1244, 1246, 1248, 1250, 1252, 1254, 1255 | 423, 432, 433, 434, 437, 440, 441, 444, 445, 446, 448, 449, 450, 452, 454, 455, 457, 461, 462, 463, 464, 477, 478, 479, 481, 482, 490, 493, 494, 506, 508, 510, 516, 522, 527, 529, 530, 531, 532, 534, 540, 543, 547, 549, 550, 554, 559, 566, 569, 573, 574, 580, 581, 586, 587, 589, 592, 595, 596, 597, 598, 604, 605, 606, 610, 612, 617, 619, 627, 629, 634, 637, 638, 639, 644, 645, 655, 660, 661, 664, 668, 673, 681, 685, 686, 691, 698, 704, 707, 718, 721, 732, 734, 747, 749, 750, 751, 752, 754, 755, 776, 777, 779, 824, 825, 832, 834, 838, 844, 854, 866, 868, 885, 1006, 1008, 1009, 1022, 1028, 1043, 1051, 1057, 1094, 1096, 1101, 1105, 1115, 1118, 1139, 1152, 1171, 1177, 1178, 1182, 1183, 1197, 1207, 1213, 1215, 1216, 1219, 1221, 1222, 1232, 1242, 1243, 1245, 1251, 1253 | |

Example 73: In Vitro Human Liver Microsome Intrinsic Clearance (HLM Cl$_{int}$)

Liver microsomes were used for in vitro determination of hepatic clearance of compounds of the present disclosure. A microsomal incubation cofactor solution was prepared with 100 mM potassium phosphate buffered to pH 7.4 (BD Biosciences, Woburn, Mass.) supplemented with 2 mM NADPH (Sigma-Aldrich, St. Louis, Mo.). 10 mM DMSO stocks of test compound were diluted and spiked into the cofactor solution to yield a 0.2 µM concentration (0.02% v/v DMSO). Aliquots of frozen human liver microsomes (Bioreclamation IVT, Baltimore Md.) were thawed and diluted into 100 mM potassium phosphate buffer to yield microsomal protein concentrations of 0.2 mg/mL. Cofactor/drug and microsomal solutions were pre-warmed separately for 4 minutes in a water bath held at 37° C. Incubations (n=1) were started by the combination of equal volumes of cofactor/drug solution with microsomal solution. The final concentration of test compound was 0.1 µM with a final protein concentration of 0.1 mg/mL and final NADPH concentration of 1 mM. Samples were collected at times 0, 3, 8, 15, 30, and 45 minutes to monitor the disappearance of test compound. At each time point, 50 µL of incubation sample was removed and spiked into 25 µL of water plus 3% formic acid plus Internal Standard for reaction termination. Samples were then injected onto an AB Sciex API 4000 triple quadrupole mass spectrometer for quantitation by LC-MS/MS. Mobile Phase A consisted of HPLC grade water with 0.2% formic acid and Mobile Phase B consisted of HPLC grade acetonitrile with 0.2% formic acid with all samples run through a Thermo HyPURITY C18 50×2.1 mm column (Waltham, Mass.). HLM $Cl_{int}$ data was reported in units of µL/min/mg. See Riley, R. J., et al., *Drug Metab. Dispos.*, 2005, September, 33(9), pp. 1304-1311. Certain compounds disclosed herein exhibited HLM $Cl_{int}$ of greater than 50 µL/min/mg or greater than 100 µL/min/mg.

Example 74: Lung PK/PD

In-Life Portion $C_{57}$bl/6n mice were acclimated for at least 3 days before use. On the day of the experiment, animals were grouped into sample sizes of 5 (n=10 for the TGF-β stimulated group). Compounds of the present disclosure (formulated in 3% glycerol in PBS; pH=4) were pre-treated via oral aspiration (OA; animals are forced to aspirate solution into the lungs by covering their nose). All oral aspirations were performed using a 50 µL dosing volume and accompanied by the appropriate vehicle control groups. Following compound OA treatment, the animals were returned to their home cages and monitored. Compound pre-treatment occurred 4 hours prior to harvest for screening and dose-response studies; duration studies had variable compound pre treatment times. One hour prior to harvest, animals were challenged via oral aspiration a second time with PBS vehicle or recombinant human TGF-β1 protein (0.01 µg per animal dissolved in 1 part 4 mM HCl and 2 parts 3% glycerol in PBS). Five minutes prior to harvest, animals were deeply anesthetized under isoflurane and euthanized via cervical dislocation. Bronchoalveolar lavage fluid (BALF), plasma and left lung lobes were collected during harvest.

Sample Collection and Processing

Blood plasma was collected via open cardiac puncture. After whole blood collection, the samples were placed in EDTA-coated tubes to prevent coagulation. Blood samples were spun at 15300×g's for 4 minutes at 4° C. to separate the plasma. Plasma was immediately isolated, frozen and submitted for bioanalytical (BA) analysis.

In order to collect BALF, the lungs were flushed via the trachea with 0.7 mL of PBS 3 times. The BALF, which consists almost entirely of tissue-derived macrophages, was immediately centrifuged at 700×g's for 15 minutes. After centrifugation, the supernatant was removed, the BALF was re-suspended in 1× cell lysis buffer, and immediately frozen. Prior to BA submission, the BALF was dethawed and sonicated for 30 minutes on cold water to lyse open the cells Left lung lobes were harvested immediately after BALF collection. Lung samples were homogenized in 500 µL of 1× cell lysis buffer. After homogenization, the samples were split: half of the sample was immediately placed on a rotisserie for 10 minutes while the other half was immediately frozen for BA analysis. The samples placed on the rotisserie were then centrifuged at 10,000×g's for 10 minutes in order to separate the protein in the supernatant from pelleted debris. Following collection of the supernatant, a total protein quantification assay (Bradford) was performed to normalize the concentrations of all samples. Using the Hamilton star liquid handling system, each sample was diluted in 1× cell lysis buffer to 2 mg/mL of protein. Samples were stored at −80° C. or immediately processed using the Meso-scale Discovery system.

Phospho-SMAD3 (pSMAD3) and Total-SMAD3 (tSMAD3) Quantification Using Meso-Scale Discovery Meso-scale Discovery (MSD) is an electrochemical protein quantification assay that requires specialized microplates with carbon electrodes attached to the bottom. These carbon electrodes allow for greater attachment of biological reagent to microplates, thus allowing for a more sensitive read-out when compared to a traditional ELISA. Similar to a standard sandwich ELISA, MSD requires use of a coating antibody that binds the target protein(s) within the sample. After sample incubation, a primary antibody is used to bind the epitope of interest. Following addition of the primary antibody, a secondary-antibody with a SULFO-TAG detection is used to allow for quantification of the epitope of interest. Lastly, the microplate is read via an electric pulse that causes the SULFO-TAG to emit light, which serves as the final read-out of the assay.

The coating antibody (SMAD3, clone=5G-11) was incubated overnight in the specialized MSD microplates at 4° C. The next day, the microplates were blocked in 3% BSA (bovine serum albumin) for 70 minutes to prevent non-specific protein binding to the bottom of the microplate. After a wash step, 50 µg of lung samples were loaded into the MSD-plate and incubated for 2 hours at room temperature. The plates were washed again to remove unbound sample; either phospo-SMAD3 (pSMAD3; clone=EP568Y) or total-SMAD3 (tSMAD3) primary antibody were incubated for 1 hour. Following a wash step, the anti-rabbit SULFO-tag detection antibody was incubated for 50 minutes. After a final wash step, MSD-read buffer was added to each sample. pSMAD3 and tSMAD3 quantification was performed using an MSD-specific plate reader (Sector S 600).

Data Analysis

Samples were immediately analyzed using an outlier analysis (Grubbs test, α=0.05). After outlier removal, the raw pSMAD3 were divided by the tSMAD3 luminescent readings. In screening and dose-response studies, the pSMAD3/tSMAD3 ratio was normalized to the TGF-β induction group (set to 100%) in order to minimize the variability between stimulation. First, the 3% glycerol/PBS group was compared with the 3% glycerol/TGF-β with a student's t-test (cut-off: p=0.05) to ensure a pSMAD3 window was present. A one-way ANOVA (fisher's uncorrected LSD) was used to compare all drug treated groups with the 3% glycerol/TGF-β group to determine if statistically significant differences are observed. Percent pSMAD3 inhibition was calculated using the vehicle pSMAD3 as a baseline value and displayed as the final readout. Dose-response curves were fitted with a 4-parameter non-linear regression algorithm; the minimum response was set to 0% pSMAD3 inhibition and the maximum response set to 100% pSMAD3 inhibition. Compound potencies were obtained from the regression and reported as ID50s.

PK Study

Plasma, lung and macrophage drug concentrations were quantified. Total macrophage concentration was normalized to the total macrophage cell volume over the total drug recovered in the BALF. The alveolar macrophage volume used in the calculation was based on a publication by Krombach et al. (*Environmental Health Perspectives*, September 1997, Vol. 105, Supplement 5, pp. 1261-1263) which estimated the rat alveolar macrophage volume to be approximately 1200 $\mu m^3$ or $1.2e^{-9}$ mL. The assumption was made that the mouse alveolar macrophage volume is similar to that of the rat. Normalized total macrophage concentration recovered=(total drug recovered from BALF)/(total cell counts*$1.2e^{-9}$ mL).

Certain compounds disclosed herein exhibited (lung $AUC_{0-t}$):(plasma $AUC_{0-t}$) ratios of greater than 10, such as greater than 50, greater than 75 or greater than 100. A compound intended for local delivery to the lung with minimal systemic exposure preferably exhibits a (lung $AUC_{0-t}$):(plasma $AUC_{0-t}$) ratio of greater than 50. Certain compounds provided in Table 2 having $pK_i$ values of greater than 9.5 exhibited a (lung $AUC_{0-t}$):(plasma $AUC_{0-t}$) ratio of greater than 75.

Example 75: Cardiac PK/PD

In-Life Portion

C57bl/6n mice were acclimated for at least 3 days before use. On the day of the experiment, animals were grouped into sample sizes of 5-10. Test compounds were pre-treated via oral aspiration (OA; animals are forced to aspirate solution into the lungs by covering their nose). All oral aspirations were performed using a 50 µL dosing volume and accompanied by a vehicle control group (3% glycerol in PBS, pH=4). Following compound OA treatment, the animals were returned to their home cages and monitored. Compound pre treatment occurred either 2 or 4 hours prior to harvest. One hour prior to harvest, animals were challenged via tail-vein intravenous injection with PBS vehicle or recombinant human TGF-β1 protein (1 µg per animal dissolved in 1 part 4 mM HCl and 2 parts 3% glycerol in PBS). Five minutes prior to harvest, animals were deeply anesthetized under isoflurane and euthanized via cervical dislocation. Plasma, left lung lobes and whole hearts were collected during harvest.

Sample Collection and Processing

Blood plasma was harvested as described above in the Lung PK/PD experiment. Whole hearts were processed in the same manners as left lung lobes in the Lung PK/PD experiment. Left lung lobes were homogenized in 500 µL of water and submitted for BA Analysis.

Phospho-SMAD3 (pSMAD3) and Total-SMAD3 (tSMAD3) Quantification Using Meso-Scale Discovery Heart samples were processed using MSD in the same manner as the left lung lobes above. Data analysis was performed in the same manners as the lung PK/PD experiment. Plasma, lung and heart drug concentrations were quantified.

There was minimal target engagement systemically following treatment with one or more compound disclosed herein, as measured by SMAD3 phosphorylation inhibition. In some examples, a compound disclosed herein exhibited less than 10% target engagement systemically as measured by SMAD3 phosphorylation inhibition.

Example 76: Efficacy Study in Syngeneic Cancer Model

One or more compounds disclosed herein, e.g., a compound provided in Table 1 having an ALK5 $pK_i$ value of greater than 9.5, preferably greater than 10.5 (a measurement reflecting the ability of the compound to inhibit ALK5 activity, measured in accordance with Example 70), are expected to suppress tumor growth in syngeneic cancer models when administered alone or in combination with an immunotherapeutic agent. Six- to 8-week old BALB/c mice are used for in vivo efficacy studies in accordance with IACUC guidelines. Commercially available 4T1 cells (0.5-$2.0 \times 10^4$ cells/mouse) are implanted subcutaneously into the right flanks of BALB/c mice. When the tumor reaches a palpable size of approximately 8-10 mm in diameter, the primary tumors are surgically removed, and the mice are randomly assigned to vehicle control or compound treatment groups. Alternatively, CT26 cells (0.5-$2.0 \times 10^4$ cells/mouse) are injected intravenously into BALB/c mice to generate the cancer model. Two days following the surgery, or 7 days following injection of CT26 cells, the mice are treated with either (1) vehicle control, (2) a compound of the present disclosure at an appropriate amount and frequency (formulated in 3% glycerol in PBS; pH=4) via oral aspiration or intranasally, (3) an immunotherapeutic agent (e.g., pembrolizumab or durvalumab) at an appropriate amount and frequency, or (4) a compound of the present disclosure and an immunotherapeutic agent, each at an appropriate amount and frequency.

Body weight is measured twice weekly. Following 2- to 4-weeks of treatment, the lung and liver of each animal is harvested, and the number of metastatic cells in each tissue sample determined using a clonogenic metastasis assay. Cells may be further subjected to one or more of FACS analysis, T-cell function assay, and RNA extraction. It is expected that the animal group treated with one or more of the ALK5 inhibitors disclosed herein exhibits reduction in lung tumor burden. Activation of an immune response by the ALK5 inhibitor may stimulate both local and systemic antitumor T-cell activation, thus a reduction in liver tumor burden may also be observed. When administered in combination with an immunotherapeutic agent, a compound of the present disclosure, such as a compound provided in Table 1, is expected to produce an increased reduction in lung tumor burden relative to the reduction in tumor burden observed in animals treated with either single agent alone. The compounds described herein are expected to interact synergistically with an immunotherapeutic agent to suppress tumor growth and increase survival.

Example 77: Prophylactic Study in Murine DSS-Induced Intestinal Fibrosis Model

One or more compounds disclosed herein, e.g., a compound provided in Table 1 having an ALK5 $pK_i$ value of greater than 9.5, preferably greater than 10.5 (a measurement reflecting the ability of the compound to inhibit ALK5 activity, measured in accordance with Example 70), are expected to slow, halt or reverse the progression of intestinal fibrosis in a murine colitis model. Six to 8-week old male C57BL/6J mice are tagged and weighed. The drinking water of the animals is treated with 2.5% dextran sulfate sodium (DSS) for 7 days to induce acute colitis, followed by 2 days of normal drinking water. Three, 3-week cycles of 2.5% DSS treatment (1 week of 2.5% DSS in water; 2 weeks of normal water) are then completed to induce intestinal fibrosis.

Starting on day one of DSS administration, mice are treated with either vehicle control or a compound of the present disclosure at an appropriate amount and frequency via oral gavage (e.g., once daily). The animals are sacrificed 9 weeks after the first DSS administration, then distal, mid and proximal sections of the colon harvested for histologic analysis, RNA extraction and cytokine measurement. A compound of the present disclosure, such as a compound provided in Table 1, is expected to decrease ALK5 activity in the colon and to slow or prevent intestinal fibrosis as evidenced by one or more of (1) reduction in the ratio of colon weight to colon length; (2) reduction in deposition of extracellular matrix as observed by histology; (3) reduction in expression of collagen 1 (Colla1) and connective tissue growth factor (Ctgf) in colon tissue; and (4) reduction in production of TGF-β 1 and IL6 in the colon, relative to vehicle-treated controls.

Example 78: Efficacy Study in Murine DSS-Induced Intestinal Fibrosis Model

One or more compounds disclosed herein, e.g., a compound provided in Table 1 having an ALK5 $pK_i$ value of greater than 9.5, preferably greater than 10.5 (a measurement reflecting the ability of the compound to inhibit ALK5 activity, measured in accordance with Example 70), are expected to slow, halt or reverse the progression of intestinal fibrosis in a murine colitis model. Six to 8-week old male C57BL/6J mice are tagged and weighed. The drinking water of the animals is treated with 2.5% dextran sulfate sodium (DSS) for 7 days to induce acute colitis, followed by 2 days of normal drinking water. Three, 3-week cycles of 2.5% DSS treatment (1 week of 2.5% DSS in water; 2 weeks of normal water) are then completed to induce intestinal fibrosis.

Following the second of the 3 cycles of DSS administration, mice are treated with either vehicle control or a compound of the present disclosure at an appropriate amount and frequency via oral gavage (e.g., once daily). Animals are sacrificed at either 6, 9 or 12 weeks after the first DSS cycle, then distal, mid and proximal sections of the colon harvested for histologic analysis, RNA extraction and cytokine measurement. A compound of the present disclosure, such as a compound provided in Table 1, is expected to decrease ALK5 activity in the colon and to slow, halt or reverse intestinal fibrosis as evidenced by one or more of (1) reduction in the ratio of colon weight to colon length; (2) reduction in deposition of extracellular matrix as observed by histology; (3) reduction in expression of collagen 1 (Colla1) and connective tissue growth factor (Ctgf) in colon tissue; and (4) reduction in production of TGF-β 1 and IL6 in the colon, relative to vehicle-treated controls.

Example 79: Efficacy Study in Adoptive T-Cell Transfer Model of Colitis

One or more compounds disclosed herein, e.g., a compound provided in Table 1 having an ALK5 $pK_i$ value of greater than 9.5, preferably greater than 10.5 (a measurement reflecting the ability of the compound to inhibit ALK5 activity, measured in accordance with Example 70), are expected to slow, halt or reverse the progression of intestinal fibrosis in an adoptive T-cell transfer model of colitis. Six- to 8-week old female CB17 SCID mice are tagged and weighed, then administered $CD4^+$ $CD25^-$ $CD62L^+$ naïve T cells isolated from the spleens of Balb/C mice (IP; $1\times10^6$ cells) to induce colitis.

Once diarrhea and a 10% or greater decrease in body weight are observed (typically around week 2), mice are treated with either vehicle control or a compound of the present disclosure at an appropriate amount and frequency via oral gavage (e.g., once daily). Animals are sacrificed 45 days after induction of colitis, then distal, mid and proximal sections of the colon harvested for histologic analysis, RNA extraction and cytokine measurement. A compound of the present disclosure, such as a compound provided in Table 1, is expected to decrease ALK5 activity in the colon and to slow, halt or reverse intestinal fibrosis as evidenced by one or more of (1) reduction in the ratio of colon weight to colon length; (2) reduction in deposition of extracellular matrix as observed by histology; (3) reduction in expression of collagen 1 (Colla1) and connective tissue growth factor (Ctgf) in colon tissue; and (4) reduction in production of TGF-β 1 and IL6 in the colon, relative to vehicle-treated controls.

Example 80: Efficacy Study in Monocrotaline Model of Severe Pulmonary Hypertension One or more compounds disclosed herein, e.g., a compound provided in Table 1 having an ALK5 $pK_i$ value of greater than 9.5, preferably greater than 10.5 (a measurement reflecting the ability of the compound to inhibit ALK5 activity, measured in accordance with Example 70), are expected to slow, halt or reverse the progression of pulmonary hypertension in a monocrotaline (MCT) model of severe pulmonary hypertension. Male Sprague-Dawley rats are tagged, weighed, and randomly divided into control and MCT-treated groups. The rats in the MCT-treated group are administered a single dose of MCT (60 mg/kg, s.c.), then treated with either (1) vehicle control; (2) sildenafil (30 mg/kg, p.o., b.i.d.); or (3) a compound of the present disclosure at an appropriate amount and frequency (formulated in 3% glycerol in PBS; pH=4) via oral aspiration.

Following 2-weeks of treatment, the animals are anesthetized with ketamine/xylazine for terminal monitoring of pulmonary and systemic arterial pressures along with heart rate. The lungs of each animal are then harvested for histologic analysis. A compound of the present disclosure, such as a compound provided in Table 1, is expected to decrease ALK5 activity in the lung and slow, halt or reverse the progression of pulmonary hypertension as evidenced by one or more of (1) reduction in systolic pulmonary arterial pressure; (2) reduction in right ventricular (RV) systolic pressure; (3) reduction in RV diastolic pressure; (4) increase in cardiac output; (5) reduction in RV hypertrophy; (6) reduction in pSmad2 or pSmad3 staining within vascular and/or alveolar cells; (7) reduction in medial thickness; (8) reduction in vascular smooth muscle cell proliferation; (9) reduction in vascular smooth muscle hypertrophy; and (10) reduction in expression of matrix metalloproteinase (MMP)-2 and/or MMP-9.

What is claimed is:

1. A compound of Formula (I-A):

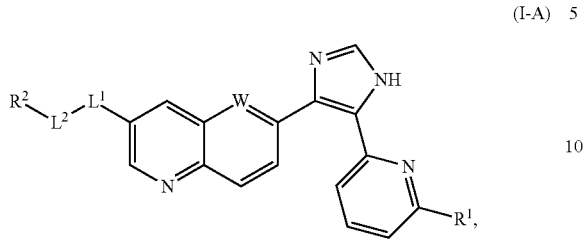

or a pharmaceutically acceptable salt thereof, wherein:
W is CH;
$R^1$ is $R^{10}$;
$L^1$ is absent; or selected from $C_{1-6}$ alkylene, $C_{2-6}$ alkenylene, $C_{2-6}$ alkynylene, $C_{3-12}$ carbocycle, and 3- to 12-membered heterocycle, each of which is optionally substituted with one or more $R^{10}$;
$L^2$ is selected from absent, —O—, —S—, —N($R^{11}$)—, —C(O)—, —C(O)O—, —OC(O)—, —OC(O)O—, —C(O)N($R^{11}$)—, —C(O)N($R^{11}$)C(O)—, —C(O)N($R^{11}$)C(O)N($R^{11}$)—, —N($R^{11}$)C(O)—, —N($R^{11}$)C(O)N($R^{11}$)—, —N($R^{11}$)C(O)O—, —OC(O)N($R^{11}$)—, —C(N$R^{11}$)—, —N($R^{11}$)C(N$R^{11}$)—, —C(N$R^{11}$)N($R^{11}$)—, —N($R^{11}$)C(N$R^{11}$)N($R^{11}$)—, —S(O)$_2$—, —OS(O)—, —S(O)O—, —S(O)—, —OS(O)$_2$, —S(O)$_2$O—, —N($R^{11}$)S(O)$_2$—, —S(O)$_2$N($R^{11}$)—, —N($R^{11}$)S(O)—, —S(O)N($R^{11}$)—, —N($R^{11}$)S(O)$_2$N($R^{11}$)—, and —N($R^{11}$)S(O)N($R^{11}$)—;
$R^2$ is $R^{10}$;
$R^{10}$ is independently selected at each occurrence from: halogen, —NO$_2$, —CN, —OR$^{12}$, —SR$^{12}$, —N(R$^{12}$)$_2$, —NR$^{13}$R$^{14}$, —S(=O)R$^{12}$, —S(=O)$_2$R$^{12}$, —S(=O)$_2$N(R$^{12}$)$_2$, —S(=O)$_2$NR$^{13}$R$^{14}$, —NR$^{12}$S(=O)$_2$R$^{12}$, —NR$^{12}$S(=O)$_2$N(R$^{12}$)$_2$, —NR$^{12}$S(=O)$_2$NR$^{13}$R$^{14}$, —C(O)R$^{12}$, —C(O)OR$^{12}$, —OC(O)R$^{12}$, —OC(O)OR$^{12}$, —OC(O)N(R$^{12}$)$_2$, —OC(O)NR$^{13}$R$^{14}$, —NR$^{12}$C(O)R$^{12}$, —NR$^{12}$C(O)OR$^{12}$, —NR$^{12}$C(O)N(R$^{12}$)$_2$, —NR$^{12}$C(O)NR$^{13}$R$^{14}$, —C(O)N(R$^{12}$)$_2$, —C(O)NR$^{13}$R$^{14}$, —P(O)(OR$^{12}$)$_2$, —P(O)(R$^{12}$)$_2$, =O, =S, =N(R$^{12}$);
$C_{1-10}$ alkyl, $C_{2-10}$ alkenyl, and $C_{2-10}$ alkynyl, each of which is independently optionally substituted at each occurrence with one or more substituents selected from halogen, —NO$_2$, —CN, —OR$^{12}$, —SR$^{12}$, —N(R$^{12}$)$_2$, —NR$^{13}$R$^{14}$, —S(=O)R$^{12}$, —S(=O)$_2$R$^{12}$, —S(=O)$_2$N(R$^{12}$)$_2$, —S(=O)$_2$NR$^{13}$R$^{14}$, —NR$^{12}$S(=O)$_2$R$^{12}$, —NR$^{12}$S(=O)$_2$N(R$^{12}$)$_2$, —NR$^{12}$S(=O)$_2$NR$^{13}$R$^{14}$, —C(O)R$^{12}$, —C(O)OR$^{12}$, —OC(O)R$^{12}$, —OC(O)OR$^{12}$, —OC(O)N(R$^{12}$)$_2$, —OC(O)NR$^{13}$R$^{14}$, —NR$^{12}$C(O)R$^{12}$, —NR$^{12}$C(O)OR$^{12}$, —NR$^{12}$C(O)N(R$^{12}$)$_2$, —NR$^{12}$C(O)NR$^{13}$R$^{14}$, —C(O)N(R$^{12}$)$_2$, —C(O)NR$^{13}$R$^{14}$, —P(O)(OR$^{12}$)$_2$, —P(O)(R$^{12}$)$_2$, =O, =S, =N(R$^{12}$), $C_{3-12}$ carbocycle, and 3- to 12-membered heterocycle; and
$C_{3-12}$ carbocycle and 3- to 12-membered heterocycle,
wherein each $C_{3-12}$ carbocycle and 3- to 12-membered heterocycle in $R^{10}$ is independently optionally substituted with one or more substituents selected from halogen, —NO$_2$, —CN, —OR$^{12}$, —SR$^{12}$, —N(R$^{12}$)$_2$, —NR$^{13}$R$^{14}$, —S(=O)R$^{12}$, —S(=O)$_2$R$^{12}$, —S(=O)$_2$N(R$^{12}$)$_2$, —S(=O)$_2$NR$^{13}$R$^{14}$, —NR$^{12}$S(=O)$_2$R$^{12}$, —NR$^{12}$S(=O)$_2$N(R$^{12}$)$_2$, —NR$^{12}$S(=O)$_2$NR$^{13}$R$^{14}$, —C(O)R$^{12}$, —C(O)OR$^{12}$, —OC(O)R$^{12}$, —OC(O)OR$^{12}$, —OC(O)N(R$^{12}$)$_2$, —OC(O)NR$^{13}$R$^{14}$, —NR$^{12}$C(O)R$^{12}$, —NR$^{12}$C(O)OR$^{12}$, —NR$^{12}$C(O)N(R$^{12}$)$_2$, —NR$^{12}$C(O)NR$^{13}$R$^{14}$, —C(O)N(R$^{12}$)$_2$, —C(O)NR$^{13}$R$^{14}$, —P(O)(OR$^{12}$)$_2$, —P(O)(R$^{12}$)$_2$, =O, =S, =N(R$^{12}$), $R^{12}$, $C_{1-6}$ alkyl, $C_{1-6}$ haloalkyl, $C_{2-6}$ alkenyl, and $C_{2-6}$ alkynyl;

$R^{11}$ is independently selected at each occurrence from: hydrogen, —C(O)R$^{12}$, —C(O)OR$^{12}$, —C(O)N(R$^{12}$)$_2$, —C(O)NR$^{13}$R$^{14}$;
$C_{1-6}$ alkyl, $C_{2-6}$ alkenyl, and $C_{2-6}$ alkynyl, each of which is independently optionally substituted at each occurrence with one or more substituents selected from halogen, —NO$_2$, —CN, —OR$^{12}$, —SR$^{12}$, —N(R$^{12}$)$_2$, —NR$^{13}$R$^{14}$, —S(=O)R$^{12}$, —S(=O)$_2$R$^{12}$, —S(=O)$_2$N(R$^{12}$)$_2$, —S(=O)$_2$NR$^{13}$R$^{14}$, —NR$^{12}$S(=O)$_2$R$^{12}$, —NR$^{12}$S(=O)$_2$N(R$^{12}$)$_2$, —NR$^{12}$S(=O)$_2$NR$^{13}$R$^{14}$, —C(O)R$^{12}$, —C(O)OR$^{12}$, —OC(O)R$^{12}$, —OC(O)OR$^{12}$, —OC(O)N(R$^{12}$)$_2$, —OC(O)NR$^{13}$R$^{14}$, —NR$^{12}$C(O)R$^{12}$, —NR$^{12}$C(O)OR$^{12}$, —NR$^{12}$C(O)N(R$^{12}$)$_2$, —NR$^{12}$C(O)NR$^{13}$R$^{14}$, —C(O)N(R$^{12}$)$_2$, —C(O)NR$^{13}$R$^{14}$, —P(O)(OR$^{12}$)$_2$, —P(O)(R$^{12}$)$_2$, =O, =S, =N(R$^{12}$), $C_{3-12}$ carbocycle, and 3- to 12-membered heterocycle; and
$C_{3-12}$ carbocycle and 3- to 12-membered heterocycle,
wherein each $C_{3-12}$ carbocycle and 3- to 12-membered heterocycle in $R^{11}$ is independently optionally substituted with one or more substituents selected from halogen, —NO$_2$, —CN, —OR$^{12}$, —SR$^{12}$, —N(R$^{12}$)$_2$, —NR$^{13}$R$^{14}$, —S(=O)R$^{12}$, —S(=O)$_2$R$^{12}$, —S(=O)$_2$N(R$^{12}$)$_2$, —S(=O)$_2$NR$^{13}$R$^{14}$, —NR$^{12}$S(=O)$_2$R$^{12}$, —NR$^{12}$S(=O)$_2$N(R$^{12}$)$_2$, —NR$^{12}$S(=O)$_2$NR$^{13}$R$^{14}$, —C(O)R$^{12}$, —C(O)OR$^{12}$, —OC(O)R$^{12}$, —OC(O)OR$^{12}$, —OC(O)N(R$^{12}$)$_2$, —OC(O)NR$^{13}$R$^{14}$, —NR$^{12}$C(O)R$^{12}$, —NR$^{12}$C(O)OR$^{12}$, —NR$^{12}$C(O)N(R$^{12}$)$_2$, —NR$^{12}$C(O)NR$^{13}$R$^{14}$, —C(O)N(R$^{12}$)$_2$, —C(O)NR$^{13}$R$^{14}$, —P(O)(OR$^{12}$)$_2$, —P(O)(R$^{12}$)$_2$, =O, =S, =N(R$^{12}$), $R^{12}$, $C_{1-6}$ alkyl, $C_{1-6}$ haloalkyl, $C_{2-6}$ alkenyl, and $C_{2-6}$ alkynyl;

$R^{12}$ is independently selected at each occurrence from hydrogen; and $C_{1-10}$ alkyl, $C_{2-10}$ alkenyl, $C_{2-10}$ alkynyl, 1- to 6-membered heteroalkyl, $C_{3-12}$ carbocycle, and 3- to 12-membered heterocycle, each of which is optionally substituted by halogen, —CN, —NO$_2$, —NH$_2$, —NHCH$_3$, —NHCH$_2$CH$_3$, =O, —OH, —OCH$_3$, —OCH$_2$CH$_3$, —CH$_3$, —CH$_2$CH$_3$, —CH(CH$_3$)$_2$, —C(CH$_3$)$_3$, $C_{3-12}$ carbocycle, or 3- to 6-membered heterocycle; and $R^{13}$ and $R^{14}$ are taken together with the nitrogen atom to which they are attached to form a heterocycle, optionally substituted with one or more $R^{12}$.

2. The compound or salt of claim 1, wherein $R^1$ is selected from halogen, $C_{1-4}$ alkyl, and $C_{1-4}$ haloalkyl.

3. The compound or salt of claim 2, wherein $R^1$ is CH$_3$.

4. The compound or salt of claim 1, wherein $L^1$ is absent, $C_{1-6}$ alkylene, $C_{3-12}$ carbocycle, or 3- to 12-membered heterocycle.

5. The compound or salt of claim 1, wherein L² is selected from absent, —O—, —N(R¹¹)—, —C(O)O—, —C(O)N(R¹¹)—, and —N(R¹¹)C(O)—.

6. The compound or salt of claim 1, wherein R² is selected from:
halogen, —CN, —OR¹², —SR¹², —N(R¹²)₂, —C(O)OR¹², —OC(O)R¹², —NR¹²C(O)R¹², —NR¹²C(O)N(R¹²)₂, —C(O)N(R¹²)₂;
C₁₋₁₀ alkyl, optionally substituted with one or more substituents selected from halogen, —CN, —OR¹², —SR¹², —N(R¹²)₂, —C(O)OR¹², —OC(O)R¹², —NR¹²C(O)R¹², —NR¹²C(O)N(R¹²)₂, —C(O)N(R¹²)₂, C₃₋₁₂ carbocycle, and 3- to 12-membered heterocycle; and
C₃₋₁₂ carbocycle and 3- to 12-membered heterocycle, wherein each C₃₋₁₂ carbocycle and 3- to 12-membered heterocycle in R² is independently optionally substituted with one or more substituents selected from halogen, —CN, —OR¹², —SR¹², —N(R¹²)₂, —C(O)OR¹², —OC(O)R¹², —NR¹²C(O)R¹², —NR¹²C(O)N(R¹²)₂, —C(O)N(R¹²)₂, =O, R¹², C₁₋₆ alkyl, and C₁₋₆ haloalkyl.

7. The compound or salt of claim 6, wherein R¹² is independently selected at each occurrence from hydrogen and C₁₋₆ alkyl, optionally substituted with one or more substituents selected from halogen, —NH₂, —NHCH₃, and —OCH₃.

8. The compound or salt of claim 1, wherein:
L¹ is selected from absent, C₃₋₁₂ carbocycle, and 3- to 12-membered heterocycle;
L² is absent; and
R² is selected from:
—CN, —OR¹², —N(R¹²)₂, —C(O)OR¹², —NR¹²C(O)R¹², —C(O)N(R¹²)₂;
C₁₋₁₀ alkyl, optionally substituted with one or more substituents selected from halogen, —CN, —OR¹², —SR¹², —N(R¹²)₂, —C(O)OR¹², C₃₋₁₂ carbocycle, and 3- to 12-membered heterocycle; and
C₃₋₁₂ carbocycle and 3- to 12-membered heterocycle, wherein each C₃₋₁₂ carbocycle and 3- to 12-membered heterocycle in R² is independently optionally substituted with one or more substituents selected from —CN, —OR¹², —N(R¹²)₂, —C(O)OR¹², —NR¹²C(O)R¹², =O, R¹², C₁₋₆ alkyl, and C₁₋₆ haloalkyl.

9. The compound or salt of claim 1, wherein:
L¹ is selected from absent;
L² is selected from —O—, —NH—, —C(O)O—, —C(O)NH—, and —NHC(O)—; and
R² is selected from:
—CN, —OR¹², —N(R¹²)₂, —C(O)OR¹², —NR¹²C(O)R¹², —C(O)N(R¹²)₂;
C₁₋₁₀ alkyl, optionally substituted with one or more substituents selected from halogen, —CN, —OR¹², —SR¹², —N(R¹²)₂, —C(O)OR¹², C₃₋₁₂ carbocycle, and 3- to 12-membered heterocycle; and
C₃₋₁₂ carbocycle and 3- to 12-membered heterocycle, wherein each C₃₋₁₂ carbocycle and 3- to 12-membered heterocycle in R² is independently optionally substituted with one or more substituents selected from —CN, —OR¹², —N(R¹²)₂, —C(O)OR¹², —NR¹²C(O)R¹², =O, R¹², C₁₋₆ alkyl, and C₁₋₆ haloalkyl.

10. The compound or salt of claim 1, wherein:
R¹ is CH₃;
L¹ is selected from absent, C₃₋₆ carbocycle, and 3- to 6-membered heterocycle;
L² is selected from absent and —NH—;
R² is selected from:
—NH₂;
C₁₋₆ alkyl, optionally substituted with one or more substituents selected from C₃₋₆ carbocycle and 3- to 6-membered heterocycle; and
C₃₋₆ carbocycle and 3- to 6-membered heterocycle, wherein each C₃₋₆ carbocycle and 3- to 6-membered heterocycle in R² is independently optionally substituted with one or more substituents selected from —N(R¹²)₂, =O, R¹², and C₁₋₆ alkyl; and
R¹² is independently selected at each occurrence from hydrogen and C₁₋₆ alkyl, optionally substituted by halogen, —NH₂, —NHCH₃, and —NHCH₂CH₃.

11. The compound or salt of claim 1, wherein the compound is provided in at least 90% enantiomeric excess.

12. A compound selected from:
N-(azetidin-3-ylmethyl)-N-methyl-6-[5-(6-methyl-2-pyridyl)-1H-imidazol-4-yl]quinolin-3-amine;
3-[(2R,6R)-2,6-dimethyl-1,2,3,6-tetrahydropyridin-4-yl]-6-[5-(6-methyl-2-pyridyl)-1H-imidazol-4-yl]quinoline;
N-(azetidin-3-ylmethyl)-6-[5-(6-methyl-2-pyridyl)-1H-imidazol-4-yl]quinolin-3-amine;
(3R)-1-[6-[5-(6-methyl-2-pyridyl)-1H-imidazol-4-yl]-3-quinolyl]pyrrolidin-3-amine;
3-(1-methyl-2,5-dihydropyrrol-3-yl)-6-[5-(6-methyl-2-pyridyl)-1H-imidazol-4-yl]quinoline;
N-methyl-2-[4-[6-[5-(6-methyl-2-pyridyl)-1H-imidazol-4-yl]-3-quinolyl]pyrazol-1-yl]ethanamine;
isopropyl 2-[4-[6-[5-(6-methyl-2-pyridyl)-1H-imidazol-4-yl]-3-quinolyl]piperazin-2-yl]acetate;
N-[4-[6-[5-(6-methyl-2-pyridyl)-1H-imidazol-4-yl]-3-quinolyl]cyclohex-3-en-1-yl]acetamide;
6-[5-(6-methyl-2-pyridyl)-1H-imidazol-4-yl]-N-(2-pyrrolidin-1-ylethyl)quinolin-3-amine;
azetidin-3-ylmethyl 4-[6-[5-(6-methyl-2-pyridyl)-1H-imidazol-4-yl]-3-quinolyl]cyclohex-3-ene-1-carboxylate;
N-[2-[(3R)-3-(methoxymethyl)piperazin-1-yl]ethyl]-6-[5-(6-methyl-2-pyridyl)-1H-imidazol-4-yl]quinolin-3-amine;
[(3R)-pyrrolidin-3-yl] 1-[6-[5-(6-methyl-2-pyridyl)-1H-imidazol-4-yl]-3-quinolyl]piperidine-4-carboxylate;
[(3R)-pyrrolidin-3-yl] 4-[6-[5-(6-methyl-2-pyridyl)-1H-imidazol-4-yl]-3-quinolyl]cyclohex-3-ene-1-carboxylate;
N-(azetidin-3-yl)-6-[5-(6-methyl-2-pyridyl)-1H-imidazol-4-yl]quinolin-3-amine;
N-[2-(2,2-dimethylpyrrolidin-1-yl)ethyl]-6-[5-(6-methyl-2-pyridyl)-1H-imidazol-4-yl]quinolin-3-amine;
methyl 2-[4-[6-[5-(6-methyl-2-pyridyl)-1H-imidazol-4-yl]-3-quinolyl]piperazin-2-yl]acetate;
[1-[6-[5-(6-methyl-2-pyridyl)-1H-imidazol-4-yl]-3-quinolyl]azetidin-3-yl]methanamine;
3-[6-[5-(6-methyl-2-pyridyl)-1H-imidazol-4-yl]-3-quinolyl]-5,6,7,8-tetrahydro-1,6-naphthyridine;
(1R)-4-[6-[5-(6-methyl-2-pyridyl)-1H-imidazol-4-yl]-3-quinolyl]cyclohex-3-en-1-amine;
N-[4-[6-[5-(6-methyl-2-pyridyl)-1H-imidazol-4-yl]-3-quinolyl]cyclohex-3-en-1-yl]-2-(2-oxotetrahydrofuran-3-yl)sulfanyl-acetamide;
4-piperidyl 5-[6-[5-(6-methyl-2-pyridyl)-1H-imidazol-4-yl]-3-quinolyl]pyridine-2-carboxylate;
N-[2-(azetidin-3-yl)ethyl]-6-[5-(6-methyl-2-pyridyl)-1H-imidazol-4-yl]quinolin-3-amine;
6-[5-(6-methyl-2-pyridyl)-1H-imidazol-4-yl]-N-(2-piperazin-1-ylethyl)quinolin-3-amine;

N-(7-isopropyl-6,8-dihydro-5H-[1,2,4]triazolo[1,5-a]pyrazin-2-yl)-6-[5-(6-methyl-2-pyridyl)-1H-imidazol-4-yl]quinolin-3-amine;
3-(2,6-diazaspiro[3.3]heptan-2-yl)-6-[5-(6-methyl-2-pyridyl)-1H-imidazol-4-yl]quinoline;
3-[6-[5-(6-methyl-2-pyridyl)-1H-imidazol-4-yl]-3-quinolyl]cyclohex-2-en-1-amine;
3-(cyclohexen-1-yl)-6-[5-(6-methyl-2-pyridyl)-1H-imidazol-4-yl]quinoline;
3-[(3R,5S)-3,5-dimethylpiperazin-1-yl]-6-[5-(6-methyl-2-pyridyl)-1H-imidazol-4-yl]quinoline;
[(3R)-1-methylpyrrolidin-3-yl] 4-[6-[5-(6-methyl-2-pyridyl)-1H-imidazol-4-yl]-3-quinolyl]benzoate;
3-(2,8-diazaspiro[3.5]nonan-2-yl)-6-[5-(6-methyl-2-pyridyl)-1H-imidazol-4-yl]quinoline;
2-[6-[5-(6-methyl-2-pyridyl)-1H-imidazol-4-yl]-3-quinolyl]-2,8-diazaspiro[4.5]decane;
5-[6-[5-(6-methyl-2-pyridyl)-1H-imidazol-4-yl]-3-quinolyl]indan-2-amine;
ethyl 4-[6-[5-(6-methyl-2-pyridyl)-1H-imidazol-4-yl]-3-quinolyl]cyclohex-3-ene-1-carboxylate;
(1S)-4-[6-[5-(6-methyl-2-pyridyl)-1H-imidazol-4-yl]-3-quinolyl]cyclohex-3-en-1-amine;
3-(2,7-diazaspiro[3.5]nonan-2-yl)-6-[5-(6-methyl-2-pyridyl)-1H-imidazol-4-yl]quinoline;
6-[5-(6-methyl-2-pyridyl)-1H-imidazol-4-yl]-N-pyrrolidin-3-yl-quinolin-3-amine;
rac-(1R,2R)-2-[3-[6-[5-(6-methyl-2-pyridyl)-1H-imidazol-4-yl]-3-quinolyl]pyrazol-1-yl]cyclohexanamine;
4-[6-[5-(6-methyl-2-pyridyl)-1H-imidazol-4-yl]-3-quinolyl]cyclohex-3-en-1-amine;
azetidin-3-yl 3-[6-[5-(6-methyl-2-pyridyl)-1H-imidazol-4-yl]-3-quinolyl]benzoate;
3-(2,7-diazaspiro[3.5]nonan-7-yl)-6-[5-(6-methyl-2-pyridyl)-1H-imidazol-4-yl]quinoline;
(3S)-1-[6-[5-(6-methyl-2-pyridyl)-1H-imidazol-4-yl]-3-quinolyl]pyrrolidin-3-amine;
6-[5-(6-methyl-2-pyridyl)-1H-imidazol-4-yl]-N-[2-(3-piperidyl)ethyl]quinolin-3-amine;
4-piperidyl 3-[6-[5-(6-methyl-2-pyridyl)-1H-imidazol-4-yl]-3-quinolyl]benzoate;
3-[2-[[1-[6-[5-(6-methyl-2-pyridyl)-1H-imidazol-4-yl]-3-quinolyl]pyrrolidin-3-yl]amino]ethylsulfanyl]tetrahydrofuran-2-one;
azetidin-3-ylmethyl 3-[6-[5-(6-methyl-2-pyridyl)-1H-imidazol-4-yl]-3-quinolyl]benzoate;
3-(1-benzyl-2,5-dihydropyrrol-3-yl)-6-[5-(6-methyl-2-pyridyl)-1H-imidazol-4-yl]quinoline;
N-benzyl-4-[6-[5-(6-methyl-2-pyridyl)-1H-imidazol-4-yl]-3-quinolyl]cyclohex-3-en-1-amine;
6-[5-(6-methyl-2-pyridyl)-1H-imidazol-4-yl]-3-[1-(piperazin-1-ylmethyl)vinyl]quinoline;
6-[5-(6-methyl-2-pyridyl)-1H-imidazol-4-yl]-3-(1,2,3,6-tetrahydropyridin-5-yl)quinoline;
[(3R)-1-methylpyrrolidin-3-yl] 5-[6-[5-(6-methyl-2-pyridyl)-1H-imidazol-4-yl]-3-quinolyl]pyridine-2-carboxylate;
5-[6-[5-(6-methyl-2-pyridyl)-1H-imidazol-4-yl]-3-quinolyl]indan-1-amine;
6-[5-(6-methyl-2-pyridyl)-1H-imidazol-4-yl]-3-(1,2,3,4-tetrahydroisoquinolin-6-yl)quinoline;
3-(2-azaspiro[3.5]non-6-en-7-yl)-6-[5-(6-methyl-2-pyridyl)-1H-imidazol-4-yl]quinoline;
4-piperidyl 4-[6-[5-(6-methyl-2-pyridyl)-1H-imidazol-4-yl]-3-quinolyl]benzoate;
N-[2-[(3R,5S)-3,5-dimethylpiperazin-1-yl]ethyl]-6-[5-(6-methyl-2-pyridyl)-1H-imidazol-4-yl]quinolin-3-amine;
3-(1-isopropyl-2,5-dihydropyrrol-3-yl)-6-[5-(6-methyl-2-pyridyl)-1H-imidazol-4-yl]quinoline;
N-methyl-1-[5-[6-[5-(6-methyl-2-pyridyl)-1H-imidazol-4-yl]-3-quinolyl]-3-pyridyl]methanamine;
N-[5-(4-isopropylpiperazin-1-yl)-2-pyridyl]-6-[5-(6-methyl-2-pyridyl)-1H-imidazol-4-yl]quinolin-3-amine;
6-[5-(6-methyl-2-pyridyl)-1H-imidazol-4-yl]-3-(2-pyridyl)quinoline;
N-[(1S)-4-[6-[5-(6-methyl-2-pyridyl)-1H-imidazol-4-yl]-3-quinolyl]cyclohex-3-en-1-yl]acetamide;
3-(2,7-diazaspiro[4.4]nonan-2-yl)-6-[5-(6-methyl-2-pyridyl)-1H-imidazol-4-yl]quinoline;
9-[6-[5-(6-methyl-2-pyridyl)-1H-imidazol-4-yl]-3-quinolyl]-3-azaspiro[5.5]undec-9-ene;
[(3R)-1-methylpyrrolidin-3-yl] 5-[6-[5-(6-methyl-2-pyridyl)-1H-imidazol-4-yl]-3-quinolyl]pyridine-3-carboxylate;
1-[3-[6-[5-(6-methyl-2-pyridyl)-1H-imidazol-4-yl]-3-quinolyl]phenyl]azetidin-3-amine;
6-[5-(6-methyl-2-pyridyl)-1H-imidazol-4-yl]-3-[1-(3-piperidyl)pyrazol-4-yl]quinoline;
6-[5-(6-methyl-2-pyridyl)-1H-imidazol-4-yl]-3-piperazin-1-yl-quinoline;
(2S)—N-[(1R)-4-[6-[5-(6-methyl-2-pyridyl)-1H-imidazol-4-yl]-3-quinolyl]cyclohex-3-en-1-yl]pyrrolidine-2-carboxamide;
3-(2,5-dihydro-1H-pyrrol-3-yl)-6-[5-(6-methyl-2-pyridyl)-1H-imidazol-4-yl]quinoline;
6-[5-(6-methyl-2-pyridyl)-1H-imidazol-4-yl]-3-(1H-pyrazol-4-yl)quinoline;
4-[6-[5-(6-methyl-2-pyridyl)-1H-imidazol-4-yl]-3-quinolyl]cyclohex-3-en-1-ol;
3-[1-(azetidin-3-yl)pyrazol-4-yl]-6-[5-(6-methyl-2-pyridyl)-1H-imidazol-4-yl]quinoline;
1-[6-[5-(6-methyl-2-pyridyl)-1H-imidazol-4-yl]-3-quinolyl]piperidin-4-amine;
N-[5-(4-methylpiperazin-1-yl)-2-pyridyl]-6-[5-(6-methyl-2-pyridyl)-1H-imidazol-4-yl]quinolin-3-amine;
3-(6,7-dihydro-5H-pyrrolo[3,4-b]pyridin-3-yl)-6-[5-(6-methyl-2-pyridyl)-1H-imidazol-4-yl]quinoline;
4-piperidyl 4-[6-[5-(6-methyl-2-pyridyl)-1H-imidazol-4-yl]-3-quinolyl]cyclohex-3-ene-1-carboxylate;
(1R,2R)-2-[4-[6-[4-(6-methyl-2-pyridyl)-1H-imidazol-5-yl]-3-quinolyl]pyrazol-1-yl]cyclohexanamine;
6-[6-[5-(6-methyl-2-pyridyl)-1H-imidazol-4-yl]-3-quinolyl]-N-(4-piperidyl)pyridin-2-amine;
3-[(2R,6S)-2,6-dimethyl-1,2,3,6-tetrahydropyridin-4-yl]-6-[5-(6-methyl-2-pyridyl)-1H-imidazol-4-yl]quinoline;
3-[[[4-[6-[5-(6-methyl-2-pyridyl)-1H-imidazol-4-yl]-3-quinolyl]cyclohex-3-en-1-yl]amino]methyl]tetrahydrofuran-2-one;
1-[6-[5-(6-methyl-2-pyridyl)-1H-imidazol-4-yl]-3-quinolyl]azetidin-3-amine;
4-[6-[5-(6-methyl-2-pyridyl)-1H-imidazol-4-yl]-3-quinolyl]cyclohex-3-ene-1-carboxylic acid;
N-[2-(4-isopropylpiperazin-1-yl)ethyl]-6-[5-(6-methyl-2-pyridyl)-1H-imidazol-4-yl]quinolin-3-amine;
6-[5-(6-methyl-2-pyridyl)-1H-imidazol-4-yl]-3-(1,2,3,6-tetrahydropyridin-4-yl)quinoline;
N-[2-(3-aminoazetidin-1-yl)ethyl]-6-[5-(6-methyl-2-pyridyl)-1H-imidazol-4-yl]quinolin-3-amine;

N-methyl-2-[3-[6-[5-(6-methyl-2-pyridyl)-1H-imidazol-4-yl]-3-quinolyl]pyrazol-1-yl]ethanamine;
6-[5-(6-methyl-2-pyridyl)-1H-imidazol-4-yl]-N-[2-(4-piperidyl)ethyl]quinolin-3-amine;
[(3S)-1-methylpyrrolidin-3-yl] 3-[6-[5-(6-methyl-2-pyridyl)-1H-imidazol-4-yl]-3-quinolyl]benzoate;
3-[6-[5-(6-methyl-2-pyridyl)-1H-imidazol-4-yl]-3-quinolyl]cyclohex-3-en-1-amine;
N-isopropyl-4-[6-[5-(6-methyl-2-pyridyl)-1H-imidazol-4-yl]-3-quinolyl]cyclohex-3-en-1-amine;
[(3S)-1-methylpyrrolidin-3-yl] 4-[6-[5-(6-methyl-2-pyridyl)-1H-imidazol-4-yl]-3-quinolyl]benzoate;
2-[4-[6-[5-(6-methyl-2-pyridyl)-1H-imidazol-4-yl]-3-quinolyl]pyrazol-1-yl]ethanamine;
6-[5-(6-methyl-2-pyridyl)-1H-imidazol-4-yl]-3-(3-piperazin-1-ylphenyl)quinoline;
5-[[[4-[6-[5-(6-methyl-2-pyridyl)-1H-imidazol-4-yl]-3-quinolyl]cyclohex-3-en-1-yl]amino]methyl]tetrahydrofuran-2-one;
6-[5-(6-methyl-2-pyridyl)-1H-imidazol-4-yl]quinolin-3-amine;
[(3R)-1-methylpyrrolidin-3-yl] 3-[6-[5-(6-methyl-2-pyridyl)-1H-imidazol-4-yl]-3-quinolyl]benzoate;
6-[5-(6-methyl-2-pyridyl)-1H-imidazol-4-yl]-3-(1,2,3,4-tetrahydroisoquinolin-7-yl)quinoline;
N-methyl-1-[6-[5-(6-methyl-2-pyridyl)-1H-imidazol-4-yl]-3-quinolyl]azetidin-3-amine;
azetidin-3-yl 5-[6-[5-(6-methyl-2-pyridyl)-1H-imidazol-4-yl]-3-quinolyl]pyridine-2-carboxylate;
2-[6-[5-(6-methyl-2-pyridyl)-1H-imidazol-4-yl]-3-quinolyl]-2-azaspiro[3.3]heptan-6-amine;
N,N-dimethyl-4-[6-[5-(6-methyl-2-pyridyl)-1H-imidazol-4-yl]-3-quinolyl]cyclohex-3-en-1-amine;
3-isoindolin-4-yl-6-[5-(6-methyl-2-pyridyl)-1H-imidazol-4-yl]quinoline;
N,N-dimethyl-1-[6-[5-(6-methyl-2-pyridyl)-1H-imidazol-4-yl]-3-quinolyl]azetidin-3-amine;
azetidin-3-ylmethyl 4-[6-[5-(6-methyl-2-pyridyl)-1H-imidazol-4-yl]-3-quinolyl]benzoate;
(1S,2S)-2-[4-[6-[4-(6-methyl-2-pyridyl)-1H-imidazol-5-yl]-3-quinolyl]pyrazol-1-yl]cyclohexanamine;
azetidin-3-yl 4-[6-[5-(6-methyl-2-pyridyl)-1H-imidazol-4-yl]-3-quinolyl]benzoate;
N-[3-[6-[5-(6-methyl-2-pyridyl)-1H-imidazol-4-yl]-3-quinolyl]phenyl]piperidin-4-amine;
isobutyl 2-[4-[6-[5-(6-methyl-2-pyridyl)-1H-imidazol-4-yl]-3-quinolyl]piperazin-2-yl]acetate;
N-[(1R)-4-[6-[5-(6-methyl-2-pyridyl)-1H-imidazol-4-yl]-3-quinolyl]cyclohex-3-en-1-yl]acetamide;
3-isoindolin-5-yl-6-[5-(6-methyl-2-pyridyl)-1H-imidazol-4-yl]quinoline;
azetidin-3-ylmethyl 6-[5-(6-methyl-2-pyridyl)-1H-imidazol-4-yl]quinoline-3-carboxylate;
[(3R)-1-methylpyrrolidin-3-yl] 1-[6-[5-(6-methyl-2-pyridyl)-1H-imidazol-4-yl]-3-quinolyl]piperidine-4-carboxylate;
N-[2-(2,8-diazaspiro[4.5]decan-2-yl)ethyl]-6-[5-(6-methyl-2-pyridyl)-1H-imidazol-4-yl]quinolin-3-amine;
[(3S)-1-methylpyrrolidin-3-yl] 5-[6-[5-(6-methyl-2-pyridyl)-1H-imidazol-4-yl]-3-quinolyl]pyridine-3-carboxylate;
methyl (2R)-1-[2-[[6-[5-(6-methyl-2-pyridyl)-1H-imidazol-4-yl]-3-quinolyl]amino]ethyl]piperidine-2-carboxylate;
[(3S)-pyrrolidin-3-yl] 3-[6-[5-(6-methyl-2-pyridyl)-1H-imidazol-4-yl]-3-quinolyl]benzoate;
N-[2-(2,6-diazaspiro[3.3]heptan-2-yl)ethyl]-6-[5-(6-methyl-2-pyridyl)-1H-imidazol-4-yl]quinolin-3-amine;
[(3R)-1-methylpyrrolidin-3-yl] 4-[6-[5-(6-methyl-2-pyridyl)-1H-imidazol-4-yl]-3-quinolyl]cyclohex-3-ene-1-carboxylate;
4-pyrrolidin-1-ylbutyl 6-[5-(6-methyl-2-pyridyl)-1H-imidazol-4-yl]quinoline-3-carboxylate;
[(3R)-pyrrolidin-3-yl] 4-[6-[5-(6-methyl-2-pyridyl)-1H-imidazol-4-yl]-3-quinolyl]benzoate;
methyl (2S)-4-[2-[[6-[5-(6-methyl-2-pyridyl)-1H-imidazol-4-yl]-3-quinolyl]amino]ethyl]piperazine-2-carboxylate;
[(3S)-pyrrolidin-3-yl] 4-[6-[5-(6-methyl-2-pyridyl)-1H-imidazol-4-yl]-3-quinolyl]benzoate;
3-[6-[5-(6-methyl-2-pyridyl)-1H-imidazol-4-yl]-3-quinolyl]-5,6,7,8-tetrahydro-1,7-naphthyridine;
[(3S)-1-methylpyrrolidin-3-yl] 5-[6-[5-(6-methyl-2-pyridyl)-1H-imidazol-4-yl]-3-quinolyl]pyridine-2-carboxylate;
[(3R)-pyrrolidin-3-yl] 5-[6-[5-(6-methyl-2-pyridyl)-1H-imidazol-4-yl]-3-quinolyl]pyridine-3-carboxylate;
6-[6-[5-(6-methyl-2-pyridyl)-1H-imidazol-4-yl]-3-quinolyl]indan-1-amine;
2-[6-[5-(6-methyl-2-pyridyl)-1H-imidazol-4-yl]-3-quinolyl]-4,5,6,7-tetrahydrothiazolo[4,5-c]pyridine;
methyl (3R)-1-[2-[[6-[5-(6-methyl-2-pyridyl)-1H-imidazol-4-yl]-3-quinolyl]amino]ethyl]piperidine-3-carboxylate;
methyl (3R)-1-[2-[[6-[5-(6-methyl-2-pyridyl)-1H-imidazol-4-yl]-3-quinolyl]amino]ethyl]pyrrolidine-3-carboxylate;
N-[2-[(3R)-3-amino-1-piperidyl]ethyl]-6-[5-(6-methyl-2-pyridyl)-1H-imidazol-4-yl]quinolin-3-amine;
methyl 6-[5-(6-methyl-2-pyridyl)-1H-imidazol-4-yl]quinoline-3-carboxylate;
3-[6-[5-(6-methyl-2-pyridyl)-1H-imidazol-4-yl]-3-quinolyl]-6,7-dihydro-5H-cyclopenta[b]pyridin-7-amine;
[(3R)-pyrrolidin-3-yl] 3-[6-[5-(6-methyl-2-pyridyl)-1H-imidazol-4-yl]-3-quinolyl]benzoate;
3-pyrrolidin-1-ylpropyl 6-[5-(6-methyl-2-pyridyl)-1H-imidazol-4-yl]quinoline-3-carboxylate;
azetidin-3-yl 6-[5-(6-methyl-2-pyridyl)-1H-imidazol-4-yl]quinoline-3-carboxylate;
4-piperidyl 6-[5-(6-methyl-2-pyridyl)-1H-imidazol-4-yl]quinoline-3-carboxylate;
4-piperidylmethyl 6-[5-(6-methyl-2-pyridyl)-1H-imidazol-4-yl]quinoline-3-carboxylate;
4-piperidyl 2-[6-[5-(6-methyl-2-pyridyl)-1H-imidazol-4-yl]-3-quinolyl]thiazole-4-carboxylate;
[(3R)-pyrrolidin-3-yl] 2-[6-[5-(6-methyl-2-pyridyl)-1H-imidazol-4-yl]-3-quinolyl]thiazole-4-carboxylate;
[(3R)-1-methylpyrrolidin-3-yl] 2-[6-[5-(6-methyl-2-pyridyl)-1H-imidazol-4-yl]-3-quinolyl]thiazole-4-carboxylate;
azetidin-3-yl 2-[6-[5-(6-methyl-2-pyridyl)-1H-imidazol-4-yl]-3-quinolyl]thiazole-4-carboxylate;
azetidin-3-ylmethyl 2-[6-[5-(6-methyl-2-pyridyl)-1H-imidazol-4-yl]-3-quinolyl]thiazole-4-carboxylate;
[(3S)-1-methylpyrrolidin-3-yl] 2-[6-[5-(6-methyl-2-pyridyl)-1H-imidazol-4-yl]-3-quinolyl]thiazole-4-carboxylate;
[(3S)-pyrrolidin-3-yl] 2-[6-[5-(6-methyl-2-pyridyl)-1H-imidazol-4-yl]-3-quinolyl]thiazole-4-carboxylate;
[(3R)-pyrrolidin-3-yl] 4-[6-[5-(6-methyl-2-pyridyl)-1H-imidazol-4-yl]-3-quinolyl]thiophene-2-carboxylate;

[(3R)-1-methylpyrrolidin-3-yl] 4-[6-[5-(6-methyl-2-pyridyl)-1H-imidazol-4-yl]-3-quinolyl]thiophene-2-carboxylate;
4-piperidyl 4-[6-[5-(6-methyl-2-pyridyl)-1H-imidazol-4-yl]-3-quinolyl]thiophene-2-carboxylate;
azetidin-3-yl 4-[6-[5-(6-methyl-2-pyridyl)-1H-imidazol-4-yl]-3-quinolyl]thiophene-2-carboxylate;
azetidin-3-ylmethyl 4-[6-[5-(6-methyl-2-pyridyl)-1H-imidazol-4-yl]-3-quinolyl]thiophene-2-carboxylate;
[(3S)-pyrrolidin-3-yl] 4-[6-[5-(6-methyl-2-pyridyl)-1H-imidazol-4-yl]-3-quinolyl]thiophene-2-carboxylate;
[(3S)-1-methylpyrrolidin-3-yl] 4-[6-[5-(6-methyl-2-pyridyl)-1H-imidazol-4-yl]-3-quinolyl]thiophene-2-carboxylate;
2-piperazin-1-ylethyl 6-[5-(6-methyl-2-pyridyl)-1H-imidazol-4-yl]quinoline-3-carboxylate;
(3-aminocyclobutyl) 6-[5-(6-methyl-2-pyridyl)-1H-imidazol-4-yl]quinoline-3-carboxylate;
(4-aminocyclohexyl) 6-[5-(6-methyl-2-pyridyl)-1H-imidazol-4-yl]quinoline-3-carboxylate;
(4-aminocyclohexyl)methyl 6-[5-(6-methyl-2-pyridyl)-1H-imidazol-4-yl]quinoline-3-carboxylate;
[rac-(1R,3R)-3-aminocyclopentyl] 6-[5-(6-methyl-2-pyridyl)-1H-imidazol-4-yl]quinoline-3-carboxylate;
[rac-(1R,3 S)-3-aminocyclohexyl]methyl 6-[5-(6-methyl-2-pyridyl)-1H-imidazol-4-yl]quinoline-3-carboxylate;
(4-amino-4-methyl-cyclohexyl) 6-[5-(6-methyl-2-pyridyl)-1H-imidazol-4-yl]quinoline-3-carboxylate;
[rac-(1S,3S)-3-aminocyclohexyl]methyl 6-[5-(6-methyl-2-pyridyl)-1H-imidazol-4-yl]quinoline-3-carboxylate;
(4-aminocyclohexyl)methyl 6-[5-(6-methyl-2-pyridyl)-1H-imidazol-4-yl]quinoline-3-carboxylate;
(4-amino-4-methyl-cyclohexyl) 6-[5-(6-methyl-2-pyridyl)-1H-imidazol-4-yl]quinoline-3-carboxylate;
[(3S)-3-piperidyl]methyl 6-[5-(6-methyl-2-pyridyl)-1H-imidazol-4-yl]quinoline-3-carboxylate;
azepan-3-yl 6-[5-(6-methyl-2-pyridyl)-1H-imidazol-4-yl]quinoline-3-carboxylate;
(2S)—N-[(1S)-4-[6-[5-(6-methyl-2-pyridyl)-1H-imidazol-4-yl]-3-quinolyl]cyclohex-3-en-1-yl]pyrrolidine-2-carboxamide;
(2R)—N-[(1R)-4-[6-[5-(6-methyl-2-pyridyl)-1H-imidazol-4-yl]-3-quinolyl]cyclohex-3-en-1-yl]pyrrolidine-2-carboxamide;
(2R)—N-[(1S)-4-[6-[5-(6-methyl-2-pyridyl)-1H-imidazol-4-yl]-3-quinolyl]cyclohex-3-en-1-yl]pyrrolidine-2-carboxamide;
[4-[6-[5-(6-methyl-2-pyridyl)-1H-imidazol-4-yl]-3-quinolyl]-3,6-dihydro-2H-pyridin-1-yl]-(4-piperidyl)methanone;
[4-[6-[5-(6-methyl-2-pyridyl)-1H-imidazol-4-yl]-3-quinolyl]-3,6-dihydro-2H-pyridin-1-yl]-[(2S)-pyrrolidin-2-yl]methanone;
(3-aminocyclobutyl) 6-[5-(6-methyl-2-pyridyl)-1H-imidazol-4-yl]quinoline-3-carboxylate;
(R)-piperidin-3-ylmethyl 6-(5-(6-methylpyridin-2-yl)-1H-imidazol-4-yl)quinoline-3-carboxylate;
(S)-piperidin-3-yl 6-(5-(6-methylpyridin-2-yl)-1H-imidazol-4-yl)quinoline-3-carboxylate;
[(3S)-pyrrolidin-3-yl] 5-[6-[5-(6-methyl-2-pyridyl)-1H-imidazol-4-yl]-3-quinolyl]thiophene-3-carboxylate;
2-((3S,5R)-3,5-dimethylpiperazin-1-yl)ethyl 6-(5-(6-methylpyridin-2-yl)-1H-imidazol-4-yl)quinoline-3-carboxylate;
2-(piperidin-1-yl)ethyl 6-(5-(6-methylpyridin-2-yl)-1H-imidazol-4-yl)quinoline-3-carboxylate;
3-(piperazin-1-yl)propyl 6-(5-(6-methylpyridin-2-yl)-1H-imidazol-4-yl)quinoline-3-carboxylate;
3-((3S,5R)-3,5-dimethylpiperazin-1-yl)propyl 6-(5-(6-methylpyridin-2-yl)-1H-imidazol-4-yl)quinoline-3-carboxylate;
azetidin-3-yl 5-(6-(5-(6-methylpyridin-2-yl)-1H-imidazol-4-yl)quinolin-3-yl)thiophene-2-carboxylate;
azetidin-3-ylmethyl 5-(6-(5-(6-methylpyridin-2-yl)-1H-imidazol-4-yl)quinolin-3-yl)thiophene-2-carboxylate;
(S)-1-methylpyrrolidin-3-yl 5-(6-(5-(6-methylpyridin-2-yl)-1H-imidazol-4-yl)quinolin-3-yl)thiophene-2-carboxylate;
(R)-1-methylpyrrolidin-3-yl 5-(6-(5-(6-methylpyridin-2-yl)-1H-imidazol-4-yl)quinolin-3-yl)thiophene-2-carboxylate;
piperidin-4-yl 5-(6-(5-(6-methylpyridin-2-yl)-1H-imidazol-4-yl)quinolin-3-yl)thiophene-2-carboxylate;
azetidin-3-yl 2-(6-(5-(6-methylpyridin-2-yl)-1H-imidazol-4-yl)quinolin-3-yl)thiazole-5-carboxylate;
[(3S)-pyrrolidin-3-yl] 4-[6-[5-(6-methyl-2-pyridyl)-1H-imidazol-4-yl]-3-quinolyl]thiazole-2-carboxylate;
2-piperazin-1-ylethyl 6-[6-[5-(6-methyl-2-pyridyl)-1H-imidazol-4-yl]-3-quinolyl]pyridine-3-carboxylate;
6-[5-(6-methyl-2-pyridyl)-1H-imidazol-4-yl]-3-[6-(piperazin-1-ylmethyl)-3-pyridyl]quinoline;
azetidin-3-yl 6-[6-[5-(6-methyl-2-pyridyl)-1H-imidazol-4-yl]-3-quinolyl]pyridine-3-carboxylate;
5-[[(3S,5R)-3,5-dimethylpiperazin-1-yl]methyl]-2-[6-[5-(6-methyl-2-pyridyl)-1H-imidazol-4-yl]-3-quinolyl]thiazole;
4-(2,5-dihydro-1H-pyrrol-3-yl)-2-[6-[5-(6-methyl-2-pyridyl)-1H-imidazol-4-yl]-3-quinolyl]thiazole;
6-[5-(6-methyl-2-pyridyl)-1H-imidazol-4-yl]-3-[6-[[rac-(3 S,5R)-3,5-dimethylpiperazin-1-yl]methyl]-3-pyridyl]quinoline;
azetidin-3-yl 4-[6-[5-(6-methyl-2-pyridyl)-1H-imidazol-4-yl]-3-quinolyl]thiazole-2-carboxylate;
2-(4-piperidyl)ethyl 6-[5-(6-methyl-2-pyridyl)-1H-imidazol-4-yl]quinoline-3-carboxylate;
2-[6-[5-(6-methyl-2-pyridyl)-1H-imidazol-4-yl]-3-quinolyl]-4-(1,2,3,6-tetrahydropyridin-4-yl)thiazole;
2-[6-[5-(6-methyl-2-pyridyl)-1H-imidazol-4-yl]-3-quinolyl]-5-(piperazin-1-ylmethyl)thiazole;
(1S)-5-[6-[5-(6-methyl-2-pyridyl)-1H-imidazol-4-yl]-3-quinolyl]indan-1-amine;
azetidin-3-yl 5-[6-[5-(6-methyl-2-pyridyl)-1H-imidazol-4-yl]-3-quinolyl]thiophene-3-carboxylate;
[(3S)-pyrrolidin-3-yl] 2-[6-[5-(6-methyl-2-pyridyl)-1H-imidazol-4-yl]-3-quinolyl]pyridine-4-carboxylate;
4-piperidyl 6-[6-[5-(6-methyl-2-pyridyl)-1H-imidazol-4-yl]-3-quinolyl]pyridine-2-carboxylate;
azetidin-3-yl 2-[6-[5-(6-methyl-2-pyridyl)-1H-imidazol-4-yl]-3-quinolyl]pyrimidine-5-carboxylate;
2-(3,4,6,7,8,8a-hexahydro-1H-pyrrolo[1,2-a]pyrazin-2-yl)ethyl 6-[5-(6-methyl-2-pyridyl)-1H-imidazol-4-yl]quinoline-3-carboxylate;
2-[6-[5-(6-methyl-2-pyridyl)-1H-imidazol-4-yl]-3-quinolyl]-4,5,6,7-tetrahydrothiazolo[5,4-c]pyridine;
azetidin-3-ylmethyl 5-[6-[5-(6-methyl-2-pyridyl)-1H-imidazol-4-yl]-3-quinolyl]thiophene-3-carboxylate;
azetidin-3-yl 2-[6-[5-(6-methyl-2-pyridyl)-1H-imidazol-4-yl]-3-quinolyl]pyridine-4-carboxylate;
[(3R)-pyrrolidin-3-yl] 2-[6-[5-(6-methyl-2-pyridyl)-1H-imidazol-4-yl]-3-quinolyl]pyrimidine-5-carboxylate;
2-[6-[5-(6-methyl-2-pyridyl)-1H-imidazol-4-yl]-3-quinolyl]-5-(1,2,3,6-tetrahydropyridin-4-yl)thiazole;

[(3R)-pyrrolidin-3-yl] 2-[6-[5-(6-methyl-2-pyridyl)-1H-imidazol-4-yl]-3-quinolyl]pyridine-4-carboxylate;
2-piperazin-1-ylethyl 5-[6-[5-(6-methyl-2-pyridyl)-1H-imidazol-4-yl]-3-quinolyl]thiophene-2-carboxylate;
[(3S)-pyrrolidin-3-yl] 6-[6-[5-(6-methyl-2-pyridyl)-1H-imidazol-4-yl]-3-quinolyl]pyridine-2-carboxylate;
4-piperidyl 6-[6-[5-(6-methyl-2-pyridyl)-1H-imidazol-4-yl]-3-quinolyl]pyridine-3-carboxylate;
2-piperazin-1-ylethyl 4-[6-[5-(6-methyl-2-pyridyl)-1H-imidazol-4-yl]-3-quinolyl]thiazole-2-carboxylate;
6-[5-(6-methyl-2-pyridyl)-1H-imidazol-4-yl]-3-(6-piperazin-1-yl-2-pyridyl)quinoline;
4-piperidyl 2-[6-[5-(6-methyl-2-pyridyl)-1H-imidazol-4-yl]-3-quinolyl]pyrimidine-5-carboxylate;
azetidin-3-ylmethyl 6-[6-[5-(6-methyl-2-pyridyl)-1H-imidazol-4-yl]-3-quinolyl]pyridine-3-carboxylate;
[(3R)-pyrrolidin-3-yl] 4-[6-[5-(6-methyl-2-pyridyl)-1H-imidazol-4-yl]-3-quinolyl]thiazole-2-carboxylate;
[(3R)-pyrrolidin-3-yl] 5-[6-[5-(6-methyl-2-pyridyl)-1H-imidazol-4-yl]-3-quinolyl]thiophene-3-carboxylate;
3-[5-[[(3 S,5R)-3,5-dimethylpiperazin-1-yl]methyl]-3-pyridyl]-6-[5-(6-methyl-2-pyridyl)-1H-imidazol-4-yl]quinoline;
[(3R)-pyrrolidin-3-yl] 6-[6-[5-(6-methyl-2-pyridyl)-1H-imidazol-4-yl]-3-quinolyl]pyridine-3-carboxylate;
4-piperidyl 2-[6-[5-(6-methyl-2-pyridyl)-1H-imidazol-4-yl]-3-quinolyl]pyridine-4-carboxylate;
6-[5-(6-methyl-2-pyridyl)-1H-imidazol-4-yl]-3-[5-(piperazin-1-ylmethyl)-3-pyridyl]quinoline;
5-(2,5-dihydro-1H-pyrrol-3-yl)-2-[6-[5-(6-methyl-2-pyridyl)-1H-imidazol-4-yl]-3-quinolyl]thiazole;
[(3S)-pyrrolidin-3-yl] 6-[6-[5-(6-methyl-2-pyridyl)-1H-imidazol-4-yl]-3-quinolyl]pyridine-3-carboxylate;
2-piperazin-1-ylethyl 2-[6-[5-(6-methyl-2-pyridyl)-1H-imidazol-4-yl]-3-quinolyl]pyridine-4-carboxylate;
2-piperazin-1-ylethyl 2-[6-[5-(6-methyl-2-pyridyl)-1H-imidazol-4-yl]-3-quinolyl]pyrimidine-5-carboxylate;
[(3R)-pyrrolidin-3-yl] 6-[6-[5-(6-methyl-2-pyridyl)-1H-imidazol-4-yl]-3-quinolyl]pyridine-2-carboxylate;
azetidin-3-yl 6-[6-[5-(6-methyl-2-pyridyl)-1H-imidazol-4-yl]-3-quinolyl]pyridine-2-carboxylate;
[4-(methylamino)cyclohexyl] 6-[5-(6-methyl-2-pyridyl)-1H-imidazol-4-yl]quinoline-3-carboxylate;
3-(4-piperidyl)propyl 6-[5-(6-methyl-2-pyridyl)-1H-imidazol-4-yl]quinoline-3-carboxylate;
4-piperidyl 5-[6-[5-(6-methyl-2-pyridyl)-1H-imidazol-4-yl]-3-quinolyl]thiophene-3-carboxylate;
2-piperazin-1-ylethyl 5-[6-[5-(6-methyl-2-pyridyl)-1H-imidazol-4-yl]-3-quinolyl]thiophene-3-carboxylate;
azetidin-3-ylmethyl 2-[6-[5-(6-methyl-2-pyridyl)-1H-imidazol-4-yl]-3-quinolyl]pyrimidine-5-carboxylate;
2-piperazin-1-ylethyl 2-[6-[5-(6-methyl-2-pyridyl)-1H-imidazol-4-yl]-3-quinolyl]thiazole-4-carboxylate;
4-piperidyl 4-[6-[5-(6-methyl-2-pyridyl)-1H-imidazol-4-yl]-3-quinolyl]thiazole-2-carboxylate;
azetidin-3-ylmethyl 4-[6-[5-(6-methyl-2-pyridyl)-1H-imidazol-4-yl]-3-quinolyl]thiazole-2-carboxylate;
[4-[6-[5-(6-methyl-2-pyridyl)-1H-imidazol-4-yl]-3-quinolyl]-3,6-dihydro-2H-pyridin-1-yl]-(3-piperidyl)methanone;
4-[6-[5-(6-methyl-2-pyridyl)-1H-imidazol-4-yl]-3-quinolyl]thiazole-2-carboxylic acid;
2-pyrrolidin-3-ylethyl 6-[5-(6-methyl-2-pyridyl)-1H-imidazol-4-yl]quinoline-3-carboxylate;
(1R)-5-[6-[5-(6-methyl-2-pyridyl)-1H-imidazol-4-yl]-3-quinolyl]indan-1-amine;
azetidin-3-ylmethyl 2-[6-[5-(6-methyl-2-pyridyl)-1H-imidazol-4-yl]-3-quinolyl]pyridine-4-carboxylate;
[(3S)-pyrrolidin-3-yl] 2-[6-[5-(6-methyl-2-pyridyl)-1H-imidazol-4-yl]-3-quinolyl]pyrimidine-5-carboxylate;
[(3S)-pyrrolidin-3-yl] 2-[6-[5-(6-methyl-2-pyridyl)-1H-imidazol-4-yl]-3-quinolyl]thiazole-5-carboxylate;
[(2S)-pyrrolidin-2-yl]methyl 6-[6-[5-(6-methyl-2-pyridyl)-1H-imidazol-4-yl]-3-quinolyl]pyridine-3-carboxylate;
[(2S)-2-piperidyl]methyl 6-[6-[5-(6-methyl-2-pyridyl)-1H-imidazol-4-yl]-3-quinolyl]pyridine-3-carboxylate;
[(3R)-pyrrolidin-3-yl] 2-[6-[5-(6-methyl-2-pyridyl)-1H-imidazol-4-yl]-3-quinolyl]thiazole-5-carboxylate;
2-[(3R)-3-aminopyrrolidin-1-yl]ethyl 6-[6-[5-(6-methyl-2-pyridyl)-1H-imidazol-4-yl]-3-quinolyl]pyridine-3-carboxylate;
2-[rac-(3S,5R)-3,5-dimethylpiperazin-1-yl]ethyl 6-[6-[5-(6-methyl-2-pyridyl)-1H-imidazol-4-yl]-3-quinolyl]pyridine-3-carboxylate;
2-(azetidin-3-yl)ethyl 4-[6-[5-(6-methyl-2-pyridyl)-1H-imidazol-4-yl]-3-quinolyl]thiophene-2-carboxylate;
[(2R)-pyrrolidin-2-yl]methyl 6-[6-[5-(6-methyl-2-pyridyl)-1H-imidazol-4-yl]-3-quinolyl]pyridine-3-carboxylate;
(4-aminocyclohexyl)methyl 4-[6-[5-(6-methyl-2-pyridyl)-1H-imidazol-4-yl]-3-quinolyl]thiophene-2-carboxylate;
2-[(3R)-3-amino-1-piperidyl]ethyl 6-[6-[5-(6-methyl-2-pyridyl)-1H-imidazol-4-yl]-3-quinolyl]pyridine-3-carboxylate;
2-[(3R)-3-amino-1-piperidyl]ethyl 4-[6-[5-(6-methyl-2-pyridyl)-1H-imidazol-4-yl]-3-quinolyl]thiophene-2-carboxylate;
[(2S)-pyrrolidin-2-yl]methyl 4-[6-[5-(6-methyl-2-pyridyl)-1H-imidazol-4-yl]-3-quinolyl]thiophene-2-carboxylate;
2-piperazin-1-ylethyl 2-[6-[5-(6-methyl-2-pyridyl)-1H-imidazol-4-yl]-3-quinolyl]thiazole-5-carboxylate;
3-bromo-6-[5-(6-methyl-2-pyridyl)-1H-imidazol-4-yl]quinoline;
[rac-(1R,3 S)-3-aminocyclohexyl]methyl 4-[6-[5-(6-methyl-2-pyridyl)-1H-imidazol-4-yl]-3-quinolyl]thiophene-2-carboxylate;
(4-amino-4-methyl-cyclohexyl) 4-[6-[5-(6-methyl-2-pyridyl)-1H-imidazol-4-yl]-3-quinolyl]thiophene-2-carboxylate;
9-[6-[5-(6-methyl-2-pyridyl)-1H-imidazol-4-yl]-3-quinolyl]-3-azaspiro[5.5]undec-9-en-4-one;
[(2R)-2-piperidyl]methyl 4-[6-[5-(6-methyl-2-pyridyl)-1H-imidazol-4-yl]-3-quinolyl]thiophene-2-carboxylate;
2-(3,4,6,7,8,8a-hexahydro-1H-pyrrolo[1,2-a]pyrazin-2-yl)ethyl 6-[6-[5-(6-methyl-2-pyridyl)-1H-imidazol-4-yl]-3-quinolyl]pyridine-3-carboxylate;
[(2S)-2-piperidyl]methyl 4-[6-[5-(6-methyl-2-pyridyl)-1H-imidazol-4-yl]-3-quinolyl]thiophene-2-carboxylate;
2-[(3 S)-3-amino-1-piperidyl]ethyl 6-[6-[5-(6-methyl-2-pyridyl)-1H-imidazol-4-yl]-3-quinolyl]pyridine-3-carboxylate;
[rac-(1R,3R)-3-aminocyclohexyl]methyl 4-[6-[5-(6-methyl-2-pyridyl)-1H-imidazol-4-yl]-3-quinolyl]thiophene-2-carboxylate;
[(2R)-pyrrolidin-2-yl]methyl 4-[6-[5-(6-methyl-2-pyridyl)-1H-imidazol-4-yl]-3-quinolyl]thiophene-2-carboxylate;

2-[(3R)-3-aminopyrrolidin-1-yl]ethyl 4-[6-[5-(6-methyl-2-pyridyl)-1H-imidazol-4-yl]-3-quinolyl]thiophene-2-carboxylate;

2-[(3 S,5R)-3,5-dimethylpiperazin-1-yl]ethyl 4-[6-[5-(6-methyl-2-pyridyl)-1H-imidazol-4-yl]-3-quinolyl]thiophene-2-carboxylate;

[(3S)-3-piperidyl]methyl 6-[6-[5-(6-methyl-2-pyridyl)-1H-imidazol-4-yl]-3-quinolyl]pyridine-3-carboxylate;

2-[(3R,5S)-3,5-dimethylpiperazin-1-yl]ethyl 2-[6-[5-(6-methyl-2-pyridyl)-1H-imidazol-4-yl]-3-quinolyl]thiazole-4-carboxylate;

methyl 2-[[6-[5-(6-methyl-2-pyridyl)-1H-imidazol-4-yl]-3-quinolyl]amino]acetate;

(4-amino-4-methyl-cyclohexyl) 4-[6-[5-(6-methyl-2-pyridyl)-1H-imidazol-4-yl]-3-quinolyl]thiophene-2-carboxylate;

2-(azetidin-3-ylamino)ethyl 4-[6-[5-(6-methyl-2-pyridyl)-1H-imidazol-4-yl]-3-quinolyl]thiophene-2-carboxylate;

azetidin-3-ylmethyl 2-[6-[5-(6-methyl-2-pyridyl)-1H-imidazol-4-yl]-3-quinolyl]thiazole-5-carboxylate;

2-(3,4,6,7,8,8a-hexahydro-1H-pyrrolo[1,2-a]pyrazin-2-yl)ethyl 2-[6-[5-(6-methyl-2-pyridyl)-1H-imidazol-4-yl]-3-quinolyl]thiazole-4-carboxylate;

2-piperazin-1-ylethyl 4-[6-[5-(6-methyl-2-pyridyl)-1H-imidazol-4-yl]-3-quinolyl]thiophene-2-carboxylate;

(3-aminocyclobutyl) 4-[6-[5-(6-methyl-2-pyridyl)-1H-imidazol-4-yl]-3-quinolyl]thiophene-2-carboxylate;

[(2R)-2-piperidyl]methyl 6-[6-[5-(6-methyl-2-pyridyl)-1H-imidazol-4-yl]-3-quinolyl]pyridine-3-carboxylate;

(4-aminocyclohexyl)methyl 4-[6-[5-(6-methyl-2-pyridyl)-1H-imidazol-4-yl]-3-quinolyl]thiophene-2-carboxylate;

2-[(3R)-3-amino-1-piperidyl]ethyl 2-[6-[5-(6-methyl-2-pyridyl)-1H-imidazol-4-yl]-3-quinolyl]thiazole-4-carboxylate; and

[(3S)-3-piperidyl]methyl 4-[6-[5-(6-methyl-2-pyridyl)-1H-imidazol-4-yl]-3-quinolyl]thiophene-2-carboxylate;

or a pharmaceutically acceptable salt thereof.

13. A pharmaceutical composition comprising the compound or salt of claim 1 and a pharmaceutically acceptable carrier.

14. The pharmaceutical composition of claim 13, wherein the pharmaceutical composition is formulated for inhalation.

15. A method of ameliorating an ALK5-mediated disease or condition, suppressing the ALK5-mediated disease or condition, or alleviating a symptom of the ALK5-mediated disease or condition in a subject, comprising administering to the subject a therapeutically effective amount of the compound or salt of claim 1.

16. The method of claim 15, wherein the disease or condition is fibrosis.

17. The method of claim 16, wherein the fibrosis is selected from cardiac fibrosis, kidney fibrosis, pulmonary fibrosis, liver fibrosis, portal vein fibrosis, skin fibrosis, bladder fibrosis, intestinal fibrosis, peritoneal fibrosis, myelofibrosis, oral submucous fibrosis, and retinal fibrosis.

18. The method of claim 17, where the pulmonary fibrosis is selected from idiopathic pulmonary fibrosis (IPF), familial pulmonary fibrosis (FPF), interstitial lung fibrosis, fibrosis associated with asthma, fibrosis associated with chronic obstructive pulmonary disease (COPD), silica-induced fibrosis, asbestos-induced fibrosis, and chemotherapy-induced lung fibrosis.

19. The method of claim 16, wherein the fibrosis is idiopathic pulmonary fibrosis (IPF).

20. The method of claim 16, wherein the fibrosis is intestinal fibrosis.

21. The method of claim 15, wherein the disease or condition is selected from breast cancer, colon cancer, prostate cancer, lung cancer, hepatocellular carcinoma, glioblastoma, melanoma, and pancreatic cancer.

22. The method of claim 21, wherein the lung cancer is non-small cell lung cancer.

23. The method of claim 15, comprising administering a second therapeutic agent.

24. The method of claim 23, wherein the second therapeutic agent is an immunotherapeutic agent.

25. The method of claim 15, wherein the compound or salt is administered by inhalation.

* * * * *